United States Patent
Altenbach et al.

(10) Patent No.: US 10,399,940 B2
(45) Date of Patent: Sep. 3, 2019

(54) SUBSTITUTED PYRROLIDINES AND METHODS OF USE

(71) Applicants: AbbVie S.à.r.l., Luxembourg (LU); Galapagos NV, Mechelen (BE)

(72) Inventors: Robert J. Altenbach, Chicago, IL (US); Andrew Bogdan, Evanston, IL (US); Nicolas Desroy, Massy (FR); Gregory A. Gfesser, Lindenhurst, IL (US); Stephen N. Greszler, Vernon Hills, IL (US); John R. Koenig, Chicago, IL (US); Philip R. Kym, Libertyville, IL (US); Bo Liu, Waukegan, IL (US); Marc J. Scanio, Libertyville, IL (US); Xenia Searle, Grayslake, IL (US); Xueqing Wang, Northbrook, IL (US); Ming C. Yeung, Grayslake, IL (US); Gang Zhao, Northbrook, IL (US)

(73) Assignees: AbbVie S.à.r.l., Luxembourg (LU); Galapagos NV, Mechelen (BE)

( * ) Notice: Subject to any disclaimer, the term of this patent is extended or adjusted under 35 U.S.C. 154(b) by 0 days.

(21) Appl. No.: 15/723,896

(22) Filed: Oct. 3, 2017

(65) Prior Publication Data

US 2018/0099932 A1 Apr. 12, 2018

Related U.S. Application Data

(60) Provisional application No. 62/405,562, filed on Oct. 7, 2016.

(51) Int. Cl.
| | | |
|---|---|---|
| *C07D 401/12* | (2006.01) | |
| *C07D 401/14* | (2006.01) | |
| *C07D 207/16* | (2006.01) | |
| *A61K 31/40* | (2006.01) | |
| *A61K 31/4439* | (2006.01) | |
| *A61K 31/4709* | (2006.01) | |
| *A61K 31/506* | (2006.01) | |
| *A61K 45/06* | (2006.01) | |
| *C07D 403/12* | (2006.01) | |
| *C07D 405/14* | (2006.01) | |

(52) U.S. Cl.
CPC ............ *C07D 207/16* (2013.01); *A61K 31/40* (2013.01); *A61K 31/4439* (2013.01); *A61K 31/4709* (2013.01); *A61K 31/506* (2013.01); *A61K 45/06* (2013.01); *C07D 401/12* (2013.01); *C07D 401/14* (2013.01); *C07D 403/12* (2013.01); *C07D 405/14* (2013.01)

(58) Field of Classification Search
CPC .................................................. C07D 401/12
See application file for complete search history.

(56) References Cited

U.S. PATENT DOCUMENTS

| | | |
|---|---|---|
| 8,999,976 B2 | 4/2015 | Binch et al. |
| 2016/0120841 A1 | 5/2016 | Kym et al. |
| 2016/0122331 A1 | 5/2016 | Kym et al. |
| 2017/0015675 A1 | 1/2017 | Altenbach et al. |
| 2017/0101405 A1 | 4/2017 | Akkari et al. |
| 2017/0101406 A1 | 4/2017 | Akkari et al. |
| 2017/0217627 A1 | 8/2017 | Earnshaw et al. |
| 2017/0233564 A1 | 8/2017 | Li et al. |

FOREIGN PATENT DOCUMENTS

| | | |
|---|---|---|
| WO | 2005120497 A2 | 12/2005 |
| WO | 2006002421 A2 | 1/2006 |
| WO | 2008147952 A1 | 12/2008 |
| WO | 2009074575 A1 | 6/2009 |
| WO | 2009076593 A1 | 6/2009 |
| WO | 2010048573 A1 | 4/2010 |
| WO | 2011072241 A1 | 6/2011 |
| WO | 2011/119984 A1 | 9/2011 |
| WO | 2011113894 A1 | 9/2011 |
| WO | 2012048181 A1 | 4/2012 |
| WO | 2013038373 A1 | 3/2013 |
| WO | 2013038378 A1 | 3/2013 |
| WO | 2013038381 A1 | 3/2013 |

(Continued)

OTHER PUBLICATIONS

Quinton, P.M., 1990. Cystic fibrosis: a disease in electrolyte transport. FASEB J. 4, 2709-2717.

Kerem, B., Rommens, J.M Buchanan, J.A., Markiewicz, D., Cox, T.K., Chakravarti, A., Buchwald, M., Tsui, L.C., Identification of the Cystic Fibrosis Gene: Genetic Analysis, Science, 1989, vol. 245, No. 4922, pp. 1073-1080.

Bobadilla, J.L., Macek, M., Jr, Fine, J.P., Farrell, P.M., 2002. Cystic fibrosis: a worldwide analysis of CFTR mutations—correlation with incidence data and application to screening. Hum. Mutat. 19, 575-606. doi:10.1002/humu.10041.

Pasyk, E.A., Foskett, J.K., 1995. Mutant (F508delCFTR) Cystic Fibrosis Transmembrane Conductance Regulator Cl—channel is functional when retained in Endoplasmic Reticulum of mammalian cells. J. Biol. Chem. 270, 12347-12350.

Morello, J.-P., Bouvier, M., Petäjä-Repo, U.E., Bichet, D.G., 2000. Pharmacological chaperones: a new twist on receptor folding. Trends Pharmacol. Sci. 21, 466-469. doi:10.1016/S0165-6147(00)01575-3.

(Continued)

*Primary Examiner* — Shawquia Jackson
(74) *Attorney, Agent, or Firm* — Quarles & Brady LLP

(57) ABSTRACT

The invention discloses compounds of Formula (I)

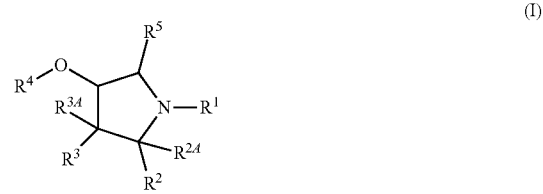

wherein $R^1$, $R^2$, $R^{2A}$, $R^3$, $R^{3A}$, $R^4$, and $R^5$ are as defined herein. The present invention relates to compounds and their use in the treatment of cystic fibrosis, methods for their production, pharmaceutical compositions comprising the same, and methods of treating cystic fibrosis by administering a compound of the invention.

21 Claims, No Drawings

(56) References Cited

FOREIGN PATENT DOCUMENTS

| WO | 2013038386 A1 | 3/2013 |
| --- | --- | --- |
| WO | 2013038390 A1 | 3/2013 |
| WO | 2013043720 A1 | 3/2013 |
| WO | 2014180562 A1 | 11/2014 |
| WO | 2015018823 A1 | 2/2015 |
| WO | 2015138909 A1 | 9/2015 |
| WO | 2015138934 A1 | 9/2015 |
| WO | 2016193812 A1 | 12/2016 |

OTHER PUBLICATIONS

Shastry, B.S. 2003. Neurodegenerative disorders of protein aggregation. Neurochem. Int. 43, 1-7. doi:10.1016/S0197-0186(02)00196-1.

Zhang W. Fujii, N., Naren, A.P., 2012. Recent advances and new perspectives in targeting CFTR for therapy of cystic fibrosis and enterotoxin-induced secretory diarrheas. (Future Med. Chem. 4, 329-345. doi:10.4155/fmc.12.1).

IUPAC 1974 Recommendations for Section E, Fundamental Stereochemistry, in Pure Appl. Chem., 1976, 45: 13-30.

Yan, X.-X., Peng, Q., Zhang, Y., Zhang, K., Hong, W., Hou, X.-L. and Wu, Y.-D., Angew. Chem., Int. Ed. 2006, 45 1979-1983.

Berge, S. M., et al. J. Pharmaceutical Sciences, 1977, 66: 1-19.

Veit G. et al, (2012) Mol Biol Cell. 23(21): 4188-4202.

European Patent Office as International Searching Authority, International Search Report and Written Opinion for corresponding International Application No. PCT/IB2017/056126, dated Dec. 21, 2017, 13 pages.

Steven M. Rowe and Alan S. Verkman, "Cystic Fibrosis Transmembrane Regulator Correctors and Potentiators", Cold Spring Harbor Perspectives in Medicine, dated Jul. 1, 2013, pp. 1-16, vol. 3, No. 7, published by Cold Spring Harbor Laboratory Press.

Puay-Wah Phuan, et al., "Synergy-Based Small-Molecule Screen Using a Human Lung Epithelial Cell Line Yields ΔF508-CFTR Correctors That Augment VX-809 Maximal Efficacy", Molecular Pharmacology, dated May 16, 2014, pp. 42-51, vol. 86, No. 1, copyright 2014 by The American Society for Pharmacology and Experimental Therapeutics.

SUBSTITUTED PYRROLIDINES AND METHODS OF USE

CROSS REFERENCE TO RELATED APPLICATIONS

This application claims priority to U.S. Provisional Application No. 62/405,562, filed Oct. 7, 2016, which is incorporated herein by its entirety for all purposes.

BACKGROUND OF THE INVENTION

Technical Field

The invention relates to substituted pyridine compounds that are modulators of the Cystic Fibrosis Transmembrane Conductance Regulator (CFTR) protein, useful in treating diseases and conditions mediated and modulated by CFTR. The invention also relates to compositions containing compounds of the invention, processes for their preparation, and methods of treatment using them.

Description of Related Technology

ABC transporters are a family of homologous membrane transporter proteins regulating the transport of a wide variety of pharmacological agents (for example drugs, xenobiotics, anions, etc.) that bind and use cellular adenosine triphosphate (ATP) for their specific activities. Some of these transporters were found to defend malignant cancer cells against chemotherapeutic agents, acting as multidrug resistance proteins (like the MDR1-P glycoprotein, or the multidrug resistance protein, MRP 1). So far, 48 ABC transporters, grouped into 7 families based on their sequence identity and function, have been identified.

ABC transporters provide protection against harmful environmental compounds by regulating a variety of important physiological roles within the body, and therefore represent important potential drug targets for the treatment of diseases associated with transporter defects, outwards cell drug transport, and other diseases in which modulation of ABC transporter activity may be beneficial.

The cAMP/ATP-mediated anion channel, CFTR, is one member of the ABC transporter family commonly associated with diseases, which is expressed in a variety of cell types, including absorptive and secretory epithelia cells, where it regulates anion flux across the membrane, as well as the activity of other ion channels and proteins. The activity of CFTR in epithelial cells is essential for the maintenance of electrolyte transport throughout the body, including respiratory and digestive tissue (Quinton, P. M., 1990. Cystic fibrosis: a disease in electrolyte transport. FASEB J. 4, 2709-2717).

The gene encoding CFTR has been identified and sequenced (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking.

Cystic fibrosis (CF) is caused by a defect in this gene which induces mutations in CFTR. Cystic fibrosis is the most common fatal genetic disease in humans, and affects ~0.04% of white individuals (Bobadilla, J. L., Macek, M., Jr, Fine, J. P., Farrell, P. M., 2002. Cystic fibrosis: a worldwide analysis of CFTR mutations--correlation with incidence data and application to screening. Hum. Mutat. 19, 575-606. doi: 10.1002/humu.10041), for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections.

In cystic fibrosis patients, mutations in endogenous respiratory epithelial CFTR fails to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects with cystic fibrosis suffer from decreased fertility, whilst males with cystic fibrosis are infertile.

A variety of disease causing mutations has been identified through sequence analysis of the CFTR gene of CF chromosomes (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). F508delCFTR, the most common CF mutation (present in at least 1 allele in ~90% of CF patients) and occurring in approximately 70% of the cases of cystic fibrosis, contains a single amino acid deletion of phenylalanine 508. This deletion prevents the nascent protein from folding correctly, which protein in turn cannot exit the endoplasmic reticulum (ER) and traffic to the plasma membrane, and then is rapidly degraded. As a result, the number of channels present in the membrane is far less than in cells expressing wild-type CFTR. In addition to impaired trafficking, the mutation results in defective channel gating. Indeed, even if F508delCFTR is allowed to reach the cell plasma membrane by low-temperature (27° C.) rescue where it can function as a cAMP-activated chloride channel, its activity is decreased significantly compared with WT-CFTR (Pasyk, E. A., Foskett, J. K., 1995. Mutant (F508delCTFR) Cystic Fibrosis Transmembrane Conductance Regulator Cl⁻channel is functional when retained in Endoplasmic Reticulum of mammalian cells. J. Biol. Chem. 270, 12347-12350).

Other mutations with lower incidence have also been identified that alter the channel regulation or the channel conductance. In case of the channel regulation mutants, the mutated protein is properly trafficked and localized to the plasma membrane but either cannot be activated or cannot function as a chloride channel (e.g. missense mutations located within the nucleotide binding domains), examples of these mutations are G551D, G178R, and G1349D. Mutations affecting chloride conductance have a CFTR protein that is correctly trafficked to the cell membrane but that generates reduced chloride flow (e.g. missense mutations located within the membrane-spanning domain), examples of these mutations are R117H and R334W.

In addition to cystic fibrosis, CFTR activity modulation may be beneficial for other diseases not directly caused by mutations in CFTR, such as, for example, chronic obstructive pulmonary disease (COPD), dry eye disease, and Sjögren's syndrome.

COPD is characterized by a progressive and non-reversible airflow limitation, which is due to mucus hypersecretion, bronchiolitis, and emphysema. A potential treatment of mucus hypersecretion and impaired mucociliary clearance that is common in COPD could consist in using activators of mutant or wild-type CFTR. In particular, the anion secretion increase across CFTR may facilitate fluid transport into the airway surface liquid to hydrate the mucus and optimize periciliary fluid viscosity. The resulting enhanced mucociliary clearance would help in reducing the symptoms associated with COPD.

Dry eye disease is characterized by a decrease in tear production and abnormal tear film lipid, protein and mucin profiles. Many factors may cause dry eye disease, some of which include age, arthritis, Lasik eye surgery, chemical/thermal burns, medications, allergies, and diseases, such as cystic fibrosis and Sjögren's syndrome. Increasing anion secretion via CFTR could enhance fluid transport from the corneal endothelial cells and secretory glands surrounding the eye, and eventually improve corneal hydration, thus helping to alleviate dry eye disease associated symptoms. Sjögren's syndrome is an autoimmune disease where the immune system harms moisture-producing glands throughout the body, including the eye, mouth, skin, respiratory tissue, liver, vagina, and gut. The ensuing symptoms, include, dry eye, mouth, and vagina, as well as lung disease. Sjögren's syndrome is also associated with rheumatoid arthritis, systemic lupus, systemic sclerosis, and polymyositis/dermatomyositis. The cause of the disease is believed to lie in defective protein trafficking, for which treatment options are limited. As a consequence, modulation of CFTR activity may help hydrating the various organs and help to elevate the associated symptoms.

In addition to CF, the defective protein trafficking induced by the 508delCFTR has been shown to be the underlying basis for a wide range of other diseases, in particular diseases where the defective functioning of the endoplasmic reticulum (ER) may either prevent the CFTR protein to exit the cell, and/or the misfolded protein is degraded (Morello, J.-P., Bouvier, M., Petäjä-Repo, U. E., Bichet, D. G., 2000. Pharmacological chaperones: a new twist on receptor folding. Trends Pharmacol. Sci. 21, 466-469. doi: 10.1016/S0165-6147(00)01575-3; Shastry, B. S., 2003. Neurodegenerative disorders of protein aggregation. Neurochem. Int. 43, 1-7. doi:10.1016/S0197-0186(02)00196-1; Zhang, W., Fujii, N., Naren, A. P., 2012. Recent advances and new perspectives in targeting CFTR for therapy of cystic fibrosis and enterotoxin-induced secretory diarrheas. (Future Med. Chem. 4, 329-345. doi:10.4155/fmc.12.1).

A number of genetic diseases are associated with a defective ER processing equivalent to the defect observed with CFTR in CF such as glycanosis CDG type 1, hereditary emphysema (α-1-antitrypsin (PiZ variant)), congenital hyperthyroidism, osteogenesis imperfecta (Type I, II, or IV procollagen), hereditary hypofibrinogenemia (fibrinogen), ACT deficiency (α-1-antichymotrypsin), diabetes insipidus (DI), neurohypophyseal DI (vasopressin hormoneN2-receptor), nephrogenic DI (aquaporin II), Charcot-Marie Tooth syndrome (peripheral myelin protein 22), Pelizaeus-Merzbacher disease, neurodegenerative diseases such as Alzheimer's disease (APP and presenilins), Parkinson's disease, amyotrophic lateral sclerosis, progressive supranuclear palsy, Pick's disease, several polyglutamine neurological disorders such as Huntington's disease, spinocerebellar ataxia type I, spinal and bulbar muscular atrophy, dentatorubral pallidoluysian, and myotonic dystrophy, as well as spongiform encephalopathies, such as hereditary Creutzfeldt-Jakob disease (prion protein processing defect), Fabry disease (lysosomal α-galactosidase A), Straussler-Scheinker syndrome, chronic obstructive pulmonary disease (COPD), dry eye disease, and Sjögren's syndrome.

In addition to up-regulation of the activity of CFTR, anion secretion reduction by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Regardless of the cause, excessive chloride transport is seen in all diarrheas, and results in dehydration, acidosis, impaired growth and death. Acute and chronic diarrheas remain a major medical problem worldwide, and are a significant factor in malnutrition, leading to death in children of less than five years old (5,000,000 deaths/year). Furthermore, in patients with chronic inflammatory bowel disease (IBD) and/or acquired immunodeficiency syndrome (AIDS), diarrhea is a dangerous condition.

Accordingly, there is a need for novel compounds able to modulate CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

In one aspect, the invention provides for compounds of Formula (I)

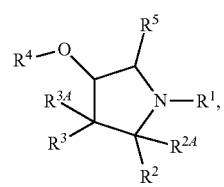

(I)

wherein
R$^1$ is selected from the group consisting of SO$_2$R$^6$, C(O)R$^6$, C(O)OR$^6$, and C(O)NR$^7$R$^8$;
R$^2$ is C(O)OH or a bioisostere thereof;
R$^{2A}$ is selected from the group consisting of hydrogen, C$_1$-C$_6$ alkyl, C$_1$-C$_6$ haloalkyl, and C$_3$-C$_6$ cycloalkyl;
R$^3$ is selected from the group consisting of C$_1$-C$_6$ alkyl, C$_3$-C$_6$ cycloalkyl, phenyl, and 5-6 membered heteroaryl; wherein the R$^3$ C$_1$-C$_6$ alkyl is optionally substituted with one or more substituents independently selected from the group consisting of C$_1$-C$_6$ alkoxy, OH, oxo, CN, NO$_2$, F, Cl, Br and I; wherein the R$^3$ C$_3$-C$_6$ cycloalkyl, phenyl, and 5-6 membered heteroaryl are optionally substituted with one or more substituents independently selected from the group consisting of C$_1$-C$_6$ alkyl, C$_1$-C$_6$ alkoxy, C$_1$-C$_6$ haloalkyl, OH, oxo, CN, NO$_2$, F, Cl, Br and I; and
R$^{3A}$ is selected from the group consisting of hydrogen, C$_1$-C$_6$ alkyl, and C$_1$-C$_6$ haloalkyl; or
R$^3$ and R$^{3A}$, together with the carbon to which they are attached, form a C$_3$-C$_6$ cycloalkyl; wherein the C$_3$-C$_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^4$ is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;

$L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo;

$R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

R²⁴, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and R²⁵ and R²⁶, at each occurrence, are each independently hydrogen or $C_1$-$C_6$ alkyl.

Another aspect of the invention relates to pharmaceutical compositions comprising a compound of the invention, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator activity. In a particular aspect, the pharmaceutical compositions may additionally comprise further therapeutically active ingredients suitable for use in combination with the compounds of the invention. In a more particular aspect, the further therapeutically active ingredient is an agent for the treatment of cystic fibrosis.

Moreover, the compounds of the invention, useful in the pharmaceutical compositions and treatment methods disclosed herein, are pharmaceutically acceptable as prepared and used.

Yet another aspect of the invention relates to a method for treating, or preventing conditions and disorders related to Cystic Fibrosis Transmembrane Conductance Regulator activity in mammals. More particularly, the method is useful for treating or preventing conditions and disorders related to cystic fibrosis, Sjögren's syndrome, pancreatic insufficiency, chronic obstructive lung disease, or chronic obstructive airway disease. Accordingly, the compounds and compositions of the invention are useful as a medicament for treating or preventing Cystic Fibrosis Transmembrane Conductance Regulator modulated disease.

The compounds, compositions comprising the compounds, methods for making the compounds, and methods for treating or preventing conditions and disorders by administering the compounds are further described herein.

In a particular aspect, the compounds of the invention are provided for use in the treatment of cystic fibrosis. In a particular aspect, the compounds of the invention are provided for use in the treatment of cystic fibrosis caused by class I, II, III, IV, V, and/or VI mutations.

The present invention also provides pharmaceutical compositions comprising a compound of the invention, and a suitable pharmaceutical carrier for use in medicine. In a particular aspect, the pharmaceutical composition is for use in the treatment of cystic fibrosis.

These and other objects of the invention are described in the following paragraphs. These objects should not be deemed to narrow the scope of the invention.

DETAILED DESCRIPTION OF THE INVENTION

Described herein are compounds of Formula (I)

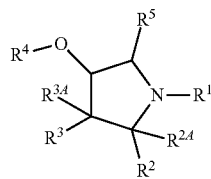

(I)

wherein R¹, R², R²⁴, R³, R³ᴬ, R⁴, and R⁵ are defined above in the Summary and below in the Detailed Description. Further, compositions comprising such compounds and methods for treating conditions and disorders using such compounds and compositions are also included.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds; reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_6$ alkenyl" means an alkenyl group containing 2-6 carbon atoms. Non-limiting examples of $C_2$-$C_6$ alkenyl include buta-1,3-dienyl, ethenyl, 2-propenyl, 2-methyl-2-propenyl, 3-butenyl, 4-pentenyl, and 5-hexenyl.

The term "$C_1$-$C_6$ alkoxy" as used herein, means a $C_1$-$C_6$ alkyl group, as defined herein, appended to the parent molecular moiety through an oxygen atom. Non-limiting examples of alkoxy include methoxy, ethoxy, propoxy, 2-propoxy, butoxy, tert-butoxy, pentyloxy, and hexyloxy.

The term "$C_1$-$C_6$ alkoxy-$C_1$-$C_6$ alkyl" as used herein, means a $C_1$-$C_6$ alkoxy group, as defined herein, appended to the parent molecular moiety through a $C_1$-$C_6$ alkyl group, as defined herein. Representative examples of $C_1$-$C_6$ alkoxy-$C_1$-$C_6$ alkyl include, but are not limited to, tert-butoxymethyl, 2-ethoxyethyl, 2-methoxyethyl, and methoxymethyl.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl. The terms "alkyl," "$C_1$-$C_6$ alkyl," "$C_1$-$C_4$ alkyl," and "$C_1$-$C_3$ alkyl" used herein are unsubstituted, unless otherwise indicated.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 1 to 3 carbon atoms ($C_1$-$C_3$ alkylenyl) or of 2 to 6 carbon atoms ($C_2$-$C_6$ alkylenyl). Examples of $C_1$-$C_6$ alkylenyl include, but are not limited to, —$CH_2$—, —$CH_2CH_2$—, —$C(CH_3)_2$—$CH_2CH_2$—, —$C(CH_3)_2$—$CH_2CH_2$—, —$CH_2CH_2CH_2CH_2$—, and —$CH_2CH(CH_3)CH_2$—.

The term, "alkenylene" as used herein, means a divalent radical derived from a straight or branched hydrocarbon chain and containing at least one carbon-carbon double bond. The term, "$C_2$-$C_6$ alkenylene" as used herein, means a divalent radical derived from a straight or branched hydrocarbon chain containing from 2 to 6 carbons and containing at least one carbon-carbon double bond.

The term, "alkynylene" as used herein, means a divalent radical derived from straight or branched chain hydrocarbon radical and containing at least one carbon-carbon triple bond. The term, "$C_2$-$C_6$ alkynylene" as used herein, means a divalent radical derived from straight or branched chain hydrocarbon radical containing from 2 to 6 carbon atoms and containing at least one carbon-carbon triple bond.

The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited to, acetylenyl, 1-propynyl, 2-propynyl, 3-butynyl, 2-pentynyl, and 1-butynyl.

The term "$C_3$-$C_{11}$ cycloalkyl" as used herein, means a hydrocarbon ring radical containing 3-11 carbon atoms, zero heteroatoms, and zero double bonds. The $C_3$-$C_{11}$ cycloalkyl group may be a single-ring (monocyclic) or have two or more rings (polycyclic or bicyclic). Monocyclic cycloalkyl groups typically contain from 3 to 8 carbon ring atoms ($C_3$-$C_8$ monocyclic cycloalkyl), and even more typically 3-6 carbon ring atoms ($C_3$-$C_6$ monocyclic cycloalkyl). Examples of monocyclic cycloalkyls include cyclopropyl, cyclobutyl, cyclopentyl, cyclohexyl, cycloheptyl, and cyclooctyl. Polycyclic cycloalkyl groups contain two or more rings, and bicyclic cycloalkyls contain two rings. In certain embodiments, the polycyclic cycloalkyl groups contain 2 or 3 rings. The rings within the polycyclic and the bicyclic cycloalkyl groups may be in a bridged, fused, or spiro orientation, or combinations thereof. In a spirocyclic cycloalkyl, one atom is common to two different rings. Examples of a spirocyclic cycloalkyl include spiro[2.5]octanyl and spiro[4.5]decanyl. In a bridged cycloalkyl, the rings share at least two non-adjacent atoms. Examples of bridged cycloalkyls include, but are not limited to bicyclo[1.1.1]pentanyl, bicyclo[2.2.2]octyl, bicyclo[3.2.1]octyl, bicyclo[3.1.1]heptyl, bicyclo[2.2.1]heptyl, bicyclo[3.2.2]nonyl, bicyclo[3.3.1]nonyl, and bicyclo[4.2.1]nonyl, tricyclo[3.3.1.0$^{3,7}$]nonyl (octahydro-2,5-methanopentalenyl or noradamantyl), tricyclo[3.3.1.1$^{3,7}$]decyl (adamantyl), and tricyclo[4.3.1.1$^{3,8}$]undecyl (homoadamantyl). In a fused ring cycloalkyl, the rings share one common bond. Examples of fused-ring cycloalkyl include, but not limited to, decalin (decahydronaphthyl), bicyclo[3.1.0]hexanyl, and bicyclo[2.2.0]octyl.

The term "$C_3$-$C_6$ cycloalkyl" as used herein, means a hydrocarbon ring radical containing 3-6 carbon atoms, zero heteroatoms, and zero double bonds. The $C_3$-$C_6$ cycloalkyl group may be a single-ring (monocyclic) or have two rings (bicyclic).

The term "$C_4$-$C_{11}$ cycloalkenyl" as used herein, means a non-aromatic hydrocarbon ring radical containing 4-11 carbon atoms, zero heteroatoms, and one or more double bonds. The $C_4$-$C_{11}$ cycloalkenyl group may be a single-ring (monocyclic) or have two or more rings (polycyclic or bicyclic). Examples of monocyclic cycloalkenyl include cyclobutenyl, cyclopentenyl, cyclohexenyl, cyclohexadienyl, cycloheptyl, cyclooctenyl, and cyclooctadienyl. Examples of bicyclic cycloalkenyl include bicyclo[2.2.1]hept-2-enyl.

The term "$C_4$-$C_8$ monocyclic cycloalkenyl" as used herein, means cyclobutenyl, cyclopentenyl, cyclohexenyl, cyclohexadienyl, cycloheptyl, cycloheptadienyl, cyclooctenyl, and cyclooctadienyl.

The term "$C_4$-$C_7$ monocyclic cycloalkenyl" as used herein, means cyclobutenyl, cyclopentenyl, cyclohexenyl, cyclohexadienyl, and cycloheptyl.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl.

The term "haloalkoxy" as used herein, means an alkoxy group, as defined herein, in which one, two, three, four, five or six hydrogen atoms are replaced by halogen. The term "$C_1$-$C_6$ haloalkoxy" means a $C_1$-$C_6$ alkoxy group, as defined herein, in which one, two, three, four, five, or six hydrogen atoms are replaced by halogen.

The term "4-12 membered heterocycle" as used herein, means a hydrocarbon ring radical of 4-12 carbon ring atoms wherein at least one carbon atom is replaced by a heteroatom(s) independently selected from the group consisting of O, N, and S. The 4-12 membered heterocycle ring may be a single ring (monocyclic) or have two or more rings (bicyclic or polycyclic). In certain embodiments, the monocyclic heterocycle is a four-, five-, six-, seven-, or eight-membered hydrocarbon ring wherein at least one carbon ring atom is replaced by a heteroatom(s) independently selected from the group consisting of O, N, and S. In certain embodiments, the monocyclic heterocycle is a 4-7 membered hydrocarbon ring wherein at least one carbon ring atom is replaced by a heteroatom(s). A four-membered monocyclic heterocycle contains zero or one double bond, and one heteroatom selected from the group consisting of O, N, and S. A five-membered monocyclic heterocycle contains zero or one double bond and one, two, or three heteroatoms selected from the group consisting of O, N, and S. Examples of five-membered monocyclic heterocycles include those containing in the ring: 1 O; 1 S; 1 N; 2 N; 3 N; 1 S and 1 N; 1 S, and 2 N; 1 O and 1 N; or 1 O and 2 N. Non limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, imidazolidinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered monocyclic heterocycle contains zero, one, or two double bonds and one, two, or three heteroatoms selected from the group consisting of O, N, and S. Examples of six-membered monocyclic heterocycles include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of six-membered monocyclic heterocycles include dihydropyranyl, 1,4-dioxanyl, 1,3-dioxanyl, 1,4-dithianyl, hexahydropyrimidine, morpholinyl, 1,4-dihydropyridinyl, piperazinyl, piperidinyl, tetrahydropyranyl, 1,2,3,6-tetrahydropyridinyl, tetrahydrothiopyranyl, thiomorpholinyl, thioxanyl, and trithianyl. Seven- and eight-membered monocyclic heterocycles contains zero, one, two, or three double bonds and one, two, or three heteroatoms selected from the group consisting of O, N, and S. Examples of monocyclic heterocycles include, but are not limited to, azetidinyl, azepanyl, aziridinyl, 1,4-diazepanyl, dihydropyranyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxazepanyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. Polycyclic heterocycle groups contain two or more rings, and bicyclic heterocycles contain two rings. In certain embodiments, the polycyclic heterocycle groups contain 2 or 3 rings. The rings within the polycyclic and the bicyclic heterocycle groups may be in a bridged, fused, or spiro orientation, or combinations thereof. In a spirocyclic heterocycle, one atom is common to two different rings. Non limiting examples of the spirocyclic heterocycle include 6-oxaspiro[2.5]octanyl, 2-azaspiro[3.3]heptyl, 5-azaspiro[2.4]heptyl, 5-azaspiro[2.5]octyl, 2-azaspiro[3.5]nonyl, 2-azaspiro[3.4]octyl, 3-azaspiro[5.5]undecyl, 5-azaspiro[3.4]octyl, 2-oxaspiro[3.3]heptyl, 2-oxa-6-azaspiro[3.3]heptyl, 6-oxa-2-azaspiro[3.4]octyl, 6-azaspiro[3.4]octyl, 7-azaspiro[3.5]nonyl, 8-azaspiro[4.5]decyl, 1-oxa-7-azaspiro[4.4]nonyl, 1-oxa-7-azaspiro[3.5]nonyl, 1-oxa-8-azaspiro[4.5]decyl, 1-oxa-3,8-diazaspiro[4.5]decyl, 1-oxa-4,9-diazaspiro[5.5]undecyl, 2-oxa-7-azaspiro[3.5]nonyl, 5-oxa-2-azaspiro[3.5]nonyl, 6-oxa-2-azaspiro[3.5]nonyl, 7-oxa-2-azaspiro[3.5]nonyl, 8-oxa-2-azaspiro[4.5]decyl, 2,7-diazaspiro[4.4]nonyl, 1,4-dioxa-8-azaspiro[4.5]decyl, 1,3,8-triazaspiro[4.5]decyl. In a fused ring heterocycle, the rings share one common bond. Examples of fused bicyclic heterocycles are a 4-6 membered monocyclic heterocycle fused to a phenyl group, or a 4-6 membered monocyclic heterocycle fused to a $C_3$-$C_6$ monocyclic cycloalkyl, or a 4-6 membered monocyclic heterocycle fused to a $C_4$-$C_7$ monocyclic cycloalkenyl, or a 4-6 membered monocyclic heterocycle fused to a 4-7 membered monocyclic heterocycle. Examples of fused bicyclic heterocycles include, but are not limited to, 1,2-dihydrophthalazinyl, 3,4-dihydro-2H-benzo[b][1,4]dioxepinyl, chromanyl, chromenyl, isochromanyl, 2,3-dihydrobenzo[b][1,4]dioxinyl, isoindolinyl, 2,3-dihydrobenzo[b]thienyl, hexahydro-1H-cyclopenta[c]furanyl, 3-oxabicyclo[3.1.0]hexanyl, 3-azabicyclo[3.1.0]hexyl, benzopyranyl, benzothiopyranyl, indolinyl, decahydropyrrolo[3,4-b]azepinyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl, hexahydropyrrolo[3,4-c]pyrrol-2(1H)-yl, hexahydrocyclopenta[c]pyrrol-3a(1H)-yl, hexahydro-1H-oxazolo[3,4-a]pyrazinyl, octahydropyrrolo[3,4-b][1,4]oxazinyl, octahydroimidazo[1,5-a]pyrazinyl, octahydropyrrolo[1,2-a]pyrazinyl, octahydro-1H-pyrrolo[3,2-c]pyridinyl, and octahydropyrrolo[3,4-c]pyrrolyl. In a bridged heterocycle, the rings share at least two non-adjacent atoms. Examples of such bridged heterocycles include, but are not limited to, 8-oxabicyclo[3.2.1]octanyl, 7-oxabicyclo[2.2.1]heptanyl, azabicyclo[2.2.1]heptyl (including 2-azabicyclo[2.2.1]hept-2-yl), 8-azabicyclo[3.2.1]oct-8-yl, octahydro-2,5-epoxypentalene, 8-oxa-3-azabicyclo[3.2.1]octyl, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl)) and the nitrogen atoms may optionally be quaternized. Non limiting examples of the polycyclic heterocycle include 6,7-dihydro-[1,3]dioxolo[4,5-f]benzofuranyl.

The term "4-6 membered heterocycle" as used herein, means a hydrocarbon ring radical of 4-6 carbon ring atoms wherein at least one carbon atom is replaced by a heteroatom(s) independently selected from the group consisting of O, N, and S. A four-membered monocyclic heterocycle contains zero or one double bond, and one heteroatom selected from the group consisting of O, N, and S. A five-membered monocyclic heterocycle contains zero or one double bond and one, two, or three heteroatoms selected from the group consisting of O, N, and S. Examples of five-membered monocyclic heterocycles include those containing in the ring: 1 O; 1 S; 1 N; 2 N; 3 N; 1 S and 1 N; 1 S, and 2 N; 1 O and 1 N; or 1 O and 2 N. Non limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, imidazolidinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered monocyclic heterocycle contains zero, one, or two double bonds and one, two, or three heteroatoms selected from the group consisting of O, N, and S. Examples of six-membered monocyclic heterocycles include those containing in the ring: 1 O; 2 O; 1 S; 2 S; 1 N; 2 N; 3 N; 1 S, 1 O, and 1 N; 1 S and 1 N; 1 S and 2N; 1 S and 1 O; 1 S and 2 O; 1 O and 1 N; and 1 O and 2 N. Examples of six-membered monocyclic heterocycles include dihydropyranyl, 1,4-dioxanyl, 1,3-dioxanyl, 1,4-dithianyl, hexahydropyrimidine, morpholinyl, 1,4-dihydropyridinyl, piperazinyl, piperidinyl, tetrahydropyranyl, 1,2,3,6-tetrahydropyridinyl, tetrahydrothiopyranyl, thiomorpholinyl, thioxanyl, and trithianyl.

The term "5-11 membered heteroaryl" as used herein, means a monocyclic heteroaryl and a bicyclic heteroaryl. The "5-7 membered heteroaryl" is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Examples of 5-6 membered monocyclic heteroaryl include, but are not limited to, furanyl, imidazolyl, isoxazolyl, isothiazolyl, oxadiazolyl, 1,3-oxazolyl, pyridazinonyl, pyridinonyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a $C_3$-$C_6$ monocyclic cycloalkyl, or a monocyclic heteroaryl fused to $C_4$-$C_7$ monocyclic cycloalkenyl, or a monocyclic heteroaryl fused to a monocyclic heteroaryl, or a monocyclic heteroaryl fused to a 4-7 membered monocyclic heterocycle. Representative examples of bicyclic heteroaryl groups include, but are not limited to, 4H-furo[3,2-b]pyrrolyl, benzofuranyl, benzothienyl, benzoisoxazolyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 4,5,6,7-tetrahydropyrazolo[1,5-a]pyridinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The nitrogen atom in the heteroaryl rings may optionally be oxidized and may optionally be alkylated.

The term "6-10 membered aryl", as used herein, means a hydrocarbon ring radical containing 6-10 carbon atoms, zero heteroatoms, and one or more aromatic rings. The 6-10 membered aryl group may be a single-ring (monocyclic) or have two rings (bicyclic). The bicyclic aryl is naphthyl, or a phenyl fused to a monocyclic cycloalkyl, or a phenyl fused to a monocyclic cycloalkenyl. Representative examples of 6-10 membered aryl groups include, but are not limited to, phenyl, indenyl, tetrahydronaphthalenyl, dihydroindenyl (indanyl), naphthyl, and the like.

The aryls, the cycloalkyls, the cycloalkenyls, the heterocycles, and the heteroaryls, including the exemplary rings, are optionally substituted unless otherwise indicated; and are attached to the parent molecular moiety through any substitutable atom contained within the ring system.

The term "heteroatom" as used herein, means a nitrogen, oxygen, and sulfur.

The term "oxo" as used herein, means a =O group.

The term "radiolabel" means a compound of the invention in which at least one of the atoms is a radioactive atom or a radioactive isotope, wherein the radioactive atom or isotope spontaneously emits gamma rays or energetic particles, for example alpha particles or beta particles, or positrons. Examples of such radioactive atoms include, but are not limited to, $^{3}H$ (tritium), $^{14}C$, $^{11}C$, $^{15}O$, $^{18}F$, $^{35}S$, $^{123}I$, and $^{125}I$.

A moiety is described as "substituted" when a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In one embodiment, the subject is a human. The terms "human," "patient," and "subject" are used interchangeably herein.

The term "one or more" refers to one to eight. In one embodiment it refers to one to eight. In one embodiment it refers to one to seven. In one embodiment it refers to one to six. In one embodiment it refers to one to five. In one embodiment it refers to one to four. In one embodiment it refers to one or three. In another embodiment it refers to one to three. In a further embodiment it refers to one to two. In yet other embodiment it refers to two. In yet other further embodiment it refers to one.

The term "bioisostere", as used herein, means a moiety with substantially similar physical or chemical properties that impart similar biological properties to the compound having Formula (I). Examples of —C(O)OH bioisosteres include —P(O)(OH)$_2$, —P(O)(OH)(H), —P(O)(OH)(O—C$_1$-C$_6$ alkyl), —P(O)(CH$_3$)(OH), —B(OH)$_2$, —SO$_3$H, —CH(OH)CF$_3$, —C(O)NH(OH), —C(O)NH(CN), —C(O)NHSO$_2$R$^{G3a}$, —SO$_2$NHC(O)R$^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$)=NC(O)R$^{G3a}$, —C(O)NHS(O)(R$^{G3a}$)=NR$^{G3b}$,

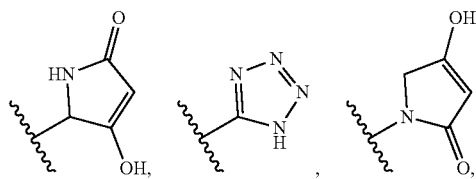

-continued

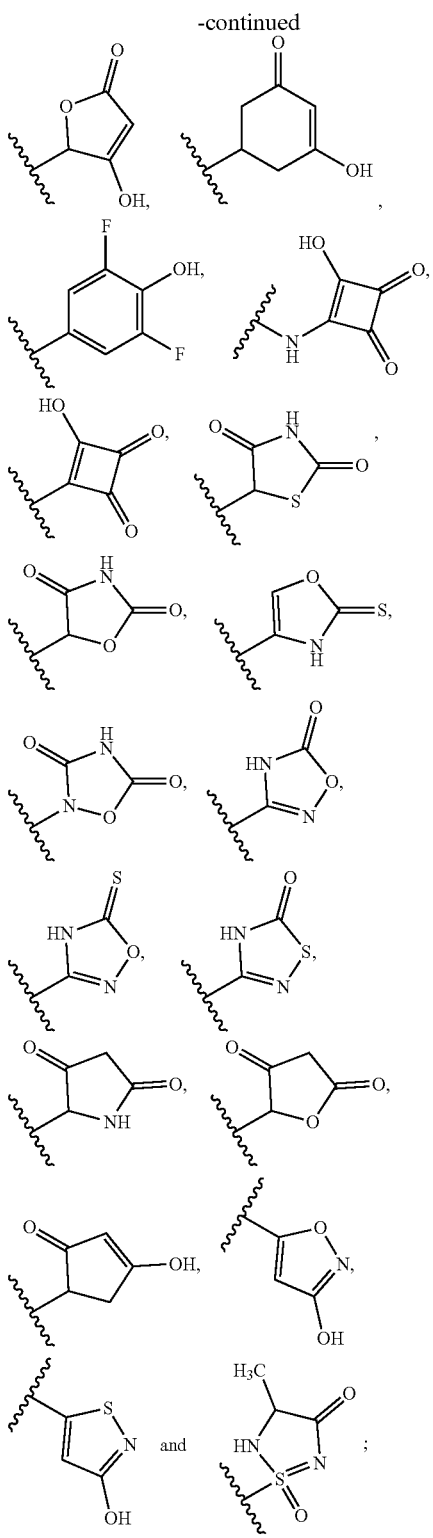

wherein
$R^{G3a}$, at each occurrence, is independently $C_1$-$C_6$ alkyl, $C_1$-$C_6$ alkyl-O—$C_1$-$C_6$ alkyl, $C_1$-$C_6$ haloalkyl, or $G^4$;
$R^{G3b}$ is hydrogen, $C_1$-$C_6$ alkyl, or $C_1$-$C_6$ haloalkyl or $G^4$;
$G^4$, at each occurrence, is independently cycloalkyl, cycloalkenyl, aryl, or heteroaryl, each of which is independently unsubstituted or substituted with 1, 2, or 3 independently selected $R^u$ groups; wherein $R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, —$NO_2$, —$OR^j$, —$OC(O)R^k$, —$OC(O)N(R^j)_2$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, or —$N(R^j)C(O)N(R^j)_2$;

$R^j$, at each occurrence, is independently selected from the group consisting of hydrogen, $C_1$-$C_6$ alkyl, or $C_1$-$C_6$ haloalkyl; and $R^k$, at each occurrence, is independently selected from the group consisting of $C_1$-$C_6$ alkyl or $C_1$-$C_6$ haloalkyl.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to Phe508del (F508del), Ile507del, or Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G, G1349D, S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10 kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326delITC, or 4279insA mutations. More particularly, Class VI mutation(s) refers to Rescued F508del mutations.

Compounds

Compounds of the invention have the general Formula (I) as described above.

Particular values of variable groups are as follows. Such values may be used where appropriate with any of the other values, definitions, claims or embodiments defined hereinbefore or hereinafter.

Formula (I)

One embodiment pertains to compounds of Formula (I),

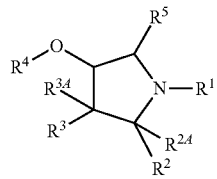

(I)

wherein $R^1$ is selected from the group consisting of $SO_2R^6$, $C(O)R^6$, $C(O)OR^6$, and $C(O)NR^7R^8$;

$R^2$ is $C(O)OH$ or a bioisostere thereof;

$R^{2A}$ is selected from the group consisting of hydrogen, $C_1$-$C_6$ alkyl, $C_1$-$C_6$ haloalkyl, and $C_3$-$C_6$ cycloalkyl;

$R^3$ is selected from the group consisting of $C_1$-$C_6$ alkyl, $C_3$-$C_6$ cycloalkyl, phenyl, and 5-6 membered heteroaryl; wherein the $R^3$ $C_1$-$C_6$ alkyl is optionally substituted with one or more substituents independently selected from the group consisting of $C_1$-$C_6$ alkoxy, OH, oxo, CN, $NO_2$, F, Cl, Br and I; wherein the $R^3$ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{3A}$ is selected from the group consisting of hydrogen, $C_1$-$C_6$ alkyl, and $C_1$-$C_6$ haloalkyl; or $R^3$ and $R^{3A}$, together with the carbon to which they are attached, form a $C_3$-$C_6$ cycloalkyl; wherein the $C_3$-$C_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^4$ is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;

$L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo;

$R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl.

In one embodiment of Formula (I), $R^1$ is selected from the group consisting of $SO_2R^6$, $C(O)R^6$, $C(O)OR^6$, and $C(O)NR^7R^8$;

$R^2$ is C(O)OH or a bioisostere thereof;

$R^{2A}$ is selected from the group consisting of hydrogen, $C_1$-$C_6$ alkyl, $C_1$-$C_6$ haloalkyl, and $C_3$-$C_6$ cycloalkyl;

$R^3$ is selected from the group consisting of $C_1$-$C_6$ alkyl, $C_3$-$C_6$ cycloalkyl, phenyl, and 5-6 membered heteroaryl; wherein the $R^3$ $C_1$-$C_6$ alkyl is optionally substituted with one or more substituents independently selected from the group consisting of $C_1$-$C_6$ alkoxy, OH, oxo, CN, $NO_2$, F, Cl, Br and I; wherein the $R^3$ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{3A}$ is selected from the group consisting of hydrogen, $C_1$-$C_6$ alkyl, and $C_1$-$C_6$ haloalkyl; or $R^3$ and $R^{3A}$, together with the carbon to which they are attached, form a $C_3$-$C_6$ cycloalkyl; wherein the $C_3$-$C_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^4$ is selected from the group consisting of ($C_1$-$C_6$ alkylene)$_x$-$C_6$-$C_{10}$ aryl, ($C_1$-$C_6$ alkylene)$_x$-5-11 membered heteroaryl, ($C_1$-$C_6$ alkylene)$_x$-4-12 membered heterocyclyl, ($C_1$-$C_6$ alkylene)$_x$-$C_3$-$C_{11}$ cycloalkyl, and ($C_1$-$C_6$ alkylene)$_x$-$C_4$-$C_{11}$ cycloalkenyl; wherein the $R^4$ $C_6$-$C_{10}$ membered aryl of ($C_1$-$C_6$ alkylene)$_x$-$C_6$-$C_{10}$ membered aryl, the 5-11 membered heteroaryl of ($C_1$-$C_6$ alkylene)$_x$-5-11 membered heteroaryl, the 4-12 membered heterocyclyl of ($C_1$-$C_6$ alkylene)$_x$-4-12 membered heterocyclyl, the $C_3$-$C_{11}$ cycloalkyl of ($C_1$-$C_6$ alkylene)$_x$-$C_3$-$C_{11}$ cycloalkyl, and the $C_4$-$C_{11}$ cycloalkenyl of ($C_1$-$C_6$ alkylene)$_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;

$R^5$ is selected from the group consisting of $C_6$-$C_{10}$ membered aryl, 5-11 membered heteroaryl, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl;

$R^{25}$ and $R^{26}$, at each occurrence, are each independently hydrogen or $C_1$-$C_6$ alkyl; and x is 0 or 1.

In one embodiment of Formula (I), $R^1$ is selected from the group consisting of $SO_2R^6$, $C(O)R^6$, $C(O)OR^6$, and $C(O)NR^7R^8$. In another embodiment of Formula (I), $R^1$ is $C(O)R^6$ or $C(O)OR^6$. In another embodiment of Formula (I), $R^1$ is $SO_2R^6$. In another embodiment of Formula (I), $R^1$ is $C(O)R^6$. In another embodiment of Formula (I), $R^1$ is $C(O)OR^6$. In another embodiment of Formula (I), $R^1$ is $C(O)NR^7R^8$.

In one embodiment of Formula (I), $R^2$ is C(O)OH or a bioisostere thereof. In another embodiment of Formula (I), $R^2$ is selected from the group consisting of —$P(O)(OH)_2$, —P(O)(OH)(H), —P(O)(OH)(O—$C_1$-$C_6$ alkyl), —P(O)($CH_3$)(OH), —$B(OH)_2$, —$SO_3H$, —CH(OH)$CF_3$, —C(O)NH(OH), —C(O)NH(CN), —C(O)NHSO$_2$R$^{G3a}$, —SO$_2$NHC(O)R$^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$)=NC(O)R$^{G3a}$, —C(O)NHS(O)(R$^{G3a}$)=NR$^{G3b}$,

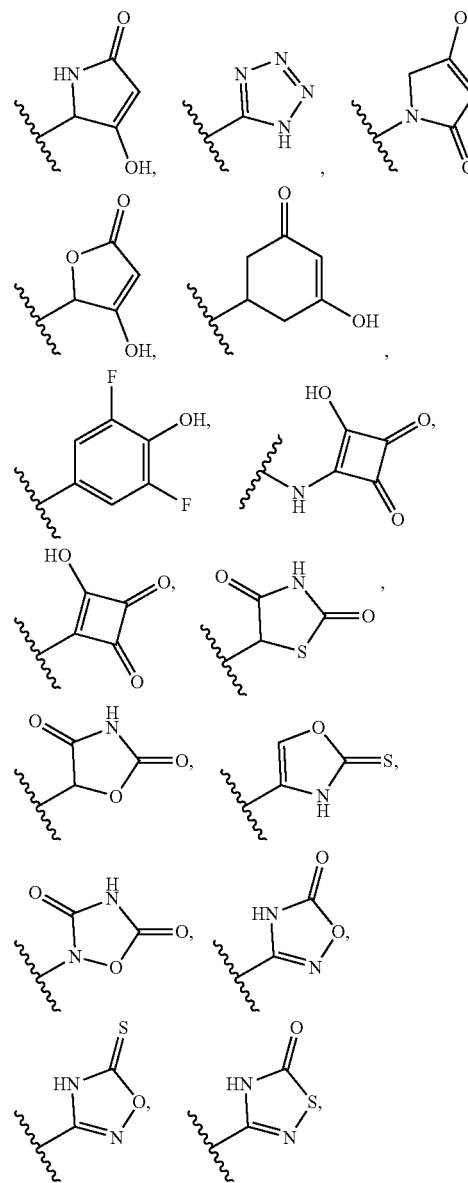

-continued

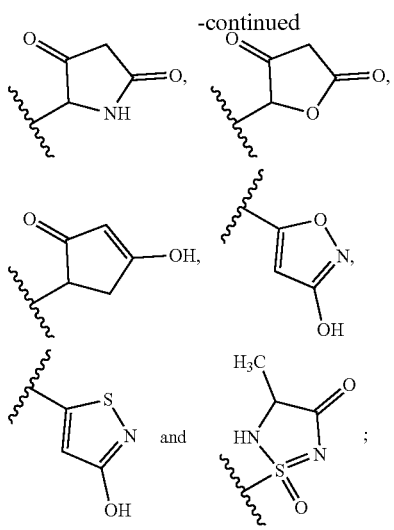

wherein
$R^{G3a}$, at each occurrence, is independently $C_1$-$C_6$ alkyl, $C_1$-$C_6$ alkyl-O—$C_1$-$C_6$ alkyl, $C_1$-$C_6$ haloalkyl, or $G^A$;
$R^{G3b}$ is hydrogen, $C_1$-$C_6$ alkyl, or $C_1$-$C_6$ haloalkyl or $G^A$;
$G^A$, at each occurrence, is independently cycloalkyl, cycloalkenyl, aryl, or heteroaryl, each of which is independently unsubstituted or substituted with 1, 2, or 3 independently selected $R^u$ groups; wherein
$R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, —NO$_2$, —OR$^j$, —OC(O)R$^k$, —OC(O)N(R$^j$)$_2$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), or —N(R$^j$)C(O)N(R$^j$)$_2$;
$R^j$, at each occurrence, is independently selected from the group consisting of hydrogen, $C_1$-$C_6$ alkyl, or $C_1$-$C_6$ haloalkyl; and
$R^k$, at each occurrence, is independently selected from the group consisting of $C_1$-$C_6$ alkyl or $C_1$-$C_6$ haloalkyl. In another embodiment of Formula (I), $R^2$ is —P(O)(OH)$_2$, —P(O)(OH)(H), —B(OH)$_2$, —SO$_3$H, —CH(OH)CF$_3$, —C(O)NH(OH), —C(O)NH(CN), —C(O)NHSO$_2$R$^{G3a}$, —SO$_2$NHC(O)R$^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$)=NC(O)R$^{G3a}$, —C(O)NHS(O)(R$^{G3a}$)=NR$^{G3b}$, or

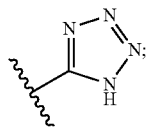

wherein
$R^{G3a}$, at each occurrence, is independently $C_1$-$C_6$ alkyl, $C_1$-$C_6$ alkyl-O—$C_1$-$C_6$ alkyl, $C_1$-$C_6$ haloalkyl, or $G^A$;
$R^{G3b}$ is hydrogen, $C_1$-$C_6$ alkyl, or $C_1$-$C_6$ haloalkyl or $G^A$;
$G^A$, at each occurrence, is independently cycloalkyl, cycloalkenyl, aryl, or heteroaryl, each of which is independently unsubstituted or substituted with 1, 2, or 3 independently selected $R^u$ groups; wherein
$R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, —NO$_2$, —OR$^j$, —OC(O)R$^k$, —OC(O)N(R$^j$)$_2$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), or —N(R$^j$)C(O)N(R$^j$)$_2$;
$R^j$, at each occurrence, is independently selected from the group consisting of hydrogen, $C_1$-$C_6$ alkyl, or $C_1$-$C_6$ haloalkyl; and
$R^k$, at each occurrence, is independently selected from the group consisting of $C_1$-$C_6$ alkyl or $C_1$-$C_6$ haloalkyl.

In another embodiment of Formula (I), $R^2$ is C(O)OH. In another embodiment of Formula (I), $R^2$ is —C(O)NHSO$_2$R$^{G3a}$ or —C(O)NHSO$_2$N(R$^{G3a}$)$_2$; $R^{G3a}$, at each occurrence, is independently $C_1$-$C_6$ alkyl, $C_1$-$C_6$ alkyl-O—$C_1$-$C_6$ alkyl, or $G^A$; and $G^A$, at each occurrence, is independently cycloalkyl, which is independently unsubstituted or substituted with 1, 2, or 3 independently selected $R^u$ groups; wherein $R^u$, at each occurrence, is independently $C_1$-$C_6$ alkyl. In another embodiment of Formula (I), $R^2$ is —C(O)NHSO$_2$R$^{G3a}$; $R^{G3a}$, at each occurrence, is independently $C_1$-$C_6$ alkyl, $C_1$-$C_6$ alkyl-O—$C_1$-$C_6$ alkyl, or $G^A$; and $G^A$, at each occurrence, is independently cycloalkyl, which is independently unsubstituted or substituted with 1, 2, or 3 independently selected $R^u$ groups; wherein $R^u$, at each occurrence, is independently $C_1$-$C_6$ alkyl. In another embodiment of Formula (I), $R^2$ is —C(O)NHSO$_2$N(R$^{G3a}$)$_2$; and $R^{G3a}$, at each occurrence, is independently $C_1$-$C_6$ alkyl.

In one embodiment of Formula (I), $R^{2A}$ is selected from the group consisting of hydrogen, $C_1$-$C_6$ alkyl, $C_1$-$C_6$ haloalkyl, and $C_3$-$C_6$ cycloalkyl. In another embodiment of Formula (I), $R^{2A}$ is hydrogen or $C_1$-$C_6$ alkyl. In another embodiment of Formula (I), $R^{2A}$ is hydrogen. In another embodiment of Formula (I), $R^{2A}$ is $C_1$-$C_6$ alkyl. In another embodiment of Formula (I), $R^{2A}$ is CH$_3$.

In one embodiment of Formula (I), $R^2$ is C(O)OH; and $R^{2A}$ is hydrogen.

In one embodiment of Formula (I),
$R^2$ is —P(O)(OH)$_2$, —P(O)(OH)(H), —B(OH)$_2$, —SO$_3$H, —CH(OH)CF$_3$, —C(O)NH(OH), —C(O)NH(CN), —C(O)NHSO$_2$R$^{G3a}$, —SO$_2$NHC(O)R$^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$)=NC(O)R$^{G3a}$, —C(O)NHS(O)(R$^{G3a}$)=NR$^{G3b}$, or

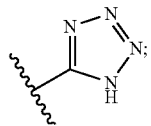 [SMILES: *c1nnn[nH]1]

$R^{G3a}$, at each occurrence, is independently $C_1$-$C_6$ alkyl, $C_1$-$C_6$ alkyl-O—$C_1$-$C_6$ alkyl, $C_1$-$C_6$ haloalkyl, or $G^A$;
$R^{G3b}$ is hydrogen, $C_1$-$C_6$ alkyl, or $C_1$-$C_6$ haloalkyl or $G^A$;
$G^A$, at each occurrence, is independently cycloalkyl, cycloalkenyl, aryl, or heteroaryl, each of which is independently unsubstituted or substituted with 1, 2, or 3 independently selected $R^u$ groups; wherein
$R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, —NO$_2$, —OR$^j$, —OC(O)R$^k$, —OC(O)N(R$^j$)$_2$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), or —N(R$^j$)C(O)N(R$^j$)$_2$;
$R^j$, at each occurrence, is independently selected from the group consisting of hydrogen, $C_1$-$C_6$ alkyl, or $C_1$-$C_6$ haloalkyl;

$R^k$, at each occurrence, is independently selected from the group consisting of $C_1$-$C_6$ alkyl or $C_1$-$C_6$ haloalkyl; and $R^{2A}$ is hydrogen. In one embodiment of Formula (I), $R^2$ is —C(O)NHSO$_2$R$^{G3a}$ or —C(O)NHSO$_2$N(R$^{G3a}$)$_2$; $R^{G3a}$, at each occurrence, is independently $C_1$-$C_6$ alkyl, $C_1$-$C_6$ alkyl-O—$C_1$-$C_6$ alkyl, or $G^4$; $G^4$, at each occurrence, is independently cycloalkyl, which is independently unsubstituted or substituted with 1, 2, or 3 independently selected $R^u$ groups; $R^u$, at each occurrence, is independently $C_1$-$C_6$ alkyl; and $R^{2A}$ is hydrogen.

In one embodiment of Formula (I), $R^3$ is selected from the group consisting of $C_1$-$C_6$ alkyl, $C_3$-$C_6$ cycloalkyl, phenyl, and 5-6 membered heteroaryl; wherein the $R^3$ $C_1$-$C_6$ alkyl is optionally substituted with one or more substituents independently selected from the group consisting of $C_1$-$C_6$ alkoxy, OH, oxo, CN, NO$_2$, F, Cl, Br and I; wherein the $R^3$ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO$_2$, F, Cl, Br and I; and $R^{3A}$ is independently selected from the group consisting of hydrogen, $C_1$-$C_6$ alkyl, and $C_1$-$C_6$ haloalkyl. In another embodiment of Formula (I), $R^3$ is selected from the group consisting of $C_1$-$C_6$ alkyl and $C_3$-$C_6$ cycloalkyl; wherein the $R^3$ $C_1$-$C_6$ alkyl is optionally substituted with one or more $C_1$-$C_6$ alkoxy; wherein the $R^3$ $C_3$-$C_6$ cycloalkyl is optionally substituted with one or more $C_1$-$C_6$ alkyl; and $R^{3A}$ is independently hydrogen. In another embodiment of Formula (I), $R^3$ is $C_1$-$C_6$ alkyl; wherein the $R^3$ $C_1$-$C_6$ alkyl is optionally substituted with one or more $C_1$-$C_6$ alkoxy; and $R^{3A}$ is independently hydrogen. In another embodiment of Formula (I), $R^3$ is $C_3$-$C_6$ cycloalkyl; wherein the $R^3$ $C_3$-$C_6$ cycloalkyl is optionally substituted with one or more $C_1$-$C_6$ alkyl; and $R^{3A}$ is hydrogen. In one embodiment of Formula (I), $R^3$ is CH$_3$, and $R^{3A}$ is hydrogen. In one embodiment of Formula (I), $R^3$ is $C_1$-$C_6$ alkyl and $R^{3A}$ is hydrogen. In one embodiment of Formula (I), $R^3$ is C(CH$_3$)$_3$, and $R^{3A}$ is hydrogen. In one embodiment of Formula (I), $R^3$ is C(OCH$_3$)(CH$_3$)$_2$, and $R^{3A}$ is hydrogen. In one embodiment of Formula (I), $R^3$ is cyclopropyl wherein the $R^3$ cyclopropyl is optionally substituted with one CH$_3$; and $R^{3A}$ is hydrogen.

In one embodiment of Formula (I), $R^3$ and $R^{3A}$, together with the carbon to which they are attached, form $C_3$-$C_6$ cycloalkyl; wherein the $C_3$-$C_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO$_2$, F, Cl, Br and I. In another embodiment of Formula (I), $R^3$ and $R^{3A}$, together with the carbon to which they are attached, form $C_3$-$C_6$ cycloalkyl, which is unsubstituted. In another embodiment of Formula (I), $R^3$ and $R^{3A}$, together with the carbon to which they are attached, form cyclopropyl.

In one embodiment of Formula (I), $R^4$ is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, OR$^9$, C(O)OR$^9$, C(O)NR$^{10}$R$^{11}$, SR$^9$, NR$^{10}$R$^{11}$, Si(R$^9$)$_3$, SF$_5$, SO$_2$R$^9$, OH, oxo, CN, NO$_2$, F, Cl, Br and I; wherein L$^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the L$^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo. In another embodiment of Formula (I), $R^4$ is selected from the group consisting of $L^1$-$C_6$-$C_{10}$ aryl, and $L^1$-5-11 membered heteroaryl; wherein the $R^4$ $C_6$-$C_{10}$ aryl and 5-11 membered heteroaryl are optionally substituted with one or more substituents independently selected from the group consisting of $R^9$, OR$^9$, NR$^{10}$R$^{11}$, OH, Cl, and Br; wherein L$^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the L$^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo. In another embodiment of Formula (I), $R^4$ is $L^1$-$C_6$-$C_{10}$ aryl; wherein the $R^4$ $C_6$-$C_{10}$ aryl is optionally substituted with one or more substituents independently selected from the group consisting of $R^9$, OR$^9$, NR$^{10}$R$^{11}$, OH, Cl, and Br; wherein L$^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the L$^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo.

In another embodiment of Formula (I), $R^4$ is $L^1$-5-11 membered heteroaryl; wherein the $R^4$ 5-11 membered heteroaryl is optionally substituted with one or more substituents independently selected from the group consisting of $R^9$, OR$^9$, NR$^{10}$R$^{11}$, OH, Cl, and Br; wherein L$^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the L$^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo.

In one embodiment of Formula (I), $R^4$ is selected from the group consisting of ($C_1$-$C_6$ alkylene)$_x$-$C_6$-$C_{10}$ aryl, ($C_1$-$C_6$ alkylene)$_x$-5-11 membered heteroaryl, ($C_1$-$C_6$ alkylene)$_x$-4-12 membered heterocyclyl, ($C_1$-$C_6$ alkylene)$_x$-$C_3$-$C_{11}$ cycloalkyl, and ($C_1$-$C_6$ alkylene)$_x$-$C_4$-$C_{11}$ cycloalkenyl; wherein the $R^4$ $C_6$-$C_{10}$ membered aryl of ($C_1$-$C_6$ alkylene)$_x$-$C_6$-$C_{10}$ membered aryl, the 5-11 membered heteroaryl of ($C_1$-$C_6$ alkylene)$_x$-5-11 membered heteroaryl, the 4-12 membered heterocyclyl of ($C_1$-$C_6$ alkylene)$_x$-4-12 membered heterocyclyl, the $C_3$-$C_{11}$ cycloalkyl of ($C_1$-$C_6$ alkylene)$_x$-$C_3$-$C_{11}$ cycloalkyl, and the $C_4$-$C_{11}$ cycloalkenyl of ($C_1$-$C_6$ alkylene)$_x$-$C_4$-$C_{11}$ cycloalkenyl are optionally substituted with one or more substituents independently selected from the group consisting of $R^9$, OR$^9$, C(O)OR$^9$, C(O)NR$^{10}$R$^{11}$, SR$^9$, NR$^{10}$R$^{11}$, Si(R$^9$)$_3$, SF$_5$, SO$_2$R$^9$, OH, oxo, CN, NO$_2$, F, Cl, Br and I; and x is 0 or 1. In another embodiment of Formula (I), $R^4$ is selected from the group consisting of ($C_1$-$C_6$ alkylene)$_x$-$C_6$-$C_{10}$ aryl, ($C_1$-$C_6$ alkylene)$_x$-5-11 membered heteroaryl, ($C_1$-$C_6$ alkylene)$_x$-4-12 membered heterocyclyl, and ($C_1$-$C_6$ alkylene)$_x$-$C_3$-$C_{11}$ cycloalkyl; wherein the $R^4$ $C_6$-$C_{10}$ membered aryl of ($C_1$-$C_6$ alkylene)$_x$-$C_6$-$C_{10}$ membered aryl, the 5-11 membered heteroaryl of ($C_1$-$C_6$ alkylene)$_x$-5-11 membered heteroaryl, the 4-12 membered heterocyclyl of ($C_1$-$C_6$ alkylene)$_x$-4-12 membered heterocyclyl, and the $C_3$-$C_{11}$ cycloalkyl of ($C_1$-$C_6$ alkylene)$_x$-$C_3$-$C_{11}$ cycloalkyl are optionally substituted with one or more substituents independently selected from the group consisting of $R^9$, OR$^9$, NR$^{10}$R$^{11}$, OH, Cl, and Br;

and x is 0 or 1. In another embodiment of Formula (I), $R^4$ is $(C_1-C_6 \text{ alkylene})_x-C_6-C_{10}$ aryl; wherein the $R^4$ $(C_1-C_6 \text{ alkylene})_x-C_6-C_{10}$ membered aryl is optionally substituted with one or more substituents independently selected from the group consisting of $R^9$, $OR^9$, $NR^{10}R^{11}$, OH, Cl, and Br; and x is 0 or 1.

In another embodiment of Formula (I), $R^4$ is $(C_1-C_6 \text{ alkylene})_x$-5-11 membered heteroaryl; wherein the $R^4$ $(C_1-C_6 \text{ alkylene})_x$-5-11 membered heteroaryl is optionally substituted with one or more substituents independently selected from the group consisting of $R^9$, $OR^9$, $NR^{10}R^{11}$, OH, Cl, and Br; and x is 0 or 1. In another embodiment of Formula (I), $R^4$ is $(C_1-C_6 \text{ alkylene})_x$-4-12 membered heterocyclyl; wherein the $R^4$ $(C_1-C_6 \text{ alkylene})_x$-4-12 membered heterocyclyl is optionally substituted with one or more substituents independently selected from the group consisting of $R^9$, $OR^9$, $NR^{10}R^{11}$, OH, Cl, and Br; and x is 0 or 1. In another embodiment of Formula (I), $R^4$ is $(C_1-C_6 \text{ alkylene})_x-C_3-C_{11}$ cycloalkyl; wherein the $R^4$ $(C_1-C_6 \text{ alkylene})_x-C_3-C_{11}$ cycloalkyl is optionally substituted with one or more substituents independently selected from the group consisting of $R^9$, $OR^9$, $NR^{10}R^{11}$, OH, Cl, and Br; and x is 0 or 1.

In one embodiment of Formula (I), $R^5$ is selected from the group consisting of $C_6-C_{10}$ membered aryl, 5-11 membered heteroaryl, 4-6 membered monocyclic heterocycle fused to a phenyl group, $C_3-C_{11}$ cycloalkyl, and $C_4-C_{11}$ cycloalkenyl; wherein the $R^5$ $C_6-C_{10}$ membered aryl, 5-11 membered heteroaryl, 4-6 membered monocyclic heterocycle fused to a phenyl group, $C_3-C_{11}$ cycloalkyl, and $C_4-C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I; $R^{12}$, at each occurrence, is independently selected from the group consisting of $C_1-C_6$ alkyl, $C_1-C_6$ haloalkyl, $C_2-C_6$ alkenyl, $C_2-C_6$ alkynyl, 6-10 membered aryl, 5-11 membered heteroaryl, $C_3-C_{11}$ cycloalkyl, $C_4-C_{11}$ cycloalkenyl, and 4-12 membered heterocyclyl; wherein each $R^{12}$ 6-10 membered aryl, 5-11 membered heteroaryl, $C_3-C_{11}$ cycloalkyl, $C_4-C_{11}$ cycloalkenyl, and 4-12 membered heterocyclyl is optionally substituted with one or more substituents independently selected from the group consisting of $C_1-C_6$ alkyl, $C_1-C_6$ alkoxy, $C_1-C_6$ haloalkyl, $C_1-C_6$ haloalkoxy, $N(C_1-C_6 \text{ alkyl})_2$, OH, oxo, CN, $NO_2$, F, Cl, Br and I; and $R^{13}$ and $R^{14}$, at each occurrence, are each independently hydrogen or $C_1-C_6$ alkyl. In another embodiment of Formula (I), $R^5$ is selected from the group consisting of $C_6-C_{10}$ membered aryl, 5-11 membered heteroaryl, and 4-6 membered monocyclic heterocycle fused to a phenyl group; wherein the $R^5$ $C_6-C_{10}$ membered aryl, 5-11 membered heteroaryl, and 4-6 membered monocyclic heterocycle fused to a phenyl group are optionally substituted with one or more substituents independently selected from the group consisting of $R^{12}$, $OR^{12}$, $NR^{13}R^{14}$, F, Cl, Br, and I; $R^{12}$, at each occurrence, is independently selected from the group consisting of $C_1-C_6$ alkyl, $C_1-C_6$ haloalkyl, 6-10 membered aryl, 5-11 membered heteroaryl, $C_3-C_{11}$ cycloalkyl, and 4-12 membered heterocyclyl; wherein each $R^{12}$ 6-10 membered aryl, 5-11 membered heteroaryl, $C_3-C_{11}$ cycloalkyl, $C_4-C_{11}$ cycloalkenyl, and 4-12 membered heterocyclyl is optionally substituted with one or more substituents independently selected from the group consisting of $C_1-C_6$ alkyl, $C_1-C_6$ alkoxy, $C_1-C_6$ haloalkyl, $C_1-C_6$ haloalkoxy, $N(C_1-C_6 \text{ alkyl})_2$, oxo, CN, F, and Cl; and $R^{13}$ and $R^{14}$, at each occurrence, are each independently $C_1-C_6$ alkyl. In another embodiment of Formula (I), $R^5$ is $C_6-C_{10}$ membered aryl and 5-11 membered heteroaryl; wherein the $R^5$ $C_6-C_{10}$ membered aryl and 5-11 membered heteroaryl are optionally substituted with one or more substituents independently selected from the group consisting of $R^{12}$, $OR^{12}$, $NR^{13}R^{14}$, F, Cl, Br, and I; $R^{12}$, at each occurrence, is independently selected from the group consisting of $C_1-C_6$ alkyl, $C_1-C_6$ haloalkyl, 6-10 membered aryl, 5-11 membered heteroaryl, $C_3-C_{11}$ cycloalkyl, and 4-12 membered heterocyclyl; wherein each $R^{12}$ 6-10 membered aryl, 5-11 membered heteroaryl, $C_3-C_{11}$ cycloalkyl, and 4-12 membered heterocyclyl is optionally substituted with one or more independently selected $C_1-C_6$ alkyl; and $R^{13}$ and $R^{14}$, at each occurrence, are each independently $C_1-C_6$ alkyl.

In another embodiment of Formula (I), $R^5$ is $C_6-C_{10}$ membered aryl; wherein the $R^5$ $C_6-C_{10}$ membered aryl is optionally substituted with one or more substituents independently selected from the group consisting of $R^{12}$, $OR^{12}$, $NR^{13}R^{14}$, F, Cl, Br, and I; $R^{12}$, at each occurrence, is independently selected from the group consisting of $C_1-C_6$ alkyl, $C_1-C_6$ haloalkyl, 6-10 membered aryl, 5-11 membered heteroaryl, $C_3-C_{11}$ cycloalkyl, and 4-12 membered heterocyclyl; wherein each $R^{12}$ 6-10 membered aryl, 5-11 membered heteroaryl, $C_3-C_{11}$ cycloalkyl, $C_4-C_{11}$ cycloalkenyl, and 4-12 membered heterocyclyl is optionally substituted with one or more substituents independently selected from the group consisting of $C_1-C_6$ alkyl, $C_1-C_6$ alkoxy, $C_1-C_6$ haloalkyl, $C_1-C_6$ haloalkoxy, $N(C_1-C_6 \text{ alkyl})_2$, oxo, CN, F, and Cl; and $R^{13}$ and $R^{14}$, at each occurrence, are each independently $C_1-C_6$ alkyl. In another embodiment of Formula (I), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, F, Cl, Br, and I; $R^{12}$, at each occurrence, is independently selected from the group consisting of $C_1-C_6$ alkyl, $C_1-C_6$ haloalkyl, 6-10 membered aryl, 5-11 membered heteroaryl, $C_3-C_{11}$ cycloalkyl, and 4-12 membered heterocyclyl; wherein each $R^{12}$ 6-10 membered aryl, 5-11 membered heteroaryl, $C_3-C_{11}$ cycloalkyl, $C_4-C_{11}$ cycloalkenyl, and 4-12 membered heterocyclyl is optionally substituted with one or more substituents independently selected from the group consisting of $C_1-C_6$ alkyl, $C_1-C_6$ alkoxy, $C_1-C_6$ haloalkyl, $C_1-C_6$ haloalkoxy, $N(C_1-C_6 \text{ alkyl})_2$, oxo, CN, F, and Cl; and $R^{13}$ and $R^{14}$, at each occurrence, are each independently $C_1-C_6$ alkyl. In another embodiment of Formula (I), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, F, Cl, Br, and I; $R^{12}$, at each occurrence, is independently selected from the group consisting of $C_1-C_6$ alkyl, $C_1-C_6$ haloalkyl, 6-10 membered aryl, 5-11 membered heteroaryl, $C_3-C_{11}$ cycloalkyl, and 4-12 membered heterocyclyl; wherein each $R^{12}$ 6-10 membered aryl, 5-11 membered heteroaryl, $C_3-C_{11}$ cycloalkyl, and 4-12 membered heterocyclyl is optionally substituted with one or more substituents independently selected from the group consisting of $C_1-C_6$ alkyl, $C_1-C_6$ alkoxy, $C_1-C_6$ haloalkyl, $C_1-C_6$ haloalkoxy, $N(C_1-C_6 \text{ alkyl})_2$, oxo, CN, F, and Cl; and $R^{13}$ and $R^{14}$, at each occurrence, are each independently $C_1-C_6$ alkyl. In another embodiment of Formula (I), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, F, Cl, and Br; $R^{12}$, at each occurrence, is independently selected from the group consisting of $C_1-C_6$ alkyl, $C_1-C_6$ haloalkyl, 6-10 membered aryl, 5-11 membered heteroaryl, $C_3-C_{11}$ cycloalkyl, and 4-12 membered heterocyclyl; wherein each $R^{12}$ 6-10 membered aryl, 5-11 membered heteroaryl, $C_3$-$C_{11}$cycloalkyl, and 4-12 membered heterocyclyl is optionally substituted with one or more independently selected $C_1$-$C_6$ alkyl; and $R^{13}$ and $R^{14}$, at each occurrence, are each independently $C_1$-$C_6$ alkyl. In another embodiment of Formula (I), $R^5$ is phenyl, which is unsubstituted. In another embodiment of Formula (I), $R^5$ is phenyl; wherein the $R^5$ phenyl is optionally substituted with one or more substituents independently selected from the group consisting of $R^{12}$, $OR^{12}$, $NR^{13}R^{14}$, F, Cl, and Br; $R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (I), $R^5$ is phenyl; which is substituted with one $R^{12}$; and $R^{12}$ is $C_1$-$C_6$ alkyl, $C_3$-$C_{11}$ cycloalkyl, or F. In another embodiment of Formula (I), $R^5$ is phenyl; which is substituted with one $R^{12}$; and $R^{12}$ is $CH_3$, $CH_2CH_3$ or $CH(CH_3)_2$. In another embodiment of Formula (I), $R^5$ is phenyl; which is substituted with one $R^{12}$; and $R^{12}$ is cyclopropyl. In another embodiment of Formula (I), $R^5$ is pyridinyl; which is substituted with one or more substituents independently selected from the group consisting of $R^{12}$, $OR^{12}$, and $NR^{13}R^{14}$; $R^{12}$ is independently $C_1$-$C_6$ alkyl; and $R^{13}$ and $R^{14}$, at each occurrence, are each independently $C_1$-$C_6$ alkyl. In another embodiment of Formula (I), $R^5$ is pyridinyl; which is substituted with one or more substituents independently selected from the group consisting of $R^{12}$, $OR^{12}$, and $NR^{13}R^{14}$; $R^{12}$ is independently $CH_3$ or $CH(CH_3)_2$; and $R^{13}$ and $R^{14}$, at each occurrence, are each independently $CH_3$. In another embodiment of Formula (I), $R^5$ is pyridinyl; wherein the $R^5$ pyridinyl is optionally substituted with one or more independently selected $R^{12}$; and $R^{12}$, at each occurrence, is independently $C_1$-$C_6$ alkyl.

In one embodiment of Formula (I), $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I; $R^{15}$ at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I; $R^{16}$ and $R^{17}$, at each occurrence, are each independently hydrogen or $C_1$-$C_6$ alkyl; and $R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I. In another embodiment of Formula (I), $R^6$ is selected from the group consisting of $C_1$-$C_6$ alkyl, $C_2$-$C_6$ alkenyl, 6-10 membered aryl, 5-11 membered heteroaryl, $C_3$-$C_{11}$cycloalkyl, and 4-12 membered heterocyclyl; wherein the $R^6$ $C_1$-$C_6$ alkyl is optionally substituted with one or more independently selected $R^{15}$ or F; wherein the $R^6$ 6-10 membered aryl, 5-11 membered heteroaryl, $C_3$-$C_{11}$ cycloalkyl, and 4-12 membered heterocyclyl are optionally substituted with one or more substituents independently selected from the group consisting of $R^{18}$ and $OR^{18}$; $R^{15}$, at each occurrence, is independently $C_3$-$C_{11}$ cycloalkyl; and $R^{18}$, at each occurrence, is independently selected $C_1$-$C_6$ alkyl; wherein each $R^{18}$ $C_1$-$C_6$ alkyl is optionally substituted with one or more F. In one embodiment of Formula (I), $R^6$ is $C_1$-$C_6$ alkyl; wherein the $R^6$ $C_1$-$C_6$ alkyl is optionally substituted with one or more independently selected $R^{15}$; and $R^{15}$, at each occurrence, is independently $C_3$-$C_{11}$ cycloalkyl. In another embodiment of Formula (I), $R^6$ is $C_1$-$C_6$ alkyl; wherein the $R^6$ $C_1$-$C_6$ alkyl is unsubstituted. In another embodiment of Formula (I), $R^6$ is —$CH_2CH_3$. In another embodiment of Formula (I), $R^6$ is —$CH(CH_3)_2$. In one embodiment of Formula (I), $R^6$ is 4-12 membered heterocyclyl; wherein the $R^6$ 4-12 membered heterocyclyl is optionally substituted with one or more substituents independently selected from the group consisting of $OR^{18}$; and $R^{18}$, at each occurrence, is independently $C_1$-$C_6$ alkyl. In another embodiment of Formula (I), $R^6$ is 4-12 membered heterocyclyl; wherein the $R^6$ 4-12 membered heterocyclyl is unsubstituted. In another embodiment of Formula (I), $R^6$ is tetrahydrofuranyl. In another embodiment of Formula (I), $R^6$ is tetrahydropyranyl. In one embodiment of Formula (I), $R^6$ is $C_3$-$C_{11}$ cycloalkyl; wherein the $R^6$ $C_3$-$C_{11}$ cycloalkyl is optionally substituted with one or more independently selected $OR^{18}$; and $R^{18}$, at each occurrence, is independently selected $C_1$-$C_6$ alkyl. In one embodiment of Formula (I), $R^6$ is cyclohexyl; wherein the $R^6$ cyclohexyl is unsubstituted.

In one embodiment of Formula (I), $R^1$ is $C(O)OR^6$; and $R^6$ is $C_1$-$C_6$ alkyl or $C_3$-$C_{11}$ cycloalkyl. In one embodiment of Formula (I), $R^1$ is $C(O)OR^6$; and $R^6$ is $C_1$-$C_6$ alkyl; wherein the $R^6$ is $C_1$-$C_6$ unsubstituted alkyl.

In one embodiment of Formula (I), $R^1$ is $C(O)R^6$; $R^6$ is 4-12 membered heterocyclyl; wherein the $R^6$ 4-12 membered heterocyclyl is optionally substituted with $OR^{18}$; and $R^{18}$, at each occurrence, is independently selected $C_1$-$C_6$ alkyl. In one embodiment of Formula (I), $R^1$ is $C(O)R^6$; and $R^6$ is 4-12 membered heterocyclyl; wherein the $R^6$ 4-12 membered heterocyclyl is unsubstituted. In one embodiment of Formula (I), $R^1$ is $C(O)R^6$; and $R^6$ is $C_3$-$C_{11}$ cycloalkyl; wherein the $R^6$ $C_3$-$C_{11}$ cycloalkyl is unsubstituted.

In one embodiment of Formula (I), $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I; $R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I; $R^{22}$ and $R^{23}$, at each occurrence, are each independently hydrogen or $C_1$-$C_6$ alkyl; $R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl. In another embodiment of Formula (I), $R^9$, at each occurrence, is independently selected from the group consisting of $C_1$-$C_6$ alkyl, 6-10 membered aryl, $C_3$-$C_{11}$ cycloalkyl, and 4-12 membered heterocyclyl; wherein each $R^9$ $C_1$-$C_6$ alkyl is optionally substituted with one or more CN or F; wherein each $R^9$ 6-10 membered aryl, $C_3$-$C_{11}$ cycloalkyl, and 4-12 membered heterocyclyl is optionally substituted with one or more substituents independently selected from the group consisting of $R^{24}$, $OR^{24}$, and F; and $R^{24}$, at each occurrence, is independently $C_1$-$C_6$ alkyl.

In one embodiment of Formula (I), $R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br, and I. In another embodiment of Formula (I), $R^{10}$ and $R^{11}$, at each occurrence, are each independently $C_1$-$C_6$ alkyl.

In one embodiment of Formula (I), $R^4$ is $L^1$-$C_6$-$C_{10}$ aryl; wherein the $R^4$ $C_6$-$C_{10}$ aryl is optionally substituted with one or more substituents independently selected from the group consisting of $R^9$ and $OR^9$; $L^1$ is absent, or is $C_1$-$C_6$ alkylene; and $R^9$, at each occurrence, is independently selected $C_1$-$C_6$ alkyl; wherein each $R^9$ $C_1$-$C_6$ alkyl is optionally substituted with one or more F. In one embodiment of Formula (I), $R^4$ is $(C_1$-$C_6$ alkylene$)_x$-$C_6$-$C_{10}$ aryl; wherein the $R^4$ $(C_1$-$C_6$ alkylene$)_x$-$C_6$-$C_{10}$ membered aryl is optionally substituted with one or more substituents independently selected from the group consisting of $R^9$ and $OR^9$; x is 0 or 1; and $R^9$, at each occurrence, is independently selected $C_1$-$C_6$ alkyl; wherein each $R^9$ $C_1$-$C_6$ alkyl is optionally substituted with one or more F. In another embodiment of Formula (I), $R^4$ is $CH_2$-phenyl; wherein the $R^4$ $CH_2$-phenyl is optionally substituted with one or more substituents independently selected from the group consisting of $R^9$ and $OR^9$; and $R^9$, at each occurrence, is independently selected from the group consisting of $CH_3$ and $CF_3$. In another embodiment of Formula (I), $R^4$ is $L^1$-5-11 membered heteroaryl; wherein the $R^4$ 5-11 membered heteroaryl is optionally substituted with one or more substituents independently selected from the group consisting of $R^9$ and $OR^9$; $L^1$ is absent, or is $C_1$-$C_6$ alkylene; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F. In another embodiment of Formula (I), $R^4$ is $(C_1$-$C_6$ alkylene$)_x$-5-11 membered heteroaryl; wherein the $R^4$ $(C_1$-$C_6$ alkylene$)_x$-5-11 membered heteroaryl is optionally substituted with one or more substituents independently selected from the group consisting of $R^9$ and $OR^9$; x is 0 or 1; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F. In another embodiment of Formula (I), $R^4$ is $CH_2$-pyridinyl; wherein the $R^4$ $CH_2$-pyridinyl is optionally substituted with one or more substituents independently selected from the group consisting of $R^9$ and $OR^9$; and $R^9$, at each occurrence, is independently selected from the group consisting of $CH_3$, $C(CH_3)_3$, $CF_3$, and cyclobutyl. In another embodiment of Formula (I), $R^4$ is $CH_2$-quinolinyl; wherein the $R^4$ $CH_2$-quinolinyl is optionally substituted with one or more substituents independently selected from the group consisting of $R^9$ and $OR^9$; and $R^9$, at each occurrence, is independently $CH_3$.

In one embodiment of Formula (I), $R^4$ is selected from the group consisting of

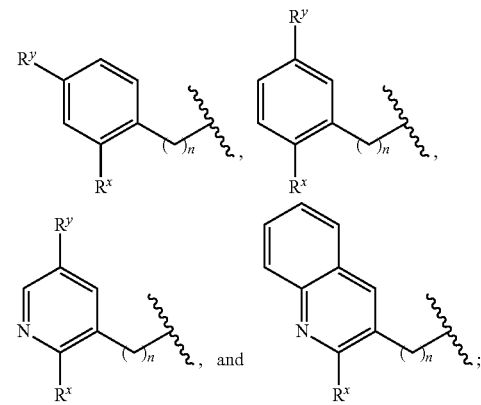

wherein $R^x$ is $OCH_3$, and $R^y$ is selected from the group consisting of $CF_3$, $C(CH_3)_3$, and cyclobutyl; and n is 1.

One embodiment pertains to compounds of Formula (I), wherein $R^1$ is $C(O)R^6$;

$R^4$ is $L^1$-5-11 membered heteroaryl; wherein the $R^4$ 5-11 membered heteroaryl is optionally substituted with one or more substituents independently selected from the group consisting of $R^9$ and $OR^9$;

$L^1$ is $C_1$-$C_6$ alkylene;

$R^5$ is $C_6$-$C_{10}$ membered aryl; wherein the $R^5$ $C_6$-$C_{10}$ membered aryl is optionally substituted with one or more $R^{12}$;

$R^6$ is 4-12 membered heterocyclyl;

$R^9$, at each occurrence, is independently selected $C_1$-$C_6$ alkyl; wherein each $R^9$ $C_1$-$C_6$ alkyl is optionally substituted with one or more F; and $R^{12}$, at each occurrence, is independently selected $C_1$-$C_6$ alkyl.

One embodiment pertains to compounds of Formula (I),

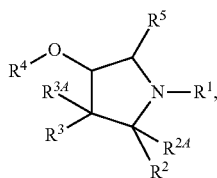

(I)

wherein
R$^1$ is selected from the group consisting of SO$_2$R$^6$, C(O)R$^6$, C(O)OR$^6$, and C(O)NR$^7$R$^8$;
R$^2$ is C(O)OH or a bioisostere thereof,
R$^{2A}$ is hydrogen;
R$^3$ is C$_1$-C$_6$ alkyl; wherein the R$^3$ C$_1$-C$_6$ alkyl is optionally substituted with one or more C$_1$-C$_6$ alkoxy;
R$^{3A}$ is hydrogen;
R$^4$ is selected from the group consisting of L$^1$-C$_6$-C$_{10}$ aryl and L$^1$-5-11 membered heteroaryl; wherein the R$^4$ C$_6$-C$_{10}$ aryl and 5-11 membered heteroaryl are optionally substituted with one or more substituents independently selected from the group consisting of R$^9$, OR$^9$, NR$^{10}$R$^{11}$, OH, Cl, and Br;
L$^1$ is absent, or is selected from the group consisting of C$_1$-C$_6$ alkylene, C$_2$-C$_6$ alkenylene, C$_2$-C$_6$ alkynylene, and C$_1$-C$_6$ alkylene-O—; wherein the L$^1$ C$_1$-C$_6$ alkylene, C$_2$-C$_6$ alkenylene, and C$_2$-C$_6$ alkynylene, alone or as part of a group, are optionally substituted with one or more substituents independently selected from the group consisting of C$_1$-C$_6$ alkoxy, OH, and oxo;
R$^5$ is selected from the group consisting of C$_6$-C$_{10}$ membered aryl, 5-11 membered heteroaryl, and 4-6 membered monocyclic heterocycle fused to a phenyl group; wherein the R$^5$ C$_6$-C$_{10}$ membered aryl, 5-11 membered heteroaryl, and 4-6 membered monocyclic heterocycle fused to a phenyl group are optionally substituted with one or more substituents independently selected from the group consisting of R$^{12}$, OR$^{12}$, NR$^{13}$R$^{14}$, F, Cl, Br and I;
R$^6$ is selected from the group consisting of C$_1$-C$_6$ alkyl, C$_2$-C$_6$ alkenyl, 6-10 membered aryl, 5-11 membered heteroaryl, C$_3$-C$_{11}$ cycloalkyl, and 4-12 membered heterocyclyl; wherein the R$^6$ C$_1$-C$_6$ alkyl is optionally substituted with one or more substituents independently selected from the group consisting of R$^5$ and F; wherein the R$^6$ 5-11 membered heteroaryl, and C$_3$-C$_{11}$ cycloalkyl are optionally substituted with one or more substituents independently selected from the group consisting of R$^{18}$ and OR$^{18}$;
R$^7$ and R$^8$ are each independently hydrogen or C$_1$-C$_6$ alkyl;
R$^9$, at each occurrence, is independently selected from the group consisting of C$_1$-C$_6$ alkyl, 6-10 membered aryl, C$_3$-C$_{11}$ cycloalkyl, and 4-12 membered heterocyclyl; wherein each R$^9$ C$_1$-C$_6$ alkyl is optionally substituted with one or more substituents independently selected from the group consisting of CN, and F; wherein each R$^9$ 6-10 membered aryl, C$_3$-C$_{11}$ cycloalkyl, and 4-12 membered heterocyclyl is optionally substituted with one or more substituents independently selected from the group consisting of R$^{24}$, OR$^{24}$, and F;
R$^{10}$ and R$^{11}$, at each occurrence, are each independently C$_1$-C$_6$ alkyl;
R$^{12}$, at each occurrence, is independently selected from the group consisting of C$_1$-C$_6$ alkyl, C$_1$-C$_6$ haloalkyl, 6-10 membered aryl, 5-11 membered heteroaryl, C$_3$-C$_{11}$ cycloalkyl, and 4-12 membered heterocyclyl; wherein each R$^{12}$ 6-10 membered aryl, 5-11 membered heteroaryl, and 4-12 membered heterocyclyl is optionally substituted with one or more substituents independently selected from the group consisting of C$_1$-C$_6$ alkyl, C$_1$-C$_6$ alkoxy, C$_1$-C$_6$ haloalkyl, C$_1$-C$_6$ haloalkoxy, N(C$_1$-C$_6$ alkyl)$_2$, oxo, CN, F, and Cl;
R$^{13}$ and R$^{14}$, at each occurrence, are each independently hydrogen or C$_1$-C$_6$ alkyl;
R$^{15}$, at each occurrence, is independently C$_3$-C$_{11}$ cycloalkyl;
R$^{18}$, at each occurrence, is independently C$_1$-C$_6$ alkyl; wherein each R$^{18}$ C$_1$-C$_6$ alkyl is optionally substituted with one or more F; and
R$^{24}$, at each occurrence, is C$_1$-C$_6$ alkyl.
In one embodiment of Formula (I),
R$^1$ is selected from the group consisting of C(O)R$^6$, C(O)OR$^6$, and C(O)NR$^7$R$^8$;
R$^2$ is C(O)OH or a bioisostere thereof;
R$^{2A}$ is hydrogen;
R$^3$ is C$_1$-C$_6$ alkyl;
R$^{3A}$ is hydrogen;
R$^4$ is selected from the group consisting of (C$_1$-C$_6$ alkylene)$_x$-C$_6$-C$_{10}$ aryl and (C$_1$-C$_6$ alkylene)$_x$-5-11 membered heteroaryl; wherein the R$^4$ C$_6$-C$_{10}$ membered aryl of (C$_1$-C$_6$ alkylene)$_x$-C$_6$-C$_{10}$ membered aryl, and the 5-11 membered heteroaryl of (C$_1$-C$_6$ alkylene)$_x$-5-11 membered heteroaryl are optionally substituted with one or more substituents independently selected from the group consisting of R$^9$, OR$^9$, NR$^{10}$R$^{11}$, OH, Cl, and Br;
R$^5$ is selected from the group consisting of C$_6$-C$_{10}$ membered aryl and 5-11 membered heteroaryl; wherein the R$^5$ C$_6$-C$_{10}$ membered aryl and 5-11 membered heteroaryl are optionally substituted with one or more substituents independently selected from the group consisting of R$^{12}$, OR$^{12}$, NR$^{13}$R$^{14}$, F, Cl, and Br;
R$^6$ is selected from the group consisting of C$_1$-C$_6$ alkyl, C$_2$-C$_6$ alkenyl, C$_3$-C$_{11}$ cycloalkyl, and 4-12 membered heterocyclyl; wherein the R$^6$ C$_1$-C$_6$ alkyl is optionally substituted with one or more independently selected R$^{15}$; wherein the R$^6$ 6C$_3$-C$_{11}$ cycloalkyl, and 4-12 membered heterocyclyl are optionally substituted with one or more independently selected OR$^{18}$;
R$^7$ and R$^8$ are each independently hydrogen or C$_1$-C$_6$ alkyl;
R$^9$, at each occurrence, is independently selected from the group consisting of C$_1$-C$_6$ alkyl, 6-10 membered aryl, C$_3$-C$_{11}$ cycloalkyl, and 4-12 membered heterocyclyl; wherein each R$^9$ C$_1$-C$_6$ alkyl, C$_2$-C$_6$ alkenyl, and C$_2$-C$_6$ alkynyl is optionally substituted with one or more F; wherein each R$^9$ 6-10 membered C$_3$-C$_{11}$ cycloalkyl, and 4-12 membered heterocyclyl is optionally substituted with one or more substituents independently selected from the group consisting of R$^{24}$, OR$^{24}$, and F;
R$^{10}$ and R$^{11}$, at each occurrence, are each independently selected C$_1$-C$_6$ alkyl;
R$^{12}$, at each occurrence, is independently selected from the group consisting of C$_1$-C$_6$ alkyl, C$_1$-C$_6$ haloalkyl, 6-10 membered aryl, 5-11 membered heteroaryl, C$_3$-C$_{11}$ cycloalkyl, and 4-12 membered heterocyclyl; wherein each R$^{12}$ 6-10 membered aryl, 5-11 membered heteroaryl, C$_3$-C$_{11}$ cycloalkyl, and 4-12 membered heterocyclyl is optionally substituted with one or more independently selected from the group consisting of $C_1$-$C_6$ alkyl;

$R^{13}$ and $R^{14}$, at each occurrence, are each independently $C_1$-$C_6$ alkyl;

$R^{15}$, at each occurrence, is independently selected $C_3$-$C_{11}$ cycloalkyl;

$R^{18}$, at each occurrence, is independently selected $C_1$-$C_6$ alkyl;

$R^{24}$, at each occurrence, is independently selected $C_1$-$C_6$ alkyl; and x is 0 or 1.

Exemplary compounds of Formula (I) include, but are not limited to rac-(2R,3S,5R)-3-tert-butyl-1-(cyclopentylacetyl)-4-[(2,5-dichlorophenyl)methoxy]-5-phenylpyrrolidine-2-carboxylic acid;

rac-(2R,3S,5R)-3-tert-butyl-1-(cyclohexanecarbonyl)-4-{[2-methoxy-5-(trifluoromethyl)phenyl]methoxy}-5-phenylpyrrolidine-2-carboxylic acid;

rac-(2R,3S,5R)-3-tert-butyl-4-[(5-chloro-2-methoxyphenyl)methoxy]-1-(cyclohexanecarbonyl)-5-phenylpyrrolidine-2-carboxylic acid;

rac-(2R,3S,5R)-3-tert-butyl-1-(cyclohexanecarbonyl)-4-[(2,5-dichlorophenyl)methoxy]-5-phenylpyrrolidine-2-carboxylic acid;

rac-(2R,3S,5R)-3-tert-butyl-1-(cyclohexanecarbonyl)-4-{[6-methyl-4-(trifluoromethyl)pyridin-2-yl]oxy}-5-phenylpyrrolidine-2-carboxylic acid;

rac-(2R,3S,5R)-3-tert-butyl-4-[(4,6-dimethoxypyrimidin-2-yl)oxy]-1-[di(propan-2-yl)carbamoyl]-5-phenylpyrrolidine-2-carboxylic acid;

rac-(2R,3S,5R)-3-tert-butyl-1-[di(propan-2-yl)carbamoyl]-4-{[2-methoxy-5-(trifluoromethyl)phenyl]methoxy}-5-phenylpyrrolidine-2-carboxylic acid;

(2R*,3S*,4R*,5R*)-3-tert-butyl-1-[di(propan-2-yl)carbamoyl]-4-{[2-methoxy-5-(trifluoromethyl)phenyl]methoxy}-5-phenylpyrrolidine-2-carboxylic acid;

(2S*,3R*,4S*,5S*)-3-tert-butyl-1-[di(propan-2-yl)carbamoyl]-4-{[2-methoxy-5-(trifluoromethyl)phenyl]methoxy}-5-phenylpyrrolidine-2-carboxylic acid;

rac-(2R,3S,4R,5R)-3-tert-butyl-1-(cyclohexanecarbonyl)-4-[(4,6-dimethoxypyrimidin-5-yl)methoxy]-5-phenylpyrrolidine-2-carboxylic acid;

rac-(2R,3S,4R,5R)-3-tert-butyl-1-(cyclohexanecarbonyl)-4-[(4,6-dimethoxypyrimidin-2-yl)methoxy]-5-phenylpyrrolidine-2-carboxylic acid;

rac-(2R,3S,4R,5R)-3-tert-butyl-1-(cyclohexanecarbonyl)-4-{[2-(dimethylamino)-5-(trifluoromethyl)pyridin-3-yl]methoxy}-5-phenylpyrrolidine-2-carboxylic acid;

rac-(2R,3S,5R)-3-tert-butyl-1-(cyclohexanecarbonyl)-5-(2-methoxyphenyl)-4-{[2-methoxy-5-(trifluoromethyl)phenyl]methoxy}pyrrolidine-2-carboxylic acid;

rac-(2R,3S,5R)-3-tert-butyl-4-[(4-chloro-2-methoxyphenyl)methoxy]-1-(cyclohexanecarbonyl)-5-(2-methoxyphenyl)pyrrolidine-2-carboxylic acid;

rac-(2R,3S,5R)-3-tert-butyl-1-(cyclohexanecarbonyl)-5-[2-(dimethylamino)pyridin-3-yl]-4-{[2-methoxy-5-(trifluoromethyl)phenyl]methoxy}pyrrolidine-2-carboxylic acid;

rac-(2R,3S,5R)-3-tert-butyl-1-(cyclohexanecarbonyl)-N-(methanesulfonyl)-4-{[2-methoxy-5-(trifluoromethyl)phenyl]methoxy}-5-phenylpyrrolidine-2-carboxamide;

rac-(2R,3S,5R)-3-tert-butyl-4-[(5-chloro-2-methoxyphenyl)methoxy]-5-phenyl-1-{[(propan-2-yl)oxy]carbonyl}pyrrolidine-2-carboxylic acid;

(2R,3S,4R,5R)-3-tert-butyl-1-(cyclohexanecarbonyl)-4-{[2-methoxy-5-(trifluoromethyl)phenyl]methoxy}-5-phenylpyrrolidine-2-carboxylic acid;

(2S,3R,4S,5S)-3-tert-butyl-1-(cyclohexanecarbonyl)-4-{[2-methoxy-5-(trifluoromethyl)phenyl]methoxy}-5-phenylpyrrolidine-2-carboxylic acid;

rac-(2R,3S,4R,5R)-3-tert-butyl-1-(cyclohexanecarbonyl)-4-{[2-methoxy-5-(trifluoromethyl)pyridin-3-yl]methoxy}-5-phenylpyrrolidine-2-carboxylic acid;

(2S,3R,4S,5S)-3-tert-butyl-1-(cyclohexanecarbonyl)-N-(2-methoxyethanesulfonyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-4-{[2-methoxy-5-(trifluoromethyl)phenyl]methoxy}-N-(1-methylcyclopropane-1-sulfonyl)-5-phenylpyrrolidine-2-carboxamide;

(2S,3R,4S,5S)-3-tert-butyl-1-(cyclohexanecarbonyl)-N-(cyclopropanesulfonyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-N-(ethanesulfonyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-N-(dimethylsulfamoyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-N-(methanesulfonyl)-4-{[2-methoxy-5-(trifluoromethyl)phenyl]methoxy}-5-phenylpyrrolidine-2-carboxamide;

(2R,3S,4R,5R)-3-tert-butyl-1-[(1S,3S)-3-methoxycyclohexane-1-carbonyl]-4-{[2-methoxy-5-(trifluoromethyl)phenyl]methoxy}-5-phenylpyrrolidine-2-carboxylic acid;

(2R,3S,4R,5R)-3-tert-butyl-1-[(1S,3S)-3-methoxycyclohexane-1-carbonyl]-4-{[6-methyl-4-(trifluoromethyl)pyridin-2-yl]oxy}-5-phenylpyrrolidine-2-carboxylic acid;

rac-(2R,3S,4R,5R)-3-(tert-butyl)-4-((2-methoxy-5-(trifluoromethyl)benzyl)oxy)-1-((1R,3R)-3-methoxycyclohexanecarbonyl)-5-phenylpyrrolidine-2-carboxylic acid;

(2S,3R,4S,5S)-3-tert-butyl-1-[(1S,3S)-3-methoxycyclohexane-1-carbonyl]-4-{[2-methoxy-5-(trifluoromethyl)phenyl]methoxy}-5-phenylpyrrolidine-2-carboxylic acid;

(2S,3R,4S,5S)-3-tert-butyl-1-[(1R,3R)-3-methoxycyclohexane-1-carbonyl]-4-{[2-methoxy-5-(trifluoromethyl)phenyl]methoxy}-5-phenylpyrrolidine-2-carboxylic acid;

(2S,3R,4S,5S)-3-tert-butyl-1-[(1S,3S)-3-methoxycyclohexane-1-carbonyl]-4-{[2-methoxy-4-(trifluoromethyl)phenyl]methoxy}-5-phenylpyrrolidine-2-carboxylic acid;

(2S,3R,4S,5S)-3-tert-butyl-1-[(1R,3R)-3-methoxycyclohexane-1-carbonyl]-4-{[2-methoxy-4-(trifluoromethyl)phenyl]methoxy}-5-phenylpyrrolidine-2-carboxylic acid;

rac-(2R,3S,4R,5R)-3-tert-butyl-1-[(cyclobutyloxy)carbonyl]-4-{[2-methoxy-4-(trifluoromethyl)phenyl]methoxy}-5-phenylpyrrolidine-2-carboxylic acid;

rac-(2R,3S,4R,5R)-3-tert-butyl-4-[(5-chloro-2-methoxyphenyl)methoxy]-1-[(cyclobutyloxy)carbonyl]-5-phenylpyrrolidine-2-carboxylic acid;

(2S,3R,4S,5S)-4-[(5-bromo-2-methoxyphenyl)methoxy]-3-tert-butyl-5-phenyl-1-{[(propan-2-yl)oxy]carbonyl}pyrrolidine-2-carboxylic acid;

(2S,3R,4S,5S)-4-[(5-bromo-2-methoxyphenyl)methoxy]-3-tert-butyl-1-[(1R,3R)-3-methoxycyclohexane-1-carbonyl]-5-phenylpyrrolidine-2-carboxylic acid;

(2S,3R,4S,5S)-3-tert-butyl-4-[(4-methoxy[1,1'-biphenyl]-3-yl)methoxy]-5-phenyl-1-{[(propan-2-yl)oxy]carbonyl}pyrrolidine-2-carboxylic acid;

(2S,3R,4S,5S)-3-tert-butyl-4-[(4-methoxy[1,1'-biphenyl]-3-yl)methoxy]-1-[(1R,3R)-3-methoxycyclohexane-1-carbonyl]-5-phenylpyrrolidine-2-carboxylic acid;

(2S,3R,4S,5S)-4-[(5-bromo-2-methoxypyridin-3-yl)methoxy]-3-tert-butyl-5-phenyl-1-{[(propan-2-yl)oxy]carbonyl}pyrrolidine-2-carboxylic acid;

(2S,3R,4S,5S)-3-tert-butyl-1-(cyclohexanecarbonyl)-4-{[2-methoxy-5-(trifluoromethyl)pyridin-3-yl]methoxy}-5-phenylpyrrolidine-2-carboxylic acid;

(2S,3R,4S,5S)-3-tert-butyl-4-[(2-methoxy-5-phenylpyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclohexyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclopentyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-tert-butyl-2-methoxyphenyl)methoxy]-1-[(1R,3R)-3-methoxycyclohexane-1-carbonyl]-5-phenylpyrrolidine-2-carboxylic acid;

(2S,3R,4S,5S)-3-tert-butyl-4-[(5-tert-butyl-2-methoxyphenyl)methoxy]-5-phenyl-1-{[(propan-2-yl)oxy]carbonyl}pyrrolidine-2-carboxylic acid;

(2S,3R,4S,5S)-3-tert-butyl-1-(cyclohexanecarbonyl)-5-(2-fluorophenyl)-4-{[2-methoxy-5-(trifluoromethyl)pyridin-3-yl]methoxy}pyrrolidine-2-carboxylic acid;

(2S,3R,4S,5S)-3-tert-butyl-1-(cyclohexanecarbonyl)-5-(2-fluorophenyl)-4-{[2-methoxy-5-(trifluoromethyl)phenyl]methoxy}pyrrolidine-2-carboxylic acid;

(2S,3R,4S,5S)-3-tert-butyl-4-[(5-tert-butyl-2-methoxyphenyl)methoxy]-1-(cyclohexanecarbonyl)-5-(2-fluorophenyl)pyrrolidine-2-carboxylic acid;

(2S,3R,4S,5S)-4-[(5-bromo-2-methoxypyridin-3-yl)methoxy]-3-tert-butyl-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-5-(2-fluorophenyl)-4-[(2-methoxy-5-phenylpyridin-3-yl)methoxy]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-phenylpyrrolidine-2-carboxylic acid;

(2S,3R,4S,5S)-3-tert-butyl-1-(cyclohexanecarbonyl)-4-[(5-cyclopentyl-2-methoxypyridin-3-yl)methoxy]-5-phenylpyrrolidine-2-carboxylic acid;

(2S,3R,4S,5S)-4-{[5-(bicyclo[2.2.1]heptan-2-yl)-2-methoxypyridin-3-yl]methoxy}-3-tert-butyl-1-(cyclohexanecarbonyl)-5-phenylpyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-4-[(5-cyclopentyl-2-methoxypyridin-3-yl)methoxy]-5-(2-fluorophenyl)pyrrolidine-2-carboxylic acid;

(2S,3R,4S,5S)-4-{[5-(bicyclo[2.2.1]heptan-2-yl)-2-methoxypyridin-3-yl]methoxy}-3-tert-butyl-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-5-(2-fluorophenyl)-4-{[2-methoxy-5-(pyrrolidin-1-yl)pyridin-3-yl]methoxy}pyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-phenylpyrrolidine-2-carboxylic acid;

(2S,3R,4S,5S)-3-tert-butyl-4-[(5-tert-butyl-2-methoxypyridin-3-yl)methoxy]-1-[(1R,3R)-3-methoxycyclohexane-1-carbonyl]-5-phenylpyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-(2-fluorophenyl)pyrrolidine-2-carboxylic acid;

(2S,3R,4S,5S)-3-tert-butyl-4-[(5-tert-butyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2-fluoro-4-methylphenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2-fluorophenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(4-fluoro-2-methylphenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2,4-difluorophenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(3,6-dihydro-2H-pyran-4-yl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(3-methoxyphenyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(4-methylphenyl)pyridin-3-yl]methoxy}-5-phenyl-1-{[propan-2-yl]oxy]carbonyl}pyrrolidine-2-carboxylic acid;

(2S,3R,4S,5S)-3-tert-butyl-4-[(6-tert-butyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-5-(2-fluorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-tert-butyl-2-methoxypyridin-3-yl)methoxy]-5-(2-fluorophenyl)-1-{[(propan-2-yl)oxy]carbonyl}pyrrolidine-2-carboxylic acid;

(2S,3R,4R,5S)-3-tert-butyl-4-[(5-tert-butyl-2-methoxypyridin-3-yl)methoxy]-5-(2-fluorophenyl)-1-{[(propan-2-yl)oxy]carbonyl}pyrrolidine-2-carboxylic acid;

(2S,3R,4S,5S)-4-[(5-bromo-2-methoxypyridin-3-yl)methoxy]-3-tert-butyl-5-(2-fluorophenyl)-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-(2-fluorophenyl)-1-{[(propan-2-yl)oxy]carbonyl}pyrrolidine-2-carboxylic acid;

(2S,3R,4S,5S)-3-tert-butyl-4-{[2-methoxy-5-(trifluoromethyl)phenyl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-tert-butyl-2-methoxypyridin-3-yl)methoxy]-5-(3-chlorophenyl)-1-{[(propan-2-yl)oxy]carbonyl}pyrrolidine-2-carboxylic acid;

(2S,3R,4S,5S)-3-tert-butyl-4-{[2-methoxy-5-(piperidin-1-yl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(pyrrolidin-1-yl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-{[(propan-2-yl)oxy]carbonyl}pyrrolidine-2-carboxylic acid;

(2S,3R,4S,5S)-3-tert-butyl-4-{[5-(3,3-difluoroazetidin-1-yl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(3,3-difluoropyrrolidin-1-yl)-2-methoxypyridin-3-yl]methoxy}-5-phenyl-1-{[(propan-2-yl)oxy]carbonyl}pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-phenylpyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-phenylpyrrolidine-2-carboxylic acid;

(2S,3R,4S,5S)-3-tert-butyl-4-{[2-methoxy-5-(trifluoromethyl)pyridin-3-yl]methoxy}-5-phenyl-1-{[(prop-2-en-1-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxane-2-carbonyl]-5-phenylpyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-[2-(propan-2-yl)phenyl]pyrrolidine-2-carboxylic acid;

(2S,3R,4R,5S)-3-tert-butyl-4-{[2-methoxy-5-(trifluoromethyl)phenyl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(propan-2-yl)phenyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(2-cyclobutyl-5-methoxypyridin-4-yl)methoxy]-5-phenyl-1-{[(propan-2-yl)oxy]carbonyl}pyrrolidine-2-carboxylic acid;

(2S,3R,4S,5S)-3-tert-butyl-5-(2-cyclobutylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxolane-2-carbonyl]-5-[2-(propan-2-yl)phenyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-{2-[(propan-2-yl)oxy]phenyl}pyrrolidine-2-carboxylic acid;

(2S,3R,4S,5S)-3-tert-butyl-4-[(2-methoxyquinolin-3-yl)methoxy]-5-phenyl-1-{[(propan-2-yl)oxy]carbonyl}pyrrolidine-2-carboxylic acid;

(2S,3R,4S,5S)-3-tert-butyl-4-{[2-hydroxy-5-(trifluoromethyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-5-[2-(3,6-dihydro-2H-pyran-4-yl)phenyl]-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(3S)-oxolane-3-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-(oxane-4-carbonyl)-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(3R)-oxolane-3-carbonyl]-5-[2-(propan-2-yl)phenyl]pyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-{[2-methoxy-5-(trifluoromethyl)phenyl]methoxy}-1-[(2S)-oxolane-2-carbonyl]-5-[2-(trifluoromethyl)pyridin-3-yl]pyrrolidine-2-carboxylic acid;

(2S,3R,4R,5S)-3-tert-butyl-4-{[2-methoxy-5-(trifluoromethyl)phenyl]methoxy}-1-[(2S)-oxolane-2-carbonyl]-5-[2-(trifluoromethyl)pyridin-3-yl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-[(2-methoxyquinolin-3-yl)methoxy]-1-[(2S)-oxolane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[3-(propan-2-yl)phenyl]pyrrolidine-2-carboxylic acid;

(2S,3R,4S,5S)-5-(3-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4R,5S)-3-tert-butyl-5-(3-tert-butylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-(3-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4R,5S)-5-(2-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[1-(propan-2-yl)-1H-pyrazol-5-yl]pyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-[2-(propan-2-yl)phenyl]pyrrolidine-2-carboxylic acid;

(2S,3R,4S,5S)-3-tert-butyl-4-[(2-methoxyquinolin-3-yl)methoxy]-1-[(2R)-oxane-2-carbonyl]-5-[2-(propan-2-yl)phenyl]pyrrolidine-2-carboxylic acid;

(2S,3R,4S,5S)-3-tert-butyl-4-[(2-methoxyquinolin-3-yl)methoxy]-1-[(2S)-oxane-2-carbonyl]-5-[2-(propan-2-yl)phenyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-(oxane-4-carbonyl)-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-[(2R)-oxane-2-carbonyl]-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid;

(2S,3R,4S,5S)-5-(2-bromophenyl)-3-tert-butyl-4-[(2-methoxyquinolin-3-yl)methoxy]-1-{[(propan-2-yl)oxy]carbonyl}pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-{[(propan-2-yl)oxy]carbonyl}pyrrolidine-2-carboxylic acid;

(2S,3R,4S,5S)-3-tert-butyl-5-(2-cyclopropylphenyl)-4-[(2-methoxyquinolin-3-yl)methoxy]-1-[(2S)-oxolane-2-carbonyl]pyrrolidine-2-carboxylic acid;

(2S,3R,4S,5S)-3-tert-butyl-5-(3-cyclobutylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-[(2S)-oxane-2-carbonyl]pyrrolidine-2-carboxylic acid;

(2S,3R,4S,5S)-3-tert-butyl-5-(3-chlorophenyl)-4-[(5-cyclobutyl-2-methoxypyridin-3-yl)methoxy]-1-{[(propan-2-yl)oxy]carbonyl}pyrrolidine-2-carboxylic acid;

(2S,3R,4S,5S)-3-tert-butyl-5-(2-cyclopropylphenyl)-4-[(2-methoxyquinolin-3-yl)methoxy]-1-{[(propan-2-yl)oxy]carbonyl}pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-[2-(trifluoromethyl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-{2-[(propan-2-yl)oxy]pyridin-3-yl}pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-[(2-methoxyquinolin-3-yl)methoxy]-1-[(2S)-oxolane-2-carbonyl]-5-[1-(propan-2-yl)-1H-pyrazol-5-yl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-(oxane-4-carbonyl)pyrrolidine-2-carboxylic acid;

(2S,3R,4S,5S)-5-(2-bromophenyl)-3-tert-butyl-4-[(2-methoxyquinolin-3-yl)methoxy]-1-[(2S)-oxolane-2-carbonyl]pyrrolidine-2-carboxylic acid;

(2S,3R,4S,5S)-3-tert-butyl-5-(3-tert-butylphenyl)-1-(ethoxycarbonyl)-4-{[2-methoxy-5-(trifluoromethyl)pyridin-3-yl]methoxy}pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(1R,2S,4S)-7-oxabicyclo[2.2.1]heptane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-[2-(trifluoromethyl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(trifluoromethyl)phenyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-1-(cyclobutanecarbonyl)-4-{[2-methoxy-5-(trifluoromethyl)pyridin-3-yl]methoxy}-5-{2-[(propan-2-yl)oxy]pyridin-3-yl}pyrrolidine-2-carboxylic acid;

(2S,3R,4S,5S)-3-tert-butyl-1-(cyclobutanecarbonyl)-4-[(5-cyclobutyl-2-methoxypyridin-3-yl)methoxy]-5-{2-[(propan-2-yl)oxy]pyridin-3-yl}pyrrolidine-2-carboxylic acid;

(2S,3R,4S,5S)-5-(2-bromophenyl)-3-tert-butyl-4-[(5-tert-butyl-2-methoxyphenyl)methoxy]-1-[(2S)-oxolane-2-carbonyl]pyrrolidine-2-carboxylic acid;

(2S,3R,4R,5S)-3-tert-butyl-1-(cyclopentanecarbonyl)-4-{[2-methoxy-5-(trifluoromethyl)pyridin-3-yl]methoxy}-5-{2-[(propan-2-yl)oxy]pyridin-3-yl}pyrrolidine-2-carboxylic acid;

(2S,3R,4R,5S)-3-tert-butyl-1-(cyclohexanecarbonyl)-4-{[2-methoxy-5-(trifluoromethyl)pyridin-3-yl]methoxy}-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-5-[2-(difluoromethyl)phenyl]-1-[(2S)-oxolane-2-carbonyl]pyrrolidine-2-carboxylic acid;

(2S,3R,4R,5S)-5-(2-bromophenyl)-3-tert-butyl-4-[(5-cyclobutyl-2-methoxypyridin-3-yl)methoxy]-1-{[(propan-2-yl)oxy]carbonyl}pyrrolidine-2-carboxylic acid;

(2S,3R,4S,5S)-3-tert-butyl-5-(2,6-difluorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-(2-cyclopropylphenyl)-1-[(2S)-oxolane-2-carbonyl]pyrrolidine-2-carboxylic acid;

(2S,3R,4S,5S)-4-[(5-bromo-2-methoxypyridin-3-yl)methoxy]-3-tert-butyl-5-(2-cyclopropylphenyl)-1-[(2S)-oxolane-2-carbonyl]pyrrolidine-2-carboxylic acid;

(2S,3R,4S,5S)-3-tert-butyl-4-{[2-methoxy-5-(trifluoromethyl)phenyl]methoxy}-5-(2-methylphenyl)-1-[(2S)-oxane-2-carbonyl]pyrrolidine-2-carboxylic acid;

(2S,3R,4S,5S)-3-tert-butyl-4-{[2-methoxy-4-(trifluoromethyl)phenyl]methoxy}-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxane-2-carbonyl]-5-[2-(propan-2-yl)phenyl]pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-[(2S)-oxane-2-carbonyl]pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2-ethylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-([1,1'-biphenyl]-2-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-6-oxo-1,6-dihydropyridin-3-yl)phenyl]-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2-cyclopropylphenyl)pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-(cyclohexanecarbonyl)pyrrolidine-2-carboxylic acid;

(2S,3R,4S,5S)-3-tert-butyl-5-(2-ethylphenyl)-4-{[2-methoxy-4-(trifluoromethyl)phenyl]methoxy}-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-ethylphenyl)-1-[(2S)-oxane-2-carbonyl]pyrrolidine-2-carboxylic acid;

(2S,3R,4S,5S)-4-[(5-bromo-2-methoxypyridin-3-yl)methoxy]-3-tert-butyl-5-(2-methylphenyl)-1-[(2S)-oxane-2-carbonyl]pyrrolidine-2-carboxylic acid;

(2S,3R,4S,5S)-3-tert-butyl-4-{[5-(2-cyanopropan-2-yl)-2-methoxyphenyl]methoxy}-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxyquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-5-(4'-fluoro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(3'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-1,2,3,6-tetrahydropyridin-4-yl)phenyl]-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-1H-pyrazol-4-yl)phenyl]-1-[(2S)-oxane-2-carbonyl]pyrrolidine-2-carboxylic acid;

(2S,3R,4S,5S)-3-tert-butyl-5-[3'-(dimethylamino)[1,1'-biphenyl]-2-yl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2'-methyl[1,1'-biphenyl]-2-yl)-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(pyridin-4-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(pyrimidin-5-yl)phenyl]pyrrolidine-2-carboxylic acid;

(2S,3R,4S,5S)-3-tert-butyl-5-[2-(furan-3-yl)phenyl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-1H-pyrrol-3-yl)phenyl]-1-[(2S)-oxane-2-carbonyl]pyrrolidine-2-carboxylic acid;

(2S,3R,4S,5S)-3-tert-butyl-5-(2'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[3'-(trifluoromethoxy)[1,1'-biphenyl]-2-yl]pyrrolidine-2-carboxylic acid;

(2S,3R,4S,5S)-3-tert-butyl-5-(4'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-[2-(2H-1,3-benzodioxol-5-yl)phenyl]-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2'-fluoro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-[2-(6-methoxypyridin-3-yl)phenyl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[4'-(trifluoromethoxy)[1,1'-biphenyl]-2-yl]pyrrolidine-2-carboxylic acid;

(2S,3R,4S,5S)-3-tert-butyl-5-(4'-cyano[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-{2-[6-(trifluoromethyl)pyridin-3-yl]phenyl}pyrrolidine-2-carboxylic acid;

(2S,3R,4S,5S)-3-tert-butyl-5-[2-(5-ethoxypyridin-3-yl)phenyl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(naphthalen-1-yl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-(naphthalen-1-yl)-1-[(2S)-oxane-2-carbonyl]pyrrolidine-2-carboxylic acid;

(2S,3R,4S,5S)-5-(1-benzofuran-7-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(2-methylpropyl)phenyl]-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-(6-methoxypyridine-2-sulfonyl)pyrrolidine-2-carboxylic acid;

(2S,3R,4S,5S)-3-tert-butyl-4-{[2-methoxy-5-(1-methylcyclobutyl)phenyl]methoxy}-5-(2-methylphenyl)-1-[(2S)-oxane-2-carbonyl]pyrrolidine-2-carboxylic acid;

(2S,3R,4S,5S)-3-tert-butyl-5-(2,3-dihydro-1-benzofuran-7-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-[(5-cyclopropyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxane-2-carbonyl]-5-(5,6,7,8-tetrahydronaphthalen-1-yl)pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-(5,6,7,8-tetrahydronaphthalen-1-yl)pyrrolidine-2-carboxylic acid;

(2S,3R,4S,5S)-3-tert-butyl-4-[(2-methoxy-7-methylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(6-tert-butyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-1-(3,4-dihydro-2H-pyran-6-carbonyl)-4-{[2-methoxy-5-(trifluoromethyl)pyridin-3-yl]methoxy}-5-(2-methylphenyl)pyrrolidine-2-carboxylic acid;

(2S,3R,4S,5S)-3-tert-butyl-4-[(5-chloro-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[2-methoxy-5-(trifluoromethoxy)phenyl]methoxy}-5-(2-methylphenyl)-1-[(2S)-oxane-2-carbonyl]pyrrolidine-2-carboxylic acid;

(2S,3R,4S,5S)—N-(6-aminopyridine-2-sulfonyl)-3-tert-butyl-4-[(5-cyclobutyl-2-methoxypyridin-3-yl)methoxy]-5-(2-cyclopropylphenyl)-1-[(2S)-oxane-2-carbonyl]pyrrolidine-2-carboxamide;

(2S,3R,4S,5S)-3-tert-butyl-4-[(6-tert-butyl-3-methoxypyridin-2-yl)methoxy]-5-(2-methylphenyl)-1-[(2S)-oxane-2-carbonyl]pyrrolidine-2-carboxylic acid;

(2S,3R,4S,5S)-3-tert-butyl-4-({[2-methoxy-5-(trifluoromethyl)pyridin-3-yl]($^{2}H_{2}$)methyl}oxy)-5-(2-methylphenyl)-1-[(2S)-oxane-2-carbonyl]pyrrolidine-2-carboxylic acid;

(2S,3R,4S,5S)-3-tert-butyl-4-{[{2-[($^{2}H_{3}$)methyloxy]-5-(trifluoromethyl)pyridin-3-yl}($^{2}H_{2}$)methyl]oxy}-5-(2-methylphenyl)-1-[(2S)-oxane-2-carbonyl]pyrrolidine-2-carboxylic acid;

(2S,3R,4S,5S)-3-tert-butyl-5-(5-chloro-2-methylphenyl)-4-[(5-cyclobutyl-2-methoxypyridin-3-yl)methoxy]-1-[(2S)-oxane-2-carbonyl]pyrrolidine-2-carboxylic acid;

(2S,3R,4S,5S)-3-tert-butyl-5-(5-chloro-2-methylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(3-chloro-2-methylphenyl)-4-[(5-cyclobutyl-2-methoxypyridin-3-yl)methoxy]-1-[(2S)-oxane-2-carbonyl]pyrrolidine-2-carboxylic acid;

(2S,3R,4S,5S)-3-tert-butyl-5-(3-chloro-2-methylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[{2-[($^{2}H_{3}$)methyloxy]-5-(trifluoromethyl)phenyl}($^{2}H_{2}$)methyl]oxy}-5-(2-methylphenyl)-1-[(2S)-oxane-2-carbonyl]pyrrolidine-2-carboxylic acid;

(2S,3R,4S,5S)-3-tert-butyl-4-{[(5-tert-butyl-2-methoxyphenyl)(²H₂)methyl]oxy}-5-(2-methylphenyl)-1-[(2S)-oxane-2-carbonyl]pyrrolidine-2-carboxylic acid;

(2S,3R,4S,5S)-3-tert-butyl-4-[(2-chloro-5,7-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxy-5,8-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxy-5,7-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-methoxyphenyl)-1-[(2S)-oxane-2-carbonyl]pyrrolidine-2-carboxylic acid;

(2S,3R,4S,5S)-3-tert-butyl-5-(2-methoxyphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-5-(2-methoxyphenyl)-1-[(2S)-oxane-2-carbonyl]pyrrolidine-2-carboxylic acid;

(2S,3R,4S,5S)-3-tert-butyl-4-[(2-methoxy-6,8-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[2-methoxy-5-(1-methylcyclopropyl)pyridin-3-yl]methoxy}-5-(2-methylphenyl)-1-[(2S)-oxane-2-carbonyl]pyrrolidine-2-carboxylic acid;

(2S,3R,4S,5S)-3-tert-butyl-4-[(2-methoxy-8-methylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-{[2-methoxy-5-(1-methylcyclobutyl)phenyl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-[(5-tert-butyl-2-methoxyphenyl)methoxy]-5-(2-methylphenyl)-1-[(2S)-oxolane-2-carbonyl]pyrrolidine-2-carboxylic acid;

(2S,3R,4S,5S)-3-tert-butyl-1-(cyclohexanecarbonyl)-4-[(2-methoxy-5,8-dimethylquinolin-3-yl)methoxy]-5-{2-[(propan-2-yl)oxy]pyridin-3-yl}pyrrolidine-2-carboxylic acid;

(2S,3R,4S,5S)-3-tert-butyl-4-({2-[2-methoxy-5-(trifluoromethyl)phenyl]prop-2-en-1-yl}oxy)-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-4-[(5-tert-butyl-2-methoxyphenyl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-1-(cyclohexanecarbonyl)-4-[(2-methoxy-5,7-dimethylquinolin-3-yl)methoxy]-5-{2-[(propan-2-yl)oxy]pyridin-3-yl}pyrrolidine-2-carboxylic acid;

(2S,3R,4S,5S)-3-tert-butyl-4-[(2-methoxy-5,7-dimethylquinolin-3-yl)methoxy]-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-5-(2-ethylphenyl)-4-[(2-methoxyquinolin-3-yl)methoxy]-1-[(2S)-oxane-2-carbonyl]pyrrolidine-2-carboxylic acid;

(2S,3R,4S,5S)-3-tert-butyl-4-[(1-methyl-1H-benzimidazol-2-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2,2-dimethyl-2,3-dihydro-1-benzofuran-7-yl)pyrrolidine-2-carboxylic acid;

(2S,3R,4S,5S)-3-tert-butyl-1-(cyclohexanecarbonyl)-5-(2,2-dimethyl-2,3-dihydro-1-benzofuran-7-yl)-4-{[2-methoxy-5-(trifluoromethyl)pyridin-3-yl]methoxy}pyrrolidine-2-carboxylic acid;

(2S,3R,4S,5S)-1-(cyclohexanecarbonyl)-3-(2-methoxypropan-2-yl)-4-{[2-methoxy-5-(trifluoromethyl)pyridin-3-yl]methoxy}-5-[2-(propan-2-yl)phenyl]pyrrolidine-2-carboxylic acid;

(2S,3R,4S,5S)-3-(2-methoxypropan-2-yl)-4-{[2-methoxy-5-(trifluoromethyl)pyridin-3-yl]methoxy}-1-{[(propan-2-yl)oxy]carbonyl}-5-[2-(propan-2-yl)phenyl]pyrrolidine-2-carboxylic acid;

(2S,3R,4S,5S)-3-(2-methoxypropan-2-yl)-4-{[2-methoxy-5-(trifluoromethyl)pyridin-3-yl]methoxy}-1-[(2S)-oxane-2-carbonyl]-5-[2-(propan-2-yl)phenyl]pyrrolidine-2-carboxylic acid;

(2S,3R,4S,5S)-3-tert-butyl-4-{2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{(2S)-2,3-dihydroxy-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{(2R)-2,3-dihydroxy-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{2-[2-methoxy-5-(trifluoromethyl)phenyl]-2-oxoethoxy}-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-{[(1,1,1-trifluoropropan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-({[(2R)-1,1,1-trifluoropropan-2-yl]oxy}carbonyl)pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-({[(2S)-1,1,1-trifluoropropan-2-yl]oxy}carbonyl)pyrrolidine-2-carboxylic acid;

(2S,3R,4S,5S)-3-tert-butyl-4-{2-hydroxy-2-[2-methoxy-5-(trifluoromethyl)phenyl]ethoxy}-5-(2-methylphenyl)-1-[(2S)-oxane-2-carbonyl]pyrrolidine-2-carboxylic acid;

(2S,3R,4S,5S)-3-tert-butyl-4-{2-methoxy-2-[2-methoxy-5-(trifluoromethyl)phenyl]ethoxy}-5-(2-methylphenyl)-1-[(2S)-oxane-2-carbonyl]pyrrolidine-2-carboxylic acid;

(2S,3R,4S,5S)-4-[(5-tert-butyl-2-methoxyphenyl)methoxy]-3-(2-methoxypropan-2-yl)-1-[(2S)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-({[(2S)-1,1,1-trifluoropropan-2-yl]oxy}carbonyl)pyrrolidine-2-carboxylic acid;

(2S,3R,4S,5S)-3-tert-butyl-4-{(2R)-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{(2S)-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-{2-[(propan-2-yl)oxy]pyridin-3-yl}-1-({[(2S)-1,1,1-trifluoropropan-2-yl]oxy}carbonyl)pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-[1-(trifluoromethyl)cyclopropane-1-carbonyl]pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-[1-(trifluoromethyl)cyclopentane-1-carbonyl]pyrrolidine-2-carboxylic acid;

(2S,3R,4S,5S)-3-tert-butyl-4-({3-[2-methoxy-5-(trifluoromethyl)pyridin-3-yl]prop-2-yn-1-yl}oxy)-5-phenyl-1-{[(propan-2-yl)oxy]carbonyl}pyrrolidine-2-carboxylic acid;

(2S,3R,4S,5S)-3-tert-butyl-5-(2-ethylphenyl)-4-({3-[2-methoxy-5-(trifluoromethyl)pyridin-3-yl]prop-2-yn-1-yl}oxy)-1-[(2S)-oxane-2-carbonyl]pyrrolidine-2-carboxylic acid;

(2S,3R,4S,5S)-3-tert-butyl-1-(cyclohexanecarbonyl)-5-{2-[(propan-2-yl)oxy]pyridin-3-yl}-4-{[5-(trifluoromethyl)-1-benzofuran-3-yl]methoxy}pyrrolidine-2-carboxylic acid;

(2S,3R,4S,5S)-3-tert-butyl-5-(2-ethylphenyl)-4-{3-[2-methoxy-5-(trifluoromethyl)pyridin-3-yl]propoxy}-1-[(2S)-oxane-2-carbonyl]pyrrolidine-2-carboxylic acid;

(2S,3R,4S,5S)-3-tert-butyl-5-(5-iodo-2-methylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-[(1R,2R)-2-(trifluoromethyl)cyclohexane-1-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-[(1S,2S)-2-(trifluoromethyl)cyclohexane-1-carbonyl]pyrrolidine-2-carboxylic acid;

(2S,3R,4S,5S)-3-tert-butyl-4-{2-[(5-chloro-2-methoxypyridin-3-yl)oxy]ethoxy}-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-1-[(2S)-oxane-2-carbonyl]-5-{2-[(propan-2-yl)oxy]pyridin-3-yl}pyrrolidine-2-carboxylic acid;

(2S,3R,4S,5S)-3-tert-butyl-4-{[2-methoxy-5-(trifluoromethyl)pyridin-3-yl]methoxy}-5-[2-($^2H_3$)methylphenyl]-1-[(2S,3S)-(2,3-$^2H_2$)oxane-2-carbonyl](2-$^2H$)pyrrolidine-2-carboxylic acid;

(2S,3R,4S,5S)-3-tert-butyl-1-(cyclohexanecarbonyl)-4-{[2-methoxy-5-(1-methylcyclopropyl)pyridin-3-yl]methoxy}-5-{2-[(propan-2-yl)oxy]pyridin-3-yl}pyrrolidine-2-carboxylic acid;

(2S,3R,4S,5S)-3-tert-butyl-4-{2-[2-methoxy-5-(trifluoromethyl)phenoxy]ethoxy}-5-(2-methylphenyl)-1-[(2S)-oxane-2-carbonyl]pyrrolidine-2-carboxylic acid;

(2S,3R,4S,5S)-4-[(5-bromo-1-benzofuran-2-yl)methoxy]-3-tert-butyl-1-[(2S)-oxane-2-carbonyl]-5-{2-[(propan-2-yl)oxy]pyridin-3-yl}pyrrolidine-2-carboxylic acid;

(2S,3R,4S,5S)-3-tert-butyl-4-[(6-tert-butyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid;

(2S,3R,4S,5S)-3-tert-butyl-4-[(6-tert-butyl-2-methoxypyridin-3-yl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-5-(2-ethylphenyl)-1-[(2S)-oxane-2-carbonyl]-4-{[7-(trifluoromethyl)-1-benzofuran-2-yl]methoxy}pyrrolidine-2-carboxylic acid;

(2S,3R,4S,5S)-3-tert-butyl-4-[(5-chloro-1-benzofuran-2-yl)methoxy]-5-(2-ethylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-(naphthalene-1-sulfonyl)-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-[2-(propan-2-yl)phenyl]pyrrolidine-2-carboxylic acid;

(2S,3R,4S,5S)-3-tert-butyl-4-[(5-cyclobutyl-1-benzofuran-2-yl)methoxy]-1-[(2S)-oxane-2-carbonyl]-5-{2-[(propan-2-yl)oxy]pyridin-3-yl}pyrrolidine-2-carboxylic acid; and pharmaceutically acceptable salts thereof.

One embodiment pertains to a compound, or a pharmaceutically acceptable salt thereof, wherein the compound is selected from the group consisting of:

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxolane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(3S)-oxolane-3-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(3R)-oxolane-3-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[3-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-[(2S)-oxolane-2-carbonyl]pyrrolidine-2-carboxylic acid; and (2S,3R,4S,5S)-3-tert-butyl-4-{[2-methoxy-5-(trifluoromethyl)pyridin-3-yl]methoxy}-5-(2-methylphenyl)-1-[(2S)-oxane-2-carbonyl]pyrrolidine-2-carboxylic acid.

One embodiment pertains to (2S,3R,4S,5S)-3-tert-butyl-4-{[2-methoxy-5-(trifluoromethyl)phenyl]methoxy}-5-(2-methylphenyl)-1-[(2S)-oxane-2-carbonyl]pyrrolidine-2-carboxylic acid; or a pharmaceutically acceptable salt thereof.

One embodiment pertains to (2S,3R,4S,5S)-3-tert-butyl-4-[(5-tert-butyl-2-methoxyphenyl)methoxy]-5-(2-methylphenyl)-1-[(2S)-oxane-2-carbonyl]pyrrolidine-2-carboxylic acid; or a pharmaceutically acceptable salt thereof.

One embodiment pertains to (2S,3R,4S,5S)-3-tert-butyl-4-{[2-methoxy-5-(trifluoromethyl)pyridin-3-yl]methoxy}-1-[(2S)-oxolane-2-carbonyl]-5-[2-(propan-2-yl)phenyl]pyrrolidine-2-carboxylic acid; or a pharmaceutically acceptable salt thereof.

One embodiment pertains to (2S,3R,4S,5S)-3-tert-butyl-4-{[2-methoxy-5-(trifluoromethyl)pyridin-3-yl]methoxy}-

1-[(2R)-oxolane-2-carbonyl]-5-[2-(propan-2-yl)phenyl]pyrrolidine-2-carboxylic acid; or a pharmaceutically acceptable salt thereof.

One embodiment pertains to a compound, or a pharmaceutically acceptable salt thereof, wherein the compound is selected from the group consisting of:
(2S,3R,4S,5S)-3-tert-butyl-4-{[2-methoxy-5-(trifluoromethyl)pyridin-3-yl]methoxy}-1-[(3S)-oxolane-3-carbonyl]-5-[2-(propan-2-yl)phenyl]pyrrolidine-2-carboxylic acid; and
(2S,3R,4S,5S)-3-tert-butyl-4-{[2-methoxy-5-(trifluoromethyl)pyridin-3-yl]methoxy}-1-[(3R)-oxolane-3-carbonyl]-5-[2-(propan-2-yl)phenyl]pyrrolidine-2-carboxylic acid;
or a pharmaceutically acceptable salt thereof.

One embodiment pertains to (2S,3R,4S,5S)-3-tert-butyl-4-{[2-methoxy-5-(trifluoromethyl)pyridin-3-yl]methoxy}-1-[(2S)-oxolane-2-carbonyl]-5-[3-(propan-2-yl)phenyl]pyrrolidine-2-carboxylic acid; or a pharmaceutically acceptable salt thereof.

One embodiment pertains to (2S,3R,4S,5S)-3-tert-butyl-4-{[2-methoxy-5-(trifluoromethyl)pyridin-3-yl]methoxy}-5-(2-methylphenyl)-1-[(2S)-oxolane-2-carbonyl]pyrrolidine-2-carboxylic acid; or a pharmaceutically acceptable salt thereof.

One embodiment pertains to (2S,3R,4S,5S)-3-tert-butyl-4-{[2-methoxy-5-(trifluoromethyl)pyridin-3-yl]methoxy}-5-(2-methylphenyl)-1-[(2S)-oxane-2-carbonyl]pyrrolidine-2-carboxylic acid; or a pharmaceutically acceptable salt thereof.

Formula (II)

One embodiment pertains to compounds of Formula (II),

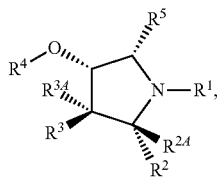

(II)

wherein
$R^1$ is selected from the group consisting of $SO_2R^6$, $C(O)R^6$, $C(O)OR^6$, and $C(O)NR^7R^8$;

$R^2$ is $C(O)OH$ or a bioisostere thereof;

$R^{2A}$ is selected from the group consisting of hydrogen, $C_1$-$C_6$ alkyl, $C_1$-$C_6$ haloalkyl, and $C_3$-$C_6$ cycloalkyl;

$R^3$ is selected from the group consisting of $C_1$-$C_6$ alkyl, $C_3$-$C_6$ cycloalkyl, phenyl, and 5-6 membered heteroaryl; wherein the $R^3$ $C_1$-$C_6$ alkyl is optionally substituted with one or more substituents independently selected from the group consisting of $C_1$-$C_6$ alkoxy, OH, oxo, CN, $NO_2$, F, Cl, Br and I; wherein the $R^3$ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{3A}$ is selected from the group consisting of hydrogen, $C_1$-$C_6$ alkyl, and $C_1$-$C_6$ haloalkyl; or $R^3$ and $R^{3A}$, together with the carbon to which they are attached, form a $C_3$-$C_6$ cycloalkyl; wherein the $C_3$-$C_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^4$ is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;

$L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo;

$R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl.

In one embodiment of Formula (II), $R^1$ is selected from the group consisting of $SO_2R^6$, $C(O)R^6$, $C(O)OR^6$, and $C(O)NR^7R^8$;

$R^2$ is $C(O)OH$ or a bioisostere thereof, $R^{2A}$ is selected from the group consisting of hydrogen, $C_1$-$C_6$ alkyl, $C_1$-$C_6$ haloalkyl, and $C_3$-$C_6$ cycloalkyl;

$R^3$ is selected from the group consisting of $C_1$-$C_6$ alkyl, $C_3$-$C_6$ cycloalkyl, phenyl, and 5-6 membered heteroaryl; wherein the $R^3$ $C_1$-$C_6$ alkyl is optionally substituted with one or more substituents independently selected from the group consisting of $C_1$-$C_6$ alkoxy, OH, oxo, CN, $NO_2$, F, Cl, Br and I; wherein the $R^3$ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{3A}$ is selected from the group consisting of hydrogen, $C_1$-$C_6$ alkyl, and $C_1$-$C_6$ haloalkyl; or $R^3$ and $R^{3A}$, together with the carbon to which they are attached, form a $C_3$-$C_6$ cycloalkyl; wherein the $C_3$-$C_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^4$ is selected from the group consisting of $(C_1$-$C_6$ alkylene$)_x$-$C_6$-$C_{10}$ aryl, $(C_1$-$C_6$ alkylene$)_x$-5-11 membered heteroaryl, $(C_1$-$C_6$ alkylene$)_x$-4-12 membered heterocyclyl, $(C_1$-$C_6$ alkylene$)_x$-$C_3$-$C_{11}$ cycloalkyl, and $(C_1$-$C_6$ alkylene$)_x$-$C_4$-$C_{11}$ cycloalkenyl; wherein the $R^4$ $C_6$-$C_{10}$ membered aryl of $(C_1$-$C_6$ alkylene$)_x$-$C_6$-$C_{10}$ membered aryl, the 5-11 membered heteroaryl of $(C_1$-$C_6$ alkylene$)_x$-5-11 membered heteroaryl, the 4-12 membered heterocyclyl of $(C_1$-$C_6$ alkylene$)_x$-4-12 membered heterocyclyl, the $C_3$-$C_{11}$ cycloalkyl of $(C_1$-$C_6$ alkylene$)_x$-$C_3$-$C_{11}$ cycloalkyl, and the $C_4$-$C_{11}$ cycloalkenyl of $(C_1$-$C_6$ alkylene$)_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;

$R^5$ is selected from the group consisting of $C_6$-$C_{10}$ membered aryl, 5-11 membered heteroaryl, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^2$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl;

$R^{25}$ and $R^{26}$, at each occurrence, are each independently hydrogen or $C_1$-$C_6$ alkyl; and x is 0 or 1.

In one embodiment of Formula (II), $R^1$ is selected from the group consisting of $SO_2R^6$, $C(O)R^6$, $C(O)OR^6$, and $C(O)NR^7R^8$. In another embodiment of Formula (II), $R^1$ is $C(O)R^6$ or $C(O)OR^6$. In another embodiment of Formula (II), $R^1$ is $SO_2R^6$. In another embodiment of Formula (II), $R^1$ is $C(O)R^6$. In another embodiment of Formula (II), $R^1$ is $C(O)OR^6$. In another embodiment of Formula (II), $R^1$ is $C(O)NR^7R^8$.

In one embodiment of Formula (II), $R^2$ is C(O)OH or a bioisostere thereof. In another embodiment of Formula (II), $R^2$ is selected from the group consisting of —$P(O)(OH)_2$, —$P(O)(OH)(H)$, —$P(O)(OH)(O$—$C_1$-$C_6$ alkyl), —$P(O)(CH_3)(OH)$, —$B(OH)_2$, —$SO_3H$, —$CH(OH)CF_3$, —$C(O)NH(OH)$, —$C(O)NH(CN)$, —$C(O)NHSO_2R^{G3a}$, —$SO_2NHC(O)R^{G3a}$, —$C(O)NHSO_2NHR^{G3a}$, —$C(O)NHSO_2N(R^{G3a})_2$, —$SO_2NH_2$, —$SO_2NHR^{G3a}$, —$SO_2N(R^{G3a})_2$, —$C(O)NHS(O)(R^{G3a})$=$NC(O)R^{G3a}$, —$C(O)NHS(O)(R^{G3a})$=$NR^{G3b}$,

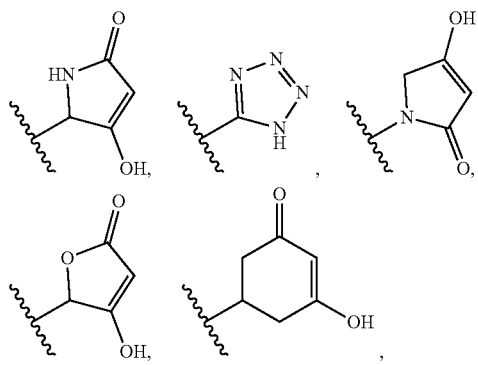

-continued

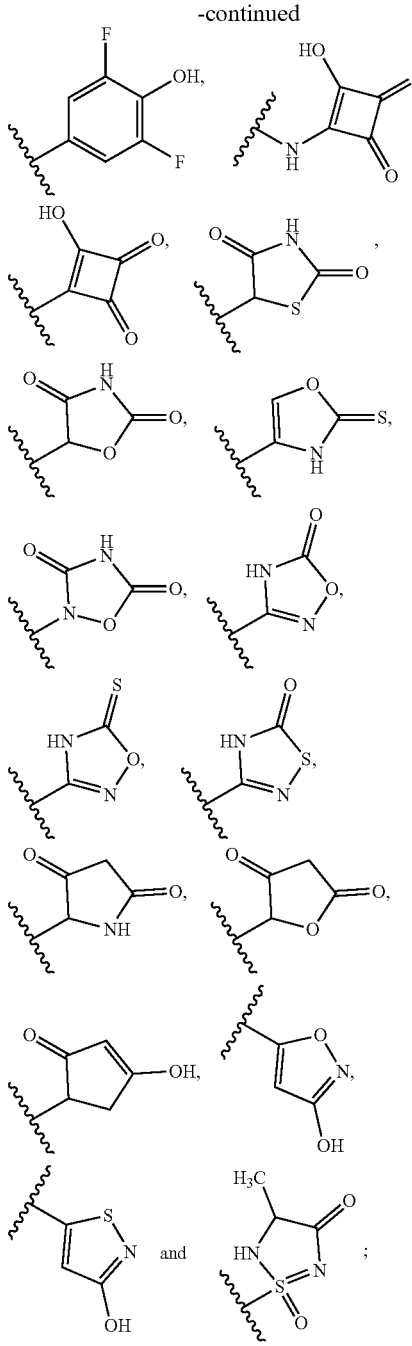

wherein
R$^{G3a}$, at each occurrence, is independently C$_1$-C$_6$ alkyl, C$_1$-C$_6$ alkyl-O—C$_1$-C$_6$ alkyl, C$_1$-C$_6$ haloalkyl, or G$^A$;
R$^{G3b}$ is hydrogen, C$_1$-C$_6$ alkyl, or C$_1$-C$_6$ haloalkyl or G$^A$;
G$^A$, at each occurrence, is independently cycloalkyl, cycloalkenyl, aryl, or heteroaryl, each of which is independently unsubstituted or substituted with 1, 2, or 3 independently selected R$^u$ groups; wherein
R$^u$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, oxo, —NO$_2$, —OR$^j$, —OC(O)R$^k$, —OC(O)N(R$^j$)$_2$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), or —N(R$^j$)C(O)N(R$^j$)$_2$;

R$^j$, at each occurrence, is independently selected from the group consisting of hydrogen, C$_1$-C$_6$ alkyl, or C$_1$-C$_6$ haloalkyl; and
R$^k$, at each occurrence, is independently selected from the group consisting of C$_1$-C$_6$ alkyl or C$_1$-C$_6$ haloalkyl. In another embodiment of Formula (II), R$^2$ is —P(O)(OH)$_2$, —P(O)(OH)(H), —B(OH)$_2$, —SO$_3$H, —CH(OH)CF$_3$, —C(O)NH(OH), —C(O)NH(CN), —C(O)NHSO$_2$R$^{G3a}$, —SO$_2$NHC(O)R$^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$)=NC(O)R$^{G3a}$, —C(O)NHS(O)(R$^{G3a}$)=NR$^{G3b}$, or

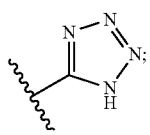

wherein
R$^{G3a}$, at each occurrence, is independently C$_1$-C$_6$ alkyl, C$_1$-C$_6$ alkyl-O—C$_1$-C$_6$ alkyl, C$_1$-C$_6$ haloalkyl, or G$^A$;
R$^{G3b}$ is hydrogen, C$_1$-C$_6$ alkyl, or C$_1$-C$_6$ haloalkyl or G$^A$;
G$^A$, at each occurrence, is independently cycloalkyl, cycloalkenyl, aryl, or heteroaryl, each of which is independently unsubstituted or substituted with 1, 2, or 3 independently selected R$^u$ groups; wherein
R$^u$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, oxo, —NO$_2$, —OR$^j$, —OC(O)R$^k$, —OC(O)N(R$^j$)$_2$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), or —N(R$^j$)C(O)N(R$^j$)$_2$;
R$^j$, at each occurrence, is independently selected from the group consisting of hydrogen, C$_1$-C$_6$ alkyl, or C$_1$-C$_6$ haloalkyl; and
R$^k$, at each occurrence, is independently selected from the group consisting of C$_1$-C$_6$ alkyl or C$_1$-C$_6$ haloalkyl. In another embodiment of Formula (II), R$^2$ is C(O)OH. In another embodiment of Formula (II), R$^2$ is —C(O)NHSO$_2$R$^{G3a}$ or —C(O)NHSO$_2$N(R$^{G3a}$)$_2$; R$^{G3a}$, at each occurrence, is independently C$_1$-C$_6$ alkyl, C$_1$-C$_6$ alkyl-O—C$_1$-C$_6$ alkyl, or G$^A$; and G$^A$, at each occurrence, is independently cycloalkyl, which is independently unsubstituted or substituted with 1, 2, or 3 independently selected R$^u$ groups; wherein R$^u$, at each occurrence, is independently C$_1$-C$_6$ alkyl. In another embodiment of Formula (II), R$^2$ is —C(O)NHSO$_2$R$^{G3a}$; R$^{G3a}$, at each occurrence, is independently C$_1$-C$_6$ alkyl, C$_1$-C$_6$ alkyl-O—C$_1$-C$_6$ alkyl, or G$^A$; and G$^A$, at each occurrence, is independently cycloalkyl, which is independently unsubstituted or substituted with 1, 2, or 3 independently selected R$^u$ groups; wherein R$^u$, at each occurrence, is independently C$_1$-C$_6$ alkyl. In another embodiment of Formula (II), R$^2$ is —C(O)NHSO$_2$N(R$^{G3a}$)$_2$; and R$^{G3a}$, at each occurrence, is independently C$_1$-C$_6$ alkyl.

In one embodiment of Formula (II), R$^{24}$ is selected from the group consisting of hydrogen, C$_1$-C$_6$ alkyl, C$_1$-C$_6$ haloalkyl, and C$_3$-C$_6$ cycloalkyl. In another embodiment of Formula (II), R$^{24}$ is hydrogen or C$_1$-C$_6$ alkyl. In another embodiment of Formula (II), R$^{24}$ is hydrogen. In another embodiment of Formula (II), R$^{24}$ is C$_1$-C$_6$ alkyl. In another embodiment of Formula (II), R$^{24}$ is CH$_3$.

In one embodiment of Formula (II), R$^2$ is C(O)OH; and R$^{24}$ is hydrogen.

In one embodiment of Formula (II),
R² is —P(O)(OH)₂, —P(O)(OH)(H), —B(OH)₂, —SO₃H, —CH(OH)CF₃, —C(O)NH(OH), —C(O)NH(CN), —C(O)NHSO₂R$^{G3a}$, —SO₂NHC(O)R$^{G3a}$, —C(O)NHSO₂NHR$^{G3a}$, —C(O)NHSO₂N(R$^{G3a}$)₂, —SO₂NH₂, —SO₂NHR$^{G3a}$, —SO₂N(R$^{G3a}$)₂, —C(O)NHS(O)(R$^{G3a}$)=NC(O)R$^{G3a}$, —C(O)NHS(O)(R$^{G3a}$)=NR$^{G3b}$, or

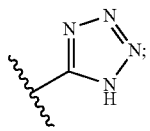 [SMILES: *c1nnn[nH]1]

R$^{G3a}$, at each occurrence, is independently $C_1$-$C_6$ alkyl, $C_1$-$C_6$ alkyl-O—$C_1$-$C_6$ alkyl, $C_1$-$C_6$ haloalkyl, or G$^A$;
R$^{G3b}$ is hydrogen, $C_1$-$C_6$ alkyl, or $C_1$-$C_6$ haloalkyl or G$^A$;
G$^A$, at each occurrence, is independently cycloalkyl, cycloalkenyl, aryl, or heteroaryl, each of which is independently unsubstituted or substituted with 1, 2, or 3 independently selected R$^u$ groups; wherein
R$^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, —NO₂, —OR$^j$, —OC(O)R$^k$, —OC(O)N(R$^j$)₂, —S(O)₂R$^j$, —S(O)₂N(R$^j$)₂, —C(O)R$^k$, —C(O)OR$^j$, —C(O)N(R$^j$)₂, —N(R$^j$)₂, —N(R$^j$)C(O)R$^k$, —N(R$^j$)S(O)₂R$^k$, —N(R$^j$)C(O)O(R$^k$), or —N(R$^j$)C(O)N(R$^j$)₂;
R$^j$, at each occurrence, is independently selected from the group consisting of hydrogen, $C_1$-$C_6$ alkyl, or $C_1$-$C_6$ haloalkyl;
R$^k$, at each occurrence, is independently selected from the group consisting of $C_1$-$C_6$ alkyl or $C_1$-$C_6$ haloalkyl; and
R$^{2A}$ is hydrogen.
In one embodiment of Formula (II),
R² is —C(O)NHSO₂R$^{G3a}$ or —C(O)NHSO₂N(R$^{G3a}$)₂;
R$^{G3a}$, at each occurrence, is independently $C_1$-$C_6$ alkyl, $C_1$-$C_6$ alkyl-O—$C_1$-$C_6$ alkyl, or G$^A$;
G$^A$, at each occurrence, is independently cycloalkyl, which is independently unsubstituted or substituted with 1, 2, or 3 independently selected R$^u$ groups;
R$^u$, at each occurrence, is independently $C_1$-$C_6$ alkyl; and R$^{2A}$ is hydrogen.
In one embodiment of Formula (II), R³ is selected from the group consisting of $C_1$-$C_6$ alkyl, $C_3$-$C_6$ cycloalkyl, phenyl, and 5-6 membered heteroaryl; wherein the R³ $C_1$-$C_6$ alkyl is optionally substituted with one or more substituents independently selected from the group consisting of $C_1$-$C_6$ alkoxy, OH, oxo, CN, NO₂, F, Cl, Br and I; wherein the R³ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO₂, F, Cl, Br and I; and R$^{3A}$ is independently selected from the group consisting of hydrogen, $C_1$-$C_6$ alkyl, and $C_1$-$C_6$ haloalkyl. In another embodiment of Formula (II), R³ is selected from the group consisting of $C_1$-$C_6$ alkyl and $C_3$-$C_6$ cycloalkyl; wherein the R³ $C_1$-$C_6$ alkyl is optionally substituted with one or more $C_1$-$C_6$ alkoxy; wherein the R³ $C_3$-$C_6$ cycloalkyl is optionally substituted with one or more $C_1$-$C_6$ alkyl; and R$^{3A}$ is independently hydrogen. In another embodiment of Formula (II), R³ is $C_1$-$C_6$ alkyl; wherein the R³ $C_1$-$C_6$ alkyl is optionally substituted with one or more $C_1$-$C_6$ alkoxy; and R$^{3A}$ is independently hydrogen. In another embodiment of Formula (II), R³ is $C_3$-$C_6$ cycloalkyl; wherein the R³ $C_3$-$C_6$ cycloalkyl is optionally substituted with one or more $C_1$-$C_6$ alkyl; and R$^{3A}$ is hydrogen. In one embodiment of Formula (II), R³ is CH₃, and R$^{3A}$ is hydrogen. In one embodiment of Formula (II), R³ is $C_1$-$C_6$ alkyl and R$^{3A}$ is hydrogen. In one embodiment of Formula (II), R³ is C(CH₃)₃, and R$^{3A}$ is hydrogen. In one embodiment of Formula (II), R³ is C(OCH₃)(CH₃)₂, and R$^{3A}$ is hydrogen. In one embodiment of Formula (II), R³ is cyclopropyl wherein the R³ cyclopropyl is optionally substituted with one CH₃; and R$^{3A}$ is hydrogen.
In one embodiment of Formula (II), R³ and R$^{3A}$, together with the carbon to which they are attached, form $C_3$-$C_6$ cycloalkyl; wherein the $C_3$-$C_6$ cycloalkyl formed from R³ and R$^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO₂, F, Cl, Br and I. In another embodiment of Formula (II), R³ and R$^{3A}$, together with the carbon to which they are attached, form $C_3$-$C_6$ cycloalkyl, which is unsubstituted. In another embodiment of Formula (II), R³ and R$^{3A}$, together with the carbon to which they are attached, form cyclopropyl.
In one embodiment of Formula (II), R⁴ is selected from the group consisting of L¹-$C_6$-$C_{10}$ aryl, L¹-5-11 membered heteroaryl, L¹-4-12 membered heterocyclyl, L¹-$C_3$-$C_{11}$ cycloalkyl, and L¹-$C_4$-$C_{11}$ cycloalkenyl; wherein the R⁴ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of R⁹, OR⁹, C(O)OR⁹, C(O)NR¹⁰R¹¹, SR⁹, NR¹⁰R¹¹, Si(R⁹)₃, SF₅, SO₂R⁹, OH, oxo, CN, NO₂, F, Cl, Br and I; wherein L¹ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the L¹ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo. In another embodiment of Formula (II), R⁴ is selected from the group consisting of L¹-$C_6$-$C_{10}$ aryl and L¹-5-11 membered heteroaryl; wherein the R⁴ $C_6$-$C_{10}$ aryl and 5-11 membered heteroaryl are optionally substituted with one or more substituents independently selected from the group consisting of R⁹, OR⁹, NR¹⁰R¹¹, OH, Cl, and Br; wherein L¹ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the L¹ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo. In another embodiment of Formula (II), R⁴ is L¹-$C_6$-$C_{10}$ aryl; wherein the R⁴ $C_6$-$C_{10}$ aryl is optionally substituted with one or more substituents independently selected from the group consisting of R⁹, OR⁹, NR¹⁰R¹¹, OH, Cl, and Br; wherein L¹ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the L¹ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo.
In another embodiment of Formula (II), R⁴ is L¹-5-11 membered heteroaryl; wherein the R⁴ 5-11 membered heteroaryl is optionally substituted with one or more substituents independently selected from the group consisting of R⁹, $OR^9$, $NR^{10}R^{11}$, OH, Cl, and Br; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo.

In one embodiment of Formula (II), $R^4$ is selected from the group consisting of ($C_1$-$C_6$ alkylene)$_x$-$C_6$-$C_{10}$ aryl, ($C_1$-$C_6$ alkylene)$_x$-5-11 membered heteroaryl, ($C_1$-$C_6$ alkylene)$_x$-4-12 membered heterocyclyl, ($C_1$-$C_6$ alkylene)$_x$-$C_3$-$C_{11}$ cycloalkyl, and ($C_1$-$C_6$ alkylene)$_x$-$C_4$-$C_{11}$ cycloalkenyl; wherein the $R^4$ $C_6$-$C_{10}$ membered aryl of ($C_1$-$C_6$ alkylene)$_x$-$C_6$-$C_{10}$ membered aryl, the 5-11 membered heteroaryl of ($C_1$-$C_6$ alkylene)$_x$-5-11 membered heteroaryl, the 4-12 membered heterocyclyl of ($C_1$-$C_6$ alkylene)$_x$-4-12 membered heterocyclyl, the $C_3$-$C_{11}$ cycloalkyl of ($C_1$-$C_6$ alkylene)$_x$$C_3$-$C_{11}$ cycloalkyl, and the $C_4$-$C_{11}$ cycloalkenyl of ($C_1$-$C_6$ alkylene)$_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I; and x is 0 or 1. In another embodiment of Formula (II), $R^4$ is selected from the group consisting of ($C_1$-$C_6$ alkylene)$_x$-$C_6$-$C_{10}$ aryl, ($C_1$-$C_6$ alkylene)$_x$-5-11 membered heteroaryl, ($C_1$-$C_6$ alkylene)$_x$-4-12 membered heterocyclyl, and ($C_1$-$C_6$ alkylene)$_x$-$C_3$-$C_{11}$ cycloalkyl; wherein the $R^4$ $C_6$-$C_{10}$ membered aryl of ($C_1$-$C_6$ alkylene)$_x$-$C_6$-$C_{10}$ membered aryl, the 5-11 membered heteroaryl of ($C_1$-$C_6$ alkylene)$_x$-5-11 membered heteroaryl, the 4-12 membered heterocyclyl of ($C_1$-$C_6$ alkylene)$_x$-4-12 membered heterocyclyl, and the $C_3$-$C_{11}$ cycloalkyl of ($C_1$-$C_6$ alkylene)$_x$$C_3$-$C_{11}$ cycloalkyl are optionally substituted with one or more substituents independently selected from the group consisting of $R^9$, $OR^9$, $NR^{10}R^{11}$, OH, Cl, and Br; and x is 0 or 1. In another embodiment of Formula (II), $R^4$ is ($C_1$-$C_6$ alkylene)$_x$-$C_6$-$C_{10}$ aryl; wherein the $R^4$ ($C_1$-$C_6$ alkylene)$_x$-$C_6$-$C_{10}$ membered aryl is optionally substituted with one or more substituents independently selected from the group consisting of $R^9$, $OR^9$, $NR^{10}R^{11}$, OH, Cl, and Br; and x is 0 or 1.

In another embodiment of Formula (II), $R^4$ is ($C_1$-$C_6$ alkylene)$_x$-5-11 membered heteroaryl; wherein the $R^4$ ($C_1$-$C_6$ alkylene)$_x$-5-11 membered heteroaryl is optionally substituted with one or more substituents independently selected from the group consisting of $R^9$, $OR^9$, $NR^{10}R^{11}$, OH, Cl, and Br; and x is 0 or 1. In another embodiment of Formula (II), $R^4$ is ($C_1$-$C_6$ alkylene)$_x$-4-12 membered heterocyclyl; wherein the $R^4$ ($C_1$-$C_6$ alkylene)$_x$-4-12 membered heterocyclyl is optionally substituted with one or more substituents independently selected from the group consisting of $R^9$, $OR^9$, $NR^{10}R^{11}$, OH, Cl, and Br; and x is 0 or 1. In another embodiment of Formula (II), $R^4$ is ($C_1$-$C_6$ alkylene)$_x$-$C_3$-$C_{11}$ cycloalkyl; wherein the $R^4$ ($C_1$-$C_6$ alkylene)$_x$-$C_3$-$C_{11}$ cycloalkyl is optionally substituted with one or more substituents independently selected from the group consisting of $R^9$, $OR^9$, $NR^{10}R^{11}$, OH, Cl, and Br; and x is 0 or 1.

In one embodiment of Formula (II), $R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I; $R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl)$_2$, OH, oxo, CN, $NO_2$, F, Cl, Br and I; and $R^{13}$ and $R^{14}$, at each occurrence, are each independently hydrogen or $C_1$-$C_6$ alkyl. In another embodiment of Formula (II), $R^5$ is selected from the group consisting of $C_6$-$C_{10}$ membered aryl, 5-11 membered heteroaryl, and 4-6 membered monocyclic heterocycle fused to a phenyl group; wherein the $R^5$ $C_6$-$C_{10}$ membered aryl, 5-11 membered heteroaryl, and 4-6 membered monocyclic heterocycle fused to a phenyl group are optionally substituted with one or more substituents independently selected from the group consisting of $R^{12}$, $OR^{12}$, $NR^{13}R^{14}$, F, Cl, Br, and I; $R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; wherein each $R^{12}$ 6-10 membered aryl, 5-11 membered heteroaryl, $C_3$-$C_{11}$cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl)$_2$, oxo, CN, F, and Cl; and $R^{13}$ and $R^{14}$, at each occurrence, are each independently $C_1$-$C_6$ alkyl. In another embodiment of Formula (II), $R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, Br, and I; $R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; wherein each $R^{12}$ 6-10 membered aryl, 5-11 membered heteroaryl, $C_3$-$C_{11}$ cycloalkyl, and 4-12 membered heterocyclyl is optionally substituted with one or more independently selected $C_1$-$C_6$ alkyl; and $R^{13}$ and $R^{14}$, at each occurrence, are each independently $C_1$-$C_6$ alkyl.

In another embodiment of Formula (II), $R^5$ is $C_6$-$C_{10}$ membered aryl; wherein the $R^5$ $C_6$-$C_{10}$ membered aryl is optionally substituted with one or more substituents independently selected from the group consisting of $R^{12}$, $OR^{12}$, $NR^{13}R^{14}$, F, Cl, Br, and I; $R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl)$_2$, oxo, CN, F, and Cl; and $R^{13}$ and $R^{14}$, at each occurrence, are each independently $C_1$-$C_6$ alkyl. In another embodiment of Formula (II), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, F, Cl, Br, and I; $R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, N($C_1$-$C_6$ alkyl)$_2$, oxo, CN, F, and Cl; and $R^{13}$ and $R^{14}$, at each occurrence, are each independently $C_1$-$C_6$ alkyl. In another embodiment of Formula (II), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, F, Cl, Br, and I; $R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; wherein each $R^{12}$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, N($C_1$-$C_6$ alkyl)$_2$, oxo, CN, F, and Cl; and $R^{13}$ and $R^{14}$, at each occurrence, are each independently $C_1$-$C_6$ alkyl. In another embodiment of Formula (II), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, F, Cl, and Br; $R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; wherein each $R^{12}$ 6-10 membered aryl, 5-11 membered heteroaryl, $C_3$-$C_{11}$cycloalkyl, and 4-12 membered heterocyclyl is optionally substituted with one or more independently selected $C_1$-$C_6$ alkyl; and $R^{13}$ and $R^{14}$, at each occurrence, are each independently $C_1$-$C_6$ alkyl. In another embodiment of Formula (II), $R^5$ is phenyl, which is unsubstituted. In another embodiment of Formula (II), $R^5$ is phenyl; wherein the $R^5$ phenyl is optionally substituted with one or more substituents independently selected from the group consisting of $R^{12}$, $OR^{12}$, $NR^{13}R^{14}$, F, Cl, and Br; $R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (II), $R^5$ is phenyl; which is substituted with one $R^{12}$; and $R^{12}$ is $C_1$-$C_6$ alkyl, $C_3$-$C_{11}$ cycloalkyl, or F. In another embodiment of Formula (II), $R^5$ is phenyl; which is substituted with one $R^{12}$; and $R^{12}$ is $CH_3$, $CH_2CH_3$ or $CH(CH_3)_2$. In another embodiment of Formula (II), $R^5$ is phenyl; which is substituted with one $R^{12}$; and $R^{12}$ is cyclopropyl. In another embodiment of Formula (II), $R^5$ is pyridinyl; which is substituted with one or more substituents independently selected from the group consisting of $R^{12}$, $OR^{12}$, and $NR^{13}R^{14}$; $R^{12}$ is independently $C_1$-$C_6$ alkyl; and $R^{13}$ and $R^{14}$, at each occurrence, are each independently $C_1$-$C_6$ alkyl. In another embodiment of Formula (II), $R^5$ is pyridinyl; which is substituted with one or more substituents independently selected from the group consisting of $R^{12}$, $OR^{12}$, and $NR^{13}R^{14}$; $R^{12}$ is independently $CH_3$ or $CH(CH_3)_2$; and $R^{13}$ and $R^{14}$, at each occurrence, are each independently $CH_3$. In another embodiment of Formula (II), $R^5$ is pyridinyl; wherein the $R^5$ pyridinyl is optionally substituted with one or more independently selected $R^{12}$; and $R^{12}$, at each occurrence, is independently $C_1$-$C_6$ alkyl.

In one embodiment of Formula (II), $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I; $R^{15}$ at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I; $R^{16}$ and $R^{17}$, at each occurrence, are each independently hydrogen or $C_1$-$C_6$ alkyl; and $R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I. In another embodiment of Formula (II), $R^6$ is selected from the group consisting of $C_1$-$C_6$ alkyl, $C_2$-$C_6$ alkenyl, 6-10 membered aryl, 5-11 membered heteroaryl, $C_3$-$C_{11}$cycloalkyl, and 4-12 membered heterocyclyl; wherein the $R^6$ $C_1$-$C_6$ alkyl is optionally substituted with one or more independently selected $R^{15}$ or F; wherein the $R^6$ 6-10 membered aryl, 5-11 membered heteroaryl, $C_3$-$C_{11}$ cycloalkyl, and 4-12 membered heterocyclyl are optionally substituted with one or more substituents independently selected from the group consisting of $R^{18}$ and $OR^{18}$; $R^{15}$, at each occurrence, is independently $C_3$-$C_{11}$ cycloalkyl; and $R^{18}$, at each occurrence, is independently selected $C_1$-$C_6$ alkyl; wherein each $R^{18}$ $C_1$-$C_6$ alkyl is optionally substituted with one or more F. In one embodiment of Formula (II), $R^6$ is $C_1$-$C_6$ alkyl; wherein the $R^6$ $C_1$-$C_6$ alkyl is optionally substituted with one or more independently selected $R^{15}$; and $R^{15}$, at each occurrence, is independently $C_3$-$C_{11}$ cycloalkyl. In another embodiment of Formula (II), $R^6$ is $C_1$-$C_6$ alkyl; wherein the $R^6$ $C_1$-$C_6$ alkyl is unsubstituted. In another embodiment of Formula (II), $R^6$ is —$CH_2CH_3$. In another embodiment of Formula (II), $R^6$ is —$CH(CH_3)_2$. In one embodiment of Formula (II), $R^6$ is 4-12 membered heterocyclyl; wherein the $R^6$ 4-12 membered heterocyclyl is optionally substituted with one or more substituents independently selected from the group consisting of $OR^{18}$; and $R^{18}$, at each occurrence, is independently $C_1$-$C_6$ alkyl. In another embodiment of Formula (II), $R^6$ is 4-12 membered heterocyclyl; wherein the $R^6$ 4-12 membered heterocyclyl is unsubstituted. In another embodiment of Formula (II), $R^6$ is tetrahydrofuranyl. In another embodiment of Formula (II), $R^6$ is tetrahydropyranyl. In one embodiment of Formula (II), $R^6$ is $C_3$-$C_{11}$ cycloalkyl; wherein the $R^6$ $C_3$-$C_{11}$ cycloalkyl is optionally substituted with one or more independently selected $OR^{18}$; and $R^{18}$, at each occurrence, is independently selected $C_1$-$C_6$ alkyl. In one embodiment of Formula (II), $R^6$ is cyclohexyl; wherein the $R^6$ cyclohexyl is unsubstituted.

In one embodiment of Formula (II), $R^1$ is $C(O)OR^6$; and $R^6$ is $C_1$-$C_6$ alkyl or $C_3$-$C_{11}$ cycloalkyl. In one embodiment of Formula (II), $R^1$ is $C(O)OR^6$; and $R^6$ is $C_1$-$C_6$ alkyl; wherein the $R^6$ is $C_1$-$C_6$ unsubstituted alkyl.

In one embodiment of Formula (II), $R^1$ is $C(O)R^6$; $R^6$ is 4-12 membered heterocyclyl; wherein the $R^6$ 4-12 membered heterocyclyl is optionally substituted with $OR^{18}$; and $R^{18}$, at each occurrence, is independently selected $C_1$-$C_6$ alkyl. In one embodiment of Formula (II), $R^1$ is $C(O)R^6$; and $R^6$ is 4-12 membered heterocyclyl; wherein the $R^6$ 4-12 membered heterocyclyl is unsubstituted. In one embodiment of Formula (II), $R^1$ is $C(O)R^6$; and $R^6$ is $C_3$-$C_{11}$ cycloalkyl; wherein the $R^6$ $C_3$-$C_{11}$ cycloalkyl is unsubstituted.

In one embodiment of Formula (II), $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I; $R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I; $R^{22}$ and $R^{23}$, at each occurrence, are each independently hydrogen or $C_1$-$C_6$ alkyl; $R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl. In another embodiment of Formula (II), $R^9$, at each occurrence, is independently selected from the group consisting of $C_1$-$C_6$ alkyl, 6-10 membered aryl, $C_3$-$C_{11}$ cycloalkyl, and 4-12 membered heterocyclyl; wherein each $R^9$ $C_1$-$C_6$ alkyl is optionally substituted with one or more CN or F; wherein each $R^9$ 6-10 membered aryl, $C_3$-$C_{11}$ cycloalkyl, and 4-12 membered heterocyclyl is optionally substituted with one or more substituents independently selected from the group consisting of $R^{24}$, $OR^{24}$, and F; and $R^{24}$, at each occurrence, is independently $C_1$-$C_6$ alkyl.

In one embodiment of Formula (II), $R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br, and I. In another embodiment of Formula (II), $R^{10}$ and $R^{11}$, at each occurrence, are each independently $C_1$-$C_6$ alkyl.

In one embodiment of Formula (II), $R^4$ is $L^1$-$C_6$-$C_{10}$ aryl; wherein the $R^4$ $C_6$-$C_{10}$ aryl is optionally substituted with one or more substituents independently selected from the group consisting of $R^9$ and $OR^9$; $L^1$ is absent or is $C_1$-$C_6$ alkylene; and $R^9$, at each occurrence, is independently selected $C_1$-$C_6$ alkyl; wherein each $R^9$ $C_1$-$C_6$ alkyl is optionally substituted with one or more F. In one embodiment of Formula (II), $R^4$ is $(C_1$-$C_6$ alkylene$)_x$-$C_6$-$C_{10}$ aryl; wherein the $R^4$ $(C_1$-$C_6$ alkylene$)_x$-$C_6$-$C_{10}$ membered aryl is optionally substituted with one or more substituents independently selected from the group consisting of $R^9$ and $OR^9$; x is 0 or 1; and $R^9$, at each occurrence, is independently selected $C_1$-$C_6$ alkyl; wherein each $R^9$ $C_1$-$C_6$ alkyl is optionally substituted with one or more F. In another embodiment of Formula (II), $R^4$ is $CH_2$-phenyl; wherein the $R^4$ $CH_2$-phenyl is optionally substituted with one or more substituents independently selected from the group consisting of $R^9$ and $OR^9$; and $R^9$, at each occurrence, is independently selected from the group consisting of $CH_3$ and $CF_3$. In another embodiment of Formula (II), $R^4$ is $L^1$-5-11 membered heteroaryl; wherein the $R^4$ 5-11 membered heteroaryl is optionally substituted with one or more substituents independently selected from the group consisting of $R^9$ and $OR^9$; $L^1$ is absent, or is $C_1$-$C_6$ alkylene; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F.

In another embodiment of Formula (II), $R^4$ is $(C_1$-$C_6$ alkylene$)_x$-5-11 membered heteroaryl; wherein the $R^4$ $(C_1$-$C_6$ alkylene$)_x$-5-11 membered heteroaryl is optionally substituted with one or more substituents independently selected from the group consisting of $R^9$ and $OR^9$; x is 0 or 1; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F. In another embodiment of Formula (II), $R^4$ is $CH_2$-pyridinyl; wherein the $R^4$ $CH_2$-pyridinyl is optionally substituted with one or more substituents independently selected from the group consisting of $R^9$ and $OR^9$; and $R^9$, at each occurrence, is independently selected from the group consisting of $CH_3$, $C(CH_3)_3$, $CF_3$, and cyclobutyl. In another embodiment of Formula (II), $R^4$ is $CH_2$-quinolinyl; wherein the $R^4$ $CH_2$-quinolinyl is optionally substituted with one or more substituents independently selected from the group consisting of $R^9$ and $OR^9$; and $R^9$, at each occurrence, is independently $CH_3$.

In one embodiment of Formula (II), $R^4$ is selected from the group consisting of

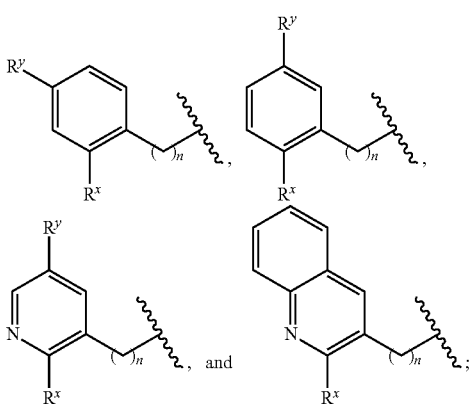

wherein $R^x$ is $OCH_3$, and $R^y$ is selected from the group consisting of $CF_3$, $C(CH_3)_3$, and cyclobutyl; and n is 1.

One embodiment pertains to compounds of Formula (II),

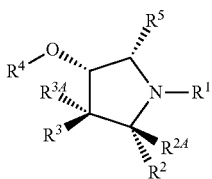

(II)

wherein
- $R^1$ is selected from the group consisting of $SO_2R^6$, $C(O)R^6$, $C(O)OR^6$, and $C(O)NR^7R^8$;
- $R^2$ is $C(O)OH$ or a bioisostere thereof;
- $R^{2A}$ is hydrogen;
- $R^3$ is $C_1$-$C_6$ alkyl; wherein the $R^3$ $C_1$-$C_6$ alkyl is optionally substituted with one or more $C_1$-$C_6$ alkoxy;
- $R^{3A}$ is hydrogen;
- $R^4$ is selected from the group consisting of $L^1$-$C_6$-$C_{10}$ aryl and $L^1$-5-11 membered heteroaryl; wherein the $R^4$ $C_6$-$C_{10}$ aryl and 5-11 membered heteroaryl are optionally substituted with one or more substituents independently selected from the group consisting of $R^9$, $OR^9$, $NR^{10}R^{11}$, OH, Cl, and Br;
- $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo;
- $R^5$ is selected from the group consisting of $C_6$-$C_{10}$ membered aryl, 5-11 membered heteroaryl, and 4-6 membered monocyclic heterocycle fused to a phenyl group; wherein the $R^5$ $C_6$-$C_{10}$ membered aryl, 5-11 membered heteroaryl, and 4-6 membered monocyclic heterocycle fused to a phenyl group are optionally substituted with one or more substituents independently selected from the group consisting of $R^{12}$, $OR^{12}$, $NR^{13}R^{14}$, F, Cl, Br and I;
- $R^6$ is selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, and 4-12 membered heterocyclyl; wherein the $R^6$ $C_1$-$C_6$ alkyl is optionally substituted with one or more substituents independently selected from the group consisting of $R^5$, and F; wherein the $R^6$ 5-11 membered heteroaryl and $C_3$-$C_{11}$ cycloalkyl are optionally substituted with one or more substituents independently selected from the group consisting of $R^{18}$ and $OR^{18}$;
- $R^7$ and $R^8$ are each independently hydrogen or $C_1$-$C_6$ alkyl;
- $R^9$, at each occurrence, is independently selected from the group consisting of $C_1$-$C_6$ alkyl, 6-10 membered aryl, $C_3$-$C_{11}$ cycloalkyl, and 4-12 membered heterocyclyl; wherein each $R^9$ $C_1$-$C_6$ alkyl is optionally substituted with one or more substituents independently selected from the group consisting of CN, and F; wherein each $R^9$ 6-10 membered aryl, $C_3$-$C_{11}$ cycloalkyl, and 4-12 membered heterocyclyl is optionally substituted with one or more substituents independently selected from the group consisting of $R^{24}$, $OR^{24}$, and F;
- $R^{10}$ and $R^{11}$, at each occurrence, are each independently $C_1$-$C_6$ alkyl;
- $R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; wherein each $R^{12}$ 6-10 membered aryl, 5-11 membered heteroaryl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, oxo, CN, F, and Cl;
- $R^{13}$ and $R^{14}$, at each occurrence, are each independently hydrogen or $C_1$-$C_6$ alkyl;
- $R^{15}$, at each occurrence, is independently $C_3$-$C_{11}$ cycloalkyl;
- $R^{18}$, at each occurrence, is independently $C_1$-$C_6$ alkyl; wherein each $R^{18}$ $C_1$-$C_6$ alkyl is optionally substituted with one or more F; and
- $R^{24}$, at each occurrence, is independently $C_1$-$C_6$ alkyl.

In one embodiment of Formula (II),
- $R^1$ is selected from the group consisting of $C(O)R^6$, $C(O)OR^6$, and $C(O)NR^7R^8$;
- $R^2$ is $C(O)OH$ or a bioisostere thereof;
- $R^{2A}$ is hydrogen;
- $R^3$ is $C_1$-$C_6$ alkyl;
- $R^{3A}$ is hydrogen;
- $R^4$ is selected from the group consisting of $(C_1$-$C_6$ alkylene$)_x$-$C_6$-$C_{10}$ aryl and $(C_1$-$C_6$ alkylene$)_x$-5-11 membered heteroaryl; wherein the $R^4$ $C_6$-$C_{10}$ membered aryl of $(C_1$-$C_6$ alkylene$)_x$-$C_6$-$C_{10}$ membered aryl, and the 5-11 membered heteroaryl of $(C_1$-$C_6$ alkylene$)_x$-5-11 membered heteroaryl are optionally substituted with one or more substituents independently selected from the group consisting of $R^9$, $OR^9$, $NR^{10}R^{11}$, OH, Cl, and Br;
- $R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, and Br;
- $R^6$ is selected from the group consisting of $C_1$-$C_6$ alkyl, $C_2$-$C_6$ alkenyl, $C_3$-$C_{11}$ cycloalkyl, and 4-12 membered heterocyclyl; wherein the $R^6$ $C_1$-$C_6$ alkyl is optionally substituted with one or more independently selected $R^{15}$; wherein the $R^6$ $6C_3$-$C_{11}$ cycloalkyl, and 4-12 membered heterocyclyl are optionally substituted with one or more independently selected $OR^{18}$;

R⁷ and R⁸ are each independently hydrogen or $C_1$-$C_6$ alkyl;

R⁹, at each occurrence, is independently selected from the group consisting of $C_1$-$C_6$ alkyl, 6-10 membered aryl, $C_3$-$C_{11}$ cycloalkyl, and 4-12 membered heterocyclyl; wherein each R⁹ $C_1$-$C_6$ alkyl, $C_2$-$C_6$ alkenyl, and $C_2$-$C_6$ alkynyl is optionally substituted with one or more F; wherein each R⁹ 6-10 membered $C_3$-$C_{11}$ cycloalkyl, and 4-12 membered heterocyclyl is optionally substituted with one or more substituents independently selected from the group consisting of R²⁴, OR²⁴, and F;

R¹⁰ and R¹¹, at each occurrence, are each independently selected $C_1$-$C_6$ alkyl;

R¹², at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; wherein each R¹² 6-10 membered aryl, 5-11 membered heteroaryl, $C_3$-$C_{11}$ cycloalkyl, and 4-12 membered heterocyclyl is optionally substituted with one or more independently selected from the group consisting of $C_1$-$C_6$ alkyl;

R¹³ and R¹⁴, at each occurrence, are each independently $C_1$-$C_6$ alkyl;

R¹⁵, at each occurrence, is independently selected $C_3$-$C_{11}$ cycloalkyl;

R¹⁸, at each occurrence, is independently selected $C_1$-$C_6$ alkyl;

R²⁴, at each occurrence, is independently selected $C_1$-$C_6$ alkyl; and x is 0 or 1.

Exemplary compounds of Formula (II) include, but are not limited to (2S*,3R*,4S*,5S*)-3-tert-butyl-1-[di(propan-2-yl)carbamoyl]-4-{[2-methoxy-5-(trifluoromethyl)phenyl]methoxy}-5-phenylpyrrolidine-2-carboxylic acid;

(2S,3R,4S,5S)-3-tert-butyl-1-(cyclohexanecarbonyl)-4-{[2-methoxy-5-(trifluoromethyl)phenyl]methoxy}-5-phenylpyrrolidine-2-carboxylic acid;

(2S,3R,4S,5S)-3-tert-butyl-1-(cyclohexanecarbonyl)-N-(2-methoxyethanesulfonyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-4-{[2-methoxy-5-(trifluoromethyl)phenyl]methoxy}-N-(1-methylcyclopropane-1-sulfonyl)-5-phenylpyrrolidine-2-carboxamide;

(2S,3R,4S,5S)-3-tert-butyl-1-(cyclohexanecarbonyl)-N-(cyclopropanesulfonyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-N-(ethanesulfonyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-N-(dimethylsulfamoyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-N-(methanesulfonyl)-4-{[2-methoxy-5-(trifluoromethyl)phenyl]methoxy}-5-phenylpyrrolidine-2-carboxamide;

(2S,3R,4S,5S)-3-tert-butyl-1-[(1S,3S)-3-methoxycyclohexane-1-carbonyl]-4-{[2-methoxy-5-(trifluoromethyl)phenyl]methoxy}-5-phenylpyrrolidine-2-carboxylic acid;

(2S,3R,4S,5S)-3-tert-butyl-1-[(1R,3R)-3-methoxycyclohexane-1-carbonyl]-4-{[2-methoxy-5-(trifluoromethyl)phenyl]methoxy}-5-phenylpyrrolidine-2-carboxylic acid;

(2S,3R,4S,5S)-3-tert-butyl-1-[(1S,3S)-3-methoxycyclohexane-1-carbonyl]-4-{[2-methoxy-4-(trifluoromethyl)phenyl]methoxy}-5-phenylpyrrolidine-2-carboxylic acid;

(2S,3R,4S,5S)-3-tert-butyl-1-[(1R,3R)-3-methoxycyclohexane-1-carbonyl]-4-{[2-methoxy-4-(trifluoromethyl)phenyl]methoxy}-5-phenylpyrrolidine-2-carboxylic acid;

(2S,3R,4S,5S)-4-[(5-bromo-2-methoxyphenyl)methoxy]-3-tert-butyl-5-phenyl-1-{[(propan-2-yl)oxy]carbonyl}pyrrolidine-2-carboxylic acid;

(2S,3R,4S,5S)-4-[(5-bromo-2-methoxyphenyl)methoxy]-3-tert-butyl-1-[(1R,3R)-3-methoxycyclohexane-1-carbonyl]-5-phenylpyrrolidine-2-carboxylic acid;

(2S,3R,4S,5S)-3-tert-butyl-4-[(4-methoxy[1,1'-biphenyl]-3-yl)methoxy]-5-phenyl-1-{[(propan-2-yl)oxy]carbonyl}pyrrolidine-2-carboxylic acid;

(2S,3R,4S,5S)-3-tert-butyl-4-[(4-methoxy[1,1'-biphenyl]-3-yl)methoxy]-1-[(1R,3R)-3-methoxycyclohexane-1-carbonyl]-5-phenylpyrrolidine-2-carboxylic acid;

(2S,3R,4S,5S)-4-[(5-bromo-2-methoxypyridin-3-yl)methoxy]-3-tert-butyl-5-phenyl-1-{[(propan-2-yl)oxy]carbonyl}pyrrolidine-2-carboxylic acid;

(2S,3R,4S,5S)-3-tert-butyl-1-(cyclohexanecarbonyl)-4-{[2-methoxy-5-(trifluoromethyl)pyridin-3-yl]methoxy}-5-phenylpyrrolidine-2-carboxylic acid;

(2S,3R,4S,5S)-3-tert-butyl-4-[(2-methoxy-5-phenylpyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclohexyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclopentyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-tert-butyl-2-methoxyphenyl)methoxy]-1-[(1R,3R)-3-methoxycyclohexane-1-carbonyl]-5-phenylpyrrolidine-2-carboxylic acid;

(2S,3R,4S,5S)-3-tert-butyl-4-[(5-tert-butyl-2-methoxyphenyl)methoxy]-5-phenyl-1-{[(propan-2-yl)oxy]carbonyl}pyrrolidine-2-carboxylic acid;

(2S,3R,4S,5S)-3-tert-butyl-1-(cyclohexanecarbonyl)-5-(2-fluorophenyl)-4-{[2-methoxy-5-(trifluoromethyl)pyridin-3-yl]methoxy}pyrrolidine-2-carboxylic acid;

(2S,3R,4S,5S)-3-tert-butyl-1-(cyclohexanecarbonyl)-5-(2-fluorophenyl)-4-{[2-methoxy-5-(trifluoromethyl)phenyl]methoxy}pyrrolidine-2-carboxylic acid;

(2S,3R,4S,5S)-3-tert-butyl-4-[(5-tert-butyl-2-methoxyphenyl)methoxy]-1-(cyclohexanecarbonyl)-5-(2-fluorophenyl)pyrrolidine-2-carboxylic acid;

(2S,3R,4S,5S)-4-[(5-bromo-2-methoxypyridin-3-yl)methoxy]-3-tert-butyl-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-5-(2-fluorophenyl)-4-[(2-methoxy-5-phenylpyridin-3-yl)methoxy]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-phenylpyrrolidine-2-carboxylic acid;

(2S,3R,4S,5S)-3-tert-butyl-1-(cyclohexane carbonyl)-4-[(5-cyclopentyl-2-methoxypyridin-3-yl)methoxy]-5-phenylpyrrolidine-2-carboxylic acid;

(2S,3R,4S,5S)-4-{[5-(bicyclo[2.2.1]heptan-2-yl)-2-methoxypyridin-3-yl]methoxy}-3-tert-butyl-1-(cyclohexanecarbonyl)-5-phenylpyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2-fluorophenyl)pyrrolidine-2-carboxylic acid;

(2S,3R,4S,5S)-3-tert-butyl-1-(cyclohexane carbonyl)-4-[(5-cyclopentyl-2-methoxypyridin-3-yl)methoxy]-5-(2-fluorophenyl)pyrrolidine-2-carboxylic acid;

(2S,3R,4S,5S)-4-{[5-(bicyclo[2.2.1]heptan-2-yl)-2-methoxypyridin-3-yl]methoxy}-3-tert-butyl-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-5-(2-fluorophenyl)-4-{[2-methoxy-5-(pyrrolidin-1-yl)pyridin-3-yl]methoxy}pyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-phenylpyrrolidine-2-carboxylic acid;

(2S,3R,4S,5S)-3-tert-butyl-4-[(5-tert-butyl-2-methoxypyridin-3-yl)methoxy]-1-[(1R,3R)-3-methoxycyclohexane-1-carbonyl]-5-phenylpyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-(2-fluorophenyl)pyrrolidine-2-carboxylic acid;

(2S,3R,4S,5S)-3-tert-butyl-4-[(5-tert-butyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2-fluoro-4-methylphenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2-fluorophenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(4-fluoro-2-methylphenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2,4-difluorophenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(3,6-dihydro-2H-pyran-4-yl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(3-methoxyphenyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(4-methylphenyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-[(6-tert-butyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-5-(2-fluorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-tert-butyl-2-methoxypyridin-3-yl)methoxy]-5-(2-fluorophenyl)-1-{[(propan-2-yl)oxy]carbonyl}pyrrolidine-2-carboxylic acid;

(2S,3R,4S,5S)-4-[(5-bromo-2-methoxypyridin-3-yl)methoxy]-3-tert-butyl-5-(2-fluorophenyl)-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-(2-fluorophenyl)-1-{[(propan-2-yl)oxy]carbonyl}pyrrolidine-2-carboxylic acid;

(2S,3R,4S,5S)-3-tert-butyl-4-{[2-methoxy-5-(trifluoromethyl)phenyl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-tert-butyl-2-methoxypyridin-3-yl)methoxy]-5-(3-chlorophenyl)-1-{[(propan-2-yl)oxy]carbonyl}pyrrolidine-2-carboxylic acid;

(2S,3R,4S,5S)-3-tert-butyl-4-{[2-methoxy-5-(piperidin-1-yl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(pyrrolidin-1-yl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-{[(propan-2-yl)oxy]carbonyl}pyrrolidine-2-carboxylic acid;

(2S,3R,4S,5S)-3-tert-butyl-4-{[5-(3,3-difluoroazetidin-1-yl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(3,3-difluoropyrrolidin-1-yl)-2-methoxypyridin-3-yl]methoxy}-5-phenyl-1-{[(propan-2-yl)oxy]carbonyl}pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-phenylpyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-phenylpyrrolidine-2-carboxylic acid;

(2S,3R,4S,5S)-3-tert-butyl-4-{[2-methoxy-5-(trifluoromethyl)pyridin-3-yl]methoxy}-5-phenyl-1-{[(prop-2-en-1-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxane-2-carbonyl]-5-phenylpyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-[2-(propan-2-yl)phenyl]pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(propan-2-yl)phenyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(2-cyclobutyl-5-methoxypyridin-4-yl)methoxy]-5-phenyl-1-{[(propan-2-yl)oxy]carbonyl}pyrrolidine-2-carboxylic acid;

(2S,3R,4S,5S)-3-tert-butyl-5-(2-cyclobutylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxolane-2-carbonyl]-5-[2-(propan-2-yl)phenyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-{2-[(propan-2-yl)oxy]phenyl}pyrrolidine-2-carboxylic acid;

(2S,3R,4S,5S)-3-tert-butyl-4-[(2-methoxyquinolin-3-yl)methoxy]-5-phenyl-1-{[(propan-2-yl)oxy]carbonyl}pyrrolidine-2-carboxylic acid;

(2S,3R,4S,5S)-3-tert-butyl-4-{[2-hydroxy-5-(trifluoromethyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-5-[2-(3,6-dihydro-2H-pyran-4-yl)phenyl]-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(3S)-oxolane-3-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-(oxane-4-carbonyl)-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(3R)-oxolane-3-carbonyl]-5-[2-(propan-2-yl)phenyl]pyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-{[2-methoxy-5-(trifluoromethyl)phenyl]methoxy}-1-[(2S)-oxolane-2-carbonyl]-5-[2-(trifluoromethyl)pyridin-3-yl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-[(2-methoxyquinolin-3-yl)methoxy]-1-[(2S)-oxolane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[3-(propan-2-yl)phenyl]pyrrolidine-2-carboxylic acid;

(2S,3R,4S,5S)-5-(3-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-(3-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[1-(propan-2-yl)-1H-pyrazol-5-yl]pyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-[2-(propan-2-yl)phenyl]pyrrolidine-2-carboxylic acid;

(2S,3R,4S,5S)-3-tert-butyl-4-[(2-methoxyquinolin-3-yl)methoxy]-1-[(2R)-oxane-2-carbonyl]-5-[2-(propan-2-yl)phenyl]pyrrolidine-2-carboxylic acid;

(2S,3R,4S,5S)-3-tert-butyl-4-[(2-methoxyquinolin-3-yl)methoxy]-1-[(2S)-oxane-2-carbonyl]-5-[2-(propan-2-yl)phenyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-(oxane-4-carbonyl)-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-[(2R)-oxane-2-carbonyl]-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid;

(2S,3R,4S,5S)-5-(2-bromophenyl)-3-tert-butyl-4-[(2-methoxyquinolin-3-yl)methoxy]-1-{[(propan-2-yl)oxy]carbonyl}pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-{[(propan-2-yl)oxy]carbonyl}pyrrolidine-2-carboxylic acid;

(2S,3R,4S,5S)-3-tert-butyl-5-(2-cyclopropylphenyl)-4-[(2-methoxyquinolin-3-yl)methoxy]-1-[(2S)-oxolane-2-carbonyl]pyrrolidine-2-carboxylic acid;

(2S,3R,4S,5S)-3-tert-butyl-5-(3-cyclobutylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-[(2S)-oxane-2-carbonyl]pyrrolidine-2-carboxylic acid;

(2S,3R,4S,5S)-3-tert-butyl-5-(3-chlorophenyl)-4-[(5-cyclobutyl-2-methoxypyridin-3-yl)methoxy]-1-{[(propan-2-yl)oxy]carbonyl}pyrrolidine-2-carboxylic acid;

(2S,3R,4S,5S)-3-tert-butyl-5-(2-cyclopropylphenyl)-4-[(2-methoxyquinolin-3-yl)methoxy]-1-{[(propan-2-yl)oxy]carbonyl}pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-[2-(trifluoromethyl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-{2-[(propan-2-yl)oxy]pyridin-3-yl}pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-[(2-methoxyquinolin-3-yl)methoxy]-1-[(2S)-oxolane-2-carbonyl]-5-[1-(propan-2-yl)-1H-pyrazol-5-yl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-(oxane-4-carbonyl)pyrrolidine-2-carboxylic acid;

(2S,3R,4S,5S)-5-(2-bromophenyl)-3-tert-butyl-4-[(2-methoxyquinolin-3-yl)methoxy]-1-[(2S)-oxolane-2-carbonyl]pyrrolidine-2-carboxylic acid;

(2S,3R,4S,5S)-3-tert-butyl-5-(3-tert-butylphenyl)-1-(ethoxycarbonyl)-4-{[2-methoxy-5-(trifluoromethyl)pyridin-3-yl]methoxy}pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(1R,2S,4S)-7-oxabicyclo[2.2.1]heptane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-[2-(trifluoromethyl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(trifluoromethyl)phenyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-1-(cyclobutanecarbonyl)-4-{[2-methoxy-5-(trifluoromethyl)pyridin-3-yl]methoxy}-5-{2-[(propan-2-yl)oxy]pyridin-3-yl}pyrrolidine-2-carboxylic acid;

(2S,3R,4S,5S)-3-tert-butyl-1-(cyclobutanecarbonyl)-4-[(5-cyclobutyl-2-methoxypyridin-3-yl)methoxy]-5-{2-[(propan-2-yl)oxy]pyridin-3-yl}pyrrolidine-2-carboxylic acid;

(2S,3R,4S,5S)-5-(2-bromophenyl)-3-tert-butyl-4-[(5-tert-butyl-2-methoxyphenyl)methoxy]-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-5-[2-(difluoromethyl)phenyl]-1-[(2S)-oxolane-2-carbonyl]pyrrolidine-2-carboxylic acid;

(2S,3R,4S,5S)-3-tert-butyl-5-(2,6-difluorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-(2-cyclopropylphenyl)-1-[(2S)-oxolane-2-carbonyl]pyrrolidine-2-carboxylic acid;

(2S,3R,4S,5S)-4-[(5-bromo-2-methoxypyridin-3-yl)methoxy]-3-tert-butyl-5-(2-cyclopropylphenyl)-1-[(2S)-oxolane-2-carbonyl]pyrrolidine-2-carboxylic acid;

(2S,3R,4S,5S)-3-tert-butyl-4-{[2-methoxy-5-(trifluoromethyl)phenyl]methoxy}-5-(2-methylphenyl)-1-[(2S)-oxane-2-carbonyl]pyrrolidine-2-carboxylic acid;

(2S,3R,4S,5S)-3-tert-butyl-4-{[2-methoxy-4-(trifluoromethyl)phenyl]methoxy}-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxane-2-carbonyl]-5-[2-(propan-2-yl)phenyl]pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-[(2S)-oxane-2-carbonyl]pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2-ethylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-([1,1'-biphenyl]-2-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-6-oxo-1,6-dihydropyridin-3-yl)phenyl]-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2-cyclopropylphenyl)pyrrolidine-2-carboxylic acid;

(2S,3R,4S,5S)-5-(2-bromophenyl)-3-tert-butyl-4-[(5-cy-clobutyl-2-methoxypyridin-3-yl)methoxy]-1-(cyclo-hexanecarbonyl)pyrrolidine-2-carboxylic acid;

(2S,3R,4S,5S)-3-tert-butyl-5-(2-ethylphenyl)-4-{[2-methoxy-4-(trifluoromethyl)phenyl]methoxy}-1-[(2S)-oxane-2-carbonyl]pyrrolidine-2-carboxylic acid;

(2S,3R,4S,5S)-3-tert-butyl-4-[(5-cyclobutyl-2-methoxy-pyridin-3-yl)methoxy]-5-(2-ethylphenyl)-1-[(2S)-oxane-2-carbonyl]pyrrolidine-2-carboxylic acid;

(2S,3R,4S,5S)-4-[(5-bromo-2-methoxypyridin-3-yl)methoxy]-3-tert-butyl-5-(2-methylphenyl)-1-[(2S)-ox-ane-2-carbonyl]pyrrolidine-2-carboxylic acid;

(2S,3R,4S,5S)-3-tert-butyl-4-{[5-(2-cyanopropan-2-yl)-2-methoxyphenyl]methoxy}-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphe-nyl)methoxy]-5-(2-methylphenyl)-1-[(2S)-oxane-2-car-bonyl]pyrrolidine-2-carboxylic acid;

(2S,3R,4S,5S)-3-tert-butyl-4-[(2-methoxyquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-5-(4'-fluoro[1,1'-biphenyl]-2-yl)-4-{[2-methoxy-5-(trifluoromethyl)pyridin-3-yl]methoxy}-1-[(2S)-oxane-2-carbonyl]pyrrolidine-2-car-boxylic acid;

(2S,3R,4S,5S)-3-tert-butyl-5-(3'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-car-boxylic acid;

(2S,3R,4S,5S)-3-tert-butyl-4-{[2-methoxy-5-(trifluorom-ethyl)pyridin-3-yl]methoxy}-5-[2-(1-methyl-1,2,3,6-tet-rahydropyridin-4-yl)phenyl]-1-[(2S)-oxane-2-carbonyl]pyrrolidine-2-carboxylic acid;

(2S,3R,4S,5S)-3-tert-butyl-4-{[2-methoxy-5-(trifluorom-ethyl)pyridin-3-yl]methoxy}-5-[2-(1-methyl-1H-pyrazol-4-yl)phenyl]-1-[(2S)-oxane-2-carbonyl]pyrrolidine-2-carboxylic acid;

(2S,3R,4S,5S)-3-tert-butyl-5-[3'-(dimethylamino)[1,1'-bi-phenyl]-2-yl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluorom-ethyl)pyridin-3-yl]methoxy}-5-(2'-methyl[1,1'-biphe-nyl]-2-yl)-1-[(2S)-oxane-2-carbonyl]pyrrolidine-2-car-boxylic acid;

(2S,3R,4S,5S)-3-tert-butyl-4-{[2-methoxy-5-(trifluorom-ethyl)pyridin-3-yl]methoxy}-1-[(2S)-oxane-2-carbonyl]-5-[2-(pyridin-4-yl)phenyl]pyrrolidine-2-carboxylic acid;

(2S,3R,4S,5S)-3-tert-butyl-4-{[2-methoxy-5-(trifluorom-ethyl)pyridin-3-yl]methoxy}-1-[(2S)-oxane-2-carbonyl]-5-[2-(pyrimidin-5-yl)phenyl]pyrrolidine-2-carboxylic acid;

(2S,3R,4S,5S)-3-tert-butyl-5-[2-(furan-3-yl)phenyl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluorom-ethyl)pyridin-3-yl]methoxy}-5-[2-(1-methyl-1H-pyrrol-3-yl)phenyl]-1-[(2S)-oxane-2-carbonyl]pyrrolidine-2-carboxylic acid;

(2S,3R,4S,5S)-3-tert-butyl-5-(2'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-car-boxylic acid;

(2S,3R,4S,5S)-3-tert-butyl-4-{[2-methoxy-5-(trifluorom-ethyl)pyridin-3-yl]methoxy}-1-[(2S)-oxane-2-carbonyl]-5-[3'-(trifluoromethoxy)[1,1'-biphenyl]-2-yl]pyrrolidine-2-carboxylic acid;

(2S,3R,4S,5S)-3-tert-butyl-5-(4'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-car-boxylic acid;

(2S,3R,4S,5S)-5-[2-(2H-1,3-benzodioxol-5-yl)phenyl]-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2'-fluoro[1,1'-biphenyl]-2-yl)-4-{[2-methoxy-5-(trifluoromethyl)pyridin-3-yl]methoxy}-1-[(2S)-oxane-2-carbonyl]pyrrolidine-2-car-boxylic acid;

(2S,3R,4S,5S)-3-tert-butyl-5-[2-(6-methoxypyridin-3-yl)phenyl]-4-{[2-methoxy-5-(trifluoromethyl)pyridin-3-yl]methoxy}-1-[(2S)-oxane-2-carbonyl]pyrrolidine-2-car-boxylic acid;

(2S,3R,4S,5S)-3-tert-butyl-4-{[2-methoxy-5-(trifluorom-ethyl)pyridin-3-yl]methoxy}-1-[(2S)-oxane-2-carbonyl]-5-[4'-(trifluoromethoxy)[1,1'-biphenyl]-2-yl]pyrrolidine-2-carboxylic acid;

(2S,3R,4S,5S)-3-tert-butyl-5-(4'-cyano[1,1'-biphenyl]-2-yl)-4-{[2-methoxy-5-(trifluoromethyl)pyridin-3-yl]methoxy}-1-[(2S)-oxane-2-carbonyl]pyrrolidine-2-car-boxylic acid;

(2S,3R,4S,5S)-3-tert-butyl-4-{[2-methoxy-5-(trifluorom-ethyl)pyridin-3-yl]methoxy}-1-[(2S)-oxane-2-carbonyl]-5-{2-[6-(trifluoromethyl)pyridin-3-yl]phenyl}pyrrolidine-2-carboxylic acid;

(2S,3R,4S,5S)-3-tert-butyl-5-[2-(5-ethoxypyridin-3-yl)phe-nyl]-4-{[2-methoxy-5-(trifluoromethyl)pyridin-3-yl]methoxy}-1-[(2S)-oxane-2-carbonyl]pyrrolidine-2-car-boxylic acid;

(2S,3R,4S,5S)-3-tert-butyl-4-{[2-methoxy-5-(trifluorom-ethyl)pyridin-3-yl]methoxy}-5-(naphthalen-1-yl)-1-[(2S)-oxane-2-carbonyl]pyrrolidine-2-carboxylic acid;

(2S,3R,4S,5S)-3-tert-butyl-4-[(5-tert-butyl-2-methoxyphe-nyl)methoxy]-5-(naphthalen-1-yl)-1-[(2S)-oxane-2-car-bonyl]pyrrolidine-2-carboxylic acid;

(2S,3R,4S,5S)-5-(1-benzofuran-7-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluorom-ethyl)pyridin-3-yl]methoxy}-5-[2-(2-methylpropyl)phe-nyl]-1-[(2S)-oxane-2-carbonyl]pyrrolidine-2-carboxylic acid;

(2S,3R,4S,5S)-3-tert-butyl-4-[(5-cyclobutyl-2-methoxy-pyridin-3-yl)methoxy]-5-(2-cyclopropylphenyl)-1-(6-methoxypyridine-2-sulfonyl)pyrrolidine-2-carboxylic acid;

(2S,3R,4S,5S)-3-tert-butyl-4-{[2-methoxy-5-(1-methylcy-clobutyl)phenyl]methoxy}-5-(2-methylphenyl)-1-[(2S)-oxane-2-carbonyl]pyrrolidine-2-carboxylic acid;

(2S,3R,4S,5S)-3-tert-butyl-5-(2,3-dihydro-1-benzofuran-7-yl)-4-{[2-methoxy-5-(trifluoromethyl)pyridin-3-yl]methoxy}-1-[(2S)-oxane-2-carbonyl]pyrrolidine-2-car-boxylic acid;

(2S,3R,4S,5S)-3-tert-butyl-4-[(5-cyclopropyl-2-methoxy-pyridin-3-yl)methoxy]-5-(2-methylphenyl)-1-[(2S)-ox-ane-2-carbonyl]pyrrolidine-2-carboxylic acid;

(2S,3R,4S,5S)-3-tert-butyl-4-[(5-cyclobutyl-2-methoxy-pyridin-3-yl)methoxy]-1-[(2S)-oxane-2-carbonyl]-5-(5,6,7,8-tetrahydronaphthalen-1-yl)pyrrolidine-2-carboxylic acid;

(2S,3R,4S,5S)-3-tert-butyl-4-{[2-methoxy-5-(trifluorom-ethyl)pyridin-3-yl]methoxy}-1-[(2S)-oxane-2-carbonyl]-5-(5,6,7,8-tetrahydronaphthalen-1-yl)pyrrolidine-2-car-boxylic acid;

(2S,3R,4S,5S)-3-tert-butyl-4-[(2-methoxy-7-methylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(6-tert-butyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-1-(3,4-dihydro-2H-pyran-6-carbonyl)-4-{[2-methoxy-5-(trifluoromethyl)pyridin-3-yl]methoxy}-5-(2-methylphenyl)pyrrolidine-2-carboxylic acid;

(2S,3R,4S,5S)-3-tert-butyl-4-[(5-chloro-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[2-methoxy-5-(trifluoromethoxy)phenyl]methoxy}-5-(2-methylphenyl)-1-[(2S)-oxane-2-carbonyl]pyrrolidine-2-carboxylic acid;

(2S,3R,4S,5S)—N-(6-aminopyridine-2-sulfonyl)-3-tert-butyl-4-[(5-cyclobutyl-2-methoxypyridin-3-yl)methoxy]-5-(2-cyclopropylphenyl)-1-[(2S)-oxane-2-carbonyl]pyrrolidine-2-carboxamide;

(2S,3R,4S,5S)-3-tert-butyl-4-[(6-tert-butyl-3-methoxypyridin-2-yl)methoxy]-5-(2-methylphenyl)-1-[(2S)-oxane-2-carbonyl]pyrrolidine-2-carboxylic acid;

(2S,3R,4S,5S)-3-tert-butyl-4-({[2-methoxy-5-(trifluoromethyl)pyridin-3-yl]($^2$H$_2$)methyl}oxy)-5-(2-methylphenyl)-1-[(2S)-oxane-2-carbonyl]pyrrolidine-2-carboxylic acid;

(2S,3R,4S,5S)-3-tert-butyl-4-{[{2-[($^2$H$_3$)methyloxy]-5-(trifluoromethyl)pyridin-3-yl}($^2$H$_2$)methyl]oxy}-5-(2-methylphenyl)-1-[(2S)-oxane-2-carbonyl]pyrrolidine-2-carboxylic acid;

(2S,3R,4S,5S)-3-tert-butyl-5-(5-chloro-2-methylphenyl)-4-[(5-cyclobutyl-2-methoxypyridin-3-yl)methoxy]-1-[(2S)-oxane-2-carbonyl]pyrrolidine-2-carboxylic acid;

(2S,3R,4S,5S)-3-tert-butyl-5-(5-chloro-2-methylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(3-chloro-2-methylphenyl)-4-[(5-cyclobutyl-2-methoxypyridin-3-yl)methoxy]-1-[(2S)-oxane-2-carbonyl]pyrrolidine-2-carboxylic acid;

(2S,3R,4S,5S)-3-tert-butyl-5-(3-chloro-2-methylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[{2-[($^2$H$_3$)methyloxy]-5-(trifluoromethyl)phenyl}($^2$H$_2$)methyl]oxy}-5-(2-methylphenyl)-1-[(2S)-oxane-2-carbonyl]pyrrolidine-2-carboxylic acid;

(2S,3R,4S,5S)-3-tert-butyl-4-{[(5-tert-butyl-2-methoxyphenyl)($^2$H$_2$)methyl]oxy}-5-(2-methylphenyl)-1-[(2S)-oxane-2-carbonyl]pyrrolidine-2-carboxylic acid;

(2S,3R,4S,5S)-3-tert-butyl-4-[(2-chloro-5,7-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxy-5,8-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxy-5,7-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-methoxyphenyl)-1-[(2S)-oxane-2-carbonyl]pyrrolidine-2-carboxylic acid;

(2S,3R,4S,5S)-3-tert-butyl-5-(2-methoxyphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-5-(2-methoxyphenyl)-1-[(2S)-oxane-2-carbonyl]pyrrolidine-2-carboxylic acid;

(2S,3R,4S,5S)-3-tert-butyl-4-[(2-methoxy-6,8-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[2-methoxy-5-(1-methylcyclopropyl)pyridin-3-yl]methoxy}-5-(2-methylphenyl)-1-[(2S)-oxane-2-carbonyl]pyrrolidine-2-carboxylic acid;

(2S,3R,4S,5S)-3-tert-butyl-4-[(2-methoxy-8-methylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-{[2-methoxy-5-(1-methylcyclobutyl)phenyl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-[(5-tert-butyl-2-methoxyphenyl)methoxy]-5-(2-methylphenyl)-1-[(2S)-oxolane-2-carbonyl]pyrrolidine-2-carboxylic acid;

(2S,3R,4S,5S)-3-tert-butyl-1-(cyclohexanecarbonyl)-4-[(2-methoxy-5,8-dimethylquinolin-3-yl)methoxy]-5-{2-[(propan-2-yl)oxy]pyridin-3-yl}pyrrolidine-2-carboxylic acid;

(2S,3R,4S,5S)-3-tert-butyl-4-({2-[2-methoxy-5-(trifluoromethyl)phenyl]prop-2-en-1-yl}oxy)-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-4-[(5-tert-butyl-2-methoxyphenyl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-1-(cyclohexanecarbonyl)-4-[(2-methoxy-5,7-dimethylquinolin-3-yl)methoxy]-5-{2-[(propan-2-yl)oxy]pyridin-3-yl}pyrrolidine-2-carboxylic acid;

(2S,3R,4S,5S)-3-tert-butyl-4-[(2-methoxy-5,7-dimethylquinolin-3-yl)methoxy]-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-5-(2-ethylphenyl)-4-[(2-methoxyquinolin-3-yl)methoxy]-1-[(2S)-oxane-2-carbonyl]pyrrolidine-2-carboxylic acid;

(2S,3R,4S,5S)-3-tert-butyl-4-[(1-methyl-1H-benzimidazol-2-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2,2-dimethyl-2,3-dihydro-1-benzofuran-7-yl)pyrrolidine-2-carboxylic acid;

(2S,3R,4S,5S)-3-tert-butyl-1-(cyclohexanecarbonyl)-5-(2,2-dimethyl-2,3-dihydro-1-benzofuran-7-yl)-4-{[2-methoxy-5-(trifluoromethyl)pyridin-3-yl]methoxy}pyrrolidine-2-carboxylic acid;

(2S,3R,4S,5S)-1-(cyclohexanecarbonyl)-3-(2-methoxypropan-2-yl)-4-{[2-methoxy-5-(trifluoromethyl)pyridin-3-yl]methoxy}-5-[2-(propan-2-yl)phenyl]pyrrolidine-2-carboxylic acid;

(2S,3R,4S,5S)-3-(2-methoxypropan-2-yl)-4-{[2-methoxy-5-(trifluoromethyl)pyridin-3-yl]methoxy}-1-{[(propan-2-yl)oxy]carbonyl}-5-[2-(propan-2-yl)phenyl]pyrrolidine-2-carboxylic acid;

(2S,3R,4S,5S)-3-(2-methoxypropan-2-yl)-4-{[2-methoxy-5-(trifluoromethyl)pyridin-3-yl]methoxy}-1-[(2S)-oxane-2-carbonyl]-5-[2-(propan-2-yl)phenyl]pyrrolidine-2-carboxylic acid;

(2S,3R,4S,5S)-3-tert-butyl-4-{2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{(2S)-2,3-dihydroxy-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{(2R)-2,3-dihydroxy-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{2-[2-methoxy-5-(trifluoromethyl)phenyl]-2-oxoethoxy}-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-{[(1,1,1-trifluoropropan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-({[(2R)-1,1,1-trifluoropropan-2-yl]oxy}carbonyl)pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-({[(2S)-1,1,1-trifluoropropan-2-yl]oxy}carbonyl)pyrrolidine-2-carboxylic acid;

(2S,3R,4S,5S)-3-tert-butyl-4-{2-hydroxy-2-[2-methoxy-5-(trifluoromethyl)phenyl]ethoxy}-5-(2-methylphenyl)-1-[(2S)-oxane-2-carbonyl]pyrrolidine-2-carboxylic acid;

(2S,3R,4S,5S)-3-tert-butyl-4-{2-methoxy-2-[2-methoxy-5-(trifluoromethyl)phenyl]ethoxy}-5-(2-methylphenyl)-1-[(2S)-oxane-2-carbonyl]pyrrolidine-2-carboxylic acid;

(2S,3R,4S,5S)-4-[(5-tert-butyl-2-methoxyphenyl)methoxy]-3-(2-methoxypropan-2-yl)-1-[(2S)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-({[(2S)-1,1,1-trifluoropropan-2-yl]oxy}carbonyl)pyrrolidine-2-carboxylic acid;

(2S,3R,4S,5S)-3-tert-butyl-4-{(2R)-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{(2S)-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-{2-[(propan-2-yl)oxy]pyridin-3-yl}-1-({[(2S)-1,1,1-trifluoropropan-2-yl]oxy}carbonyl)pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-[1-(trifluoromethyl)cyclopropane-1-carbonyl]pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-[1-(trifluoromethyl)cyclopentane-1-carbonyl]pyrrolidine-2-carboxylic acid;

(2S,3R,4S,5S)-3-tert-butyl-4-({3-[2-methoxy-5-(trifluoromethyl)pyridin-3-yl]prop-2-yn-1-yl}oxy)-5-phenyl-1-{[(propan-2-yl)oxy]carbonyl}pyrrolidine-2-carboxylic acid;

(2S,3R,4S,5S)-3-tert-butyl-5-(2-ethylphenyl)-4-({3-[2-methoxy-5-(trifluoromethyl)pyridin-3-yl]prop-2-yn-1-yl}oxy)-1-[(2S)-oxane-2-carbonyl]pyrrolidine-2-carboxylic acid;

(2S,3R,4S,5S)-3-tert-butyl-1-(cyclohexanecarbonyl)-5-{2-[(propan-2-yl)oxy]pyridin-3-yl}-4-{[5-(trifluoromethyl)-1-benzofuran-3-yl]methoxy}pyrrolidine-2-carboxylic acid;

(2S,3R,4S,5S)-3-tert-butyl-5-(2-ethylphenyl)-4-{3-[2-methoxy-5-(trifluoromethyl)pyridin-3-yl]propoxy}-1-[(2S)-oxane-2-carbonyl]pyrrolidine-2-carboxylic acid;

(2S,3R,4S,5S)-3-tert-butyl-5-(5-iodo-2-methylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-[(1R,2R)-2-(trifluoromethyl)cyclohexane-1-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-[(1S,2S)-2-(trifluoromethyl)cyclohexane-1-carbonyl]pyrrolidine-2-carboxylic acid;

(2S,3R,4S,5S)-3-tert-butyl-4-{2-[(5-chloro-2-methoxypyridin-3-yl)oxy]ethoxy}-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-1-[(2S)-oxane-2-carbonyl]-5-{2-[(propan-2-yl)oxy]pyridin-3-yl}pyrrolidine-2-carboxylic acid;

(2S,3R,4S,5S)-3-tert-butyl-4-{[2-methoxy-5-(trifluoromethyl)pyridin-3-yl]methoxy}-5-[2-($^2H_3$)methylphenyl]-1-[(2S,3S)-(2,3-$^2H_2$)oxane-2-carbonyl](2-$^2H$)pyrrolidine-2-carboxylic acid;

(2S,3R,4S,5S)-3-tert-butyl-1-(cyclohexanecarbonyl)-4-{[2-methoxy-5-(1-methylcyclopropyl)pyridin-3-yl]methoxy}-5-{2-[(propan-2-yl)oxy]pyridin-3-yl}pyrrolidine-2-carboxylic acid;

(2S,3R,4S,5S)-3-tert-butyl-4-{2-[2-methoxy-5-(trifluoromethyl)phenoxy]ethoxy}-5-(2-methylphenyl)-1-[(2S)-oxane-2-carbonyl]pyrrolidine-2-carboxylic acid;

(2S,3R,4S,5S)-4-[(5-bromo-1-benzofuran-2-yl)methoxy]-3-tert-butyl-1-[(2S)-oxane-2-carbonyl]-5-{2-[(propan-2-yl)oxy]pyridin-3-yl}pyrrolidine-2-carboxylic acid;

(2S,3R,4S,5S)-3-tert-butyl-4-[(6-tert-butyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid;

(2S,3R,4S,5S)-3-tert-butyl-4-[(6-tert-butyl-2-methoxypyridin-3-yl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-5-(2-ethylphenyl)-1-[(2S)-oxane-2-carbonyl]-4-{[7-(trifluoromethyl)-1-benzofuran-2-yl]methoxy}pyrrolidine-2-carboxylic acid;

(2S,3R,4S,5S)-3-tert-butyl-4-[(5-chloro-1-benzofuran-2-yl)methoxy]-5-(2-ethylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-(naphthalene-1-sulfonyl)-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-[2-(propan-2-yl)phenyl]pyrrolidine-2-carboxylic acid;

(2S,3R,4S,5S)-3-tert-butyl-4-[(5-cyclobutyl-1-benzofuran-2-yl)methoxy]-1-[(2S)-oxane-2-carbonyl]-5-{2-[(propan-2-yl)oxy]pyridin-3-yl}pyrrolidine-2-carboxylic acid; and pharmaceutically acceptable salts thereof.

Formula (III)

One embodiment pertains to compounds of Formula (III)

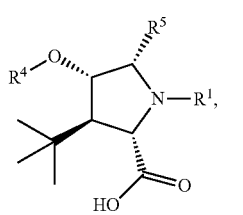

(III)

wherein
- $R^1$ is selected from the group consisting of $SO_2R^6$, $C(O)R^6$, $C(O)OR^6$, and $C(O)NR^7R^8$;
- $R^4$ is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;
- $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo;
- $R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;
- $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;
- $R^7$ and $R^8$ are each independently hydrogen or $C_1$-$C_6$ alkyl;
- $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;
- $R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;
- $R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;
- $R^{13}$ and $R^{14}$, at each occurrence, are each independently hydrogen or $C_1$-$C_6$ alkyl;
- $R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;
- $R^{16}$ and $R^{17}$, at each occurrence, are each independently hydrogen or $C_1$-$C_6$ alkyl;
- $R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl.

In one embodiment of Formula (III), $R^1$ is selected from the group consisting of $SO_2R^6$, $C(O)R^6$, $C(O)OR^6$, and $C(O)NR^7R^8$;

$R^4$ is selected from the group consisting of $(C_1$-$C_6$ alkylene$)_x$-$C_6$-$C_{10}$ aryl, $(C_1$-$C_6$ alkylene$)_x$-5-11 membered heteroaryl, $(C_1$-$C_6$ alkylene$)_x$-4-12 membered heterocyclyl, $(C_1$-$C_6$ alkylene$)_x$-$C_3$-$C_{11}$ cycloalkyl, and $(C_1$-$C_6$ alkylene$)_x$-$C_4$-$C_{11}$ cycloalkenyl; wherein the $R^4$ $C_6$-$C_{10}$ membered aryl of $(C_1$-$C_6$ alkylene$)_x$-$C_6$-$C_{10}$ membered aryl, the 5-11 membered heteroaryl of $(C_1$-$C_6$ alkylene$)_x$-5-11 membered heteroaryl, the 4-12 membered heterocyclyl of $(C_1$-$C_6$ alkylene$)_x$-4-12 membered heterocyclyl, the $C_3$-$C_{11}$ cycloalkyl of $(C_1$-$C_6$ alkylene$)_x$-$C_3$-$C_{11}$ cycloalkyl, and the $C_4$-$C_{11}$ cycloalkenyl of $(C_1$-$C_6$ alkylene$)_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;

$R^5$ is selected from the group consisting of $C_6$-$C_{10}$ membered aryl, 5-11 membered heteroaryl, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl;

$R^{25}$ and $R^{26}$, at each occurrence, are each independently hydrogen or $C_1$-$C_6$ alkyl; and x is 0 or 1.

In one embodiment of Formula (III), $R^1$ is selected from the group consisting of $SO_2R^6$, $C(O)R^6$, $C(O)OR^6$, and $C(O)NR^7R^8$. In another embodiment of Formula (III), $R^1$ is $C(O)R^6$ or $C(O)OR^6$. In another embodiment of Formula (III), $R^1$ is $SO_2R^6$. In another embodiment of Formula (III), $R^1$ is $C(O)R^6$. In another embodiment of Formula (III), $R^1$ is $C(O)OR^6$. In another embodiment of Formula (III), $R^1$ is $C(O)NR^7R^8$.

In one embodiment of Formula (III), $R^4$ is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo. In another embodiment of Formula (III), $R^4$ is selected from the group consisting of $L^1$-$C_6$-$C_{10}$ aryl, and $L^1$-5-11 membered heteroaryl; wherein the $R^4$ $C_6$-$C_{10}$ aryl, and 5-11 membered heteroaryl are optionally substituted with one or more substituents independently selected from the group consisting of $R^9$, $OR^9$, $NR^{10}R^{11}$, OH, Cl, and Br; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo. In another embodiment of Formula (III), $R^4$ is $L^1$-$C_6$-$C_{10}$ aryl; wherein the $R^4$ $C_6$-$C_{10}$ aryl is optionally substituted with one or more substituents independently selected from the group consisting of $R^9$, $OR^9$, $NR^{10}R^{11}$, OH, Cl, and Br; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo.

In another embodiment of Formula (III), $R^4$ is $L^1$-5-11 membered heteroaryl; wherein the $R^4$ 5-11 membered heteroaryl is optionally substituted with one or more substituents independently selected from the group consisting of $R^9$, $OR^9$, $NR^{10}R^{11}$, OH, Cl, and Br; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo.

In one embodiment of Formula (III), $R^4$ is selected from the group consisting of $(C_1$-$C_6$ alkylene$)_x$-$C_6$-$C_{10}$ aryl, $(C_1$-$C_6$ alkylene$)_x$-5-11 membered heteroaryl, $(C_1$-$C_6$ alkylene$)_x$-4-12 membered heterocyclyl, $(C_1$-$C_6$ alkylene$)_x$-$C_3$-$C_{11}$ cycloalkyl, and $(C_1$-$C_6$ alkylene$)_x$-$C_4$-$C_{11}$ cycloalkenyl; wherein the $R^4$ $C_6$-$C_{10}$ membered aryl of $(C_1$-$C_6$ alkylene$)_x$-$C_6$-$C_{10}$ membered aryl, the 5-11 membered heteroaryl of $(C_1$-$C_6$ alkylene$)_x$-5-11 membered heteroaryl, the 4-12 membered heterocyclyl of $(C_1$-$C_6$ alkylene$)_x$-4-12 membered heterocyclyl, the $C_3$-$C_{11}$ cycloalkyl of $(C_1$-$C_6$ alkylene$)_x$$C_3$-$C_{11}$ cycloalkyl, and the $C_4$-$C_{11}$ cycloalkenyl of $(C_1$-$C_6$ alkylene$)_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I; and x is 0 or 1.

In another embodiment of Formula (III), $R^4$ is selected from the group consisting of $(C_1$-$C_6$ alkylene$)_x$-$C_6$-$C_{10}$ aryl, $(C_1$-$C_6$ alkylene$)_x$-5-11 membered heteroaryl, $(C_1$-$C_6$ alkylene$)_x$-4-12 membered heterocyclyl, and $(C_1$-$C_6$ alkylene$)_x$-$C_3$-$C_{11}$ cycloalkyl; wherein the $R^4$ $C_6$-$C_{10}$ membered aryl of $(C_1$-$C_6$ alkylene$)_x$-$C_6$-$C_{10}$ membered aryl, the 5-11 membered heteroaryl of $(C_1$-$C_6$ alkylene$)_x$-5-11 membered heteroaryl, the 4-12 membered heterocyclyl of $(C_1$-$C_6$ alkylene$)_x$-4-12 membered heterocyclyl, and the $C_3$-$C_{11}$ cycloalkyl of $(C_1$-$C_6$ alkylene$)_x$$C_3$-$C_{11}$ cycloalkyl are optionally substituted with one or more substituents independently selected from the group consisting of $R^9$, $OR^9$, $NR^{10}R^{11}$, OH, Cl, and Br; and x is 0 or 1. In another embodiment of Formula (III), $R^4$ is $(C_1$-$C_6$ alkylene$)_x$-$C_6$-$C_{10}$ aryl; wherein the $R^4$ $(C_1$-$C_6$ alkylene$)_x$-$C_6$-$C_{10}$ membered aryl is optionally substituted with one or more substituents independently selected from the group consisting of $R^9$, $OR^9$, $NR^{10}R^{11}$, OH, Cl, and Br; and x is 0 or 1.

In another embodiment of Formula (III), $R^4$ is $(C_1$-$C_6$ alkylene$)_x$-5-11 membered heteroaryl; wherein the $R^4$ $(C_1$-$C_6$ alkylene$)_x$-5-11 membered heteroaryl is optionally substituted with one or more substituents independently selected from the group consisting of $R^9$, $OR^9$, $NR^{10}R^{11}$, OH, Cl, and Br; and x is 0 or 1. In another embodiment of Formula (III), $R^4$ is $(C_1$-$C_6$ alkylene$)_x$-4-12 membered heterocyclyl; wherein the $R^4$ $(C_1$-$C_6$ alkylene$)_x$-4-12 membered heterocyclyl is optionally substituted with one or more substituents independently selected from the group consisting of $R^9$, $OR^9$, $NR^{10}R^{11}$, OH, Cl, and Br; and x is 0 or 1. In another embodiment of Formula (III), $R^4$ is $(C_1$-$C_6$ alkylene$)_x$-$C_3$-$C_{11}$ cycloalkyl; wherein the $R^4$ $(C_1$-$C_6$ alkylene)$_x$-C$_3$-C$_{11}$ cycloalkyl is optionally substituted with one or more substituents independently selected from the group consisting of R$^9$, OR$^9$, NR$^{10}$R$^{11}$, OH, Cl, and Br; and x is 0 or 1.

In one embodiment of Formula (III), R$^5$ is selected from the group consisting of C$_6$-C$_{10}$ membered aryl, 5-11 membered heteroaryl, 4-6 membered monocyclic heterocycle fused to a phenyl group, C$_3$-C$_{11}$ cycloalkyl, and C$_4$-C$_{11}$ cycloalkenyl; wherein the R$^5$ C$_6$-C$_{10}$ membered aryl, 5-11 membered heteroaryl, 4-6 membered monocyclic heterocycle fused to a phenyl group, C$_3$-C$_{11}$ cycloalkyl, and C$_4$-C$_{11}$cycloalkenyl are optionally substituted with one or more substituents independently selected from the group consisting of R$^{12}$, OR$^{12}$, NR$^{13}$R$^{14}$, OH, oxo, CN, NO$_2$, F, Cl, Br and I; R$^{12}$, at each occurrence, is independently selected from the group consisting of C$_1$-C$_6$ alkyl, C$_1$-C$_6$ haloalkyl, C$_2$-C$_6$ alkenyl, C$_2$-C$_6$ alkynyl, 6-10 membered aryl, 5-11 membered heteroaryl, C$_3$-C$_{11}$ cycloalkyl, C$_4$-C$_{11}$ cycloalkenyl, and 4-12 membered heterocyclyl; wherein each R$^{12}$ 6-10 membered aryl, 5-11 membered heteroaryl, C$_3$-C$_{11}$ cycloalkyl, C$_4$-C$_{11}$ cycloalkenyl, and 4-12 membered heterocyclyl is optionally substituted with one or more substituents independently selected from the group consisting of C$_1$-C$_6$ alkyl, C$_1$-C$_6$ alkoxy, C$_1$-C$_6$ haloalkyl, C$_1$-C$_6$ haloalkoxy, N(C$_1$-C$_6$ alkyl)$_2$, OH, oxo, CN, NO$_2$, F, Cl, Br and I; and R$^{13}$ and R$^{14}$, at each occurrence, are each independently hydrogen or C$_1$-C$_6$ alkyl. In another embodiment of Formula (III), R$^5$ is selected from the group consisting of C$_6$-C$_{10}$ membered aryl, 5-11 membered heteroaryl, and 4-6 membered monocyclic heterocycle fused to a phenyl group; wherein the R$^5$ C$_6$-C$_{10}$ membered aryl, 5-11 membered heteroaryl, and 4-6 membered monocyclic heterocycle fused to a phenyl group are optionally substituted with one or more substituents independently selected from the group consisting of R$^{12}$, OR$^{12}$, NR$^{13}$R$^{14}$, F, Cl, Br, and I; R$^{12}$, at each occurrence, is independently selected from the group consisting of C$_1$-C$_6$ alkyl, C$_1$-C$_6$ haloalkyl, 6-10 membered aryl, 5-11 membered heteroaryl, C$_3$-C$_{11}$ cycloalkyl, and 4-12 membered heterocyclyl; wherein each R$^{12}$ 6-10 membered aryl, 5-11 membered heteroaryl, C$_3$-C$_{11}$cycloalkyl, C$_4$-C$_{11}$ cycloalkenyl, and 4-12 membered heterocyclyl is optionally substituted with one or more substituents independently selected from the group consisting of C$_1$-C$_6$ alkyl, C$_1$-C$_6$ alkoxy, C$_1$-C$_6$ haloalkyl, C$_1$-C$_6$ haloalkoxy, N(C$_1$-C$_6$ alkyl)$_2$, oxo, CN, F, and Cl; and R$^{13}$ and R$^{14}$, at each occurrence, are each independently C$_1$-C$_6$ alkyl. In another embodiment of Formula (III), R$^5$ is selected from the group consisting of C$_6$-C$_{10}$ membered aryl and 5-11 membered heteroaryl; wherein the R$^5$ C$_6$-C$_{10}$ membered aryl and 5-11 membered heteroaryl are optionally substituted with one or more substituents independently selected from the group consisting of R$^{12}$, OR$^{12}$, NR$^{13}$R$^{14}$, F, Cl, Br, and I; R$^{12}$, at each occurrence, is independently selected from the group consisting of C$_1$-C$_6$ alkyl, C$_1$-C$_6$ haloalkyl, 6-10 membered aryl, 5-11 membered heteroaryl, C$_3$-C$_{11}$ cycloalkyl, and 4-12 membered heterocyclyl; wherein each R$^{12}$ 6-10 membered aryl, 5-11 membered heteroaryl, C$_3$-C$_{11}$ cycloalkyl, and 4-12 membered heterocyclyl is optionally substituted with one or more independently selected C$_1$-C$_6$ alkyl; and R$^{13}$ and R$^{14}$, at each occurrence, are each independently C$_1$-C$_6$ alkyl.

In another embodiment of Formula (III), R$^5$ is C$_6$-C$_{10}$ membered aryl; wherein the R$^5$ C$_6$-C$_{10}$ membered aryl is optionally substituted with one or more substituents independently selected from the group consisting of R$^{12}$, OR$^{12}$, NR$^{13}$R$^{14}$, F, Cl, Br, and I; R$^{12}$, at each occurrence, is independently selected from the group consisting of C$_1$-C$_6$ alkyl, C$_1$-C$_6$ haloalkyl, 6-10 membered aryl, 5-11 membered heteroaryl, C$_3$-C$_{11}$ cycloalkyl, and 4-12 membered heterocyclyl; wherein each R$^{12}$ 6-10 membered aryl, 5-11 membered heteroaryl, C$_3$-C$_{11}$ cycloalkyl, C$_4$-C$_{11}$ cycloalkenyl, and 4-12 membered heterocyclyl is optionally substituted with one or more substituents independently selected from the group consisting of C$_1$-C$_6$ alkyl, C$_1$-C$_6$ alkoxy, C$_1$-C$_6$ haloalkyl, C$_1$-C$_6$ haloalkoxy, N(C$_1$-C$_6$ alkyl)$_2$, oxo, CN, F, and Cl; and R$^{13}$ and R$^{14}$, at each occurrence, are each independently C$_1$-C$_6$ alkyl. In another embodiment of Formula (III), R$^5$ is 5-11 membered heteroaryl; wherein the R$^5$ 5-11 membered heteroaryl is optionally substituted with one or more substituents independently selected from the group consisting of R$^{12}$, OR$^{12}$, NR$^{13}$R$^{14}$, F, Cl, Br, and I; R$^{12}$, at each occurrence, is independently selected from the group consisting of C$_1$-C$_6$ alkyl, C$_1$-C$_6$ haloalkyl, 6-10 membered aryl, 5-11 membered heteroaryl, C$_3$-C$_{11}$ cycloalkyl, and 4-12 membered heterocyclyl; wherein each R$^{12}$ 6-10 membered aryl, 5-11 membered heteroaryl, C$_3$-C$_{11}$ cycloalkyl, C$_4$-C$_{11}$cycloalkenyl, and 4-12 membered heterocyclyl is optionally substituted with one or more substituents independently selected from the group consisting of C$_1$-C$_6$ alkyl, C$_1$-C$_6$ alkoxy, C$_1$-C$_6$ haloalkyl, C$_1$-C$_6$ haloalkoxy, N(C$_1$-C$_6$ alkyl)$_2$, oxo, CN, F, and Cl; and R$^{13}$ and R$^{14}$, at each occurrence, are each independently C$_1$-C$_6$ alkyl. In another embodiment of Formula (III), R$^5$ is 5-11 membered heteroaryl; wherein the R$^5$ 5-11 membered heteroaryl is optionally substituted with one or more substituents independently selected from the group consisting of R$^{12}$, OR$^{12}$, NR$^{13}$R$^{14}$, F, Cl, and Br; R$^{12}$, at each occurrence, is independently selected from the group consisting of C$_1$-C$_6$ alkyl, C$_1$-C$_6$ haloalkyl, 6-10 membered aryl, 5-11 membered heteroaryl, C$_3$-C$_{11}$ cycloalkyl, and 4-12 membered heterocyclyl; wherein each R$^{12}$ 6-10 membered aryl, 5-11 membered heteroaryl, C$_3$-C$_{11}$cycloalkyl, and 4-12 membered heterocyclyl is optionally substituted with one or more independently selected C$_1$-C$_6$ alkyl; and R$^{13}$ and R$^{14}$, at each occurrence, are each independently C$_1$-C$_6$ alkyl. In another embodiment of Formula (III), R$^5$ is phenyl, which is unsubstituted. In another embodiment of Formula (III), R$^5$ is phenyl; wherein the R$^5$ phenyl is optionally substituted with one or more substituents independently selected from the group consisting of R$^{12}$, OR$^{12}$, NR$^{13}$R$^{14}$, F, Cl, and Br; R$^{12}$, at each occurrence, is independently selected from the group consisting of C$_1$-C$_6$ alkyl, C$_1$-C$_6$ haloalkyl, 6-10 membered aryl, 5-11 membered heteroaryl, C$_3$-C$_{11}$ cycloalkyl, and 4-12 membered heterocyclyl; and R$^{13}$ and R$^{14}$, at each occurrence, are each independently C$_1$-C$_6$ alkyl. In another embodiment of Formula (III), R$^5$ is phenyl; which is substituted with one R$^{12}$; and R$^{12}$ is C$_1$-C$_6$ alkyl, C$_3$-C$_{11}$ cycloalkyl, or F. In another embodiment of Formula (III), R$^5$ is phenyl; which is substituted with one R$^{12}$; and R$^{12}$ is CH$_3$, CH$_2$CH$_3$ or CH(CH$_3$)$_2$. In another embodiment of Formula (III), $R^5$ is phenyl; which is substituted with one $R^{12}$; and $R^{12}$ is cyclopropyl. In another embodiment of Formula (III), $R^5$ is pyridinyl; which is substituted with one or more substituents independently selected from the group consisting of $R^{12}$, $OR^{12}$, and $NR^{13}R^{14}$; $R^{12}$ is independently $C_1$-$C_6$ alkyl; and $R^{13}$ and $R^{14}$, at each occurrence, are each independently $C_1$-$C_6$ alkyl. In another embodiment of Formula (III), $R^5$ is pyridinyl; which is substituted with one or more substituents independently selected from the group consisting of $R^{12}$, $OR^{12}$, and $NR^{13}R^{14}$; $R^{12}$ is independently $CH_3$ or $CH(CH_3)_2$; and $R^{13}$ and $R^{14}$, at each occurrence, are each independently $CH_3$. In another embodiment of Formula (III), $R^5$ is pyridinyl; wherein the $R^5$ pyridinyl is optionally substituted with one or more independently selected $R^{12}$; and $R^{12}$, at each occurrence, is independently $C_1$-$C_6$ alkyl.

In one embodiment of Formula (III), $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I; $R^{15}$ at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I; $R^{16}$ and $R^{17}$, at each occurrence, are each independently hydrogen or $C_1$-$C_6$ alkyl; and $R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I. In another embodiment of Formula (III), $R^6$ is selected from the group consisting of $C_1$-$C_6$ alkyl, $C_2$-$C_6$ alkenyl, 6-10 membered aryl, 5-11 membered heteroaryl, $C_3$-$C_{11}$cycloalkyl, and 4-12 membered heterocyclyl; wherein the $R^6$ $C_1$-$C_6$ alkyl is optionally substituted with one or more independently selected $R^{15}$ or F; wherein the $R^6$ 6-10 membered aryl, 5-11 membered heteroaryl, $C_3$-$C_{11}$ cycloalkyl, and 4-12 membered heterocyclyl are optionally substituted with one or more substituents independently selected from the group consisting of $R^{18}$ and $OR^{18}$; $R^{15}$, at each occurrence, is independently $C_3$-$C_{11}$ cycloalkyl; and $R^{18}$, at each occurrence, is independently selected $C_1$-$C_6$ alkyl; wherein each $R^{18}$ $C_1$-$C_6$ alkyl is optionally substituted with one or more F. In one embodiment of Formula (III), $R^6$ is $C_1$-$C_6$ alkyl; wherein the $R^6$ $C_1$-$C_6$ alkyl is optionally substituted with one or more independently selected $R^{15}$; and $R^{15}$, at each occurrence, is independently $C_3$-$C_{11}$ cycloalkyl. In another embodiment of Formula (III), $R^6$ is $C_1$-$C_6$ alkyl; wherein the $R^6$ $C_1$-$C_6$ alkyl is unsubstituted. In another embodiment of Formula (III), $R^6$ is —$CH_2CH_3$. In another embodiment of Formula (III), $R^6$ is —$CH(CH_3)_2$. In one embodiment of Formula (III), $R^6$ is 4-12 membered heterocyclyl; wherein the $R^6$ 4-12 membered heterocyclyl is optionally substituted with one or more substituents independently selected from the group consisting of $OR^{18}$; and $R^{18}$, at each occurrence, is independently $C_1$-$C_6$ alkyl. In another embodiment of Formula (III), $R^6$ is 4-12 membered heterocyclyl; wherein the $R^6$ 4-12 membered heterocyclyl is unsubstituted. In another embodiment of Formula (III), $R^6$ is tetrahydrofuranyl. In another embodiment of Formula (III), $R^6$ is tetrahydropyranyl. In one embodiment of Formula (III), $R^6$ is $C_3$-$C_{11}$ cycloalkyl; wherein the $R^6$ $C_3$-$C_{11}$ cycloalkyl is optionally substituted with one or more independently selected $OR^{18}$; and $R^{18}$, at each occurrence, is independently selected $C_1$-$C_6$ alkyl. In one embodiment of Formula (III), $R^6$ is cyclohexyl; wherein the $R^6$ cyclohexyl is unsubstituted.

In one embodiment of Formula (III), $R^1$ is $C(O)OR^6$; and $R^6$ is $C_1$-$C_6$ alkyl or $C_3$-$C_{11}$ cycloalkyl. In one embodiment of Formula (III), $R^1$ is $C(O)OR^6$; and $R^6$ is $C_1$-$C_6$ alkyl; wherein the $R^6$ is $C_1$-$C_6$ unsubstituted alkyl.

In one embodiment of Formula (III), $R^1$ is $C(O)R^6$; $R^6$ is 4-12 membered heterocyclyl; wherein the $R^6$ 4-12 membered heterocyclyl is optionally substituted with $OR^{18}$; and $R^{18}$, at each occurrence, is independently selected $C_1$-$C_6$ alkyl. In one embodiment of Formula (III), $R^1$ is $C(O)R^6$; and $R^6$ is 4-12 membered heterocyclyl; wherein the $R^6$ 4-12 membered heterocyclyl is unsubstituted. In one embodiment of Formula (III), $R^1$ is $C(O)R^6$; and $R^6$ is $C_3$-$C_{11}$ cycloalkyl; wherein the $R^6$ $C_3$-$C_{11}$ cycloalkyl is unsubstituted.

In one embodiment of Formula (III), $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I; $R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I; $R^{22}$ and $R^{23}$, at each occurrence, are each independently hydrogen or $C_1$-$C_6$ alkyl; $R^{24}$, at each occurrence, is independently selected from the group consisting of $C_1$-$C_6$ alkyl, $C_1$-$C_6$ haloalkyl, C$_1$-C$_6$ alkoxy-C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$ cycloalkyl, C$_4$-C$_{11}$ cycloalkenyl, and 4-12 membered heterocyclyl; and R$^{25}$ and R$^{26}$, at each occurrence, are each independently hydrogen or C$_1$-C$_6$ alkyl. In another embodiment of Formula (III), R$^9$, at each occurrence, is independently selected from the group consisting of C$_1$-C$_6$ alkyl, 6-10 membered aryl, C$_3$-C$_{11}$ cycloalkyl, and 4-12 membered heterocyclyl; wherein each R$^9$ C$_1$-C$_6$ alkyl is optionally substituted with one or more CN or F; wherein each R$^9$ 6-10 membered aryl, C$_3$-C$_{11}$ cycloalkyl, and 4-12 membered heterocyclyl is optionally substituted with one or more substituents independently selected from the group consisting of R$^{24}$, OR$^{24}$, and F; and R$^{24}$, at each occurrence, is independently C$_1$-C$_6$ alkyl.

In one embodiment of Formula (III), R$^{10}$ and R$^{11}$, at each occurrence, are each independently selected from the group consisting of hydrogen, C$_1$-C$_6$ alkyl, phenyl, and 5-6 membered heteroaryl; wherein each R$^{10}$ and R$^{11}$ phenyl and 5-6 membered heteroaryl is optionally substituted with one or more substituents independently selected from the group consisting of C$_1$-C$_6$ alkyl, C$_1$-C$_6$ alkoxy, C$_1$-C$_6$ haloalkyl, OH, oxo, CN, NO$_2$, F, Cl, Br, and I. In another embodiment of Formula (III), R$^{10}$ and R$^{11}$, at each occurrence, are each independently C$_1$-C$_6$ alkyl.

In one embodiment of Formula (III), R$^4$ is L$^1$-C$_6$-C$_{10}$ aryl; wherein the R$^4$ C$_6$-C$_{10}$ aryl is optionally substituted with one or more substituents independently selected from the group consisting of R$^9$ and OR$^9$; L$^1$ is absent, or is C$_1$-C$_6$ alkylene; and R$^9$, at each occurrence, is independently selected C$_1$-C$_6$ alkyl; wherein each R$^9$ C$_1$-C$_6$ alkyl is optionally substituted with one or more F. In one embodiment of Formula (III), R$^4$ is (C$_1$-C$_6$ alkylene)$_x$-C$_6$-C$_{10}$ aryl; wherein the R$^4$ (C$_1$-C$_6$ alkylene)$_x$-C$_6$-C$_{10}$ membered aryl is optionally substituted with one or more substituents independently selected from the group consisting of R$^9$ and OR$^9$; x is 0 or 1; and R$^9$, at each occurrence, is independently selected C$_1$-C$_6$ alkyl; wherein each R$^9$ C$_1$-C$_6$ alkyl is optionally substituted with one or more F. In another embodiment of Formula (III), R$^4$ is CH$_2$-phenyl; wherein the R$^4$ CH$_2$-phenyl is optionally substituted with one or more substituents independently selected from the group consisting of R$^9$ and OR$^9$; and R$^9$, at each occurrence, is independently selected from the group consisting of CH$_3$ and CF$_3$. In another embodiment of Formula (III), R$^4$ is L$^1$-5-11 membered heteroaryl; wherein the R$^4$ 5-11 membered heteroaryl is optionally substituted with one or more substituents independently selected from the group consisting of R$^9$ and OR$^9$; L$^1$ is absent, or is C$_1$-C$_6$ alkylene; and R$^9$, at each occurrence, is independently selected from the group consisting of C$_1$-C$_6$ alkyl and C$_3$-C$_{11}$ cycloalkyl; wherein each R$^9$ C$_1$-C$_6$ alkyl is optionally substituted with one or more F. In another embodiment of Formula (III), R$^4$ is (C$_1$-C$_6$ alkylene)$_x$-5-11 membered heteroaryl; wherein the R$^4$ (C$_1$-C$_6$ alkylene)$_x$-5-11 membered heteroaryl is optionally substituted with one or more substituents independently selected from the group consisting of R$^9$ and OR$^9$; x is 0 or 1; and R$^9$, at each occurrence, is independently selected from the group consisting of C$_1$-C$_6$ alkyl and C$_3$-C$_{11}$ cycloalkyl; wherein each R$^9$ C$_1$-C$_6$ alkyl is optionally substituted with one or more F. In another embodiment of Formula (III), R$^4$ is CH$_2$-pyridinyl; wherein the R$^4$ CH$_2$-pyridinyl is optionally substituted with one or more substituents independently selected from the group consisting of R$^9$ and OR$^9$; and R$^9$, at each occurrence, is independently selected from the group consisting of CH$_3$, C(CH$_3$)$_3$, CF$_3$, and cyclobutyl. In another embodiment of Formula (III), R$^4$ is CH$_2$-quinolinyl; wherein the R$^4$ CH$_2$-quinolinyl is optionally substituted with one or more substituents independently selected from the group consisting of R$^9$ and OR$^9$; and R$^9$, at each occurrence, is independently CH$_3$.

In one embodiment of Formula (III), R$^4$ is selected from the group consisting of

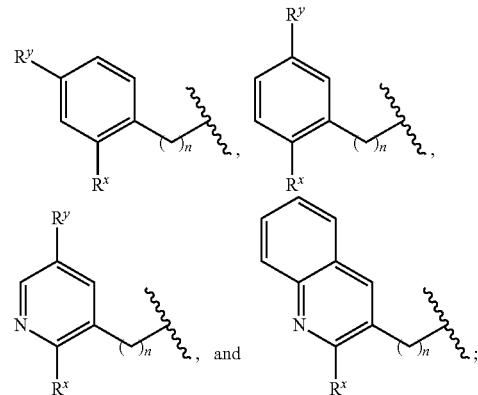

wherein R$^x$ is OCH$_3$, and R$^y$ is selected from the group consisting of CF$_3$, C(CH$_3$)$_3$, and cyclobutyl; and n is 1.

One embodiment pertains to compounds of Formula (III), wherein
R$^1$ is C(O)R$^6$;
R$^4$ is L$^1$-5-11 membered heteroaryl; wherein the R$^4$ 5-11 membered heteroaryl is optionally substituted with one or more substituents independently selected from the group consisting of R$^9$ and OR$^9$;
L$^1$ is C$_1$-C$_6$ alkylene;
R$^5$ is C$_6$-C$_{10}$ membered aryl; wherein the R$^5$ C$_6$-C$_{10}$ membered aryl is optionally substituted with one or more R$^{12}$;
R$^6$ is 4-12 membered heterocyclyl;
R$^9$, at each occurrence, is independently selected C$_1$-C$_6$ alkyl; wherein each R$^9$ C$_1$-C$_6$ alkyl is optionally substituted with one or more F; and
R$^{12}$, at each occurrence, is independently selected C$_1$-C$_6$ alkyl.

One embodiment pertains to compounds of Formula (III),

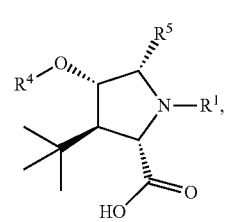

(III)

wherein
R$^1$ is selected from the group consisting of SO$_2$R$^6$, C(O)R$^6$, C(O)OR$^6$, and C(O)NR$^7$R$^8$;
R$^4$ is selected from the group consisting of L$^1$-C$_6$-C$_{10}$ aryl and L$^1$-5-11 membered heteroaryl; wherein the R$^4$ C$_6$-C$_{10}$ aryl and 5-11 membered heteroaryl are optionally substituted with one or more substituents independently selected from the group consisting of R$^9$, OR$^9$, NR$^{10}$R$^{11}$, OH, Cl, and Br;
L$^1$ is absent, or is selected from the group consisting of C$_1$-C$_6$ alkylene, C$_2$-C$_6$ alkenylene, C$_2$-C$_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo;

$R^5$ is selected from the group consisting of $C_6$-$C_{10}$ membered aryl, 5-11 membered heteroaryl, and 4-6 membered monocyclic heterocycle fused to a phenyl group; wherein the $R^5$ $C_6$-$C_{10}$ membered aryl, 5-11 membered heteroaryl, and 4-6 membered monocyclic heterocycle fused to a phenyl group, are optionally substituted with one or more substituents independently selected from the group consisting of $R^{12}$, $OR^{12}$, $NR^{13}R^{14}$, F, Cl, Br and I;

$R^6$ is selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, and 4-12 membered heterocyclyl; wherein the $R^6$ $C_1$-$C_6$ alkyl is optionally substituted with one or more substituents independently selected from the group consisting of $R^{15}$, and F; wherein the $R^6$ 5-11 membered heteroaryl, and $C_3$-$C_{11}$ cycloalkyl are optionally substituted with one or more substituents independently selected from the group consisting of $R^{18}$ and $OR^{18}$;

$R^7$ and $R^8$ are each independently hydrogen or $C_1$-$C_6$ alkyl;

$R^9$, at each occurrence, is independently selected from the group consisting of $C_1$-$C_6$ alkyl, 6-10 membered aryl, and $C_3$-$C_{11}$ cycloalkyl; wherein each $R^9$ $C_1$-$C_6$ alkyl is optionally substituted with one or more substituents independently selected from the group consisting of CN, and F; wherein each $R^9$ 6-10 membered aryl, $C_3$-$C_{11}$ cycloalkyl, and 4-12 membered heterocyclyl is optionally substituted with one or more substituents independently selected from the group consisting of $R^{24}$, $OR^{24}$, and F;

$R^{10}$ and $R^{11}$, at each occurrence, are each independently $C_1$-$C_6$ alkyl;

$R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; wherein each $R^{12}$ 6-10 membered aryl, 5-11 membered heteroaryl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, N($C_1$-$C_6$ alkyl)$_2$, oxo, CN, F, and Cl;

$R^{13}$ and $R^{14}$, at each occurrence, are each independently hydrogen or $C_1$-$C_6$ alkyl;

$R^{15}$, at each occurrence, is independently $C_3$-$C_{11}$ cycloalkyl;

$R^{18}$, at each occurrence, is independently $C_1$-$C_6$ alkyl; wherein each $R^{18}$ $C_1$-$C_6$ alkyl is optionally substituted with one or more F; and $R^{24}$, at each occurrence, is independently $C_1$-$C_6$ alkyl.

In one embodiment of Formula (III), $R^1$ is selected from the group consisting of $C(O)R^6$, $C(O)OR^6$, and $C(O)NR^7R^8$;

$R^4$ is selected from the group consisting of ($C_1$-$C_6$ alkylene)$_x$-$C_6$-$C_{10}$ aryl and ($C_1$-$C_6$ alkylene)$_x$-5-11 membered heteroaryl; wherein the $R^4$ $C_6$-$C_{10}$ membered aryl of ($C_1$-$C_6$ alkylene)$_x$-$C_6$-$C_{10}$ membered aryl, and the 5-11 membered heteroaryl of ($C_1$-$C_6$ alkylene)$_x$-5-11 membered heteroaryl are optionally substituted with one or more substituents independently selected from the group consisting of $R^9$, $OR^9$, $NR^{10}R^{11}$, OH, Cl, and Br;

$R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, and Br;

$R^6$ is selected from the group consisting of $C_1$-$C_6$ alkyl, $C_2$-$C_6$ alkenyl, $C_3$-$C_{11}$ cycloalkyl, and 4-12 membered heterocyclyl; wherein the $R^6$ $C_1$-$C_6$ alkyl is optionally substituted with one or more independently selected $R^{15}$; wherein the $R^6$ $C_3$-$C_{11}$ cycloalkyl, and 4-12 membered heterocyclyl are optionally substituted with one or more independently selected $OR^{18}$;

$R^7$ and $R^8$ are each independently hydrogen or $C_1$-$C_6$ alkyl;

$R^9$, at each occurrence, is independently selected from the group consisting of $C_1$-$C_6$ alkyl, 6-10 membered aryl, $C_3$-$C_{11}$ cycloalkyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more F; wherein each $R^9$ 6-10 membered $C_3$-$C_{11}$ cycloalkyl, and 4-12 membered heterocyclyl is optionally substituted with one or more substituents independently selected from the group consisting of $R^{24}$, $OR^{24}$, and F;

$R^{10}$ and $R^{11}$, at each occurrence, are each independently selected $C_1$-$C_6$ alkyl;

$R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; wherein each $R^{12}$ 6-10 membered aryl, 5-11 membered heteroaryl, $C_3$-$C_{11}$ cycloalkyl, and 4-12 membered heterocyclyl is optionally substituted with one or more independently selected from the group consisting of $C_1$-$C_6$ alkyl;

$R^{13}$ and $R^{14}$, at each occurrence, are each independently $C_1$-$C_6$ alkyl;

$R^{15}$, at each occurrence, is independently selected $C_3$-$C_{11}$ cycloalkyl;

$R^{18}$, at each occurrence, is independently selected $C_1$-$C_6$ alkyl;

$R^{24}$, at each occurrence, is independently selected $C_1$-$C_6$ alkyl; and x is 0 or 1.

Exemplary compounds of Formula (III) include, but are not limited to (2S*,3R*,4S*,5S*)-3-tert-butyl-1-[di(propan-2-yl)carbamoyl]-4-{[2-methoxy-5-(trifluoromethyl)phenyl]methoxy}-5-phenylpyrrolidine-2-carboxylic acid;

(2S,3R,4S,5S)-3-tert-butyl-1-(cyclohexanecarbonyl)-4-{[2-methoxy-5-(trifluoromethyl)phenyl]methoxy}-5-phenylpyrrolidine-2-carboxylic acid;

(2S,3R,4S,5S)-3-tert-butyl-1-[(1S,3S)-3-methoxycyclohexane-1-carbonyl]-4-{[2-methoxy-5-(trifluoromethyl)phenyl]methoxy}-5-phenylpyrrolidine-2-carboxylic acid;

(2S,3R,4S,5S)-3-tert-butyl-1-[(1R,3R)-3-methoxycyclohexane-1-carbonyl]-4-{[2-methoxy-5-(trifluoromethyl)phenyl]methoxy}-5-phenylpyrrolidine-2-carboxylic acid;

(2S,3R,4S,5S)-3-tert-butyl-1-[(1S,3S)-3-methoxycyclohexane-1-carbonyl]-4-{[2-methoxy-4-(trifluoromethyl)phenyl]methoxy}-5-phenylpyrrolidine-2-carboxylic acid;

(2S,3R,4S,5S)-3-tert-butyl-1-[(1R,3R)-3-methoxycyclohexane-1-carbonyl]-4-{[2-methoxy-4-(trifluoromethyl)phenyl]methoxy}-5-phenylpyrrolidine-2-carboxylic acid;

(2S,3R,4S,5S)-4-[(5-bromo-2-methoxyphenyl)methoxy]-3-tert-butyl-5-phenyl-1-{[(propan-2-yl)oxy]carbonyl}pyrrolidine-2-carboxylic acid;

(2S,3R,4S,5S)-4-[(5-bromo-2-methoxyphenyl)methoxy]-3-tert-butyl-1-[(1R,3R)-3-methoxycyclohexane-1-carbonyl]-5-phenylpyrrolidine-2-carboxylic acid;

(2S,3R,4S,5S)-3-tert-butyl-4-[(4-methoxy[1,1'-biphenyl]-3-yl)methoxy]-5-phenyl-1-{[(propan-2-yl)oxy]carbonyl}pyrrolidine-2-carboxylic acid;

(2S,3R,4S,5S)-3-tert-butyl-4-[(4-methoxy[1,1'-biphenyl]-3-yl)methoxy]-1-[(1R,3R)-3-methoxycyclohexane-1-carbonyl]-5-phenylpyrrolidine-2-carboxylic acid;

(2S,3R,4S,5S)-4-[(5-bromo-2-methoxypyridin-3-yl)methoxy]-3-tert-butyl-5-phenyl-1-{[(propan-2-yl)oxy]carbonyl}pyrrolidine-2-carboxylic acid;

(2S,3R,4S,5S)-3-tert-butyl-1-(cyclohexanecarbonyl)-4-{[2-methoxy-5-(trifluoromethyl)pyridin-3-yl]methoxy}-5-phenylpyrrolidine-2-carboxylic acid;

(2S,3R,4S,5S)-3-tert-butyl-4-[(2-methoxy-5-phenylpyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclohexyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclopentyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-tert-butyl-2-methoxyphenyl)methoxy]-1-[(1R,3R)-3-methoxycyclohexane-1-carbonyl]-5-phenylpyrrolidine-2-carboxylic acid;

(2S,3R,4S,5S)-3-tert-butyl-4-[(5-tert-butyl-2-methoxyphenyl)methoxy]-5-phenyl-1-{[(propan-2-yl)oxy]carbonyl}pyrrolidine-2-carboxylic acid;

(2S,3R,4S,5S)-3-tert-butyl-1-(cyclohexanecarbonyl)-5-(2-fluorophenyl)-4-{[2-methoxy-5-(trifluoromethyl)pyridin-3-yl]methoxy}pyrrolidine-2-carboxylic acid;

(2S,3R,4S,5S)-3-tert-butyl-1-(cyclohexanecarbonyl)-5-(2-fluorophenyl)-4-{[2-methoxy-5-(trifluoromethyl)phenyl]methoxy}pyrrolidine-2-carboxylic acid;

(2S,3R,4S,5S)-3-tert-butyl-4-[(5-tert-butyl-2-methoxyphenyl)methoxy]-1-(cyclohexanecarbonyl)-5-(2-fluorophenyl)pyrrolidine-2-carboxylic acid;

(2S,3R,4S,5S)-4-[(5-bromo-2-methoxypyridin-3-yl)methoxy]-3-tert-butyl-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-5-(2-fluorophenyl)-4-[(2-methoxy-5-phenylpyridin-3-yl)methoxy]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-phenylpyrrolidine-2-carboxylic acid;

(2S,3R,4S,5S)-3-tert-butyl-1-(cyclohexanecarbonyl)-4-[(5-cyclopentyl-2-methoxypyridin-3-yl)methoxy]-5-phenylpyrrolidine-2-carboxylic acid;

(2S,3R,4S,5S)-4-{[5-(bicyclo[2.2.1]heptan-2-yl)-2-methoxypyridin-3-yl]methoxy}-3-tert-butyl-1-(cyclohexanecarbonyl)-5-phenylpyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-4-[(5-cyclopentyl-2-methoxypyridin-3-yl)methoxy]-5-(2-fluorophenyl)pyrrolidine-2-carboxylic acid;

(2S,3R,4S,5S)-4-{[5-(bicyclo[2.2.1]heptan-2-yl)-2-methoxypyridin-3-yl]methoxy}-3-tert-butyl-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-5-(2-fluorophenyl)-4-{[2-methoxy-5-(pyrrolidin-1-yl)pyridin-3-yl]methoxy}pyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-phenylpyrrolidine-2-carboxylic acid;

(2S,3R,4S,5S)-3-tert-butyl-4-[(5-tert-butyl-2-methoxypyridin-3-yl)methoxy]-1-[(1R,3R)-3-methoxycyclohexane-1-carbonyl]-5-phenylpyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-(2-fluorophenyl)pyrrolidine-2-carboxylic acid;

(2S,3R,4S,5S)-3-tert-butyl-4-[(5-tert-butyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2-fluoro-4-methylphenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2-fluorophenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(4-fluoro-2-methylphenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2,4-difluorophenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(3,6-dihydro-2H-pyran-4-yl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(3-methoxyphenyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(4-methylphenyl)pyridin-3-yl]methoxy}-5-phenyl-1-{[propan-2-yl)oxy]carbonyl}pyrrolidine-2-carboxylic acid;

(2S,3R,4S,5S)-3-tert-butyl-4-[(6-tert-butyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-5-(2-fluorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-tert-butyl-2-methoxypyridin-3-yl)methoxy]-5-(2-fluorophenyl)-1-{[(propan-2-yl)oxy]carbonyl}pyrrolidine-2-carboxylic acid;

(2S,3R,4S,5S)-4-[(5-bromo-2-methoxypyridin-3-yl)methoxy]-3-tert-butyl-5-(2-fluorophenyl)-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-(2-fluorophenyl)-1-{[(propan-2-yl)oxy]carbonyl}pyrrolidine-2-carboxylic acid;

(2S,3R,4S,5S)-3-tert-butyl-4-{[2-methoxy-5-(trifluoromethyl)phenyl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-tert-butyl-2-methoxypyridin-3-yl)methoxy]-5-(3-chlorophenyl)-1-{[(propan-2-yl)oxy]carbonyl}pyrrolidine-2-carboxylic acid;

(2S,3R,4S,5S)-3-tert-butyl-4-{[2-methoxy-5-(piperidin-1-yl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(pyrrolidin-1-yl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-{[(propan-2-yl)oxy]carbonyl}pyrrolidine-2-carboxylic acid;

(2S,3R,4S,5S)-3-tert-butyl-4-{[5-(3,3-difluoroazetidin-1-yl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(3,3-difluoropyrrolidin-1-yl)-2-methoxypyridin-3-yl]methoxy}-5-phenyl-1-{[(propan-2-yl)oxy]carbonyl}pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-phenylpyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-phenylpyrrolidine-2-carboxylic acid;

(2S,3R,4S,5S)-3-tert-butyl-4-{[2-methoxy-5-(trifluoromethyl)pyridin-3-yl]methoxy}-5-phenyl-1-{[(prop-2-en-1-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxane-2-carbonyl]-5-phenylpyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-[2-(propan-2-yl)phenyl]pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(propan-2-yl)phenyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(2-cyclobutyl-5-methoxypyridin-4-yl)methoxy]-5-phenyl-1-{[(propan-2-yl)oxy]carbonyl}pyrrolidine-2-carboxylic acid;

(2S,3R,4S,5S)-3-tert-butyl-5-(2-cyclobutylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxolane-2-carbonyl]-5-[2-(propan-2-yl)phenyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2S)-oxane-2-carbonyl]pyrrolidine-2-carboxylic acid (2S,3R,4S,5S)-3-tert-butyl-5-(2-chlorophenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-{2-[(propan-2-yl)oxy]phenyl}pyrrolidine-2-carboxylic acid;

(2S,3R,4S,5S)-3-tert-butyl-4-[(2-methoxyquinolin-3-yl)methoxy]-5-phenyl-1-{[(propan-2-yl)oxy]carbonyl}pyrrolidine-2-carboxylic acid;

(2S,3R,4S,5S)-3-tert-butyl-4-{[2-hydroxy-5-(trifluoromethyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-5-[2-(3,6-dihydro-2H-pyran-4-yl)phenyl]-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(3S)-oxolane-3-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-(oxane-4-carbonyl)-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(3R)-oxolane-3-carbonyl]-5-[2-(propan-2-yl)phenyl]pyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-{[2-methoxy-5-(trifluoromethyl)phenyl]methoxy}-1-[(2S)-oxolane-2-carbonyl]-5-[2-(trifluoromethyl)pyridin-3-yl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-[(2-methoxyquinolin-3-yl)methoxy]-1-[(2S)-oxolane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[3-(propan-2-yl)phenyl]pyrrolidine-2-carboxylic acid;

(2S,3R,4S,5S)-5-(3-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-(3-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[1-(propan-2-yl)-1H-pyrazol-5-yl]pyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-[2-(propan-2-yl)phenyl]pyrrolidine-2-carboxylic acid;

(2S,3R,4S,5S)-3-tert-butyl-4-[(2-methoxyquinolin-3-yl)methoxy]-1-[(2R)-oxane-2-carbonyl]-5-[2-(propan-2-yl)phenyl]pyrrolidine-2-carboxylic acid;

(2S,3R,4S,5S)-3-tert-butyl-4-[(2-methoxyquinolin-3-yl)methoxy]-1-[(2S)-oxane-2-carbonyl]-5-[2-(propan-2-yl)phenyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-(oxane-4-carbonyl)-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-[(2R)-oxane-2-carbonyl]-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid;

(2S,3R,4S,5S)-5-(2-bromophenyl)-3-tert-butyl-4-[(2-methoxyquinolin-3-yl)methoxy]-1-{[(propan-2-yl)oxy]carbonyl}pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-{[(propan-2-yl)oxy]carbonyl}pyrrolidine-2-carboxylic acid;

(2S,3R,4S,5S)-3-tert-butyl-5-(2-cyclopropylphenyl)-4-[(2-methoxyquinolin-3-yl)methoxy]-1-[(2S)-oxolane-2-carbonyl]pyrrolidine-2-carboxylic acid;

(2S,3R,4S,5S)-3-tert-butyl-5-(3-cyclobutylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-[(2S)-oxane-2-carbonyl]pyrrolidine-2-carboxylic acid;

(2S,3R,4S,5S)-3-tert-butyl-5-(3-chlorophenyl)-4-[(5-cyclobutyl-2-methoxypyridin-3-yl)methoxy]-1-{[(propan-2-yl)oxy]carbonyl}pyrrolidine-2-carboxylic acid;

(2S,3R,4S,5S)-3-tert-butyl-5-(2-cyclopropylphenyl)-4-[(2-methoxyquinolin-3-yl)methoxy]-1-{[(propan-2-yl)oxy]carbonyl}pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-[2-(trifluoromethyl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-{2-[(propan-2-yl)oxy]pyridin-3-yl}pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-[(2-methoxyquinolin-3-yl)methoxy]-1-[(2S)-oxolane-2-carbonyl]-5-[1-(propan-2-yl)-1H-pyrazol-5-yl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-(oxane-4-carbonyl)pyrrolidine-2-carboxylic acid;

(2S,3R,4S,5S)-5-(2-bromophenyl)-3-tert-butyl-4-[(2-methoxyquinolin-3-yl)methoxy]-1-[(2S)-oxolane-2-carbonyl]pyrrolidine-2-carboxylic acid;

(2S,3R,4S,5S)-3-tert-butyl-5-(3-tert-butylphenyl)-1-(ethoxycarbonyl)-4-{[2-methoxy-5-(trifluoromethyl)pyridin-3-yl]methoxy}pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(1R,2S,4S)-7-oxabicyclo[2.2.1]heptane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-[2-(trifluoromethyl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(trifluoromethyl)phenyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-1-(cyclobutanecarbonyl)-4-{[2-methoxy-5-(trifluoromethyl)pyridin-3-yl]methoxy}-5-{2-[(propan-2-yl)oxy]pyridin-3-yl}pyrrolidine-2-carboxylic acid;

(2S,3R,4S,5S)-3-tert-butyl-1-(cyclobutanecarbonyl)-4-[(5-cyclobutyl-2-methoxypyridin-3-yl)methoxy]-5-{2-[(propan-2-yl)oxy]pyridin-3-yl}pyrrolidine-2-carboxylic acid;

(2S,3R,4S,5S)-5-(2-bromophenyl)-3-tert-butyl-4-[(5-tert-butyl-2-methoxyphenyl)methoxy]-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-5-[2-(difluoromethyl)phenyl]-1-[(2S)-oxolane-2-carbonyl]pyrrolidine-2-carboxylic acid;

(2S,3R,4S,5S)-3-tert-butyl-5-(2,6-difluorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-(2-cyclopropylphenyl)-1-[(2S)-oxolane-2-carbonyl]pyrrolidine-2-carboxylic acid;

(2S,3R,4S,5S)-4-[(5-bromo-2-methoxypyridin-3-yl)methoxy]-3-tert-butyl-5-(2-cyclopropylphenyl)-1-[(2S)-oxolane-2-carbonyl]pyrrolidine-2-carboxylic acid;

(2S,3R,4S,5S)-3-tert-butyl-4-{[2-methoxy-5-(trifluoromethyl)phenyl]methoxy}-5-(2-methylphenyl)-1-[(2S)-oxane-2-carbonyl]pyrrolidine-2-carboxylic acid;

(2S,3R,4S,5S)-3-tert-butyl-4-{[2-methoxy-4-(trifluoromethyl)phenyl]methoxy}-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxane-2-carbonyl]-5-[2-(propan-2-yl)phenyl]pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-[(2S)-oxane-2-carbonyl]pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2-ethylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-([1,1'-biphenyl]-2-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-6-oxo-1,6-dihydropyridin-3-yl)phenyl]-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2-cyclopropylphenyl)pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-(cyclohexanecarbonyl)pyrrolidine-2-carboxylic acid;

(2S,3R,4S,5S)-3-tert-butyl-5-(2-ethylphenyl)-4-{[2-methoxy-4-(trifluoromethyl)phenyl]methoxy}-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-ethylphenyl)-1-[(2S)-oxane-2-carbonyl]pyrrolidine-2-carboxylic acid;

(2S,3R,4S,5S)-4-[(5-bromo-2-methoxypyridin-3-yl)methoxy]-3-tert-butyl-5-(2-methylphenyl)-1-[(2S)-oxane-2-carbonyl]pyrrolidine-2-carboxylic acid;

(2S,3R,4S,5S)-3-tert-butyl-4-{[5-(2-cyanopropan-2-yl)-2-methoxyphenyl]methoxy}-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxyquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-5-(4'-fluoro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(3'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-1,2,3,6-tetrahydropyridin-4-yl)phenyl]-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-1H-pyrazol-4-yl)phenyl]-1-[(2S)-oxane-2-carbonyl]pyrrolidine-2-carboxylic acid;

(2S,3R,4S,5S)-3-tert-butyl-5-[3'-(dimethylamino)[1,1'-biphenyl]-2-yl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2'-methyl[1,1'-biphenyl]-2-yl)-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(pyridin-4-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(pyrimidin-5-yl)phenyl]pyrrolidine-2-carboxylic acid;

(2S,3R,4S,5S)-3-tert-butyl-5-[2-(furan-3-yl)phenyl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-1H-pyrrol-3-yl)phenyl]-1-[(2S)-oxane-2-carbonyl]pyrrolidine-2-carboxylic acid;

(2S,3R,4S,5S)-3-tert-butyl-5-(2'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[3'-(trifluoromethoxy)[1,1'-biphenyl]-2-yl]pyrrolidine-2-carboxylic acid;

(2S,3R,4S,5S)-3-tert-butyl-5-(4'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-[2-(2H-1,3-benzodioxol-5-yl)phenyl]-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2'-fluoro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-[2-(6-methoxypyridin-3-yl)phenyl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[4'-(trifluoromethoxy)[1,1'-biphenyl]-2-yl]pyrrolidine-2-carboxylic acid;

(2S,3R,4S,5S)-3-tert-butyl-5-(4'-cyano[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-{2-[6-(trifluoromethyl)pyridin-3-yl]phenyl}pyrrolidine-2-carboxylic acid;

(2S,3R,4S,5S)-3-tert-butyl-5-[2-(5-ethoxypyridin-3-yl)phenyl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(naphthalen-1-yl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-(naphthalen-1-yl)-1-[(2S)-oxane-2-carbonyl]pyrrolidine-2-carboxylic acid;

(2S,3R,4S,5S)-5-(1-benzofuran-7-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(2-methylpropyl)phenyl]-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-(6-methoxypyridine-2-sulfonyl)pyrrolidine-2-carboxylic acid;

(2S,3R,4S,5S)-3-tert-butyl-4-{[2-methoxy-5-(1-methylcyclobutyl)phenyl]methoxy}-5-(2-methylphenyl)-1-[(2S)-oxane-2-carbonyl]pyrrolidine-2-carboxylic acid;

(2S,3R,4S,5S)-3-tert-butyl-5-(2,3-dihydro-1-benzofuran-7-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-[(5-cyclopropyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxane-2-carbonyl]-5-(5,6,7,8-tetrahydronaphthalen-1-yl)pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-(5,6,7,8-tetrahydronaphthalen-1-yl)pyrrolidine-2-carboxylic acid;

(2S,3R,4S,5S)-3-tert-butyl-4-[(2-methoxy-7-methylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(6-tert-butyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-1-(3,4-dihydro-2H-pyran-6-carbonyl)-4-{[2-methoxy-5-(trifluoromethyl)pyridin-3-yl]methoxy}-5-(2-methylphenyl)pyrrolidine-2-carboxylic acid;

(2S,3R,4S,5S)-3-tert-butyl-4-[(5-chloro-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[2-methoxy-5-(trifluoromethoxy)phenyl]methoxy}-5-(2-methylphenyl)-1-[(2S)-oxane-2-carbonyl]pyrrolidine-2-carboxylic acid;

(2S,3R,4S,5S)-3-tert-butyl-4-[(6-tert-butyl-3-methoxypyridin-2-yl)methoxy]-5-(2-methylphenyl)-1-[(2S)-oxane-2-carbonyl]pyrrolidine-2-carboxylic acid;

(2S,3R,4S,5S)-3-tert-butyl-4-({[2-methoxy-5-(trifluoromethyl)pyridin-3-yl]($^2$H$_2$)methyl}oxy)-5-(2-methylphenyl)-1-[(2S)-oxane-2-carbonyl]pyrrolidine-2-carboxylic acid;

(2S,3R,4S,5S)-3-tert-butyl-4-{[{2-[($^2$H$_3$)methyloxy]-5-(trifluoromethyl)pyridin-3-yl}($^2$H$_2$)methyl]oxy}-5-(2-methylphenyl)-1-[(2S)-oxane-2-carbonyl]pyrrolidine-2-carboxylic acid;

(2S,3R,4S,5S)-3-tert-butyl-5-(5-chloro-2-methylphenyl)-4-[(5-cyclobutyl-2-methoxypyridin-3-yl)methoxy]-1-[(2S)-oxane-2-carbonyl]pyrrolidine-2-carboxylic acid;

(2S,3R,4S,5S)-3-tert-butyl-5-(5-chloro-2-methylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(3-chloro-2-methylphenyl)-4-[(5-cyclobutyl-2-methoxypyridin-3-yl)methoxy]-1-[(2S)-oxane-2-carbonyl]pyrrolidine-2-carboxylic acid;

(2S,3R,4S,5S)-3-tert-butyl-5-(3-chloro-2-methylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[{2-[($^2$H$_3$)methyloxy]-5-(trifluoromethyl)phenyl}($^2$H$_2$)methyl]oxy}-5-(2-methylphenyl)-1-[(2S)-oxane-2-carbonyl]pyrrolidine-2-carboxylic acid;

(2S,3R,4S,5S)-3-tert-butyl-4-{[(5-tert-butyl-2-methoxyphenyl)($^2$H$_2$)methyl]oxy}-5-(2-methylphenyl)-1-[(2S)-oxane-2-carbonyl]pyrrolidine-2-carboxylic acid;

(2S,3R,4S,5S)-3-tert-butyl-4-[(2-chloro-5,7-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxy-5,8-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxy-5,7-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-methoxyphenyl)-1-[(2S)-oxane-2-carbonyl]pyrrolidine-2-carboxylic acid;

(2S,3R,4S,5S)-3-tert-butyl-5-(2-methoxyphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-5-(2-methoxyphenyl)-1-[(2S)-oxane-2-carbonyl]pyrrolidine-2-carboxylic acid;

(2S,3R,4S,5S)-3-tert-butyl-4-[(2-methoxy-6,8-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[2-methoxy-5-(1-methylcyclopropyl)pyridin-3-yl]methoxy}-5-(2-methylphenyl)-1-[(2S)-oxane-2-carbonyl]pyrrolidine-2-carboxylic acid;

(2S,3R,4S,5S)-3-tert-butyl-4-[(2-methoxy-8-methylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-{[2-methoxy-5-(1-methylcyclobutyl)phenyl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-[(5-tert-butyl-2-methoxyphenyl)methoxy]-5-(2-methylphenyl)-1-[(2S)-oxolane-2-carbonyl]pyrrolidine-2-carboxylic acid;

(2S,3R,4S,5S)-3-tert-butyl-1-(cyclohexanecarbonyl)-4-[(2-methoxy-5,8-dimethylquinolin-3-yl)methoxy]-5-{2-[(propan-2-yl)oxy]pyridin-3-yl}pyrrolidine-2-carboxylic acid;

(2S,3R,4S,5S)-3-tert-butyl-4-({2-[2-methoxy-5-(trifluoromethyl)phenyl]prop-2-en-1-yl}oxy)-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-4-[(5-tert-butyl-2-methoxyphenyl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-1-(cyclohexanecarbonyl)-4-[(2-methoxy-5,7-dimethylquinolin-3-yl)methoxy]-5-{2-[(propan-2-yl)oxy]pyridin-3-yl}pyrrolidine-2-carboxylic acid;

(2S,3R,4S,5S)-3-tert-butyl-4-[(2-methoxy-5,7-dimethylquinolin-3-yl)methoxy]-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-5-(2-ethylphenyl)-4-[(2-methoxyquinolin-3-yl)methoxy]-1-[(2S)-oxane-2-carbonyl]pyrrolidine-2-carboxylic acid;

(2S,3R,4S,5S)-3-tert-butyl-4-[(1-methyl-1H-benzimidazol-2-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2,2-dimethyl-2,3-dihydro-1-benzofuran-7-yl)pyrrolidine-2-carboxylic acid;

(2S,3R,4S,5S)-3-tert-butyl-1-(cyclohexanecarbonyl)-5-(2,2-dimethyl-2,3-dihydro-1-benzofuran-7-yl)-4-{[2-methoxy-5-(trifluoromethyl)pyridin-3-yl]methoxy}pyrrolidine-2-carboxylic acid;

(2S,3R,4S,5S)-3-tert-butyl-4-{2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{(2S)-2,3-dihydroxy-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{(2R)-2,3-dihydroxy-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{2-[2-methoxy-5-(trifluoromethyl)phenyl]-2-oxoethoxy}-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-{[(1,1,1-trifluoropropan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-({[(2R)-1,1,1-trifluoropropan-2-yl]oxy}carbonyl)pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-({[(2S)-1,1,1-trifluoropropan-2-yl]oxy}carbonyl)pyrrolidine-2-carboxylic acid;

(2S,3R,4S,5S)-3-tert-butyl-4-{2-hydroxy-2-[2-methoxy-5-(trifluoromethyl)phenyl]ethoxy}-5-(2-methylphenyl)-1-[(2S)-oxane-2-carbonyl]pyrrolidine-2-carboxylic acid;

(2S,3R,4S,5S)-3-tert-butyl-4-{2-methoxy-2-[2-methoxy-5-(trifluoromethyl)phenyl]ethoxy}-5-(2-methylphenyl)-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-({[(2S)-1,1,1-trifluoropropan-2-yl]oxy}carbonyl)pyrrolidine-2-carboxylic acid;

(2S,3R,4S,5S)-3-tert-butyl-4-{(2R)-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-{(2S)-2-[2-methoxy-5-(trifluoromethyl)phenyl]propoxy}-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-{2-[(propan-2-yl)oxy]pyridin-3-yl}-1-({[(2S)-1,1,1-trifluoropropan-2-yl]oxy}carbonyl)pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-[1-(trifluoromethyl)cyclopropane-1-carbonyl]pyrrolidine-2-carboxylic acid;

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-[1-(trifluoromethyl)cyclopentane-1-carbonyl]pyrrolidine-2-carboxylic acid;

(2S,3R,4S,5S)-3-tert-butyl-4-({3-[2-methoxy-5-(trifluoromethyl)pyridin-3-yl]prop-2-yn-1-yl}oxy)-5-phenyl-1-{[(propan-2-yl)oxy]carbonyl}pyrrolidine-2-carboxylic acid;

(2S,3R,4S,5S)-3-tert-butyl-5-(2-ethylphenyl)-4-({3-[2-methoxy-5-(trifluoromethyl)pyridin-3-yl]prop-2-yn-1-yl}oxy)-1-[(2S)-oxane-2-carbonyl]pyrrolidine-2-carboxylic acid;

(2S,3R,4S,5S)-3-tert-butyl-1-(cyclohexanecarbonyl)-5-{2-[(propan-2-yl)oxy]pyridin-3-yl}-4-{[5-(trifluoromethyl)-1-benzofuran-3-yl]methoxy}pyrrolidine-2-carboxylic acid;

(2S,3R,4S,5S)-3-tert-butyl-5-(2-ethylphenyl)-4-{3-[2-methoxy-5-(trifluoromethyl)pyridin-3-yl]propoxy}-1-[(2S)-oxane-2-carbonyl]pyrrolidine-2-carboxylic acid;

(2S,3R,4S,5S)-3-tert-butyl-5-(5-iodo-2-methylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-[(1R,2R)-2-(trifluoromethyl)cyclohexane-1-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-[(1S,2S)-2-(trifluoromethyl)cyclohexane-1-carbonyl]pyrrolidine-2-carboxylic acid;

(2S,3R,4S,5S)-3-tert-butyl-4-{2-[(5-chloro-2-methoxypyridin-3-yl)oxy]ethoxy}-5-(2-methylphenyl)-1-[(2S)-oxane-2-carbonyl]pyrrolidine-2-carboxylic acid;
(2S,3R,4S,5S)-3-tert-butyl-4-[(5-tert-butyl-2-methoxyphenyl)methoxy]-1-[(2S)-oxane-2-carbonyl]-5-{2-[(propan-2-yl)oxy]pyridin-3-yl}pyrrolidine-2-carboxylic acid;
(2S,3R,4S,5S)-3-tert-butyl-4-{[2-methoxy-5-(trifluoromethyl)pyridin-3-yl]methoxy}-5-[2-($^2$H$_3$)methylphenyl]-1-[(2S,3S)-(2,3-$^2$H$_2$)oxane-2-carbonyl](2-$^2$H)pyrrolidine-2-carboxylic acid;
(2S,3R,4S,5S)-3-tert-butyl-1-(cyclohexanecarbonyl)-4-{[2-methoxy-5-(1-methylcyclopropyl)pyridin-3-yl]methoxy}-5-{2-[(propan-2-yl)oxy]pyridin-3-yl}pyrrolidine-2-carboxylic acid;
(2S,3R,4S,5S)-3-tert-butyl-4-{2-[2-methoxy-5-(trifluoromethyl)phenoxy]ethoxy}-5-(2-methylphenyl)-1-[(2S)-oxane-2-carbonyl]pyrrolidine-2-carboxylic acid;
(2S,3R,4S,5S)-4-[(5-bromo-1-benzofuran-2-yl)methoxy]-3-tert-butyl-1-[(2S)-oxane-2-carbonyl]-5-{2-[(propan-2-yl)oxy]pyridin-3-yl}pyrrolidine-2-carboxylic acid;
(2S,3R,4S,5S)-3-tert-butyl-4-[(6-tert-butyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid;
(2S,3R,4S,5S)-3-tert-butyl-4-[(6-tert-butyl-2-methoxypyridin-3-yl)methoxy]-1-(cyclohexanecarbonyl)-5-{2-[(propan-2-yl)oxy]pyridin-3-yl}pyrrolidine-2-carboxylic acid;
(2S,3R,4S,5S)-3-tert-butyl-5-(2-ethylphenyl)-1-[(2S)-oxane-2-carbonyl]-4-{[7-(trifluoromethyl)-1-benzofuran-2-yl]methoxy}pyrrolidine-2-carboxylic acid;
(2S,3R,4S,5S)-3-tert-butyl-4-[(5-chloro-1-benzofuran-2-yl)methoxy]-5-(2-ethylphenyl)-1-[(2S)-oxane-2-carbonyl]pyrrolidine-2-carboxylic acid;
(2S,3R,4S,5S)-3-tert-butyl-4-[(5-cyclobutyl-2-methoxypyridin-3-yl)methoxy]-1-(naphthalene-1-sulfonyl)-5-{2-[(propan-2-yl)oxy]pyridin-3-yl}pyrrolidine-2-carboxylic acid;
(2S,3R,4S,5S)-3-tert-butyl-4-[(5-cyclobutyl-2-methoxypyridin-3-yl)methoxy]-1-(cyclohexanecarbonyl)-5-[2-(propan-2-yl)phenyl]pyrrolidine-2-carboxylic acid;
(2S,3R,4S,5S)-3-tert-butyl-4-[(5-cyclobutyl-1-benzofuran-2-yl)methoxy]-1-[(2S)-oxane-2-carbonyl]-5-{2-[(propan-2-yl)oxy]pyridin-3-yl}pyrrolidine-2-carboxylic acid; and pharmaceutically acceptable salts thereof.

Compounds of the invention are named by using Name 2015 Pack 2 naming algorithm by Advanced Chemical Development or Struct=Name naming algorithm as part of CHEMDRAW® ULTRA v. 12.0.2.1076 or Professional Version 15.0.0.106.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by precipitation or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by precipitation or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of Formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula (I) for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (I) may generally be prepared by conventional techniques known to those skilled in the art or by processes analogous to those described in the accompanying Examples using an appropriate isotopically-labelled reagents in place of the non-labelled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of Formula (I), (II), and (III) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of Formula (I), (II), and (III) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid, and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, refers to derivatives of the compounds of the invention which have cleavable groups. Such derivatives become, by solvolysis or under physiological conditions, the compounds of the invention which are pharmaceutically active in vivo. Prodrugs of the compounds of the invention are, within the scope of sound medical judgement, suitable for use in contact with the tissues of humans and lower animals without undue toxicity, irritation, allergic response, and the like, commensurate with a reasonable benefit/risk ratio, and effective for their intended use.

The invention contemplates compounds of Formula (I), (II), and (III) formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

When employed as a pharmaceutical, a compound of the invention is typically administered in the form of a pharmaceutical composition. Such compositions can be prepared in a manner well known in the pharmaceutical art and comprise a therapeutically effective amount of a compound of Formula (I), (II), (III), or a pharmaceutically acceptable salt thereof together with a pharmaceutically acceptable carrier. The phrase "pharmaceutical composition" refers to a composition suitable for administration in medical or veterinary use.

The term "pharmaceutically acceptable carrier" as used herein, means a non-toxic, inert solid, semi-solid or liquid filler, diluent, encapsulating material or formulation auxiliary of any type.

Methods of Use

The compounds and compositions using any amount and any route of administration may be administered to a subject for the treatment or prevention of cystic fibrosis, pancreatic insufficiency, Sjögren's syndrome (SS), chronic obstructive lung disease (COLD), or chronic obstructive airway disease (COAD).

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, and via implantation. In certain embodiments, the compounds and compositions thereof may be delivered orally. The compounds may also be delivered rectally, bucally, intravaginally, ocularly, or by insufflation. CFTR-modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as modulators of CFTR. Thus, the compounds and compositions are particularly useful for treating or lessening the severity or progression of a disease, disorder, or a condition where hyperactivity or inactivity of CFTR is involved. Accordingly, the invention provides a method for treating cystic fibrosis, pancreatic insufficiency, Sjögren's syndrome (SS), chronic obstructive lung disease (COLD), or chronic obstructive airway disease (COAD) in a subject, wherein the method comprises the step of administering to said subject a therapeutically effective amount of a compound of Formula (I), or a pharmaceutically acceptable salt thereof, or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, V, and/or VI mutation.

In a particular embodiment, the present invention provides compounds of the invention, or a pharmaceutically acceptable salt thereof, or a pharmaceutical composition comprising a compound of the invention, for use in medicine. In a particular embodiment, the present invention provides compounds of the invention, or a pharmaceutically acceptable salt thereof, or pharmaceutical compositions comprising a compound of the invention, for use in the treatment of cystic fibrosis, pancreatic insufficiency, Sjögren's syndrome (SS), chronic obstructive lung disease (COLD) or chronic obstructive airway disease (COAD). In a more particular embodiment, the present invention provides compounds of the invention or pharmaceutical compositions comprising a compound of the invention, for use in the treatment of cystic fibrosis. In a more particular embodiment, the cystic fibrosis is caused by a Class I, II, III, IV, V, and/or VI mutation.

One embodiment is directed to the use of a compound according to Formula (I), (II), (III), or a pharmaceutically acceptable salt thereof in the preparation of a medicament. The medicament optionally can comprise one or more additional therapeutic agents. In some embodiments, the medicament is for use in the treatment of cystic fibrosis, pancreatic insufficiency, Sjögren's syndrome (SS), chronic obstructive lung disease (COLD) or chronic obstructive airway disease (COAD). In a particular embodiment, the medicament is for use in the treatment of cystic fibrosis. In a more particular embodiment, the cystic fibrosis is caused by a Class I, II, III, IV, V, and/or VI mutation.

This invention also is directed to the use of a compound according to Formula (I), (II), (III), or a pharmaceutically acceptable salt thereof in the manufacture of a medicament for the treatment of cystic fibrosis, Sjögren's syndrome, pancreatic insufficiency, chronic obstructive lung disease, and chronic obstructive airway disease. The medicament optionally can comprise one or more additional therapeutic agents. In a particular embodiment, the invention is directed to the use of a compound according to Formula (I) II), (III), or a pharmaceutically acceptable salt thereof in the manufacture of a medicament for the treatment of cystic fibrosis. In a more particular embodiment, the cystic fibrosis is caused by a Class I, II, III, IV, V, and/or VI mutation.

In one embodiment, the present invention provides pharmaceutical compositions comprising a compound of the invention, or a pharmaceutically acceptable salt thereof, and one or more additional therapeutic agents. In another embodiment, the present invention provides pharmaceutical compositions comprising a compound of the invention, or a pharmaceutically acceptable salt thereof, and one or more additional therapeutic agents wherein the additional therapeutic agents are selected from the group consisting of CFTR modulators and CFTR amplifiers. In another embodiment, the present invention provides pharmaceutical compositions comprising a compound of the invention, or a pharmaceutically acceptable salt thereof, and one or more additional therapeutic agents wherein the additional therapeutic agents are CFTR modulators.

In one embodiment, the present invention provides pharmaceutical compositions comprising a compound of the invention, or a pharmaceutically acceptable salt thereof, and one or more additional therapeutic agents. In one embodiment, the present invention provides pharmaceutical compositions comprising a compound of the invention, or a pharmaceutically acceptable salt thereof, one potentiator, and one or more additional correctors. In one embodiment, the present invention provides pharmaceutical compositions comprising a compound of the invention, and another therapeutic agent. In a particular embodiment, the other therapeutic agent is a cystic fibrosis treatment agent. In one embodiment, the present invention provides a method for treating cystic fibrosis in a subject comprising administering a compound of the invention, or a pharmaceutically acceptable salt thereof, and one or more additional therapeutic agents. In another embodiment, the present invention provides a method for treating cystic fibrosis in a subject comprising administering a compound of the invention, or a pharmaceutically acceptable salt thereof, and one or more additional therapeutic agents wherein the additional therapeutic agents are selected from the group consisting of CFTR modulators and CFTR amplifiers. In one embodiment, the present invention provides a method for treating cystic fibrosis in a subject comprising administering a compound of the invention, or a pharmaceutically acceptable salt thereof, and one or more additional therapeutic agents wherein the additional therapeutic agents are CFTR modulators. In one embodiment, the present invention provides a method for treating cystic fibrosis in a subject comprising administering a compound of the invention, or a pharmaceutically acceptable salt thereof, and, and another therapeutic agent. In a particular embodiment, the other therapeutic agent is a cystic fibrosis treatment agent. In one embodiment, the present invention provides a method for treating cystic fibrosis in a subject comprising administering a therapeutically effective amount of a compound of the invention, or a pharmaceutically acceptable salt thereof. In a particular embodiment, the additional therapeutic agent(s) are one potentiator, and one or more additional correctors. In another embodiment, the additional therapeutic agent(s) is selected from the group consisting of CFTR modulators and CFTR amplifiers. In another embodiment, the other therapeutic agent(s) is a CFTR modulator. In a more particular embodiment, the cystic fibrosis is caused by a Class I, II, III, IV, V, and/or VI mutation.

The present compounds or pharmaceutically acceptable salts thereof may be administered as the sole active agent or it may be co-administered with other therapeutic agents, including other compounds or pharmaceutically acceptable salts thereof, that demonstrate the same or a similar therapeutic activity and that are determined to be safe and efficacious for such combined administration. The present compounds may be co-administered to a subject. The term "co-administered" means the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or pharmaceutically acceptable salts thereof may be co-administered with a therapeutically effective amount of one or more additional therapeutic agents to treat a CFTR mediated disease, where examples of therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers. In one embodiment, the CFTR mediated disease is cystic fibrosis, chronic obstructive pulmonary disease (COPD), dry eye disease, pancreatic insufficiency, or Sjögren's syndrome. In one embodiment, the CFTR mediated disease is cystic fibrosis.

In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulators. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of CFTR potentiators include, but are not limited to, Ivacaftor (VX-770), CTP-656, NVS-QBW251, FD1860293, GLPG2451, GLPG3067, GLPG1837, PTI-808, N-(3-carbamoyl-5,5,7,7-tetramethyl-5,7-dihydro-4H-thieno[2,3-c]pyran-2-yl)-1H-pyrazole-5-carboxamide, and 3-amino-N-[(2S)-2-hydroxypropyl]-5-{[4-(trifluoromethoxy)phenyl]sulfonyl}pyridine-2-carboxamide.
Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823, WO2014/180562, WO2015018823, WO 2016193812 and U.S. application Ser. No. 15/502,892.

In one embodiment, the potentiator can be selected from the group consisting of
Ivacaftor (VX-770, N-(2,4-di-tert-butyl-5-hydroxyphenyl)-4-oxo-1,4-dihydroquinoline-3-carboxamide);
GLPG1837;
GLP-2451;
PTI-808;
CTP-656;
NVS-QBW251;
GLPG3067;
FD1860293;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-4,7-dihydro-5H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide
2-(1-hydroxycyclopropanecarboxamido)-5,5,7,7-tetramethyl-5,7-dihydro-4H-thieno[2,3-c]pyran-3-carboxamide;
5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;
N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;
N-(3-carbamoyl-5,5,7,7-tetramethyl-5,7-dihydro-4H-thieno[2,3-c]pyran-2-yl)-5-(trifluoromethyl)-1H-pyrazole-3-carboxamide;
5-tert-butyl-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-5-ethyl-1H-pyrazole-3-carboxamide;
N-(3-carbamoyl-5,5,7,7-tetramethyl-5,7-dihydro-4H-thieno[2,3-c]pyran-2-yl)-3-ethyl-4-methyl-1H-pyrazole-5-carboxamide;
2-(2-hydroxypropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-4-chloro-1H-pyrazole-3-carboxamide;
N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;
4-bromo-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-4-chloro-5-methyl-1H-pyrazole-3-carboxamide;
N-(3-carbamoyl-5,5,7,7-tetramethyl-5,7-dihydro-4H-thieno[2,3-c]pyran-2-yl)-4-methyl-1H-pyrazole-3-carboxamide;
2-(2-hydroxy-3,3-dimethylbutanamido)-5,5,7,7-tetramethyl-5,7-dihydro-4H-thieno[2,3-c]pyran-3-carboxamide;
2-[(2-hydroxy-4-methyl-pentanoyl)amino]-5,5,7,7-tetramethyl-4H-thieno[2,3-c]pyran-3-carboxamide;
5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;
N-(3-carbamoyl-5,5,7,7-tetramethyl-4H-thieno[2,3-c]pyran-2-yl)-4-(3-methoxypropyl)-1H-pyrazole-3-carboxamide;
N-(3-carbamoyl-5,5,7,7-tetramethyl-4H-thieno[2,3-c]pyran-2-yl)-4-(2-ethoxyethyl)-1H-pyrazole-3-carboxamide;
2-[[(2S)-2-hydroxy-3,3-dimethyl-butanoyl]amino]-5,5,7,7-tetramethyl-4H-thieno[2,3-c]pyran-3-carboxamide;

2-[[(2R)-2-hydroxy-3,3-dimethyl-butanoyl]amino]-5,5,7,7-tetramethyl-4H-thieno[2,3-c]pyran-3-carboxamide;
2-[(2-hydroxy-2,3,3-trimethyl-butanoyl)amino]-5,5,7,7-tetramethyl-4H-thieno[2,3-c]pyran-3-carboxamide;
[5-[(3-carbamoyl-5,5,7,7-tetramethyl-4H-thieno[2,3-c]pyran-2-yl)carbamoyl]pyrazol-1-yl]methyl dihydrogen phosphate;
[3-[(3-carbamoyl-5,5,7,7-tetramethyl-4H-thieno[2,3-c]pyran-2-yl)carbamoyl]pyrazol-1-yl]methyl dihydrogen phosphate;
N-(3-carbamoyl-5,5,7,7-tetramethyl-4H-thieno[2,3-c]pyran-2-yl)-4-(1,4-dioxan-2-yl)-1H-pyrazole-3-carboxamide;
5,5,7,7-tetramethyl-2-[[(2S)-3,3,3-trifluoro-2-hydroxy-2-methyl-propanoyl]amino]-4H-thieno[2,3-c]pyran-3-carboxamide;
2-[[(2S)-2-hydroxypropanoyl]amino]-5,5,7,7-tetramethyl-4H-thieno[2,3-c]pyran-3-carboxamide;
3-amino-N-(2-hydroxy-2-methylpropyl)-5-{[4-(trifluoromethoxy)phenyl]sulfonyl}pyridine-2-carboxamide;
3-amino-N-[(4-hydroxy-1-methylpiperidin-4-yl)methyl]-5-{[4-(trifluoromethoxy)phenyl]sulfonyl}pyridine-2-carboxamide;
3-amino-N-(3-hydroxy-2, 2-dimethylpropyl)-5-{[4-(trifluoromethoxy)phenyl]sulfonyl}pyridine-2-carboxamide;
3-amino-5-[(4-fluorophenyl)sulfonyl]-N-[(1-hydroxycyclopropyl)methyl]pyridine-2-carboxamide;
3-amino-5-[(4-fluorophenyl)sulfonyl]-N-[(2R)-3,3,3-trifluoro-2-hydroxypropyl]pyridine-2-carboxamide;
3-amino-5-[(3-fluorophenyl)sulfonyl]-N-(2-hydroxy-2-methylpropyl)pyridine-2-carboxamide;
3-amino-N-[2-(cyclopropylamino)-2-oxoethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(azetidin-1-yl)methanone;
(3-amino-5-{[4-(trifluoromethoxy)phenyl]sulfonyl}pyridin-2-yl)[3-(hydroxymethyl)azetidin-1-yl]methanone;
(3-amino-5-{[4-(trifluoromethoxy)phenyl]sulfonyl}pyridin-2-yl)(3-fluoroazetidin-1-yl)methanone;
3-amino-N-[(2R)-2-hydroxy-3-methoxypropyl]-5-{[4-(trifluoromethyl)phenyl]sulfonyl}pyridine-2-carboxamide;
(3-amino-5-{[2-fluoro-4-(trifluoromethoxy)phenyl]sulfonyl}pyridin-2-yl)(3-hydroxyazetidin-1-yl)methanone;
(3-amino-5-{[2-(trifluoromethoxy)phenyl]sulfonyl}pyridin-2-yl)(3,3-difluoroazetidin-1-yl)methanone;
rac-3-amino-N-[(3R,4S)-4-hydroxytetrahydro-2H-pyran-3-yl]-5-{[2-(trifluoromethoxy)phenyl]sulfonyl}pyridine-2-carboxamide;
3-amino-5-[(4,4-difluoropiperidin-1-yl)sulfonyl]-N-(3,3,3-trifluoro-2-hydroxypropyl)pyridine-2-carboxamide;
(3-amino-5-{[2-(trifluoromethoxy)phenyl]sulfonyl}pyridin-2-yl)[3-hydroxy-3-(trifluoromethyl)azetidin-1-yl]methanone;
3-amino-N-(2-hydroxy-4-methylpentyl)-5-{[4-(trifluoromethoxy)phenyl]sulfonyl}pyridine-2-carboxamide;
(3-amino-5-{[4-(trifluoromethyl)phenyl]sulfonyl}pyridin-2-yl)(3-hydroxy-3-methylazetidin-1-yl)methanone;
3-amino-N-(3,3,3-trifluoro-2-hydroxypropyl)-5-{[4-(trifluoromethyl)piperidin-1-yl]sulfonyl}pyridine-2-carboxamide;
3-amino-N-[2-hydroxy-1-(4-methoxyphenyl)ethyl]-5-{[4-(trifluoromethoxy)phenyl]sulfonyl}pyridine-2-carboxamide;
3-amino-5-[(3,3-difluoroazetidin-1-yl)sulfonyl]-N-(3,3,3-trifluoro-2-hydroxypropyl)pyridine-2-carboxamide;
3-amino-5-{[2-fluoro-4-(trifluoromethyl)phenyl]sulfonyl}-N-[(2S)-2-hydroxypropyl]pyridine-2-carboxamide;
3-amino-5-{[2-fluoro-4-(trifluoromethyl)phenyl]sulfonyl}-N-[(2R)-2-hydroxy-3-methoxypropyl]pyridine-2-carboxamide;
3-amino-N-[2-oxo-2-(propan-2-ylamino)ethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3R)-tetrahydrofuran-3-ylmethyl]pyridine-2-carboxamide;
(3-amino-5-{[2-fluoro-4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3S)-tetrahydrofuran-3-ylmethyl]pyridine-2-carboxamide;
3-amino-5-{[2-fluoro-4-(trifluoromethoxy)phenyl]sulfonyl}-N-[(3S)-tetrahydrofuran-3-ylmethyl]pyridine-2-carboxamide;
3-amino-N-[2-hydroxy-3-(2,2,2-trifluoroethoxy)propyl]-5-{[4-(trifluoromethyl)phenyl]sulfonyl}pyridine-2-carboxamide;
3-amino-N-(3-tert-butoxy-2-hydroxypropyl)-5-{[2-fluoro-4-(trifluoromethyl)phenyl]sulfonyl}pyridine-2-carboxamide;
[3-amino-5-(phenylsulfonyl)pyridin-2-yl][3-hydroxy-3-(trifluoromethyl)azetidin-1-yl]methanone;
{3-amino-5-[(3-fluorophenyl)sulfonyl]pyridin-2-yl}[3-hydroxy-3-(trifluoromethyl)azetidin-1-yl]methanone; and
3-amino-N-[(2S)-2-hydroxypropyl]-5-{[4-(trifluoromethoxy)phenyl]sulfonyl}pyridine-2-carboxamide.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2851, GLPG2222, GLPG2665, GLPG2737, GLPG3221, PTI-801, VX-152, VX-440, VX-445, VX-659, FDL169, FDL304, FD2052160, and FD2035659. Examples of correctors are also disclosed in U.S. application Ser. Nos. 14/925,649, 14/926,727, 15/205,512, 15/287,922, 15/287,911, 15/287,922, 15/287,911, and 15/492,094.

In one embodiment, the corrector(s) can be selected from the group consisting of
Lumacaftor (VX-809);
1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);
PTI-801;
VX-983;
GLPG2665;
GLPG2851;
GLPG2222;
VX-152;
VX-440;
VX-659;
VX-445;
FDL169
FDL304;
FD2052160;
FD2035659;

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-3,4-dihydro-2H-chromen-2-yl]benzoic acid;

3-[(2R,4S)-4-({[1-(2,2-difluoro-1,3-benzodioxol-5-yl)cyclopropyl]carbonyl}amino)-6-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;

3-[(2R,4R)-4-{[1-(2,2-difluoro-1,3-benzodioxol-5-yl)cyclopropyl]carbonyl}amino)-7-fluoro-3,4-dihydro-2H-chromen-2-yl]benzoic acid;

3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;

3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;

3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

4-[(2R,4S)-4-({[1-(2,2-difluoro-1,3-benzodioxol-5-yl)cyclopropyl]carbonyl}amino)tetrahydro-2H-pyran-2-yl]benzoic acid;

3-cyclobutyl-4-[4-(morpholin-4-yl)piperidin-1-yl]-1-phenyl-1H-pyrazolo[3,4-b]pyridine-6-carboxylic acid;

3-cyclobutyl-1-phenyl-4-{4-[(pyrrolidin-1-yl)methyl]piperidin-1-yl}-1H-pyrazolo[3,4-b]pyridine-6-carboxylic acid;

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid;

6-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3, 4-dihydro-2H-1-benzopyran-2-yl]cyclohexane-1-carboxylic acid;

6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;

cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2S,4S)-7-(difluoromethoxy)-4-{[(7R)-2,2-difluoro-7-methyl-6, 7-dihydro-2H-furo[2, 3-1][1,3]benzodioxole-7-carbonyl]amino}-3,4-dihydro-2H-1-benzopyran-2-yl]cyclohexane-1-carboxylic acid;

1-[(2R,4R)-4-{[(7R)-2,2-difluoro-7-methyl-6,7-dihydro-2H-furo[2,3-][1,3]benzodioxole-7-carbonyl]amino}-7-(trifluoromethoxy)-3,4-dihydro-2H-1-benzopyran-2-yl]cyclopropane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-][1,3]benzodioxole-7-carbonyl]amino}-7-methoxy-3,4-dihydro-2H-1-benzopyran-2-yl]cyclohexane-1-carboxylic acid;

trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid; and trans-4-[(2R,4R)-4-{[(7R)-2,2-difluoro-7-methyl-6,7-dihydro-2H-furo[2,3-][1,3]benzodioxole-7-carbonyl]amino}-7-(trifluoromethoxy)-3,4-dihydro-2H-1-benzopyran-2-yl]cyclohexane-1-carboxylic acid.

In one embodiment, the additional therapeutic agent is a CFTR amplifier. CFTR amplifiers enhance the effect of known CFTR modulators, such as potentiators and correctors. Examples of CFTR amplifiers are PTI130 and PTI-428. Examples of amplifiers are also disclosed in publications: WO2015138909 and WO2015138934.

In one embodiment, the additional therapeutic agent is a CFTR stabilizer. CFTR stabilizers enhance the stability of corrected CFTR that has been treated with a corrector, corrector/potentiator or other CFTR modulator combination(s). An example of a CFTR stabilizer is cavosonstat (N91115). Examples of stabilizers are also disclosed in publication: WO2012048181.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in PCT Publication No. WO2009074575 and WO2013043720; and U.S. Pat. No. 8,999,976.

In one embodiment, the ENaC inhibitor is VX-371.

In one embodiment, the ENaC inhibitor is SPX-101 (S18).

In one embodiment, the present invention provides pharmaceutical compositions comprising a compound of the invention, or a pharmaceutically acceptable salt thereof, and one or more additional therapeutic agents. In a particular embodiment, the additional therapeutic agents are selected from the group consisting of CFTR modulators and CFTR amplifiers. In a further embodiment, the additional therapeutic agents are CFTR modulators. In one embodiment, the present invention provides pharmaceutical compositions comprising a compound of the invention, or a pharmaceutically acceptable salt thereof, one potentiator, and one or more additional correctors.

This invention also is directed to kits that comprise one or more compounds and/or salts of the invention, and, optionally, one or more additional therapeutic agents.

This invention also is directed to methods of use of the compounds, salts, compositions, and/or kits of the invention to, with or without one or more additional therapeutic agents, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

Chemical Synthetic Procedures

General

The compounds of the invention can be prepared from readily available starting materials using the following general methods and procedures. It will be appreciated that where typical or preferred process conditions (i.e. reaction temperatures, times, mole ratios of reactants, solvents, pressures, etc.) were given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Protective Groups in Organic Synthesis Third Edition; Greene, T W and Wuts, P G M, Eds.; Wiley-Interscience: New York, 1991).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). $^1$H NMR spectra were recorded on a Bruker Advance 300 NMR spectrometer (300 MHz), an Agilent 400 MHz NMR spectrometer or a 500 MHz spectrometer. Chemical shifts (δ ppm) for $^1$H NMR spectra were reported in parts per million (ppm) relative to tetramethylsilane (δ ppm 0.00) or the appropriate residual solvent peak, i.e. CHCl$_3$ (δ ppm 7.27), as internal reference. Multiplicities were given as singlet (s), doublet (d), doublet of doublets (dd), doublet of doublets of doublets (ddd), doublet of doublets of doublets of doublets (dddd), doublet of doublets of quartets (ddq), doublet of doublets of triplets (ddt), doublet of quartets (dq), doublet of triplets of doublets (dtd), heptet (hept), triplet (t), triplet of doublets of doublets (tdd), triplet of quartets (tq), quartet (q), quartet of doublets (qd), quartet of triplets (qt), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 μm, 2.1 mm ID×50 mm L, Waters Acquity UPLC BEH C18 1.7 μm, 2.1 mm ID×30 mm L, or Waters Xterra® MS 5 μm C18, 100×4.6 mm. The methods were using either MeCN/H$_2$O gradients (H$_2$O contains either 0.1% TFA or 0.1% NH$_3$) or MeOH/H$_2$O gradients (H$_2$O contains 0.05% TFA). Microwave heating was performed with a Biotage® Initiator.

Racemic mixtures were separated on an Agilent HP1100 system with UV detection. Column used: Chiralpak® IA (10×250 mm, 5 μm). Solvents used: iPrOH and tBME. Enantiomeric purity was determined on an Agilent HP1100 system with UV detection. Column used: Chiralpak® IA (4.6×250 mm, 5 µm). Solvents used: iPrOH and tBME.

Reverse Phase Purification Methods

Prep LC/MS Method TFA6

Samples were purified by reverse phase preparative HPLC on a Phenomenex® Luna® C8(2) 5 µm 100 Å AXIA™ column (50 mm×21.2 mm). A gradient of acetonitrile (A) and 0.1% trifluoroacetic acid in water (B) was used, at a flow rate of 40 mL/minute (0-0.5 min 15% A, 0.5-8.0 min linear gradient 15-100% A, 8.0-9.0 min 100% A, 7.0-8.9 min 100% A, 9.0-9.1 min linear gradient 100-15% A, 9.1-10 min 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method TFA7

Samples were purified by reverse phase preparative HPLC on a Phenomenex® Luna® C8(2) 5 µm 100 Å AXIA™ column (50 mm×21.2 mm). A gradient of acetonitrile (A) and 0.1% trifluoroacetic acid in water (B) was used, at a flow rate of 40 mL/minute (0-0.5 min 25% A, 0.5-8.0 min linear gradient 25-100% A, 8.0-9.0 min 100% A, 7.0-8.9 min 100% A, 9.0-9.1 min linear gradient 100-25% A, 9.1-10 min 25% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method TFA8

Samples were purified by reverse phase preparative HPLC on a Phenomenex® Luna® C8(2) 5 µm 100 Å AXIA™ column (50 mm×21.2 mm). A gradient of acetonitrile (A) and 0.1% trifluoroacetic acid in water (B) was used, at a flow rate of 40 mL/minute (0-0.5 min 35% A, 0.5-8.0 min linear gradient 35-100% A, 8.0-9.0 min 100% A, 7.0-8.9 min 100% A, 9.0-9.1 min linear gradient 100-35% A, 9.1-10 min 35% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method TFA10

Samples were purified by reverse phase preparative HPLC on a Phenomenex® Luna® C8(2) 5 µm 100 Å AXIA™ column (50 mm×21.2 mm). A gradient of acetonitrile (A) and 0.1% trifluoroacetic acid in water (B) was used, at a flow rate of 30 mL/minute (0-0.2 min 5% A, 0.2-3.0 min linear gradient 5-100% A, 4.1-4.5 min 100-5% A, 4.5-5.0 min 5% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method AA6

Samples were purified by reverse phase preparative HPLC on a Phenomenex® Luna® C8(2) 5 µm 100 Å AXIA™ column (50 mm×21.2 mm). A gradient of acetonitrile (A) and 0.1% ammonium acetate in water (B) was used, at a flow rate of 40 mL/minute (0-0.5 min 15% A, 0.5-8.0 min linear gradient 15-100% A, 8.0-9.0 min 100% A, 7.0-8.9 min 100% A, 9.0-9.1 min linear gradient 100-15% A, 9.1-10 min 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method AA7

Samples were purified by reverse phase preparative HPLC on a Phenomenex® Luna® C8(2) 5 µm 100 Å AXIA™ (50 mm×21.2 mm). A gradient of acetonitrile (A) and 0.1% ammonium acetate in water (B) was used, at a flow rate of 40 mL/minute (0-0.5 min 25% A, 0.5-8.0 min linear gradient 25-100% A, 8.0-9.0 min 100% A, 7.0-8.9 min 100% A, 9.0-9.1 min linear gradient 100-25% A, 9.1-10 min 25% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method AA8

Samples were purified by reverse phase preparative HPLC on a Phenomenex® Luna® C8(2) 5 m 100 Å AXIA™ column (50 mm×21.2 mm). A gradient of acetonitrile (A) and 0.1% ammonium acetate in water (B) was used, at a flow rate of 40 mL/minute (0-0.5 min 35% A, 0.5-8.0 min linear gradient 35-100% A, 8.0-9.0 min 100% A, 7.0-8.9 min 100% A, 9.0-9.1 min linear gradient 100-35% A, 9.1-10 min 35% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Stereochemistry of final compounds was arbitrarily assigned in some cases, based on the order of elution and/or activity with respect to existing analogs.

List of abbreviations that may be used in the experimental section:

| Abbreviation | Definition |
|---|---|
| MeCN | acetonitrile |
| eq | equivalents |
| TFA | trifluoroacetic acid |
| NMR | nuclear magnetic resonance |
| DMSO | dimethyl sulfoxide |
| LC/MS or LCMS | liquid chromatography - mass spectrometry |
| MeOH | methanol |
| tBME | tert-butyl methyl ether |
| s | singlet |
| br s | broad singlet |
| d | duplet or doublet |
| dd | double duplet or doublet of doublets |
| m | multiplet |
| min | minute |
| mL or mL | milliliter |
| μL | microliter |
| g | gram |
| mg | milligram |
| mmol | millimoles |
| HPLC | high pressure liquid chromatography |
| ppm | parts per million |
| Xantphos | 4,5-bis(diphenylphosphino)-9,9-dimethylxanthene |
| μm | micrometer |
| iPrOH | iso-propanol |
| DBU | 1,8-diazabicycloundec-7-ene |
| HATU | 1-[bis(dimethylamino)methylene]-1H-1,2,3-triazolo[4,5-b]pyridinium 3-oxid hexafluorophosphate |
| EDC or EDCI | N-(3-dimethylaminopropyl)-N'-ethylcarbodiimide |

Synthetic Preparation of the Compounds of the Invention Schemes

The compounds of the present disclosure can be better understood in connection with the following synthetic schemes and methods which illustrate a means by which the compounds can be prepared. The compounds of this disclosure can be prepared by a variety of synthetic procedures. Representative procedures are shown in, but are not limited to, Schemes 1-7.

Scheme 1

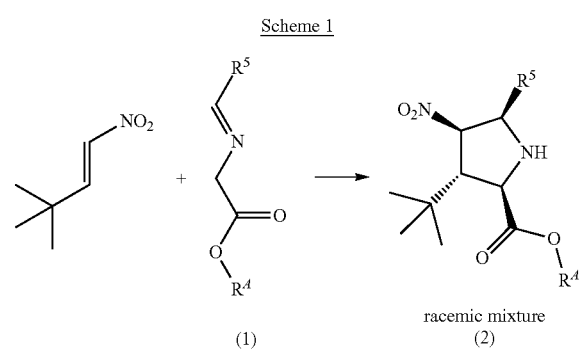

racemic mixture
(1)     (2)

As shown in Scheme 1, core compounds of formula (2) can be prepared from compounds of formula (1). Compounds of formula (1), wherein $R^A$ is typically $C_1$-$C_6$ alkyl and $R^5$ is as described herein, can be treated first with lithium bromide, followed by (E)-3, 3-dimethyl-1-nitrobut-1-ene in the presence of a base such as, but not limited to, 1,8-diazabicyclo[5.4.0]undec-7-ene, triethylamine, or potassium carbonate in a solvent such as but not limited to toluene, or tetrahydrofuran to provide a racemic mixture of compounds of formula (2). The reaction is typically performed at a reduced temperature, such as −78° C., before quenching with aqueous saturated ammonium chloride.

Alternatively, a mixture of compounds of formula (1) and (E)-3, 3-dimethyl-1-nitrobut-1-ene, wherein $R^A$ is typically $C_1$-$C_6$ alkyl and $R^5$ is as described herein, can be treated with acetyl(oxo)silver in the presence of molecular sieves and a base such as, but not limited to, 1,8-diazabicyclo[5.4.0] undec-7-ene, triethylamine, or potassium carbonate in a solvent such as but not limited to toluene or tetrahydrofuran to provide a racemic mixture of core compounds of formula (2). The reaction is typically performed in an ice bath before warming to room temperature and quenching with aqueous saturated aqueous ammonium chloride.

Scheme 2

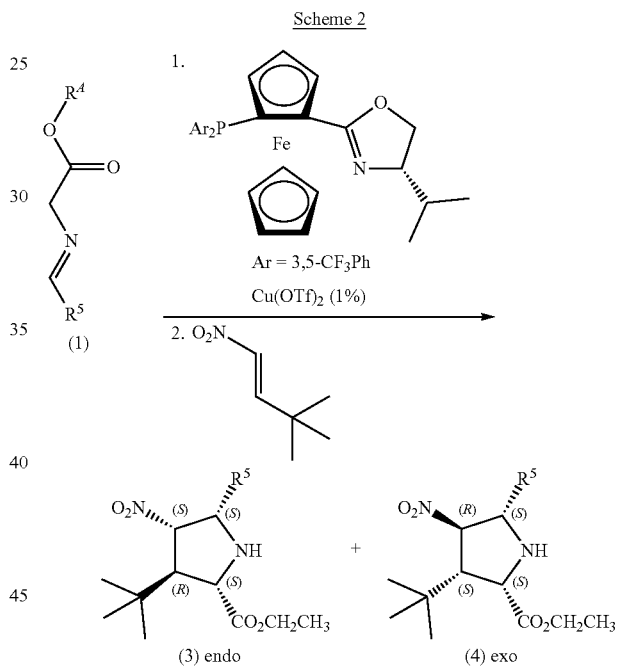

(3) endo     (4) exo

As shown in Scheme 2, core compounds of formula (3) and (4) can be prepared from compounds of formula (1). Compounds of formula (1), wherein $R^A$ is typically $C_1$-$C_6$ alkyl and $R^5$ is as described herein, can be added to a prepared mixture of (2-(bis(3,5-bis(trifluoromethyl)phenyl) phosphino)-3-((S)-4-isopropyl-4,5-dihydrooxazol-2-yl)cyclopenta-2,4-dien-1-yl)(cyclopenta-2,4-dien-1-yl)iron and copper (I) triflate dimer in a solvent such as, but not limited to, tetrahydrofuran, under an inert gas such as but not limited to argon or nitrogen, followed by the addition of (E)-3, 3-dimethyl-1-nitrobut-1-ene, and a base such as, but not limited to potassium tert-butoxide, to provide core compounds of formula (3) and (4). The reaction is typically performed at reduced temperature, such as but not limited to 0° C. Core compounds (3) and (4) may be obtained as a mixture or may be separated by precipitation or chromatography. Core compound (3) is typically the major isomer.

Scheme 3

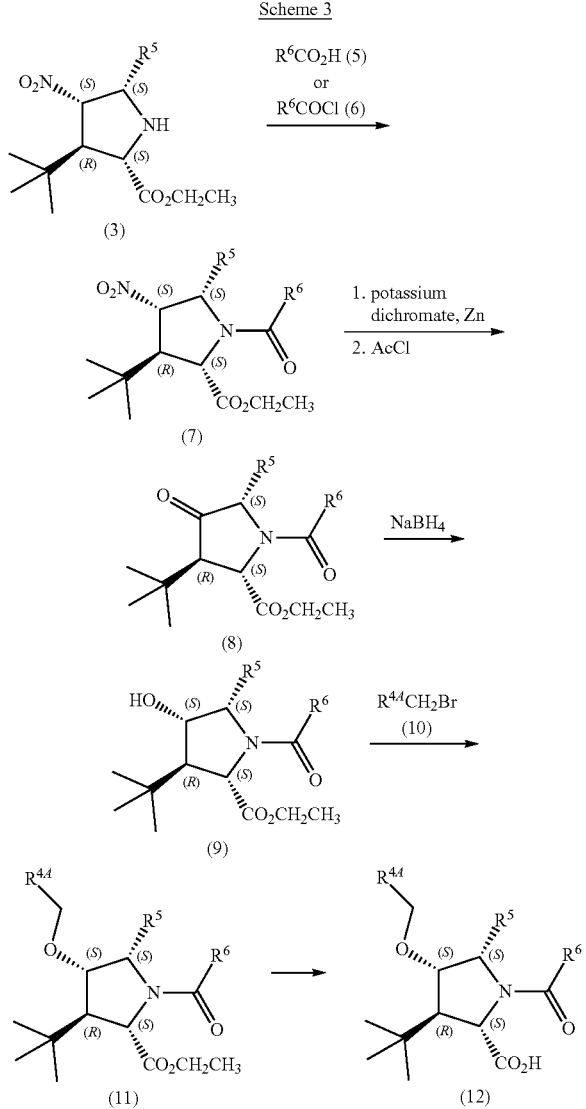

As shown in Scheme 3, compounds of formula (12) can be prepared from compounds of formula (3).

Carboxylic acids of formula (5) can be coupled with amine cores of formula (3) to provide compounds of formula (7). Examples of conditions known to generate compounds of formula (7) from a mixture of a carboxylic acid and an amine include, but are not limited to, adding a coupling reagent such as, but not limited to, N-(3-dimethylaminopropyl)-N-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to 4-(dimethylamino)pyridine (DMAP), 1-hydroxy-7-azabenzotriazole (HOAT) and 1-hydroxybenzotriazole (HOBT). The reaction may be carried out optionally in the presence of a base such as, but not limited to, triethylamine, N,N-diisopropylethylamine or pyridine. The coupling reaction may be carried out in solvents such as, but not limited to, tetrahydrofuran, N,N-dimethylformamide, N,N-dimethylacetamide, dimethyl sulfoxide, dichloromethane, and ethyl acetate. The reactions may be carried out at ambient temperature or heated. The heating can be accomplished either conventionally or with microwave irradiation.

Alternatively, carboxylic acids of formula (5) can be converted to the corresponding acid chlorides of formula (6) by reaction with thionyl chloride, $PCl_3$, $PCl_5$, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides of formula (6) (or commercially available acid chlorides of formula (6)) can then reacted with core amines of formula (3) optionally in the presence of a base such as a tertiary amine base such as but not limited to triethylamine or N,N-diisopropylethylamine or an aromatic base such as pyridine, at room temperature or heated in a solvent such as dichloromethane to provide compounds of formula (7).

Compounds of formula (7) can be reacted with a freshly prepared solution of chromium (II) chloride at to provide compounds of formula (8). The reaction is typically performed under nitrogen at an elevated temperature such as reflux, in a solvent such as, but not limited to, ethanol. Remaining hydrolyzed acid, if any, can be converted back to the ester using esterification conditions known in the art and literature such as acetyl chloride in refluxing ethanol. Compounds of formula (9) can be prepared from compounds of formula (8) by treating the latter with a reducing agent such as, but not limited to, sodium borohydride. The reaction is typically performed at a reduced temperature such as 0° C. or below, in a solvent such as, but not limited to, ethanol, methanol and the like. Alcohols of formula (9) can be treated with a base such as, but not limited to, sodium hydride, potassium carbonate, or potassium tert-butoxide and compounds of formula (10), wherein $R^{4,4}$ is the ring of $R^4$ as described herein, to provide compounds of formula (11). The addition may be performed at reduced temperature, such as 0° C., before warming up to ambient or elevated temperature in a solvent such as, but not limited to, dimethylformamide, tetrahydrofuran, and the like. Esters of formula (10) can be hydrolyzed in an aqueous hydroxide solution to provide acids of formula (12) which are representative of Formula (I). The reaction is typically performed in a solvent such as but not limited to methanol, tetrahydrofuran, or mixtures thereof, and may be performed at ambient temperature or an elevated temperature.

Scheme 4
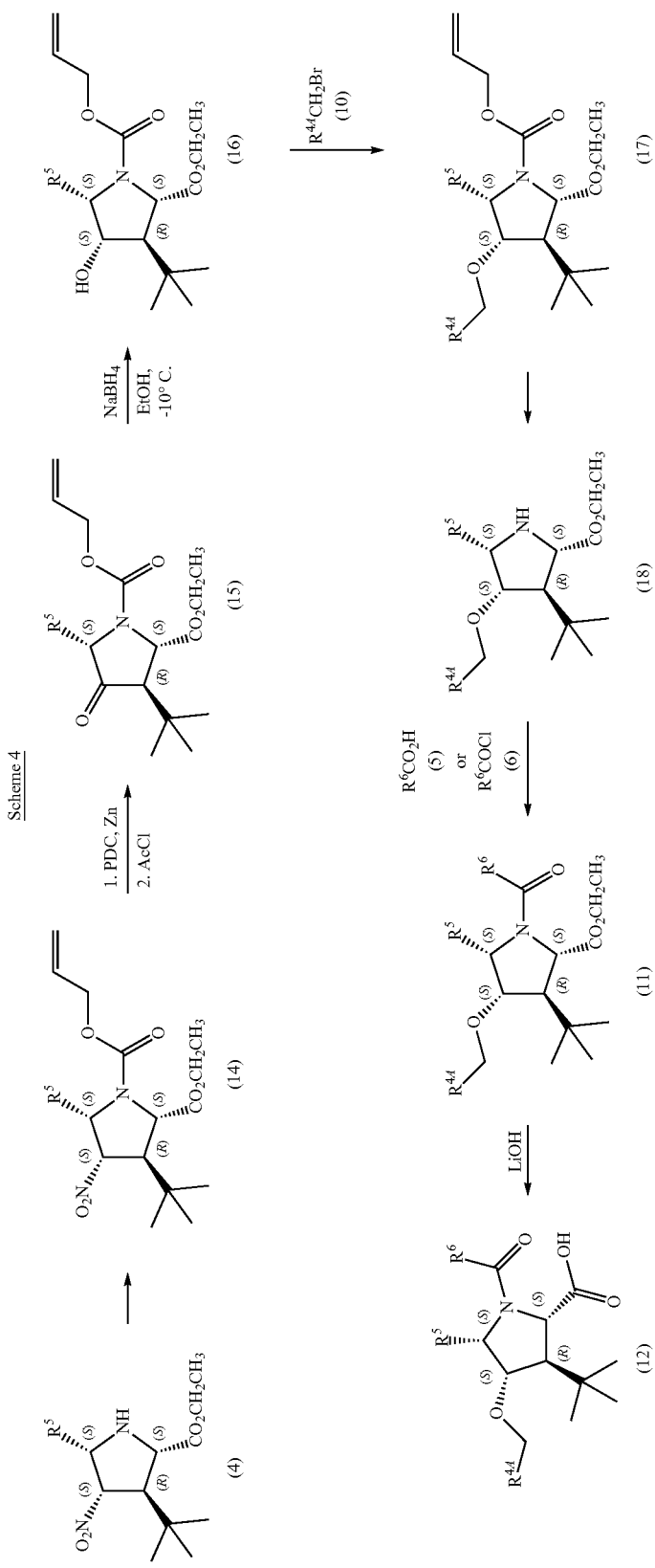

As shown in Scheme 4, compounds of formula (12), which are representative of compounds of Formula (I), can be prepared from compounds of formula (4). Compounds of formula (4) in saturated aqueous NaHCO$_3$ and a solvent such as, but not limited to, toluene, can be treated with allyl carbonochloridate to provide compounds of formula (14). The reaction is typically performed at ambient temperature. Compounds of formula (14) can be reacted with a freshly prepared solution of chromium (II) chloride at to provide compounds of formula (15). The reaction is typically performed under nitrogen at an elevated temperature such as reflux in a solvent such as, but not limited to, ethanol. Remaining hydrolyzed acid, if any, can be converted back to the ester using esterification conditions known in the art and literature such as acetyl chloride in refluxing ethanol. Compounds of formula (16) can be prepared from compounds of formula (15) by treating the latter with a reducing agent such as, but not limited to, sodium borohydride. The reaction is typically performed at a reduced temperature such as 0° C. or below, in a solvent such as but not limited to ethanol, methanol and the like. Alcohols of formula (16) can be treated with a base such as, but not limited to, sodium hydride, potassium carbonate, or potassium tert-butoxide and compounds of formula (10) wherein $R^{4.4}$ is the ring of $R^4$ as described herein, to provide compounds of formula (17). The addition may be performed at reduced temperature, such as 0° C., before warming up to ambient or elevated temperature in a solvent such as, but not limited to, N,N-dimethylformamide, tetrahydrofuran, and the like. Removal of the allyl carbamate protecting group in compounds of formula (17) to provide compounds of formula (18) can be accomplished by reacting the former with a palladium catalyst such as, but not limited to, tetrakis(triphenylphosphine)palladium(0) in the presence of 1,3-dimethylpyrimidine-2,4,6(1H,3H,5H)-trione. The reaction is typically performed at ambient temperature in a solvent such as, but not limited to, dichloromethane, ethyl acetate, acetonitrile, water or mixtures thereof.

Carboxylic acids of formula (5) can be coupled with amine cores of formula (18) to provide compounds of formula (11). Examples of conditions known to generate compounds of formula (11) from a mixture of a carboxylic acid and an amine include, but are not limited to, adding a coupling reagent such as, but not limited to, N-(3-dimethylaminopropyl)-N'-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to 4-(dimethylamino) pyridine (DMAP), 1-hydroxy-7-azabenzotriazole (HOAT) and 1-hydroxybenzotriazole (HOBT). The reaction may be carried out optionally in the presence of a base such as, but not limited to, triethylamine, N,N-diisopropylethylamine or pyridine. The coupling reaction may be carried out in solvents such as, but not limited to, tetrahydrofuran, N,N-dimethylformamide, N,N-dimethylacetamide, dimethyl sulfoxide, dichloromethane, and ethyl acetate. The reactions may be carried out at ambient temperature or heated. The heating can be accomplished either conventionally or with microwave irradiation.

Alternatively, carboxylic acids of formula (5) can be converted to the corresponding acid chlorides of formula (6) by reaction with thionyl chloride, PCl$_3$, PCl$_5$, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides of formula (6) (or commercially available acid chlorides of formula (6)) can then reacted with core amines of formula (18) optionally in the presence of a base such as a tertiary amine base such as but not limited to triethylamine or N,N-diisopropylethylamine or an aromatic base such as pyridine, at room temperature or heated in a solvent such as dichloromethane to provide compounds of formula (11).

Esters of formula (11) can be hydrolyzed in an aqueous hydroxide solution to provide compounds of formula (12) which are representative of Formula (I). The reaction is typically performed in a solvent such as, but not limited to, methanol, tetrahydrofuran, or mixtures thereof, and may be performed at ambient temperature or an elevated temperature.

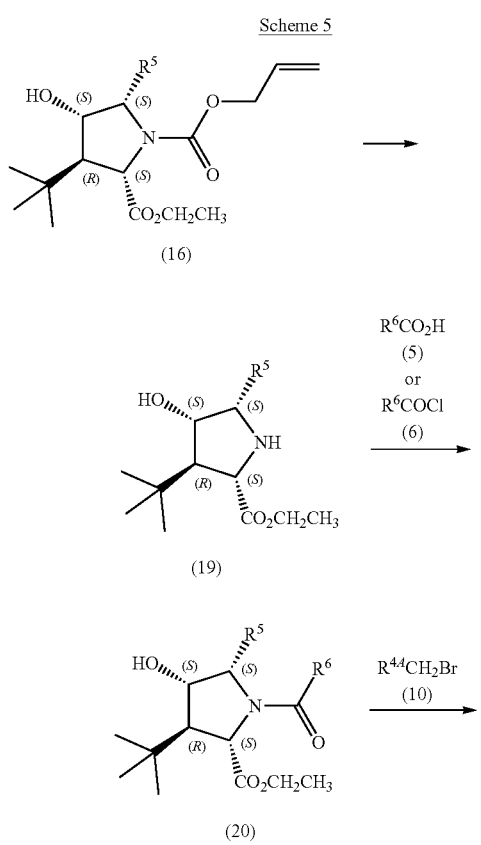

Scheme 5

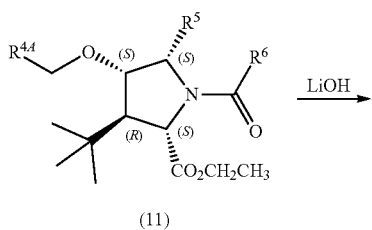

(11)

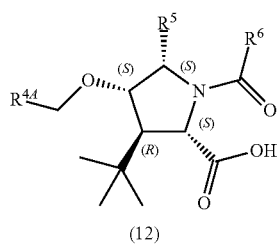

(12)

An alternative sequence for the preparation of compounds of Formula (12) is shown in Scheme 5. Removal of the allyl carbamate protecting group in compounds of formula (16) to provide compounds of formula (19) can be accomplished by reacting the former with a palladium catalyst such as, but not limited to, tetrakis(triphenylphosphine)palladium(0) in the presence of 1,3-dimethylpyrimidine-2,4,6(1H,3H,5H)-trione. The reaction is typically performed at ambient temperature in a solvent such as, but not limited to, dichloromethane, ethyl acetate, acetonitrile, water or mixtures thereof.

Carboxylic acids of formula (5) can be coupled with amine cores of formula (19) to provide compounds of formula (20). Examples of conditions known to generate compounds of formula (20) from a mixture of a carboxylic acid and an amine include, but are not limited to, adding a coupling reagent such as, but not limited to, 1-chloro-N,N,2-trimethylprop-1-en-1-amine (Ghosez reagent), N-(3-dimethylaminopropyl)-N-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide, 2-(7-azabenzotriazol-1-yl)-N,N,N',N'-tetramethyluronium hexafluorophosphate, 1-[bis(dimethylamino)methylene]-1H-1,2,3-triazolo[4,5-b]pyridinium 3-oxid hexafluorophosphate (HATU), O-(benzotriazol-1-yl)-N,N,N',N-tetramethyluronium tetrafluoroborate (TBTU), 2-(1H-benzo[d][1,2,3]triazol-1-yl)-1,1,3,3-tetramethylisouronium hexafluorophosphate(V) (HBTU), or 2,4,6-tripropyl-1,3,5,2,4,6-trioxatriphosphinane 2,4,6-trioxide (T3P). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to 4-(dimethylamino) pyridine (DMAP), 1-hydroxy-7-azabenzotriazole (HOAT) and 1-hydroxybenzotriazole (HOBT). The reaction may be carried out optionally in the presence of a base such as, but not limited to, triethylamine, N,N-diisopropylethylamine or pyridine. The coupling reaction may be carried out in solvents such as, but not limited to, tetrahydrofuran, N,N-dimethylformamide, N,N-dimethylacetamide, dimethyl sulfoxide, dichloromethane, and ethyl acetate. The reactions may be carried out at ambient temperature or heated. The heating can be accomplished either conventionally or with microwave irradiation.

Alternatively, carboxylic acids of formula (5) can be converted to the corresponding acid chlorides of formula (6) by reaction with thionyl chloride, $PCl_3$, $PCl_5$, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides of formula (6) (or commercially available acid chlorides of formula (6)) can then reacted with core amines of formula (19) optionally in the presence of a base such as a tertiary amine base such as, but not limited to, triethylamine or N,N-diisopropylethylamine or an aromatic base such as pyridine, at room temperature or heated in a solvent such as dichloromethane to provide compounds of formula (20).

Compounds of formula (20) can be treated with a base such as, but not limited to, sodium hydride, potassium carbonate, or potassium tert-butoxide and compounds of formula (10) wherein $R^{4A}$ is the ring of $R^4$ as described herein to provide compounds of formula (11). The addition may be performed at reduced temperature, such as 0° C., before warming up to ambient or elevated temperature in a solvent such as, but not limited to, dimethylformamide, tetrahydrofuran, and the like. Esters of formula (11) can be hydrolyzed in an aqueous hydroxide solution to provide compounds of formula (12) which are representative of formula (I). The reaction is typically performed in a solvent such as, but not limited to, methanol, tetrahydrofuran, or mixtures thereof, and may be performed at ambient temperature or an elevated temperature.

Scheme 6

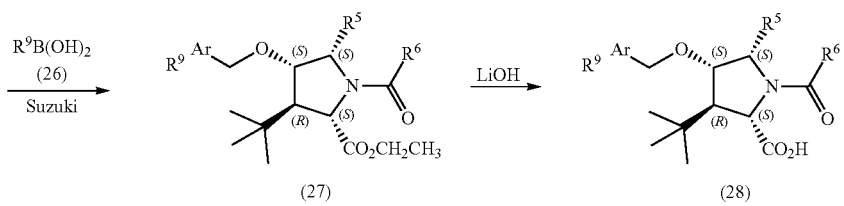

-continued

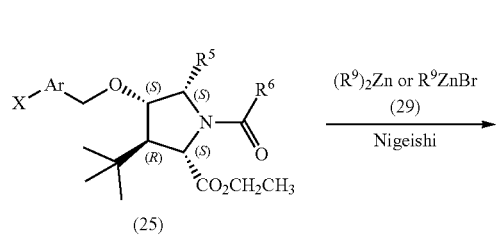 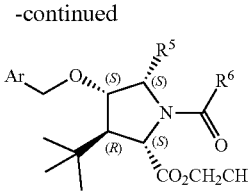 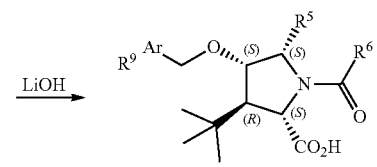

(25) (27) (28)

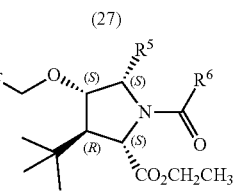 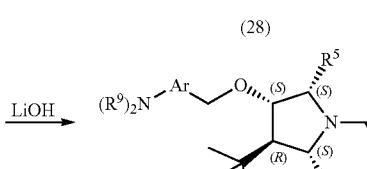

(31) (32)

Scheme 6 depicts examples of ways to diversify the substituents on an aromatic ring of the $R^4$ group. Compounds of formula (25), wherein X is I, Br, Cl or triflate and Ar is aryl or heteroaryl, can be prepared as described in Schemes 3, 4, or 5.

Compounds of formula (27) can be prepared by reacting compounds of formula (25) wherein X is I, Br, Cl or triflate with boronic acid compounds of formula (26), wherein $R^9$ is as described herein (or the boronic ester equivalents), under Suzuki coupling conditions known to those skilled in the art and widely available in the literature. The reaction typically requires the use of a base and a catalyst. Examples of bases include, but are not limited to, potassium carbonate, potassium t-butoxide, sodium carbonate, cesium carbonate, and cesium fluoride. Examples of catalysts include, but are not limited to, tetrakis(triphenylphosphine)palladium(0), [1,1'-bis(diphenylphosphino)ferrocene]dichloropalladium(II) dichloromethane, bis(triphenylphosphine)palladium(II) dichloride, and tris(dibenzylideneacetone)dipalladium(0). The reaction may be conducted in a solvent such as, but not limited to, water, dioxane, 1,2-dimethoxyethane, N,N-dimethylformamide, toluene, ethanol, tetrahydrofuran and the like or mixtures thereof. The reaction may be conducted at ambient or elevated temperatures, and optionally in a microwave oven. Esters of formula (27) can be hydrolyzed in an aqueous hydroxide solution to provide compounds of formula (28) which are representative of formula (I). The reaction is typically performed in a solvent such as, but not limited to, methanol, tetrahydrofuran, or mixtures thereof, and may be performed at ambient temperature or an elevated temperature.

Compounds of formula (27) can be prepared by reacting compounds of formula (25) wherein X is I, Br, Cl or triflate with organozinc compounds of formula (29), wherein $R^9$ is as described herein, under Negishi coupling conditions known to those skilled in the art and widely available in the literature. The reaction typically requires the use of a palladium or nickel catalyst. Examples of catalysts include, but are not limited to, dichloro[4,5-dichloro-1,3-bis(2,6-di-3-pentylphenyl)imidazol-2-ylidene](3-chloropyridyl)palladium(II) (PEPPSI-IPentCl), tetrakis(triphenylphosphine)nickel(0), tetrakis(triphenylphosphine)palladium(0), bis(triphenylphosphine)palladium(II) dichloride, [1,1'-bis(diphenylphosphino)ferrocene]dichloropalladium(II) dichloromethane, tris(dibenzylideneacetone)dipalladium(0), and palladium(II) acetate. The reaction may be conducted in a solvent such as, but not limited to, water, dioxane, 1-methyl-2-pyrrolidinone, N,N-dimethylacetamide, 1,2-dimethoxyethane, N,N-dimethylformamide, toluene, ethanol, tetrahydrofuran and the like, or mixtures thereof. The reaction may be conducted at ambient or elevated temperatures, and optionally in a microwave oven. Esters of formula (27) can be hydrolyzed in an aqueous hydroxide solution to provide compounds of formula (28) which are representative of Formula (I). The reaction is typically performed in a solvent such as, but not limited to, methanol, tetrahydrofuran, or mixtures thereof, and may be performed at ambient temperature or an elevated temperature.

Compounds of formula (31) can be prepared by reacting compounds of formula (25) wherein X is I, Br, Cl or triflate with amines compounds of formula (30), wherein $R^9$ is H or is as described herein, under Buchwald-Hartwig amination conditions known to those skilled in the art and widely available in the literature. The reaction typically requires the use of a base, catalyst, and optionally, a ligand. Examples of bases include, but are not limited to, potassium carbonate, potassium t-butoxide, sodium t-butoxide, sodium carbonate, cesium carbonate, and cesium fluoride. Examples of catalysts include, but are not limited to, dichloro[4,5-dichloro-1,3-bis(2,6-di-3-pentylphenyl)imidazol-2-ylidene](3-chloropyridyl)palladium(II) (PEPPSI-IPentCl), chloro-(2-dicyclohexylphosphino-2',6'-diisopropoxy-1,1'-biphenyl)[2-(2-aminoethyl)phenyl]palladium(II)-methyl-t-butyl ether adduct (RuPhos palladacycle), tetrakis(triphenylphosphine)nickel(0), tetrakis(triphenylphosphine)palladium(0), bis(triphenylphosphine)palladium(II) dichloride, [1,1'-bis(diphenylphosphino)ferrocene]dichloropalladium(II) dichloromethane, tris(dibenzylideneacetone)dipalladium(0), and palladium(II) acetate. Examples of optional ligands include, but are not limited to, BINAP (2,2'-bis(diphenylphosphino)-1,1'-binaphthyl), DPPF (1,1'-bis(diphenylphosphino)ferrocene), and Xantphos (4,5-bis(diphenylphosphino)-9,9-dimethylxanthene). The reaction may be conducted in a solvent such as, but not limited to, water, dioxane, 1-methyl-2-pyrrolidinone, N,N-dimethylacetamide, dimethoxyethane, N,N-dimethylformamide, toluene, ethanol, tetrahydrofuran, and the like or mixtures thereof. The reaction may be conducted at ambient or elevated temperatures, and optionally in a microwave oven. Esters of formula (31) can be hydrolyzed in an aqueous hydroxide solution to provide compounds of formula (32) which are representative of Formula (I). The reaction is typically performed in a solvent such as, but not limited to, methanol, tetrahydrofuran, or mixtures thereof, and may be performed at ambient temperature or an elevated temperature.

Scheme 7

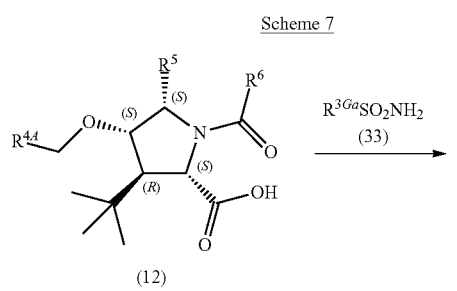

(12)

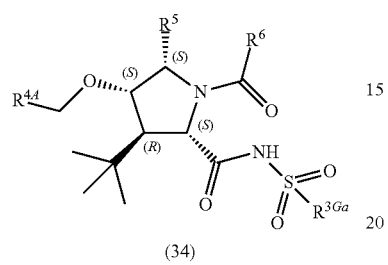

(34)

As shown in Scheme 7, compounds of formula (34), which are representative of compounds of Formula (I), can be prepared from compounds of formula (12). Compounds of formula (12) can be reacted with compounds of formula (33) in the presence of a coupling agent such as, but not limited to, carbonyldiimidazole and a base such as, but not limited to, 1,8-diazabicyclo[5.4.0]undec-7-ene (DBU). The reaction is typically performed at an elevated temperature in a solvent such as, but not limited to, dichloromethane, dichloroethane, or the like.

EXAMPLES

Catalyst and Intermediate Synthesis

Catalyst 1

(2-(bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron The procedure for preparation of the chiral ligand was modified from Yan, X.-X., Peng, Q., Zhang, Y., Zhang, K., Hong, W., Hou, X.-L. and Wu, Y.-D., Angew. Chem., Int. Ed. 2006, 45 1979-1983.
Cyclopenta-2,4-dien-1-yl(3-((S)-4-isopropyl-4,5-dihydrooxazol-2-yl)cyclopenta-2,4-dien-1-yl)iron (515 mg, 1.733 mmol) was dissolved in 2-methyltetrahydrofuran (17 mL). The resulting solution was cooled to −78° C. in an acetone-dry ice bath, and tetramethylethylenediamine (0.340 mL, 2.253 mmol) was added, followed by dropwise addition of sec-butyllithium (1.485 mL, 2.080 mmol), maintaining an internal temperature <−70° C. After stirring for 30 minutes, the reaction mixture was treated with bis(3,5-bis(trifluoromethyl)phenyl)chlorophosphine (1110 mg, 2.253 mmol) in one portion. After stirring at −78° C. for 1 hour, the reaction flask was removed from the bath and warmed to ambient temperature before diluting with 20 mL of methyl tert-butyl ether and quenching with 10 mL of saturated aqueous ammonium chloride. The layers were separated, and the organic layer was washed with 10 mL of saturated ammonium chloride and 10 mL of brine, dried over sodium sulfate, filtered and concentrated. The crude material was purified via chromatography, eluting with isocratic 93:7 heptanes:methyl tert-butyl ether on an 80 g silica gel column for 20 minutes to provide 920 mg of the title compound. $^1$H NMR (300 MHz, CDCl$_3$) δ ppm 0.86 (d, J=6.6 Hz, 3H), 0.92 (d, J=6.3 Hz, 3H), 1.69-1.77 (m, 1H), 3.49-3.50 (m, 1H), 3.73-3.81 (m, 1H), 3.96 (t, J=7.8 Hz, 1H), 4.21-4.27 (m, 6H), 4.46-4.48 (m, 1H), 5.00-5.01 (m, 1H), 7.65 (d, J=6.3 Hz, 2H), 7.80 (s, 1H), 7.89 (d, J=6.0 Hz, 2H), 7.93 (s, 1H); MS(ESI+) m/z 754.0 (M+H)$^+$.

Intermediate 1

(E)-3,3-dimethyl-1-nitrobut-1-ene

Intermediate 1A 3,3-dimethyl-1-nitrobutan-2-ol

To a slurry of lithium aluminum hydride (0.881 g, 23.22 mmol) in dry tetrahydrofuran (140 mL), which had been stirred for 30 minutes at 0° C., nitromethane (70.9 g, 1161 mmol) was added dropwise. After 30 minutes, pivalaldehyde (20 g, 232 mmol) was added dropwise. The mixture was stirred at 0° C. for 5 hours, and was quenched with 1N aqueous HCl. The reaction mixture was poured into water, extracted with CH$_2$Cl$_2$ (2×250 mL), washed with brine (2×200 mL), dried over Na$_2$SO$_4$, filtered, and concentrated to provide the title compound (17 g, 107 mmol, 46.3% yield). LC-MS (ESI$^-$) m/z146.7 (M–H)$^-$.

Intermediate 1B (E)-3,3-dimethyl-1-nitrobut-1-ene

A solution of 3,3-dimethyl-1-nitrobutan-2-ol (10 g, 67.9 mmol) in dichloromethane (100 mL) was cooled to −10° C. under N$_2$, treated with 2,2,2-trifluoroacetic anhydride (15.70 g, 74.7 mmol), stirred at −15° C. for 5 minutes, treated dropwise with triethylamine (20.84 mL, 149 mmol) keeping the bath at −15° C. during the addition, stirred at 0° C. for 3 hours, treated with saturated aqueous NH$_4$Cl solution (300 mL), and stirred for 5 minutes. The CH$_2$Cl$_2$ layer was isolated and the aqueous layer was extracted with CH$_2$Cl$_2$ (2×150 mL). The combined CH$_2$Cl$_2$ layers were dried (Na$_2$SO$_4$), filtered, and concentrated. The crude material was purified by column chromatography (ethyl acetate/petroleum ether=1/200) to provide the title compound (6.8 g, 48.4 mmol, 71.3% yield). $^1$H NMR (400 MHz, CDCl$_3$) δ ppm 7.19 (d, J=13.2 Hz, 1H), 6.83 (d, J=13.6 Hz, 1H), 1.09 (s, 9H).

Intermediate 2

5-bromo-3-(bromomethyl)-2-methoxypyridine

To a solution of 5-bromo-2-methoxy-3-methylpyridine (Ark, 2.981 g, 14.75 mmol) in CCl$_4$ (12 mL) was added N-bromosuccinimide (2.89 g, 16.23 mmol) and (E)-2,2'-(diazene-1,2-diyl)bis(2-methylpropanenitrile) (0.036 g, 0.221 mmol). The reaction mixture was stirred at 80° C. for 2 hours, cooled in an ice bath, and filtered through diatomaceous earth. The solution was concentrated in vacuo to afford the title compound (2.0538 g, 50% yield). $^1$H NMR (501 MHz, CDCl$_3$) δ ppm 8.17 (d, J=2.4 Hz, 1H), 7.74 (d, J=2.4, 1H), 4.43 (s, 2H), 4.01 (s, 3H).

Intermediate 3

3-(bromomethyl)-2-methoxyquinoline

Intermediate 3A (2-methoxyquinolin-3-yl)methanol

2-Methoxyquinoline-3-carbaldehyde (1.45 g, 7.75 mmol) was suspended in methanol (20 mL) and the mixture was cooled to 0° C. Sodium borohydride (600 mg, 15.86 mmol) was added, causing bubbling. The reaction mixture was stirred and gradually warmed to room temperature overnight (let ice bath melt). The reaction mixture was concentrated, and the crude material was taken up in saturated aqueous bicarbonate solution (50 mL) and extracted with dichloromethane (2×50 mL). The combined organic layers were dried over Na$_2$SO$_4$, filtered, and concentrated to afford the title compound (1.46 g, 7.72 mmol, 100% yield). $^1$H NMR (500 MHz, DMSO-d$_6$) δ ppm 8.19 (q, J=1.2 Hz, 1H), 7.90 (dd, J=8.0, 1.5 Hz, 1H), 7.82-7.72 (m, 1H), 7.62 (ddd, J=8.4, 6.9, 1.5 Hz, 1H), 7.42 (ddd, J=8.1, 6.9, 1.2 Hz, 1H), 5.44-5.30 (m, 1H), 4.66-4.54 (m, 2H), 4.01 (s, 3H); MS (ESI+) m/z 190 (M+H)$^+$.

Intermediate 3B 3-(bromomethyl)-2-methoxyquinoline

Intermediate 3A (1.46 g, 7.72 mmol) and triphenylphosphine (4.00 g, 15.25 mmol) were dissolved in dichloromethane (25 mL) and cooled in an ice bath. N-bromosuccinimide (1.373 g, 7.72 mmol) was added gradually using a solid addition funnel, keeping the internal temperature below 10° C. The ice bath was removed, and after stirring for 15 minutes the reaction was complete. The reaction was quenched by adding 10 mL of water, stirred for 5 minutes, and the layers were separated. The organic layer was washed twice with water and filtered through a fritted cartridge layered with a pad of silica (1 cm), eluting with heptanes. The filtrates were reduced in volume to provide a solid which was filtered and washed with 3×30 mL of 50:50 methyl tert-butyl ether:heptanes. The material was dried in vacuo to provide a residue, and the residue was purified using a 40 g silica gel cartridge, eluting with dichloromethane to provide the title compound (1.01 g, 4.01 mmol, 51.9% yield). $^1$H NMR (500 MHz, DMSO-d$_6$) δ ppm 8.35 (s, 1H), 7.86 (dd, J=8.1, 1.4 Hz, 1H), 7.77 (d, J=8.2 Hz, 1H), 7.67 (ddd, J=8.3, 6.9, 1.5 Hz, 1H), 7.44 (ddd, J=8.2, 6.8, 1.2 Hz, 1H), 4.74 (s, 2H), 4.05 (s, 3H); MS (ESI+) m/z 252 (M+H)$^+$.

Intermediate 4

3-(bromomethyl)-5-cyclobutyl-2-methoxypyridine

Intermediate 4A methyl 5-cyclobutyl-2-methoxynicotinate

Methyl 5-bromo-2-methoxynicotinate (CombiBlocks, 2.516 g, 10.23 mmol) and [1,1'-bis(diphenylphosphino)ferrocene]dichloropalladium(II) (PdCl$_2$(dppf), 0.383 g, 0.523 mmol) were suspended in tetrahydrofuran (100 mL), and the orange suspension was purged with N$_2$. A commercial solution of cyclobutylzinc(II) bromide (Aldrich, 0.5 M tetrahydrofuran, 24 mL, 12.00 mmol) was added dropwise, and the reaction mixture was allowed to stir at room temperature for 16 hours. The reaction mixture was quenched by the addition of 100 mL saturated aqueous ammonium chloride, and the product was extracted into 300 mL of dichloromethane. The combined extracts were dried over sodium sulfate, filtered and concentrated in vacuo. Silica gel chromatography, eluting with 5-100% ethyl acetate/heptanes, afforded the title compound (1.110 g, 49% yield). $^1$H NMR (400 MHz, CDCl$_3$) δ ppm 8.16 (d, J=2.6 Hz, 1H), 8.05 (d, J=2.6 Hz, 1H), 4.04 (s, 3H), 3.93 (s, 3H), 3.53 (p, J=8.6 Hz, 1H), 2.43-2.33 (m, 2H), 2.21-2.01 (m, 3H), 1.96-1.88 (m, 1H); MS (ESI+) m/z 222 (M+H)$^+$.

Intermediate 4B (5-cyclobutyl-2-methoxypyridin-3-yl)methanol

Intermediate 4A (1.110 g, 5.02 mmol) was dissolved in tetrahydrofuran (24 mL), and the solution was cooled in an ice bath. A solution of lithium aluminum hydride (2M in tetrahydrofuran, 2.51 mL, 5.02 mmol) was added dropwise over 3 minutes via syringe. The reaction mixture was then diluted with 200 mL of methyl tert-butyl ether, quenched with 10 mL of saturated aqueous potassium sodium tartrate (Rochelle's salt), and the mixture was stirred for another 30 minutes at room temperature before separating the layers. The organic layer was dried over sodium sulfate and filtered, and the solvent was removed to provide the title compound, 0.943 g (97% yield). The compound was dried azeotropically with toluene and then used directly in the next step. $^1$H NMR (400 MHz, CDCl$_3$) δ ppm 7.94 (d, J=2.4 Hz, 1H), 7.51 (d, J=2.4 Hz, 1H), 4.67 (d, J=6.3 Hz, 2H), 4.00 (d, J=0.8 Hz, 3H), 3.51 (p, J=8.5 Hz, 1H), 2.36 (dtd, J=10.3, 8.0, 2.7 Hz, 2H), 2.29 (t, J=6.5 Hz, 1H), 2.22-2.00 (m, 3H), 1.97-1.84 (m, 1H); MS (ESI+) m/z 194 (M+H)$^+$.

Intermediate 4C 3-(bromomethyl)-5-cyclobutyl-2-methoxypyridine

Intermediate 4B (0.943 g, 4.88 mmol) and triphenylphosphine (2.56 g, 9.76 mmol) were dissolved in dichloromethane (24.4 mL) and cooled in an ice bath. N-Bromosuccinimide (1.737 g, 9.76 mmol) was added gradually using a solid addition funnel, keeping the internal temperature below 10° C. After completion of the addition, the ice bath was removed, and the reaction was stirred at room temperature for 15 minutes. Water was added (10 mL), and the mixture was stirred for 5 minutes before the layers were separated. The organic layer was washed twice with water and then filtered through a fritted cartridge layered with a pad of silica (1 cm), eluting with heptanes. The filtrates were reduced in volume. The solid was collected by filtration and washed with 3×30 mL of 50:50 methyl tert-butyl ether: heptanes. The filtrate was concentrated, and the residue was purified by silica gel chromatography, eluting with 5-50% ethyl acetate/heptanes, to yield the title compound (1.07 g, 86% yield). $^1$H NMR (400 MHz, CDCl$_3$) δ ppm 7.97 (d, J=2.4 Hz, 1H), 7.52 (d, J=2.4 Hz, 1H), 4.52 (s, 2H), 4.02 (s, 3H), 3.59-3.38 (m, 1H), 2.44-2.31 (m, 2H), 2.21-2.00 (m, 3H), 1.95-1.85 (m, 1H); MS (ESI+) m/z 256 (M+H)$^+$.

Intermediate 5

(S)-tetrahydro-2H-pyran-2-carboxylic acid

Intermediate 5A

(S)-4-benzyl-3-((S)-tetrahydro-2H-pyran-2-carbonyl)oxazolidin-2-one

Intermediate 5B

(S)-4-benzyl-3-((R)-tetrahydro-2H-pyran-2-carbonyl)oxazolidin-2-one

Tetrahydro-2H-pyran-2-carboxylic acid (8.9 g, 68.4 mmol) was dissolved in 15 mL of dichloromethane and oxalyl chloride (11.97 mL, 137 mmol) was added. Two drops of dimethylformamide were added to catalyze the reaction and it was stirred at room temperature for 1 hour before concentrating in vacuo. The bath temperature was kept at 25° C. The tetrahydro-2H-pyran-2-carbonyl chloride was azeotroped one time with tetrahydrofuran (30 mL), dissolved in 3 mL of tetrahydrofuran and used immediately in the coupling reaction.

(S)-4-Benzyloxazolidin-2-one (11.54 g, 65.1 mmol) was dissolved in 15 mL of tetrahydrofuran and n-butyllithium (25.9 mL, 65.1 mmol) was added, maintaining an internal temperature <−60° C. After the addition was complete, a solution of tetrahydro-2H-pyran-2-carbonyl chloride (10.16 g, 68.4 mmol) in 3 mL of tetrahydrofuran was added dropwise, and slight exotherms were noted (<5° C.). TLC immediately after the addition was complete and showed complete conversion to the desired product. The first eluting peak A was the desired (S) diastereomer using methyl tert-butyl ether/heptanes. The crude 1:1 mix was loaded onto a 330 g silica gel column, eluting with 0:100 to 50:50 methyl tert-butyl ether:heptanes over 30 minutes then isocratic 50:50 methyl tert-butyl ether:heptanes until the complete elution of the second diastereomer. A total of 8.9 g of the title compound was obtained. First eluting peak 51A: (S)-4-benzyl-3-((S)-tetrahydro-2H-pyran-2-carbonyl)oxazolidin-2-one. $^1$H NMR (400 MHz, CDCl$_3$) δ ppm 7.42-7.17 (m, 5H), 5.05 (dd, J=10.5, 2.0 Hz, 1H), 4.68 (ddt, J=10.1, 6.7, 3.4 Hz, 1H), 4.32-4.08 (m, 3H), 3.62 (td, J=11.5, 2.5 Hz, 1H), 3.38 (dd, J=13.4, 3.3 Hz, 1H), 2.79 (dd, J=13.4, 9.7 Hz, 1H), 2.01-1.85 (m, 2H), 1.78-1.55 (m, 4H); MS (ESI+) m/z 290.0 (M+H)$^+$. Second-eluting peak 51B: (S)-4-benzyl-3-((R)-tetrahydro-2H-pyran-2-carbonyl)oxazolidin-2-one. $^1$H NMR (400 MHz, CDCl$_3$) δ ppm 7.43-7.17 (m, 5H), 4.96 (dd, J=10.5, 2.1 Hz, 1H), 4.75 (ddt, J=9.2, 7.9, 3.3 Hz, 1H), 4.34-4.16 (m, 2H), 4.18-4.06 (m, 1H), 3.58 (td, J=11.6, 2.6 Hz, 1H), 3.30-3.18 (m, 1H), 2.84 (dd, J=13.5, 9.2 Hz, 1H), 2.09-1.90 (m, 2H), 1.77-1.52 (m, 4H); MS (ESI+) m/z 290.0 (M+H)$^+$.

Intermediate 5C

(S)-tetrahydro-2H-pyran-2-carboxylic acid

Lithium hydroxide hydrate (6.36 g, 152 mmol) was dissolved in 180 mL of water. A separate solution of (S)-4-benzyl-3-((S)-tetrahydro-2H-pyran-2-carbonyl)oxazolidin-2-one (27.4 g, 95 mmol) in 50 mL of tetrahydrofuran was prepared, and the solution was cooled to 0° C. in an ice-water bath before adding hydrogen peroxide (30% aqueous) (36 mL, 352 mmol). Lithium hydroxide solution was added via syringe (over 30 minutes, maintaining an internal temperature below 5° C.). The reaction was stirred at the same temperature for 90 minutes, at which point it was complete. The reaction was quenched by addition of aqueous sodium sulfite (48 g of Na$_2$SO$_3$ in 280 mL of water) slowly via addition funnel, maintaining an internal temperature below 10° C. The tetrahydrofuran was removed in vacuo (water bath at 25° C.). The auxiliary was removed by extraction with dichloromethane (3×150 mL). To the aqueous layer was added 200 mL of dichloromethane and the resulting mixture was stirred in an ice-water bath while the aqueous layer was acidified with 6M aqueous HCl via addition funnel. The internal temperature was maintained below 10° C. during the addition. The layers were separated, the aqueous layer was extracted with dichloromethane (9×150 mL), and the combined dichloromethane layers were dried over sodium sulfate, filtered, and concentrated to provide the desired product. $^1$H NMR (400 MHz, CDCl$_3$) δ ppm 8.89 (s, 1H), 4.20-4.08 (m, 1H), 4.04-3.85 (m, 1H), 3.54 (td, J=11.3, 2.7 Hz, 1H), 2.05 (dq, J=8.9, 3.6, 3.2 Hz, 1H), 1.92 (dqd, J=6.9, 5.3, 4.4, 1.7 Hz, 1H), 1.69-1.45 (m, 4H). [α]23=−6.8° (c=1.0, methanol).

Intermediate 6

2-(bromomethyl)-4-(tert-butyl)-1-methoxybenzene

Intermediate 6A

(5-(tert-butyl)-2-methoxyphenyl)methanol

To a cooled (ice bath) solution of 5-tert-butyl-2-methoxybenzoic acid (0.828 g, 3.98 mmol) in tetrahydrofuran (19.88 mL) was added LAH (lithium aluminum hydride) (0.151 g, 3.98 mmol) in portions. The mixture was allowed to warm to room temperature and was stirred for 1 hour. Additional lithium aluminum hydride was added (2 mL of a 2M solution in tetrahydrofuran) and after 3 hours the reaction was quenched by slow addition of sodium sulfate decahydrate. The mixture was diluted with ether and was stirred at room temperature for 15 hours. The mixture was filtered and the solids were washed with ether (2×50 mL). The filtrate was concentrated to provide (5-(tert-butyl)-2-methoxyphenyl)methanol (0.770 g, 3.96 mmol, 100% yield), which was used in the next step without further purification. $^1$H NMR (400 MHz, CDCl$_3$) δ ppm 7.35-7.27 (m, 2H), 6.92-6.77 (m, 1H), 4.72 (d, J=6.2 Hz, 2H), 3.88 (s, 3H), 2.37 (t, J=6.5 Hz, 1H), 1.34 (s, 9H); MS (ESI+) m/z 195 (M+H)$^+$.

Intermediate 6B

2-(bromomethyl)-4-(tert-butyl)-1-methoxybenzene

Intermediate 6A (0.77 g, 3.96 mmol) was combined with triphenylphosphine (2.079 g, 7.93 mmol) and dissolved in dichloromethane (19.82 mL). N-Bromosuccinimide (1.411 g, 7.93 mmol) was added in several portions and an exotherm/bubbling was noted (temperature did not exceed 23° C.). After stirring for 15 minutes, the reaction was quenched by adding 5 mL of water. The mixture was stirred for 5 minutes, the layers were separated, and the organic layer was washed twice with water and filtered through a fritted cartridge layered with a pad of silica (2 cm), eluting with heptanes. The filtrate was concentrated to approximately 4 mL and was loaded directly onto a 40 g silica gel column and eluted with 0-15% ethyl acetate/heptanes over 30 minutes to provide 2-(bromomethyl)-4-(tert-butyl)-1-methoxybenzene (0.250 g, 0.972 mmol, 24.53% yield). $^1$H NMR (400 MHz, DMSO-d$_6$) δ ppm 7.39 (d, J=2.5 Hz, 1H), 7.17 (dd, J=8.5, 2.6 Hz, 1H), 6.82 (d, J=8.5 Hz, 1H), 4.49 (s, 2H), 3.74 (s, 3H), 1.26 (s, 9H).

Intermediate 7

3-(bromomethyl)-2-methoxyquinoline

Intermediate 7A (2-methoxyquinolin-3-yl)methanol

2-Methoxyquinoline-3-carbaldehyde (1.45 g, 7.75 mmol) was suspended in methanol (20 mL) and the mixture was cooled to 0° C. in an ice bath. Sodium borohydride (600 mg, 15.86 mmol) was added, causing bubbling. The reaction mixture was stirred and was allowed to warm to room temperature overnight (ice bath was allowed to melt). The reaction mixture was concentrated, and the crude material was taken up in saturated aqueous bicarbonate solution (50 mL) and was extracted with dichloromethane (2×50 mL). The combined organic layers were dried over Na$_2$SO$_4$, filtered, and concentrated to afford the product (1.46 g, 7.72 mmol, 100% yield). $^1$H NMR (500 MHz, DMSO-d$_6$) δ ppm 8.19 (q, J=1.2 Hz, 1H), 7.90 (dd, J=8.0, 1.5 Hz, 1H), 7.82-7.72 (m, 1H), 7.62 (ddd, J=8.4, 6.9, 1.5 Hz, 1H), 7.42 (ddd, J=8.1, 6.9, 1.2 Hz, 1H), 5.44-5.30 (m, 1H), 4.66-4.54 (m, 2H), 4.01 (s, 3H); MS (ESI+) m/z 190 (M+H)$^+$.

Intermediate 7B 3-(bromomethyl)-2-methoxyquinoline

Intermediate 7A (1.46 g, 7.72 mmol) and triphenylphosphine (4.00 g, 15.25 mmol) were dissolved in dichloromethane (25 mL) and cooled in an ice bath. N-Bromosuccinimide (1.373 g, 7.72 mmol) was added gradually using a solid addition funnel, keeping the internal temperature below 10° C. The ice bath was removed, and after stirring for 15 minutes the reaction was complete. The reaction was quenched by adding 10 mL of water. The mixture was stirred for 5 minutes. The layers were separated and the organic layer was washed twice with water and filtered through a fritted cartridge layered with a pad of silica (1 cm), eluting with heptanes. The filtrates were reduced in volume. The mixture was filtered and washed with 3×30 mL of 50:50 methyl tert-butyl ether:heptanes. The solvent was removed in vacuo, and the crude material was purified using a 40 g silica gel cartridge eluting with dichloromethane to provide the title compound (1.01 g, 4.01 mmol, 51.9% yield). $^1$H NMR (500 MHz, DMSO-d$_6$) δ ppm 8.35 (s, 1H), 7.86 (dd, J=8.1, 1.4 Hz, 1H), 7.77 (d, J=8.2 Hz, 1H), 7.67 (ddd, J=8.3, 6.9, 1.5 Hz, 1H), 7.44 (ddd, J=8.2, 6.8, 1.2 Hz, 1H), 4.74 (s, 2H), 4.05 (s, 3H); MS (ESI+) m/z 252 (M+H)$^+$.

Intermediate 8

3-(bromomethyl)-2-methoxy-5-(trifluoromethyl) pyridine

Intermediate 8A methyl 2-methoxy-5-(trifluoromethyl)nicotinate

To 3-bromo-2-methoxy-5-(trifluoromethyl)pyridine (50 g, 195 mmol) and Pd-dppf ([1,1'-bis(diphenylphosphino)ferrocene]dichloropalladium(II), Heraeus, 1.32 g, 1.804 mmol) in a 300 mL stainless steel reactor was added methanol (250 mL) and triethylamine (54.4 mL, 391 mmol). The reactor was degassed with nitrogen several times and carbon monoxide and was heated to 100±5° C. for 16.38 hours and at 60 psi.±4 psi for 2.7 hours and 21±7 psi (~14 hours). Additional Pd-dppf (Heraeus) (0.82 g, 1.121 mmol) catalyst was added. The crude product was concentrated to remove methanol. Ethyl acetate (400 mL) was added, followed by addition of 150 mL of saturated aqueous NH$_4$Cl, and the organic layer was isolated. The aqueous layer was extracted with ethyl acetate (200 mL). The organic layers were combined, washed with brine, dried over Na$_2$SO$_4$, filtered, and passed through a silica gel plug to remove dark Pt/C. The filtrate was concentrated to provide 40.62 g of the desired crude product, which was used directly in the next step. $^1$H NMR (400 MHz, DMSO-d$_6$) δ ppm=3.84 (s, 3 H) 3.96 (s, 3 H) 8.40 (br s, 1 H) 8.81 (br s, 1 H); MS (ESI$^+$) m/z 236.1 (M+H)$^+$.

Intermediate 8B (2-methoxy-5-(trifluoromethyl)pyridin-3-yl)methanol

Ethyl 2-methoxy-5-(trifluoromethyl)nicotinate (59.54 g, 253 mmol) was dissolved in tetrahydrofuran (506 mL). After cooling to <5° C., a solution of lithium aluminum hydride (177 mL, 177 mmol) in tetrahydrofuran was added over 40 minutes, maintaining an internal temperature <10° C. After 1 hour, the reaction was quenched by the addition of 50 mL of acetone, diluted with methyl tert-butyl ether (300 mL) and stirred with 300 mL of saturated aqueous potassium sodium tartrate (Rochelle's salt) until two clear layers were present. The reaction mixture was extracted with ethyl acetate and the combined extracts were washed with brine, dried over sodium sulfate, filtered, and concentrated to provide a residue, which was purified by flash chromatography (0 to 30% ethyl acetate in heptane) to provide (2-methoxy-5-(trifluoromethyl)pyridin-3-yl)methanol (40.28 g, 194 mmol, 77% yield). $^1$H NMR (400 MHz, 10740717-864-P1A, DMSO-d$_6$) δ ppm 3.96 (s, 3 H) 4.50 (d, J=5.73 Hz, 2 H) 5.45 (t, J=5.73 Hz, 1 H) 7.89-8.01 (m, 1 H) 8.47 (s, 1 H); MS (ESI$^+$) m/z 208.0 (M+H)$^+$.

Intermediate 8C 3-(bromomethyl)-2-methoxy-5-(trifluoromethyl) pyridine

Intermediate 8B (21.6 g, 104 mmol) and triphenylphosphine (54.7 g, 209 mmol) were dissolved in dichloromethane (521 mL) and the reaction mixture was cooled to 0° C. N-Bromosuccinimide (37.1 g, 209 mmol) was added in several portions and an exotherm/bubbling was noted (temperature did not exceed 25° C.). After stirring for 5 minutes in the ice bath, the reaction was warmed to room temperature for 30 minutes. The reaction mixture was cooled in the ice bath before addition of 300 mL of water, stirred for 5 minutes, and the organic layer was separated. The organic layer was washed with water (2×30 mL) then concentrated to approximately 50 mL and filtered through a fritted funnel layered with a pad of silica (1.5 inch), eluting with heptanes. The filtrates were concentrated to provide a viscous mixture and were diluted with 50:50 methyl tert-butyl ether:heptanes. The resulting solid was filtered. The filtrate was concentrated and was purified with a 330 g silica gel cartridge using a gradient of 5% ethyl acetate in heptane to provide desired product (22.12 g, 79%). $^1$H NMR (400 MHz, CDCl$_3$) δ ppm 4.04-4.10 (m, 3 H) 4.46-4.50 (m, 2 H) 7.83 (d, J=2.43 Hz, 1 H) 8.40 (d, J=1.10 Hz, 1 H).

Intermediate 9

5-bromo-3-(bromomethyl)-2-methoxypyridine

To a solution of 5-bromo-2-methoxy-3-methylpyridine (Ark, 2.981 g, 14.75 mmol) in CCl$_4$ (12 mL) was added N-bromosuccinimide (2.89 g, 16.23 mmol) and (E)-2,2'-(diazene-1,2-diyl)bis(2-methylpropanenitrile) (0.036 g, 0.221 mmol). The reaction mixture was stirred at 80° C. for 2 hours, and cooled in an ice bath and filtered through diatomaceous earth. The solution was concentrated in vacuo to afford the title compound (2.0538 g, 50% yield). $^1$H NMR (501 MHz, CDCl$_3$) δ ppm 8.17 (d, J=2.4 Hz, 1H), 7.74 (d, J=2.4, 1H), 4.43 (s, 2H), 4.01 (s, 3H).

Intermediate 10

3-(bromomethyl)-5-(tert-butyl)-2-methoxypyridine

Intermediate 10A (5-bromo-2-methoxypyridin-3-yl)methanol

5-Bromo-2-methoxynicotinaldehyde (2 g, 9.26 mmol) was suspended in methanol (40 mL) and cooled to 0° C. Sodium borohydride (0.350 g, 9.26 mmol) was added, causing bubbling. The reaction mixture was stirred at 0° C. for 15 minutes, the flask was removed from the ice bath, and the mixture was allowed to stir at room temperature for 2 hours. The reaction mixture was concentrated, and the crude material was taken up in methyl tert-butyl ether and saturated aqueous sodium bicarbonate. The phases were separated, and the organic layer was dried over Na$_2$SO$_4$, filtered and concentrated to afford the title compound (1.876 g, 8.60 mmol, 93% yield). $^1$H NMR (400 MHz, CDCl$_3$) δ ppm 8.15 (d, J=2.5 Hz, 1H), 7.75 (d, J=2.4 Hz, 1H), 4.66 (d, J=6.2 Hz, 2H), 3.99 (s, 3H), 2.15 (t, J=6.3 Hz, 1H); MS (DCI+) m/z 217.8 (M+H)$^+$.

Intermediate 10B 5-bromo-3-(((tert-butyldimethylsilyl)oxy)methyl)-2-methoxypyridine (5-Bromo-2-methoxypyridin-3-yl)methanol (1.876 g, 8.60 mmol), tert-butyldimethylsilyl chloride (1.556 g, 10.32 mmol), and imidazole (0.879 g, 12.91 mmol) were stirred in dichloromethane (35 mL) overnight at room temperature. Methanol (3 mL) was added to quench the tert-butyldimethylsilyl chloride, and the reaction mixture was stirred at room temperature for 10 minutes. The mixture was diluted with dichloromethane and washed twice with saturated aqueous sodium bicarbonate and once with brine. The organic layer was dried over sodium sulfate, filtered and concentrated to afford 5-bromo-3-(((tert-butyldimethylsilyl)oxy)methyl)-2-methoxypyridine (2.71 g, 8.16 mmol, 95% yield). $^1$H NMR (400 MHz, CDCl$_3$) δ ppm 8.08 (dt, J=2.5, 0.9 Hz, 1H), 7.81 (dt, J=2.5, 1.2 Hz, 1H), 4.65 (m, 2H), 3.93 (s, 3H), 0.93 (s, 9H), 0.14 (s, 6H); MS (ESI+) m/z 332 (M+H)$^+$.

Intermediate 10C 5-(tert-butyl)-3-(((tert-butyldimethylsilyl)oxy)methyl)-2-methoxypyridine A 50 mL round bottom flask containing a solution of 5-bromo-3-(((tert-butyldimethylsilyl)oxy)methyl)-2-methoxypyridine (1.624 g, 4.89 mmol) in tetrahydrofuran (12.22 mL) was degassed by bubbling nitrogen through the mixture for 20 minutes. To this solution was added nickel chloride dimethoxyethane adduct (0.107 g, 0.489 mmol) and 1,3-dicyclohexyl-1H-imidazol-3-ium tetrafluoroborate (0.156 g, 0.489 mmol) and degassing continued for another 15 minutes. The reaction was cooled to −10° C. tert-Butylmagnesium chloride (1M in tetrahydrofuran) (9.77 mL, 9.77 mmol) was added dropwise. The reaction was stirred at −10° C. for 100 minutes. The reaction was quenched with chips of ice and was allowed to warm to room temperature. The mixture was poured into saturated aqueous NH$_4$Cl solution and was extracted three times with ethyl acetate. The combined organic extracts were washed with brine, dried over sodium sulfate, filtered and concentrated. The crude material was purified using an 80 g silica gel cartridge, eluting with 0 to 50% methyl tert-butyl ether-heptanes over 40 minutes to provide 5-(tert-butyl)-3-(((tert-butyldimethylsilyl)oxy)methyl)-2-methoxypyridine (1.12 g, 3.62 mmol). $^1$H NMR (500 MHz, CDCl$_3$) δ ppm 8.06 (dt, J=2.7, 0.8 Hz, 1H), 7.82 (dt, J=2.4, 1.2 Hz, 1H), 4.71 (t, J=1.0 Hz, 2H), 3.95 (s, 3H), 1.34 (s, 9H), 1.02-0.95 (m, 15H).

Intermediate 10D (5-(tert-butyl)-2-methoxypyridin-3-yl)methanol 5-(tert-Butyl)-3-(((tert-butyldimethylsilyl)oxy)methyl)-2-methoxypyridine (1.124 g, 3.63 mmol) was dissolved in tetrahydrofuran (22 mL) and treated with tetrabutylammonium fluoride trihydrate (2.19 g, 6.94 mmol), and the reaction mixture was stirred at room temperature for 1 hour. The reaction mixture was poured into saturated aqueous NH$_4$Cl, and the mixture was extracted three times with ethyl acetate. The combined extracts were dried over Na$_2$SO$_4$, filtered, and concentrated. The crude material was purified using a 40 g silica gel cartridge with a gradient of 5-100% ethyl acetate/heptanes over 40 minutes to provide (5-(tert-butyl)-2-methoxypyridin-3-yl)methanol (0.6128 g, 3.14 mmol, 86% yield). $^1$H NMR (400 MHz, CDCl$_3$) δ ppm 8.10 (d, J=2.5 Hz, 1H), 7.70-7.53 (m, 1H), 4.65 (d, J=5.3 Hz, 2H), 3.98 (s, 3H), 2.52-2.37 (m, 1H), 1.32 (s, 9H).

Intermediate 10E 3-(bromomethyl)-5-(tert-butyl)-2-methoxypyridine (5-(tert-Butyl)-2-methoxypyridin-3-yl)methanol (0.502 g, 2.57 mmol) and triphenylphosphine (1.349 g, 5.14 mmol) were dissolved in dichloromethane (12.85 mL). N-Bromosuccinimide (0.915 g, 5.14 mmol) was added in several portions and an exotherm/bubbling were noted (temp did not exceed 23° C.). After stirring for 15 minutes, the reaction was quenched by adding 5 mL of water. The mixture was stirred for 5 minutes and the layers were separated. The organic layer was washed twice with water, and filtered through a fritted cartridge layered with a pad of silica (2 cm), eluting with heptanes. The filtrates were concentrated, triturated with 50:50 methyl tert-butyl ether:heptanes, and filtered. The solid was washed with 50:50 methyl tert-butyl ether/heptanes (2×10 mL) and the solvent was removed in vacuo to provide 3-(bromomethyl)-5-(tert-butyl)-2-methoxypyridine (0.582 g, 2.254 mmol, 88% yield). $^1$H NMR (400 MHz, CDCl$_3$) δ ppm 8.14 (d, J=2.6 Hz, 1H), 7.63 (d, J=2.6 Hz, 1H), 4.50 (s, 2H), 4.01 (s, 3H), 1.33 (s, 9H).

Core Synthesis

Core 1 rac-(2R,3R,4R,5R)-ethyl 3-(tert-butyl)-4-nitro-5-phenylpyrrolidine-2-carboxylate

Core 1A

(E)-ethyl 2-(benzylideneamino)acetate

To a mixture of glycine ethyl ester hydrochloride (7.23 g, 51.8 mmol) and magnesium sulfate (7.09 g, 58.9 mmol) in dichloromethane (80 mL) was added triethylamine (7.22 mL, 51.8 mmol). The mixture was stirred at ambient temperature for 20 minutes, and benzaldehyde (4.79 mL, 47.1 mmol) was added dropwise. The mixture was stirred overnight. The reaction mixture was filtered and the solid was washed with dichloromethane (20 mL×2). The combined organic layers were washed with brine, dried over MgSO$_4$, filtered and concentrated to yield (E)-ethyl 2-(benzylideneamino)acetate 8.2 g, (91% yield). $^1$H NMR (400 MHz, CDCl$_3$) δ ppm 8.30 (s, 1H), 7.83-7.71 (m, 2H), 7.48-7.37 (m, 2H), 4.40 (d, J=1.4 Hz, 2H), 4.24 (q, J=7.1 Hz, 2H), 1.30 (t, J=7.1 Hz, 3H); MS (ESI+) m/z 292.1 (M+H)$^+$.

Core 1B rac-(2R,3R,4R,5R)-ethyl 3-(tert-butyl)-4-nitro-5-phenylpyrrolidine-2-carboxylate To a solution of Core 1A (1.0 g, 5.23 mmol) and (E)-3,3-dimethyl-1-nitrobut-1-ene (0.810 g, 6.28 mmol) in toluene (30 mL) cooled in an ice-bath was added acetyl(oxo)silver (1.309 g, 7.84 mmol) and 3A molecular sieves. Triethylamine (1.458 mL, 10.46 mmol) was added slowly to the well stirred reaction mixture. After stirring at 0° C. for 10 minutes, the reaction mixture was allowed to warm to ambient temperature and was stirred for another 4 hours. Saturated aqueous ammonium chloride was added, the precipitate was filtered off and the residue was extracted with ether. The combined organic fractions were dried over MgSO$_4$, filtered, concentrated, and purified by chromatography on 40 g silica gel cartridge, eluting with ethyl acetate in heptane, 0-40% gradient to provide the title compound (1.6 g, 95% yield). $^1$H NMR (400 MHz, CDCl$_3$) δ ppm 7.39-7.26 (m, 5H), 5.12 (dd, J=6.0, 2.5 Hz, 1H), 4.44 (d, J=5.7 Hz, 1H), 4.31 (q, J=7.2 Hz, 2H), 3.81 (d, J=7.1 Hz, 1H), 3.30 (s, 1H), 2.95 (dd, J=7.1, 2.5 Hz, 1H), 1.34 (t, J=7.2 Hz, 3H), 1.06 (s, 9H); MS(ESI+) m/z 321 (M+H)$^+$.

Core 2 rac-(2R,3S,4R,5R)-ethyl 3-(tert-butyl)-5-(2-methoxyphenyl)-4-nitropyrrolidine-2-carboxylate

Core 2A

(E)-ethyl 2-((2-methoxybenzylidene)amino)acetate

To a mixture of ethyl 2-aminoacetate hydrochloride (10.76 g, 77.12 mmol) and magnesium sulfate (10.61 g, 88.2 mmol) in dichloromethane (100 mL) was added triethylamine (11.2 mL, 80.8 mmol). The mixture was stirred at room temperature for 20 minutes and then 2-methoxybenzaldehyde (10.0 g, 73.45 mmol) was added dropwise. The resulting mixture was stirred at room temperature overnight. The solid was filtered off and washed with dichloromethane (300 mL). The combined filtrate was washed with water (150 mL) and brine (150 mL), dried over magnesium sulfate, filtered and concentrated to provide the title compound (E)-ethyl 2-((2-methoxybenzylidene)amino)acetate (16 g, 50.60 mmol, 68.9% yield). $^1$H NMR (400 MHz, CDCl$_3$) δ ppm 8.73 (s, 1H), 8.01 (d, J=8.0 Hz, 1H), 7.37-7.44 (m, 1H), 6.89-7.00 (m, 2H), 4.40 (s, 2H), 4.20-4.26 (m, 2H), 3.85 (s, 3H), 1.28-1.31 (m, 3H).

Core 2B rac-(2R,3S,4R,5R)-ethyl 3-(tert-butyl)-5-(2-methoxyphenyl)-4-nitropyrrolidine-2-carboxylate To a solution of (E)-ethyl 2-((2-methoxybenzylidene)amino)acetate (26.72 g, 120.94 mmol) and lithium bromide (13.90 g, 131.02 mmol) in tetrahydrofuran (220 mL) at −78° C. was added (E)-3,3-dimethyl-1-nitrobut-1-ene (13.0 g, 110.78 mmol) in tetrahydrofuran (20 mL) and DBU (1,8-diazabicyclo[5.4.0]undec-7-ene, 22.6 mL, 151.18 mmol) dropwise. The mixture was stirred at −78° C. for 2.5 hours and quenched with saturated aqueous ammonium chloride (100 mL), extracted with ethyl acetate (2×150 mL), washed with brine (2×150 mL), dried over sodium sulfate, filtered and concentrated. The residue was triturated with petroleum ether (100 mL). The solid was collected by filtration and dried in vacuo to provide the title compound rac-(2R,3S,4R,5R)-ethyl 3-(tert-butyl)-5-(2-methoxyphenyl)-4-nitropyrrolidine-2-carboxylate (10.3 g, 29.43 mmol, 28.3% yield). $^1$H NMR (400 MHz, CDCl$_3$) δ ppm 7.22-7.28 (m, 2H), 6.86-6.95 (m, 2H), 5.33-5.35 (m, 1H), 4.56 (s, 1H), 4.30-4.32 (m, 2H), 3.89 (s, 3H), 3.77 (d, J=8.0 Hz, 1H), 3.36 (d, J=7.2 Hz, 1H), 2.88-2.90 (m, 1H), 1.34 (d, J=7.2 Hz, 3H), 1.05 (s, 9H); LC-MS (ESI+) m/z 351 (M+H)$^+$.

Core 3

(2R,3S,4R,5R)-benzyl 3-(tert-butyl)-4-nitro-5-phenylpyrrolidine-2-carboxylate

Core 3A

(E)-benzyl 2-(benzylideneamino)acetate

To the mixture of benzyl 2-aminoacetate hydrochloride (CAS#2462-31-9) (5 g, 21.00 mmol) and magnesium sulfate (3.16 g, 26.2 mmol) in dichloromethane (80 mL) was added triethylamine (3.22 mL, 23.10 mmol). The mixture was stirred for 20 minutes, benzaldehyde (2.348 mL, 23.10 mmol) was added dropwise, and the mixture was stirred at ambient temperature overnight. The mixture was filtered and the solid was washed with dichloromethane. The combined organic layers were washed with brine, dried over MgSO$_4$, filtered, and concentrated to yield (E)-benzyl 2-(benzylideneamino)acetate (5.3 g, 100% yield). $^1$H NMR (400 MHz, CDCl$_3$) δ ppm 8.28 (s, 1H), 7.84-7.70 (m, 2H), 7.48-7.26 (m, 8H), 5.21 (s, 2H), 4.44 (d, J=1.3 Hz, 2H); MS (ESI+) m/z 254 (M+H)$^+$.

Core 3B rac-(2R,3S,4R,5R)-benzyl 3-(tert-butyl)-4-nitro-5-phenylpyrrolidine-2-carboxylate The title compound was synthesized with the same procedure as Core 1B using Core 3A as starting material. LC/MS (ESI+) m/z 378.37 (M+H)+.

Core 4 rac-(2R,3S,4R,5R)-ethyl 3-(tert-butyl)-5-(2-(dimethylamino)pyridin-3-yl)-4-nitropyrrolidine-2-carboxylate

Core 4A

2-(dimethylamino)nicotinaldehyde

Dimethylamine (aqueous solution, 10 mL, 79 mmol) was diluted with 10 mL of methanol and 2-chloronicotinaldehyde (5.0 g, 35.3 mmol) was added all at once. The reaction mixture was heated to 55° C. for 24 hours and another 10 mL of dimethylamine solution was added. After an additional 24 hours, the starting material had been consumed. The reaction mixture was cooled to room temperature, diluted with saturated aqueous ammonium chloride and extracted with dichloromethane. The combined extracts were concentrated and purified via flash chromatography, eluting with 0-20% ethyl acetate/heptanes over 20 minutes on an 80 g silica gel column to provide the title compound (3.9988 g, 75%). $^1$H NMR (501 MHz, CDCl$_3$) δ ppm 9.96 (s, 1H), 8.31 (dd, J=4.6, 2.0 Hz, 1H), 7.94 (dd, J=7.6, 2.0 Hz, 1H), 6.77 (dd, J=7.6, 4.6 Hz, 1H), 3.13 (s, 6H); LC-MS (ESI+) m/z 151.1 (M+H)+.

Core 4B

(E)-ethyl 2-(((2-(dimethylamino)pyridin-3-yl)methylene)amino)acetate

Ethyl 2-aminoacetate hydrochloride (3.72 g, 26.6 mmol) and magnesium sulfate (6.41 g, 53.3 mmol) were suspended in dichloromethane (44.4 mL). The suspension was treated with 2-(dimethylamino)nicotinaldehyde (4 g, 26.6 mmol) and triethylamine (3.71 mL, 26.6 mmol) and the mixture was stirred at room temperature for 16 hours. The solid material was removed via filtration and the filtrate was washed with water, dried over sodium sulfate, filtered and concentrated to provide the crude imine (5.76 g, 92%), which was used in the next step without additional purification. $^1$H NMR (400 MHz, CDCl$_3$) δ ppm 8.42-8.37 (m, 1H), 8.26 (dd, J=4.8, 2.0 Hz, 1H), 8.06 (dd, J=7.6, 1.9 Hz, 1H), 6.84 (ddd, J=7.6, 4.8, 0.6 Hz, 1H), 4.40 (d, J=1.3 Hz, 2H), 4.23 (q, J=7.1 Hz, 2H), 2.97 (s, 6H), 1.29 (t, J=7.1 Hz, 3H).

Core 4C rac-(2R,3S,4R,5R)-ethyl 3-(tert-butyl)-5-(2-(dimethylamino)pyridin-3-yl)-4-nitropyrrolidine-2-carboxylate (E)-Ethyl 2-(((2-(dimethylamino)pyridin-3-yl)methylene)amino)acetate (3.31 g, 14.07 mmol) was dissolved in 60 mL of tetrahydrofuran. The resulting solution was cooled in an acetone-dry ice bath to −78° C. before adding (E)-3,3-dimethyl-1-nitrobut-1-ene (1.58 g, 12.23 mmol), and lithium bromide (10.60 mL, 15.90 mmol). 2,3,4,6,7,8,9,10-Octahydropyrimido[1,2-a]azepine (2.104 mL, 14.07 mmol) was added dropwise via syringe, and the resulting mixture was stirred at −78° C. for 2 hours then warmed to ambient temperature before quenching with saturated aqueous ammonium chloride (30 mL). The mixture was extracted with 3×15 mL of methyl tert-butyl ether and was concentrated in vacuo to provide crude material, which was purified via flash chromatography, eluting with 0:100 to 30:70 ethyl acetate:heptanes over 20 minutes on an 80 g silica gel column to provide 2.20 g of the title compound. $^1$H NMR (501 MHz, CDCl$_3$) δ ppm 8.30 (dd, J=4.8, 1.8 Hz, 1H), 7.62 (ddd, J=7.6, 1.8, 0.8 Hz, 1H), 6.99 (dd, J=7.7, 4.8 Hz, 1H), 5.48 (dd, J=5.7, 2.4 Hz, 1H), 4.62 (dd, J=12.3, 5.7 Hz, 1H), 4.31 (qd, J=7.2, 1.6 Hz, 2H), 3.80 (dd, J=9.7, 7.1 Hz, 1H), 3.18 (t, J=11.2 Hz, 1H), 2.94-2.90 (m, 1H), 2.79 (s, 6H), 1.34 (t, J=7.1 Hz, 3H), 1.07 (s, 10H); MS (ESI+) m/z 365.2 (M+H)+.

Core 5

(2S,3R,4S,5S)-ethyl 3-(tert-butyl)-4-nitro-5-phenylpyrrolidine-2-carboxylate

Core 5A

(E)-ethyl 2-(benzylideneamino)acetate

Ethyl 2-aminoacetate hydrochloride (30 g, 215 mmol) and magnesium sulfate (51.7 g, 430 mmol) were stirred in dichloromethane (358 mL) at ambient temperature, and triethylamine (30.0 mL, 215 mmol) was added. The resulting suspension was stirred for 5 minutes and benzaldehyde (21.78 mL, 215 mmol) was added dropwise via syringe. The mixture was then stirred at ambient temperature for 16 hours. The solid material was removed via filtration through a fritted funnel, and the filter cake was washed with 20 mL of dichloromethane. The filtrate was washed with 2×20 mL of water, dried over sodium sulfate, filtered, and concentrated to provide the title compound. $^1$H NMR (501 MHz, CDCl$_3$) δ ppm 8.30 (d, J=1.4 Hz, 1H), 7.82-7.74 (m, 2H), 7.50-7.36 (m, 3H), 4.40 (d, J=1.3 Hz, 2H), 4.24 (q, J=7.2 Hz, 2H), 1.30 (t, J=7.2 Hz, 3H).

Core 5B

(2S,3R,4S,5S)-ethyl 3-(tert-butyl)-4-nitro-5-phenylpyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (2.98 g, 3.96 mmol) and copper (I) triflate dimer, benzene complex (0.859 g, 1.707 mmol; 90% technical grade, Aldrich) were dissolved in tetrahydrofuran (697 mL) that had been sparged with a nitrogen stream for 2 hours. The resulting mixture was stirred for 90 minutes at ambient temperature, at which point the flask was cooled to an internal temperature below 5° C. (E)-Ethyl 2-(benzylideneamino)acetate (73.3 g, 383 mmol) was added in one portion via syringe. Potassium 2-methylpropan-2-olate (2.73 mL, 2.73 mmol, 1M solution in tetrahydrofuran) was added dropwise, followed by addition of (E)-3,3-dimethyl-1-nitrobut-1-ene (45 g, 348 mmol) neat over 25 minutes via syringe, maintaining an internal temperature <10° C. After the addition was complete, the reaction was stirred for an additional 5 minutes at the same temperature, at which point LC-MS showed complete conversion of the starting nitroalkene. The reaction mixture was diluted with 300 mL of methyl tert-butyl ether and stirred with 300 mL of saturated aqueous ammonium chloride at ambient temperature for 15 minutes. The layers were separated, and the organic layer was washed with saturated aqueous ammonium chloride and brine and dried over sodium sulfate. After filtration, the organic extracts were concentrated in vacuo to provide a crude residue (140 g), which was precipitated from 800 mL of heptanes. The resulting material was removed via filtration using a fritted funnel, washed with 200 mL of cold heptanes, and dried to constant weight in a vacuum oven to provide 72.5 g of the title compound. $^1$H NMR (400 MHz, CDCl$_3$) δ ppm 7.37-7.18 (m, 5H), 5.13 (dd, J=6.0, 2.5 Hz, 1H), 4.45 (dd, J=12.4, 6.0 Hz, 1H), 4.32 (qd, J=7.2, 1.2 Hz, 2H), 3.82 (dd, J=9.7, 7.1 Hz, 1H), 3.30 (dd, J=12.3, 9.8 Hz, 1H), 2.96 (dd, J=7.2, 2.5 Hz, 1H), 1.35 (t, J=7.1 Hz, 3H), 1.06 (s, 9H); MS (ESI+) m/z 321.1 (M+H)$^+$;[α]$^{24.8}$=+16.1° (c=1, methanol).

Core 6

(2S,3R,4S,5S)-ethyl 3-(tert-butyl)-5-(2-fluorophenyl)-4-nitropyrrolidine-2-carboxylate Core 6A (E)-ethyl 2-((2-fluorobenzylidene)amino)acetate To a mixture of ethyl 2-aminoacetate hydrochloride (11.8 g, 84.7 mmol) and magnesium sulfate (11.7 g, 96.7 mmol) in dichloromethane (100 mL) was added triethylamine (12.5 mL, 88.7 mmol). The mixture was stirred for 20 minutes and 2-fluorobenzaldehyde (10.0 g, 80.6 mmol) was added dropwise. The resulting mixture was stirred at room temperature overnight. The solid was filtered off and washed with dichloromethane (200 mL). The filtrate was washed with water (100 mL) and brine (100 mL), dried over MgSO$_4$, filtered and concentrated to give the title compound (E)-ethyl 2-((2-fluorobenzylidene)amino)acetate (16.0 g, 76.6 mmol, 95% yield). $^1$H NMR (400 MHz, CDCl$_3$) δ ppm 8.60 (s, 1H), 8.03-8.07 (m, 1H), 7.39-7.45 (m, 1H), 7.11-7.20 (m, 1H), 7.06-7.08 (m, 1H), 4.43 (s, 2H), 4.27, 4.24 (dd, J=7.2 Hz, 14.4 Hz, 2H), 1.32-1.36 (m, 3H), 1.26-1.33 (m, 3H); LC-MS (ESI+) m/z 210 (M+H)$^+$.

Core 6B (2S,3R,4S,5S)-ethyl 3-(tert-butyl)-5-(2-fluorophenyl)-4-nitropyrrolidine-2-carboxylate To a flame-dried Schlenk tube charged with activated 4A molecular sieves and a stirring bar was added [Cu(OTf)]$_2$.benzene (copper(II) trifluoromethanesulfonate, 417.8 mg, 0.83 mmol) and (2-(bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (1.45 g, 1.93 mmol) in freshly distilled anhydrous tetrahydrofuran (160 mL) under an inert atmosphere. The mixture was stirred for 15 minutes and cooled to 0° C. (E)-Ethyl 2-((2-fluorobenzylidene) amino) acetate (16.0 g, 76.6 mmol) was added, followed by addition of potassium tert-butoxide (1.33 mL, 1.33 mmol) and (E)-3, 3-dimethyl-1-nitrobut-1-ene (8.56 g, 66.36 mmol). The reaction mixture was stirred at 0° C. for 2 hours, and then filtered through a short plug of silica gel. The filtrate was concentrated. The residue was purified by silica gel column chromatography (eluted with 10% petroleum ether/ethyl acetate) to provide the title compound (13.55 g, 40.09 mmol, 58.6% yield, ee=95.3%). $^1$H NMR (400 MHz, CDCl$_3$) δ ppm 7.30-7.33 (m, 2H), 7.15-7.17 (m, 1H), 7.07 (t, J=8.4 Hz, 1H), 5.22-5.24 (m, 1H), 4.60 (t, J=6.0 Hz, 1H), 4.29-4.35(m, 2H), 3.80 (t, J=3.6 Hz, 1H), 3.33 (t, J=11.2 Hz, 1H), 2.93-2.96 (m, 1H), 1.35 (t, J=7.2 Hz, 3H), 1.06(s, 9H); LC-MS(ESI+) m/z 339 (M+H)$^+$.

Core 7

(2S,3R,4S,5S)-ethyl 3-(tert-butyl)-5-(2-isopropoxypyridin-3-yl)-4-nitropyrrolidine-2-carboxylate Core 7A (E)-ethyl 2-(((2-isopropoxypyridin-3-yl)methylene)amino)acetate Ethyl 2-aminoacetate hydrochloride (4.97 g, 35.6 mmol) and magnesium sulfate (6.86 g, 57.0 mmol) were suspended in dichloromethane (47.5 mL) and the suspension was treated with 2-isopropoxynicotinaldehyde (4.8 g, 28.5 mmol) and triethylamine (4.96 mL, 35.6 mmol). The mixture was stirred for 16 hours at room temperature. The solid material was removed via filtration and the filtrate was washed with water (twice) and brine, dried over sodium sulfate, filtered and concentrated to provide the crude (E)-ethyl 2-(((2-isopropoxypyridin-3-yl)methylene)amino)acetate (7.14 g, 28.5 mmol, 100% yield), which was used without additional purification. $^1$H NMR (400 MHz, DMSO-d$_6$) δ ppm 8.51 (s, 1H), 8.25 (dd, J=4.9, 2.0 Hz, 1H), 8.13 (dd, J=7.5, 2.1 Hz, 1H), 7.00 (ddd, J=7.5, 4.9, 0.7 Hz, 1H), 5.34 (hept, J=6.2 Hz, 1H), 4.41 (d, J=1.3 Hz, 2H), 4.15-3.99 (m, 2H), 1.30 (d, J=6.2 Hz, 6H), 1.18 (t, J=7.1 Hz, 3H). MS (DCI+) m/z 251.0 (M+H)$^+$.

Core 7B (2S,3R,4S,5S)-ethyl 3-(tert-butyl)-5-(2-isopropoxypyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.141 g, 0.187 mmol) and copper (I) triflate dimer, benzene complex (0.036 g, 0.072 mmol) were dissolved in tetrahydrofuran (22.13 mL) that had been sparged with a nitrogen stream for 2 hours. The resulting mixture was stirred for 1.5 hours at room temperature, and neat (E)-ethyl 2-(((2-isopropoxypyridin-3-yl)methylene)amino)acetate (3.6 g, 14.38 mmol) was added after cooling to <5° C. in an ice-water bath. Potassium 2-methylpropan-2-olate (0.144 mL, 0.144 mmol) was added drop wise, followed by addition of neat (E)-3,3-dimethyl-1-nitrobut-1-ene (1.858 g, 14.38 mmol) over 25 minutes, maintaining an internal temperature <10° C. After the addition was complete, the reaction mixture was stirred for 15 minutes at the same temperature. The reaction mixture was diluted with methyl tert-butyl ether (100 mL) and stirred with 75 mL of saturated aqueous ammonium chloride at room temperature for 15 minutes. The organic layer was separated and washed with saturated sodium bicarbonate solution and brine, dried over sodium sulfate, filtered, and concentrated. The residue was purified by flash chromatography (0 to 20% ethyl acetate in heptane) to provide title compound (2S,3R,4S,5S)-ethyl 3-(tert-butyl)-5-(2-isopropoxypyridin-3-yl)-4-nitropyrrolidine-2-carboxylate carboxylate (4.51 g, 11.89 mmol, 83% yield). $^1$H NMR (400

MHz, DMSO-d₆) δ ppm 8.04 (dd, J=5.0, 1.8 Hz, 1H), 7.64 (dt, J=7.4, 1.4 Hz, 1H), 6.90 (dd, J=7.3, 5.0 Hz, 1H), 5.33-5.19 (m, 2H), 4.41 (dd, J=9.5, 6.1 Hz, 1H), 4.19 (qd, J=7.1, 5.3 Hz, 2H), 3.77 (dd, J=8.4, 7.3 Hz, 1H), 3.55 (t, J=8.9 Hz, 1H), 2.92 (dd, J=7.3, 2.6 Hz, 1H), 1.32 (dd, J=13.6, 6.1 Hz, 6H), 1.23 (t, J=7.1 Hz, 3H), 0.95 (s, 9H). MS (ESI⁺) m/z 380.0 (M+H)⁺.

Core 8

(2S,3R,4S,5S)-ethyl 3-(tert-butyl)-5-(3-chlorophenyl)-4-nitropyrrolidine-2-carboxylate

Core 8A (E)-ethyl 2-((3-chlorobenzylidene)amino)acetate

Ethyl 2-aminoacetate hydrochloride (5.96 g, 42.7 mmol) and magnesium sulfate (5.14 g, 42.7 mmol) were suspended in dichloromethane (50.8 mL). Triethylamine (5.95 mL, 42.7 mmol) was added, and the reaction mixture was stirred for 1 hour at ambient temperature before addition of 3-chlorobenzaldehyde (4.03 mL, 35.6 mmol) via syringe. The reaction mixture was stirred overnight at ambient temperature. Solids were removed via filtration using a fritted funnel and the filter cake was washed with dichloromethane (10 mL). The filtrate was quickly washed twice with 10 mL of water and 10 mL of brine and dried over sodium sulfate, filtered and concentrated in vacuo to provide a residue, which was used without additional purification. ¹H NMR (400 MHz, CDCl₃) δ ppm 8.24 (d, J=1.3 Hz, 1H), 7.81 (t, J=1.8 Hz, 1H), 7.62 (dt, J=7.6, 1.4 Hz, 1H), 7.48-7.29 (m, 2H), 4.40 (d, J=1.3 Hz, 2H), 4.24 (q, J=7.1 Hz, 2H), 1.31 (t, J=7.1 Hz, 3H).

Core 8B (2S,3R,4S,5S)-ethyl 3-(tert-butyl)-5-(3-chlorophenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.192 g, 0.255 mmol) and copper (I) triflate dimer, benzene complex (0.056 g, 0.111 mmol) were dissolved in tetrahydrofuran (50 mL) that had been sparged with an N₂ stream for 1 hour. The resulting mixture was stirred for 1 hour at ambient temperature, and 4 Å molecular sieves (6 g, 22.16 mmol) were added, followed by addition of the (E)-ethyl 2-((3-chlorobenzylidene)amino)acetate (6.0 g, 26.6 mmol) as a solution in 3 mL of tetrahydrofuran. The resulting suspension was cooled to <5° C. in an ice-water bath. Potassium 2-methylpropan-2-olate (0.177 mL, 0.177 mmol) was added dropwise, followed by addition of (E)-3,3-dimethyl-1-nitrobut-1-ene (2.86 g, 22.16 mmol) as a solution in 2 mL of tetrahydrofuran over 10 minutes, maintaining a temperature less than 10° C. The reaction was complete after 10 minutes at the same temperature as determined by LC-MS. The reaction was quenched with 5 mL of saturated aqueous ammonium chloride and filtered through diatomaceous earth after diluting with methyl tert-butyl ether (50 mL). The filtrate was stirred at ambient temperature with saturated aqueous ammonium chloride (20 mL) for 15 minutes and the layers were separated. The organic layer was washed with saturated ammonium chloride and brine, dried over sodium sulfate, filtered, and concentrated in vacuo. The crude material was loaded onto a 120 g silica gel column and was eluted with 0:100 to 30:70 methyl tert-butyl ether:heptanes over 20 minutes to provide 5.83 g of the title compound. ¹H NMR (501 MHz, CDCl₃) δ ppm 7.33 (dq, J=1.7, 1.0 Hz, 1H), 7.30-7.24 (m, 2H), 7.22-7.16 (m, 1H), 5.11 (dd, J=6.0, 2.5 Hz, 1H), 4.40 (dd, J=12.0, 6.0 Hz, 1H), 4.31 (qd, J=7.1, 1.1 Hz, 2H), 3.79 (dd, J=9.6, 7.1 Hz, 1H), 3.21 (dd, J=11.9, 9.7 Hz, 1H), 2.96 (dd, J=7.2, 2.6 Hz, 1H), 1.34 (t, J=7.1 Hz, 3H), 1.05 (s, 9H). MS (ESI+) m/z355.1 (M+H)⁺.

Core 9

(2S,3R,4S,5S)-ethyl 3-(tert-butyl)-4-nitro-5-(o-tolyl)pyrrolidine-2-carboxylate

Core 9A (E)-ethyl 2-((2-methylbenzylidene)amino)acetate

Ethyl 2-aminoacetate hydrochloride (3.97 g, 28.5 mmol) and magnesium sulfate (3.43 g, 28.5 mmol) were stirred in dichloromethane (43.1 mL) at ambient temperature, and triethylamine (3.97 mL, 28.5 mmol) was added. The mixture was stirred for 5 minutes and 2-methylbenzaldehyde (2.97 mL, 25.9 mmol) was added dropwise. The mixture was stirred at ambient temperature for 16 hours. The solid material was filtered through a disposable plastic frit and washed with dichloromethane. The organic layer was washed with 30 mL of water, dried over sodium sulfate, filtered, and concentrated. ¹H NMR (500 MHz, CDCl₃) δ ppm 8.63 (d, J=1.4 Hz, 1H), 7.96 (dd, J=7.7, 1.4 Hz, 1H), 7.35 (td, J=7.5, 1.5 Hz, 1H), 7.32-7.25 (m, 1H), 7.25-7.18 (m, 1H), 4.45 (d, J=1.4 Hz, 2H), 4.28 (q, J=7.2 Hz, 2H), 2.55 (s, 3H), 1.34 (t, J=7.1 Hz, 3H). MS (ESI+) m/z 206 (M+H)⁺.

Core 9B (2S,3R,4S,5S)-ethyl 3-(tert-butyl)-4-nitro-5-(o-tolyl)pyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.222 g, 0.294 mmol) and copper (I) triflate dimer, benzene complex (0.064 g, 0.127 mmol) were dissolved in tetrahydrofuran (51.7 mL) that had been sparged with a stream of nitrogen for 4 hours. The resulting mixture was stirred for 1.5 hours at ambient temperature, and (E)-ethyl 2-((2-methylbenzylidene)amino)acetate (5.31 g, 25.9 mmol) was added after cooling to <5° C. in an ice-water bath. Potassium 2-methylpropan-2-olate (0.203 mL, 0.203 mmol) was added dropwise, followed by addition of (E)-3,3-dimethyl-1-nitrobut-1-ene (3.51 g, 27.2 mmol) neat over 25 minutes, maintaining an internal temperature <10° C. After the addition was complete, the reaction was stirred for 90 minutes at the same temperature. The reaction mixture was diluted with methyl tert-butyl ether (100 mL) and stirred with 50 mL of saturated aqueous ammonium chloride at ambient temperature for 15 minutes. The organic layer was washed with saturated sodium bicarbonate and brine, dried over sodium sulfate, and filtered. The filtrate was concentrated and was diluted with 80 mL of heptanes and the solvent was reduced in volume until a solid precipitated out. The mixture was cooled in an ice bath to <5° C. for 15 minutes, and the resulting material was filtered, washed with 20 mL of heptanes, and dried to constant weight in a vacuum oven to provide (2S,3R,4S,5S)-ethyl 3-(tert-butyl)-4-nitro-5-(o-tolyl)pyrrolidine-2-carboxylate (4.85 g, 14.50 mmol, 56% yield). ¹H NMR (501

MHz, CDCl₃) δ ppm 7.34-7.27 (m, 1H), 7.27-7.16 (m, 3H), 5.18 (dd, J=6.1, 2.6 Hz, 1H), 4.55 (dd, J=10.1, 5.9 Hz, 1H), 4.35 (qd, J=7.2, 1.2 Hz, 2H), 3.81 (t, J=7.1 Hz, 1H), 3.31 (s, 1H), 3.07 (dd, J=7.3, 2.6 Hz, 1H), 2.41 (s, 3H), 1.38 (t, J=7.1 Hz, 3H), 1.08 (s, 9H). MS (APCI+) m/z 335 (M+H)⁺.

Core 10

(2S,3R,4S,5S)-ethyl 5-(2-bromophenyl)-3-(tert-butyl)-4-nitropyrrolidine-2-carboxylate Core 10A (E)-ethyl 2-((2-bromobenzylidene)amino)acetate Ethyl 2-aminoacetate hydrochloride (2.63 g, 18.85 mmol) and magnesium sulfate (2.269 g, 18.85 mmol) were stirred in dichloromethane (28.6 mL) at ambient temperature, and triethylamine (2.63 mL, 18.85 mmol) was added. The mixture was stirred for 5 minutes, 2-bromobenzaldehyde (2.0 mL, 17.13 mmol) was added dropwise, and the mixture was stirred at ambient temperature for 16 hours. The solid material was filtered through a disposable plastic frit and washed with dichloromethane. The organic layer was washed with 30 mL of water then dried over sodium sulfate, filtered, and concentrated to provide (E)-ethyl 2-((2-bromobenzylidene)amino)acetate (4.6 g, 17.03 mmol, 99% yield). ¹H NMR (400 MHz, CDCl₃) δ ppm 8.70 (d, J=1.6 Hz, 1H), 8.12 (dd, J=7.7, 1.9 Hz, 1H), 7.60 (dd, J=7.8, 1.3 Hz, 1H), 7.38 (tt, J=7.6, 1.1 Hz, 1H), 7.35-7.27 (m, 1H), 4.48 (d, J=1.4 Hz, 2H), 4.28 (q, J=7.1 Hz, 2H), 1.34 (t, J=7.1 Hz, 3H); MS (ESI+) m/z 270 (M+H)⁺.

Core 10B (2S,3R,4S,5S)-ethyl 5-(2-bromophenyl)-3-(tert-butyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.147 g, 0.195 mmol) and copper (I) triflate dimer, benzene complex (0.042 g, 0.084 mmol) were dissolved in tetrahydrofuran (34.3 mL) that had been sparged with stream of nitrogen for 1 hour. The resulting mixture was stirred for 1.5 hours at ambient temperature, and (E)-ethyl 2-((2-bromobenzylidene)amino)acetate (4.63 g, 17.14 mmol) was added after cooling to <5° C. in an ice-water bath. Potassium 2-methylpropan-2-olate (0.134 mL, 0.134 mmol) was added dropwise, followed by addition of (E)-3,3-dimethyl-1-nitrobut-1-ene (2.324 g, 18.00 mmol) neat over 25 minutes, maintaining an internal temperature <10° C. After the addition was complete and stirred for 90 minutes, LC-MS showed complete conversion. The mixture was diluted with methyl tert-butyl ether (150 mL) and stirred with 50 mL of saturated aqueous ammonium chloride at ambient temperature for 15 minutes. The layers were separated and the organic layer was washed with saturated aqueous sodium bicarbonate and brine. The organic layer was dried over sodium sulfate, filtered, and concentrated, and precipitated from 50 mL of heptane. The mixture was cooled in an ice bath to <5° C. for 15 minutes, and the resulting material was filtered and washed with 20 mL of heptanes to provide (2S,3R,4S,5S)-ethyl 5-(2-bromophenyl)-3-(tert-butyl)-4-nitropyrrolidine-2-carboxylate (4.303 g, 10.78 mmol, 62.9% yield). ¹H NMR (400 MHz, CDCl₃) δ ppm 7.58 (dd, J=8.0, 1.2 Hz, 1H), 7.41-7.29 (m, 2H), 7.24-7.14 (m, 1H), 5.43 (dd, J=5.9, 2.3 Hz, 1H), 4.70 (dd, J=10.7, 5.9 Hz, 1H), 4.33 (qd, J=7.1, 1.2 Hz, 2H), 3.82 (t, J=7.5 Hz, 1H), 3.22 (t, J=9.8 Hz, 1H), 3.03 (dd, J=7.0, 2.3 Hz, 1H), 1.36 (t, J=7.1 Hz, 3H), 1.08 (s, 9H); MS (APCI+) m/z 399 (M+H)⁺.

Core 11

(2S,3R,4S,5S)-tert-butyl 3-(tert-butyl)-5-(2-isopropylphenyl)-4-nitropyrrolidine-2-carboxylate Core 11A (E)-tert-butyl 2-((2-isopropylbenzylidene)amino)acetate To a stirred suspension of tert-butyl 2-aminoacetate hydrochloride (2.55 g, 14.74 mmol) and magnesium sulfate (3.55 g, 29.5 mmol) in anhydrous CH₂Cl₂ (50 mL) at room temperature was slowly added triethylamine (2.158 mL, 15.48 mmol). The mixture was stirred for 15 minutes, treated with 2-isopropylbenzaldehyde (2.3 g, 14.74 mmol), and stirred overnight. The solid material was removed via filtration and the filtrate was washed with water (quick wash twice) and brine, then dried over sodium sulfate, filtered and concentrated to provide (E)-tert-butyl 2-((2-isopropylbenzylidene)amino)acetate (3.85 g, 14.74 mmol, 100% yield). ¹H NMR (400 MHz, DMSO-d₆) δ ppm 8.68 (s, 1H), 7.75 (dd, J=7.8, 1.4 Hz, 1H), 7.44-7.32 (m, 2H), 7.21 (ddd, J=8.1, 7.0, 1.7 Hz, 1H), 4.30 (d, J=1.2 Hz, 2H), 3.58 (hept, J=6.8 Hz, 1H), 1.40 (s, 9H), 1.24-1.15 (m, 6H). MS (DCI+) m/z 262.1 (M+H)⁺.

Core 11B (2S,3R,4S,5S)-tert-butyl 3-(tert-butyl)-5-(2-isopropylphenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.075 g, 0.100 mmol) and copper (I) triflate dimer, benzene complex (0.019 g, 0.038 mmol) were dissolved in tetrahydrofuran (11.83 mL) that had been sparged with an nitrogen stream for 2 hours. The resulting mixture was stirred for 1.5 hours at room temperature, and (E)-tert-butyl 2-((2-isopropylbenzylidene)amino)acetate (2.01 g, 7.69 mmol) neat was added after cooling to <5° C. in an ice-water bath. Potassium 2-methylpropan-2-olate (0.077 mL, 0.077 mmol) was added drop wise, followed by addition of (E)-3,3-dimethyl-1-nitrobut-1-ene (0.993 g, 7.69 mmol) neat over 25 minutes, maintaining an internal temperature <10° C. After the addition was complete, the reaction mixture was stirred for 15 minutes at the same temperature. The reaction mixture was diluted with methyl tert-butyl ether (60 mL) and stirred with 40 mL of saturated aqueous ammonium chloride at room temperature for 15 minutes. The organic layer was separated and washed with saturated aqueous sodium bicarbonate and brine, dried over sodium sulfate, filtered, and concentrated. The residue was purified by flash chromatography (0 to 30% ethyl acetate in heptane) to provide (2S,3R,4S,5S)-tert-butyl 3-(tert-butyl)-5-(2-isopropylphenyl)-4-nitropyrrolidine-2-carboxylate (2.48 g, 6.35 mmol, 83% yield). ¹H NMR (501 MHz, DMSO-d₆) δ ppm 7.35 (dd, J=7.9, 1.4 Hz, 1H), 7.31-7.18 (m, 2H), 7.10 (ddd, J=8.5, 7.3, 1.5 Hz, 1H), 5.08 (dd, J=7.0, 3.6 Hz, 1H), 4.70 (dd, J=8.5, 6.9 Hz, 1H), 3.61 (t, J=7.7 Hz, 1H), 3.40 (t, J=8.1 Hz, 1H), 3.10 (hept, J=6.8

Hz, 1H), 3.00 (dd, J=7.8, 3.5 Hz, 1H), 1.47 (s, 9H), 1.28 (d, J=6.8 Hz, 3H), 1.16 (d, J=6.7 Hz, 3H), 0.95 (s, 9H). MS (ESI$^+$) m/z 390.9 (M+H)$^+$.

Core 12

(2S,3R,4S,5S)-ethyl 3-(tert-butyl)-5-(2-cyclopropyl-phenyl)-4-nitropyrrolidine-2-carboxylate Core 12A (E)-ethyl 2-((2-cyclopropylbenzylidene)amino)acetate Ethyl 2-aminoacetate hydrochloride (4.50 g, 32.2 mmol) and magnesium sulfate (6.21 g, 51.6 mmol) were suspended in dichloromethane (43.0 mL) and the suspension was treated with triethylamine (4.49 mL, 32.2 mmol). After 1 hour, 2-cyclopropylbenzaldehyde (3.77 g, 25.8 mmol) in 5 mL of dichloromethane was added and the reaction was stirred at room temperature for 16 hours. The solid material was removed via filtration and the filtrate was washed with water and brine, dried over sodium sulfate, filtered, and concentrated to provide (E)-ethyl 2-((2-cyclopropylben-zylidene)amino)acetate (5.68 g, 24.56 mmol, 95% yield), which was used in the next step without further purification. $^1$H NMR (400 MHz, DMSO-d$_6$) δ ppm 8.92 (d, J=1.5 Hz, 1H), 7.81 (dd, J=7.8, 1.5 Hz, 1H), 7.35 (td, J=7.6, 1.5 Hz, 1H), 7.22 (td, J=7.6, 1.2 Hz, 1H), 7.05 (dd, J=7.8, 1.2 Hz, 1H), 4.45 (d, J=1.3 Hz, 2H), 4.13 (q, J=7.1 Hz, 2H), 2.33 (tt, J=8.5, 5.3 Hz, 1H), 1.21 (t, J=7.1 Hz, 3H), 1.03-0.90 (m, 2H), 0.75-0.63 (m, 2H). MS (ESI$^+$) m/z 232.1 (M+H)$^+$.

Core 12B (2S,3R,4S,5S)-ethyl 3-(tert-butyl)-5-(2-cyclopropyl-phenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.241 g, 0.319 mmol) and copper (I) triflate dimer, benzene complex (0.062 g, 0.123 mmol) were dissolved in tetrahydrofuran (63.0 mL) that had been sparged with an nitrogen stream for 2 hours. The resulting mixture was stirred for 1.5 hours at room temperature, and (E)-ethyl 2-((2-cyclopropylbenzylidene) amino)acetate (5.68 g, 24.56 mmol) in tetrahydrofuran (8 mL) was added after cooling to <5° C. in an ice-water bath. Potassium 2-methylpropan-2-olate (0.246 mL, 0.246 mmol) was added drop wise, followed by addition of (E)-3,3-dimethyl-1-nitrobut-1-ene (3.17 g, 24.56 mmol) neat over 25 minutes, maintaining an internal temperature <10° C. After the addition was complete, the reaction was stirred for 15 minutes at the same temperature, diluted with methyl tert-butyl ether (100 mL) and stirred with 75 mL of saturated ammonium chloride at room temperature for 15 minutes. The organic layer was separated, washed with saturated sodium bicarbonate and brine, dried over sodium sulfate, and filtered. The filtrate was concentrated and purified by flash chromatography (0 to 30% ethyl acetate in heptane) to provide (2S,3R,4S,5S)-ethyl 3-(tert-butyl)-5-(2-cyclopropy-lphenyl)-4-nitropyrrolidine-2-carboxylate (6.85 g, 19.00 mmol, 77% yield). ee>97%. $^1$H NMR (501 MHz, DMSO-d$_6$) δ ppm 7.34 (dd, J=7.6, 1.5 Hz, 1H), 7.15 (dtd, J=25.3, 7.5, 1.6 Hz, 2H), 7.07-7.01 (m, 1H), 5.31 (dd, J=6.7, 3.1 Hz, 1H), 4.92 (dd, J=8.4, 6.6 Hz, 1H), 4.27-4.12 (m, 2H), 3.75 (t, J=7.7 Hz, 1H), 3.51 (t, J=8.1 Hz, 1H), 3.04 (dd, J=7.6, 3.1 Hz, 1H), 2.06 (tt, J=8.5, 5.4 Hz, 1H), 1.24 (t, J=7.1 Hz, 3H), 0.95 (s, 9H), 1.00-0.78 (m, 2H), 0.81-0.68 (m, 1H), 0.64-0.55 (m, 1H). MS (ESI$^+$) m/z 361.2 (M+H)$^+$.

Core 13

(2S,3R,4S,5S)-ethyl 3-(tert-butyl)-5-(2-isopropyl-phenyl)-4-nitropyrrolidine-2-carboxylate Core 13A (E)-ethyl 2-((2-isopropylbenzylidene)amino)acetate Ethyl 2-aminoacetate hydrochloride (5.02 g, 36.0 mmol) and magnesium sulfate (5.20 g, 43.2 mmol) were suspended in dichloromethane (45 mL) and treated with triethylamine (9.9 mL, 71.0 mmol). The mixture was stirred for 20 minutes and was treated dropwise with 2-isopropylbenzaldehyde (5 g, 33.7 mmol). The reaction mixture stirred at room temperature for 3 days. The mixture was filtered (fritted glass funnel), and the filter pad was washed with copious amount of CH$_2$Cl$_2$. The filtrates were washed twice with water and once with brine, dried over Na$_2$SO$_4$, filtered, and concentrated in vacuo to yield the title compound, 7.066 g (90% yield). $^1$H NMR (400 MHz, CDCl$_3$) δ ppm 8.73 (m, 1H), 7.94 (dd, J=7.9, 1.5 Hz, 1H), 7.42 (m, 1H), 7.35 (dd, J=7.9, 1.4 Hz, 1H), 7.24 (m, 1H), 4.44 (d, J=1.4 Hz, 2H), 4.26 (q, J=7.1 Hz, 2H), 3.53 (hept, J=6.8 Hz, 1H), 1.34-1.29 (m, 9H). MS (ESI$^+$) m/z 234.1 (M+H)$^+$.

Core 13B (2S,3R,4S,5S)-ethyl 3-(tert-butyl)-5-(2-isopropyl-phenyl)-4-nitropyrrolidine-2-carboxylate Tetrahydrofuran (30 mL) was sparged with nitrogen for 75 minutes, then it was treated with copper(I) triflate dimer, benzene complex (0.033 g, 0.065 mmol) and (2-(bis(3,5-bis (trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.098 g, 0.129 mmol). The mixture was stirred at room temperature for 1 hour. The mixture was cooled to <5° C. and treated dropwise with a solution of the product of Step 13A (4.15 g, 17.80 mmol) in 8 mL tetrahydrofuran, followed by dropwise addition of potassium 2-methylpropan-2-olate (1M in tetrahydrofuran; 0.1 mL, 0.100 mmol), keeping the temperature <5° C. Neat (E)-3,3-dimethyl-1-nitrobut-1-ene (2.09 g, 16.18 mmol) was then added dropwise over about 10 minutes to keep the temperature <10° C. After completion of the addition, the reaction continued to stir in the ice bath for 25 minutes. The reaction mixture was then quenched with 25 mL of saturated aqueous NH$_4$Cl solution and warmed up to room temperature. The mixture was diluted with methyl tert-butyl ether and washed twice with saturated aqueous NH$_4$Cl solution and once with brine. The organic layer was dried over Na$_2$SO$_4$, filtered, and concentrated in vacuo. Silica gel chromatography, eluting with 10 to 50% ethyl acetate-heptanes, afforded the title compound, 1.902 g, (32% yield). $^1$H NMR (400 MHz, DMSO-d$_6$) δ ppm 7.42-7.34 (m, 1H), 7.30-7.17 (m, 2H), 7.08 (ddd, J=7.5, 6.9, 1.7 Hz, 1H), 5.08 (dd, J=6.9, 3.6 Hz, 1H), 4.77 (d, J=6.9 Hz, 1H), 4.23 (q, J=7.1 Hz, 2H), 3.77 (d, J=7.6 Hz, 1H), 3.25 (br s, 1H), 3.21-3.06 (m, 2H), 1.33-1.14 (m, 9H), 0.98 (s, 9H). MS (ESI$^+$) m/z 363.1 (M+H)$^+$.

Core 14

(2S,3R,4S,5S)-ethyl 3-(tert-butyl)-5-(2-chlorophenyl)-4-nitropyrrolidine-2-carboxylate

Core 14A

(E)-ethyl 2-((2-chlorobenzylidene)amino)acetate

A mixture of ethyl 2-aminoacetate hydrochloride (1.85 g, 13.25 mmol) and magnesium sulfate (3.19 g, 26.5 mmol) in dichloromethane (22.09 mL) (anhydrous) was treated with triethylamine (1.847 mL, 13.25 mmol), stirred for 30 minutes, and treated with the 2-chlorobenzaldehyde (1.86 g, 13.25 mmol) as a solution in 3 mL of dichloromethane. The reaction was stirred at ambient temperature overnight. The solid material was filtered and the filtrate was concentrated. Toluene (5 mL) was added, the mixture was filtered again and concentrated, giving (E)-ethyl 2-((2-chlorobenzylidene) amino)acetate (2.76 g, 12.23 mmol, 92% yield) which was used directly in the next step. $^1$H NMR (400 MHz, CDCl$_3$) δ ppm 8.77 (d, J=1.5 Hz, 1H), 8.19-8.04 (m, 1H), 7.45-7.39 (m, 2H), 7.34 (ddd, J=8.3, 6.0, 2.6 Hz, 1H), 4.48 (d, J=1.5 Hz, 2H), 4.28 (q, J=7.2 Hz, 2H), 1.34 (t, J=7.1 Hz, 3H).

Core 14B

(2S,3R,4S,5S)-ethyl 3-(tert-butyl)-5-(2-chlorophenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.175 g, 0.232 mmol) and copper (I) triflate dimer, benzene complex (0.047 g, 0.093 mmol) were dissolved in tetrahydrofuran (19.36 mL) that had been sparged with an N$_2$ stream for 1 hour. The resulting mixture was stirred for 1 hour at ambient temperature (continue nitrogen sparge), and (E)-ethyl 2-((2-chlorobenzylidene)amino)acetate (2.75 g, 12.19 mmol) was added as a solution in 2 mL of tetrahydrofuran and the resulting solution was cooled to <5° C. in an ice-water bath. Potassium 2-methylpropan-2-olate in tetrahydrofuran (0.209 mL, 0.209 mmol) was added dropwise, followed by addition of neat (E)-3,3-dimethyl-1-nitrobut-1-ene (1.5 g, 11.61 mmol) over 20 minutes, maintaining a temperature less than 7° C. The reaction mixture was stirred for 1 hour at 0° C. and quenched with 60 mL of saturated aqueous ammonium chloride and 100 mL of ethyl acetate and warmed to ambient temperature. The organic layer was separated and washed with saturated aqueous ammonium chloride (2×50 mL) and brine and filtered through a pad of silica gel. The organic layer was concentrated. Heptane (70 mL) was added, and the resulting precipitate was filtered. The filtrate was purified by chromatography using a 40 g silica gel cartridge eluting with a gradient of 0-60% heptanes/ethyl acetate over a period of 20 minutes to provide additional product (2S,3R,4S,5S)-ethyl 3-(tert-butyl)-5-(2-chlorophenyl)-4-nitropyrrolidine-2-carboxylate (2.85 g, 8.03 mmol, 69.2% yield). $^1$H NMR (400 MHz, DMSO-d$_6$) δ ppm 7.56-7.48 (m, 1H), 7.45-7.38 (m, 1H), 7.35-7.24 (m, 2H), 5.25 (dd, J=6.7, 3.0 Hz, 1H), 4.71 (t, J=7.0 Hz, 1H), 4.19 (qq, J=7.3, 3.7 Hz, 2H), 3.78 (t, J=7.3 Hz, 1H), 3.68 (t, J=7.3 Hz, 1H), 3.07 (dd, J=7.4, 3.0 Hz, 1H), 1.24 (t, J=7.1 Hz, 3H), 0.94 (s, 9H), 0.96 (s, 9H); MS (APCI+) m/z 355 (M+H)$^+$.

Core 15

(2S,3R,4S,5S)-ethyl 3-(tert-butyl)-5-(2-isopropoxyphenyl)-4-nitropyrrolidine-2-carboxylate

Core 15A

(E)-ethyl 2-((2-isopropoxybenzylidene)amino)acetate

To ethyl 2-aminoacetate hydrochloric acid (CAS#623-33-6) (4.68 g, 33.5 mmol) and magnesium sulfate (4.03 g, 33.5 mmol) in dichloromethane (80 ml) was added triethylamine (4.67 mL, 33.5 mmol). The mixture was stirred at ambient temperature for 5 minutes, and 2-isopropoxybenzaldehyde [CAS#22921-58-0] (5 g, 30.5 mmol) was added dropwise and stirred overnight. The solid was filtered and the solid was washed with dichloromethane (10 mL×2). The combined organic layer was washed with brine, dried over MgSO$_4$, filtered and concentrated to provide the title compound, 7.28 g (96% yield). $^1$H NMR (501 MHz, Chloroform-d) δ ppm 8.74 (d, J=1.5 Hz, 1H), 8.04 (dd, J=7.8, 1.8 Hz, 1H), 7.38 (ddd, J=8.4, 7.3, 1.8 Hz, 1H), 7.00-6.95 (m, 1H), 6.95-6.91 (m, 1H), 4.66-4.60 (m, 1H), 4.42 (d, J=1.4 Hz, 2H), 4.26 (q, J=7.1 Hz, 2H), 1.38 (d, J=6.1 Hz, 6H), 1.32 (t, J=7.1 Hz, 3H).

Core 15B

(2S,3R,4S,5S)-ethyl 3-(tert-butyl)-5-(2-isopropoxyphenyl)-4-nitropyrrolidine-2-carboxylate A mixture of (2-(bis(3,5-bis(trifluoromethyl)phenyl) phosphino)-3-((S)-4-isopropyl-4,5-dihydrooxazol-2-yl)cyclopenta-2,4-dien-1-yl)(cyclopenta-2,4-dien-1-yl)iron (0.109 g, 0.144 mmol) and copper(I) triflate dimer, benzene complex (0.030 g, 0.060 mmol) in tetrahydrofuran (40 mL) cooled in an ice-bath was sparged with N$_2$ for 1 hour. Example 15A (7 g, 28.1 mmol) in 10 mL tetrahydrofuran was added, followed by potassium 2-methylpropan-2-olate (10.80 mg, 0.096 mmol), and (E)-3,3-dimethyl-1-nitrobut-1-ene (1.632 g, 12.64 mmol) dropwise, maintaining an internal temperature <10° C. The mixture was stirred at the same temperature for 2 hours, diluted with ethyl acetate (50 mL) and saturated aqueous ammonium chloride (50 mL). The organic layer was washed with saturated aqueous NaHCO$_3$ and brine, dried over Na$_2$SO$_4$, filtered, and concentrated. Purification via chromatography on a 80 g silica gel cartridge, eluting with ethyl acetate in heptane at 0-40% gradient provided the title compound 2.84 g (62.4% yield). $^1$H NMR (501 MHz, Chloroform-d) δ ppm 7.29-7.22 (m, 2H), 6.93 (td, J=7.6, 1.1 Hz, 1H), 6.87 (dt, J=8.3, 0.7 Hz, 1H), 5.44 (dd, J=5.5, 2.2 Hz, 1H), 4.69 (dtd, J=12.1, 6.0, 0.7 Hz, 1H), 4.54 (s, 1H), 4.34 (qd, J=7.1, 2.0 Hz, 2H), 3.81 (s, 1H), 3.45 (s, 1H), 2.87 (dd, J=7.1, 2.2 Hz, 1H), 1.48 (d, J=6.0 Hz, 3H), 1.41-1.34 (m, 6H), 1.09 (s, 9H); MS (ESI+) m/z 379.1 (M+H)$^+$.

Core 16

(2S,3R,4S,5S)-ethyl 3-(tert-butyl)-4-nitro-5-(2-(trifluoromethyl)pyridin-3-yl)pyrrolidine-2-carboxylate

Core 16A

(E)-ethyl 2-(((2-(trifluoromethyl)pyridin-3-yl)methylene)amino)acetate

Ethyl 2-aminoacetate hydrochloride (3.49 g, 24.98 mmol) and magnesium sulfate (4.81 g, 40.0 mmol) were suspended in dichloromethane (33.3 mL) and the suspension was treated with triethylamine (3.48 mL, 24.98 mmol). After 1 hour, 2-(trifluoromethyl)nicotinaldehyde (3.5 g, 19.99 mmol) in dichloromethane (5 mL) was added and the reaction mixture was stirred at room temperature for 16 hours. The solid material was removed via filtration and the filtrate was washed with water and brine, dried over sodium sulfate, filtered, and concentrated to provide (E)-ethyl 2-(((2-(trifluoromethyl)pyridin-3-yl)methylene)amino)acetate (5.08 g, 19.52 mmol, 98% yield), which was used without further purification. $^1$H NMR (400 MHz, DMSO-d$_6$) δ ppm 8.80 (dd, J=4.6, 1.6 Hz, 1H), 8.68 (td, J=2.5, 1.4 Hz, 1H), 8.62-8.45 (m, 1H), 7.87-7.62 (m, 1H), 4.56 (d, J=1.3 Hz, 2H), 4.13 (m, 2H), 1.19 (m, 3H). MS (ESI$^+$) m/z 261.0 (M+H)$^+$.

Core 16B (2S,3R,4S,5S)-ethyl 3-(tert-butyl)-4-nitro-5-(2-(trifluoromethyl)pyridin-3-yl)pyrrolidine-2-carboxylate To a 250 mL flask was added tetrahydrofuran (50 mL). The mixture was sparged with a nitrogen stream for 2 hours, and (2-(bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.191 g, 0.254 mmol), and copper (I) triflate dimer, benzene complex (0.049 g, 0.098 mmol) were added. The reaction mixture was sparged with a nitrogen stream for 90 minutes at room temperature, and (E)-ethyl 2-(((2-(trifluoromethyl)pyridin-3-yl)methylene)amino)acetate (5.08 g, 19.52 mmol) in tetrahydrofuran (8 mL) was added after cooling to <5° C. in an ice-water bath. Potassium 2-methylpropan-2-olate (0.195 mL, 0.195 mmol) was added drop wise, followed by addition of (E)-3,3-dimethyl-1-nitrobut-1-ene (2.52 g, 19.52 mmol) neat over 25 minutes, maintaining an internal temperature <10° C. After the addition was complete, the reaction mixture was stirred for 15 minutes, diluted with methyl tert-butyl ether (100 mL), and stirred with 75 mL of saturated aqueous ammonium chloride at room temperature for 15 minutes. The organic layer was separated and washed with saturated aqueous sodium bicarbonate and brine, then dried over sodium sulfate. The mixture was filtered, concentrated and purified by flash chromatography (0 to 30% ethyl acetate in heptane) to provide (2S,3R,4S,5S)-ethyl 3-(tert-butyl)-4-nitro-5-(2-(trifluoromethyl)pyridin-3-yl) pyrrolidine-2-carboxylate (4.56 g, 11.71 mmol, 60.0% yield). ee=95.4%. $^1$H NMR (501 MHz, DMSO-d$_6$) δ ppm 8.65 (m, 1H), 8.27 (dd, J=8.1, 1.5 Hz, 1H), 7.72 (ddd, J=19.7, 8.0, 4.6 Hz, 1H), 5.02 (dd, J=7.1, 3.3 Hz, 1H), 4.84 (t, J=6.5 Hz, 1H), 4.20 (qq, J=7.0, 3.7 Hz, 2H), 3.94 (t, J=5.9 Hz, 1H), 3.83 (dd, J=7.3, 6.3 Hz, 1H), 3.19 (dd, J=7.4, 3.3 Hz, 1H), 1.25 (t, J=7.1 Hz, 3H), 0.93 (s, 9H). MS (ESI$^+$) m/z 390.1 (M+H)$^+$.

Core 17

(2S,3R,4S,5S)-ethyl 5-(3-bromophenyl)-3-(tert-butyl)-4-nitropyrrolidine-2-carboxylate Core 17A (E)-ethyl 2-((3-bromobenzylidene)amino)acetate Ethyl 2-aminoacetate hydrochloride (2.490 g, 17.84 mmol) and magnesium sulfate (2.147 g, 17.84 mmol) were stirred in dichloromethane (24.13 mL) at ambient temperature, and triethylamine (2.486 mL, 17.84 mmol) was added. The mixture was stirred for 5 minutes and 3-bromobenzaldehyde (1.890 mL, 16.21 mmol) was added dropwise. The mixture was stirred at ambient temperature for 16 hours. The solid material was filtered through a disposable plastic frit and washed with dichloromethane. The organic layer was washed with 30 mL of water, dried over sodium sulfate, filtered, then concentrated to provide (E)-ethyl 2-((3-bromobenzylidene)amino)acetate (4.38 g, 16.21 mmol, 100% yield). $^1$H NMR (500 MHz, CDCl$_3$) δ ppm 8.27 (d, J=1.4 Hz, 1H), 8.01 (t, J=1.8 Hz, 1H), 7.70 (dt, J=7.7, 1.3 Hz, 1H), 7.61 (ddd, J=8.0, 2.0, 1.0 Hz, 1H), 7.33 (t, J=7.8 Hz, 1H), 4.44 (d, J=1.3 Hz, 2H), 4.28 (q, J=7.1 Hz, 2H), 1.35 (t, J=7.1 Hz, 3H); MS (ESI+) m/z 224 (M+H)$^+$.

Core 17B (2S,3R,4S,5S)-ethyl 5-(3-bromophenyl)-3-(tert-butyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.139 g, 0.184 mmol) and copper (I) triflate dimer, benzene complex (0.040 g, 0.079 mmol) were dissolved in tetrahydrofuran (32.4 mL) that had been sparged with a nitrogen stream for 1 hour. The resulting mixture was stirred for 1.5 hours at ambient temperature, and (E)-ethyl 2-((3-bromobenzylidene)amino) acetate (4.38 g, 16.21 mmol) was added after cooling to <5° C. in an ice-water bath. Potassium 2-methylpropan-2-olate (0.127 mL, 0.127 mmol) was added dropwise, followed by addition of (E)-3,3-dimethyl-1-nitrobut-1-ene (2.199 g, 17.03 mmol) neat over 25 minutes, maintaining an internal temperature <10° C. After the addition was complete, the mixture was stirred for 2 hours. Additional potassium 2-methylpropan-2-olate (0.127 mL, 0.127 mmol) was added. After 30 minutes, the reaction mixture was diluted with methyl tert-butyl ether (150 mL) and stirred with 50 mL of saturated aqueous ammonium chloride at ambient temperature for 15 minutes. The layers were separated. The organic layer was washed with saturated aqueous sodium bicarbonate and brine, dried over sodium sulfate, filtered, and concentrated to provide a crude material, which was triturated with 3×5 mL of heptanes. The heptane insolubles were chromatographed using an 80 g silica gel cartridge with a gradient of 5-50% ethyl acetate/heptanes over 40 minutes to provide (2S,3R,4S,5S)-ethyl 5-(3-bromophenyl)-3-(tert-butyl)-4-nitropyrrolidine-2-carboxylate (2.76 g, 6.91 mmol, 42.6% yield). n-Hexane (about 1 mL) was added to about 50 mg of the crude material, and the mixture was warmed to 45° C. The mixture was cooled to provide the title compound. Relative and absolute stereochemistry were confirmed by X-ray analysis. $^1$H NMR (501 MHz, CDCl$_3$) δ ppm 7.50 (d, J=1.9 Hz, 1H), 7.45 (dt, J=7.5, 1.7 Hz, 1H), 7.29-7.19 (m, 2H), 5.13 (dd, J=6.0, 2.6 Hz, 1H), 4.41 (dd, J=11.9, 6.0 Hz, 1H), 4.33 (qd, J=7.1, 1.1 Hz, 2H), 3.81 (dd, J=9.5, 7.2 Hz, 1H), 3.27-3.17 (m, 1H), 2.98 (dd, J=7.2, 2.5 Hz, 1H), 1.37 (t, J=7.2 Hz, 3H), 1.07 (s, 9H); MS (APCI+) m/z 399 (M+H)$^+$.

Core 18

(2S,3R,4S,5S)-ethyl 3-(tert-butyl)-5-(3-(tert-butyl)phenyl)-4-nitropyrrolidine-2-carboxylate

Core 18A

(E)-ethyl 2-((3-(tert-butyl)benzylidene)amino)acetate

To ethyl 2-aminoacetate, hydrochloric acid (CAS#623-33-6, 776 mg, 5.56 mmol) and magnesium sulfate (669 mg, 5.56 mmol) in $CH_2Cl_2$ (10 mL) was added triethylamine (0.775 mL, 5.56 mmol). The mixture was stirred at ambient temperature for 5 minutes, 3-(tert-butyl)benzaldehyde (820 mg, 5.05 mmol) was added dropwise, and the mixture was stirred overnight. The mixture was filtered and the solid was washed with $CH_2Cl_2$ (10 mL×2). The combined organics were washed with water and brine, dried over $MgSO_4$, filtered, and concentrated to provide (E)-ethyl 2-((3-(tert-butyl)benzylidene)amino)acetate (1.08 g, 86% yield). $^1H$ NMR (400 MHz, $CDCl_3$) δ ppm 8.31 (s, 1H), 7.81 (t, J=1.9 Hz, 1H), 7.60 (dt, J=7.5, 1.4 Hz, 1H), 7.50 (ddd, J=7.8, 2.1, 1.2 Hz, 1H), 7.37 (t, J=7.7 Hz, 1H), 4.41 (d, J=1.2 Hz, 2H), 4.25 (q, J=7.1 Hz, 2H), 1.36 (s, 9H), 1.32 (t, J=7.1 Hz, 3H).

Core 18B

(2S,3R,4S,5S)-ethyl 3-(tert-butyl)-5-(3-(tert-butyl)phenyl)-4-nitropyrrolidine-2-carboxylate A mixture of (2-(bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (37 mg, 0.049 mmol) and copper(I) triflate dimer, benzene complex (CAS#42152-46-5, 10.18 mg, 0.020 mmol) in tetrahydrofuran (10 mL) was spurred with $N_2$ for one hour, and Core 18A (1 g, 4.04 mmol) in tetrahydrofuran (5 mL) was added at 0° C., followed by addition of potassium 2-methylpropan-2-olate (3.63 mg, 0.032 mmol) dropwise, and finally (E)-3,3-dimethyl-1-nitrobut-1-ene (548 mg, 4.25 mmol) maintaining an internal temperature <10° C. The mixture was stirred at the same temperature for one hour, diluted with ethyl acetate (20 mL) and saturated aqueous ammonium chloride (20 mL) and stirred at ambient temperature for 30 minutes. The organic layer washed with $NaHCO_3$ and brine, dried over $Na_2SO_4$, filtered, and concentrated to provide title compound which was used in next step without purification. LC/MS (APCI+) m/z 377 (M+1)$^+$.

Core 19

(2S,3R,4S,5R)-ethyl 3-(tert-butyl)-5-(1-isopropyl-1H-pyrazol-5-yl)-4-nitropyrrolidine-2-carboxylate

Core 19A

(E)-ethyl 2-(((1-isopropyl-1H-pyrazol-5-yl)methylene)amino)acetate

Ethyl 2-aminoacetate hydrochloride (2.223 g, 15.92 mmol) and magnesium sulfate (1.917 g, 15.92 mmol) were stirred in dichloromethane (24.13 mL) at ambient temperature, and triethylamine (2.185 mL, 15.67 mmol) was added. The mixture was stirred for 5 minutes and 1-isopropyl-1H-pyrazole-5-carbaldehyde (2.0 g, 14.48 mmol) was added dropwise. The mixture was stirred at ambient temperature for 16 hours. The solid material was filtered through a disposable plastic frit and washed with dichloromethane. The organic layer was washed with 30 mL of water, dried over sodium sulfate, filtered, and concentrated to provide (E)-ethyl 2-(((1-isopropyl-1H-pyrazol-5-yl)methylene)amino)acetate (3.23 g, 14.47 mmol, 100% yield). $^1H$ NMR (400 MHz, $CDCl_3$) δ ppm 8.29 (t, J=1.3 Hz, 1H), 7.52 (d, J=1.9 Hz, 1H), 6.58 (d, J=2.0 Hz, 1H), 5.48 (p, J=6.6 Hz, 1H), 4.38 (d, J=1.3 Hz, 2H), 4.24 (q, J=7.2 Hz, 2H), 1.50 (d, J=6.6 Hz, 6H), 1.31 (t, J=7.1 Hz, 3H); MS (ESI+) m/z 224 (M+H)$^+$.

Core 19B

(2S,3R,4S,5R)-ethyl 3-(tert-butyl)-5-(1-isopropyl-1H-pyrazol-5-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.124 g, 0.164 mmol) and copper (I) triflate dimer, benzene complex (0.036 g, 0.071 mmol) were dissolved in tetrahydrofuran (28.9 mL) that had been sparged with a nitrogen stream for 1 hour. The resulting mixture was stirred for 1.5 hours at ambient temperature, and (E)-ethyl 2-(((1-isopropyl-1H-pyrazol-5-yl)methylene)amino)acetate (3.23 g, 14.47 mmol) was added after cooling to <5° C. in an ice-water bath. Potassium 2-methylpropan-2-olate (0.113 mL, 0.113 mmol) was added dropwise, followed by addition of (E)-3,3-dimethyl-1-nitrobut-1-ene (1.962 g, 15.19 mmol) neat over 25 minutes, maintaining an internal temperature <10° C. After the addition was complete the reaction was stirred for 2 hours. The mixture was diluted with methyl tert-butyl ether (150 mL) and stirred with 50 mL of saturated aqueous ammonium chloride at ambient temperature for 15 minutes. The layers were separated, and the organic layer was washed with saturated sodium bicarbonate and brine, and dried over sodium sulfate. After filtration, the combined organic layers were concentrated and triturated with 3×5 mL of heptanes and left in dry ice overnight in heptanes. The solvent was removed and the resulting material concentrated. n-Hexane was added and the mixture was triturated and stirred at ambient temperature for an hour. The mixture was filtered and washed with 10 mL of heptanes to provide (2S,3R,4S,5R)-ethyl 3-(tert-butyl)-5-(1-isopropyl-1H-pyrazol-5-yl)-4-nitropyrrolidine-2-carboxylate (2.556 g, 7.25 mmol, 50.1% yield). $^1H$ NMR (500 MHz, $CDCl_3$) δ ppm 7.50 (d, J=1.9 Hz, 1H), 6.21 (d, J=1.9 Hz, 1H), 5.04 (dd, J=5.9, 2.3 Hz, 1H), 4.47 (ddd, J=21.6, 12.9, 6.2 Hz, 2H), 4.35 (qd, J=7.2, 1.8 Hz, 2H), 3.82 (dd, J=9.4, 6.6 Hz, 1H), 3.30 (dd, J=12.3, 9.5 Hz, 1H), 3.02 (dd, J=6.7, 2.3 Hz, 1H), 1.60 (d, J=6.6 Hz, 3H), 1.56 (d, J=6.5 Hz, 3H), 1.37 (t, J=7.1 Hz, 3H), 1.10 (s, 9H); MS (APCI+) m/z 353 (M+H)$^+$. Absolute chemistry confirmed by X-ray diffraction analysis.

Core 20

(2S,3R,4S,5S)-ethyl 3-(tert-butyl)-5-(2-methoxypyridin-3-yl)-4-nitropyrrolidine-2-carboxylate

Core 20A

(E)-ethyl 2-(((2-methoxypyridin-3-yl)methylene)amino)acetate

Ethyl 2-aminoacetate hydrochloride (14.50 g, 104 mmol) and magnesium sulfate (20.01 g, 166 mmol) were suspended in 130 mL of dichloromethane. A solution of 2-methoxynicotinaldehyde (11.4 g, 83 mmol) in 9 mL of dichloromethane was added to the stirring mixture, followed by addition of triethylamine (14.48 mL, 104 mmol) and the reaction mixture was stirred for 16 hours at ambient temperature. The solid material was removed via filtration and the filtrate was washed quickly with cold water (2×10 mL) and brine (10 mL) and dried over sodium sulfate, filtered, and concentrated to provide the crude imine, which was used without additional purification. $^1$H NMR (500 MHz, DMSO-$d_6$) δ ppm 8.58 (d, J=1.6 Hz, 1H), 8.31 (dd, J=4.9, 2.0 Hz, 1H), 8.19 (dd, J=7.4, 2.0 Hz, 1H), 7.09 (ddd, J=7.4, 4.9, 0.7 Hz, 1H), 4.45 (d, J=1.4 Hz, 2H), 4.14 (q, J=7.2 Hz, 2H), 3.96 (s, 3H), 1.22 (t, J=7.1 Hz, 3H).

Core 20B (2S,3R,4S,5S)-ethyl 3-(tert-butyl)-5-(2-methoxypyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.642 g, 0.853 mmol) and copper (I) triflate dimer, benzene complex (0.185 g, 0.367 mmol) were dissolved in tetrahydrofuran (150 mL) that had been sparged with an $N_2$ stream for 4 hours. The resulting mixture was stirred for 1.5 hours ambient temperature, and (E)-ethyl 2-(((2-methoxypyridin-3-yl)methylene)amino)acetate (17.50 g, 79 mmol) was then added via syringe after cooling the flask to an internal temperature of <5° C. in an ice-water bath. Potassium 2-methylpropan-2-olate (0.588 mL, 0.588 mmol) was added dropwise via syringe, followed by addition of (E)-3,3-dimethyl-1-nitrobut-1-ene (9.69 g, 75.0 mmol) neat via syringe over 25 minutes, maintaining an internal temperature <10° C. The reaction mixture was stirred for an additional 20 minutes at the same temperature, at which point LC-MS indicated complete consumption of the nitroalkene. The reaction mixture was diluted with methyl tert-butyl ether (300 mL) and stirred with 300 mL of saturated aqueous ammonium chloride at ambient temperature for 15 minutes. The layers were separated and the organic layer was washed with saturated sodium bicarbonate and brine, dried over sodium sulfate, filtered and concentrated. The crude material was purified via silica gel chromatography, eluting with 0:100 to 50:50 ethyl acetate:heptanes over 30 minutes on a 330 g column to provide 17.5 g of the title compound. $^1$H NMR (400 MHz, CDCl$_3$) δ ppm 8.13 (dd, J=5.0, 1.5 Hz, 1H), 7.62-7.34 (m, 1H), 6.96-6.71 (m, 1H), 5.36 (dt, J=5.7, 1.8 Hz, 1H), 4.54-4.38 (m, 1H), 4.41-4.25 (m, 2H), 4.04 (s, 3H), 3.82-3.65 (m, 1H), 3.28 (s, 1H), 2.93 (dt, J=7.3, 1.8 Hz, 1H), 1.37 (td, J=7.2, 1.2 Hz, 3H), 1.08 (s, 9H). MS(ESI+) m/z 352.1 (M+H)$^+$.

Core 21

(2S,3R,4S,5S)-ethyl 3-(tert-butyl)-4-nitro-5-(2-(trifluoromethyl)phenyl)pyrrolidine-2-carboxylate Core 21A (E)-ethyl 2-((2-(trifluoromethyl)benzylidene)amino)acetate A slurry of ethyl 2-aminoacetate hydrochloride (6.01 g, 43.1 mmol) and magnesium sulfate (5.88 g, 48.8 mmol) in dichloromethane (100 mL) was stirred at 0° C. Triethylamine (6.00 mL, 43.1 mmol) was added drop wise and the mixture was stirred at room temperature for 1 hour. 2-(Trifluoromethyl)benzaldehyde (5 g, 28.7 mmol) was added. After 15 hours, the solid was filtered and washed with dichloromethane (3×200 mL). The dichloromethane layer was washed with water (2×100 mL), dried (Na$_2$SO$_4$), filtered, and concentrated, to provide (E)-ethyl 2-((2-(trifluoromethyl)benzylidene)amino)acetate (7.2 g, 25.8 mmol, 90% yield). $^1$H NMR (400 MHz, CDCl$_3$) δ ppm 8.64 (s, 1H), 8.28 (d, J=7.6 Hz, 1H), 7.61-7.51 (m, 2H), 7.69-7.67 (m, 1H), 4.45 (s, 2H), 4.24 (q, J=6.8 Hz, 2H), 1.30 (t, J=7.0 Hz, 3H).

Core 21B (2S,3R,4S,5S)-ethyl 3-(tert-butyl)-4-nitro-5-(2-(trifluoromethyl)phenyl)pyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.169 g, 0.225 mmol) and copper (I) triflate dimer, benzene complex (0.048 g, 0.095 mmol) were added under an argon atmosphere to a flame-dried flask, containing activated 4A molecular sieves and a stirring bar. The freshly distilled anhydrous tetrahydrofuran (20 mL) was added. After being stirred for 15 minutes, the solution was cooled to 0° C. before (E)-ethyl 2-((2-(trifluoromethyl)benzylidene)amino)acetate (2.408 g, 9.29 mmol) was added, followed by potassium tert-butoxide (0.155 mL, 0.155 mmol). (E)-3,3-Dimethyl-1-nitrobut-1-ene (1 g, 7.74 mmol) was added slowly. The reaction mixture was stirred at 0° C. for 5 hours, and water (80 mL) was added to the flask. The aqueous layer was extracted with ethyl acetate (2×100 mL). The organic layers were combined, washed with brine (2×80 mL), dried over Na$_2$SO$_4$, filtered, and concentrated. The crude material was purified by chromatography on silica gel (ethyl acetate/petroleum mixture 1:40) to provide title compound (2 g, 5.10 mmol, 65.8% yield). $^1$H NMR (400 MHz, CDCl$_3$) δ ppm 7.69-7.41 (m, 4H), 5.07-5.06 (m, 1H), 4.81-4.78 (m, 1H), 4.32 (q, 2H), 3.82 (t, J=7.2 Hz, 1H), 3.15-3.13 (m, 1H), 3.01 (t, J=8.6 Hz, 1H), 1.34 (t, J=7.2 Hz, 3H), 1.03 (s, 9H).

Core 22

(2S,3R,4S,5S)-ethyl 3-(tert-butyl)-5-(2-(difluoromethyl)phenyl)-4-nitropyrrolidine-2-carboxylate Core 22A (E)-ethyl 2-((2-(difluoromethyl)benzylidene)amino)acetate A mixture of ethyl 2-aminoacetate hydrochloride (1.788 g, 12.81 mmol) and magnesium sulfate (3.08 g, 25.6 mmol) in dichloromethane (21.35 mL) (anhydrous) was treated with triethylamine (1.785 mL, 12.81 mmol), stirred for 10 minutes and treated with 2-(difluoromethyl)benzaldehyde (2.00 g, 12.81 mmol) as a solution in 4 mL of dichloromethane. The mixture was stirred at ambient temperature overnight. The solid material was filtered, the filtrate was concentrated, toluene (25 mL) was added, and the mixture was filtered again. The mixture was concentrated to provide (E)-ethyl 2-((2-(difluoromethyl)benzylidene)amino)acetate (3.0 g, 12.44 mmol, 97% yield) which was used directly on to the next step. $^1$H NMR (400 MHz, CDCl$_3$) δ ppm 8.59 (t, J=1.4 Hz, 1H), 8.00-7.87 (m, 1H), 7.70 (dd, J=6.6, 2.3 Hz, 1H), 7.63-7.52 (m, 2H), 7.35 (t, J=55.1 Hz, 1H), 4.47 (d, J=1.3 Hz, 2H), 4.28 (q, J=7.1 Hz, 2H), 1.34 (t, J=7.1 Hz, 3H).

Core 22B (2S,3R,4S,5S)-ethyl 3-(tert-butyl)-5-(2-(difluoromethyl)phenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.187 g, 0.249 mmol) and copper (I) triflate dimer, benzene complex (0.050 g, 0.099 mmol) were dissolved in tetrahydrofuran (12.9 mL) that had been sparged with an $N_2$ stream for 1 hour. The resulting mixture was stirred for 1 hour at ambient temperature (continue nitrogen sparge), and (E)-ethyl 2-((2-(difluoromethyl)benzylidene)amino)acetate (3.0 g, 12.44 mmol) was added as a solution in 1.5 mL of tetrahydrofuran and the resulting solution was cooled to <5° C. in an ice-water bath. Potassium 2-methylpropan-2-olate in tetrahydrofuran (0.224 mL, 0.224 mmol) was added dropwise, followed by addition of neat (E)-3,3-dimethyl-1-nitrobut-1-ene (1.606 g, 12.44 mmol) over 2 minutes, maintaining a temperature less than 7° C. The reaction mixture was stirred for 3 hours at 0° C. The mixture was quenched with 10 mL of saturated aqueous ammonium chloride and 30 mL of ethyl acetate and it was warmed to ambient temperature. The organic layer was separated and washed with saturated aqueous ammonium chloride (2×20 mL) and brine and filtered through a pad of silica gel. The filtrate was concentrated. The residue was triturated with heptane, decanted, precipitated in hot heptane, and filtered to provide (2S,3R,4S,5S)-ethyl 3-(tert-butyl)-5-(2-(difluoromethyl)phenyl)-4-nitropyrrolidine-2-carboxylate (2.48 g, 6.70 mmol, 53.8% yield). $^1$H NMR (400 MHz, DMSO-$d_6$) δ ppm 7.64 (d, J=7.7 Hz, 1H), 7.57-7.53 (m, 1H), 7.48 (t, J=7.4 Hz, 1H), 7.45-7.39 (m, 1H), 7.38 (t, J=54.4 Hz, 1H), 5.19 (dd, J=7.0, 3.4 Hz, 1H), 4.79 (t, J=6.5 Hz, 1H), 4.19 (qd, J=7.1, 2.4 Hz, 2H), 3.83-3.61 (m, 2H), 3.11 (dd, J=6.9, 3.5 Hz, 1H), 1.24 (t, J=7.1 Hz, 3H), 0.93 (s, 9H); MS (ESI+) m/z 371 (M+H)$^+$.

Core 23

(2S,3R,4S,5S)-ethyl 3-(tert-butyl)-5-(2,6-difluorophenyl)-4-nitropyrrolidine-2-carboxylate Core 23A (E)-ethyl 2-((2,6-difluorobenzylidene)amino)acetate A mixture of ethyl 2-aminoacetate hydrochloride (1.85 g, 13.25 mmol) and magnesium sulfate (3.19 g, 26.5 mmol) in dichloromethane (22.09 mL) (anhydrous) was treated with triethylamine (1.847 mL, 13.25 mmol), stirred for 30 minutes and treated with 2,6-difluorobenzaldehyde (1.88 g, 13.25 mmol) as a solution in 3 mL of dichloromethane. The vial was capped and stirred at ambient temperature overnight. The solid material was filtered. The filtrate was concentrated, toluene (5 mL) was added, and the mixture was filtered again and concentrated, to provide (E)-ethyl 2-((2,6-difluorobenzylidene)amino)acetate (2.9 g, 12.76 mmol, 96% yield) which was used directly in the next step. $^1$H NMR (400 MHz, CDCl$_3$) δ ppm 8.54 (d, J=1.3 Hz, 1H), 7.13-6.81 (m, 3H), 4.49 (s, 2H), 4.28 (q, J=7.1 Hz, 2H), 1.34 (t, J=7.1 Hz, 3H).

Core 23B (2S,3R,4S,5S)-ethyl 3-(tert-butyl)-5-(2,6-difluorophenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.175 g, 0.232 mmol) and copper (I) triflate dimer, benzene complex (0.047 g, 0.093 mmol) were dissolved in tetrahydrofuran (19.36 mL mL) that had been sparged with an $N_2$ stream for 1 hour. The resulting mixture was stirred for 1 hour at ambient temperature (continue nitrogen sparge), and (E)-ethyl 2-((2,6-difluorobenzylidene)amino)acetate (2.9 g, 12.76 mmol) was added as a solution in 2 mL of tetrahydrofuran. The resulting solution was cooled to <5° C. in an ice-water bath. Potassium 2-methylpropan-2-olate in tetrahydrofuran (0.244 mL, 0.244 mmol) was added dropwise, followed by addition of (E)-3,3-dimethyl-1-nitrobut-1-ene (1.5 g, 11.61 mmol) in 2 mL tetrahydrofuran over 2 minutes, maintaining a temperature less than 7° C. The reaction mixture was stirred for 1 hour at 0° C. The mixture was quenched with 4 mL of saturated aqueous ammonium chloride and 10 mL of diethyl ether and warmed to ambient temperature. The ether layer was separated and washed with saturated aqueous ammonium chloride (2×20 mL) and brine and filtered through a pad of silica gel. The filtrate was concentrated, and heptane (60 mL) was added. The precipitate was collected by filtration and the filtrate was concentrated and purified by chromatography using a 24 g silica gel cartridge eluting with a gradient of 0-60% heptanes/ethyl acetate over a period of 20 minutes to provide a combined yield of (2S,3R,4S,5S)-ethyl 3-(tert-butyl)-5-(2,6-difluorophenyl)-4-nitropyrrolidine-2-carboxylate (1.9 g, 5.33 mmol, 45.9% yield). $^1$H NMR (400 MHz, DMSO-$d_6$) δ ppm 7.44 (tt, J=8.3, 6.5 Hz, 1H), 7.12 (dd, J=9.5, 8.4 Hz, 2H), 5.21 (dd, J=6.2, 3.3 Hz, 1H), 4.67 (dd, J=13.1, 6.2 Hz, 1H), 4.21 (qd, J=7.1, 4.5 Hz, 2H), 3.83 (dd, J=13.3, 10.5 Hz, 1H), 3.73 (dd, J=10.7, 7.6 Hz, 1H), 2.88 (dd, J=7.6, 3.3 Hz, 1H), 1.23 (t, J=7.1 Hz, 3H), 0.96 (s, 9H); MS (APCI+) m/z 357 (M+H)$^+$.

Core 24

(2S,3R,4S,5S)-ethyl 3-(tert-butyl)-5-(2-ethylphenyl)-4-nitropyrrolidine-2-carboxylate Core 24A (E)-ethyl 2-((2-ethylbenzylidene)amino)acetate A mixture of ethyl 2-aminoacetate hydrochloride (1.85 g, 13.25 mmol) and magnesium sulfate (3.19 g, 26.5 mmol) in dichloromethane (22 mL) (anhydrous) was treated with triethylamine (1.847 mL, 13.25 mmol), stirred for 10 minutes and treated with 2-ethylbenzaldehyde (1.78 g, 13.25 mmol) as a solution in 1 mL of dichloromethane. The flask was capped and stirred at ambient temperature overnight. The solid material was filtered, the filtrate was washed with water, and the organic layer was dried with $Na_2SO_4$ and filtered again. The filtrate was concentrated, giving (E)-ethyl 2-((2-ethylbenzylidene)amino)acetate (2.65 g, 12.09 mmol, 91% yield). $^1$H NMR (400 MHz, CDCl$_3$) δ ppm 8.63 (s, 1H), 7.96 (dd, J=7.8, 1.5 Hz, 1H), 7.37 (td, J=7.5, 1.5 Hz, 1H), 7.26 (d, J=6.1 Hz, 1H), 7.25-7.19 (m, 1H), 4.43 (d, J=1.4 Hz, 2H), 4.26 (q, J=7.1 Hz, 2H), 2.89 (q, J=7.5 Hz, 2H), 1.32 (t, J=7.1 Hz, 3H), 1.26 (t, J=7.6 Hz, 3H).

Core 24B (2S,3R,4S,5S)-ethyl 3-(tert-butyl)-5-(2-ethylphenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.182 g, 0.242 mmol) and copper (I) triflate dimer, benzene complex (0.049 g, 0.097 mmol) were dissolved in tetrahydrofuran (18 mL) that had been sparged with an $N_2$ stream for 1 hour. The resulting mixture was stirred for 1 hour at ambient temperature (continued nitrogen sparge), and (E)-ethyl 2-((2-ethylbenzylidene)amino)acetate (2.65 g, 12.09 mmol) in 1 mL tetrahydrofuran was added. The resulting solution was cooled to <5° C. in an ice-water bath. Potassium 2-methylpropan-2-olate in tetrahydrofuran (0.218 mL, 0.218 mmol) was added dropwise, followed by addition of (E)-3,3-dimethyl-1-nitrobut-1-ene (1.561 g, 12.09 mmol) in 1 mL tetrahydrofuran over 2 minutes, maintaining a temperature less than 7° C. The reaction mixture was stirred for 1.5 hours at 0° C. The mixture was quenched with 20 mL of saturated aqueous ammonium chloride and 50 mL of ethyl acetate and warmed to ambient temperature. The organic layer was separated and washed with saturated aqueous ammonium chloride (2×50 mL) and brine and filtered through a pad of silica gel. The filtrate was concentrated. The crude material was purified by chromatography using a 40 g silica gel cartridge eluting with a gradient of 0-60% heptanes/ethyl acetate over a period of 20 minutes. The crude material was triturated with heptane and the precipitate was filtered to provide (2S,3R,4S,5S)-ethyl 3-(tert-butyl)-5-(2-ethylphenyl)-4-nitropyrrolidine-2-carboxylate (2.11 g, 6.06 mmol, 50.1% yield). $^1$H NMR (501 MHz, DMSO-$d_6$) δ ppm 7.40-7.29 (m, 1H), 7.25-7.15 (m, 2H), 7.11 (td, J=7.4, 1.8 Hz, 1H), 5.17 (dd, J=7.0, 3.5 Hz, 1H), 4.64 (t, J=7.4 Hz, 1H), 4.19 (qd, J=7.1, 3.8 Hz, 2H), 3.72 (t, J=7.6 Hz, 1H), 3.47 (t, J=7.5 Hz, 1H), 3.07 (dd, J=7.9, 3.5 Hz, 1H), 2.72 (dt, J=15.0, 7.5 Hz, 1H), 2.63 (dt, J=15.0, 7.5 Hz, 1H), 1.22 (dt, J=16.4, 7.3 Hz, 6H), 0.93 (s, 9H); MS (APCI+) m/z 349 (M+H)$^+$.

Example 1 rac-(2R,3S,5R)-3-tert-butyl-1-(cyclopentylacetyl)-4-[(2,5-dichlorophenyl)methoxy]-5-phenylpyrrolidine-2-carboxylic acid Example 1A rac-(2R,3S,4R,5R)-ethyl 3-(tert-butyl)-1-(2-cyclopentylacetyl)-4-nitro-5-phenylpyrrolidine-2-carboxylate To a cooled (ice bath) solution of Core 1 (1.6 g, 4.99 mmol) and triethylamine (1.047 mL, 7.49 mmol) in dichloromethane (10 mL) was treated with 2-cyclopentylacetyl chloride (0.436 mL, 3.23 mmol). The reaction mixture was stirred in an ice-bath for 30 minutes and allowed to warm to ambient temperature. Dichloromethane (20 mL) was added. The organics were washed with saturated aqueous NaHCO$_3$ and brine, dried over MgSO$_4$, filtered and concentrated. The residue was chromatographed on a 40 g silica gel cartridge, eluting with ethyl acetate in heptanes at 0-40% gradient to provide title compound, 1.43 g (66.5% yield). $^1$H NMR (400 MHz, CDCl$_3$) δ ppm 7.65 (d, J=6.9 Hz, 2H), 7.38 (d, J=7.2 Hz, 3H), 5.52-5.22 (m, 2H), 4.86 (d, J=4.5 Hz, 1H), 4.37 (d, J=8.8 Hz, 2H), 3.14 (t, J=3.8 Hz, 1H), 2.52-1.40 (m, 9H), 1.39 (dd, J=11.8, 4.9 Hz, 3H), 1.08 (d, J=5.4 Hz, 9H), 0.95-0.84 (m, 2H); MS (ESI+) m/z 431 (M+H)$^+$.

Example 1B rac-(2R,3S,5R)-methyl 3-(tert-butyl)-1-(2-cyclopentylacetyl)-4-oxo-5-phenylpyrrolidine-2-carboxylate To potassium dichromate (1.8 g, 6.12 mmol) in 6 M aqueous HCl acid (50 mL) was added zinc powder (3.4 g) under a N$_2$ atmosphere. After the complete dissolution of zinc, the formed chromium (II) chloride was transferred via cannula to the refluxing solution of Example 1A (0.439 g, 1.020 mmol) in methanol (50 mL). After 4 hours of refluxing, LC/MS showed two main peaks, one was desired product and the other was intermediate oxime. The reaction mixture was cooled and concentrated to half of its volume, and extracted with dichloromethane (50 mL×3). The organic phase was washed with saturated aqueous NaHCO$_3$ and brine, dried over MgSO$_4$, filtered, and concentrated. Purification via chromatography on a 40 g silica gel cartridge, eluting with ethyl acetate in heptanes at 0-100% gradient, provided two major products, one was the title compound 0.12 g (30.5% yield). $^1$H NMR (400 MHz, CDCl$_3$) δ ppm 7.72-7.60 (m, 2H), 7.41 (dd, J=8.4, 6.6 Hz, 2H), 7.38-7.30 (m, 1H), 4.95-4.79 (m, 2H), 3.83 (s, 3H), 2.57 (d, J=5.2 Hz, 1H), 2.22 (hept, J=7.6 Hz, 1H), 2.13-1.96 (m, 2H), 1.73 (ddt, J=38.6, 12.8, 6.3 Hz, 2H), 1.44 (dddt, J=23.5, 15.7, 8.5, 4.6 Hz, 4H), 1.10 (s, 9H), 0.98-0.86 (m, 2H); MS (ESI+) m/z 386 (M+H)$^+$.

Example 1C rac-(2R,3S,5R)-methyl 3-(tert-butyl)-1-(2-cyclopentylacetyl)-4-hydroxy-5-phenylpyrrolidine-2-carboxylate A solution of Example 1B (100 mg, 0.259 mmol) in methanol (6 mL) was cooled to 0° C., treated with sodium borohydride (11.78 mg, 0.311 mmol), stirred at 0° C. for 30 minutes, and warmed to ambient temperature for another 30 minutes. LC/MS indicated the starting material was consumed. The solvent was removed and the residue was diluted with dichloromethane. The organics were washed with saturated aqueous NaHCO$_3$ and brine, dried over Na$_2$SO$_4$, filtered, and concentrated. Purification via chromatography on a 12 g silica gel cartridge, eluting with ethyl acetate in heptanes at 0-50% gradient provided rac-(2R,3S,5R)-methyl 3-(tert-butyl)-1-(2-cyclopentylacetyl)-4-hydroxy-5-phenylpyrrolidine-2-carboxylate (62 mg, 61.7% yield). $^1$H NMR (400 MHz, CDCl$_3$) δ ppm 7.74-7.64 (m, 2H), 7.53-7.42 (m, 2H), 7.41-7.34 (m, 1H), 5.03 (d, J=6.4 Hz, 1H), 4.64 (d, J=4.6 Hz, 1H), 4.40 (td, J=6.8, 4.1 Hz, 1H), 3.84 (s, 3H), 2.28 (t, J=4.4 Hz, 1H), 2.19 (h, J=7.8 Hz, 1H), 2.02 (dd, J=15.7, 7.4 Hz, 1H), 1.90 (dd, J=15.6, 6.9 Hz, 1H), 1.77 (dq, J=13.0, 6.4 Hz, 1H), 1.68-1.61 (m, 1H), 1.60 (s, 1H), 1.51-1.37 (m, 4H), 1.06 (s, 9H), 0.89 (dtt, J=16.1, 7.9, 4.1 Hz, 2H); MS (ESI+) m/z 388 (M+H)$^+$.

Example 1D rac-(2R,3S,5R)-3-tert-butyl-1-(cyclopentylacetyl)-4-[(2,5-dichlorophenyl)methoxy]-5-phenylpyrrolidine-2-carboxylic acid To 2-(bromomethyl)-1,4-dichlorobenzene (33.4 mg, 0.139 mmol) and Example 1C (45 mg, 0.116 mmol) in dimethylformamide (1.0 mL) at ambient temperature was added sodium hydride (6.97 mg, 0.174 mmol) portionwise. The mixture was stirred at 60° C. for 3 hours, and then cooled to room temperature. Aqueous LiOH solution (6M, 1.0 mL) was added and the reaction was stirred for another 2 hours. The mixture was adjusted pH to 1~2 by adding 2M aqueous HCl and was concentrated. Dichloromethane (2 mL) was added and the mixture was filtered through a syringe filter. Purification of the residue via chromatography, eluting with ethyl acetate/methanol (95:5) in heptanes in 0-40 gradient provided rac-(2R,3S,5R)-3-(tert-butyl)-1-(2-cyclopentylacetyl)-4-((2,5-dichlorobenzyl)oxy)-5-phenylpyrrolidine-2-carboxylic acid, 19 mg (30.7% yield). $^1$H NMR (400 MHz, CDCl$_3$) δ ppm 7.40-7.26 (m, 5H), 7.14-6.99 (m, 2H), 6.51 (d, J=2.4 Hz, 1H), 5.13 (d, J=6.6 Hz, 1H), 4.73 (d, J=3.5 Hz, 1H), 4.48 (d, J=13.7 Hz, 1H), 4.18 (dd, J=6.6, 3.3 Hz, 1H), 4.10 (d, J=13.7 Hz, 1H), 2.27-1.98 (m, 3H), 1.76 (dt, J=12.6, 6.3 Hz, 1H), 1.62 (dq, J=12.3, 6.4 Hz, 1H), 1.55-1.32 (m, 4H), 1.04 (s, 9H), 0.99-0.90 (m, 1H), 0.81 (dq, J=12.4, 7.9 Hz, 1H); MS (ESI+) m/z 532 (M+H)$^+$.

Example 2 rac-(2R,3S,5R)-3-tert-butyl-1-(cyclohexanecarbonyl)-4-{[2-methoxy-5-(trifluoromethyl)phenyl]methoxy}-5-phenylpyrrolidine-2-carboxylic acid Example 2A rac-(2R,3S,4R,5R)-ethyl 3-(tert-butyl)-1-(cyclohexanecarbonyl)-4-nitro-5-phenylpyrrolidine-2-carboxylate A solution of Core 1 (5.0 g, 15.61 mmol) and triethylamine (3.27 mL, 23.41 mmol) in dichloromethane (40 mL) cooling in an ice-bath was treated with cyclohexanecarbonyl chloride (2.71 mL, 20.29 mmol). The mixture was stirred at 0° C. for 30 minutes and was allowed to warm to room temperature. Dichloromethane (20 mL) was added. The mixture was washed with saturated aqueous NaHCO$_3$ and brine, and dried over MgSO$_4$, filtered and concentrated. Purification via chromatography on an 80 g silica gel cartridge eluting with ethyl acetate in heptanes at 0-40% gradient provided the title compound 6.2 g (92% yield). $^1$H NMR (400 MHz, CDCl$_3$) δ ppm 7.64 (d, J=7.1 Hz, 2H), 7.42-7.31 (m, 3H), 5.43 (d, J=9.1 Hz, 1H), 5.34 (dd, J=9.0, 4.4 Hz, 1H), 4.79 (d, J=4.6 Hz, 1H), 4.33 (q, J=7.2 Hz, 2H), 3.12 (t, J=4.7 Hz, 1H), 2.03 (dd, J=13.3, 10.0 Hz, 1H), 1.85-1.65 (m, 2H), 1.61 (d, J=13.1 Hz, 1H), 1.54-1.38 (m, 4H), 1.35 (d, J=7.2 Hz, 3H), 1.27 (d, J=13.7 Hz, 1H), 1.15 (d, J=14.5 Hz, 1H), 1.04 (s, 9H), 0.56 (q, J=13.2 Hz, 1H); MS (ESI+) m/z 431 (M+H).

Example 2B rac-(2R,3S,5R)-methyl 3-(tert-butyl)-1-(cyclohexanecarbonyl)-4-oxo-5-phenylpyrrolidine-2-carboxylate Potassium dichromate (5.11 g, 17.37 mmol) was dissolved in 6 M aqueous HCl acid (60 mL) and zinc (6 g, 92 mmol) was added under N$_2$ atmosphere. Complete dissolution of the zinc provided a clear light blue solution. The formed chromium(II) chloride was transferred to a refluxing solution of Example 2A (1.1 g, 2.55 mmol) in ethanol (60 mL) under N$_2$. The reaction mixture was refluxed for 16 hours. LC/MS indicated conversion was complete and two products were formed, one was desired product and another was hydrolyzed acid. The mixture was cooled to ambient temperature and extracted with ethyl acetate (60 mL×3). The organics were washed with saturated aqueous NaHCO$_3$ solution and brine, dried over MgSO$_4$, filtered, and concentrated. The residue was dissolved in ethanol (5 mL), cooled in an ice-bath, and acetyl chloride (1 mL) in ethanol (2 mL) was slowly added. The mixture was stirred at 60° C. for 2 hours and LC/MS indicated all acid was converted to the ester. The solvent was reduced in volume and the crude material was purified via chromatography on a 80 g silica gel cartridge, eluting with ethyl acetate in heptanes using a 0-40% gradient to provide the title compound (860 mg, 86% yield). $^1$H NMR (400 MHz, CDCl$_3$) δ ppm 7.68 (dd, J=7.3, 1.7 Hz, 2H), 7.45-7.38 (m, 2H), 7.37-7.31 (m, 1H), 4.90 (s, 1H), 4.84 (d, J=5.0 Hz, 1H), 4.28 (q, J=7.2 Hz, 2H), 2.54 (dd, J=5.0, 1.0 Hz, 1H), 2.08 (tt, J=11.4, 3.3 Hz, 1H), 1.70 (t, J=14.9 Hz, 2H), 1.54-1.48 (m, 2H), 1.47-1.37 (m, 2H), 1.32 (t, J=7.2 Hz, 3H), 1.10 (s, 9H), 0.92-0.82 (m, 4H); MS (ESI+) m/z 400.1 (M+H).

Example 2C rac-(2R,3S,5R)-ethyl 3-(tert-butyl)-1-(cyclohexanecarbonyl)-4-hydroxy-5-phenylpyrrolidine-2-carboxylate A solution of Example 2B (200 mg, 0.501 mmol) in methanol (10 mL) was cooled in an ice-bath and was treated with sodium borohydride (37.9 mg, 1.001 mmol). The mixture was stirred at 0° C. for 30 minutes, and was allowed to warm to ambient temperature. The solvent was removed and dichloromethane (20 mL) was added. The mixture was washed with saturated aqueous NaHCO$_3$ and brine, dried over Na$_2$SO$_4$, filtered, and concentrated to provide title compound, 196 mg (98% yield) which used in next step without further purification. LC/MS (APCI+) m/z 402 (M+H)$^+$.

Example 2D rac-(2R,3S,5R)-3-tert-butyl-1-(cyclohexanecarbonyl)-4-{[2-methoxy-5-(trifluoromethyl)phenyl]methoxy}-5-phenylpyrrolidine-2-carboxylic acid To 2-(bromomethyl)-1-methoxy-4-(trifluoromethyl)benzene (40 mg, 0.149 mmol) and Example 2C (49.7 mg, 0.124 mmol) in dimethylformamide (1.0 mL) in an ice-bath was added sodium hydride (7.43 mg, 0.186 mmol) portionwise. The mixture was warmed to 60° C. and stirred for 3 hours. Ethyl acetate and water were added. The organic layer was washed with brine, dried over MgSO$_4$, filtered, and concentrated. The residue was dissolved in methanol (2 mL) and 6M aqueous LiOH (0.5 mL) and stirred at 50° C. overnight. The mixture was adjusted to pH 1~2 by adding 2M aqueous HCl. The reaction mixture was extracted with ethyl acetate. The organic layers were combined, dried over sodium sulfate, and concentrated. The residue was purified via chromatography, eluting with ethyl acetate/methanol (9:1) in heptanes using a 0-40% gradient to provide the title compound, 22 mg (35% yield). $^1$H NMR (400 MHz, CDCl$_3$) δ ppm 7.42-7.37 (m, 1H), 7.33 (qd, J=7.7, 6.7, 3.8 Hz, 3H), 7.25-7.20 (m, 2H), 6.81-6.75 (m, 2H), 5.17 (d, J=6.6 Hz, 1H), 4.66 (d, J=3.7 Hz, 1H), 4.56 (d, J=13.3 Hz, 1H), 4.22-4.11 (m, 2H), 3.77 (s, 3H), 3.15 (t, J=3.5 Hz, 1H), 2.35-2.23 (m, 1H), 1.77 (d, J=7.1 Hz, 1H), 1.68 (d, J=13.2

Hz, 2H), 1.55-1.41 (m, 2H), 1.40-1.20 (m, 2H), 1.14 (t, J=10.5 Hz, 2H), 1.02 (s, 9H), 0.73 (t, J=12.8 Hz, 1H); MS (ESI−) m/z 560 (M−H)−.

Example 3 rac-(2R,3S,5R)-3-tert-butyl-4-[(5-chloro-2-methoxyphenyl)methoxy]-1-(cyclohexanecarbonyl)-5-phenylpyrrolidine-2-carboxylic acid The title compound was prepared according to the procedure described in Example 2D, substituting 2-(bromomethyl)-4-chloro-1-methoxybenzene for 2-(bromomethyl)-1-methoxy-4-(trifluoromethyl)benzene. $^1$H NMR (400 MHz, CDCl$_3$) δ ppm 7.40-7.30 (m, 3H), 7.28 (d, J=1.9 Hz, 2H), 7.07 (dd, J=8.6, 2.7 Hz, 1H), 6.63 (d, J=8.6 Hz, 1H), 6.44 (d, J=2.7 Hz, 1H), 5.14 (d, J=6.6 Hz, 1H), 4.67 (d, J=3.6 Hz, 1H), 4.45 (d, J=13.3 Hz, 1H), 4.16-4.10 (m, 2H), 3.70 (s, 3H), 3.08 (t, J=3.5 Hz, 1H), 2.29 (tt, J=11.6, 3.3 Hz, 1H), 2.00 (s, 2H), 1.77-1.74 (d, J=13.3 Hz, 1H), 1.68 (d, J=13.3 Hz, 1H), 1.61-1.39 (m, 3H), 1.36-1.24 (m, 1H), 1.19-1.09 (m, 2H), 1.07 (s, 1H), 1.01 (s, 9H), 0.76-0.69 (m, 1H); MS (ESI+) m/z 527 (M+H).

Example 4 rac-(2R,3S,5R)-3-tert-butyl-1-(cyclohexanecarbonyl)-4-[(2,5-dichlorophenyl)methoxy]-5-phenylpyrrolidine-2-carboxylic acid The title compound was prepared according to the procedure described in Example 2D, substituting 2-(bromomethyl)-1,4-dichlorobenzene (35.9 mg, 0.149 mmol) for 2-(bromomethyl)-1-methoxy-4-(trifluoromethyl)benzene. $^1$H NMR (400 MHz, CDCl$_3$) δ ppm 7.40-7.31 (m, 3H), 7.28 (dd, J=6.5, 1.8 Hz, 2H), 7.11 (d, J=8.4 Hz, 1H), 7.04 (dd, J=8.5, 2.6 Hz, 1H), 6.52 (d, J=2.5 Hz, 1H), 5.18 (d, J=6.5 Hz, 1H), 4.71 (d, J=3.0 Hz, 1H), 4.51 (d, J=13.8 Hz, 1H), 4.18 (dd, J=6.6, 2.6 Hz, 1H), 4.10 (d, J=13.8 Hz, 1H), 3.13 (t, J=2.9 Hz, 1H), 2.37-2.21 (m, 1H), 1.1.77 (d, J=13.2 Hz, 1H), 1.68 (d, J=13.2 Hz, 1H), 1.61-1.39 (m, 3H), 1.34-1.24 (m, 1H), 1.13 (s, 2H), 1.04 (s, 9H), 0.69 (d, J=12.4 Hz, 1H); MS (ESI−) m/z 531 (M−H)−.

Example 5 rac-(2R,3S,5R)-3-tert-butyl-1-(cyclohexanecarbonyl)-4-{[6-methyl-4-(trifluoromethyl)pyridin-2-yl]oxy}-5-phenylpyrrolidine-2-carboxylic acid To Example 2C (67 mg, 0.167 mmol) and 2-chloro-6-methyl-4-(trifluoromethyl)pyridine (65.3 mg, 0.334 mmol) in dimethylformamide (1.0 mL), cooled in an ice-bath, was added sodium hydride (13.35 mg, 0.334 mmol) portionwise. The mixture was stirred at ambient temperature for 24 hours. Dichloromethane (10 mL) was added and the mixture was washed with 1M aqueous HCl and brine, dried over Na$_2$SO$_4$, filtered, and concentrated. The residue was purified via flash chromatography on 12 g silica gel cartridge, eluting with ethyl acetate in heptanes at 5-60% gradient to provide the title compound, 18 mg (20.25% yield). $^1$H NMR (400 MHz, CDCl$_3$) δ ppm 7.17 (s, 3H), 7.13-7.08 (m, 2H), 6.85 (s, 1H), 6.35 (s, 1H), 5.80 (t, J=6.6 Hz, 1H), 5.46 (d, J=7.3 Hz, 1H), 4.67 (d, J=5.4 Hz, 1H), 3.17 (t, J=5.7 Hz, 1H), 2.50 (s, 3H), 2.29 (tt, J=11.7, 3.2 Hz, 1H), 1.80 (d, J=10.1 Hz, 2H), 1.60-1.44 (m, 3H), 1.31 (td, J=12.4, 11.7, 3.5 Hz, 1H), 1.18 (d, J=12.2 Hz, 2H), 1.05 (s, 9H), 0.81-0.67 (m, 1H); MS (ESI−) m/z 531 (M−H)−.

Example 6 rac-(2R,3S,5R)-3-tert-butyl-4-[(4,6-dimethoxypyrimidin-2-yl)oxy]-1-[di(propan-2-yl)carbamoyl]-5-phenylpyrrolidine-2-carboxylic acid Example 6A rac-(2R,3S,4R,5R)-benzyl 3-(tert-butyl)-1-(diisopropylcarbamoyl)-4-nitro-5-phenylpyrrolidine-2-carboxylate To Core 3 (3 g, 7.84 mmol) and triethylamine (3.28 mL, 23.53 mmol) in dichloromethane (30 mL) was added diisopropylcarbamic chloride (1.540 g, 9.41 mmol) in dichloromethane (10 mL) dropwise. The reaction mixture was stirred at ambient temperature for 2 hours, warmed to 40° C. overnight, and ethyl acetate (30 mL) and saturated aqueous ammonium chloride (20 mL) were added. The aqueous layer was extracted with ethyl acetate. The combined organic fractions were dried over MgSO$_4$, filtered, and concentrated. Purification via chromatography on an 80 g silica gel cartridge, eluting with ethyl acetate in heptanes at 0-40% gradient provided the title compound, 2.15 g (53.8% yield). $^1$H NMR (400 MHz, CDCl$_3$) δ ppm 7.45-7.30 (m, 7H), 7.26-7.19 (m, 3H), 5.40 (d, J=8.9 Hz, 1H), 5.27 (q, J=12.1 Hz, 2H), 5.19 (dd, J=8.9, 5.3 Hz, 1H), 4.66 (d, J=5.7 Hz, 1H), 3.75 (hept, J=6.7 Hz, 2H), 3.34 (t, J=5.5 Hz, 1H), 1.07 (d, J=6.7 Hz, 6H), 1.03 (d, J=6.7 Hz, 6H), 0.97 (s, 9H); MS (ESI+) m/z 510 (M+H)+.

Example 6B rac-(2R,3S,5R)-ethyl 3-(tert-butyl)-1-(diisopropylcarbamoyl)-4-oxo-5-phenylpyrrolidine-2-carboxylate The title compound was prepared according to the procedure described in Example 2B, substituting Example 6A for Example 2A. During the reaction, transesterification from benzyl to ethyl ester occurred. Purification via chromatography on 40 g silica gel cartridge, eluting with ethyl acetate in heptanes at 0-40% gradient, provided the title compound, 1.03 g (63.0% yield). $^1$H NMR (400 MHz, CDCl$_3$) δ ppm 7.48 (dd, J=7.2, 2.0 Hz, 2H), 7.33 (t, J=7.4 Hz, 1H), 7.28 (s, 2H), 5.04 (s, 1H), 4.61 (d, J=4.6 Hz, 1H), 4.31-4.13 (m, 2H), 3.70 (p, J=6.7 Hz, 2H), 2.49 (dd, J=4.5, 1.0 Hz, 1H), 1.27 (t, J=7.1 Hz, 3H), 1.17 (d, J=6.7 Hz, 6H), 1.11-1.06 (m, 15H); MS (ESI+) m/z 417 (M+H)+.

Example 6C rac-(2R,3S,5R)-ethyl 3-(tert-butyl)-1-(diisopropylcarbamoyl)-4-hydroxy-5-phenylpyrrolidine-2-carboxylate Example 6C was prepared according to the procedure described in Example 1C, substituting Example 6B for Example 1B, and 2-chloro-4,6-dimethoxypyrimidine for 2-chloro-6-methyl-4-(trifluoromethyl)pyridine. $^1$H NMR (400 MHz, CDCl$_3$) δ ppm 7.66-7.56 (m, 2H), 7.38 (t, J=7.6 Hz, 2H), 7.31-7.26 (m, 1H), 5.39 (d, J=6.0 Hz, 1H), 4.30 (pd, J=7.3, 2.8 Hz, 4H), 3.68 (p, J=6.7 Hz, 2H), 2.26 (t, J=2.0

Hz, 1H), 2.14 (d, J=6.0 Hz, 1H), 1.34 (t, J=7.1 Hz, 3H), 1.26 (d, J=6.6 Hz, 6H), 1.13 (d, J=6.7 Hz, 6H), 1.06 (s, 9H); MS (ESI−) m/z 527.3 (M−H)−, MS (ESI+) m/z 419.1 (M+H)+.

Example 6D rac-(2R,3S,5R)-3-(tert-butyl)-1-(diisopropylcarbamoyl)-4-((4,6-dimethoxypyrimidin-2-yl)oxy)-5-phenylpyrrolidine-2-carboxylic acid Example 6D was prepared according to the procedure described in Example 5, substituting Example 6C for Example 2C, and 2-chloro-4,6-dimethoxypyrimidine for 2-chloro-6-methyl-4-(trifluoromethyl)pyridine. $^1$H NMR (500 MHz, CDCl$_3$) δ ppm 7.27-7.17 (m, 5H), 5.70 (s, 1H), 5.58 (t, J=7.5 Hz, 1H), 5.30 (d, J=7.2 Hz, 1H), 4.64 (d, J=6.5 Hz, 1H), 3.90 (s, 6H), 3.60 (hept, J=6.6 Hz, 2H), 3.20 (dd, J=7.7, 6.5 Hz, 1H), 1.23 (d, J=6.6 Hz, 6H), 1.17 (d, J=6.6 Hz, 6H), 1.08 (s, 9H); MS (ESI−) m/z 527.3 (M−H)−.

Example 7 rac-(2R,3S,5R)-3-tert-butyl-1-[di(propan-2-yl)carbamoyl]-4-{[2-methoxy-5-(trifluoromethyl)phenyl]methoxy}-5-phenylpyrrolidine-2-carboxylic acid Example 7 was prepared according to the procedure described in Example 1D, substituting Example 6C for Example 1C, and 2-(bromomethyl)-1-methoxy-4-(trifluoromethyl)benzene for 2-(bromomethyl)-1,4-dichlorobenzene. $^1$H NMR (400 MHz, CDCl$_3$) δ ppm 7.67 (d, J=2.3 Hz, 1H), 7.61 (dd, J=8.7, 2.3 Hz, 1H), 7.55-7.49 (m, 2H), 7.35-7.29 (m, 2H), 7.27-7.23 (m, 1H), 5.41 (d, J=5.9 Hz, 1H), 5.38 (s, 1H), 5.23 (d, J=12.9 Hz, 1H), 4.37-4.32 (m, 2H), 3.86 (s, 3H), 3.63 (h, J=6.4 Hz, 2H), 2.30 (t, J=1.8 Hz, 1H), 1.22 (d, J=6.7 Hz, 6H), 1.10-0.98 (m, 15H); MS (ESI+) m/z 579.2 (M+H)+.

Example 8

(2R*,3S*,4R*,5R*)-3-tert-butyl-1-[di(propan-2-yl)carbamoyl]-4-{[2-methoxy-5-(trifluoromethyl)phenyl]methoxy}-5-phenylpyrrolidine-2-carboxylic acid Example 8 was obtained via SFC purification of Example 7 using a chiral Column (WHELK-O S.S, Column Size: 21×250 mm, 5 micron, Serial Number: 09210901, Concentration: 30 mg/mL in methanol, Co-Solvent: isopropyl alcohol) to provide title compound as the second eluent. The stereochemistry was arbitrarily assigned. $^1$H NMR (400 MHz, DMSO-d$_6$) δ ppm 7.69 (s, 2H), 7.47-7.42 (m, 2H), 7.25-7.13 (m, 4H), 5.18 (d, J=3.3 Hz, 2H), 4.88 (d, J=6.3 Hz, 1H), 4.43 (d, J=5.2 Hz, 1H), 4.34 (d, J=4.5 Hz, 1H), 4.18 (q, J=5.2 Hz, 1H), 3.87 (s, 3H), 3.58 (p, J=6.6 Hz, 2H), 2.21 (t, J=4.4 Hz, 1H), 0.99 (d, J=6.5 Hz, 6H), 0.97-0.85 (m, 15H); MS (ESI+) m/z 579.2 (M+H).

Example 9

(2S*,3R*,4S*,5S*)-3-tert-butyl-1-[di(propan-2-yl)carbamoyl]-4-{[2-methoxy-5-(trifluoromethyl)phenyl]methoxy}-5-phenylpyrrolidine-2-carboxylic acid The title compound was isolated via SFC chiral separation described in Example 8 as the first eluent. The stereochemistry was arbitrarily assigned. $^1$H NMR (400 MHz, DMSO-d$_6$) δ ppm 7.69 (s, 2H), 7.47-7.42 (m, 2H), 7.25-7.13 (m, 4H), 5.18 (d, J=3.3 Hz, 2H), 4.88 (d, J=6.2 Hz, 1H), 4.43 (d, J=5.3 Hz, 1H), 4.34 (d, J=4.5 Hz, 1H), 4.18 (q, J=5.2 Hz, 1H), 3.87 (s, 3H), 3.58 (p, J=6.6 Hz, 2H), 2.21 (t, J=4.4 Hz, 1H), 0.99 (d, J=6.6 Hz, 6H), 0.94 (d, J=6.7 Hz, 6H), 0.91 (s, 9H); MS (ESI+) m/z 579.1 (M+H).

Example 10 rac-(2R,3S,4R,5R)-3-tert-butyl-1-(cyclohexanecarbonyl)-4-[(4,6-dimethoxypyrimidin-5-yl)methoxy]-5-phenylpyrrolidine-2-carboxylic acid

Example 10A 5-(bromomethyl)-4,6-dimethoxypyrimidine (4,6-Dimethoxypyrimidin-5-yl)methanol (600 mg, 3.53 mmol) was dissolved in 35 mL of dichloromethane. The solution was cooled to <5° C. in an ice bath and PBr$_3$ (0.133 mL, 1.410 mmol) was added dropwise. The reaction was stirred for 10 minutes at ambient temperature, at which point TLC indicated complete consumption of the starting material. Saturated aqueous sodium bicarbonate (5 mL) was added, and the mixture was stirred for 5 minutes and extracted with ethyl acetate (3×20 mL). The combined organic extracts were washed with brine (20 mL), dried over sodium sulfate, filtered, and concentrated. The crude material was purified via flash chromatography, eluting with 0:100 to 10:90 ethyl acetate:heptanes over 20 minutes on a 12 g silica gel column to provide 190 mg of the title compound. $^1$H NMR (400 MHz, CDCl$_3$) δ ppm 8.38 (s, 1H), 4.47 (s, 2H), 4.04 (s, 6H).

Example 10B rac-(2R,3S,4R,5R)-ethyl 3-(tert-butyl)-1-(cyclohexanecarbonyl)-4-((4,6-dimethoxypyrimidin-5-yl)methoxy)-5-phenylpyrrolidine-2-carboxylate Example 2C (44 mg, 0.110 mmol) and Example 10A (38.3 mg, 0.164 mmol) were dissolved in 1 mL of dry dimethylformamide and the reaction was cooled to <5° C. in an ice bath. Potassium 2-methylpropan-2-olate (1M in tetrahydrofuran, 0.12 mL, 0.12 mmol) solution was added dropwise. After the addition was complete, full conversion of Example 10A was observed by LC/MS. The reaction mixture was diluted with methyl tert-butyl ether (10 mL) and quenched with saturated aqueous ammonium chloride (5 mL). The layers were separated and the organic layer was washed with water (10 mL), concentrated in vacuo, and loaded onto a 12 g silica gel column. The column was eluted with 0:100 to 35:65 ethyl acetate:heptanes over 20 minutes to provide 56 mg of the title compound. $^1$H NMR (400 MHz, DMSO-d$_6$) δ ppm 8.29 (s, 1H), 7.55 (d, J=7.2 Hz, 2H), 7.20 (dq, J=13.9, 7.2 Hz, 3H), 5.11 (d, J=6.4 Hz, 1H), 4.40 (d, J=4.0 Hz, 1H), 4.13 (dd, J=6.4, 3.8 Hz, 1H), 4.06 (q, J=7.1 Hz, 2H), 4.02 (d, J=10.0 Hz, 1H), 3.97 (d, J=10.0 Hz, 1H), 3.80 (s, 6H), 2.34 (br s, 1H), 2.18 (br s, 1H), 1.68-1.37 (m, 4H), 1.31-1.02 (m, 6H), 1.15 (t, J=7.1 Hz, 3H), 0.94 (s, 9H); MS (ESI+) m/z 554.2 (M+H)+.

Example 10C rac-(2R,3S,4R,5R)-3-tert-butyl-1-(cyclohexanecarbonyl)-4-[(4,6-dimethoxypyrimidin-5-yl)methoxy]-5-phenylpyrrolidine-2-carboxylic acid Example 10B (56 mg, 0.101 mmol) was dissolved in 0.25 mL of tetrahydrofuran and 0.25 mL of methanol. Lithium hydroxide (1M aqueous, 0.506 mL, 0.506 mmol) was added, and the resulting solution was heated to 40° C. for 16 hours. The vial was cooled to ambient temperature, acidified with 6M aqueous HCl to pH=3, and extracted with dichloromethane (3×10 mL). The combined organic extracts were concentrated, loaded onto a 4 g silica gel column, and eluted with 5:95 to 100:0 ethyl acetate:heptanes over 10 minutes to provide 34 mg of the title compound. $^1$H NMR (400 MHz, DMSO-d$_6$) δ ppm 8.30 (s, 1H), 7.56 (d, J=7.2 Hz, 2H), 7.21 (qd, J=7.6, 6.7, 3.5 Hz, 3H), 5.10 (d, J=6.6 Hz, 1H), 4.38 (d, J=4.0 Hz, 1H), 4.20-4.10 (m, 1H), 4.00 (d, J=2.9 Hz, 2H), 3.81 (s, 6H), 2.39 (br s, 1H), 2.21 (br s, 1H), 1.62 (d, J=12.7 Hz, 2H), 1.47 (s, 2H), 1.26-0.98 (m, 6H), 0.94 (s, 9H); MS (ESI+) m/z 526.1 (M+H)$^+$.

Example 11 rac-(2R,3S,4R,5R)-3-tert-butyl-1-(cyclohexanecarbonyl)-4-[(4,6-dimethoxypyrimidin-2-yl)methoxy]-5-phenylpyrrolidine-2-carboxylic acid Example 11A 2-(bromomethyl)-4,6-dimethoxypyrimidine 4,6-Dimethoxy-2-methylpyrimidine (5 g, 32.4 mmol) was dissolved in carbon tetrachloride (54.1 mL) and N-bromosuccinimide (5.77 g, 32.4 mmol) and azobisisobutyronitrile (0.266 g, 1.622 mmol) were added sequentially to the pressure tube, which was sealed and heated to 80° C. for 4 hours and 100° C. for 16 hours. The reaction vessel was cooled to ambient temperature, concentrated in vacuo, and the resulting crude material was purified via flash chromatography, eluting with 0:100 to 25:75 ethyl acetate:heptanes on a 120 g silica gel column over 20 minutes to provide the title compound. $^1$H NMR (400 MHz, CDCl$_3$) δ ppm 5.92 (s, 1H), 4.39 (s, 2H), 3.95 (s, 6H); MS (ESI+) m/z 235.0 (M+H)$^+$.

Example 11B rac-(2R,3S,4R,5R)-ethyl 3-(tert-butyl)-1-(cyclohexanecarbonyl)-4-((4,6-dimethoxypyrimidin-2-yl)methoxy)-5-phenylpyrrolidine-2-carboxylate Example 11A (44 mg, 0.110 mmol) and Example 2C (76.6 mg, 0.328 mmol) were dissolved in 1 mL of dry dimethylformamide and the resulting solution was cooled to <5° C. in an ice-water bath. Potassium tert-butoxide (1M in tetrahydrofuran, 0.22 mL, 0.22 mmol) was added dropwise over 1 minute. After 10 minutes at the same temperature, LC/MS indicated complete conversion. The reaction mixture was diluted with methyl tert-butyl ether and quenched with saturated aqueous ammonium chloride. The organic layer was washed with water, concentrated in vacuo, loaded onto a 12 g silica gel column, and eluted with 0:100 to 35:65 ethyl acetate:heptanes over 20 minutes to provide 53 mg of the title compound. $^1$H NMR (400 MHz, DMSO-d$_6$, 120° C.) δ ppm 7.63 (d, J=7.2 Hz, 2H), 7.32-7.10 (m, 3H), 5.94 (s, 1H), 5.17 (d, J=6.3 Hz, 1H), 4.47 (d, J=3.8 Hz, 1H), 4.35 (dd, J=6.3, 3.3 Hz, 1H), 4.11 (q, J=7.1 Hz, 2H), 4.05-3.92 (m, 2H), 3.82 (s, 6H), 2.54 (s, 1H), 2.18 (s, 1H), 1.61-1.55 (m, 2H), 1.53-1.47 (m, 2H), 1.30-1.0 (m, 6H), 1.19 (t, J=7.1 Hz, 3H), 0.97 (s, 9H); MS (ESI+) m/z 554.2 (M+H)$^+$.

Example 11C rac-(2R,3S,4R,5R)-3-tert-butyl-1-(cyclohexanecarbonyl)-4-[(4,6-dimethoxypyrimidin-2-yl)methoxy]-5-phenylpyrrolidine-2-carboxylic acid Example 11B (53 mg, 0.096 mmol) was dissolved in a mixture of tetrahydrofuran (0.25 mL) and methanol (0.250 mL). Aqueous Lithium hydroxide (1M, 0.479 mL, 0.479 mmol) solution was added. After heating to 40° C. for 3 hours, additional lithium hydroxide monohydrate (20.08 mg, 0.479 mmol) was added, and heating was continued overnight, at which point complete conversion was noted by LC/MS. The reaction flask was cooled to room temperature and acidified with 6M aqueous HCl to pH=3. The mixture was extracted with dichloromethane, the organics were concentrated in vacuo, and the crude material was loaded onto a 4 g silica gel column eluting with 5:95 to 100:0 ethyl acetate:heptanes over 10 minutes to provide 31 mg of the title compound. $^1$H NMR (400 MHz, DMSO-d$_6$, 120° C.) δ ppm 7.64 (d, J=7.4 Hz, 2H), 7.20 (dt, J=25.1, 7.3 Hz, 3H), 5.95 (s, 1H), 5.16 (d, J=6.4 Hz, 1H), 4.44 (d, J=3.5 Hz, 1H), 4.35 (dd, J=6.4, 3.0 Hz, 1H), 3.97 (s, 2H), 3.83 (s, 6H), 2.60 (s, 1H), 2.22 (br s, 1H), 1.64 (d, J=9.5 Hz, 2H), 1.48 (s, 2H), 1.31-1.04 (m, 6H), 0.97 (s, 9H); MS (ESI+) m/z 526.1 (M+H)$^+$.

Example 12 rac-(2R,3S,4R,5R)-3-tert-butyl-1-(cyclohexanecarbonyl)-4-{[2-(dimethylamino)-5-(trifluoromethyl)pyridin-3-yl]methoxy}-5-phenylpyrrolidine-2-carboxylic acid Example 12A 2-(dimethylamino)-5-(trifluoromethyl)nicotinaldehyde 3-Bromo-2-chloro-5-(trifluoromethyl)pyridine (5 g, 19.20 mmol) and dimethylformamide (1.932 mL, 24.96 mmol) were dissolved in 100 mL of toluene, and the reaction mixture was cooled to <−70° C. before n-butyllithium (9.94 mL, 24.96 mmol) was added dropwise. The reaction mixture was stirred at the same temperature for 30 minutes, quenched by the addition of 10 mL of 1M aqueous HCl, and warmed to ambient temperature. The resulting biphasic mixture was stirred for 15 minutes, the layers were separated, and the organic layer was concentrated in vacuo. The crude material was purified via flash chromatography, eluting with 0:100 to 20:80 ethyl acetate:heptanes over 20 minutes on an 80 g silica gel column to provide 1.91 g of the title compound. $^1$H NMR (501 MHz, CDCl$_3$) δ ppm 9.93 (s, 1H), 8.57-8.38 (m, 1H), 8.12 (dd, J=2.0, 1.2 Hz, 1H), 3.20 (s, 6H); MS (ESI+) m/z 219.1 (M+H)$^+$.

Example 12B (2-(dimethylamino)-5-(trifluoromethyl)pyridin-3-yl)methanol

Example 12A (1.8 g, 8.25 mmol) was dissolved in 17 mL of methanol and the mixture was cooled in an ice bath to <5° C. before sodium borohydride (0.312 g, 8.25 mmol) was added in one portion. After stirring for 15 minutes at the same temperature, the reaction was complete. The volatiles were removed in vacuo and the crude residue was partitioned between ethyl acetate and saturated aqueous sodium bicarbonate. The organic extracts were dried over sodium sulfate, filtered, and concentrated to provide the title compound (1.55 g). $^1$H NMR (400 MHz, CDCl$_3$) δ ppm 8.39 (dd, J=2.5, 1.1 Hz, 1H), 7.84 (d, J=2.3 Hz, 1H), 4.72 (d, J=5.1 Hz, 2H), 2.99 (s, 6H), 2.54 (t, J=5.5 Hz, 1H); MS (ESI+) m/z 221.0 (M+H)$^+$.

Example 12C 3-(bromomethyl)-N,N-dimethyl-5-(trifluoromethyl)pyridin-2-amine

Example 12B (1.32, 6.0 mmol) and triphenylphosphine (2.36 g, 9.0 mmol) were dissolved in tetrahydrofuran (30 mL) and the mixture was cooled to <5° C. in an ice bath before adding N-bromosuccinimide (1.6 g, 9.0 mmol) in one portion. After 15 minutes, complete conversion was observed as indicated by LC/MS. The reaction mixture was concentrated to approximately 5 mL, loaded onto a 40 g silica gel column, and eluted with 0:100 to 30:70 methyl tert-butyl ether:heptanes over 20 minutes to provide 240 mg of the title compound. $^1$H NMR (400 MHz, CDCl$_3$) δ ppm 8.39-8.34 (m, 1H), 7.76 (d, J=2.3 Hz, 1H), 4.54 (s, 2H), 3.11 (s, 6H).

Example 12D rac-(2R,3S,4R,5R)-ethyl 3-(tert-butyl)-1-(cyclohexanecarbonyl)-4-((2-(dimethylamino)-5-(trifluoromethyl)pyridin-3-yl)methoxy)-5-phenylpyrrolidine-2-carboxylate Example 2C (60 mg, 0.149 mmol) was dissolved in 1 mL of dimethylformamide. Example 12C (42.3 mg, 0.149 mmol) was added, and the solution was cooled to <0° C. in an acetone-ice bath. Potassium tert-butoxide (1M in tetrahydrofuran, 0.149 mL, 0.149 mmol) was added dropwise. After stirring for 15 minutes at the same temperature, the reaction mixture was diluted with saturated aqueous ammonium chloride and extracted with methyl tert-butyl ether. The combined methyl tert-butyl ether extracts were concentrated in vacuo, which was loaded onto a 12 g silica gel column and was eluted with 0:100 to 35:65 ethyl acetate:heptanes over 20 minutes to provide 67 mg of the title compound as an inseparable mixture of compounds that was carried to the subsequent step without additional purification. MS (ESI+) m/z 604.1 (M+H)$^+$.

Example 12E rac-(2R,3S,4R,5R)-3-tert-butyl-1-(cyclohexanecarbonyl)-4-{[2-(dimethylamino)-5-(trifluoromethyl)pyridin-3-yl]methoxy}-5-phenylpyrrolidine-2-carboxylic acid Lithium hydroxide (24.99 mg, 1.044 mmol) was dissolved in 0.5 mL of water and the solution was added to a mixture of Example 12D (63 mg, 0.104 mmol) in 0.250 mL of methanol and 0.250 mL of tetrahydrofuran. The reaction mixture was heated to 40° C. for 16 hours. After cooling to ambient temperature, the reaction was neutralized with 6M aqueous HCl to pH=3 and extracted with dichloromethane. The combined organic extracts were concentrated in vacuo and purified via flash chromatography, eluting with 10:90 to 100:0 ethyl acetate:heptanes on a 4 g silica gel column over 20 minutes to provide 16 mg of the title compound. $^1$H NMR (400 MHz, DMSO-d$_6$, 120° C.) δ ppm 8.22 (t, J=1.5 Hz, 1H), 7.65 (d, J=7.3 Hz, 2H), 7.37-6.95 (m, 4H), 5.20 (d, J=6.2 Hz, 1H), 4.52 (d, J=2.7 Hz, 1H), 4.36-4.18 (m, 2H), 3.95 (d, J=12.6 Hz, 1H), 2.81 (s, 6H), 2.50 (br s, 1H), 2.21 (br s, 1H), 1.64 (d, J=10.2 Hz, 2H), 1.48 (s, 2H), 1.32-1.01 (m, 6H), 0.99 (s, 9H); MS (DCI$^+$) m/z 576.2 (M+H)$^+$.

Example 13 rac-(2R,3S,5R)-3-tert-butyl-1-(cyclohexanecarbonyl)-5-(2-methoxyphenyl)-4-{[2-methoxy-5-(trifluoromethyl)phenyl]methoxy}pyrrolidine-2-carboxylic acid

Example 13A rac-(2R,3S,4R,5R)-ethyl 3-(tert-butyl)-1-(cyclohexanecarbonyl)-5-(2-methoxyphenyl)-4-nitropyrrolidine-2-carboxylate A mixture of Core 2 (12.26 g, 35.03 mmol) and triethylamine (11.2 mL, 80.57 mmol) in dichloromethane (120 mL) at 0° C. was treated with cyclohexanecarbonyl chloride (6.1 mL, 45.54 mmol). The mixture was stirred at 0° C. for 30 minutes and at 25° C. for 1 hour. The mixture was diluted with dichloromethane (150 mL), washed with saturated aqueous sodium bicarbonate (80 mL) and with brine (100 mL), dried over magnesium sulfate, filtered and concentrated. The residue was purified by silica gel column chromatography (eluted with 1/2 ethyl acetate/petroleum ether) to provide the title compound (16.0 g, 34.78 mmol, 100% yield). LC/MS (ESI) m/z 461 (M+H)$^+$.

Example 13B rac-(2R,3S,5R)-ethyl 3-(tert-butyl)-1-(cyclohexanecarbonyl)-5-(2-methoxyphenyl)-4-oxopyrrolidine-2-carboxylate To a solution of potassium dichromate (53.73 g, 182.63 mmol) in 6 M aqueous hydrochloric acid (480 mL) was added zinc powder (87.01 g, 1330.59 mmol) under nitrogen atmosphere. Upon the complete dissolution of zinc, the freshly prepared chromium(II) chloride solution was transferred via syringe to a refluxing solution of Example 13A (12 g, 26.09 mmol) in ethanol (480 mL) under nitrogen. The mixture was stirred at reflux for 1 hour and was cooled to room temperature. The mixture was concentrated. The residue was extracted with dichloromethane (200 mL). The organic layer was washed with aqueous sodium bicarbonate solution (100 mL) and brine (150 mL), dried over magnesium sulfate, filtered and concentrated to provide a residue which was purified by silica gel column chromatography (eluted with 1/3 ethyl acetate/petroleum ether) to provide the title compound (4.32 g, 10.07 mmol, 29.4% yield). LC/MS (ESI) m/z 430 (M+H)$^+$.

Example 13C rac-(2R,3S,5R)-ethyl 3-(tert-butyl)-1-(cyclohexanecarbonyl)-4-hydroxy-5-(2-methoxyphenyl)pyrrolidine-2-carboxylate To a solution of rac-(2R,3S,5R)-ethyl 3-(tert-butyl)-1-(cyclohexanecarbonyl)-5-(2-methoxyphenyl)-4-oxopyrrolidine-2-carboxylate (Example 13B, 4.32 g, 10.07 mmol) in ethanol (30 mL) was added sodium borohydride (0.761 g, 20.14 mmol) at 0° C. The mixture was stirred at 0° C. for 1 hour and was diluted with water (20 mL). The mixture was concentrated. The residue was extracted with dichloromethane (20 mL×3). The combined organic layers were washed with brine (100 mL), dried over magnesium sulfate, filtered and concentrated to provide a residue which was purified by silica gel column chromatography (eluted with 1/2 ethyl acetate/petroleum ether) to provide the title compound (3.23 g, 7.49 mmol, 29.4% yield). $^1$H NMR (400 MHz, CDCl$_3$) δ ppm 8.00-8.02 (m, 1H), 7.31 (t, J=8.0 Hz, 1H), 7.05 (t, J=12.4 Hz, 1H), 6.93 (d, J=8.0 Hz, 1H), 5.49 (d, J=6.0 Hz, 1H), 4.61 (d, J=4.0 Hz, 1H),4.80 (d, J=6.0 Hz, 1H),4.23-4.26 (m, 2H), 3.91 (s, 3H), 2.26 (s, 1H), 1.84 (d, J=5.6 Hz, 1H), 1.26-1.70 (m, 4H), 1.26-1.35 (m,6H), 1.04-1.06 (m, 12H), 0.56-0.65 (m, 1H); LC/MS (ESI) m/z 432 (M+H)$^+$.

Example 13D rac-(2R,3S,5R)-3-tert-butyl-1-(cyclohexanecarbonyl)-5-(2-methoxyphenyl)-4-{[2-methoxy-5-(trifluoromethyl)phenyl]methoxy}pyrrolidine-2-carboxylic acid To rac-(2R,3S,5R)-ethyl 3-(tert-butyl)-1-(cyclohexanecarbonyl)-4-hydroxy-5-(2-methoxyphenyl)pyrrolidine-2-carboxylate (Example 13C, 60 mg, 0.139 mmol) and 2-(bromomethyl)-1-methoxy-4-(trifluoromethyl)benzene (56.1 mg, 0.209 mmol) in dimethylformamide (1 mL) cooled in an ice bath was added potassium 2-methylpropan-2-olate (23.40 mg, 0.209 mmol) drop wise keeping the temperature below 0° C. After the addition, the temperature was slowly raised to ambient temperature. Methanol (2 mL) and 6M aqueous LiOH (0.5 mL) were added. The mixture was stirred at 45° C. overnight, adjusted pH to 1~2 by adding 4M HCl in dioxane, and concentrated. Purification via chromatography, eluting with ethyl acetate:methanol (9:1) in heptanes provided the title compound 25 mg (30.4% yield). $^1$H NMR (400 MHz, DMSO-d$_6$) δ ppm 7.91 (s, 1H), 7.43 (dd, J=8.7, 2.4 Hz, 1H), 7.17-7.11 (m, 1H), 7.00 (d, J=8.6 Hz, 1H), 6.93 (s, 1H), 6.92-6.79 (m, 2H), 5.50 (d, J=6.2 Hz, 1H), 4.49 (d, J=3.1 Hz, 1H), 4.32 (d, J=13.2 Hz, 1H), 4.22 (dd, J=6.4, 2.4 Hz, 1H), 3.99 (d, J=13.2 Hz, 1H), 3.78 (s, 3H), 3.76 (s, 3H), 2.51 (s, 1H), 2.23-2.10 (m, 1H), 1.65 (d, J=10.0 Hz, 2H), 1.48 (s, 2H), 1.23-1.00 (m, 6H), 0.98 (s, 9H); MS (ESI+) m/z 592.1 (M+H)$^+$.

Example 14 rac-(2R,3S,5R)-3-tert-butyl-4-[(4-chloro-2-methoxyphenyl)methoxy]-1-(cyclohexanecarbonyl)-5-(2-methoxyphenyl)pyrrolidine-2-carboxylic acid The title compound was prepared according to the procedure described in Example 13D, substituting 1-(bromomethyl)-4-chloro-2-methoxybenzene for 2-(bromomethyl)-1-methoxy-4-(trifluoromethyl)benzene. $^1$H NMR (400 MHz, DMSO-d$_6$) δ ppm 7.88 (s, 1H), 7.18 (t, J=7.8 Hz, 1H), 6.91 (d, J=8.2 Hz, 1H), 6.85 (q, J=3.0 Hz, 2H), 6.70 (dd, J=8.1, 2.0 Hz, 1H), 6.59 (d, J=8.1 Hz, 1H), 5.46 (d, J=6.0 Hz, 1H), 4.49 (d, J=3.0 Hz, 1H), 4.25-4.14 (m, 2H), 3.92 (d, J=12.9 Hz, 1H), 3.79 (s, 3H), 3.68 (s, 3H), 1.65 (d, J=10.1 Hz, 2H), 1.49 (s, 2H), 1.06 (s, 3H), 0.96 (s, 9H); MS (ESI+) m/z 558.1 (M+H)$^+$.

Example 15 rac-(2R,3S,5R)-3-tert-butyl-1-(cyclohexanecarbonyl)-5-[2-(dimethylamino)pyridin-3-yl]-4-{[2-methoxy-5-(trifluoromethyl)phenyl]methoxy}pyrrolidine-2-carboxylic acid Example 15A rac-(2R,3S,4R,5R)-ethyl 3-(tert-butyl)-1-(cyclohexanecarbonyl)-5-(2-(dimethylamino)pyridin-3-yl)-4-nitropyrrolidine-2-carboxylate A solution of Core 4 (2.0 g, 5.49 mmol) and triethylamine (1.151 mL, 8.23 mmol) in dichloromethane (20 mL) at 0° C. was treated with cyclohexanecarbonyl chloride (0.954 mL, 7.13 mmol). The reaction mixture was stirred at 0° C. for 30 minutes, and was allowed to warm to ambient temperature. Dichloromethane (20 mL) was added. The mixture was washed with saturated aqueous NaHCO$_3$ and brine, dried over MgSO$_4$, filtered and concentrated. The residue was chromatographed on a 25 g silica gel cartridge eluting with 0-50% ethyl acetate in heptanes to provide the title compound 1.58 g, (60.7% yield). $^1$H NMR (501 MHz, CDCl$_3$) δ ppm 8.39-7.87 (m, 2H), 7.07 (dd, J=7.8, 4.8 Hz, 1H), 5.87 (t, J=8.0 Hz, 1H), 5.53-5.47 (m, 1H), 4.98 (d, J=2.5 Hz, 1H), 4.45-4.33 (m, 2H), 3.09-3.02 (m, 1H), 2.88 (d, J=31.3 Hz, 6H), 2.41 (t, J=11.8 Hz, 1H), 1.88-1.69 (m, 3H), 1.62 (s, 5H), 1.41 (dt, J=21.4, 7.2 Hz, 3H), 1.34-1.22 (m, 3H), 1.12 (d, J=12.4 Hz, 9H); MS (ESI+) m/z 475.2 (M+H).

Example 15B rac-(2R,3S,5R)-ethyl 3-(tert-butyl)-1-(cyclohexanecarbonyl)-5-(2-(dimethylamino)pyridin-3-yl)-4-oxopyrrolidine-2-carboxylate To potassium dichromate (3.37 g, 11.46 mmol) in 6 M aqueous HCl (60 mL) in an ice-bath, zinc (3.86 g, 35 mmol) was added slowly keeping the internal temperature below 15° C. Complete dissolution of the zinc provided a clear light blue solution. The formed chromium(II) chloride was transferred to a refluxing solution of Example 15A (0.8 g, 1.686 mmol) in ethanol (60 mL). After the addition, LC/MS confirmed the conversion to the intermediate of oxime. The reaction mixture was refluxed overnight, cooled to ambient temperature and concentrated to half of its volume. The mixture was extracted with ethyl acetate (50 mL×3). The organic phase was washed with saturated aqueous NaHCO$_3$ solution and brine, dried over MgSO$_4$, filtered, and concentrated to provide a residue which was purified via chromatography on a 24 g silica gel cartridge, eluting with ethyl acetate in heptanes at 0-40% gradient to provide the title compound (120 mg, 16.05% yield). $^1$H NMR (400 MHz, DMSO-d$_6$) δ ppm 8.27 (dd, J=4.7, 1.9 Hz, 1H), 8.17 (dd, J=7.7, 1.9 Hz, 1H), 7.09 (dd, J=7.7, 4.7 Hz, 1H), 5.56 (s, 1H), 4.55 (d, J=4.6 Hz, 1H), 4.16 (dddd, J=17.9, 10.6, 7.1, 3.6 Hz, 2H), 2.85 (s, 6H), 2.80 (d, J=4.6 Hz, 1H), 1.87-1.77 (m, 1H), 1.69-1.40 (m, 4H), 1.28 (t, J=12.6 Hz, 2H), 1.04 (d, J=6.8 Hz, 9H), 1.00-0.80 (m, 4H), 0.52-0.28 (m, 2H); MS (ESI+) m/z 444.2 (M+H)$^+$.

Example 15C rac-(2R,3S,4R,5R)-ethyl 3-(tert-butyl)-1-(cyclohexanecarbonyl)-5-(2-(dimethylamino)pyridin-3-yl)-4-hydroxypyrrolidine-2-carboxylate To a solution of Example 15B (120 mg, 0.271 mmol) in ethanol (5 mL) cooled in an ice-bath was added sodium borohydride (20.47 mg, 0.541 mmol) slowly. The reaction mixture was stirred for 30 minutes, and was allowed to warm to ambient temperature. The mixture was concentrated and the residue was dissolved in dichloromethane and water. The water layer was extracted with dichloromethane. The combined organics were washed with brine, dried over MgSO$_4$, filtered, and concentrated to provide the title compound (120 mg, 100% yield) which was used in next step. LC/MS (APCI+) m/z 446.47 (M+H)$^+$.

Example 15D rac-(2R,3S,5R)-3-(tert-butyl)-1-(cyclohexanecarbonyl)-5-(2-(dimethylamino)pyridin-3-yl)-4-((2-methoxy-5-(trifluoromethyl)benzyl)oxy)pyrrolidine-2-carboxylic acid To a mixture of Example 15C (60 mg, 0.135 mmol) and 2-(bromomethyl)-1-methoxy-4-(trifluoromethyl)benzene (54.3 mg, 0.202 mmol) in dimethylformamide (1 mL) cooled in an ice-bath was added potassium 2-methylpropan-2-olate (30.2 mg, 0.269 mmol, 0.27 mL, 1.0 M in tetrahydrofuran) drop wise. The mixture was stirred at 0-5° C. for 20 minutes. LC/MS showed the reaction was complete, and methanol (1.5 mL) and 6M aqueous LiOH (0.5 mL) were added. The mixture was stirred at 50° C. overnight, adjusted to pH 1~2 by adding 2M aqueous HCl, and concentrated. The residue was dispersed in dichloromethane (2 mL) and filtered. Purification by reverse-phase HPLC (Phenomenex® Luna® C8(2) 5 μm 100 Å AXIA™ column (30 mm×75 mm) A gradient of acetonitrile (A) and 0.1% trifluoroacetic acid in water (B) was used, at a flow rate of 50 mL/minute (0-1.0 min 5% A, 1.0-8.5 minute linear gradient 5-100% A, 8.5-11.5 minute 100% A, 11.5-12.0 minute linear gradient 95-5% A)) provided the title compound (18 mg, 22.07% yield). $^1$H NMR (400 MHz, DMSO-d$_6$) δ ppm 8.63-8.47 (m, 1H), 8.25-8.14 (m, 1H), 7.52 (d, J=8.3 Hz, 1H), 7.19-6.93 (m, 3H), 5.35 (d, J=5.7 Hz, 1H), 4.52 (d, J=12.8 Hz, 1H), 4.42-4.31 (m, 1H), 4.16 (d, J=13.8 Hz, 1H), 3.91-3.82 (m, 1H), 3.73 (d, J=10.3 Hz, 3H), 2.87 (s, 3H), 2.73 (s, 3H), 2.62 (d, J=17.2 Hz, 1H), 1.84-1.08 (m, 9H), 1.00 (d, J=7.4 Hz, 9H), 0.48 (dd, J=61.9, 12.8 Hz, 2H); MS (ESI+) m/z 606.3 (M+H)$^+$.

Example 16 rac-(2R,3S,5R)-3-tert-butyl-1-(cyclohexanecarbonyl)-N-(methanesulfonyl)-4-{[2-methoxy-5-(trifluoromethyl)phenyl]methoxy}-5-phenylpyrrolidine-2-carboxamide A mixture of Example 2D (50 mg, 0.089 mmol) and di(1H-imidazol-1-yl)methanone (31.8 mg, 0.196 mmol) in dichloromethane (2 mL) was stirred at 40° C. for 2 hours, and methanesulfonamide (33.9 mg, 0.356 mmol) and 2,3,4,6,7,8,9,10-octahydropyrimido[1,2-a]azepine (0.053 mL, 0.356 mmol) were added. The mixture was stirred at 40° C. overnight, and dichloromethane and water were added. The organic layer was washed with brine, dried over MgSO$_4$, filtered, and concentrated. The residue was purified with reverse-phase HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 min linear gradient 95-5% A) to provide the title compound (30 mg, 52.8% yield). $^1$H NMR (501 MHz, DMSO-d$_6$) δ ppm 11.95 (s, 2H), 7.82-7.76 (m, 2H), 7.53 (dd, J=8.7, 2.4 Hz, 1H), 7.31-7.25 (m, 2H), 7.23-7.18 (m, 1H), 7.07 (d, J=8.6 Hz, 1H), 6.90 (d, J=2.4 Hz, 1H), 5.46 (d, J=7.9 Hz, 1H), 4.50 (d, J=12.5 Hz, 1H), 4.39-4.29 (m, 2H), 4.17 (d, J=9.1 Hz, 1H), 3.79 (s, 3H), 3.14 (s, 3H), 2.44 (t, J=9.3 Hz, 1H), 2.19 (tt, J=11.6, 3.2 Hz, 1H), 1.68 (dd, J=28.2, 12.7 Hz, 2H), 1.45 (d, J=12.7 Hz, 1H), 1.34-1.22 (m, 2H), 1.15-0.94 (m, 3H), 0.92 (s, 9H), 0.67 (d, J=12.7 Hz, 1H), 0.56 (m, 1H),); MS (ESI+) m/z 639.1 (M+H)$^+$.

Example 17 rac-(2R,3S,5R)-3-tert-butyl-4-[(5-chloro-2-methoxyphenyl)methoxy]-5-phenyl-1-{[(propan-2-yl)oxy]carbonyl}pyrrolidine-2-carboxylic acid Example 17A rac-(2R,3S,4R,5R)-2-ethyl 1-isopropyl 3-(tert-butyl)-4-nitro-5-phenylpyrrolidine-1,2-dicarboxylate Core 1 (0.800 g, 2.497 mmol) in dichloromethane (5 mL) was treated with triethylamine (0.7 mL, 5.02 mmol) followed by isopropyl chloroformate (1M in toluene) (4.2 mL, 4.20 mmol). The reaction mixture was stirred at room temperature overnight. The mixture was then diluted with 50 mL dichloromethane and washed twice with 1N aqueous HCl (20 mL each) and once with brine (20 mL). The organic layer was dried over Na$_2$SO$_4$, filtered, and concentrated in vacuo. The resulting crude residue was purified by silica gel chromatography, eluting with 0 to 40% ethyl acetate-heptanes to provide the title compound (0.344 g, 34% yield). $^1$H NMR (400 MHz, DMSO-d$_6$) δ ppm 7.49 (m, 2H), 7.20 (m, 3H), 5.59 (m, 1H), 5.42 (m, 1H), 4.65 (m, 1H), 4.47 (m, 1H), 4.23 (m, 2H), 2.98 (m, 1H), 1.27 (m, 3H), 1.05 (d, J=6.3 Hz, 3H), 1.00 (s, 9H), 0.91 (d, J=5.9 Hz, 3H); MS (ESI$^+$) m/z 407.0 (M+H)$^+$.

Example 17B rac-(2R,3S,5R)-2-ethyl 1-isopropyl 3-(tert-butyl)-4-oxo-5-phenylpyrrolidine-1,2-dicarboxylate Potassium dichromate (0.846 g, 2.88 mmol) was dissolved in 6N aqueous HCl (14 mL), and the solution was chilled in an ice bath. Zinc dust (1.522 g, 23.27 mmol) was added under nitrogen in portions over a few minutes. After the last addition of zinc, the flask was removed from the ice bath and allowed to stir at room temperature for 45 minutes under nitrogen until the zinc had fully dissolved. The initially green-blue mixture became clear and brilliant blue. Meanwhile, a solution of Example 17A (0.344 g, 0.846 mmol) in ethanol (14 mL) was heated to 75° C. The chromium solution was transferred via syringe to a dropping funnel and added dropwise over 5 minutes to the reaction mixture, which turned emerald green. The reaction mixture was refluxed for 20 hours. The mixture was cooled to room temperature, and the ethanol was evaporated in vacuo. Water (25 mL) was added, and the resulting mixture was extracted three times with dichloromethane (25 mL each). The combined organics were dried over Na$_2$SO$_4$, filtered and concentrated in vacuo. Chromatography on silica gel, eluting with 0 to 30% ethyl acetate-heptanes, provided the title compound, 0.066 g (21% yield). $^1$H NMR (500 MHz, DMSO-d$_6$) δ ppm 7.51 (m, 2H), 7.34-7.25 (m, 3H), 4.99 (s, 1H), 4.65 (m, 1H), 4.55 (d, J=4.5 Hz, 1H), 4.25-4.14 (m, 2H), 2.62 (m, 1H), 1.37-1.00 (m, 18H); MS (ESI+) m/z 376.0 (M+H)+.

Example 17C rac-(2R,3S,5R)-2-ethyl 1-isopropyl 3-(tert-butyl)-4-hydroxy-5-phenylpyrrolidine-1,2-dicarboxylate Example 17B (0.079 g, 0.210 mmol) in ethanol (2.5 mL) was cooled in an ice bath and then treated in one portion with sodium borohydride (0.021 g, 0.568 mmol). The mixture stirred in the ice bath for 10 minutes and at room temperature overnight. The reaction mixture was quenched with 2 mL water and concentrated in vacuo. Excess water was removed azeotropically with acetonitrile, and the residue was purified by silica gel chromatography, eluting with 0 to 30% ethyl acetate-heptanes. The crude title compound was obtained as a residue (34 mg) and the material was used directly into the next step without additional purification. MS (APCI+) m/z 378.2 (M+H)+.

Example 17D rac-(2R,3S,5R)-2-ethyl 1-isopropyl 3-(tert-butyl)-4-((5-chloro-2-methoxybenzyl)oxy)-5-phenylpyrrolidine-1,2-dicarboxylate Example 17C (0.019 g, 0.050 mmol) and 2-(bromomethyl)-4-chloro-1-methoxybenzene (Enamine; 0.024 g, 0.101 mmol) in dimethylformamide (0.5 mL) were cooled to 0° C., and the mixture was treated dropwise with potassium tert-butoxide solution (1M in tetrahydrofuran) (0.101 mL, 0.101 mmol). The reaction mixture was stirred in an ice bath for 1 hour. The mixture was diluted with ethyl acetate (5 mL) and washed three times with water (1 mL each time). The combined extracts were then dried over $Na_2SO_4$, filtered, and concentrated in vacuo. The crude material was used in the next step without further purification. MS (APCI+) m/z 532.6 (M+H)+.

Example 17E rac-(2R,3S,5R)-3-tert-butyl-4-[(5-chloro-2-methoxyphenyl)methoxy]-5-phenyl-1-{[(propan-2-yl)oxy]carbonyl}pyrrolidine-2-carboxylic acid Example 17D (0.027 g, 0.05 mmol) in tetrahydrofuran (1.600 mL) and methanol (0.4 mL) was treated with lithium hydroxide (1M aqueous, 0.400 mL, 0.400 mmol), and the reaction mixture was stirred overnight at 35° C. The reaction mixture was then concentrated in vacuo, and excess moisture was removed azeotropically with acetonitrile. The material thus obtained was purified by reverse-phase HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A) to provide the title compound, 0.0025 g, 9% yield. $^1$H NMR (500 MHz, CDCl$_3$) δ ppm 7.40-7.27 (m, 5H), 7.09 (dd, J=8.7, 2.6 Hz, 1H), 6.65 (d, J=8.7 Hz, 1H), 6.56 (d, J=2.7 Hz, 1H), 5.02 (d, J=6.1 Hz, 1H), 4.85 (m, 1H), 4.49 (d, J=3.1 Hz, 1H), 4.36 (d, J=13.3 Hz, 1H), 4.09 (dd, J=6.1, 2.7 Hz, 1H), 4.04 (d, J=13.2 Hz, 1H), 3.71 (s, 3H), 2.95 (m, 1H), 1.18 (d, J=6.2 Hz, 3H), 1.09-1.03 (m, 12H); MS (ESI+) m/z 504.0 (M+H)+.

Example 18

(2R,3S,4R,5R)-3-tert-butyl-1-(cyclohexanecarbonyl)-4-{[2-methoxy-5-(trifluoromethyl)phenyl]methoxy}-5-phenylpyrrolidine-2-carboxylic acid Example 2 (6.55 g) was separated by chiral preparative SFC chromatography using a CHIRALPAK OZ-H, column size 30×250 mm, 5 micron, serial Number: OZHO-SANG001-101201, using a concentration of 65 mg/mL in methanol with 2-propanol cosolvent (30%) at a flow rate of 56 g/min $CO_2$ to provide 2.10 g of the title compound. $R_T$ (chiral SFC)=7.9 min; $^1$H NMR (400 MHz, DMSO-d$_6$, 120° C.) δ ppm 7.66 (d, J=7.4 Hz, 2H), 7.44 (dd, J=8.8, 2.4 Hz, 1H), 7.19 (dt, J=26.6, 7.3 Hz, 3H), 7.07-6.89 (m, 2H), 5.21 (d, J=6.4 Hz, 1H), 4.49 (d, J=3.4 Hz, 1H), 4.32 (d, J=13.2 Hz, 1H), 4.25 (dd, J=6.5, 2.7 Hz, 1H), 3.98 (d, J=13.2 Hz, 1H), 3.77 (s, 3H), 2.51 (s, 1H), 2.24 (s, 1H), 1.65 (d, J=9.8 Hz, 2H), 1.48 (s, 2H), 1.36-1.03 (m, 5H), 0.99 (s, 9H), 0.79 (d, J=38.3 Hz, 1H); MS (ESI+) m/z 562.3 (M+H)+.

Example 19

(2S,3R,4S,5S)-3-tert-butyl-1-(cyclohexanecarbonyl)-4-{[2-methoxy-5-(trifluoromethyl)phenyl]methoxy}-5-phenylpyrrolidine-2-carboxylic acid Example 2 (6.55 g) was separated by chiral preparative SFC chromatography using a CHIRALPAK OZ-H, column size 30×250 mm, 5 micron, serial Number: OZH0SANG001-101201, using a concentration of 65 mg/mL in methanol with 2-propanol cosolvent (30%) at a flow rate of 56 g/min $CO_2$ and UV monitoring at 220 nm to provide 1.92 g of (2S,3R,4S,5S)-3-(tert-butyl)-1-(cyclohexanecarbonyl)-4-((2-methoxy-5-(trifluoromethyl)benzyl)oxy)-5-phenylpyrrolidine-2-carboxylic acid. The absolute structure of the title compound was determined by X-ray crystallography. $R_T$ (chiral SFC)=6.0 min; $^1$H NMR (400 MHz, DMSO-d$_6$, 120° C.) δ ppm 7.66 (d, J=7.4 Hz, 2H), 7.44 (dd, J=8.8, 2.4 Hz, 1H), 7.19 (dt, J=26.6, 7.3 Hz, 3H), 7.07-6.89 (m, 2H), 5.21 (d, J=6.4 Hz, 1H), 4.49 (d, J=3.4 Hz, 1H), 4.32 (d, J=13.2 Hz, 1H), 4.25 (dd, J=6.5, 2.7 Hz, 1H), 3.98 (d, J=13.2 Hz, 1H), 3.77 (s, 3H), 2.51 (s, 1H), 2.24 (s, 1H), 1.65 (d, J=9.8 Hz, 2H), 1.48 (s, 2H), 1.36-1.03 (m, 5H), 0.99 (s, 9H), 0.79 (d, J=38.3 Hz, 1H); MS (ESI+) m/z 562.3 (M+H)+; $[α]^{24.8}$=+83.9° (c=0.85, methanol)+.

Example 20 rac-(2R,3S,4R,5R)-3-tert-butyl-1-(cyclohexanecarbonyl)-4-{[2-methoxy-5-(trifluoromethyl)pyridin-3-yl]methoxy}-5-phenylpyrrolidine-2-carboxylic acid The title compound was prepared according to the procedure described in Example 2D, substituting 3-(chloromethyl)-2-methoxy-5-(trifluoromethyl)pyridine for 2-(bromomethyl)-1-methoxy-4-(trifluoromethyl)benzene. $^1$H NMR (400 MHz, DMSO-d$_6$) δ ppm 8.2 (s, 2H),7.65 (d, J=7.3 Hz, 2H), 7.20 (dd, J=8.6, 5.4 Hz, 3H), 7.13 (t, J=7.2 Hz, 1H), 5.22 (d, J=6.3 Hz, 1H), 4.51 (d, J=3.1 Hz, 1H), 4.38-4.26 (m, 2H), 3.94 (d, J=13.8 Hz, 1H), 3.88 (d, J=0.9 Hz, 3H), 2.50 (s, 1H), 2.23 (s, 1H), 1.71-1.58 (m, 2H), 1.48

(s, 2H), 1.21-1.12 (m, 2H), 1.00 (d, J=1.0 Hz, 9H), 0.85 (t, J=6.4 Hz, 2H); MS (ESI+) m/z 563.1 (M+H)$^+$.

Example 21

(2S,3R,4S,5S)-3-tert-butyl-1-(cyclohexanecarbonyl)-N-(2-methoxyethanesulfonyl)-4-{[2-methoxy-5-(trifluoromethyl)phenyl]methoxy}-5-phenylpyrrolidine-2-carboxamide A 4 mL vial was charged with a stir bar, a solution of Example 19 (20.0 mg, 0.036 mmol) in dichloroethane, and a solution of carbonyldiimidazole (12.8 mg, 2.22 eq, 0.08 mmol) in dichloroethane. The vial was capped and stirred at 42° C. for 2 hours. To the mixture of 2-methoxyethanesulfonamide (16.3 mg, 3 eq, 0.107 mmol) in dichloromethane was added 1,8-diazabicyclo[5.4.0]undec-7-ene (DBU, 16.1 µL, 3 eq, 0.107 mmol) and the vial was capped. The vial was stirred at 60° C. for another 2 hours. Upon completion, the compound was concentrated to dryness and redissolved in 1400 µL of DMSO/methanol (1:1 v/v). The material was purified using reverse phase HPLC method TFA8 to obtain title compound (15.4 mg, 63.4%). $^1$H NMR (400 MHz, DMSO-d$_6$) δ ppm 7.61 (d, J=7.5 Hz, 2H), 7.51-7.43 (m, 1H), 7.24 (dt, J=14.2, 6.8 Hz, 3H), 7.04 (d, J=8.7 Hz, 1H), 7.00-6.98 (m, 1H), 5.34 (d, J=7.2 Hz, 1H), 4.48-4.39 (m, 1H), 4.38 (d, J=5.9 Hz, 1H), 4.30 (t, J=6.6 Hz, 1H), 4.19 (d, J=12.6 Hz, 1H), 3.79 (s, 3H), 3.73 (t, J=6.3 Hz, 2H), 3.57-3.52 (m, 2H), 3.22 (s, 3H), 2.64 (t, J=6.1 Hz, 1H), 2.33-2.27 (m, 1H), 1.75-1.64 (m, 2H), 1.55-1.40 (m, 2H), 1.36-1.25 (m, 1H), 1.19-1.04 (m, 3H), 0.98 (s, 9H); MS (APCI+) m/z 683.4 (M+H)$^+$.

Example 22

(2S,3R,4S,5S)-3-tert-butyl-1-(cyclohexanecarbonyl)-4-{[2-methoxy-5-(trifluoromethyl)phenyl]methoxy}-N-(1-methylcyclopropane-1-sulfonyl)-5-phenylpyrrolidine-2-carboxamide The title compound was prepared according to the procedure described in Example 21 substituting 1-methylcyclopropane-1-sulfonamide for 2-methoxyethanesulfonamide. $^1$H NMR (400 MHz, DMSO-d$_6$) δ ppm 7.56 (d, J=7.3 Hz, 2H), 7.50-7.44 (m, 1H), 7.24 (dt, J=12.8, 6.9 Hz, 3H), 7.04 (d, J=8.9 Hz, 1H), 7.00 (s, 1H), 5.36 (d, J=7.4 Hz, 1H), 4.47-4.41 (m, 2H), 4.34-4.26 (m, 2H), 4.16 (d, J=12.7 Hz, 1H), 3.79 (s, 3H), 2.70 (t, J=6.0 Hz, 1H), 2.42-2.34 (m, 1H), 1.69 (s, 3H), 1.55-1.45 (m, 3H), 1.42 (s, 3H), 1.35 (dd, J=21.3, 9.9 Hz, 0H), 1.13 (dt, J=22.9, 11.5 Hz, 2H), 1.01 (s, 2H), 0.98 (s, 9H), 0.81 (s, 2H); MS (APCI+) m/z 679.4 (M+H)$^+$.

Example 23

(2S,3R,4S,5S)-3-tert-butyl-1-(cyclohexanecarbonyl)-N-(cyclopropanesulfonyl)-4-{[2-methoxy-5-(trifluoromethyl)phenyl]methoxy}-5-phenylpyrrolidine-2-carboxamide The title compound was prepared according to the procedure described in Example 21 substituting cyclopropanesulfonamide for 2-methoxyethanesulfonamide. $^1$H NMR (400 MHz, DMSO-d$_6$) δ ppm 7.60 (d, J=7.0 Hz, 2H), 7.48 (dd, J=8.4, 2.4 Hz, 1H), 7.29-7.18 (m, 3H), 7.04 (d, J=8.7 Hz, 1H), 6.99 (s, 1H), 5.35 (d, J=7.4 Hz, 1H), 4.44 (d, J=12.7 Hz, 1H), 4.40 (d, J=5.9 Hz, 1H), 4.30 (t, J=6.6 Hz, 1H), 4.19 (d, J=12.7 Hz, 1H), 3.79 (s, 3H), 2.88-2.79 (m, 1H), 2.68-2.65 (m, 1H), 2.39-2.29 (m, 1H), 1.74-1.66 (m, 2H), 1.54-1.41 (m, 2H), 1.37-1.26 (m, 2H), 1.23-1.04 (m, 5H), 0.98 (s, 9H), 0.97-0.91 (m, 2H); MS (APCI+) m/z 665.4 (M+H)$^+$.

Example 24

(2S,3R,4S,5S)-3-tert-butyl-1-(cyclohexanecarbonyl)-N-(ethanesulfonyl)-4-{[2-methoxy-5-(trifluoromethyl)phenyl]methoxy}-5-phenylpyrrolidine-2-carboxamide The title compound was prepared according to the procedure described in Example 21 substituting ethanesulfonamide for 2-methoxyethanesulfonamide. $^1$H NMR (400 MHz, DMSO-d$_6$) δ ppm 7.61 (d, J=7.5 Hz, 2H), 7.48 (d, J=8.9 Hz, 1H), 7.23 (dq, J=13.0, 7.2 Hz, 3H), 7.04 (d, J=8.6 Hz, 1H), 7.00 (d, J=2.5 Hz, 1H), 5.34 (d, J=7.3 Hz, 1H), 4.47-4.37 (m, 2H), 4.31 (t, J=6.7 Hz, 1H), 4.18 (d, J=12.6 Hz, 1H), 3.79 (s, 3H), 3.29 (dq, J=14.3, 7.2 Hz, 1H), 2.64 (t, J=6.0 Hz, 1H), 2.33-2.27 (m, 1H), 1.74-1.65 (m, 2H), 1.54-1.41 (m, 2H), 1.37-1.25 (m, 1H), 1.21 (t, J=7.4 Hz, 3H), 1.18-1.05 (m, 3H), 0.98 (s, 9H), 0.78-0.70 (m, 1H); MS (APCI+) m/z 653.4 (M+H)$^+$.

Example 25

(2S,3R,4S,5S)-3-tert-butyl-1-(cyclohexanecarbonyl)-N-(dimethylsulfamoyl)-4-{[2-methoxy-5-(trifluoromethyl)phenyl]methoxy}-5-phenylpyrrolidine-2-carboxamide The title compound was prepared according to the procedure described in Example 21 substituting N,N-dimethylsulfonamide for 2-methoxyethanesulfonamide. $^1$H NMR (400 MHz, DMSO-d$_6$) δ ppm 7.58 (d, J=7.5 Hz, 2H), 7.50-7.46 (m, 1H), 7.25 (dt, J=13.1, 7.0 Hz, 3H), 7.04 (d, J=8.7 Hz, 1H), 7.02-6.99 (m, 1H), 5.35 (d, J=7.3 Hz, 1H), 4.44 (d, J=12.7 Hz, 1H), 4.41 (d, J=5.8 Hz, 1H), 4.33-4.29 (m, 1H), 4.18 (d, J=12.7 Hz, 1H), 3.79 (s, 3H), 2.79 (s, 5H), 2.69-2.67 (m, 1H), 2.37-2.30 (m, 1H), 1.74-1.66 (m, 3H), 1.54-1.41 (m, 1H), 1.32 (s, 1H), 1.13 (dd, J=22.0, 11.4 Hz, 3H), 0.97 (s, 9H), 0.77-0.71 (m, 1H); MS (APCI+) m/z 668.4 (M+H)$^+$.

Example 26

(2S,3R,4S,5S)-3-tert-butyl-1-(cyclohexanecarbonyl)-N-(methanesulfonyl)-4-{[2-methoxy-5-(trifluoromethyl)phenyl]methoxy}-5-phenylpyrrolidine-2-carboxamide The title compound was prepared according to the procedure described in Example 21 substituting methanesulfonamide for 2-methoxyethanesulfonamide. $^1$H NMR (400 MHz, DMSO-d$_6$) δ ppm 7.64-7.59 (m, 2H), 7.50-7.46 (m, 1H), 7.24 (dt, J=15.2, 7.1 Hz, 3H), 7.04 (d, J=8.7 Hz, 1H), 7.00 (d, J=2.4 Hz, 1H), 5.34 (d, J=7.3 Hz, 1H), 4.45 (d, J=12.6 Hz, 1H), 4.37 (d, J=6.4 Hz, 1H), 4.31 (t, J=6.9 Hz, 1H), 4.21 (d, J=12.6 Hz, 1H), 3.79 (s, 3H), 3.12 (s, 3H), 2.63 (t, J=6.4 Hz, 1H), 2.31 (m, 1H), 1.74-1.65 (m, 2H), 1.53-1.40 (m, 2H), 1.36-1.25 (m, 1H), 1.20-1.03 (m, 4H), 0.98 (s, 9H), 0.79-0.69 (m, 1H); MS (APCI+) m/z 639.3 (M+H)$^+$.

Example 27

(2R,3S,4R,5R)-3-tert-butyl-1-[(1S,3S)-3-methoxycyclohexane-1-carbonyl]-4-{[2-methoxy-5-(trifluoromethyl)phenyl]methoxy}-5-phenylpyrrolidine-2-carboxylic acid The title compound was prepared according to the procedure described in Example 31 substituting Core 1 for Core 5 in Example 31A. $^1$H NMR (400 MHz, DMSO-$d_6$) δ ppm 7.65 (s, 2H), 7.43 (dd, J=8.6, 2.5 Hz, 1H), 7.19 (t, J=7.4 Hz, 2H), 7.12 (d, J=7.1 Hz, 1H), 7.00 (d, J=8.7 Hz, 1H), 6.96 (s, 1H), 5.20 (d, J=6.5 Hz, 1H), 4.42 (s, 1H), 4.31 (d, J=13.2 Hz, 1H), 4.22 (s, 1H), 3.97 (d, J=13.3 Hz, 1H), 3.76 (s, 3H), 3.33 (s, 1H), 2.68-2.60 (m, 1H), 2.56-2.50 (m, 1H), 1.61 (s, 2H), 1.40 (t, J=5.1 Hz, 2H), 1.33-1.27 (m, 1H), 1.25 (s, 3H), 0.98 (s, 10H), 0.85 (td, J=6.0, 5.4, 3.7 Hz, 2H); MS (ESI+) m/z 593 (M+H)$^+$.

Example 28

(2R,3S,4R,5R)-3-tert-butyl-1-[(1S,3S)-3-methoxycyclohexane-1-carbonyl]-4-{[6-methyl-4-(trifluoromethyl)pyridin-2-yl]oxy}-5-phenylpyrrolidine-2-carboxylic acid The title compound was prepared according to the procedure described in Example 31 substituting Core 1 for Core 5 in Example 31A and 2-chloro-6-methyl-4-(trifluoromethyl)pyridine for 2-(bromomethyl)-1-methoxy-4-(trifluoromethyl)benzene in Example 31D. $^1$H NMR (400 MHz, DMSO-$d_6$) δ ppm 7.52 (d, J=7.6 Hz, 2H), 7.11 (t, J=7.4 Hz, 2H), 7.05 (d, J=7.1 Hz, 1H), 6.95 (s, 1H), 6.13 (s, 1H), 5.90 (dd, J=6.5, 3.3 Hz, 1H), 5.35 (d, J=6.4 Hz, 1H), 4.51 (d, J=3.8 Hz, 1H), 3.32 (s, 1H), 2.54 (s, 1H), 2.42 (s, 3H), 1.69-1.50 (m, 2H), 1.43-1.34 (m, 2H), 1.34-1.19 (m, 3H), 1.05 (s, 9H), 0.99-0.96 (m, 3H), 0.88-0.80 (m, 2H); MS (ESI+) m/z 563 (M+H)$^+$.

Example 29 rac-(2R,3S,4R,5R)-3-(tert-butyl)-4-((2-methoxy-5-(trifluoromethyl)benzyl)oxy)-1-((1R,3R)-3-methoxycyclohexanecarbonyl)-5-phenylpyrrolidine-2-carboxylic acid The title compound was prepared according to the procedure described in Example 31 substituting Core 1 for Core 5 in Example 31A. $^1$H NMR (400 MHz, DMSO-$d_6$) δ ppm 7.69-7.60 (m, 2H), 7.43 (dd, J=8.6, 2.3 Hz, 1H), 7.20 (t, J=7.3 Hz, 2H), 7.14 (d, J=6.8 Hz, 1H), 6.99 (d, J=8.6 Hz, 1H), 6.96 (d, J=2.1 Hz, 1H), 5.14 (d, J=6.5 Hz, 1H), 4.49-4.39 (m, 1H), 4.31 (d, J=13.2 Hz, 1H), 4.27-4.21 (m, 1H), 3.96 (d, J=13.2 Hz, 1H), 3.76 (s, 3H), 3.50-3.39 (m, 1H), 3.19 (s, 2H), 2.66-2.61 (m, 1H), 2.57-2.49 (m, 0H), 1.82-1.69 (m, 1H), 1.66-1.54 (m, 1H), 1.41 (t, J=12.4 Hz, 1H), 1.25 (s, 3H), 1.23-1.09 (m, 3H), 0.98 (s, 9H), 0.89-0.78 (m, 1H); MS (ESI+) m/z 592 (M+H)$^+$.

Example 30

(2S,3R,4S,5S)-3-tert-butyl-1-[(1S,3S)-3-methoxycyclohexane-1-carbonyl]-4-{[2-methoxy-5-(trifluoromethyl)phenyl]methoxy}-5-phenylpyrrolidine-2-carboxylic acid The title compound was prepared according to the procedure described in Example 31 using the second eluting diastereomer in Example 31C and treating as described in Example 31D-31E. $^1$H NMR (400 MHz, DMSO-$d_6$) δ ppm 7.65 (s, 2H), 7.43 (dd, J=8.6, 2.5 Hz, 1H), 7.19 (t, J=7.4 Hz, 2H), 7.12 (d, J=7.1 Hz, 1H), 7.00 (d, J=8.7 Hz, 1H), 6.96 (s, 1H), 5.20 (d, J=6.5 Hz, 1H), 4.42 (s, 1H), 4.31 (d, J=13.2 Hz, 1H), 4.22 (s, 1H), 3.97 (d, J=13.3 Hz, 1H), 3.76 (s, 3H), 3.33 (s, 1H), 2.68-2.60 (m, 1H), 2.56-2.50 (m, 1H), 1.61 (s, 2H), 1.40 (t, J=5.1 Hz, 2H), 1.33-1.27 (m, 1H), 1.25 (s, 3H), 0.98 (s, 10H), 0.85 (td, J=6.0, 5.4, 3.7 Hz, 2H); MS (ESI+) m/z 592 (M+H)$^+$.

Example 31

(2S,3R,4S,5S)-3-tert-butyl-1-[(1R,3R)-3-methoxycyclohexane-1-carbonyl]-4-{[2-methoxy-5-(trifluoromethyl)phenyl]methoxy}-5-phenylpyrrolidine-2-carboxylic acid

Example 31A (2S,3R,4S,5S)-ethyl 3-(tert-butyl)-1-((1R,3R)-3-methoxycyclohexanecarbonyl)-4-nitro-5-phenylpyrrolidine-2-carboxylate and (2S,3R,4S,5S)-ethyl 3-(tert-butyl)-1-((1S,3S)-3-methoxycyclohexanecarbonyl)-4-nitro-5-phenylpyrrolidine-2-carboxylate To a solution of Core 5 (1.037 g, 3.24 mmol) and triethylamine (1.353 mL, 9.71 mmol) in dichloromethane (8 mL) at 25° C. was added dropwise rac-(1R,3R)-3-methoxycyclohexanecarbonyl chloride (1.143 g, 6.47 mmol) as a solution in 4 mL of dichloromethane. After 30 minutes, the reaction mixture was quenched with saturated aqueous ammonium chloride (50 mL) and extracted with 200 mL of dichloromethane. The organic extracts were concentrated in vacuo and purified using a 80 g silica gel cartridge with 5-100% ethyl acetate/heptanes over 40 minutes to provide (2S,3R,4S,5S)-ethyl 3-(tert-butyl)-1-((1S,3S)-3-methoxycyclohexanecarbonyl)-4-nitro-5-phenylpyrrolidine-2-carboxylate (1.395 g, 3.03 mmol, 94% yield) (mixture of diastereomers). $^1$H NMR (400 MHz, DMSO-$d_6$) δ ppm 7.56 (t, J=6.6 Hz, 2H), 7.25 (p, J=7.3 Hz, 3H), 5.74-5.53 (m, 2H), 4.66 (dd, J=7.3, 3.7 Hz, 1H), 4.24 (qd, J=7.0, 1.6 Hz, 2H), 3.49-3.28 (m, 1H), 3.19 (s, 3H), 2.99 (dt, J=5.9, 3.4 Hz, 1H), 2.55 (s, 1H), 1.80 (d, J=13.2 Hz, 1H), 1.69-1.54 (m, 2H), 1.48-1.38 (m, 2H), 1.28 (td, J=7.1, 1.6 Hz, 3H), 1.21-1.12 (m, 2H), 1.00 (d, J=2.0 Hz, 9H), 0.88-0.79 (m, 1H); MS (ESI+) m/z 461 (M+H)$^+$.

Example 31B (2S,3R,5S)-ethyl 3-(tert-butyl)-1-((1R,3R)-3-methoxycyclohexanecarbonyl)-4-oxo-5-phenylpyrrolidine-2-carboxylate and (2S,3R,5S)-ethyl 3-(tert-butyl)-1-((1S,3S)-3-methoxycyclohexanecarbonyl)-4-oxo-5-phenylpyrrolidine-2-carboxylate Example 31A (1.350 g, 2.93 mmol) was dissolved in ethanol (75 mL), the solution was degassed with bubbling nitrogen for about 20 minutes, and the mixture was heated to 75° C. under nitrogen. A separate solution of CrCl$_2$ was prepared by dissolving potassium dichromate (2.93 g, 9.97 mmol) in aqueous hydrochloric acid, 6M (75 mL) and adding Zn (in portions while cooling in an ice bath, keeping the internal temperature around 25° C.), keeping the system under nitrogen. The color of the solution changed from dark brown to dark green to clear light blue. The mixture was added via cannula over 20 minutes to the solution of starting material. The reaction was warmed to 80° C. and was heated for 19 hours. The reaction mixture was cooled to room temperature and the ethanol was removed in vacuo. The mixture was diluted with water (50 mL) and extracted with dichloromethane (3×200 mL). The combined extracts were dried over sodium sulfate, filtered, concentrated and purified using a 40 g silica gel cartridge and eluting with 0-15% ethyl acetate/heptanes over 20 minutes then 10 minutes at 30% ethyl acetate/heptanes and 30-100% ethyl acetate/heptanes over 10 minutes to provide (2S,3R,5S)-ethyl 3-(tert-butyl)-1-((1S,3S)-3-methoxycyclohexanecarbonyl)-4-oxo-5-phenylpyrrolidine-2-carboxylate (0.752 g, 1.751 mmol, 59.7% yield) as a mixture of diastereomers. $^1$H NMR (90° C., 400 MHz, DMSO-$d_6$) δ ppm 7.56 (s, 2H), 7.30 (dt, J=32.7, 7.4 Hz, 3H), 5.10 (s, 1H), 4.72 (d, J=4.3 Hz, 1H), 4.16 (dtd, J=7.4, 6.2, 5.5, 1.9 Hz, 2H), 3.46-3.39 (m, 1H), 3.19 (d, J=8.3 Hz, 1H), 3.17 (s, 3H), 2.67-2.49 (m, 1H), 1.88-1.73 (m, 1H), 1.72-1.52 (m, 1H), 1.49-1.34 (m, 2H), 1.29-1.25 (m, 1H), 1.21 (td, J=7.1, 2.0 Hz, 3H), 1.03 (d, J=3.9 Hz, 10H), 1.00 (d, J=2.5 Hz, 1H), 0.93-0.86 (m, 1H); MS (ESI+) m/z 430 (M+H)$^+$.

Example 31C (2S,3R,4S,5S)-ethyl 3-(tert-butyl)-4-hydroxy-1-((1R,3R)-3-methoxycyclohexanecarbonyl)-5-phenylpyrrolidine-2-carboxylate Example 31B (0.750 g, 1.746 mmol) was dissolved in ethanol (8.73 mL) and sodium borohydride (0.132 g, 3.49 mmol) was added in one portion after cooling the reaction to <5° C. in an ice-water bath. The reaction mixture was stirred at the same temperature for 30 minutes, concentrated, and partitioned between ethyl acetate and saturated aqueous sodium bicarbonate. The organics were concentrated and purified using a 40 g silica gel cartridge and eluting with 0-100% ethyl acetate/heptanes over 30 minutes to provide (2S,3R,4S,5S)-ethyl 3-(tert-butyl)-4-hydroxy-1-((1R,3R)-3-methoxycyclohexanecarbonyl)-5-phenylpyrrolidine-2-carboxylate (0.242 g, 0.561 mmol, 32.1% yield) as the second eluent. $^1$H NMR (400 MHz, DMSO-$d_6$) δ ppm 7.57 (d, J=7.5 Hz, 2H), 7.26 (t, J=7.5 Hz, 2H), 7.19 (t, J=7.3 Hz, 1H), 4.95 (d, J=6.8 Hz, 1H), 4.41-4.32 (m, 2H), 4.14 (q, J=7.1 Hz, 2H), 3.96 (s, 1H), 3.42 (d, J=4.2 Hz, 1H), 3.17 (s, 3H), 2.53 (s, 1H), 2.22 (s, 1H), 1.73 (d, J=13.9 Hz, 1H), 1.60 (d, J=13.4 Hz, 1H), 1.38 (ddd, J=13.9, 11.4, 2.7 Hz, 1H), 1.26 (d, J=3.4 Hz, 1H), 1.27-1.19 (m, 4H), 1.22-1.08 (m, 1H), 1.18-1.10 (m, 1H), 0.98 (s, 9H), 0.88-0.79 (m, 1H); MS (ESI+) m/z 432 (M+H)$^+$. The other diastereomer was also isolated (2S,3R,4S,5S)-ethyl 3-(tert-butyl)-4-hydroxy-1-((1S,3S)-3-methoxycyclohexanecarbonyl)-5-phenylpyrrolidine-2-carboxylate (0.245 g, 0.568 mmol, 32.5% yield) as the first eluent. $^1$H NMR (400 MHz, DMSO-$d_6$) δ ppm 7.58 (d, J=7.3 Hz, 2H), 7.27 (t, J=7.6 Hz, 3H), 7.18 (d, J=7.3 Hz, 1H), 5.00 (d, J=6.8 Hz, 1H), 4.40-4.30 (m, 2H), 4.14 (q, J=7.1 Hz, 2H), 3.92 (s, 1H), 3.29 (s, 1H), 2.72 (s, 3H), 2.53 (s, 3H), 2.20 (s, 1H), 1.70-1.49 (m, 2H), 1.44-1.32 (m, 3H), 1.32-1.18 (m, 5H), 0.97 (s, 9H); MS (ESI+) m/z 432 (M+H)$^+$.

Example 31D (2S,3R,4S,5S)-ethyl 3-(tert-butyl)-4-((2-methoxy-5-(trifluoromethyl)benzyl)oxy)-1-((1R,3R)-3-methoxycyclohexanecarbonyl)-5-phenylpyrrolidine-2-carboxylate Example 31C (90 mg, 0.209 mmol) and 2-(bromomethyl)-1-methoxy-4-(trifluoromethyl)benzene (84 mg, 0.313 mmol) were dissolved in dry dimethylformamide (0.5 mL). After cooling in an ice bath, potassium 2-methylpropan-2-olate (0.30 mL, 0.250 mmol) solution was added dropwise over 2 minutes. The reaction mixture was stirred in the ice bath for 30 minutes, acidified with 1M aqueous HCl (10 drops), warmed to room temperature, diluted with water (0.5 mL), and extracted with dichloromethane (2×3 mL). The organics were concentrated and loaded onto a 12 g silica gel column and were eluted with 5-100% ethyl acetate/heptanes over 20 minutes to provide (2S,3R,4S,5S)-ethyl 3-(tert-butyl)-4-((2-methoxy-5-(trifluoromethyl)benzyl)oxy)-1-((1R,3R)-3-methoxycyclohexanecarbonyl)-5-phenylpyrrolidine-2-carboxylate (116 mg, 0.187 mmol, 90% yield). $^1$H NMR (400 MHz, DMSO-$d_6$) δ ppm 7.63 (d, J=17.2 Hz, 2H), 7.44 (dd, J=8.8, 2.3 Hz, 1H), 7.21 (t, J=7.4 Hz, 2H), 7.15 (d, J=7.1 Hz, 1H), 7.03-6.97 (m, 2H), 5.16 (d, J=6.2 Hz, 1H), 4.52 (d, J=3.3 Hz, 1H), 4.29 (d, J=13.1 Hz, 2H), 4.13-4.04 (m, 2H), 3.93 (d, J=13.1 Hz, 1H), 3.75 (d, J=0.8 Hz, 3H), 3.43 (s, 1H), 3.18 (d, J=0.9 Hz, 3H), 2.60 (s, 1H), 1.74 (d, J=13.8 Hz, 1H), 1.61 (d, J=12.9 Hz, 1H), 1.48-1.36 (m, 1H), 1.25-1.18 (m, 2H), 1.15 (td, J=7.1, 0.9 Hz, 3H), 0.99 (d, J=1.0 Hz, 9H), 0.89-0.78 (m, 4H); MS (APCI+) m/z 620 (M+H)$^+$.

Example 31E (2S,3R,4S,5S)-3-tert-butyl-1-[(1R,3R)-3-methoxycyclohexane-1-carbonyl]-4-{[2-methoxy-5-(trifluoromethyl)phenyl]methoxy}-5-phenylpyrrolidine-2-carboxylic acid Example 31D (64 mg, 0.103 mmol) was dissolved in methanol (0.5 mL) and tetrahydrofuran (0.500 mL). LiOH (20 mg, 0.835 mmol) in water (0.250 mL) was added. The reaction mixture was warmed at 35° C. for 48 hours. The solvent was removed, and the reaction mixture was acidified with 1M aqueous HCl (30 drops). The crude material was loaded onto a 12 g silica gel column and was eluted with an ethyl acetate/ethanol/heptanes solvent system over 20 minutes to provide (2S,3R,4S,5S)-3-(tert-butyl)-4-((2-methoxy-5-(trifluoromethyl)benzyl)oxy)-1-((1R,3R)-3-methoxycyclohexanecarbonyl)-5-phenylpyrrolidine-2-carboxylic acid (50 mg, 0.085 mmol, 82% yield). $^1$H NMR (400 MHz, DMSO-$d_6$) δ ppm 7.69-7.60 (m, 2H), 7.43 (dd, J=8.6, 2.3 Hz, 1H), 7.20 (t, J=7.3 Hz, 2H), 7.14 (d, J=6.8 Hz, 1H), 6.99 (d, J=8.6 Hz, 1H), 6.96 (d, J=2.1 Hz, 1H), 5.14 (d, J=6.5 Hz, 1H), 4.49-4.39 (m, 1H), 4.31 (d, J=13.2 Hz, 1H), 4.27-4.21 (m, 1H), 3.96 (d, J=13.2 Hz, 1H), 3.76 (s, 3H), 3.50-3.39 (m, 1H), 3.19 (s, 2H), 2.66-2.61 (m, 1H), 2.57-2.49 (m, 0H), 1.82-1.69 (m, 1H), 1.66-1.54 (m, 1H), 1.41 (t, J=12.4 Hz, 1H), 1.25 (s, 3H), 1.23-1.09 (m, 3H), 0.98 (s, 9H), 0.89-0.78 (m, 1H); MS (ESI+) m/z 592 (M+H)$^+$.

Example 32

(2S,3R,4S,5S)-3-tert-butyl-1-[(1S,3S)-3-methoxycyclohexane-1-carbonyl]-4-{[2-methoxy-4-(trifluoromethyl)phenyl]methoxy}-5-phenylpyrrolidine-2-carboxylic acid The title compound was prepared according to the procedure described in Example 31 using the first eluting diastereomer from Example 31C and substituting 1-(bromomethyl)-2-methoxy-4-(trifluoromethyl)benzene for 2-(bromomethyl)-1-methoxy-4-(trifluoromethyl)benzene in Example 31D. $^1$H NMR (400 MHz, DMSO-d$_6$) δ ppm 7.71-7.51 (m, 2H), 7.21 (t, J=7.3 Hz, 2H), 7.15 (d, J=7.1 Hz, 1H), 7.05 (s, 1H), 6.99 (d, J=7.9 Hz, 1H), 6.81 (d, J=7.9 Hz, 1H), 5.18 (d, J=6.4 Hz, 1H), 4.44 (s, 1H), 4.28 (d, J=13.6 Hz, 1H), 4.20 (d, J=6.3 Hz, 1H), 3.96 (d, J=13.6 Hz, 1H), 3.75 (s, 3H), 3.33 (s, 1H), 2.70-2.59 (m, 2H), 2.51 (s, 1H), 1.61 (s, 2H), 1.48-1.34 (m, 2H), 1.27 (d, J=10.7 Hz, 4H), 0.98 (s, 9H), 0.89-0.78 (m, 2H); MS (ESI+) m/z 592 (M+H)$^+$.

Example 33

(2S,3R,4S,5S)-3-tert-butyl-1-[(1R,3R)-3-methoxycyclohexane-1-carbonyl]-4-{[2-methoxy-4-(trifluoromethyl)phenyl]methoxy}-5-phenylpyrrolidine-2-carboxylic acid The title compound was prepared according to the procedure described in Example 31 substituting 1-(bromomethyl)-2-methoxy-4-(trifluoromethyl)benzene for 2-(bromomethyl)-1-methoxy-4-(trifluoromethyl)benzene in Example 31D. $^1$H NMR (400 MHz, DMSO-d$_6$) δ ppm 7.65 (d, J=7.4 Hz, 2H), 7.26-7.09 (m, 3H), 7.05 (d, J=1.6 Hz, 1H), 6.99 (dd, J=7.9, 1.6 Hz, 1H), 6.83 (d, J=7.9 Hz, 1H), 5.13 (d, J=6.3 Hz, 1H), 4.46 (d, J=3.2 Hz, 1H), 4.28 (d, J=13.6 Hz, 1H), 4.23 (d, J=6.2 Hz, 1H), 3.96 (d, J=13.6 Hz, 1H), 3.74 (s, 3H), 3.43 (s, 1H), 3.19 (s, 3H), 2.71-2.58 (m, 1H), 2.52 (s, 1H), 1.77 (d, J=12.3 Hz, 1H), 1.61 (d, J=12.5 Hz, 1H), 1.42 (ddd, J=13.9, 11.2, 2.7 Hz, 1H), 1.31-1.13 (m, 4H), 0.99 (s, 9H), 0.89-0.79 (m, 1H); MS (ESI+) m/z 592 (M+H)$^+$.

Example 34 rac-(2R,3S,4R,5R)-3-tert-butyl-1-[(cyclobutyloxy) carbonyl]-4-{[2-methoxy-4-(trifluoromethyl)phenyl] methoxy}-5-phenylpyrrolidine-2-carboxylic acid Example 34A cyclobutylchloroformate Cyclobutanol (1.02 g, 14.15 mmol) was dissolved in dichloromethane (10 mL) and pyridine (1.2 mL, 14.84 mmol) was added to the reaction mixture. The reaction mixture was cooled to 0° C. with an ice bath. Triphosgene (2.06 g, 6.94 mmol) was added in portions to the well stirred reaction mixture. The reaction mixture was stirred at 0° C. for 1 hour and was allowed to warm to ambient temperature and stir for an additional 3 hours. The reaction mixture was poured into 1 M aqueous HCl (50 mL) and extracted with dichloromethane (3×50 mL). The combined organic layers were dried over Na$_2$SO$_4$, filtered, and concentrated to provide the title compound (1.3 g, 68%), which was used without additional purification. $^1$H NMR (400 MHz, CDCl$_3$) 4.85-4.93 (m, 1H), 2.31-2.38 (m, 2H), 2.06-2.16 (m, 2H), 1.57-1.64 (m, 2H).

Example 34B rac-1-cyclobutyl 2-ethyl (2R,3S,4R,5R)-3-(tert-butyl)-4-nitro-5-phenylpyrrolidine-1,2-dicarboxylate rac-(2R,3S,4R,5R)-Ethyl 3-(tert-butyl)-4-nitro-5-phenylpyrrolidine-2-carboxylate (Core 1, 1.01 g, 3.15 mmol) was dissolved in dichloromethane (10 mL) and trimethylamine (0.9 mL, 6.46 mmol) was added, followed by cyclobutyl chloroformate (Example 34A, 1.3 g, 9.66 mmol). The reaction mixture was stirred at ambient temperature for 4 hours, at which point it was complete. The reaction mixture was diluted with dichloromethane (50 mL) and washed with 1M aqueous HCl (2×50 mL) and brine. The organic layer was dried over sodium sulfate, filtered and concentrated to provide ~2 g of crude product. The residue was purified by silica gel chromatography (dichloromethane, R$_f$=0.25) to provide the title compound (1.31 g, 99%). $^1$H NMR (400 MHz, DMSO-d$_6$, 120° C.) δ ppm 7.56-7.45 (m, 2H), 7.30-7.15 (m, 3H), 5.66-5.54 (m, 1H), 5.45 (d, J=8.8 Hz, 1H), 4.79-4.70 (m, 1H), 4.50 (d, J=3.8 Hz, 1H), 4.25 (q, J=7.1 Hz, 2H), 2.99 (t, J=3.7 Hz, 1H), 2.40-1.36 (m, 6H), 1.28 (t, J=7.1 Hz, 3H), 1.01 (s, 9H); MS (ESI+) m/z 419 (M+H)$^+$.

Example 34C rac-1-cyclobutyl 2-ethyl (2R,3S,5R)-3-(tert-butyl)-4-oxo-5-phenylpyrrolidine-1,2-dicarboxylate rac-(2R,3S,4R,5R)-1-Cyclobutyl 2-ethyl 3-(tert-butyl)-4-nitro-5-phenylpyrrolidine-1,2-dicarboxylate (Example 34 B, 700 mg, 1.673 mmol) was dissolved in 30 mL of ethanol and the solution was heated to 75° C. A separate solution of CrCl$_2$ was prepared by dissolving pyridinium dichromate (1673 mg, 5.69 mmol) in 30 mL of 6M aqueous HCl and adding Zn (3.00 g, 27.5 mmol, in portions while cooling in an ice bath). The suspension was stirred until all Zn dissolved, leaving a brilliant blue solution. The CrCl$_2$ solution was transferred via cannula over 15 minutes to the solution of starting material and heating was continued for 16 hours. The temperature was maintained between 70 and 75° C. during the addition. Immediately after the addition was complete, very clean conversion to the oxime intermediate was observed. Heating was continued between 75 and 80° C. overnight (total 16 hours). The reaction was cooled to room temperature, diluted with water and extracted with dichloromethane (3×30 mL). The combined organic extracts were washed with brine and dried over sodium sulfate. After filtration and concentration, the crude residue was dissolved ethanol (10 mL). A separate solution of HCl/ethanol was prepared by the addition of 1 mL of acetyl chloride to 5 mL of ethanol at 0° C. The mixture was poured into the reaction flask and the mixture was heated to 45° C. for 1 hour. The reaction mixture was concentrated in vacuo and loaded onto a 12 g silica gel column. The column was eluted with 0-30% ethyl acetate/heptanes over 20 minutes to provide the title compound (373 mg, 58%). $^1$H NMR (400 MHz, DMSO-d$_6$, 120° C.) δ ppm 7.50-7.45 (m, 2H), 7.33-7.28 (m, 2H), 7.27-7.21 (m, 1H), 4.94 (s, 1H), 4.87-4.75 (m, 1H), 4.62 (d, J=4.5 Hz, 1H), 4.19 (qd, J=7.0, 1.5 Hz, 2H), 2.57 (dd, J=4.5, 1.1 Hz, 1H), 2.28-2.07 (m, 2H), 1.91-1.45 (m, 4H), 1.23 (t, J=7.1 Hz, 3H), 1.05 (s, 9H); MS (ESI+) m/z 388 (M+H)$^+$.

Example 34D rac-1-cyclobutyl 2-ethyl (2R,3S,4R,5R)-3-(tert-butyl)-4-hydroxy-5-phenylpyrrolidine-1,2-dicarboxylate Example 34C (310 mg, 0.80 mmol) was dissolved in methanol (4 mL), and the reaction mixture was cooled to 0° C. Sodium borohydride (62.9 mg, 1.66 mmol) was added and the reaction mixture was stirred at 0° C. for 1 hour. The mixture was warmed to ambient temperature for another 1 hour. The solvent was removed in vacuo, the residue was extracted with dichloromethane (50 mL), and the organics were washed with saturated aqueous NaHCO$_3$ (50 mL) and brine (50 mL), dried over Na$_2$SO$_4$, filtered, and concentrated to provide crude product, which was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (117.5 mg, 38%). $^1$H NMR (400 MHz, DMSO-d$_6$, 120° C.) δ ppm 7.54-7.48 (m, 2H), 7.27-7.19 (m, 2H), 7.19-7.12 (m, 1H), 4.83 (d, J=6.7 Hz, 1H), 4.71 (p, J=7.0 Hz, 1H), 4.31 (dd, J=6.7, 4.4 Hz, 1H), 4.23 (d, J=4.8 Hz, 1H), 4.16 (q, J=7.1 Hz, 2H), 2.24 (t, J=4.7 Hz, 1H), 2.20-2.03 (m, 2H), 1.81-1.41 (m, 4H), 1.24 (t, J=7.0 Hz, 3H), 0.98 (s, 9H); MS (ESI+) m/z 390 (M+H)$^+$.

Example 34E rac-1-cyclobutyl 2-ethyl (2R,3S,4R,5R)-3-(tert-butyl)-4-((2-methoxy-4-(trifluoromethyl)benzyl)oxy)-5-phenylpyrrolidine-1,2-dicarboxylate Example 34D (33.6 mg, 0.086 mmol) and 2-methoxy-4-(trifluoromethyl)benzyl bromide (36.9 mg, 0.137 mmol) were dissolved in dimethylformamide (1 mL). The reaction mixture was cooled to 0° C., potassium tert-butoxide (1M in tetrahydrofuran, 0.14 mL, 0.14 mmol) was added dropwise and the reaction was stirred at ambient temperature for 1 hour. The reaction was diluted with methanol (1 mL) and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (36.6 mg, 73%). $^1$H NMR (400 MHz, DMSO-d$_6$, 120° C.) δ ppm 7.59-7.52 (m, 2H), 7.24-7.12 (m, 3H), 7.06 (d, J=1.5 Hz, 1H), 7.01 (d, J=7.9 Hz, 1H), 6.83 (d, J=7.9 Hz, 1H), 5.01 (d, J=6.2 Hz, 1H), 4.73 (p, J=7.0 Hz, 1H), 4.34 (d, J=3.4 Hz, 1H), 4.26 (d, J=13.3 Hz, 1H), 4.20 (dd, J=6.2, 2.8 Hz, 1H), 4.15-4.07 (m, 2H), 3.95 (d, J=13.3 Hz, 1H), 3.74 (s, 3H), 2.44 (t, J=3.2 Hz, 1H), 2.21-2.04 (m, 2H), 1.82-1.40 (m, 4H), 1.17 (t, J=7.1 Hz, 3H), 0.99 (s, 9H); MS (ESI+) m/z 578 (M+H)$^+$.

Example 34F rac-(2R,3S,4R,5R)-3-tert-butyl-1-[(cyclobutyloxy)carbonyl]-4-{[2-methoxy-4-(trifluoromethyl)phenyl]methoxy}-5-phenylpyrrolidine-2-carboxylic acid Example 34E (33.6 mg, 0.058 mmol) was dissolved in methanol (1 mL) and tetrahydrofuran (1 mL). LiOH (1 M, 0.5 mL, 0.5 mmol) was added and the reaction mixture was heated to 50° C. for 16 hours. The reaction mixture was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (18.6 mg, 58%). $^1$H NMR (400 MHz, DMSO-d$_6$, 120° C.) δ ppm 7.62-7.55 (m, 2H), 7.23-7.11 (m, 3H), 7.05 (d, J=1.6 Hz, 1H), 7.00 (dd, J=7.5, 1.5 Hz, 1H), 6.86 (d, J=7.9 Hz, 1H), 4.99 (d, J=6.2 Hz, 1H), 4.77-4.68 (m, 1H), 4.31 (d, J=3.2 Hz, 1H), 4.26 (d, J=13.5 Hz, 1H), 4.18 (dd, J=6.2, 2.5 Hz, 1H), 3.96-3.90 (m, 1H), 3.74 (s, 3H), 2.48-2.47 (m, 1H), 2.21-2.03 (m, 2H), 1.83-1.38 (m, 4H), 0.99 (s, 9H); MS (ESI+) m/z 550 (M+H)$^+$.

Example 35 rac-(2R,3S,4R,5R)-3-tert-butyl-4-[(5-chloro-2-methoxyphenyl)methoxy]-1-[(cyclobutyloxy)carbonyl]-5-phenylpyrrolidine-2-carboxylic acid Example 35A rac-1-cyclobutyl 2-ethyl (2R,3S,4R,5R)-3-(tert-butyl)-4-((5-chloro-2-methoxybenzyl)oxy)-5-phenylpyrrolidine-1,2-dicarboxylate Example 34D (47.0 mg, 0.121 mmol) and 2-(bromomethyl)-4-chloro-1-methoxybenzene (41.1 mg, 0.175 mmol) were dissolved in N,N-dimethylformamide (1 mL). The reaction was cooled to 0° C., and potassium tert-butoxide (1M in tetrahydrofuran, 0.18 mL, 0.18 mmol) was added dropwise and the reaction was stirred at ambient temperature for 1 hours. The reaction mixture was diluted with methanol (1 mL) and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (47.4 mg, 72%). $^1$H NMR (400 MHz, DMSO-d$_6$, 120° C.) δ ppm 7.60-7.54 (m, 2H), 7.25-7.19 (m, 2H), 7.19-7.13 (m, 1H), 7.10 (dd, J=8.7, 2.8 Hz, 1H), 6.82 (d, J=8.7 Hz, 1H), 6.64 (d, J=2.7 Hz, 1H), 5.01 (d, J=6.2 Hz, 1H), 4.73 (p, J=7.0 Hz, 1H), 4.34 (d, J=3.3 Hz, 1H), 4.23-4.09 (m, 4H), 3.88 (d, J=13.0 Hz, 1H), 3.66 (s, 3H), 2.44 (t, J=3.0 Hz, 1H), 2.21-2.04 (m, 2H), 1.82-1.40 (m, 4H), 1.19 (t, J=7.1 Hz, 3H), 0.99 (s, 9H); MS (ESI+) m/z 544 (M+H)$^+$.

Example 35B rac-(2R,3S,4R,5R)-3-tert-butyl-4-[(5-chloro-2-methoxyphenyl)methoxy]-1-[(cyclobutyloxy)carbonyl]-5-phenylpyrrolidine-2-carboxylic acid Example 35B (44.4 mg, 0.082 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction mixture was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (22.2 mg, 53%). $^1$H NMR (400 MHz, DMSO-d$_6$, 120° C.) δ ppm 7.60-7.54 (m, 2H), 7.25-7.18 (m, 2H), 7.18-7.12 (m, 1H), 7.10 (dd, J=8.7, 2.7 Hz, 1H), 6.82 (d, J=8.7 Hz, 1H), 6.62 (d, J=2.7 Hz, 1H), 4.99 (d, J=6.3 Hz, 1H), 4.73 (p, J=7.0 Hz, 1H), 4.30 (d, J=3.2 Hz, 1H), 4.24-4.18 (m, 1H), 4.17 (dd, J=6.3, 2.5 Hz, 1H), 3.88 (d, J=13.1 Hz, 1H), 3.66 (s, 3H), 2.36 (s, 1H), 2.21-2.02 (m, 2H), 1.84-1.39 (m, 4H), 0.99 (s, 9H); MS (ESI+) m/z 516 (M+H)+.

Example 36

(2S,3R,4S,5S)-4-[(5-bromo-2-methoxyphenyl) methoxy]-3-tert-butyl-5-phenyl-1-{[(propan-2-yl) oxy]carbonyl}pyrrolidine-2-carboxylic acid The title compound was prepared according to the procedure described in Example 38F substituting Example 38D for Example 34E. $^1$H NMR (400 MHz, DMSO-$d_6$) δ ppm 7.65-7.56 (m, 2H), 7.27-7.11 (m, 4H), 6.78 (d, J=8.7 Hz, 1H), 6.75 (d, J=2.5 Hz, 1H), 4.97 (d, J=6.4 Hz, 1H), 4.64 (p, J=6.2 Hz, 1H), 4.29 (d, J=3.3 Hz, 1H), 4.22 (d, J=13.1 Hz, 1H), 4.16 (dd, J=6.3, 2.5 Hz, 1H), 3.89 (d, J=13.1 Hz, 1H), 3.80 (s, 1H), 3.67 (s, 3H), 1.06 (d, J=6.3 Hz, 3H), 0.99 (s, 9H), 0.89 (d, J=6.2 Hz, 3H); MS (APCI+) m/z 548 (M+H)+.

Example 37

(2S,3R,4S,5S)-4-[(5-bromo-2-methoxyphenyl) methoxy]-3-tert-butyl-1-[(1R,3R)-3-methoxycyclohexane-1-carbonyl]-5-phenylpyrrolidine-2-carboxylic acid The title compound was prepared according to the procedure described in Example 31 substituting 4-bromo-2-(bromomethyl)-1-methoxybenzene for 2-(bromomethyl)-1-methoxy-4-(trifluoromethyl)benzene in Example 31D. $^1$H NMR (400 MHz, DMSO-$d_6$) δ ppm 7.65 (d, J=7.4 Hz, 2H), 7.28-7.10 (m, 4H), 6.78 (d, J=8.7 Hz, 1H), 6.72 (d, J=2.6 Hz, 1H), 5.13 (d, J=6.5 Hz, 1H), 4.44 (d, J=3.2 Hz, 1H), 4.27-4.17 (m, 2H), 3.92 (d, J=13.2 Hz, 1H), 3.67 (s, 3H), 3.44 (s, 1H), 3.20 (s, 3H), 2.72-2.59 (m, 2H), 2.53 (s, 1H), 1.77 (d, J=13.6 Hz, 1H), 1.62 (d, J=12.8 Hz, 1H), 1.42 (ddd, J=13.9, 11.2, 2.7 Hz, 1H), 1.32-1.17 (m, 2H), 0.99 (s, 9H), 0.90-0.78 (m, 2H); MS (APCI+) m/z 602 (M+H)+.

Example 38

(2S,3R,4S,5S)-3-tert-butyl-4-[(4-methoxy[1,1'-biphenyl]-3-yl)methoxy]-5-phenyl-1-{[(propan-2-yl) oxy]carbonyl}pyrrolidine-2-carboxylic acid Example 38A (2S,3R,4S,5S)-2-ethyl 1-isopropyl 3-(tert-butyl)-4-nitro-5-phenylpyrrolidine-1,2-dicarboxylate To a solution of Core 5 (2.193, 6.84 mmol) in dichloromethane (20 mL) and triethylamine (4 mL, 28.7 mmol) was added a 1M solution of isopropyl chloroformate (15 mL, 15.00 mmol) in toluene dropwise via addition funnel over about 3 minutes. After 30 minutes, additional 1M isopropyl chloroformate (6 mL) was added and after another 30 minutes additional 1M isopropyl chloroformate (6 mL) was added. The reaction mixture was stirred at room temperature for 3 hours more. The reaction mixture was diluted with dichloromethane (200 mL) and a small amount of ethanol and washed with saturated aqueous sodium bicarbonate (50 mL), dried over sodium sulfate, filtered, and concentrated. The crude material was purified using a 40 g silica gel cartridge with a gradient of 5-100% ethyl acetate/heptanes over 30 minutes to provide (2S,3R,4S,5S)-2-ethyl 1-isopropyl 3-(tert-butyl)-4-nitro-5-phenylpyrrolidine-1,2-dicarboxylate (2.790 g, 6.88 mmol, 100% yield). $^1$H NMR (400 MHz, 120° C., DMSO-$d_6$) δ ppm 7.56-7.46 (m, 2H), 7.30-7.15 (m, 3H), 5.61 (dd, J=8.8, 3.3 Hz, 1H), 5.43 (d, J=8.8 Hz, 1H), 5.33 (dd, J=6.6, 3.2 Hz, 0H), 4.67 (pd, J=6.1, 0.7 Hz, 1H), 4.50 (d, J=3.8 Hz, 1H), 4.25 (qd, J=7.1, 0.6 Hz, 2H), 2.98 (t, J=3.6 Hz, 1H), 1.29 (td, J=7.0, 0.7 Hz, 3H), 1.06 (d, J=6.2 Hz, 3H), 1.03-0.98 (m, 9H), 0.92 (d, J=6.2 Hz, 3H); MS (APCI+) m/z 407 (M+H)+.

Example 38B (2S,3R,5S)-2-ethyl 1-isopropyl 3-(tert-butyl)-4-oxo-5-phenylpyrrolidine-1,2-dicarboxylate Example 38A (2.366 g, 5.82 mmol) was dissolved in ethanol (75 mL) and the solution was heated to 71° C. A separate solution of CrCl$_2$ was prepared by dissolving pyridinium dichromate (5.82 g, 19.79 mmol) in hydrochloric acid (6M, 75 mL) and adding Zn (10.47 g, 160 mmol) in portions while cooling in an ice bath. The suspension was stirred until all almost all of the Zn dissolved, leaving a brilliant blue solution. The CrCl$_2$ solution was transferred via cannula over 15 minutes to the solution of starting material (cooled to 65° C. during the addition) and heating was continued at 80° C. for 16 hours. The mixture was cooled to room temperature, reduced in volume in vacuo, diluted with water, and extracted with 3×200 mL of dichloromethane. The combined extracts were washed with brine, dried over sodium sulfate, filtered, and concentrated in vacuo. The crude material was loaded onto a 80 g silica gel column and eluted with 0-100% ethyl acetate/heptanes over 40 minutes to provide (2S,3R,5S)-2-ethyl 1-isopropyl 3-(tert-butyl)-4-oxo-5-phenylpyrrolidine-1,2-dicarboxylate (0.793 g, 2.112 mmol, 36.3% yield). $^1$H NMR (400 MHz, DMSO-$d_6$) δ ppm 7.48-7.40 (m, 2H), 7.33-7.27 (m, 2H), 7.26-7.19 (m, 1H), 4.91 (s, 1H), 4.77-4.69 (m, 1H), 4.62 (d, J=4.4 Hz, 1H), 4.19 (qd, J=7.1, 1.4 Hz, 2H), 2.56 (dd, J=4.5, 0.9 Hz, 1H), 1.22 (t, J=7.1 Hz, 3H), 1.11 (d, J=6.2 Hz, 3H), 1.05 (s, 9H), 0.98 (d, J=6.2 Hz, 3H); MS (APCI+) m/z 376 (M+H)+.

Example 38C (2S,3R,4S,5S)-2-ethyl 1-isopropyl 3-(tert-butyl)-4-hydroxy-5-phenylpyrrolidine-1,2-dicarboxylate Example 38B (0.611 g, 1.627 mmol) was dissolved in ethanol (8.14 mL) and sodium borohydride (0.123 g, 3.25 mmol) was added in one portion after cooling the reaction to <5° C. in an ice-water bath. The reaction was stirred at the same temperature for 30 minutes, concentrated, and partitioned between ethyl acetate and saturated aqueous sodium bicarbonate. The organics were concentrated and purified using a 40 g silica gel cartridge and eluting with 0-100% ethyl acetate/heptanes over 40 minutes on to provide (2S, 3R,4S,5S)-2-ethyl 1-isopropyl 3-(tert-butyl)-4-hydroxy-5-phenylpyrrolidine-1,2-dicarboxylate (0.506 g, 1.340 mmol, 82% yield). $^1$H NMR (400 MHz, DMSO-$d_6$) δ ppm 7.50 (dd, J=8.1, 1.5 Hz, 2H), 7.19-7.27 (m, 2H), 7.09-7.19 (m, 1H), 4.82 (d, J=6.7 Hz, 1H), 4.62 (pd, J=6.2, 1.1 Hz, 1H), 4.27-4.35 (m, 1H), 4.22 (dd, J=4.8, 1.2 Hz, 1H), 4.10-4.19 (m, 2H), 3.84 (d, J=7.4 Hz, 1H), 2.21-2.28 (m, 1H), 1.24 (td, J=7.1, 1.0 Hz, 3H), 1.04 (dd, J=6.3, 1.2 Hz, 3H), 0.98 (d, J=1.1 Hz, 9H), 0.90 (d, J=6.2 Hz, 3H); MS (APCI+) m/z 378 (M+H)+.

Example 38D (2S,3R,4S,5S)-2-ethyl 1-isopropyl 4-((5-bromo-2-methoxybenzyl)oxy)-3-(tert-butyl)-5-phenylpyrrolidine-1,2-dicarboxylate Example 38C (36 mg, 0.095 mmol) and 4-bromo-2-(bromomethyl)-1-methoxybenzene (53.4 mg, 0.191 mmol) were dissolved in dry dimethylformamide (0.5 mL). After cooling in an ice bath, potassium 2-methylpropan-2-olate (0.200 mL, 0.200 mmol) solution was added dropwise over 2 minutes. After 30 minutes, the reaction was acidified with 1M aqueous HCl (10 drops) and warmed to room temperature. The mixture was concentrated and loaded onto a 12 g silica gel column and eluted with 5-100% ethyl acetate/heptanes over 20 minutes to provide (2S,3R,4S,5S)-2-ethyl 1-isopropyl 4-((5-bromo-2-methoxybenzyl)oxy)-3-(tert-butyl)-5-phenylpyrrolidine-1,2-dicarboxylate (57 mg, 0.099 mmol, 104% yield). $^1$H NMR (400 MHz, DMSO-$d_6$) δ ppm 7.56 (dd, J=7.1, 1.6 Hz, 2H), 7.26-7.13 (m, 4H), 6.81-6.74 (m, 2H), 4.99 (d, J=6.0 Hz, 1H), 4.65 (dt, J=12.4, 6.2 Hz, 1H), 4.35 (d, J=3.2 Hz, 1H), 4.24-4.17 (m, 2H), 4.14 (qd, J=7.1, 2.6 Hz, 2H), 3.88 (dd, J=12.9, 0.9 Hz, 1H), 3.68-3.63 (m, 3H), 2.44 (t, J=2.9 Hz, 1H), 1.20 (t, J=7.1 Hz, 3H), 1.06 (d, J=6.2 Hz, 3H), 1.00 (s, 9H), 0.92 (d, J=7.5 Hz, 3H); MS (APCI+) m/z 577 (M+H)$^+$.

Example 38E (2S,3R,4S,5S)-2-ethyl 1-isopropyl 3-(tert-butyl)-4-((4-methoxy-[1,1'-biphenyl]-3-yl)methoxy)-5-phenylpyrrolidine-1,2-dicarboxylate Example 38D (125 mg, 0.217 mmol), phenylboronic acid (31.7 mg, 0.260 mmol), cesium carbonate (212 mg, 0.650 mmol) and dichlorobis(triphenylphosphine)palladium(II) (10 mg, 0.014 mmol) were combined in a 4 mL vial and put under nitrogen. To this mixture was added degassed dioxane (1084 μL). The reaction mixture was heated in an aluminum block at 95° C. for 2 hours, concentrated, loaded onto a 12 g silica gel column, and eluted with 5-100% ethyl acetate/heptanes over 20 minutes to provide (2S,3R,4S,5S)-2-ethyl 1-isopropyl 3-(tert-butyl)-4-((4-methoxy-[1,1'-biphenyl]-3-yl)methoxy)-5-phenylpyrrolidine-1,2-dicarboxylate (91 mg, 0.159 mmol, 73.2% yield). MS (APCI+) m/z 574 (M+H)$^+$.

Example 38F (2S,3R,4S,5S)-3-tert-butyl-4-[(4-methoxy[1,1'-biphenyl]-3-yl)methoxy]-5-phenyl-1-{[(propan-2-yl)oxy]carbonyl}pyrrolidine-2-carboxylic acid Example 38E (91 mg, 0.159 mmol) was dissolved in methanol (0.5 mL). LiOH (25 mg, 1.044 mmol) in water (0.500 mL) was added and a precipitate formed. Tetrahydrofuran (0.500 mL) was added and everything dissolved. The reaction mixture was warmed at 45° C. for 16 hours. The solvent was removed, and the reaction was acidified with 1M aqueous HCl (30 drops). The crude material was loaded onto a 12 g silica gel column and eluted with an ethyl acetate/ethanol/heptanes solvent system over 20 minutes to provide (2S,3R,4S,5S)-3-(tert-butyl)-1-(isopropoxycarbonyl)-4-((4-methoxy-[1,1'-biphenyl]-3-yl)methoxy)-5-phenylpyrrolidine-2-carboxylic acid (48 mg, 0.088 mmol, 55.5% yield). $^1$H NMR (400 MHz, DMSO-$d_6$) δ ppm 7.64-7.59 (m, 2H), 7.47-7.36 (m, 5H), 7.32-7.24 (m, 1H), 7.16 (dd, J=8.2, 6.7 Hz, 2H), 7.11-7.07 (m, 1H), 7.04 (d, J=2.4 Hz, 1H), 6.91 (d, J=8.5 Hz, 1H), 5.00 (d, J=6.4 Hz, 1H), 4.64 (p, J=6.2 Hz, 1H), 4.35-4.28 (m, 2H), 4.22 (dd, J=6.4, 2.7 Hz, 1H), 4.01 (d, J=12.6 Hz, 1H), 3.72 (s, 3H), 2.52 (t, J=3.0 Hz, 1H), 1.06 (d, J=6.2 Hz, 3H), 1.00 (s, 9H), 0.89 (d, J=6.2 Hz, 3H); MS (APCI+) m/z 546 (M+H)$^+$.

Example 39

(2S,3R,4S,5S)-3-tert-butyl-4-[(4-methoxy[1,1'-biphenyl]-3-yl)methoxy]-1-[(1R,3R)-3-methoxycyclohexane-1-carbonyl]-5-phenylpyrrolidine-2-carboxylic acid The title compound was prepared according to the procedure described in Example 31, substituting 4-bromo-2-(bromomethyl)-1-methoxybenzene for 2-(bromomethyl)-1-methoxy-4-(trifluoromethyl)benzene in Example 31D and treating the resulting product as described in Example 38E-38F. $^1$H NMR (400 MHz, DMSO-$d_6$) δ ppm 7.67 (d, J=6.7 Hz, 2H), 7.48-7.36 (m, 5H), 7.33-7.23 (m, 1H), 7.19 (t, J=7.3 Hz, 2H), 7.15-7.05 (m, 1H), 7.01 (d, J=2.5 Hz, 1H), 6.92 (d, J=8.5 Hz, 1H), 5.15 (d, J=6.5 Hz, 1H), 4.44 (d, J=3.1 Hz, 1H), 4.33 (d, J=12.6 Hz, 1H), 4.30-4.23 (m, 1H), 4.03 (d, J=12.6 Hz, 1H), 3.73 (s, 3H), 3.44 (s, 1H), 3.19 (s, 3H), 2.69-2.60 (m, 2H), 2.61-2.52 (m, 1H), 1.77 (d, J=11.6 Hz, 1H), 1.67-1.57 (m, 2H), 1.42 (td, J=13.4, 12.3, 2.7 Hz, 1H), 1.21-1.10 (m, 2H), 0.99 (s, 9H), 0.92-0.77 (m, 1H); MS (APCI+) m/z 600 (M+H)$^+$.

Example 40

(2S,3R,4S,5S)-4-[(5-bromo-2-methoxypyridin-3-yl)methoxy]-3-tert-butyl-5-phenyl-1-{[(propan-2-yl)oxy]carbonyl}pyrrolidine-2-carboxylic acid

Example 40A (2S,3R,4S,5S)-2-ethyl 1-isopropyl 4-((5-bromo-2-methoxypyridin-3-yl)methoxy)-3-(tert-butyl)-5-phenylpyrrolidine-1,2-dicarboxylate Example 38C (140 mg, 0.371 mmol) and 5-bromo-3-(bromomethyl)-2-methoxypyridine (157 mg, 0.559 mmol) were dissolved in dry dimethylformamide (0.8 mL). After cooling in an ice bath, potassium 2-methylpropan-2-olate (0.80 mL, 0.80 mmol) solution was added dropwise over 20 minutes. After 20 minutes, the reaction was acidified with 1M aqueous HCl (10 drops) and warmed to room temperature. The mixture was concentrated and loaded onto a 24 g silica gel column and eluted with 5-50% ethyl acetate/heptanes over 20 minutes to provide (2S,3R,4S,5S)-2-ethyl 1-isopropyl 4-((5-bromo-2-methoxypyridin-3-yl)methoxy)-3-(tert-butyl)-5-phenylpyrrolidine-1,2-dicarboxylate (0.170 g, 0.294 mmol, 79% yield). $^1$H NMR (400 MHz, DMSO-$d_6$) δ ppm 8.00 (d, J=2.5 Hz, 1H), 7.58-7.52 (m, 2H), 7.25-7.15 (m, 3H), 7.02 (dd, J=2.4, 1.1 Hz, 1H), 5.00 (d, J=6.2 Hz, 1H), 4.65 (p, J=6.2 Hz, 1H), 4.36 (d, J=3.1 Hz, 1H), 4.25-4.18 (m, 2H), 4.13 (qd, J=7.1, 2.8 Hz, 2H), 3.85 (d, J=13.5 Hz, 1H), 3.78 (s, 3H), 2.44 (t, J=2.8 Hz, 1H), 1.20-1.16 (m, 3H), 1.06 (d, J=6.2 Hz, 3H), 1.01 (s, 9H), 0.90 (d, J=6.2 Hz, 3H); MS (APCI+) m/z 577 (M+H)$^+$.

Example 40B (2S,3R,4S,5S)-4-[(5-bromo-2-methoxypyridin-3-yl)methoxy]-3-tert-butyl-5-phenyl-1-{[(propan-2-yl)oxy]carbonyl}pyrrolidine-2-carboxylic acid Example 40A (38 mg, 0.066 mmol) was dissolved in methanol (0.5 mL). LiOH (12 mg, 0.501 mmol) in water (0.500 mL) was added followed by tetrahydrofuran (0.500 mL). The reaction was warmed at 45° C. for 16 hours. The solvent was removed and the reaction was acidified with 1M aqueous HCl (30 drops). The crude material was loaded onto a 12 g silica gel column and purified twice with an ethyl acetate/ethanol/heptanes solvent system over 20 minutes to provide (2S,3R,4S,5S)-4-((5-bromo-2-methoxypyridin-3-yl)methoxy)-3-(tert-butyl)-1-(isopropoxycarbonyl)-5-phenylpyrrolidine-2-carboxylic acid (20 mg, 0.036 mmol, 55.3% yield). $^1$H NMR (400 MHz, DMSO-d$_6$) δ ppm 8.00 (d, J=2.5 Hz, 1H), 7.63-7.55 (m, 2H), 7.24-7.17 (m, 2H), 7.17-7.11 (m, 1H), 7.00 (dd, J=2.4, 1.2 Hz, 1H), 4.99 (d, J=6.3 Hz, 1H), 4.64 (p, J=6.3 Hz, 1H), 4.30 (d, J=3.0 Hz, 1H), 4.24-4.17 (m, 2H), 3.86 (dd, J=13.8, 1.1 Hz, 1H), 3.78 (s, 3H), 1.26 (s, 1H), 1.06 (d, J=6.2 Hz, 3H), 1.00 (s, 9H), 0.89 (d, J=6.2 Hz, 3H); MS (APCI+) m/z 549 (M+H)$^+$.

Example 41

(2S,3R,4S,5S)-3-tert-butyl-1-(cyclohexanecarbonyl)-4-{[2-methoxy-5-(trifluoromethyl)pyridin-3-yl]methoxy}-5-phenylpyrrolidine-2-carboxylic acid Example 41A (2S,3R,4S,5S)-ethyl 3-(tert-butyl)-1-(cyclohexanecarbonyl)-4-nitro-5-phenylpyrrolidine-2-carboxylate To a cooled (ice bath) mixture of Core 5 (2.0 g, 6.24 mmol) and triethylamine (2.61 mL, 18.73 mmol) in dichloromethane (20 mL) was added cyclohexanecarbonyl chloride (1.002 mL, 7.49 mmol) dropwise. The mixture was stirred in the ice-bath for 10 minutes and allowed to warm to room temperature. Dichloromethane (10 mL) was added. The mixture was washed with brine, dried over MgSO$_4$, filtered, and concentrated to provide the title compound (2.45 g, 91%). $^1$H NMR (400 MHz, CDCl$_3$) δ ppm 7.73-7.61 (m, 2H), 7.38 (q, J=8.2, 7.4 Hz, 3H), 5.46 (d, J=9.0 Hz, 1H), 5.37 (dd, J=8.9, 4.5 Hz, 1H), 4.82 (d, J=4.7 Hz, 1H), 4.36 (q, J=7.2 Hz, 2H), 3.15 (d, J=4.6 Hz, 1H), 2.06 (ddt, J=11.5, 7.0, 3.5 Hz, 1H), 1.68 (dd, J=33.2, 12.5 Hz, 2H), 1.55-1.41 (m, 4H), 1.38 (t, J=7.1 Hz, 3H), 1.34-1.13 (m, 3H), 1.07 (s, 9H), 0.59 (d, J=12.6 Hz, 1H); MS (ESI+) m/z 431 (M+H)$^+$.

Example 41B (2S,3R,5S)-ethyl 3-(tert-butyl)-1-(cyclohexanecarbonyl)-4-oxo-5-phenylpyrrolidine-2-carboxylate To potassium dichromate (4.65 g, 15.79 mmol) in 6 M aqueous HCl (60 mL), zinc (5.3 g, 81 mmol) was added under N$_2$ atmosphere. Complete dissolution of zinc provided a clear light blue solution. The formed chromium(II) chloride was transferred to the refluxing solution of Example 41A (1 g, 2.323 mmol) in ethanol (60 mL). The reaction mixture was refluxed overnight. The mixture was cooled and concentrated to half of its volume and extracted with dichloromethane (30 mL×3). The combined organic phase was washed with brine, dried over MgSO$_4$, filtered, and concentrated. The residue was dissolved in ethanol (2 mL) and added to a prepared solution of acetyl chloride (1 mL) in ethanol (4 mL) cooling in an ice-bath. The mixture was heated to 60° C. for 2 hours, concentrated, and dissolved in ethyl acetate (50 mL) and saturated aqueous NaHCO$_3$ (30 mL). The organic layer was washed with brine, dried over MgSO$_4$, filtered, and concentrated to provide a residue which purified via chromatography on a 40 g silica gel cartridge, eluting with ethyl acetate in heptanes at 0-30% gradient to provide the title compound (688 mg, 74.1% yield).

Example 41C (2S,3R,4S,5S)-ethyl 3-(tert-butyl)-1-(cyclohexanecarbonyl)-4-hydroxy-5-phenylpyrrolidine-2-carboxylate To Example 41B (730 mg, 1.827 mmol) in ethanol (10 mL) cooled in an ice-bath was added sodium borohydride (138 mg, 3.65 mmol) portionwise. The mixture was stirred in ice-bath for 30 minutes and was allowed to warm to room temperature. LC/MS indicated the reaction was finished and showed two product peaks at ratio about 3 to 1, with the title compound as the major isomer. Saturated NH$_4$Cl (2 mL) was added, and the mixture was concentrated, dissolved in dichloromethane (30 mL), washed with brine, dried over MgSO$_4$, filtered, and concentrated. Purification via chromatography on a 40 g silica gel cartridge eluting with ethyl acetate/methanol (9:1) in heptanes at 0-40% gradient provided the title compound (480 mg, 65.4% yield). LC/MS (APCI+) m/z 402 (M+H)$^+$.

Example 41D (2S,3R,4S,5S)-3-tert-butyl-1-(cyclohexanecarbonyl)-4-{[2-methoxy-5-(trifluoromethyl)pyridin-3-yl]methoxy}-5-phenylpyrrolidine-2-carboxylic acid To Example 41C and 3-(bromomethyl)-2-methoxy-5-(trifluoromethyl)pyridine (121 mg, 0.448 mmol) in dimethylformamide (2 mL) cooled in an ice-bath, potassium 2-methylpropan-2-olate (62.9 mg, 0.560 mmol, 0.56 mL, 1.0 M in tetrahydrofuran) was added dropwise. The mixture was stirred in the ice-bath for 20 minutes, and allowed to warm to room temperature. Methanol (1.5 mL) and 6M aqueous LiOH (0.5 mL) was added. The mixture was stirred at 50° C. overnight, and adjusted to pH 1~2 by adding 2M aqueous HCl. The solvent was removed and dichloromethane was (1 mL) added. The reaction mixture was filtered through a syringe filter and the filtrate was purified via chromatography, eluting with methanol in dichloromethane at 0-20% gradient to provide title compound, 130 mg (61.9% yield). $^1$H NMR (400 MHz, DMSO-d$_6$) δ ppm 8.29 (td, J=1.9, 0.8 Hz, 1H), 7.66 (d, J=7.3 Hz, 2H), 7.28-7.08 (m, 4H), 5.23 (d, J=6.3 Hz, 1H), 4.51 (d, J=3.1 Hz, 1H), 4.38-4.24 (m, 2H), 3.95 (d, J=13.9 Hz, 1H), 3.89 (s, 3H), 2.51 (s, 1H), 2.23 (s, 1H), 1.65 (d, J=9.5 Hz, 2H), 1.49 (s, 2H), 1.17 (d, J=73.3 Hz, 6H), 1.01 (s, 9H); MS (ESI+) m/z 563 (M+H)$^+$.

Example 42

(2S,3R,4S,5S)-3-tert-butyl-4-[(2-methoxy-5-phenylpyridin-3-yl)methoxy]-5-phenyl-1-{[(propan-2-yl)oxy]carbonyl}pyrrolidine-2-carboxylic acid The title compound was prepared following the procedures used in Example 38E-38F using the material from Example 40A. $^1$H NMR (400 MHz, DMSO-d$_6$) δ ppm 8.20 (d, J=2.6 Hz, 1H), 7.67-7.58 (m, 2H), 7.44 (d, J=4.9 Hz, 4H), 7.37-7.30 (m, 1H), 7.28 (dd, J=2.5, 1.1 Hz, 1H), 7.14 (t, J=7.5 Hz, 2H), 7.09-7.02 (m, 1H), 5.00 (d, J=6.3 Hz, 1H), 4.68-4.59 (m, 1H), 4.34-4.28 (m, 2H), 4.24 (dd, J=6.4, 2.4 Hz, 1H), 3.97 (d, J=13.2 Hz, 1H), 3.85 (d, J=0.7 Hz, 3H), 2.54 (t, J=2.8 Hz, 1H), 1.06 (d, J=6.2 Hz, 3H), 1.01 (s, 9H), 0.90-0.85 (m, 3H); MS (APCI+) m/z 547 (M+H)+.

Example 43

(2S,3R,4S,5S)-3-tert-butyl-4-[(5-cyclohexyl-2-methoxypyridin-3-yl)methoxy]-5-phenyl-1-{[(propan-2-yl)oxy]carbonyl}pyrrolidine-2-carboxylic acid

Example 43A (2S,3R,4S,5S)-2-ethyl 1-isopropyl 3-(tert-butyl)-4-((5-cyclohexyl-2-methoxypyridin-3-yl)methoxy)-5-phenylpyrrolidine-1,2-dicarboxylate In a 4 mL vial, Example 40A (22.7 mg, 0.039 mmol, 1.0 eq) and dichloro[4,5-dichloro-1,3-bis(2,6-Di-3-pentylphenyl)imidazol-2-ylidene](3-chloropyridyl)palladium(II) (PEPPSI-IPentCl, 3.38 mg, 0.0039 mmol, 0.1 eq) were dissolved in tetrahydrofuran (500 μL), flushed with nitrogen and stirred at room temperature. Cyclohexylzinc bromide (0.5 M, 235 μL, 0.12 mmol, 3.0 eq) was added and the reaction was stirred at room temperature for 30 minutes. The solvent was removed under a stream of nitrogen, reconstituted in DMSO, and purified reverse phase HPLC/MS method TFA7. MS (APCI+) m/z 581.1 (M+H)+.

Example 43B (2S,3R,4S,5S)-3-tert-butyl-4-[(5-cyclohexyl-2-methoxypyridin-3-yl)methoxy]-5-phenyl-1-{[(propan-2-yl)oxy]carbonyl}pyrrolidine-2-carboxylic acid Example 43A was dissolved in 3:2 tetrahydrofuran/methanol (500 μL). LiOH monohydrate (16 mg, 0.39 mmol, 10 eq) in H₂O (100 μL) was added and the reaction mixture was stirred at 45° C. After material started to precipitate, a few drops methanol were added. After 4 hours the solvent was removed under a stream of nitrogen. The residue was acidified using 800 μL 1 M aqueous HCl, and was diluted with 400 μL CH₃CN. The reaction was loaded directly into an injection loop and was purified using prep LC method TFA8 to provide the title compound (8.8 mg, 40.6% yield). ¹H NMR (400 MHz, 120° C., DMSO-d₆:D₂O=9:1 (v/v)) δ ppm 7.75 (d, J=2.5 Hz, 1H), 7.60-7.52 (m, 2H), 7.25-7.18 (m, 2H), 7.18-7.10 (m, 1H), 6.83 (d, J=2.5 Hz, 1H), 4.97 (d, J=6.3 Hz, 1H), 4.63 (p, J=6.2 Hz, 1H), 4.31 (d, J=3.2 Hz, 1H), 4.27-4.12 (m, 2H), 3.87 (d, J=13.2 Hz, 1H), 3.75 (s, 3H), 2.48-2.45 (m, 1H), 2.35-2.27 (m, 1H), 1.73 (d, J=38.3 Hz, 5H), 1.45-1.11 (m, 5H), 1.05 (d, J=6.2 Hz, 3H), 0.98 (s, 9H), 0.88 (d, J=6.1 Hz, 3H); MS (APCI+) m/z 553.1 (M+H)+.

Example 44

(2S,3R,4S,5S)-3-tert-butyl-4-[(5-cyclopentyl-2-methoxypyridin-3-yl)methoxy]-5-phenyl-1-{[(propan-2-yl)oxy]carbonyl}pyrrolidine-2-carboxylic acid

Example 44A (2S,3R,4S,5S)-2-ethyl 1-isopropyl 3-(tert-butyl)-4-((5-cyclopentyl-2-methoxypyridin-3-yl)methoxy)-5-phenylpyrrolidine-1,2-dicarboxylate In a 4 mL vial, Example 40A (22.7 mg, 0.039 mmol, 1.0 eq) and dichloro[4,5-dichloro-1,3-bis(2,6-Di-3-pentylphenyl)imidazol-2-ylidene](3-chloropyridyl)palladium(II) (PEPPSI-IPentCl, 3.38 mg, 0.0039 mmol, 0.1 eq) were dissolved in tetrahydrofuran (500 μL), flushed with nitrogen and stirred at room temperature. Cyclopentylzinc bromide (0.5 M, 235 μL, 0.12 mmol, 3.0 eq) was added and reaction was stirred at room temperature for 30 minutes. The solvent was removed under a stream of nitrogen, reconstituted in DMSO, and purified using reverse phase method TFA8. MS (APCI+) m/z 567.1 (M+H)+.

Example 44B (2S,3R,4S,5S)-3-tert-butyl-4-[(5-cyclopentyl-2-methoxypyridin-3-yl)methoxy]-5-phenyl-1-{[(propan-2-yl)oxy]carbonyl}pyrrolidine-2-carboxylic acid Example 44A was dissolved in 3:2 tetrahydrofuran/methanol (500 μL). LiOH monohydrate (16 mg, 0.39 mmol, 10 eq) in H₂O (100 μL) was added and the reaction mixture was stirred at 45° C. After material started to precipitate, a few drops methanol were added. After 4 hours, the solvent was removed under a stream of nitrogen. The residue was acidified using 800 μL 1 M aqueous HCl, and diluted with 400 μL CH₃CN. The reaction was loaded directly into an injection loop and purified using prep LC method TFA8 to provide the title compound (11.0 mg, 52.1% yield). ¹H NMR (400 MHz, 120° C., DMSO-d₆:D₂O=9:1 (v/v)) δ ppm 7.77 (d, J=2.4 Hz, 1H), 7.60-7.53 (m, 2H), 7.24-7.09 (m, 3H), 6.90 (d, J=2.3 Hz, 1H), 4.97 (d, J=6.3 Hz, 1H), 4.62 (p, J=6.3 Hz, 1H), 4.30 (d, J=3.2 Hz, 1H), 4.23-4.13 (m, 2H), 3.86 (d, J=13.2 Hz, 1H), 3.75 (s, 3H), 2.83-2.78 (m, 1H), 2.46 (t, J=2.9 Hz, 1H), 1.94-1.88 (m, 2H), 1.78-1.58 (m, 4H), 1.56-1.30 (m, 2H), 1.05 (d, J=6.3 Hz, 3H), 0.98 (s, 9H), 0.88 (d, J=6.2 Hz, 3H); MS (APCI+) m/z 539.1 (M+H)+.

Example 45

(2S,3R,4S,5S)-3-tert-butyl-4-[(5-cyclobutyl-2-methoxypyridin-3-yl)methoxy]-5-phenyl-1-{[(propan-2-yl)oxy]carbonyl}pyrrolidine-2-carboxylic acid

Example 45A (2S,3R,4S,5S)-2-ethyl 1-isopropyl 3-(tert-butyl)-4-((5-cyclobutyl-2-methoxypyridin-3-yl)methoxy)-5-phenylpyrrolidine-1,2-dicarboxylate Example 40A (0.140 g, 0.242 mmol) in tetrahydrofuran (2.4 mL) was treated with PdCl₂(dppf) ([1,1'-bis(diphenylphosphino)ferrocene]dichloropalladium(II), 8.8 mg, 0.012 mmol), followed by dropwise addition of cyclobutylzinc(II) bromide (0.5M in tetrahydrofuran) (0.97 mL, 0.48 mmol) at room temperature. The reaction was allowed to stir for a total of 2 hours at room temperature. The reaction mixture was quenched with saturated aqueous NH₄Cl solution and the solvent was reduced under a stream of nitrogen. The crude product was purified using a 25 g silica gel cartridge with a gradient of 5-50% ethyl acetate/heptanes over 20 minutes to provide (2S,3R,4S,5S)-2-ethyl 1-isopropyl 3-(tert-butyl)-4-((5-cyclobutyl-2-methoxypyridin-3-yl)methoxy)-5-phenylpyrrolidine-1,2-dicarboxylate (113 mg, 0.204 mmol, 84% yield). ¹H NMR (400 MHz, DMSO-d₆) δ ppm 7.76 (d, J=2.5 Hz, 1H), 7.60-7.54 (m, 2H), 7.26-7.11 (m, 3H), 6.93 (d, J=2.4 Hz, 1H), 5.00 (d, J=6.2 Hz, 1H), 4.64 (p, J=6.2 Hz, 1H), 4.34 (d, J=3.3 Hz, 1H), 4.23-4.17 (m, 2H), 4.10 (qd, J=7.1, 2.8 Hz, 2H), 3.87 (dd, J=13.0, 0.8 Hz, 1H), 3.75 (s, 3H), 3.41-3.27 (m, 1H), 2.50-2.42 (m, 2H), 2.24 (ddt, J=9.0, 6.1, 2.5 Hz, 2H), 2.01-1.79 (m, 3H), 1.15 (t, J=7.0 Hz, 3H), 1.05 (d, J=6.2 Hz, 3H), 0.99 (s, 9H), 0.89 (d, J=6.1 Hz, 3H); MS (ESI+) m/z 552 (M+H)$^+$.

Example 45B (2S,3R,4S,5S)-3-tert-butyl-4-[(5-cyclobutyl-2-methoxypyridin-3-yl)methoxy]-5-phenyl-1-{[(propan-2-yl)oxy]carbonyl}pyrrolidine-2-carboxylic acid To a solution of Example 45A (113 mg, 0.204 mmol) in tetrahydrofuran (1 mL) and methanol (1.0 mL) was added lithium hydroxide (34 mg, 1.420 mmol) in water (1 mL) and the reaction was heated at 45° C. overnight. The solvent was removed under a stream of nitrogen. The crude material was acidified with 2M aqueous HCl (342 uL) and purified using a 24 g silica gel column. The column was eluted with an ethyl acetate/ethanol/heptanes solvent system to provide (2S,3R,4S,5S)-3-(tert-butyl)-4-((5-cyclobutyl-2-methoxypyridin-3-yl)methoxy)-1-(isopropoxycarbonyl)-5-phenylpyrrolidine-2-carboxylic acid (80 mg, 0.152 mmol, 74.6% yield). $^1$H NMR (400 MHz, DMSO-d$_6$) δ ppm 7.76 (d, J=2.4 Hz, 1H), 7.61-7.57 (m, 2H), 7.24-7.10 (m, 3H), 6.93 (td, J=1.7, 0.9 Hz, 1H), 4.98 (d, J=6.3 Hz, 1H), 4.63 (ddd, J=11.8, 6.6, 5.8 Hz, 1H), 4.29 (d, J=3.2 Hz, 1H), 4.24-4.15 (m, 2H), 3.88 (dd, J=13.1, 0.9 Hz, 1H), 3.76 (d, J=0.7 Hz, 3H), 3.39-3.26 (m, 1H), 2.71-2.57 (m, 1H), 2.32-2.16 (m, 2H), 2.03-1.81 (m, 3H), 1.06 (d, J=6.2 Hz, 3H), 0.99 (d, J=0.8 Hz, 9H), 0.89 (d, J=6.2 Hz, 3H), 0.87-0.79 (m, 1H); MS (APCI+) m/z 525 (M+H)$^+$.

Example 46

(2S,3R,4S,5S)-3-tert-butyl-4-[(5-tert-butyl-2-methoxyphenyl)methoxy]-1-[(1R,3R)-3-methoxycyclohexane-1-carbonyl]-5-phenylpyrrolidine-2-carboxylic acid Example 46A (2S,3R,4S,5S)-ethyl 3-(tert-butyl)-4-((5-(tert-butyl)-2-methoxybenzyl)oxy)-1-((1R,3R)-3-methoxycyclohexanecarbonyl)-5-phenylpyrrolidine-2-carboxylate Example 31C (27 mg, 0.063 mmol) and 2-(bromomethyl)-4-(tert-butyl)-1-methoxybenzene (30 mg, 0.117 mmol) were dissolved in dry dimethylformamide (0.5 mL). After cooling in an ice bath, potassium 2-methylpropan-2-olate (0.100 mL, 0.100 mmol) solution was added dropwise over 2 minutes. The mixture was acidified with 1M aqueous HCl (10 drops) and warmed to room temperature. The mixture was concentrated and loaded onto a 12 g silica gel column and was eluted with 5-100% methyl tert-butyl ether/heptanes over 20 minutes to provide (2S,3R,4S,5S)-ethyl 3-(tert-butyl)-4-((5-(tert-butyl)-2-methoxybenzyl)oxy)-1-((1R,3R)-3-methoxycyclohexanecarbonyl)-5-phenylpyrrolidine-2-carboxylate (33 mg, 0.054 mmol, 87% yield). MS (APCI+) m/z 608 (M+H)$^+$.

Example 46B (2S,3R,4S,5S)-3-tert-butyl-4-[(5-tert-butyl-2-methoxyphenyl)methoxy]-1-[(1R,3R)-3-methoxycyclohexane-1-carbonyl]-5-phenylpyrrolidine-2-carboxylic acid Example 46A (33 mg, 0.054 mmol) was dissolved in methanol (0.5 mL). Lithium hydroxide (17 mg, 0.710 mmol) and water (0.500 mL) were added and a precipitate formed. Tetrahydrofuran (0.500 mL) was added and everything dissolved. The reaction mixture was warmed at 45° C. overnight. The solvent was removed, and the reaction was acidified with 1M aqueous HCl (30 drops). The crude material was loaded onto a 12 g silica gel column and was eluted with an ethyl acetate/ethanol/heptanes solvent system over 20 minutes to provide (2S,3R,4S,5S)-3-(tert-butyl)-4-((5-(tert-butyl)-2-methoxybenzyl)oxy)-1-((1R,3R)-3-methoxycyclohexanecarbonyl)-5-phenylpyrrolidine-2-carboxylic acid (24 mg, 0.041 mmol, 76% yield). $^1$H NMR (400 MHz, DMSO-d$_6$) δ ppm 7.67 (d, J=7.4 Hz, 2H), 7.22 (t, J=7.4 Hz, 2H), 7.16 (d, J=7.1 Hz, 1H), 7.12 (dd, J=8.6, 2.6 Hz, 1H), 6.87 (d, J=2.6 Hz, 1H), 6.74 (d, J=8.6 Hz, 1H), 5.13 (d, J=6.6 Hz, 1H), 4.38 (d, J=3.7 Hz, 1H), 4.26-4.16 (m, 2H), 3.94 (d, J=12.2 Hz, 1H), 3.65 (s, 3H), 3.44 (s, 1H), 3.20 (s, 3H), 3.04-3.00 (m, 1H), 2.70-2.58 (m, 1H), 2.52 (s, 1H), 1.76 (d, J=13.7 Hz, 1H), 1.62 (d, J=12.7 Hz, 1H), 1.42 (ddd, J=13.8, 11.2, 2.7 Hz, 1H), 1.30-1.21 (m, 2H), 1.18 (s, 9H), 0.96 (s, 9H), 0.90-0.81 (m, 2H); MS (APCI+) m/z 580 (M+H)$^+$.

Example 47

(2S,3R,4S,5S)-3-tert-butyl-4-[(5-tert-butyl-2-methoxyphenyl)methoxy]-5-phenyl-1-{[(propan-2-yl)oxy]carbonyl}pyrrolidine-2-carboxylic acid Example 47A (2S,3R,4S,5S)-2-ethyl 1-isopropyl 3-(tert-butyl)-4-((5-(tert-butyl)-2-methoxybenzyl)oxy)-5-phenylpyrrolidine-1,2-dicarboxylate Example 38C and 2-(bromomethyl)-4-(tert-butyl)-1-methoxybenzene (53 mg, 0.206 mmol) were dissolved in dry dimethylformamide (0.5 mL). After cooling in an ice bath, potassium 2-methylpropan-2-olate (0.216 mL, 0.216 mmol) solution was added dropwise over 2 minutes. After 30 minutes, the reaction was acidified with 1M aqueous HCl (10 drops) and warmed to room temperature. The mixture was concentrated, loaded onto a 12 g silica gel column, and eluted with 5-100% methyl tert-butyl ether/heptanes over 20 minutes to provide (2S,3R,4S,5S)-2-ethyl 1-isopropyl 3-(tert-butyl)-4-((5-(tert-butyl)-2-methoxybenzyl)oxy)-5-phenylpyrrolidine-1,2-dicarboxylate (73 mg, 0.132 mmol, 98% yield). MS (APCI+) m/z 554 (M+H)$^+$.

Example 47B (2S,3R,4S,5S)-3-tert-butyl-4-[(5-tert-butyl-2-methoxyphenyl)methoxy]-5-phenyl-1-{[(propan-2-yl)oxy]carbonyl}pyrrolidine-2-carboxylic acid Example 47A (78 mg, 0.141 mmol) was dissolved in methanol (0.5 mL). LiOH (23 mg, 0.960 mmol) in water (0.500 mL) was added and a precipitate formed. Tetrahydrofuran was added (0.500 mL) and everything dissolved. The reaction mixture was warmed at 45° C. After warming at 45° C. overnight, LC/MS showed some desired product but mostly starting material. Additional LiOH (20 mg) was added in addition to 0.3 mL tetrahydrofuran. The reaction mixture was warmed at 45° C. for 6 hours. The solvent was removed, and the reaction was acidified with 1M aqueous HCl (30 drops). The crude material was loaded onto a 12 g silica gel column and was eluted with an ethyl acetate/ethanol/heptanes solvent system over 20 minutes to provide (2S,3R,4S,5S)-3-(tert-butyl)-4-((5-(tert-butyl)-2-methoxybenzyl)oxy)-1-(isopropoxycarbonyl)-5-phenylpyrrolidine-2-carboxylic acid (51 mg, 0.097 mmol, 68.9% yield). $^1$H NMR (400 MHz, DMSO-$d_6$) δ ppm 7.65-7.59 (m, 2H), 7.19 (td, J=7.1, 1.1 Hz, 2H), 7.15-7.09 (m, 2H), 6.89 (d, J=2.5 Hz, 1H), 6.77-6.71 (m, 1H), 4.96 (d, J=6.4 Hz, 1H), 4.62 (ddd, J=11.8, 6.8, 5.8 Hz, 1H), 4.24 (d, J=3.7 Hz, 1H), 4.19 (d, J=12.3 Hz, 1H), 4.17-4.13 (m, 1H), 3.91 (d, J=12.3 Hz, 1H), 3.64 (d, J=1.0 Hz, 3H), 1.26 (s, 1H), 1.18 (d, J=1.1 Hz, 9H), 1.06 (dd, J=6.2, 1.0 Hz, 3H), 0.97 (d, J=1.0 Hz, 9H), 0.89 (d, J=6.2 Hz, 3H); MS (APCI+) m/z 526 (M+H)$^+$.

Example 48

(2S,3R,4S,5S)-3-tert-butyl-1-(cyclohexanecarbonyl)-5-(2-fluorophenyl)-4-{[2-methoxy-5-(trifluoromethyl)pyridin-3-yl]methoxy}pyrrolidine-2-carboxylic acid Example 48A (2S,3R,4S,5S)-ethyl 3-(tert-butyl)-1-(cyclohexanecarbonyl)-5-(2-fluorophenyl)-4-nitropyrrolidine-2-carboxylate A solution of Core 6 (5.00 g, 14.78 mmol) and triethylamine (4.74 mL, 34.0 mmol) in dichloromethane, 50 mL) at 0° C. was treated with cyclohexanecarbonyl chloride (2.57 mL, 19.21 mmol), and stirred at 0° C. for 30 minutes and at 25° C. for 1 hour. The reaction was diluted with dichloromethane (50 mL) and the mixture was washed with saturated aqueous NaHCO$_3$. The organics were washed with brine, dried over MgSO$_4$, filtered, and concentrated. The crude material was purified by silica column chromatography on silica gel eluting with petroleum ether/ethyl acetate 10:1 to provide (2S,3R,4S,5S)-ethyl 3-(tert-butyl)-1-(cyclohexanecarbonyl)-5-(2-fluorophenyl)-4-nitropyrrolidine-2-carboxylate (3.5596 g, 7.54 mmol, 51.0% yield). $^1$H NMR (400 MHz, CDCl$_3$) δ ppm 8.06 (td, J=7.8, 1.7 Hz, 1H), 7.61-7.49 (m, 0H), 7.33 (tdd, J=7.5, 5.4, 1.7 Hz, 1H), 7.25-7.14 (m, 1H), 7.11-7.03 (m, 1H), 7.03-6.94 (m, 0H), 5.78 (dd, J=17.0, 8.4 Hz, 1H), 5.43-5.33 (m, 1H), 4.93 (d, J=3.2 Hz, 1H), 4.66 (d, J=1.7 Hz, 0H), 4.48-4.27 (m, 2H), 3.14-3.01 (m, 1H), 2.37 (td, J=11.4, 5.8 Hz, 0H), 1.94 (ddt, J=11.3, 6.6, 3.5 Hz, 1H), 1.85-1.76 (m, 2H), 1.76-1.56 (m, 3H), 1.51 (dd, J=12.9, 3.6 Hz, 2H), 1.37 (dt, J=21.9, 7.1 Hz, 3H), 1.25 (d, J=7.5 Hz, 2H), 1.08 (d, J=15.7 Hz, 9H), 0.63 (dd, J=14.9, 11.2 Hz, 1H).

Example 48B (2S,3R,5S)-ethyl 3-(tert-butyl)-1-(cyclohexanecarbonyl)-5-(2-fluorophenyl)-4-oxopyrrolidine-2-carboxylate Example 48A (2.227 g, 4.97 mmol) was dissolved in ethanol (75 mL) and the solution was degassed by bubbling nitrogen through for about 20 minutes. The mixture was heated to 75° C. under nitrogen. A separate solution of CrCl$_2$ was prepared under nitrogen by dissolving potassium dichromate (4.97 g, 16.88 mmol) in aqueous hydrochloric acid, 6M (75 mL) and adding Zn (8.93 g, 137 mmol) (in portions while cooling in an ice bath, keeping the internal temperature around 25° C.). The color of the solution went from dark brown to dark green to clear light blue. The solution bubbled steadily. The CrCl$_2$ solution was added via cannula over 20 minutes to the solution of starting material. The reaction was warmed to 80° C. (internal temperature) and heating was continued for 19 hours. The mixture was cooled to room temperature, concentrated, diluted with water (50 mL), and extracted with dichloromethane (3×200 mL). The extracts were combined, dried over sodium sulfate, filtered, and concentrated. The material was re-esterified using the following procedure: The crude residue was dissolved in 20 mL of ethanol. A separate solution of HCl/ethanol was prepared by addition of 3 mL of acetyl chloride to 10 mL of ethanol cooled in an ice bath. The mixtures were combined and heated to 45° C. for 1 hour, at which point all acid had converted to the desired ester product. The mixture was concentrated in vacuo and the crude material was loaded onto a 80 g silica gel column and eluted with 0-30% ethyl acetate/heptanes over 20 minutes to provide (2S,3R,5S)-ethyl 3-(tert-butyl)-1-(cyclohexanecarbonyl)-5-(2-fluorophenyl)-4-oxopyrrolidine-2-carboxylate (1.041 g, 2.493 mmol, 50.2% yield). $^1$H NMR (400 MHz, DMSO-$d_6$) δ ppm 7.72 (d, J=8.2 Hz, 1H), 7.42-7.31 (m, 1H), 7.24-7.10 (m, 2H), 5.41 (s, 1H), 4.82 (d, J=3.9 Hz, 1H), 4.25-4.12 (m, 2H), 2.66 (d, J=3.9 Hz, 1H), 2.25 (s, 1H), 1.69 (d, J=11.0 Hz, 2H), 1.53 (d, J=10.9 Hz, 2H), 1.39-1.27 (m, 2H), 1.22 (td, J=7.1, 0.8 Hz, 3H), 1.17-1.10 (m, 2H), 1.06 (d, J=0.8 Hz, 9H), 0.96-0.76 (m, 2H); MS (ESI+) m/z 418 (M+H)$^+$.

Example 48C (2S,3R,4S,5S)-ethyl 3-(tert-butyl)-1-(cyclohexanecarbonyl)-5-(2-fluorophenyl)-4-hydroxypyrrolidine-2-carboxylate Example 48B (1.00 g, 2.395 mmol) was dissolved in ethanol (11.98 mL) and sodium borohydride (0.181 g, 4.79 mmol) was added after cooling the reaction to <−7° C. in an ice/acetone bath. The reaction mixture was stirred at the same temperature for 30 minutes, concentrated and partitioned between ethyl acetate and saturated aqueous sodium bicarbonate. The organics were concentrated and the crude material was purified on a 40 g silica gel column, eluting with 0-100% methyl tert-butyl ether/heptanes over 40 minutes. The purified material was precipitated from ethyl acetate/hexane to provide (2S,3R,4S,5S)-ethyl 3-(tert-butyl)-1-(cyclohexanecarbonyl)-5-(2-fluorophenyl)-4-hydroxypyrrolidine-2-carboxylate (0.703 g, 1.676 mmol, 70.0% yield). $^1$H NMR (400 MHz, DMSO-$d_6$) δ ppm 7.94 (s, 1H), 7.35-7.20 (m, 1H), 7.16-6.97 (m, 2H), 5.29 (d, J=6.7 Hz, 1H), 4.42 (t, J=4.7 Hz, 2H), 4.36 (s, 1H), 4.17 (q, J=7.1 Hz, 2H), 2.84-2.77 (m, 1H), 2.29 (t, J=4.3 Hz, 1H), 2.13 (s, 1H), 1.67 (dt, J=11.0, 4.3 Hz, 2H), 1.51 (d, J=9.6 Hz, 2H), 1.25 (t, J=7.1 Hz, 4H), 1.17-1.05 (m, 2H), 0.99 (s, 9H), 0.91-0.67 (m, 1H); MS (APCI+) m/z 420 (M+H)$^+$. Relative and absolute stereochemistry confirmed by X-ray diffraction analysis.

Example 48D (2S,3R,4S,5S)-ethyl 3-(tert-butyl)-1-(cyclohexanecarbonyl)-5-(2-fluorophenyl)-4-((2-methoxy-5-(trifluoromethyl)pyridin-3-yl)methoxy)pyrrolidine-2-carboxylate Example 48C (64 mg, 0.153 mmol) and 3-(bromomethyl)-2-methoxy-5-(trifluoromethyl)pyridine (65 mg, 0.241 mmol) were dissolved in dry dimethylformamide (0.4 mL). After cooling in an ice bath, potassium 2-methylpropan-2-olate (0.244 mL, 0.244 mmol) solution was added dropwise over 2 minutes. After 30 minutes, the reaction was acidified with 1M aqueous HCl (13 drops) and warmed to room temperature. The mixture was concentrated and loaded onto a 12 g silica gel column and was eluted with 5-100% methyl tert-butyl ether/heptanes over 20 minutes to provide (2S,3R,4S,5S)-ethyl 3-(tert-butyl)-1-(cyclohexanecarbonyl)-5-(2-fluorophenyl)-4-((2-methoxy-5-(trifluoromethyl)pyridin-3-yl)methoxy)pyrrolidine-2-carboxylate (51 mg, 0.084 mmol, 54.9% yield). $^1$H NMR (400 MHz, DMSO-$d_6$) δ ppm 8.31 (s, 1H), 7.88 (s, 1H), 7.25-7.18 (m, 1H), 7.16 (s, 1H), 7.03 (dt, J=19.3, 8.5 Hz, 2H), 5.45 (d, J=6.2 Hz, 1H), 4.61 (d, J=3.0 Hz, 1H), 4.38 (d, J=13.6 Hz, 2H), 4.17-4.01 (m, 3H), 3.89 (s, 3H), 2.53 (s, 1H), 2.31-2.11 (m, 1H), 1.68 (s, 2H), 1.53 (s, 2H), 1.34-1.22 (m, 2H), 1.15 (t, J=7.1 Hz, 3H), 1.12-1.06 (m, 2H), 1.02 (s, 9H), 0.89-0.80 (m, 2H); MS (APCI+) m/z 609 (M+H)$^+$.

Example 48E (2S,3R,4S,5S)-3-tert-butyl-1-(cyclohexanecarbonyl)-5-(2-fluorophenyl)-4-{[2-methoxy-5-(trifluoromethyl)pyridin-3-yl]methoxy}pyrrolidine-2-carboxylic acid Example 48D (51 mg, 0.084 mmol) was dissolved in methanol (0.5 mL). Lithium hydroxide (26 mg, 1.086 mmol) and water (0.500 mL) were added and a precipitate formed. Tetrahydrofuran (0.500 mL) was added and everything dissolved. The reaction was warmed at 45° C. overnight. The solvent was removed, and the reaction was acidified with 1M aqueous HCl (30 drops). The crude material was loaded onto a 12 g silica gel column and was eluted with an ethyl acetate/ethanol/heptanes solvent system over 20 minutes to provide (2S,3R,4S,5S)-3-(tert-butyl)-1-(cyclohexanecarbonyl)-5-(2-fluorophenyl)-4-((2-methoxy-5-(trifluoromethyl)pyridin-3-yl)methoxy)pyrrolidine-2-carboxylic acid (41 mg, 0.071 mmol, 84% yield). $^1$H NMR (400 MHz, DMSO-$d_6$) δ ppm 8.29 (d, J=2.3 Hz, 1H), 8.16-8.01 (m, 1H), 7.25-7.10 (m, 2H), 7.09-6.91 (m, 2H), 5.44 (d, J=6.4 Hz, 1H), 4.53-4.45 (m, 1H), 4.40 (d, J=13.8 Hz, 1H), 4.34-4.28 (m, 1H), 4.06 (d, J=13.8 Hz, 1H), 3.90 (s, 3H), 2.62 (s, 1H), 2.40-2.17 (m, 1H), 1.68 (d, J=10.5 Hz, 2H), 1.54 (s, 2H), 1.25 (d, J=4.2 Hz, 2H), 1.14 (d, J=19.4 Hz, 2H), 1.01 (s, 9H), 0.90-0.80 (m, 2H); MS (APCI+) m/z 581 (M+H)$^+$.

Example 49

(2S,3R,4S,5S)-3-tert-butyl-1-(cyclohexanecarbonyl)-5-(2-fluorophenyl)-4-{[2-methoxy-5-(trifluoromethyl)phenyl]methoxy}pyrrolidine-2-carboxylic acid The title compound was prepared using the procedures described for Example 48 substituting 2-(bromomethyl)-1-methoxy-4-(trifluoromethyl)benzene for 3-(bromomethyl)-2-methoxy-5-(trifluoromethyl)pyridine in Example 48D. $^1$H NMR (400 MHz, DMSO-$d_6$) δ ppm 8.05 (s, 1H), 7.44 (dd, J=8.8, 2.4 Hz, 1H), 7.18 (d, J=6.8 Hz, 1H), 7.10-6.89 (m, 4H), 5.44 (d, J=6.5 Hz, 1H), 4.48 (d, J=3.0 Hz, 1H), 4.40 (d, J=13.1 Hz, 1H), 4.30-4.24 (m, 1H), 4.08 (d, J=13.2 Hz, 1H), 3.77 (s, 3H), 2.60 (s, 1H), 2.40-2.15 (m, 1H), 1.77-1.64 (m, 2H), 1.60-1.48 (m, 2H), 1.34-1.21 (m, 2H), 1.19-1.06 (m, 2H), 1.00 (s, 9H), 0.91-0.81 (m, 2H); MS (APCI+) m/z 580 (M+H)$^+$.

Example 50

(2S,3R,4S,5S)-3-tert-butyl-4-[(5-tert-butyl-2-methoxyphenyl)methoxy]-1-(cyclohexanecarbonyl)-5-(2-fluorophenyl)pyrrolidine-2-carboxylic acid Example 50A (2S,3R,4S,5S)-ethyl 3-(tert-butyl)-4-((5-(tert-butyl)-2-methoxybenzyl)oxy)-1-(cyclohexanecarbonyl)-5-(2-fluorophenyl)pyrrolidine-2-carboxylate Example 48C (60 mg, 0.143 mmol) and 2-(bromomethyl)-4-(tert-butyl)-1-methoxybenzene (45 mg, 0.175 mmol) were dissolved in dry dimethylformamide (0.4 mL). After cooling in an ice bath, potassium 2-methylpropan-2-olate (0.229 mL, 0.229 mmol) solution was added dropwise over 2 minutes. After 30 minutes, the reaction was acidified with 1M aqueous HCl (10 drops) and warmed to room temperature. The mixture was concentrated and loaded onto a 12 g silica gel column and was eluted with 5-100% methyl tert-butyl ether/heptanes over 20 minutes to provide (2S,3R,4S,5S)-ethyl 3-(tert-butyl)-4-((5-(tert-butyl)-2-methoxybenzyl)oxy)-1-(cyclohexanecarbonyl)-5-(2-fluorophenyl)pyrrolidine-2-carboxylate (72 mg, 0.121 mmol, 84% yield). $^1$H NMR (400 MHz, DMSO-$d_6$) δ ppm 7.94 (s, 1H), 7.23 (d, J=7.2 Hz, 1H), 7.13 (dd, J=8.6, 2.6 Hz, 1H), 7.06 (dt, J=18.6, 8.6 Hz, 2H), 6.83 (d, J=2.5 Hz, 1H), 6.75 (d, J=8.5 Hz, 1H), 5.44 (d, J=6.3 Hz, 1H), 4.54 (d, J=3.4 Hz, 1H), 4.33-4.24 (m, 2H), 4.08 (qd, J=7.0, 1.2 Hz, 2H), 4.02 (d, J=12.1 Hz, 1H), 3.64 (s, 3H), 2.50 (s, 1H), 2.25-2.10 (m, 1H), 1.68 (d, J=8.2 Hz, 2H), 1.52 (s, 2H), 1.32-1.19 (m, 2H), 1.17 (s, 9H), 1.14 (t, J=7.1 Hz, 3H), 1.11-1.04 (m, 2H), 0.97 (s, 9H), 0.90-0.76 (m, 2H); MS (APCI+) m/z 596 (M+H)$^+$.

Example 50B (2S,3R,4S,5S)-3-tert-butyl-4-[(5-tert-butyl-2-methoxyphenyl)methoxy]-1-(cyclohexanecarbonyl)-5-(2-fluorophenyl)pyrrolidine-2-carboxylic acid Example 50A (70 mg, 0.117 mmol) was dissolved in methanol (0.5 mL). Lithium hydroxide (26 mg, 1.086 mmol) and water (0.500 mL) were added and a precipitate formed. Tetrahydrofuran (0.500 mL) was added and everything dissolved. The reaction was warmed at 45° C. overnight. The solvent was removed, and the reaction was acidified with 1M aqueous HCl (30 drops). The crude material was loaded onto a 12 g silica gel column and was eluted with an ethyl acetate/ethanol/heptanes solvent system over 20 minutes to provide (2S,3R,4S,5S)-3-(tert-butyl)-4-((5-(tert-butyl)-2-methoxybenzyl)oxy)-1-(cyclohexanecarbonyl)-5-(2-fluorophenyl)pyrrolidine-2-carboxylic acid (46 mg, 0.081 mmol, 69.0% yield). $^1$H NMR (400 MHz, DMSO-$d_6$) δ ppm 8.08 (s, 1H), 7.20 (d, J=6.2 Hz, 1H), 7.13 (dd, J=8.6, 2.6 Hz, 1H), 7.10-6.96 (m, 2H), 6.85 (d, J=2.5 Hz, 1H), 6.75 (d, J=8.6 Hz, 1H), 5.43 (d, J=6.6 Hz, 1H), 4.44 (d, J=3.4 Hz, 1H), 4.28 (d, J=12.3 Hz, 1H), 4.23 (d, J=7.2 Hz, 1H), 4.03 (d, J=12.3 Hz, 1H), 3.65 (s, 3H), 2.56 (s, 1H), 2.27 (d, J=21.7 Hz, 1H), 1.68 (d, J=7.8 Hz, 2H), 1.53 (s, 2H), 1.34-1.21 (m, 2H), 1.17 (d, J=0.8 Hz, 9H), 1.15-1.06 (m, 2H), 0.96 (s, 9H), 0.91-0.79 (m, 2H); MS (APCI+) m/z 568 (M+H)$^+$.

Example 51

(2S,3R,4S,5S)-4-[(5-bromo-2-methoxypyridin-3-yl)
methoxy]-3-tert-butyl-1-(cyclohexanecarbonyl)-5-
(2-fluorophenyl)pyrrolidine-2-carboxylic acid

Example 51A (2S,3R,4S,5S)-ethyl 4-((5-bromo-2-methoxypyridin-
3-yl)methoxy)-3-(tert-butyl)-1-(cyclohexanecarbo-
nyl)-5-(2-fluorophenyl)pyrrolidine-2-carboxylate Example 48C (273 mg, 0.651 mmol) and 5-bromo-3-(bromomethyl)-2-methoxypyridine (273 mg, 0.972 mmol) were dissolved in dry dimethylformamide (2.0 mL). After cooling in an ice bath, potassium 2-methylpropan-2-olate (1.041 mL, 1.041 mmol) solution was added dropwise over 2 minutes. After 30 minutes, the reaction was acidified with 1M aqueous HCl (20 drops) and warmed to ambient temperature. The crude material was concentrated and loaded onto a 24 g silica gel column and was eluted with 5-100% methyl tert-butyl ether/heptanes over 25 minutes to provide (2S,3R,4S,5S)-ethyl 4-((5-bromo-2-methoxypyridin-3-yl)methoxy)-3-(tert-butyl)-1-(cyclohexanecarbonyl)-5-(2-fluorophenyl)pyrrolidine-2-carboxylate (0.373 g, 0.602 mmol, 93% yield). $^1$H NMR (400 MHz, DMSO-$d_6$) δ ppm 8.02 (d, J=2.5 Hz, 1H), 7.88 (s, 1H), 7.26 (d, J=6.7 Hz, 1H), 7.12 (d, J=7.5 Hz, 1H), 7.04 (dd, J=10.7, 8.4 Hz, 1H), 6.97 (s, 1H), 5.44 (d, J=6.2 Hz, 1H), 4.60 (d, J=2.9 Hz, 1H), 4.30 (d, J=13.6 Hz, 2H), 4.13 (qd, J=7.1, 2.9 Hz, 2H), 4.02-3.95 (m, 1H), 3.79 (s, 3H), 2.51 (s, 1H), 2.33-2.10 (m, 1H), 1.68 (s, 2H), 1.53 (s, 2H), 1.26 (s, 2H), 1.18 (t, J=7.1 Hz, 3H), 1.14-1.06 (m, 2H), 1.01 (s, 9H), 0.89-0.79 (m, 2H); MS (APCI+) m/z 621 (M+H)$^+$.

Example 51B (2S,3R,4S,5S)-4-[(5-bromo-2-methoxypyridin-3-yl)
methoxy]-3-tert-butyl-1-(cyclohexanecarbonyl)-5-
(2-fluorophenyl)pyrrolidine-2-carboxylic acid Example 51A (33 mg, 0.053 mmol) was dissolved in methanol (0.5 mL). Lithium hydroxide (14 mg, 0.585 mmol) and water (0.500 mL) were added and a precipitate formed. Tetrahydrofuran (0.500 mL) was added and everything dissolved. The reaction was warmed at 45° C. overnight. The solvent was removed, and the reaction was acidified with 1M aqueous HCl (30 drops). The crude material was purified directly using a 12 g silica gel cartridge eluting with an ethyl acetate/ethanol/heptanes solvent system over 20 minutes to provide (2S,3R,4S,5S)-4-((5-bromo-2-methoxy-pyridin-3-yl)methoxy)-3-(tert-butyl)-1-(cyclohexanecarbonyl)-5-(2-fluorophenyl)pyrrolidine-2-carboxylic acid (29 mg, 0.049 mmol, 92% yield). $^1$H NMR (400 MHz, DMSO-$d_6$) δ ppm 8.13-8.03 (m, 1H), 8.01 (d, J=2.5 Hz, 1H), 7.29-7.17 (m, 1H), 7.13-7.04 (m, 1H), 7.05-6.95 (m, 1H), 6.94 (s, 1H), 5.42 (s, 1H), 4.47 (s, 1H), 4.32 (d, J=13.7 Hz, 1H), 4.27 (s, 1H), 3.99 (d, J=13.6 Hz, 1H), 3.80 (s, 3H), 2.60 (s, 1H), 1.79-1.63 (m, 3H), 1.62-1.48 (m, 2H), 1.34-1.20 (m, 3H), 1.20-1.04 (m, 2H), 1.01 (s, 9H), 0.93-0.79 (m, 2H); MS (APCI+) m/z 580 (M+H)$^+$.

Example 52

(2S,3R,4S,5S)-3-tert-butyl-1-(cyclohexanecarbonyl)-
5-(2-fluorophenyl)-4-[(2-methoxy-5-phenylpyridin-
3-yl)methoxy]pyrrolidine-2-carboxylic acid The title compound was prepared using the procedures described for Example 48 substituting 5-bromo-3-(bromomethyl)-2-methoxypyridine for 3-(bromomethyl)-2-methoxy-5-(trifluoromethyl)pyridine in Example 48D then following the procedures described in Example 38E-38F. $^1$H NMR (400 MHz, DMSO-$d_6$) δ ppm 8.21 (d, J=2.5 Hz, 1H), 8.08 (s, 1H), 7.48-7.39 (m, 4H), 7.37-7.30 (m, 1H), 7.22 (s, 1H), 7.14-7.06 (m, 1H), 7.06-6.98 (m, 1H), 6.98-6.89 (m, 1H), 5.44 (d, J=6.5 Hz, 1H), 4.49 (s, 1H), 4.40 (d, J=13.3 Hz, 1H), 4.31 (s, 1H), 4.09 (d, J=13.3 Hz, 1H), 3.86 (s, 3H), 2.63 (s, 1H), 1.77-1.61 (m, 3H), 1.61-1.46 (m, 2H), 1.34-1.20 (m, 2H), 1.19-1.06 (m, 2H), 1.01 (s, 9H), 0.91-0.78 (m, 2H); MS (APCI+) m/z 589 (M+H)$^+$.

Example 53

(2S,3R,4S,5S)-3-tert-butyl-4-[(5-cyclobutyl-2-
methoxypyridin-3-yl)methoxy]-1-(cyclohexanecar-
bonyl)-5-phenylpyrrolidine-2-carboxylic acid

Example 53A (2S,3R,4S,5S)-ethyl 4-((5-bromo-2-methoxypyridin-
3-yl)methoxy)-3-(tert-butyl)-1-(cyclohexanecarbo-
nyl)-5-phenylpyrrolidine-2-carboxylate The title compound was prepared according to the procedure described in Example 51A, substituting Example 41C for Example 48C. LC/MS (APCI+) m/z 603.0 (M+H)$^+$.

Example 53B (2S,3R,4S,5S)-3-tert-butyl-4-[(5-cyclobutyl-2-
methoxypyridin-3-yl)methoxy]-1-(cyclohexanecar-
bonyl)-5-phenylpyrrolidine-2-carboxylic acid In a 4 mL vial, Example 53A (50.0 mg, 0.083 mmol, 1.0 eq) and dichloro[4,5-dichloro-1,3-bis(2,6-Di-3-pentylphenyl)imidazol-2-ylidene](3-chloropyridyl)palladium(II) (PEPPSI-IPentCl, 7.15 mg, 0.0083 mmol, 0.1 eq) were dissolved in tetrahydrofuran (1.0 mL), flushed with nitrogen and stirred at room temperature. Cyclobutylzinc bromide (0.5 M, 498 μL, 0.25 mmol, 3.0 eq) was added and the reaction was stirred at room temperature for 30 minutes. The solvent was removed under a stream of nitrogen, and the crude material was reconstituted in 3:2 tetrahydrofuran/methanol (1.0 mL). LiOH monohydrate (34 mg, 0.83 mmol, 10 eq) in H$_2$O (300 μL) was added and reaction was stirred overnight at 45° C. The solvent was removed under a stream of nitrogen. The residue was acidified with 1 M aqueous HCl and was extracted with dichloromethane (3×2 mL). The solvent was removed and the crude material was reconstituted in acetonitrile. The reaction mixture was loaded directly into an injection loop and purified using prep LC method TFA8 to provide the title compound (23.8 mg, 43.0% yield). $^1$H NMR (400 MHz, 120° C., DMSO-$d_6$: D$_2$O=9:1 (v/v)) δ ppm 7.76 (d, J=2.5 Hz, 1H), 7.65 (d, J=7.2 Hz, 2H), 7.29-7.15 (m, 3H), 6.92 (d, J=2.4 Hz, 1H), 5.19 (d, J=6.4 Hz, 1H), 4.50 (d, J=3.2 Hz, 1H), 4.30-4.16 (m, 2H), 3.90 (d, J=13.1 Hz, 1H), 3.76 (s, 3H), 3.40-3.27 (m, 1H), 2.29-2.19 (m, 3H), 2.03-1.80 (m, 4H), 1.67-1.60 (m, 2H), 1.50-1.45 (m, 2H), 0.98 (s, 15H), 0.90-0.50 (m, 1H); MS (APCI+) m/z 549.1 (M+H)$^+$.

Example 54

(2S,3R,4S,5S)-3-tert-butyl-1-(cyclohexanecarbonyl)-
4-[(5-cyclopentyl-2-methoxypyridin-3-yl)methoxy]-
5-phenylpyrrolidine-2-carboxylic acid In a 4 mL vial, Example 53A (50.0 mg, 0.083 mmol, 1.0 eq) and dichloro[4,5-dichloro-1,3-bis(2,6-Di-3-pentylphenyl)imidazol-2-ylidene](3-chloropyridyl)palladium(II) (PEPPSI-IPentCl, 7.15 mg, 0.0083 mmol, 0.1 eq) were dissolved in tetrahydrofuran (1.0 mL), flushed with nitrogen, and stirred at room temperature. Cyclopentylzinc bromide (0.5 M, 498 µL, 0.25 mmol, 3.0 eq) was added and reaction was stirred at room temperature for 30 minutes. The solvent was removed under a stream of nitrogen, and the crude material was reconstituted in 3:2 tetrahydrofuran/methanol (1.0 mL). LiOH monohydrate (34 mg, 0.83 mmol, 10 eq) in H$_2$O (300 µL) was added and reaction was stirred overnight at 45° C. The solvent was removed under a stream of nitrogen. The residue was acidified with 1 M aqueous HCl and extracted with dichloromethane (3×2 mL). The solvent was removed and the crude material was reconstituted in acetonitrile. The reaction was loaded directly into an injection loop and purified using prep LC method TFA8 to provide the title compound (36.0 mg, 64.0% yield). $^1$H NMR (400 MHz, 120° C., DMSO-d$_6$:D$_2$O=9:1 (v/v)) δ ppm 7.78 (d, J=2.4 Hz, 1H), 7.64 (d, J=7.3 Hz, 2H), 7.28-7.13 (m, 3H), 6.90 (d, J=2.4 Hz, 1H), 5.19 (d, J=6.3 Hz, 1H), 4.49 (d, J=3.3 Hz, 1H), 4.25-4.16 (m, 2H), 3.90 (d, J=13.0 Hz, 1H), 3.76 (s, 3H), 2.88-2.74 (m, 1H), 2.50-2.46 (m, 1H), 2.29-2.13 (m, 1H), 1.95-1.87 (m, 2H), 1.81-1.70 (m, 2H), 1.68-1.59 (m, 4H), 1.50-1.45 (m, 2H), 1.46-1.30 (m, 2H), 1.27-1.03 (m, 5H), 0.98 (s, 9H), 0.81-0.56 (m, 1H); MS (APCI+) m/z 563.1 (M+H)$^+$.

Example 55

(2S,3R,4S,5S)-4-{[5-(bicyclo[2.2.1]heptan-2-yl)-2-methoxypyridin-3-yl]methoxy}-3-tert-butyl-1-(cyclohexanecarbonyl)-5-phenylpyrrolidine-2-carboxylic acid In a 4 mL vial, Example 53A (50.0 mg, 0.083 mmol, 1.0 eq) and dichloro[4,5-dichloro-1,3-bis(2,6-Di-3-pentylphenyl)imidazol-2-ylidene](3-chloropyridyl)palladium(II) (PEPPSI-IPentCl, 7.15 mg, 0.0083 mmol, 0.1 eq) were dissolved in tetrahydrofuran (1.0 mL), flushed with nitrogen and stirred at room temperature. exo-2-Norbornylzinc bromide (0.5 M, 498 µL, 0.25 mmol, 3.0 eq) was added and reaction was stirred at room temperature for 30 minutes. The solvent was removed under a stream of nitrogen, and reconstituted in 3:2 tetrahydrofuran/methanol (1.0 mL). LiOH monohydrate (34 mg, 0.83 mmol, 10 eq) in H$_2$O (300 µL) was added and reaction was stirred overnight at 45° C. The solvent was removed under a stream of nitrogen. The residue was acidified with 1 M aqueous HCl and was extracted with dichloromethane (3×2 mL). The solvent was removed and the crude material was reconstituted in acetonitrile. The reaction mixture was loaded directly into an injection loop and purified using prep LC method TFA8 to provide the title compound (25.9 mg, 44% yield). $^1$H NMR (400 MHz, 120° C., DMSO-d$_6$:D$_2$O=9:1 (v/v)) δ ppm 7.80-7.73 (m, 1H), 7.67-7.61 (m, 2H), 7.29-7.10 (m, 3H), 6.94-6.84 (m, 1H), 5.19 (d, J=6.4 Hz, 1H), 4.51-4.44 (m, 1H), 4.28-4.16 (m, 2H), 3.94-3.86 (m, 1H), 3.79-3.73 (m, 3H), 3.01-2.93 (m, 1H), 2.49 (s, 1H), 2.35-2.08 (m, 3H), 1.68-1.60 (m, 2H), 1.60-1.36 (m, 5H), 1.34-1.03 (m, 9H), 1.00-0.95 (m, 10H), 0.88-0.54 (m, 1H); MS (APCI+) m/z 589.1 (M+H)$^+$.

Example 56

(2S,3R,4S,5S)-3-tert-butyl-4-[(5-cyclobutyl-2-methoxypyridin-3-yl)methoxy]-1-(cyclohexanecarbonyl)-5-(2-fluorophenyl)pyrrolidine-2-carboxylic acid The title compound was prepared according to the procedure described in Example 53, substituting Example 51A for Example 53A. $^1$H NMR (400 MHz, 120° C., DMSO-d$_6$:D$_2$O=9:1 (v/v)) δ ppm 7.97-7.92 (m, 1H), 7.77 (d, J=2.4 Hz, 1H), 7.27-7.22 (m, 1H), 7.12-6.98 (m, 2H), 6.89 (s, 1H), 5.42 (d, J=6.3 Hz, 1H), 4.54 (d, J=2.9 Hz, 1H), 4.34-4.20 (m, 2H), 4.00 (d, J=13.0 Hz, 1H), 3.77 (s, 3H), 3.39-3.26 (m, 1H), 2.54 (s, 1H), 2.23 (s, 2H), 2.02-1.80 (m, 4H), 1.74-1.60 (m, 2H), 1.58-1.45 (m, 2H), 1.32-1.04 (m, 5H), 1.01-0.96 (m, 10H), 0.86-0.67 (m, 1H); MS (APCI+) m/z 567.1 (M+H)$^+$.

Example 57

(2S,3R,4S,5S)-3-tert-butyl-1-(cyclohexanecarbonyl)-4-[(5-cyclopentyl-2-methoxypyridin-3-yl)methoxy]-5-(2-fluorophenyl)pyrrolidine-2-carboxylic acid The title compound was prepared according to the procedure described in Example 54, substituting Example 51A for Example 53A. $^1$H NMR (400 MHz, 120° C., DMSO-d$_6$:D$_2$O=9:1 (v/v)) δ ppm 7.93 (s, 1H), 7.79 (d, J=2.5 Hz, 1H), 7.26-7.19 (m, 1H), 7.11-6.98 (m, 2H), 6.90-6.85 (m, 1H), 5.42 (d, J=6.3 Hz, 1H), 4.53 (d, J=2.9 Hz, 1H), 4.34-4.21 (m, 2H), 3.99 (d, J=13.0 Hz, 1H), 3.76 (s, 3H), 2.87-2.73 (m, 1H), 2.53 (s, 1H), 2.17 (s, 1H), 1.91-1.86 (m, 2H), 1.80-1.59 (m, 6H), 1.55-1.50 (m, 2H), 1.43-1.03 (m, 7H), 0.98 (s, 9H), 0.88-0.59 (m, 1H); MS (APCI+) m/z 581.1 (M+H)$^+$.

Example 58

(2S,3R,4S,5S)-4-{[5-(bicyclo[2.2.1]heptan-2-yl)-2-methoxypyridin-3-yl]methoxy}-3-tert-butyl-1-(cyclohexanecarbonyl)-5-(2-fluorophenyl)pyrrolidine-2-carboxylic acid The title compound was prepared according to the procedure described in Example 55, substituting Example 51A for Example 53A. $^1$H NMR (400 MHz, 120° C., DMSO-d$_6$:D$_2$O=9:1 (v/v)) δ ppm 8.00-7.89 (m, 1H), 7.82-7.73 (m, 1H), 7.25-7.20 (m, 1H), 7.10-7.00 (m, 2H), 6.87 (d, J=17.2 Hz, 1H), 5.42 (d, J=6.2 Hz, 1H), 4.55-4.48 (m, 1H), 4.34-4.19 (m, 2H), 4.04-3.94 (m, 1H), 3.80-3.74 (m, 3H), 3.04-2.90 (m, 1H), 2.53 (s, 1H), 2.34-2.06 (m, 3H), 1.78-1.59 (m, 3H), 1.59-0.92 (m, 23H), 0.82 (s, 1H); MS (APCI+) m/z 607.1 (M+H)$^+$.

Example 59

(2S,3R,4S,5S)-3-tert-butyl-1-(cyclohexanecarbonyl)-5-(2-fluorophenyl)-4-{[2-methoxy-5-(pyrrolidin-1-yl)pyridin-3-yl]methoxy}pyrrolidine-2-carboxylic acid In a 4 mL vial, (2S,3R,4S,5S)-ethyl 4-((5-bromo-2-methoxypyridin-3-yl)methoxy)-3-(tert-butyl)-1-(cyclohexanecarbonyl)-5-(2-fluorophenyl)pyrrolidine-2-carboxylate (Example 51A, 0.050 g, 0.081 mmol), sodium tert-butoxide (0.039 g, 0.404 mmol), and RuPhos palladacycle (0.012 g, 0.016 mmol) were treated with dioxane (1.6 mL) and pyrrolidine (0.01 mL, 0.121 mmol). The vial was sealed with a screw cap, and the reaction was placed in a preheated heating block and stirred at 85° C. overnight. The reaction mixture was then concentrated in vacuo, and the residue was purified by reverse-phase HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A) to provide the title compound, 0.0024 g (5% yield). $^1$H NMR (400 MHz, DMSO-d$_6$) δ ppm 7.98 (s, 1H), 7.30-7.16 (m, 2H), 7.04 (m, 2H), 6.45 (d, J=3.0 Hz, 1H), 5.42 (m, 1H), 4.54 (d, J=2.9 Hz, 1H), 4.29-4.26 (m, 2H), 4.04-3.92 (m, 1H), 3.71 (s, 3H), 3.05 (m, 4H), 2.55 (m, 1H), 2.20 (m, 1H), 1.93 (m, 4H), 1.75-1.06 (m, 10H), 1.00 (s, 9H); MS (ESI$^+$) m/z 582.1 (M+H)$^+$.

Example 60

(2S,3R,4S,5S)-3-tert-butyl-4-[(5-tert-butyl-2-methoxypyridin-3-yl)methoxy]-1-(cyclohexanecarbonyl)-5-phenylpyrrolidine-2-carboxylic acid The title compound was prepared according to the procedure described in Example 41D, substituting 3-(bromomethyl)-5-(tert-butyl)-2-methoxypyridine for 3-(bromomethyl)-2-methoxy-5-(trifluoromethyl)pyridine. $^1$H NMR (400 MHz, DMSO-d$_6$) δ ppm 7.94 (d, J=3.5 Hz, 1H), 7.68 (d, J=7.5 Hz, 2H), 7.30-7.10 (m, 4H), 5.21 (d, J=6.4 Hz, 1H), 4.47 (d, J=3.5 Hz, 1H), 4.23 (dd, J=11.2, 5.5 Hz, 2H), 3.91 (d, J=13.0 Hz, 1H), 3.77 (s, 3H), 2.5 (m, 1H), 2.24 (s, 1H), 1.65 (d, J=9.8 Hz, 2H), 1.49 (s, 2H), 1.25 (d, J=10.0 Hz, 2H), 1.21 (s, 9H), 1.08 (td, J=10.1, 9.5, 4.0 Hz, 3H), 0.99 (s, 9H), 0.87-0.82 (m, 1H); MS (ESI-) m/z 549.3 (M-H)$^-$.

Example 61

(2S,3R,4S,5S)-3-tert-butyl-4-[(5-tert-butyl-2-methoxypyridin-3-yl)methoxy]-1-[(1R,3R)-3-methoxycyclohexane-1-carbonyl]-5-phenylpyrrolidine-2-carboxylic acid The title compound was prepared according to the procedure described in Example 31 substituting 3-(bromomethyl)-5-(tert-butyl)-2-methoxypyridine for 2-(bromomethyl)-1-methoxy-4-(trifluoromethyl)benzene in Example 31D. $^1$H NMR (400 MHz, DMSO-d$_6$) δ ppm 7.93 (d, J=2.7 Hz, 1H), 7.69 (d, J=7.4 Hz, 2H), 7.21 (t, J=7.1 Hz, 2H), 7.15 (d, J=2.8 Hz, 2H), 5.15 (d, J=6.6 Hz, 1H), 4.41 (s, 1H), 4.23 (d, J=13.0 Hz, 1H), 3.97-3.87 (m, 1H), 3.78 (s, 3H), 3.44 (s, 1H), 3.20 (s, 3H), 2.73-2.61 (m, 1H), 2.56 (s, 1H), 1.85-1.72 (m, 1H), 1.68-1.56 (m, 1H), 1.48-1.38 (m, 1H), 1.28-1.24 (m, 2H), 1.20 (s, 9H), 1.19-1.04 (m, 2H), 0.99 (s, 9H), 0.89-0.78 (m, 2H); MS (APCI+) m/z 581 (M+H)$^+$.

Example 62

(2S,3R,4S,5S)-3-tert-butyl-4-[(5-tert-butyl-2-methoxypyridin-3-yl)methoxy]-1-(cyclohexanecarbonyl)-5-(2-fluorophenyl)pyrrolidine-2-carboxylic acid The title compound was prepared using the procedures described for Example 48 substituting 3-(bromomethyl)-5-(tert-butyl)-2-methoxypyridine for 3-(bromomethyl)-2-methoxy-5-(trifluoromethyl)pyridine in Example 48D. $^1$H NMR (400 MHz, DMSO-d$_6$) δ ppm 8.20 (s, 1H), 7.94 (d, J=2.7 Hz, 1H), 7.18 (s, 1H), 7.12 (s, 1H), 7.02 (s, 2H), 5.45 (s, 1H), 4.40 (s, 1H), 4.30 (d, J=13.0 Hz, 1H), 4.24 (s, 1H), 4.11-3.99 (m, 1H), 3.78 (s, 3H), 2.65 (s, 1H), 1.68 (d, J=11.2 Hz, 2H), 1.55 (s, 2H), 1.29-1.23 (m, 3H), 1.18 (s, 9H), 1.15-1.07 (m, 2H), 0.98 (s, 9H), 0.89-0.81 (m, 2H); MS (APCI+) m/z 569 (M+H)$^+$.

Example 63

(2S,3R,4S,5S)-3-tert-butyl-4-[(5-tert-butyl-2-methoxypyridin-3-yl)methoxy]-5-phenyl-1-{[(propan-2-yl)oxy]carbonyl}pyrrolidine-2-carboxylic acid The title compound was prepared using the procedures described for Example 38A-38D and Example 38F substituting 3-(bromomethyl)-5-(tert-butyl)-2-methoxypyridine for 4-bromo-2-(bromomethyl)-1-methoxybenzene in Example 38D. $^1$H NMR (400 MHz, DMSO-d$_6$) δ ppm 7.93 (d, J=2.6 Hz, 1H), 7.70-7.65 (m, 2H), 7.21-7.06 (m, 4H), 4.98 (d, J=6.6 Hz, 1H), 4.62 (p, J=6.2 Hz, 1H), 4.24-4.18 (m, 2H), 4.16 (dd, J=6.7, 3.2 Hz, 1H), 3.93-3.87 (m, 1H), 3.77 (s, 3H), 2.55 (t, J=3.4 Hz, 1H), 1.20 (s, 9H), 1.07 (d, J=6.2 Hz, 3H), 0.98 (s, 9H), 0.88 (d, J=6.2 Hz, 3H); MS (APCI+) m/z 527 (M+H)$^+$.

Example 64

(2S,3R,4S,5S)-3-tert-butyl-4-{[2-methoxy-5-(trifluoromethyl)pyridin-3-yl]methoxy}-5-phenyl-1-{[(propan-2-yl)oxy]carbonyl}pyrrolidine-2-carboxylic acid

Example 64A (2S,3R,4S,5S)-2-ethyl 1-isopropyl 3-(tert-butyl)-4-((2-methoxy-5-(trifluoromethyl)pyridin-3-yl)methoxy)-5-phenylpyrrolidine-1,2-dicarboxylate Example 38C (37 mg, 0.098 mmol) and 3-(bromomethyl)-2-methoxy-5-(trifluoromethyl)pyridine (47.6 mg, 0.176 mmol) were dissolved in dry dimethylformamide (0.5 mL). After cooling in an ice bath, potassium 2-methylpropan-2-olate (0.157 mL, 0.157 mmol) solution was added dropwise over 2 minutes. LC/MS showed desired product. The mixture was acidified with 1M aqueous HCl (10 drops) and warmed to room temperature. The mixture was concentrated and loaded onto a 12 g silica gel column and eluted with 5-100% ethyl acetate/heptanes over 20 minutes to provide (2S,3R,4S,5S)-2-ethyl 1-isopropyl 3-(tert-butyl)-4-((2-methoxy-5-(trifluoromethyl)pyridin-3-yl)methoxy)-5-phenylpyrrolidine-1,2-dicarboxylate (52 mg, 0.092 mmol, 94% yield). $^1$H NMR (400 MHz, DMSO-d$_6$) δ ppm 8.28 (s, 1H), 7.58-7.53 (m, 2H), 7.22 (d, J=2.3 Hz, 1H), 7.17 (dd, J=8.2, 6.6 Hz, 2H), 7.13-7.07 (m, 1H), 5.02 (d, J=6.1 Hz, 1H), 4.64 (pd, J=6.2, 0.9 Hz, 1H), 4.37 (d, J=3.1 Hz, 1H), 4.30-4.24 (m, 2H), 4.16-4.03 (m, 2H), 3.87 (d, J=0.9 Hz, 3H), 2.87-2.81 (m, 2H), 1.15 (td, J=7.1, 0.9 Hz, 3H), 1.05 (d, J=6.2 Hz, 3H), 1.01 (d, J=0.9 Hz, 9H), 0.90 (d, J=6.2 Hz, 3H); MS (APCI+) m/z 567 (M+H)$^+$.

Example 64B (2S,3R,4S,5S)-3-tert-butyl-4-{[2-methoxy-5-(trifluoromethyl)pyridin-3-yl]methoxy}-5-phenyl-1-{[(propan-2-yl)oxy]carbonyl}pyrrolidine-2-carboxylic acid Example 64A (52 mg, 0.092 mmol) was dissolved in methanol (0.5 mL) and a 2M aqueous solution of lithium hydroxide (0.459 mL, 0.918 mmol) was added. The reaction was warmed at 45° C. overnight, acidified with 2M aqueous HCl (0.460 mL), and concentrated. The residue was loaded onto a 12 g silica gel column and eluted with 5-100% ethyl acetate/ethanol/heptanes over 20 minutes to provide (2S,3R, 4S,5S)-3-(tert-butyl)-1-(isopropoxycarbonyl)-4-((2-methoxy-5-(trifluoromethyl)pyridin-3-yl)methoxy)-5-phenylpyrrolidine-2-carboxylic acid (22 mg, 0.041 mmol, 44.5% yield). $^1$H NMR (400 MHz, DMSO-d$_6$) δ ppm 7.68-7.62 (m, 2H), 7.20-7.16 (m, 2H), 7.16-7.12 (m, 2H), 7.13-7.05 (m, 1H), 5.00 (d, J=6.5 Hz, 1H), 4.63 (p, J=6.2 Hz, 1H), 4.30 (d, J=14.0 Hz, 1H), 4.26 (d, J=3.1 Hz, 1H), 4.21 (dd, J=6.5, 2.5 Hz, 1H), 3.93 (d, J=13.9 Hz, 1H), 3.88 (s, 3H), 2.55 (t, J=2.8 Hz, 1H), 1.06 (d, J=6.2 Hz, 3H), 1.00 (s, 9H), 0.89 (d, J=6.2 Hz, 3H); MS (APCI+) m/z 539 (M+H)$^+$.

Example 65

(2S,3R,4S,5S)-3-tert-butyl-4-{[5-(2-fluoro-4-methyl-phenyl)-2-methoxypyridin-3-yl]methoxy}-5-phenyl-1-{[(propan-2-yl)oxy]carbonyl}pyrrolidine-2-carboxylic acid Example 40A (25 mg, 0.043 mmol, 1.0 eq) and PdCl$_2$(dppf) ([1,1'-bis(diphenylphosphino)ferrocene]dichloropalladium(II), 3.2 mg, 0.0043 mmol, 0.1 eq) suspended in 500 L dioxane was placed under a nitrogen atmosphere. (2-Fluoro-4-methylphenyl)boronic acid (0.4 M, 215 µL, 0.086 mmol, 2.0 eq) was added and the mixture was stirred at room temperature for 5 minutes. Cs$_2$CO$_3$ (1 M, 129 µL, 0.129 mmol, 3.0 eq) was added and reaction mixture was heated to 100° C. for 1 hour. The solvent was removed under a stream of nitrogen, and the residue was reconstituted in 500 µL 3:2 tetrahydrofuran/methanol. LiOH monohydrate (20 mg/100 uL) was added and reaction was stirred at 45° C. overnight. The solvent was removed under a stream of nitrogen. The residue was acidified with 1 M aqueous HCl and extracted with dichloromethane (3×1 mL). The reaction was loaded directly into an injection loop and purified using prep LC method TFA8 to provide the title compound (12.8 mg, 33% yield). $^1$H NMR (400 MHz, 120° C., DMSO-d$_6$:D$_2$O=9:1 (v/v)) δ ppm 8.10-8.04 (m, 1H), 7.53 (d, J=7.5 Hz, 2H), 7.22-6.95 (m, 7H), 4.97 (d, J=6.3 Hz, 1H), 4.62 (p, J=6.2 Hz, 1H), 4.31 (d, J=3.1 Hz, 1H), 4.26 (d, J=13.2 Hz, 1H), 4.20 (dd, J=6.2, 2.5 Hz, 1H), 3.93 (d, J=13.1 Hz, 1H), 3.83 (s, 3H), 2.49-2.45 (m, 1H), 2.37 (s, 3H), 1.04 (d, J=6.2 Hz, 3H), 0.99 (s, 9H), 0.87 (d, J=6.1 Hz, 3H); MS (APCI+) m/z 579.0 (M+H)$^+$.

Example 66

(2S,3R,4S,5S)-3-tert-butyl-4-{[5-(2-fluorophenyl)-2-methoxypyridin-3-yl]methoxy}-5-phenyl-1-{[(propan-2-yl)oxy]carbonyl}pyrrolidine-2-carboxylic acid The title compound was prepared according to the procedure described in Example 65 substituting 2-(2-fluorophenyl)-4,4,5,5-tetramethyl-1,3,2-dioxaborolane for (2-fluoro-4-methylphenyl)boronic acid. $^1$H NMR (400 MHz, 120° C., DMSO-d$_6$:D$_2$O=9:1 (v/v)) δ ppm 8.09 (s, 1H), 7.53 (d, J=7.9 Hz, 2H), 7.44-7.36 (m, 1H), 7.34-7.19 (m, 3H), 7.17-7.11 (m, 1H), 7.08 (t, J=7.6 Hz, 2H), 6.97 (t, J=7.4 Hz, 1H), 4.97 (d, J=6.3 Hz, 1H), 4.62 (p, J=6.3 Hz, 1H), 4.31 (d, J=3.1 Hz, 1H), 4.27 (d, J=13.3 Hz, 1H), 4.21 (dd, J=6.3, 2.4 Hz, 1H), 3.95 (d, J=13.3 Hz, 1H), 3.84 (s, 3H), 2.50-2.46 (m, 1H), 1.04 (d, J=6.2 Hz, 3H), 0.99 (s, 9H), 0.87 (d, J=6.2 Hz, 3H); MS (APCI+) m/z 565.1 (M+H)$^+$.

Example 67

(2S,3R,4S,5S)-3-tert-butyl-4-{[5-(4-fluoro-2-methyl-phenyl)-2-methoxypyridin-3-yl]methoxy}-5-phenyl-1-{[(propan-2-yl)oxy]carbonyl}pyrrolidine-2-carboxylic acid The title compound was prepared according to the procedure described in Example 65 substituting 2-(4-fluoro-2-methylphenyl)-4,4,5,5-tetramethyl-1,3,2-dioxaborolane for (2-fluoro-4-methylphenyl)boronic acid. $^1$H NMR (400 MHz, 120° C., DMSO-d$_6$:D$_2$O=9:1 (v/v)) δ ppm 7.86-7.80 (m, 1H), 7.54-7.47 (m, 2H), 7.12-6.97 (m, 5H), 6.97-6.89 (m, 1H), 6.89-6.84 (m, 1H), 4.96 (d, J=6.1 Hz, 1H), 4.61 (hept, J=6.0 Hz, 1H), 4.30 (d, J=3.1 Hz, 1H), 4.27 (d, J=13.5 Hz, 1H), 4.19 (dd, J=6.3, 2.4 Hz, 1H), 3.96-3.89 (m, 1H), 3.83 (s, 3H), 2.46 (s, 1H), 2.10 (s, 3H), 1.04 (d, J=6.2 Hz, 3H), 0.99 (s, 9H), 0.87 (d, J=6.2 Hz, 3H); MS (APCI+) m/z 579.0 (M+H)$^+$.

Example 68

(2S,3R,4S,5S)-3-tert-butyl-4-{[5-(2,4-difluorophenyl)-2-methoxypyridin-3-yl]methoxy}-5-phenyl-1-{[(propan-2-yl)oxy]carbonyl}pyrrolidine-2-carboxylic acid The title compound was prepared according to the procedure described in Example 65 substituting 2-(2,4-difluorophenyl)-4,4,5,5-tetramethyl-1,3,2-dioxaborolane for (2-fluoro-4-methylphenyl)boronic acid. $^1$H NMR (400 MHz, 120° C., DMSO-d$_6$:D$_2$O=9:1 (v/v)) δ ppm 8.09-8.00 (m, 1H), 7.53 (d, J=7.8 Hz, 2H), 7.38-7.27 (m, 1H), 7.21-7.04 (m, 5H), 7.02-6.94 (m, 1H), 4.97 (d, J=6.2 Hz, 1H), 4.61 (h, J=6.3 Hz, 1H), 4.32 (d, J=3.1 Hz, 1H), 4.27 (d, J=13.1 Hz, 1H), 4.20 (dd, J=6.3, 2.2 Hz, 1H), 3.94 (d, J=13.4 Hz, 1H), 3.84 (s, 3H), 2.49-2.45 (m, 1H), 1.04 (d, J=6.2 Hz, 3H), 0.99 (s, 9H), 0.87 (d, J=6.2 Hz, 3H); MS (APCI+) m/z 583.0 (M+H)$^+$.

Example 69

(2S,3R,4S,5S)-3-tert-butyl-4-{[5-(3,6-dihydro-2H-pyran-4-yl)-2-methoxypyridin-3-yl]methoxy}-5-phenyl-1-{[(propan-2-yl)oxy]carbonyl}pyrrolidine-2-carboxylic acid The title compound was prepared according to the procedure described in Example 65 substituting 2-(3,6-dihydro-2H-pyran-4-yl)-4,4,5,5-tetramethyl-1,3,2-dioxaborolane for (2-fluoro-4-methylphenyl)boronic acid. $^1$H NMR (400 MHz, 120° C., DMSO-d$_6$:D$_2$O=9:1 (v/v)) δ ppm 7.96 (d, J=2.6 Hz, 1H), 7.60-7.52 (m, 2H), 7.22-7.05 (m, 4H), 5.97-5.90 (m, 1H), 4.97 (d, J=6.2 Hz, 1H), 4.63 (hept, J=12.5 Hz, 1H), 4.32 (d, J=3.0 Hz, 1H), 4.26-4.16 (m, 4H), 3.85 (d, J=12.7 Hz, 1H), 3.85-3.76 (m, 5H), 2.48-2.46 (m, 1H), 2.34-2.26 (m, 2H), 1.05 (d, J=6.2 Hz, 3H), 0.99 (s, 9H), 0.88 (d, J=6.2 Hz, 3H); MS (APCI+) m/z 533.1 (M+H)$^+$.

Example 70

(2S,3R,4S,5S)-3-tert-butyl-4-{[2-methoxy-5-(3-methoxyphenyl)pyridin-3-yl]methoxy}-5-phenyl-1-{[(propan-2-yl)oxy]carbonyl}pyrrolidine-2-carboxylic acid The title compound was prepared according to the procedure described in Example 65 substituting 2-(3-methoxyphenyl)-4,4,5,5-tetramethyl-1,3,2-dioxaborolane for (2-fluoro-4-methylphenyl)boronic acid. $^1$H NMR (400 MHz, 120° C., DMSO-d$_6$:D$_2$O=9:1 (v/v)) δ ppm 8.19 (d, J=2.6 Hz, 1H), 7.61-7.54 (m, 2H), 7.41-7.30 (m, 1H), 7.28 (d, J=2.6 Hz, 1H), 7.14 (t, J=7.5 Hz, 2H), 7.10-6.97 (m, 3H), 6.93 (ddd, J=8.3, 2.5, 0.9 Hz, 1H), 4.99 (d, J=6.2 Hz, 1H), 4.63 (p, J=6.1 Hz, 1H), 4.33 (d, J=3.1 Hz, 1H), 4.28 (d, J=13.2 Hz, 1H), 4.23 (dd, J=6.2, 2.4 Hz, 1H), 3.98-3.91 (m, 1H), 3.85 (s, 3H), 3.84 (s, 3H), 2.56-2.50 (m, 1H), 1.05 (d, J=6.2 Hz, 3H), 0.97 (s, 9H), 0.88 (d, J=6.2 Hz, 3H); MS (APCI+) m/z 577.0 (M+H)$^+$.

Example 71

(2S,3R,4S,5S)-3-tert-butyl-4-{[2-methoxy-5-(4-methylphenyl)pyridin-3-yl]methoxy}-5-phenyl-1-{[(propan-2-yl)oxy]carbonyl}pyrrolidine-2-carboxylic acid The title compound was prepared according to the procedure described in Example 65 substituting 4,4,5,5-tetramethyl-2-(p-tolyl)-1,3,2-dioxaborolane for (2-fluoro-4-methylphenyl)boronic acid. $^1$H NMR (400 MHz, 120° C., DMSO-d$_6$:D$_2$O=9:1 (v/v)) δ ppm 8.16 (d, J=2.5 Hz, 1H), 7.61-7.54 (m, 2H), 7.36-7.29 (m, 2H), 7.29-7.20 (m, 3H), 7.14 (d, J=7.8 Hz, 2H), 7.11-7.03 (m, 1H), 5.00 (d, J=6.2 Hz, 1H), 4.64 (h, J=6.1 Hz, 1H), 4.33 (d, J=3.0 Hz, 1H), 4.28 (d, J=13.2 Hz, 1H), 4.23 (dd, J=6.2, 2.3 Hz, 1H), 3.95 (d, J=13.6 Hz, 1H), 3.83 (s, 3H), 2.52-2.50 (m, 1H), 2.37-2.32 (m, 3H), 1.05 (d, J=6.2 Hz, 3H), 1.00 (s, 9H), 0.88 (d, J=6.2 Hz, 3H); MS (APCI+) m/z 561.0 (M+H)$^+$.

Example 72

(2S,3R,4S,5S)-3-tert-butyl-4-[(6-tert-butyl-2-methoxypyridin-3-yl)methoxy]-5-phenyl-1-{[(propan-2-yl)oxy]carbonyl}pyrrolidine-2-carboxylic acid The title compound was prepared using the procedures described for Example 38A-38D and Example 38F substituting 3-(bromomethyl)-6-(tert-butyl)-2-methoxypyridine for 4-bromo-2-(bromomethyl)-1-methoxybenzene in Example 38D. $^1$H NMR (400 MHz, DMSO-d$_6$) δ ppm 7.60-7.54 (m, 2H), 7.23-7.07 (m, 3H), 6.96-6.90 (m, 1H), 6.69 (d, J=7.6 Hz, 1H), 4.95 (d, J=6.3 Hz, 1H), 4.62 (p, J=6.2 Hz, 1H), 4.26 (d, J=3.3 Hz, 1H), 4.17-4.08 (m, 2H), 3.84 (dd, J=12.9, 1.0 Hz, 1H), 3.78 (s, 3H), 2.45-2.41 (m, 1H), 1.24 (s, 9H), 1.05 (d, J=6.2 Hz, 3H), 0.97 (s, 9H), 0.88 (d, J=6.3 Hz, 3H); MS (ESI+) m/z 527 (M+H)$^+$.

Example 73

(2S,3R,4S,5S)-3-tert-butyl-5-(2-fluorophenyl)-4-{[2-methoxy-5-(trifluoromethyl)pyridin-3-yl]methoxy}-1-{[(propan-2-yl)oxy]carbonyl}pyrrolidine-2-carboxylic acid Example 73A (2S,3R,4S,5S)-2-ethyl 1-isopropyl 3-(tert-butyl)-5-(2-fluorophenyl)-4-nitropyrrolidine-1,2-dicarboxylate Core 6 (1.042 g, 3.08 mmol) was dissolved in toluene (6.16 mL) and triethylamine (1.073 mL, 7.70 mmol) was added, followed by the slow addition of isopropyl carbonochloridate (1.848 mL, 3.70 mmol) solution after cooling in an ice-water bath to ~10° C. The addition was at such a rate that the temperature was maintained at or below room temperature during the addition (2-3 minutes). After the addition was complete, the reaction mixture was removed from the water bath and stirred at room temperature for 45 minutes. The mixture was diluted with ethyl acetate and stirred with saturated aqueous sodium bicarbonate for 20 minutes. The layers were separated, and the organic layer was washed with 1M aqueous HCl and brine, dried over sodium sulfate, filtered and concentrated. The crude material was purified using a 40 g silica gel cartridge with a gradient of 5-100% ethyl acetate/heptanes over 40 minutes to provide (2S,3R,4S,5S)-2-ethyl 1-isopropyl 3-(tert-butyl)-5-(2-fluorophenyl)-4-nitropyrrolidine-1,2-dicarboxylate (1.176 g, 2.77 mmol, 90% yield). $^1$H NMR (400 MHz, DMSO-d$_6$) δ ppm 7.81 (td, J=7.7, 1.8 Hz, 1H), 7.34-7.24 (m, 1H), 7.16-6.99 (m, 2H), 5.66 (d, J=8.8 Hz, 1H), 5.55 (dd, J=8.8, 3.6 Hz, 1H), 4.68 (dt, J=12.5, 6.2 Hz, 1H), 4.50 (d, J=4.1 Hz, 1H), 4.25 (q, J=7.1 Hz, 2H), 3.10-3.02 (m, 1H), 1.29 (t, J=7.1 Hz, 3H), 1.08 (d, J=6.2 Hz, 3H), 1.01 (s, 9H), 0.93 (d, J=6.2 Hz, 3H); MS (ESI+) m/z 425 (M+H)$^+$.

Example 73B (2S,3R,5S)-2-ethyl 1-isopropyl 3-(tert-butyl)-5-(2-fluorophenyl)-4-oxopyrrolidine-1,2-dicarboxylate Example 73A (1.080 g, 2.54 mmol) was dissolved in ethanol (22 mL) and the solution was heated to 75° C. A separate solution of CrCl$_2$ was prepared by dissolving pyridinium dichromate (2.393 g, 6.36 mmol) in 6M aqueous hydrochloric acid (22 mL) and adding Zn (2.39 g, 6.36 mmol) (in portions while cooling in an ice bath-large exotherms). The suspension was stirred at room temperature for 30 minutes after removing from the ice bath, and the solution remained cloudy. Additional 6M aqueous hydrochloric acid (22 mL) was added and the suspension was stirred for another 30 minutes, resulting in a clear brilliant blue solution. The CrCl$_2$ solution was transferred via cannula/addition funnel over 20 minutes to the solution of starting material, and the mixture was heated for 16 hours, and allowed to cool to room temperature. The mixture was poured into a separatory funnel and extracted with 3×250 mL of dichloromethane. The solvent was removed in vacuo and the crude material was chromatographed using a 40 g silica gel cartridge with a gradient of 5-100% ethyl acetate/heptanes to provide (2S,3R,5S)-2-ethyl 1-isopropyl 3-(tert-butyl)-5-(2-fluorophenyl)-4-oxopyrrolidine-1,2-dicarboxylate (0.409 g, 1.040 mmol, 40.9% yield). $^1$H NMR (400 MHz, DMSO-d$_6$) δ ppm 7.64 (td, J=7.6, 1.8 Hz, 1H), 7.32 (tdd, J=7.3, 5.3, 1.8 Hz, 1H), 7.21-7.02 (m, 2H), 5.16 (s, 1H), 4.73 (hept, J=5.9 Hz, 1H), 4.62 (d, J=4.2 Hz, 1H), 4.19 (qd, J=7.1, 1.6 Hz, 2H), 2.64 (dd, J=4.3, 1.0 Hz, 1H), 1.22 (t, J=7.1 Hz, 3H), 1.12 (d, J=6.2 Hz, 3H), 1.06 (s, 9H), 0.97 (d, J=6.3 Hz, 3H); MS (APCI+) m/z 394 (M+H)$^+$.

Example 73C (2S,3R,4S,5S)-2-ethyl 1-isopropyl 3-(tert-butyl)-5-(2-fluorophenyl)-4-hydroxypyrrolidine-1,2-dicarboxylate Example 73B (0.411 g, 1.045 mmol) was dissolved in ethanol (5.22 mL) and sodium borohydride (0.079 g, 2.089 mmol) was added after cooling the mixture to <−60° C. in a dry ice-acetone bath. The ice bath was removed and the reaction was to warm to room temperature over 20 minutes. The reaction mixture was concentrated then partitioned between ethyl acetate and saturated sodium bicarbonate. The organics were concentrated and purified on a 40 g silica gel cartridge, eluting with 0-100% methyl tert-butyl ether/heptanes over 40 minutes to provide (2S,3R,4S,5S)-2-ethyl 1-isopropyl 3-(tert-butyl)-5-(2-fluorophenyl)-4-hydroxypyrrolidine-1,2-dicarboxylate (0.345 g, 0.872 mmol, 84% yield). $^1$H NMR (400 MHz, DMSO-$d_6$) δ ppm 7.86 (td, J=7.8, 1.8 Hz, 1H), 7.19 (tdd, J=7.6, 5.3, 1.9 Hz, 1H), 7.10-7.04 (m, 1H), 6.99 (ddd, J=10.6, 8.1, 1.2 Hz, 1H), 5.12 (d, J=6.6 Hz, 1H), 4.64 (p, J=6.2 Hz, 1H), 4.41-4.34 (m, 1H), 4.26 (s, 1H), 4.16 (q, J=7.1 Hz, 3H), 2.26 (t, J=4.1 Hz, 1H), 1.24 (t, J=7.1 Hz, 3H), 1.05 (d, J=6.2 Hz, 3H), 0.98 (d, J=3.0 Hz, 9H), 0.91 (d, J=6.2 Hz, 3H); MS (APCI+) m/z 396 (M+H)$^+$.

Example 73D (2S,3R,4S,5S)-2-ethyl 1-isopropyl 3-(tert-butyl)-5-(2-fluorophenyl)-4-((2-methoxy-5-(trifluoromethyl)pyridin-3-yl)methoxy)pyrrolidine-1,2-dicarboxylate Example 73C (75 mg, 0.190 mmol) and 3-(bromomethyl)-2-methoxy-5-(trifluoromethyl)pyridine (68 mg, 0.252 mmol) were dissolved in dry dimethylformamide (948 μL). After cooling in an ice bath, potassium 2-methylpropan-2-olate (303 μL, 0.303 mmol) solution was added dropwise over 2 minutes. LC/MS showed desired product. The mixture was acidified with 1M aqueous HCl (10 drops) and warmed to room temperature. The mixture was diluted with water (2 mL) and extracted with dichloromethane. The organic extracts were loaded onto a 25 g silica gel column and eluted with 5-100% ethyl acetate/heptanes over 20 minutes to provide (2S,3R,4S,5S)-2-ethyl 1-isopropyl 3-(tert-butyl)-5-(2-fluorophenyl)-4-((2-methoxy-5-(trifluoromethyl)pyridin-3-yl)methoxy)pyrrolidine-1,2-dicarboxylate (72 mg, 0.123 mmol, 64.9% yield). MS (APCI+) m/z 584 (M+H)$^+$.

Example 73E (2S,3R,4S,5S)-3-tert-butyl-5-(2-fluorophenyl)-4-{[2-methoxy-5-(trifluoromethyl)pyridin-3-yl]methoxy}-1-{[(propan-2-yl)oxy]carbonyl}pyrrolidine-2-carboxylic acid To a solution of Example 73D (52 mg, 0.089 mmol) in tetrahydrofuran (222 μL) and methanol (222 μL) was added lithium hydroxide (23 mg, 0.960 mmol) and the reaction was heated at 45° C. overnight. The solvent was removed under a stream of nitrogen. The crude material was acidified with 2M aqueous HCl (480 uL) and was purified using a 12 g silica gel column eluting with an ethyl acetate/ethanol/heptanes solvent system to provide (2S,3R,4S,5S)-3-(tert-butyl)-5-(2-fluorophenyl)-1-(isopropoxycarbonyl)-4-((2-methoxy-5-(trifluoromethyl)pyridin-3-yl)methoxy)pyrrolidine-2-carboxylic acid (18.7 mg, 0.034 mmol, 37.8% yield). $^1$H NMR (400 MHz, DMSO-$d_6$) δ ppm 8.29 (s, 1H), 8.12 (t, J=7.7 Hz, 1H), 7.20-7.09 (m, 2H), 7.01 (t, J=7.5 Hz, 1H), 6.97-6.86 (m, 1H), 5.27 (d, J=6.5 Hz, 1H), 4.67-4.61 (m, 1H), 4.38 (d, J=13.9 Hz, 1H), 4.31 (d, J=2.9 Hz, 1H), 4.26 (dd, J=6.6, 2.0 Hz, 1H), 4.07-3.99 (m, 2H), 3.89 (s, 3H), 2.57 (d, J=2.5 Hz, 1H), 1.07 (d, J=6.3 Hz, 3H), 1.00 (s, 9H), 0.91 (d, J=6.2 Hz, 3H); MS (APCI+) m/z 557 (M+H)$^+$.

Example 74

(2S,3R,4S,5S)-3-tert-butyl-4-[(5-tert-butyl-2-methoxypyridin-3-yl)methoxy]-5-(2-fluorophenyl)-1-{[(propan-2-yl)oxy]carbonyl}pyrrolidine-2-carboxylic acid Example 74A (2S,3R,4S,5S)-2-ethyl 1-isopropyl 3-(tert-butyl)-4-((5-(tert-butyl)-2-methoxypyridin-3-yl)methoxy)-5-(2-fluorophenyl)pyrrolidine-1,2-dicarboxylate and Example 74B (2S,3R,4R,5S)-2-ethyl 1-isopropyl 3-(tert-butyl)-4-((5-(tert-butyl)-2-methoxypyridin-3-yl)methoxy)-5-(2-fluorophenyl)pyrrolidine-1,2-dicarboxylate The title compound was prepared using the procedure described for Example 73D substituting 3-(bromomethyl)-5-(tert-butyl)-2-methoxypyridine for 3-(bromomethyl)-2-methoxy-5-(trifluoromethyl)pyridine but subjecting the product to reverse phase chromatography to provide two diastereomers, the major diastereomer identified as (2S,3R,4S,5S)-2-ethyl 1-isopropyl 3-(tert-butyl)-4-((5-(tert-butyl)-2-methoxypyridin-3-yl)methoxy)-5-(2-fluorophenyl)pyrrolidine-1,2-dicarboxylate. $^1$H NMR (400 MHz, DMSO-$d_6$) δ ppm 7.94 (d, J=2.7 Hz, 1H), 7.89 (td, J=7.7, 1.8 Hz, 1H), 7.18 (tdd, J=7.6, 5.3, 1.8 Hz, 1H), 7.14-7.11 (m, 1H), 7.09-6.93 (m, 2H), 5.27 (d, J=6.2 Hz, 1H), 4.66 (p, J=6.2 Hz, 1H), 4.39 (d, J=3.1 Hz, 1H), 4.31-4.23 (m, 2H), 4.09 (qd, J=7.1, 1.5 Hz, 2H), 3.96 (d, J=12.8 Hz, 1H), 3.76 (s, 3H), 1.19 (s, 9H), 1.13 (t, J=7.1 Hz, 3H), 1.06 (d, J=6.3 Hz, 3H), 0.99 (s, 9H), 0.91 (d, J=6.2 Hz, 3H); MS (ESI+) m/z 573 (M+H)$^+$. The minor diastereomer Example 74B was identified as (2S,3R,4R,5S)-2-ethyl 1-isopropyl 3-(tert-butyl)-4-((5-(tert-butyl)-2-methoxypyridin-3-yl)methoxy)-5-(2-fluorophenyl)pyrrolidine-1,2-dicarboxylate. $^1$H NMR (400 MHz, DMSO-$d_6$) δ ppm 8.09 (d, J=2.7 Hz, 1H), 7.98 (td, J=8.0, 1.7 Hz, 1H), 7.69 (d, J=2.6 Hz, 1H), 7.32 (tdd, J=7.5, 5.3, 1.7 Hz, 1H), 7.22-7.11 (m, 2H), 5.25 (s, 1H), 4.77 (d, J=12.2 Hz, 1H), 4.71 (p, J=6.2 Hz, 1H), 4.52 (d, J=12.3 Hz, 1H), 4.35 (d, J=11.1 Hz, 1H), 4.20 (qd, J=7.1, 5.3 Hz, 2H), 4.01 (dd, J=3.7, 1.7 Hz, 1H), 3.88 (s, 3H), 2.13 (dd, J=11.1, 3.7 Hz, 1H), 1.31 (d, J=7.1 Hz, 3H), 1.28 (s, 9H), 1.09 (d, J=6.2 Hz, 3H), 1.06-1.00 (m, 3H), 0.93 (s, 9H); MS (ESI+) m/z 573 (M+H)$^+$.

Example 74C (2S,3R,4S,5S)-3-tert-butyl-4-[(5-tert-butyl-2-methoxypyridin-3-yl)methoxy]-5-(2-fluorophenyl)-1-{[(propan-2-yl)oxy]carbonyl}pyrrolidine-2-carboxylic acid The major diastereomer Example 74A was treated as described in Example 73 to provide the title compound. $^1$H NMR (400 MHz, DMSO-$d_6$) δ ppm 8.18-8.08 (m, 1H), 7.93 (dd, J=2.6, 0.6 Hz, 1H), 7.20-7.11 (m, 2H), 7.06-6.92 (m, 2H), 5.26 (d, J=6.5 Hz, 1H), 4.64 (p, J=6.2 Hz, 1H), 4.32-4.24 (m, 2H), 4.21 (dd, J=6.4, 2.4 Hz, 1H), 3.97 (dt, J=12.9, 0.8 Hz, 1H), 3.77 (s, 3H), 2.55 (t, J=2.8 Hz, 1H), 1.18 (s, 9H), 1.06 (d, J=6.2 Hz, 3H), 0.98 (s, 9H), 0.90 (d, J=6.2 Hz, 3H); MS (ESI+) m/z 545 (M+H)$^+$.

Example 75

(2S,3R,4R,5S)-3-tert-butyl-4-[(5-tert-butyl-2-methoxypyridin-3-yl)methoxy]-5-(2-fluorophenyl)-1-{[(propan-2-yl)oxy]carbonyl}pyrrolidine-2-carboxylic acid The title compound was prepared using Example 74B and the procedures described in Example 73E. $^1$H NMR (400 MHz, DMSO-$d_6$) δ ppm 8.42 (t, J=8.0 Hz, 1H), 8.07 (d, J=2.7 Hz, 1H), 7.70 (d, J=2.6 Hz, 1H), 7.26 (dt, J=7.9, 6.2 Hz, 1H), 7.15-7.05 (m, 2H), 5.21 (s, 1H), 4.75-4.60 (m, 2H), 4.48 (d, J=12.4 Hz, 1H), 4.23 (d, J=10.4 Hz, 1H), 4.00-3.91 (m, 1H), 3.87 (s, 3H), 2.19-2.13 (m, 1H), 1.31-1.22 (m, 12H), 1.09 (d, J=6.2 Hz, 3H), 0.99 (s, 9H); MS (ESI+) m/z 545 (M+H)$^+$.

Example 76

(2S,3R,4S,5S)-4-[(5-bromo-2-methoxypyridin-3-yl)methoxy]-3-tert-butyl-5-(2-fluorophenyl)-1-{[(propan-2-yl)oxy]carbonyl}pyrrolidine-2-carboxylic acid The title compound was prepared using the procedures described for Example 73E, substituting Example 77A for Example 73D. $^1$H NMR (400 MHz, DMSO-$d_6$, 90° C.) δ ppm 8.06-7.99 (m, 2H), 7.21 (tdd, J=7.5, 5.2, 1.8 Hz, 1H), 7.07 (td, J=7.5, 1.2 Hz, 1H), 7.02-6.95 (m, 1H), 6.92 (d, J=2.4 Hz, 1H), 5.24 (d, J=6.3 Hz, 1H), 4.65 (p, J=6.2 Hz, 1H), 4.34-4.27 (m, 2H), 4.24 (dd, J=6.4, 1.8 Hz, 1H), 3.96 (d, J=13.8 Hz, 1H), 3.78 (s, 3H), 2.50 (t, J=2.2 Hz, 1H), 1.06 (d, J=6.2 Hz, 3H), 0.99 (s, 9H), 0.94-0.87 (m, 3H); MS (APCI+) m/z 567 (M+H)$^+$.

Example 77

(2S,3R,4S,5S)-3-tert-butyl-4-[(5-cyclobutyl-2-methoxypyridin-3-yl)methoxy]-5-(2-fluorophenyl)-1-{[(propan-2-yl)oxy]carbonyl}pyrrolidine-2-carboxylic acid

Example 77A (2S,3R,4S,5S)-2-ethyl 1-isopropyl 4-((5-bromo-2-methoxypyridin-3-yl)methoxy)-3-(tert-butyl)-5-(2-fluorophenyl)pyrrolidine-1,2-dicarboxylate Example 73C (109 mg, 0.276 mmol) and 5-bromo-3-(bromomethyl)-2-methoxypyridine (105 mg, 0.374 mmol) were dissolved in dry dimethylformamide (612 μL). After cooling in an ice bath, potassium 2-methylpropan-2-olate (441 μL, 0.441 mmol) solution was added dropwise over 2 minutes. After 30 minutes, the reaction was acidified with 1M aqueous HCl (10 drops) and warmed to room temperature. The mixture was concentrated and loaded onto a 24 g silica gel column and was eluted with 5-50% ethyl acetate/heptanes over 40 minutes to provide 100 mg of desired product as a mixture of diastereomers. The material was rechromatographed using reverse phase HPLC (CH$_3$CN/H$_2$O/TFA) to provide (2S,3R,4S,5S)-2-ethyl 1-isopropyl 4-((5-bromo-2-methoxypyridin-3-yl)methoxy)-3-(tert-butyl)-5-(2-fluorophenyl)pyrrolidine-1,2-dicarboxylate (76 mg, 0.128 mmol, 46.3% yield). $^1$H NMR (400 MHz, DMSO-$d_6$) δ ppm 8.02 (d, J=2.5 Hz, 1H), 7.86 (td, J=7.8, 1.8 Hz, 1H), 7.22 (tdd, J=7.5, 5.3, 1.8 Hz, 1H), 7.08 (td, J=7.6, 1.1 Hz, 1H), 7.04-6.92 (m, 2H), 5.26 (d, J=6.1 Hz, 1H), 4.68 (p, J=6.2 Hz, 1H), 4.40 (d, J=2.9 Hz, 1H), 4.32-4.25 (m, 2H), 4.17-4.08 (m, 2H), 3.96 (d, J=13.5 Hz, 1H), 3.79 (d, J=0.8 Hz, 3H), 1.18 (td, J=7.1, 0.9 Hz, 3H), 1.07 (d, J=6.2 Hz, 3H), 1.01 (d, J=0.9 Hz, 9H), 0.95-0.91 (m, 4H); MS (ESI+) m/z 596 (M+H)$^+$.

Example 77B (2S,3R,4S,5S)-2-ethyl 1-isopropyl 3-(tert-butyl)-4-((5-cyclobutyl-2-methoxypyridin-3-yl)methoxy)-5-(2-fluorophenyl)pyrrolidine-1,2-dicarboxylate Example 77A (45 mg, 0.076 mmol) in tetrahydrofuran (756 μL) treated with PdCl$_2$(dppf) (2.76 mg, 3.78 μmol), followed by dropwise addition of cyclobutylzinc(II) bromide (0.5M in tetrahydrofuran) (302 μL, 0.151 mmol) at room temperature. The reaction was stirred at ambient temperature for 2 hours. The reaction mixture was quenched with saturated aqueous NH$_4$Cl solution and the solvent was concentrated under a stream of nitrogen. The crude product was purified using a 12 g silica gel cartridge with a gradient of 5-10% ethyl acetate/heptanes over 20 minutes to provide (2S,3R,4S,5S)-2-ethyl 1-isopropyl 3-(tert-butyl)-4-((5-cyclobutyl-2-methoxypyridin-3-yl)methoxy)-5-(2-fluorophenyl)pyrrolidine-1,2-dicarboxylate (21 mg, 0.037 mmol, 48.7% yield). MS (ESI+) m/z 552 (M+H)$^+$.

Example 77C (2S,3R,4S,5S)-3-tert-butyl-4-[(5-cyclobutyl-2-methoxypyridin-3-yl)methoxy]-5-(2-fluorophenyl)-1-{[(propan-2-yl)oxy]carbonyl}pyrrolidine-2-carboxylic acid To a solution of Example 77B (21 mg, 0.037 mmol) in tetrahydrofuran (1 mL) and methanol (1.000 mL) was added lithium hydroxide (0.2 mL, 0.400 mmol) in water (1 mL) and the reaction was heated at 45° C. for 72 hours. The solvent was removed under a stream of nitrogen. The crude material was acidified with 2M aqueous HCl (400 uL) and was purified using a 12 g silica gel column eluting with an ethyl acetate/ethanol/heptanes solvent system to provide a mixture of cylobutyl and bromo products as identified by LC/MS. The material was repurified by reverse phase HPLC using acetonitrile/water/trifluoroacetic acid to provide (2S,3R,4S,5S)-3-(tert-butyl)-4-((5-cyclobutyl-2-methoxypyridin-3-yl)methoxy)-5-(2-fluorophenyl)-1-(isopropoxycarbonyl)pyrrolidine-2-carboxylic acid (7 mg, 0.013 mmol, 35.1% yield). $^1$H NMR (400 MHz, DMSO-$d_6$) δ ppm 7.95 (td, J=7.8, 1.8 Hz, 1H), 7.77 (d, J=2.4 Hz, 1H), 7.19 (tdd, J=7.6, 5.3, 1.8 Hz, 1H), 7.06 (td, J=7.5, 1.2 Hz, 1H), 6.98 (ddd, J=10.8, 8.2, 1.3 Hz, 1H), 6.90 (d, J=2.3 Hz, 1H), 5.26 (d, J=6.3 Hz, 1H), 4.66 (p, J=6.2 Hz, 1H), 4.35 (d, J=2.9 Hz, 1H), 4.28 (d, J=13.0 Hz, 1H), 4.24 (dd, J=6.2, 2.0 Hz, 1H), 3.98 (d, J=13.1 Hz, 1H), 3.76 (s, 3H), 3.39-3.26 (m, 1H), 2.50 (t, J=2.6 Hz, 1H), 2.23 (ddd, J=9.0, 7.1, 3.0 Hz, 2H), 2.01-1.79 (m, 4H), 1.07 (d, J=6.1 Hz, 3H), 0.99 (s, 9H), 0.91 (d, J=6.2 Hz, 3H); MS (ESI+) m/z 543 (M+H)$^+$.

Example 78

(2S,3R,4S,5S)-3-tert-butyl-4-{[2-methoxy-5-(trifluoromethyl)phenyl]methoxy}-1-{[(propan-2-yl)oxy]carbonyl}-5-{2-[(propan-2-yl)oxy]pyridin-3-yl}pyrrolidine-2-carboxylic acid The title compound was prepared according to the procedure described in Example 95E, substituting 2-(bromomethyl)-1-methoxy-4-(trifluoromethyl)benzene for 3-(bromomethyl)-5-cyclobutyl-2-methoxypyridine. $^1$H NMR (400 MHz, DMSO-d$_6$) δ ppm 8.11 (ddd, J=7.4, 2.0, 0.7 Hz, 1H), 7.90 (dd, J=4.9, 1.9 Hz, 1H), 7.43 (dd, J=8.5, 2.4 Hz, 1H), 7.00 (d, J=8.6 Hz, 1H), 6.91 (t, J=1.6 Hz, 1H), 6.78 (dd, J=7.4, 4.9 Hz, 1H), 5.27-5.20 (m, 1H), 5.18 (d, J=5.9 Hz, 1H), 4.67 (hept, J=6.2 Hz, 1H), 4.40 4.32 (m, 3H), 4.00 (d, J=13.3 Hz, 1H), 3.75 (s, 3H), 2.6 (s, 1H), 1.28 (d, J=6.1 Hz, 3H), 1.20 (d, J=6.2 Hz, 3H), 1.06 (d, J=6.2 Hz, 3H), 1.00 (s, 9H), 0.92 (d, J=6.2 Hz, 3H); MS (ESI+) m/z 597.1 (M+H)$^+$.

Example 79

(2S,3R,4S,5S)-3-tert-butyl-5-(3-chlorophenyl)-4-{[2-methoxy-5-(trifluoromethyl)pyridin-3-yl]methoxy}-1-{[(propan-2-yl)oxy]carbonyl}pyrrolidine-2-carboxylic acid Example 79A (2S,3R,4S,5S)-2-ethyl 1-isopropyl 3-(tert-butyl)-5-(3-chlorophenyl)-4-nitropyrrolidine-1,2-dicarboxylate Core 8 (2.003 g, 5.64 mmol) was dissolved in toluene (6.64 mL) and triethylamine (1.967 mL, 14.11 mmol) was added, followed by slow addition of isopropyl carbonochloridate (3.39 mL, 6.77 mmol) solution after cooling in an ice-water bath to ~10° C. After the addition was complete, the reaction mixture was removed from the water bath and the mixture was stirred at room temperature for 1 hour. LC/MS showed a small amount of starting material. Additional isopropyl chloroformate (0.4 mL) solution was added, and the reaction mixture was stirred at room temperature for 30 more minutes, at which point complete conversion was noted. The reaction mixture was diluted with diethyl ether and stirred with saturated aqueous sodium bicarbonate for 20 minutes. The layers were separated and the organic layer was washed twice with 1M aqueous HCl and brine, dried over sodium sulfate, filtered, and concentrated. The crude material was loaded onto a 40 g silica gel cartridge, eluting with a gradient of 5-100% ethyl acetate/heptanes over a period of 40 minutes. The product was precipitated from hexanes to provide (2S,3R,4S,5S)-2-ethyl 1-isopropyl 3-(tert-butyl)-5-(3-chlorophenyl)-4-nitropyrrolidine-1,2-dicarboxylate (2.086 g, 4.73 mmol, 84% yield). $^1$H NMR (400 MHz, DMSO-d$_6$) δ ppm 7.63 (t, J=1.5 Hz, 1H), 7.48-7.41 (m, 1H), 7.29-7.20 (m, 2H), 5.64 (dd, J=8.7, 3.0 Hz, 1H), 5.44 (d, J=8.7 Hz, 1H), 4.70 (p, J=6.2 Hz, 1H), 4.51 (d, J=3.6 Hz, 1H), 4.25 (q, J=7.1 Hz, 2H), 2.96 (t, J=3.3 Hz, 1H), 1.30 (t, J=7.1 Hz, 3H), 1.08 (d, J=6.2 Hz, 3H), 1.01 (s, 9H), 0.95 (d, J=6.2 Hz, 3H); MS (ESI+) m/z 441 (M+H)$^+$.

Example 79B (2S,3R,5S)-2-ethyl 1-isopropyl 3-(tert-butyl)-5-(3-chlorophenyl)-4-oxopyrrolidine-1,2-dicarboxylate Example 79A (1.4 g, 3.18 mmol) was dissolved in ethanol (28.6 mL) and the solution was heated to 75° C. A separate solution of CrCl$_2$ was prepared by dissolving pyridinium dichromate (2.99 g, 7.94 mmol) in 6M aqueous hydrochloric acid (57.2 mL) and adding Zn (5.71 g, 87 mmol) in portions while cooling in an ice bath. The suspension was stirred at room temperature for 30 minutes after removing from the ice bath, leaving a brilliant blue solution. The CrCl$_2$ solution was transferred via cannula over 60 minutes to the solution of starting material and heating was continued for 16 hours. The mixture was cooled to room temperature, poured into a separatory funnel, extracted three times with dichloromethane, dried over sodium sulfate, filtered, and concentrated. The crude material was redissolved in ethanol and subjected to re-esterification. Acetyl chloride (3 mL, 42.2 mmol) was added slowly to ice-cooled flask containing ethanol (9 mL). After the addition was complete, the reaction was stirred at room temperature for 5 minutes before pouring the resulting HCl/ethanol solution into a separate flask containing the crude ester/acid mixture. The mixture was heated to 65° C. for an additional hour, at which point nearly complete conversion was noted. The mixture was cooled to room temperature, concentrated and diluted with ether. The mixture was poured into a separatory funnel and washed three times with 1M aqueous HCl, three times with saturated aqueous sodium bicarbonate, and once with brine. The combined organics were dried over sodium sulfate, filtered, and concentrated to provide the crude product. The crude product was purified on a 24 g cartridge eluting with a gradient of 0-70% ethyl acetate/heptanes over a period of 20 minutes to provide the desired product (2S,3R,5S)-2-ethyl 1-isopropyl 3-(tert-butyl)-5-(3-chlorophenyl)-4-oxopyrrolidine-1,2-dicarboxylate (0.28 g, 0.683 mmol). $^1$H NMR (400 MHz, DMSO-d$_6$) δ ppm 7.62 (s, 1H), 7.46 (dd, J=7.5, 1.5 Hz, 1H), 7.37 (t, J=7.7 Hz, 1H), 7.35-7.30 (m, 1H), 5.09 (s, 1H), 4.66 (d, J=13.2 Hz, 1H), 4.55 (d, J=4.3 Hz, 1H), 4.19 (dd, J=10.4, 3.9 Hz, 2H), 2.64 (d, J=4.4 Hz, 1H), 1.23 (t, J=7.1 Hz, 3H), 1.13 (m, 3H), 1.02 (s, 9H), 0.72 (s, 3H); MS (APCI+) m/z 410 (M+H)$^+$.

Example 79C (2S,3R,4S,5S)-2-ethyl 1-isopropyl 3-(tert-butyl)-5-(3-chlorophenyl)-4-hydroxypyrrolidine-1,2-dicarboxylate Example 79B (0.28 g, 0.683 mmol) was dissolved in ethanol (3.42 mL) and sodium borohydride (0.052 g, 1.366 mmol) was added after cooling the reaction to <−60° C. in a dry ice/acetone bath. The ice bath was removed and the mixture was allowed to warm to room temperature over about 20 minutes, at which point LC/MS showed the starting material to be completely consumed. The mixture was concentrated then partitioned between ethyl acetate and saturated sodium bicarbonate. The organic layer was concentrated and purified on a 40 g silica gel cartridge, eluting with 0-70% ethyl acetate/heptanes over 20 minutes. The desired product was precipitated from hexane to provide (2S,3R,4S,5S)-2-ethyl 1-isopropyl 3-(tert-butyl)-5-(3-chlorophenyl)-4-hydroxypyrrolidine-1,2-dicarboxylate (160 mg, 0.388 mmol, 56.9% yield). $^1$H NMR (500 MHz, DMSO-d$_6$) δ ppm 7.66 (s, 1H), 7.44 (dt, J=7.6, 1.4 Hz, 1H), 7.28 (t, J=7.8 Hz, 1H), 7.22 (ddd, J=8.0, 2.2, 1.2 Hz, 1H), 4.79 (t, J=5.5 Hz, 2H), 4.61 (d, J=40.7 Hz, 1H), 4.32 (dd, J=6.5, 4.2 Hz, 1H), 4.20 (s, 1H), 4.18-4.10 (m, 2H), 2.16 (t, J=4.4 Hz, 1H), 1.25 (t, J=7.1 Hz, 3H), 1.11 (m, 3H), 0.96 (s, 9H), 0.88-0.59 (m, 3H); MS (APCI+) m/z 396 (M+H)$^+$.

Example 79D (2S,3R,4S,5S)-2-ethyl 1-isopropyl 3-(tert-butyl)-5-(3-chlorophenyl)-4-((2-methoxy-5-(trifluoromethyl)pyridin-3-yl)methoxy)pyrrolidine-1,2-dicarboxylate Example 79C (50 mg, 0.121 mmol) and 3-(bromomethyl)-2-methoxy-5-(trifluoromethyl)pyridine (68.0 mg, 0.252 mmol) were dissolved in dry dimethylformamide (0.607 mL). After cooling in an ice bath, potassium 2-methylpropan-2-olate (0.194 mL, 0.194 mmol) solution was added dropwise over 2 minutes. The reaction was stirred for 30 minutes, then acidified with 1M aqueous HCl (5 drops) and warmed to room temperature. The reaction mixture was diluted with water (2 mL) and extracted with dichloromethane. The extracts were loaded onto a 12 g silica gel cartridge and eluted with 0-60% ethyl acetate/heptanes over 20 minutes to provide (2S,3R,4S,5S)-2-ethyl 1-isopropyl 3-(tert-butyl)-5-(3-chlorophenyl)-4-((2-methoxy-5-(trifluoromethyl)pyridin-3-yl)methoxy)pyrrolidine-1,2-dicarboxylate, 2096-1 (61 mg, 0.101 mmol, 84% yield). $^1$H NMR (400 MHz, DMSO-$d_6$) δ ppm 8.37 (s, 1H), 7.71 (s, 1H), 7.50 (d, J=7.5 Hz, 1H), 7.22 (t, J=7.7 Hz, 1H), 7.17 (d, J=8.6 Hz, 2H), 5.04 (s, 1H), 4.60 (s, 1H), 4.40-4.28 (m, 3H), 4.07 (td, J=10.9, 10.3, 7.1 Hz, 2H), 3.90 (d, J=13.7 Hz, 1H), 3.85 (s, 3H), 2.41 (s, 1H), 1.30-1.04 (m, 6H), 0.99 (s, 9H), 0.89-0.59 (m, 3H); MS (APCI+) m/z 602 (M+H)$^+$.

Example 79E (2S,3R,4S,5S)-3-tert-butyl-5-(3-chlorophenyl)-4-{[2-methoxy-5-(trifluoromethyl)pyridin-3-yl] methoxy}-1-{[(propan-2-yl)oxy] carbonyl}pyrrolidine-2-carboxylic acid To a mixture of Example 79D (60 mg, 0.100 mmol) in tetrahydrofuran (300 μL), methanol (300 μL) and water (300 μL) was added lithium hydroxide hydrate (29.3 mg, 0.699 mmol) and the reaction heated at 45° C. over the weekend. LC/MS showed the desired product and the solvent was removed under a stream of nitrogen. The crude material was acidified with 2M aqueous HCl (350 uL), extracted with dichloromethane and purified using a 4 g silica gel column eluting with a gradient 0-10% methanol/dichloromethane over a period of 15 minutes to provide (2S,3R,4S,5S)-3-(tert-butyl)-5-(3-chlorophenyl)-1-(isopropoxycarbonyl)-4-((2-methoxy-5-(trifluoromethyl)pyridin-3-yl)methoxy)pyrrolidine-2-carboxylic acid (39 mg, 0.068 mmol, 68.2% yield). $^1$H NMR (400 MHz, DMSO-$d_6$) δ ppm 12.67 (bs, 1H), 8.37-8.31 (m, 1H), 7.77 (s, 1H), 7.54 (d, J=7.4 Hz, 1H), 7.18 (t, J=7.7 Hz, 1H), 7.13 (d, J=8.2 Hz, 1H), 7.06 (s, 1H), 4.99 (d, J=6.0 Hz, 1H), 4.57 (s, 1H), 4.33 (d, J=14.4 Hz, 1H), 4.28 (d, J=6.3 Hz, 1H), 4.25 (d, J=2.3 Hz, 1H), 3.91 (d, J=14.4 Hz, 1H), 3.84 (s, 3H), 2.44 (s, 1H), 1.18-1.02 (m, 3H), 0.96 (s, 9H), 0.65 (s, 3H); MS (APCI+) m/z 574 (M+H)$^+$.

Example 80

(2S,3R,4S,5S)-3-tert-butyl-4-[(5-tert-butyl-2-methoxypyridin-3-yl)methoxy]-5-(3-chlorophenyl)-1-{[(propan-2-yl)oxy]carbonyl}pyrrolidine-2-carboxylic acid The title compound was prepared using the procedure described in Example 79 substituting 3-(bromomethyl)-5-(tert-butyl)-2-methoxypyridine for 3-(bromomethyl)-2-methoxy-5-(trifluoromethyl)pyridine. $^1$H NMR (501 MHz, DMSO-$d_6$) δ ppm 12.62 (bs, 1H), 7.92 (d, J=2.7 Hz, 1H), 7.81 (s, 1H), 7.59 (d, J=7.5 Hz, 1H), 7.23 (t, J=7.8 Hz, 1H), 7.17 (d, J=7.9 Hz, 1H), 7.09 (s, 1H), 4.99 (s, 1H), 4.61 (d, J=43.6 Hz, 1H), 4.26 (d, J=13.5 Hz, 1H), 3.88 (d, J=13.6 Hz, 1H), 3.74 (s, 3H), 2.44 (s, 1H), 1.17 (s, 9H), 1.11 (m, 3H), 0.97 (s, 9H), 0.66 (s, 3H); MS (APCI+) m/z 562 (M+H)$^+$.

Example 81

(2S,3R,4S,5S)-3-tert-butyl-4-{[2-methoxy-5-(piperidin-1-yl)pyridin-3-yl]methoxy}-5-phenyl-1-{[(propan-2-yl)oxy]carbonyl}pyrrolidine-2-carboxylic acid To a 4 mL vial was added dichloro[4,5-dichloro-1,3-bis (2,6-Di-3-pentylphenyl)imidazol-2-ylidene](3-chloropyridyl)palladium(II) (PEPPSI-IPentCl, 3.73 mg, 4.33 μmol 0.1 eq) and potassium t-butoxide (12.14 mg, 0.108 mmol (2.5 eq) in dimethoxyethane (DME) (0.5 mL) to provide a yellow suspension. The vial was placed under nitrogen. Example 40A (25 mg, 0.043 mmol, 1.0 eq) and piperidine (6.41 μL, 0.065 mmol, 1.5 eq) in dimethoxyethane (0.5 mL) were added. The reaction was stirred at 90° C. for 4 hours. The solvent was removed under a stream of nitrogen. The residue was reconstituted in 500 uL 3:2 tetrahydrofuran/methanol. LiOH monohydrate (5 M, 200 μL) was added and the reaction was stirred at 45° C. overnight. The solvent was removed under a stream of nitrogen. The mixture was acidified with 2 M aqueous HCl and extracted with dichloromethane (3×1 mL). The solvent was removed under a stream of nitrogen. The residue was reconstituted in dimethyl sulfoxide/methanol and purified on reverse phase HPLC using method AA6 to provide the title compound (7.5 mg, 31% yield). $^1$H NMR (400 MHz, 120° C., DMSO-$d_6$: D$_2$O=9:1 (v/v)) δ ppm 7.66-7.60 (m, 2H), 7.50 (d, J=3.0 Hz, 1H), 7.23-7.06 (m, 3H), 6.70 (d, J=3.1 Hz, 1H), 4.95 (d, J=6.5 Hz, 1H), 4.60 (p, J=6.2 Hz, 1H), 4.23 (d, J=3.2 Hz, 1H), 4.18 (d, J=13.3 Hz, 1H), 4.13 (dd, J=6.5, 2.5 Hz, 1H), 3.85 (d, J=13.2 Hz, 1H), 3.71 (s, 3H), 2.93-2.80 (m, 5H), 1.67-1.56 (m, 4H), 1.56-1.45 (m, 2H), 1.04 (d, J=6.3 Hz, 3H), 0.97 (s, 9H), 0.87 (d, J=6.1 Hz, 3H); MS (APCI+) m/z 554.1 (M+H)$^+$.

Example 82

(2S,3R,4S,5S)-3-tert-butyl-4-{[2-methoxy-5-(pyrrolidin-1-yl)pyridin-3-yl]methoxy}-5-phenyl-1-{[(propan-2-yl)oxy]carbonyl}pyrrolidine-2-carboxylic acid The title compound was prepared according to the procedure described in Example 81 substituting pyrrolidine for piperidine. $^1$H NMR (400 MHz, 120° C., DMSO-$d_6$: D$_2$O=9:1 (v/v)) δ ppm 7.60-7.53 (m, 2H), 7.28-7.07 (m, 4H), 6.52 (s, 1H), 4.96 (d, J=6.2 Hz, 1H), 4.62 (p, J=6.2 Hz, 1H), 4.31 (d, J=3.1 Hz, 1H), 4.22-4.12 (m, 2H), 3.84 (d, J=13.1 Hz, 1H), 3.69 (s, 3H), 3.06-2.99 (m, 4H), 2.49-2.43 (m, 1H), 1.96-1.87 (m, 4H), 1.04 (d, J=6.2 Hz, 3H), 0.98 (s, 9H), 0.87 (d, J=6.2 Hz, 3H); MS (APCI+) m/z 540.1 (M+H)$^+$.

Example 83

(2S,3R,4S,5S)-3-tert-butyl-4-{[2-methoxy-5-(trifluoromethyl)pyridin-3-yl]methoxy}-5-(2-methylphenyl)-1-{[(propan-2-yl)oxy]carbonyl}pyrrolidine-2-carboxylic acid Example 83A (2S,3R,4S,5S)-2-ethyl 1-isopropyl 3-(tert-butyl)-4-nitro-5-(o-tolyl)pyrrolidine-1,2-dicarboxylate To a cooled (ice bath) solution of Core 9 (1.86 g, 5.56 mmol) in dichloromethane (11.12 mL) was added triethylamine (2.326 mL, 16.69 mmol) followed by addition of isopropyl carbonochloridate (3.34 mL, 6.67 mmol) as a solution in toluene maintaining an internal temperature <10° C. After the addition was complete, the ice bath was removed and the mixture was stirred at room temperature. After 6 hours, additional triethylamine (1 mL, 7.17 mmol) was added, followed by 1 mL of 2M isopropyl chloroformate solution. The reaction was stirred at room temperature overnight, diluted with methyl tert-butyl ether (200 mL), and stirred with 50 mL of saturated aqueous ammonium chloride at room temperature for 15 minutes. The organic layer was separated and washed with 1N aqueous HCl and brine then dried over sodium sulfate. After filtration, the solvent was removed to provide 2.22 g of starting material and product, which was resubjected to the reaction conditions and worked up as described. The resulting crude material was chromatographed using an 80 g silica gel cartridge with a gradient of 5-50% methyl tert-butyl ether/heptanes to provide (2S,3R,4S,5S)-2-ethyl 1-isopropyl 3-(tert-butyl)-4-nitro-5-(o-tolyl)pyrrolidine-1,2-dicarboxylate (1.44 g, 3.42 mmol, 61.6% yield). $^1$H NMR (400 MHz, DMSO-$d_6$) δ ppm 7.78 (dd, J=7.9, 1.8 Hz, 1H), 7.14-7.02 (m, 3H), 5.54 (d, J=2.7 Hz, 2H), 4.64 (p, J=6.2 Hz, 1H), 4.49 (d, J=4.0 Hz, 1H), 4.26 (q, J=7.1 Hz, 2H), 3.07 (dd, J=4.1, 2.4 Hz, 1H), 2.36 (s, 3H), 1.30 (t, J=7.1 Hz, 3H), 1.05 (d, J=6.2 Hz, 3H), 1.02 (s, 9H), 0.88 (d, J=6.2 Hz, 3H); MS (APCI+) m/z 421 (M+H)$^+$.

Example 83B (2S,3R,5S)-2-ethyl 1-isopropyl 3-(tert-butyl)-4-oxo-5-(o-tolyl)pyrrolidine-1,2-dicarboxylate Example 83A (0.900 g, 2.140 mmol) was dissolved in ethanol (22 mL) and the solution was heated to 75° C. A separate solution of $CrCl_2$ was prepared by dissolving pyridinium dichromate (2.013 g, 5.35 mmol) in aqueous hydrochloric acid (6M, 44 mL) and adding Zn (3.85 g, 58.9 mmol) in portions while cooling in an ice bath. The suspension was stirred at room temperature for 30 minutes after removing from the ice bath, and the suspension stirred for another 30 minutes, leaving a clear brilliant blue solution. The $CrCl_2$ solution was transferred via cannula over 20 minutes to the solution of starting material. The reaction mixture was heated between 75 and 80° C. for 10 hours, allowed to cool to room temperature, poured into a separatory funnel, and extracted with 3×200 mL of dichloromethane. The extracts were dried over sodium sulfate and filtered and the solvent was removed in vacuo. The crude material was re-esterified, dissolving it in 6 mL of ethanol and adding a prepared solution of 4 mL ethanol and 1 mL of acetyl chloride (combined at 0° C.). The mixture was warmed at 65° C. for an hour, the solvent was reduced in volume, and the crude material was chromatographed using a 40 g silica gel cartridge with a gradient of 5-100% ethyl acetate/heptanes to provide (2S,3R,5S)-2-ethyl 1-isopropyl 3-(tert-butyl)-4-oxo-5-(o-tolyl)pyrrolidine-1,2-dicarboxylate (0.540 g, 1.386 mmol, 64.8% yield). $^1$H NMR (400 MHz, DMSO-$d_6$) δ ppm 7.67-7.59 (m, 1H), 7.13 (dtt, J=14.2, 7.2, 3.9 Hz, 3H), 5.17 (s, 1H), 4.69 (ddd, J=12.4, 6.6, 5.8 Hz, 1H), 4.57 (d, J=5.2 Hz, 1H), 4.23 (qd, J=7.1, 2.1 Hz, 2H), 2.61 (d, J=5.2 Hz, 1H), 2.38 (s, 3H), 1.26 (t, J=7.1 Hz, 3H), 1.08 (d, J=6.2 Hz, 3H), 1.06 (s, 9H), 0.90 (d, J=6.1 Hz, 3H); MS (APCI+) m/z 389 (M+H)$^+$.

Example 83C (2S,3R,4S,5S)-2-ethyl 1-isopropyl 3-(tert-butyl)-4-hydroxy-5-(o-tolyl)pyrrolidine-1,2-dicarboxylate Example 83B (0.54 g, 1.386 mmol) was dissolved in ethanol (6.93 mL) and sodium borohydride (0.105 g, 2.77 mmol) was added after cooling the reaction to <−10° C. in a dry ice/acetone bath. The ice bath was removed and the mixture was allowed the reaction to warm to room temperature. The reaction mixture was concentrated and partitioned between ethyl acetate and saturated aqueous sodium bicarbonate. The organics were concentrated and purified on a 24 g silica gel cartridge, eluting with 0-70% ethyl acetate/heptanes over 20 minutes to provide (2S,3R,4S,5S)-2-ethyl 1-isopropyl 3-(tert-butyl)-4-hydroxy-5-(o-tolyl)pyrrolidine-1,2-dicarboxylate, 2101-T (0.348 g, 0.889 mmol, 64.1% yield). $^1$H NMR (400 MHz, DMSO-$d_6$) δ ppm 7.94-7.78 (m, 1H), 7.15-6.96 (m, 3H), 4.96 (d, J=6.7 Hz, 1H), 4.58 (d, J=5.1 Hz, 1H), 4.54 (bs, 1H), 4.40-4.32 (m, 1H), 4.17 (d, J=5.1 Hz, 1H), 4.14 (q, J=7.1, 2H), 2.27 (s, 3H), 2.22 (t, J=4.8 Hz, 1H), 1.23 (t, J=7.1 Hz, 3H), 1.05 (bs, 3H), 0.95 (s, 9H), 0.57 (s, 3H); MS (APCI+) m/z 392 (M+H)$^+$.

Example 83D 2-ethyl 1-isopropyl (2S,3R,4S,5S)-3-(tert-butyl)-4-((2-methoxy-5-(trifluoromethyl)pyridin-3-yl)methoxy)-5-(o-tolyl)pyrrolidine-1,2-dicarboxylate To a solution of (2S,3R,4S,5S)-2-ethyl 1-isopropyl 3-(tert-butyl)-4-((2-methoxy-5-(trifluoromethyl)pyridin-3-yl)methoxy)-5-(o-tolyl)pyrrolidine-1,2-dicarboxylate, Example 83C (70 mg, 0.179 mmol) and 3-(bromomethyl)-2-methoxy-5-(trifluoromethyl)pyridine (100 mg, 0.371 mmol) were dissolved in dry dimethylformamide (0.894 mL). After cooling in an ice bath, potassium 2-methylpropan-2-olate (0.194 mL, 0.194 mmol) solution was added dropwise over 2 minutes. After 30 minutes, the mixture was acidified with 1M aqueous HCl (5 drops) and the mixture was warmed to room temperature. The mixture was diluted with water (2 mL) and extracted with dichloromethane. The extracts were loaded onto a 12 g silica gel cartridge and were eluted with 0-60% ethyl acetate/heptanes over 20 minutes to provide (2S,3R,4S,5S)-2-ethyl 1-isopropyl 3-(tert-butyl)-4-((2-methoxy-5-(trifluoromethyl)pyridin-3-yl)methoxy)-5-(o-tolyl)pyrrolidine-1,2-dicarboxylate (59 mg, 0.102 mmol, 56.8% yield). $^1$H NMR (400 MHz, DMSO-$d_6$) δ ppm 8.34 (d, J=2.4 Hz, 1H), 7.88 (s, 1H), 7.02 (d, J=3.5 Hz, 4H), 5.10 (d, J=5.5 Hz, 1H), 4.57 (s, 2H), 4.46-4.24 (m, 3H), 4.18-3.99 (m, 2H), 3.84 (m, 4H), 2.31 (s,3H), 1.25-1.13 (m, 3H), 1.10 (t, J=7.1 Hz, 3H), 1.01 (s, 9H), 0.87-0.48 (m, 3H); MS (APCI+) m/z 582 (M+H)$^+$.

Example 83E (2S,3R,4S,5S)-3-tert-butyl-4-{[2-methoxy-5-(trifluoromethyl)pyridin-3-yl]methoxy}-5-(2-methylphenyl)-1-{[(propan-2-yl)oxy]carbonyl}pyrrolidine-2-carboxylic acid To a solution of Example 83D (58 mg, 0.100 mmol) in tetrahydrofuran (300 μL), methanol (300 μL) and water (300 μL) was added lithium hydroxide (29.3 mg, 0.699 mmol) and the reaction was heated at 45° C. for 72 hours. The solvent was removed under a stream of nitrogen. The crude material was acidified with 2M aqueous HCl (350 uL) to pH-5, extracted with dichloromethane, and purified using a 4 g silica gel column. The column was eluted with a gradient of 0-10% methanol/dichloromethane over a period of 20 minutes to provide (2S,3R,4S,5S)-3-(tert-butyl)-1-(isopropoxycarbonyl)-4-((2-methoxy-5-(trifluoromethyl)pyridin-3-yl)methoxy)-5-(o-tolyl)pyrrolidine-2-carboxylic acid (28 mg, 0.051 mmol, 50.7% yield). $^1$H NMR (400 MHz, DMSO-$d_6$) δ ppm 12.60 (s, 1H), 8.38-8.22 (m, 1H), 7.94 (s, 1H), 7.00 (m, 4H), 5.06 (d, J=5.7 Hz, 1H), 4.54 (m, 2H), 4.32 (d, J=3.2 Hz, 2H), 4.30 (d, J=5.7 Hz, 1H), 3.87 (d, J=14.5 Hz, 1H), 3.83 (s, 3H), 2.27 (s, 3H), 1.21-1.02 (m, 3H), 0.99 (s, 9H), 0.82-0.5 (m, 3H); MS (APCI+) m/z 553 (M+H)$^+$.

Example 84

(2S,3R,4S,5S)-3-tert-butyl-4-{[5-(3,3-difluoroazetidin-1-yl)-2-methoxypyridin-3-yl]methoxy}-5-phenyl-1-{[(propan-2-yl)oxy]carbonyl}pyrrolidine-2-carboxylic acid To a 4 mL vial was added dichloro[4,5-dichloro-1,3-bis(2,6-di-3-pentylphenyl)imidazol-2-ylidene](3-chloropyridyl)palladium(II) (1.1 mg, 0.0013 mmol 0.05 eq) and potassium t-butoxide (8.74 mg, 0.078 mmol, 3.0 eq) in dimethoxyethane (DME, 0.5 mL) to provide a yellow suspension. The vial was placed under nitrogen. 3,3-Difluoroazetidine hydrochloride (5.05 mg, 0.039 mmol, 1.5 eq) was added. The mixture was stirred at 85° C. for 30 minutes. Example 40A (15 mg, 0.026 mmol, 1.0 eq) was added. The reaction was stirred at 85° C. for 4 hours. The solvent was removed under a stream of nitrogen. The residue was reconstituted in 500 uL 3:2 tetrahydrofuran:methanol. LiOH monohydrate (5 M, 200 μL) was added and the reaction was stirred at 45° C. overnight. The solvent was removed under a stream of nitrogen. The reaction was acidified with 2 M aqueous HCl and was extracted with dichloromethane (3×1 mL). The solvent was removed under a stream of nitrogen. The residue was reconstituted in DMSO/methanol and purified on reverse phase HPLC using method AA6 to provide the title compound (4.0 mg, 27% yield). $^1$H NMR (400 MHz, 120° C., DMSO-$d_6$:D$_2$O=9:1 (v/v)) δ ppm 7.64-7.53 (m, 2H), 7.26 (d, J=3.0 Hz, 1H), 7.23-7.00 (m, 3H), 6.46-6.40 (m, 1H), 4.95 (d, J=6.2 Hz, 1H), 4.62 (hept, J=6.1 Hz, 1H), 4.31 (d, J=2.9 Hz, 1H), 4.22-4.03 (m, 6H), 3.82 (d, J=13.3 Hz, 1H), 3.71 (s, 3H), 2.45 (t, J=2.6 Hz, 1H), 1.04 (d, J=6.1 Hz, 3H), 0.98 (s, 9H), 0.87 (d, J=6.2 Hz, 3H); MS (APCI+) m/z 561.9 (M+H)$^+$.

Example 85

(2S,3R,4S,5S)-3-tert-butyl-4-{[5-(3,3-difluoropyrrolidin-1-yl)-2-methoxypyridin-3-yl]methoxy}-5-phenyl-1-{[(propan-2-yl)oxy]carbonyl}pyrrolidine-2-carboxylic acid The title compound was prepared according to the procedure described in Example 84 substituting 3,3-difluoropyrrolidine hydrochloride for 3,3-difluoroazetidine hydrochloride and using 4.0 eq of potassium t-butoxide instead of 3.0 eq. $^1$H NMR (400 MHz, 120° C., DMSO-$d_6$:D$_2$O=9:1 (v/v)) δ ppm 7.56 (d, J=7.4 Hz, 2H), 7.31 (d, J=3.0 Hz, 1H), 7.14 (dt, J=28.0, 7.4 Hz, 3H), 6.51 (d, J=3.1 Hz, 1H), 4.96 (d, J=6.2 Hz, 1H), 4.62 (p, J=6.2 Hz, 1H), 4.32 (d, J=2.9 Hz, 1H), 4.24-4.13 (m, 2H), 3.85 (d, J=13.3 Hz, 1H), 3.70 (s, 3H), 3.45 (td, J=13.2, 3.8 Hz, 2H), 3.30 (td, J=7.2, 4.3 Hz, 2H), 2.47-2.37 (m, 3H), 1.04 (d, J=6.2 Hz, 3H), 0.99 (s, 9H), 0.87 (d, J=6.2 Hz, 3H); MS (APCI+) m/z 576.2 (M+H)$^+$.

Example 86

(2S,3R,4S,5S)-5-(2-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid

Example 86A (2S,3R,4S,5S)-2-ethyl 1-isopropyl 5-(2-bromophenyl)-3-(tert-butyl)-4-nitropyrrolidine-1,2-dicarboxylate To a solution of Core 10 (1.487 g, 3.72 mmol) in pyridine (10 mL) was added isopropyl carbonochloridate (6 mL, 6.00 mmol) as a solution in toluene. The reaction was stirred at room temperature for 18 hours. Additional carbamoyl chloride (4 mL, 4 mmol) was added and the mixture was stirred for 1 hour more. The mixture was diluted with methyl tert-butyl ether and filtered through diatomaceous earth. The solvent was removed in vacuo. The crude material was diluted with dichloromethane (200 mL), washed with 50 mL of 1M aqueous HCl, and concentrated. The bright yellow residue was purified on an 80 g silica gel cartridge with a gradient of 5-50% ethyl acetate in heptanes to provide (2S,3R,4S,5S)-2-ethyl 1-isopropyl 5-(2-bromophenyl)-3-(tert-butyl)-4-nitropyrrolidine-1,2-dicarboxylate (1.486 g, 3.06 mmol, 82% yield). $^1$H NMR (400 MHz, DMSO-$d_6$) δ ppm 7.87 (dd, J=7.9, 1.7 Hz, 1H), 7.52 (dd, J=8.0, 1.2 Hz, 1H), 7.30 (td, J=7.6, 1.2 Hz, 1H), 7.18 (td, J=7.7, 1.7 Hz, 1H), 5.66 (d, J=8.5 Hz, 1H), 5.50 (dd, J=8.5, 2.7 Hz, 1H), 4.72-4.63 (m, 1H), 4.55 (d, J=3.4 Hz, 1H), 4.27 (qd, J=7.1, 0.8 Hz, 2H), 3.04 (t, J=3.1 Hz, 1H), 1.30 (td, J=7.0, 0.8 Hz, 3H), 1.07 (d, J=6.2 Hz, 3H), 1.03 (d, J=0.9 Hz, 9H), 0.91 (d, J=6.2 Hz, 3H); MS (APCI+) m/z 485 (M+H)$^+$.

Example 86B (2S,3R,5S)-2-ethyl 1-isopropyl 5-(2-bromophenyl)-3-(tert-butyl)-4-oxopyrrolidine-1,2-dicarboxylate Example 86A (1.48 g, 3.05 mmol) was dissolved in ethanol (35 mL) and the solution was heated to 75° C. A separate solution of CrCl$_2$ was prepared by dissolving pyridinium dichromate (2.87 g, 7.62 mmol) in aqueous hydrochloric acid (6M, 70 mL) and adding Zn (5.48 g, 84 mmol) in portions while cooling in an ice bath. The suspension was stirred at room temperature for 30 minutes after removing from the ice bath, and the suspension was stirred for another 30 minutes, leaving a clear brilliant blue solution. The CrCl$_2$ solution was transferred via cannula over 20 minutes to the solution of starting material (internal temp 79° C.). The reaction mixture was stirred at this temperature for 23 hours, heating was continued for 7 more hours at 91° C., and the mixture was cooled to room temperature. The mixture was poured into a separatory funnel and extracted with 3×150 mL of dichloromethane. The extracts were dried over sodium sulfate, filtered, and the solvent was removed in vacuo. The crude material was re-esterified by dissolving in 6 mL of ethanol and adding a prepared solution of 4 mL ethanol and 1.5 mL of acetyl chloride (combined at 0° C.), and then warming at 65° C. for an hour. The solvent was removed and the crude material was taken up in 100 mL of ethyl acetate and washed with saturated aqueous sodium bicarbonate. The organics were dried over sodium sulfate and filtered. The solvent was removed in vacuo to provide (2S,3R,5S)-2-ethyl 1-isopropyl 5-(2-bromophenyl)-3-(tert-butyl)-4-oxopyrrolidine-1,2-dicarboxylate (1.38 g, 2.430 mmol, 80% yield). $^1$H NMR (400 MHz, DMSO-d$_6$) δ ppm 7.80 (dd, J=7.8, 1.8 Hz, 1H), 7.59 (dd, J=8.0, 1.3 Hz, 1H), 7.32 (td, J=7.5, 1.4 Hz, 1H), 7.20 (dd, J=7.6, 1.8 Hz, 1H), 5.41 (s, 1H), 4.74-4.66 (m, 1H), 4.58 (dd, J=4.6, 0.6 Hz, 1H), 4.27-4.22 (m, 2H), 2.61 (dd, J=4.6, 0.9 Hz, 1H), 1.26 (t, J=7.0 Hz, 3H), 1.09 (d, J=6.3 Hz, 3H), 1.06 (s, 9H), 0.89 (d, J=6.1 Hz, 3H); MS (APCI+) m/z 455 (M+H)$^+$.

Example 86C (2S,3R,5S)-2-ethyl 1-isopropyl 5-(2-bromophenyl)-3-(tert-butyl)-4-hydroxypyrrolidine-1,2-dicarboxylate Example 86B (1.38 g, 3.04 mmol) was dissolved in ethanol (20 mL) and the mixture was cooled in an acetone/ice bath to ~−9° C. Sodium tetrahydroborate (0.138 g, 3.64 mmol) was added, initially in small portions but then all at once. The mixture was allowed to stir in the bath for 30 minutes, and concentrated in vacuo. Ethyl acetate (200 mL) and saturated aqueous sodium bicarbonate (50 mL) were added and the mixture was stirred for 30 minutes at room temperature. The organic layer was washed with brine, dried over sodium sulfate, filtered, and concentrated. The crude material was loaded onto a 40 g silica gel column and was eluted with 0-100% methyl tert-butyl ether/heptanes to provide (2S,3R,4S,5S)-2-ethyl 1-isopropyl 5-(2-bromophenyl)-3-(tert-butyl)-4-hydroxypyrrolidine-1,2-dicarboxylate and (2S,3R,4R,5S)-2-ethyl 1-isopropyl 5-(2-bromophenyl)-3-(tert-butyl)-4-hydroxypyrrolidine-1,2-dicarboxylate as a 2:1 mixture (0.650 g, 1.424 mmol, 46.9% yield). This mixture was carried forward for subsequent reactions $^1$H NMR (400 MHz, DMSO-d$_6$) δ ppm 7.93 (dd, J=7.8, 1.8 Hz, 1H), 7.47 (dd, J=8.0, 1.2 Hz, 1H), 7.25 (td, J=7.6, 1.2 Hz, 1H), 7.09 (td, J=7.6, 1.8 Hz, 1H), 5.17 (d, J=6.0 Hz, 1H), 4.62 (p, J=6.2 Hz, 1H), 4.44 (td, J=5.5, 2.3 Hz, 1H), 4.32 (d, J=3.2 Hz, 1H), 4.23-4.14 (m, 3H), 2.28 (t, J=2.8 Hz, 1H), 1.25 (t, J=7.1 Hz, 3H), 1.04 (d, J=6.1 Hz, 3H), 0.99 (s, 9H), 0.87 (d, J=6.2 Hz, 3H); MS (APCI+) m/z 457 (M+H)$^+$ Br doublet.

Example 86D (2S,3R,4S,5S)-2-ethyl 1-isopropyl 5-(2-bromophenyl)-3-(tert-butyl)-4-((2-methoxy-5-(trifluoromethyl)pyridin-3-yl)methoxy)pyrrolidine-1,2-dicarboxylate 3-(Bromomethyl)-2-methoxy-5-(trifluoromethyl)pyridine (0.433 g, 1.603 mmol) and Example 86C (0.500 g, 1.096 mmol) were dissolved in dimethylformamide (3.0 mL) cooled in an ice bath, and KOtBu (potassium tert-butoxide) (1.5 mL, 1.500 mmol) was added dropwise. After 30 minutes, the mixture was diluted with 100 mL of methyl tert-butyl ether and quenched with 15 mL of saturated aqueous ammonium chloride. The organic layer was washed with 20 mL of water and brine, dried over sodium sulfate, filtered, and concentrated. The crude material was purified using a 40 g silica gel cartridge with a gradient of 5-50% methyl tert-butyl ether/heptanes over 40 minutes to provide desired (2S,3R,4S,5S)-2-ethyl 1-isopropyl 5-(2-bromophenyl)-3-(tert-butyl)-4-((2-methoxy-5-(trifluoromethyl)pyridin-3-yl)methoxy)pyrrolidine-1,2-dicarboxylate (0.304 g, 0.471 mmol, 43.0% yield). $^1$H NMR (400 MHz, DMSO-d$_6$) δ ppm 8.33-8.26 (m, 1H), 7.96 (dd, J=7.8, 1.8 Hz, 1H), 7.44 (dd, J=8.0, 1.3 Hz, 1H), 7.21 (td, J=7.6, 1.3 Hz, 1H), 7.16 (d, J=2.4 Hz, 1H), 7.07 (td, J=7.6, 1.8 Hz, 1H), 5.29 (d, J=5.7 Hz, 1H), 4.66 (p, J=6.2 Hz, 1H), 4.47 (d, J=2.1 Hz, 1H), 4.37 (dd, J=5.7, 1.2 Hz, 1H), 4.32 (dt, J=13.6, 0.9 Hz, 1H), 4.11 (qd, J=7.1, 2.3 Hz, 2H), 3.98-3.92 (m, 1H), 3.87 (s, 3H), 2.52-2.48 (m, 1H), 1.15 (t, J=7.1 Hz, 3H), 1.06 (d, J=6.2 Hz, 3H), 1.03 (s, 9H), 0.90 (d, J=6.2 Hz, 3H); MS (ESI+) m/z 645 (M+H).

Example 86E (2S,3R,4S,5S)-5-(2-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid Example 86D (58 mg, 0.090 mmol) and lithium hydroxide (20.4 mg, 0.852 mmol) were dissolved in methanol (0.5 mL), tetrahydrofuran (0.500 mL) and water (0.500 mL). The reaction was warmed at 45° C. overnight. The solvent was removed under a stream of nitrogen and the mixture was acidified with of 2N aqueous HCl (0.422 mL). The mixture was chromatographed using a 12 g silica gel cartridge with an ethanol/ethyl acetate/heptanes solvent system to provide (2S,3R,4S,5S)-5-(2-bromophenyl)-3-(tert-butyl)-1-(isopropoxycarbonyl)-4-((2-methoxy-5-(trifluoromethyl)pyridin-3-yl)methoxy)pyrrolidine-2-carboxylic acid (43 mg, 0.070 mmol, 78% yield). $^1$H NMR (400 MHz, DMSO-d$_6$) δ ppm 8.29 (d, J=2.5 Hz, 1H), 8.08 (dd, J=7.8, 1.8 Hz, 1H), 7.42 (dd, J=7.9, 1.3 Hz, 1H), 7.19 (td, J=7.6, 1.3 Hz, 1H), 7.15 (s, 1H), 7.05 (td, J=7.6, 1.8 Hz, 1H), 5.28 (d, J=5.9 Hz, 1H), 4.65 (p, J=6.2 Hz, 1H), 4.40 (d, J=2.1 Hz, 1H), 4.38-4.29 (m, 2H), 4.01-3.94 (m, 1H), 3.87 (s, 3H), 2.53 (d, J=1.7 Hz, 1H), 1.06 (d, J=6.2 Hz, 3H), 1.02 (s, 9H), 0.89 (d, J=6.2 Hz, 3H); MS (APCI+) m/z 617 (M+H)$^+$.

Example 87

(2S,3R,4S,5S)-3-tert-butyl-4-{[2-methoxy-5-(trifluoromethyl)pyridin-3-yl]methoxy}-1-{[(propan-2-yl)oxy]carbonyl}-5-[2-(propan-2-yl)phenyl]pyrrolidine-2-carboxylic acid Example 87A 2-ethyl 1-isopropyl (2S,3R,4S,5S)-3-(tert-butyl)-5-(2-isopropylphenyl)-4-nitropyrrolidine-1,2-dicarboxylate Core 13 (500 mg, 1.38 mmol) was dissolved in dichloromethane (4 mL) and trimethylamine (1.54 mL, 11.0 mmol) was added, followed by isopropyl chloroformate (1M in toluene, 4.14 mL, 8.28 mmol). The reaction was stirred at ambient temperature for 4 hours, at which point it was complete. The reaction was diluted with dichloromethane (50 mL) and washed with 1M aqueous HCl (2×50 mL) and brine. The organic layer was dried over sodium sulfate, filtered, and concentrated to provide the crude product. The residue was purify by silica gel chromatography (0% to 20% ethyl acetate in heptanes) to provide the title compound (363 mg, 59%). $^1$H NMR (400 MHz, DMSO-d$_6$, 120° C.) δ ppm 7.88-7.81 (m, 1H), 7.24-7.11 (m, 2H), 7.04 (ddd, J=8.4, 6.5, 2.1 Hz, 1H), 5.65 (d, J=8.9 Hz, 1H), 5.51 (dd, J=8.9, 3.5 Hz, 1H), 4.65 (m, 1H), 4.49 (d, J=4.2 Hz, 1H), 4.26 (q, J=7.1 Hz, 2H), 3.22 (h, J=6.8 Hz, 1H), 3.06 (m, 1H), 1.34-1.17 (m, 9H), 1.03 (d, J=6.2 Hz, 3H), 1.02 (s, 9H), 0.84 (d, J=6.4 Hz, 3H); MS (ESI+) m/z 449 (M+H)+.

Example 87B 2-ethyl 1-isopropyl (2S,3R,5S)-3-(tert-butyl)-5-(2-isopropylphenyl)-4-oxopyrrolidine-1,2-dicarboxylate Example 87A (363 mg, 0.809 mmol) was dissolved in 9 mL of ethanol and the solution was heated to 75° C. A separate solution of $CrCl_2$ was prepared by dissolving pyridinium dichromate (761 mg, 2.02 mmol) in 18 mL of 6M aqueous HCl and adding Zn (1.455 g, 22.25 mmol) in portions while cooling in an ice bath. The suspension was stirred until all the Zn dissolved, leaving a brilliant blue solution. The $CrCl_2$ solution was transferred via cannula over 15 minutes to the solution of starting material and heating was continued for 16 hours. The temperature was maintained between 70° C. and 75° C. during the addition. The reaction mixture was continuously heated between 75° C. and 80° C. overnight, cooled to room temperature, diluted with water and extracted with dichloromethane (3×30 mL). The combined extracts were washed with brine, dried over sodium sulfate, filtered and concentrated. The crude residue was dissolved in ethanol (5 mL). A separate solution of HCl/ethanol was prepared by addition of 0.5 mL of acetyl chloride to 1.5 mL of ethanol at 0° C., and it was poured into the reaction flask and heated to 45° C. for 1 hour. The reaction mixture was concentrated in vacuo and loaded onto a 40 g silica gel cartridge, eluting with 5-100% ethyl acetate/heptanes over to provide the title compound (156 mg, 46%). $^1$H NMR (400 MHz, DMSO-$d_6$, 120° C.) δ ppm 7.68 (dd, J=7.8, 1.4 Hz, 1H), 7.29 (dd, J=7.8, 1.5 Hz, 1H), 7.20 (td, J=7.5, 1.5 Hz, 1H), 7.09 (td, J=7.5, 1.5 Hz, 1H), 5.28 (m, 1H), 4.69 (p, J=6.2 Hz, 1H), 4.57 (d, J=5.5 Hz, 1H), 4.23 (m, 2H), 3.32 (p, J=6.8 Hz, 1H), 2.62 (dd, J=5.5, 0.9 Hz, 1H), 1.30-1.23 (m, 6H), 1.21 (d, J=6.8 Hz, 3H), 1.06 (m, 12H), 0.87 (d, J=6.2 Hz, 3H); MS (ESI+) m/z 418 (M+H)+.

Example 87C (2S,3R,4S,5S)-2-ethyl 1-isopropyl 3-(tert-butyl)-4-hydroxy-5-(2-isopropylphenyl)pyrrolidine-1,2-dicarboxylate Example 87B (156 mg, 0.374 mmol) was dissolved in ethanol (5 mL), and the reaction mixture was cooled to 0° C. Sodium borohydride (25.9 mg, 0.685 mmol) was added and the reaction was stirred at 0° C. for 1 hour, and warmed to ambient temperature for another hour. The solvent was removed in vacuo and the residue was extracted with ethyl acetate (50 mL), washed with saturated aqueous $NaHCO_3$ (50 mL) and brine (50 mL), dried over $Na_2SO_4$, filtered, and concentrated to provide crude product. The crude material was purified by silica gel chromatography (0 to 5% ethyl acetate in dichloromethane) to provide the title compound (107.5 mg, 69%). $^1$H NMR (400 MHz, DMSO-$d_6$, 120° C.) δ ppm 7.90 (dd, J=7.8, 1.4 Hz, 1H), 7.20 (dd, J=7.8, 1.4 Hz, 1H), 7.13 (td, J=7.4, 1.4 Hz, 1H), 7.05 (td, J=7.5, 1.4 Hz, 1H), 5.17 (d, J=6.6 Hz, 1H), 4.60 (pd, J=6.2, 0.9 Hz, 1H), 4.33 (dd, J=6.6, 3.8 Hz, 1H), 4.25 (d, J=4.5 Hz, 1H), 4.18 (qd, J=7.1, 0.9 Hz, 2H), 3.19 (hept, J=6.8 Hz, 1H), 2.26 (t, J=4.2 Hz, 1H), 1.29-1.20 (m, 9H), 1.02-0.98 (m, 12H), 0.82 (d, J=6.2 Hz, 3H); MS (ESI+) m/z 420 (M+H)+.

Example 87D 2-ethyl 1-isopropyl (2S,3R,4S,5S)-3-(tert-butyl)-5-(2-isopropylphenyl)-4-((2-methoxy-5-(trifluoromethyl)pyridin-3-yl)methoxy)pyrrolidine-1,2-dicarboxylate Example 87C (48.0 mg, 0.114 mmol) and 3-(bromomethyl)-2-methoxy-5-(trifluoromethyl)pyridine (57.7 mg, 0.214 mmol) were dissolved in dimethylformamide (1 mL). The reaction was cooled to 0° C., then potassium tert-butoxide (1M in tetrahydrofuran, 0.18 mL, 0.18 mmol) was added dropwise and the reaction was stirred at ambient temperature for 1 hour. The reaction was quenched by the addition of 1M aqueous HCl (0.1 mL) and was purified by silica gel chromatography (0 to 5% ethyl acetate in dichloromethane) to provide the title compound (107.5 mg, 69%). $^1$H NMR (400 MHz, DMSO-$d_6$, 120° C.) δ ppm 8.27 (s, 1H), 7.92 (dd, J=7.9, 1.4 Hz, 1H), 7.23-6.92 (m, 4H), 5.26 (d, J=5.6 Hz, 1H), 4.70-4.57 (m, J=6.2 Hz, 1H), 4.44 (d, J=2.1 Hz, 1H), 4.29-4.19 (m, 2H), 4.17-4.08 (m, 2H), 3.85 (s, 3H), 3.78 (d, J=13.8 Hz, 1H), 3.21 (dq, J=12.9, 6.6 Hz, 1H), 1.24 (d, J=6.8 Hz, 3H), 1.21-1.15 (m, 6H), 1.04 (s, 9H), 1.00 (d, J=8.1 Hz, 3H), 0.83 (d, J=6.2 Hz, 4H); MS (ESI+) m/z 609 (M+H)+.

Example 87E (2S,3R,4S,5S)-3-tert-butyl-4-{[2-methoxy-5-(trifluoromethyl)pyridin-3-yl]methoxy}-1-{[(propan-2-yl)oxy]carbonyl}-5-[2-(propan-2-yl)phenyl]pyrrolidine-2-carboxylic acid Example 87D (42.8 mg, 0.070 mmol) was dissolved in methanol (1 mL), and tetrahydrofuran (1 mL). LiOH (1 M, 0.5 mL, 0.5 mmol) was added and the reaction was heated to 50° C. for 16 hours. The reaction was quenched by the addition of 1M aqueous HCl (0.5 mL) and was purified by silica gel chromatography (5 to 100% ethyl acetate in dichloromethane) to provide the title compound (21.8 mg, 53%). $^1$H NMR (400 MHz, DMSO-$d_6$, 120° C.) δ ppm 8.26 (s, 1H), 7.24-7.11 (m, 2H), 7.12-7.03 (m, 1H), 6.97 (t, J=7.5 Hz, 1H), 5.29-5.20 (m, 1H), 4.69-4.58 (m, 1H), 4.39 (d, J=2.1 Hz, 1H), 4.32-4.23 (m, 1H), 4.21 (t, J=5.5 Hz, 1H), 3.89-3.73 (m, 5H), 3.27-3.16 (m, 1H), 2.52 (t, J=1.3 Hz, 1H), 1.24 (d, J=6.7 Hz, 3H), 1.17 (d, J=7.0 Hz, 3H), 1.06-0.98 (m, 12H), 0.82 (dd, J=6.3, 3.8 Hz, 3H).); MS (ESI+) m/z 581 (M+H)+.

Example 88

(2S,3R,4S,5S)-3-tert-butyl-4-{[2-methoxy-5-(trifluoromethyl)pyridin-3-yl]methoxy}-1-[(2S)-oxolane-2-carbonyl]-5-phenylpyrrolidine-2-carboxylic acid Example 88A (2S,3R,4S,5S)-1-allyl 2-ethyl 3-(tert-butyl)-4-nitro-5-phenylpyrrolidine-1,2-dicarboxylate To (2S,3R,4S,5S)-ethyl 3-(tert-butyl)-4-nitro-5-phenylpyrrolidine-2-carboxylate (1.0 g, 3.12 mmol) (Core 5) in toluene (3 mL) and saturated $NaHCO_3$ (3.00 mL) was added allyl carbonochloridate (0.332 mL, 3.12 mmol) drop wise at ambient temperature, and the mixture was stirred for 30 minutes. LC/MS indicated the conversion was finished. Dichloromethane (20 mL) and water (10 mL) were added and the organic layer washed with brine, dried over MgSO$_4$, filtered, and concentrated. The residue was purified via silica gel chromatography, eluting with ethyl acetate in heptane at 0-40% gradient to provide the title compound (1.0 g, 95% yield). $^1$H NMR (501 MHz, CDCl$_3$) δ ppm 7.58-7.51 (m, 2H), 7.37-7.26 (m, 3H), 5.61 (s, 2H), 5.43 (d, J=8.7 Hz, 1H), 5.30 (dd, J=8.7, 2.6 Hz, 1H), 5.00 (s, 1H), 4.70 (s, 1H), 4.56 (s, 2H), 4.39 (qd, J=7.1, 1.8 Hz, 2H), 3.11 (t, J=2.9 Hz, 1H), 1.40 (t, J=7.1 Hz, 3H), 1.10 (s, 9H); MS (ESI+) m/z 405 (M+H)$^+$.

Example 88B (2S,3R,5S)-1-allyl 2-ethyl 3-(tert-butyl)-4-oxo-5-phenylpyrrolidine-1,2-dicarboxylate Example 88B was prepared according to the procedure described in Example 2B, substituting Example 88A for Example 2A. LC/MS (ESI+)=374.45 (M+H)$^+$.

Example 88C (2S,3R,4S,5S)-1-allyl 2-ethyl 3-(tert-butyl)-4-hydroxy-5-phenylpyrrolidine-1,2-dicarboxylate and

Example 88D (2S,3R,4R,5S)-1-allyl 2-ethyl 3-(tert-butyl)-4-hydroxy-5-phenylpyrrolidine-1,2-dicarboxylate To Example 88B (560 mg, 1.5 mmol) in ethanol (4 mL) cooling in an ice-bath was added sodium borohydride (113 mg, 3.00 mmol) portionwise. The mixture was stirred in the ice-bath for 30 minutes, and allowed to warm to ambient temperature. LC/MS showed two product peaks, the ratio was about 6 to 1. The solvent was removed, dichloromethane (20 mL) was added and the organics were washed with brine. The organics were dried over MgSO$_4$, filtered, and concentrated. Purification via chromatography, eluting with ethyl acetate/methanol (9:1) in heptanes at 0-40% gradient provided title compound as the second eluent (340 mg, 60.4% yield). $^1$H NMR (400 MHz, CDCl$_3$) δ ppm 7.64-7.56 (m, 2H), 7.43-7.36 (m, 2H), 7.33-7.28 (m, 1H), 5.55 (s, 1H), 5.04 (s, 1H), 4.97-4.70 (m, 1H), 4.64-4.38 (m, 3H), 4.35-4.31 (m, 1H), 4.27 (ddd, J=10.8, 7.0, 3.4 Hz, 2H), 2.41-2.32 (m, 1H), 1.47 (d, J=5.0 Hz, 1H), 1.34 (t, J=7.1 Hz, 3H), 1.07 (s, 9H); LC/MS (ESI+) m/z 376.5 (M+H)$^+$. Also obtained was the other diastereomer (2S,3R,4R,5S)-1-allyl 2-ethyl 3-(tert-butyl)-4-hydroxy-5-phenylpyrrolidine-1,2-dicarboxylate as the first eluent (56 mg, 9.95% yield).

Example 88E (2S,3R,4S,5S)-1-allyl 2-ethyl 3-(tert-butyl)-4-((2-methoxy-5-(trifluoromethyl)pyridin-3-yl)methoxy)-5-phenylpyrrolidine-1,2-dicarboxylate To Example 88C (340 mg, 0.906 mmol) and 3-(bromomethyl)-2-methoxy-5-(trifluoromethyl)pyridine (293 mg, 1.087 mmol) in dimethylformamide (2 mL) in an ice-bath was added potassium 2-methylpropan-2-olate (152 mg, 1.358 mmol, 1.6 mL, 1.0 M in tetrahydrofuran) dropwise. The mixture was stirred in ice-bath for 20 minutes, and allowed to warm to room temperature. Saturated aqueous NH$_4$Cl (2 mL) was added, and dichloromethane (20 mL) was added. The mixture was washed with brine, dried over MgSO$_4$, filtered, and concentrated. Purification of the residue via chromatography, eluting with ethyl acetate/methanol (9:1) in heptanes at 0-40% gradient provided the title compound (380 mg, 71% yield). $^1$H NMR (400 MHz, DMSO-d$_6$) δ ppm 8.29 (t, J=1.5 Hz, 1H), 7.62-7.52 (m, 2H), 7.26-7.15 (m, 3H), 7.13-7.05 (m, 1H), 5.73-5.66 (m, 1H), 5.08 (d, J=6.1 Hz, 1H), 5.04 (dq, J=3.2, 1.8 Hz, 1H), 5.01 (t, J=1.7 Hz, 1H), 4.41 (ddd, J=5.1, 3.6, 2.3 Hz, 3H), 4.30-4.25 (m, 2H), 4.10 (qd, J=7.1, 2.3 Hz, 2H), 3.87 (s, 3H), 1.15 (t, J=7.0 Hz, 3H), 1.01 (s, 9H); MS (ESI+) m/z 565 (M+H)$^+$.

Example 88F (2S,3R,4S,5S)-ethyl 3-(tert-butyl)-4-((2-methoxy-5-(trifluoromethyl)pyridin-3-yl)methoxy)-5-phenylpyrrolidine-2-carboxylate To Example 88E (320 mg, 0.567 mmol) in a mixture of acetonitrile and water (3.3 mL, 10:1) was added diethylamine (0.117 mL, 1.134 mmol) and tetrakis(triphenylphosphine) palladium(0) (14.41 mg, 0.012 mmol). The mixture was stirred at ambient temperature overnight. Dichloromethane (10 mL) and water (10 mL) were added. The organic layer was washed with brine, dried over magnesium sulfate, filtered, and concentrated. Purification via chromatography, eluting with ethyl acetate/methanol (10:1) in heptanes at 0-50% gradient provided the title compound (260 mg, 95% yield). $^1$H NMR (400 MHz, CDCl$_3$) δ ppm 8.24 (dt, J=1.9, 0.9 Hz, 1H), 7.46-7.41 (m, 2H), 7.37 (d, J=2.4 Hz, 1H), 7.35-7.29 (m, 2H), 7.28-7.23 (m, 1H), 4.33 (dt, J=14.0, 0.9 Hz, 1H), 4.25 (qd, J=7.2, 0.8 Hz, 2H), 4.17 (d, J=4.1 Hz, 1H), 3.94 (dd, J=4.2, 1.4 Hz, 1H), 3.93-3.88 (m, 4H), 3.74 (d, J=6.2 Hz, 1H), 2.85 (s, 1H), 2.43 (dd, J=6.3, 1.3 Hz, 1H), 1.30 (t, J=7.1 Hz, 3H), 1.06 (s, 9H); MS (ESI+) m/z 563 (M+H)$^+$.

Example 88G (2S,3R,4S,5S)-ethyl 3-(tert-butyl)-4-((2-methoxy-5-(trifluoromethyl)pyridin-3-yl)methoxy)-5-phenyl-1-((S)-tetrahydrofuran-2-carbonyl)pyrrolidine-2-carboxylate To (S)-tetrahydrofuran-2-carboxylic acid (CAS#87392-07-2) (24.16 mg, 0.208 mmol) and a drop of dimethylformamide in dichloromethane (5 mL) was added oxalyl dichloride (52.8 mg, 0.416 mmol) (0.21 mL, 2M in dichloromethane). The mixture was stirred for 30 minutes. The solvent was removed under pressure and fresh dichloromethane was added and the solvent was removed again. The residue was dissolved in dichloromethane (1 mL) and added dropwise to the solution of Example 88F (50 mg, 0.104 mmol) and triethylamine (0.139 mL, 0.999 mmol) in dichloromethane (2 mL) in an ice-bath. The mixture was stirred and was allowed to warm to ambient temperature. Saturated aqueous NH$_4$Cl (1 mL) and dichloromethane (10 mL) were added. The organic layer was washed with brine, dried over MgSO$_4$, filtered, and concentrated. The residue was purified via chromatography, eluting with ethyl acetate in heptanes at 0-40% gradient to provide title compound. $^1$H NMR (400 MHz, CDCl$_3$) δ ppm 8.22 (dd, J=2.8, 1.3 Hz, 1H), 7.71-7.63 (m, 2H), 7.37-7.22 (m, 4H), 7.07 (d, J=2.3 Hz, 1H), 5.46 (d, J=6.1 Hz, 1H), 4.78 (d, J=3.3 Hz, 1H), 4.35 (d, J=13.9 Hz, 1H), 4.27-4.13 (m, 4H), 3.94-3.85 (m, 4H), 3.89-3.78 (m, 2H), 3.74 (td, J=7.7, 5.6 Hz, 1H), 2.58 (t, J=2.9 Hz, 1H), 2.12-2.01 (m, 1H), 1.98-1.86 (m, 1H), 1.72-1.61 (m, 1H), 1.43-1.31 (m, 1H), 1.26 (t, J=7.1 Hz, 3H), 1.10 (d, J=9.1 Hz, 1H), 1.08 (s, 9H); MS (ESI+) m/z 579 (M+H)+.

Example 88H (2S,3R,4S,5S)-3-(tert-butyl)-4-((2-methoxy-5-(trifluoromethyl)pyridin-3-yl)methoxy)-5-phenyl-1-((S)-tetrahydrofuran-2-carbonyl)pyrrolidine-2-carboxylic acid Example 88G was dissolved in methanol (1.5 mL) and 6M aqueous LiOH (0.5 mL) and stirred at 45° C. overnight. The reaction mixture was adjusted pH to 1~2 by adding 2M aqueous HCl. The reaction mixture was concentrated, taken up in dichloromethane and filtered through a syringe filter. The filtrate was purified via chromatography on a 4 g silica gel cartridge, eluting with methanol in dichloromethane at a 0-20% gradient yield the title compound 30 mg (52.4% yield in two steps). $^1$H NMR (400 MHz, CDCl$_3$) δ ppm 8.22 (dd, J=2.6, 1.3 Hz, 1H), 7.72-7.63 (m, 2H), 7.36-7.24 (m, 3H), 7.07 (d, J=2.3 Hz, 1H), 5.46 (d, J=6.1 Hz, 1H), 4.78 (d, J=3.3 Hz, 1H), 4.35 (d, J=13.9 Hz, 1H), 4.24-4.14 (m, 3H), 3.91 (s, 3H), 3.88-3.79 (m, 2H), 3.74 (td, J=7.7, 5.7 Hz, 1H), 2.58 (t, J=2.9 Hz, 1H), 2.07 (dddd, J=12.5, 8.6, 6.3, 4.8 Hz, 1H), 1.98-1.82 (m, 1H), 1.66 (ddq, J=11.9, 8.9, 7.0 Hz, 1H), 1.37 (dddd, J=12.4, 8.8, 7.8, 6.0 Hz, 1H), 1.26 (t, J=7.1 Hz, 3H), 1.08 (s, 9H); MS (ESI+) m/z 551 (M+H)+.

Example 89

(2S,3R,4S,5S)-3-tert-butyl-4-{[2-methoxy-5-(trifluoromethyl)pyridin-3-yl]methoxy}-1-[(2S)-oxane-2-carbonyl]-5-phenylpyrrolidine-2-carboxylic acid Example 89A (2S,3R,4S,5S)-ethyl 3-(tert-butyl)-4-((2-methoxy-5-(trifluoromethyl)pyridin-3-yl)methoxy)-5-phenyl-1-((S)-tetrahydro-2H-pyran-2-carbonyl)pyrrolidine-2-carboxylate and Example 89B (2S,3R,4S,5S)-ethyl 3-(tert-butyl)-4-((2-methoxy-5-(trifluoromethyl)pyridin-3-yl)methoxy)-5-phenyl-1-((R)-tetrahydro-2H-pyran-2-carbonyl)pyrrolidine-2-carboxylate To tetrahydro-2H-pyran-2-carboxylic acid (65.0 mg, 0.499 mmol) in dichloromethane (6 mL) and a drop of dimethylformamide was added oxalyl dichloride (127 mg, 1.0 mmol, 0.5 mL, 2M in dichloromethane). The mixture was stirred for 30 minutes and the solvent was removed under pressure and fresh dichloromethane was added and removed again. The residue was dissolved in dichloromethane (1 mL) and was added dropwise to the solution of Example 88F (120 mg, 0.250 mmol) and triethylamine (0.139 mL, 1.0 mmol) in dichloromethane (6 mL) cooled with an ice-bath. The mixture was stirred in an ice-bath for 30 minutes and was warmed to room temperature. LC/MS indicated the reaction was finished and showed two diastereoisomers peaks at the ratio about 1:1. Saturated aqueous NH$_4$Cl (2 mL) and dichloromethane (10 mL) were added. The organic layer was washed with brine, dried over MgSO$_4$, filtered, and concentrated. Purification via chromatography on a 24 g silica gel cartridge, eluting with ethyl acetate in heptanes at 0-40% gradient provided Example 89A as the first eluent (55 mg, 37.2% yield). $^1$H NMR (400 MHz, CDCl$_3$) δ ppm 8.29-8.16 (m, 1H), 7.75-7.61 (m, 2H), 7.40-7.24 (m, 3H), 7.12 (d, J=2.3 Hz, 1H), 5.52 (d, J=6.1 Hz, 1H), 4.74 (d, J=3.1 Hz, 1H), 4.32 (d, J=14.1 Hz, 1H), 4.21 (qq, J=7.1, 3.7 Hz, 2H), 4.15-4.06 (m, 1H), 3.91 (s, 3H), 3.85 (dd, J=13.7, 4.5 Hz, 2H), 3.38 (dd, J=10.3, 2.7 Hz, 1H), 2.95 (td, J=11.5, 2.5 Hz, 1H), 2.51 (t, J=2.7 Hz, 1H), 1.77-1.29 (m, 6H), 1.26 (t, J=7.1 Hz, 3H), 1.07 (s, 9H); MS (ESI+) m/z 593.1 (M+H)+. Example 89B was obtained as the second eluent (52 mg, 35.1% yield). $^1$H NMR (400 MHz, CDCl$_3$) δ ppm 8.22 (tt, J=2.5, 1.2 Hz, 1H), 7.72-7.61 (m, 1H), 7.52-7.48 (m, 1H), 7.36-7.31 (m, 1H), 7.30-7.23 (m, 2H), 7.19-7.13 (m, 1H), 5.24 (d, J=5.6 Hz, 1H), 5.19 (d, J=1.5 Hz, 1H), 4.34 (dd, J=24.7, 14.0 Hz, 1H), 4.28-4.12 (m, 3H), 4.11-3.94 (m, 3H), 3.91 (d, J=7.2 Hz, 3H), 3.83-3.73 (m, 1H), 3.47 (td, J=11.1, 2.6 Hz, 1H), 2.70 (s, 1H), 1.99-1.60 (m, 4H), 1.56-1.48 (m, 2H), 1.24 (t, J=7.2 Hz, 3H), 1.08 (d, J=13.1 Hz, 9H); MS (ESI+) m/z 593.2 (M+H)+.

Example 89C (2S,3R,4S,5S)-3-(tert-butyl)-4-((2-methoxy-5-(trifluoromethyl)pyridin-3-yl)methoxy)-5-phenyl-1-((S)-tetrahydro-2H-pyran-2-carbonyl)pyrrolidine-2-carboxylic acid The mixture of Example 89A (50 mg, 0.084 mmol) in methanol (1.5 mL) and 6M aqueous LiOH (0.5 mL) was stirred at 45° C. for overnight. The mixture was adjusted to pH to 1~2 by adding 2M aqueous HCl. The reaction mixture was concentrated, taken up in dichloromethane, and filtered through a syringe filter. The filtrate was purified via chromatography on a 4 g silica gel cartridge, eluting with methanol in dichloromethane at 0-20% gradient to provide the title compound (30 mg, 63.0% yield). $^1$H NMR (400 MHz, DMSO-d$_6$) δ ppm 8.37-8.29 (m, 1H), 7.66 (d, J=7.4 Hz, 2H), 7.21 (d, J=7.5 Hz, 3H), 7.16 (d, J=7.5 Hz, 1H), 5.42 (s, 1H), 4.55 (s, 1H), 4.33-4.25 (m, 2H), 3.91 (d, J=13.9 Hz, 1H), 3.88 (s, 3H), 3.79 (d, J=11.3 Hz, 1H), 3.51 (s, 1H), 2.84 (s, 2H), 1.72-1.26 (m, 6H), 1.00 (s, 9H); MS (ESI+) m/z 565.1 (M+H)+.

Example 90

(2S,3R,4S,5S)-3-tert-butyl-4-{[2-methoxy-5-(trifluoromethyl)pyridin-3-yl]methoxy}-5-phenyl-1-{[(prop-2-en-1-yl)oxy]carbonyl}pyrrolidine-2-carboxylic acid A mixture of Example 88E (45 mg, 0.080 mmol) and lithium hydroxide (19.09 mg, 0.797 mmol) in methanol/water (2 mL, 4:1) was stirred at 50° C. overnight, and LC/MS indicated conversion was complete. The mixture was adjusted pH to 1~2 by adding 2M aqueous HCl. The reaction mixture was concentrated, taken up in dichloromethane, and filtered through a syringe filter. The filtrate was purified via chromatography on a 4 g silica gel cartridge, eluting with methanol in dichloromethane at 0-20% gradient to provide the title compound (38 mg, 89% yield). $^1$H NMR (400 MHz, DMSO-d$_6$) δ ppm 8.28 (d, J=2.2 Hz, 1H), 7.64-7.52 (m, 2H), 7.23-7.12 (m, 3H), 7.13-7.05 (m, 1H), 5.06 (d, J=6.1 Hz, 1H), 5.04-4.99 (m, 1H), 4.40 (dt, J=5.0, 1.7 Hz, 2H), 4.37 (d, J=3.0 Hz, 1H), 4.32-4.24 (m, 2H), 3.91 (d, J=13.9 Hz, 1H), 3.87 (s, 3H), 2.50 (t, J=2.6 Hz, 1H), 1.01 (s, 9H); MS (ESI+) m/z 538 (M+H)+.

Example 91

(2S,3R,4S,5S)-3-tert-butyl-4-{[2-methoxy-5-(trifluoromethyl)pyridin-3-yl]methoxy}-1-[(2R)-oxane-2-carbonyl]-5-phenylpyrrolidine-2-carboxylic acid The title compound was prepared according to the procedure described in Example 89C, substituting Example 89B for Example 89A. $^1$H NMR (400 MHz, DMSO-$d_6$) δ ppm 8.28 (s, 1H), 7.55 (s, 2H), 7.26-7.13 (m, 3H), 7.10 (d, J=6.9 Hz, 1H), 5.19 (d, J=6.2 Hz, 1H), 4.81 (s, 1H), 4.36-4.20 (m, 2H), 3.88 (s, 4H), 3.79 (d, J=12.0 Hz, 1H), 2.58 (s, 1H), 1.82-1.27 (m, 7H), 1.01 (d, J=3.6 Hz, 9H); MS (ESI+) m/z 565.1 (M+H)+.

Example 92

(2S,3R,4S,5S)-3-tert-butyl-5-(2-cyclopropylphenyl)-4-{[2-methoxy-5-(trifluoromethyl)pyridin-3-yl]methoxy}-1-{[(propan-2-yl)oxy]carbonyl}pyrrolidine-2-carboxylic acid Example 92A 2-ethyl 1-isopropyl (2S,3R,4S,5S)-3-(tert-butyl)-5-(2-cyclopropylphenyl)-4-nitropyrrolidine-1,2-dicarboxylate Core 12 (1.32 g, 3.66 mmol) was dissolved in dichloromethane (10 mL) and trimethylamine (2 mL, 14.35 mmol) was added, followed by isopropyl chloroformate (2M in toluene, 7 mL, 14 mmol). The reaction was stirred at ambient temperature for 4 hours, at which point it was complete. The reaction was diluted with dichloromethane (50 mL) and washed with 1M aqueous HCl (2×50 mL) and brine. The organic layer was dried over sodium sulfate, filtered, and concentrated to provide the crude product. The residue was purified by silica gel chromatography (5% ethyl acetate in dichloromethane) to provide the title compound (1.3 g, 99%). $^1$H NMR (400 MHz, DMSO-$d_6$, 120° C.) δ ppm 7.74 (dd, J=7.5, 1.7 Hz, 1H), 7.16-7.04 (m, 2H), 6.98 (dd, J=7.4, 1.6 Hz, 1H), 5.88 (d, J=8.5 Hz, 1H), 5.62 (dd, J=8.5, 2.1 Hz, 1H), 4.72 (hept, J=6.2 Hz, 0H), 4.51 (d, J=3.0 Hz, 1H), 4.23 (q, J=7.1 Hz, 2H), 2.98 (t, J=2.6 Hz, 1H), 2.10 (ddd, J=13.6, 8.3, 5.5 Hz, 1H), 1.26 (t, J=7.1 Hz, 3H), 1.14 (d, J=6.2 Hz, 4H), 1.04-0.79 (m, 16H). MS (ESI+) m/z 447 (M+H)+.

Example 92B 2-ethyl 1-isopropyl (2S,3R,5S)-3-(tert-butyl)-5-(2-cyclopropylphenyl)-4-oxopyrrolidine-1,2-dicarboxylate Example 92A (875 mg, 1.96 mmol) was dissolved in 22 mL of ethanol and the solution was heated to 75° C. A separate solution of CrCl$_2$ was prepared by dissolving pyridinium dichromate (2.063 g, 5.48 mmol) in 44 mL of 6M aqueous HCl and adding Zn (3.882 g, 54.4 mmol) in portions while cooling in an ice bath. The suspension was stirred until all Zn dissolved, leaving a brilliant blue solution. The CrCl$_2$ solution was transferred via cannula over 15 minutes to the mixture of starting material and heating was continued for 16 hours. The temperature was maintained between 70° C. and 75° C. during the addition. The reaction mixture was continuously heated between 75° C. and 80° C. overnight, cooled to room temperature, diluted with water, and extracted with dichloromethane (3×100 mL). The combined extracts were washed with brine, dried over sodium sulfate, filtered, and concentrated. The crude residue was dissolved in ethanol (6 mL). A separate solution of HCl/ethanol was prepared by addition of 1 mL of acetyl chloride to 4 mL of ethanol at 0° C., and poured into the reaction flask and heated to 45° C. for 1 hour. The reaction mixture was concentrated in vacuo and loaded onto a 40 g silica gel column, eluting with 5% ethyl acetate in dichloromethane to provide the title compound (366.7 mg, 44%). $^1$H NMR (400 MHz, DMSO-$d_6$, 120° C.) δ ppm 7.68 (dd, J=7.3, 1.8 Hz, 1H), 7.18-7.05 (m, 3H), 5.63 (s, 1H), 4.69 (heptd, J=6.1, 2.1 Hz, 1H), 4.59 (dd, J=5.0, 1.0 Hz, 1H), 4.24 (qt, J=7.1, 1.4 Hz, 2H), 2.61 (d, J=5.0 Hz, 1H), 2.13 (ddd, J=13.8, 8.5, 5.4 Hz, 1H), 1.27 (td, J=7.1, 0.9 Hz, 3H), 1.06 (d, J=1.0 Hz, 12H), 0.96-0.83 (m, 5H), 0.83-0.74 (m, 1H), 0.53 (dqt, J=8.7, 3.5, 1.6 Hz, 1H); MS (ESI+) m/z 416 (M+H)+.

Example 92C 2-ethyl 1-isopropyl (2S,3R,4S,5S)-3-(tert-butyl)-5-(2-cyclopropylphenyl)-4-hydroxypyrrolidine-1,2-dicarboxylate Example 92B (333.4 mg, 0.802 mmol) was dissolved in ethanol (5 mL), and the reaction was cooled to 0° C. Sodium borohydride (51.2 mg, 1.353 mmol) was added and the reaction was stirred at 0° C. for 1 hour, and warmed to ambient temperature for another 1 hour. The solvent was removed in vacuo and the residue was extracted with ethyl acetate (50 mL) and washed with saturated aqueous NaHCO$_3$ (50 mL) and brine (50 mL), dried over Na$_2$SO$_4$, filtered and concentrated to provide crude product, which was purified by silica gel chromatography (5% ethyl acetate in dichloromethane) to provide the title compound (201.3 mg, 60%). $^1$H NMR (400 MHz, DMSO-$d_6$, 120° C.) δ ppm 7.89-7.82 (m, 1H), 7.11-7.03 (m, 2H), 7.02-6.95 (m, 1H), 5.61 (d, J=0.9 Hz, 0H), 5.47 (d, J=6.2 Hz, 1H), 4.60 (p, J=6.2 Hz, 1H), 4.43 (dd, J=6.3, 2.9 Hz, 1H), 4.30 (d, J=3.7 Hz, 1H), 4.18 (q, J=7.1 Hz, 2H), 2.29 (t, J=3.3 Hz, 1H), 2.02-1.90 (m, 1H), 1.26 (t, J=7.1 Hz, 3H), 1.04-0.97 (m, 12H), 0.96-0.78 (m, 5H), 0.74 (dtd, J=9.5, 5.5, 3.9 Hz, 1H), 0.55 (dtd, J=9.1, 5.6, 3.5 Hz, 1H); MS (ESI+) m/z 418 (M+H)+.

Example 92D 2-ethyl 1-isopropyl (2S,3R,4S,5S)-3-(tert-butyl)-5-(2-isopropylphenyl)-4-((2-methoxy-5-(trifluoromethyl)pyridin-3-yl)methoxy)pyrrolidine-1,2-dicarboxylate Example 92D (98.2 mg, 0.235 mmol) and 3-(bromomethyl)-2-methoxy-5-(trifluoromethyl)pyridine (102.3 mg, 0.380 mmol) were dissolved in dimethylformamide (1 mL). The reaction was cooled to 0° C., potassium tert-butoxide (1M in tetrahydrofuran, 0.30 mL, 0.30 mmol) was added dropwise, and the reaction was stirred at ambient temperature for 1 hour. The reaction was quenched by the addition of 1M aqueous HCl (0.1 mL) and was purified by silica gel chromatography (5% to 100% ethyl acetate) to provide the title compound (65.4 mg, 46%). $^1$H NMR (400 MHz, DMSO-$d_6$, 120° C.) δ ppm 8.27 (s, 1H), 7.95 (dd, J=6.7, 2.4 Hz, 1H), 7.16 (d, J=2.4 Hz, 1H), 7.01 (tt, J=7.3, 5.4 Hz, 2H), 6.93 (dd, J=6.8, 2.3 Hz, 1H), 5.58 (d, J=5.7 Hz, 1H), 4.63 (hept, J=6.2 Hz, 1H), 4.41 (d, J=2.0 Hz, 1H), 4.31 (s, 1H), 4.29 (d, J=8.2 Hz, 1H), 3.91-3.84 (m, 4H), 3.21 (dq, J=12.9, 6.6 Hz, 1H), 2.57-2.50 (m, 1H), 2.01-1.91 (m, 1H), 1.26 (t, J=7.1 Hz, 3H), 1.07-0.99 (m, 12H), 0.95-0.78 (m, 5H), 0.63-0.52 (m, 2H); MS (ESI+) m/z 607 (M+H)+.

Example 92E (2S,3R,4S,5S)-3-tert-butyl-5-(2-cyclopropylphenyl)-4-{[2-methoxy-5-(trifluoromethyl)pyridin-3-yl]methoxy}-1-{[(propan-2-yl)oxy]carbonyl}pyrrolidine-2-carboxylic acid Example 92D (55.1 mg, 0.091 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction mixture was quenched by the addition of 1M aqueous HCl (0.5 mL) and was purified by silica gel chromatography (ethyl acetate) to provide the title compound (51.7 mg, 98%). 1H NMR (400 MHz, DMSO-d6, 120° C.) δ ppm 8.27 (s, 1H), 7.95 (dd, J=6.7, 2.4 Hz, 1H), 7.16 (d, J=2.4 Hz, 1H), 7.01 (tt, J=7.3, 5.4 Hz, 2H), 6.93 (dd, J=6.8, 2.3 Hz, 1H), 5.58 (d, J=5.7 Hz, 1H), 4.63 (hept, J=6.2 Hz, 1H), 4.41 (d, J=2.0 Hz, 1H), 4.31 (s, 1H), 4.29 (d, J=8.2 Hz, 1H), 3.91-3.84 (m, 4H), 2.57-2.50 (m, 1H), 2.01-1.91 (m, 1H), 1.07-0.99 (m, 12H), 0.95-0.78 (m, 5H), 0.63-0.52 (m, 2H); MS (ESI+) m/z 579 (M+H)+.

Example 93

(2S,3R,4S,5S)-3-tert-butyl-4-[(5-cyclobutyl-2-methoxypyridin-3-yl)methoxy]-1-{[(propan-2-yl)oxy]carbonyl}-5-[2-(propan-2-yl)phenyl]pyrrolidine-2-carboxylic acid Example 93A 2-ethyl 1-isopropyl (2S,3R,4S,5S)-3-(tert-butyl)-4-((5-cyclobutyl-2-methoxypyridin-3-yl)methoxy)-5-(2-isopropylphenyl)pyrrolidine-1,2-dicarboxylate Example 87C (94.0 mg, 0.224 mmol) and 3-(bromomethyl)-5-cyclobutyl-2-methoxypyridine (92.3 mg, 0.360 mmol) were dissolved in dimethylformamide (1.1 mL). The reaction was cooled to 0° C., then potassium tert-butoxide (1M in tetrahydrofuran, 0.30 mL, 0.30 mmol) was added dropwise and the reaction was stirred at ambient temperature for 1 hour. The reaction mixture was quenched by the addition of 1M aqueous HCl (0.1 mL) and was purified by silica gel chromatography (5% to 100% ethyl acetate in heptanes) to provide the title compound (95.7 mg, 72%). 1H NMR (400 MHz, DMSO-d6, 120° C.) δ ppm 7.94 (dd, J=8.1, 1.4 Hz, 1H), 7.75 (d, J=2.4 Hz, 1H), 7.18 (dd, J=7.9, 1.5 Hz, 1H), 7.16-7.10 (m, 1H), 7.07-6.98 (m, 1H), 6.88 (d, J=2.4 Hz, 1H), 5.25 (d, J=5.6 Hz, 1H), 4.63 (hept, J=6.2 Hz, 1H), 4.43 (d, J=2.1 Hz, 1H), 4.23-4.06 (m, 6H), 3.73 (s, 3H), 3.37-3.14 (m, 2H), 2.31-2.17 (m, 2H), 2.03-1.80 (m, 4H), 1.25 (d, J=6.8 Hz, 3H), 1.21-1.12 (m, 6H), 1.02 (d, J=1.8 Hz, 12H), 0.82 (d, J=6.2 Hz, 3H); MS (ESI+) m/z 595 (M+H)+.

Example 93B (2S,3R,4S,5S)-3-tert-butyl-4-[(5-cyclobutyl-2-methoxypyridin-3-yl)methoxy]-1-{[(propan-2-yl)oxy]carbonyl}-5-[2-(propan-2-yl)phenyl]pyrrolidine-2-carboxylic acid Example 93A (82.7 mg, 0.139 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction was quenched by the addition of 1M aqueous HCl (0.5 mL) and was purified by silica gel chromatography (5 to 100% ethyl acetate in dichloromethane) to provide the title compound (66.4 mg, 84%). 1H NMR (400 MHz, DMSO-d6, 120° C.) δ ppm 8.00 (dd, J=7.9, 1.4 Hz, 1H), 7.77-7.72 (m, 1H), 7.21-7.09 (m, 2H), 7.02 (ddd, J=8.4, 7.1, 1.6 Hz, 1H), 6.86 (d, J=2.4 Hz, 1H), 5.24 (d, J=5.7 Hz, 1H), 4.63 (p, J=6.2 Hz, 1H), 4.38 (d, J=2.1 Hz, 1H), 4.22-4.13 (m, 2H), 3.81-3.72 (m, 4H), 3.30 (p, J=8.5 Hz, 1H), 3.21 (p, J=6.8 Hz, 1H), 2.50 (t, J=1.4 Hz, 1H), 2.29-2.13 (m, 2H), 2.03-1.78 (m, 4H), 1.25 (d, J=6.7 Hz, 3H), 1.17 (d, J=6.8 Hz, 3H), 1.07-0.96 (m, 12H), 0.81 (d, J=6.2 Hz, 3H); MS (ESI+) m/z 567 (M+H)+.

Example 94

(2S,3R,4R,5S)-3-tert-butyl-4-{[2-methoxy-5-(trifluoromethyl)phenyl]methoxy}-1-{[(propan-2-yl)oxy]carbonyl}-5-{2-[(propan-2-yl)oxy]pyridin-3-yl}pyrrolidine-2-carboxylic acid The title compound was prepared according to the procedure described in Example 95F, substituting 2-(bromomethyl)-1-methoxy-4-(trifluoromethyl)benzene for 3-(bromomethyl)-5-cyclobutyl-2-methoxypyridine, and Example 95E for Example 95D. 1H NMR (400 MHz, DMSO-d6) δ ppm 8.33 (ddd, J=7.4, 1.9, 0.8 Hz, 1H), 8.03 (dd, J=4.9, 1.9 Hz, 1H), 7.64-7.58 (m, 2H), 7.18 (d, J=8.4 Hz, 1H), 6.91 (dd, J=7.4, 4.9 Hz, 1H), 5.51-5.44 (m, 1H), 5.11 (s, 1H), 5.03 (d, J=13.1 Hz, 1H), 4.71-4.65 (m, 1H), 4.62 (d, J=13.1 Hz, 1H), 4.31 (d, J=11.3 Hz, 1H), 3.97 (d, J=3.6 Hz, 1H), 3.89 (s, 3H), 3.74 (d, J=9.1 Hz, 1H), 2.10-2.03 (m, 1H), 1.40 (d, J=6.1 Hz, 3H), 1.34 (d, J=6.2 Hz, 3H), 1.11-1.01 (m, 6H), 0.99 (s, 9H); MS (ESI−) m/z 595.3 (M−H).

Example 95

(2S,3R,4S,5S)-3-tert-butyl-4-[(5-cyclobutyl-2-methoxypyridin-3-yl)methoxy]-1-{[(propan-2-yl)oxy]carbonyl}-5-{2-[(propan-2-yl)oxy]pyridin-3-yl}pyrrolidine-2-carboxylic acid Example 95A (2S,3R,4S,5S)-2-ethyl 1-isopropyl 3-(tert-butyl)-5-(2-isopropoxypyridin-3-yl)-4-nitropyrrolidine-1,2-dicarboxylate To (2S,3R,4S,5S)-ethyl 3-(tert-butyl)-5-(2-isopropoxypyridin-3-yl)-4-nitropyrrolidine-2-carboxylate (Core 7) (2.00 g, 5.27 mmol) and triethylamine (5.88 mL, 42.2 mmol) in dichloromethane (10 mL) was added isopropyl carbonochloridate (3.88 g, 31.6 mmol) drop wise at ambient temperature. The mixture was stirred for 2 hours, and dichloromethane (20 mL) and water (10 mL) added. The organic layer was washed with brine, dried over MgSO4, filtered, and concentrated. Purification of the residue via chromatography, eluting with ethyl acetate in heptanes provided the title compound (2.26 g, 92% yield). 1H NMR (400 MHz, CDCl3) δ ppm 8.04 (dd, J=5.0, 1.8 Hz, 2H), 6.82 (dd, J=7.4, 5.0 Hz, 1H), 5.50 (d, J=8.0 Hz, 1H), 5.37 (dd, J=12.7, 6.8 Hz, 2H), 4.88 (s, 1H), 4.70 (s, 1H), 4.34 (qd, J=7.2, 2.3 Hz, 2H), 2.94 (t, J=1.6 Hz, 1H), 1.43-1.33 (m, 9H), 1.15-1.123 (m, 6H), 1.08 (s, 9H); MS (ESI+) m/z 466 (M+H)+.

Example 95B (2S,3R,5S)-2-ethyl 1-isopropyl 3-(tert-butyl)-5-(2-hydroxypyridin-3-yl)-4-oxopyrrolidine-1,2-dicarboxylate To potassium dichromate (6.07 g, 20.62 mmol) in 6M aqueous HCl (60 mL) was added zinc (6.75 g, 103 mmol) under $N_2$ atmosphere. After the complete dissolution of zinc, providing a clear light blue solution, the formed chromium (II) chloride was transferred to the refluxing solution of Example 95A (1.6 g, 3.44 mmol) in ethanol (60 mL) under $N_2$. The reaction mixture was refluxed at 85° C. for 16 hours. LC/MS indicated the reaction was finished and showed two peaks, one was desired title compound and another was saponified acid. The mixture was cooled, concentrated to half of its volume, and extracted with ethyl acetate (60 mL×3). The combined organic phase was washed with saturated aqueous $NaHCO_3$ solution and brine, dried over $MgSO_4$, filtered, and concentrated. To the residue in ethanol (5 mL) was added a prepared solution of acetyl chloride (1 mL) in ethanol (5 mL) slowly. The mixture was heated at 60° C. for 2 hours. The solvent was removed and the residue was dissolved in dichloromethane (30 mL) and washed with $NaHCO_3$ and brine, dried over $MgSO_4$, filtered, and concentrated. The residue was purified via chromatography, eluting with methanol in ethyl acetate at 0-20% gradient to provide the title compound (1.05 g, 78%). LC/MS (APCI+) m/z 393.17 $(M+H)^+$.

Example 95C (2S,3R,5S)-2-ethyl 1-isopropyl 3-(tert-butyl)-5-(2-isopropoxypyridin-3-yl)-4-oxopyrrolidine-1,2-dicarboxylate To the mixture of Example 95B (500 mg, 1.274 mmol) and silver carbonate (CAS#534-16-7) (703 mg, 2.55 mmol) in $CHCl_3$ (10 mL) was added 2-iodopropane (CAS#75-30-9) (325 mg, 1.911 mmol) dropwise. The mixture was refluxed for 3 hours, and was stirred at ambient temperature overnight to complete the reaction. The reaction mixture was filtered and the solid was washed with dichloromethane (5 mL×2). The combined organics were washed with brine and concentrated to provide the title compound (550 mg, 99% yield) which used in next step without further purification. LC/MS (APCI+) m/z 435.4 $(M+H)^+$.

Example 95D (2S,3R,4S,5S)-2-ethyl 1-isopropyl 3-(tert-butyl)-4-hydroxy-5-(2-isopropoxypyridin-3-yl)pyrrolidine-1,2-dicarboxylate and

Example 95E (2S,3R,4R,5S)-2-ethyl 1-isopropyl 3-(tert-butyl)-4-hydroxy-5-(2-isopropoxypyridin-3-yl)pyrrolidine-1,2-dicarboxylate To Example 95C (180 mg, 0.414 mmol) in ethanol (5 mL) cooled with an ice-bath was added sodium borohydride (31.3 mg, 0.828 mmol) portionwise. The mixture was stirred in ice-bath for 30 minutes and was allowed to warm to ambient temperature. LC/MS indicated the conversion was finished and showed two diastereoisomeric peaks with ratio about 2:1. Aqueous saturated $NH_4Cl$ (1 mL) and dichloromethane (20 mL) were added. The mixture was washed with brine, dried over $MgSO_4$, filtered, and concentrated. The residue was purified via chromatography, eluting with ethyl acetate/methanol (9:1) in heptane. The first eluent was Example 95E (2S,3R,4R,5S)-2-ethyl 1-isopropyl 3-(tert-butyl)-4-hydroxy-5-(2-isopropoxypyridin-3-yl)pyrrolidine-1,2-dicarboxylate (60 mg, 33.2% yield); and the second eluent was the title compound Example 95D (121 mg, 66.5% yield). LC/MS (APCI+) m/z 437.5 $(M+H)^+$.

Example 95F (2S,3R,4S,5S)-3-(tert-butyl)-4-((5-cyclobutyl-2-methoxypyridin-3-yl)methoxy)-1-(isopropoxycarbonyl)-5-(2-isopropoxypyridin-3-yl)pyrrolidine-2-carboxylic acid To Example 95D (51 mg, 0.117 mmol) and 3-(bromomethyl)-5-cyclobutyl-2-methoxypyridine (30 mg, 0.117 mmol) in dimethylformamide (1 mL) cooling in an ice bath, potassium 2-methylpropan-2-olate (19.71 mg, 0.176 mmol, 0.18 mL, 1.0 M in tetrahydrofuran) was added drop wise. The mixture was stirred in an ice-bath for 30 minutes, and was allowed to warm to room temperature. Methanol (1.5 mL) and 6M aqueous LiOH (0.5 mL) were added. The mixture was stirred at 50° C. overnight, and adjusted to pH 1~2 with the addition of 2M aqueous HCl. The reaction mixture was concentrated, and the residue was taken up in dichloromethane and filtered through a syringe filter. The filtrate was purified via chromatography, on a 4 g silica gel cartridge, eluting with methanol in dichloromethane at 0-20% gradient to provide the title compound (35 mg, 51.2% yield). $^1$H NMR (400 MHz, DMSO-$d_6$) δ ppm 8.13 (dd, J=7.4, 1.9 Hz, 1H), 7.93 (dd, J=4.9, 2.0 Hz, 1H), 7.76 (d, J=2.0 Hz, 1H), 6.86-6.79 (m, 2H), 5.23 (p, J=6.2 Hz, 1H), 5.16 (d, J=6.0 Hz, 1H), 4.67 (hept, J=6.2 Hz, 1H), 4.37 (d, J=2.5 Hz, 1H), 4.28 (d, J=13.2 Hz, 1H), 4.22 (dd, J=6.0, 1.6 Hz, 1H), 3.95 (d, J=13.1 Hz, 1H), 3.76 (s, 3H), 3.32 (hept, J=6.2 Hz, 1H), 2.49-2.48 (m, 1H), 2.29-2.19 (m, 2H), 2.01-1.83 (m, 4H), 1.29 (d, J=6.1 Hz, 3H), 1.21 (d, J=6.1 Hz, 3H), 1.06 (d, J=6.2 Hz, 3H), 0.99 (s, 9H), 0.93 (d, J=6.2 Hz, 3H); MS (ESI+) m/z 584.1 $(M+H)^+$.

Example 96

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(propan-2-yl)phenyl]pyrrolidine-2-carboxylic acid

Example 96A (2S,3R,4S,5S)-1-allyl 2-ethyl 3-(tert-butyl)-5-(2-isopropylphenyl)-4-nitropyrrolidine-1,2-dicarboxylate Core 11 (12.3 g, 33.9 mmol) was dissolved in toluene (120 mL) and saturated aqueous sodium bicarbonate (120 mL) was added. Allyl chloroformate (3.98 mL, 37.3 mmol) was added, and the reaction mixture was stirred at ambient temperature for 20 minutes, at which point LC/MS indicated complete conversion of the starting material. The reaction was diluted with methyl tert-butyl ether (70 mL) and the layers were separated. The organic layer was washed with 1M aqueous HCl (2×30 mL), 1M aqueous NaOH (2×30 mL) and brine (30 mL). The organic layer was dried over sodium sulfate, filtered, concentrated, and purified via flash chromatography, eluting with 0:100 to 30:70 methyl tert-butyl ether:heptanes over 30 minutes on a 330 g silica gel column to provide 12.3 g of the title compound. $^1$H NMR (400 MHz, DMSO-d$_6$, 120° C.) δ ppm 7.86 (dd, J=8.0, 1.2 Hz, 1H), 7.32-7.14 (m, 2H), 7.05 (ddd, J=8.4, 6.5, 2.1 Hz, 1H), 5.72 (d, J=9.0 Hz, 1H), 5.65 (ddd, J=17.2, 10.7, 5.3 Hz, 1H), 5.53 (dd, J=8.9, 3.6 Hz, 1H), 5.08-4.93 (m, 2H), 4.55 (d, J=4.3 Hz, 1H), 4.41 (d, J=5.2 Hz, 2H), 4.27 (qd, J=7.0, 0.9 Hz, 2H), 3.24 (p, J=6.7 Hz, 1H), 3.14-3.05 (m, 1H), 1.31 (t, J=7.1 Hz, 3H), 1.27 (d, J=6.6 Hz, 3H), 1.19 (d, J=6.7 Hz, 3H), 1.03 (s, 9H); MS (ESI+) m/z 447.3 (M+H)$^+$.

Example 96B (2S,3R,5S)-1-allyl 2-ethyl 3-(tert-butyl)-5-(2-isopropylphenyl)-4-oxopyrrolidine-1,2-dicarboxylate Example 96A (11.2 g, 25.08 mmol) was dissolved in ethanol (226 mL) and the solution was heated to 75° C. A separate solution of CrCl$_2$ was prepared by dissolving pyridinium dichromate (23.59 g, 62.7 mmol) in aqueous hydrochloric acid, (6M, 452 mL) and adding Zn (44.3 g, 667 mmol) in portions while cooling in an ice bath, maintaining an internal temperature below 35° C. The resulting suspension was stirred at ambient temperature for 30 minutes after removing the flask from the ice bath, leaving a blue solution of CrCl$_2$, which was added via cannula over 20 minutes to the reaction flask containing the solution of the starting material in ethanol at 75° C. Heating was continued at 85° C. for 36 hours. The flask was cooled to ambient temperature, and the organic material was extracted with dichloromethane (3×200 mL). The combined extracts were dried over sodium sulfate, filtered, and concentrated. The material was redissolved in an anhydrous solution of HCl in ethanol that was prepared by the addition of acetyl chloride (8.9 mL, 125 mmol) to 100 mL of ethanol via syringe while cooling in an ice-water bath. The resulting solution was heated to 45° C. for 1 hour, at which point complete re-esterification had occurred. The reaction mixture was concentrated and the crude material was partitioned between saturated aqueous sodium bicarbonate and methyl tert-butyl ether (300 mL each). The organic extracts were dried over sodium sulfate, filtered, and concentrated to provide (2S,3R,5S)-1-allyl 2-ethyl 3-(tert-butyl)-5-(2-isopropylphenyl)-4-oxopyrrolidine-1,2-dicarboxylate (10 g) as an inseparable mixture with unreacted oxime. The mixture was used in the next step without additional purification.

Example 96C (2S,3R,4S,5S)-1-allyl 2-ethyl 3-(tert-butyl)-4-hydroxy-5-(2-isopropylphenyl)pyrrolidine-1,2-dicarboxylate Example 96B (10 g, 24.07 mmol) was dissolved in 100 mL of ethanol and sodium borohydride (0.910 g, 24.07 mmol) was added in one portion after cooling to −5° C. The reaction was complete in 10 minutes at this temperature, as indicated by LC/MS. Acetone (10 mL) was added to quench the excess borohydride, and the reaction mixture was stirred at the same temperature for 15 minutes. The flask was warmed to ambient temperature, concentrated in vacuo, and partitioned between methyl tert-butyl ether and saturated sodium bicarbonate (100 mL each). The organic extracts were concentrated in vacuo to provide crude material, which was purified via flash chromatography, eluting with 0:100 to 30:70 methyl tert-butyl ether:heptanes over 40 minutes on a 220 g silica gel column to provide 5.5 g of the desired diastereomer (2S,3R,4S,5S)-1-allyl 2-ethyl 3-(tert-butyl)-4-hydroxy-5-(2-isopropylphenyl)pyrrolidine-1,2-dicarboxylate as an inseparable mixture with the oxime from the previous step. $^1$H NMR (400 MHz, DMSO-d$_6$, 120° C.) δ ppm 7.90 (dd, J=7.8, 1.5 Hz, 1H), 7.20 (ddd, J=7.7, 4.4, 1.5 Hz, 1H), 7.13 (tdd, J=7.6, 2.8, 1.5 Hz, 1H), 7.05 (ddd, J=8.9, 7.2, 1.5 Hz, 1H), 5.70-5.59 (m, 1H), 5.22 (d, J=6.6 Hz, 1H), 5.04-4.84 (m, 2H), 4.35 (m, 3H), 4.30 (d, J=4.6 Hz, 1H), 4.24-4.14 (m, 2H), 3.75 (br s, 1H), 3.19 (dt, J=13.6, 6.9 Hz, 1H), 2.37-2.25 (m, 1H), 1.26 (d, J=5.7 Hz, 3H), 1.24 (t, J=4 Hz, 3H), 1.20 (d, J=5.7 Hz, 3H), 1.00 (s, 9H); MS (ESI+) m/z 418.1 (M+H)$^+$.

Example 96D (2S,3R,4S,5S)-1-allyl 2-ethyl 3-(tert-butyl)-5-(2-isopropylphenyl)-4-((2-methoxy-5-(trifluoromethyl)pyridin-3-yl)methoxy)pyrrolidine-1,2-dicarboxylate Example 96C (1.75 g, 3.14 mmol) was dissolved in 1.2 mL of dry dimethylformamide. After cooling to 0° C. in an ice bath, potassium tert-butoxide (1M in tetrahydrofuran, 4.6 mL, 4.6 mmol) solution was added dropwise, followed immediately by addition of 3-(bromomethyl)-2-methoxy-5-(trifluoromethyl)pyridine (1.36 g, 5.0 mmol) dropwise via syringe. LC/MS after 10 minutes showed complete conversion of the starting alcohol. The reaction was quenched with saturated aqueous ammonium chloride (10 mL) and extracted with methyl tert-butyl ether (3×20 mL). The combined organic extracts were concentrated in vacuo and purified via flash chromatography, eluting on a 120 g silica gel column with 0:100 to 20:80 methyl tert-butyl ether: heptanes over 20 minutes to provide 955 mg of the title compound. $^1$H NMR (400 MHz, DMSO-d$_6$, 120° C.) δ ppm 8.33-8.21 (m, 1H), 7.92 (dd, J=7.9, 1.4 Hz, 1H), 7.17 (dt, J=5.7, 1.5 Hz, 2H), 7.10 (td, J=7.5, 1.4 Hz, 1H), 7.01-6.93 (m, 1H), 5.66 (ddt, J=16.2, 10.4, 5.1 Hz, 1H), 5.33 (d, J=5.7 Hz, 1H), 5.04-4.87 (m, 2H), 4.50 (d, J=2.2 Hz, 1H), 4.39 (d, J=5.2 Hz, 2H), 4.29-4.22 (m, 2H), 4.13 (qd, J=7.1, 1.2 Hz, 2H), 3.86 (s, 3H), 3.78 (d, J=13.8 Hz, 1H), 3.24 (p, J=6.8 Hz, 1H), 2.52 (t, J=1.6 Hz, 1H), 1.23 (d, J=6.7 Hz, 3H), 1.19 (d, J=7.0 Hz, 3H), 1.15 (t, J=8 Hz, 3H), 1.05 (s, 9H); MS (ESI+) m/z 607.0 (M+H)$^+$.

Example 96E (2S,3R,4S,5S)-ethyl 3-(tert-butyl)-5-(2-isopropylphenyl)-4-((2-methoxy-5-(trifluoromethyl)pyridin-3-yl)methoxy)pyrrolidine-2-carboxylate Example 96D (850 mg, 1.401 mmol) and 1,3-dimethylpyrimidine-2,4,6(1H,3H,5H)-trione (438 mg, 2.80 mmol) were dissolved in 14 mL of a 1:1 mixture of dichloromethane and ethyl acetate that had been degassed for 5 minutes. Palladium tetrakis(triphenylphosphine)palladium (16.19 mg, 0.014 mmol) was added, and the reaction mixture was stirred at ambient temperature for 15 minutes, at which point the reaction was complete as indicated by LC/MS. The reaction mixture was diluted with methyl tert-butyl ether (50 mL) and stirred with 10 mL of 10% aqueous sodium carbonate solution for 10 minutes. The organic layer was washed with brine and concentrated in vacuo to provide crude material. The crude material was purified via flash chromatography, eluting with 0:100 to 30:70 methyl tert-butyl ether:heptanes over 20 minutes on a 40 g silica gel column to provide 623 mg of (2S,3R,4S,5S)-ethyl 3-(tert-butyl)-5-(2-isopropylphenyl)-4-((2-methoxy-5-(trifluoromethyl)pyridin-3-yl)methoxy)pyrrolidine-2-carboxylate. ¹H NMR (400 MHz, DMSO-d$_6$, 120° C.) δ ppm 8.34-8.26 (m, 1H), 7.63 (dd, J=7.9, 1.4 Hz, 1H), 7.39 (d, J=2.4 Hz, 1H), 7.22 (dd, J=7.8, 1.5 Hz, 1H), 7.14 (td, J=7.5, 1.4 Hz, 1H), 7.02 (td, J=7.6, 1.4 Hz, 1H), 4.42 (d, J=4.5 Hz, 1H), 4.22 (d, J=13.6 Hz, 1H), 4.15 (q, J=8 Hz, 2H), 3.96 (dd, J=4.6, 1.8 Hz, 1H), 3.85 (s, 3H), 3.77 (d, J=13.7 Hz, 1H), 3.65 (d, J=6.5 Hz, 1H), 3.24 (p, J=6.8 Hz, 1H), 2.42 (dd, J=6.5, 1.8 Hz, 1H), 1.22 (t, J=8 Hz, 3H), 1.21 (br s, 3H), 1.19 (br s, 3H) 1.00 (s, 9H); MS (ESI+) m/z 523.1 (M+H)⁺.

Example 96F (2S,3R,4S,5S)-ethyl 3-(tert-butyl)-5-(2-isopropylphenyl)-4-((2-methoxy-5-(trifluoromethyl)pyridin-3-yl)methoxy)-1-((S)-tetrahydro-2H-pyran-2-carbonyl)pyrrolidine-2-carboxylate and Example 96G (2S,3R,4S,5S)-ethyl 3-(tert-butyl)-5-(2-isopropylphenyl)-4-((2-methoxy-5-(trifluoromethyl)pyridin-3-yl)methoxy)-1-((R)-tetrahydro-2H-pyran-2-carbonyl)pyrrolidine-2-carboxylate Example 96D (370 mg, 0.71 mmol) was dissolved in dichloromethane (7.1 mL) and triethylamine (0.30 mL, 2.1 mmol) was added. After cooling in an ice bath to <10° C., a solution of freshly-prepared tetrahydro-2H-pyran-2-carbonyl chloride (158 mg, 1.062 mmol) was added dropwise, and the reaction was complete as soon as the addition was done, as indicated by LC/MS. The reaction mixture was diluted with methyl tert-butyl ether (10 mL) and 1M aqueous HCl (10 mL) was added. The layers were separated, and the organic layer was washed with 1M aqueous HCl (2×5 mL) and brine (10 mL), dried over sodium sulfate, filtered, and concentrated in vacuo to provide a crude residue. The crude material was purified via flash chromatography, eluting with 0:100 to 20:80 methyl tert-butyl ether:heptanes over 5 minutes then isocratic 20:80 methyl tert-butyl ether:heptanes for 40 minutes on an 80 g silica gel column to provide Example 96F (144 mg) as the first-eluting diastereomer and Example 96G (120 mg) as the second-eluting diastereomer. Example 96F (first eluting)¹H NMR (400 MHz, DMSO-d$_6$, 120° C.) δ ppm 8.33-8.19 (m, 1H), 8.00 (dd, J=7.9, 1.5 Hz, 1H), 7.24 (d, J=7.6 Hz, 1H), 7.15 (s, 2H), 7.03 (d, J=7.9 Hz, 1H), 5.61 (d, J=0.8 Hz, 1H), 4.74 (d, J=1.8 Hz, 1H), 4.29 (d, J=13.8 Hz, 1H), 4.24 (d, J=5.7 Hz, 1H), 4.09 (qd, J=7.1, 2.9 Hz, 2H), 3.86 (s, 3H), 3.80 (d, J=13.9 Hz, 1H), 3.73 (s, 1H), 3.24 (p, J=6.8 Hz, 1H), 3.18-2.93 (m, 1H), 2.45 (d, J=1.7 Hz, 2H), 1.74-1.61 (m, 1H), 1.54 (t, J=10.7 Hz, 2H), 1.37 (s, 3H), 1.30 (d, J=6.7 Hz, 3H), 1.16 (d, J=6.6 Hz, 3H), 1.13 (t, J=7.1 Hz, 3H), 1.05 (s, 9H); MS (ESI+) m/z 635.1 (M+H)⁺. Example 96G (second eluting)¹H NMR (400 MHz, DMSO-d$_6$, 120° C.) δ ppm 8.35-8.15 (m, 1H), 7.80 (s, 1H), 7.22-6.88 (m, 4H), 5.40 (d, J=5.6 Hz, 1H), 4.97 (s, 1H), 4.28 (d, J=13.8 Hz, 1H), 4.21 (d, J=5.5 Hz, 1H), 4.19-4.08 (m, 2H), 3.86 (s, 3H), 3.79 (d, J=13.8 Hz, 1H), 3.24 (hept, J=6.6 Hz, 1H), 2.59 (s, 1H), 1.90-1.85 (br s, 1H), 1.85-1.35 (m, 6H), 1.29-1.22 (m, 3H), 1.19 (dd, J=6.6, 1.1 Hz, 3H), 1.16 (t, J=7.1 Hz, 3H), 1.05 (s, 9H); MS (ESI+) m/z 635.1 (M+H)⁺.

Example 96H (2S,3R,4S,5S)-3-tert-butyl-4-{[2-methoxy-5-(trifluoromethyl)pyridin-3-yl]methoxy}-1-[(2S)-oxane-2-carbonyl]-5-[2-(propan-2-yl)phenyl]pyrrolidine-2-carboxylic acid Example 96F (140 mg, 0.22 mmol) was dissolved in a mixture of 0.9 mL of tetrahydrofuran, 0.9 mL of water, and 0.45 mL of methanol. Lithium hydroxide hydrate (93 mg, 2.21 mmol) was added, and the reaction mixture was heated to 50° C. for 16 hours. The reaction mixture was cooled to room temperature, diluted with dichloromethane (10 mL), acidified with 1M aqueous HCl to pH=3, and extracted with 3×5 mL dichloromethane. The organic extracts were combined, dried over sodium sulfate, filtered, and concentrated in vacuo to provide Example 96H. X-ray confirmation of the absolute stereochemistry confirmed the identity of the title compound. ¹H NMR (400 MHz, DMSO-d$_6$, 120° C.) δ ppm 8.33-8.18 (m, 1H), 8.06 (dd, J=8.0, 1.3 Hz, 1H), 7.32-6.93 (m, 4H), 5.63 (s, 1H), 4.71 (d, J=1.7 Hz, 1H), 4.33 (d, J=14.0 Hz, 1H), 4.24 (d, J=5.8 Hz, 1H), 3.87 (s, 3H), 3.84 (d, J=8.0 Hz, 1H), 3.75 (d, J=11.2 Hz, 1H), 3.24 (p, J=6.8 Hz, 1H), 3.20-2.80 (br s, 2H), 2.52 (d, J=1.7 Hz, 1H), 1.73-1.22 (m, 6H), 1.30 (d, J=6.7 Hz, 3H), 1.13 (d, J=6.7 Hz, 3H), 1.04 (s, 9H); MS (ESI+) m/z 607.1 (M+H)⁺.

Example 97

(2S,3R,4S,5S)-3-tert-butyl-4-{[2-methoxy-5-(trifluoromethyl)pyridin-3-yl]methoxy}-1-[(2R)-oxane-2-carbonyl]-5-[2-(propan-2-yl)phenyl]pyrrolidine-2-carboxylic acid Example 96G (120 mg, 0.189 mmol) was dissolved in a mixture of 0.8 mL of tetrahydrofuran, 0.8 mL of water, and 0.4 mL of methanol in a 20-mL scintillation vial. Lithium hydroxide hydrate (79 mg, 1.9 mmol) was added, and the reaction mixture was heated to 50° C. for 16 hours in a heating block. The vial was cooled to room temperature, diluted with dichloromethane (5 mL), acidified with 1M aqueous HCl to pH=3, and extracted into dichloromethane (3×5 mL). The combined organic extracts were dried over sodium sulfate, filtered, and concentrated in vacuo to provide the title compound. ¹H NMR (400 MHz, DMSO-d$_6$, 120° C.) δ ppm 8.29-8.20 (m, 1H), 7.85 (s, 1H), 7.16 (d, J=7.8 Hz, 1H), 7.13-7.00 (m, 2H), 6.94 (t, J=7.5 Hz, 1H), 5.39 (d, J=5.8 Hz, 1H), 4.90 (s, 1H), 4.30 (d, J=14.0 Hz, 1H), 4.19 (d, J=5.8 Hz, 1H), 3.98 (br s, 1H), 3.86 (s, 3H), 3.82 (d, J=14.0 Hz, 1H), 3.82-3.75 (br s, 1H), 3.23 (p, J=6.8 Hz, 2H), 2.64 (s, 1H), 1.79 (s, 1H), 1.65-1.35 (m, 5H), 1.26 (d, J=6.7 Hz, 3H), 1.16 (d, J=6.8 Hz, 3H), 1.04 (s, 9H); MS (ESI+) m/z 607.1 (M+H)⁺.

Example 98

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(propan-2-yl)phenyl]pyrrolidine-2-carboxylic acid Example 98A (2S,3R,4S,5S)-ethyl 3-(tert-butyl)-5-(2-isopropylphenyl)-4-((2-methoxy-5-(trifluoromethyl)pyridin-3-yl)methoxy)-1-((S)-tetrahydrofuran-2-carbonyl)pyrrolidine-2-carboxylate (S)-Tetrahydrofuran-2-carboxylic acid (0.040 g, 0.344 mmol) was refluxed in thionyl chloride (0.65 mL, 8.96 mmol) for 1 hour, and the mixture was cooled to room temperature and concentrated in vacuo. Excess thionyl chloride was chased three times with dichloromethane (1 mL each), and the residue was treated with a solution of (2S,3R,4S,5S)-ethyl 3-(tert-butyl)-5-(2-isopropylphenyl)-4-((2-methoxy-5-(trifluoromethyl)pyridin-3-yl)methoxy)pyrrolidine-2-carboxylate (Example 96E) 0.180 g, 0.344 mmol) in dichloromethane (1 mL) and with pyridine (0.33 mL, 4.13 mmol). The mixture was stirred at room temperature for 2 hours. The reaction mixture was then diluted with 10 mL of ethyl acetate and washed with water (3×3 mL) and with brine (3 mL). The organic layer was dried over $Na_2SO_4$, filtered and concentrated in vacuo, and the crude product was used directly in the next reaction without further purification. MS (ESI+) m/z 621.6 (M+H)+.

Example 98B (2S,3R,4S,5S)-3-tert-butyl-4-{[2-methoxy-5-(trifluoromethyl)pyridin-3-yl]methoxy}-1-[(2S)-oxolane-2-carbonyl]-5-[2-(propan-2-yl)phenyl]pyrrolidine-2-carboxylic acid Example 98A (0.214 g, 0.344 mmol) and lithium hydroxide (1M aqueous) (3.5 mL, 3.50 mmol) were stirred in tetrahydrofuran (3.5 mL) and methanol (3.50 mL) overnight at 45° C. After this time, the reaction mixture was carefully acidified to pH 2 with 1N aqueous HCl, and the entire mixture was concentrated in vacuo. Excess moisture was removed azeotropically with acetonitrile, and the residue was subjected to silica gel chromatography, eluting with 0 to 20% methanol-dichloromethane. The still-impure material thus obtained was purified further by silica gel chromatography eluting with 5 to 25% 3:1 ethyl acetate-ethanol in heptanes to provide the title compound (45.9 mg). $^1$H NMR (400 MHz, DMSO-$d_6$) δ ppm 8.26 (m, 1H), 8.03 (d, J=7.7 Hz, 1H), 7.16 (m, 3H), 7.00 (t, J=7.5 Hz, 1H), 5.65 (m, 1H), 4.69 (d, J=1.9 Hz, 1H), 4.37-4.19 (m, 2H), 4.09 (m, 1H), 3.86-3.80 (m, 4H), 3.77-3.48 (m, 2H), 3.25 (m, 1H), 2.55 (m, 1H), 2.08-1.63 (m, 4H), 1.24 (d, J=6.7 Hz, 3H), 1.15 (d, J=6.7 Hz, 3H), 1.03 (s, 9H); MS (ESI+) m/z 593.1 (M+H)+.

Example 99

(2S,3R,4S,5S)-3-tert-butyl-5-(2-chlorophenyl)-4-{[2-methoxy-5-(trifluoromethyl)pyridin-3-yl]methoxy}-1-{[(propan-2-yl)oxy]carbonyl}pyrrolidine-2-carboxylic acid The title compound was prepared using the procedures described in Example 86 substituting Core 14 for Core 10. $^1$H NMR (500 MHz, DMSO-$d_6$) δ ppm 8.38 (d, J=2.3 Hz, 1H), 8.27 (s, 1H), 7.29 (d, J=7.6 Hz, 1H), 7.21 (td, J=7.2, 3.4 Hz, 2H), 6.94 (d, J=44.3 Hz, 1H), 5.29 (s, 1H), 4.65 (d, J=62.1 Hz, 1H), 4.42 (d, J=14.4 Hz, 1H), 4.35 (d, J=7.6 Hz, 2H), 4.02 (d, J=14.4 Hz, 1H), 3.87 (s, 3H), 2.58 (s, 1H), 1.21-1.12 (m, 3H), 1.01 (s, 12H); MS (APCI+) m/z 574 (M+H)+.

Example 100

(2S,3R,4S,5S)-3-tert-butyl-4-[(2-cyclobutyl-5-methoxypyridin-4-yl)methoxy]-5-phenyl-1-{[(propan-2-yl)oxy]carbonyl}pyrrolidine-2-carboxylic acid Example 100A (2S,3R,4S,5S)-2-ethyl 1-isopropyl 3-(tert-butyl)-4-nitro-5-phenylpyrrolidine-1,2-dicarboxylate A solution of Core 5 (30 g, 94 mmol) in toluene (187 mL) was treated with triethylamine (32.6 mL, 234 mmol) and was cooled in an ice bath to ~10° C. Isopropyl carbonochloridate (56.2 mL, 112 mmol, 2M solution in toluene) was added at such a rate that the temperature was maintained at or below room temperature during the addition (2-3 minutes). After the addition was complete, the flask was removed from the cold bath and stirred at room temperature for 45 minutes. The mixture was diluted with ethyl acetate and stirred with saturated aqueous sodium bicarbonate for 20 minutes. The phases were separated, and the organic layer was washed with 1M aqueous HCl three times and once with brine. The organic layer was dried over $Na_2SO_4$, filtered, and concentrated in vacuo. The crude product was treated with 50 mL of heptane and stirred vigorously. The mixture was stirred in an ice bath for an additional 30 minutes. The material was collected by filtration, washed with cold heptane, and air-dried to provide the title compound, 35 g (92%). $^1$H NMR (400 MHz, DMSO-$d_6$) δ ppm 7.54-7.47 (m, 2H), 7.28-7.15 (m, 3H), 5.60 (ddd, J=8.9, 3.4, 1.0 Hz, 1H), 5.43 (d, J=8.8 Hz, 1H), 4.67 (hept, J=6.2 Hz, 1H), 4.50 (d, J=3.8 Hz, 1H), 4.28-4.19 (m, 2H), 2.98 (t, J=3.5 Hz, 1H), 1.29 (t, J=7.1 Hz, 3H), 1.10-0.98 (m, 12H), 0.95 (m, 3H); MS (APCI+) m/z 407.3 (M+H)+.

Example 100B (2S,3R,5S)-2-ethyl 1-isopropyl 3-(tert-butyl)-4-oxo-5-phenylpyrrolidine-1,2-dicarboxylate Example 100A (20 g, 49.2 mmol) was dissolved in ethanol (443 mL), and the solution was heated to 75° C. A separate solution of chromium(II) chloride was prepared by dissolving pyridinium dichromate (48.1 g, 128 mmol) in 6M aqueous hydrochloric acid (887 mL) and adding zinc dust (88 g, 1.34 mol) in portions while cooling in an ice bath. The suspension was stirred at room temperature for 60 minutes after removing from the ice bath, leaving a brilliant blue solution. The solution was transferred via cannula over 90 minutes to the heated solution of starting material, Example 100A. The temperature was maintained between 70° C. and 75° C. during the addition. After completion of the addition, the heating was continued between 75° C. and 80° C. for 12 hours, and the reaction was brought to room temperature. The mixture was poured into a separatory funnel and extracted three times with dichloromethane (total 750 mL). The combined extracts were dried over sodium sulfate, filtered, and concentrated in vacuo. The crude material was then redissolved in ethanol (295 mL) and treated with a solution (prepared at 0° C.) of acetyl chloride (26.2 mL, 369 mmol) in ethanol (295 mL). The resulting solution was heated to 40° C. for 90 minutes, and cooled to room temperature. The solution was concentrated in vacuo to a volume of approximately 20 mL and was diluted with methyl tert-butyl ether. The solution was poured into a separatory funnel and washed three times with 1M aqueous HCl, three times with saturated sodium bicarbonate, and once with brine. The solution was dried over sodium sulfate, filtered, and concentrated in vacuo to provide the crude title compound, 26.84 g. The title compound was used directly in the subsequent reaction. MS (APCI$^+$) m/z 376.5 (M+H)$^+$.

Example 100C (2S,3R,4S,5S)-2-ethyl 1-isopropyl 3-(tert-butyl)-4-hydroxy-5-phenylpyrrolidine-1,2-dicarboxylate Example 100B (26.84 g, 71.5 mmol) was dissolved in ethanol (357 mL) in a 1 L round bottom flask. After cooling in an acetone-ice bath to ~-9° C., sodium borohydride (3.25 g, 86 mmol) was added in portions. After the addition, the cold bath was allowed to warm to −5° C., and excess sodium borohydride was quenched by slow addition of acetone (~5 mL). A delayed exotherm from 0 to 22° C. was noted. After the exotherm had subsided, the mixture continued stirring in the ice bath for another 20 minutes and was concentrated in vacuo to approximately 50 mL. Ethyl acetate (300 mL) was added, followed by 200 mL of saturated sodium bicarbonate, and the entire mixture was then stirred for 30 minutes at room temperature. The phases were separated, and the organic layer was washed with 1M aqueous NaOH (2×100 mL), 1M aqueous HCl (2×100 mL), and brine (100 mL). The organic layer was dried over sodium sulfate, filtered, and concentrated in vacuo. Heptanes (100 mL) were added, and the mixture was heated to dissolve the material (~60° C.). The mixture was allowed to cool slowly with stirring. After stirring at room temperature overnight, the solid was collected by filtration, washed with cold heptanes, and dried under vacuum. Silica gel chromatography of the crude material, eluting with 0 to 20% methyl tert-butyl ether-heptanes, provided the title compound, 18.7 g (67% yield over two steps). $^1$H NMR (400 MHz, DMSO-d$_6$) δ ppm 7.54-7.46 (m, 2H), 7.22 (m, 1H), 7.23-7.10 (m, 2H), 4.82 (d, J=6.7 Hz, 1H), 4.62 (hept, J=6.2 Hz, 1H), 4.31 (ddd, J=6.7, 5.3, 4.4 Hz, 1H), 4.25-4.09 (m, 3H), 3.84 (m, 1H), 2.24 (m, 1H), 1.24 (t, J=7.1 Hz, 3H), 1.04 (d, J=6.2 Hz, 3H), 0.98 (s, 9H), 0.90 (d, J=6.2 Hz, 3H); MS (ESI$^+$) m/z 378.0 (M+H)$^+$.

Example 100D 2-bromo-4-(bromomethyl)-5-methoxypyridine

To a solution of 2-bromo-5-methoxy-4-methylpyridine (1.00 g, 4.95 mmol) in CCl$_4$ (8 mL) was added N-bromosuccinimide (0.969 g, 5.44 mmol) and (E)-2,2'-(diazene-1,2-diyl)bis(2-methylpropanenitrile) (0.012 g, 0.074 mmol). The reaction was stirred at 80° C. for 2 hours, and cooled in an ice bath and filtered through diatomaceous earth. The solution was concentrated, and the crude product was purified with silica gel chromatography (5-50% ethyl acetate/heptanes, eluent) to provide the title compound, 0.280 g (20% yield). $^1$H NMR (400 MHz, CDCl$_3$) δ ppm 8.04 (s, 1H), 7.46 (s, 1H), 4.41 (s, 2H), 4.00 (s, 3H).

Example 100E (2S,3R,4S,5S)-2-ethyl 1-isopropyl 4-((2-bromo-5-methoxypyridin-4-yl)methoxy)-3-(tert-butyl)-5-phenylpyrrolidine-1,2-dicarboxylate Example 100C (0.380 g, 1.007 mmol) and Example 100D (0.280 g, 0.997 mmol) were dissolved in dry dimethylformamide (2.2 mL), and the resulting solution was cooled in an ice bath. A 1M solution of potassium 2-methylpropan-2-olate in tetrahydrofuran (1.6 mL, 1.6 mmol) was added dropwise over 10 minutes. The mixture was acidified with 1M aqueous HCl (40 drops) and warmed to room temperature. The mixture was diluted with 15 mL of water and 75 mL of methyl tert-butyl ether. The aqueous layer was removed, and the organics were washed with water and brine and then concentrated in vacuo. Silica gel chromatography (5 to 100% ethyl acetate-heptanes, eluent) provided the title compound, 85 mg (15% yield). $^1$H NMR (400 MHz, DMSO-d$_6$) δ ppm 7.92 (s, 1H), 7.59-7.51 (m, 2H), 7.25-7.10 (m, 3H), 6.71 (d, J=1.2 Hz, 1H), 5.00 (d, J=6.1 Hz, 1H), 4.65 (p, J=6.2 Hz, 1H), 4.37 (d, J=3.0 Hz, 1H), 4.29-4.21 (m, 2H), 4.15 (qd, J=7.1, 2.9 Hz, 2H), 3.86 (dd, J=14.6, 1.1 Hz, 1H), 3.76 (s, 3H), 2.44 (t, J=2.6 Hz, 1H), 1.20 (t, J=7.1 Hz, 3H), 1.05 (d, J=6.2 Hz, 3H), 1.01 (s, 9H), 0.90 (d, J=6.2 Hz, 3H); MS (APCI+) m/z 577 (M+H)$^+$.

Example 100F (2S,3R,4S,5S)-2-ethyl 1-isopropyl 3-(tert-butyl)-4-((2-cyclobutyl-5-methoxypyridin-4-yl)methoxy)-5-phenylpyrrolidine-1,2-dicarboxylate Example 100E (84 mg, 0.145 mmol) in tetrahydrofuran (1.45 mL) was treated with dichloro[4,5-dichloro-1,3-bis(2,6-Di-3-pentylphenyl)imidazol-2-ylidene](3-chloropyridyl)palladium(II) (PEPPSI-IPentCl, 12.5 mg, 0.015 mmol), followed by dropwise addition of cyclobutylzinc(II) bromide (0.5M in tetrahydrofuran) (0.35 mL, 0.175 mmol) at room temperature. After 30 minutes, an additional amount of cyclobutylzinc(II) bromide solution was added, (0.5M in tetrahydrofuran, 0.23 mL, 0.116 mmol), and the reaction continued to stir at room temperature for 2 hours. The reaction mixture was then quenched with saturated aqueous NH$_4$Cl solution, and the solvent was then evaporated under a stream of nitrogen. The crude product was purified by silica gel chromatography using 5-50% ethyl acetate/heptanes as the eluent to obtain the title compound, 71 mg (88% yield). $^1$H NMR (400 MHz, DMSO-d$_6$) δ ppm 8.05 (s, 1H), 7.61-7.51 (m, 2H), 7.25-7.10 (m, 3H), 6.52 (s, 1H), 5.00 (d, J=6.1 Hz, 1H), 4.64 (p, J=6.2 Hz, 1H), 4.36 (d, J=3.1 Hz, 1H), 4.30-4.18 (m, 2H), 4.11 (qd, J=7.1, 2.7 Hz, 2H), 3.89 (d, J=13.8 Hz, 1H), 3.73 (s, 3H), 3.40 (p, J=8.4 Hz, 1H), 2.27-2.06 (m, 4H), 1.97 (dq, J=10.7, 8.7 Hz, 1H), 1.83 (dddd, J=9.9, 8.9, 7.9, 4.1 Hz, 1H), 1.16 (t, J=7.1 Hz, 3H), 1.05 (d, J=6.2 Hz, 3H), 1.00 (s, 9H), 0.89 (d, J=6.3 Hz, 3H), 0.85 (dt, J=7.5, 2.8 Hz, 1H); MS (ESI+) m/z 552 (M+H)$^+$.

Example 100G (2S,3R,4S,5S)-3-tert-butyl-4-[(2-cyclobutyl-5-methoxypyridin-4-yl)methoxy]-5-phenyl-1-{[(propan-2-yl)oxy]carbonyl}pyrrolidine-2-carboxylic acid Example 100F (0.054 g, 0.098 mmol) in tetrahydrofuran (0.78 mL) and methanol (0.78 mL) was treated with lithium hydroxide (1M aqueous) (0.78 mL, 0.780 mmol), and the reaction was stirred at 45° C. overnight. An additional amount of 1M aqueous LiOH was added (0.2 mL), and stirring was continued at 50° C. for 6 hours and at room temperature for 3 days. After this time, the pH was adjusted carefully to pH 2 with 1N aqueous HCl, and the whole mixture was concentrated in vacuo. The residue was dried azeotropically with acetonitrile, and the resulting material was purified by silica gel chromatography, eluting with 5 to 25% 3:1 ethyl acetate/ethanol-heptanes to obtain the title compound, 43 mg (84% yield). $^1$H NMR (400 MHz, DMSO-d$_6$) δ ppm 8.04 (s, 1H), 7.61 (d, J=7.4 Hz, 2H), 7.23-7.10 (m, 3H), 6.49 (s, 1H), 4.97 (d, J=6.4 Hz, 1H), 4.66-4.58 (m, 1H), 4.24 (m, 2H), 4.16 (dd, J=6.3, 2.4 Hz, 1H), 3.90 (d, J=13.8 Hz, 1H), 3.73 (s, 3H), 3.39 (m, 1H), 2.52 (m, 1H), 2.22-1.81 (m, 6H), 1.05 (d, J=6.3 Hz, 3H), 0.98 (s, 9H), 0.87 (d, J=6.2 Hz, 3H); MS (ESI$^+$) m/z 525.3 (M+H)$^+$.

Example 101

(2S,3R,4S,5S)-3-tert-butyl-5-(2-cyclobutylphenyl)-4-{[2-methoxy-5-(trifluoromethyl)pyridin-3-yl]methoxy}-1-{[(propan-2-yl)oxy]carbonyl}pyrrolidine-2-carboxylic acid The title compound was prepared according to the procedure described in Example 43, substituting Example 86D for Example 40A, and cyclobutylzinc(II) bromide for cyclohexylzinc bromide in Example 43A. $^1$H NMR (400 MHz, 120° C., DMSO-d$_6$:D$_2$O=9:1 (v/v)) δ ppm 8.24 (d, J=2.1 Hz, 1H), 8.07 (d, J=7.8 Hz, 1H), 7.20-7.06 (m, 3H), 6.98 (t, J=7.3 Hz, 1H), 5.08 (d, J=5.8 Hz, 1H), 4.58 (p, J=6.3 Hz, 1H), 4.30 (d, J=1.7 Hz, 1H), 4.22 (d, J=14.0 Hz, 1H), 4.09 (d, J=5.9 Hz, 1H), 3.90-3.76 (m, 4H), 3.70 (p, J=8.6 Hz, 1H), 2.53 (s, 1H), 2.42-2.27 (m, 1H), 2.07 (ddq, J=46.2, 27.2, 9.8, 9.0 Hz, 4H), 1.81 (t, J=9.5 Hz, 1H), 1.01 (d, J=5.5 Hz, 12H), 0.79 (d, J=6.2 Hz, 3H); MS (APCI+) m/z 593.0 (M+H)$^+$.

Example 102

(2S,3R,4S,5S)-3-tert-butyl-4-{[2-methoxy-5-(trifluoromethyl)pyridin-3-yl]methoxy}-1-[(2R)-oxolane-2-carbonyl]-5-[2-(propan-2-yl)phenyl]pyrrolidine-2-carboxylic acid Example 102A (2S,3R,4S,5S)-ethyl 3-(tert-butyl)-5-(2-isopropylphenyl)-4-((2-methoxy-5-(trifluoromethyl)pyridin-3-yl)methoxy)-1-((R)-tetrahydrofuran-2-carbonyl)pyrrolidine-2-carboxylate The title compound was prepared according to the procedure of Example 98A, substituting (R)-tetrahydrofuran-2-carboxylic acid for (S)-tetrahydrofuran-2-carboxylic acid. The crude product was taken directly into the next step without further purification. MS (ESI$^+$) m/z 621.4 (M+H)$^+$.

Example 102B (2S,3R,4S,5S)-3-(tert-butyl)-5-(2-isopropylphenyl)-4-((2-methoxy-5-(trifluoromethyl)pyridin-3-yl)methoxy)-1-((R)-tetrahydrofuran-2-carbonyl)pyrrolidine-2-carboxylic acid The title compound was prepared according to the procedure of Example 98B, substituting Example 102A for Example 98A. $^1$H NMR (400 MHz, DMSO-d$_6$) δ ppm 8.25 (m, 1H), 7.85 (m, 1H), 7.20-7.13 (m, 1H), 7.13-7.04 (m, 2H), 6.95 (t, J=7.5 Hz, 1H), 5.39 (d, J=5.8 Hz, 1H), 4.93 (m, 1H), 4.44 (m, 1H), 4.31 (d, J=14.0 Hz, 1H), 4.21 (d, J=5.8 Hz, 1H), 3.86 (s, 3H), 3.83 (m, 1H), 3.76-3.66 (m, 2H), 3.23 (m, 1H), 2.65 (s, 1H), 1.99 (m, 1H), 1.95-1.73 (m, 3H), 1.25 (d, J=6.7 Hz, 3H), 1.15 (d, J=6.8 Hz, 3H), 1.05 (s, 9H); MS (ESI$^+$) m/z 593.0 (M+H)$^+$.

Example 103

(2S,3R,4S,5S)-3-tert-butyl-5-(2-chlorophenyl)-4-{[2-methoxy-5-(trifluoromethyl)pyridin-3-yl]methoxy}-1-[(2S)-oxane-2-carbonyl]pyrrolidine-2-carboxylic acid The title compound was prepared using the procedures described in Example 179 substituting Core 14 for Core 24, using the first eluting diastereomer as described in Example 179F. $^1$H NMR (400 MHz, DMSO-d$_6$) δ ppm 8.31 (s, 1H), 8.28 (s, 1H), 7.27 (s, 1H), 7.17 (s, 2H), 7.09 (d, J=2.2 Hz, 1H), 5.80 (s, 1H), 4.63-4.54 (m, 1H), 4.37 (d, J=14.0 Hz, 1H), 4.32 (d, J=6.3 Hz, 1H), 4.00 (d, J=14.0 Hz, 1H), 3.88 (s, 3H), 3.80 (d, J=11.2 Hz, 1H), 3.25 (bs, 2H), 2.58 (s, 1H), 1.70 (s, 1H), 1.54 (s, 2H), 1.37 (bs, 3H), 1.01 (s, 9H); MS (ESI+) m/z 599 (M+H)$^+$.

Example 104

(2S,3R,4S,5S)-3-tert-butyl-5-(2-chlorophenyl)-4-{[2-methoxy-5-(trifluoromethyl)pyridin-3-yl]methoxy}-1-[(2R)-oxane-2-carbonyl]pyrrolidine-2-carboxylic acid The title compound was prepared using the procedures described in Example 179 substituting Core 14 for Core 24 using the second eluting diastereomer as described in Example 179F. $^1$H NMR (400 MHz, DMSO-d$_6$) δ ppm 8.27 (s, 1H), 8.18 (s, 1H), 7.20 (d, J=6.4 Hz, 1H), 7.09 (s, 2H), 6.98 (s, 1H), 5.41 (s, 1H), 4.70 (s, 1H), 4.38 (d, J=14.2 Hz, 1H), 4.28 (d, J=6.5 Hz, 1H), 4.01 (d, J=14.2 Hz, 1H), 3.89 (s, 3H), 3.85 (bs, 1H), 2.79 (s,1H), 3.44 (bs,2H), 1.81 (s, 1H), 1.61 (s, 1H), 1.51 (d, J=13.9 Hz, 1H), 1.46 (s, 3H), 1.01 (s, 9H); MS (ESI+) m/z 599 (M+H)$^+$.

Example 105

(2S,3R,4S,5S)-3-tert-butyl-4-{[2-methoxy-5-(trifluoromethyl)pyridin-3-yl]methoxy}-1-{[(propan-2-yl)oxy]carbonyl}-5-{2-[(propan-2-yl)oxy]phenyl}pyrrolidine-2-carboxylic acid The title compound was prepared according to the procedure described in Example 73A-73E, Core 15 for Core 6 in Example 73A. $^1$H NMR (400 MHz, DMSO-d$_6$) δ ppm 8.29-8.24 (m, 1H), 7.82 (dd, J=7.6, 1.8 Hz, 1H), 7.17-7.11 (m, 1H), 7.09-7.00 (m, 1H), 6.84-6.72 (m, 2H), 5.30 (d, J=5.8 Hz, 1H), 4.66 (hept, J=6.2 Hz, 1H), 4.52 (hept, J=6.0 Hz, 1H), 4.40-4.28 (m, 2H), 4.22 (dd, J=5.8, 1.5 Hz, 1H), 3.94 (dt, J=13.9, 1.0 Hz, 1H), 3.87 (s, 3H), 2.58 (m, 1H), 1.25 (dd, J=10.5, 6.0 Hz, 6H), 1.04 (d, J=6.2 Hz, 3H), 1.01 (s, 9H), 0.90 (d, J=6.2 Hz, 3H); MS (ESI+) m/z 597 (M+H)$^+$.

Example 106

(2S,3R,4S,5S)-3-tert-butyl-4-[(2-methoxyquinolin-3-yl)methoxy]-5-phenyl-1-{[(propan-2-yl)oxy]carbonyl}pyrrolidine-2-carboxylic acid Example 106A (2-methoxyquinolin-3-yl)methanol 2-Methoxyquinoline-3-carbaldehyde (1.45 g, 7.75 mmol) was suspended in methanol (20 mL) and cooled to 0° C.

Sodium borohydride (600 mg, 15.86 mmol) was added, causing bubbling. The reaction mixture stirred at 0° C. to room temperature overnight (ice bath melted). The reaction mixture was concentrated, and the crude material was taken up in saturated aqueous sodium bicarbonate solution (50 mL) and extracted with dichloromethane (2×50 mL). The combined organic layers were dried over $Na_2SO_4$, filtered, and concentrated to provide the title compound (1.46 g, 7.72 mmol, 100% yield). $^1$H NMR (500 MHz, DMSO-$d_6$) δ ppm 8.19 (q, J=1.2 Hz, 1H), 7.90 (dd, J=8.0, 1.5 Hz, 1H), 7.82-7.72 (m, 1H), 7.62 (ddd, J=8.4, 6.9, 1.5 Hz, 1H), 7.42 (ddd, J=8.1, 6.9, 1.2 Hz, 1H), 5.44-5.30 (m, 1H), 4.66-4.54 (m, 2H), 4.01 (s, 3H); MS (ESI+) m/z 190 (M+H)$^+$.

Example 106B 3-(bromomethyl)-2-methoxyquinoline

Example 106A (1.46 g, 7.72 mmol) and triphenylphosphine (4.00 g, 15.25 mmol) were dissolved in dichloromethane (25 mL) and cooled in an ice bath. N-bromosuccinimide (1.373 g, 7.72 mmol) was added gradually using a solid addition funnel, keeping the internal temperature below 10° C. The ice bath was removed, and after stirring for 15 minutes the reaction was complete. The reaction was quenched by adding 10 mL of water, stirred for 5 minutes, and the layers were separated. The organics were washed twice with water, and filtered through a fritted cartridge layered with a pad of silica (1 cm), eluting with heptanes. The filtrates were reduced in volume. The mixture was filtered and washed with 3×30 mL of 50:50 methyl tert-butyl ether:heptanes, and the solvent was removed in vacuo. The crude material was purified using a 40 g silica gel cartridge eluting with dichloromethane to provide the title compound (1.01 g, 4.01 mmol, 51.9% yield). $^1$H NMR (500 MHz, DMSO-$d_6$) δ ppm 8.35 (s, 1H), 7.86 (dd, J=8.1, 1.4 Hz, 1H), 7.77 (d, J=8.2 Hz, 1H), 7.67 (ddd, J=8.3, 6.9, 1.5 Hz, 1H), 7.44 (ddd, J=8.2, 6.8, 1.2 Hz, 1H), 4.74 (s, 2H), 4.05 (s, 3H); MS (ESI+) m/z 252 (M+H)$^+$.

Example 106C 2-ethyl 1-isopropyl (2S,3R,4S,5S)-3-(tert-butyl)-4-((2-methoxyquinolin-3-yl)methoxy)-5-phenylpyrrolidine-1,2-dicarboxylate Example 38C (100.6 mg, 0.267 mmol) and 3-(bromomethyl)-2-methoxyquinoline (Example 106B, 112.6 mg, 0.447 mmol) were dissolved in dimethylformamide (1.5 mL). The reaction was cooled to 0° C., potassium tert-butoxide (1M in tetrahydrofuran, 0.30 mL, 0.30 mmol) was added dropwise, and the reaction was stirred at ambient temperature for 1 hour. The reaction was quenched by the addition of 1M aqueous HCl (0.1 mL) and purified by silica gel chromatography (5% to 100% ethyl acetate in heptanes) to provide the title compound (71.9 mg, 49.2%). $^1$H NMR (400 MHz, DMSO-$d_6$, 120° C.) δ ppm 7.67 (dt, J=8.8, 1.0 Hz, 1H), 7.63-7.57 (m, 2H), 7.57-7.50 (m, 2H), 7.34 (ddd, J=8.0, 6.9, 1.2 Hz, 1H), 7.31 (q, J=1.0 Hz, 1H), 7.26-7.20 (m, 2H), 7.20-7.14 (m, 1H), 5.04 (d, J=6.2 Hz, 1H), 4.65 (hept, J=6.2 Hz, 1H), 4.38 (d, J=3.2 Hz, 1H), 4.34 (dd, J=13.6, 1.2 Hz, 1H), 4.28 (dd, J=6.2, 2.6 Hz, 1H), 4.12 (qd, J=7.1, 0.9 Hz, 2H), 4.02 (dd, J=13.7, 1.3 Hz, 1H), 3.92 (s, 3H), 2.50 (t, J=2.9 Hz, 1H), 1.16 (t, J=7.1 Hz, 3H), 1.06 (d, J=6.2 Hz, 3H), 1.01 (s, 9H), 0.91 (d, J=6.3 Hz, 3H); MS (ESI+) m/z 549 (M+H)$^+$.

Example 106D (2S,3R,4S,5S)-3-tert-butyl-4-[(2-methoxyquinolin-3-yl)methoxy]-5-phenyl-1-{[(propan-2-yl)oxy]carbonyl}pyrrolidine-2-carboxylic acid Example 106C (62.3 mg, 0.114 mmol) was dissolved in methanol (1 mL), and tetrahydrofuran (1 mL). LiOH (1 M aqueous, 0.5 mL, 0.5 mmol) was added and the reaction was heated to 50° C. for 16 hours. The reaction was quenched by the addition of 1M aqueous HCl (0.5 mL) and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (48.1 mg, 67%) as the TFA salt. $^1$H NMR (400 MHz, DMSO-$d_6$, 120° C.) δ ppm 7.70-7.50 (m, 5H), 7.38-7.30 (m, 2H), 7.25-7.13 (m, 3H), 5.02 (d, J=6.2 Hz, 1H), 4.65 (hept, J=6.2 Hz, 1H), 4.39-4.31 (m, 2H), 4.26 (dd, J=6.2, 2.2 Hz, 1H), 4.01 (dd, J=13.9, 1.3 Hz, 1H), 3.92 (s, 3H), 2.53 (t, J=2.6 Hz, 1H), 1.06 (d, J=6.2 Hz, 3H), 1.02 (s, 9H), 0.90 (d, J=6.2 Hz, 3H); MS (ESI+) m/z 521 (M+H)$^+$.

Example 107

(2S,3R,4S,5S)-3-tert-butyl-4-{[2-hydroxy-5-(trifluoromethyl)pyridin-3-yl]methoxy}-5-phenyl-1-{[(propan-2-yl)oxy]carbonyl}pyrrolidine-2-carboxylic acid Example 64 (250 mg, 0.464 mmol) was dissolved in 2 mL of 1,4-dioxane in a 20-mL scintillation vial, and hydrochloric acid (6M in water, 2.0 mL, 12 mmol) was added. The vial was capped and heated to 60° C. for 6 hours, at which point complete demethylation had occurred as indicated by LC/MS. The vial was cooled to ambient temperature. The material was removed via filtration through a fritted funnel and dried to constant weight in a vacuum oven at 50° C. to provide 197 mg of the title compound. $^1$H NMR (400 MHz, DMSO-$d_6$, 120° C.) δ ppm 7.66-7.49 (m, 3H), 7.28-6.98 (m, 3H), 6.81 (dt, J=2.9, 1.4 Hz, 1H), 5.00 (d, J=6.2 Hz, 1H), 4.64 (hept, J=6.2 Hz, 1H), 4.33 (d, J=3.0 Hz, 1H), 4.24 (dd, J=6.2, 2.2 Hz, 1H), 4.15 (dt, J=14.5, 1.0 Hz, 1H), 3.74 (dt, J=14.6, 1.1 Hz, 1H), 2.48 (m, J=1.9 Hz, 1H), 1.06 (d, J=6.2 Hz, 3H), 1.02 (s, 9H), 0.89 (d, J=6.2 Hz, 3H); MS (ESI+) m/z 524.9 (M+H)$^+$.

Example 108

(2S,3R,4S,5S)-3-tert-butyl-5-[2-(3,6-dihydro-2H-pyran-4-yl)phenyl]-4-{[2-methoxy-5-(trifluoromethyl)pyridin-3-yl]methoxy}-1-{[(propan-2-yl)oxy]carbonyl}pyrrolidine-2-carboxylic acid The title compound was prepared according to the procedure described in Example 65 substituting Example 86D for Example 40A, and 2-(3,6-dihydro-2H-pyran-4-yl)-4,4,5,5-tetramethyl-1,3,2-dioxaborolane for (2-fluoro-4-methylphenyl)boronic acid. $^1$H NMR (400 MHz, 120° C., DMSO-$d_6$:$D_2O$=9:1 (v/v)) δ ppm 8.27 (s, 1H), 8.00-7.92 (m, 1H), 7.23 (d, J=2.4 Hz, 1H), 7.20-7.02 (m, 2H), 6.96 (dd, J=7.2, 1.7 Hz, 1H), 5.50 (s, 1H), 5.08 (d, J=5.4 Hz, 1H), 4.62 (p, J=6.2 Hz, 1H), 4.38 (d, J=1.6 Hz, 1H), 4.34-4.25 (m, 1H), 4.14 (q, J=2.8 Hz, 2H), 3.98 (d, J=5.4 Hz, 1H), 3.92-3.68 (m, 6H), 2.43 2.12 (m, 2H), 1.00 (d, J=11.0 Hz, 12H), 0.81 (d, J=6.2 Hz, 3H); MS (APCI+) m/z 621.3 (M+H)+.

Example 109

(2S,3R,4S,5S)-3-tert-butyl-4-{[2-methoxy-5-(trifluoromethyl)pyridin-3-yl]methoxy}-1-[(3S)-oxolane-3-carbonyl]-5-[2-(propan-2-yl)phenyl]pyrrolidine-2-carboxylic acid

Example 109A (2S,3R,4S,5S)-ethyl 3-(tert-butyl)-5-(2-isopropylphenyl)-4-((2-methoxy-5-(trifluoromethyl)pyridin-3-yl)methoxy)-1-((S)-tetrahydrofuran-3-carbonyl)pyrrolidine-2-carboxylate The title compound was prepared according to the procedure of Example 98A, substituting (S)-tetrahydrofuran-3-carboxylic acid for (S)-tetrahydrofuran-2-carboxylic acid. The crude product was taken directly into the next step without further purification. MS (ESI+) m/z 621.8 (M+H)+.

Example 109B (2S,3R,4S,5S)-3-tert-butyl-4-{[2-methoxy-5-(trifluoromethyl)pyridin-3-yl]methoxy}-1-[(3S)-oxolane-3-carbonyl]-5-[2-(propan-2-yl)phenyl]pyrrolidine-2-carboxylic acid The title compound was prepared according to the procedure of Example 98B, substituting Example 109A for Example 98A. $^1$H NMR (400 MHz, DMSO-d$_6$) δ ppm 8.27 (s, 1H), 8.00-7.93 (m, 1H), 7.25-7.06 (m, 3H), 7.02 (t, J=7.5 Hz, 1H), 5.45 (d, J=5.8 Hz, 1H), 4.65 (m, 1H), 4.36-4.23 (m, 2H), 3.86 (s, 3H), 3.84 (m, 1H), 3.74 (m, 1H), 3.68 (m, 1H), 3.57-3.44 (m, 2H), 3.26 (m, 1H), 2.99 (m, 1H), 2.59 (m, 1H), 1.90 (m, 2H), 1.25 (m, 3H), 1.16 (d, J=6.7 Hz, 3H), 1.04 (s, 9H); MS (ESI+) m/z 593.2 (M+H)+.

Example 110

(2S,3R,4S,5S)-3-tert-butyl-4-{[2-methoxy-5-(trifluoromethyl)pyridin-3-yl]methoxy}-1-(oxane-4-carbonyl)-5-[2-(propan-2-yl)phenyl]pyrrolidine-2-carboxylic acid

Example 110A (2S,3R,4S,5S)-ethyl 3-(tert-butyl)-5-(2-isopropylphenyl)-4-((2-methoxy-5-(trifluoromethyl)pyridin-3-yl)methoxy)-1-(tetrahydro-2H-pyran-4-carbonyl)pyrrolidine-2-carboxylate The title compound was prepared according to the procedure of Example 98A, substituting tetrahydro-2H-pyran-4-carboxylic acid for (S)-tetrahydrofuran-2-carboxylic acid. The crude product was taken directly into the next step without further purification. MS (ESI+) m/z 635.6 (M+H)+.

Example 110B (2S,3R,4S,5S)-3-(tert-butyl)-5-(2-isopropylphenyl)-4-((2-methoxy-5-(trifluoromethyl)pyridin-3-yl)methoxy)-1-(tetrahydro-2H-pyran-4-carbonyl)pyrrolidine-2-carboxylic acid The title compound was prepared according to the procedure of Example 98B, substituting Example 110A for Example 98A. $^1$H NMR (400 MHz, DMSO-d$_6$) δ ppm 8.26 (m, 1H), 7.99 (m, 1H), 7.22 (m, 1H), 7.11 (m, 2H), 7.00 (m, 1H), 5.42 (d, J=5.9 Hz, 1H), 4.63 (m, 1H), 4.36-4.22 (m, 2H), 3.86 (s, 3H), 3.84 (m, 1H), 3.77 (m, 2H), 3.67 (m, 1H), 3.26 (m, 1H), 3.10 (m, 1H), 2.83 (m, 1H), 2.58 (m, 1H), 1.53 (m, 4H), 1.27 (d, J=6.8 Hz, 3H), 1.16 (d, J=6.8 Hz, 3H), 1.03 (s, 9H); MS (ESI+) m/z 607.1 (M+H)+.

Example 111

(2S,3R,4S,5S)-3-tert-butyl-4-{[2-methoxy-5-(trifluoromethyl)pyridin-3-yl]methoxy}-1-[(3R)-oxolane-3-carbonyl]-5-[2-(propan-2-yl)phenyl]pyrrolidine-2-carboxylic acid

Example 111A (2S,3R,4S,5S)-ethyl 3-(tert-butyl)-5-(2-isopropylphenyl)-4-((2-methoxy-5-(trifluoromethyl)pyridin-3-yl)methoxy)-1-((R)-tetrahydrofuran-3-carbonyl)pyrrolidine-2-carboxylate The title compound was prepared according to the procedure of Example 98A, substituting (R)-tetrahydrofuran-3-carboxylic acid for (S)-tetrahydrofuran-2-carboxylic acid. The crude product was taken directly into the next step without further purification. MS (ESI+) m/z 621.7 (M+H)+.

Example 111B (2S,3R,4S,5S)-3-tert-butyl-4-{[2-methoxy-5-(trifluoromethyl)pyridin-3-yl]methoxy}-1-[(3R)-oxolane-3-carbonyl]-5-[2-(propan-2-yl)phenyl]pyrrolidine-2-carboxylic acid The title compound was prepared according to the procedure of Example 98B, substituting Example 111A for Example 98A. $^1$H NMR (400 MHz, DMSO-d$_6$) δ ppm 8.27 (m, 1H), 7.94 (m, 1H), 7.20-6.98 (m, 4H), 5.42 (d, J=5.9 Hz, 1H), 4.66 (d, J=1.9 Hz, 1H), 4.36-4.22 (m, 2H), 3.86 (s, 3H), 3.89-3.75 (m, 2H), 3.66 (m, 1H), 3.53 (m, 2H), 3.24 (h, J=6.9 Hz, 1H), 2.99 (m, 1H), 2.61 (m, 1H), 1.88-1.59 (m, 2H), 1.24 (d, J=6.8 Hz, 3H), 1.15 (d, J=6.8 Hz, 3H), 1.04 (s, 9H); MS (ESI+) m/z 593.2 (M+H)+.

Example 112

(2S,3R,4S,5S)-3-tert-butyl-5-(2-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid

Example 112A 1-allyl 2-ethyl (2S,3R,4S,5S)-3-(tert-butyl)-5-(2-cyclopropylphenyl)-4-nitropyrrolidine-1,2-dicarboxylate Core 12 (2.00 g, 5.55 mmol) was dissolved in toluene (10 mL) and saturated aqueous NaHCO$_3$ (10 mL) was added followed by allyl chloroformate (0.708 mL, 6.66 mmol). The reaction was stirred at ambient temperature for 17 hours, at which point it was complete. The reaction was diluted with dichloromethane (50 mL) and washed with 1M aqueous HCl (2×50 mL) and brine. The organic layer was dried over sodium sulfate, filtered, and concentrated to provide the crude product. The residue was purified by silica gel chromatography (5% ethyl acetate in dichloromethane) to provide the title compound (1.76 g, 71%). $^1$H NMR (400 MHz, DMSO-d$_6$, 120° C.) δ ppm 7.78 (dd, J=7.6, 1.7 Hz, 1H), 7.17-7.04 (m, 2H), 7.01-6.95 (m, 1H), 6.00 (d, J=8.6 Hz, 1H), 5.67 (ddt, J=17.2, 10.4, 5.2 Hz, 1H), 5.56 (dd, J=8.6, 2.5 Hz, 1H), 5.05-4.89 (m, 2H), 4.60 (d, J=3.4 Hz, 1H), 4.41 (dq, J=5.2, 1.5 Hz, 2H), 4.27 (qd, J=7.1, 1.0 Hz, 2H), 3.05 (ddd, J=3.3, 2.5, 0.7 Hz, 1H), 2.06 (tt, J=8.5, 5.4 Hz, 1H), 1.30 (t, J=7.1 Hz, 3H), 1.04 (s, 9H), 1.02-0.88 (m, 2H), 0.85-0.75 (m, 1H), 0.54 (dtd, J=7.9, 5.1, 2.9 Hz, 1H); MS (ESI+) m/z 445 (M+H)$^+$.

Example 112B 1-allyl 2-ethyl (2S,3R,5S)-3-(tert-butyl)-5-(2-cyclopropylphenyl)-4-oxopyrrolidine-1,2-dicarboxylate Example 112A (1.79 g, 3.93 mmol) was dissolved in 44 mL of ethanol and the solution was heated to 75° C. A separate solution of CrCl$_2$ was prepared by dissolving pyridinium dichromate (4.066 g, 10.81 mmol) in 88 mL of 6M aqueous HCl and adding Zn (7.904 g, 119 mmol) in portions while cooling in an ice bath. The suspension was stirred until all Zn dissolved, leaving a brilliant blue solution. The CrCl$_2$ solution was transferred via cannula over 15 minutes to the solution of starting material and heating was continued for 16 hours. The temperature was maintained between 70° C. and 75° C. during the addition, and was maintained between 75° C. and 80° C. overnight (total 16 hours). The reaction mixture was cooled to room temperature, diluted with water and extracted with dichloromethane (3×200 mL). The combined extracts were washed with brine, and dried over sodium sulfate, filtered, and concentrated. The crude residue was dissolved ethanol (6 mL). A separate solution of HCl/ethanol was prepared by addition of 1 mL of acetyl chloride to 4 mL of ethanol at 0° C., and poured into the reaction flask and the mixture was heated to 45° C. for 1 hour. The reaction mixture was concentrated in vacuo and loaded onto a 40 g silica gel column and was eluted with 5% ethyl acetate in dichloromethane over to provide the title compound (518.9 mg, 32%). $^1$H NMR (400 MHz, DMSO-d$_6$, 120° C.) δ ppm 7.69 (dd, J=7.1, 2.0 Hz, 1H), 7.19-7.05 (m, 3H), 5.74-5.63 (m, 2H), 5.07-4.94 (m, 2H), 4.65 (d, J=5.0 Hz, 1H), 4.45 (dd, J=5.3, 1.8 Hz, 2H), 4.28-4.18 (m, 2H), 2.63 (dd, J=5.0, 0.9 Hz, 1H), 2.13 (tt, J=8.5, 5.4 Hz, 1H), 1.26 (td, J=7.1, 0.8 Hz, 3H), 1.07 (d, J=0.8 Hz, 9H), 0.95-0.83 (m, 2H), 0.83-0.72 (m, 1H), 0.52 (dddd, J=7.8, 6.6, 3.9, 1.5 Hz, 1H); MS (ESI+) m/z 414 (M+H)$^+$.

Example 112C 1-allyl 2-ethyl (2S,3R,4S,5S)-3-(tert-butyl)-5-(2-cyclopropylphenyl)-4-hydroxypyrrolidine-1,2-dicarboxylate Example 112B (504.6 mg, 1.220 mmol) was dissolved in ethanol (5 mL), and the reaction was cooled to 0° C. Sodium borohydride (75.0 mg, 1.982 mmol) was added and the reaction was stirred at 0° C. for 1 hour, and warmed to ambient temperature for another 1 hour. The solvent was removed in vacuo and the residue was extracted with ethyl acetate (50 mL), washed with saturated aqueous NaHCO$_3$ (50 mL) and brine (50 mL), dried over Na$_2$SO$_4$, filtered, and concentrated to provide crude product, which was purified by silica gel chromatography (5% ethyl acetate in dichloromethane) to provide the title compound (280 mg, 55%). $^1$H NMR (400 MHz, DMSO-d$_6$, 120° C.) δ ppm 7.89-7.83 (m, 1H), 7.10-7.04 (m, 2H), 7.01-6.95 (m, 1H), 5.72-5.60 (m, 1H), 5.51 (d, J=6.2 Hz, 1H), 5.03-4.91 (m, 2H), 4.45 (td, J=5.6, 2.9 Hz, 1H), 4.36 (td, J=3.5, 2.1 Hz, 3H), 4.18 (q, J=7.1 Hz, 2H), 3.71 (s, 1H), 2.31 (t, J=3.4 Hz, 1H), 1.97 (tt, J=7.9, 5.4 Hz, 1H), 1.25 (t, J=7.1 Hz, 3H), 1.01 (s, 9H), 0.88 (ttd, J=12.7, 8.9, 5.6 Hz, 2H), 0.73 (dtd, J=9.4, 5.4, 3.6 Hz, 1H), 0.61-0.49 (m, 1H); MS (ESI+) m/z 416 (M+H)$^+$.

Example 112D 1-allyl 2-ethyl (2S,3R,4S,5S)-3-(tert-butyl)-5-(2-cyclopropylphenyl)-4-((2-methoxy-5-(trifluoromethyl)pyridin-3-yl)methoxy)pyrrolidine-1,2-dicarboxylate Example 112C (275.0 mg, 0.662 mmol) and 3-(bromomethyl)-2-methoxy-5-(trifluoromethyl)pyridine (312.1 mg, 1.156 mmol) were dissolved in dimethylformamide (2.6 mL). The reaction was cooled to 0° C., and potassium tert-butoxide (1M in tetrahydrofuran, 0.80 mL, 0.80 mmol) was added dropwise. The reaction mixture was stirred at ambient temperature for 1 hour. The reaction mixture was poured into saturated aqueous NH$_4$Cl (35 mL), extracted with methyl tert-butyl ether (3×35 mL), and purified by silica gel chromatography (5% ethyl acetate in dichloromethane) to provide the title compound (350.8 mg, 88%). $^1$H NMR (400 MHz, DMSO-d$_6$, 120° C.) δ ppm 8.33-8.25 (m, 1H), 7.88 (dd, J=7.3, 2.1 Hz, 1H), 7.20-7.15 (m, 1H), 7.02 (ddd, J=7.0, 4.5, 1.9 Hz, 2H), 6.94 (dd, J=6.9, 2.1 Hz, 1H), 5.73-5.58 (m, 2H), 5.05-4.90 (m, 2H), 4.52 (d, J=2.0 Hz, 1H), 4.41-4.37 (m, 2H), 4.37-4.33 (m, 1H), 4.27 (d, J=13.8 Hz, 1H), 4.11 (dtd, J=8.0, 6.9, 1.2 Hz, 2H), 3.87-3.79 (m, 4H), 2.52 (t, J=1.3 Hz, 1H), 1.99 (td, J=8.4, 4.2 Hz, 1H), 1.15 (td, J=7.1, 0.7 Hz, 3H), 1.05 (s, 9H), 0.96-0.83 (m, 2H), 0.59 (dd, J=5.2, 2.6 Hz, 2H); MS (ESI+) m/z 605 (M+H)$^+$.

Example 112E ethyl (2S,3R,4S,5S)-3-(tert-butyl)-5-(2-cyclopropylphenyl)-4-((2-methoxy-5-(trifluoromethyl)pyridin-3-yl)methoxy)pyrrolidine-2-carboxylate Example 112D (350 mg, 0.579 mmol) was dissolved in ethyl acetate (2.5 mL) and dichloromethane (2.5 mL) and treated with 1,3-dimethylpyrimidine-2,4,6(1H,3H,5H)-trione (183.2 mg, 1.173 mmol) and tetrakis(triphenylphosphine)palladium (7.2 mg, 6.23 µmol). The reaction mixture was stirred at ambient temperature. After 1 hour, the reaction mixture was diluted with methyl tert-butyl ether (50 mL) and stirred with 15 mL of 10% aqueous Na$_2$CO$_3$ (50 mL) solution for 30 minutes. The phases were separated, and the organic layer was washed with brine, dried over Na$_2$SO$_4$, filtered, and concentrated. The residue was purified by silica gel chromatography, eluting with 5% to 10% ethyl acetate in dichloromethane to provide the title compound (220.4 mg, 73%). $^1$H NMR (400 MHz, DMSO-d$_6$, 120° C.) δ ppm 8.29 (s, 1H), 7.59 (dd, J=7.5, 1.7 Hz, 1H), 7.36 (d, J=2.4 Hz, 1H), 7.12-7.00 (m, 2H), 6.95 (dd, J=7.2, 1.7 Hz, 1H), 4.65 (d, J=4.4 Hz, 1H), 4.23 (d, J=13.8 Hz, 1H), 4.19-4.08 (m, 3H), 3.85 (s, 3H), 3.80 (d, J=13.8 Hz, 1H), 3.66 (d, J=6.4 Hz, 1H), 2.40 (dd, J=6.3, 1.6 Hz, 1H), 1.99 (tt, J=8.5, 5.5 Hz, 1H), 1.21 (t, J=7.1 Hz, 3H), 1.01 (s, 10H), 0.90 (dq, J=8.3, 2.1 Hz, 2H), 0.68-0.55 (m, 2H); MS (ESI+) m/z 521 (M+H)$^+$.

Example 112F ethyl (2S,3R,4S,5S)-3-(tert-butyl)-5-(2-cyclopropylphenyl)-4-((2-methoxy-5-(trifluoromethyl)pyridin-3-yl)methoxy)-1-((S)-tetrahydrofuran-2-carbonyl)pyrrolidine-2-carboxylate (S)-(−)-tetrahydro-2-furoic acid (44.3 mg, 0.382 mmol) was dissolved in dichloromethane (2 mL). Oxalyl chloride (2M, 250 µL, 0.50 mmol) was added followed by dimethylformamide (25 µL). The reaction mixture was stirred at room temperature for 3 hours, at which point it was concentrated, redissolved in dichloromethane (1 mL), and concentrated again. The residue was taken up in dichloromethane (3×1 mL) and added to a solution of Example 112E (81.3 mg, 0.156 mmol) and triethylamine (100 µL, 0.717 mmol) and dichloromethane (3 mL). The reaction was stirred at ambient temperature for 17 hours. After this time, the mixture was diluted with dichloromethane (100 mL) and washed twice with saturated aqueous NaHCO$_3$ and once with brine. The organic layer was dried over Na$_2$SO$_4$, filtered, and concentrated to provide the title compound (79.8 mg, 83%). $^1$H NMR (400 MHz, DMSO-d$_6$, 120° C.) δ ppm 8.27 (s, 1H), 7.94 (d, J=7.2 Hz, 1H), 7.14 (d, J=2.4 Hz, 1H), 7.13-7.00 (m, 2H), 6.99-6.93 (m, 1H), 5.92 (s, 1H), 4.77 (s, 1H), 4.38 (d, J=5.7 Hz, 1H), 4.28 (d, J=13.9 Hz, 1H), 4.09 (qd, J=7.0, 1.3 Hz, 2H), 3.89-3.81 (m, 5H), 3.66 (dd, J=19.4, 12.3 Hz, 2H), 2.50 (s, 1H), 2.07-1.89 (m, 1H), 1.89-1.56 (m, 4H), 1.14 (t, J=7.1 Hz, 3H), 1.05 (s, 9H), 0.91 (tdd, J=8.2, 5.3, 3.6 Hz, 2H), 0.71-0.52 (m, 2H); MS (ESI+) m/z 619 (M+H)$^+$.

Example 112G (2S,3R,4S,5S)-3-tert-butyl-5-(2-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid Example 112F (73.1 mg, 0.118 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction was quenched by the addition of 1M aqueous HCl (0.5 mL), concentrated and purified by silica gel chromatography eluting with ethyl acetate to provide the title compound (61.5 mg, 88%). $^1$H NMR (400 MHz, DMSO-d$_6$, 120° C.) δ ppm 8.27 (s, 1H), 8.00 (d, J=7.2 Hz, 1H), 7.12 (d, J=2.5 Hz, 1H), 7.06 (q, J=6.7 Hz, 2H), 6.95 (dd, J=7.1, 2.0 Hz, 1H), 5.93 (d, J=11.0 Hz, 1H), 4.71 (d, J=1.8 Hz, 1H), 4.37 (d, J=5.8 Hz, 1H), 4.31 (d, J=14.0 Hz, 1H), 3.93-3.82 (m, 6H), 3.70 (q, J=6.9 Hz, 1H), 3.61 (d, J=7.3 Hz, 1H), 2.56 (s, 1H), 2.09-1.87 (m, 2H), 1.87-1.72 (m, 1H), 1.63 (s, 1H), 1.04 (s, 9H), 0.97-0.77 (m, 2H), 0.71-0.60 (m, 1H), 0.60-0.48 (m, 1H); MS (ESI+) m/z 591 (M+H)$^+$.

Example 113

(2S,3R,4S,5S)-3-tert-butyl-4-{[2-methoxy-5-(trifluoromethyl)phenyl]methoxy}-1-[(2S)-oxolane-2-carbonyl]-5-[2-(trifluoromethyl)pyridin-3-yl]pyrrolidine-2-carboxylic acid Example 113A (2S,3R,4S,5S)-1-allyl 2-ethyl 3-(tert-butyl)-4-hydroxy-5-(2-(trifluoromethyl)pyridin-3-yl)pyrrolidine-1,2-dicarboxylate and Example 113B (2R,3S,4S,5R)-1-allyl 2-ethyl 3-(tert-butyl)-4-hydroxy-5-(2-(trifluoromethyl)pyridin-3-yl)pyrrolidine-1,2-dicarboxylate The title compound was prepared according to the procedure described in Example 88A-Example 88C, substituting Core 16 for Core 5 in Example 88A. Both diastereomers were isolated. The first eluent was Example 113A. LC/MS (APCI+) m/z 445.40 (M+H)$^+$. The second eluent was Example 113B. LC/MS (APCI+) m/z 445.45 (M+H)$^+$.

Example 113C (2S,3R,4S,5S)-3-tert-butyl-4-{[2-methoxy-5-(trifluoromethyl)phenyl]methoxy}-1-[(2S)-oxolane-2-carbonyl]-5-[2-(trifluoromethyl)pyridin-3-yl]pyrrolidine-2-carboxylic acid The title compound was prepared according to the procedure described in Example 88D-Example 88G, substituting Example 113A for Example 88C, and 2-(bromomethyl)-1-methoxy-4-(trifluoromethyl)benzene for 3-(bromomethyl)-2-methoxy-5-(trifluoromethyl)pyridine.
$^1$H NMR (400 MHz, DMSO-d$_6$) δ ppm 8.77 (d, J=8.1 Hz, 1H), 8.48 (d, J=4.6 Hz, 1H), 7.55-7.38 (m, 2H), 6.99 (d, J=8.6 Hz, 1H), 6.87 (d, J=2.3 Hz, 1H), 5.55 (s, 1H), 4.83-4.70 (m, 1H), 4.33 (d, J=13.1 Hz, 1H), 4.15 (d, J=6.0 Hz, 1H), 3.97 (d, J=13.1 Hz, 1H), 3.71 (s, 3H), 3.67 (d, J=14.8 Hz, 2H), 3.32 (m, 1H), 2.59 (s, 1H), 1.86 (dtd, J=74.6, 13.8, 12.8, 7.3 Hz, 4H), 1.01 (s, 9H); MS (ESI+) m/z 619.2 (M+H)$^+$.

Example 114

(2S,3R,4R,5S)-3-tert-butyl-4-{[2-methoxy-5-(trifluoromethyl)phenyl]methoxy}-1-[(2S)-oxolane-2-carbonyl]-5-[2-(trifluoromethyl)pyridin-3-yl]pyrrolidine-2-carboxylic acid The title compound was prepared according to the procedure described in Example 88D-Example 88G, substituting Example 113B for Example 88C, and 2-(bromomethyl)-1-methoxy-4-(trifluoromethyl)benzene for 3-(bromomethyl)-2-methoxy-5-(trifluoromethyl)pyridine.
$^1$H NMR (400 MHz, DMSO-d$_6$) δ ppm 9.19 (d, J=8.2 Hz, 1H), 8.63 (s, 1H), 7.69 (s, 1H), 7.62-7.54 (m, 2H), 7.16 (d, J=8.6 Hz, 1H), 5.88 (s, 1H), 4.75 (s, 1H), 4.55 (d, J=11.6 Hz, 1H), 4.41 (d, J=10.5 Hz, 1H), 4.15 (s, 1H), 3.87 (s, 3H), 3.74-3.58 (m, 3H), 2.19 (d, J=10.8 Hz, 1H), 1.77 (d, J=67.9 Hz, 4H), 1.00 (s, 9H); MS (ESI+) m/z 619.2 (M+H)$^+$.

Example 115

(2S,3R,4S,5S)-3-tert-butyl-5-(2-chlorophenyl)-4-{[2-methoxy-5-(trifluoromethyl)pyridin-3-yl]methoxy}-1-[(2S)-oxolane-2-carbonyl]pyrrolidine-2-carboxylic acid The title compound was prepared using the procedures described in Example 144 substituting Core 14 for Core 10 and 3-(bromomethyl)-5-trifluromethyl-2-methoxypyridine for 3-(bromomethyl)-5-cyclobutyl-2-methoxypyridine. $^1$H NMR (400 MHz, DMSO-d$_6$) δ ppm 8.28 (s, 1H), 8.21 (s, 1H), 7.24 (t, J=4.4 Hz, 1H), 7.15 (s, 2H), 7.11-7.00 (m, 1H), 5.64 (s, 1H), 4.61 (s, 1H), 4.37 (d, J=13.9 Hz, 2H), 4.01 (d, J=13.9 Hz, 1H), 3.88 (s, 3H), 3.74 (s, 1H), 3.66 (s, 1H), 2.63 (s, 1H), 1.93 (q, J=5.5, 4.1 Hz, 1H), 1.87-1.74 (m, 1H), 1.70 (s, 1H), 1.02 (s, 9H); MS (APCI+) m/z 585 (M+H)$^+$.

Example 116

(2S,3R,4S,5S)-3-tert-butyl-4-[(2-methoxyquinolin-3-yl)methoxy]-1-[(2S)-oxolane-2-carbonyl]-5-[2-(propan-2-yl)phenyl]pyrrolidine-2-carboxylic acid

Example 116A 1-allyl 2-ethyl (2S,3R,4S,5S)-3-(tert-butyl)-5-(2-isopropylphenyl)-4-((2-methoxyquinolin-3-yl)methoxy)pyrrolidine-1,2-dicarboxylate Example 96C (458.5 mg, 1.098 mmol) and 3-(bromomethyl)-2-methoxyquinoline (Example 106B, 300.1 mg, 1.190 mmol) were dissolved in dimethylformamide (2.5 mL). The reaction was cooled to 0° C., and potassium tert-butoxide (1M in tetrahydrofuran, 1.20 mL, 1.20 mmol) was added dropwise. The reaction mixture was stirred at ambient temperature for 1 hour. The reaction mixture was poured into saturated aqueous NH$_4$Cl (35 mL), extracted with methyl tert-butyl ether (3×35 mL), and purified by silica gel chromatography (5% ethyl acetate in dichloromethane) to provide the title compound (291.2 mg, 45%). $^1$H NMR (400 MHz, DMSO-d$_6$, 120° C.) δ ppm 8.27 (s, 1H), 7.88 (dd, J=7.0, 2.2 Hz, 1H), 7.18 (s, 1H), 7.07-6.86 (m, 3H), 5.58 (d, J=5.6 Hz, 1H), 4.64 (p, J=6.2 Hz, 1H), 4.46 (d, J=2.0 Hz, 1H), 4.32 (d, J=5.5 Hz, 1H), 4.27 (d, J=13.9 Hz, 1H), 4.11 (qd, J=7.1, 3.0 Hz, 2H), 3.88-3.80 (m, 4H), 2.50 (d, J=1.9 Hz, 1H), 2.01-1.92 (m, 1H), 1.15 (td, J=7.0, 0.8 Hz, 3H), 1.03 (d, J=10.3 Hz, 12H), 0.90 (ddd, J=10.8, 8.5, 2.1 Hz, 2H), 0.84 (d, J=6.3 Hz, 3H), 0.60 (dd, J=5.5, 2.4 Hz, 2H); MS (ESI+) m/z 589 (M+H)$^+$.

Example 116B ethyl (2S,3R,4S,5S)-3-(tert-butyl)-5-(2-isopropylphenyl)-4-((2-methoxyquinolin-3-yl)methoxy)pyrrolidine-2-carboxylate Example 116A (298 mg, 0.506 mmol) was dissolved in ethyl acetate (2.4 mL) and dichloromethane (2.4 mL), and treated with 1,3-dimethylpyrimidine-2,4,6(1H,3H,5H)-trione (155.6 mg, 0.997 mmol) and tetrakis(triphenylphosphine)palladium (5.9 mg, 5.11 μmol). The reaction mixture was stirred at ambient temperature. After 1 hour, the reaction mixture was diluted with methyl tert-butyl ether (50 mL) and stirred with 15 mL of 10% aqueous Na$_2$CO$_3$ (50 mL) solution for 30 minutes. The phases were separated, and the organic layer was washed with brine, dried over Na$_2$SO$_4$, filtered, and concentrated. The residue was purified by silica gel chromatography 5% to 10% ethyl acetate in dichloromethane to provide the title compound (186.6 mg, 73%). $^1$H NMR (400 MHz, DMSO-d$_6$) δ ppm 7.68 (t, J=7.9 Hz, 2H), 7.61-7.50 (m, 2H), 7.45 (s, 1H), 7.37-7.30 (m, 1H), 7.27-7.17 (m, 2H), 7.10 (td, J=7.5, 1.6 Hz, 1H), 4.41 (d, J=4.4 Hz, 1H), 4.28 (d, J=13.7 Hz, 1H), 4.16 (q, J=7.1 Hz, 2H), 3.97 (dt, J=4.5, 1.4 Hz, 1H), 3.93-3.85 (m, 5H), 3.65 (d, J=6.5 Hz, 1H), 3.23 (dq, J=13.7, 6.8 Hz, 1H), 1.27-1.16 (m, 9H), 1.00 (d, J=1.0 Hz, 9H); MS (ESI+) m/z 506 (M+H)$^+$.

Example 116C ethyl (2S,3R,4S,5S)-3-(tert-butyl)-5-(2-isopropylphenyl)-4-((2-methoxyquinolin-3-yl)methoxy)-1-((S)-tetrahydrofuran-2-carbonyl)pyrrolidine-2-carboxylate (S)-(−)-tetrahydro-2-furoic acid (27.6 mg, 0.238 mmol) was dissolved in dichloromethane (2 mL). Oxalyl chloride (2M, 180 μL, 0.36 mmol) was added followed by dimethylformamide (25 μL). The reaction mixture was stirred at room temperature for 3 hours, concentrated, redissolved in dichloromethane (1 mL), and concentrated again. The residue was taken up in dichloromethane (3×1 mL) and added to a solution of Example 116B (61.7 mg, 0.122 mmol) and triethyl amine (100 μL, 0.717 mmol) in dichloromethane (3 mL). The reaction was stirred at ambient temperature for 18 hours. The mixture was diluted with dichloromethane (100 mL) and washed twice with saturated aqueous NaHCO$_3$ and once with brine. The organic layer was dried over Na$_2$SO$_4$, filtered, and concentrated to provide the title compound (57.0 mg, 77%). $^1$H NMR (400 MHz, DMSO-d$_6$, 120° C.) δ ppm 8.04 (d, J=7.9 Hz, 1H), 7.66 (d, J=8.3 Hz, 1H), 7.57-7.47 (m, 2H), 7.37-7.30 (m, 1H), 7.25 (d, J=6.2 Hz, 2H), 7.14 (d, J=11.3 Hz, 2H), 5.68 (s, 1H), 4.76 (s, 1H), 4.39-4.30 (m, 1H), 4.27 (d, J=5.6 Hz, 1H), 4.11 (q, J=7.1 Hz, 2H), 3.97-3.88 (m, 5H), 3.73-3.55 (m, 2H), 3.26 (p, J=6.7 Hz, 1H), 2.54 (s, 1H), 2.07-1.93 (m, 1H), 1.87-1.56 (m, 3H), 1.25 (d, J=6.7 Hz, 3H), 1.17-1.10 (m, 6H), 1.05 (s, 9H), 0.91 (tdd, J=8.2, 5.3, 3.6 Hz, 2H), 0.71-0.52 (m, 2H); MS (ESI+) m/z 603 (M+H)$^+$.

Example 116D (2S,3R,4S,5S)-3-tert-butyl-4-[(2-methoxyquinolin-3-yl)methoxy]-1-[(2S)-oxolane-2-carbonyl]-5-[2-(propan-2-yl)phenyl]pyrrolidine-2-carboxylic acid Example 116C (54.0 mg, 0.090 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction was quenched by the addition of 1M aqueous HCl (0.5 mL), concentrated, and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (47.6 mg, 77%) as the TFA salt. $^1$H NMR (400 MHz, DMSO-d$_6$, 120° C.) δ ppm 8.13-8.06 (m, 1H), 7.68-7.63 (m, 1H), 7.53 (td, J=8.1, 1.3 Hz, 1H), 7.33 (ddd, J=8.1, 6.9, 1.2 Hz, 1H), 7.24 (d, J=7.1 Hz, 2H), 7.17 (s, 1H), 7.11 (t, J=7.3 Hz, 1H), 5.68 (s, 1H), 4.73 (d, J=1.8 Hz, 1H), 4.37 (dd, J=14.1, 1.4 Hz, 1H), 4.26 (d, J=5.8 Hz, 1H), 4.20-4.00 (m, 1H), 3.93 (dd, J=14.2, 1.5 Hz, 1H), 3.91 (s, 3H), 3.70 (q, J=7.0, 5.5 Hz, 1H), 3.65-3.55 (m, 1H), 3.26 (p, J=6.8 Hz, 1H), 2.60 (s, 1H), 2.05-1.93 (m, 1H), 1.87-1.74 (m, 1H), 1.73-1.55 (m, 2H), 1.25 (d, J=6.8 Hz, 3H), 1.12 (d, J=6.7 Hz, 3H), 1.04 (s, 9H); MS (ESI+) m/z 575 (M+H)+.

Example 117

(2S,3R,4S,5S)-3-tert-butyl-4-{[2-methoxy-5-(trifluoromethyl)pyridin-3-yl]methoxy}-1-[(2S)-oxolane-2-carbonyl]-5-[3-(propan-2-yl)phenyl]pyrrolidine-2-carboxylic acid Example 117A (2S,3R,4S,5S)-ethyl 5-(3-bromophenyl)-3-(tert-butyl)-4-((2-methoxy-5-(trifluoromethyl)pyridin-3-yl)methoxy)-1-((S)-tetrahydrofuran-2-carbonyl)pyrrolidine-2-carboxylate To a cooled (ice bath) solution of (2S,3R,4S,5S)-ethyl 5-(3-bromophenyl)-3-(tert-butyl)-4-((2-methoxy-5-(trifluoromethyl)pyridin-3-yl)methoxy)pyrrolidine-2-carboxylate (Example 124E, 435 mg, 0.778 mmol) in dichloromethane (5 mL) was added triethylamine (0.636 mL, 4.56 mmol) followed by dropwise addition of (S)-tetrahydrofuran-2-carbonyl chloride (220 mg, 1.633 mmol) as a solution in 3 mL dichloromethane. After stirring at room temperature for 5 minutes, the reaction was quenched with 10 mL of saturated aqueous sodium bicarbonate. The organic layer was separated, dried with $Na_2SO_4$, filtered, and concentrated. The resulting crude material was chromatographed using a 24 g silica gel cartridge with a gradient of 0-70% ethyl acetate/heptanes to provide the title compound (0.490 g, 0.745 mmol, 96% yield). $^1$H NMR (400 MHz, DMSO-$d_6$) δ ppm 8.36-8.26 (m, 1H), 7.85 (s, 1H), 7.59 (d, J=7.5 Hz, 1H), 7.31 (d, J=7.9 Hz, 1H), 7.24 (d, J=2.3 Hz, 1H), 7.15 (t, J=7.8 Hz, 1H), 5.50-5.28 (m, 1H), 4.75-4.59 (m, 1H), 4.42-4.25 (m, 2H), 4.10 (qq, J=6.5, 3.7 Hz, 2H), 4.00-3.84 (m, 4H), 3.77-3.58 (m, 2H), 2.44 (s, 1H), 2.03-1.85 (m, 1H), 1.85-1.73 (m, 1H), 1.73-1.58 (m, 1H), 1.16 (td, J=7.1, 0.9 Hz, 3H), 1.01 (s, 9H), 0.94-0.74 (m, 2H); MS (APCI+) m/z 659 (M+H)+.

Example 117B (2S,3R,4S,5S)-ethyl 3-(tert-butyl)-4-((2-methoxy-5-(trifluoromethyl)pyridin-3-yl)methoxy)-5-(3-(prop-1-en-2-yl)phenyl)-1-((S)-tetrahydrofuran-2-carbonyl)pyrrolidine-2-carboxylate A mixture of (2S,3R,4S,5S)-ethyl 5-(3-bromophenyl)-3-(tert-butyl)-4-((2-methoxy-5-(trifluoromethyl)pyridin-3-yl)methoxy)-1-((S)-tetrahydrofuran-2-carbonyl)pyrrolidine-2-carboxylate (Example 117A, 150 mg, 0.228 mmol), 4,4,5,5-tetramethyl-2-(prop-1-en-2-yl)-1,3,2-dioxaborolane (65.2 mg, 0.388 mmol) and cesium fluoride (120 mg, 0.787 mmol) in dioxane (2 mL) was degassed for 5 minutes, then 1,1'-bis(diphenylphosphino)ferrocene-palladium(ii)dichloride dichloromethane complex (11.36 mg, 0.014 mmol) was added. The reaction mixture was purged with nitrogen and heated to 100° C. for 2 hours. The reaction mixture was cooled to room temperature before dichloromethane (10 mL) was added. The resulting mixture was filtered over a pad of silica gel, washed with 35% ethyl acetate in heptanes solution (10 mL), and concentrated. Purification of the residue via chromatography on a 12 g silica gel cartridge eluting with 0 to 30% ethyl acetate in heptanes provided the title compound (125 mg, 89% yield). LC/MS (APCI+) m/z 619.58 (M+H)+.

Example 117C (2S,3R,4S,5S)-ethyl 3-(tert-butyl)-5-(3-isopropylphenyl)-4-((2-methoxy-5-(trifluoromethyl)pyridin-3-yl)methoxy)-1-((S)-tetrahydrofuran-2-carbonyl)pyrrolidine-2-carboxylate Example 117B (120 mg, 0.194 mmol) in ethanol (1.2 mL) was added to 5% Pt/C (75 mg, 0.158 mmol) in a 20 mL pressure bottle. The mixture was stirred under 50 psi of hydrogen at ambient temperature for 75 minutes. LC/MS indicated the reaction was complete. The mixture was diluted with ethanol and filtered through a polypropylene membrane and filtered again through a diatomaceous earth column. The filtrate was concentrated. The residue (100 mg, 84%) was used in the next step without further purification. LC/MS (APCI+) m/z 621.9 (M+H)+.

Example 117D (2S,3R,4S,5S)-3-(tert-butyl)-5-(3-isopropylphenyl)-4-((2-methoxy-5-(trifluoromethyl)pyridin-3-yl)methoxy)-1-((S)-tetrahydrofuran-2-carbonyl)pyrrolidine-2-carboxylic acid The mixture of Example 117C (100 mg, 0.161 mmol) in methanol (2 mL) and 6M aqueous LiOH (0.5 mL) was stirred at 50° C. for overnight, adjusted pH to 1~2 by adding 2M aqueous HCl and was concentrated. The residue was purified by silica gel chromatography, eluting with methanol in dichloromethane at 0-20% gradient to provide the title compound, 80 mg (84% yield). $^1$H NMR (400 MHz, DMSO-$d_6$) δ ppm 8.28 (s, 1H), 7.59 (s, 1H), 7.44 (d, J=7.7 Hz, 1H), 7.18 (d, J=2.4 Hz, 1H), 7.11 (t, J=7.6 Hz, 1H), 7.00 (d, J=7.8 Hz, 1H), 5.37 (s, 1H), 4.57 (s, 1H), 4.32-4.25 (m, 2H), 4.20 (s, 1H), 3.90 (d, J=7.6 Hz, 1H), 3.87 (s, 3H), 3.74 (q, J=7.2 Hz, 1H), 3.63 (s, 1H), 1.70 (d, J=77.7 Hz, 4H), 1.25 (s, 1H), 1.10 (d, J=6.9 Hz, 6H), 1.00 (s, 9H); MS (ESI+) m/z 593 (M+H)+.

Example 118

(2S,3R,4S,5S)-5-(3-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid Example 117A (54.0 mg, 0.082 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction was quenched by the addition of 1M aqueous HCl (0.5 mL), concentrated, and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (51.7 mg, 85%) as the TFA salt. $^1$H NMR (400 MHz, DMSO-$d_6$, 120° C.) δ ppm 8.30 (d, J=2.3 Hz, 1H), 7.89 (s, 1H), 7.62 (d, J=7.6 Hz, 1H), 7.30 (d, J=8.0 Hz, 1H), 7.22 (s, 1H), 7.15 (q, J=8.8, 7.8 Hz, 1H), 5.38 (s, 1H), 4.61 (s, 1H), 4.38-4.28 (m, 2H), 4.19 (s, 1H), 3.96 (d, J=13.8 Hz, 1H), 3.89 (d, J=0.9 Hz, 3H), 3.80-3.58 (m, 2H), 2.51-2.48 (m, 1H), 1.97-1.60 (m, 4H), 1.00 (d, J=0.9 Hz, 9H); MS (ESI+) m/z 629 & 631 (M+H)+.

Example 119

(2S,3R,4S,5S)-3-tert-butyl-5-(3-chlorophenyl)-4-{[2-methoxy-5-(trifluoromethyl)pyridin-3-yl]methoxy}-1-[(2S)-oxolane-2-carbonyl]pyrrolidine-2-carboxylic acid The title compound was prepared using the procedures described in Example 144 substituting Core 8 for Core 10 and 3-(bromomethyl)-5-trifluromethyl-2-methoxypyridine for 3-(bromomethyl)-5-cyclobutyl-2-methoxypyridine. $^1$H NMR (400 MHz, DMSO-$d_6$) δ ppm 8.30 (s, 1H), 7.76 (s, 1H), 7.57 (d, J=7.5 Hz, 1H), 7.27-7.11 (m, 3H), 5.38 (s, 1H), 4.61 (s, 1H), 4.38-4.27 (m, 2H), 4.14 (bs, 1H), 3.97 (d, J=13.8 Hz, 1H), 3.89 (s, 3H), 3.74 (q, J=7.2 Hz, 1H), 3.65 (m, 1H), 2.49 (s, 1H), 1.89 (s, 1H), 1.80 (dt, J=13.5, 6.6 Hz, 1H), 1.67 (s, 1H), 1.01 (s, 9H); MS (APCI+) m/z 585 (M+H)+.

Example 120

(2S,3R,4S,5S)-3-tert-butyl-5-(3-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid Example 120A ethyl (2S,3R,4S,5S)-3-(tert-butyl)-5-(3-cyclopropylphenyl)-4-((2-methoxy-5-(trifluoromethyl)pyridin-3-yl)methoxy)-1-((S)-tetrahydrofuran-2-carbonyl)pyrrolidine-2-carboxylate Example 117A (172.3 mg, 0.262 mmol), cyclopropylboronic acid (38.2 mg, 0.445 mmol) and cesium fluoride (137.5 mg, 0.905 mmol) were dissolved in dioxane (2 mL). The reaction was degassed for 5 minutes, and 1,1'-bis(diphenylphosphino)ferrocene-palladium(II)dichloride dichloromethane complex (13.0 mg, 0.016 mmol) was added. The reaction mixture was purged with nitrogen and heated to 100° C. The reaction mixture was filtered and purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (51.7 mg, 85%). $^1$H NMR (400 MHz, DMSO-$d_6$, 120° C.) δ ppm 8.29 (d, J=2.3 Hz, 1H), 7.43-7.31 (m, 2H), 7.22 (d, J=2.4 Hz, 1H), 7.08 (t, J=7.6 Hz, 1H), 6.90 (d, J=7.7 Hz, 1H), 5.35 (s, 1H), 4.62 (s, 1H), 4.32-4.23 (m, 2H), 4.19-4.03 (m, 3H), 3.91-3.80 (m, 5H), 3.71 (q, J=7.1 Hz, 1H), 3.63 (t, J=6.7 Hz, 1H), 2.43 (d, J=2.8 Hz, 1H), 1.90-1.71 (m, 3H), 1.62 (s, 1H), 1.15 (td, J=7.1, 0.8 Hz, 3H), 1.00 (s, 9H), 0.88-0.76 (m, 2H), 0.59-0.44 (m, 2H); MS (ESI+) m/z 619 (M+H)+.

Example 120B (2S,3R,4S,5S)-3-tert-butyl-5-(3-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid Example 120A (114.4 mg, 0.185 mmol) was dissolved in methanol (1 mL), and tetrahydrofuran (1 mL). Aqueous LiOH (1 M, 1.0 mL, 1.0 mmol) was added and the reaction was heated to 50° C. for 16 hours. The reaction was quenched by the addition of 1M aqueous HCl (1 mL), concentrated, and purified by silica gel chromatography (ethyl acetate) to provide the title compound (90.3 mg, 88%). $^1$H NMR (400 MHz, DMSO-$d_6$, 120° C.) δ ppm 8.32-8.24 (m, 1H), 7.38 (d, J=8.9 Hz, 2H), 7.22-7.14 (m, 1H), 7.07 (t, J=7.5 Hz, 1H), 6.91 (d, J=7.6 Hz, 1H), 5.35 (s, 1H), 4.57 (s, 1H), 4.35-4.24 (m, 2H), 4.18 (s, 1H), 3.94-3.84 (m, 5H), 3.73 (q, J=7.2 Hz, 1H), 3.64 (t, J=6.8 Hz, 1H), 2.49-2.48 (m, 1H), 1.90-1.54 (m, 4H), 1.00 (s, 9H), 0.82 (ddd, J=8.4, 4.2, 2.8 Hz, 2H), 0.54 (ddt, J=6.2, 5.1, 1.4 Hz, 2H); MS (ESI+) m/z 591 (M+H)+.

Example 121

(2S,3R,4S,5S)-3-tert-butyl-5-(3-tert-butylphenyl)-4-{[2-methoxy-5-(trifluoromethyl)pyridin-3-yl]methoxy}-1-[(2S)-oxolane-2-carbonyl]pyrrolidine-2-carboxylic acid Example 121A (2S,3R,5S)-1-allyl 2-ethyl 3-(tert-butyl)-5-(3-(tert-butyl)phenyl)-4-nitropyrrolidine-1,2-dicarboxylate To Core 18 (1.5 g, 3.98 mmol) in toluene (10 mL) and saturated aqueous NaHCO$_3$ (10 mL) was added allyl carbonochloridate (1.059 mL, 9.96 mmol) dropwise at room temperature. The mixture was stirred at room temperature for 2 hours. Ethyl acetate (20 mL) was added and the organic layer was washed with brine and concentrated. Purification of the residue by chromatography on a 24 g silica gel cartridge eluting with ethyl acetate in heptane at 0-40% gradient provided (2S,3R,4S,5S)-1-allyl 2-ethyl 3-(tert-butyl)-5-(3-(tert-butyl)phenyl)-4-nitropyrrolidine-1,2-dicarboxylate, (1.2 g, 2.61 mmol, 65.4% yield). $^1$H NMR (400 MHz, CDCl$_3$) δ ppm 7.52 (s, 1H), 7.37 (dt, J=7.4, 1.7 Hz, 1H), 7.32-7.29 (m, 1H), 7.26 (q, J=7.6, 7.0 Hz, 1H), 5.60 (s, 1H), 5.42 (d, J=8.6 Hz, 1H), 5.29 (dd, J=8.7, 2.4 Hz, 1H), 4.98 (s, 1H), 4.71 (s, 1H), 4.58 (d, J=10.2 Hz, 1H), 4.43-4.33 (m, 2H), 3.11 (t, J=2.7 Hz, 1H), 1.39 (t, J=7.1 Hz, 3H), 1.33 (s, 9H), 1.10 (s, 9H); LC/MS (APCI+) m/z 461.5 (M+H)+.

Example 121B (2S,3R,5S)-1-allyl 2-ethyl 3-(tert-butyl)-5-(3-(tert-butyl)phenyl)-4-oxopyrrolidine-1,2-dicarboxylate To potassium dichromate (4.22 g, 14.33 mmol) in 6M aqueous HCl (60 mL) was added zinc (4.68 g, 71.7 mmol) portionwise under N$_2$ atmosphere. After the complete dissolution of zinc yielded a clear light blue solution, the formed chromium(II) chloride was transferred to the refluxing solution of Example 121A (1.1 g, 2.388 mmol) in ethanol (60 mL) under N$_2$. The reaction mixture was refluxed for 16 hours. The mixture was cooled and concentrated to half of its volume, and extracted with dichloromethane (60 mL×3). The organic phase was washed with saturated aqueous NaHCO$_3$ solution and brine, dried over MgSO$_4$, filtered, and concentrated. To the residue in ethanol (5 mL) was added prepared acetyl chloride (1.5 mL) in ethanol (5 mL). The mixture was heated at 60° C. for 1 hour and the solvent was removed. The residue was dissolved in dichloromethane (30 mL), washed with brine, dried over MgSO$_4$, filtered, and concentrated. Purification by chromatography, eluting with methanol/ethyl acetate (1:9) in heptanes at 0-40% gradient provided the title compound 635 mg, (61.9% yield). $^1$H NMR (501 MHz, CDCl$_3$) δ ppm 7.62 (s, 1H), 7.40 (dt, J=7.0, 1.8 Hz, 1H), 7.35-7.29 (m, 2H), 5.66 (s, 2H), 5.00 (s, 1H), 4.91 (s, 1H), 4.79-4.74 (m, 1H), 4.61 (d, J=13.6 Hz, 1H), 4.50 (s, 1H), 4.34-4.24 (m, 2H), 2.59 (dd, J=4.6, 1.1 Hz, 1H), 1.35 (s, 9H), 1.32 (d, J=7.2 Hz, 3H), 1.14 (s, 9H); MS (ESI+) m/z 430 (M+H)$^+$.

Example 121C (2S,3R,4S,5S)-1-allyl 2-ethyl 3-(tert-butyl)-5-(3-(tert-butyl)phenyl)-4-hydroxypyrrolidine-1,2-dicarboxylate and Example 121D (2S,3R,4R,5S)-1-allyl 2-ethyl 3-(tert-butyl)-5-(3-(tert-butyl)phenyl)-4-hydroxypyrrolidine-1,2-dicarboxylate To Example 121B (630 mg, 1.467 mmol) in ethanol (10 mL) cooled in an ice-bath was added sodium borohydride (83 mg, 2.200 mmol) portionwise. The mixture was stirred in an ice-bath for 30 minutes, and was allowed to warm to ambient temperature. LC/MS showed two product peaks; the ratio was about 4/1. The solvent was removed and dichloromethane was added. The organics were washed with brine, dried over MgSO$_4$, filtered, and concentrated. The crude material was purified via chromatography, eluting with ethyl acetate/methanol (9:1) in heptane. The first eluent was title compound Example 121C (2S,3R,4S,5S)-1-allyl 2-ethyl 3-(tert-butyl)-5-(3-(tert-butyl)phenyl)-4-hydroxypyrrolidine-1,2-dicarboxylate (422 mg, 66.7% yield); $^1$H NMR (500 MHz, DMSO-d$_6$) δ ppm 7.60 (s, 1H), 7.38 (dt, J=6.9, 1.7 Hz, 1H), 7.27-7.13 (m, 2H), 5.55 (s, 1H), 4.84 (s, 1H), 4.63 (d, J=4.4 Hz, 1H), 4.47-4.38 (m, 1H), 4.32 (d, J=5.9 Hz, 1H), 4.24 (s, 1H), 4.16 (q, J=7.1 Hz, 2H), 2.20 (t, J=5.1 Hz, 1H), 1.29 (s, 9H), 1.23 (t, J=7.1 Hz, 3H), 0.98 (s, 9H); MS (ESI+) m/z 432 (M+H)$^+$. The second eluent was Example 121D (2S,3R,4R,5S)-1-allyl 2-ethyl 3-(tert-butyl)-5-(3-(tert-butyl)phenyl)-4-hydroxypyrrolidine-1,2-dicarboxylate (105 mg, 16.59% yield) $^1$H NMR (501 MHz, DMSO-d$_6$) δ ppm 7.64 (d, J=24.0 Hz, 1H), 7.35 (tt, J=7.9, 2.9 Hz, 1H), 7.23 (dd, J=5.0, 1.4 Hz, 1H), 7.22-7.13 (m, 1H), 5.54 (t, J=4.7 Hz, 1H), 5.30-5.14 (m, 1H), 4.95-4.80 (m, 1H), 4.75 (d, J=6.3 Hz, 1H), 4.45 (tdd, J=9.4, 6.6, 4.7 Hz, 1H), 4.39-4.31 (m, 1H), 4.23-4.03 (m, 3H), 3.99 (dt, J=10.6, 3.8 Hz, 1H), 1.93 (ddd, J=17.0, 11.2, 3.3 Hz, 1H), 1.28-1.25 (m, 9H), 1.25-1.17 (m, 3H), 0.96 (s, 9H);); MS (ESI+) m/z 432 (M+H)$^+$.

Example 121E (2S,3R,4S,5S)-1-allyl 2-ethyl 3-(tert-butyl)-5-(3-(tert-butyl)phenyl)-4-((2-methoxy-5-(trifluoromethyl)pyridin-3-yl)methoxy)pyrrolidine-1,2-dicarboxylate To Example 121C (410 mg, 0.950 mmol) and 3-(bromomethyl)-2-methoxy-5-(trifluoromethyl)pyridine (308 mg, 1.140 mmol) in dimethylformamide (4 mL) cooling in an ice bath, potassium 2-methylpropan-2-olate (139 mg, 1.235 mmol, 1.3 mL, 1.0M in tetrahydrofuran) was added dropwise. The mixture was stirred in an ice-bath for 30 minutes, and was allowed to warm to room temperature. Saturated NH$_4$Cl was added. The organic layer washed with brine, dried over MgSO$_4$, filtered, and concentrated. The residue was purified via chromatography, eluting with ethyl acetate in heptanes at 0-40% gradient to provide (2S,3R,4S,5S)-1-allyl 2-ethyl 3-(tert-butyl)-5-(3-(tert-butyl)phenyl)-4-((2-methoxy-5-(trifluoromethyl)pyridin-3-yl)methoxy)pyrrolidine-1,2-dicarboxylate (495 mg, 84% yield). LC/MS (APCI+) m/z 621.3 (M+H)$^+$.

Example 121F (2S,3R,4S,5S)-ethyl 3-(tert-butyl)-5-(3-(tert-butyl)phenyl)-4-((2-methoxy-5-(trifluoromethyl)pyridin-3-yl)methoxy)pyrrolidine-2-carboxylate To a solution of Example 121E (495 mg, 0.797 mmol) in acetonitrile/water (6.6 mL, 10:1) was added diethylamine (0.165 mL, 1.595 mmol) and tetrakis(triphenylphosphine)palladium(0) (20.27 mg, 0.018 mmol). The mixture was stirred at ambient temperature overnight; LC/MS showed conversion was finished. Dichloromethane (30 mL) and water (20 mL) were added and the organic layer was washed with brine, dried over MgSO$_4$, filtered, and concentrated. Purification of the residue via silica gel chromatography, eluting with ethyl acetate/methanol (10:1) in heptanes at 0-50% gradient provided the title compound (320 mg, 74.8% yield). LC/MS (APCI+) m/z 537.57 (M+H)$^+$.

Example 121G (2S,3R,4S,5S)-3-tert-butyl-5-(3-tert-butylphenyl)-4-{[2-methoxy-5-(trifluoromethyl)pyridin-3-yl]methoxy}-1-[(2S)-oxolane-2-carbonyl]pyrrolidine-2-carboxylic acid To (S)-tetrahydrofuran-2-carboxylic acid (34.6 mg, 0.298 mmol) and a drop of dimethylformamide in dichloromethane (4 mL) was added oxalyl dichloride (56.8 mg, 0.447 mmol, 2.2 mL, 2 M in dichloromethane). The mixture was stirred at room temperature for 30 minutes. The solvent was removed under pressure and fresh dichloromethane was added and reaction mixture was concentrated again. The residue was dissolved in dichloromethane (1 mL) and added dropwise to a solution of Example 121F (80 mg, 0.149 mmol) and triethylamine (0.083 mL, 0.596 mmol) in dichloromethane (4 mL) in an ice-bath. The mixture was stirred at 0° C. for 30 minutes, and allowed to warm to room temperature. Dichloromethane and saturated aqueous NH$_4$Cl were added and the organic layer was washed with brine, dried over MgSO$_4$, filtered, and concentrated. The residue was dissolved in methanol (1.5 mL) and 6M aqueous LiOH (0.5 mL), and was stirred at 50° C. for 6 hours. The pH was adjusted to 1~2 by adding 2M aqueous HCl. The reaction mixture was concentrated, taken up in dichloromethane and filtered through a syringe filter. The filtrate was purified via chromatography, eluting with methanol in dichloromethane on a 12 g silica gel cartridge at 0-20% gradient to provide the title compound (65 mg, 0.107 mmol, 71.9% yield). $^1$H NMR (400 MHz, DMSO-d$_6$) δ ppm 8.28(s, 1H), 7.79 (s, 1H), 7.40 (d, J=7.0 Hz, 1H), 7.13 (dd, J=16.1, 7.7 Hz, 3H), 5.39 (s, 1H), 4.57 (s, 1H), 4.30 (dd, J=6.5, 2.6 Hz, 1H), 4.25 (d, J=13.7 Hz, 1H), 4.19 (s, 1H), 3.86 (d, J=0.7 Hz, 3H), 3.74 (q, J=7.2 Hz, 1H), 3.62 (d, J=5.8 Hz, 1H), 2.57 (m, 1H), 1.76 (dd, J=12.1, 6.4 Hz, 2H), 1.59 (s, 1H), 1.25 (m, 1H), 1.18 (d, J=0.7 Hz, 9H), 1.01 (s, 9H); MS (ESI+) m/z 607.1 (M+H)$^+$.

Example 122

(2S,3R,4R,5S)-3-tert-butyl-5-(3-tert-butylphenyl)-4-{[2-methoxy-5-(trifluoromethyl)pyridin-3-yl]methoxy}-1-[(2S)-oxolane-2-carbonyl]pyrrolidine-2-carboxylic acid The title compound was prepared according to the procedure described from Example 121C to 121 G, substituting Example 121D for Example 121C. $^1$H NMR (400 MHz, DMSO-d$_6$) δ ppm 8.47 (s, 1H), 7.99-7.87 (m, 2H), 7.36 (d, J=5.1 Hz, 1H), 7.27 (d, J=4.3 Hz, 2H), 5.39 (s, 1H), 4.83 (d, J=12.5 Hz, 1H), 4.64 (d, J=12.5 Hz, 1H), 4.38 (d, J=11.0 Hz, 1H), 4.17 (d, J=11.3 Hz, 1H), 3.70 (t, J=7.1 Hz, 1H), 3.62 (dd, J=9.5, 4.0 Hz, 1H), 2.19 (dd, J=11.0, 3.7 Hz, 1H), 1.87-1.75 (m, 2H), 1.63 (s, 1H), 1.45 (s, 1H), 1.29 (s, 9H), 1.27-0.99 (m, 4H), 0.97 (s, 9H); MS (ESI+) m/z 607.2 (M+H)$^+$.

Example 123

(2S,3R,4S,5S)-3-tert-butyl-5-(3-chlorophenyl)-4-{[2-methoxy-5-(trifluoromethyl)pyridin-3-yl]methoxy}-1-[(2S)-oxane-2-carbonyl]pyrrolidine-2-carboxylic acid The title compound was prepared using the procedures described in Example 179 substituting Core 8 for Core 24. $^1$H NMR (400 MHz, DMSO-d$_6$) δ ppm 8.30 (s, 1H), 7.82 (s, 1H), 7.62 (d, J=7.5 Hz, 1H), 7.23 (d, J=2.5 Hz, 1H), 7.21-7.12 (m, 2H), 5.39 (s, 1H), 4.51 (d, J=2.8 Hz, 1H), 4.32 (d, J=13.9 Hz, 1H), 4.27 (d, J=6.4 Hz, 1H), 3.95 (d, J=13.9 Hz, 1H), 3.89 (s, 3H), 3.80 (d, J=11.5 Hz, 1H), 2.62 (s, 1H), 1.68 (s, 1H), 1.52 (d, J=10.6 Hz, 1H), 1.46-1.30 (m, 2H), 0.99 (s, 9H); MS (ESI+) m/z 600 (M+H)$^+$.

Example 124

(2S,3R,4S,5S)-5-(3-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid

Example 124A (2S,3R,4S,5S)-1-allyl 2-ethyl 5-(3-bromophenyl)-3-(tert-butyl)-4-nitropyrrolidine-1,2-dicarboxylate To Core 17 (1.974 g, 4.94 mmol) in toluene (24 mL) and saturated aqueous NaHCO$_3$ (24 mL) was added allyl carbonochloridate (0.788 mL, 7.42 mmol) dropwise at ambient temperature. The mixture was stirred at ambient temperature for 30 minutes. Methyl tert-butyl ether (100 mL) was added and the organic layer was washed with brine, dried over sodium sulfate, filtered and concentrated. The crude material was purified using an 80 g silica gel cartridge with a gradient of 5-100% ethyl acetate/heptanes over 40 minutes to provide (2S,3R,4S,5S)-1-allyl 2-ethyl 5-(3-bromophenyl)-3-(tert-butyl)-4-nitropyrrolidine-1,2-dicarboxylate (2.263 g, 4.68 mmol, 95% yield). $^1$H NMR (400 MHz, DMSO-d$_6$) δ ppm 7.78 (t, J=1.9 Hz, 1H), 7.51 (ddt, J=7.7, 1.6, 0.8 Hz, 1H), 7.39 (ddd, J=8.0, 2.2, 1.1 Hz, 1H), 7.21 (t, J=7.9 Hz, 1H), 5.73 (ddt, J=16.4, 11.2, 5.2 Hz, 1H), 5.66 (dd, J=8.7, 2.9 Hz, 1H), 5.49 (d, J=8.7 Hz, 1H), 5.08 (dt, J=1.7, 1.1 Hz, 1H), 5.05 (dq, J=8.0, 1.6 Hz, 1H), 4.56 (d, J=3.5 Hz, 1H), 4.46 (dt, J=5.2, 1.6 Hz, 2H), 4.26 (qd, J=7.1, 0.7 Hz, 2H), 2.99-2.93 (m, 1H), 1.30 (t, J=7.1 Hz, 3H), 1.01 (s, 9H); MS (APCI+) m/z 483 (M+H)$^+$.

Example 124B (2S,3R,5S)-1-allyl 2-ethyl 5-(3-bromophenyl)-3-(tert-butyl)-4-oxopyrrolidine-1,2-dicarboxylate To potassium dichromate (8.25 g, 28.1 mmol) in 6 N aqueous HCl (80 mL) was added zinc (10.70 g, 164 mmol) under N$_2$ atmosphere. After the almost complete dissolution of the zinc yielded a clear bright blue solution, the formed chromium(II) chloride was transferred to a refluxing solution of Example 124A (2.26 g, 4.68 mmol) in ethanol (50 mL) under N$_2$ using an addition funnel over 1 hour. The reaction mixture was refluxed at 90° C. overnight, cooled and diluted with 600 mL of dichloromethane. The organic phase was and dried over sodium sulfate, filtered and concentrated. The crude material was then taken up in anhydrous ethanol and treated with a solution of HCl in ethanol (prepared by adding 2.5 mL of acetyl chloride to an ice bath cooled solution of 6 mL of ethanol), and the mixture was heated at 65° C. for one hour. The ethanol was removed and the crude material was diluted with 300 mL of methyl tert-butyl ether, washed with 50 mL each of saturated aqueous sodium bicarbonate and brine, dried over sodium sulfate, and filtered. The solvent was removed in vacuo to provide (2S,3R,5S)-1-allyl 2-ethyl 5-(3-bromophenyl)-3-(tert-butyl)-4-oxopyrrolidine-1,2-dicarboxylate (2.04 g, 3.61 mmol, 77% yield). $^1$H NMR (400 MHz, DMSO-d$_6$) δ ppm 7.70 (t, J=1.9 Hz, 1H), 7.48 (ddd, J=6.9, 1.7, 0.8 Hz, 1H), 7.43 (ddd, J=7.9, 2.0, 1.0 Hz, 1H), 7.28 (d, J=7.9 Hz, 1H), 5.82-5.70 (m, 1H), 5.11 (dt, J=4.7, 1.6 Hz, 1H), 5.09-5.01 (m, 2H), 4.67 (d, J=4.2 Hz, 1H), 4.54-4.48 (m, 2H), 4.24-4.16 (m, 2H), 2.59 (dd, J=4.3, 1.1 Hz, 1H), 1.23 (dd, J=7.4, 6.8 Hz, 3H), 1.05 (s, 9H); MS (APCI+) m/z 452 (M+H)$^+$.

Example 124C (2S,3R,4S,5S)-1-allyl 2-ethyl 5-(3-bromophenyl)-3-(tert-butyl)-4-hydroxypyrrolidine-1,2-dicarboxylate Example 124B (2.04 g, 4.51 mmol) was dissolved in ethanol (20 mL) and cooled in an ice bath. Sodium tetrahydroborate (0.205 g, 5.41 mmol) was added initially in small portions but then all at once. The mixture was allowed to stir in the bath for 30 minutes. The mixture was concentrated in vacuo. Methyl tert-butyl ether (300 mL) and saturated sodium bicarbonate (50 mL) were added and the mixture was stirred for 30 minutes at room temperature. The layers were separated, and the organic layer was washed with brine, dried over sodium sulfate, filtered, and concentrated. The resulting residue was loaded onto an 80 g silica gel column and was eluted with 5-50% ethyl acetate/heptanes to provide (2S,3R,4S,5S)-1-allyl 2-ethyl 5-(3-bromophenyl)-3-(tert-butyl)-4-hydroxypyrrolidine-1,2-dicarboxylate (1.062 g, 2.337 mmol, 51.8% yield). $^1$H NMR (400 MHz, DMSO-d$_6$) δ ppm 7.75 (t, J=1.9 Hz, 1H), 7.49 (ddd, J=7.6, 2.0, 1.1 Hz, 1H), 7.32 (ddd, J=7.9, 2.0, 1.0 Hz, 1H), 7.18 (t, J=7.8 Hz, 1H), 5.71 (ddt, J=17.7, 10.2, 5.1 Hz, 1H), 5.10-5.00 (m, 2H), 4.87 (d, J=6.6 Hz, 1H), 4.43-4.38 (m, 2H), 4.38-4.31 (m, 1H), 4.28 (d, J=4.6 Hz, 1H), 4.26-4.21 (m, 1H), 4.17 (q, J=7.1 Hz, 2H), 2.24 (t, J=4.4 Hz, 1H), 1.25 (td, J=7.2, 0.7 Hz, 3H), 0.99 (d, J=0.7 Hz, 9H); MS (APCI+) m/z 455 (M+H)$^+$ Br doublet.

Example 124D (2S,3R,4S,5S)-1-allyl 2-ethyl 5-(3-bromophenyl)-3-(tert-butyl)-4-((2-methoxy-5-(trifluoromethyl)pyridin-3-yl)methoxy)pyrrolidine-1,2-dicarboxylate Example 124C (788 mg, 1.734 mmol) and 3-(bromomethyl)-2-methoxy-5-(trifluoromethyl)pyridine (940 mg, 3.48 mmol) were dissolved in dry dimethylformamide (6 mL). After cooling in an ice bath, 1 M potassium 2-methylpropan-2-olate (2.5 mL, 2.500 mmol) solution in tetrahydrofuran was added dropwise over 15 minutes. After 30 minutes, the reaction was acidified with 1M aqueous HCl (0.5 mL) and warmed to room temperature. The reaction mixture was diluted with 100 mL of methyl tert-butyl ether and washed with water (25 mL). The organics were separated and dried over sodium sulfate, filtered, and concentrated. The crude material was purified using a 40 g silica gel column and was eluted with 5-50% ethyl acetate/heptanes over 40 minutes to provide (2S,3R,4S,5S)-1-allyl 2-ethyl 5-(3-bromophenyl)-3-(tert-butyl)-4-((2-methoxy-5-(trifluoromethyl)pyridin-3-yl)methoxy)pyrrolidine-1,2-dicarboxylate (0.593 g, 0.922 mmol, 53.1% yield). $^1$H NMR (400 MHz, DMSO-$d_6$) δ ppm 8.31 (s, 1H), 7.80 (d, J=1.9 Hz, 1H), 7.53 (d, J=7.7 Hz, 1H), 7.30-7.26 (m, 1H), 7.24 (d, J=2.4 Hz, 1H), 7.12 (t, J=7.8 Hz, 1H), 5.71 (ddd, J=18.4, 10.3, 5.1 Hz, 1H), 5.09-5.01 (m, 3H), 4.43 (dd, J=3.9, 2.1 Hz, 3H), 4.34-4.27 (m, 3H), 4.11 (qd, J=7.1, 2.5 Hz, 2H), 3.93 (d, J=13.5 Hz, 1H), 3.88 (s, 3H), 1.16 (t, J=7.1 Hz, 3H), 1.01 (s, 9H); MS (APCI+) m/z 643 (M+H)$^+$.

Example 124E (2S,3R,4S,5S)-ethyl 5-(3-bromophenyl)-3-(tert-butyl)-4-((2-methoxy-5-(trifluoromethyl)pyridin-3-yl)methoxy)pyrrolidine-2-carboxylate Example 124D (160 mg, 0.249 mmol) was dissolved in ethyl acetate (2.5 mL) and dichloromethane (2.5 mL), degassed with a stream of nitrogen, and treated with 1,3-dimethylpyrimidine-2,4,6(1H,3H,5H)-trione (78 mg, 0.497 mmol) and tetrakis(triphenylphosphine)palladium (2.87 mg, 2.486 mol). The reaction was stirred at ambient temperature for 10 minutes. The reaction mixture was quenched with 15 mL of 2M aqueous Na$_2$CO$_3$ and was diluted with 50 mL of methyl tert-butyl ether. The phases were separated, and the organic layer was washed with brine, dried over Na$_2$SO$_4$, filtered, and concentrated. The crude material was purified using a 24 g silica gel cartridge with a gradient of 5-100% ethyl acetate/heptanes over 20 minutes to provide (2S,3R,4S,5S)-ethyl 5-(3-bromophenyl)-3-(tert-butyl)-4-((2-methoxy-5-(trifluoromethyl)pyridin-3-yl)methoxy)pyrrolidine-2-carboxylate (103 mg, 0.184 mmol, 74.0% yield). $^1$H NMR (400 MHz, DMSO-$d_6$) δ ppm 8.32 (s, 1H), 7.67 (t, J=1.9 Hz, 1H), 7.46-7.37 (m, 2H), 7.31 (ddd, J=7.9, 2.1, 1.1 Hz, 1H), 7.15 (t, J=7.8 Hz, 1H), 4.30 (dt, J=13.6, 0.8 Hz, 1H), 4.22 (d, J=4.9 Hz, 1H), 4.17-4.06 (m, 3H), 3.93 (dt, J=13.6, 0.9 Hz, 1H), 3.88 (s, 3H), 3.66 (d, J=6.1 Hz, 1H), 3.01 (s, 1H), 2.40 (dd, J=6.1, 2.2 Hz, 1H), 1.20 (t, J=7.1 Hz, 3H), 0.98 (s, 9H); (APCI+) m/z 559 (M+H)$^+$.

Example 124F (2S,3R,4S,5S)-2-ethyl 1-isopropyl 5-(3-bromophenyl)-3-(tert-butyl)-4-((2-methoxy-5-(trifluoromethyl)pyridin-3-yl)methoxy)pyrrolidine-1,2-dicarboxylate To a solution of Example 124E (75 mg, 0.134 mmol) in toluene (1 mL) and saturated aqueous NaHCO$_3$ (1.000 mL) was added dropwise 2M isopropyl carbonochloridate (0.141 mL, 0.282 mmol) as a solution in toluene. After stirring at room temperature for 20 minutes, LC/MS showed desired product with no starting material left. The organics were concentrated and chromatographed using an 12 g silica gel cartridge with a gradient of 5-100% ethyl acetate/heptanes to provide (2S,3R,4S,5S)-2-ethyl 1-isopropyl 5-(3-bromophenyl)-3-(tert-butyl)-4-((2-methoxy-5-(trifluoromethyl)pyridin-3-yl)methoxy)pyrrolidine-1,2-dicarboxylate (59 mg, 0.091 mmol, 68.2% yield). $^1$H NMR (400 MHz, DMSO-$d_6$) δ ppm 8.31 (d, J=2.4 Hz, 1H), 7.79 (t, J=1.8 Hz, 1H), 7.52 (dt, J=7.7, 1.3 Hz, 1H), 7.31-7.23 (m, 2H), 7.12 (t, J=7.8 Hz, 1H), 5.01 (d, J=6.0 Hz, 1H), 4.66 (p, J=6.2 Hz, 1H), 4.37 (d, J=2.9 Hz, 1H), 4.33-4.27 (m, 2H), 4.11 (qd, J=7.1, 4.9 Hz, 2H), 3.93 (dt, J=13.6, 0.9 Hz, 1H), 3.88 (s, 3H), 2.45-2.42 (m, 1H), 1.17 (t, J=7.1 Hz, 3H), 1.06 (d, J=6.2 Hz, 3H), 1.01 (s, 9H), 0.93 (d, J=6.3 Hz, 3H); MS (APCI+) m/z 645 (M+H)$^+$.

Example 124G (2S,3R,4S,5S)-5-(3-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid Example 124F (58 mg, 0.090 mmol) and lithium hydroxide (20.4 mg, 0.852 mmol) were dissolved in methanol (0.5 mL), tetrahydrofuran (0.500 mL) and water (0.500 mL). The reaction mixture was warmed at 45° C. overnight. The solvent was removed under a stream of nitrogen and was acidified with 0.422 mL of 2N aqueous HCl. The crude material was chromatographed using a 12 g silica gel cartridge with an ethanol/ethyl acetate/heptanes solvent system to provide (2S,3R,4S,5S)-5-(3-bromophenyl)-3-(tert-butyl)-1-(isopropoxycarbonyl)-4-((2-methoxy-5-(trifluoromethyl)pyridin-3-yl)methoxy)pyrrolidine-2-carboxylic acid (32 mg, 0.052 mmol, 57.7% yield). $^1$H NMR (400 MHz, DMSO-$d_6$) δ ppm 8.32-8.27 (m, 1H), 7.89 (t, J=1.8 Hz, 1H), 7.66-7.60 (m, 1H), 7.29-7.22 (m, 1H), 7.22-7.17 (m, 1H), 7.09 (t, J=7.8 Hz, 1H), 4.99 (d, J=6.4 Hz, 1H), 4.64 (p, J=6.2 Hz, 1H), 4.32 (d, J=13.9 Hz, 1H), 4.28-4.22 (m, 2H), 4.00-3.93 (m, 1H), 3.89 (s, 3H), 2.52 (t, J=2.7 Hz, 1H), 1.06 (d, J=6.2 Hz, 3H), 0.99 (s, 9H), 0.91 (d, J=6.2 Hz, 3H); MS (APCI+) m/z 617 (M+H)$^+$.

Example 125

(2S,3R,4S,5S)-3-tert-butyl-5-(3-chlorophenyl)-4-{[2-methoxy-5-(trifluoromethyl)pyridin-3-yl]methoxy}-1-[(2R)-oxane-2-carbonyl]pyrrolidine-2-carboxylic acid The title compound was prepared using the procedures described in Example 179 substituting Core 8 for Core 24. $^1$H NMR (400 MHz, DMSO-$d_6$) δ ppm 8.30 (s, 1H), 7.66 (s, 1H), 7.49 (s, 1H), 7.25-7.04 (m, 3H), 5.18 (s, 1H), 4.81 (s, 1H), 4.33 (d, J=13.9 Hz, 1H), 4.29-4.23 (m, 1H), 3.96 (d, J=13.9 Hz, 2H), 3.89 (d, J=0.7 Hz, 3H), 3.81 (s, 1H), 2.60 (s, 1H), 1.78 (s, 1H), 1.54 (s, 2H), 1.43 (s, 3H), 1.01 (s, 9H); MS (ESI+) m/z 600 (M+H)$^+$.

Example 126

(2S,3R,4R,5S)-5-(2-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid

Example 126A 1-allyl 2-ethyl (2S,3R,4R,5S)-5-(2-bromophenyl)-3-(tert-butyl)-4-hydroxypyrrolidine-1,2-dicarboxylate Example 144B (633 mg, 1.399 mmol) was dissolved in ethanol (10 mL). Sodium borohydride (52.9 mg, 1.399 mmol) was added after cooling the reaction to ~−10° C. in an ice-acetone bath. The ice bath was removed and the reaction was allowed to warm to room temperature, which took about 20 minutes, at which point LC/MS showed the starting material was completely consumed. The reaction mixture was concentrated and stirred in ethyl acetate (50 mL) and saturated sodium bicarbonate (50 mL) for 30 minutes. The organics were concentrated and purified by silica gel chromatography, eluting with 0 to 5% ethyl acetate in dichloromethane to provide the desired product (101.5 mg, 16%). $^1$H NMR (400 MHz, DMSO-$d_6$, 120° C.) δ ppm 8.10 (dd, J=7.8, 1.7 Hz, 1H), 7.57 (dd, J=7.9, 1.2 Hz, 1H), 7.34 (td, J=7.6, 1.3 Hz, 1H), 7.17 (td, J=7.6, 1.7 Hz, 1H), 5.76 (s, 1H), 5.24 (d, J=5.8 Hz, 1H), 5.08 (d, J=10.6 Hz, 2H), 4.98 (s, 1H), 4.48-4.39 (m, 3H), 4.28-4.08 (m, 3H), 2.01-1.86 (m, 1H), 1.29 (t, J=7.1 Hz, 3H), 0.97 (s, 9H); MS (ESI+) m/z 454 (M+H)$^+$.

Example 126B 1-allyl 2-ethyl (2S,3R,4R,5S)-5-(2-bromophenyl)-3-(tert-butyl)-4-((2-methoxy-5-(trifluoromethyl)pyridin-3-yl)methoxy)pyrrolidine-1,2-dicarboxylate Example 126A (92.2 mg, 0.203 mmol) and 3-(bromomethyl)-2-methoxy-5-(trifluoromethyl)pyridine (123.8 mg, 0.458 mmol) were dissolved in dimethylformamide (1 mL). The reaction mixture was cooled to 0° C., potassium tert-butoxide (1M in tetrahydrofuran, 0.30 mL, 0.30 mmol) was added dropwise and the reaction was stirred at ambient temperature for 1 hour. The reaction mixture was poured into saturated aqueous NH$_4$Cl (35 mL), extracted with methyl tert-butyl ether (3×35 mL), and purified by silica gel chromatography (5% ethyl acetate in dichloromethane) to provide the title compound (57.1 mg, 44%). $^1$H NMR (400 MHz, DMSO-$d_6$, 120° C.) δ ppm 8.46 (d, J=2.1 Hz, 1H), 8.25 (dd, J=7.9, 1.8 Hz, 1H), 7.94 (d, J=2.5 Hz, 1H), 7.60 (dd, J=7.9, 1.3 Hz, 1H), 7.39 (td, J=7.6, 1.3 Hz, 1H), 7.23 (td, J=7.6, 1.7 Hz, 1H), 5.80-5.67 (m, 1H), 5.28 (s, 1H), 5.07 (t, J=10.9 Hz, 2H), 4.72 (d, J=12.6 Hz, 1H), 4.46-4.39 (m, 3H), 4.31-4.12 (m, 3H), 4.08 (d, J=3.5 Hz, 1H), 3.98 (s, 3H), 2.21 (dd, J=11.1, 3.4 Hz, 1H), 1.29 (t, J=7.1 Hz, 3H), 0.95 (s, 9H); MS (ESI+) m/z 643 & 645 (M+H)$^+$.

Example 126C ethyl (2S,3R,4R,5S)-5-(2-bromophenyl)-3-(tert-butyl)-4-((2-methoxy-5-(trifluoromethyl)pyridin-3-yl)methoxy)pyrrolidine-2-carboxylate Example 126B (54.0 mg, 0.084 mmol) was dissolved in ethyl acetate (1 mL) and dichloromethane (1 mL) and was treated with 1,3-dimethylpyrimidine-2,4,6(1H,3H,5H)-trione (26.2 mg, 0.168 mmol) and tetrakis(triphenylphosphine)palladium (1.0 mg, 0.865 μmol). The reaction was stirred at ambient temperature. After 1 hour, the reaction mixture was diluted with methyl tert-butyl ether (25 mL) and stirred with 15 mL of 10% aqueous Na$_2$CO$_3$ (50 mL) solution for 30 minutes. The phases were separated, and the organic layer was washed with brine, dried over Na$_2$SO$_4$, filtered, and concentrated. The residue was purified by silica gel chromatography, eluting with 5% to 10% ethyl acetate in dichloromethane to provide the title compound (47.0 mg, 100%). $^1$H NMR (400 MHz, DMSO-$d_6$) δ ppm 8.54 (dd, J=2.6, 1.2 Hz, 1H), 8.36 (dd, J=7.9, 1.8 Hz, 1H), 8.04 (d, J=2.5 Hz, 1H), 7.54 (dd, J=8.0, 1.3 Hz, 1H), 7.39 (td, J=7.4, 1.2 Hz, 1H), 7.18 (td, J=7.6, 1.8 Hz, 1H), 5.07 (d, J=12.8 Hz, 1H), 5.04 (d, J=1.1 Hz, 1H), 4.66-4.59 (m, 2H), 4.14 (qq, J=7.2, 3.8 Hz, 2H), 4.06-3.98 (m, 1H), 3.97 (s, 3H), 3.91 (d, J=3.5 Hz, 1H), 2.04 (dd, J=10.3, 3.5 Hz, 1H), 1.25 (t, J=7.1 Hz, 3H), 0.88 (s, 9H); MS (ESI+) m/z 559 & 561 (M+H)$^+$.

Example 126D ethyl (2S,3R,4R,5S)-5-(2-bromophenyl)-3-(tert-butyl)-4-((2-methoxy-5-(trifluoromethyl)pyridin-3-yl)methoxy)-1-((S)-tetrahydrofuran-2-carbonyl)pyrrolidine-2-carboxylate (S)-(−)-tetrahydro-2-furoic acid (40.2 mg, 0.345 mmol) was dissolved in dichloromethane (2 mL). Oxalyl chloride (2M in dichloromethane, 200 μL, 0.40 mmol) was added followed by dimethylformamide (25 μL). The reaction mixture was stirred at room temperature for 3 hours, at which point it was concentrated, redissolved in dichloromethane (1 mL), and concentrated again. The residue was taken up in dichloromethane (3×1 mL) and was added to a solution of Example 126C (47.0 mg, 0.084 mmol) and triethylamine (100 μL, 0.717 mmol) and dichloromethane (3 mL). The reaction mixture was stirred at ambient temperature for 17 hours. After this time, the mixture was diluted with dichloromethane (50 mL) and washed twice with saturated NaHCO$_3$ and once with brine. The organic layer was dried over Na$_2$SO$_4$, filtered, and concentrated to provide the title compound (43.0 mg, 78%). $^1$H NMR (400 MHz, DMSO-$d_6$, 120° C.) δ ppm 8.46 (s, 1H), 8.32 (d, J=7.9 Hz, 1H), 7.93 (d, J=2.5 Hz, 1H), 7.64 (d, J=7.9 Hz, 1H), 7.43 (t, J=7.5 Hz, 1H), 7.26 (t, J=7.7 Hz, 1H), 5.71 (s, 1H), 5.07 (d, J=12.4 Hz, 1H), 4.73 (d, J=12.3 Hz, 1H), 4.44 (d, J=11.4 Hz, 1H), 4.28-4.10 (m, 3H), 4.00 (s, 3H), 3.73-3.57 (m, 2H), 2.48-2.47 (m, 1H), 2.19 (dd, J=11.3, 3.5 Hz, 1H), 1.92-1.47 (m, 4H), 1.28 (t, J=7.1 Hz, 3H), 0.95 (s, 9H); MS (ESI+) m/z 657 & 659 (M+H)$^+$.

Example 126E (2S,3R,4R,5S)-5-(2-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid Example 126D (40.0 mg, 0.061 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction was quenched by the addition of 1M aqueous HCl (0.5 mL), concentrated and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (29.6 mg, 55%) as the TFA salt. $^1$H NMR (400 MHz, DMSO-d$_6$, 120° C.) δ ppm 7.69 (dq, J=8.4, 0.9 Hz, 1H), 7.63 (dd, J=7.9, 1.5 Hz, 1H), 7.56 (ddd, J=8.4, 6.9, 1.5 Hz, 1H), 7.47 (s, 1H), 7.39-7.31 (m, 2H), 6.49 (d, J=1.8 Hz, 1H), 5.76 (ddt, J=17.3, 10.5, 5.3 Hz, 1H), 5.29 (d, J=6.5 Hz, 1H), 5.16-5.04 (m, 2H), 4.76 (p, J=6.5 Hz, 1H), 4.49-4.30 (m, 5H), 4.16-4.00 (m, 3H), 3.95 (s, 3H), 2.58 (t, J=3.4 Hz, 1H), 1.35 (d, J=6.5 Hz, 3H), 1.28 (d, J=6.5 Hz, 3H), 1.13 (t, J=7.1 Hz, 3H), 1.01 (s, 9H); MS (ESI+) m/z 629 & 631 (M+H)$^+$.

Example 127

(2S,3R,4S,5S)-3-tert-butyl-4-{[2-methoxy-5-(trifluoromethyl)pyridin-3-yl]methoxy}-1-[(2S)-oxolane-2-carbonyl]-5-[1-(propan-2-yl)-1H-pyrazol-5-yl]pyrrolidine-2-carboxylic acid The title compound was prepared using the procedure described in Example 144 substituting Core 19:for Core 10 and 3-(bromomethyl)-5-trifluoromethyl-2-methoxypyridine for 3-(bromomethyl)-5-cyclobutyl-2-methoxypyridine. $^1$H NMR (400 MHz, DMSO-d$_6$) δ ppm 8.32 (d, J=2.3 Hz, 1H), 7.35 (s, 1H), 7.24 (s, 1H), 6.56 (s, 1H), 5.65-5.47 (m, 1H), 4.70 (p, J=6.4 Hz, 1H), 4.62 (s, 1H), 4.41-4.30 (m, 2H), 3.99 (d, J=13.8 Hz, 1H), 3.91 (s, 3H), 3.69 (dt, J=13.4, 6.9 Hz, 2H), 2.55 (s, 1H), 2.11-1.97 (m, 1H), 1.87-1.75 (m, 1H), 1.76-1.64 (m, 2H), 1.38 (d, J=6.4 Hz, 3H), 1.29 (d, J=6.5 Hz, 3H), 1.26 (s, OH), 1.01 (s, 9H), 0.91-0.78 (m, 1H); MS (APCI+) m/z 583 (M+H)$^+$.

Example 128

(2S,3R,4S,5S)-3-tert-butyl-5-(2-cyclopropylphenyl)-4-{[2-methoxy-5-(trifluoromethyl)pyridin-3-yl]methoxy}-1-[(2S)-oxane-2-carbonyl]pyrrolidine-2-carboxylic acid Example 128A ethyl (2S,3R,4S,5S)-3-(tert-butyl)-5-(2-cyclopropylphenyl)-4-((2-methoxy-5-(trifluoromethyl)pyridin-3-yl)methoxy)-1-((S)-tetrahydro-2H-pyran-2-carbonyl)pyrrolidine-2-carboxylate Tetrahydropyran-2-carboxylic acid (53.7 mg, 0.413 mmol) was dissolved in dichloromethane (2 mL). Oxalyl chloride (2M in dichloromethane, 250 µL, 0.50 mmol) was added followed by dimethylformamide (25 µL). The reaction was stirred at room temperature for 3 hours, at which point it was concentrated, redissolved in dichloromethane (1 mL), and concentrated again. The residue was taken up in dichloromethane (3×1 mL) and was added to a solution of Example 112E (90.4 mg, 0.174 mmol) and triethylamine (100 µL, 0.717 mmol) in dichloromethane (3 mL). The reaction was stirred at ambient temperature for 17 hours. After this time, the mixture was diluted with dichloromethane (100 mL) and washed twice with saturated aqueous NaHCO$_3$ and once with brine. The organic layer was dried over Na$_2$SO$_4$, filtered, and concentrated. The residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The title compound was the second eluting diastereomer and was isolated as the TFA salt (43.7 mg, 34%). $^1$H NMR (400 MHz, DMSO-d$_6$, 120° C.) δ ppm 8.27 (s, 1H), 7.96 (dd, J=7.6, 1.7 Hz, 1H), 7.16 (d, J=2.5 Hz, 1H), 7.06 (t, J=9.6 Hz, 2H), 6.95 (d, J=7.1 Hz, 1H), 5.90 (s, 1H), 4.72 (s, 1H), 4.36 (d, J=5.6 Hz, 1H), 4.28 (d, J=13.9 Hz, 1H), 4.08 (qd, J=7.1, 3.0 Hz, 2H), 3.89-3.80 (m, 5H), 3.75 (d, J=11.4 Hz, 1H), 3.45 (s, 1H), 2.44 (d, J=1.8 Hz, 1H), 2.06-1.94 (m, 1H), 1.72-1.26 (m, 6H), 1.13 (t, J=7.1 Hz, 3H), 1.04 (s, 9H), 0.99-0.84 (m, 2H), 0.80-0.67 (m, 1H), 0.57-0.46 (m, 1H); MS (ESI+) m/z 633 (M+H)$^+$.

Example 128B (2S,3R,4S,5S)-3-tert-butyl-5-(2-cyclopropylphenyl)-4-{[2-methoxy-5-(trifluoromethyl)pyridin-3-yl]methoxy}-1-[(2S)-oxane-2-carbonyl]pyrrolidine-2-carboxylic acid Example 128A (40.7 mg, 0.055 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction mixture was quenched by the addition of 1M aqueous HCl (0.5 mL), concentrated and purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (27.3 mg, 70%) as the TFA salt. $^1$H NMR (400 MHz, DMSO-d$_6$, 120° C.) δ ppm 8.27 (d, J=2.4 Hz, 1H), 8.02 (dd, J=7.5, 1.8 Hz, 1H), 7.13 (s, 1H), 7.11-6.99 (m, 2H), 6.94 (dd, J=7.3, 1.7 Hz, 1H), 5.90 (s, 1H), 4.69 (s, 1H), 4.35 (d, J=5.8 Hz, 1H), 4.31 (d, J=14.0 Hz, 1H), 3.95-3.84 (m, 5H), 3.76 (d, J=11.5 Hz, 1H), 3.47 (s, 1H), 2.50 (d, J=1.8 Hz, 1H), 2.07-1.94 (m, 1H), 1.71-1.25 (m, 6H), 1.04 (s, 9H), 0.98-0.84 (m, 2H), 0.78-0.65 (m, 1H), 0.49 (dtd, J=9.1, 5.3, 3.0 Hz, 1H); MS (ESI+) m/z 605 (M+H)$^+$.

Example 129

(2S,3R,4S,5S)-3-tert-butyl-4-{[2-methoxy-5-(trifluoromethyl)pyridin-3-yl]methoxy}-5-(2-methylphenyl)-1-[(2S)-oxolane-2-carbonyl]pyrrolidine-2-carboxylic acid Example 129A (2S,3R,4S,5S)-1-allyl 2-ethyl 3-(tert-butyl)-4-nitro-5-(o-tolyl)pyrrolidine-1,2-dicarboxylate To a mixture of Core 9 (946 mg, 2.83 mmol) in toluene (3 mL) and saturated aqueous NaHCO$_3$ (3 mL) was added allyl carbonochloridate (360 µL, 3.39 mmol) dropwise at room temperature. The mixture was stirred at room temperature overnight. The reaction was poured into water (50 mL) and extracted with dichloromethane (50 mL). The organic layer was washed with brine and concentrated in vacuo. Purification by silica gel chromatography, eluting with ethyl acetate in heptane, provided the title compound, 1.22 g (quantitative yield). $^1$H NMR (400 MHz, DMSO-d$_6$) δ ppm 7.79 (dd, J=7.8, 1.9 Hz, 1H), 7.24-7.04 (m, 3H), 5.69 (ddt, J=17.4, 10.5, 5.1 Hz, 1H), 5.60 (d, J=8.9 Hz, 1H), 5.55

(dd, J=8.9, 3.1 Hz, 1H), 5.07-4.96 (m, 2H), 4.56 (d, J=3.9 Hz, 1H), 4.42 (dtd, J=5.2, 1.7, 0.7 Hz, 2H), 4.26 (q, J=7.1 Hz, 2H), 3.08 (t, J=3.5 Hz, 1H), 2.36 (s, 3H), 1.29 (td, J=7.1, 0.7 Hz, 3H), 1.03 (d, J=0.8 Hz, 9H); MS (ESI$^+$) m/z 419.0 (M+H)$^+$.

Example 129B (2S,3R,5S)-1-allyl 2-ethyl 3-(tert-butyl)-4-oxo-5-(o-tolyl)pyrrolidine-1,2-dicarboxylate Pyridinium dichromate (2.74 g, 7.29 mmol) was dissolved in 6N aqueous HCl (64.0 mL) and cooled in an ice bath. Zinc dust (5.24 g, 80 mmol) was added in portions, then the flask was removed from the ice bath, and the reaction mixture was stirred at room temperature for 75 minutes (until zinc had dissolved and bubbling had stopped). The blue solution was transferred via cannula over about 20 minutes to a refluxing solution of Example 129A (1.22 g, 2.92 mmol) in ethanol (32 mL). The reaction mixture was refluxed overnight. The reaction mixture was cooled to room temperature, and extracted three times with dichloromethane. The combined organic extracts were dried over Na$_2$SO$_4$, filtered, and concentrated in vacuo. The resulting material was taken up in 5.5 mL of ethanol and treated with a solution (prepared at 0° C.) of 1.85 mL acetyl chloride in 9 mL ethanol. The reaction mixture was refluxed for 1 hour. After this time, the mixture was concentrated in vacuo, and the residue was purified by silica gel chromatography, eluting with 0 to 40% ethyl acetate-heptanes to provide the title compound, 0.693 g, (61% yield). $^1$H NMR (400 MHz, DMSO-d$_6$) δ ppm 7.68-7.61 (m, 1H), 7.21-7.06 (m, 3H), 5.70 (m, 1H), 5.23 (s, 1H), 5.08-4.97 (m, 2H), 4.63 (d, J=5.1 Hz, 1H), 4.46 (m, 2H), 4.28-4.18 (m, 2H), 2.64 (dd, J=5.3, 1.0 Hz, 1H), 2.38 (s, 3H), 1.26 (t, J=7.1 Hz, 3H), 1.06 (s, 9H); MS (ESI$^+$) m/z 388.0 (M+H)$^+$.

Example 129C (2S,3R,4S,5S)-1-allyl 2-ethyl 3-(tert-butyl)-4-hydroxy-5-(o-tolyl)pyrrolidine-1,2-dicarboxylate A solution of Example 129B (0.693 g, 1.789 mmol) in ethanol (8.9 mL) was cooled to −10° and then treated with one portion of sodium borohydride (0.081 g, 2.146 mmol). The reaction stirred at −10° C. to −5° C. for 90 minutes, and it was quenched carefully with 0.6 mL acetone. The mixture was concentrated in vacuo, and the resulting material was taken up in 10 mL ethyl acetate and stirred vigorously with 10 mL of saturated aqueous NaHCO$_3$ solution for 30 minutes. The mixture was transferred to a separatory funnel, the phases were separated, and the aqueous layer was extracted twice more with ethyl acetate (10 mL each). The combined organics were dried over Na$_2$SO$_4$, filtered, and concentrated in vacuo, and the crude product was purified by silica gel chromatography, eluting with 5 to 40% ethyl acetate-heptanes to provide the title compound, 0.280 g (40% yield). $^1$H NMR (400 MHz, DMSO-d$_6$) δ ppm 7.85 (m, 1H), 7.11-7.01 (m, 3H), 5.73-5.61 (m, 1H), 5.08 (d, J=6.6 Hz, 1H), 4.99 (m, 2H), 4.45-4.33 (m, 3H), 4.30 (m, 1H), 4.22-4.12 (m, 2H), 3.82 (m, 1H), 2.29 (s, 3H), 2.28 (m, 1H), 1.24 (t, J=7.1 Hz, 3H), 0.99 (s, 9H); MS (ESI$^+$) m/z 390.1 (M+H)$^+$.

Example 129D methyl 2-methoxy-5-(trifluoromethyl)nicotinate

To 3-bromo-2-methoxy-5-(trifluoromethyl)pyridine (50 g, 195 mmol) and Pd-dppf (Heraeus) (1.32 g, 1.804 mmol) in a 300 mL stainless steel reactor was added methanol (250 mL) and triethylamine (54.4 mL, 391 mmol). The reactor was degassed with nitrogen several times carbon monoxide was added and the reaction was heated to 100±5° C., for about 16.38 hours. The pressure was at 60 psi±4 psi for 2.7 hours and at 21±7 psi for rest of the reaction time ~14 hours. Additional Pd-dppf (Heraeus) (0.82 g, 1.121 mmol) catalyst was added. The reactor was repeatedly degassed with nitrogen several times, carbon monoxide was added and the reaction was heated to 100±5° C. for 10 hours. The crude product was concentrated to remove methanol. Ethyl acetate (400 mL) was added, followed by the addition of 150 mL saturated aqueous NH$_4$Cl, and the organic layer was isolated. The aqueous layer was extracted with ethyl acetate (200 mL). The organic layers were combined, washed with brine, dried over Na$_2$SO$_4$, filtered, and passed through a silica gel plug to remove dark Pt/C. The filtrate was concentrated to provide 40.62 g of the desired crude product, which was directly used in the next step. $^1$H NMR (400 MHz, DMSO-d$_6$) δ ppm=3.84 (s, 3 H) 3.96 (s, 3 H) 8.40 (br s, 1 H) 8.81 (br s, 1 H); MS (ESI$^+$) m/z 236.1 (M+H)$^+$.

Example 129E (2-methoxy-5-(trifluoromethyl)pyridin-3-yl)methanol

Ethyl 2-methoxy-5-(trifluoromethyl)nicotinate (59.54 g, 253 mmol) was dissolved in tetrahydrofuran (506 mL). After cooling to <5° C., a solution of lithium aluminum hydride (177 mL, 177 mmol) in tetrahydrofuran was added over 40 minutes, maintaining an internal temperature <10° C. After 1 hour, the reaction was quenched by the addition of 50 mL of acetone then diluted with methyl tert-butyl ether (300 mL) and stirred with 300 mL of saturated aqueous Rochelle's salt (potassium sodium tartrate tetrahydrate) until two clear layers were present. The reaction mixture was extracted with ethyl acetate and the combined extracts were washed with brine, dried over sodium sulfate, filtered, and concentrated. The crude material was purified by flash column (0 to 30% ethyl acetate in heptane) to provide the title compound (2-methoxy-5-(trifluoromethyl)pyridin-3-yl) methanol (40.28 g, 194 mmol, 77% yield). $^1$H NMR (400 MHz, DMSO-d$_6$) δ ppm=3.96 (s, 3 H) 4.50 (d, J=5.73 Hz, 2 H) 5.45 (t, J=5.73 Hz, 1 H) 7.89-8.01 (m, 1 H) 8.47 (s, 1 H); MS (ESI$^+$) m/z 208.0 (M+H)$^+$.

Example 129F 3-(bromomethyl)-2-methoxy-5-(trifluoromethyl) pyridine

Example 129E (21.6 g, 104 mmol) and triphenylphosphine (54.7 g, 209 mmol) were dissolved in dichloromethane (521 mL) and the reaction mixture was cooled to 0° C. N-bromosuccinimide (37.1 g, 209 mmol) was added in several portions and an exotherm/bubbling was noted (temperature did not exceed 25° C.). After stirring for 5 minutes in the ice bath, the reaction was warmed to room temperature for 30 minutes. The reaction mixture was recooled in the ice bath before addition of 300 mL of water, stirred for 5 minutes, and the organic layer was separated. The organic layer was washed with water (2×30 mL), concentrated to approximately 50 mL and filtered through a fritted funnel layered with a pad of silica (1.5 inch), eluting with heptanes. The filtrates were concentrated to provide a viscous mixture, diluted with 50:50 methyl tert-butyl ether:heptanes and filtered. The filtrate was concentrated and purified with a 330 g silica gel cartridge using a gradient of 5% ethyl acetate in heptanes to provide desired product (22.12 g, 79%). $^1$H NMR (400 MHz, CDCl$_3$) δ ppm=4.04-4.10 (m, 3 H) 4.46-4.50 (m, 2 H) 7.83 (d, J=2.43 Hz, 1 H) 8.40 (d, J=1.10 Hz, 1 H).

Example 129G (2S,3R,4S,5S)-1-allyl 2-ethyl 3-(tert-butyl)-4-((2-methoxy-5-(trifluoromethyl)pyridin-3-yl)methoxy)-5-(o-tolyl)pyrrolidine-1,2-dicarboxylate Example 129C (0.280 g, 0.719 mmol), dried azeotropically with toluene, was dissolved in dimethylformamide (7.2 mL), and the solution was cooled to 0° C. Potassium 2-methylpropan-2-olate solution (1M in tetrahydrofuran) (0.79 mL, 0.79 mmol) was added dropwise, followed by dropwise addition of Example 129F (0.233 g, 0.863 mmol). The reaction mixture stirred at 0° C. for 45 minutes, the mixture was poured into 30 mL of saturated aqueous NH$_4$Cl solution and extracted three times with methyl tert-butyl ether (3×30 mL). The combined organics were dried over Na$_2$SO$_4$, filtered and concentrated in vacuo, and the crude product was purified by silica gel chromatography, eluting with 0 to 30% methyl tert-butyl ether-heptanes to provide the title compound, 0.224 g (54% yield). $^1$H NMR (400 MHz, DMSO-d$_6$) δ ppm 8.28 (m, 1H), 7.85 (tt, J=4.6, 3.0 Hz, 0H), 7.18-7.13 (m, 1H), 7.04-6.96 (m, 3H), 5.69 (ddt, J=16.3, 10.5, 5.1 Hz, 1H), 5.19 (d, J=5.8 Hz, 1H), 5.06-4.95 (m, 2H), 4.48 (d, J=2.3 Hz, 1H), 4.40 (dq, J=5.1, 1.5 Hz, 2H), 4.34-4.22 (m, 2H), 4.11 (q, J=7.0 Hz, 2H), 3.86 (s, 3H), 3.83 (dt, J=13.7, 1.1 Hz, 1H), 2.86-2.79 (m, 1H), 2.51 (m, 1H), 2.31 (s, 3H), 1.15 (t, J=7.1 Hz, 3H), 1.03 (s, 9H); MS (ESI$^+$) m/z 578.9 (M+H)$^+$.

Example 129H (2S,3R,4S,5S)-ethyl 3-(tert-butyl)-4-((2-methoxy-5-(trifluoromethyl)pyridin-3-yl)methoxy)-5-(o-tolyl)pyrrolidine-2-carboxylate Example 129G (0.224 g, 0.387 mmol) was dissolved in ethyl acetate (2 mL) and dichloromethane (2 mL), and the solution was treated with 1,3-dimethylpyrimidine-2,4,6(1H, 3H,5H)-trione (0.121 g, 0.774 mmol) and tetrakis(triphenylphosphine)palladium (4.5 mg, 3.87 μmol). The reaction stirred at room temperature overnight. After this time, the reaction mixture was diluted with methyl tert-butyl ether (20 mL) and stirred with 20 mL of 10% aqueous Na$_2$CO$_3$ solution for 15 minutes. The phases were then separated, and the organic layer was washed with brine, dried over Na$_2$SO$_4$, filtered, and concentrated in vacuo. Silica gel chromatography, eluting with 0 to 30% methyl tert-butyl ether-heptanes, provided the title compound, 0.176 g (92% yield). $^1$H NMR (400 MHz, DMSO-d$_6$) δ ppm 8.30 (s, 1H), 7.66-7.50 (m, 1H), 7.35 (d, J=2.4 Hz, 1H), 7.05 (m, 3H), 4.34-4.10 (m, 5H), 4.10-3.99 (m, 1H), 3.86 (s, 3H), 3.79 (d, J=13.9 Hz, 1H), 3.63 (s, 1H), 2.38 (dd, J=6.5, 1.7 Hz, 1H), 2.32 (s, 3H), 1.21 (t, J=7.0 Hz, 3H), 0.99 (s, 9H); MS (APCI$^+$) m/z 495.6 (M+H)$^+$.

Example 129I (2S,3R,4S,5S)-ethyl 3-(tert-butyl)-4-((2-methoxy-5-(trifluoromethyl)pyridin-3-yl)methoxy)-1-((S)-tetrahydrofuran-2-carbonyl)-5-(o-tolyl)pyrrolidine-2-carboxylate The title compound was prepared according to the procedure of Example 98A, substituting Example 129H for (2S,3R,4S,5S)-ethyl 3-(tert-butyl)-5-(2-isopropylphenyl)-4-((2-methoxy-5-(trifluoromethyl)pyridin-3-yl)methoxy)pyrrolidine-2-carboxylate (Example 96E). The crude product was used in the next reaction without further purification. MS (APCI$^+$) m/z 593.5 (M+H)$^+$.

Example 129J (2S,3R,4S,5S)-3-tert-butyl-4-{[2-methoxy-5-(trifluoromethyl)pyridin-3-yl]methoxy}-5-(2-methylphenyl)-1-[(2S)-oxolane-2-carbonyl]pyrrolidine-2-carboxylic acid The title compound was prepared according to the procedure for Example 98B, substituting Example 129F for Example 98A. $^1$H NMR (400 MHz, DMSO-d$_6$) δ ppm 8.28 (s, 1H), 8.00 (d, J=5.5 Hz, 1H), 7.14 (s, 1H), 7.04 (m, 3H), 5.53 (s, 1H), 4.66 (s, 1H), 4.34-4.25 (m, 2H), 4.05 (m, 1H), 3.87 (d, J=14.0 Hz, 1H), 3.87 (s, 3H), 3.70-3.62 (m, 2H), 2.54 (m, 1H), 2.33 (s, 3H), 1.97 (m, 1H), 1.79 (m, 1H), 1.64 (m, 2H), 1.03 (s, 9H); MS (ESI$^+$) m/z 565.2 (M+H)$^+$.

Example 130

(2S,3R,4S,5S)-3-tert-butyl-4-[(5-cyclobutyl-2-methoxypyridin-3-yl)methoxy]-1-[(2S)-oxolane-2-carbonyl]-5-[2-(propan-2-yl)phenyl]pyrrolidine-2-carboxylic acid Example 130A methyl 5-cyclobutyl-2-methoxynicotinate Methyl 5-bromo-2-methoxynicotinate (CombiBlocks, 2.516 g, 10.23 mmol) and PdCl$_2$(dppf) (0.383 g, 0.523 mmol) were suspended in tetrahydrofuran (100 mL), and the orange suspension was purged with N$_2$. A commercial solution of cyclobutylzinc(II) bromide (Aldrich, 0.5 M tetrahydrofuran, 24 mL, 12.00 mmol) was added dropwise, and the reaction was allowed to stir at room temperature for 16 hours. After this time, the reaction mixture was quenched by addition of 100 mL saturated aqueous ammonium chloride, and the product was extracted into 300 mL of dichloromethane. The combined extracts were dried over sodium sulfate, filtered, and concentrated in vacuo. Silica gel chromatography, eluting with 5-100% ethyl acetate/heptanes, provided the title compound (1.110 g, 49% yield). $^1$H NMR (400 MHz, CDCl$_3$) δ ppm 8.16 (d, J=2.6 Hz, 1H), 8.05 (d, J=2.6 Hz, 1H), 4.04 (s, 3H), 3.93 (s, 3H), 3.53 (p, J=8.6 Hz, 1H), 2.43-2.33 (m, 2H), 2.21-2.01 (m, 3H), 1.96-1.88 (m, 1H); MS (ESI+) m/z 222 (M+H)$^+$.

Example 130B (5-cyclobutyl-2-methoxypyridin-3-yl)methanol

Example 130A (1.110 g, 5.02 mmol) was dissolved in tetrahydrofuran (24 mL), and the solution was cooled in an ice bath. A solution of lithium aluminum hydride (2M in tetrahydrofuran, 2.51 mL, 5.02 mmol) was added dropwise over 3 minutes via syringe. The reaction mixture was diluted with 200 mL of methyl tert-butyl ether and quenched with 10 mL of saturated aqueous Rochelle's salt (potassium sodium tartrate tetrahydrate). The mixture was stirred for another 30 minutes at room temperature before separating the layers. The organic layer was dried over sodium sulfate and filtered. The solvent was removed to provide the title compound, 0.943 g (97% yield). The compound was dried azeotropically with toluene and used directly in the next reaction. $^1$H NMR (400 MHz, CDCl$_3$) δ ppm 7.94 (d, J=2.4 Hz, 1H), 7.51 (d, J=2.4 Hz, 1H), 4.67 (d, J=6.3 Hz, 2H), 4.00 (d, J=0.8 Hz, 3H), 3.51 (p, J=8.5 Hz, 1H), 2.36 (dtd, J=10.3, 8.0, 2.7 Hz, 2H), 2.29 (t, J=6.5 Hz, 1H), 2.22-2.00 (m, 3H), 1.97-1.84 (m, 1H); MS (ESI+) m/z 194 (M+H)$^+$.

Example 130C 3-(bromomethyl)-5-cyclobutyl-2-methoxypyridine

Example 130B (0.943 g, 4.88 mmol) and triphenylphosphine (2.56 g, 9.76 mmol) were dissolved in dichloromethane (24.4 mL) and cooled in an ice bath. N-bromosuccinimide (1.737 g, 9.76 mmol) was added gradually using a solid addition funnel, keeping the internal temperature below 10° C. After completion of the addition, the ice bath was removed, and the reaction was stirred at room temperature for 15 minutes. Water was added (10 mL), and the mixture was stirred for 5 minutes before the layers were separated. The organic layer was washed twice with water and then filtered through a fritted cartridge layered with a pad of silica (1 cm), eluting with heptanes. The filtrates were reduced in volume. The material was collected by filtration and washed with 3×30 mL of 50:50 methyl tert-butyl ether:heptanes. The filtrate was concentrated, and the residue was purified by silica gel chromatography, eluting with 5-50% ethyl acetate/heptanes, to provide the title compound (1.07 g, 86% yield). $^1$H NMR (400 MHz, CDCl$_3$) δ ppm 7.97 (d, J=2.4 Hz, 1H), 7.52 (d, J=2.4 Hz, 1H), 4.52 (s, 2H), 4.02 (s, 3H), 3.59-3.38 (m, 1H), 2.44-2.31 (m, 2H), 2.21-2.00 (m, 3H), 1.95-1.85 (m, 1H); MS (ESI+) m/z 256 (M+H)$^+$.

Example 130D (2S,3R,4S,5S)-1-allyl 2-ethyl 3-(tert-butyl)-5-(2-isopropylphenyl)-4-nitropyrrolidine-1,2-dicarboxylate Core 13 (18.1 g, 49.9 mmol) was dissolved in toluene (125 mL), and saturated aqueous sodium bicarbonate (125 mL) was added. After cooling to approximately 10° C., the mixture was treated with allyl chloroformate (5.59 mL, 52.4 mmol), and the flask was removed from the bath. The reaction mixture was stirred overnight at room temperature. The phases were separated, and the aqueous layer was extracted with additional methyl tert-butyl ether. The combined organics were washed twice with water, dried over Na$_2$SO$_4$, filtered and concentrated in vacuo. The title compound thus obtained (22 g, 99% yield) was used directly in the next reaction without further purification. $^1$H NMR (400 MHz, DMSO-d$_6$) δ ppm 7.86 (dd, J=7.9, 1.2 Hz, 1H), 7.24-7.15 (m, 2H), 7.05 (ddd, J=8.3, 6.5, 2.1 Hz, 1H), 5.76-5.60 (m, 2H), 5.53 (dd, J=8.9, 3.6 Hz, 1H), 5.06-4.93 (m, 2H), 4.55 (d, J=4.3 Hz, 1H), 4.41 (dt, J=5.2, 1.6 Hz, 2H), 4.32-4.22 (m, 2H), 3.24 (hept, J=6.7 Hz, 1H), 3.13-3.06 (m, 1H), 1.36-1.22 (m, 6H), 1.19 (dd, J=6.6, 0.8 Hz, 3H), 1.03 (s, 9H); MS (ESI$^+$) m/z 447.0 (M+H)$^+$.

Example 130E (2S,3R,5S)-1-allyl 2-ethyl 3-(tert-butyl)-5-(2-isopropylphenyl)-4-oxopyrrolidine-1,2-dicarboxylate The title compound was prepared according to the procedure of Example 17B, substituting Example 130D for Example 17A. $^1$H NMR (400 MHz, DMSO-d$_6$) δ ppm 7.70 (m, 1H), 7.31 (m, 1H), 7.19 (m, 1H), 7.09 (m, 1H), 5.75-5.60 (m, 1H), 5.35 (s, 1H), 5.09-4.92 (m, 2H), 4.63 (d, J=5.5 Hz, 1H), 4.45 (m, 2H), 4.23 (m, 2H), 3.32 (m, 1H), 2.65 (m, 1H), 1.33-1.14 (m, 9H), 1.10-0.97 (m, 9H); MS (ESI$^+$) m/z 415.8 (M+H)$^+$.

Example 130F (2S,3R,4S,5S)-1-allyl 2-ethyl 3-(tert-butyl)-4-hydroxy-5-(2-isopropylphenyl)pyrrolidine-1,2-dicarboxylate The title compound was prepared according to the procedure of Example 129C, substituting Example 130E for Example 129B. $^1$H NMR (400 MHz, DMSO-d$_6$) δ ppm 7.90 (dd, J=7.8, 1.5 Hz, 1H), 7.24-7.00 (m, 3H), 5.72-5.52 (m, 1H), 5.22 (d, J=6.6 Hz, 1H), 5.03-4.91 (m, 2H), 4.44-4.27 (m, 4H), 4.18 (m, 2H), 3.72 (m, 1H), 3.20 (m, 1H), 2.29 (t, J=4.2 Hz, 1H), 1.29-1.16 (m, 9H), 1.04 (s, 1H), 1.00 (s, 9H); MS (APCI$^+$) m/z 418.3 (M+H)$^+$.

Example 130G (2S,3R,4S,5S)-1-allyl 2-ethyl 3-(tert-butyl)-4-((5-cyclobutyl-2-methoxypyridin-3-yl)methoxy)-5-(2-isopropylphenyl)pyrrolidine-1,2-dicarboxylate The title compound was prepared according to the procedure of Example 100E, substituting Example 130C for Example 100D and substituting Example 130F for Example 100C. $^1$H NMR (400 MHz, DMSO-d$_6$) δ ppm 7.94 (d, J=7.9 Hz, 1H), 7.75 (d, J=2.5 Hz, 1H), 7.25-7.08 (m, 2H), 7.03 (t, J=7.6 Hz, 1H), 6.86 (d, J=2.4 Hz, 1H), 5.65 (m, 1H), 5.30 (d, J=5.7 Hz, 1H), 5.05-4.88 (m, 2H), 4.47 (d, J=2.2 Hz, 1H), 4.38 (m, 2H), 4.24-4.02 (m, 4H), 3.77 (m, 1H), 3.73 (s, 3H), 3.42-3.13 (m, 2H), 2.50 (m, 1H), 2.35-2.14 (m, 2H), 2.05-1.78 (m, 4H), 1.22 (d, J=6.8 Hz, 3H), 1.18 (d, J=6.8 Hz, 3H), 1.15 (t, J=7.1 Hz, 3H), 1.02 (s, 9H); MS (ESI$^+$) m/z 593.3 (M+H)$^+$.

Example 130H (2S,3R,4S,5S)-ethyl 3-(tert-butyl)-4-((5-cyclobutyl-2-methoxypyridin-3-yl)methoxy)-5-(2-isopropylphenyl)pyrrolidine-2-carboxylate The title compound was prepared according to the procedure for Example 129H, substituting Example 130G for Example 129G. The crude product was taken directly into the next reaction without further purification. MS (ESI$^+$) m/z 509.4 (M+H)$^+$.

Example 130I (2S,3R,4S,5S)-ethyl 3-(tert-butyl)-4-((5-cyclobutyl-2-methoxypyridin-3-yl)methoxy)-5-(2-isopropylphenyl)-1-((S)-tetrahydrofuran-2-carbonyl)pyrrolidine-2-carboxylate The title compound was prepared according to the procedure of Example 98A, substituting Example 13 OH for (2S,3R,4S,5S)-ethyl 3-(tert-butyl)-5-(2-isopropylphenyl)-4-((2-methoxy-5-(trifluoromethyl)pyridin-3-yl)methoxy)pyrrolidine-2-carboxylate (Example 96E). The crude product was taken directly into the next reaction without further purification. MS (APCI$^+$) m/z 607.7 (M+H)$^+$.

Example 130J (2S,3R,4S,5S)-3-tert-butyl-4-[(5-cyclobutyl-2-methoxypyridin-3-yl)methoxy]-1-[(2S)-oxolane-2-carbonyl]-5-[2-(propan-2-yl)phenyl]pyrrolidine-2-carboxylic acid The title compound was prepared according to the procedure of Example 98B, substituting Example 130I for Example 98A. $^1$H NMR (400 MHz, DMSO-d$_6$) δ ppm 8.04 (d, J=7.8 Hz, 1H), 7.74 (d, J=2.4 Hz, 1H), 7.21 (dd, J=18.1, 7.4 Hz, 2H), 7.06 (t, J=7.5 Hz, 1H), 6.83 (s, 1H), 5.64 (m, 1H), 4.68 (m, 1H), 4.26-4.16 (m, 2H), 4.06 (m, 1H), 3.83-3.64 (m, 5H), 3.59 (m, 1H), 3.35-3.18 (m, 2H), 2.52 (m, 1H), 2.23 (m, 2H), 2.02-1.74 (m, 6H), 1.62 (m, 2H), 1.25 (d, J=6.7 Hz, 3H), 1.15 (d, J=6.8 Hz, 3H), 1.02 (s, 9H); MS (ESI$^+$) m/z 579.2 (M+H)$^+$.

Example 131

(2S,3R,4S,5S)-3-tert-butyl-4-[(2-methoxyquinolin-3-yl)methoxy]-1-[(2R)-oxane-2-carbonyl]-5-[2-(propan-2-yl)phenyl]pyrrolidine-2-carboxylic acid

Example 131A ethyl (2S,3R,4S,5S)-3-(tert-butyl)-5-(2-isopropylphenyl)-4-((2-methoxyquinolin-3-yl)methoxy)-1-((R)-tetrahydro-2H-pyran-2-carbonyl)pyrrolidine-2-carboxylate Tetrahydropyran-2-carboxylic acid (57.8 mg, 0.444 mmol) was dissolved in dichloromethane (2 mL). Oxalyl chloride (2M in dichloromethane, 300 μL, 0.60 mmol) was added followed by dimethylformamide (25 μL). The reaction was stirred at room temperature for 3 hours, at which point it was concentrated, redissolved in dichloromethane (1 mL), and concentrated again. The residue was taken up in dichloromethane (3×1 mL) and added to a solution of Example 116B (107.9 mg, 0.214 mmol) and triethylamine (100 μL, 0.717 mmol) in dichloromethane (3 mL). The reaction mixture was stirred at ambient temperature for 17 hours. After this time, the mixture was diluted with dichloromethane (100 mL) and washed twice with saturated aqueous NaHCO$_3$ and once with brine. The organic layer was dried over Na$_2$SO$_4$, filtered, and concentrated. The residue was purified by reverse-phase preparative HPLC on a Waters Nova-Pak® HR C18 6 μm 60 Å Prep-Pak® cartridge column (40 mm×100 mm) and eluting with a gradient of 10% to 100% acetonitrile in 10 mM aqueous ammonium acetate over 12 minutes, at a flow rate of 70 mL/minute. The title compound was the first eluting diastereomer (58.8 mg, 45%). $^1$H NMR (400 MHz, DMSO-d$_6$, 120° C.) δ ppm 7.86 (s, 1H), 7.66 (dq, J=8.4, 0.9 Hz, 1H), 7.53 (ddd, J=8.4, 6.9, 1.5 Hz, 1H), 7.48 (dd, J=8.0, 1.5 Hz, 1H), 7.33 (ddd, J=8.1, 6.9, 1.3 Hz, 1H), 7.21 (d, J=7.6 Hz, 2H), 7.09 (d, J=16.6 Hz, 2H), 5.41 (d, J=5.6 Hz, 1H), 4.97 (s, 1H), 4.35 (dd, J=14.0, 1.3 Hz, 1H), 4.23 (d, J=5.6 Hz, 1H), 4.14 (q, J=7.1 Hz, 2H), 3.98-3.87 (m, 4H), 3.82 (s, 1H), 3.24 (h, J=6.8 Hz, 1H), 2.69-2.58 (m, 1H), 2.50 (s, 1H), 1.80 (s, 1H), 1.66-1.33 (m, 5H), 1.26 (d, J=6.7 Hz, 3H), 1.18-1.09 (m, 6H), 1.05 (s, 9H); MS (ESI+) m/z 617 (M+H)$^+$.

Example 131B (2S,3R,4S,5S)-3-tert-butyl-4-[(2-methoxyquinolin-3-yl)methoxy]-1-[(2R)-oxane-2-carbonyl]-5-[2-(propan-2-yl)phenyl]pyrrolidine-2-carboxylic acid Example 131A (55.8 mg, 0.090 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction was quenched by the addition of 1M aqueous HCl (0.5 mL), concentrated and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (21.1 mg, 33%) as the TFA salt. $^1$H NMR (400 MHz, DMSO-d$_6$, 120° C.) δ ppm 7.91 (s, 1H), 7.65 (d, J=8.3 Hz, 1H), 7.57-7.48 (m, 2H), 7.33 (ddd, J=7.9, 6.8, 1.2 Hz, 1H), 7.20 (q, J=8.0 Hz, 2H), 7.14 (s, 1H), 7.04 (t, J=7.4 Hz, 1H), 5.41 (d, J=5.7 Hz, 1H), 4.94 (s, 1H), 4.37 (dd, J=14.2, 1.3 Hz, 1H), 4.22 (d, J=5.7 Hz, 1H), 3.98-3.89 (m, 6H), 3.84 (s, 1H), 3.24 (hept, J=6.7 Hz, 1H), 2.69 (s, 1H), 1.80 (s, 1H), 1.68-1.33 (m, 5H), 1.27 (d, J=6.7 Hz, 3H), 1.13 (d, J=6.8 Hz, 3H), 1.05 (s, 9H); MS (ESI+) m/z 589 (M+H)$^+$.

Example 132

(2S,3R,4S,5S)-3-tert-butyl-4-[(2-methoxyquinolin-3-yl)methoxy]-1-[(2S)-oxane-2-carbonyl]-5-[2-(propan-2-yl)phenyl]pyrrolidine-2-carboxylic acid

Example 132A ethyl (2S,3R,4S,5S)-3-(tert-butyl)-5-(2-isopropylphenyl)-4-((2-methoxyquinolin-3-yl)methoxy)-1-((S)-tetrahydro-2H-pyran-2-carbonyl)pyrrolidine-2-carboxylate Tetrahydropyran-2-carboxylic acid (57.8 mg, 0.444 mmol) was dissolved in dichloromethane (2 mL). Oxalyl chloride (2M in dichloromethane, 300 μL, 0.60 mmol) was added followed by dimethylformamide (25 μL). The reaction was stirred at room temperature for 3 hours, at which point it was concentrated, redissolved in dichloromethane (1 mL), and concentrated again. The residue was taken up in dichloromethane (3×1 mL) and added to a solution of Example 116B (107.9 mg, 0.214 mmol) and triethylamine (100 μL, 0.717 mmol) in dichloromethane (3 mL). The reaction was stirred at ambient temperature for 17 hours. After this time, the mixture was diluted with dichloromethane (100 mL) and washed twice with saturated aqueous NaHCO$_3$ and once with brine. The organic layer was dried over Na$_2$SO$_4$, filtered and concentrated. The residue was purified by reverse-phase preparative HPLC on a Waters Nova-Pak® HR C18 6 μm 60 Å Prep-Pak® cartridge column (40 mm×100 mm), eluting with a gradient of 10% to 100% acetonitrile in 10 mM aqueous ammonium acetate over 12 minutes, at a flow rate of 70 mL/minute. The title compound was the second eluting diastereomer (58.2 mg, 44%). $^1$H NMR (400 MHz, DMSO-$d_6$, 120° C.) δ ppm 8.06 (d, J=7.9 Hz, 1H), 7.66 (d, J=8.3 Hz, 1H), 7.58-7.45 (m, 2H), 7.37-7.21 (m, 3H), 7.13 (s, 2H), 5.64 (s, 1H), 4.75 (d, J=1.8 Hz, 1H), 4.36 (d, J=13.9 Hz, 1H), 4.26 (d, J=5.7 Hz, 1H), 4.09 (q, J=7.1 Hz, 2H), 3.97-3.88 (m, 4H), 3.78-3.71 (m, 1H), 3.25 (hept, J=6.9 Hz, 1H), 3.18-2.98 (m, 2H), 2.50 (d, J=1.9 Hz, 1H), 1.73-1.49 (m, 2H), 1.48-1.23 (m, 7H), 1.17-1.08 (m, 6H), 1.05 (s, 9H); MS (ESI+) m/z 617 (M+H)$^+$.

Example 132B (2S,3R,4S,5S)-3-tert-butyl-4-[(2-methoxyquinolin-3-yl)methoxy]-1-[(2S)-oxane-2-carbonyl]-5-[2-(propan-2-yl)phenyl]pyrrolidine-2-carboxylic acid Example 132A (55.2 mg, 0.089 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction was quenched by the addition of 1M aqueous HCl (0.5 mL), concentrated, and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (33.1 mg, 53%) as the TFA salt. $^1$H NMR (400 MHz, DMSO-$d_6$, 120° C.) δ ppm 8.11 (d, J=7.9 Hz, 1H), 7.66 (d, J=8.3 Hz, 1H), 7.57-7.47 (m, 2H), 7.33 (ddd, J=8.0, 7.0, 1.3 Hz, 1H), 7.26 (d, J=8.1 Hz, 2H), 7.14 (d, J=15.2 Hz, 2H), 5.65 (s, 1H), 4.73 (d, J=1.7 Hz, 1H), 4.39 (d, J=14.1 Hz, 1H), 4.26 (d, J=5.8 Hz, 1H), 3.94 (dd, J=14.1, 1.4 Hz, 1H), 3.91 (s, 3H), 3.76 (d, J=11.3 Hz, 1H), 3.64 (s, 1H), 3.24 (h, J=6.9 Hz, 1H), 3.10 (s, 1H), 2.57 (d, J=1.6 Hz, 1H), 1.74-1.52 (m, 2H), 1.37 (d, J=10.2 Hz, 4H), 1.30 (d, J=6.7 Hz, 3H), 1.10 (d, J=6.8 Hz, 3H), 1.05 (s, 9H); MS (ESI+) m/z 589 (M+H)$^+$.

Example 133

(2S,3R,4S,5S)-3-tert-butyl-4-[(5-cyclobutyl-2-methoxypyridin-3-yl)methoxy]-1-[(2S)-oxolane-2-carbonyl]-5-{2-[(propan-2-yl)oxy]pyridin-3-yl}pyrrolidine-2-carboxylic acid Example 133A (2S,3R,4S,5S)-1-allyl 2-ethyl 3-(tert-butyl)-5-(2-methoxypyridin-3-yl)-4-nitropyrrolidine-1,2-dicarboxylate To a mixture of Core 12 (5.0 g, 14.23 mmol) in toluene (30 mL) and saturated aqueous NaHCO$_3$ (30 mL) was added allyl carbonochloridate (3.78 mL, 35.6 mmol) dropwise at ambient temperature and the mixture was stirred for 1 hour. Ethyl acetate (30 mL) was added. The organic layer was washed with brine, dried over MgSO$_4$, filtered, and concentrated. Purification of the residue via chromatography on a 80 g silica gel cartridge, eluting with ethyl acetate in heptanes at 0-40% gradient provided the title compound (5.4 g, 87% yield). LC/MS (APCI+) m/z 436.41 (M+H)$^+$.

Example 133B (2S,3R,5S)-1-allyl 2-ethyl 3-(tert-butyl)-5-(2-hydroxypyridin-3-yl)-4-oxopyrrolidine-1,2-dicarboxylate A solution of CrCl$_2$ was prepared by dissolving pyridinium dichromate (10.80 g, 28.7 mmol) in aqueous hydrochloric acid, (6 M, 207 mL) and adding Zn (20.27 g, 310 mmol) in portions over 20 minutes while cooling in an ice bath, maintaining the internal temperature below 35° C. The resulting suspension was stirred at room temperature for 30 minutes after removing from the ice bath, leaving a brilliant blue solution. In a separate flask, Example 133A (5 g, 11.48 mmol) was dissolved in ethanol (103 mL) and the resulting solution was heated to 75° C. The CrCl$_2$ solution was added via addition funnel over 20 minutes to the solution of the starting material, and the temperature was increased to 85° C. after the addition was complete. Heating was continued for 16 hours at the same temperature, at which point the intermediate oxime had been fully consumed. A mixture of the title compound and (2S,3R,5S)-1-((allyloxy)carbonyl)-3-(tert-butyl)-5-(2-hydroxypyridin-3-yl)-4-oxopyrrolidine-2-carboxylic acid was produced at this point. The reaction mixture was cooled to ambient temperature and poured into a separatory funnel. The product mixture was extracted into 3×100 mL of dichloromethane and the combined extracts were dried over sodium sulfate, filtered and concentrated to provide a crude material (4.5 g), which was re-esterified according to the following procedure: The crude material (4.5 g) was dissolved in a solution of HCl-ethanol prepared by addition of acetyl chloride (4.08 mL, 57.4 mmol) to ethanol (45.9 mL) while cooling in an ice-water bath. The resulting yellow solution was heated to 45° C. for 3 hours, at which point complete re-esterification had occurred. The flask was cooled to ambient temperature, concentrated in vacuo and partitioned between saturated aqueous sodium bicarbonate and ethyl acetate. The combined organic extracts were washed with brine, dried over sodium sulfate, filtered, and concentrated to provide the title compound (3.5 g), which was used without additional purification. $^1$H NMR (400 MHz, DMSO-$d_6$) δ ppm 11.23 (br s, 1H), 7.52 (dd, J=6.7, 2.1 Hz, 1H), 7.30-7.08 (m, 2H), 6.14 (t, J=6.6 Hz, 1H), 5.86 (ddt, J=17.3, 10.5, 5.3 Hz, 1H), 5.26-5.09 (m, 2H), 4.77-4.51 (m, 4H), 4.06 (q, J=7.1 Hz, 2H), 1.13 (t, J=7.1 Hz, 3H), 1.02 (s, 9H); MS (ESI+) m/z 391.2 (M+H)$^+$.

Example 133C (2S,3R,5S)-1-allyl 2-ethyl 3-(tert-butyl)-5-(2-isopropoxypyridin-3-yl)-4-oxopyrrolidine-1,2-dicarboxylate Example 133B (3.4 g, 8.71 mmol) was dissolved in 35 mL of chloroform. Silver carbonate (4.80 g, 17.42 mmol) was added, followed by 2-iodopropane (2.61 mL, 26.1 mmol) and the reaction mixture was heated to 60° C. for 3.5 hours. The reaction mixture was cooled to ambient temperature, diluted with methyl tert-butyl ether (50 mL), filtered through diatomaceous earth, and concentrated to provide 3.8 g of the title compound. $^1$H NMR (400 MHz, DMSO-$d_6$) δ ppm 8.04 (dd, J=4.9, 1.9 Hz, 1H), 7.86 (dd, J=7.4, 1.9 Hz, 1H), 6.88 (dd, J=7.4, 4.9 Hz, 1H), 5.84-5.69 (m, 1H), 5.28-5.19 (m, 1H), 5.17-5.06 (m, 3H), 4.64 (d, J=4.2 Hz, 1H), 4.49 (dt, J=5.2, 1.6 Hz, 2H), 4.18 (qd, J=7.1, 3.0 Hz, 2H), 2.67 (dd, J=4.3, 0.9 Hz, 1H), 1.29 (d, J=6.1 Hz, 3H), 1.22 (d, J=6.1 Hz, 3H), 1.20 (t, J=6.7 Hz, 3H), 1.06 (s, 9H); MS (ESI+) m/z 433.3 (M+H)$^+$.

Example 133D (2S,3R,4S,5S)-1-allyl 2-ethyl 3-(tert-butyl)-4-hydroxy-5-(2-isopropoxypyridin-3-yl)pyrrolidine-1,2-dicarboxylate and Example 133E (2S,3R,4R,5S)-1-allyl 2-ethyl 3-(tert-butyl)-4-hydroxy-5-(2-isopropoxypyridin-3-yl)pyrrolidine-1,2-dicarboxylate Example 133C (3.77 g, 8.72 mmol) was dissolved in ethanol (43.6 mL) and the solution was cooled to ~−10° C. before addition of sodium borohydride (0.429 g, 11.33 mmol) in small portions over 2 minutes. After stirring for 45 minutes at the same temperature, TLC indicated complete conversion to the desired mixture of alcohols. Acetone (5 mL) was added slowly due to delayed exotherms to quench the excess reducing agent, and the reaction was warmed to ambient temperature. The mixture was concentrated in vacuo and diluted with a mixture of methyl tert-butyl ether and saturated sodium bicarbonate (50 mL each). The mixture was stirred for 30 minutes at ambient temperature and the layers were separated. The product was extracted into methyl tert-butyl ether (2×25 mL) and the combined organic extracts were washed with brine, dried over sodium sulfate, filtered and concentrated to provide the crude material. The crude material was purified via flash chromatography, eluting on an 80 g silica gel column with 0:100 to 10:90 ethyl acetate:heptanes over 5 minutes, isocratic 10:90 ethyl acetate:heptanes until complete elution of the first diastereomer ((2S,3R,4R,5S)-1-allyl 2-ethyl 3-(tert-butyl)-4-hydroxy-5-(2-isopropoxypyridin-3-yl)pyrrolidine-1,2-dicarboxylate, Example 133E) which was isolated as a mixture of compounds, and the gradient was increased to 20:80 ethyl acetate:heptanes over 10 minutes and maintained at 20:80 ethyl acetate:heptanes until complete elution of the second diastereomer (2S,3R,4S,5S)-1-allyl 2-ethyl 3-(tert-butyl)-4-hydroxy-5-(2-isopropoxypyridin-3-yl)pyrrolidine-1,2-dicarboxylate (1.79 g, Example 133D). For Example 133D (second eluent)$^1$H NMR (400 MHz, DMSO-d$_6$) δ ppm 8.06-7.82 (m, 2H), 6.83 (dd, J=7.4, 4.9 Hz, 1H), 5.71 (ddt, J=18.8, 10.2, 5.1 Hz, 1H), 5.27 (p, J=6.1 Hz, 1H), 5.13-4.89 (m, 2H), 4.46-4.27 (m, 2H), 4.16 (q, J=7.1 Hz, 2H), 4.00 (d, J=6.6 Hz, 1H), 2.26 (t, J=2.7 Hz, 1H), 1.32 (d, J=6.1 Hz, 3H), 1.29 (d, J=6.2 Hz, 3H), 1.23 (t, J=7.1 Hz, 3H), 1.11 (s, 3H), 0.99 (s, 9H); MS (ESI+) m/z 435.3 (M+H). For Example 133E (first eluting,) MS (ESI+) m/z 435.3 (M+H)$^+$.

Example 133F (2S,3R,4S,5S)-1-allyl 2-ethyl 3-(tert-butyl)-4-((5-cyclobutyl-2-methoxypyridin-3-yl)methoxy)-5-(2-isopropoxypyridin-3-yl)pyrrolidine-1,2-dicarboxylate Example 133D (1.79 g, 4.12 mmol) was dissolved in 20 mL of dry dimethylformamide and the solution was cooled to <5° C. before dropwise addition of potassium tert-butoxide (1 M in tetrahydrofuran, 4.53 mL, 4.53 mmol). After the addition was completed, 3-(bromomethyl)-5-cyclobutyl-2-methoxypyridine (1.266 g, 4.94 mmol) was added dropwise as a solution in 1 mL tetrahydrofuran and the reaction was stirred at the same temperature for 5 minutes. The reaction was quenched with saturated aqueous ammonium chloride (10 mL) and extracted with methyl tert-butyl ether (3×10 mL). The combined organic extracts were washed with water (20 mL) and brine (20 mL). The organics were concentrated in vacuo and purified via flash chromatography, eluting with 0:100 to 30:70 ethyl acetate:heptanes to provide 1.79 g of the title compound. $^1$H NMR (400 MHz, DMSO-d$_6$) δ ppm 8.03 (ddd, J=7.4, 1.9, 0.8 Hz, 1H), 7.95 (dd, J=5.0, 2.0 Hz, 1H), 7.77 (dd, J=2.4, 0.8 Hz, 1H), 6.87-6.79 (m, 2H), 5.82-5.66 (m, 1H), 5.30-5.18 (m, 2H), 5.13-5.00 (m, 2H), 4.49 (d, J=2.4 Hz, 1H), 4.32-4.26 (m, 2H), 4.11-4.00 (m, 2H), 3.99-3.92 (m, 1H), 3.76 (s, 3H), 3.36-3.30 (m, 1H), 2.47-1.77 (m, 6H), 1.30 (d, J=6.2 Hz, 3H), 1.23 (d, J=6.1 Hz, 3H), 1.18 (t, J=7.1 Hz, 3H), 1.12 (t, J=7.1 Hz, 3H), 1.02 (s, 9H); MS (ESI$^+$) m/z 610.5 (M+H)$^+$.

Example 133G (2S,3R,4S,5S)-ethyl 3-(tert-butyl)-4-((5-cyclobutyl-2-methoxypyridin-3-yl)methoxy)-5-(2-isopropoxypyridin-3-yl)pyrrolidine-2-carboxylate Example 133F (1.78 g, 2.92 mmol) was dissolved in a mixture of dichloromethane (14.60 mL) and ethyl acetate (14.60 mL). 1,3-Dimethylpyrimidine-2,4,6(1H,3H,5H)-trione (0.912 g, 5.84 mmol) was added, followed by tetrakis (triphenylphosphine)palladium (0.034 g, 0.029 mmol) and the reaction mixture was stirred at ambient temperature for 10 minutes, at which point complete conversion was achieved. The mixture was diluted with methyl tert-butyl ether (50 mL), 10% sodium carbonate (50 mL) was added, and the mixture was stirred for 10 minutes. The layers were separated, the aqueous layer was extracted with methyl tert-butyl ether (3×25 mL), and the combined organic extracts were washed with brine (50 mL). The organics were dried over sodium sulfate, filtered, and concentrated to provide the title compound, which was used without additional purification. MS (ESI+) m/z 526.5 (M+H)$^+$.

Example 133H (2S,3R,4S,5S)-3-tert-butyl-4-[(5-cyclobutyl-2-methoxypyridin-3-yl)methoxy]-1-[(2S)-oxolane-2-carbonyl]-5-{2-[(propan-2-yl)oxy]pyridin-3-yl}pyrrolidine-2-carboxylic acid The title compound was prepared according to the procedure described in Example 121G, substituting (2S,3R,4S,5S)-ethyl 3-(tert-butyl)-4-((5-cyclobutyl-2-methoxypyridin-3-yl)methoxy)-5-(2-isopropoxypyridin-3-yl)pyrrolidine-2-carboxylate (Example 133G) for Example 121F. $^1$H NMR (400 MHz, DMSO-d$_6$) δ ppm 8.42 (s, 1H), 7.95 (s, 1H), 7.76 (d, J=2.4 Hz, 1H), 6.79 (d, J=14.1 Hz, 2H), 4.45 (s, 1H), 4.32 (d, J=13.2 Hz, 1H), 4.22 (s, 1H), 4.00 (d, J=13.5 Hz, 1H), 3.78 (s, 1H), 3.77 (d, J=1.0 Hz, 3H), 3.66 (s, 1H), 3.32 (q, J=8.5 Hz, 1H), 2.63 (s, 2H), 2.27-2.17 (m, 2H), 2.00-1.79 (m, 6H), 1.28 (d, J=6.0 Hz, 3H), 1.18 (d, J=6.1 Hz, 3H), 1.05-0.93 (m, 9H); MS (ESI+) m/z 596 (M+1)$^+$.

Example 134

(2S,3R,4S,5S)-3-tert-butyl-4-[(5-cyclobutyl-2-methoxypyridin-3-yl)methoxy]-1-(oxane-4-carbonyl)-5-{2-[(propan-2-yl)oxy]pyridin-3-yl}pyrrolidine-2-carboxylic acid The title compound was prepared according to the procedure described in Example 121G, substituting Example 133G for Example 121F, and tetrahydro-2H-pyran-4-carboxylic acid for (S)-tetrahydrofuran-2-carboxylic acid. $^1$H NMR (400 MHz, DMSO-$d_6$) δ ppm 8.19 (s, 1H), 7.97 (s, 1H), 7.77 (d, J=2.3 Hz, 1H), 6.82 (s, 2H), 5.36 (s, 1H), 5.26 (p, J=6.1 Hz, 1H), 4.53 (d, J=2.8 Hz, 1H), 4.30 (d, J=13.1 Hz, 1H), 4.25 (dd, J=6.3, 2.1 Hz, 1H), 3.98 (d, J=13.2 Hz, 1H), 3.82 (dt, J=11.2, 3.5 Hz, 1H), 3.76 (s, 3H), 3.32 (p, J=8.4 Hz, 2H), 2.56 (s, 1H), 2.35-2.17 (m, 3H), 2.11-1.79 (m, 6H), 1.57 (s, 4H), 1.32 (d, J=6.1 Hz, 3H), 1.22 (d, J=6.1 Hz, 3H), 0.99 (s, 9H); MS (ESI+) m/z 610.2 (M+H)$^+$.

Example 135

(2S,3R,4S,5S)-3-tert-butyl-4-[(5-cyclobutyl-2-methoxypyridin-3-yl)methoxy]-1-[(2R)-oxane-2-carbonyl]-5-{2-[(propan-2-yl)oxy]pyridin-3-yl}pyrrolidine-2-carboxylic acid Example 135A (2S,3R,4S,5S)-ethyl 3-(tert-butyl)-4-((5-cyclobutyl-2-methoxypyridin-3-yl)methoxy)-5-(2-isopropoxypyridin-3-yl)-1-((R)-tetrahydro-2H-pyran-2-carbonyl)pyrrolidine-2-carboxylate and Example 135B (2S,3R,4S,5S)-ethyl 3-(tert-butyl)-4-((5-cyclobutyl-2-methoxypyridin-3-yl)methoxy)-5-(2-isopropoxypyridin-3-yl)-1-((S)-tetrahydro-2H-pyran-2-carbonyl)pyrrolidine-2-carboxylate To tetrahydro-2H-pyran-2-carboxylic acid (CAS#51673-83-7) (89 mg, 0.685 mmol) and a drop of dimethylformamide in dichloromethane (6 mL) was added oxalyl dichloride (130 mg, 1.027 mmol, 0.5 mL, 2M in dichloromethane). The mixture was stirred for 30 minutes. The solvent was removed under pressure and fresh dichloromethane was added and removed again. The residue was dissolved in dichloromethane (1 mL) and added dropwise to the solution of Example 133G (180 mg, 0.342 mmol) and triethylamine (0.191 mL, 1.370 mmol) in dichloromethane (6 mL) in an ice-bath. The mixture was stirred at 0° C. for 30 minutes, and allowed to warm to ambient temperature. Dichloromethane and saturated aqueous NH$_4$Cl were added and the organic layer was washed with brine, dried over MgSO$_4$, filtered, and concentrated. Purification of the residue by chromatography, eluting with ethyl acetate in heptanes at 0-40% gradient provided (2S,3R,4S,5S)-ethyl 3-(tert-butyl)-4-((5-cyclobutyl-2-methoxypyridin-3-yl)methoxy)-5-(2-isopropoxypyridin-3-yl)-1-((R)-tetrahydro-2H-pyran-2-carbonyl)pyrrolidine-2-carboxylate (Example 135A, 65 mg, 29.8% yield) as the first eluent. LC/MS (APCI+) m/z 638.8 (M+H)$^+$. (2S,3R,4S,5S)-ethyl 3-(tert-butyl)-4-((5-cyclobutyl-2-methoxypyridin-3-yl)methoxy)-5-(2-isopropoxypyridin-3-yl)-1-((S)-tetrahydro-2H-pyran-2-carbonyl)pyrrolidine-2-carboxylate (Example 135B, 50 mg, 22.89% yield) was obtained as the second eluent. LC/MS (APCI+) m/z 638.8 (M+H)$^+$.

Example 135C (2S,3R,4S,5S)-3-tert-butyl-4-[(5-cyclobutyl-2-methoxypyridin-3-yl)methoxy]-1-[(2R)-oxane-2-carbonyl]-5-{2-[(propan-2-yl)oxy]pyridin-3-yl}pyrrolidine-2-carboxylic acid The mixture of Example 135A (60 mg, 0.094 mmol) in methanol (1.5 mL) and 6M aqueous LiOH (0.5 mL) was stirred at 45° C. for overnight. LC/MS indicated conversion was finished. The mixture was adjusted to pH to 1~2 using 2N aqueous HCl and was purified by chromatography on a 12 g silica gel cartridge eluting with methanol in dichloromethane at 0-20% gradient to provide the title compound 41 mg (71.5% yield). $^1$H NMR (400 MHz, DMSO-$d_6$) δ ppm 7.93 (d, J=4.6 Hz, 2H), 7.76 (d, J=2.4 Hz, 1H), 6.79 (s, 2H), 5.24 (dd, J=12.9, 6.8 Hz, 2H), 4.94 (s, 1H), 4.30 (d, J=13.2 Hz, 1H), 4.24 (dd, J=6.0, 1.2 Hz, 1H), 3.94 (d, J=13.3 Hz, 3H), 3.76 (s, 3H), 3.31 (p, J=8.3 Hz, 1H), 2.86-2.81 (m, 1H), 2.58 (s, 1H), 2.22 (ddt, J=6.3, 4.9, 3.3 Hz, 2H), 2.04-1.85 (m, 4H), 1.86-1.74 (m, 2H), 1.49 (d, J=43.0 Hz, 4H), 1.31 (d, J=6.1 Hz, 3H), 1.20 (d, J=6.1 Hz, 3H), 1.00 (s, 9H); MS (ESI+) m/z 610.2 (M+H)$^+$.

Example 136

(2S,3R,4S,5S)-3-tert-butyl-4-[(5-cyclobutyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid (2S,3R,4S,5S)-ethyl 3-(tert-butyl)-4-((5-cyclobutyl-2-methoxypyridin-3-yl)methoxy)-5-(2-isopropoxypyridin-3-yl)-1-((S)-tetrahydro-2H-pyran-2-carbonyl)pyrrolidine-2-carboxylate (Example 135B, 45 mg, 0.071 mmol) dissolved in methanol (1.5 mL) and 6N aqueous NaOH (0.5 mL) was stirred at 45° C. for overnight. The mixture adjusted pH to 1~2 by 2N aqueous HCl and the mixture was purified by chromatography, eluting with methanol in CH$_2$Cl$_2$ at 0-20% gradient to yield title compound (33 mg, 0.054 mmol, 77% yield)$^1$H NMR (400 MHz, DMSO-$d_6$) δ ppm 8.35 (s, 1H), 7.96 (s, 1H), 7.76 (d, J=2.5 Hz, 1H), 6.82 (d, J=2.6 Hz, 2H), 5.65 (s, 1H), 5.24 (dq, J=11.6, 5.9 Hz, 1H), 4.56 (s, 1H), 4.30 (d, J=13.2 Hz, 1H), 4.21 (dd, J=6.5, 2.2 Hz, 1H), 3.98 (d, J=13.2 Hz, 1H), 3.85 (s, 1H), 3.80 (d, J=10.8 Hz, 1H), 3.76 (s, 3H), 3.33 (q, J=8.1 Hz, 2H), 2.52 (s, 1H), 2.25-2.21 (m, 1H), 1.96-1.79 (m, 5H), 1.74-1.34 (d, J=62.2 Hz, 6H), 1.32 (d, J=6.2 Hz, 3H), 1.19 (d, J=6.1 Hz, 3H), 0.98 (s, 9H); MS (ESI+) m/z 610.2 (M+1)$^+$.

Example 137

(2S,3R,4S,5S)-5-(2-bromophenyl)-3-tert-butyl-4-[(2-methoxyquinolin-3-yl)methoxy]-1-{[(propan-2-yl)oxy]carbonyl}pyrrolidine-2-carboxylic acid Example 137A 2-ethyl 1-isopropyl (2S,3R,4S,5S)-5-(2-bromophenyl)-3-(tert-butyl)-4-((2-methoxyquinolin-3-yl)methoxy)pyrrolidine-1,2-dicarboxylate Example 86C (72.2 mg, 0.158 mmol) and Example 106B (60.0 mg, 0.238 mmol) were dissolved in dimethylformamide (1.5 mL). The reaction was cooled to 0° C., then potassium tert-butoxide (1M in tetrahydrofuran, 0.20 mL, 0.20 mmol) was added dropwise and the reaction was stirred at ambient temperature for 1 hour. The reaction was quenched by the addition of 1M aqueous HCl (0.1 mL) and purified by silica gel chromatography (0% to 5% ethyl acetate in dichloromethane) to provide the title compound (43.6 mg, 37%). $^1$H NMR (400 MHz, DMSO-$d_6$, 120° C.) δ ppm 8.03 (dd, J=7.8, 1.7 Hz, 1H), 7.67 (d, J=8.3 Hz, 1H), 7.55 (td, J=8.4, 1.7 Hz, 2H), 7.47 (dd, J=8.1, 1.2 Hz, 1H), 7.39-7.23 (m, 3H), 7.14 (td, J=7.6, 1.8 Hz, 1H), 5.31 (d, J=5.7 Hz, 1H), 4.67 (hept, J=6.2 Hz, 1H), 4.48 (d, J=2.1 Hz, 1H), 4.43-4.34 (m, 2H), 4.13 (qd, J=7.1, 0.8 Hz, 2H), 4.06 (d, J=13.4 Hz, 1H), 3.92 (d, J=0.8 Hz, 3H), 2.56-2.49 (m, 1H), 1.16 (td, J=7.1, 0.8 Hz, 3H), 1.07 (d, J=6.2 Hz, 3H), 1.03 (d, J=0.8 Hz, 9H), 0.90 (d, J=6.2 Hz, 3H); MS (ESI+) m/z 627 & 629 (M+H)+.

Example 137B (2S,3R,4S,5S)-5-(2-bromophenyl)-3-tert-butyl-4-[(2-methoxyquinolin-3-yl)methoxy]-1-{[(propan-2-yl)oxy]carbonyl}pyrrolidine-2-carboxylic acid Example 137A (40.6 mg, 0.055 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction was quenched by the addition of 1M aqueous HCl (0.5 mL) and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (22.2 mg, 57%) as the TFA salt. $^1$H NMR (400 MHz, DMSO-d$_6$, 120° C.) δ ppm 8.10 (dd, J=7.9, 1.7 Hz, 1H), 7.67 (d, J=8.1 Hz, 1H), 7.55 (t, J=7.5 Hz, 2H), 7.47 (d, J=7.9 Hz, 1H), 7.35 (t, J=7.5 Hz, 1H), 7.31-7.25 (m, 2H), 7.16-7.09 (m, 1H), 5.31 (d, J=5.8 Hz, 1H), 4.66 (hept, J=6.3 Hz, 1H), 4.44 (d, J=2.0 Hz, 1H), 4.42-4.35 (m, 2H), 4.06 (dd, J=13.8, 1.2 Hz, 1H), 3.92 (s, 3H), 2.57 (t, J=1.4 Hz, 1H), 1.07 (d, J=6.2 Hz, 3H), 1.03 (s, 9H), 0.90 (d, J=6.2 Hz, 3H); MS (ESI+) m/z 599 & 601 (M+H)+.

Example 138

(2S,3R,4S,5S)-5-(2-bromophenyl)-3-tert-butyl-4-[(5-cyclobutyl-2-methoxypyridin-3-yl)methoxy]-1-{[(propan-2-yl)oxy]carbonyl}pyrrolidine-2-carboxylic acid Example 138A 2-ethyl 1-isopropyl (2S,3R,4S,5S)-5-(2-bromophenyl)-3-(tert-butyl)-4-((5-cyclobutyl-2-methoxypyridin-3-yl)methoxy)pyrrolidine-1,2-dicarboxylate Example 86C (81.3 mg, 0.178 mmol) and 3-(bromomethyl)-5-cyclobutyl-2-methoxypyridine (70.6 mg, 0.276 mmol) were dissolved in dimethylformamide (1.5 mL). The reaction was cooled to 0° C., potassium tert-butoxide (1M in tetrahydrofuran, 0.20 mL, 0.20 mmol) was added dropwise, and the reaction mixture was stirred at ambient temperature for 1 hour. The reaction was quenched by the addition of 1M aqueous HCl (0.1 mL) and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (44.5 mg, 34%) as the TFA salt. $^1$H NMR (400 MHz, DMSO-d$_6$, 120° C.) δ ppm 7.99 (dd, J=7.9, 1.8 Hz, 1H), 7.77 (d, J=2.4 Hz, 1H), 7.47 (dd, J=8.0, 1.3 Hz, 1H), 7.25 (td, J=7.6, 1.3 Hz, 1H), 7.11 (td, J=7.6, 1.8 Hz, 1H), 6.87 (d, J=2.4 Hz, 1H), 5.27 (d, J=5.7 Hz, 1H), 4.65 (hept, J=6.2 Hz, 1H), 4.45 (d, J=2.1 Hz, 1H), 4.33 (dd, J=5.7, 1.3 Hz, 1H), 4.22 (d, J=13.0 Hz, 1H), 4.11 (qd, J=7.0, 1.0 Hz, 2H), 3.91 (dt, J=13.0, 0.8 Hz, 1H), 3.75 (s, 3H), 3.38-3.28 (m, 1H), 2.48 (s, 1H), 2.25 (dddd, J=12.1, 8.6, 4.9, 2.5 Hz, 2H), 2.05-1.79 (m, 4H), 1.15 (t, J=7.0 Hz, 3H), 1.06 (d, J=6.2 Hz, 3H), 1.01 (s, 9H), 0.89 (d, J=6.2 Hz, 3H); MS (ESI+) m/z 631 & 633 (M+H)+.

Example 138B (2S,3R,4S,5S)-5-(2-bromophenyl)-3-tert-butyl-4-[(5-cyclobutyl-2-methoxypyridin-3-yl)methoxy]-1-{[(propan-2-yl)oxy]carbonyl}pyrrolidine-2-carboxylic acid Example 138A (41.5 mg, 0.056 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction mixture was quenched by the addition of 1M aqueous HCl (0.5 mL) and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (28.0 mg, 70%) as the TFA salt. $^1$H NMR (400 MHz, DMSO-d$_6$, 120° C.) δ ppm 8.05 (dd, J=7.9, 1.7 Hz, 1H), 7.77 (d, J=2.4 Hz, 1H), 7.46 (dd, J=8.0, 1.2 Hz, 1H), 7.24 (t, J=7.6 Hz, 1H), 7.10 (td, J=7.6, 1.7 Hz, 1H), 6.88 (d, J=2.4 Hz, 1H), 5.27 (d, J=5.8 Hz, 1H), 4.64 (hept, J=6.3 Hz, 1H), 4.40 (d, J=2.1 Hz, 1H), 4.31 (dd, J=5.8, 1.1 Hz, 1H), 4.24 (d, J=13.1 Hz, 1H), 3.92 (d, J=13.2 Hz, 1H), 3.76 (s, 3H), 3.33 (p, J=8.5 Hz, 1H), 2.50 (t, J=1.5 Hz, 1H), 2.33-2.19 (m, 2H), 1.99-1.77 (m, 4H), 1.06 (d, J=6.2 Hz, 3H), 1.01 (s, 9H), 0.88 (d, J=6.2 Hz, 3H); MS (ESI+) m/z 603 & 605 (M+H)+.

Example 139

(2S,3R,4S,5S)-3-tert-butyl-5-(2-cyclopropylphenyl)-4-[(2-methoxyquinolin-3-yl)methoxy]-1-[(2S)-oxolane-2-carbonyl]pyrrolidine-2-carboxylic acid Example 139A 1-allyl 2-ethyl (2S,3R,4S,5S)-3-(tert-butyl)-5-(2-cyclopropylphenyl)-4-((2-methoxyquinolin-3-yl)methoxy)pyrrolidine-1,2-dicarboxylate Example 112C (324 mg, 0.780 mmol) and Example 106B (205.6 mg, 1.046 mmol) were dissolved in dimethylformamide (2.5 mL). The reaction was cooled to 0° C., then potassium tert-butoxide (1M in tetrahydrofuran, 1.00 mL, 1.00 mmol) was added dropwise and the reaction was stirred at ambient temperature for 1 hour. The reaction mixture was poured into saturated aqueous NH$_4$Cl (35 mL) and extracted with methyl tert-butyl ether (3×35 mL). The organic layer was concentrated and the crude material was purified by silica gel chromatography (0% to 5% ethyl acetate in dichloromethane) to provide the title compound (378.4 mg, 83%). $^1$H NMR (400 MHz, DMSO-d$_6$, 120° C.) δ ppm 7.99-7.91 (m, 1H), 7.66 (d, J=8.3 Hz, 1H), 7.57-7.48 (m, 2H), 7.34 (ddd, J=8.0, 6.8, 1.2 Hz, 1H), 7.19-7.10 (m, 3H), 7.01-6.94 (m, 1H), 5.75-5.61 (m, 2H), 5.07-4.92 (m, 2H), 4.53 (d, J=2.0 Hz, 1H), 4.45-4.38 (m, 2H), 4.38-4.29 (m, 2H), 4.13 (q, J=7.0 Hz, 2H), 3.98 (dd, J=13.9, 1.3 Hz, 1H), 3.91 (s, 3H), 2.61-2.53 (m, 1H), 1.97 (tt, J=8.4, 5.4 Hz, 1H), 1.15 (t, J=7.1 Hz, 3H), 1.06 (s, 9H), 0.95-0.77 (m, 2H), 0.64-0.48 (m, 2H); MS (ESI+) m/z 587 (M+H)$^+$.

Example 139B ethyl (2S,3R,4S,5S)-3-(tert-butyl)-5-(2-cyclopropylphenyl)-4-((2-methoxyquinolin-3-yl)methoxy)pyrrolidine-2-carboxylate Example 139A (375.4 mg, 0.641 mmol) was dissolved in ethyl acetate (3.2 mL) and dichloromethane (3.2 mL) and was treated with 1,3-dimethylpyrimidine-2,4,6(1H,3H,5H)-trione (207.7 mg, 1.330 mmol) and tetrakis(triphenylphosphine)palladium (7.9 mg, 6.84 µmol). The reaction mixture was stirred at ambient temperature. After 1 hour, the reaction mixture was diluted with methyl tert-butyl ether (50 mL) and stirred with 15 mL of aqueous 10% $Na_2CO_3$ (50 mL) solution for 30 minutes. The phases were then separated, and the organic layer was washed with brine, dried over $Na_2SO_4$, filtered, and concentrated. The residue was purified by silica gel chromatography 5% to 10% ethyl acetate in dichloromethane to provide the title compound (305.4 mg, 95%). $^1$H NMR (400 MHz, DMSO-$d_6$, 120° C.) δ ppm 7.69-7.64 (m, 2H), 7.59-7.50 (m, 2H), 7.43 (s, 1H), 7.34 (ddd, J=8.1, 7.0, 1.2 Hz, 1H), 7.18-7.10 (m, 2H), 7.01-6.94 (m, 1H), 4.65 (d, J=4.3 Hz, 1H), 4.30 (dd, J=13.8, 1.3 Hz, 1H), 4.21-4.11 (m, 3H), 3.93 (dd, J=13.8, 1.3 Hz, 1H), 3.90 (s, 3H), 3.66 (d, J=6.3 Hz, 1H), 2.94 (s, 1H), 2.44 (dd, J=6.3, 1.6 Hz, 1H), 2.04-1.93 (m, 1H), 1.22 (t, J=7.1 Hz, 3H), 1.01 (s, 9H), 0.92-0.80 (m, 2H), 0.66-0.51 (m, 2H); MS (ESI+) m/z 503 (M+H)$^+$.

Example 139C ethyl (2S,3R,4S,5S)-3-(tert-butyl)-5-(2-cyclopropylphenyl)-4-((2-methoxy-5-(trifluoromethyl)pyridin-3-yl)methoxy)-1-((S)-tetrahydrofuran-2-carbonyl)pyrrolidine-2-carboxylate (S)-(−)-tetrahydro-2-furoic acid (44.3 mg, 0.382 mmol) was dissolved in dichloromethane (2 mL). Oxalyl chloride (2M in dichloromethane, 250 µL, 0.50 mmol) was added followed by dimethylformamide (25 µL). The reaction mixture was stirred at room temperature for 3 hours, concentrated, redissolved in dichloromethane (1 mL), and concentrated again. The residue was taken up in dichloromethane (3×1 mL) and added to a solution of Example 139B (140.0 mg, 0.279 mmol) and triethylamine (150 µL, 1.076 mmol) in dichloromethane (3 mL). The reaction mixture was stirred at ambient temperature for 17 hours. The mixture was diluted with dichloromethane (100 mL) and washed twice with saturated aqueous $NaHCO_3$ and once with brine. The organic layer was dried over $Na_2SO_4$, filtered and concentrated. The residue was purified by silica gel chromatography, eluting with 5% to 10% ethyl acetate in dichloromethane to provide the title compound (105.4 mg, 63%). $^1$H NMR (400 MHz, DMSO-$d_6$, 120° C.) δ ppm 8.01 (d, J=6.0 Hz, 1H), 7.66 (d, J=8.3 Hz, 1H), 7.57-7.47 (m, 2H), 7.37-7.31 (m, 1H), 7.17 (d, J=10.4 Hz, 3H), 7.05-6.97 (m, 1H), 5.93 (s, 1H), 4.78 (s, 1H), 4.41 (d, J=5.7 Hz, 1H), 4.35 (dd, J=13.9, 1.2 Hz, 1H), 4.16-4.06 (m, 2H), 3.99 (dd, J=14.0, 1.3 Hz, 1H), 3.91 (d, J=0.8 Hz, 3H), 3.67 (d, J=19.3, 12.3 Hz, 2H), 2.55 (s, 1H), 2.06-1.91 (m, 2H), 1.86-1.55 (m, 4H), 1.14 (td, J=7.1, 0.9 Hz, 3H), 1.05 (d, J=0.8 Hz, 9H), 0.87 (dtd, J=27.2, 9.1, 4.6 Hz, 2H), 0.64 (dq, J=9.5, 5.1 Hz, 1H), 0.53 (dq, J=9.6, 5.1 Hz, 1H); MS (ESI+) m/z 601 (M+H)$^+$.

Example 139D (2S,3R,4S,5S)-3-tert-butyl-5-(2-cyclopropylphenyl)-4-[(2-methoxyquinolin-3-yl)methoxy]-1-[(2S)-oxolane-2-carbonyl]pyrrolidine-2-carboxylic acid Example 139C (73.1 mg, 0.118 mmol) was dissolved in methanol (1 mL), and tetrahydrofuran (1 mL). Aqueous LiOH (1 M, 1.0 mL, 1.0 mmol) was added and the reaction mixture was heated to 50° C. for 16 hours. The reaction mixture was concentrated, and 2 mL of water and 3 mL of dichloromethane were added. The aqueous layer was acidified with 1 M aqueous HCl to pH ~2, then diluted to 25 mL with water. The aqueous layer was extracted with dichloromethane (2×25 mL). The combined organic layers were washed with brine (25 mL), dried over $Na_2SO_4$, filtered and concentrated to provide the title compound (97.3 mg, 100%). $^1$H NMR (400 MHz, DMSO-$d_6$, 120° C.) δ ppm 8.06 (d, J=7.1 Hz, 1H), 7.66 (dt, J=8.1, 1.0 Hz, 1H), 7.57-7.46 (m, 2H), 7.34 (ddd, J=8.1, 7.0, 1.1 Hz, 1H), 7.17 (d, J=13.7 Hz, 3H), 7.00 (dd, J=7.2, 2.1 Hz, 1H), 5.93 (s, 1H), 4.74 (d, J=1.7 Hz, 1H), 4.42-4.34 (m, 2H), 4.21-4.03 (m, 1H), 3.99 (dd, J=14.0, 1.3 Hz, 1H), 3.91 (d, J=0.8 Hz, 3H), 3.71 (t, J=7.3 Hz, 1H), 3.62 (d, J=7.6 Hz, 1H), 2.61 (s, 1H), 2.48-2.47 (m, 1H), 2.07-1.89 (m, 2H), 1.87-1.73 (m, 1H), 1.64 (s, 1H), 1.05 (d, J=0.9 Hz, 9H), 0.96-0.77 (m, 2H), 0.68-0.58 (m, 1H), 0.52 (dtd, J=9.5, 5.4, 3.6 Hz, 1H); MS (ESI+) m/z 593 (M+H)$^+$.

Example 140

(2S,3R,4S,5S)-3-tert-butyl-5-(3-cyclobutylphenyl)-4-{[2-methoxy-5-(trifluoromethyl)pyridin-3-yl]methoxy}-1-[(2S)-oxolane-2-carbonyl]pyrrolidine-2-carboxylic acid The title compound was prepared according to the procedure described in Example 43A-Example 43B, substituting Example 117A for Example 40A, and cyclobutylzinc(II) bromide for cyclohexylzinc bromide in Example 43A. $^1$H NMR (400 MHz, 120° C., DMSO-$d_6$:$D_2O$=9:1 (v/v)) δ ppm 8.26 (s, 1H), 7.56 (s, 1H), 7.39 (d, J=7.7 Hz, 1H), 7.20-7.05 (m, 2H), 6.97 (d, J=7.7 Hz, 1H), 5.36 (s, 1H), 4.58 (s, 1H), 4.31-4.23 (m, 2H), 4.19 (s, 1H), 3.86 (s, 4H), 3.73 (q, J=7.3 Hz, 1H), 3.65 (d, J=20.0 Hz, 1H), 3.46-3.34 (m, 1H), 2.27-2.15 (m, 2H), 1.99-1.85 (m, 3H), 1.76 (tdd, J=12.9, 8.0, 5.2 Hz, 3H), 1.60 (s, 1H), 0.99 (s, 9H); MS (APCI+) m/z 605.2 (M+H)$^+$.

Example 141

(2S,3R,4S,5S)-3-tert-butyl-4-{[2-methoxy-5-(trifluoromethyl)pyridin-3-yl]methoxy}-5-(2-methylphenyl)-1-[(2S)-oxane-2-carbonyl]pyrrolidine-2-carboxylic acid

Example 141A ethyl (2S,3R,4S,5S)-3-(tert-butyl)-4-((2-methoxy-5-(trifluoromethyl)pyridin-3-yl)methoxy)-1-((S)-tetrahydro-2H-pyran-2-carbonyl)-5-(o-tolyl)pyrrolidine-2-carboxylate Tetrahydropyran-2-carboxylic acid (64.1 mg, 0.493 mmol) was dissolved in dichloromethane (2 mL). Oxalyl chloride (2M in dichloromethane, 300 µL, 0.60 mmol) was added followed by dimethylformamide (25 µL). The reaction was stirred at ambient temperature for 3 hours, at which point it was concentrated, redissolved in dichloromethane (1 mL), and concentrated again. The residue was taken up in dichloromethane (3×1 mL) and added to a solution of Example 129H (116 mg, 0.235 mmol) and triethylamine (130 µL, 0.933 mmol) in dichloromethane (3 mL). The reaction was stirred at ambient temperature for 17 hours. After this time, the mixture was diluted with dichloromethane (100 mL) and washed twice with saturated aqueous NaHCO$_3$, and once with brine. The organic layer was dried over Na$_2$SO$_4$, filtered, and concentrated. The residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The title compound was the second eluting diastereomer and was isolated as the TFA salt (43.1 mg, 26%). $^1$H NMR (400 MHz, DMSO-d$_6$, 120° C.) δ ppm 8.28 (s, 1H), 8.01-7.91 (m, 1H), 7.20 (d, J=2.4 Hz, 1H), 7.13-6.91 (m, 3H), 5.56 (s, 1H), 4.68 (s, 1H), 4.33-4.21 (m, 3H), 4.09 (qd, J=7.1, 2.8 Hz, 2H), 3.86 (s, 3H), 3.82 (d, J=13.9 Hz, 1H), 3.75 (d, J=11.4 Hz, 1H), 2.90 (s, 1H), 2.42 (t, J=1.3 Hz, 1H), 2.34 (s, 3H), 1.77-1.22 (m, 6H), 1.14 (t, J=7.0 Hz, 3H), 1.02 (s, 9H); MS (ESI+) m/z 607 (M+H)$^+$.

Example 141B (2S,3R,4S,5S)-3-tert-butyl-4-{[2-methoxy-5-(trifluoromethyl)pyridin-3-yl]methoxy}-5-(2-methylphenyl)-1-[(2S)-oxane-2-carbonyl]pyrrolidine-2-carboxylic acid Example 141A (40.7 mg, 0.056 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction was quenched by the addition of 1M aqueous HCl (0.5 mL), concentrated and purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (27.0 mg, 69%) as the TFA salt. $^1$H NMR (400 MHz, DMSO-d$_6$, 120° C.) δ ppm 8.31-8.24 (m, 1H), 8.08-7.99 (m, 1H), 7.18 (d, J=2.4 Hz, 1H), 7.11-6.98 (m, 3H), 5.56 (s, 1H), 4.64 (s, 1H), 4.32-4.24 (m, 2H), 3.91-3.82 (m, 5H), 3.76 (d, J=11.3 Hz, 2H), 2.50 (s, 1H), 2.33 (s, 3H), 1.74-1.23 (m, 6H), 1.02 (s, 9H); MS (ESI+) m/z 579 (M+H)$^+$.

Example 142

(2S,3R,4S,5S)-3-tert-butyl-5-(3-chlorophenyl)-4-[(5-cyclobutyl-2-methoxypyridin-3-yl)methoxy]-1-{[(propan-2-yl)oxy]carbonyl}pyrrolidine-2-carboxylic acid Example 142A 2-ethyl 1-isopropyl (2S,3R,4S,5S)-3-(tert-butyl)-5-(3-chlorophenyl)-4-((5-cyclobutyl-2-methoxypyridin-3-yl)methoxy)pyrrolidine-1,2-dicarboxylate Example 79C (40.0 mg, 0.097 mmol) and 3-(bromomethyl)-5-cyclobutyl-2-methoxypyridine (35.0 mg, 0.137 mmol) were dissolved in dimethylformamide (1.1 mL). The reaction was cooled to 0° C., and potassium tert-butoxide (1M in tetrahydrofuran, 0.12 mL, 0.12 mmol) was added dropwise and the reaction was stirred at ambient temperature for 1 hour. The reaction was quenched by the addition of 1M aqueous HCl (0.1 mL) and purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The title compound was the second eluting diastereomer and was isolated as the TFA salt (30.0 mg, 44%). $^1$H NMR (400 MHz, DMSO-d$_6$, 120° C.) δ ppm 7.81-7.77 (m, 1H), 7.67 (t, J=1.8 Hz, 1H), 7.48 (dt, J=7.6, 1.5 Hz, 1H), 7.22 (t, J=7.7 Hz, 1H), 7.19-7.14 (m, 1H), 6.94 (d, J=2.4 Hz, 1H), 5.00 (d, J=6.1 Hz, 1H), 4.66 (p, J=6.2 Hz, 1H), 4.35 (d, J=3.0 Hz, 1H), 4.28-4.19 (m, 2H), 4.10 (qd, J=7.1, 2.3 Hz, 2H), 3.96-3.87 (m, 1H), 3.76 (s, 3H), 3.36 (p, J=8.4 Hz, 1H), 2.43 (t, J=2.8 Hz, 1H), 2.32-2.19 (m, 2H), 2.04-1.78 (m, 4H), 1.16 (t, J=7.1 Hz, 3H), 1.06 (d, J=6.2 Hz, 3H), 1.00 (s, 9H), 0.92 (d, J=6.2 Hz, 3H); MS (ESI+) m/z 587 (M+H)$^+$.

Example 142B (2S,3R,4S,5S)-3-tert-butyl-5-(3-chlorophenyl)-4-[(5-cyclobutyl-2-methoxypyridin-3-yl)methoxy]-1-{[(propan-2-yl)oxy]carbonyl}pyrrolidine-2-carboxylic acid Example 142A (27.0 mg, 0.039 mmol) was dissolved in methanol (1 mL), and tetrahydrofuran (1 mL). Aqueous LiOH (1 M, 0.5 mL, 0.5 mmol) was added and the reaction was heated to 50° C. for 16 hours. The reaction was quenched by the addition of 1M aqueous HCl (0.5 mL) and purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The title compound was the second eluting diastereomer and was isolated as the TFA salt (30.0 mg, 44%) $^1$H NMR (400 MHz, DMSO-d$_6$, 120° C.) δ ppm 7.79 (d, J=2.5 Hz, 1H), 7.70 (t, J=1.8 Hz, 1H), 7.50 (dt, J=7.3, 1.5 Hz, 1H), 7.21 (t, J=7.7 Hz, 1H), 7.16 (dt, J=8.4, 1.5 Hz, 1H), 6.95-6.89 (m, 1H), 4.99 (d, J=6.3 Hz, 1H), 4.65 (hept, J=6.2 Hz, 1H), 4.31 (d, J=3.0 Hz, 1H), 4.27-4.20 (m, 2H), 3.92 (d, J=13.1 Hz, 1H), 3.77 (s, 3H), 3.35 (p, J=8.3 Hz, 1H), 2.50 (s, 1H), 2.32-2.19 (m, 2H), 2.04-1.79 (m, 4H), 1.06 (d, J=6.3 Hz, 3H), 0.99 (s, 9H), 0.92 (d, J=6.2 Hz, 3H); MS (ESI+) m/z 559 (M+H)$^+$.

Example 143

(2S,3R,4S,5S)-3-tert-butyl-5-(2-cyclopropylphenyl)-4-[(2-methoxyquinolin-3-yl)methoxy]-1-{[(propan-2-yl)oxy]carbonyl}pyrrolidine-2-carboxylic acid The title compound was prepared according to the procedure described in Example 92D to Example 92E, substituting Example 106B for 3-(bromomethyl)-2-methoxy-5-(trifluoromethyl)pyridine in Example 92D. $^1$H NMR (400 MHz, DMSO-d$_6$, 120° C.) δ ppm 8.05-7.97 (m, 1H), 7.66 (dd, J=8.5, 1.4 Hz, 1H), 7.58-7.49 (m, 2H), 7.34 (ddd, J=8.0, 7.0, 1.2 Hz, 1H), 7.22 (s, 1H), 7.12 (td, J=6.9, 6.1, 4.0 Hz, 2H), 6.98 (dd, J=6.4, 2.5 Hz, 1H), 5.59 (d, J=5.7 Hz, 1H), 4.64 (hept, J=6.3 Hz, 1H), 4.44 (d, J=1.9 Hz, 1H), 4.39-4.30 (m, 2H), 3.98 (dd, J=14.1, 1.4 Hz, 1H), 3.91 (s, 3H), 2.61-2.55 (m, 1H), 1.96 (tt, J=8.5, 5.4 Hz, 1H), 1.08-0.99 (m, 12H), 0.95-0.77 (m, 5H), 0.58 (dtt, J=9.3, 7.1, 4.6 Hz, 2H); MS (ESI+) m/z 565 (M+H)+.

Example 144

(2S,3R,4S,5S)-5-(2-bromophenyl)-3-tert-butyl-4-[(5-cyclobutyl-2-methoxypyridin-3-yl)methoxy]-1-[(2S)-oxolane-2-carbonyl]pyrrolidine-2-carboxylic acid Example 144A (2S,3R,4S,5S)-1-allyl 2-ethyl 5-(2-bromophenyl)-3-(tert-butyl)-4-nitropyrrolidine-1,2-dicarboxylate To Core 10 (957 mg, 2.397 mmol) in toluene (10 mL) and saturated aqueous NaHCO$_3$ (10 mL) was added allyl carbonochloridate (0.3 mL, 2.82 mmol) dropwise at ambient temperature. The mixture was stirred at ambient temperature overnight. The reaction was poured into water (50 mL) and extracted with dichloromethane (3×50 mL). The organic layer was washed with brine and concentrated and purified by silica gel chromatography using a 40 g cartridge and eluting with 0->5% ethyl acetate in dichloromethane to provide (2S,3R,4S,5S)-1-allyl 2-ethyl 5-(2-bromophenyl)-3-(tert-butyl)-4-nitropyrrolidine-1,2-dicarboxylate (1.16 g, 2.400 mmol, 100% yield). $^1$H NMR (400 MHz, DMSO-d$_6$, 120° C.) δ ppm 7.78 (dd, J=7.7, 1.5 Hz, 1H), 7.24-7.04 (m, 2H), 6.99 (dd, J=7.5, 1.5 Hz, 1H), 6.00 (d, J=8.6 Hz, 1H), 5.67 (ddt, J=17.2, 10.5, 5.2 Hz, 1H), 5.56 (dd, J=8.6, 2.5 Hz, 1H), 5.05-4.92 (m, 2H), 4.60 (d, J=3.4 Hz, 1H), 4.41 (dq, J=4.8, 1.5 Hz, 2H), 4.31-4.21 (m, 2H), 3.06 (t, J=3.0 Hz, 1H), 2.06 (tt, J=8.4, 5.4 Hz, 1H), 1.30 (t, J=7.1 Hz, 3H), 1.04 (s, 9H), 1.02-0.89 (m, 2H), 0.80 (dtd, J=9.4, 5.2, 3.4 Hz, 1H), 0.59-0.48 (m, 1H); MS (APCI+) m/z 483/485 (M+H)+ Br doublet.

Example 144B (2S,3R,5S)-1-allyl 2-ethyl 5-(2-bromophenyl)-3-(tert-butyl)-4-oxopyrrolidine-1,2-dicarboxylate To a solution of potassium dichromate (3.72 g, 12.65 mmol) in 6 N aqueous HCl (50 mL) was added zinc (4.41 g, 67.5 mmol) under N$_2$ atmosphere. After the almost complete dissolution of zinc yielded a clear bright blue solution, the formed chromium(II) chloride was transferred to the refluxing solution of Example 144A (1.14 g, 2.359 mmol) in ethanol (25 mL) under N$_2$ using an addition funnel (internal temp 78° C.). The reaction mixture was refluxed at 85° C. overnight and cooled and diluted with 300 mL of dichloromethane. The organic phase was separated, dried over sodium sulfate, filtered and concentrated. The crude material was then taken up in anhydrous ethanol and treated with a solution of HCl in ethanol (prepared by adding 2.0 mL of acetyl chloride to an ice bath cooled solution of 6 mL of ethanol), and heated at 65° C. for one hour. The ethanol was removed and the crude material was diluted with 300 mL of methyl tert-butyl ether, washed with 50 mL each of saturated aqueous sodium bicarbonate and brine, and dried over sodium sulfate. After filtration, the solvent was removed in vacuo to provide (2S,3R,5S)-1-allyl 2-ethyl 5-(2-bromophenyl)-3-(tert-butyl)-4-oxopyrrolidine-1,2-dicarboxylate (1.067 g, 2.359 mmol, 100% yield). $^1$H NMR (400 MHz, DMSO-d$_6$) δ ppm 7.81 (dd, J=7.8, 1.7 Hz, 1H), 7.59 (dd, J=8.0, 1.3 Hz, 1H), 7.33 (td, J=7.6, 1.3 Hz, 1H), 7.19 (ddd, J=8.0, 7.3, 1.7 Hz, 1H), 5.71 (ddt, J=16.9, 11.0, 5.2 Hz, 1H), 5.45 (s, 1H), 5.10-4.99 (m, 2H), 4.64 (dd, J=4.6, 0.6 Hz, 1H), 4.46 (dtd, J=5.2, 1.5, 0.7 Hz, 2H), 4.29-4.16 (m, 2H), 2.63 (dd, J=4.6, 0.9 Hz, 1H), 1.30-1.22 (m, 3H), 1.06 (s, 9H); MS (APCI+) m/z 452 (M+H)+.

Example 144C (2S,3R,4S,5S)-1-allyl 2-ethyl 5-(2-bromophenyl)-3-(tert-butyl)-4-hydroxypyrrolidine-1,2-dicarboxylate Example 144B (850 mg, 1.879 mmol) was dissolved in ethanol (10 mL) and cooled in an ice/acetone bath. Sodium tetrahydroborate (85 mg, 2.255 mmol) was added in small portions over 30 minutes. The reaction mixture was concentrated in vacuo (no heat) and 10 mL of saturated aqueous sodium bicarbonate and 15 mL of ethyl acetate were added. The reaction mixture was stirred at room temperature for 30 minutes. The organics were diluted with 50 mL more ethyl acetate, separated, washed with brine, dried over sodium sulfate, filtered, and concentrated. The crude residue was loaded onto a 24 g silica gel column and eluted with 5-100% ethyl acetate/heptanes to provide a 0.584 g of a mixture of diastereomers. The crude material was rechromatographed using a 24 g silica gel cartridge with a gradient of 5-30% ethyl acetate/heptanes over 20 minutes to provide (2S,3R,4S,5S)-1-allyl 2-ethyl 5-(2-bromophenyl)-3-(tert-butyl)-4-hydroxypyrrolidine-1,2-dicarboxylate (0.465 g, 1.023 mmol, 54.5% yield). $^1$H NMR (400 MHz, DMSO-d$_6$) δ ppm 7.93 (dd, J=7.9, 1.7 Hz, 1H), 7.47 (dd, J=8.0, 1.2 Hz, 1H), 7.25 (t, J=7.6 Hz, 1H), 7.09 (td, J=7.7, 1.7 Hz, 1H), 5.69 (ddt, J=17.7, 10.1, 5.0 Hz, 1H), 5.20 (d, J=6.0 Hz, 1H), 5.05-4.94 (m, 2H), 4.51-4.42 (m, 2H), 4.41-4.33 (m, 3H), 4.20 (d, J=7.0 Hz, 2H), 2.29 (t, J=2.8 Hz, 1H), 1.25 (t, J=7.1 Hz, 3H), 1.00 (s, 9H); MS (APCI+) m/z 454 (M+H)+.

Example 144D (2S,3R,4S,5S)-ethyl 5-(2-bromophenyl)-3-(tert-butyl)-4-hydroxy-1-((S)-tetrahydrofuran-2-carbonyl)pyrrolidine-2-carboxylate Example 144C (0.465 g, 1.023 mmol) was dissolved in ethyl acetate (5 mL) and dichloromethane (5 mL), degassed with a stream of nitrogen bubbling through, and treated with 1,3-dimethylpyrimidine-2,4,6(1H,3H,5H)-trione (0.320 g, 2.047 mmol) and tetrakis(triphenylphosphine)palladium (0.008 g, 6.92 µmol). The reaction stirred at room temperature. After 10 minutes, the reaction was complete. To the reaction mixture was added triethylamine (0.856 mL, 6.14 mmol) followed by dropwise addition of (S)-tetrahydrofuran-2-carbonyl chloride (0.164 g, 1.219 mmol) as a solution in 0.2 mL of dichloromethane. The reaction mixture was quenched with 5 mL of saturated aqueous NaHCO$_3$ and concentrated. The phases were separated and the crude organics were purified twice using a 12 g silica gel cartridge with a gradient of 5-100% ethyl acetate/heptanes over 20 minutes to provide (2S,3R,4S,5S)-ethyl 5-(2-bromophenyl)-3-(tert-butyl)-4-hydroxy-1-((S)-tetrahydrofuran-2-carbonyl) pyrrolidine-2-carboxylate (0.392 g, 0.837 mmol, 82% yield). $^1$H NMR (400 MHz, DMSO-d$_6$) δ ppm 8.16 (d, J=7.8 Hz, 0H), 7.99 (s, 1H), 7.51 (d, J=8.0 Hz, 1H), 7.27 (t, J=7.5 Hz, 1H), 7.12 (t, J=7.7 Hz, 1H), 5.50 (s, 1H), 4.58 (s, 1H), 4.50 (d, J=6.1 Hz, 1H), 4.17 (qd, J=7.1, 1.1 Hz, 2H), 3.70 (q, J=7.2 Hz, 1H), 3.66-3.56 (m, 1H), 2.28 (t, J=2.7 Hz, 1H), 2.18 (d, J=6.6 Hz, 0H), 2.02-1.83 (m, 1H), 1.77 (dp, J=14.0, 6.8, 6.3 Hz, 1H), 1.66 (s, 1H), 1.33-1.18 (m, 3H), 0.99 (d, J=4.8 Hz, 10H), 0.85 (ddt, J=9.0, 6.3, 3.5 Hz, 1H); (APCI+) m/z 468 (M+H)+.

Example 144E (2S,3R,4S,5S)-ethyl 5-(2-bromophenyl)-3-(tert-butyl)-4-((5-cyclobutyl-2-methoxypyridin-3-yl)methoxy)-1-((S)-tetrahydrofuran-2-carbonyl)pyrrolidine-2-carboxylate Example 144D (108 mg, 0.231 mmol) was dried azeotropically three times with toluene, dissolved in dimethyl formamide (1 mL), and cooled to 0° C. Potassium 2-methylpropan-2-olate (1M in tetrahydrofuran, 0.277 mL, 0.277 mmol) was added dropwise, followed by dropwise addition of 3-(bromomethyl)-5-cyclobutyl-2-methoxypyridine (70.9 mg, 0.277 mmol). After 10 minutes, the reaction was quenched with 2 mL of saturated aqueous NH$_4$Cl and the organics were taken up in dichloromethane and purified using a 10 g silica gel cartridge, eluting with 5-100% ethyl acetate-heptanes over 20 minutes to provide (2S,3R,4S,5S)-ethyl 5-(2-bromophenyl)-3-(tert-butyl)-4-((5-cyclobutyl-2-methoxypyridin-3-yl)methoxy)-1-((S)-tetrahydrofuran-2-carbonyl)pyrrolidine-2-carboxylate (108 mg, 0.168 mmol, 72.8% yield). $^1$H NMR (400 MHz, DMSO-d$_6$) δ ppm 8.03 (s, 1H), 7.77 (d, J=2.5 Hz, 1H), 7.49 (d, J=7.9 Hz, 1H), 7.26 (t, J=7.3 Hz, 1H), 7.13 (t, J=7.7 Hz, 1H), 6.86 (d, J=2.4 Hz, 1H), 5.60 (s, 1H), 4.78 (s, 1H), 4.38 (d, J=5.8 Hz, 1H), 4.25 (s, 1H), 4.10 (q, J=7.1 Hz, 2H), 3.92 (d, J=13.0 Hz, 1H), 3.86 (d, J=10.3 Hz, 1H), 3.75 (s, 3H), 3.73-3.59 (m, 2H), 3.40-3.31 (m, 1H), 2.30-2.18 (m, 2H), 2.06-1.90 (m, 3H), 1.90-1.73 (m, 2H), 1.69 (s, 1H), 1.32-1.23 (m, 1H), 1.14 (t, J=7.1 Hz, 3H), 1.02 (s, 9H), 0.95 (s, 1H), 0.85 (tt, J=5.4, 2.6 Hz, 1H); MS (APCI+) m/z 643 (M+H)+.

Example 144F (2S,3R,4S,5S)-5-(2-bromophenyl)-3-tert-butyl-4-[(5-cyclobutyl-2-methoxypyridin-3-yl)methoxy]-1-[(2S)-oxolane-2-carbonyl]pyrrolidine-2-carboxylic acid Example 144E (108 mg, 0.168 mmol) and lithium hydroxide (33.7 mg, 1.407 mmol) were dissolved in methanol (0.5 mL), tetrahydrofuran (1 mL) and water (1 mL). The reaction was warmed at 45° C. overnight. The solvents were removed under a stream of nitrogen. The residue was acidified with 0.705 mL of 2N aqueous HCl and chromatographed using a 12 g silica gel cartridge with an ethanol/ethyl acetate/heptanes solvent system to provide 127 mg of impure product. The material was purified again using reverse phase HPLC method TFA8 to provide (2S,3R,4S,5S)-5-(2-bromophenyl)-3-(tert-butyl)-4-((5-cyclobutyl-2-methoxypyridin-3-yl)methoxy)-1-((S)-tetrahydrofuran-2-carbonyl)pyrrolidine-2-carboxylic acid (68 mg, 0.110 mmol, 65.8% yield). $^1$H NMR (400 MHz, DMSO-d$_6$) δ ppm 8.09 (s, 1H), 7.77 (dd, J=2.5, 0.7 Hz, 1H), 7.49 (d, J=7.9 Hz, 1H), 7.26 (t, J=7.6 Hz, 1H), 7.12 (t, J=7.6 Hz, 1H), 6.87-6.82 (m, 1H), 5.60 (s, 1H), 4.72 (s, 1H), 4.36 (d, J=6.0 Hz, 1H), 4.25 (dt, J=13.3, 0.8 Hz, 1H), 3.94 (dt, J=13.3, 0.9 Hz, 1H), 3.76 (s, 3H), 3.76-3.67 (m, 1H), 3.68-3.60 (m, 1H), 3.39-3.26 (m, 1H), 2.53 (s, 1H), 2.30-2.17 (m, 2H), 2.03-1.87 (m, 5H), 1.91-1.69 (m, 2H), 1.74-1.62 (m, 2H), 1.01 (s, 9H); MS (APCI+) m/z 617 (M+H)+ (Br doublet).

Example 145

(2S,3R,4S,5S)-3-tert-butyl-4-[(5-cyclobutyl-2-methoxypyridin-3-yl)methoxy]-1-{[(propan-2-yl)oxy]carbonyl}-5-[2-(trifluoromethyl)phenyl]pyrrolidine-2-carboxylic acid The title compound was prepared using the procedures described in Example 86 substituting Core 21 for Core 10 in Example 86A and 3-(bromomethyl)-5-cyclobutyl-2-methoxypyridine for 3-(bromomethyl)-5-trifluromethyl-2-methoxypyridine in Example 86D. $^1$H NMR (400 MHz, DMSO-d$_6$) δ ppm 12.72 (s, 1H), 8.40 (d, J=7.9 Hz, 1H), 7.75 (d, J=2.4 Hz, 1H), 7.61 (dd, J=8.0, 1.2 Hz, 1H), 7.56 (t, J=7.9 Hz, 1H), 7.41 (t, J=7.6 Hz, 1H), 6.84 (s, 1H), 5.15 (d, J=5.3 Hz, 1H), 4.51 (s, 1H), 4.35 (d, J=1.4 Hz, 1H), 4.21 (d, J=13.7 Hz, 1H), 4.05 (d, J=5.4 Hz, 1H), 3.83 (d, J=13.7 Hz, 1H), 3.68 (s, 3H), 2.23-2.10 (m, 2H), 1.98-1.76 (m, 4H), 1.18-1.04 (m, 2H), 0.96 (s, 9H), 0.89 (bs, 2H), 0.51 (bs, 2H); MS (ESI+) m/z 593 (M+H)+.

Example 146

(2S,3R,4S,5S)-3-tert-butyl-4-{[2-methoxy-5-(trifluoromethyl)pyridin-3-yl]methoxy}-1-[(2S)-oxolane-2-carbonyl]-5-{2-[(propan-2-yl)oxy]pyridin-3-yl}pyrrolidine-2-carboxylic acid

Example 146A (2S,3R,4S,5S)-1-allyl 2-ethyl 3-(tert-butyl)-5-(2-isopropoxypyridin-3-yl)-4-((2-methoxy-5-(trifluoromethyl)pyridin-3-yl)methoxy)pyrrolidine-1,2-dicarboxylate To Example 133D (244 mg, 0.562 mmol) and 3-(bromomethyl)-2-methoxy-5-(trifluoromethyl)pyridine (182 mg, 0.674 mmol) in dimethylformamide (2 mL) while cooling in an ice bath, potassium 2-methylpropan-2-olate (82 mg, 0.730 mmol, 0.73 mL, 1.0 M in tetrahydrofuran) was added dropwise. The mixture was stirred in ice-bath for 30 minutes, and was allowed to warm to room temperature. Dichloromethane and saturated aqueous NH$_4$Cl were added. The organic layer was separated, washed with brine, dried over MgSO$_4$, filtered, and concentrated. The residue was purified via chromatography, eluting with ethyl acetate in heptanes at a 0-40% gradient to provide the title compound (260 mg, 74.2% yield). LC/MS (APCI+) m/z 624.24 (M+H)+.

Example 146B (2S,3R,4S,5S)-ethyl 3-(tert-butyl)-5-(2-isopropoxypyridin-3-yl)-4-((2-methoxy-5-(trifluoromethyl)pyridin-3-yl)methoxy)pyrrolidine-2-carboxylate To a solution of Example 146A (250 mg, 0.401 mmol) and diethylamine (0.083 mL, 0.802 mmol) in acetonitrile/water (8.8 mL, 10:1) was added tetrakis(triphenylphosphine)palladium(0) (10.19 mg, 8.82 µmol). The mixture was stirred at ambient temperature overnight, and LC/MS showed the conversion was complete. Dichloromethane (20 mL) and water (10 mL) were added, and the organic layer was washed with brine, dried over MgSO$_4$, filtered, and concentrated to provide the title compound 200 mg (92% yield) which used in the next step without further purification. LC/MS (APCI+) m/z 540.32 (M+H)+.

Example 146C (2S,3R,4S,5S)-ethyl 3-(tert-butyl)-5-(2-isopropoxy-pyridin-3-yl)-4-((2-methoxy-5-(trifluoromethyl)pyridin-3-yl)methoxy)-1-((S)-tetrahydrofuran-2-carbonyl)pyrrolidine-2-carboxylate To (S)-tetrahydrofuran-2-carboxylic acid (34.4 mg, 0.297 mmol) and a drop of dimethylformamide in dichloromethane (2 mL) was added oxalyl dichloride (56.5 mg, 0.445 mmol, 0.23 mL, 2M in dichloromethane). The mixture was stirred at ambient temperature for 30 minutes. The solvent was removed under pressure and fresh dichloromethane was added and removed again. The residue in dichloromethane (1 mL) was added dropwise to a solution of Example 146B (80 mg, 0.148 mmol) and triethylamine (0.083 mL, 0.593 mmol) in dichloromethane (6 mL) in an ice-bath. The mixture was stirred in an ice-bath for 30 minutes, and then at ambient temperature for 30 minutes. Dichloromethane and saturated aqueous NH$_4$Cl were added and the organic layer washed with brine, dried over MgSO$_4$, filtered, and concentrated. The residue was purified by chromatography, eluting with ethyl acetate in heptanes at 0-40% gradient to provide the title compound.

Example 146D (2S,3R,4S,5S)-3-tert-butyl-4-{[2-methoxy-5-(trifluoromethyl)pyridin-3-yl]methoxy}-1-[(2S)-oxolane-2-carbonyl]-5-{2-[(propan-2-yl)oxy]pyridin-3-yl}pyrrolidine-2-carboxylic acid Example 146C was dissolved in methanol (1.5 mL) and aqueous LiOH (6M, 0.5 mL). The mixture was stirred at 45° C. overnight. LC/MS indicated the conversion was finished, and the mixture was adjusted pH to 1~2 by adding 2M aqueous HCl. The resulting mixture was purified via silica gel chromatography, eluting with methanol in dichloromethane using a gradient of 0-20% to provide title compound 36 mg (39.8% yield). $^1$H NMR (400 MHz, DMSO-d$_6$) δ ppm 8.57-8.26 (m, 2H), 7.90 (s, 1H), 7.08-7.00 (m, 1H), 6.77 (s, 1H), 5.60 (s, 2H), 5.20 (p, J=6.2 Hz, 1H), 4.48 (s, 1H), 4.40 (d, J=14.0 Hz, 1H), 4.26 (s, 1H), 4.05 (d, J=14.8 Hz, 1H), 3.89 (s, 3H), 3.78 (s, 1H), 3.66 (s, 1H), 2.64 (d, J=4.6 Hz, 1H), 1.77 (d, J=64.0 Hz, 4H), 1.28 (dd, J=6.1, 4.4 Hz, 3H), 1.16 (d, J=6.1 Hz, 3H), 1.01 (d, J=4.9 Hz, 9H); MS (ESI+) m/z 610 (M+H)+.

Example 147

(2S,3R,4S,5S)-3-tert-butyl-4-{[2-methoxy-5-(trifluoromethyl)pyridin-3-yl]methoxy}-1-{[(propan-2-yl)oxy]carbonyl}-5-{2-[(propan-2-yl)oxy]pyridin-3-yl}pyrrolidine-2-carboxylic acid The title compound was prepared according to the procedure described in Example 146C-146D substituting isopropyl carbonochloridate for (S)-tetrahydrofuran-2-carboxylic acid. $^1$H NMR (400 MHz, DMSO-d$_6$) δ ppm 8.29 (d, J=9.2 Hz, 2H), 7.87 (dd, J=4.9, 1.9 Hz, 1H), 7.09 (d, J=2.4 Hz, 1H), 6.75 (dd, J=7.4, 4.9 Hz, 1H), 5.25-5.16 (m, 2H), 4.67 (dq, J=12.4, 6.2 Hz, 1H), 4.37 (d, J=14.0 Hz, 1H), 4.32 (d, J=2.7 Hz, 1H), 4.23 (dd, J=6.2, 1.8 Hz, 1H), 4.00 (d, J=14.0 Hz, 1H), 3.88 (s, 3H), 2.54 (t, J=2.2 Hz, 1H), 1.28 (d, J=6.1 Hz, 3H), 1.18 (d, J=6.1 Hz, 3H), 1.06 (d, J=6.2 Hz, 3H), 1.00 (s, 9H), 0.91 (d, J=6.2 Hz, 3H); MS (ESI+) m/z (M+H)+.

Example 148

(2S,3R,4S,5S)-3-tert-butyl-4-[(2-methoxyquinolin-3-yl)methoxy]-1-[(2S)-oxolane-2-carbonyl]-5-[1-(propan-2-yl)-1H-pyrazol-5-yl]pyrrolidine-2-carboxylic acid The title compound was prepared using the procedures described in Example 112A-112G, substituting Core 19 for Core 12 in Example 112A, and substituting 3-(bromomethyl)-2-methoxyquinoline (Example 106B) for 3-(bromomethyl)-2-methoxy-5-(trifluoromethyl)pyridine in Example 112D. $^1$H NMR (400 MHz, DMSO-d$_6$, 120° C.) δ ppm 7.69 (d, J=8.4 Hz, 1H), 7.65 (dd, J=8.0, 1.4 Hz, 1H), 7.55 (ddd, J=8.4, 6.9, 1.5 Hz, 1H), 7.44 (s, 1H), 7.35 (ddd, J=8.1, 6.8, 1.2 Hz, 2H), 6.62 (s, 1H), 5.59 (s, 1H), 4.72 (p, J=6.4 Hz, 1H), 4.65 (s, 1H), 4.43 (dd, J=14.0, 1.2 Hz, 1H), 4.37 (s, 1H), 4.22 (s, 1H), 4.10 (d, J=13.9 Hz, 1H), 3.95 (d, J=0.8 Hz, 3H), 3.69 (dt, J=13.7, 6.9 Hz, 2H), 2.61 (s, 1H), 2.06 (q, J=5.6 Hz, 1H), 1.88-1.65 (m, 3H), 1.39 (d, J=6.3 Hz, 3H), 1.28 (d, J=6.5 Hz, 3H), 1.02 (s, 9H); MS (ESI+) m/z 565 (M+H)+.

Example 149

(2S,3R,4S,5S)-3-tert-butyl-4-[(5-cyclobutyl-2-methoxypyridin-3-yl)methoxy]-5-(2-cyclopropylphenyl)-1-[(2S)-oxolane-2-carbonyl]pyrrolidine-2-carboxylic acid Example 149A (2S,3R,5S)-1-allyl 2-ethyl 3-(tert-butyl)-5-(2-cyclopropylphenyl)-4-oxopyrrolidine-1,2-dicarboxylate Pyridinium dichromate (8.72 g, 23.17 mmol) in 6N aqueous HCl (200 mL) was cooled to 0° C. and treated with zinc dust (16.66 g, 255 mmol) in portions over about 20 minutes. After completion of the addition, the mixture was brought to room temperature and stirred until all zinc dissolved and bubbling stopped (~2 h). The deep blue solution was then transferred via cannula to a refluxing solution of Example 112A (4.12 g, 9.27 mmol) in ethanol (100 mL) over about 35 minutes. The reaction mixture was heated at strong reflux (heating block temp: 98° C.) overnight. After this time, heating was discontinued, and the mixture was transferred to a separatory funnel and extracted three times with dichloromethane (100 mL each). The combined organics were then dried over Na$_2$SO$_4$, filtered and concentrated in vacuo, and the crude residue was taken up in 28 mL ethanol and treated with a prepared solution of 5.8 mL of acetyl chloride in 17 mL ethanol (solution prepared at 0° C.). The reaction mixture was refluxed for 1 hour, then was cooled to room temperature and concentrated in vacuo. Silica gel chromatography, eluting with 0 to 20% ethyl acetate-heptanes, provided the title compound, 1.566 g (41% yield). $^1$H NMR (400 MHz, DMSO-d$_6$) δ ppm 7.69 (dd, J=6.8, 1.9 Hz, 1H), 7.11 (m, 3H), 5.73-5.63 (m, 2H), 5.06-4.94 (m, 2H), 4.65 (d, J=5.0 Hz, 1H), 4.44 (d, J=5.3 Hz, 2H), 4.24 (q, J=7.1 Hz, 2H), 2.64 (d, J=5.0 Hz, 1H), 2.13 (tt, J=8.5, 5.4 Hz, 1H), 1.26 (t, J=7.1 Hz, 3H), 1.07 (s, 9H), 0.97-0.73 (m, 3H), 0.52 (m, 1H); MS (ESI+) m/z 414.1 (M+H)+.

Example 149B (2S,3R,4S,5S)-1-allyl 2-ethyl 3-(tert-butyl)-5-(2-cyclopropylphenyl)-4-hydroxypyrrolidine-1,2-dicarboxylate Example 149A (1.566 g, 3.79 mmol) in ethanol (15.5 mL) was cooled to −10° C. and the solution was treated in one portion with sodium borohydride (0.233 g, 6.15 mmol). The reaction mixture was stirred in the cold bath for a few minutes, then removed from the cold bath and allowed to warm to room temperature (~40 minutes). After this time, the mixture was concentrated in vacuo, and the residue was taken up in ethyl acetate (50 mL) and saturated aqueous NaHCO$_3$ solution (50 mL), and the mixture was stirred for 30 minutes. The mixture was transferred to a separatory funnel, and the phases were separated. The organic layer was dried over Na$_2$SO$_4$, filtered and concentrated in vacuo, and the crude material was purified by silica gel chromatography, eluting with 0 to 30% ethyl acetate-heptanes to provide the title compound, 700 mg (45% yield). $^1$H NMR (400 MHz, DMSO-d$_6$) δ ppm 7.91-7.82 (m, 1H), 7.12-7.03 (m, 2H), 7.03-6.95 (m, 1H), 5.64 (m, 1H), 5.51 (d, J=6.3 Hz, 1H), 5.03-4.90 (m, 2H), 4.45 (dd, J=6.2, 2.9 Hz, 1H), 4.36 (dt, J=6.1, 2.6 Hz, 3H), 4.18 (q, J=7.0 Hz, 2H), 3.72 (m, 1H), 2.31 (t, J=3.3 Hz, 1H), 1.96 (tt, J=8.4, 5.4 Hz, 1H), 1.25 (t, J=7.1 Hz, 3H), 1.00 (s, 9H), 0.96-0.79 (m, 2H), 0.73 (dtd, J=9.4, 5.4, 3.6 Hz, 1H), 0.55 (dtd, J=8.4, 5.4, 3.3 Hz, 1H); MS (ESI+) m/z 416.1 (M+H)+.

Example 149C (2S,3R,4S,5S)-1-allyl 2-ethyl 3-(tert-butyl)-4-((5-cyclobutyl-2-methoxypyridin-3-yl)methoxy)-5-(2-cyclopropylphenyl)pyrrolidine-1,2-dicarboxylate Example 149B (0.350 g, 0.842 mmol), dried azeotropically with toluene, was dissolved in dimethylformamide (8.4 mL) and the mixture was cooled to 0° C. Potassium 2-methylpropan-2-olate (1M in tetrahydrofuran, 0.93 mL, 0.930 mmol) was added dropwise, followed by dropwise addition of Example 130C (0.259 g, 1.011 mmol). The reaction mixture was stirred at 0° C. for 45 minutes, poured into saturated aqueous NH$_4$Cl and extracted three times with methyl tert-butyl ether. The combined organics were dried over Na$_2$SO$_4$, filtered, and concentrated in vacuo. Silica gel chromatography, eluting with 0 to 30% methyl tert-butyl ether-heptanes, provided the title compound, 0.353 g (71% yield). $^1$H NMR (400 MHz, DMSO-d$_6$) δ ppm 7.90 (m, 1H), 7.75 (m, 1H), 7.14-7.02 (m, 2H), 6.96 (m, 1H), 6.92-6.78 (m, 1H), 5.79-5.51 (m, 2H), 5.08-4.88 (m, 2H), 4.50 (d, J=2.0 Hz, 1H), 4.39 (dq, J=4.7, 1.5 Hz, 2H), 4.29 (dd, J=5.7, 1.1 Hz, 1H), 4.24-4.01 (m, 3H), 3.81 (dt, J=13.1, 0.9 Hz, 1H), 3.74 (s, 3H), 3.31 (m, 1H), 2.51 (m, 1H), 2.31-2.11 (m, 2H), 2.08-1.75 (m, 5H), 1.14 (t, J=7.1 Hz, 3H), 1.03 (s, 9H), 0.95-0.78 (m, 2H), 0.65-0.52 (m, 2H); MS (ESI+) m/z 591.2 (M+H)+.

Example 149D (2S,3R,4S,5S)-ethyl 3-(tert-butyl)-4-((5-cyclobutyl-2-methoxypyridin-3-yl)methoxy)-5-(2-cyclopropylphenyl)pyrrolidine-2-carboxylate Example 149C (0.353 g, 0.598 mmol) was dissolved in ethyl acetate (3 mL) and dichloromethane (3 mL), and the solution was treated with 1,3-dimethylpyrimidine-2,4,6(1H,3H,5H)-trione (0.187 g, 1.195 mmol) and tetrakistriphenylphosphine palladium (6.9 mg, 5.98 µmol). The reaction mixture was stirred at room temperature for 30 minutes, and was diluted with 20 mL methyl tert-butyl ether and stirred vigorously with 20 mL of 10% aqueous Na$_2$CO$_3$ solution for 15 minutes. The phases were separated, and the organic layer was washed with brine, dried over Na$_2$SO$_4$, filtered, and concentrated in vacuo. The residue was used directly into the next reaction without further purification. MS (ESI+) m/z 507.2 (M+H)+.

Example 149E (2S,3R,4S,5S)-ethyl 3-(tert-butyl)-4-((5-cyclobutyl-2-methoxypyridin-3-yl)methoxy)-5-(2-cyclopropylphenyl)-1-((S)-tetrahydrofuran-2-carbonyl)pyrrolidine-2-carboxylate (S)-Tetrahydrofuran-2-carboxylic acid (0.069 g, 0.598 mmol) was refluxed in thionyl chloride (0.57 mL, 7.77 mmol) for 1 hour. The mixture was cooled to room temperature and concentrated in vacuo. Excess thionyl chloride was chased three times with dichloromethane (1 mL each), and the resulting crude acid chloride was treated with a solution of Example 149D (0.151 g, 0.299 mmol) in dichloromethane (1.4 mL) and with pyridine (0.29 mL, 3.59 mmol). The reaction was stirred at room temperature. After 1 hour, the reaction mixture was diluted with ethyl acetate (10 mL) and washed with water (3×3 mL) and with brine (3 mL). The organic layer was dried over Na$_2$SO$_4$, filtered, and concentrated in vacuo. The crude product was taken directly into the next reaction without further purification. MS (APCI+) m/z 605.7 (M+H)+.

Example 149F (2S,3R,4S,5S)-3-tert-butyl-4-[(5-cyclobutyl-2-methoxypyridin-3-yl)methoxy]-5-(2-cyclopropylphenyl)-1-[(2S)-oxolane-2-carbonyl]pyrrolidine-2-carboxylic acid Example 149E (0.181 g, 0.299 mmol) and lithium hydroxide (1M aqueous, 3 mL, 3 mmol) were stirred in tetrahydrofuran (3 mL) and methanol (3 mL) at 45° C. overnight. The reaction mixture was cooled to room temperature and acidified to pH 2 with 1N aqueous HCl. The mixture was concentrated in vacuo, and excess moisture was removed azeotropically with acetonitrile. The residue was chromatographed on silica gel, eluting with 0 to 5% methanol-ethyl acetate, to obtain the still-impure product. The crude material was further purified by silica gel chromatography, eluting with 5 to 25% 3:1 ethyl acetate-ethanol/heptanes, to provide the title compound, 0.0235 g (14% yield). $^1$H NMR (400 MHz, DMSO-d$_6$) δ ppm 8.02 (d, J=7.0 Hz, 1H), 7.75 (d, J=2.5 Hz, 1H), 7.12 (m, 2H), 7.02-6.95 (m, 1H), 6.82 (d, J=2.3 Hz, 1H), 5.89 (m, 1H), 4.69 (d, J=1.7 Hz, 1H), 4.32 (d, J=5.8 Hz, 1H), 4.22 (d, J=13.3 Hz, 1H), 4.05 (m, 1H), 3.85 (d, J=13.5 Hz, 1H), 3.75 (s, 3H), 3.70 (m, 1H), 3.61 (m, 1H), 3.30 (p, J=8.5 Hz, 1H), 2.55 (m, 1H), 2.27-2.17 (m, 2H), 2.01-1.80 (m, 7H), 1.63 (m, 1H), 1.02 (s, 9H), 0.96-0.81 (m, 3H), 0.69-0.51 (m, 2H); MS (ESI+) m/z 577.2 (M+H)+.

Example 150

(2S,3R,4S,5S)-3-tert-butyl-4-[(5-cyclobutyl-2-methoxypyridin-3-yl)methoxy]-5-(2-cyclopropylphenyl)-1-(oxane-4-carbonyl)pyrrolidine-2-carboxylic acid

Example 150A (2S,3R,4S,5S)-ethyl 3-(tert-butyl)-4-((5-cyclobutyl-2-methoxypyridin-3-yl)methoxy)-5-(2-cyclopropylphenyl)-1-(tetrahydro-2H-pyran-4-carbonyl)pyrrolidine-2-carboxylate The title compound was prepared according to the procedure of Example 149E, substituting tetrahydro-2H-pyran-4-carboxylic acid for (S)-tetrahydrofuran-2-carboxylic acid. The crude product was taken directly into the following reaction without further purification. MS (APCI$^+$) m/z 619.7 (M+H)$^+$.

Example 150B (2S,3R,4S,5S)-3-tert-butyl-4-[(5-cyclobutyl-2-methoxypyridin-3-yl)methoxy]-5-(2-cyclopropylphenyl)-1-(oxane-4-carbonyl)pyrrolidine-2-carboxylic acid The title compound was prepared according to the procedure of Example 149F, substituting Example 150A for Example 149E. $^1$H NMR (400 MHz, DMSO-$d_6$) δ ppm 8.00 (m, 1H), 7.76 (d, J=2.4 Hz, 1H), 7.10 (m, 2H), 6.99 (dd, J=7.2, 1.7 Hz, 1H), 6.86-6.80 (m, 1H), 5.68 (d, J=5.8 Hz, 1H), 4.64 (d, J=1.8 Hz, 1H), 4.34 (d, J=5.8 Hz, 1H), 4.23 (d, J=13.3 Hz, 1H), 3.89-3.80 (m, 2H), 3.75 (s, 3H), 3.65 (m, 1H), 3.31 (m, 1H), 3.11 (m, 2H), 2.83 (m, 2H), 2.57 (m, 1H), 2.26-2.17 (m, 2H), 2.07-1.80 (m, 4H), 1.52 (m, 4H), 1.02 (s, 9H), 0.97 (m, 1H), 0.90 (m, 1H), 0.67 (m, 1H), 0.58 (m, 1H); MS (ESI$^+$) m/z 591.4 (M+H)$^+$.

Example 151

(2S,3R,4S,5S)-5-(2-bromophenyl)-3-tert-butyl-4-[(2-methoxyquinolin-3-yl)methoxy]-1-[(2S)-oxolane-2-carbonyl]pyrrolidine-2-carboxylic acid The title compound was prepared according to the procedure described in Example 144 substituting 3-(bromomethyl)-2-methoxyquinoline (Example 106B) for 3-(bromomethyl)-5-cyclobutyl-2-methoxypyridine in Example 144E. $^1$H NMR (400 MHz, DMSO-$d_6$, 120° C.) δ ppm 8.14 (s, 1H), 7.67 (d, J=8.5 Hz, 1H), 7.55 (dd, J=8.0, 6.1 Hz, 2H), 7.49 (d, J=7.9 Hz, 1H), 7.39-7.24 (m, 3H), 7.15 (t, J=7.7 Hz, 1H), 5.64 (s, 1H), 4.76 (s, 1H), 4.48-4.37 (m, 2H), 4.07 (d, J=13.8 Hz, 1H), 3.96-3.88 (m, 4H), 3.76-3.61 (m, 2H), 2.60 (s, 1H), 2.05-1.91 (m, 1H), 1.89-1.59 (m, 3H), 1.04 (s, 9H); MS (ESI+) m/z 5611 & 613 (M+H)$^+$.

Example 152

(2S,3R,4S,5S)-3-tert-butyl-5-(3-tert-butylphenyl)-1-(ethoxycarbonyl)-4-{[2-methoxy-5-(trifluoromethyl)pyridin-3-yl]methoxy}pyrrolidine-2-carboxylic acid Example 121F (50 mg, 0.093 mmol, 1.0 eq) and trimethylamine (39.2 μL, 0.279 mmol, 3.0 eq) were dissolved in dichloromethane (1 mL). Ethyl chloroformate (12.1 mg, 0.11 mmol, 1.3 eq) was added neat. The reaction was stirred for 2 hours at room temperature. The reaction was concentrated and the residue was dissolved in 3:2 tetrahydrofuran/methanol (1 mL). Aqueous LiOH (5 M, 300 uL) was added and the reaction was stirred at 45° C. overnight. The solvent was removed under a stream of nitrogen, and the residue was acidified with 2 M aqueous HCl and diluted with CH$_3$CN. Purification was carried out using preparative reverse phase HPLC MS method TFA 8 (37.5 mg, 58% yield). $^1$H NMR (400 MHz, 120° C., DMSO-$d_6$:D$_2$O=9:1 (v/v)) δ ppm 8.28-8.22 (m, 1H), 7.73-7.60 (m, 1H), 7.38-7.28 (m, 1H), 7.17-7.03 (m, 3H), 5.02 (d, J=6.4 Hz, 1H), 4.31 (d, J=3.4 Hz, 1H), 4.27-4.18 (m, 2H), 3.96-3.80 (m, 6H), 2.47 (s, 1H), 1.17 (s, 9H), 0.99 (s, 9H), 0.94 (t, J=7.0 Hz, 3H); MS (APCI+) m/z 581.1 (M+H)$^+$.

Example 153

(2S,3R,4S,5S)-3-tert-butyl-5-(3-tert-butylphenyl)-4-{[2-methoxy-5-(trifluoromethyl)pyridin-3-yl]methoxy}-1-{[(propan-2-yl)oxy]carbonyl}pyrrolidine-2-carboxylic acid Example 153 was prepared using the procedure from Example 152, substituting isopropyl chloroformate for ethyl chloroformate. $^1$H NMR (400 MHz, 120° C., DMSO-$d_6$:D$_2$O=9:1 (v/v)) δ ppm 8.25 (s, 1H), 7.66 (d, J=2.0 Hz, 1H), 7.34 (dt, J=6.9, 1.8 Hz, 1H), 7.16 (s, 1H), 7.14-7.03 (m, 2H), 4.98 (d, J=6.3 Hz, 1H), 4.70-4.55 (m, 1H), 4.30 (d, J=3.4 Hz, 1H), 4.26-4.18 (m, 2H), 3.88-3.82 (m, 4H), 2.50-2.44 (m, 1H), 1.17 (s, 9H), 1.04 (d, J=6.2 Hz, 3H), 0.99 (s, 9H), 0.85 (d, J=6.3 Hz, 3H); MS (APCI+) m/z 595.1 (M+H)$^+$.

Example 154

(2S,3R,4S,5S)-3-tert-butyl-5-(3-tert-butylphenyl)-4-{[2-methoxy-5-(trifluoromethyl)pyridin-3-yl]methoxy}-1-[(1R,2S,4S)-7-oxabicyclo[2.2.1]heptane-2-carbonyl]pyrrolidine-2-carboxylic acid (1R,2S,4S)-7-oxabicyclo[2.2.1]heptane-2-carboxylic acid (15.9 mg, 0.11 mmol, 1.2 eq) was dissolved in dichloromethane (500 μL). Ghosez reagent (1-chloro-N,N,2-trimethyl-1-propenylamine) (25 μL, 0.25 mmol, 2.0 eq) was added neat and the reaction was stirred at room temperature for 10 minutes. Example 121F (50 mg, 0.093 mmol, 1.0 eq) in 1:1 tetrahydrofuran/pyridine (500 μL) was added and the reaction was stirred for 2 hours at room temperature. The solvent was removed under a stream of nitrogen and the residue was dissolved in 3:2 tetrahydrofuran/methanol (1 mL). Aqueous LiOH monohydrate (5 M, 300 uL) was added and the reaction was stirred at 45° C. overnight. The solvent was removed under a stream of nitrogen. The residue was acidified with 2 M aqueous HCl and diluted with CH$_3$CN. Purification was carried out using preparative reverse phase HPLC MS method TFA 8 (37.5 mg, 58% yield). $^1$H NMR (400 MHz, 120° C., DMSO-$d_6$:D$_2$O=9:1 (v/v)) δ ppm 8.26 (s, 1H), 7.89-7.68 (m, 1H), 7.50-7.39 (m, 1H), 7.20-7.09 (m, 3H), 5.21 (d, J=6.6 Hz, 1H), 4.53-4.44 (m, 2H), 4.42-4.33 (m, 1H), 4.29-4.20 (m, 2H), 4.01-3.83 (m, 4H), 2.44 (s, 1H), 1.86-1.66 (m, 1H), 1.60-1.31 (m, 2H), 1.20-1.13 (m, 11H), 1.03-0.95 (m, 10H); MS (APCI+) m/z 633.1 (M+H)$^+$.

Example 155

(2S,3R,4S,5S)-3-tert-butyl-4-[(5-cyclobutyl-2-methoxypyridin-3-yl)methoxy]-1-[(2S)-oxolane-2-carbonyl]-5-[2-(trifluoromethyl)phenyl]pyrrolidine-2-carboxylic acid The title compound was prepared using the procedures described in Example 144 substituting Core 21 for Core 10.

¹H NMR (400 MHz, DMSO-d₆) δ ppm 8.46 (d, J=8.0 Hz, 1H), 7.77 (s, 1H), 7.60 (d, J=7.8 Hz, 1H), 7.49 (d, J=7.9 Hz, 1H), 7.39 (d, J=7.7 Hz, 1H), 6.82 (s, 1H), 5.54 (s, 1H), 4.69 (s, 1H), 4.19 (d, J=13.3 Hz, 1H), 4.13 (d, J=5.5 Hz, 1H), 3.82 (d, J=13.2 Hz, 1H), 3.73 (d, J=1.3 Hz, 4H), 3.63 (s, 1H), 3.31 (t, J=8.2 Hz, 1H), 2.57 (s, 1H), 2.24 (d, J=8.2 Hz, 2H), 2.01-1.83 (m, 6H), 1.83-1.74 (m, 1H), 1.68 (s, 1H), 1.00 (d, J=1.2 Hz, 9H); MS (APCI+) m/z 605 (M+H)⁺.

Example 156

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(trifluoromethyl)phenyl]pyrrolidine-2-carboxylic acid The title compound was prepared using the procedures described in Example 144 substituting Core 21 for Core 10 and 3-(bromomethyl)-5-triflurormethyl-2-methoxypyridine for 3-(bromomethyl)-5-cyclobutyl-2-methoxypyridine. ¹H NMR (400 MHz, DMSO-d₆) δ ppm 8.49 (d, J=8.1 Hz, 1H), 8.28 (s, 1H), 7.57 (d, J=7.9 Hz, 1H), 7.45 (m, 1H), 7.35 (m, 1H), 7.06 (s, 1H), 5.55 (s, 1H), 4.66 (s, 1H), 4.31 (d, J=13.9 Hz, 1H), 4.14 (s, 1H), 3.89 (d, J=14.0 Hz, 1H), 3.85 (s, 3H), 3.73 (d, J=7.1 Hz, 1H), 3.63 (s, 1H), 2.62 (s, 1H), 1.90 (s, 1H), 1.84-1.74 (m, 1H), 1.68 (s, 1H), 1.01 (s, 9H); MS (ESI+) m/z 619 (M+H)⁺.

Example 157

(2S,3R,4S,5S)-3-tert-butyl-5-(3-tert-butylphenyl)-4-{[2-methoxy-5-(trifluoromethyl)pyridin-3-yl]methoxy}-1-[(2R)-oxane-2-carbonyl]pyrrolidine-2-carboxylic acid

Example 157A (2S,3R,4S,5S)-ethyl 3-(tert-butyl)-5-(3-(tert-butyl)phenyl)-4-((2-methoxy-5-(trifluoromethyl)pyridin-3-yl)methoxy)-1-((R)-tetrahydro-2H-pyran-2-carbonyl)pyrrolidine-2-carboxylate and

Example 157B (2S,3R,4S,5S)-ethyl 3-(tert-butyl)-5-(3-(tert-butyl)phenyl)-4-((2-methoxy-5-(trifluoromethyl)pyridin-3-yl)methoxy)-1-((S)-tetrahydro-2H-pyran-2-carbonyl)pyrrolidine-2-carboxylate Into a 4 mL vial was added tetrahydro-2H-pyran-2-carboxylic acid (24.25 mg, 0.186 mmol) and Ghosez reagent (37.0 μL, 0.280 mmol) in dichloromethane (0.5 mL) to provide a colorless solution. The reaction was stirred at room temperature for 10 minutes. Example 121F (50 mg, 0.093 mmol) in 1 mL 1:1 tetrahydrofuran/pyridine was added. The reaction immediately turned yellow. The reaction was stirred for 1 hour at room temperature. The solvent was removed under a stream of nitrogen. The residue was reconstituted in DMSO/methanol and purified on reverse phase HPLC using HPLC method TFA8. Two diastereomers were isolated.

Example 157C (2S,3R,4S,5S)-3-tert-butyl-5-(3-tert-butylphenyl)-4-{[2-methoxy-5-(trifluoromethyl)pyridin-3-yl]methoxy}-1-[(2R)-oxane-2-carbonyl]pyrrolidine-2-carboxylic acid Example 157A, the first eluting fraction, was diluted with 1 mL 3:2 tetrahydrofuran/methanol and 5 M aqueous LiOH (300 uL) and heated to 45° C. overnight. The solvent was removed under a stream of nitrogen. The residue was acidified with 2 M aqueous HCl, and extracted with dichloromethane (3×1 mL). The solvent was removed under N₂ and residue was dissolved in CH₃CN. Purification was carried out using preparative reverse phase HPLC MS method TFA 8 (22.5 mg, 39% yield). The stereochemistry of the title compound was arbitrarily assigned. ¹H NMR (400 MHz, 120° C., DMSO-d₆:D₂O=9:1 (v/v)) δ ppm 8.25 (s, 1H), 7.64 (s, 1H), 7.32 (s, 1H), 7.15-7.06 (m, 3H), 5.19 (d, J=6.2 Hz, 1H), 4.94-4.51 (m, 1H), 4.37-4.16 (m, 2H), 3.98-3.59 (m, 6H), 2.54 (s, 1H), 1.87-1.70 (m, 1H), 1.65-1.23 (m, 6H), 1.16 (s, 9H), 1.00 (s, 9H); MS (APCI+) m/z 621.3 (M+H)⁺.

Example 158

(2S,3R,4S,5S)-3-tert-butyl-5-(3-tert-butylphenyl)-4-{[2-methoxy-5-(trifluoromethyl)pyridin-3-yl]methoxy}-1-[(2S)-oxane-2-carbonyl]pyrrolidine-2-carboxylic acid The title compound was synthesized according to the procedure described in Example 157C, substituting Example 157B (second eluting isomer) for Example 157A. ¹H NMR (400 MHz, 120° C., DMSO-d₆:D₂O=9:1 (v/v)) δ ppm 8.25 (d, J=2.2 Hz, 1H), 7.74 (s, 1H), 7.42 (d, J=7.0 Hz, 1H), 7.15 (d, J=7.7 Hz, 3H), 5.39 (s, 1H), 4.54 (s, 1H), 4.29-4.19 (m, 2H), 3.85 (s, 5H), 3.59 (s, 1H), 2.44 (t, J=3.0 Hz, 1H), 1.69-1.25 (m, 7H), 1.17 (s, 9H), 0.99 (s, 9H); MS (APCI+) m/z 621.3 (M+H)⁺.

Example 159

(2S,3R,4S,5S)-5-(2-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid

Example 159A ethyl (2S,3R,4S,5S)-5-(2-bromophenyl)-3-(tert-butyl)-4-((2-methoxy-5-(trifluoromethyl)pyridin-3-yl)methoxy)-1-((S)-tetrahydrofuran-2-carbonyl)pyrrolidine-2-carboxylate Example 144D (96.4 mg, 0.206 mmol) and 3-(bromomethyl)-2-methoxy-5-(trifluoromethyl)pyridine (80.0 mg, 0.296 mmol) were dissolved in dimethylformamide (1 mL). The reaction was cooled to 0° C., potassium tert-butoxide (1M in tetrahydrofuran, 0.30 mL, 0.30 mmol) was added dropwise and the reaction was stirred at ambient temperature for 1 hour. The reaction was quenched by the addition of 1M aqueous HCl (0.3 mL) and was purified by silica gel chromatography (0 to 5% ethyl acetate in dichloromethane) to provide the title compound (81.5 mg, 60%). ¹H NMR (400 MHz, DMSO-d₆, 120° C.) δ ppm 8.30 (s, 1H), 8.00 (s, 1H), 7.47 (d, J=8.1 Hz, 1H), 7.23 (t, J=7.5 Hz, 1H), 7.16-7.04 (m, 2H), 5.61 (d, J=1.2 Hz, 1H), 4.79 (s, 1H), 4.42 (d, J=5.8 Hz, 1H), 4.33 (d, J=13.6 Hz, 1H), 4.10 (qd, J=7.1, 1.4 Hz, 2H), 4.01-3.92 (m, 2H), 3.87 (s, 3H), 3.77-3.55 (m, 2H), 2.49 (s, 1H), 2.06-1.91 (m, 1H), 1.86-1.61 (m, 3H), 1.14 (t, J=7.1 Hz, 3H), 1.03 (s, 9H); MS (ESI+) m/z 657 & 659 (M+H)⁺.

Example 159B (2S,3R,4S,5S)-5-(2-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid Example 159A (67.0 mg, 0.102 mmol) was dissolved in methanol (1 mL), and tetrahydrofuran (1 mL). Aqueous LiOH (1 M, 1.0 mL, 1.0 mmol) was added and the reaction was heated to 50° C. for 16 hours. The reaction was quenched by the addition of 1M aqueous HCl (1 mL), concentrated and purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (57.8 mg, 76%) as the TFA salt. $^1$H NMR (400 MHz, DMSO-$d_6$, 120° C.) δ ppm 8.29 (s, 1H), 8.08 (s, 1H), 7.45 (d, J=7.9 Hz, 1H), 7.22 (t, J=7.4 Hz, 1H), 7.14-7.02 (m, 2H), 5.62 (s, 1H), 4.74 (s, 1H), 4.40 (d, J=6.1 Hz, 1H), 4.36 (d, J=13.8 Hz, 1H), 4.01-3.94 (m, 2H), 3.88 (s, 3H), 3.78-3.61 (m, 2H), 2.55 (s, 1H), 2.02-1.88 (m, 1H), 1.86-1.58 (m, 3H), 1.03 (s, 9H); MS (ESI+) m/z 629 & 631 (M+H)$^+$.

Example 160

(2S,3R,4S,5S)-3-tert-butyl-1-(cyclobutanecarbonyl)-4-{[2-methoxy-5-(trifluoromethyl)pyridin-3-yl]methoxy}-5-{2-[(propan-2-yl)oxy]pyridin-3-yl}pyrrolidine-2-carboxylic acid The title compound was synthesized according to the procedure described in Example 146A-146D, substituting Example 133E for Example 133D in Example 146A, and cyclobutanecarboxylic acid for (S)-tetrahydrofuran-2-carboxylic acid in Example 146C. $^1$H NMR (400 MHz, DMSO-$d_6$) δ ppm 8.29 (s, 1H), 8.07 (s, 1H), 7.91 (d, J=4.8 Hz, 1H), 7.08 (s, 1H), 6.78 (t, J=6.2 Hz, 1H), 5.26 (dd, J=11.0, 6.0 Hz, 2H), 4.50 (s, 1H), 4.38 (d, J=13.7 Hz, 1H), 4.29 (dd, J=6.1, 2.0 Hz, 1H), 4.04-3.97 (m, 1H), 3.88 (d, J=0.8 Hz, 3H), 2.52 (s, 1H), 2.21-1.96 (m, 5H), 1.72 (s, 2H), 1.32 (d, J=6.1 Hz, 3H), 1.20 (d, J=6.1 Hz, 3H), 1.00 (s, 9H); MS (ESI+) m/z 594.1 (M+H)$^+$.

Example 161

(2S,3R,4S,5S)-3-tert-butyl-1-(cyclobutanecarbonyl)-4-[(5-cyclobutyl-2-methoxypyridin-3-yl)methoxy]-5-{2-[(propan-2-yl)oxy]pyridin-3-yl}pyrrolidine-2-carboxylic acid

Example 161A (2S,3R,4R,5S)-1-allyl 2-ethyl 3-(tert-butyl)-4-((5-cyclobutyl-2-methoxypyridin-3-yl)methoxy)-5-(2-isopropoxypyridin-3-yl)pyrrolidine-1,2-dicarboxylate The title compound was synthesized according to the procedure described in Example 133F, substituting Example 133E for Example 133D.

Example 161B (2S,3R,4R,5S)-ethyl 3-(tert-butyl)-4-((5-cyclobutyl-2-methoxypyridin-3-yl)methoxy)-5-(2-isopropoxypyridin-3-yl)pyrrolidine-2-carboxylate The title compound was synthesized according to the procedure described in Example 133G, substituting Example 161A for Example 133F.

Example 161C (2S,3R,4S,5S)-3-tert-butyl-1-(cyclobutanecarbonyl)-4-[(5-cyclobutyl-2-methoxypyridin-3-yl)methoxy]-5-{2-[(propan-2-yl)oxy]pyridin-3-yl}pyrrolidine-2-carboxylic acid The title compound was prepared according to the procedure described in Example 121G, substituting Example 161B for Example 121F, and cyclobutanecarboxylic acid for (S)-tetrahydrofuran-2-carboxylic acid. $^1$H NMR (400 MHz, DMSO-$d_6$) δ ppm 8.08 (s, 1H), 7.96 (d, J=4.8 Hz, 1H), 7.76 (d, J=2.5 Hz, 1H), 6.82 (dd, J=10.5, 4.2 Hz, 2H), 5.27 (dd, J=8.8, 6.2 Hz, 2H), 4.47 (d, J=13.9 Hz, 1H), 4.29 (d, J=13.1 Hz, 1H), 4.24 (dd, J=6.2, 2.1 Hz, 1H), 3.96 (d, J=13.2 Hz, 1H), 3.76 (s, 3H), 3.33 (q, J=8.4 Hz, 1H), 3.27 (s, 1H), 3.2 (m, 1H), 3.03 (m, 1H), 2.30-1.80 (m, 12H), 1.32 (d, J=6.1 Hz, 3H), 1.21 (d, J=6.1 Hz, 3H), 0.98 (s, 9H); MS (ESI+) m/z 580.2 (M+H)$^+$.

Example 162

(2S,3R,4S,5S)-5-(2-bromophenyl)-3-tert-butyl-4-[(5-tert-butyl-2-methoxyphenyl)methoxy]-1-[(2S)-oxolane-2-carbonyl]pyrrolidine-2-carboxylic acid

Example 162A (2S,3R,4S,5S)-ethyl 5-(2-bromophenyl)-3-(tert-butyl)-4-((5-(tert-butyl)-2-methoxybenzyl)oxy)-1-((S)-tetrahydrofuran-2-carbonyl)pyrrolidine-2-carboxylate Example 144D (68 mg, 0.145 mmol) and 2-(bromomethyl)-4-(tert-butyl)-1-methoxybenzene (49 mg, 0.191 mmol) were dried azeotropically with toluene, then dissolved in dimethylformamide (1 mL) and cooled to 0° C. Potassium 2-methylpropan-2-olate (1M in tetrahydrofuran, 0.174 mL, 0.174 mmol) was added dropwise. After 15 minutes, the reaction was quenched with 2 mL of saturated aqueous NH$_4$Cl and 10 drops of HCl. The organics were taken up in dichloromethane and purified using a 10 g silica gel cartridge, eluting with 5-100% methyl tert-butyl ether-heptanes over 20 minutes to provide (2S,3R,4S,5S)-ethyl 5-(2-bromophenyl)-3-(tert-butyl)-4-((5-(tert-butyl)-2-methoxybenzyl)oxy)-1-((S)-tetrahydrofuran-2-carbonyl)pyrrolidine-2-carboxylate (89 mg, 0.138 mmol, 95% yield). MS (APCI+) m/z 644 (M+H)$^+$.

Example 162B (2S,3R,4S,5S)-5-(2-bromophenyl)-3-tert-butyl-4-[(5-tert-butyl-2-methoxyphenyl)methoxy]-1-[(2S)-oxolane-2-carbonyl]pyrrolidine-2-carboxylic acid Example 144D (89 mg, 0.138 mmol) and lithium hydroxide (0.552 mL, 1.104 mmol) were dissolved in methanol (0.5 mL), tetrahydrofuran (1 mL) and water (1 mL). The reaction was warmed at 45° C. overnight. The solvent was removed under a stream of nitrogen and acidified with 0.552 mL of 2N aqueous HCl. The crude material was chromatographed using a 12 g silica gel cartridge with an ethanol/ethyl acetate/heptanes solvent system to provide (2S,3R,4S,5S)-5-(2-bromophenyl)-3-(tert-butyl)-4-((5-(tert-butyl)-2-methoxybenzyl)oxy)-1-((S)-tetrahydrofuran-2-carbonyl)pyrrolidine-2-carboxylic acid (39 mg, 0.063 mmol, 45.8% yield). $^1$H NMR (400 MHz, DMSO-d$_6$) δ ppm 8.12 (d, J=7.7 Hz, 1H), 7.48 (d, J=7.9 Hz, 1H), 7.24 (t, J=7.7 Hz, 1H), 7.11 (dd, J=8.6, 2.7 Hz, 2H), 6.83 (d, J=2.6 Hz, 1H), 6.73 (d, J=8.6 Hz, 1H), 5.58 (s, 1H), 4.66 (s, 1H), 4.33 (d, J=6.1 Hz, 1H), 4.21 (d, J=12.4 Hz, 1H), 3.92 (d, J=12.4 Hz, 1H), 3.76-3.69 (m, 1H), 3.63 (s, 3H), 2.52 (s, 1H), 1.95 (s, 1H), 1.80 (dt, J=13.5, 6.5 Hz, 1H), 1.68 (s, 1H), 1.25 (d, J=1.8 Hz, 1H), 1.17 (s, 9H), 0.98 (s, 9H), 0.91-0.78 (m, 1H); MS (APCI+) m/z 615/617 (M+H)$^+$ (Br doublet).

Example 163

(2S,3R,4R,5S)-3-tert-butyl-1-(cyclopentanecarbonyl)-4-{[2-methoxy-5-(trifluoromethyl)pyridin-3-yl]methoxy}-5-{2-[(propan-2-yl)oxy]pyridin-3-yl}pyrrolidine-2-carboxylic acid The title compound was synthesized according to the procedure described in Example 146A-146D, substituting Example 133E for Example 133D in Example 146A, and cyclopentanecarboxylic acid for (S)-tetrahydrofuran-2-carboxylic acid in Example 146C. $^1$H NMR (400 MHz, DMSO-d$_6$) δ ppm 8.51-8.33 (m, 2H), 8.11-8.05 (m, 1H), 7.90 (d, J=2.4 Hz, 1H), 6.96 (t, J=6.2 Hz, 1H), 5.53-5.45 (m, 1H), 5.24 (s, 1H), 4.99 (d, J=13.4 Hz, 1H), 4.64 (d, J=13.3 Hz, 1H), 4.38 (d, J=11.3 Hz, 1H), 4.04 (d, J=3.6 Hz, 1H), 4.01 (d, J=1.1 Hz, 3H), 2.34 (s, 1H), 2.11 (d, J=11.5 Hz, 1H), 1.68 (dd, J=11.5, 8.1 Hz, 1H), 1.55 (s, 4H), 1.42 (d, J=6.2 Hz, 3H), 1.36 (s, 1H), 1.34 (d, J=6.1 Hz, 3H), 1.00 (d, J=1.1 Hz, 9H); MS (ESI+) m/z 608.1 (M+H)$^+$.

Example 164

(2S,3R,4R,5S)-3-tert-butyl-1-(cyclohexanecarbonyl)-4-{[2-methoxy-5-(trifluoromethyl)pyridin-3-yl]methoxy}-5-{2-[(propan-2-yl)oxy]pyridin-3-yl}pyrrolidine-2-carboxylic acid The title compound was synthesized according to the procedure described in Example 146A-146D, substituting Example 133E for Example 133D in Example 146A, and cyclohexanecarboxylic acid for (S)-tetrahydrofuran-2-carboxylic acid in Example 146C. $^1$H NMR (400 MHz, DMSO-d$_6$) δ ppm 8.48 8.45 (m, 1H), 8.41 (s, 1H), 8.09 (d, J=4.7 Hz, 1H), 7.88 (d, J=2.4 Hz, 1H), 6.96 (t, J=6.2 Hz, 1H), 5.51 (p, J=6.1 Hz, 1H), 5.19 (s, 1H), 4.98 (d, J=13.3 Hz, 1H), 4.63 (d, J=13.3 Hz, 1H), 4.36 (d, J=11.4 Hz, 1H), 4.02 (d, J=3.6 Hz, 1H), 4.00 (s, 3H), 2.13 (dd, J=11.4, 3.6 Hz, 1H), 1.68-1.45 (m, 4H), 1.42 (d, J=6.2 Hz, 3H), 1.35 (d, J=6.2 Hz, 3H), 1.33-1.02 (m, 6H), 1.00 (s, 9H); MS (ESI+) m/z 622.1 (M+H)$^+$.

Example 165

(2S,3R,4S,5S)-3-tert-butyl-4-[(5-cyclobutyl-2-methoxypyridin-3-yl)methoxy]-5-[2-(difluoromethyl)phenyl]-1-[(2S)-oxolane-2-carbonyl]pyrrolidine-2-carboxylic acid The title compound was prepared using the procedures described in Example 144 substituting Core 22 for Core 10.

$^1$H NMR (400 MHz, DMSO-d$_6$) δ ppm 8.33 (d, J=7.8 Hz, 1H), 7.75 (d, J=2.4 Hz, 1H), 7.48 (d, J=7.6 Hz, 1H), 7.42-7.29 (m, 2H), 7.34 (t, J=55.0 Hz, 1H), 6.80 (s, 1H), 5.54 (s, 1H), 4.58 (s, 1H), 4.21-4.12 (m, 2H), 3.79 (d, J=13.3 Hz, 1H), 3.74 (m, 4H), 3.62 (s, 1H), 3.30 (p, J=8.4 Hz, 1H), 2.58 (s, 1H), 2.33-2.14 (m, 2H), 2.02-1.73 (m, 4H), 1.65 (s, 2H), 1.00 (s, 9H); MS (APCI+) m/z 587 (M+H)$^+$.

Example 166

(2S,3R,4R,5S)-5-(2-bromophenyl)-3-tert-butyl-4-[(5-cyclobutyl-2-methoxypyridin-3-yl)methoxy]-1-{[(propan-2-yl)oxy]carbonyl}pyrrolidine-2-carboxylic acid The title compound was prepared using the procedure described in Example 138A-138B, and was isolated as the minor diastereomer. $^1$H NMR (400 MHz, DMSO-d$_6$) δ ppm 8.30 (dd, J=7.8, 1.7 Hz, 1H), 7.92 (d, J=2.4 Hz, 1H), 7.57 (d, J=1.7 Hz, 2H), 7.36 (td, J=7.5, 1.3 Hz, 1H), 7.20 (td, J=7.6, 1.7 Hz, 1H), 5.24 (s, 1H), 4.98 (d, J=12.1 Hz, 1H), 4.67 (q, J=6.2 Hz, 1H), 4.62 (d, J=12.2 Hz, 1H), 4.32 (d, J=10.8 Hz, 1H), 4.00 (d, J=3.5 Hz, 1H), 3.86 (s, 3H), 3.48 (p, J=8.4 Hz, 1H), 2.37-2.26 (m, 2H), 2.20 (dd, J=10.8, 3.5 Hz, 1H), 2.12-1.92 (m, 3H), 1.87 (t, J=7.9 Hz, 1H), 1.11 (s, 2H), 1.06 (d, J=6.2 Hz, 1H), 1.03-0.91 (m, 12H); MS (APCI+) m/z 603/605 (M+H)$^+$ Br doublet.

Example 167

(2S,3R,4S,5S)-3-tert-butyl-5-(2,6-difluorophenyl)-4-{[2-methoxy-5-(trifluoromethyl)pyridin-3-yl]methoxy}-1-{[(propan-2-yl)oxy]carbonyl}pyrrolidine-2-carboxylic acid The title compound was prepared using the procedure described in Example 86, substituting Core 23 for Core 10. $^1$H NMR (501 MHz, DMSO-d$_6$) δ ppm 8.38 (d, J=2.4 Hz, 1H), 7.35 (s, 1H), 7.24 (p, J=7.6 Hz, 1H), 6.87 (t, J=8.7 Hz, 2H), 5.42 (d, J=7.6 Hz, 1H), 4.63 (s, 1H), 4.43 (d, J=13.6 Hz, 1H), 4.39 (dd, J=7.7, 4.6 Hz, 1H), 4.14 (d, J=4.9 Hz, 1H), 3.93 (d, J=13.6 Hz, 1H), 3.82 (s, 3H), 2.61 (t, J=4.8 Hz, 1H), 1.07 (d, J=6.2 Hz, 3H), 0.97 (s, 9H), 0.93-0.73 (m, 3H); MS (APCI+) m/z 575 (M+H)$^+$.

Example 168

(2S,3R,4S,5S)-3-tert-butyl-4-[(5-cyclobutyl-2-methoxypyridin-3-yl)methoxy]-5-(2-cyclopropylphenyl)-1-{[(propan-2-yl)oxy]carbonyl}pyrrolidine-2-carboxylic acid Example 168A 1-allyl 2-ethyl (2S,3R,4S,5S)-3-(tert-butyl)-4-((5-cyclobutyl-2-methoxypyridin-3-yl)methoxy)-5-(2-cyclopropylphenyl)pyrrolidine-1,2-dicarboxylate Example 112C (104 g, 2.503 mmol) and 3-(bromomethyl)-5-cyclobutyl-2-methoxypyridine (761.3 mg, 2.97 mmol) were dissolved in dimethylformamide (10 mL). The reaction was cooled to 0° C., and potassium tert-butoxide (1M in tetrahydrofuran, 3.00 mL, 3.00 mmol) was added dropwise. The reaction was stirred at ambient temperature for 1 hour. The reaction was poured into saturated aqueous NH$_4$Cl (50 mL), extracted with methyl tert-butyl ether (3×50 mL), and purified by silica gel chromatography (0% to 10% ethyl acetate in dichloromethane) to provide the title compound (1.11 g, 75%). $^1$H NMR (400 MHz, DMSO-d$_6$, 120° C.) δ ppm 7.96-7.91 (m, 1H), 7.78 (d, J=2.4 Hz, 1H), 7.13-7.05 (m, 2H), 7.03-6.94 (m, 1H), 6.88 (d, J=2.4 Hz, 1H), 5.69 (ddt, J=16.2, 10.4, 5.1 Hz, 1H), 5.63 (d, J=5.6 Hz, 1H), 5.07-4.93 (m, 2H), 4.53 (d, J=2.0 Hz, 1H), 4.42 (dq, J=5.0, 1.7 Hz, 2H), 4.33 (dd, J=5.6, 1.0 Hz, 1H), 4.22 (d, J=13.2 Hz, 1H), 4.14 (q, J=7.0 Hz, 2H), 3.84 (dd, J=13.1, 0.9 Hz, 1H), 3.77 (s, 3H), 3.34 (p, J=8.8 Hz, 1H), 2.57-2.52 (m, 1H), 2.31-2.19 (m, 2H), 2.05-1.81 (m, 5H), 1.17 (t, J=7.0 Hz, 3H), 1.06 (s, 9H), 0.98-0.85 (m, 2H), 0.68-0.55 (m, 2H); MS (ESI+) m/z 591 (M+H)$^+$.

Example 168B ethyl (2S,3R,4S,5S)-3-(tert-butyl)-4-((5-cyclobutyl-2-methoxypyridin-3-yl)methoxy)-5-(2-cyclopropyl-phenyl)pyrrolidine-2-carboxylate Example 168A (1.09 g, 1.845 mmol) was dissolved in ethyl acetate (5 mL) and dichloromethane (5 mL) and treated with 1,3-dimethylpyrimidine-2,4,6(1H,3H,5H)-trione (513.0 mg, 3.29 mmol) and tetrakis(triphenylphosphine) palladium (29.7 mg, 0.26 mmol). The reaction mixture was stirred at ambient temperature. After 1 hour, the reaction mixture was diluted with methyl tert-butyl ether (100 mL) and was stirred with 15 mL of 10% aqueous Na$_2$CO$_3$ (100 mL) solution for 30 minutes. The phases were then separated, and the organic layer was washed with brine, dried over Na$_2$SO$_4$, filtered, and concentrated. The residue was purified by silica gel chromatography eluting with 5% to 10% ethyl acetate in dichloromethane to provide the title compound (706.3 mg, 76%). $^1$H NMR (400 MHz, DMSO-d$_6$, 120° C.) δ ppm 7.77 (d, J=2.4 Hz, 1H), 7.62-7.56 (m, 1H), 7.18-7.11 (m, 2H), 7.03-6.97 (m, 1H), 6.89 (d, J=2.4 Hz, 1H), 4.59-4.50 (m, 1H), 4.20-4.02 (m, 5H), 3.71 (s, 3H), 3.60 (t, J=6.7 Hz, 1H), 3.32-3.27 (m, 1H), 3.11 (dt, J=15.9, 6.4 Hz, 1H), 2.31 (dd, J=6.7, 1.3 Hz, 1H), 2.23-2.09 (m, 2H), 2.02-1.73 (m, 4H), 1.19 (t, J=7.1 Hz, 3H), 0.95 (s, 9H), 0.87 (dd, J=8.4, 1.8 Hz, 2H), 0.64-0.53 (m, 2H); MS (ESI+) m/z 507 (M+H)$^+$.

Example 168C 2-ethyl 1-isopropyl (2S,3R,4S,5S)-3-(tert-butyl)-4-((5-cyclobutyl-2-methoxypyridin-3-yl)methoxy)-5-(2-cyclopropylphenyl)pyrrolidine-1,2-dicarboxylate Example 168B (201.1 mg, 0.397 mmol) was dissolved in dichloromethane (3 mL). Triethylamine (0.25 mL, 1.794 mmol) was added followed by isopropyl chloroformate (1 M, 0.60 mL, 0.60 mmol). The reaction was stirred at ambient temperature for 1 hour. The reaction was concentrated and purified by silica gel chromatography (5%->10% ethyl acetate in dichloromethane) to provide the title compound (235.5 mg, 100%). $^1$H NMR (400 MHz, DMSO-d$_6$, 120° C.) δ ppm 7.97-7.88 (m, 1H), 7.78 (d, J=2.4 Hz, 1H), 7.13-7.05 (m, 2H), 7.00 (dt, J=6.1, 3.3 Hz, 1H), 6.90 (d, J=2.3 Hz, 1H), 5.59 (d, J=5.6 Hz, 1H), 4.66 (hept, J=6.2 Hz, 1H), 4.47 (d, J=1.9 Hz, 1H), 4.30 (dd, J=5.6, 1.0 Hz, 1H), 4.21 (d, J=13.2 Hz, 1H), 4.14 (qd, J=7.0, 1.8 Hz, 2H), 3.84 (d, J=13.2 Hz, 1H), 3.77 (s, 3H), 3.34 (p, J=8.8 Hz, 1H), 2.53-2.51 (m, 1H), 2.26 (dddq, J=11.8, 9.2, 5.7, 3.2 Hz, 2H), 2.05-1.83 (m, 5H), 1.18 (t, J=7.0 Hz, 3H), 1.06 (s, 12H), 0.99-0.80 (m, 5H), 0.62 (dd, J=6.6, 2.9 Hz, 2H); MS (ESI+) m/z 593 (M+H)$^+$.

Example 168D (2S,3R,4S,5S)-3-tert-butyl-4-[(5-cyclobutyl-2-methoxypyridin-3-yl)methoxy]-5-(2-cyclopropyl-phenyl)-1-{[(propan-2-yl)oxy]carbonyl}pyrrolidine-2-carboxylic acid Example 168C (235.5 mg, 0.397 mmol) was dissolved in methanol (2 mL) and tetrahydrofuran (2 mL). Aqueous LiOH (1 M, 2 mL, 2 mmol) was added and the reaction was heated to 50° C. for 16 hours. The reaction was acidified with 2 M aqueous HCl to pH ~3 and stirred for 15 minutes. The reaction was diluted with water (50 mL) and extracted with dichloromethane (2×50 mL). The combined organic layers were washed with brine (50 mL), dried over Na$_2$SO$_4$, filtered and concentrated to provide the title compound (222.3 mg, 99%). $^1$H NMR (400 MHz, DMSO-d$_6$, 120° C.) δ ppm 8.04-7.96 (m, 1H), 7.78 (d, J=2.4 Hz, 1H), 7.09 (td, J=7.3, 6.5, 3.6 Hz, 2H), 6.99 (dd, J=6.5, 2.6 Hz, 1H), 6.88 (d, J=2.3 Hz, 1H), 5.58 (d, J=5.8 Hz, 1H), 4.65 (hept, J=6.2 Hz, 1H), 4.42 (d, J=1.9 Hz, 1H), 4.28 (d, J=5.7 Hz, 1H), 4.23 (d, J=13.4 Hz, 1H), 3.86 (d, J=13.4 Hz, 1H), 3.77 (d, J=1.4 Hz, 3H), 3.33 (p, J=8.6 Hz, 1H), 2.55 (d, J=1.9 Hz, 1H), 2.31-2.19 (m, 2H), 2.03-1.81 (m, 5H), 1.10-0.99 (m, 12H), 0.98-0.80 (m, 5H), 0.62 (p, J=4.8 Hz, 2H); MS (ESI+) m/z 565 (M+H)$^+$.

Example 169

(2S,3R,4S,5S)-3-tert-butyl-4-[(5-cyclobutyl-2-methoxypyridin-3-yl)methoxy]-1-(cyclohexanecarbonyl)-5-{2-[(propan-2-yl)oxy]pyridin-3-yl}pyrrolidine-2-carboxylic acid Example 169A (2S,3R,4S,5S)-ethyl 3-(tert-butyl)-4-hydroxy-5-(2-isopropoxypyridin-3-yl)pyrrolidine-2-carboxylate Example 133D (30 g, 69.0 mmol) and 1,3-dimethylpyrimidine-2,4,6(1H,3H,5H)-trione (21.56 g, 138 mmol) were dissolved in a mixture of dichloromethane and ethyl acetate (340 mL each). Tetrakis(triphenylphosphine) palladium(0) (0.798 g, 0.690 mmol) was added, and the flask was sealed with a septum and the reaction was stirred at ambient temperature for 15 minutes. The reaction was diluted with methyl tert-butyl ether (500 mL), 200 mL of 10% aqueous sodium carbonate was added, and the mixture was stirred for 10 minutes. The layers were separated, and the organic layer was dried over sodium sulfate, filtered, and concentrated in vacuo. The crude material was purified via flash chromatography, eluting with 0:100 to 60:40 ethyl acetate:heptanes over 30 minutes on a 330 g silica gel column to provide 19 g of the title compound. $^1$H NMR (400 MHz, CDCl$_3$) δ ppm 8.06 (dd, J=5.0, 1.9 Hz, 1H), 7.73 (ddd, J=7.3, 1.8, 0.9 Hz, 1H), 6.87 (dd, J=7.3, 5.0 Hz, 1H), 5.36 (p, J=6.1 Hz, 1H), 4.37 (t, J=4.8 Hz, 1H), 4.31-4.17 (m, 3H), 3.69 (d, J=6.2 Hz, 1H), 2.62 (s, 1H), 2.19 (dd, J=6.3, 1.1 Hz, 1H), 1.69 (br s, 1H), 1.39 (d, J=6.2 Hz, 3H), 1.36 (d, J=6.2 Hz, 3H), 1.31 (t, J=7.1 Hz, 3H), 1.04 (s, 9H); MS (ESI+) m/z 351.2 (M+H)$^+$.

Example 169B (2S,3R,4S,5S)-ethyl 3-(tert-butyl)-1-(cyclohexanecarbonyl)-4-hydroxy-5-(2-isopropoxypyridin-3-yl)pyrrolidine-2-carboxylate To the solution of Example 169A (100 mg, 0.285 mmol) and triethylamine (0.119 mL, 0.856 mmol) in dichloromethane (3 mL) was added cyclohexanecarbonyl chloride (0.057 mL, 0.428 mmol) in an ice-bath. The mixture was stirred in ice-bath for 30 minutes, and was allowed to warm to ambient temperature. Dichloromethane (10 mL) and saturated aqueous NH$_4$Cl (10 mL) were added and the organic layer was washed with brine, dried over MgSO$_4$, filtered, and concentrated. The residue was purified via chromatography, on a 4 g silica gel cartridge, eluting with ethyl acetate in heptanes at 0-40% gradient to provide title compound 106 mg (81% yield). LC/MS (APCI+) m/z 461.45 (M+H)$^+$.

Example 169C (2S,3R,4S,5S)-ethyl 3-(tert-butyl)-4-((5-cyclobutyl-2-methoxypyridin-3-yl)methoxy)-1-(cyclohexanecarbonyl)-5-(2-isopropoxypyridin-3-yl)pyrrolidine-2-carboxylate To Example 169B (46 mg, 0.100 mmol) and 3-(bromomethyl)-5-cyclobutyl-2-methoxypyridine (25.6 mg, 0.100 mmol) in dimethylformamide (1 mL) cooling in an ice bath, potassium 2-methylpropan-2-olate (16.81 mg, 0.150 mmol, 0.75 mL, 1.0M in tetrahydrofuran) was added dropwise. The mixture was stirred in ice-bath for 30 minutes, and allowed to warm to ambient temperature. Dichloromethane and saturated aqueous NH$_4$Cl were added. The organic layer was washed with brine, dried over MgSO$_4$, filtered, and concentrated. The residue was purified by chromatography, eluting with ethyl acetate in heptane, on a 4 g silica gel cartridge using a 0-40% gradient to provide the title compound.

Example 169D (2S,3R,4S,5S)-3-(tert-butyl)-4-((5-cyclobutyl-2-methoxypyridin-3-yl)methoxy)-1-(cyclohexanecarbonyl)-5-(2-isopropoxypyridin-3-yl)pyrrolidine-2-carboxylic acid Example 169C was dissolved in methanol/6M aqueous LiOH (2 mL, 4:1) and the mixture was stirred at 45° C. overnight. The mixture was adjusted pH to 1~2 by adding 2M aqueous HCl and the resulting mixture was purified via reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A to provide title compound 25 mg (41.2% yield). $^1$H NMR (400 MHz, DMSO-d$_6$) δ ppm 8.20 (s, 1H), 7.98 (s, 1H), 7.77 (d, J=2.5 Hz, 1H), 6.84 (s, 2H), 5.35 (s, 1H), 5.25 (m, 1H), 4.53 (d, J=2.9 Hz, 1H), 4.29 (d, J=13.1 Hz, 1H), 4.25 (dd, J=6.2, 2.2 Hz, 1H), 3.98 (d, J=13.2 Hz, 1H), 3.76 (s, 3H), 3.36-3.30 (m, 1H), 2.51 (s, 1H), 2.27-2.20 (m, 2H), 1.97-1.82 (m, 4H), 1.59 (d, J=63.4 Hz, 5H), 1.31 (d, J=6.1 Hz, 3H), 1.28-1.17 (m, 6H), 1.09 (s, 2H), 0.99 (s, 9H); MS (ESI+) m/z 608.2 (M+H)$^+$.

Example 170

(2S,3R,4S,5S)-3-tert-butyl-4-[(5-cyclobutyl-2-methoxypyridin-3-yl)methoxy]-5-(2-methylphenyl)-1-[(2S)-oxane-2-carbonyl]pyrrolidine-2-carboxylic acid

Example 170A (2S,3R,4S,5S)-ethyl 3-(tert-butyl)-4-hydroxy-5-(o-tolyl)pyrrolidine-2-carboxylate To a solution of Example 129C (430 mg, 1.104 mmol) and 1,3-dimethylpyrimidine-2,4,6(1H,3H,5H)-trione (345 mg, 2.208 mmol) in ethyl acetate/dichloromethane (1:1, 4 mL) was added tetrakis(triphenylphosphine)palladium(0) (22.78 mg, 0.022 mmol). The mixture was stirred at ambient temperature for 30 minutes, and LC/MS showed the conversion was finished. Dichloromethane (10 mL) and aqueous Na$_2$CO$_3$ (2 M, 2 mL) were added and the mixture was stirred for 10 minutes. The organic layer was washed with brine, dried over MgSO$_4$, filtered, and concentrated. The residue was purified via silica gel chromatography, eluting with ethyl acetate in heptanes at 0-50% gradient to provide title compound 300 mg, (89% yield). LC/MS (APCI+), m/z 306.3 (M+H)$^+$.

Example 170B (2S,3R,4S,5S)-ethyl 3-(tert-butyl)-4-hydroxy-1-((S)-tetrahydro-2H-pyran-2-carbonyl)-5-(o-tolyl)pyrrolidine-2-carboxylate To Example 170A (200 mg, 0.655 mmol) and triethylamine (0.274 mL, 1.965 mmol) in dichloromethane (2 mL) cooling in an ice-bath was added (S)-tetrahydro-2H-pyran-2-carbonyl chloride (117 mg, 0.786 mmol). The mixture was stirred in an ice-bath for 20 minutes, and allowed to warm to room temperature. Dichloromethane (10 mL) and brine (10 mL) were added. The organic layer washed with water, dried over MgSO$_4$, filtered, and concentrated to provide title compound (270 mg, 99% yield) which was used in the next step. LC/MS (APCI+) m/z 418.42 (M+H)$^+$.

Example 170C (2S,3R,4S,5S)-3-(tert-butyl)-4-((5-cyclobutyl-2-methoxypyridin-3-yl)methoxy)-1-((S)-tetrahydro-2H-pyran-2-carbonyl)-5-(o-tolyl)pyrrolidine-2-carboxylic acid To Example 170B (50 mg, 0.120 mmol) and 3-(bromomethyl)-5-cyclobutyl-2-methoxypyridine (36.8 mg, 0.144 mmol) in dimethylformamide (1 mL) cooling in an ice-bath, potassium 2-methylpropan-2-olate (20.16 mg, 0.180 mmol, 0.18 mL, 1.0M in tetrahydrofuran) was added dropwise. The mixture was stirred in ice-bath for 20 minutes, and was allowed to warm to ambient temperature. LC/MS showed the conversion was finished. Dichloromethane and saturated aqueous NH$_4$Cl (2 mL) were added. The organic layer was washed with brine, dried over MgSO$_4$, filtered, and concentrated. The residue was purified via chromatography, eluting with ethyl acetate in heptanes at a 0-40% gradient to provide the ester of (2S,3R,4S,5S)-ethyl 3-(tert-butyl)-4-((5-cyclobutyl-2-methoxypyridin-3-yl)methoxy)-1-((S)-tetrahydro-2H-pyran-2-carbonyl)-5-(o-tolyl)pyrrolidine-2-carboxylate which was dissolved in methanol (1.5 mL) and 6M aqueous LiOH (0.5 mL) and stirred at 450 for 17 hours. The mixture was adjusted pH to 1~2 by adding 2M aqueous HCl and the reaction mixture was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to provide the title compound 28 mg (41.4% yield). $^1$H NMR (400 MHz, DMSO-d$_6$) δ ppm 8.07-8.01 (m, 1H), 7.76 (dd, J=2.4, 0.8 Hz, 1H), 7.10 (s, 3H), 6.88 (dq, J=2.4, 0.9 Hz, 1H), 5.54 (s, 1H), 4.63 (s, 1H), 4.23 (d, J=5.9 Hz, 1H), 4.20-4.15 (dt, J=13.3, 0.9 Hz, 1H), 3.82 (dt, J=13.3, 0.9 Hz, 1H), 3.77 (s, 1H), 3.75 (s, 3H), 3.34-3.30 (m, 2H), 2.64 (s, 1H), 2.48 (s, 1H), 2.32 (s, 3H), 2.27-2.16 (m, 2H), 2.03-1.78 (m, 4H), 1.71-1.24 (m, 6H), 1.00 (s, 9H); MS (ESI+) m/z 565.33 (M+H)$^+$.

Example 171

(2S,3R,4S,5S)-3-tert-butyl-4-[(5-cyclobutyl-2-methoxypyridin-3-yl)methoxy]-5-(2-cyclopropyl-phenyl)-1-[(2S)-oxane-2-carbonyl]pyrrolidine-2-carboxylic acid Example 171A ethyl (2S,3R,4S,5S)-3-(tert-butyl)-4-((5-cyclobutyl-2-methoxypyridin-3-yl)methoxy)-5-(2-cyclopropyl-phenyl)-1-((S)-tetrahydro-2H-pyran-2-carbonyl)pyrrolidine-2-carboxylate Example 168B (172.5 mg, 0.340 mmol) was dissolved in dichloromethane (3 mL). Triethylamine (0.25 mL, 1.794 mmol) was added followed by (S)-tetrahydro-2H-pyran-2-carbonyl chloride (70.0 mg, 0.471 mmol). The reaction was stirred at ambient temperature for 1 hour. The reaction was concentrated and purified by silica gel chromatography (5%->10% ethyl acetate in dichloromethane) to provide the title compound (188.1 mg, 89%). $^1$H NMR (400 MHz, DMSO-d$_6$, 120° C.) δ ppm 7.99 (dd, J=7.3, 1.9 Hz, 1H), 7.75 (d, J=2.4 Hz, 1H), 7.10 (d, J=8.3 Hz, 2H), 6.98 (dd, J=7.1, 1.9 Hz, 1H), 6.86 (d, J=2.4 Hz, 1H), 5.87 (s, 1H), 4.71 (s, 1H), 4.31 (d, J=5.6 Hz, 1H), 4.19 (d, J=13.2 Hz, 1H), 4.08 (qd, J=7.1, 1.1 Hz, 2H), 3.81 (dt, J=13.2, 0.9 Hz, 1H), 3.73 (s, 4H), 3.31 (p, J=9.1, 8.7 Hz, 1H), 2.44 (d, J=1.8 Hz, 1H), 2.31-2.11 (m, 2H), 2.07-1.78 (m, 5H), 1.73-1.21 (m, 8H), 1.13 (t, J=7.1 Hz, 3H), 1.02 (s, 9H), 0.99-0.83 (m, 2H), 0.78-0.66 (m, 1H), 0.51 (dtd, J=9.0, 5.2, 3.0 Hz, 1H); MS (ESI+) m/z 593 (M+H)$^+$.

Example 171B (2S,3R,4S,5S)-3-tert-butyl-4-[(5-cyclobutyl-2-methoxypyridin-3-yl)methoxy]-5-(2-cyclopropyl-phenyl)-1-[(2S)-oxane-2-carbonyl]pyrrolidine-2-carboxylic acid Example 171A (161.9 mg, 0.262 mmol) was dissolved in methanol (1 mL), and tetrahydrofuran (1 mL). Aqueous LiOH (1 M, 1 mL, 1 mmol) was added and the reaction was heated to 50° C. for 16 hours. The reaction was acidified with 2 M aqueous HCl to pH ~3 and stirred for 15 minutes. The reaction was diluted with water (25 mL) and extracted with dichloromethane (2×25 mL). The combined organic layers were washed with brine (25 mL), dried over Na$_2$SO$_4$, filtered and concentrated to provide the title compound (138.9 mg, 90%)$^1$H NMR (400 MHz, DMSO-d$_6$, 120° C.) δ ppm 8.04-7.96 (m, 1H), 7.78 (d, J=2.4 Hz, 1H), 7.09 (td, J=7.3, 6.5, 3.6 Hz, 2H), 6.99 (dd, J=6.5, 2.6 Hz, 1H), 6.88 (d, J=2.3 Hz, 1H), 5.58 (d, J=5.8 Hz, 1H), 4.65 (hept, J=6.2 Hz, 1H), 4.42 (d, J=1.9 Hz, 1H), 4.28 (d, J=5.7 Hz, 1H), 4.23 (d, J=13.4 Hz, 1H), 3.86 (d, J=13.4 Hz, 1H), 3.77 (d, J=1.4 Hz, 3H), 3.49 (s, 2H), 3.33 (p, J=8.6 Hz, 1H), 2.55 (d, J=1.9 Hz, 1H), 2.31-2.19 (m, 2H), 2.03-1.81 (m, 5H), 1.10-0.99 (m, 12H), 0.98-0.80 (m, 5H), 0.62 (p, J=4.8 Hz, 2H); MS (ESI+) m/z 565 (M+H)$^+$.

Example 172

(2S,3R,4S,5S)-3-tert-butyl-4-[(5-tert-butyl-2-methoxyphenyl)methoxy]-5-(2-cyclopropylphenyl)-1-[(2S)-oxolane-2-carbonyl]pyrrolidine-2-carboxylic acid Example 172A (2S,3R,4S,5S)-1-allyl 2-ethyl 3-(tert-butyl)-4-((5-(tert-butyl)-2-methoxybenzyl)oxy)-5-(2-cyclopropyl-phenyl)pyrrolidine-1,2-dicarboxylate Example 149B (0.135 g, 0.324 mmol), dried azeotropically with toluene, was dissolved in dimethylformamide (3.2 mL) and the mixture was cooled to 0° C. Potassium 2-methylpropan-2-olate (1M in tetrahydrofuran, 0.36 mL, 0.360 mmol) was added dropwise, followed by dropwise addition of 2-(bromomethyl)-4-(tert-butyl)-1-methoxybenzene (0.100 g, 0.389 mmol). The reaction mixture was stirred at 0° C. for 45 minutes, and it was poured into saturated aqueous NH$_4$Cl and extracted three times with methyl tert-butyl ether. The combined organics were dried over Na$_2$SO$_4$, filtered and concentrated in vacuo. Silica gel chromatography, eluting with 0 to 30% methyl tert-butyl ether-heptanes, provided the title compound, 0.051 g (27% yield). $^1$H NMR (500 MHz, DMSO-d$_6$) δ ppm 7.94 (m, 1H), 7.16-7.05 (m, 3H), 7.01-6.94 (m, 1H), 6.86 (d, J=2.6 Hz, 1H), 6.74 (m, 1H), 5.74-5.59 (m, 2H), 5.05-4.95 (m, 2H), 4.54-4.47 (m, 1H), 4.40 (dq, J=4.8, 1.4 Hz, 2H), 4.29 (dd, J=5.7, 1.1 Hz, 1H), 4.22-4.08 (m, 3H), 3.88 (m, 1H), 3.63 (s, 3H), 2.52 (m, 1H), 1.99 (ddd, J=13.7, 8.5, 5.4 Hz, 1H), 1.19-1.16 (m, 12H), 1.04 (s, 9H), 0.97-0.85 (m, 2H), 0.63 (m, 2H); MS (ESI$^+$) m/z 592.1 (M+H)$^+$.

Example 172B (2S,3R,4S,5S)-ethyl 3-(tert-butyl)-4-((5-(tert-butyl)-2-methoxybenzyl)oxy)-5-(2-cyclopropylphenyl)pyrrolidine-2-carboxylate Example 172A (0.051 g, 0.086 mmol) in ethyl acetate (0.5 mL) and dichloromethane (0.5 mL) was treated with 1,3-dimethylpyrimidine-2,4,6(1H,3H,5H)-trione (0.027 g, 0.172 mmol) and tetrakis(triphenylphosphine)palladium(0) (1 mg, 0.865 µmol), and the reaction was stirred at room temperature. After 1 hour, the reaction mixture was diluted with 3 mL methyl tert-butyl ether and was stirred with 3 mL of 10% aqueous Na$_2$CO$_3$ solution for 30 minutes. The phases were separated, and the organic layer was washed with brine, dried over Na$_2$SO$_4$, filtered, and concentrated in vacuo to provide the crude title compound (38 mg, 87% yield), which was used in the following reaction without further purification. MS (APCI$^+$) m/z 508.6 (M+H)$^+$.

Example 172C (2S,3R,4S,5S)-ethyl 3-(tert-butyl)-4-((5-(tert-butyl)-2-methoxybenzyl)oxy)-5-(2-cyclopropylphenyl)-1-((S)-tetrahydrofuran-2-carbonyl)pyrrolidine-2-carboxylate A stock solution of (S)-tetrahydrofuran-2-carbonyl chloride was prepared as follows: 101 mg (0.87 mmol) of (S)-tetrahydrofuran-2-carboxylic acid was refluxed in 0.9 mL of thionyl chloride for 1 hour, and the solution was cooled to room temperature and concentrated in vacuo, with excess thionyl chloride chased by dichloromethane (3×1 mL). The resulting crude acid chloride was dissolved in 2.2 mL dichloromethane and was used in the present reaction and that of Example 173D. Stock solution (0.4 mL, 0.150 mmol) of crude (S)-tetrahydrofuran-2-carbonyl chloride was added to a solution of Example 172B (0.038 g, 0.075 mmol) in 1 mL dichloromethane. Pyridine (0.073 mL, 0.898 mmol) was added, and the reaction was stirred at room temperature for 1 hour. After this time, the mixture was diluted with ethyl acetate and washed three times with water and once with brine. The organic layer was dried over $Na_2SO_4$, filtered, and concentrated in vacuo, and the crude title compound thus obtained was taken directly into the next reaction without further purification. MS (APCI$^+$) m/z 606.6 (M+H)$^+$.

Example 172D (2S,3R,4S,5S)-3-tert-butyl-4-[(5-tert-butyl-2-methoxyphenyl)methoxy]-5-(2-cyclopropylphenyl)-1-[(2S)-oxolane-2-carbonyl]pyrrolidine-2-carboxylic acid Example 172C (0.045 g, 0.075 mmol) and lithium hydroxide (1M aqueous, 0.75 mL, 0.75 mmol) were stirred in tetrahydrofuran (0.75 mL) and methanol (0.75 mL) overnight at 45° C., and at 50° C. for 1 hour. The reaction mixture was cooled to room temperature and acidified to pH ~2 with 1N aqueous HCl, and the mixture was extracted with dichloromethane (3×3 mL). The combined organic extracts were dried over $Na_2SO_4$, filtered and concentrated in vacuo, and the crude product was purified by silica gel chromatography, eluting with 0 to 100% ethyl acetate-heptanes to provide the title compound, 0.006 g (14% yield). $^1$H NMR (400 MHz, DMSO-d$_6$) δ ppm 8.07 (m, 1H), 7.08 (m, 3H), 6.96 (m, 1H), 6.81 (m, 1H), 6.71 (d, J=8.5 Hz, 1H), 5.84 (m, 1H), 4.61 (m, 1H), 4.27 (m, 1H), 4.18 (d, J=12.6 Hz, 1H), 3.83 (d, J=12.6 Hz, 1H), 3.70 (m, 1H), 3.60 (s, 3H), 3.57 (m, 2H), 2.56 (m, 1H), 2.04-1.83 (m, 3H), 1.62 (m, 2H), 1.15 (s, 9H), 0.99 (s, 9H), 0.90 (m, 2H), 0.68-0.51 (m, 2H); MS (ESI$^+$) m/z 578.2 (M+H)$^+$.

Example 173

(2S,3R,4S,5S)-4-[(5-bromo-2-methoxypyridin-3-yl)methoxy]-3-tert-butyl-5-(2-cyclopropylphenyl)-1-[(2S)-oxolane-2-carbonyl]pyrrolidine-2-carboxylic acid Example 173A 5-bromo-3-(bromomethyl)-2-methoxypyridine To a solution of 5-bromo-2-methoxy-3-methylpyridine (Ark; 2.981 g, 14.75 mmol) in CCl$_4$ (12 mL) was added N-bromosuccinimide (2.89 g, 16.23 mmol) and (E)-2,2'-(diazene-1,2-diyl)bis(2-methylpropanenitrile) (0.036 g, 0.221 mmol). The reaction mixture was stirred at 80° C. for 2 hours, and it was cooled in an ice bath and filtered through diatomaceous earth. The solution was concentrated in vacuo to provide the title compound (2.0538 g, 50% yield). $^1$H NMR (501 MHz, CDCl$_3$) δ ppm 8.17 (d, J=2.4 Hz, 1H), 7.74 (d, J=2.4 Hz, 1H), 4.43 (s, 2H), 4.01 (s, 3H).

Example 173B (2S,3R,4S,5S)-1-allyl 2-ethyl 4-((5-bromo-2-methoxypyridin-3-yl)methoxy)-3-(tert-butyl)-5-(2-cyclopropylphenyl)pyrrolidine-1,2-dicarboxylate Example 149B (0.370 g, 0.890 mmol), dried azeotropically with toluene, was dissolved in dimethyl formamide (3.2 mL) and cooled to 0° C. Potassium 2-methylpropan-2-olate (1M in tetrahydrofuran, 0.98 mL, 0.980 mmol) was added dropwise, followed by Example 173A (0.300 g, 1.068 mmol). The reaction mixture was stirred at 0° C. for 45 minutes, and the mixture was poured into saturated aqueous NH$_4$Cl and extracted three times with methyl tert-butyl ether. The combined organics were dried over $Na_2SO_4$, filtered, and concentrated in vacuo. Silica gel chromatography, eluting with 0 to 40% methyl tert-butyl ether-heptanes, provided the impure title compound, 0.246 g (45% yield). $^1$H NMR (500 MHz, DMSO-d$_6$) δ ppm 8.02 (m, 1H), 7.94-7.87 (m, 1H), 7.14-7.06 (m, 2H), 7.05-6.97 (m, 1H), 6.94 (m, 1H), 5.75-5.61 (m, 2H), 5.02 (m, 2H), 4.53 (m, 1H), 4.43 (m, 2H), 4.33 (m, 1H), 4.24-4.14 (m, 3H), 3.96-3.89 (m, 1H), 3.79 (s, 3H), 2.52 (m, 1H), 2.04-1.94 (m, 1H), 1.21 (t, J=6.6 Hz, 3H), 1.07 (s, 9H), 0.90 (m, 2H), 0.67-0.54 (m, 2H); MS (ESI$^+$) m/z 615.0 (M+H)$^+$.

Example 173C (2S,3R,4S,5S)-ethyl 4-((5-bromo-2-methoxypyridin-3-yl)methoxy)-3-(tert-butyl)-5-(2-cyclopropylphenyl)pyrrolidine-2-carboxylate The impure product from Example 173B (0.246 g, 0.400 mmol) in ethyl acetate (2 mL) and dichloromethane (2 mL) was treated with 1,3-dimethylpyrimidine-2,4,6(1H,3H,5H)-trione (0.125 g, 0.799 mmol) and tetrakis(triphenylphosphine)palladium(0) (4.6 mg, 4.00 μmol), and the reaction mixture was stirred at room temperature. After 1 hour, the reaction mixture was diluted with 15 mL methyl tert-butyl ether and the mixture was stirred with 15 mL of 10% aqueous Na$_2$CO$_3$ solution for 30 minutes. The mixture was transferred to a separatory funnel, the phases were separated, and the organic layer was washed with brine, dried over $Na_2SO_4$, filtered, and concentrated in vacuo to provide the crude title compound, which was taken directly into the following reaction without further purification. MS (APCI$^+$) m/z 533.5 (M+H)$^+$.

Example 173D (2S,3R,4S,5S)-ethyl 4-((5-bromo-2-methoxypyridin-3-yl)methoxy)-3-(tert-butyl)-5-(2-cyclopropylphenyl)-1-((S)-tetrahydrofuran-2-carbonyl)pyrrolidine-2-carboxylate Stock (S)-tetrahydrofuran-2-carbonyl chloride solution from Example 172C (1.8 mL, 0.723 mmol) was added to a solution of Example 173C (0.192 g, 0.361 mmol) in 1 mL dichloromethane. Pyridine (0.35 mL, 4.34 mmol) was added, and the reaction mixture was stirred at room temperature for 1 hour. The reaction mixture was diluted with ethyl acetate and washed three times with water and once with brine. The organic layer was dried over $Na_2SO_4$, filtered, and concentrated in vacuo to provide the crude title compound, which was taken directly into the next reaction without further purification. MS (APCI$^+$) m/z 631.5 (M+H)$^+$.

Example 173E (2S,3R,4S,5S)-4-[(5-bromo-2-methoxypyridin-3-yl)methoxy]-3-tert-butyl-5-(2-cyclopropylphenyl)-1-[(2S)-oxolane-2-carbonyl]pyrrolidine-2-carboxylic acid Example 173D (0.227 g, 0.361 mmol) and lithium hydroxide (1M aqueous, 3 mL, 3 mmol) were stirred in tetrahydrofuran (3 mL) and methanol (3 mL) at 45° C. overnight. The reaction mixture was cooled to room temperature and acidified to pH~2 with 1N aqueous HCl, and the mixture was extracted with dichloromethane (3×10 mL). The combined organic extracts were dried over $Na_2SO_4$, filtered, and concentrated in vacuo. The crude product was subjected to silica gel chromatography, eluting with 0 to 5% methanol-ethyl acetate. The material thus obtained was further purified by reverse-phase HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A) to provide the title compound, 0.048 g (22% yield). $^1$H NMR (400 MHz, DMSO-$d_6$) δ ppm 7.98 (m, 2H), 7.16-7.05 (m, 2H), 6.98 (dd, J=7.0, 2.0 Hz, 1H), 6.87 (dd, J=2.4, 1.2 Hz, 1H), 5.90 (m, 1H), 4.71 (d, J=1.8 Hz, 1H), 4.32 (d, J=5.7 Hz, 1H), 4.23 (m, 1H), 4.07 (m, 1H), 3.84 (m, 1H), 3.77 (s, 3H), 3.70 (m, 1H), 3.61 (m, 1H), 2.53 (m, 1H), 2.05-1.88 (m, 3H), 1.87-1.72 (m, 1H), 1.63 (m, 1H), 1.03 (s, 9H), 0.98-0.81 (m, 2H), 0.65 (m, 1H), 0.60-0.49 (m, 1H); MS (ESI$^+$) m/z 601.1 (M+H)$^+$.

Example 174

(2S,3R,4S,5S)-3-tert-butyl-4-{[2-methoxy-5-(trifluoromethyl)phenyl]methoxy}-5-(2-methylphenyl)-1-[(2S)-oxane-2-carbonyl]pyrrolidine-2-carboxylic acid Example 174A (2S,3R,4S,5S)-ethyl 3-(tert-butyl)-4-((2-methoxy-5-(trifluoromethyl)benzyl)oxy)-1-((S)-tetrahydro-2H-pyran-2-carbonyl)-5-(o-tolyl)pyrrolidine-2-carboxylate To a solution Example 170 (80 mg, 0.192 mmol) and 2-(bromomethyl)-1-methoxy-4-(trifluoromethyl)benzene (61.9 mg, 0.230 mmol) in dimethylformamide (5 mL) cooled in an ice bath was added potassium 2-methylpropan-2-olate (32.2 mg, 0.287 mmol) dropwise. The reaction was stirred in an ice-bath for 20 minutes, and stirred at room temperature for 30 minutes. Dichloromethane and saturated aqueous ammonium chloride solution were added. The organic layer was washed with brine, dried over $MgSO_4$, filtered, and concentrated. The residue was purified via chromatography, eluting with ethyl acetate in heptane, using a 0-30% gradient to provide the title compound. LC/MS (APCI+) m/z 606 (M+H)$^+$.

Example 174B (2S,3R,4S,5S)-3-tert-butyl-4-{[2-methoxy-5-(trifluoromethyl)phenyl]methoxy}-5-(2-methylphenyl)-1-[(2S)-oxane-2-carbonyl]pyrrolidine-2-carboxylic acid Example 174A was dissolved in methanol (2 mL) and aqueous LiOH solution (6N, 0.5 mL). The mixture was stirred at 45° C. overnight, adjusted pH to 1~2 by adding 2M aqueous HCl. The reaction mixture was purified by reverse-phase HPLC on a Phenomenex Luna C8(2) 5 um 100 Å AXIA column (30 mm×75 mm), with a gradient of acetonitrile (A) and 0.1% trifluoroacetic acid in water (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A) to provide the title compound (48 mg, 0.083 mmol, 43.4% yield). $^1$H NMR (400 MHz, DMSO-$d_6$) δ ppm 8.08-7.99 (m, 1H), 7.43 (dd, J=8.7, 2.4 Hz, 1H), 7.07 (s, 3H), 7.03-6.93 (m, 2H), 5.54 (s, 1H), 4.62 (d, J=1.9 Hz, 2H), 4.30-4.20 (m, 2H), 3.78 (s, 2H), 3.74 (s, 3H), 2.31 (s, 3H), 1.68-1.28 (m, 6H), 1.00 (s, 9H); MS (ESI+) m/z 578 (M+H)$^+$.

Example 175

(2S,3R,4S,5S)-3-tert-butyl-4-{[2-methoxy-4-(trifluoromethyl)phenyl]methoxy}-5-(2-methylphenyl)-1-[(2S)-oxane-2-carbonyl]pyrrolidine-2-carboxylic acid Example 175A (2S,3R,4S,5S)-ethyl 3-(tert-butyl)-4-((2-methoxy-4-(trifluoromethyl)benzyl)oxy)-1-((S)-tetrahydro-2H-pyran-2-carbonyl)-5-(o-tolyl)pyrrolidine-2-carboxylate To a solution Example 170B (80 mg, 0.192 mmol) and 1-(bromomethyl)-2-methoxy-4-(trifluoromethyl)benzene (56.7 mg, 0.217 mmol) in dimethylformamide (5 mL) cooled in an ice bath was added potassium 2-methylpropan-2-olate (32.2 mg, 0.287 mmol) dropwise. The reaction was stirred in an ice-bath for 20 minutes, and stirred at room temperature for 30 minutes. Dichloromethane and saturated aqueous ammonium chloride solution were added. The organic layer washed with brine, dried over $MgSO_4$, filtered, and concentrated. The residue was purified through chromatography, eluting with ethyl acetate in heptane, using a 0-30% gradient to provide the title compound. LC/MS (APCI+) m/z 606 (M+H)$^+$.

Example 175B (2S,3R,4S,5S)-3-tert-butyl-4-{[2-methoxy-4-(trifluoromethyl)phenyl]methoxy}-5-(2-methylphenyl)-1-[(2S)-oxane-2-carbonyl]pyrrolidine-2-carboxylic acid Example 175A was dissolved in methanol (2 mL) and aqueous LiOH solution (6N, 0.5 mL). The mixture was stirred at 45° C. overnight, and adjusted pH to 1~2 by adding 2M aqueous HCl. The reaction mixture was purified by reverse-phase HPLC on a Phenomenex Luna C8(2) 5 um 100 Å AXIA column (30 mm×75 mm), with a gradient of acetonitrile (A) and 0.1% trifluoroacetic acid in water (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A) to provide the title compound (40 mg, 36.1% yield). $^1$H NMR (400 MHz, DMSO-$d_6$) δ ppm 8.07-7.96 (m, 1H), 7.17 (d, J=7.9 Hz, 1H), 7.10 (s, 2H), 7.05 (d, J=1.6 Hz, 1H), 7.01-6.94 (m, 1H), 6.79 (d, J=7.9 Hz, 1H), 5.52 (s, 1H), 4.63 (s, 2H), 4.27-4.22 (m, 1H), 4.20 (d, J=5.8 Hz, 1H), 3.88 (d, J=13.8 Hz, 1H), 3.79 (s, 2H), 3.73 (s, 3H), 2.45 (s, 1H), 2.31 (s, 3H), 1.71-1.27 (m, 6H), 1.00 (s, 9H); MS (ESI+) m/z 578.1 (M+H)$^+$.

Example 176

(2S,3R,4S,5S)-3-tert-butyl-4-[(5-cyclobutyl-2-methoxypyridin-3-yl)methoxy]-1-[(2S)-oxane-2-carbonyl]-5-[2-(propan-2-yl)phenyl]pyrrolidine-2-carboxylic acid

Example 176A (2S,3R,4S,5S)-1-((allyloxy)carbonyl)-3-(tert-butyl)-4-((5-cyclobutyl-2-methoxypyridin-3-yl)methoxy)-5-(2-isopropylphenyl)pyrrolidine-2-carboxylic acid Example 130F (0.217 g, 0.520 mmol), dried azeotropically with toluene, was dissolved in dimethyl formamide (5.2 mL) and the mixture was cooled to 0° C. Potassium 2-methylpropan-2-olate (1M in tetrahydrofuran, 0.64 mL, 0.640 mmol) was added dropwise, followed by dropwise addition of Example 130C (0.177 g, 0.691 mmol). The reaction mixture was stirred at 0° C. for 45 minutes, poured into saturated aqueous NH$_4$Cl and extracted three times with methyl tert-butyl ether. The combined organics were dried over Na$_2$SO$_4$, filtered, and concentrated in vacuo. Silica gel chromatography, eluting with 0 to 30% methyl tert-butyl ether-heptanes and flushing the column with 3:1:4 ethyl acetate-ethanol-heptanes, provided the impure title compound as a colorless residue, 0.059 g (20% yield). The compound was used in the next step without further purification. MS (APCI$^+$) m/z 565.6 (M+H)$^+$.

Example 176B (2S,3R,4S,5S)-3-(tert-butyl)-4-((5-cyclobutyl-2-methoxypyridin-3-yl)methoxy)-5-(2-isopropylphenyl)pyrrolidine-2-carboxylic acid Example 176A (0.063 g, 0.112 mmol) was dissolved in ethyl acetate (0.6 mL) and dichloromethane (0.6 mL) and treated with 1,3-dimethylpyrimidine-2,4,6(1H,3H,5H)-trione (0.035 g, 0.223 mmol) and tetrakis(triphenylphosphine) palladium (1.3 mg, 1.116 μmol). The reaction was stirred at room temperature for 30 minutes, diluted with 5 mL methyl tert-butyl ether, and stirred with 4 mL of 10% aqueous Na$_2$CO$_3$ solution for 15 minutes. The phases were separated, and the organic layer was washed with brine, dried over Na$_2$SO$_4$, filtered, and concentrated in vacuo. The crude title compound thus obtained was taken directly into the next reaction without further purification. MS (APCI$^+$) m/z 481.5 (M+H)$^+$.

Example 176C (2S,3R,4S,5S)-3-tert-butyl-4-[(5-cyclobutyl-2-methoxypyridin-3-yl)methoxy]-1-[(2S)-oxane-2-carbonyl]-5-[2-(propan-2-yl)phenyl]pyrrolidine-2-carboxylic acid A solution of (S)-tetrahydro-2H-pyran-2-carbonyl chloride (200 mg/mL in dichloromethane, prepared from (S)-tetrahydro-2H-pyran carboxylic acid and oxalyl chloride; 0.16 mL of solution used, 0.032 g, 0.212 mmol) was added to a solution of Example 176B (0.051 g, 0.106 mmol) and pyridine (0.103 mL, 1.272 mmol) in dichloromethane (1.5 mL). The reaction mixture was stirred at room temperature. After 1 hour, the mixture was diluted with dichloromethane (5 mL), washed three times with water (1 mL each), and once with brine (1 mL). The organic layer was dried over Na$_2$SO$_4$, filtered and concentrated in vacuo. The crude product was purified by reverse-phase HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A to provide the title compound, 0.012 g (19% yield). $^1$H NMR (400 MHz, DMSO-d$_6$) δ ppm 8.06 (dd, J=7.8, 1.4 Hz, 1H), 7.73 (m, 1H), 7.22 (m, 2H), 7.07 (t, J=7.5 Hz, 1H), 6.82 (d, J=2.3 Hz, 1H), 5.60 (m, 1H), 4.69 (d, J=1.7 Hz, 1H), 4.28-4.16 (m, 2H), 3.77 (m, 2H), 3.74 (s, 3H), 3.56 (m, 1H), 3.34-3.17 (m, 2H), 3.06 (m, 2H), 2.50 (m, 1H), 2.22 (m, 2H), 2.02-1.78 (m, 4H), 1.66 (m, 1H), 1.54 (m, 1H), 1.42-1.27 (m, 6H), 1.13 (d, J=6.8 Hz, 3H), 1.02 (s, 9H); MS (ESI$^+$) m/z 593.5 (M+H)$^+$.

Example 177

(2S,3R,4S,5S)-5-(2-bromophenyl)-3-tert-butyl-4-[(5-cyclobutyl-2-methoxypyridin-3-yl)methoxy]-1-[(2S)-oxane-2-carbonyl]pyrrolidine-2-carboxylic acid The title compound was prepared according to the procedure described in Example 144E-Example 144F, substituting (S)-tetrahydro-2H-pyran-2-carboxylic acid for (S)-tetrahydrofuran-2-carboxylic acid in Example 144E. $^1$H NMR (400 MHz, DMSO-d$_6$, 120° C.) δ ppm 8.05-7.97 (m, 1H), 7.66 (dd, J=8.5, 1.4 Hz, 1H), 7.58-7.49 (m, 2H), 7.34 (ddd, J=8.0, 7.0, 1.2 Hz, 1H), 7.22 (s, 1H), 7.12 (td, J=6.9, 6.1, 4.0 Hz, 2H), 6.98 (dd, J=6.4, 2.5 Hz, 1H), 5.59 (d, J=5.7 Hz, 1H), 4.64 (hept, J=6.3 Hz, 1H), 4.44 (d, J=1.9 Hz, 1H), 4.39-4.30 (m, 2H), 3.98 (dd, J=14.1, 1.4 Hz, 1H), 3.91 (s, 3H), 2.61-2.55 (m, 1H), 1.96 (tt, J=8.5, 5.4 Hz, 1H), 1.08-0.99 (m, 12H), 0.95-0.77 (m, 5H), 0.58 (dtt, J=9.3, 7.1, 4.6 Hz, 2H); MS (ESI+) m/z 565 (M+H)$^+$.

Example 178

(2S,3R,4S,5S)-5-(2-bromophenyl)-3-tert-butyl-4-{[2-methoxy-5-(trifluoromethyl)pyridin-3-yl]methoxy}-1-[(2S)-oxane-2-carbonyl]pyrrolidine-2-carboxylic acid

Example 178A 1-allyl 2-ethyl (2S,3R,4S,5S)-5-(2-bromophenyl)-3-(tert-butyl)-4-((2-methoxy-5-(trifluoromethyl)pyridin-3-yl)methoxy)pyrrolidine-1,2-dicarboxylate Example 144C (6.92 g, 15.23 mmol) and 3-(bromomethyl)-2-methoxy-5-(trifluoromethyl)pyridine (5.16 g, 19.11 mmol) were dissolved in dimethylformamide (61 mL). The reaction was cooled to 0° C., and potassium tert-butoxide (1M in tetrahydrofuran, 19.0 mL, 19.0 mmol) was added dropwise. The reaction was stirred at ambient temperature for 1 hour. The reaction was poured into saturated aqueous NH$_4$Cl (50 mL), diluted with water (100 mL) and extracted with methyl tert-butyl ether (3×100 mL). The combined organics were washed with water (100 mL) and brine (100 mL), dried over Na$_2$SO$_4$, filtered and concentrated. The residue was purified by silica gel chromatography (0% to 5% ethyl acetate in dichloromethane) to provide the title compound (9.80 mg, 52%). $^1$H NMR (400 MHz, DMSO-d$_6$, 120° C.) δ ppm 8.34-8.25 (m, 1H), 7.96 (dd, J=7.8, 1.8 Hz, 1H), 7.45 (dd, J=8.0, 1.3 Hz, 1H), 7.22 (td, J=7.6, 1.3 Hz, 1H), 7.15 (d, J=2.4 Hz, 1H), 7.08 (td, J=7.6, 1.8 Hz, 1H), 5.72 (ddt, J=17.5, 10.0, 5.0 Hz, 1H), 5.33 (d, J=5.6 Hz, 1H), 5.09-4.99 (m, 2H), 4.54 (d, J=2.0 Hz, 1H), 4.47-4.37 (m, 4H), 4.34 (dd, J=13.6, 0.9 Hz, 1H), 4.12 (qd, J=7.1, 1.2 Hz, 2H), 3.88 (s, 3H), 2.52 (t, J=1.5 Hz, 1H), 1.15 (t, J=7.1 Hz, 3H), 1.05 (s, 9H); MS (ESI+) m/z 643 & 645 (M+H)+.

Example 178B ethyl (2S,3R,4S,5S)-5-(2-bromophenyl)-3-(tert-butyl)-4-((2-methoxy-5-(trifluoromethyl)pyridin-3-yl)methoxy)pyrrolidine-2-carboxylate Example 178A (4.925 mg, 7.65 mmol) was dissolved in ethyl acetate (15 mL) and dichloromethane (15 mL) and treated with 1,3-dimethylpyrimidine-2,4,6(1H,3H,5H)-trione (2.39 g, 15.31 mmol) and tetrakis(triphenylphosphine)palladium (94.5 mg, 0.082 mmol). The reaction mixture was stirred at ambient temperature. After 1 hour, the reaction mixture was diluted with methyl tert-butyl ether (100 mL) and stirred with 10% aqueous $Na_2CO_3$ (100 mL) solution for 30 minutes. The phases were then separated, and the organic layer was washed with brine, dried over $Na_2SO_4$, filtered, and concentrated to provide the title compound (4.28 g, 100%). $^1$H NMR (400 MHz, DMSO-$d_6$, 120° C.) δ ppm 8.35 (dd, J=2.5, 1.2 Hz, 1H), 7.75 (dd, J=7.8, 1.8 Hz, 1H), 7.48 (dd, J=7.9, 1.2 Hz, 1H), 7.26 (td, J=7.5, 1.3 Hz, 1H), 7.15 (d, J=2.5 Hz, 1H), 7.12 (td, J=7.6, 1.8 Hz, 1H), 5.61-5.43 (m, 1H), 5.07-4.92 (m, 1H), 4.35 (t, J=5.5 Hz, 1H), 4.28 (d, J=14.1 Hz, 1H), 4.18-4.04 (m, 2H), 3.89-3.78 (m, 4H), 3.65 (t, J=6.2 Hz, 1H), 1.16 (t, J=7.1 Hz, 3H), 0.95 (s, 9H); MS (ESI+) m/z 559 & 561 (M+H)+.

Example 178C ethyl (2S,3R,4S,5S)-5-(2-bromophenyl)-3-(tert-butyl)-4-((2-methoxy-5-(trifluoromethyl)pyridin-3-yl)methoxy)-1-((S)-tetrahydro-2H-pyran-2-carbonyl)pyrrolidine-2-carboxylate (S)-Tetrahydro-2H-pyran-2-carboxylic acid (1.21 g, 9.30 mmol) was dissolved in dichloromethane (40 mL). Oxalyl chloride (2M in dichloromethane, 4.65 mL, 9.30 mmol) was added followed by dimethylformamide (50 µL). The reaction was stirred at ambient temperature for 3 hours. The reaction was chilled to 0° C. and Example 178B (4.28 g, 7.65 mmol) and triethylamine (4 mL, 28.7 mmol) dissolved in dichloromethane (20 mL) were added. The reaction was allowed to warm to ambient temperature and was stirred at ambient temperature for 17 hours. The mixture was diluted with dichloromethane (100 mL) and washed twice with saturated aqueous $NaHCO_3$ and once with brine. The organic layer was dried over $Na_2SO_4$, filtered, and concentrated. The residue was purified by silica gel chromatography, eluting with 5% ethyl acetate in dichloromethane to provide the title compound (3.33 g, 65%). $^1$H NMR (400 MHz, DMSO-$d_6$, 120° C.) δ ppm 8.29 (d, J=1.7 Hz, 1H), 8.05 (d, J=7.9 Hz, 1H), 7.49 (d, J=7.9 Hz, 1H), 7.24 (s, 1H), 7.17 (d, J=2.4 Hz, 1H), 7.11 (s, 1H), 5.77 (s, 1H), 4.73 (s, 1H), 4.38 (d, J=6.0 Hz, 1H), 4.32 (d, J=13.7 Hz, 1H), 4.09 (qd, J=7.1, 2.2 Hz, 2H), 3.98-3.90 (m, 1H), 3.87 (s, 3H), 3.83-3.73 (m, 1H), 3.51-3.20 (m, 2H), 2.45-2.38 (m, 1H), 1.68 (s, 1H), 1.45 (d, J=54.8 Hz, 5H), 1.14 (t, J=7.1 Hz, 3H), 1.02 (s, 9H); MS (ESI+) m/z 671 & 673 (M+H)+.

Example 178D (2S,3R,4S,5S)-5-(2-bromophenyl)-3-tert-butyl-4-{[2-methoxy-5-(trifluoromethyl)pyridin-3-yl]methoxy}-1-[(2S)-oxane-2-carbonyl]pyrrolidine-2-carboxylic acid Example 178C (66.9 mg, 0.100 mmol) was dissolved in methanol (1 mL), and tetrahydrofuran (1 mL). Aqueous LiOH (1 M, 1.0 mL, 01.0 mmol) was added and the reaction was heated to 50° C. for 16 hours. The reaction was acidified with 1 M aqueous HCl to pH ~2, then diluted to 25 mL with water. The aqueous layer was extracted with dichloromethane (2×25 mL). The combined organic layers were washed with brine (25 mL), dried over $Na_2SO_4$, filtered and concentrated to provide the title compound (62.4 mg, 97%). $^1$H NMR (400 MHz, DMSO-$d_6$, 120° C.) δ ppm 8.32-8.24 (m, 1H), 8.13 (d, J=7.9 Hz, 1H), 7.48 (d, J=8.0 Hz, 1H), 7.23 (s, 1H), 7.15 (d, J=2.4 Hz, 1H), 7.10 (s, 1H), 5.74 (s, 1H), 4.69 (s, 1H), 4.42-4.28 (m, 2H), 3.97 (dd, J=13.8, 0.9 Hz, 1H), 3.87 (d, J=0.9 Hz, 3H), 3.80 (d, J=11.5 Hz, 1H), 2.48 (s, 1H), 1.67 (d, J=12.3 Hz, 1H), 1.61-1.19 (m, 5H), 1.02 (d, J=1.0 Hz, 9H); MS (ESI+) m/z 643 & 645 (M+H)+.

Example 179

(2S,3R,4S,5S)-3-tert-butyl-5-(2-ethylphenyl)-4-{[2-methoxy-5-(trifluoromethyl)pyridin-3-yl]methoxy}-1-[(2S)-oxane-2-carbonyl]pyrrolidine-2-carboxylic acid Example 179A (2S,3R,4S,5S)-1-allyl 2-ethyl 3-(tert-butyl)-5-(2-ethylphenyl)-4-nitropyrrolidine-1,2-dicarboxylate To Core 24 (1.43 g, 4.10 mmol) in toluene (4.77 mL) and saturated aqueous $NaHCO_3$ (4.77 mL) was added allyl carbonochloridate (0.463 mL, 4.23 mmol) dropwise at ambient temperature. The mixture was stirred at ambient temperature for 16 hours. Ethyl acetate (30 mL) and water (25 mL) were added and the organic layer was washed with brine and concentrated. The resulting material was purified on a 24 g silica gel cartridge eluting with a gradient of 0-65% ethyl acetate/heptanes over a period of 20 minutes to provide (2S,3R,4S,5S)-1-allyl 2-ethyl 3-(tert-butyl)-5-(2-ethylphenyl)-4-nitropyrrolidine-1,2-dicarboxylate (1.64 g, 3.79 mmol, 92% yield). $^1$H NMR (400 MHz, DMSO-$d_6$) δ ppm 7.83 (d, J=7.7 Hz, 1H), 7.19-7.13 (m, 1H), 7.13-7.05 (m, 2H), 5.72 (bs, 1H), 5.66 (dd, J=8.8, 2.9 Hz, 1H), 5.58 (d, J=8.8 Hz, 1H), 4.97 (d, 2H), 4.53 (d, J=3.8 Hz, 1H), 4.42 (s, 2H), 4.24 (q, J=7.1 Hz, 2H), 3.03 (d, J=3.5 Hz, 1H), 2.84 (dq, J=14.8, 7.4 Hz, 1H), 2.58 (dq, J=15.1, 7.6 Hz, 1H), 1.26 (t, J=7.1 Hz, 3H), 1.18 (t, J=7.5 Hz, 3H), 1.00 (s, 9H); MS (APCI+) m/z 433 (M+H)+.

Example 179B (2S,3R,5S)-1-allyl 2-ethyl 3-(tert-butyl)-5-(2-ethylphenyl)-4-oxopyrrolidine-1,2-dicarboxylate To potassium dichromate (6.02 g, 20.48 mmol) in 6N aqueous HCl (93 mL) was added zinc (6.84 g, 105 mmol) portionwise under $N_2$ atmosphere at room temperature. After the almost complete dissolution of zinc (~2 hours) provided a clear light blue solution, the formed chromium(II) chloride was transferred via cannula to the refluxing solution of Example 179A (1.64 g, 3.79 mmol) in ethanol (79 mL) under $N_2$. The reaction mixture was refluxed at 86° C. internally for 20 hours, cooled, and concentrated. The mixture was extracted with dichloromethane three times. The organic phase was washed with saturated aqueous $NaHCO_3$ solution and brine, dried over $MgSO_4$, filtered, and concentrated. The residue (1.65 g) was subjected to re-esterification. Acetyl chloride (2 mL, 28.13 mmol) was added slowly to an ice-cooled flask containing ethanol (6 mL). After the addition was complete, the reaction was stirred at room temperature for 5 minutes before pouring the resulting HCl/ethanol solution into a separate flask containing the crude ester/acid mixture. The mixture was heated to 65° C. for an additional hour, at which point nearly complete conversion was noted. The mixture was cooled to room temperature and concentrated. The crude material was purified on a 24 g cartridge eluting with a gradient of 0-70% ethyl acetate/heptanes over a period of 20 minutes to provide (2S,3R,5S)-1-allyl 2-ethyl 3-(tert-butyl)-5-(2-ethylphenyl)-4-oxopyrrolidine-1,2-dicarboxylate (0.802 g, 1.998 mmol, 52.7% yield). $^1$H NMR (400 MHz, DMSO-$d_6$) δ ppm 7.77 (d, J=7.6 Hz, 1H), 7.25-7.05 (m, 3H), 5.69 (d, J=101.2 Hz, 1H), 5.26 (s, 1H), 4.90 (d, 1H), 4.73-4.29 (m, 4H), 4.20 (qd, J=7.1, 1.6 Hz, 2H), 2.73 (tt, J=14.5, 7.1 Hz, 3H), 1.24 (t, J=7.1 Hz, 3H), 1.16 (t, J=7.5 Hz, 3H), 1.03 (s, 9H); MS (APCI+) m/z 402 (M+H)$^+$.

Example 179C (2S,3R,4S,5S)-1-allyl 2-ethyl 3-(tert-butyl)-5-(2-ethylphenyl)-4-hydroxypyrrolidine-1,2-dicarboxylate Example 179B (0.8 g, 1.993 mmol) was dissolved in ethanol (9.96 mL) and sodium borohydride (0.151 g, 3.99 mmol) was added after cooling the reaction to <−10° C. in an ice/acetone bath. The ice bath was removed and the mixture was allowed to warm to room temperature over 20 minutes. The reaction mixture was concentrated and partitioned between ethyl acetate and saturated aqueous sodium bicarbonate. The organics were concentrated and purified using a 40 g silica gel cartridge and eluting with 0-2% methanol/dichloromethane over a period of 20 minutes to provide (2S,3R,4S,5S)-1-allyl 2-ethyl 3-(tert-butyl)-5-(2-ethylphenyl)-4-hydroxypyrrolidine-1,2-dicarboxylate, 2173 (601 mg, 1.489 mmol, 74.7% yield). $^1$H NMR (400 MHz, DMSO-$d_6$) δ ppm 7.92 (s, 1H), 7.13-7.02 (m, 3H), 5.67 (d, J=107.5 Hz, 1H), 5.23 (m, 1H), 5.07 (d, J=6.6 Hz, 1H), 4.85 (m, 1H), 4.61 (s, 1H), 4.47-4.27 (m, 3H), 4.24 (d, J=4.9 Hz, 1H), 4.14 (qd, J=7.1, 1.9 Hz, 2H), 2.69 (dq, J=14.4, 7.2 Hz, 1H), 2.54 (dd, J=14.7, 7.5 Hz, 1H), 2.23 (s, 1H), 1.22 (t, J=7.1 Hz, 3H), 1.16 (t, J=7.4 Hz, 3H), 0.95 (s, 9H); MS (APCI+) m/z 404 (M+H)$^+$.

Example 179D (2S,3R,4S,5S)-1-allyl 2-ethyl 3-(tert-butyl)-5-(2-ethylphenyl)-4-((2-methoxy-5-(trifluoromethyl)pyridin-3-yl)methoxy)pyrrolidine-1,2-dicarboxylate Example 179C (400 mg, 0.991 mmol) and 3-(bromomethyl)-2-methoxy-5-(trifluoromethyl)pyridine (428 mg, 1.586 mmol) were dissolved in dry dimethylformamide (5 mL). After cooling in an ice bath, potassium 2-methylpropan-2-olate (1.437 mL, 1.437 mmol) solution was added dropwise over 4 minutes. After 60 minutes, the reaction was acidified with 1M aqueous HCl (1.2 mL) and warmed to room temperature. The reaction mixture was diluted with water (20 mL) and extracted with dichloromethane. The organic extracts were loaded onto a 24 g silica gel column and eluted with a gradient of 0-80% ethyl acetate/heptanes over 20 minutes to provide (2S,3R,4S,5S)-1-allyl 2-ethyl 3-(tert-butyl)-5-(2-ethylphenyl)-4-((2-methoxy-5-(trifluoromethyl)pyridin-3-yl)methoxy)pyrrolidine-1,2-dicarboxylate (421 mg, 0.710 mmol, 71.7% yield). $^1$H NMR (400 MHz, DMSO-$d_6$) δ ppm 8.33 (dd, J=2.5, 1.2 Hz, 1H), 7.91 (s, 1H), 7.15-6.93 (m, 4H), 5.66 (d, J=128.9 Hz, 1H), 5.18 (d, J=5.4 Hz, 3H), 5.00-4.53 (m, 1H), 4.47 (d, J=1.8 Hz, 2H), 4.31 (s, 2H), 4.28 (d, J=14.6 Hz, 2H), 4.06 (qt, J=7.1, 3.6 Hz, 2H), 3.82 (d, J=14.6 Hz, 4H), 2.73 (dq, J=14.9, 7.4 Hz, 1H), 2.54 (dt, J=14.7, 7.5 Hz, 1H), 1.14 (t, J=7.6 Hz, 3H), 1.08 (t, J=7.1 Hz, 3H), 1.00 (s, 9H); MS (APCI+) m/z 593 (M+H)$^+$.

Example 179E (2S,3R,4S,5S)-ethyl 3-(tert-butyl)-5-(2-ethylphenyl)-4-((2-methoxy-5-(trifluoromethyl)pyridin-3-yl)methoxy)pyrrolidine-2-carboxylate To a solution of Example 179D (420 mg, 0.709 mmol) in acetonitrile/water (1.24 mL, 10:1) was added tetrakis(triphenylphosphine)palladium(0) (18.02 mg, 0.016 mmol) and diethylamine (0.147 mL, 1.417 mmol) The mixture was stirred at room temperature overnight. Dichloromethane and water were added, and the organic layer was washed with brine, dried over $MgSO_4$, filtered, and concentrated. The crude material was purified by chromatography, eluting on 12 g silica gel cartridge with a gradient of 0-70% ethyl acetate/heptanes over 20 minutes to provide (2S,3R,4S,5S)-ethyl 3-(tert-butyl)-5-(2-ethylphenyl)-4-((2-methoxy-5-(trifluoromethyl)pyridin-3-yl)methoxy)pyrrolidine-2-carboxylate (321 mg, 0.631 mmol, 89% yield). $^1$H NMR (501 MHz, DMSO-$d_6$) δ ppm 8.41-8.30 (s, 1H), 7.67-7.55 (d, 1H), 7.27 (d, J=2.5 Hz, 1H), 7.19-7.09 (m, 2H), 7.05 (ddd, J=8.5, 5.7, 3.0 Hz, 1H), 4.25 (d, J=4.5 Hz, 1H), 4.22 (d, J=13.8 Hz, 2H), 4.17-4.07 (m, 2H), 3.96 (dd, J=4.5, 1.6 Hz, 1H), 3.83 (s, 3H), 3.72 (d, J=13.9 Hz, 1H), 3.59 (t, J=7.1 Hz, 1H), 3.12 (t, J=7.8 Hz, 1H), 2.68 (dq, J=15.0, 7.5 Hz, 1H), 2.59 (dq, J=14.9, 7.5 Hz, 1H), 2.34 (dd, J=6.8, 1.5 Hz, 1H), 1.22-1.17 (t, 3H), 1.17-1.13 (t, 3H), 0.95 (s, 9H); MS (APCI+) m/z 509 (M+H)$^+$.

Example 179F (2S,3R,4S,5S)-ethyl 3-(tert-butyl)-5-(2-ethylphenyl)-4-((2-methoxy-5-(trifluoromethyl)pyridin-3-yl)methoxy)-1-((S)-tetrahydro-2H-pyran-2-carbonyl)pyrrolidine-2-carboxylate To a solution of Example 179E (320 mg, 0.629 mmol) in dichloromethane (2.5 mL) at 0° C. was added triethylamine (0.395 mL, 2.83 mmol) followed by tetrahydro-2H-pyran-2-carbonyl chloride (159 mg, 1.070 mmol) as a solution in 2 mL dichloromethane. After stirring for 15 minutes, the reaction was quenched with 5 mL of saturated aqueous sodium bicarbonate. The crude material was chromatographed three times using a 24 g silica gel cartridge (3 times with a gradient of 0-80% ethyl acetate/heptanes over a period of 20 minutes to provide (2S,3R,4S,5S)-ethyl 3-(tert-butyl)-5-(2-ethylphenyl)-4-((2-methoxy-5-(trifluoromethyl)pyridin-3-yl)methoxy)-1-((S)-tetrahydro-2H-pyran-2-carbonyl)pyrrolidine-2-carboxylate (166 mg, 0.267 mmol, 42.5% yield). ¹H NMR (400 MHz, DMSO-d₆) δ ppm 8.27 (d, J=2.4 Hz, 1H), 8.02-7.94 (d, 1H), 7.20 (s, 1H), 7.13 (s, 2H), 7.04 (d, J=7.5 Hz, 1H), 5.56 (s, 1H), 4.69 (s, 1H), 4.32-4.20 (m, 2H), 4.09 (qd, J=7.0, 3.0 Hz, 2H), 3.85 (s, 3H), 3.80 (d, J=13.8 Hz, 1H), 3.72 (d, J=11.4 Hz, 1H), 3.41 (bs, 2H), 2.75 (dt, J=15.1, 7.6 Hz, 1H), 2.66 (dd, J=14.9, 7.4 Hz, 1H), 2.42 (d, J=1.8 Hz, 1H), 1.65 (d, J=12.9 Hz, 1H), 1.52 (d, J=11.9 Hz, 2H), 1.34 (s, 3H), 1.22 (t, J=7.5 Hz, 3H), 1.14 (t, J=7.1 Hz, 3H), 1.03 (s, 9H); MS (APCI+) m/z 621 (M+H)⁺. Also obtained was (2S,3R,4S,5S)-ethyl 3-(tert-butyl)-5-(2-ethylphenyl)-4-((2-methoxy-5-(trifluoromethyl)pyridin-3-yl)methoxy)-1-((R)-tetrahydro-2H-pyran-2-carbonyl)pyrrolidine-2-carboxylate (168 mg, 0.271 mmol, 43.0% yield). ¹H NMR (400 MHz, DMSO-d₆) δ ppm 8.27 (s, 1H), 7.78 (s, 1H), 7.15 (d, J=2.4 Hz, 1H), 7.09-7.03 (m, 2H), 6.97 (d, J=8.3 Hz, 1H), 5.31 (d, J=5.6 Hz, 1H), 4.94 (s, 1H), 4.29-4.20 (m, 2H), 4.13 (qd, J=7.1, 2.2 Hz, 2H), 3.91 (bs, 2H), 3.85 (s, 3H), 3.83-3.76 (m, 1H), 3.26 (bs, 1H), 2.75 (dq, J=14.9, 7.6 Hz, 1H), 2.63 (dt, J=14.8, 7.5 Hz, 1H), 2.57 (d, J=2.4 Hz, 1H), 1.77 (s, 1H), 1.51 (s, 2H), 1.41 (s, 3H), 1.22 (t, J=7.5 Hz, 3H), 1.15 (t, J=7.1 Hz, 3H), 1.03 (s, 9H); MS (APCI+) m/z 621 (M+H)⁺.

Example 179G (2S,3R,4S,5S)-3-tert-butyl-5-(2-ethylphenyl)-4-{[2-methoxy-5-(trifluoromethyl)pyridin-3-yl]methoxy}-1-[(2S)-oxane-2-carbonyl]pyrrolidine-2-carboxylic acid To a solution of the first eluting diastereomer from Example 179F (156 mg, 0.251 mmol) in tetrahydrofuran (0.760 mL), methanol (0.760 mL), and water (0.760 mL) was added lithium hydroxide, H₂O (73.8 mg, 1.759 mmol). The reaction mixture was heated at 45° C. for 16 hours. LC/MS showed desired product and the solvent was removed under a stream of nitrogen. Water (0.5 mL) was added to the crude material. The mixture was acidified with 1M aqueous HCl (1.53 mL) to pH-6, extracted once with heptanes (discarded), and once with dichloromethane. The solvent was evaporated in vacuo. The resulted crude material was chromatographed using a 4 g silica gel cartridge with a gradient of 0-10% methanol/dichloromethane over a period of 10 minutes to provide (2S,3R,4S,5S)-3-(tert-butyl)-5-(2-ethylphenyl)-4-((2-methoxy-5-(trifluoromethyl)pyridin-3-yl)methoxy)-1-((S)-tetrahydro-2H-pyran-2-carbonyl)pyrrolidine-2-carboxylic acid (87 mg, 0.147 mmol, 58.4% yield). ¹H NMR (400 MHz, DMSO-d₆) δ ppm 8.26 (s, 1H), 8.05 (d, J=7.3 Hz, 1H), 7.16 (s, 1H), 7.10 (s, 2H), 7.03 (m, 1H), 5.56 (s, 1H), 4.65 (s, 1H), 4.28 (d, J=14.0 Hz, 1H), 4.23 (d, J=5.8 Hz, 1H), 3.86 (d, 4H), 3.73 (d, J=11.5 Hz, 1H), 3.42 (bs, 2H), 2.79-2.69 (m, 1H), 2.64 (dq, J=15.0, 7.6 Hz, 1H), 2.48 (m, 1H), 1.71-1.60 (m, 1H), 1.52 (m, 2H), 1.34 (m, 3H), 1.21 (t, J=7.5 Hz, 3H), 1.02 (s, 9H); MS (APCI+) m/z 593 (M+H)⁺.

Example 180

(2S,3R,4S,5S)-5-([1,1'-biphenyl]-2-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid Example 178C (98.5 mg, 0.147 mmol), phenylboronic acid (30.5 mg, 0.250 mmol) and cesium fluoride (75.2 mg, 0.495 mmol) were dissolved in dioxane (1 mL). The reaction was purged with nitrogen for 5 minutes, and 1,1'-bis(diphenylphosphino)ferrocene-palladium(II)dichloride dichloromethane complex (9.0 mg, 0.011 mmol) was added. The reaction was purged with nitrogen and heated to 100° C. for 1 hour. Methanol (1 mL) and aqueous LiOH (1M, 1 mL) was added and the reaction was heated to 50° C. for 16 hours. The reaction mixture was filtered and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound (41.3 mg, 37%) as the TFA salt. ¹H NMR (400 MHz, DMSO-d₆, 120° C.) δ ppm 8.31 (dd, J=2.5, 1.1 Hz, 1H), 8.14-8.06 (m, 1H), 7.46-7.32 (m, 3H), 7.28-7.18 (m, 5H), 7.10 (s, 1H), 5.27 (d, J=5.5 Hz, 1H), 4.62 (d, J=1.5 Hz, 1H), 4.33 (d, J=13.9 Hz, 1H), 3.94-3.84 (m, 4H), 3.76-3.61 (m, 4H), 2.39 (d, J=1.6 Hz, 1H), 1.75-1.20 (m, 6H), 0.77 (s, 9H); MS (ESI+) m/z 641 (M+H)⁺.

Example 181

(2S,3R,4S,5S)-3-tert-butyl-4-{[2-methoxy-5-(trifluoromethyl)pyridin-3-yl]methoxy}-5-[2-(1-methyl-6-oxo-1,6-dihydropyridin-3-yl)phenyl]-1-[(2S)-oxane-2-carbonyl]pyrrolidine-2-carboxylic acid Into a 4 mL vial was added (2S,3R,4S,5S)-ethyl 5-(2-bromophenyl)-3-(tert-butyl)-4-((2-methoxy-5-(trifluoromethyl)pyridin-3-yl)methoxy)-1-((S)-tetrahydro-2H-pyran-2-carbonyl)pyrrolidine-2-carboxylate (Example 178C, 38.6 mg, 0.057 mmol), (1-methyl-6-oxo-1,6-dihydropyridin-3-yl)boronic acid (115 μL, 0.069 mmol), and PdCl₂(dppf) (4.21 mg, 5.75 μmol) in dioxane (1 mL) to provide an orange suspension. Cesium carbonate (86 μL, 0.172 mmol) in H₂O was added and the reaction was stirred at 85° C. for 1 hour. The solvent was removed under a stream of nitrogen. The residue was dissolved in 1 mL dichloromethane and extracted with H₂O (2×2 mL). The organic phase was dried and dissolved in 3:2 tetrahydrofuran/methanol. Aqueous lithium hydroxide monohydrate (200 μL, 1.000 mmol) was added and the reaction was stirred overnight at 45° C. The solvent was removed under a stream of nitrogen. The residue was acidified with 2 M aqueous HCl and extracted with dichloromethane (2×2 mL). The solvent was removed under a stream of nitrogen. The residue was dissolved in CH₃CN and purified by prep HPLC using HPLC TFA method 8. The desired product co-eluted with dppf ligand. The desired fractions were collected, combined and concentrated. The crude material was dissolved in CH₃CN and repurified using HPLC method AA6 (17.0 mg, 44% yield). ¹H NMR (400 MHz, 120° C., DMSO-d₆:D₂O=9:1 (v/v)) δ ppm 8.35-8.24 (m, 2H), 7.46-7.38 (m, 1H), 7.38-7.29 (m, 1H), 7.26-7.14 (m, 3H), 7.07 (s, 1H), 6.43 (d, J=9.3 Hz, 1H), 5.23 (s, 1H), 4.47 (s, 1H), 4.31 (d, J=13.9 Hz, 1H), 3.87 (s, 6H), 3.44 (s, 3H), 2.58-2.53 (m, 1H), 1.77-1.04 (m, 6H), 0.86 (s, 9H); MS (APCI+) m/z 672.4 (M+H)⁺.

Example 182

(2S,3R,4S,5S)-3-tert-butyl-4-[(5-cyclobutyl-2-methoxypyridin-3-yl)methoxy]-1-(cyclohexanecarbonyl)-5-(2-cyclopropylphenyl)pyrrolidine-2-carboxylic acid The title compound was prepared according to the procedure described in Example 149E-F-146D, substituting cyclohexanecarbonyl chloride for (S)-tetrahydrofuran-2-carboxylic acid. $^1$H NMR (400 MHz, DMSO-d$_6$, 120° C.) δ ppm 8.00 (s, 1H), 7.75 (dd, J=2.4, 0.8 Hz, 1H), 7.10 (h, J=6.4, 5.8 Hz, 2H), 6.99 (dd, J=7.1, 2.0 Hz, 1H), 6.83 (d, J=2.4 Hz, 1H), 5.66 (d, J=5.8 Hz, 1H), 4.62 (d, J=2.1 Hz, 1H), 4.33 (d, J=5.8 Hz, 1H), 4.22 (dt, J=13.4, 0.8 Hz, 1H), 3.86 (dt, J=13.3, 0.9 Hz, 1H), 3.75 (s, 3H), 3.30 (p, J=8.3 Hz, 1H), 2.54 (s, 1H), 2.29-2.15 (m, 2H), 2.06 (s, 1H), 2.02-1.77 (m, 5H), 1.64 (d, J=10.2 Hz, 2H), 1.52-1.37 (m, 2H), 1.23 (ddd, J=23.0, 12.9, 7.1 Hz, 6H), 1.02 (s, 11H), 0.67 (s, 1H), 0.61-0.48 (m, 1H); MS (ESI+) m/z 589 (M+H)$^+$.

Example 183

(2S,3R,4S,5S)-5-(2-bromophenyl)-3-tert-butyl-4-[(5-cyclobutyl-2-methoxypyridin-3-yl)methoxy]-1-(cyclohexanecarbonyl)pyrrolidine-2-carboxylic acid The title compound was prepared according to the procedure described in Example 144D-Example 144F, substituting cyclohexanecarbonyl chloride for (S)-tetrahydrofuran-2-carboxylic acid in Example 144D. $^1$H NMR (400 MHz, DMSO-d$_6$, 120° C.) δ ppm 8.08 (s, 1H), 7.77 (dd, J=2.4, 0.7 Hz, 1H), 7.51 (d, J=7.9 Hz, 1H), 7.26 (t, J=7.4 Hz, 1H), 7.13 (t, J=7.6 Hz, 1H), 6.85 (d, J=2.4 Hz, 1H), 5.42 (d, J=5.8 Hz, 1H), 4.59 (d, J=2.1 Hz, 1H), 4.33 (dd, J=6.0, 1.3 Hz, 1H), 4.25 (dt, J=13.2, 0.8 Hz, 1H), 3.98-3.90 (m, 1H), 3.76 (s, 3H), 3.39-3.24 (m, 1H), 2.54 (s, 1H), 2.33-2.17 (m, 2H), 2.02-1.79 (m, 3H), 1.59 (d, J=61.5 Hz, 4H), 1.36-1.04 (m, 6H), 1.00 (s, 9H); MS (ESI+) m/z 627 & 629 (M+H)$^+$.

Example 184

(2S,3R,4S,5S)-3-tert-butyl-5-(2-ethylphenyl)-4-{[2-methoxy-4-(trifluoromethyl)phenyl]methoxy}-1-[(2S)-oxane-2-carbonyl]pyrrolidine-2-carboxylic acid

Example 184A (2S,3R,4S,5S)-1-allyl 2-ethyl 3-(tert-butyl)-5-(2-ethylphenyl)-4-((2-methoxy-4-(trifluoromethyl)benzyl)oxy)pyrrolidine-1,2-dicarboxylate To a mixture of (2S,3R,4S,5S)-1-allyl 2-ethyl 3-(tert-butyl)-5-(2-ethylphenyl)-4-hydroxypyrrolidine-1,2-dicarboxylate from Example 179C (100 mg, 0.248 mmol) and 1-(bromomethyl)-2-methoxy-4-(trifluoromethyl)benzene (73.3 mg, 0.273 mmol) in dimethyl formamide (N,N-dimethylformamide) (1.25 mL) cooling in an ice bath, potassium 2-methylpropan-2-olate (0.273 mL, 0.273 mmol) solution was added dropwise over 4 minutes. After 60 minutes, the reaction mixture was acidified with 1M aqueous HCl (0.23 mL) and warmed to ambient temperature. The mixture was diluted with water (10 mL) and extracted with dichloromethane. The extracts were loaded onto a 24 g silica gel column and the column was eluted with a gradient of 0-65% ethyl acetate/heptanes over 20 minutes to give the title compound. $^1$H NMR (400 MHz, DMSO-d$_6$) δ ppm 7.92 (s, 1H), 7.15-7.02 (m, 4H), 6.98 (dt, J=8.0, 1.1 Hz, 1H), 6.62 (d, J=7.9 Hz, 1H), 5.66 (d, J=120.3 Hz, 1H), 5.17-5.09 (m, 1H), 4.84 (d, 1H), 4.44 (d, J=1.9 Hz, 1H), 4.35 (bs, 3H), 4.24 (d, 1H), 4.21 (d, 1H), 4.09 (q, J=7.1 Hz, 2H), 3.83 (d, J=14.1 Hz, 1H), 3.71 (s, 3H), 2.69 (dq, J=15.0, 7.5 Hz, 1H), 2.56-2.48 (m, 1H), 2.43 (d, J=1.7 Hz, 1H), 1.12 (td, J=7.3, 5.1 Hz, 6H), 0.98 (s, 9H); MS (APCI+) m/z 592 (M+H)$^+$.

Example 184B (2S,3R,4S,5S)-ethyl 3-(tert-butyl)-5-(2-ethylphenyl)-4-((2-methoxy-4-(trifluoromethyl)benzyl)oxy)pyrrolidine-2-carboxylate To a solution of (2S,3R,4S,5S)-1-allyl 2-ethyl 3-(tert-butyl)-5-(2-ethylphenyl)-4-((2-methoxy-4-(trifluoromethyl)benzyl)oxy)pyrrolidine-1,2-dicarboxylate from Example 184A (75 mg, 0.127 mmol) in acetonitrile/water (1.24 mL, 10:1) was added tetrakis(triphenylphosphine)palladium(0) (3.22 mg, 2.79 mol) and diethylamine (0.026 mL, 0.254 mmol) The mixture was stirred at ambient temperature for 16 hours. Dichloromethane and water were added. The organic layer was washed with brine, dried over MgSO$_4$, filtered, and concentrated. The residue was purified by chromatography, eluting on 12 g cartridge with a gradient 0-60% ethyl acetate/heptanes over 20 minutes to yield (2S,3R,4S,5S)-ethyl 3-(tert-butyl)-5-(2-ethylphenyl)-4-((2-methoxy-4-(trifluoromethyl)benzyl)oxy)pyrrolidine-2-carboxylate. $^1$H NMR (500 MHz, DMSO-d$_6$) δ ppm 7.64-7.58 (m, 1H), 7.21-7.08 (m, 5H), 6.94 (d, J=8.0 Hz, 1H), 4.21 (dd, J=8.1, 4.3 Hz, 1H), 4.18-4.09 (m, 3H), 3.89 (dd, J=4.5, 1.7 Hz, 1H), 3.73 (s, 3H), 3.70 (d, 1H), 3.57 (t, J=7.2 Hz, 1H), 3.08 (t, J=7.9 Hz, 1H), 2.69 (dq, J=15.0, 7.5 Hz, 1H), 2.60 (dq, J=14.8, 7.5 Hz, 1H), 2.31 (dd, J=7.1, 1.6 Hz, 1H), 1.20 (t, J=7.1 Hz, 3H), 1.17 (t, J=7.6 Hz, 3H), 0.94 (s, 9H); MS (APCI+) m/z 508 (M+H)$^+$.

Example 184C (2S,3R,4S,5S)-ethyl 3-(tert-butyl)-5-(2-ethylphenyl)-4-((2-methoxy-4-(trifluoromethyl)benzyl)oxy)-1-((S)-tetrahydro-2H-pyran-2-carbonyl)pyrrolidine-2-carboxylate To a solution of (2S,3R,4S,5S)-ethyl 3-(tert-butyl)-5-(2-ethylphenyl)-4-((2-methoxy-4-(trifluoromethyl)benzyl)oxy) pyrrolidine-2-carboxylate from Example 184B (57 mg, 0.112 mmol) in dichloromethane (0.6 mL) at 0° C. was added triethylamine (0.070 mL, 0.505 mmol) followed by addition of (S)-tetrahydro-2H-pyran-2-carbonyl chloride (28.4 mg, 0.191 mmol) as a solution in 1 mL dichloromethane. After stirring for 15 minutes, the reaction mixture was quenched with 5 mL of saturated aqueous sodium bicarbonate. The crude organics were chromatographed using a 12 g silica gel cartridge with a gradient of 0-65% ethyl acetate/heptanes over a period of 20 minutes to give (2S,3R,4S,5S)-ethyl 3-(tert-butyl)-5-(2-ethylphenyl)-4-((2-methoxy-4-(trifluoromethyl)benzyl)oxy)-1-((S)-tetrahydro-2H-pyran-2-carbonyl)pyrrolidine-2-carboxylate. $^1$H NMR (400 MHz, DMSO-d$_6$) δ ppm 8.06-7.90 (m, 1H), 7.12 (m, 3H), 7.04 (d, J=1.6 Hz, 1H), 6.98 (d, J=7.5 Hz, 1H), 6.75 (d, J=7.8 Hz, 1H), 5.52 (s, 1H), 4.67 (s, 1H), 4.22 (d, J=13.6 Hz, 1H), 4.16 (d, J=5.7 Hz, 1H), 4.10 (q, J=7.1 Hz, 2H), 3.86 (d, J=13.5 Hz, 1H), 3.72 (m, 4H), 2.74 (dt, J=15.0, 7.6 Hz, 1H), 2.63 (dt, J=15.0, 7.5 Hz, 1H), 2.40 (d, J=1.9 Hz, 1H), 1.65 (m, 1H), 1.51 (m, 2H), 1.35 (m, 2H), 1.21 (t, J=7.5 Hz, 3H), 1.16 (t, J=7.1 Hz, 3H), 1.00 (s, 9H); MS (APCI+) m/z 621 (M+H)$^+$.

Example 184D (2S,3R,4S,5S)-3-tert-butyl-5-(2-ethylphenyl)-4-{[2-methoxy-4-(trifluoromethyl)phenyl]methoxy}-1-[(2S)-oxane-2-carbonyl]pyrrolidine-2-carboxylic acid To a solution of (2S,3R,4S,5S)-ethyl 3-(tert-butyl)-5-(2-ethylphenyl)-4-((2-methoxy-4-(trifluoromethyl)benzyl)

oxy)-1-((S)-tetrahydro-2H-pyran-2-carbonyl)pyrrolidine-2-carboxylate from Example 184C (57 mg, 0.092 mmol) in tetrahydrofuran (0.3 mL), methanol (0.300 mL) and water (0.300 mL) was added lithium hydroxide hydrate (27.0 mg, 0.644 mmol) and the reaction was heated at 45° C. for 16 hours. The solvent was removed under a stream of nitrogen. Water (0.5 mL) was added to the crude material. The mixture was acidified with 1M aqueous HCl (0.6 mL) to pH-6, extracted once with heptane (discarded), and filtered. The precipitate was dissolved in dichloromethane, and the solvent was evaporated in vacuo. The crude residue was chromatographed using a 4 g silica gel cartridge with a gradient of 0-10% methanol/dichloromethane over a period of 9 minutes to give (2S,3R,4S,5S)-3-(tert-butyl)-5-(2-ethylphenyl)-4-((2-methoxy-4-(trifluoromethyl)benzyl)oxy)-1-((S)-tetrahydro-2H-pyran-2-carbonyl)pyrrolidine-2-carboxylic acid. $^1$H NMR (400 MHz, DMSO-$d_6$) δ ppm 8.20 (d, J=7.8 Hz, 1H), 7.19-6.99 (m, 4H), 6.97-6.88 (d, 1H), 6.72 (d, J=8.0 Hz, 1H), 5.51 (s, 1H), 4.55 (s, 1H), 4.25 (d, J=13.9 Hz, 1H), 4.13 (d, J=6.0 Hz, 1H), 3.89 (d, J=13.8 Hz, 1H), 3.72 (m, 4H), 3.48 (bs, 2H) 2.78-2.66 (m, 1H), 2.61 (dt, J=15.0, 7.5 Hz, 1H), 2.56 (s, 1H), 1.65 (s, 1H), 1.51 (t, J=11.5 Hz, 1H), 1.33 (s, 2H), 1.19 (t, J=7.5 Hz, 3H), 0.99 (s, 9H); MS (APCI+) m/z 592 (M+H)$^+$.

Example 185

(2S,3R,4S,5S)-3-tert-butyl-4-[(5-cyclobutyl-2-methoxypyridin-3-yl)methoxy]-5-(2-ethylphenyl)-1-[(2S)-oxane-2-carbonyl]pyrrolidine-2-carboxylic acid Example 185A (2S,3R,4S,5S)-ethyl 3-(tert-butyl)-4-((5-cyclobutyl-2-methoxypyridin-3-yl)methoxy)-5-(2-ethylphenyl)-1-((S)-tetrahydro-2H-pyran-2-carbonyl)pyrrolidine-2-carboxylate (2S,3R,4S,5S)-Ethyl 3-(tert-butyl)-5-(2-ethylphenyl)-4-hydroxy-1-((S)-tetrahydro-2H-pyran-2-carbonyl)pyrrolidine-2-carboxylate from Example 278C (184 mg, 0.426 mmol) and 3-(bromomethyl)-5-cyclobutyl-2-methoxypyridine (158 mg, 0.618 mmol) were dissolved in dry N,N-dimethylformamide (2.2 mL). After cooling in an ice bath, potassium 2-methylpropan-2-olate (0.640 mL, 0.640 mmol) solution was added dropwise over 2 minutes. After 30 minutes, the mixture was quenched with saturated aqueous NH$_4$Cl solution and was extracted with dichloromethane. The organic solvent was evaporated and the residue was loaded onto a 24 g silica gel column and was eluted with 0-70% ethyl acetate/heptanes over 20 minutes to give (2S,3R,4S,5S)-ethyl 3-(tert-butyl)-4-((5-cyclobutyl-2-methoxypyridin-3-yl)methoxy)-5-(2-ethylphenyl)-1-((S)-tetrahydro-2H-pyran-2-carbonyl)pyrrolidine-2-carboxylate. $^1$H NMR (400 MHz, DMSO-$d_6$) δ ppm 8.02 (d, J=7.7 Hz, 1H), 7.75 (d, J=2.5 Hz, 1H), 7.16 (s, 2H), 7.09 (s, 1H), 6.90 (d, J=2.4 Hz, 1H), 5.54 (s, 1H), 4.68 (s, 1H), 4.20 (d, 1H), 4.17 (d, J=13.8 Hz, 2H), 4.09 (qd, J=7.1, 1.1 Hz, 2H), 3.77 (d, J=13.2 Hz, 1H), 3.74 (s, 3H), 3.72 (m, 1H), 3.40-3.24 (m, 1H), 2.70 (dp, J=30.3, 7.5 Hz, 2H), 2.41 (d, J=1.8 Hz, 1H), 2.35-2.17 (m, 3H), 2.05-1.79 (m, 5H), 1.65 (d, J=12.4 Hz, 1H), 1.51 (d, J=11.9 Hz, 1H), 1.32 (d, J=16.9 Hz, 3H), 1.22 (t, J=7.5 Hz, 3H), 1.14 (t, J=7.1 Hz, 3H), 1.01 (s, 9H); MS (APCI+) m/z 607 (M+H)$^+$.

Example 185B (2S,3R,4S,5S)-3-tert-butyl-4-[(5-cyclobutyl-2-methoxypyridin-3-yl)methoxy]-5-(2-ethylphenyl)-1-[(2S)-oxane-2-carbonyl]pyrrolidine-2-carboxylic acid To a solution of (2S,3R,4S,5S)-ethyl 3-(tert-butyl)-4-((5-cyclobutyl-2-methoxypyridin-3-yl)methoxy)-5-(2-ethylphenyl)-1-((S)-tetrahydro-2H-pyran-2-carbonyl)pyrrolidine-2-carboxylate (205 mg, 0.338 mmol) in tetrahydrofuran (1.0 mL), methanol (1.000 mL) and water (1.000 mL) was added lithium hydroxide hydrate (99 mg, 2.365 mmol) and the reaction was heated at 45° C. for 16 hours. The solvent was removed under a stream of nitrogen. Water (2 mL) was added to the crude material. The mixture was extracted with 2×10 mL heptane (discarded), and extracted with diethyl ether. The mixture was concentrated, and 2 mL of water was added. The mixture was acidified with 1M aqueous HCl (0.4 mL) to pH-6, and filtered to give the title compound. $^1$H NMR (400 MHz, DMSO-$d_6$) δ ppm 8.14 (d, J=7.7 Hz, 1H), 7.76 (d, J=2.5 Hz, 1H), 7.15 (s, 2H), 7.09 (s, 1H), 6.87 (d, J=2.4 Hz, 1H), 5.54 (s, 1H), 4.60 (s, 1H), 4.23-4.16 (m, 3H), 3.81 (d, J=13.5 Hz, 1H), 3.75 (s, 3H), 3.73 (bs, 2H), 3.32 (p, J=8.5 Hz, 1H), 2.78-2.69 (m, 1H), 2.65 (dt, J=14.8, 7.5 Hz, 1H), 2.52 (s, 1H), 2.24 (m, 2H), 2.01-1.91 (m, 3H), 1.91-1.82 (m, 1H), 1.66 (m, 1H), 1.53 (m, 2H), 1.42-1.25 (m, 3H), 1.22 (t, J=7.5 Hz, 3H), 1.01 (s, 9H); MS (APCI+) m/z 579 (M+H)$^+$.

Example 186

(2S,3R,4S,5S)-4-[(5-bromo-2-methoxypyridin-3-yl)methoxy]-3-tert-butyl-5-(2-methylphenyl)-1-[(2S)-oxane-2-carbonyl]pyrrolidine-2-carboxylic acid The title compound was prepared according to the procedure described in Example 188, substituting Intermediate 2 for Intermediate 6. $^1$H NMR (400 MHz, DMSO-$d_6$) δ ppm 7.94 (s, 1H), 7.11 (d, J=4.2 Hz, 3H), 5.44 (s, 1H), 4.48-4.35 (m, 2H), 4.15 (q, J=7.1 Hz, 2H), 3.95 (s, 2H), 3.84-3.75 (m, 2H), 3.34 (s, 1H), 2.95 (s, 1H), 2.32 (s, 3H), 2.21 (t, J=3.9 Hz, 1H), 1.36 (d, J=24.9 Hz, 5H), 1.24 (t, J=7.1 Hz, 6H), 0.98 (s, 9H); MS (ESI+) m/z 418.2 (M+H)$^+$.

Example 187

(2S,3R,4S,5S)-3-tert-butyl-4-{[5-(2-cyanopropan-2-yl)-2-methoxyphenyl]methoxy}-5-(2-methylphenyl)-1-[(2S)-oxane-2-carbonyl]pyrrolidine-2-carboxylic acid Example 187A ((5-bromo-2-methoxybenzyl)oxy)(tert-butyl)dimethylsilane 5-Bromo-2-methoxyphenyl)methanol (1.89 g, 8.71 mmol) was dissolved in 25 mL of dichloromethane. Imidazole (0.711 g, 10.45 mmol) was added, followed by addition of tert-butyldimethylsilyl chloride (1.378 g, 9.14 mmol) in one portion. After stirring at room temperature for 30 minutes, methanol (1 mL) was added, and the reaction mixture was stirred for 5 minutes. The mixture was washed with 1M aqueous HCl (3×5 mL) and brine (5 mL) and the organics were dried over sodium sulfate, filtered, and concentrated in vacuo to give the title compound which was used without additional purification. $^1$H NMR (400 MHz, Chloroform-d) δ ppm 7.54 (dt, J=2.3, 1.1 Hz, 1H), 7.32-7.24 (m, 1H), 6.65 (d, J=8.6 Hz, 1H), 4.68 (d, J=1.0 Hz, 2H), 3.76 (s, 3H), 0.94 (s, 9H), 0.10 (s, 6H); MS (ESI) m/z 331.0 (M+H)$^+$.

Example 187B 2-(3-(((tert-butyldimethylsilyl)oxy)methyl)-4-methoxyphenyl)-2-methylpropanenitrile A 250-mL round bottom flask was charged with Example 187A (2.7 g, 8.15 mmol), BINAP (2,2'-bis(diphenylphosphino)-1,1'-binaphthyl, 0.507 g, 0.815 mmol), and diacetoxypalladium (0.183 g, 0.815 mmol). Toluene (20 mL) was added, and the suspension was sparged with N$_2$ for 15 minutes. A separate 100-mL round-bottomed flask was charged with a solution of sodium bis(trimethylsilyl)amide (0.6 M in toluene, 20.37 mL, 12.22 mmol), and isobutyronitrile (0.841 mL, 9.37 mmol) was added dropwise. After stirring for 10 minutes, the solution of deprotonated nitrile was added to the suspension of the remaining reagents. The flask was then heated to 100° C. for 16 hours. The reaction flask was cooled to room temperature. The mixture was extracted with methyl tert-butyl ether after diluting with saturated aqueous ammonium chloride. The organic extracts were concentrated in vacuo and purified via flash chromatography, eluting with 0:100 to 20:80 ethyl acetate:heptanes over 20 minutes on a 40 g silica gel column to give the title compound. $^1$H NMR (400 MHz, Chloroform-d) δ ppm 7.50 (dd, J=2.6, 1.4 Hz, 1H), 7.28 (dd, J=8.5, 2.7 Hz, 1H), 6.74 (d, J=8.5 Hz, 1H), 4.69 (s, 2H), 3.75 (s, 3H), 1.64 (s, 6H), 0.90 (s, 9H), 0.05 (s, 6H); MS (ESI) m/z 320.0 (M+H)$^+$.

Example 187C 2-(3-(hydroxymethyl)-4-methoxyphenyl)-2-methylpropanenitrile

Example 187B (2 g, 6.26 mmol) was dissolved in methanol (10 mL) and HCl (3M in cyclopropyl methyl ether, 0.209 mL, 0.626 mmol) was added. Stirring was continued for 10 minutes, at which point complete deprotection had occurred. The reaction was concentrated in vacuo to give the title compound, which was used without additional purification. $^1$H NMR (400 MHz, Chloroform-d) δ ppm 7.39 (d, J=8.4 Hz, 2H), 6.88 (d, J=8.2 Hz, 1H), 4.70 (s, 2H), 3.87 (s, 3H), 2.16 (br s, 1H), 1.71 (s, 6H); MS (ESI) m/z 188.0 (M-OH)$^+$.

Example 187D 2-(3-(bromomethyl)-4-methoxyphenyl)-2-methylpropanenitrile

To 2-(3-(hydroxymethyl)-4-methoxyphenyl)-2-methylpropanenitrile (470 mg, 2.290 mmol) dissolved in dichloromethane (11.4 mL) was added dibromotriphenylphosphorane (1063 mg, 2.52 mmol) all at once, and the resulting solution was stirred at room temperature for 30 minutes. The mixture was diluted with methyl tert-butyl ether, filtered, and the filtrate was concentrated. The residue was loaded onto a 12 g silica gel column and was eluted with 0-15% methyl tert-butyl ether in heptane over 15 minutes to give the title compound. $^1$H NMR (400 MHz, Chloroform-d) δ ppm 7.48-7.32 (m, 2H), 6.93-6.84 (m, 1H), 4.56 (s, 2H), 3.91 (s, 3H), 1.72 (s, 6H).

Example 187E (2S,3R,4S,5S)-3-tert-butyl-4-{[5-(2-cyanopropan-2-yl)-2-methoxyphenyl]methoxy}-5-(2-methylphenyl)-1-[(2S)-oxane-2-carbonyl]pyrrolidine-2-carboxylic acid The title compound was prepared according to the procedure described in Example 188, substituting Example 187D for Intermediate 6. $^1$H NMR (400 MHz, DMSO-d$_6$) δ ppm 7.26 (dd, J=8.6, 2.7 Hz, 1H), 7.08 (d, J=3.9 Hz, 3H), 6.89 (d, J=2.7 Hz, 1H), 6.84 (d, J=8.6 Hz, 1H), 5.51 (s, 1H), 4.63-4.57 (m, 1H), 4.22 (d, J=5.9 Hz, 1H), 4.18 (d, J=12.8 Hz, 1H), 3.78 (dd, J=20.3, 12.1 Hz, 3H), 3.66 (s, 3H), 2.45-2.43 (m, 1H), 2.33 (s, 3H), 1.68-1.61 (m, 1H), 1.56 (d, J=5.3 Hz, 6H), 1.50 (d, J=12.4 Hz, 1H), 1.31 (d, J=8.7 Hz, 4H), 0.98 (s, 9H); MS (ESI+) m/z 577 (M+H)$^+$.

Example 188

(2S,3R,4S,5S)-3-tert-butyl-4-[(5-tert-butyl-2-methoxyphenyl)methoxy]-5-(2-methylphenyl)-1-[(2S)-oxane-2-carbonyl]pyrrolidine-2-carboxylic acid Example 188A (2S,3R,4S,5S)-ethyl 3-(tert-butyl)-4-hydroxy-5-(o-tolyl)pyrrolidine-2-carboxylate To a solution of (2S,3R,4S,5S)-1-allyl 2-ethyl 3-(tert-butyl)-4-hydroxy-5-(o-tolyl)pyrrolidine-1,2-dicarboxylate (1.44 g, 3.70 mmol) (Example 129C) and 1,3-dimethylpyrimidine-2,4,6(1H,3H,5H)-trione (1.155 g, 7.39 mmol) in ethyl acetate/dichloromethane(1:1) (8 mL) was added tetrakis(triphenylphosphine)palladium(0) (0.076 g, 0.074 mmol). The mixture was stirred at room temperature for 30 minutes. Dichloromethane and aqueous Na$_2$CO$_3$ (2N, 2 mL) were added and the mixture was stirred for 10 minutes. The organic layer was washed with brine, dried over MgSO$_4$, filtered, and concentrated. The residue was purified by chromatography on a 24 g silica gel cartridge, eluting with ethyl acetate in heptane at a 0-50% gradient to provide the title compound. MS (APCI+) m/z 306 (M+H)$^+$.

Example 188B (2S,3R,4S,5S)-ethyl 3-(tert-butyl)-4-hydroxy-1-((S)-tetrahydro-2H-pyran-2-carbonyl)-5-(o-tolyl)pyrrolidine-2-carboxylate To (S)-tetrahydro-2H-pyran-2-carboxylic acid (0.469 g, 3.60 mmol) (Intermediate 5) and a drop of N,N-dimethylformamide in CH$_2$Cl$_2$ (2 mL) was added oxalyl dichloride (0.831 g, 6.55 mmol) dropwise. The mixture was stirred at room temperature for 20 minutes. The solvent was removed and fresh CH$_2$Cl$_2$ was added. The solvent was removed again. The residue was added to CH$_2$Cl$_2$ (2 mL) and added to a mixture of Example 188A (1.0 g, 3.27 mmol) and triethylamine (1.369 mL, 9.82 mmol) in CH$_2$Cl$_2$ (8 mL) cooling in an ice bath. During the addition, the temperature was kept around 0° C. The mixture was stirred in ice bath for 20 minutes, and allowed to warm to ambient temperature. CH$_2$Cl$_2$ (20 mL) and water (10 mL) were added. The organic layer was washed with brine, dried over MgSO$_4$, filtered and concentrated to yield the title compound, which was used in the next step. $^1$H NMR (400 MHz, DMSO-d$_6$) δ ppm 7.94

(s, 1H), 7.11 (d, J=4.2 Hz, 3H), 5.44 (s, 1H), 4.48-4.35 (m, 2H), 4.15 (q, J=7.1 Hz, 2H), 3.95 (s, 2H), 3.84-3.75 (m, 2H), 3.34 (s, 1H), 2.95 (s, 1H), 2.32 (s, 3H), 2.21 (t, J=3.9 Hz, 1H), 1.36 (d, J=24.9 Hz, 5H), 1.24 (t, J=7.1 Hz, 6H), 0.98 (s, 9H); MS (ESI+) m/z 418.2 (M+H)+.

Example 188C (2S,3R,4S,5S)-3-tert-butyl-4-[(5-tert-butyl-2-methoxyphenyl)methoxy]-5-(2-methylphenyl)-1-[(2S)-oxane-2-carbonyl]pyrrolidine-2-carboxylic acid To Example 188B (100 mg, 0.239 mmol) and 2-(bromomethyl)-4-(tert-butyl)-1-methoxybenzene(Intermediate 6) (67.8 mg, 0.263 mmol) in N,N-dimethylformamide (2 mL) cooling in an ice bath was added potassium 2-methylpropan-2-olate (0.36 mL, 1.0 M in $CH_2Cl_2$) dropwise. The mixture was stirred in ice bath for 20 minutes, warmed to ambient temperature, and stirred for 30 minutes. Dichloromethane (10 mL) and saturated aqueous $NH_4Cl$ (10 mL) were added and the organic layer was washed with brine, dried over $MgSO_4$, filtered, and concentrated. The residue was purified via chromatography on a 10 g silica gel cartridge, eluting with ethyl acetate in heptane at a 0-60% gradient to yield the intermediate, (2S,3R,4S,5S)-ethyl 3-(tert-butyl)-4-((5-(tert-butyl)-2-methoxybenzyl)oxy)-1-((S)-tetrahydro-2H-pyran-2-carbonyl)-5-(o-tolyl)pyrrolidine-2-carboxylate, which was dissolved in methanol (2 mL) and 6 N aqueous LiOH (0.5 mL). The mixture was stirred at 45° C. for 4 hours, and the pH was adjusted to 1~2 by adding 2N aqueous HCl. The mixture was extracted with dichloromethane, dried over $MgSO_4$, filtered, and concentrated. Purification via chromatography, eluting with methanol in $CH_2Cl_2$, 0-20% gradient, provided the title compound. $^1H$ NMR (400 MHz, DMSO-$d_6$) δ ppm 8.07-8.01 (m, 1H), 7.14-7.05 (m, 4H), 6.85 (d, J=2.6 Hz, 1H), 6.72 (d, J=8.6 Hz, 1H), 5.50 (s, 1H), 4.59 (d, J=2.0 Hz, 1H), 4.22-4.10 (m, 3H), 3.77 (dd, J=16.6, 12.1 Hz, 3H), 3.61 (s, 3H), 2.44 (d, J=2.0 Hz, 1H), 2.32 (s, 3H), 1.70-1.29 (m, 6H), 1.17 (s, 9H), 0.97 (s, 9H); MS (ESI+) m/z 566 (M+H)+.

Example 189

(2S,3R,4S,5S)-3-tert-butyl-4-[(2-methoxyquinolin-3-yl)methoxy]-5-(2-methylphenyl)-1-[(2S)-oxane-2-carbonyl]pyrrolidine-2-carboxylic acid To (2S,3R,4S,5S)-ethyl 3-(tert-butyl)-4-hydroxy-1-((S)-tetrahydro-2H-pyran-2-carbonyl)-5-(o-tolyl)pyrrolidine-2-carboxylate (Example 188B) (100 mg, 0.239 mmol) and 3-(bromomethyl)-2-methoxyquinoline [CAS#85-46-1](66.4 mg, 0.263 mmol) in N,N-dimethylformamide (2 mL) cooling in an ice bath, potassium 2-methylpropan-2-olate (40.3 mg, 0.359 mmol), (0.36 mL, 1.0 M in dichloromethane) was added dropwise. The mixture was stirred in an ice bath for 20 minutes, and stirred at room temperature for 30 minutes. Dichloromethane (20 mL) and saturated aqueous $NH_4Cl$ (5 mL) were added. The organic layer was washed with brine, dried over $MgSO_4$, filtered, and concentrated. The residue was purified via chromatography, eluting with ethyl acetate in heptane, using a 0-40% gradient to give (2S,3R,4S,5S)-ethyl 3-(tert-butyl)-4-((2-methoxyquinolin-3-yl)methoxy)-1-((S)-tetrahydro-2H-pyran-2-carbonyl)-5-(o-tolyl)pyrrolidine-2-carboxylate, which dissolved in methanol (2 mL) and 6 M aqueous LiOH (0.5 mL). The mixture was stirred at 50° C. for 4 hours. The pH was adjusted to 1~2 by adding 2 M aqueous HCl. The mixture was concentrated to dryness. The residue was purified by chromatography, eluting with ethyl acetate/methanol (9:1) in heptane, at a 0-50% gradient to yield the title compound. $^1H$ NMR (400 MHz, DMSO-$d_6$) δ ppm 8.12-8.06 (m, 1H), 7.66 (dq, J=7.9, 1.0 Hz, 1H), 7.54 (dd, J=8.3, 7.3 Hz, 2H), 7.34 (td, J=7.2, 1.2 Hz, 1H), 7.26 (q, J=1.1 Hz, 1H), 7.13 (d, J=4.6 Hz, 3H), 5.59 (d, J=9.3 Hz, 1H), 4.69-4.65 (m, 1H), 4.34 (dd, J=14.0, 1.3 Hz, 1H), 4.30 (d, J=5.8 Hz, 1H), 3.97 (dd, J=14.0, 1.3 Hz, 1H), 3.91 (s, 3H), 3.77 (d, J=11.3 Hz, 1H), 3.40 (s, 2H), 2.53 (d, J=1.9 Hz, 1H), 2.32 (s, 3H), 1.71-1.30 (m, 6H), 1.02 (s, 9H); MS (ESI+) m/e 561 (M+H)+.

Example 190

(2S,3R,4S,5S)-3-tert-butyl-5-(4'-fluoro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid A 4 mL vial was charged with Pd(dppf)$Cl_2$ ([1,1'-bis(diphenylphosphino)ferrocene]dichloropalladium(II), 2.72 mg, 0.0037 mmol, 0.1 eq) and stir bar. To this was added a stock solution of Example 178C (0.074 M in dioxane, 500 µL, 0.037 mmol, 1.0 eq) and 4-fluorophenylboronic acid (0.6 M in dioxane, 74 µL, 0.044 mmol, 1.2 eq), followed by the addition of $Cs_2CO_3$ (1 M in water, 111 µL, 0.11 mmol, 3.0 eq). The vial was capped and placed to stir at 85° C. for 2 hours. The solvent was removed under a stream of nitrogen and the reaction vial was charged with tetrahydrofuran (1 mL). To this was added 1 mL of a 1M aqueous solution of LiOH in 75% methanol. The reaction was placed to stir at 60° C. until the hydrolysis was complete. The material was dried in vacuo, dissolved in methanol, passed through a diatomaceous earth cartridge and washed with methanol (2×1 mL). The sample was dried in vacuo and dissolved in DMSO and filtered and purified via preparative reverse phase HPLC/MS to provide the title compound. $^1H$ NMR (400 MHz, 120° C., DMSO-$d_6$:$D_2O$=9:1 (v/v)) δ ppm 8.35-8.26 (m, 1H), 8.20-8.07 (m, 1H), 7.32-7.18 (m, 7H), 7.17-7.01 (m, 1H), 5.28-5.17 (m, 1H), 4.61 (s, 1H), 4.40-4.26 (m, 1H), 4.02-3.79 (m, 4H), 3.78-3.59 (m, 2H), 3.29-3.04 (m, 2H), 2.44 (s, 1H), 1.76-1.11 (m, 6H), 0.80 (s, 9H); MS (APCI+) m/z 659.4 (M+H)+.

Example 191

(2S,3R,4S,5S)-3-tert-butyl-5-(3'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid Example 191 was prepared following the general procedure used to prepare Example 190, substituting 3-chlorophenylboronic acid for 4-fluorophenylboronic acid. $^1H$ NMR (400 MHz, 120° C., DMSO-$d_6$:$D_2O$=9:1 (v/v)) δ ppm 8.37-8.26 (m, 1H), 8.21-8.11 (m, 1H), 7.53-7.37 (m, 2H), 7.36-7.03 (m, 6H), 5.30-5.12 (m, 1H), 4.61 (s, 1H), 4.33 (d, J=13.9 Hz, 1H), 4.00-3.82 (m, 4H), 3.71 (s, 2H), 3.29-3.05 (m, 2H), 2.45 (s, 1H), 1.84-1.06 (m, 6H), 0.81 (s, 9H); MS (APCI+) m/z 675.3 (M+H)+.

Example 192

(2S,3R,4S,5S)-3-tert-butyl-4-{[2-methoxy-5-(trifluoromethyl)pyridin-3-yl]methoxy}-5-[2-(1-methyl-1,2,3,6-tetrahydropyridin-4-yl)phenyl]-1-[(2S)-oxane-2-carbonyl]pyrrolidine-2-carboxylic acid Example 192 was prepared following the general procedure used to prepare Example 190, substituting 1-methyl- 4-(4,5,5-tetramethyl-1,3,2-dioxaborolan-2-yl)-1,2,3,6-tetrahydropyridine for 4-fluorophenylboronic acid. $^1$H NMR (400 MHz, 120° C., DMSO-d$_6$:D$_2$O=9:1 (v/v)) δ ppm 8.29 (s, 1H), 8.11-7.90 (m, 1H), 7.25-6.91 (m, 4H), 5.45 (s, 1H), 5.43-5.31 (m, 1H), 4.71 (s, 1H), 4.34 (d, J=14.0 Hz, 1H), 4.11-4.04 (m, 1H), 3.93-3.84 (m, 4H), 3.79-3.65 (m, 2H), 3.36-3.03 (m, 2H), 2.67 (d, J=30.9 Hz, 2H), 2.56-2.43 (m, 2H), 2.37 (s, 5H), 1.76-1.29 (m, 6H), 1.01 (s, 9H); MS (APCI+) m/z 660.4 (M+H)$^+$.

Example 193

(2S,3R,4S,5S)-3-tert-butyl-4-{[2-methoxy-5-(trifluoromethyl)pyridin-3-yl]methoxy}-5-[2-(1-methyl-1H-pyrazol-4-yl)phenyl]-1-[(2S)-oxane-2-carbonyl]pyrrolidine-2-carboxylic acid Example 193 was prepared following the general procedure used to prepare Example 190, substituting 1-methyl-4-(4,4,5,5-tetramethyl-1,3,2-dioxaborolan-2-yl)-1H-pyrazole for 4-fluorophenylboronic acid. $^1$H NMR (400 MHz, 120° C., DMSO-d$_6$:D$_2$O=9:1 (v/v)) δ ppm 8.27 (s, 1H), 8.19 (d, J=7.3 Hz, 1H), 7.62 (s, 1H), 7.40 (s, 1H), 7.19 (d, J=18.7 Hz, 4H), 5.56-5.43 (m, 1H), 4.62-4.50 (m, 1H), 4.29 (d, J=13.9 Hz, 1H), 3.97-3.83 (m, 7H), 3.68-3.16 (m, 4H), 1.89 (s, 1H), 1.67-1.20 (m, 6H), 0.91 (s, 9H); MS (APCI+) m/z 645.4 (M+H)$^+$.

Example 194

(2S,3R,4S,5S)-3-tert-butyl-5-[3'-(dimethylamino)[1,1'-biphenyl]-2-yl]-4-{[2-methoxy-5-(trifluoromethyl)pyridin-3-yl]methoxy}-1-[(2S)-oxane-2-carbonyl]pyrrolidine-2-carboxylic acid Example 194 was prepared following the general procedure used to prepare Example 190, substituting (3-(dimethylamino)phenyl)boronic acid for 4-fluorophenylboronic acid. $^1$H NMR (400 MHz, 120° C., DMSO-d$_6$:D$_2$O=9:1 (v/v)) δ ppm 8.36-8.25 (m, 1H), 8.09-8.01 (m, 1H), 7.30-7.08 (m, 5H), 6.80-6.66 (m, 1H), 6.61-6.56 (m, 1H), 6.53 (d, J=7.4 Hz, 1H), 5.41 (d, J=5.7 Hz, 1H), 4.64 (s, 1H), 4.32 (d, J=14.0 Hz, 1H), 3.93-3.85 (m, 4H), 3.81-3.65 (m, 2H), 3.25-3.06 (m, 2H), 2.84 (s, 6H), 2.41 (d, J=1.5 Hz, 1H), 1.76-1.13 (m, 6H), 0.79 (s, 9H); MS (APCI+) m/z 684.4 (M+H)$^+$.

Example 195

(2S,3R,4S,5S)-3-tert-butyl-4-{[2-methoxy-5-(trifluoromethyl)pyridin-3-yl]methoxy}-5-(2'-methyl[1,1'-biphenyl]-2-yl)-1-[(2S)-oxane-2-carbonyl]pyrrolidine-2-carboxylic acid Example 195 was prepared following the general procedure used to prepare Example 190, substituting o-tolylboronic acid for 4-fluorophenylboronic acid. $^1$H NMR (400 MHz, 120° C., DMSO-d$_6$:D$_2$O=9:1 (v/v)) δ ppm 8.37-8.26 (m, 1H), 8.16-8.03 (m, 1H), 7.34-7.13 (m, 7H), 7.05-6.98 (m, 1H), 5.30-5.21 (m, 1H), 4.74-4.69 (m, 1H), 4.62 (s, 1H), 4.38 (d, J=13.8 Hz, 1H), 4.02-3.89 (m, 4H), 3.85-3.72 (m, 2H), 3.66-3.23 (m, 2H), 2.45 (s, 1H), 1.99 (s, 3H), 1.53 (d, J=67.9 Hz, 6H), 0.73 (d, J=2.5 Hz, 9H); MS (APCI+) m/z 655.4 (M+H)$^+$.

Example 196

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(pyridin-4-yl)phenyl]pyrrolidine-2-carboxylic acid Example 196 was prepared following the general procedure used to prepare Example 190, substituting pyridin-4-ylboronic acid for 4-fluorophenylboronic acid. $^1$H NMR (400 MHz, 120° C., DMSO-d$_6$:D$_2$O=9:1 (v/v)) δ ppm 8.68-8.54 (m, 2H), 8.37-8.27 (m, 1H), 8.20-8.11 (m, 1H), 7.40-7.02 (m, 6H), 5.28-5.17 (m, 1H), 4.65 (s, 1H), 4.37-4.30 (m, 1H), 4.01-3.84 (m, 4H), 3.80-3.65 (m, 2H), 3.29-3.01 (m, 2H), 2.43 (s, 1H), 1.67-1.36 (m, 6H), 0.81 (s, 9H); MS (APCI+) m/z 642.3 (M+H)$^+$.

Example 197

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(pyrimidin-5-yl)phenyl]pyrrolidine-2-carboxylic acid Example 197 was prepared following the general procedure used to prepare Example 190, substituting pyrimidin-5-ylboronic acid for 4-fluorophenylboronic acid. $^1$H NMR (400 MHz, 120° C., DMSO-d$_6$:D$_2$O=9:1 (v/v)) δ ppm 9.18 (s, 1H), 8.72 (s, 2H), 8.42-8.30 (m, 1H), 8.30-8.16 (m, 1H), 7.30 (d, J=29.9 Hz, 4H), 5.16-5.04 (m, 1H), 4.66-4.59 (m, 1H), 4.33 (d, J=13.7 Hz, 1H), 4.03-3.87 (m, 4H), 3.79-3.60 (m, 2H), 3.27-2.99 (m, 2H), 2.47 (s, 1H), 1.82-1.12 (m, 6H), 0.82 (s, 9H); MS (APCI+) m/z 643.4 (M+H)$^+$.

Example 198

(2S,3R,4S,5S)-3-tert-butyl-5-[2-(furan-3-yl)phenyl]-4-{[2-methoxy-5-(trifluoromethyl)pyridin-3-yl]methoxy}-1-[(2S)-oxane-2-carbonyl]pyrrolidine-2-carboxylic acid Example 198 was prepared following the general procedure used to prepare Example 190, substituting furan-3-ylboronic acid for 4-fluorophenylboronic acid. $^1$H NMR (400 MHz, 120° C., DMSO-d$_6$:D$_2$O=9:1 (v/v)) δ ppm 8.32-8.28 (m, 1H), 8.21-8.11 (m, 1H), 7.76-7.66 (m, 1H), 7.62-7.55 (m, 1H), 7.30-7.12 (m, 4H), 6.56 (dd, J=1.8, 0.9 Hz, 1H), 5.68-5.40 (m, 1H), 4.63 (s, 1H), 4.30 (d, J=14.0 Hz, 1H), 4.06-3.93 (m, 1H), 3.92-3.81 (m, 4H), 3.75-3.61 (m, 1H), 3.11-3.03 (m, 2H), 2.47 (s, 1H), 1.74-1.23 (m, 6H), 0.92 (s, 9H); MS (APCI+) m/z 631.3 (M+H)$^+$.

Example 199

(2S,3R,4S,5S)-3-tert-butyl-4-{[2-methoxy-5-(trifluoromethyl)pyridin-3-yl]methoxy}-5-[2-(1-methyl-1H-pyrrol-3-yl)phenyl]-1-[(2S)-oxane-2-carbonyl]pyrrolidine-2-carboxylic acid Example 199 was prepared following the general procedure used to prepare Example 190, substituting 1-methyl-3-(4,4,5,5-tetramethyl-1,3,2-dioxaborolan-2-yl)-1H-pyrrole for 4-fluorophenylboronic acid. $^1$H NMR (400 MHz, 120° C., DMSO-d$_6$:D$_2$O=9:1 (v/v)) δ ppm 8.29 (s, 1H), 8.05 (d, J=7.8 Hz, 1H), 7.30-7.24 (m, 1H), 7.21-7.07 (m, 3H), 6.77-6.72 (m, 1H), 6.68-6.63 (m, 1H), 6.08 (t, J=2.3 Hz, 1H), 5.71 (s, 1H), 4.62 (s, 1H), 4.29 (d, J=14.0 Hz, 1H), 3.88

(s, 4H), 3.74-3.34 (m, 5H), 3.18-2.90 (m, 2H), 2.44 (d, J=1.6 Hz, 1H), 1.71-1.24 (m, 6H), 0.92 (s, 9H); MS (APCI+) m/z 644.4 (M+H)+.

Example 200

(2S,3R,4S,5S)-3-tert-butyl-5-(2'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid Example 200 was prepared following the general procedure used to prepare Example 190, substituting 2-chlorophenylboronic acid for 4-fluorophenylboronic acid. $^1$H NMR (400 MHz, 120° C., DMSO-d$_6$:D$_2$O=9:1 (v/v)) δ ppm 8.29 (d, J=12.5 Hz, 1H), 8.17-8.11 (m, 1H), 7.57-7.49 (m, 2H), 7.45-7.38 (m, 2H), 7.27 (s, 2H), 7.16-7.02 (m, 2H), 4.69-4.52 (m, 1H), 4.46-4.26 (m, 1H), 4.01-3.82 (m, 5H), 3.81-3.59 (m, 2H), 3.33-2.92 (m, 2H), 2.46 (s, 1H), 1.85-1.13 (m, 6H), 0.82-0.66 (m, 9H); MS (APCI+) m/z 675.4 (M+H)+.

Example 201

(2S,3R,4S,5S)-3-tert-butyl-4-{[2-methoxy-5-(trifluoromethyl)pyridin-3-yl]methoxy}-1-[(2S)-oxane-2-carbonyl]-5-[3'-(trifluoromethoxy) [1,1'-biphenyl]-2-yl]pyrrolidine-2-carboxylic acid Example 201 was prepared following the general procedure used to prepare Example 190, substituting (3-(trifluoromethoxy)phenyl)boronic acid for 4-fluorophenylboronic acid. $^1$H NMR (400 MHz, 120° C., DMSO-d$_6$:D$_2$O=9:1 (v/v)) δ ppm 8.37-8.27 (m, 1H), 8.25-8.10 (m, 1H), 7.58 (t, J=8.0 Hz, 1H), 7.43-7.24 (m, 4H), 7.24-7.15 (m, 1H), 7.15-7.07 (m, 2H), 5.26 (s, 1H), 4.64 (s, 1H), 4.32 (d, J=13.9 Hz, 1H), 3.96-3.85 (m, 4H), 3.83-3.50 (m, 2H), 3.26-2.94 (m, 2H), 2.43 (s, 1H), 1.79-1.13 (m, 6H), 0.78 (s, 9H); MS (APCI+) m/z 725.4 (M+H)+.

Example 202

(2S,3R,4S,5S)-3-tert-butyl-5-(4'-chloro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid Example 202 was prepared following the general procedure used to prepare Example 190, substituting 4-chlorophenylboronic acid for 4-fluorophenylboronic acid. $^1$H NMR (400 MHz, 120° C., DMSO-d$_6$:D$_2$O=9:1 (v/v)) δ ppm 8.32 (s, 1H), 8.17-8.09 (m, 1H), 7.53-7.44 (m, 2H), 7.33-7.21 (m, 5H), 7.18-7.06 (m, 1H), 5.26-5.19 (m, 1H), 4.69-4.58 (m, 1H), 4.33 (d, J=13.8 Hz, 1H), 3.99-3.83 (m, 4H), 3.79-3.61 (m, 2H), 3.20-2.94 (m, 2H), 2.43 (d, J=1.4 Hz, 1H), 1.80-1.09 (m, 6H), 0.81 (s, 9H); MS (APCI+) m/z 675.3 (M+H)+.

Example 203

(2S,3R,4S,5S)-5-[2-(2H-1,3-benzodioxol-5-yl)phenyl]-3-tert-butyl-4-{[2-methoxy-5-(trifluoromethyl)pyridin-3-yl]methoxy}-1-[(2S)-oxane-2-carbonyl]pyrrolidine-2-carboxylic acid Example 203 was prepared following the general procedure used to prepare Example 190, substituting benzo[d][1,3]dioxol-5-ylboronic acid for 4-fluorophenylboronic acid. $^1$H NMR (400 MHz, 120° C., DMSO-d$_6$:D$_2$O=9:1 (v/v)) δ ppm 8.37-8.26 (m, 1H), 8.21-8.06 (m, 1H), 7.26-7.15 (m, 3H), 7.15-7.07 (m, 1H), 6.93 (d, J=7.9 Hz, 1H), 6.76-6.73 (m, 1H), 6.69 (dd, J=7.9, 1.7 Hz, 1H), 5.99 (s, 2H), 5.30 (s, J=5.6 Hz, 1H), 4.60 (s, 1H), 4.33 (d, J=13.8 Hz, 1H), 3.94-3.87 (m, 4H), 3.85-3.62 (m, 2H), 3.22-2.97 (m, 2H), 2.47-2.42 (m, 1H), 1.78-1.08 (m, 6H), 0.83 (s, 9H); MS (APCI+) m/z 685.4 (M+H)+.

Example 204

(2S,3R,4S,5S)-3-tert-butyl-5-(2'-fluoro[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid Example 204 was prepared following the general procedure used to prepare Example 190, substituting 2-fluorophenylboronic acid for 4-fluorophenylboronic acid. $^1$H NMR (400 MHz, 120° C., DMSO-d$_6$:D$_2$O=9:1 (v/v)) δ ppm 8.30 (s, 1H), 8.20-8.05 (m, 1H), 7.54-7.40 (m, 1H), 7.34-7.07 (m, 7H), 5.10 (s, 1H), 4.63 (s, 1H), 4.35 (d, J=14.0 Hz, 1H), 3.97-3.86 (m, 4H), 3.77-3.62 (m, 2H), 3.35-3.15 (m, 2H), 2.43 (s, 1H), 1.77-1.11 (m, 6H), 0.78 (s, 9H); MS (APCI+) m/z 659.4 (M+H)+.

Example 205

(2S,3R,4S,5S)-3-tert-butyl-5-[2-(6-methoxypyridin-3-yl)phenyl]-4-{[2-methoxy-5-(trifluoromethyl)pyridin-3-yl]methoxy}-1-[(2S)-oxane-2-carbonyl]pyrrolidine-2-carboxylic acid Example 205 was prepared following the general procedure used to prepare Example 190, substituting 2-methoxy-5-(4,4,5,5-tetramethyl-1,3,2-dioxaborolan-2-yl)pyridine for 4-fluorophenylboronic acid. $^1$H NMR (400 MHz, 120° C., DMSO-d$_6$:D$_2$O=9:1 (v/v)) δ ppm 8.36-8.28 (m, 1H), 8.17-8.12 (m, 1H), 8.02 (d, J=2.7 Hz, 1H), 7.60 (dd, J=8.5, 2.5 Hz, 1H), 7.34-7.21 (m, 3H), 7.18-7.09 (m, 1H), 6.87 (d, J=8.5 Hz, 1H), 5.34-5.09 (m, 1H), 4.62 (s, 1H), 4.33 (d, J=13.8 Hz, 1H), 3.95-3.84 (m, 7H), 3.82-3.58 (m, 2H), 3.27-3.00 (m, 2H), 2.45 (s, 1H), 1.80-1.18 (m, 6H), 0.82 (s, 9H); MS (APCI+) m/z 672.4 (M+H)+.

Example 206

(2S,3R,4S,5S)-3-tert-butyl-4-{[2-methoxy-5-(trifluoromethyl)pyridin-3-yl]methoxy}-1-[(2S)-oxane-2-carbonyl]-5-[4'-(trifluoromethoxy) [1,1'-biphenyl]-2-yl]pyrrolidine-2-carboxylic acid Example 206 was prepared following the general procedure used to prepare Example 190, substituting (4-(trifluoromethoxy)phenyl)boronic acid for 4-fluorophenylboronic acid. $^1$H NMR (400 MHz, 120° C., DMSO-d$_6$:D$_2$O=9:1 (v/v)) δ ppm 8.35-8.25 (m, 1H), 8.18-8.06 (m, 1H), 7.43-7.31 (m, 4H), 7.31-7.19 (m, 3H), 7.16-7.07 (m, 1H), 5.24-5.12 (m, 1H), 4.64-4.57 (m, 1H), 4.33 (d, J=13.7 Hz, 1H), 3.95-3.87 (m, 4H), 3.86-3.52 (m, 2H), 3.33-3.00 (m, 2H), 2.46-2.37 (m, 1H), 1.49 (d, J=63.4 Hz, 6H), 0.78 (s, 9H); MS (APCI+) m/z 725.4 (M+H)+.

Example 207

(2S,3R,4S,5S)-3-tert-butyl-5-(4'-cyano[1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid Example 207 was prepared following the general procedure used to prepare Example 190, substituting (4-cyanophenyl)boronic acid for 4-fluorophenylboronic acid. $^1$H NMR (400 MHz, 120° C., DMSO-d$_6$:D$_2$O=9:1 (v/v)) δ ppm 8.34-8.27 (m, 1H), 8.21-8.14 (m, 1H), 7.85 (d, J=8.1 Hz, 2H), 7.46 (d, J=8.1 Hz, 2H), 7.36-7.18 (m, 3H), 7.17-7.09 (m, 1H), 5.30-5.00 (m, 1H), 4.68-4.57 (m, 1H), 4.39-4.26 (m, 1H), 3.96-3.84 (m, 4H), 3.81-3.55 (m, 2H), 3.27-2.95 (m, 2H), 2.43 (s, 1H), 1.83-1.15 (m, 6H), 0.80 (s, 9H); MS (APCI+) m/z 666.4 (M+H)$^+$.

Example 208

(2S,3R,4S,5S)-3-tert-butyl-4-{[2-methoxy-5-(trifluoromethyl)pyridin-3-yl]methoxy}-1-[(2S)-oxane-2-carbonyl]-5-{2-[6-(trifluoromethyl)pyridin-3-yl]phenyl}pyrrolidine-2-carboxylic acid Example 208 was prepared following the general procedure used to prepare Example 190, substituting (6-(trifluoromethyl)pyridin-3-yl)boronic acid for 4-fluorophenylboronic acid. $^1$H NMR (400 MHz, 120° C., DMSO-d$_6$:D$_2$O=9:1 (v/v)) δ ppm 8.64 (s, 1H), 8.32 (d, J=2.2 Hz, 1H), 8.28-8.20 (m, 1H), 8.02-7.87 (m, 2H), 7.39-7.29 (m, 2H), 7.29-7.15 (m, 2H), 5.20-4.96 (m, 1H), 4.61 (s, 1H), 4.34 (d, J=13.8 Hz, 1H), 3.99-3.83 (m, 4H), 3.78-3.60 (m, 2H), 3.31-2.99 (m, 2H), 2.46 (s, 1H), 1.83-1.12 (m, 6H), 0.79 (s, 9H); MS (APCI+) m/z 710.4 (M+H)$^+$.

Example 209

(2S,3R,4S,5S)-3-tert-butyl-5-[2-(5-ethoxypyridin-3-yl)phenyl]-4-{[2-methoxy-5-(trifluoromethyl)pyridin-3-yl]methoxy}-1-[(2S)-oxane-2-carbonyl]pyrrolidine-2-carboxylic acid Example 209 was prepared following the general procedure used to prepare Example 190, substituting (5-ethoxypyridin-3-yl)boronic acid for 4-fluorophenylboronic acid. $^1$H NMR (400 MHz, 120° C., DMSO-d$_6$:D$_2$O=9:1 (v/v)) δ ppm 8.38-8.23 (m, 2H), 8.18-7.96 (m, 2H), 7.36-7.03 (m, 5H), 5.27-5.20 (m, 1H), 4.66 (s, 1H), 4.30 (s, 1H), 4.20-4.00 (m, 2H), 3.90 (s, 4H), 3.78-3.57 (m, 2H), 3.15-2.94 (m, 2H), 2.43 (s, 1H), 1.82-1.37 (m, 6H), 1.33 (t, J=7.0 Hz, 3H), 0.81 (s, 9H); MS (APCI+) m/z 685.5 (M+H)$^+$.

Example 210

(2S,3R,4S,5S)-3-tert-butyl-4-{[2-methoxy-5-(trifluoromethyl)pyridin-3-yl]methoxy}-5-(naphthalen-1-yl)-1-[(2S)-oxane-2-carbonyl]pyrrolidine-2-carboxylic acid

Example 210A (E)-ethyl 2-((naphthalen-2-ylmethylene)amino)acetate

Ethyl 2-aminoacetate hydrochloride (1.117 g, 8.00 mmol) and magnesium sulfate (1.541 g, 12.81 mmol) were suspended in dichloromethane (10.67 mL) and the suspension was treated with triethylamine (1.116 mL, 8.00 mmol). The mixture stirred at room temperature for 1 hour, and 2-naphthaldehyde (1.0 g, 6.40 mmol) was added. The mixture was stirred at room temperature for 20 hours. The solid material was removed via filtration and the filtrate was washed with water (quick wash twice) and brine. The organic layer was dried over sodium sulfate, filtered, and concentrated to give the title compound. $^1$H NMR (400 MHz, DMSO-d$_6$) δ ppm 9.03 (dt, J=8.7, 1.0 Hz, 1H), 8.96 (d, J=1.4 Hz, 1H), 8.07-7.85 (m, 3H), 7.64-7.50 (m, 3H), 4.52 (d, J=1.2 Hz, 2H), 4.14 (q, J=7.1 Hz, 2H), 1.25-1.10 (t, 3H); MS (ESI$^+$) m/z 242.2 (M+H)$^+$.

Example 210B (2S,3R,4S,5S)-ethyl 3-(tert-butyl)-5-(naphthalen-2-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.063 g, 0.084 mmol) and copper (I) triflate dimer, benzene complex (0.016 g, 0.032 mmol) were dissolved in tetrahydrofuran (16.47 mL) that had been sparged with a N$_2$ stream for 4 hours. The resulting solution was stirred for 1.5 hours at room temperature. (E)-ethyl 2-((naphthalen-2-ylmethylene)amino)acetate (1.55 g, 6.42 mmol) in tetrahydrofuran (1 mL) was added after cooling to <5° C. in an ice water bath. Potassium 2-methylpropan-2-olate (0.064 mL, 0.064 mmol) was added dropwise, followed by addition of (E)-3,3-dimethyl-1-nitrobut-1-ene (0.830 g, 6.42 mmol) neat over 25 minutes, maintaining an internal temperature <10° C. After the addition was complete, the mixture was stirred for 15 minutes at the same temperature. The reaction mixture was diluted with methyl tert-butyl ether (30 mL) and stirred with 30 mL of saturated aqueous ammonium chloride at room temperature for 15 minutes. The organic layer was washed with saturated aqueous sodium bicarbonate and brine, dried over sodium sulfate, and filtered. The filtrate was concentrated and the residue was purified by flash chromatography (0 to 30% ethyl acetate in heptane) to provide the title compound. $^1$H NMR (400 MHz, Chloroform-d) δ ppm 7.92 (dd, J=8.1, 1.3 Hz, 1H), 7.85 (dd, J=8.3, 3.4 Hz, 2H), 7.63 (ddd, J=8.2, 6.6, 1.4 Hz, 1H), 7.61-7.51 (m, 2H), 7.53-7.43 (m, 1H), 5.39 (dd, J=6.0, 2.5 Hz, 1H), 5.18 (dd, J=10.7, 5.9 Hz, 1H), 4.44-4.32 (m, 2H), 3.93 (t, J=7.7 Hz, 1H), 3.45 (t, J=9.9 Hz, 1H), 3.15 (dd, J=7.2, 2.4 Hz, 1H), 1.40 (td, J=7.2, 0.6 Hz, 3H), 1.16 (s, 9H); MS (ESI$^+$) m/z 371.3

Example 210C (2S,3R,4S,5S)-3-tert-butyl-4-{[2-methoxy-5-(trifluoromethyl)pyridin-3-yl]methoxy}-5-(naphthalen-1-yl)-1-[(2S)-oxane-2-carbonyl]pyrrolidine-2-carboxylic acid The title compound was prepared according to the procedure described from Example 88A-H, substituting Example 210B for Core 5, and Intermediate 5 for (S)-tetrahydrofuran-2-carboxylic acid, respectively. $^1$H NMR (400 MHz, DMSO-d$_6$) δ ppm 8.30 (s, 1H), 8.21-8.07 (m, 2H), 7.91-7.67 (m, 2H), 7.51 (s, 3H), 6.83 (s, 1H), 6.32 (s, 1H), 4.66 (s, 1H), 4.51 (d, J=6.1 Hz, 1H), 4.20 (d, J=13.9 Hz, 1H), 3.71 (s, 3H), 3.62 (s, 1H), 3.44 (s, 1H), 2.51 (s, 1H), 2.24 (s, 1H), 1.51 (s, 4H), 1.08 (s, 9H), 0.74 (s, 2H); MS (ESI+) m/z 615 (M+H)$^+$.

Example 211

(2S,3R,4S,5S)-3-tert-butyl-4-[(5-tert-butyl-2-methoxyphenyl)methoxy]-5-(naphthalen-1-yl)-1-[(2S)-oxane-2-carbonyl]pyrrolidine-2-carboxylic acid The title compound was prepared according to the procedure described in Example 88A-H, substituting Example 210B for Core 5, Intermediate 6 for Intermediate 8, and Intermediate 5 for (S)-tetrahydrofuran-2-carboxylic acid, respectively. $^1$H NMR (400 MHz, DMSO-$d_6$) δ ppm 8.31 (d, J=7.3 Hz, 1H), 8.15 (d, J=8.5 Hz, 1H), 7.87 (d, J=8.2 Hz, 1H), 7.75 (d, J=8.2 Hz, 1H), 7.57-7.51 (m, 1H), 7.44 (dt, J=15.3, 7.7 Hz, 2H), 7.01 (dd, J=8.5, 2.6 Hz, 1H), 6.63-6.55 (m, 2H), 6.20 (s, 1H), 4.66 (s, 1H), 4.41 (dd, J=6.2, 1.5 Hz, 1H), 4.01 (d, J=12.4 Hz, 1H), 3.59 (d, J=12.4 Hz, 1H), 3.52 (d, J=18.8 Hz, 1H), 3.48 (s, 3H), 3.30 (s, 1H), 2.52 (s, 1H), 1.51 (d, J=35.5 Hz, 4H), 1.08 (s, 9H), 1.04 (s, 9H); MS (ESI+) m/z 602 (M+H)$^+$.

Example 212

(2S,3R,4S,5S)-5-(1-benzofuran-7-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid

Example 212A (E)-ethyl 2-((benzofuran-7-ylmethylene)amino)acetate

Ethyl 2-aminoacetate hydrochloride (1.089 g, 7.80 mmol) and magnesium sulfate (1.502 g, 12.48 mmol) were suspended in dichloromethane (10.40 mL) and the suspension was treated with triethylamine (1.087 mL, 7.80 mmol). The mixture was stirred at room temperature for 1 hour before benzofuran-7-carbaldehyde (0.94 g, 6.24 mmol) in 1 mL of dichloromethane was added. The reaction mixture was stirred at room temperature for 20 hours. The solid material was removed via filtration and the filtrate was washed with water (quick wash twice) and brine, dried over sodium sulfate, filtered, and concentrated to give the title compound. $^1$H NMR (400 MHz, DMSO-$d_6$) δ ppm 8.80 (d, J=1.5 Hz, 1H), 8.08 (d, J=2.2 Hz, 1H), 7.77 (ddd, J=12.1, 7.6, 1.2 Hz, 2H), 7.33 (t, J=7.6 Hz, 1H), 7.03 (d, J=2.2 Hz, 1H), 4.50 (d, J=1.3 Hz, 2H), 4.13 (q, J=7.1 Hz, 2H), 1.21 (t, J=7.1 Hz, 3H); MS (ESI$^+$) m/z 232.2 (M+H)$^+$.

Example 212B (2S,3R,4S,5S)-ethyl 5-(benzofuran-7-yl)-3-(tert-butyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.061 g, 0.081 mmol) and copper (I) triflate dimer, benzene complex (0.016 g, 0.031 mmol) were dissolved in tetrahydrofuran (15.97 mL) that had been sparged with a $N_2$ stream for 4 hours. The resulting solution was stirred for 1.5 hours at room temperature, and (E)-ethyl 2-((benzofuran-7-ylmethylene)amino)acetate (1.44 g, 6.23 mmol) in tetrahydrofuran (1 mL) was added after cooling to <5° C. in an ice water bath. Potassium 2-methylpropan-2-olate (0.062 mL, 0.062 mmol) was added dropwise, followed by addition of (E)-3,3-dimethyl-1-nitrobut-1-ene (0.804 g, 6.23 mmol) neat over 25 minutes, maintaining an internal temperature <10° C. After the addition was complete, the mixture was stirred for 15 minutes at the same temperature. The mixture was diluted with methyl tert-butyl ether (30 mL) and stirred with 30 mL of saturated aqueous ammonium chloride at room temperature for 15 minutes. The organic layer was washed with saturated aqueous sodium bicarbonate and brine, dried over sodium sulfate, and filtered. The filtrate was concentrated and the residue was purified by flash chromatography (0 to 30% ethyl acetate in heptane) to give the title compound. $^1$H NMR (400 MHz, Chloroform-d) δ ppm 7.68 (d, J=2.2 Hz, 1H), 7.58 (dd, J=7.0, 1.9 Hz, 1H), 7.27 (dd, J=9.4, 7.1 Hz, 2H), 6.82 (d, J=2.2 Hz, 1H), 5.46 (dd, J=5.7, 2.3 Hz, 1H), 4.90 (dd, J=12.0, 5.7 Hz, 1H), 4.36 (qd, J=7.2, 1.3 Hz, 2H), 3.91 (t, J=7.8 Hz, 1H), 3.64 (d, J=11.1 Hz, 1H), 2.98 (dd, J=7.0, 2.3 Hz, 1H), 1.38 (t, J=7.1 Hz, 3H), 1.14 (s, 9H); MS (ESI$^+$) m/z 361.1 (M+H)$^+$.

Example 212C (2S,3R,4S,5S)-5-(1-benzofuran-7-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid The title compound was prepared according to the procedure described from Example 88A-H, substituting Example 212B for Core 5, Intermediate 5 for (S)-tetrahydrofuran-2-carboxylic acid, respectively. $^1$H NMR (400 MHz, DMSO-$d_6$) δ ppm 8.26-8.17 (m, 1H), 7.90 (d, J=7.5 Hz, 1H), 7.78 (d, J=2.2 Hz, 1H), 7.43 (d, J=7.7 Hz, 1H), 7.11 (t, J=7.6 Hz, 1H), 6.97 (d, J=2.4 Hz, 1H), 6.80 (d, J=2.2 Hz, 1H), 6.06 (s, 2H), 4.59 (s, 1H), 4.40 (dd, J=6.5, 2.7 Hz, 1H), 4.29 (d, J=13.7 Hz, 1H), 3.86 (d, J=13.7 Hz, 1H), 3.82 (s, 3H), 3.65 (d, J=13.6 Hz, 2H), 2.53 (t, J=3.1 Hz, 1H), 1.67-1.27 (m, 6H), 1.03 (s, 9H); MS (ESI+) m/z 605 (M+H)$^+$.

Example 213

(2S,3R,4S,5S)-3-tert-butyl-4-{[2-methoxy-5-(trifluoromethyl)pyridin-3-yl]methoxy}-5-[2-(2-methylpropyl)phenyl]-1-[(2S)-oxane-2-carbonyl]pyrrolidine-2-carboxylic acid oxane-2-carbonyl]pyrrolidine-2-carboxylic acid

Example 213A (2S,3R,4S,5S)-ethyl 3-(tert-butyl)-5-(2-isobutylphenyl)-4-((2-methoxy-5-(trifluoromethyl)pyridin-3-yl)methoxy)-1-((S)-tetrahydro-2H-pyran-2-carbonyl)pyrrolidine-2-carboxylate (2S,3R,4S,5S)-Ethyl 5-(2-bromophenyl)-3-(tert-butyl)-4-((2-methoxy-5-(trifluoromethyl)pyridin-3-yl)methoxy)-1-((S)-tetrahydro-2H-pyran-2-carbonyl)pyrrolidine-2-carboxylate (Example 178C, 174 mg, 0.259 mmol), isobutylboronic acid (52.8 mg, 0.518 mmol) and potassium carbonate (107 mg, 0.777 mmol) were suspended in toluene (2.5 mL). The reaction was purged with nitrogen for 2 minutes, and [1,1'-bis(diphenylphosphino)ferrocene]dichloropalladium(II) (10.58 mg, 0.013 mmol) was added. The reaction was capped and heated at 110° C. for 4 hours. The solvent was reduced under a stream of nitrogen and the crude material was purified using a 10 g silica gel cartridge with a gradient of 5-100% ethyl acetate/heptanes over 20 minutes to give the title compound. ¹H NMR (400 MHz, DMSO-d6) δ ppm 8.28 (s, 1H), 8.00 (dd, J=7.7, 1.4 Hz, 1H), 7.22 (s, 1H), 7.13-6.97 (m, 3H), 5.48 (s, 1H), 4.71 (s, 1H), 4.40-4.28 (m, 1H), 4.25 (d, J=13.8 Hz, 1H), 4.21 (d, J=5.6 Hz, 1H), 4.08 (qd, J=7.1, 3.3 Hz, 2H), 3.94 (d, J=13.6 Hz, 1H), 3.87 (s, 1H), 3.84 (s, 3H), 3.78 (d, J=13.8 Hz, 1H), 3.73 (d, J=12.9 Hz, 2H), 2.55 (d, J=7.0 Hz, 1H), 2.43 (d, J=1.8 Hz, 1H), 1.94 (td, J=15.7, 14.3, 5.8 Hz, 1H), 1.66 (s, 1H), 1.52 (d, J=12.1 Hz, 1H), 1.36 (s, 3H), 1.14 (t, J=7.1 Hz, 3H), 1.02 (d, J=2.0 Hz, 9H), 0.93 (t, J=6.4 Hz, 6H); MS (APCI+) m/z 649 (M+H)⁺.

Example 213B (2S,3R,4S,5S)-3-tert-butyl-4-{[2-methoxy-5-(trifluoromethyl)pyridin-3-yl]methoxy}-5-[2-(2-methylpropyl)phenyl]-1-[(2S)-oxane-2-carbonyl]pyrrolidine-2-carboxylic acid Example 213A (160 mg, 0.247 mmol) was dissolved in methanol (822 µL) and tetrahydrofuran (822 µL). A solution of lithium hydroxide (56 mg, 2.338 mmol) in water (822 µL) was added. The reaction was heated at 45° C. for 16 hours. The solvent was reduced in volume, and acidified with 1M aqueous HCl to pH ~3. The reaction was extracted with dichloromethane. The solvent was removed and the crude material was purified by reverse-phase preparative HPLC on a Phenomenex® Luna® C8(2) 5 µm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to give the title compound. ¹H NMR (400 MHz, DMSO-d₆) δ ppm 8.27 (dq, J=2.0, 1.0 Hz, 1H), 8.06 (dd, J=7.6, 1.5 Hz, 1H), 7.20 (d, J=2.4 Hz, 1H), 7.06 (q, J=8.8, 7.1 Hz, 3H), 5.50 (s, 1H), 4.67 (d, J=1.7 Hz, 1H), 4.29 (d, J=13.9 Hz, 1H), 4.21 (d, J=5.7 Hz, 1H), 4.07-3.97 (m, 1H), 3.86 (s, 3H), 3.84-3.79 (m, 1H), 3.78-3.70 (m, 1H), 3.18 (d, J=6.3 Hz, 1H), 2.53 (dd, J=7.1, 4.0 Hz, 2H), 2.49 (d, J=1.7 Hz, 1H), 1.91 (dd, J=13.3, 6.8 Hz, 1H), 1.69-1.61 (m, 1H), 1.54 (q, J=11.5 Hz, 1H), 1.35 (d, J=11.8 Hz, 3H), 1.03 (s, 9H), 1.00 (d, J=3.3 Hz, 1H), 0.92 (t, J=6.8 Hz, 6H); MS (ESI+) m/z 621 (M+H)⁺.

Example 214

(2S,3R,4S,5S)-3-tert-butyl-4-[(5-cyclobutyl-2-methoxypyridin-3-yl)methoxy]-5-(2-cyclopropylphenyl)-1-(6-methoxypyridine-2-sulfonyl)pyrrolidine-2-carboxylic acid Example 214A 6-fluoropyridine-2-sulfonyl chloride Di-n-butylmagnesium (1 M in tetrahydrofuran) (3.17 mL, 3.17 mmol) and n-butyllithium (1.6 M in heptanes) (1.979 mL, 3.17 mmol) were combined to give a suspension. To this cooled solution was added dropwise a solution of 2-bromo-6-fluoropyridine (1.393 g, 7.92 mmol) in tetrahydrofuran (8 mL), keeping the internal temperature below −10° C. The reaction was stirred at −10° C. for 1 hour. The solution was added dropwise via cannula to a cooled solution of sulfuryl chloride (16 mL, 16.00 mmol) as a 1 M solution in dichloromethane while stirring in a dry ice/acetone bath keeping the temperature around −10° C. The solvent was reduced in volume and the material was filtered and washed with heptanes to give the title compound. MS (APCI+) m/z 177 (M+H)⁺.

Example 214B (2S,3R,4S,5S)-ethyl 3-(tert-butyl)-4-((5-cyclobutyl-2-methoxypyridin-3-yl)methoxy)-5-(2-cyclopropylphenyl)-1-((6-fluoropyridin-2-yl)sulfonyl)pyrrolidine-2-carboxylate To a solution of Example 149C (50 mg, 0.099 mmol) and pyridine (1 mL) and 1 mL of dichloromethane was added dropwise a solution of 6-fluoropyridine-2-sulfonyl chloride (Example 214A, 50 mg, 0.256 mmol) in dichloromethane. After 45 minutes, the solvent was reduced under a stream of nitrogen. The organics were washed with brine, dried over sodium sulfate, filtered, and concentrated. The crude material was purified using a 25 g silica gel cartridge with a gradient of 5-100% ethyl acetate/heptanes to give the title compound. ¹H NMR (501 MHz, Chloroform-d) δ ppm 7.84-7.71 (m, 2H), 7.59 (d, J=7.8 Hz, 1H), 7.37-7.30 (m, 1H), 7.11-7.07 (m, 2H), 7.07-7.02 (m, 1H), 6.83 (dt, J=8.2, 4.1 Hz, 1H), 6.81-6.78 (m, 1H), 6.06 (d, J=5.6 Hz, 1H), 5.00 (d, J=2.3 Hz, 1H), 4.28-4.15 (m, 4H), 3.85-3.79 (m, 5H), 3.28 (q, J=8.4 Hz, 1H), 2.65 (d, J=2.1 Hz, 1H), 2.32-2.14 (m, 1H), 2.12-1.94 (m, 3H), 1.94-1.80 (m, 2H), 1.24 (t, J=7.1 Hz, 3H), 1.17 (s, 9H), 1.02-0.93 (m, 1H), 0.93-0.83 (m, 2H), 0.59-0.48 (m, 1H); MS (APCI+) m/z 666 (M+H)⁺.

Example 214C (2S,3R,4S,5S)-3-tert-butyl-4-[(5-cyclobutyl-2-methoxypyridin-3-yl)methoxy]-5-(2-cyclopropylphenyl)-1-(6-methoxypyridine-2-sulfonyl)pyrrolidine-2-carboxylic acid Example 214B (61 mg, 0.092 mmol) was dissolved in methanol (0.500 mL) and tetrahydrofuran (0.5 mL). A solution of 2 M aqueous lithium hydroxide (0.458 mL, 0.916 mmol) was added. The reaction was heated at 45° C. for 16 hours. The solvent was removed and the reaction was acidified with 0.458 mL of 2 M aqueous HCl. The reaction was diluted with dichloromethane and the organics were purified using a 10 g silica gel cartridge with an ethyl acetate/ethanol/heptanes solvent system to give the title compound. ¹H NMR (400 MHz, DMSO-d₆) δ ppm 12.71 (s, 1H), 7.93-7.80 (m, 2H), 7.74 (d, J=2.4 Hz, 1H), 7.26 (d, J=7.3 Hz, 1H), 7.06 (dd, J=7.8, 5.3 Hz, 2H), 6.98-6.88 (m, 2H), 6.78 (d, J=2.4 Hz, 1H), 5.81 (d, J=6.1 Hz, 1H), 4.48 (d, J=3.5 Hz, 1H), 4.22 (dd, J=6.2, 2.1 Hz, 1H), 4.17 (d, J=13.4 Hz, 1H), 3.87 (s, 3H), 3.74 (d, J=13.4 Hz, 1H), 3.69 (s, 3H), 3.28-3.18 (m, 2H), 2.42 (dd, J=3.6, 2.0 Hz, 1H), 2.15 (tdd, J=7.8, 5.7, 2.4 Hz, 2H), 2.01 (td, J=8.6, 4.5 Hz, 1H), 1.96-1.76 (m, 4H), 0.89 (s, 9H), 0.86-0.76 (m, 1H), 0.73-0.61 (m, 1H), 0.56 (qd, J=5.5, 2.6 Hz, 1H); MS (APCI+) m/z 650 (M+H)⁺.

Example 215

(2S,3R,4S,5S)-3-tert-butyl-4-{[2-methoxy-5-(1-methylcyclobutyl)phenyl]methoxy}-5-(2-methylphenyl)-1-[(2S)-oxane-2-carbonyl]pyrrolidine-2-carboxylic acid Example 215A 1-(4-methoxyphenyl)cyclobutanol (4-Methoxyphenyl)magnesium bromide (56.9 mL, 28.5 mmol, 0.5 M in tetrahydrofuran) solution was cooled to -78° C. before dropwise addition of cyclobutanone (2.239 mL, 30.0 mmol) via syringe. After the addition was complete, the mixture was warmed to ambient temperature and quenched with saturated aqueous ammonium chloride (10 mL). The mixture was diluted with methyl tert-butyl ether (20 mL) and the layers were separated. The organic layer was washed with saturated aqueous ammonium chloride (20 mL) and brine (20 mL), dried over sodium sulfate, filtered, and concentrated to provide the title compound which was used without additional purification. $^1$H NMR (400 MHz, Chloroform-d) δ ppm 7.45 (d, J=8.8 Hz, 2H), 6.93 (d, J=8.8 Hz, 2H), 3.84 (s, 3H), 2.57 (dddd, J=12.4, 6.5, 2.8, 1.7 Hz, 2H), 2.43-2.27 (m, 2H), 2.18-1.89 (m, 2H), 1.76-1.60 (m, 1H).

Example 215B 1-methoxy-4-(1-methylcyclobutyl)benzene

Example 215A (3 g, 16.83 mmol) was dissolved in dichloromethane (84 mL) and the resulting solution was cooled to −78° C. in a dry ice acetone bath. Titanium(IV) chloride (neat, 3.69 mL, 33.7 mmol) was added via syringe and the solution was stirred for 1 hour at the same temperature before the addition of dimethylzinc (50.5 mL, 50.5 mmol) solution slowly as a 1 M solution in heptanes. After the addition was complete, the reaction flask was warmed to ambient temperature before pouring into 300 mL of ice in a beaker while stirring vigorously. The resulting suspension was diluted with dichloromethane (100 mL) and stirred for 5 minutes before filtering through diatomaceous earth and washing the organic layer with brine (50 mL). The organic layer was dried over sodium sulfate, filtered, and concentrated to provide the title compound, which was used without additional purification. $^1$H NMR (500 MHz, Chloroform-d) δ ppm 7.14 (d, J=8.7 Hz, 2H), 6.90 (d, J=8.7 Hz, 2H), 3.84 (s, 3H), 2.40 (qd, J=9.4, 8.9, 2.1 Hz, 2H), 2.21-2.04 (m, 3H), 1.92-1.81 (m, 1H), 1.48 (s, 3H).

Example 215C 2-methoxy-5-(1-methylcyclobutyl)benzaldehyde

Example 215B (3 g, 17.02 mmol) was dissolved in 110 mL of dichloromethane, and the resulting solution was cooled to <0° C. in an ice brine bath. After addition of dichloro(methoxy)methane (1.70 mL, 18.7 mmol), titanium tetrachloride (2.065 mL, 18.72 mmol) was added dropwise as a solution in 10 mL of dichloromethane over 2 minutes, maintaining an internal temperature <5° C. After 15 minutes at the same temperature, thin layer chromatography indicated complete conversion. The resulting solution was quenched with 40 mL of water, the layers were separated, and the organic layer was concentrated and loaded onto an 80 g silica gel column, eluting with 0:100 to 15:85 ethyl acetate:heptanes over 20 minutes to provide the title compound. $^1$H NMR (400 MHz, Chloroform-d) δ ppm 10.49 (d, J=1.0 Hz, 1H), 7.67 (dd, J=2.6, 0.9 Hz, 1H), 7.40 (ddd, J=8.6, 2.6, 1.0 Hz, 1H), 6.96 (d, J=8.6 Hz, 1H), 3.94 (d, J=0.9 Hz, 3H), 2.37 (td, J=10.3, 9.7, 7.2 Hz, 2H), 2.19-2.01 (m, 3H), 1.89-1.73 (m, 1H), 1.46 (s, 3H); MS (ESI+) m/z=205.1 (M+H)$^+$.

Example 215D (2-methoxy-5-(1-methylcyclobutyl)phenyl)methanol

To 2-methoxy-5-(1-methylcyclobutyl)benzaldehyde (1.0 g, 4.90 mmol) in ethanol (10 mL) cooling in an ice bath, sodium borohydride (0.204 g, 5.39 mmol) was added in portions. The mixture was stirred in an ice bath for 30 minutes, saturated aqueous NH$_4$Cl (2 mL) was added, and the solvent was removed under reduced pressure. The residue was partitioned between ethyl acetate and saturated aqueous sodium bicarbonate. The organics were washed with brine, dried over sodium sulfate, filtered, and concentrated to give the title compound. MS (APCI+) m/z 207 (M+H)$^+$.

Example 215E 2-(bromomethyl)-1-methoxy-4-(1-methylcyclobutyl) benzene

To triphenylphosphine (2365 mg, 9.02 mmol) in dichloromethane (10 mL) cooling in an ice bath was added 1-bromopyrrolidine-2,5-dione (1605 mg, 9.02 mmol) in portions. The mixture was stirred for 30 minutes maintaining an internal temperature <10° C., and (2-methoxy-5-(1-methylcyclobutyl)phenyl)methanol (930 mg, 4.51 mmol) in dichloromethane (2 mL) was added slowly at <10. The mixture stirred in an ice bath for 1 hour. Saturated aqueous NH$_4$Cl (2 mL) was added and the organic layer was washed with saturated aqueous sodium bicarbonate and brine, dried over sodium sulfate, filtered, and concentrated. The residue was purified via chromatography, eluting with ethyl acetate in heptane at a 0-40% gradient to give the title compound. $^1$H NMR (501 MHz, Chloroform-d) δ ppm 7.17-7.11 (m, 2H), 6.84 (s, 1H), 4.60 (s, 2H), 3.91 (s, 3H), 2.40-2.30 (m, 2H), 2.16-1.98 (m, 3H), 1.87-1.77 (m, 1H), 1.46 (d, J=0.7 Hz, 3H).

Example 215F (2S,3R,4S,5S)-3-tert-butyl-4-{[2-methoxy-5-(1-methylcyclobutyl)phenyl]methoxy}-5-(2-methylphenyl)-1-[(2S)-oxane-2-carbonyl]pyrrolidine-2-carboxylic acid To Example 188B (70 mg, 0.168 mmol) and Example 215E (54.2 mg, 0.201 mmol) in N,N-dimethylformamide (2 mL) cooling in an ice bath, potassium 2-methylpropan-2-olate (0.25 mL, 1.0 M in tetrahydrofuran) was added dropwise. The mixture was stirred in ice bath for 20 minutes, and stirred at room temperature for 30 minutes. Dichloromethane (15 mL) and saturated aqueous NH$_4$Cl (5 mL) were added. The organic layer was washed with brine, dried over MgSO$_4$, filtered, and concentrated. The residue was purified via chromatography, eluting with ethyl acetate in heptane, 0-40% gradient to yield ester of (2S,3R,4S,5S)-ethyl 3-(tert-butyl)-4-((2-methoxy-5-(1-methylcyclobutyl)benzyl)oxy)-1-((S)-tetrahydro-2H-pyran-2-carbonyl)-5-(o-tolyl)pyrrolidine-2-carboxylate, which dissolved in methanol (2 mL) and 6N aqueous LiOH (0.5 mL). The mixture was stirred at 45° C. for 4 hours. The solvent was removed and the residue was adjusted pH to 1~2 by adding 2N aqueous HCl. The mixture was extracted with dichloromethane (10 mL×3). The combined organics were washed with brine, dried over MgSO$_4$, filtered, and concentrated. The residue was purified via chromatography, eluting with ethyl acetate/methanol (9:1) in heptane at 0-60% to provide the title compound. $^1$H NMR (400 MHz, DMSO-d$_6$) δ ppm 8.07-8.00 (m, 1H), 7.08 (d, J=4.1 Hz, 3H), 6.93 (dd, J=8.4, 2.5 Hz, 1H), 6.73 (d, J=8.4 Hz, 1H), 6.64 (d, J=2.5 Hz, 1H), 5.50 (s, 1H), 4.59 (d, J=2.1 Hz, 1H), 4.19 (d, J=6.0 Hz, 1H), 4.15 (d, J=12.5 Hz, 1H), 3.81 (d, J=12.6 Hz, 1H), 3.78-3.72 (m, 1H), 3.62 (s, 3H), 3.37 (s, 1H), 3.19 (s, 1H), 2.45 (d, J=2.0 Hz, 1H), 2.32 (s, 3H), 2.17 (qd, J=10.3, 8.7, 4.5 Hz, 2H), 2.07-1.89 (m, 4H), 1.78-1.69 (m, 1H), 1.65 (d, J=13.6 Hz, 1H), 1.49 (t, J=12.2 Hz, 1H), 1.37 (dd, J=21.2, 9.3 Hz, 2H), 1.30 (s, 3H), 1.25 (d, J=5.8 Hz, 1H), 0.97 (s, 9H); MS (ESI+) m/z 578.1 (M+H)+.

Example 216

(2S,3R,4S,5S)-3-tert-butyl-5-(2,3-dihydro-1-benzo-furan-7-yl)-4-{[2-methoxy-5-(trifluoromethyl)pyridin-3-yl]methoxy}-1-[(2S)-oxane-2-carbonyl]pyrrolidine-2-carboxylic acid (2S,3R,4S,5S)-Ethyl 5-(benzofuran-7-yl)-3-(tert-butyl)-4-((2-methoxy-5-(trifluoromethyl)pyridin-3-yl)methoxy)-1-((S)-tetrahydro-2H-pyran-2-carbonyl)pyrrolidine-2-carboxylate (Example 212, 55 mg, 0.087 mmol) in tetrahydrofuran (1.5 mL) was added to Ra—Ni 2800, water slurry (11.34 mg, 0.087 mmol) in a 5 mL Barnstead reactor. The reactor was purged with argon for 5 minutes and stirred under 50 psi of hydrogen at 50° C. for 10 hours. The mixture was cooled down and filtered through a polypropylene membrane. The solvent was removed to yield (2S,3R,4S,5S)-ethyl 3-(tert-butyl)-5-(2,3-dihydrobenzofuran-7-yl)-4-((2-methoxy-5-(trifluoromethyl)pyridin-3-yl)methoxy)-1-((S)-tetrahydro-2H-pyran-2-carbonyl)pyrrolidine-2-carboxylate, which was dissolved in methanol (1.5 mL) and 6 N aqueous LiOH (0.5 mL) and stirred at 50° C. for 4 hours. The pH was adjusted to 1~2 by adding 2 M aqueous HCl. The mixture was concentrated to dryness. Purification by chromatography on a 12 g silica gel cartridge, eluting with ethyl acetate/methanol (9:1) in heptane using a 0-60% gradient gave the title compound. $^1$H NMR (400 MHz, DMSO-$d_6$) δ ppm 8.29 (d, J=2.0 Hz, 1H), 7.69 (d, J=7.8 Hz, 1H), 7.21 (d, J=2.4 Hz, 1H), 7.00 (d, J=7.3 Hz, 1H), 6.69 (t, J=7.5 Hz, 1H), 5.60 (s, 1H), 4.51-4.48 (m, 1H), 4.47-4.42 (m, 1H), 4.42-4.37 (m, 1H), 4.37-4.33 (m, 1H), 4.23 (dd, J=6.6, 3.0 Hz, 1H), 4.04 (d, J=13.9 Hz, 1H), 3.90 (s, 3H), 3.83-3.76 (m, 1H), 3.17-3.09 (m, 2H), 2.99 (dd, J=16.2, 7.9 Hz, 4H), 1.67 (d, J=13.0 Hz, 1H), 1.56-1.31 (m, 4H), 1.25 (s, 1H), 0.98 (s, 9H); MS (ESI+) m/z 607.2 (M+1)+.

Example 217

(2S,3R,4S,5S)-3-tert-butyl-4-[(5-cyclopropyl-2-methoxypyridin-3-yl)methoxy]-5-(2-methylphenyl)-1-[(2S)-oxane-2-carbonyl]pyrrolidine-2-carboxylic acid Example 217A
5-cyclopropyl-2-methoxynicotinaldehyde 5-Bromo-2-methoxynicotinaldehyde (4 gg, 18.52 mmol) in 1,4-dioxane (40 mL) was degassed with nitrogen for 5 minutes, and cyclopropylboronic acid (2.39 g, 27.78 mmol), cesium fluoride (7.84 g, 51.0 mmol) and PdCl$_2$dppf ([1,1'-bis(diphenylphosphino)ferrocene]dichloropalladium(II), 0.756 g, 0.926 mmol) were added. The mixture was degassed again with nitrogen and heated to 100° C. under nitrogen for 2 hours. The mixture was cooled to room temperature and ethyl acetate (50 mL) was added. The mixture was stirred for 5 minutes, filtered over a pad of silica gel, washed with ethyl acetate/heptane (1:1), concentrated and purified via flash chromatography (0 to 20% methyl tert-butyl ether in heptane) to provide the title compound. $^1$H NMR (400 MHz, DMSO-$d_6$) δ ppm 10.18 (s, 1H), 8.26 (d, J=2.7 Hz, 1H), 7.67 (d, J=2.7 Hz, 1H), 3.94 (s, 3H), 1.95 (tt, J=8.4, 5.0 Hz, 1H), 0.99-0.90 (m, 2H), 0.70-0.63 (m, 2H); MS (ESI+) m/z 178 (M+H)+.

Example 217B (5-cyclopropyl-2-methoxypyridin-3-yl)methanol

To Example 217A (2 g, 11.29 mmol) in ethanol (10 mL) cooling in an ice bath, sodium borohydride (0.470 g, 12.42 mmol) was added in portions. The mixture was stirred in an ice bath for 30 minutes. Saturated aqueous NH$_4$Cl (2 mL) was added, the solvent was removed, and the residue was partitioned between ethyl acetate and saturated aqueous sodium bicarbonate. The water layer was extracted with ethyl acetate (10 mL×3) and the organic extracts were washed with brine, dried over sodium sulfate, filtered, and concentrated to give the title compound which was used in next step. MS (APCI+) m/z 180.2 (M+1)+.

Example 217C 3-(bromomethyl)-5-cyclopropyl-2-methoxypyridine

To triphenylphosphine (4.83 g, 18.41 mmol) in dichloromethane (10 mL) cooling in an ice bath was added 1-bromopyrrolidine-2,5-dione (3.28 g, 18.41 mmol) portionwise. The mixture was stirred for 30 minutes maintaining an internal temperature <10° C., and Example 217B in dichloromethane (2 mL) was added slowly at <10° C. The mixture stirred in an ice bath for 1 hour. Saturated aqueous NH$_4$Cl (2 mL) was added and the organic layer was washed with brine, dried over sodium sulfate, filtered, and concentrated. Purification via chromatography on a 40 g silica gel cartridge, eluting with ethyl acetate in heptane at a 0-30% gradient gave the title compound. $^1$H NMR (400 MHz, Chloroform-d) δ ppm 7.96 (dd, J=4.7, 2.4 Hz, 1H), 7.31 (d, J=2.4 Hz, 1H), 4.59 (s, 1H), 4.48 (s, 1H), 3.99 (s, 3H), 1.89-1.78 (m, 1H), 0.96 (ddd, J=7.0, 4.6, 1.0 Hz, 2H), 0.67-0.60 (m, 2H); MS (APCI+) m/z 242.2 (M+H)+.

Example 217D (2S,3R,4S,5S)-3-tert-butyl-4-[(5-cyclopropyl-2-methoxypyridin-3-yl)methoxy]-5-(2-methylphenyl)-1-[(2S)-oxane-2-carbonyl]pyrrolidine-2-carboxylic acid To (2S,3R,4S,5S)-ethyl 3-(tert-butyl)-4-hydroxy-1-((S)-tetrahydro-2H-pyran-2-carbonyl)-5-(o-tolyl)pyrrolidine-2-carboxylate (Example 188B) (60 mg, 0.144 mmol) and 3-(bromomethyl)-5-cyclopropyl-2-methoxypyridine (52.2 mg, 0.216 mmol) in N,N-dimethylformamide (2 mL) cooling in an ice bath, potassium 2-methylpropan-2-olate (24.19 mg, 0.216 mmol), (0.25 mL, 1.0 M in dichloromethane) was added dropwise. The mixture was stirred in an ice bath for 20 minutes, and was stirred at room temperature for 30 minutes. Dichloromethane (20 mL) and saturated aqueous NH$_4$Cl (5 mL) were added. The organic layer was washed with brine, dried over MgSO$_4$, filtered, and concentrated. The residue was purified via chromatography, eluting with ethyl acetate in heptane, at 0-50% gradient to yield the intermediate (2S,3R,4S,5S)-ethyl 3-(tert-butyl)-4-((5-cyclopropyl-2-methoxypyridin-3-yl)methoxy)-1-((S)-tetrahydro-2H-pyran-2-carbonyl)-5-(o-tolyl)pyrrolidine-2-carboxylate, which was dissolved in methanol (2 mL) and 6M aqueous LiOH (0.5 mL). The mixture was stirred at 45° C. for 4 hours, and the pH was adjusted to 1~2 by adding 2M aqueous HCl. The mixture was filtered and purified via reverse-phase preparative HPLC with trifluoroacetic acid method to yield the title compound. $^1$H NMR (400 MHz, DMSO-$d_6$) δ ppm 8.03 (dd, J=6.5, 2.9 Hz, 1H), 7.72 (d, J=2.5 Hz, 1H), 7.10 (s, 3H), 6.66 (d, J=2.4 Hz, 1H), 5.53 (s, 1H), 4.63 (s, 1H), 4.21 (d, J=5.9 Hz, 1H), 4.16 (dd, J=13.4, 0.9 Hz, 1H), 3.83-3.73 (m, 5H), 2.45 (s, 3H), 2.32 (s, 3H), 1.79-1.14 (m, 7H), 1.00 (d, J=0.7 Hz, 9H), 0.92-0.79 (m, 2H), 0.56-0.41 (m, 2H);); MS (ESI+) m/z 551.2 (M+H)$^+$.

Example 218

(2S,3R,4S,5S)-3-tert-butyl-4-[(5-cyclobutyl-2-methoxypyridin-3-yl)methoxy]-1-[(2S)-oxane-2-carbonyl]-5-(5,6,7,8-tetrahydronaphthalen-1-yl)pyrrolidine-2-carboxylic acid Example 218A (E)-ethyl 2-(((5,6,7,8-tetrahydronaphthalen-1-yl)methylene)amino)acetate Ethyl 2-aminoacetate hydrochloride (1.089 g, 7.80 mmol) and magnesium sulfate (1.503 g, 12.48 mmol) were suspended in dichloromethane (10.40 mL) and the suspension was treated with triethylamine (1.087 mL, 7.80 mmol). After stirring for 1 hour, 5,6,7,8-tetrahydronaphthalene-1-carbaldehyde (1.0 g, 6.24 mmol) was added and stirring was continued for 20 hours at room temperature. The solid material was removed via filtration and the filtrate was washed with water (quick wash twice) and brine, then dried over sodium sulfate, filtered, and concentrated to provide the title compound. $^1$H NMR (400 MHz, DMSO-$d_6$) δ ppm 8.60 (d, J=1.4 Hz, 1H), 7.57 (dd, J=6.5, 2.7 Hz, 1H), 7.17-7.06 (m, 2H), 4.38 (d, J=1.3 Hz, 2H), 4.10 (q, J=7.1 Hz, 2H), 2.90 (t, J=6.3 Hz, 2H), 2.72 (t, J=6.1 Hz, 2H), 1.79-1.61 (m, 4H), 1.23-1.11 (m, 3H); MS (ESI$^+$) m/z 246.2 (M+H)$^+$.

Example 218B (2S,3R,4S,5S)-ethyl 3-(tert-butyl)-4-nitro-5-(5,6,7,8-tetrahydronaphthalen-1-yl)pyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.061 g, 0.081 mmol) and copper (I) triflate dimer, benzene complex (0.016 g, 0.031 mmol) were dissolved in tetrahydrofuran (15.99 mL) that had been sparged with a $N_2$ stream for 4 hours. The resulting solution was stirred for 1.5 hours at room temperature, and Example 218A in tetrahydrofuran (1 mL) was added after cooling to <5° C. in an ice water bath. Potassium 2-methylpropan-2-olate (0.062 mL, 0.062 mmol) was added dropwise, followed by addition of (E)-3,3-dimethyl-1-nitrobut-1-ene (0.806 g, 6.24 mmol) neat over 25 minutes, maintaining an internal temperature <10° C. After the addition was complete, the mixture was stirred for 15 minutes at the same temperature. The reaction mixture was diluted with methyl tert-butyl ether (30 mL) and stirred with 30 mL of saturated aqueous ammonium chloride at room temperature for 15 minutes. The organic layer was separated and washed with saturated aqueous sodium bicarbonate and brine, then dried over sodium sulfate. After filtration, the solution was concentrated and the residue was purified by flash chromatography (0 to 30% ethyl acetate in heptane) to provide the title compound. $^1$H NMR (501 MHz, Chloroform-d) δ ppm 7.17-7.08 (m, 2H), 7.06 (dd, J=6.8, 2.1 Hz, 1H), 5.17 (dd, J=6.1, 2.6 Hz, 1H), 4.54 (dd, J=11.0, 6.0 Hz, 1H), 4.35 (qd, J=7.1, 1.1 Hz, 2H), 3.79 (t, J=7.8 Hz, 1H), 3.28 (t, J=10.3 Hz, 1H), 3.06 (dd, J=7.4, 2.6 Hz, 1H), 2.89-2.81 (m, 1H), 2.84-2.73 (m, 2H), 2.75-2.65 (m, 1H), 2.03-1.91 (m, 1H), 1.89-1.76 (m, 2H), 1.63 (s, 1H), 1.38 (t, J=7.1 Hz, 3H), 1.08 (s, 9H); MS (ESI$^+$) m/z 375.2 (M+H)$^+$.

Example 218C (2S,3R,4S,5S)-3-tert-butyl-4-[(5-cyclobutyl-2-methoxypyridin-3-yl)methoxy]-1-[(2S)-oxane-2-carbonyl]-5-(5,6,7,8-tetrahydronaphthalen-1-yl)pyrrolidine-2-carboxylic acid The title compound was synthesized according to the procedure described in Example 144A to Example 144F, substituting Example 218B for Core 10, and substituting (S)-tetrahydro-2H-pyran-2-carbonyl chloride for of (S)-tetrahydrofuran-2-carbonyl chloride. $^1$H NMR (400 MHz, DMSO-$d_6$) δ ppm 7.87 (d, J=7.6 Hz, 1H), 7.76 (dd, J=2.4, 0.8 Hz, 1H), 6.98 (t, J=7.6 Hz, 1H), 6.95-6.84 (m, 2H), 5.52 (s, 1H), 4.61 (s, 1H), 4.21 (d, J=5.8 Hz, 1H), 4.17 (dt, J=13.3, 0.8 Hz, 1H), 3.80 (dt, J=13.4, 0.9 Hz, 1H), 3.75 (s, 3H), 3.38-3.24 (m, 2H), 2.75-2.64 (m, 4H), 2.57 (dt, J=16.5, 6.4 Hz, 2H), 2.25-2.22 (m, 1H), 2.00-1.60 (m, 10H), 1.50 (d, J=11.8 Hz, 2H), 1.43-1.22 (m, 4H), 0.99 (s, 9H); MS (ESI+) m/z 605 (M+H)$^+$.

Example 219

(2S,3R,4S,5S)-3-tert-butyl-4-{[2-methoxy-5-(trifluoromethyl)pyridin-3-yl]methoxy}-1-[(2S)-oxane-2-carbonyl]-5-(5,6,7,8-tetrahydronaphthalen-1-yl)pyrrolidine-2-carboxylic acid The title compound was synthesized according to the procedure described in Example 144A to Example 144F, substituting Example 218B for Core 10, substituting Intermediate 8 for Intermediate 4, and substituting (S)-tetrahydro-2H-pyran-2-carbonyl chloride for (S)-tetrahydrofuran-2-carbonyl chloride. $^1$H NMR (400 MHz, DMSO-$d_6$) δ ppm 8.27 (d, J=2.1 Hz, 1H), 7.90-7.80 (m, 1H), 7.19 (d, J=2.4 Hz, 1H), 6.97-6.82 (m, 2H), 5.57 (d, J=21.5 Hz, 1H), 4.62 (s, 1H), 4.31-4.24 (m, 2H), 3.87 (s, 3H), 3.83 (d, J=14.0 Hz, 1H), 3.76 (d, J=11.4 Hz, 1H), 3.37 (s, 2H), 2.87 (s, 1H), 2.73-2.55 (m, 5H), 1.80-1.63 (m, 4H), 1.51 (d, J=11.9 Hz, 2H), 1.38-1.12 (m, 4H), 1.01 (s, 9H); MS (ESI+) m/z 619 (M+H)$^+$.

Example 220

(2S,3R,4S,5S)-3-tert-butyl-4-[(2-methoxy-7-methylquinolin-3-yl)methoxy]-5-(2-methylphenyl)-1-[(2S)-oxane-2-carbonyl]pyrrolidine-2-carboxylic acid Example 220A (2-methoxy-7-methylquinolin-3-yl)methanol To 2-methoxy-7-methylquinoline-3-carbaldehyde [CAS#842972-37-6] (1.0 g, 4.97 mmol) in ethanol (10 mL) cooling in an ice bath, sodium borohydride (0.207 g, 5.47 mmol) was added in portions. The mixture was stirred in an ice bath for 30 minutes. Saturated aqueous NH$_4$Cl (2 mL) was added, the solvent was removed under vacuum, and the residue was partitioned between ethyl acetate and saturated aqueous sodium bicarbonate. The organic layer was washed with brine, dried over sodium sulfate, filtered, and concentrated to provide the title compound which was used in the next step. MS (APCI+) m/z 204.4 (M+H)⁺.

Example 220B 3-(bromomethyl)-2-methoxy-7-methylquinoline

To triphenylphosphine (2.25 g, 8.56 mmol) in dichloromethane (10 mL) cooling in an ice bath was added 1-bromopyrrolidine-2,5-dione (1.52 mg, 8.56 mmol) portionwise. The mixture was stirred for 30 minutes, maintaining an internal temperature <10° C. Example 220A (870 mg, 4.28 mmol) in dichloromethane (2 mL) was added slowly at <10° C. The mixture was stirred at room temperature for 1 hour. Saturated aqueous NH₄Cl (2 mL) was added, and the residue was partitioned between ethyl acetate and saturated aqueous sodium bicarbonate. The organic layer was washed with brine, dried over sodium sulfate, filtered, and concentrated. Purification via chromatography on a 40 g silica gel cartridge, eluting with ethyl acetate in heptane at a 0-50% gradient provided the title compound. MS (APCI+) m/z m/z 266 (M+H)⁺.

Example 220C (2S,3R,4S,5S)-3-tert-butyl-4-[(2-methoxy-7-methylquinolin-3-yl)methoxy]-5-(2-methylphenyl)-1-[(2S)-oxane-2-carbonyl]pyrrolidine-2-carboxylic acid The title compound was prepared according the procedure described in Example 188C, substituting Example 220B for Intermediate 6. ¹H NMR (400 MHz, DMSO-d₆) δ ppm 8.08 (dd, J=7.0, 2.5 Hz, 1H), 7.47 (dq, J=1.6, 0.8 Hz, 1H), 7.44 (d, J=8.1 Hz, 1H), 7.20 (s, 1H), 7.18 (dd, J=8.2, 1.8 Hz, 1H), 7.16-7.05 (m, 3H), 5.60 (s, 1H), 4.66 (s, 1H), 4.34-4.25 (m, 2H), 3.94 (dd, J=13.8, 1.3 Hz, 1H), 3.89 (s, 3H), 3.77 (d, J=11.4 Hz, 1H), 2.86 (s, 3H), 2.51 (m, 1H), 2.43 (d, J=0.8 Hz, 3H), 2.31 (s, 3H), 1.75-1.16 (m, 6H), 1.02 (s, 9H); MS (ESI+) m/z 575 (M+H)⁺.

Example 221

(2S,3R,4S,5S)-3-tert-butyl-4-[(6-tert-butyl-2-methoxypyridin-3-yl)methoxy]-5-(2-methylphenyl)-1-[(2S)-oxane-2-carbonyl]pyrrolidine-2-carboxylic acid Example 221A 6-(tert-butyl)-2-methoxynicotinaldehyde A 500 mL flask was charged with palladium acetate (0.511 g, 2.277 mmol), 2-di-tert-butylphosphino-2',4',6'-triisopropylbiphenyl (1.933 g, 4.55 mmol), and cesium carbonate (37.1 g, 114 mmol). After purging the flask with N₂, toluene (75 mL) was added, and the mixture was heated in a preheated heating block to 80° C. After 5 minutes, the flask was cooled to room temperature, and 6-(tert-butyl)-2-chloronicotinaldehyde (15 g, 76 mmol) was added as a solution in methanol (75 mL). The mixture was heated at 67° C. for 2 hours, and cooled to room temperature. The reaction was quenched by the addition of saturated aqueous ammonium chloride solution, the mixture was partitioned between water and methyl tert-butyl ether, and the organic phase was washed with brine and dried over sodium sulfate. After filtration, the mixture was concentrated in vacuo, and the residue was purified by silica gel chromatography, eluting with 0 to 10% ethyl acetate/heptanes, to afford the title compound. ¹H NMR (501 MHz, CDCl₃) δ ppm 10.35 (s, 1H), 8.06 (d, J=7.8 Hz, 1H), 7.06-6.99 (m, 1H), 4.09 (s, 3H), 1.38 (s, 9H); MS (ESI⁺) m/z 194.1 (M+H)⁺.

Example 221B (6-(tert-butyl)-2-methoxypyridin-3-yl)methanol

The title compound was prepared according to the method described for the preparation of Intermediate 3A, substituting Example 221A for 2-methoxyquinoline-3-carbaldehyde. ¹H NMR (501 MHz, Chloroform-d) δ ppm 7.48 (dd, J=7.5, 0.7 Hz, 1H), 6.88 (d, J=7.4 Hz, 1H), 4.64 (d, J=6.4 Hz, 2H), 4.02 (s, 3H), 2.31 (t, J=6.5 Hz, 1H), 1.35 (s, 9H); MS (ESI⁺) 196.1 (M+H)⁺.

Example 221C 3-(bromomethyl)-6-(tert-butyl)-2-methoxypyridine

The title compound was prepared according to the method described for the preparation of Intermediate 3B, substituting Example 221B for Intermediate 3A. ¹H NMR (400 MHz, Chloroform-d) δ ppm 7.52 (d, J=7.6 Hz, 1H), 6.86 (d, J=7.6 Hz, 1H), 4.51 (s, 2H), 4.02 (s, 3H), 1.34 (s, 9H); MS (ESI⁺)m/z 258.1 (M+H)⁺.

Example 221D (2S,3R,4S,5S)-ethyl 3-(tert-butyl)-4-hydroxy-5-(o-tolyl)pyrrolidine-2-carboxylate The title compound was prepared according to the procedure described for Example 129H, substituting Example 129C for Example 129G. ¹H NMR (400 MHz, DMSO-d₆) δ ppm 7.41 (d, J=6.8 Hz, 1H), 7.14-7.01 (m, 3H), 4.20-4.02 (m, 4H), 3.94 (m, 1H), 3.45 (m, 1H), 2.95 (m, 1H), 2.23 (s, 3H), 2.07 (m, 1H), 1.19 (t, J=7.1 Hz, 3H), 0.91 (s, 9H); MS (ESI⁺) m/z 306.2 (M+H)⁺.

Example 221E (2S,3R,4S,5S)-ethyl 3-(tert-butyl)-4-hydroxy-1-((S)-tetrahydro-2H-pyran-2-carbonyl)-5-(o-tolyl)pyrrolidine-2-carboxylate The title compound was prepared according to the method described for Example 98A, substituting Example 221D for Example 96E and substituting (S)-tetrahydro-2H-pyran-2-carboxylic acid for (S)-tetrahydrofuran-2-carboxylic acid. ¹H NMR (400 MHz, DMSO-d₆) δ ppm 7.94 (m, 1H), 7.11 (m, 3H), 5.45 (m, 1H), 4.41 (m, 2H), 4.15 (q, J=7.1 Hz, 2H), 3.95-3.64 (m, 2H), 3.32 (m, 1H), 2.98 (m, 1H), 2.32 (s, 3H), 2.21 (t, J=3.8 Hz, 1H), 1.76-1.06 (m, 6H), 1.24 (t, J=7.1 Hz, 3H), 0.98 (s, 9H); MS (ESI⁺) m/z 418.3 (M+H)⁺.

Example 221F (2S,3R,4S,5S)-ethyl 3-(tert-butyl)-4-((6-(tert-butyl)-2-methoxypyridin-3-yl)methoxy)-1-((S)-tetrahydro-2H-pyran-2-carbonyl)-5-(o-tolyl)pyrrolidine-2-carboxylate The title compound was prepared according to the procedure of Example 129G, substituting Example 221E for Example 129C and substituting Example 221C for Example 129F. The crude title compound thus obtained was used directly without further purification. MS (APCI$^+$) m/z 595.5 (M+H)$^+$.

Example 221G (2S,3R,4S,5S)-3-tert-butyl-4-[(6-tert-butyl-2-methoxypyridin-3-yl)methoxy]-5-(2-methylphenyl)-1-[(2S)-oxane-2-carbonyl]pyrrolidine-2-carboxylic acid The title compound was prepared according to the procedure of Example 98B, substituting Example 221F for Example 98A. $^1$H NMR (400 MHz, DMSO-d$_6$) δ ppm 7.99 (m, 1H), 7.11 (m, 3H), 6.83 (d, J=7.6 Hz, 1H), 6.67 (d, J=7.7 Hz, 1H), 5.54 (m, 1H), 4.57 (m, 1H), 4.16 (d, J=5.6 Hz, 1H), 4.07 (d, J=13.1 Hz, 1H), 3.84-3.71 (m, 4H), 3.75 (s, 3H), 2.35 (m, 1H), 2.29 (m, 2H), 2.27 (s, 3H), 1.66-1.17 (m, 4H), 1.23 (s, 9H), 0.96 (s, 9H); MS (ESI$^+$) m/z 567.2 (M+H)$^+$.

Example 222

(2S,3R,4S,5S)-3-tert-butyl-1-(3,4-dihydro-2H-pyran-6-carbonyl)-4-{[2-methoxy-5-(trifluoromethyl)pyridin-3-yl]methoxy}-5-(2-methylphenyl)pyrrolidine-2-carboxylic acid Example 222A (2S,3R,4S,5S)-ethyl 3-(tert-butyl)-1-(3,4-dihydro-2H-pyran-6-carbonyl)-4-hydroxy-5-(o-tolyl)pyrrolidine-2-carboxylate The title compound was prepared according to the procedure described in Example 170B, substituting 3,4-dihydro-2H-pyran-6-carbonyl chloride for (S)-tetrahydro-2H-pyran-2-carbonyl chloride. MS (ESI+) m/z 416 (M+H)$^+$.

Example 222B (2S,3R,4S,5S)-ethyl 3-(tert-butyl)-1-(3,4-dihydro-2H-pyran-6-carbonyl)-4-((2-methoxy-5-(trifluoromethyl)pyridin-3-yl)methoxy)-5-(o-tolyl)pyrrolidine-2-carboxylate (2S,3R,4S,5S)-Ethyl 3-(tert-butyl)-1-(3,4-dihydro-2H-pyran-6-carbonyl)-4-hydroxy-5-(o-tolyl)pyrrolidine-2-carboxylate (Example 222A, 60 mg, 0.144 mmol) and 3-(bromomethyl)-2-methoxy-5-(trifluoromethyl)pyridine (60 mg, 0.222 mmol) were dissolved in dry N,N-dimethylformamide (1 mL). After cooling in an ice bath, potassium 2-methylpropan-2-olate (0.217 mL, 0.217 mmol) 1 M solution in tetrahydrofuran was added dropwise over 15 minutes. After 30 minutes, the reaction was acidified with 1M aqueous HCl (5 drops mL) and warmed to ambient temperature. The mixture was diluted with 1 mL of water and the organics were taken up in 1 mL of dichloromethane. The crude material was purified using a 10 g silica gel column and was eluted with 5-50% ethyl acetate/heptanes over 40 minutes to provide the title compound. $^1$H NMR (400 MHz, DMSO-d$_6$) δ ppm 8.27 (s, 1H), 7.91 (dd, J=7.1, 2.0 Hz, 1H), 7.21 (d, J=2.4 Hz, 1H), 6.99 (dqd, J=12.2, 7.1, 2.3 Hz, 3H), 5.46 (d, J=5.7 Hz, 1H), 5.25 (d, J=4.2 Hz, 1H), 4.62 (d, J=1.6 Hz, 1H), 4.31-4.22 (m, 2H), 4.15-4.02 (m, 2H), 3.86 (s, 3H), 3.81 (d, J=13.9 Hz, 1H), 3.73 (s, 1H), 3.50 (s, 1H), 2.39 (d, J=1.6 Hz, 1H), 2.32 (s, 3H), 1.97-1.75 (m, 2H), 1.58 (s, 1H), 1.18-1.10 (m, 3H), 1.03 (s, 9H), 0.90-0.80 (m, 1H); MS (APCI+) m/z 605 (M+H)$^+$.

Example 222C (2S,3R,4S,5S)-3-tert-butyl-1-(3,4-dihydro-2H-pyran-6-carbonyl)-4-{[2-methoxy-5-(trifluoromethyl)pyridin-3-yl]methoxy}-5-(2-methylphenyl)pyrrolidine-2-carboxylic acid (2S,3R,4S,5S)-Ethyl 3-(tert-butyl)-1-(3,4-dihydro-2H-pyran-6-carbonyl)-4-((2-methoxy-5-(trifluoromethyl)pyridin-3-yl)methoxy)-5-(o-tolyl)pyrrolidine-2-carboxylate from Example 222B (74 mg, 0.122 mmol) and lithium hydroxide (29.3 mg, 1.224 mmol) were dissolved in methanol (1 mL) and water (0.5 mL) and tetrahydrofuran (0.5 mL). The reaction mixture was warmed at 45° C. for 16 hours. The solvent was removed and the reaction was acidified with 2 M aqueous HCl (0.612 mL). The crude material was purified using a 12 g silica gel column and was eluted with an ethyl acetate/heptanes/ethanol solvent system to provide the title compound. $^1$H NMR (400 MHz, DMSO-d$_6$) δ ppm 8.30-8.22 (m, 1H), 7.99 (dd, J=6.5, 2.4 Hz, 1H), 7.20 (d, J=2.4 Hz, 1H), 7.00 (dtt, J=10.5, 7.3, 3.7 Hz, 3H), 5.47 (d, J=5.8 Hz, 1H), 5.22 (s, 1H), 4.60 (d, J=1.9 Hz, 1H), 4.32-4.25 (m, 2H), 3.87 (s, 4H), 3.71 (d, J=9.4 Hz, 1H), 3.50 (s, 1H), 2.31 (s, 3H), 1.96-1.85 (m, 1H), 1.82 (s, 1H), 1.57 (s, 1H), 1.40 (s, 1H), 1.03 (s, 9H), 0.91-0.82 (m, 1H); MS (APCI+) m/z 577 (M+H)$^+$.

Example 223

(2S,3R,4S,5S)-3-tert-butyl-4-[(5-chloro-2-methoxypyridin-3-yl)methoxy]-5-(2-methylphenyl)-1-[(2S)-oxane-2-carbonyl]pyrrolidine-2-carboxylic acid The title compound was prepared according to the procedure described in Example 170C, substituting 3-(bromomethyl)-5-chloro-2-methoxypyridine for 3-(bromomethyl)-5-cyclobutyl-2-methoxypyridine. $^1$H NMR (400 MHz, DMSO-d$_6$, 120° C.) δ ppm 8.06-7.99 (m, 1H), 7.91 (dt, J=2.6, 0.7 Hz, 1H), 7.11 (s, 3H), 6.84 (dt, J=2.8, 1.0 Hz, 1H), 5.55 (s, 1H), 4.65 (s, 1H), 4.28-4.16 (m, 2H), 3.97 (s, 1H), 3.85-3.71 (m, 5H), 3.36 (s, 2H), 2.32 (s, 3H), 1.75-1.25 (m, 6H), 1.02 (s, 9H); MS (ESI+) m/z 545 (M+H)$^+$.

Example 224

(2S,3R,4S,5S)-3-tert-butyl-4-{[2-methoxy-5-(trifluoromethoxy)phenyl]methoxy}-5-(2-methylphenyl)-1-[(2S)-oxane-2-carbonyl]pyrrolidine-2-carboxylic acid The title compound was prepared according to the procedure described in Example 170C, substituting 2-(bromomethyl)-1-methoxy-4-(trifluoromethoxy)benzene for 3-(bromomethyl)-5-cyclobutyl-2-methoxypyridine. $^1$H NMR (400 MHz, DMSO-d$_6$, 120° C.) δ ppm 8.07-7.96 (m, 1H), 7.15-6.99 (m, 4H), 6.89 (d, J=8.9 Hz, 1H), 6.55-6.51 (m, 1H), 5.54 (s, 1H), 4.63 (s, 1H), 4.27-4.19 (m, 2H), 3.85 (dt, J=13.5, 0.8 Hz, 1H), 3.77 (d, J=11.3 Hz, 1H), 3.69 (s, 3H), 3.37 (s, 2H), 2.46 (s, 1H), 2.32 (s, 3H), 1.72-1.26 (m, 6H), 1.00 (s, 9H); MS (ESI+) m/z 594 (M+H)$^+$.

Example 225

(2S,3R,4S,5S)—N-(6-aminopyridine-2-sulfonyl)-3-tert-butyl-4-[(5-cyclobutyl-2-methoxypyridin-3-yl)methoxy]-5-(2-cyclopropylphenyl)-1-[(2S)-oxane-2-carbonyl]pyrrolidine-2-carboxamide (2S,3R,4S,5S)-3-(tert-Butyl)-4-((5-cyclobutyl-2-methoxypyridin-3-yl)methoxy)-5-(2-cyclopropylphenyl)-1-((S)-tetrahydro-2H-pyran-2-carbonyl)pyrrolidine-2-carboxylic acid (Example 171B) (48.8 mg, 0.083 mmol) and di(1H-imidazol-1-yl)methanone (20.09 mg, 0.124 mmol) were combined in N,N-dimethylformamide (1 mL) and warmed to 65° C. for 1 hour. 6-Aminopyridine-2-sulfonamide (14.31 mg, 0.083 mmol) was dissolved in 0.3 mL of N,N-dimethylformamide and sodium hydride (3.47 mg, 0.087 mmol) (60% dispersion in mineral oil) was added in portions. The reaction was stirred at ambient temperature for one hour, the mixture was added to the NaH/sulfonamide suspension and the resulting mixture was stirred at ambient temperature for 16 hours. The solvent was reduced in volume and the crude material was quenched with water and 1N aqueous HCl was added dropwise to acidic pH. The resulting precipitate was filtered and washed with water. The crude precipitate was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as the trifluoroacetic acid salt. $^1$H NMR (400 MHz, DMSO-$d_6$) δ ppm 7.74 (d, J=2.5 Hz, 1H), 7.63 (dd, J=7.5, 1.7 Hz, 1H), 7.44 (dd, J=8.3, 7.3 Hz, 1H), 7.13 (dd, J=7.3, 0.9 Hz, 1H), 7.11-7.04 (m, 2H), 6.94 (dd, J=7.5, 1.6 Hz, 1H), 6.78 (d, J=2.4 Hz, 1H), 6.64 (dd, J=8.4, 0.8 Hz, 1H), 5.89 (d, J=6.1 Hz, 1H), 4.57 (d, J=2.6 Hz, 1H), 4.31 (dd, J=6.1, 1.7 Hz, 1H), 4.23 (d, J=13.4 Hz, 1H), 3.95 (d, J=9.0 Hz, 1H), 3.91 (s, 1H), 3.77 (s, 1H), 3.74 (s, 3H), 3.69-3.56 (m, 1H), 3.33-3.27 (m, 3H), 2.55 (t, J=2.2 Hz, 1H), 2.27-2.13 (m, 2H), 2.04-1.79 (m, 4H), 1.71-1.62 (m, 1H), 1.54-1.43 (m, 1H), 1.36 (dt, J=8.8, 4.3 Hz, 2H), 1.22-1.07 (m, 1H), 1.00 (s, 9H), 0.96-0.82 (m, 2H), 0.71 (ddd, J=9.1, 5.5, 3.8 Hz, 1H), 0.46 (ddd, J=9.5, 6.4, 3.7 Hz, 1H); MS (APCI+) m/z 746 (M+H)$^+$.

Example 226

(2S,3R,4S,5S)-3-tert-butyl-4-[(6-tert-butyl-3-methoxypyridin-2-yl)methoxy]-5-(2-methylphenyl)-1-[(2S)-oxane-2-carbonyl]pyrrolidine-2-carboxylic acid

Example 226A (6-bromo-3-methoxypyridin-2-yl)methanol

6-Bromo-3-methoxypicolinaldehyde (0.880 g, 4.07 mmol) was suspended in CH$_3$OH (20 mL) and the mixture was cooled to 0° C. Sodium borohydride (0.154 g, 4.07 mmol) was added, causing bubbling. The reaction mixture was stirred at 0° C. for 15 minutes, and the flask was removed from the ice bath and was allowed to stir at room temperature for 2 hours. The reaction mixture was then concentrated in vacuo, and the crude material was taken up in methyl tert-butyl ether and saturated aqueous NaHCO$_3$ solution. The phases were separated, and the organic layer was dried over Na$_2$SO$_4$, filtered, and concentrated in vacuo to provide the title compound. $^1$H NMR (501 MHz, CDCl$_3$) δ ppm 8.15 (d, J=2.4 Hz, 1H), 7.75 (m 1H), 4.66 (dt, J=6.3, 0.7 Hz, 2H), 2.16 (t, J=6.3 Hz, 1H); MS (ESI$^+$)m/z 218.0 (M+H)$^+$.

Example 226B 6-bromo-2-(((tert-butyldimethylsilyl)oxy)methyl)-3-methoxypyridine (6-Bromo-3-methoxypyridin-2-yl)methanol (0.718 g, 3.29 mmol), tert-butyldimethylsilyl chloride (0.596 g, 3.95 mmol), and imidazole (0.336 g, 4.94 mmol) were stirred in CH$_2$Cl$_2$ (13 mL) overnight at room temperature. The reaction was then quenched with 3 mL of CH$_3$OH, and the reaction mixture was stirred at room temperature for 10 minutes. The mixture was diluted with CH$_2$Cl$_2$ and washed twice with saturated aqueous NaHCO$_3$ solution and once with brine. The organic solution was dried over Na$_2$SO$_4$, filtered and concentrated in vacuo to provide the title compound. $^1$H NMR (400 MHz, CDCl$_3$) δ ppm 7.34 (d, J=8.5 Hz, 1H), 7.05 (d, J=8.5 Hz, 1H), 4.80 (s, 2H), 3.84 (s, 3H), 0.92 (s, 9H), 0.12 (s, 6H).

Example 226C 6-(tert-butyl)-2-(((tert-butyldimethylsilyl)oxy)methyl)-3-methoxypyridine To a 100 mL 2-neck round bottom flask was added nickel chloride-dimethoxyethane adduct (0.066 g, 0.300 mmol) and 1,3-dicyclohexyl-1H-imidazol-3-ium tetrafluoroborate (0.096 g, 0.300 mmol), followed by a solution of 6-bromo-2-(((tert-butyldimethylsilyl)oxy)methyl)-3-methoxypyridine (0.997 g, 3.00 mmol) in tetrahydrofuran (12 mL). The system was evacuated and back-filled with nitrogen seven times, then the reaction was cooled to −10° C., and tert-butylmagnesium chloride (1M in tetrahydrofuran) (6.00 mL, 6.00 mmol) was added dropwise. The reaction mixture was stirred at −10° C. for 150 minutes. The reaction was then quenched with chips of ice and allowed to warm to room temperature. The mixture was poured into saturated aqueous NH$_4$Cl solution and was extracted three times with ethyl acetate. The combined organic extracts were washed with brine, dried over Na$_2$SO$_4$, filtered, and concentrated in vacuo. Silica gel chromatography, eluting with 0 to 40% ethyl acetate-heptanes, afforded the crude title compound. $^1$H NMR (400 MHz, CDCl$_3$) δ ppm 7.18 (d, J=8.5 Hz, 1H), 7.06 (d, J=8.5 Hz, 1H), 4.86 (s, 2H), 3.82 (s, 3H), 1.35 (s, 9H), 0.92 (s, 9H), 0.10 (s, 6H); MS (ESI$^+$) m/z 310.1 (M+H)$^+$.

Example 226D (6-(tert-butyl)-3-methoxypyridin-2-yl)methanol 6-(tert-Butyl)-2-(((tert-butyldimethylsilyl)oxy)methyl)-3-methoxypyridine (0.356 g, 1.150 mmol) in tetrahydrofuran (11 mL) was treated with tetrabutylammonium fluoride trihydrate (1.814 g, 5.75 mmol), and the reaction was stirred overnight at room temperature. The reaction mixture was poured into a mixture of saturated aqueous NH$_4$Cl and brine solution in a separatory funnel, and the mixture was extracted three times with ethyl acetate. The combined extracts were dried over Na$_2$SO$_4$, filtered, and concentrated in vacuo to provide the title compound, which was taken directly into the next step without further purification. MS (APCI⁺) m/z 196.3 (M+H)⁺.

Example 226E 2-(bromomethyl)-6-(tert-butyl)-3-methoxypyridine (6-(tert-Butyl)-3-methoxypyridin-2-yl)methanol (970 mg, 4.97 mmol) and triphenylphosphine (1.99 g, 7.59 mmol) were dissolved in dichloromethane (25 mL) and cooled in an ice bath. N-Bromosuccinimide (1.31 g, 7.36 mmol) was added in portions, keeping the internal temperature below 10° C. The ice bath was removed, and after stirring for 15 minutes, the reaction was complete. The reaction was quenched by adding 25 mL of water, and was stirred for 5 minutes. The layers were separated, and the organics were washed twice with water and filtered through a fritted cartridge layered with a pad of silica (1 cm), eluting with heptanes. The filtrates were concentrated. The crude residue was taken up in pure heptanes and filtered through a fritted cartridge layered with a pad of silica (3 cm), eluting with heptanes to give the title compound. ¹H NMR (501 MHz, DMSO-d₆) δ ppm 7.40 (d, J=8.7 Hz, 1H), 7.37 (d, J=8.6 Hz, 1H), 4.60 (s, 2H), 3.86 (s, 3H), 1.28 (s, 9H); MS (ESI⁺) m/z 258 & 260 (M+H)⁺.

Example 226F ethyl (2S,3R,4S,5S)-3-(tert-butyl)-4-((6-(tert-butyl)-3-methoxypyridin-2-yl)methoxy)-1-((S)-tetrahydro-2H-pyran-2-carbonyl)-5-(o-tolyl)pyrrolidine-2-carboxylate Example 170B (98.7 mg, 0.236 mmol), after being azeotroped with toluene (3×2 mL), and Example 226E (91.4 mg, 0.354 mmol) were dissolved in dry N,N-dimethylformamide (1 mL). After cooling in an ice bath, a potassium 2-methylpropan-2-olate (300 µL, 0.300 mmol) solution was added dropwise over 2 minutes. The reaction was diluted with methanol (1 mL), filtered and purified by reverse phase chromatography (trifluoroacetic acid method) to give the title compound as the trifluoroacetic acid salt. ¹H NMR (400 MHz, DMSO-d₆, 120° C.) δ ppm 7.95-7.88 (m, 1H), 7.22 (d, J=8.5 Hz, 1H), 7.15 (d, J=8.6 Hz, 1H), 7.13-7.01 (m, 3H), 5.41 (s, 1H), 4.56 (s, 1H), 4.30 (dd, J=5.8, 1.1 Hz, 1H), 4.12 (q, J=7.1 Hz, 2H), 3.95 (d, J=11.4 Hz, 1H), 3.90 (d, J=11.3 Hz, 1H), 3.76-3.67 (m, 1H), 3.54 (s, 3H), 2.93 (s, 2H), 2.31 (d, J=2.1 Hz, 1H), 2.21 (s, 3H), 1.63 (d, J=12.9 Hz, 1H), 1.55-1.27 (m, 5H), 1.25 (s, 9H), 1.19 (t, J=7.1 Hz, 3H), 0.89 (s, 9H). MS (ESI⁺) m/z 595 (M+H)⁺.

Example 226G (2S,3R,4S,5S)-3-tert-butyl-4-[(6-tert-butyl-3-methoxypyridin-2-yl)methoxy]-5-(2-methylphenyl)-1-[(2S)-oxane-2-carbonyl]pyrrolidine-2-carboxylic acid Example 226F (106.8 mg, 0.150 mmol) and lithium hydroxide (1M aqueous) (1.0 mL, 1.0 mmol) in tetrahydrofuran (1 mL) and methanol (1 mL) was stirred at 50° C. for 16 hours. The reaction mixture was acidified with 1.2 mL 1N aqueous HCl, and concentrated in vacuo. The residue was purified by reverse phase using the trifluoroacetic acid method to provide the title compound as the trifluoroacetic acid salt. ¹H NMR (400 MHz, DMSO-d₆, 120° C.) δ ppm 7.97 (dd, J=5.6, 3.7 Hz, 1H), 7.24 (d, J=8.6 Hz, 1H), 7.17 (d, J=8.6 Hz, 1H), 7.13-7.00 (m, 3H), 5.41 (s, 1H), 4.54 (d, J=2.0 Hz, 1H), 4.34 (d, J=6.0 Hz, 1H), 3.94 (q, J=11.6 Hz, 2H), 3.74 (d, J=11.8 Hz, 1H), 3.56 (s, 3H), 3.37 (s, 1H), 2.89 (s, 1H), 2.36 (d, J=1.7 Hz, 1H), 2.18 (s, 3H), 1.69-1.58 (m, 1H), 1.57-1.29 (m, 5H), 1.27 (s, 9H), 0.89 (s, 9H); MS (ESI+) m/z 567 (M+H)⁺.

Example 227

(2S,3R,4S,5S)-3-tert-butyl-4-({[2-methoxy-5-(trifluoromethyl)pyridin-3-yl](²H₂)methyl}oxy)-5-(2-methylphenyl)-1-[(2S)-oxane-2-carbonyl]pyrrolidine-2-carboxylic acid Example 227A methyl 2-methoxy-5-(trifluoromethyl)nicotinate Methanol (12.5 mL) was added to 3-bromo-2-methoxy-5-(trifluoromethyl)pyridine [CAS#124432-63-9] (5 g, 19.53 mmol) and triethylamine (4.25 mL, 30.5 mmol) in a 50 mL Hast C reactor, and [1,1'-bis(diphenylphosphino)ferrocene]dichloropalladium(II) dichloromethane (0.143 g, 0.195 mmol) was added. The mixture was purged with argon and pressurized with CO. Agitation was set for 1200 RPM and the mixture was stirred under 60 psi of carbon monoxide at 100° C. for 10 hours. The mixture was allowed to cool to room temperature. The reaction solution was concentrated and filtered via a short silica gel column eluting with ethyl acetate. The filtrate was concentrated to provide the title compound, which used in next step without further purification. ¹H NMR (400 MHz, Chloroform-d) δ ppm 8.60 (td, J=1.9, 0.9 Hz, 1H), 8.46-8.29 (m, 1H), 4.13 (s, 3H), 3.96 (s, 3H); MS (ESI+) m/z 236 (M+H)⁺.

Example 227B (2-methoxy-5-(trifluoromethyl)pyridin-3-yl)methanol-d₂

To methyl 2-methoxy-5-(trifluoromethyl)nicotinate (1.23 g, 5.23 mmol) in methanol-d₄ (2 mL) and tetrahydrofuran (6 mL) was added sodium borodeuteride (0.263 g, 6.28 mmol) portionwise. The mixture was stirred at room temperature for 30 minutes, at which point another 0.2 equivalent of NaBD₄ was added and stirring was continued for another 30 minutes. Saturated aqueous NH₄Cl (2 mL) and ethyl acetate (30 mL) were added. The mixture was washed with brine, dried over sodium sulfate, filtered, and concentrated. Purification via chromatography on a 40 g silica gel cartridge, eluting with ethyl acetate in heptane at 0-30% gradient provided the title compound. ¹H NMR (400 MHz, Chloroform-d) δ ppm 8.38 (dq, J=2.3, 1.2 Hz, 1H), 7.86 (d, J=2.4 Hz, 1H), 4.05 (s, 3H); MS (ESI+) m/z 210 (M+H)⁺.

Example 227C 3-(bromomethy-d₂)-2-methoxy-5-(trifluoromethyl)pyridine

To triphenylphosphine (2031 mg, 7.75 mmol) in dichloromethane (10 mL) cooling in an ice bath was added 1-bromopyrrolidine-2,5-dione (1379 mg, 7.75 mmol) portionwise. The mixture was stirred for 30 minutes maintaining an internal temperature <10° C. (2-Methoxy-5-(trifluoromethyl)pyridin-3-yl)methanol-d₂ (810 mg, 3.87 mmol) in dichloromethane (2 mL) was added slowly at <10° C. The mixture was stirred at room temperature for 1 hour. Saturated aqueous NH₄Cl (2 mL) was added and the solvent was removed. The residue was partitioned between ethyl acetate and saturated aqueous sodium bicarbonate. The organic layer was washed with brine, dried over sodium sulfate, filtered, and concentrated. Purification via chromatography on a 40 g silica gel cartridge, eluting with ethyl acetate in heptane at 0-30% gradient provided the title compound. MS (APCI+) m/z 274 (M+H)⁺.

Example 227D (2S,3R,4S,5S)-3-tert-butyl-4-({[2-methoxy-5-(trifluoromethyl)pyridin-3-yl]($^2$H$_2$)methyl}oxy)-5-(2-methylphenyl)-1-[(2S)-oxane-2-carbonyl]pyrrolidine-2-carboxylic acid To (2S,3R,4S,5S)-ethyl 3-(tert-butyl)-4-hydroxy-1-((S)-tetrahydro-2H-pyran-2-carbonyl)-5-(o-tolyl)pyrrolidine-2-carboxylate (Example 188B, 70 mg, 0.168 mmol) and Example 227C (68.4 mg, 0.251 mmol) in N,N-dimethylformamide (2 mL) cooling in an ice bath, potassium 2-methylpropan-2-olate (28.2 mg, 0.251 mmol) (0.25 mL, 1.0 M in tetrahydrofuran) was added dropwise. The mixture was stirred in the ice bath for 20 minutes, and stirred at room temperature for 30 minutes. Dichloromethane (20 mL) and saturated aqueous NH₄Cl (5 mL) were added. The organic layer was washed with brine, dried over MgSO₄, filtered, and concentrated. The residue was purified via chromatography, eluting with ethyl acetate/methanol (9:1) in heptane, at 0-30% gradient to yield the intermediate ester which was dissolved in methanol (2 mL) and 6 N aqueous LiOH (0.5 mL). The mixture was stirred at 45° C. for 4 hours. The pH was adjusted to 1~2 by adding 2N aqueous HCl. Dichloromethane (10 mL) was added and the organics were washed with brine, dried over MgSO₄, filtered, and concentrated. Purification via chromatography on a 12 g silica gel cartridge, eluting with ethyl acetate/methanol (9:1) in heptane at 0-50% gradient provided the title compound. $^1$H NMR (400 MHz, DMSO-d$_6$) δ ppm 8.28 (dt, J=2.4, 1.2 Hz, 1H), 8.06-7.98 (m, 1H), 7.18 (d, J=2.6 Hz, 1H), 7.06 (t, J=6.6 Hz, 3H), 5.55 (s, 1H), 4.64 (d, J=1.9 Hz, 1H), 4.27 (d, J=5.9 Hz, 1H), 3.87 (s, 3H), 3.76 (d, J=11.4 Hz, 1H), 3.38 (s, 2H), 2.64 (m, 1H), 2.32 (s, 3H), 1.75-1.24 (m, 6H), 1.02 (s, 9H); MS (ESI+) m/z 581 (M+H)⁺.

Example 228

(2S,3R,4S,5S)-3-tert-butyl-4-{[{2-[($^2$H$_3$)methyloxy]-5-(trifluoromethyl)pyridin-3-yl}($^2$H$_2$)methyl]oxy}-5-(2-methylphenyl)-1-[(2S)-oxane-2-carbonyl]pyrrolidine-2-carboxylic acid Example 228A 3-bromo-2-methoxy-d₃-5-(trifluoromethyl)pyridine To the mixture of 3-bromo-2-chloro-5-(trifluoromethyl)pyridine (5.0 g, 19.20 mmol) and methanol-d₃ (1.165 mL, 28.8 mmol) in N,N-dimethylformamide (10 mL) was added sodium hydride (1.152 g, 28.8 mmol) portionwise. The reaction was stirred at room temperature for 1 hour. Ethyl acetate (20 mL) and saturated aqueous NH₄Cl (2 mL) were added. The organics were washed with brine, dried over Na₂SO₄, filtered, and concentrated to provide the title compound. MS (APCI+) m/z 239.2 (M+H)⁺.

Example 228B methyl 2-methoxy-d₃-5-(trifluoromethyl)nicotinate

To Example 228A (3.9 g, 15.06 mmol) and [1,1'-bis(diphenylphosphino)ferrocene]dichloropalladium(II) (Heraeus) (121 mg, 0.166 mmol) in a 100 mL Hast C reactor were add methanol (50 mL) and triethylamine (4.2 mL, 30.1 mmol). The reactor was degassed with nitrogen several times. Carbon monoxide was added and the reaction was heated to 100° C. for 2.18 hours at 60 psi±8 psi of carbon monoxide, and at 100° C. for 10 hours. The mixture was allowed to cool to room temperature and was filtered via a short silica gel column eluting with ethyl acetate. The filtrate was concentrated to provide the title compound. $^1$H NMR (400 MHz, Chloroform-d) δ ppm 8.60 (q, J=1.1 Hz, 1H), 8.46-8.30 (m, 1H), 3.96 (s, 3H), 0.10 (d, J=2.7 Hz, 1H); MS (ESI+) m/z 239 (M+H)⁺.

Example 228C (2-methoxy-d₃-5-(trifluoromethyl)pyridin-3-yl)methanol-d₂

To methyl 2-methoxy-d₃-5-(trifluoromethyl)nicotinate (1.7 g, 7.14 mmol) in tetrahydrofuran (8 mL) and methanol-d₄ (2 mL) was added sodium borodeuteride (0.359 g, 8.57 mmol) in portions at ambient temperature. The mixture was stirred for 2 hours. Saturated aqueous NH₄Cl (2 mL) and ethyl acetate (50 mL) were added. The organic layer was washed with brine, dried over sodium sulfate, filtered, and concentrated. Purification via chromatography on a 40 g silica gel cartridge, eluting with ethyl acetate in heptane at 0-30% gradient, provided the title compound. $^1$H NMR (501 MHz, Chloroform-d) δ ppm 8.40 (p, J=1.1 Hz, 1H), 7.88 (d, J=2.4 Hz, 1H); MS (ESI+) m/z 213 (M+H)⁺.

Example 228D 3-(bromomethyl-d₂)-2-methoxy-d₃-5-(trifluoromethyl)pyridine

To triphenylphosphine (2.72 g, 10.37 mmol) in dichloromethane (10 mL) cooling in an ice bath was added 1-bromopyrrolidine-2,5-dione (1.845 g, 10.37 mmol) portionwise. The mixture was stirred for 30 minutes maintaining an internal temperature <10° C., and Example 228C (1.1 g, 5.18 mmol) in dichloromethane (2 mL) was added slowly at <10° C. The mixture was stirred at room temperature for 1 hour. Saturated aqueous NH₄Cl (2 mL) was added and the solvent was removed. The residue was partitioned between ethyl acetate and saturated aqueous sodium bicarbonate. The organic layer was washed with brine, dried over sodium sulfate, filtered, and concentrated. Purification via chromatography on a 40 g silica gel cartridge, eluting with ethyl acetate in heptane at 0-30% gradient provided the title compound. $^1$H NMR (500 MHz, Chloroform-d) δ ppm 8.43 (ddq, J=6.9, 2.1, 1.0 Hz, 1H), 7.87 (ddd, J=28.3, 2.5, 0.6 Hz, 1H).

Example 228E (2S,3R,4S,5S)-3-tert-butyl-4-{[{2-[($^2$H$_3$)methyloxy]-5-(trifluoromethyl)pyridin-3-yl}($^2$H$_2$)methyl]oxy}-5-(2-methylphenyl)-1-[(2S)-oxane-2-carbonyl]pyrrolidine-2-carboxylic acid To (2S,3R,4S,5S)-ethyl 3-(tert-butyl)-4-hydroxy-1-((S)-tetrahydro-2H-pyran-2-carbonyl)-5-(o-tolyl)pyrrolidine-2- carboxylate (Example 188B, 70 mg, 0.168 mmol) and Example 228D (69.2 mg, 0.251 mmol) in N,N-dimethylformamide (2 mL) cooling in an ice bath, potassium 2-methylpropan-2-olate (28.2 mg, 0.251 mmol) (0.25 mL, 1.0 M in tetrahydrofuran) was added dropwise. The mixture was stirred in ice bath for 20 minutes, and stirred at room temperature for 30 minutes. Dichloromethane (20 mL) and saturated aqueous NH$_4$Cl (5 mL) were added. The organic layer was washed with brine, dried over MgSO$_4$, filtered, and concentrated. The residue was purified via chromatography on a 12 g silica gel cartridge, eluting with ethyl acetate/methanol (9:1) in heptane, at 0-50% gradient to yield the intermediate ester which was dissolved in methanol (2 mL) and 6N aqueous LiOH (0.5 mL). The mixture was stirred at 45° C. for 4 hours and the pH was adjusted to 1~2 by adding 2M aqueous HCl. The mixture was dissolved in dichloromethane (10 mL), washed with brine, dried over Na$_2$SO$_4$, filtered, and concentrated. The residue was purified via chromatography on a 12 g silica gel cartridge, eluting with ethyl acetate/methanol (9:1) in heptane at 0-50% gradient to provide the title compound. $^1$H NMR (400 MHz, DMSO-d$_6$) δ ppm 8.27 (q, J=1.2 Hz, 1H), 8.06-7.99 (m, 1H), 7.17 (d, J=1.2 Hz, 1H), 7.05 (t, J=6.6 Hz, 3H), 5.55 (s, 1H), 4.64 (s, 1H), 4.27 (d, J=5.8 Hz, 1H), 3.76 (d, J=11.4 Hz, 1H), 3.38 (s, 2H), 2.64 (m, 1H), 2.32 (s, 3H), 1.71-1.22 (m, 6H), 1.02 (s, 9H); MS (ESI+) m/z 584 (M+H)$^+$.

Example 229

(2S,3R,4S,5S)-3-tert-butyl-5-(5-chloro-2-methylphenyl)-4-[(5-cyclobutyl-2-methoxypyridin-3-yl)methoxy]-1-[(2S)-oxane-2-carbonyl]pyrrolidine-2-carboxylic acid Example 229A (E)-ethyl 2-((5-chloro-2-methylbenzylidene)amino)acetate A mixture of ethyl 2-aminoacetate hydrochloride (2.4 g, 17.19 mmol) and magnesium sulfate (4.14 g, 34.4 mmol) in dichloromethane (29 mL) (anhydrous) was treated with triethylamine (2.397 mL, 17.19 mmol), stirred for 10 minutes and treated with 5-chloro-2-methylbenzaldehyde (2.66 g, 17.19 mmol) as a solution in 1 mL dichloromethane. The flask was capped and stirred at ambient temperature for 16 hours. The solid material was filtered, and the filtrate was washed with water. The organics were dried with Na$_2$SO$_4$, filtered, and concentrated to provide the title compound. $^1$H NMR (501 MHz, Chloroform-d) δ ppm 8.56 (t, J=1.4 Hz, 1H), 7.97 (d, J=2.4 Hz, 1H), 7.31 (dd, J=8.2, 2.4 Hz, 1H), 7.22-7.01 (m, 1H), 4.45 (d, J=1.3 Hz, 2H), 4.28 (q, J=7.1 Hz, 2H), 2.50 (s, 3H), 1.34 (t, J=7.1 Hz, 3H).

Example 229B (2S,3R,4S,5S)-ethyl 3-(tert-butyl)-5-(5-chloro-2-methylphenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.220 g, 0.292 mmol) and copper(II) trifluoromethanesulfonate (0.059 g, 0.117 mmol) were dissolved in tetrahydrofuran (28 mL) that had been sparged with a N$_2$ stream for 1 hour. The resulting solution was stirred for 1 hour at ambient temperature (continued nitrogen sparge), and (E)-ethyl 2-((5-chloro-2-methylbenzylidene)amino)acetate from Example 229A (3.5 g, 14.60 mmol) in 1 mL tetrahydrofuran was added. The resulting solution was cooled to <5° C. in an ice water bath. Potassium 2-methylpropan-2-olate, 1M in tetrahydrofuran (0.263 mL, 0.263 mmol) was added dropwise, followed by addition of (E)-3,3-dimethyl-1-nitrobut-1-ene (1.886 g, 14.60 mmol) in 1 mL tetrahydrofuran over 2 minutes, maintaining a temperature less than 7° C. The reaction mixture was stirred for 2 hours at 0° C. The mixture was quenched with 30 mL of saturated aqueous ammonium chloride and 75 mL of ethyl acetate and warmed to ambient temperature. The organic layer was separated and washed with saturated aqueous ammonium chloride (2×30 mL) and brine and filtered through a pad of silica gel. The filtrate was concentrated, and the crude material was triturated with 70 mL heptane, and filtered to provide the title compound. $^1$H NMR (500 MHz, DMSO-d$_6$) δ ppm 7.46 (d, J=2.3 Hz, 1H), 7.23 (dd, J=8.1, 2.3 Hz, 1H), 7.19 (d, J=8.2 Hz, 1H), 5.28 (dd, J=7.1, 3.6 Hz, 1H), 4.64 (t, J=6.8 Hz, 1H), 4.22 (qq, J=6.9, 3.7 Hz, 2H), 3.74 (dd, J=7.7, 6.6 Hz, 1H), 3.66 (t, J=6.6 Hz, 1H), 3.13 (dd, J=7.7, 3.6 Hz, 1H), 2.36 (s, 3H), 1.27 (t, J=7.1 Hz, 3H), 0.95 (s, 9H); MS (APCI+) m/z 369 (M+H)$^+$.

Example 229C (2S,3R,4S,5S)-1-allyl 2-ethyl 3-(tert-butyl)-5-(5-chloro-2-methylphenyl)-4-nitropyrrolidine-1,2-dicarboxylate To (2S,3R,4S,5S)-ethyl 3-(tert-butyl)-5-(5-chloro-2-methylphenyl)-4-nitropyrrolidine-2-carboxylate from Example 229B (2.5 g, 6.78 mmol) in toluene (8 mL) and saturated aqueous NaHCO$_3$ (8 mL) was added allyl carbonochloridate (0.743 mL, 6.78 mmol) dropwise at ambient temperature. The mixture was stirred at ambient temperature for 16 hours. Ethyl acetate (30 mL) and water (25 mL) were added and the organic layer was separated, washed with brine and concentrated. The resulting material was purified on a 24 g cartridge eluting with a gradient of 0-100% ethyl acetate/heptanes over a period of 20 minute to provide the title compound. $^1$H NMR (400 MHz, DMSO-d$_6$) δ ppm 7.83 (s, 1H), 7.17 (dd, J=8.1, 2.3 Hz, 1H), 7.12 (d, J=8.2 Hz, 1H), 5.80 (s, 1H), 5.70-5.60 (m, 1H), 5.48 (d, J=8.6 Hz, 1H), 5.15 (m, 1H), 4.92-4.63 (m, 1H), 4.54 (d, J=3.4 Hz, 1H), 4.47 (s, 2H), 4.23 (qd, J=7.1, 2.4 Hz, 2H), 3.01 (t, J=3.0 Hz, 1H), 2.33 (s, 3H), 1.27 (t, J=7.1 Hz, 3H), 0.98 (s, 9H); MS (APCI+) m/z 453 (M+H)$^+$.

Example 229D (2S,3R,5S)-1-allyl 2-ethyl 3-(tert-butyl)-5-(5-chloro-2-methylphenyl)-4-oxopyrrolidine-1,2-dicarboxylate To potassium dichromate (8.77 g, 29.8 mmol) in 6N aqueous HCl (136 mL) was added zinc (9.96 g, 152 mmol) portionwise under N$_2$ atmosphere at ambient temperature. After the almost complete dissolution of zinc (after ~2 hours), the formed chromium(II) chloride was transferred via cannula to a refluxing solution of (2S,3R,4S,5S)-1-allyl 2-ethyl 3-(tert-butyl)-5-(5-chloro-2-methylphenyl)-4-nitropyrrolidine-1,2-dicarboxylate (Example 229C, 2.5 g, 5.52 mmol) in ethanol (115 mL) under N$_2$. The reaction mixture was refluxed at 86° C. internally for 20 hours, cooled, and concentrated. The mixture was extracted with dichloromethane three times. The organic phase was washed with brine, dried over Na$_2$SO$_4$, filtered, and concentrated. The residue (2.15 g) was subjected to re-esterification. Acetyl chloride (2 mL, 28.13 mmol) was added slowly to an ice cooled flask containing ethanol (6 mL). After the addition was complete, the reaction was stirred at ambient temperature for 5 minutes before pouring the resulting HCl/ethanol solution into a separate flask containing the crude ester/acid mixture. The mixture was heated to 65° C. for an additional hour. The mixture was cooled to ambient temperature, concentrated and the residue was purified on a 40 g cartridge eluting with a gradient of 0-65% ethyl acetate/heptanes over a period of 20 minutes to provide the title compound. $^1$H NMR (400 MHz, DMSO-$d_6$) δ ppm 7.83 (s, 1H), 7.20 (d, J=2.1 Hz, 2H), 5.72 (d, J=99.1 Hz, 1H), 5.22 (d, J=40.3 Hz, 2H), 4.80 (d, J=89.9 Hz, 1H), 4.56 (s, 1H), 4.47 (d, J=14.1 Hz, 1H), 4.36 (s, 1H), 4.19 (qd, J=7.1, 4.0 Hz, 2H), 2.75 (d, J=5.4 Hz, 1H), 2.34 (s, 3H), 1.24 (t, J=7.1 Hz, 3H), 1.01 (s, 9H); MS (APCI+) m/z 422 (M+H)$^+$.

Example 229E (2S,3R,4S,5S)-1-allyl 2-ethyl 3-(tert-butyl)-5-(5-chloro-2-methylphenyl)-4-hydroxypyrrolidine-1,2-dicarboxylate (2S,3R,5S)-1-Allyl 2-ethyl 3-(tert-butyl)-5-(5-chloro-2-methylphenyl)-4-oxopyrrolidine-1,2-dicarboxylate from Example 229D (1.3 g, 3.08 mmol) was dissolved in ethanol (15.41 mL). Sodium borohydride (0.233 g, 6.16 mmol) was added after cooling the reaction to <-10° C. in an ice acetone bath. The ice bath was removed and the mixture was allowed to warm to room temperature over about 20 minutes. The mixture was concentrated and partitioned between ethyl acetate and saturated aqueous sodium bicarbonate for about 30 minutes. The organics were concentrated and purified on a 24 g silica gel cartridge, eluting with 0-60% ethyl acetate/heptanes over period of 20 minutes. The enriched fractions were combined and rechromatographed on a 12 g silica gel cartridge eluting with 100% dichloromethane over a period of 12 minutes to provide the title compound. $^1$H NMR (400 MHz, DMSO-$d_6$) δ ppm 7.94 (s, 1H), 7.09 (d, J=1.5 Hz, 2H), 5.73 (m, 1H), 5.18 (s, 1H), 4.97 (s, 1H), 4.80 (s, 1H), 4.68 (m, 1H), 4.46 (m, 1H), 4.39 (s, 2H), 4.27 (s, 1H), 4.20-4.07 (m, 2H), 2.25 (s, 3H), 2.22 (s, 1H), 1.24 (t, J=7.1 Hz, 3H), 0.95 (s, 9H); MS (APCI+) m/z 424 (M+H+).

Example 229F (2S,3R,4S,5S)-1-allyl 2-ethyl 3-(tert-butyl)-5-(5-chloro-2-methylphenyl)-4-((5-cyclobutyl-2-methoxypyridin-3-yl)methoxy)pyrrolidine-1,2-dicarboxylate (2S,3R,4S,5S)-1-Allyl 2-ethyl 3-(tert-butyl)-5-(5-chloro-2-methylphenyl)-4-hydroxypyrrolidine-1,2-dicarboxylate from Example 229E (200 mg, 0.472 mmol) and 3-(bromomethyl)-5-cyclobutyl-2-methoxypyridine (175 mg, 0.684 mmol) were dissolved in dry N,N-dimethylformamide (2.4 mL). After cooling in an ice bath, potassium 2-methylpropan-2-olate (0.684 mL, 0.684 mmol) 1 M solution in tetrahydrofuran was added dropwise over 2 minutes. After 60 minutes, the mixture was acidified with 1M aqueous HCl (0.17 mL) and warmed to ambient temperature. The mixture was diluted with water (10 mL), extracted with dichloromethane, and loaded onto a 12 g silica gel column, eluting with 0-70% ethyl acetate/heptanes over 20 minutes to provide the title compound. $^1$H NMR (501 MHz, DMSO-$d_6$) δ ppm 7.94 (d, J=31.4 Hz, 1H), 7.78 (d, J=2.4 Hz, 1H), 7.21-7.04 (m, 2H), 6.79 (d, J=2.4 Hz, 1H), 5.73 (d, J=142.7 Hz, 1H), 5.33-5.14 (m, 1H), 5.10 (s, 1H), 4.99-4.60 (m, 1H), 4.51 (m, 3H), 4.37 (s, 1H), 4.27 (d, J=13.6 Hz, 1H), 4.09 (dd, J=7.1, 3.6 Hz, 2H), 3.85 (d, J=13.6 Hz, 1H), 3.72 (s, 3H), 2.27 (s, 3H), 2.22-2.07 (m, 2H), 2.04-1.87 (m, 3H), 1.81-1.71 (m, 1H), 1.11 (t, J=7.1 Hz, 3H), 1.01 (s, 9H); MS (APCI+) m/z 599 (M+H)$^+$.

Example 229G (2S,3R,4S,5S)-ethyl 3-(tert-butyl)-5-(5-chloro-2-methylphenyl)-4-((5-cyclobutyl-2-methoxypyridin-3-yl)methoxy)pyrrolidine-2-carboxylate To a solution of (2S,3R,4S,5S)-1-allyl 2-ethyl 3-(tert-butyl)-5-(5-chloro-2-methylphenyl)-4-((5-cyclobutyl-2-methoxypyridin-3-yl)methoxy)pyrrolidine-1,2-dicarboxylate from Example 229F (150 mg, 0.250 mmol) in acetonitrile/water (4.29 mL, 10:1) was added tetrakis(triphenylphosphine)palladium(0) (6.36 mg, 5.51 μmol) and diethylamine (0.052 mL, 0.501 mmol). The mixture was stirred at ambient temperature for 16 hours. Dichloromethane and water were added, and the organic layer was washed with brine, dried over Na$_2$SO$_4$, filtered, and concentrated. The crude material was purified by chromatography, eluting on a 12 g cartridge with a gradient of 0-70% ethyl acetate/heptanes over 20 minutes to provide the title compound. $^1$H NMR (501 MHz, DMSO-$d_6$) δ ppm 7.80 (d, J=2.4 Hz, 1H), 7.69 (d, J=2.3 Hz, 1H), 7.17 (dd, J=8.1, 2.4 Hz, 1H), 7.13 (d, J=8.1 Hz, 1H), 6.87 (d, J=2.4 Hz, 1H), 4.25-4.22 (m, 1H), 4.20 (d, J=12.8 Hz, 1H), 4.15-4.06 (m, 2H), 4.01 (dd, J=4.6, 1.5 Hz, 1H), 3.72 (s, 3H), 3.67 (d, J=12.9 Hz, 1H), 3.60 (t, J=6.8 Hz, 1H), 3.22 (t, J=7.2 Hz, 1H), 2.34 (dd, J=6.6, 1.5 Hz, 1H), 2.27 (s, 3H), 2.23-2.16 (m, 2H), 2.01-1.88 (m, 3H), 1.83-1.76 (m, 1H), 1.18 (t, J=7.1 Hz, 3H), 0.95 (s, 9H); MS (APCI+) m/z 515 (M+H)$^+$.

Example 229H (2S,3R,4S,5S)-ethyl 3-(tert-butyl)-5-(5-chloro-2-methylphenyl)-4-((5-cyclobutyl-2-methoxypyridin-3-yl)methoxy)-1-((S)-tetrahydro-2H-pyran-2-carbonyl)pyrrolidine-2-carboxylate To a solution of (2S,3R,4S,5S)-ethyl 3-(tert-butyl)-5-(5-chloro-2-methylphenyl)-4-((5-cyclobutyl-2-methoxypyridin-3-yl)methoxy)pyrrolidine-2-carboxylate from Example 229G (116 mg, 0.225 mmol) in dichloromethane (0.6 mL) at 0° C. was added triethylamine (0.141 mL, 1.013 mmol) followed by addition of (S)-tetrahydro-2H-pyran-2-carbonyl chloride (56.9 mg, 0.383 mmol) as a solution in 1 mL dichloromethane. After stirring for 15 minutes, the mixture was quenched with 5 mL of saturated aqueous sodium bicarbonate. The crude organics were chromatographed using a 12 g silica gel cartridge with a gradient of 0-65% ethyl acetate/heptanes over a period of 20 minutes to provide the title compound. $^1$H NMR (400 MHz, DMSO-$d_6$) δ ppm 8.06-7.90 (m, 1H), 7.12 (m, 3H), 7.04 (d, J=1.6 Hz, 1H), 6.98 (d, J=7.5 Hz, 1H), 6.75 (d, J=7.8 Hz, 1H), 5.52 (s, 1H), 4.67 (s, 1H), 4.22 (d, J=13.6 Hz, 1H), 4.16 (d, J=5.7 Hz, 1H), 4.10 (q, J=7.1 Hz, 2H), 3.86 (d, J=13.5 Hz, 1H), 3.72 (m, 4H), 2.74 (dt, J=15.0, 7.6 Hz, 1H), 2.63 (dt, J=15.0, 7.5 Hz, 1H), 2.40 (d, J=1.9 Hz, 1H), 1.65 (m, 1H), 1.51 (m, 2H), 1.35 (m, 2H), 1.21 (t, J=7.5 Hz, 3H), 1.16 (t, J=7.1 Hz, 3H), 1.00 (s, 9H); MS (APCI+) m/z 621 (M+H)$^+$.

Example 229I (2S,3R,4S,5S)-3-tert-butyl-5-(5-chloro-2-methylphenyl)-4-[(5-cyclobutyl-2-methoxypyridin-3-yl)methoxy]-1-[(2S)-oxane-2-carbonyl]pyrrolidine-2-carboxylic acid To a solution of (2S,3R,4S,5S)-ethyl 3-(tert-butyl)-5-(5-chloro-2-methylphenyl)-4-((5-cyclobutyl-2-methoxypyridin-3-yl)methoxy)-1-((S)-tetrahydro-2H-pyran-2-carbonyl)pyrrolidine-2-carboxylate from Example 229H (110 mg, 0.175 mmol) in tetrahydrofuran (0.5 mL), methanol (0.500 mL) and water (0.500 mL) was added lithium hydroxide hydrate(51.5 mg, 1.228 mmol) and the reaction was heated at 45° C. for 16 hours. The solvent was removed under a stream of nitrogen. Water (1 mL) was added to the crude material, and the mixture was extracted with 5 mL heptane (discarded). The mixture was extracted with diethyl ether, and the extract was concentrated. Water was added (2 mL), and the mixture was acidified with 1M aqueous HCl (10 drops) to pH~6. The mixture was filtered to provide the title compound. $^1$H NMR (400 MHz, DMSO-$d_6$) δ ppm 8.15 (s, 1H), 7.79 (d, J=2.4 Hz, 1H), 7.09 (s, 2H), 6.87 (d, J=2.4 Hz, 1H), 5.47 (s, 1H), 4.63 (s, 1H), 4.26-4.18 (m, 2H), 3.85 (d, J=13.2 Hz, 1H), 3.76 (m, 4H), 3.40-3.29 (m, 1H), 2.28 (s, 3H), 2.27-2.19 (m, 2H), 2.03-1.90 (m, 3H), 1.85 (pd, J=4.4, 2.2 Hz, 1H), 1.69 (m, 1H), 1.54 (m, 2H), 1.37 (m, 3H), 0.99 (s, 9H); MS (APCI+) m/z 599 (M+H)$^+$.

Example 230

(2S,3R,4S,5S)-3-tert-butyl-5-(5-chloro-2-methylphenyl)-4-{[2-methoxy-5-(trifluoromethyl)pyridin-3-yl]methoxy}-1-[(2S)-oxane-2-carbonyl]pyrrolidine-2-carboxylic acid

Example 230A (2S,3R,4S,5S)-1-allyl 2-ethyl 3-(tert-butyl)-5-(5-chloro-2-methylphenyl)-4-((2-methoxy-5-(trifluoromethyl)pyridin-3-yl)methoxy)pyrrolidine-1,2-dicarboxylate (2S,3R,4S,5S)-1-Allyl 2-ethyl 3-(tert-butyl)-5-(5-chloro-2-methylphenyl)-4-hydroxypyrrolidine-1,2-dicarboxylate from Example 229E (200 mg, 0.472 mmol) and 3-(bromomethyl)-2-methoxy-5-(trifluoromethyl)pyridine (185 mg, 0.684 mmol) were dissolved in dry N,N-dimethylformamide (2.4 mL). After cooling in an ice bath, potassium 2-methylpropan-2-olate (0.684 mL, 0.684 mmol) 1M solution in tetrahydrofuran was added dropwise over 4 minutes. After 60 minutes, the mixture was acidified with 1M aqueous HCl (1.2 mL) and warmed to ambient temperature. The mixture was diluted with water (20 mL) and extracted with dichloromethane. The extracts were purified on a 24 g silica gel column and were eluted with a gradient of 0-80% ethyl acetate/heptanes over 20 minutes to provide the title compound. $^1$H NMR (501 MHz, DMSO-$d_6$) δ ppm 8.36 (dd, J=2.5, 1.2 Hz, 1H), 7.91 (d, J=30.3 Hz, 1H), 7.07 (d, J=1.5 Hz, 3H), 5.73 (d, J=143.5 Hz, 1H), 5.34-5.15 (m, 1H), 5.11 (s, 1H), 4.96-4.62 (m, 1H), 4.60-4.46 (m, 3H), 4.42 (s, 3H), 4.33 (d, J=14.3 Hz, 1H), 4.10 (p, J=6.8 Hz, 2H), 3.87 (d, J=14.6 Hz, 1H), 3.84 (s, 3H), 2.28 (s, 3H), 1.12 (t, J=7.1 Hz, 3H), 1.02 (s, 9H); MS (APCI+) m/z 613 (M+H)$^+$.

Example 230B (2S,3R,4S,5S)-ethyl 3-(tert-butyl)-5-(5-chloro-2-methylphenyl)-4-((2-methoxy-5-(trifluoromethyl)pyridin-3-yl)methoxy)pyrrolidine-2-carboxylate To a solution of (2S,3R,4S,5S)-1-allyl 2-ethyl 3-(tert-butyl)-5-(5-chloro-2-methylphenyl)-4-((2-methoxy-5-(trifluoromethyl)pyridin-3-yl)methoxy)pyrrolidine-1,2-dicarboxylate from Example 230A (180 mg, 0.294 mmol) in acetonitrile/water (4.29 mL, 10:1) was added tetrakis(triphenylphosphine)palladium(0) (7.46 mg, 6.46 μmol) and diethylamine (0.061 mL, 0.587 mmol) The mixture was stirred at ambient temperature for 16 hours. Dichloromethane and water were added. The organic layer was washed with brine, dried over Na$_2$SO$_4$, filtered, and concentrated. The residue was purified by chromatography, eluting on 12 g cartridge with a gradient 0-70% ethyl acetate/heptanes over 20 minutes to provide the title compound. $^1$H NMR (501 MHz, DMSO-$d_6$) δ ppm 8.38-8.36 (m, 1H), 7.67 (d, J=1.9 Hz, 1H), 7.22 (d, J=2.4 Hz, 1H), 7.13-7.05 (m, 2H), 4.28 (d, J=14.0 Hz, 1H), 4.24 (dd, J=6.8, 4.6 Hz, 1H), 4.16-4.07 (m, 2H), 4.06 (dd, J=5.1, 1.6 Hz, 1H), 3.84 (s, 3H), 3.75 (d, J=14.0 Hz, 1H), 3.62 (t, J=6.7 Hz, 1H), 3.25 (t, J=7.1 Hz, 1H), 2.37 (dd, J=6.4, 1.5 Hz, 1H), 2.26 (s, 3H), 1.18 (t, J=7.1 Hz, 3H), 0.95 (s, 9H); MS (APCI+) m/z 529 (M+H)$^+$.

Example 230C (2S,3R,4S,5S)-ethyl 3-(tert-butyl)-5-(5-chloro-2-methylphenyl)-4-((2-methoxy-5-(trifluoromethyl)pyridin-3-yl)methoxy)-1-((S)-tetrahydro-2H-pyran-2-carbonyl)pyrrolidine-2-carboxylate To a solution of (2S,3R,4S,5S)-ethyl 3-(tert-butyl)-5-(5-chloro-2-methylphenyl)-4-((2-methoxy-5-(trifluoromethyl)pyridin-3-yl)methoxy)pyrrolidine-2-carboxylate from Example 230B (140 mg, 0.265 mmol) in dichloromethane (0.6 mL) at 0° C. was added triethylamine (0.166 mL, 1.191 mmol) followed by addition of (S)-tetrahydro-2H-pyran-2-carbonyl chloride (66.9 mg, 0.450 mmol) as a solution in 1 mL dichloromethane. After stirring for 15 minutes, the mixture was quenched with 5 mL of saturated aqueous sodium bicarbonate. The crude material was chromatographed using a 12 g silica gel cartridge with a gradient of 0-65% ethyl acetate/heptanes over a period of 20 minutes to provide the title compound. $^1$H NMR (400 MHz, DMSO-$d_6$) δ ppm 8.31 (t, J=1.5 Hz, 1H), 8.00 (s, 1H), 7.24 (d, J=2.4 Hz, 1H), 7.09 (s, 2H), 5.48 (s, 1H), 4.71 (s, 1H), 4.33-4.26 (m, 2H), 4.12 (qd, J=7.1, 4.1 Hz, 2H), 3.88 (d, 4H), 3.76 (m, 2H), 2.43 (d, J=1.7 Hz, 1H), 2.32 (s, 3H), 1.69 (m, 1H), 1.54 (m, 2H), 1.39 (m, 3H), 1.18 (t, J=7.1 Hz, 3H), 1.03 (s, 9H); MS (APCI+) m/z 641 (M+H+).

Example 230D (2S,3R,4S,5S)-3-tert-butyl-5-(5-chloro-2-methylphenyl)-4-{[2-methoxy-5-(trifluoromethyl)pyridin-3-yl]methoxy}-1-[(2S)-oxane-2-carbonyl]pyrrolidine-2-carboxylic acid To a solution of (2S,3R,4S,5S)-ethyl 3-(tert-butyl)-5-(5-chloro-2-methylphenyl)-4-((2-methoxy-5-(trifluoromethyl)pyridin-3-yl)methoxy)-1-((S)-tetrahydro-2H-pyran-2-carbonyl)pyrrolidine-2-carboxylate from Example 230C (130 mg, 0.203 mmol) in tetrahydrofuran (0.6 mL), methanol (0.600 mL) and water (0.600 mL) was added lithium hydroxide hydrate (59.6 mg, 1.419 mmol) and the reaction was heated at 45° C. for 16 hours. The solvent was removed under a stream of nitrogen. Water (2 mL) was added to the crude material, and the mixture was extracted with 5 mL heptane (discarded). The desired product was extracted into diethyl ether, and the mixture was concentrated. Water (1 mL) was added and the mixture was acidified with 1M aqueous HCl (14 drops mL) to pH~6. The mixture was filtered to provide the title compound. $^1$H NMR (400 MHz, DMSO-$d_6$) δ ppm 8.29 (d, J=2.4 Hz, 1H), 8.16 (s, 1H), 7.18 (d, J=2.4 Hz, 1H), 7.06 (s, 2H), 5.48 (s, 1H), 4.62 (d, J=1.9 Hz, 1H), 4.31 (d, J=14.0 Hz, 1H), 4.27 (d, J=6.1 Hz, 1H), 3.87 (m, 4H), 3.77 (d, J=11.3 Hz, 1H), 2.49 (s, 1H), 2.28 (s, 3H), 1.69 (m, 1H), 1.55 (m, 2H), 1.37 (m, 3H), 1.01 (s, 9H); MS (APCI+) m/z 613 (M+H)$^+$.

Example 231

(2S,3R,4S,5S)-3-tert-butyl-5-(3-chloro-2-methylphenyl)-4-[(5-cyclobutyl-2-methoxypyridin-3-yl)methoxy]-1-[(2S)-oxane-2-carbonyl]pyrrolidine-2-carboxylic acid Example 231A (E)-ethyl 2-((3-chloro-2-methylbenzylidene)amino)acetate A mixture of ethyl 2-aminoacetate hydrochloride (4.8 g, 34.4 mmol) and magnesium sulfate (8.28 g, 68.8 mmol) in dichloromethane (58 mL) (anhydrous) was treated with triethylamine (4.79 mL, 34.4 mmol). The mixture was stirred for 10 minutes and treated with 3-chloro-2-methylbenzaldehyde (5.60 g, 34.4 mmol) (as a solution in 1 mL dichloromethane). The flask was capped and the mixture was stirred at ambient temperature for 16 hours. The solid material was filtered, the filtrate was washed with water, and the organic layer was dried with $Na_2SO_4$, filtered and concentrated to provide the title compound. $^1$H NMR (400 MHz, Chloroform-d) δ ppm 8.63 (d, J=1.4 Hz, 1H), 7.84 (dd, J=7.8, 1.3 Hz, 1H), 7.45 (dd, J=8.0, 1.3 Hz, 1H), 7.19 (t, J=7.9 Hz, 1H), 4.44 (d, J=1.3 Hz, 2H), 4.26 (q, J=7.1 Hz, 2H), 2.56 (s, 3H), 1.32 (t, J=7.1 Hz, 3H).

Example 231B (2S,3R,4S,5S)-ethyl 3-(tert-butyl)-5-(3-chloro-2-methylphenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.440 g, 0.584 mmol) and Cu(OTf)$_2$ (copper(II) trifluoromethanesulfonate, 0.118 g, 0.234 mmol) were dissolved in tetrahydrofuran (46 mL) that had been sparged with a $N_2$ stream for 1 hour. The resulting mixture was stirred for 1 hour at ambient temperature (continued nitrogen sparge). (E)-ethyl 2-((3-chloro-2-methylbenzylidene)amino)acetate (7 g, 29.2 mmol) in 5 mL tetrahydrofuran was added and the resulting solution was cooled to <5° C. in an ice water bath. Potassium 2-methylpropan-2-olate in tetrahydrofuran (0.526 mL, 0.526 mmol) was added dropwise, followed by addition of (E)-3,3-dimethyl-1-nitrobut-1-ene (Example 231A, 3.77 g, 29.2 mmol) in 1 mL tetrahydrofuran over 2 minutes, maintaining a temperature less than 7° C. The reaction mixture was stirred for 2 hours at 0° C. The mixture was quenched with 60 mL of saturated aqueous ammonium chloride and 75 mL of ethyl acetate and warmed to ambient temperature. The organic layer was separated and washed with saturated aqueous ammonium chloride (2×30 mL) and brine and filtered through a pad of silica gel. The mixture was concentrated, triturated with 100 mL heptane, and filtered to provide the title compound. $^1$H NMR (500 MHz, DMSO-$d_6$) δ ppm 7.43 (d, J=7.8 Hz, 1H), 7.37 (dd, J=8.0, 1.2 Hz, 1H), 7.17 (t, J=7.9 Hz, 1H), 5.29 (dd, J=7.1, 3.7 Hz, 1H), 4.71 (t, J=7.1 Hz, 1H), 4.21 (qd, J=7.1, 4.5 Hz, 2H), 3.73 (dd, J=7.9, 6.9 Hz, 1H), 3.59 (t, J=7.0 Hz, 1H), 3.12 (dd, J=8.0, 3.6 Hz, 1H), 2.41 (s, 3H), 1.26 (t, J=7.1 Hz, 3H), 0.96 (s, 9H); MS (APCI+) m/z 369 (M+H)$^+$.

Example 231C (2S,3R,4S,5S)-1-allyl 2-ethyl 3-(tert-butyl)-5-(3-chloro-2-methylphenyl)-4-nitropyrrolidine-1,2-dicarboxylate To (2S,3R,4S,5S)-ethyl 3-(tert-butyl)-5-(3-chloro-2-methylphenyl)-4-nitropyrrolidine-2-carboxylate from Example 231B (5 g, 13.56 mmol) in toluene (16 mL) and saturated aqueous NaHCO$_3$ (16 mL) was added allyl carbonochloridate (1.485 mL, 13.56 mmol) dropwise at ambient temperature. The mixture was stirred at ambient temperature for 16 hours. Ethyl acetate (30 mL) and water (25 mL) were added and the organic layer was washed with brine and concentrated. The resulting material was purified on a 24 g cartridge eluting with a gradient of 0-100% ethyl acetate/heptanes over a period of 20 minutes to provide the title compound. $^1$H NMR (400 MHz, DMSO-$d_6$) δ ppm 7.81 (s, 1H), 7.30 (dd, J=8.1, 1.2 Hz, 1H), 7.12 (t, J=7.9 Hz, 1H), 5.78 (s, 1H), 5.67 (d, J=9.0 Hz, 1H), 5.57 (d, J=8.7 Hz, 1H), 5.14 (m, 1H), 4.92-4.62 (m, 1H), 4.54 (d, J=3.4 Hz, 1H), 4.43 (s, 2H), 4.22 (q, J=7.0 Hz, 2H), 3.02 (d, J=2.9 Hz, 1H), 2.39 (s, 3H), 1.24 (t, J=7.1 Hz, 3H), 0.99 (s, 9H); MS (APCI+) m/z 453 (M+H)$^+$.

Example 231D (2S,3R,5S)-1-allyl 2-ethyl 3-(tert-butyl)-5-(3-chloro-2-methylphenyl)-4-oxopyrrolidine-1,2-dicarboxylate To potassium dichromate (8.77 g, 29.8 mmol) in 6N aqueous HCl (136 mL) was added zinc (9.96 g, 152 mmol) portionwise under a $N_2$ atmosphere at ambient temperature. After the almost complete dissolution of zinc (~2 hours), the formed chromium(II) chloride was transferred via cannula to a refluxing solution of (2S,3R,4S,5S)-1-allyl 2-ethyl 3-(tert-butyl)-5-(3-chloro-2-methylphenyl)-4-nitropyrrolidine-1,2-dicarboxylate from Example 231C (2.5 g, 5.52 mmol) in ethanol (115 mL) under $N_2$. The reaction mixture was refluxed at 86° C. internally for 20 hours, and cooled. The mixture was concentrated and extracted with dichloromethane three times. The combined organic phase was washed with brine and dried over $Na_2SO_4$, filtered, and concentrated. The residue (2.2 g) was subjected to re-esterification. Acetyl chloride (2 mL, 28.13 mmol) was added slowly to an ice cooled flask containing ethanol (6 mL). After the addition was complete, the mixture was stirred at ambient temperature for 5 minutes before pouring the resulting HCl/ethanol solution into a separate flask containing the crude ester/acid mixture. The mixture was heated at 65° C. for an additional hour, cooled to ambient temperature, and concentrated. The residue was purified on a 24 g cartridge eluting with a gradient of 0-70% ethyl acetate/heptanes over a period of 20 minute to provide the title compound. $^1$H NMR (400 MHz, DMSO-$d_6$) δ ppm 7.75 (d, J=7.8 Hz, 1H), 7.33 (dd, J=8.0, 1.2 Hz, 1H), 7.17 (t, J=7.9 Hz, 1H), 5.71 (d, J=95.0 Hz, 1H), 5.39 (s, 1H), 5.18 (m, 1H), 4.79 (d, J=97.1 Hz, 1H), 4.57 (s, 1H), 4.45 (m, 2H), 4.18 (qd, J=7.2, 1.5 Hz, 2H), 2.71 (d, J=5.4 Hz, 1H), 2.40 (s, 3H), 1.21 (t, J=7.1 Hz, 3H), 1.01 (s, 9H); MS (APCI+) m/z 422 (M+H)$^+$.

Example 231E (2S,3R,4S,5S)-1-allyl 2-ethyl 3-(tert-butyl)-5-(3-chloro-2-methylphenyl)-4-hydroxypyrrolidine-1,2-dicarboxylate (2S,3R,5S)-1-Allyl 2-ethyl 3-(tert-butyl)-5-(3-chloro-2-methylphenyl)-4-oxopyrrolidine-1,2-dicarboxylate from Example 231D (1.38 g, 3.27 mmol) was dissolved in ethanol (16.35 mL) and sodium borohydride (0.247 g, 6.54 mmol) was added after cooling the reaction to <−10° C. in an ice acetone bath. The ice bath was removed and the mixture was allowed to warm to room temperature over 20 minutes. The mixture was concentrated and partitioned between ethyl acetate and saturated aqueous sodium bicarbonate for 30 minutes. The organics were concentrated and purified via flash chromatography, eluting with 0-80% ethyl acetate/heptanes on 24 g silica gel cartridge over a period of 20 minutes to give crude product which was further purified by eluting with 0-2% methanol/dichloromethane over a period of 20 minute on a 24 g silica gel cartridge to provide the title compound. $^1$H NMR (501 MHz, DMSO-$d_6$) δ ppm 7.91 (s, 1H), 7.28-7.19 (m, 1H), 7.11 (t, J=7.9 Hz, 1H), 5.70 (d, J=120.3 Hz, 1H), 5.30-4.98 (m, 2H), 4.97-4.59 (m, 2H), 4.41 (s, 2H), 4.33 (s, 1H), 4.25 (s, 1H), 4.13 (qd, J=7.1, 2.4 Hz, 2H), 2.31 (s, 3H), 2.20 (s, 1H), 1.21 (t, J=7.1 Hz, 3H), 0.95 (s, 9H); MS (APCI+) m/z 424 (M+H)$^+$.

Example 231F (2S,3R,4S,5S)-1-allyl 2-ethyl 3-(tert-butyl)-5-(3-chloro-2-methylphenyl)-4-((5-cyclobutyl-2-methoxypyridin-3-yl)methoxy)pyrrolidine-1,2-dicarboxylate (2S,3R,4S,5S)-1-Allyl 2-ethyl 3-(tert-butyl)-5-(3-chloro-2-methylphenyl)-4-hydroxypyrrolidine-1,2-dicarboxylate from Example 231E (200 mg, 0.472 mmol) and 3-(bromomethyl)-5-cyclobutyl-2-methoxypyridine (175 mg, 0.684 mmol) were dissolved in dry N,N-dimethylformamide (2.4 mL). After cooling in an ice bath, potassium 2-methylpropan-2-olate (0.684 mL, 0.684 mmol, 1 M solution in tetrahydrofuran) was added dropwise over 2 minutes. After 60 minutes, the reaction was acidified with 1M aqueous HCl (0.17 mL) and warmed to ambient temperature. The mixture was diluted with water (10 mL) and was extracted with dichloromethane. The extracts were loaded onto a 12 g silica gel column and were eluted with 0-70% ethyl acetate/heptanes over 20 minutes to provide the title compound. $^1$H NMR (400 MHz, DMSO-$d_6$) δ ppm 7.91 (d, J=19.7 Hz, 1H), 7.74 (d, J=2.4 Hz, 1H), 7.25 (d, J=7.9 Hz, 1H), 7.11 (t, J=7.9 Hz, 1H), 6.72 (d, J=2.4 Hz, 1H), 5.70 (d, J=111.3 Hz, 1H), 5.21 (m, 3H), 4.96-4.57 (m, 1H), 4.48 (m, 2H), 4.36 (s, 2H), 4.25 (d, J=13.6 Hz, 1H), 4.13-3.96 (m, 2H), 3.90 (d, J=13.5 Hz, 1H), 3.71 (s, 3H), 3.28-3.20 (m, 1H), 2.31 (s, 3H), 2.15 (dddt, J=6.4, 4.9, 3.6, 1.9 Hz, 2H), 1.99-1.84 (m, 2H), 1.84-1.73 (m, 2H), 1.05 (t, J=7.1 Hz, 3H), 1.00 (s, 9H); MS (APCI+) m/z 599 (M+H)$^+$.

Example 231G (2S,3R,4S,5S)-ethyl 3-(tert-butyl)-5-(3-chloro-2-methylphenyl)-4-((5-cyclobutyl-2-methoxypyridin-3-yl)methoxy)pyrrolidine-2-carboxylate To a solution of (2S,3R,4S,5S)-1-allyl 2-ethyl 3-(tert-butyl)-5-(3-chloro-2-methylphenyl)-4-((5-cyclobutyl-2-methoxypyridin-3-yl)methoxy)pyrrolidine-1,2-dicarboxylate from Example 231F (146 mg, 0.244 mmol) in acetonitrile/water (4.18 mL, 10:1) was added tetrakis(triphenylphosphine)palladium(0) (6.19 mg, 5.36 µmol) and diethylamine (0.050 mL, 0.487 mmol) The mixture was stirred at ambient temperature for 16 hours. Dichloromethane and water were added, and the organic layer was washed with brine, dried over $Na_2SO_4$, filtered, and concentrated. The residue was purified by chromatography, eluting on 12 g cartridge with a gradient of 0-70% ethyl acetate/heptanes over 20 minutes to provide the title compound. $^1$H NMR (501 MHz, DMSO-$d_6$) δ ppm 7.78 (d, J=2.4 Hz, 1H), 7.64 (dd, J=7.8, 1.3 Hz, 1H), 7.31 (dd, J=8.0, 1.3 Hz, 1H), 7.16 (t, J=7.9 Hz, 1H), 6.85 (d, J=2.4 Hz, 1H), 4.25 (dd, J=7.8, 4.5 Hz, 1H), 4.19 (d, J=13.2 Hz, 1H), 4.16-4.07 (m, 2H), 4.02 (dd, J=4.6, 1.5 Hz, 1H), 3.77 (d, J=13.2 Hz, 1H), 3.72 (s, 3H), 3.60 (t, J=7.0 Hz, 1H), 3.17 (t, J=7.7 Hz, 1H), 2.33 (d, J=2.2 Hz, 1H), 2.32 (s, 3H), 2.23-2.13 (m, 2H), 2.01-1.87 (m, 3H), 1.87-1.78 (m, 1H), 1.18 (t, J=7.1 Hz, 3H), 0.95 (s, 9H); MS (APCI+) m/z 515 (M+H)$^+$.

Example 231H (2S,3R,4S,5S)-ethyl 3-(tert-butyl)-5-(3-chloro-2-methylphenyl)-4-((5-cyclobutyl-2-methoxypyridin-3-yl)methoxy)-1-((S)-tetrahydro-2H-pyran-2-carbonyl)pyrrolidine-2-carboxylate To a solution of (2S,3R,4S,5S)-ethyl 3-(tert-butyl)-5-(3-chloro-2-methylphenyl)-4-((5-cyclobutyl-2-methoxypyridin-3-yl)methoxy)pyrrolidine-2-carboxylate from Example 231G (98 mg, 0.190 mmol) in dichloromethane (0.6 mL) at 0° C. was added triethylamine (0.119 mL, 0.856 mmol) followed by addition (S)-tetrahydro-2H-pyran-2-carbonyl chloride (48.1 mg, 0.323 mmol) as a solution in 1 mL dichloromethane. After stirring for 15 minutes, the reaction was quenched with 5 mL of saturated aqueous sodium bicarbonate. The crude material was chromatographed using a 24 g silica gel cartridge, eluting with a gradient of 0-65% ethyl acetate/heptanes over a period of 20 minutes to provide the title compound. $^1$H NMR (400 MHz, DMSO-$d_6$) δ ppm 8.00 (d, J=7.8 Hz, 1H), 7.78 (d, J=2.5 Hz, 1H), 7.26 (d, J=7.1 Hz, 1H), 7.10 (m, 1H), 6.88 (d, J=2.4 Hz, 1H), 5.57 (s, 1H), 4.69 (s, 1H), 4.28 (d, J=5.9 Hz, 1H), 4.21 (d, J=13.1 Hz, 1H), 4.10 (qd, J=7.1, 0.9 Hz, 2H), 3.87 (d, J=13.1 Hz, 1H), 3.76 (m, 4H), 3.34 (p, J=8.4 Hz, 1H), 2.42 (t, J=1.4 Hz, 1H), 2.37 (m, 4H), 2.31-2.19 (m, 2H), 2.05-1.90 (m, 3H), 1.90-1.81 (m, 1H), 1.67 (m, 1H), 1.51 (m, 2H), 1.38 (m, 3H), 1.14 (t, J=7.0 Hz, 3H), 1.02 (s, 9H); MS (APCI+) m/z 627 (M+H)$^+$.

Example 231I (2S,3R,4S,5S)-3-tert-butyl-5-(3-chloro-2-methylphenyl)-4-[(5-cyclobutyl-2-methoxypyridin-3-yl)methoxy]-1-[(2S)-oxane-2-carbonyl]pyrrolidine-2-carboxylic acid To a solution of (2S,3R,4S,5S)-ethyl 3-(tert-butyl)-5-(3-chloro-2-methylphenyl)-4-((5-cyclobutyl-2-methoxypyridin-3-yl)methoxy)-1-((S)-tetrahydro-2H-pyran-2-carbonyl) pyrrolidine-2-carboxylate from Example 231H (88 mg, 0.140 mmol) in tetrahydrofuran (0.45 mL), methanol (0.450 mL) and water (0.450 mL) was added lithium hydroxide hydrate (41.2 mg, 0.982 mmol) and the reaction was heated at 45° C. for 40 hours. The solvent was removed under a stream of nitrogen. Water (1 mL) was added to the crude material, and the mixture was extracted with 5 mL heptane (discarded). The desired product was extracted into diethyl ether and the organics were concentrated. Water (2 mL) was added, and the mixture was acidified with 1M aqueous HCl (8 drops) to pH~6, and filtered to provide the title compound. $^1$H NMR (400 MHz, DMSO-$d_6$) δ ppm 8.25 (d, J=7.9 Hz, 1H), 7.78 (d, J=2.4 Hz, 1H), 7.24 (d, J=7.9 Hz, 1H), 7.07 (m, 1H), 6.78 (d, J=2.4 Hz, 1H), 5.57 (s, 1H), 4.56 (s, 1H), 4.25 (d, J=13.5 Hz, 2H), 3.94-3.86 (m, 1H), 3.80 (s, 1H), 3.77 (s, 3H), 3.33 (q, J=8.4 Hz, 1H), 2.59 (s, 1H), 2.34 (s, 3H), 2.30-2.16 (m, 2H), 2.03-1.79 (m, 4H), 1.68 (m, 1H), 1.54 (m, 2H), 1.37 (s, 3H), 1.00 (s, 9H); MS (APCI+) m/z 599 (M+H)$^+$.

Example 232

(2S,3R,4S,5S)-3-tert-butyl-5-(3-chloro-2-methylphenyl)-4-{[2-methoxy-5-(trifluoromethyl)pyridin-3-yl]methoxy}-1-[(2S)-oxane-2-carbonyl]pyrrolidine-2-carboxylic acid Example 232A (2S,3R,4S,5S)-1-allyl 2-ethyl 3-(tert-butyl)-5-(3-chloro-2-methylphenyl)-4-((2-methoxy-5-(trifluoromethyl)pyridin-3-yl)methoxy)pyrrolidine-1,2-dicarboxylate (2S,3R,4S,5S)-1-Allyl 2-ethyl 3-(tert-butyl)-5-(3-chloro-2-methylphenyl)-4-hydroxypyrrolidine-1,2-dicarboxylate from Example 231E (200 mg, 0.472 mmol) and 3-(bromomethyl)-2-methoxy-5-(trifluoromethyl)pyridine (185 mg, 0.684 mmol) were dissolved in dry N,N-dimethylformamide (2.4 mL). After cooling in an ice bath, potassium 2-methylpropan-2-olate (0.684 mL, 0.684 mmol) as a 1 M solution in tetrahydrofuran was added dropwise over 4 minutes. After 60 minutes, the reaction was acidified with 1M aqueous HCl (1.2 mL) and warmed to ambient temperature. The mixture was diluted with water (20 mL) and extracted with dichloromethane. The extracts were loaded onto a 24 g silica gel column eluting with a gradient of 0-80% ethyl acetate/heptanes over 20 minutes to provide the title compound. $^1$H NMR (501 MHz, DMSO-$d_6$) δ ppm 8.36 (dd, J=2.6, 1.2 Hz, 1H), 7.89 (d, J=26.3 Hz, 1H), 7.21 (d, J=7.9 Hz, 1H), 7.07 (s, 1H), 6.98 (d, J=2.4 Hz, 1H), 5.72 (d, J=140.0 Hz, 1H), 5.19 (m, 2H), 4.99-4.63 (m, 1H), 4.50 (s, 2H), 4.43 (s, 2H), 4.34 (d, J=14.2 Hz, 1H), 4.06 (qq, J=7.4, 3.9 Hz, 2H), 3.96 (d, J=14.2 Hz, 1H), 3.85 (s, 3H), 2.51 (s, 1H), 2.34 (s, 3H), 1.07 (t, J=7.1 Hz, 3H), 1.02 (s, 9H); MS (APCI+) m/z 613 (M+H)$^+$.

Example 232B (2S,3R,4S,5S)-ethyl 3-(tert-butyl)-5-(3-chloro-2-methylphenyl)-4-((2-methoxy-5-(trifluoromethyl)pyridin-3-yl)methoxy)pyrrolidine-2-carboxylate To a solution of (2S,3R,4S,5S)-1-allyl 2-ethyl 3-(tert-butyl)-5-(3-chloro-2-methylphenyl)-4-((2-methoxy-5-(trifluoromethyl)pyridin-3-yl)methoxy)pyrrolidine-1,2-dicarboxylate from Example 232A (190 mg, 0.310 mmol) in acetonitrile/water (4.29 mL, 10:1) was added tetrakis(triphenylphosphine)palladium(0) (7.88 mg, 6.82 μmol) and diethylamine (0.064 mL, 0.620 mmol) The mixture was stirred at ambient temperature for 16 hours. Dichloromethane and water were added, and the organic layer was washed with brine, dried over Na$_2$SO$_4$, filtered, and concentrated. The mixture was purified by chromatography, eluting on 12 g cartridge with a gradient of 0-70% ethyl acetate/heptanes over 20 minutes to provide the title compound. $^1$H NMR (400 MHz, DMSO-$d_6$) δ ppm 8.37 (d, J=2.1 Hz, 1H), 7.63 (dd, J=7.5, 1.3 Hz, 1H), 7.24 (dd, J=8.0, 1.3 Hz, 1H), 7.20 (d, J=2.5 Hz, 1H), 7.08 (t, J=7.9 Hz, 1H), 4.32-4.24 (m, 2H), 4.17-4.05 (m, 3H), 3.84 (s, 4H), 3.62 (t, J=7.0 Hz, 1H), 3.21 (t, J=7.5 Hz, 1H), 2.36 (dd, J=6.6, 1.4 Hz, 1H), 2.33 (s, 3H), 1.18 (t, J=7.1 Hz, 3H), 0.96 (s, 9H); MS (APCI+) m/z 529 (M+H)$^+$.

Example 232C (2S,3R,4S,5S)-ethyl 3-(tert-butyl)-5-(3-chloro-2-methylphenyl)-4-((2-methoxy-5-(trifluoromethyl)pyridin-3-yl)methoxy)-1-((S)-tetrahydro-2H-pyran-2-carbonyl)pyrrolidine-2-carboxylate To a solution of (2S,3R,4S,5S)-ethyl 3-(tert-butyl)-5-(3-chloro-2-methylphenyl)-4-((2-methoxy-5-(trifluoromethyl)pyridin-3-yl)methoxy)pyrrolidine-2-carboxylate from Example 232B (132 mg, 0.250 mmol) in dichloromethane (0.6 mL) at 0° C. was added triethylamine (0.157 mL, 1.123 mmol) followed by addition of (S)-tetrahydro-2H-pyran-2-carbonyl chloride (63.0 mg, 0.424 mmol) of as a solution in 1 mL dichloromethane. After stirring for 15 minutes, the mixture was quenched with 5 mL of saturated aqueous sodium bicarbonate. The crude material was chromatographed using a 12 g silica gel cartridge with a gradient of 0-65% ethyl acetate/heptanes over a period of 20 minutes to provide the title compound. $^1$H NMR (400 MHz, DMSO-$d_6$) δ ppm 8.30 (d, J=1.4 Hz, 1H), 7.98 (d, J=7.9 Hz, 1H), 7.20 (m, 2H), 7.05 (m, 1H), 5.60 (s, 1H), 4.71 (s, 1H), 4.33 (d, J=6.0 Hz, 1H), 4.30 (d, J=13.7 Hz, 1H), 4.09 (qd, J=7.1, 2.1 Hz, 2H), 3.88 (d, 4H), 3.76 (m, 2H), 2.43 (d, J=1.9 Hz, 1H), 2.39 (s, 3H), 1.68 (d, J=11.9 Hz, 1H), 1.52 (m, 2H), 1.38 (s, 3H), 1.14 (m, 3H), 1.04 (s, 9H); MS (APCI+) m/z 641 (M+H)$^+$.

Example 232D (2S,3R,4S,5S)-3-tert-butyl-5-(3-chloro-2-methylphenyl)-4-{[2-methoxy-5-(trifluoromethyl)pyridin-3-yl]methoxy}-1-[(2S)-oxane-2-carbonyl]pyrrolidine-2-carboxylic acid To a solution of (2S,3R,4S,5S)-ethyl 3-(tert-butyl)-5-(3-chloro-2-methylphenyl)-4-((2-methoxy-5-(trifluoromethyl)pyridin-3-yl)methoxy)-1-((S)-tetrahydro-2H-pyran-2-carbonyl)pyrrolidine-2-carboxylate from Example 232C (121 mg, 0.189 mmol) in tetrahydrofuran (0.55 mL), methanol (0.550 mL) and water (0.550 mL) was added lithium hydroxide hydrate (55.4 mg, 1.321 mmol) and the reaction was heated at 45° C. for 40 hours. The solvent was removed under a stream of nitrogen. Water (2 mL) was added to the crude material, and the mixture was extracted with 5 mL heptane (discarded). The desired product was extracted into diethyl ether, and concentrated. Water (2 mL) was added, and the mixture was acidified with 1M aqueous HCl (13 drops) to pH~6. The precipitate was filtered to provide the title compound. ¹H NMR (400 MHz, DMSO-$d_6$) δ ppm 8.29 (d, J=2.5, 1H), 8.13 (d, J=7.9 Hz, 1H), 7.20 (d, J=7.9 Hz, 1H), 7.14 (d, J=2.5 Hz, 1H), 7.04 (m, 1H), 5.60 (s, 1H), 4.62 (d, J=2.0 Hz, 1H), 4.35-4.31 (m, 2H), 4.30 (s, 1H), 3.93 (d, J=13.9 Hz, 1H), 3.89 (s, 3H), 3.78 (d, J=11.3 Hz, 1H), 2.54 (s, 1H), 2.37 (s, 3H), 1.68 (s, 1H), 1.53 (m, 2H), 1.37 (m, 3H), 1.03 (s, 9H); MS (APCI+) m/z 613 (M+H+).

Example 233

(2S,3R,4S,5S)-3-tert-butyl-4-[(5-tert-butyl-2-methoxypyridin-3-yl)methoxy]-5-(2-methylphenyl)-1-[(2S)-oxane-2-carbonyl]pyrrolidine-2-carboxylic acid The title compound was prepared according to the procedure described in Example 188 substituting 3-(bromomethyl)-5-(tert-butyl)-2-methoxypyridine (Intermediate 10) for Intermediate 6. ¹H NMR (400 MHz, DMSO-$d_6$) δ ppm 8.06-8.01 (m, 1H), 7.91 (d, J=2.7 Hz, 1H), 7.17-7.13 (m, 1H), 5.53 (s, 2H), 4.65-4.59 (m, 1H), 4.23 (d, J=5.9 Hz, 1H), 4.17 (d, J=13.1 Hz, 1H), 3.78 (d, J=8.4 Hz, 2H), 3.75 (s, 3H), 3.35 (s, 1H), 2.63 (s, 6H), 2.33 (s, 3H), 1.68-1.28 (m, 6H), 1.19 (s, 9H), 1.00 (s, 9H); MS (ESI+) m/z 567 (M+H)⁺.

Example 234

(2S,3R,4S,5S)-3-tert-butyl-4-{[{2-[(²H₃)methyloxy]-5-(trifluoromethyl)phenyl}(²H₂)methyl]oxy}-5-(2-methylphenyl)-1-[(2S)-oxane-2-carbonyl]pyrrolidine-2-carboxylic acid Example 234A 2-bromo-1-methoxy-4-(trifluoromethyl)benzene-d3

A mixture of 2-bromo-4-(trifluoromethyl)phenol (5.0 g, 20.75 mmol) and potassium carbonate (5.73 g, 41.5 mmol) in N,N-dimethylformamide (10 mL) stirred at room temperature for 30 minutes, and iodomethane-d₃ (4.51 g, 31.1 mmol) was added. The reaction was stirred at room temperature overnight. The solvent was removed and residue was dissolved in methanol, filtered and purified by reverse phase HPLC with trifluoroacetic acid method to provide the title compound.

Example 234B 2-($d_3$-methoxy-5-(trifluoromethyl)benzoate

2-Bromo-1-methoxy-4-(trifluoromethyl)benzene-d₃ (5 g, 19.38 mmol), and Pd-dppf ([1,1'-bis(diphenylphosphino)ferrocene]dichloropalladium(II), Heraeus) (0.1395 g, 0.191 mmol) were added in a 50 mL Hast C reactor. Methanol (15 mL) and triethylamine (5 mL, 35.9 mmol) were added and the reactor was degassed with nitrogen several times. Carbon monoxide was added and the mixture was heated to 100° C. for 16 hours at 60 psi. The reaction mixture was concentrated and purified via an 80 g silica gel cartridge, eluting with ethyl acetate in heptane at 0-40% gradient to provide the title compound. ¹H NMR (400 MHz, Chloroform-d) δ ppm 8.08 (d, J=2.4 Hz, 1H), 7.73 (dd, J=8.8, 2.4 Hz, 1H), 7.06 (d, J=8.8 Hz, 1H), 3.92 (s, 3H).

Example 234C (2-($d_3$-methoxy-5-(trifluoromethyl)phenyl)($d_2$)methanol

To methyl 2-($d_3$-methoxy-5-(trifluoromethyl)benzoate (3.7148 g, 15.66 mmol) in tetrahydrofuran (20 mL) cooling in an ice bath was added sodium borodeuteride (0.656 g, 15.66 mmol) portionwise. The mixture was stirred for 10 minutes in an ice bath, warmed to room temperature, and heated to reflux at 67° C. for 2 hours. To the mixture was added CH₃OD (4 mL) slowly, and the reaction mixture was stirred at room temperature overnight, when more NaBD4 (0.328 g, 7.83 mmol) and 1 mL of CH₃OD were added. Stirring was continued for 2 hours, before the reaction was quenched with saturated aqueous NH₄Cl (20 mL). Ethyl acetate (60 mL) was added into the reaction mixture. The organic layer was washed with brine and dried over sodium sulfate, filtered, concentrated and purified by flash chromatography on a 40 g silica gel cartridge, eluting with ethyl acetate in heptane at 0-20% gradient to provide the title compound. ¹H NMR (400 MHz, DMSO-$d_6$) δ ppm 7.65 (d, J=2.4 Hz, 1H), 7.57 (ddd, J=8.5, 2.5, 0.9 Hz, 1H), 7.14-7.07 (m, 1H), 5.21 (s, 1H); MS (DCI+) m/z 229.1 (M+NH₄)⁺.

Example 234D 2-(bromo-$d_2$-methyl)-1-($d_3$)-methoxy-4-(trifluoromethyl)benzene Into a 200 mL 3 neck round bottom flask was added triphenylphosphine (3.92 g, 14.96 mmol) and dichloromethane (57.5 mL) The resulting solution was cooled in an ice water bath to <5° C. and 1-bromo-5-methylenepyrrolidin-2-one (2.63 g, 14.96 mmol) was added portionwise over 3-5 minutes, maintaining an internal temperature <10° C. After stirring for 30 minutes, (2-($d_3$-methoxy-5-(trifluoromethyl)phenyl)($d_2$)methanol (2.43 g, 11.51 mmol) in dichloromethane (5 mL) was added slowly into it, maintaining an internal temperature <10° C. for 1 hour. Saturated aqueous NH₄Cl (6 mL) was added and the solvent was removed. The residue was partitioned between ethyl acetate and saturated aqueous sodium bicarbonate. The organic layer was dried over sodium sulfate, filtered, and concentrated. Purification via chromatography on a 40 g silica gel cartridge, eluting with ethyl acetate in heptane using a 0-30% gradient provided the title compound. ¹H NMR (400 MHz, Chloroform-d) δ ppm 7.65-7.55 (m, 2H), 6.97 (d, J=8.6 Hz, 1H).

Example 234E (2S,3R,4S,5S)-3-tert-butyl-4-{[{2-[(²H₃)methyloxy]-5-(trifluoromethyl)phenyl}(²H₂)methyl]oxy}-5-(2-methylphenyl)-1-[(2S)-oxane-2-carbonyl]pyrrolidine-2-carboxylic acid To (2S,3R,4S,5S)-ethyl 3-(tert-butyl)-4-hydroxy-1-((S)-tetrahydro-2H-pyran-2-carbonyl)-5-(o-tolyl)pyrrolidine-2-carboxylate (Example 188B, 70 mg, 0.168 mmol) and 2-(bromomethyl-$d_2$)-1-methoxy-$d_3$-4-(trifluoromethyl)benzene (Example 234D, 68.9 mg, 0.251 mmol) in N,N-dimethylformamide (2 mL) cooling in an ice bath, was added potassium 2-methylpropan-2-olate (28.2 mg, 0.251 mmol) (0.22 mL, 1.0M in tetrahydrofuran) dropwise. The mixture was stirred in an ice bath for 20 minutes, and was allowed to warm to ambient temperature. Dichloromethane (20 mL) and saturated aqueous NH₄Cl (5 mL) were added. The organic layer was washed with brine, dried over MgSO$_4$, filtered, and concentrated. The residue was purified via chromatography, eluting with ethyl acetate in heptane, 0-40% gradient to provide the intermediate ester; which was dissolved in methanol (2 mL) and 6M aqueous LiOH (0.5 mL). The mixture was stirred at 45° C. for 4 hours. The pH was adjusted to 1~2. Purification via chromatography on a 12 g silica gel cartridge, eluting with ethyl acetate/methanol (9:1) in heptane at 0-45% gradient provided the title compound. $^1$H NMR (400 MHz, DMSO-d$_6$) δ ppm 8.02 (q, J=3.8, 2.8 Hz, 1H), 7.43 (dd, J=8.7, 2.4 Hz, 1H), 7.07 (s, 3H), 6.98 (d, J=8.6 Hz, 1H), 6.95 (d, J=2.4 Hz, 1H), 5.54 (s, 1H), 4.64-4.60 (m, 1H), 4.22 (d, J=5.9 Hz, 1H), 3.76 (d, J=11.3 Hz, 1H), 3.37 (s, 2H), 2.63(s, 1H), 2.31 (s, 3H), 1.70-1.24 (m, 6H), 1.00 (s, 9H); MS (ESI+) m/z 583 (M+H)$^+$.

Example 235

(2S,3R,4S,5S)-3-tert-butyl-4-{[(5-tert-butyl-2-methoxyphenyl)($^2$H$_2$)methyl]oxy}-5-(2-methylphenyl)-1-[(2S)-oxane-2-carbonyl]pyrrolidine-2-carboxylic acid Example 235A 2-bromo-4-(tert-butyl)-1-methoxybenzene To 2-bromo-4-(tert-butyl)phenol [CAS#2198-66-5] (5 g, 21.82 mmol) and potassium carbonate (6.03 g, 43.6 mmol) in N,N-dimethylformamide (12 mL) was added iodomethane (2.72 mL, 43.6 mmol) slowly at room temperature. The mixture was stirred at room temperature for 10 minutes and 40° C. overnight. The mixture was filtered and the cake was washed with CH$_2$Cl$_2$. The combined organics were washed with brine, dried over Na$_2$SO$_4$, filtered, and concentrated. The residue was purified via chromatography on a 40 g silica gel cartridge, eluting with ethyl acetate in heptane at 0-25% gradient to provide the title compound. MS (APCI+) m/z 244 (M+H)$^+$.

Example 235B methyl 5-(tert-butyl)-2-methoxybenzoate

Example 235A (5 g, 20.56 mmol) in methanol (15 mL) and triethylamine (2.87 mL, 20.56 mmol) were added to Pd-dppf ([1,1'-bis(diphenylphosphino)ferrocene]dichloropalladium(II) dichloromethane, Heraeus, CAS#95464-05-4)) (870 mg, 1.189 mmol) in a 250 mL pressure bottle under argon. The mixture was pressurized with 70 psi of carbon monoxide and stirred at 100° C. for 16 hours. The solvent was removed and the residue was purified via chromatography, eluting with ethyl acetate in heptane at a 0-30% gradient to provide the title compound. $^1$H NMR (400 MHz, Chloroform-d) δ ppm 7.80 (d, J=2.6 Hz, 1H), 7.49 (dd, J=8.8, 2.7 Hz, 1H), 6.92 (d, J=8.8 Hz, 1H), 3.90 (s, 3H), 3.89 (s, 3H), 1.32 (s, 9H); MS (APCI+) m/z 223 (M+H)$^+$.

Example 235C (5-(tert-butyl)-2-methoxyphenyl)-dideuterio methanol

To Example 235B (1.0 g, 4.50 mmol) in tetrahydrofuran (5 mL) and methanol (5.00 mL) cooling in an ice bath was added sodium borodeuteride (0.377 g, 9.00 mmol) slowly. The mixture was stirred at ambient temperature for 2 hours, and saturated aqueous NH$_4$Cl (2 mL) and ethyl acetate (30 mL) were added to the reaction mixture. The mixture was washed with brine, dried over sodium sulfate, filtered, and concentrated. Purification via chromatography on a 40 g silica gel cartridge, eluting with ethyl acetate in heptane at 0-30% gradient provided the title compound. $^1$H NMR (400 MHz, Chloroform-d) δ ppm 7.38-7.27 (m, 2H), 6.86 (dd, J=8.5, 1.4 Hz, 1H), 3.88 (d, J=1.0 Hz, 3H), 2.36 (s, 1H), 1.34 (s, 9H).

Example 235D 2-(dideuterio-bromomethyl)-4-(tert-butyl)-1-methoxybenzene

To triphenylphosphine (695 mg, 2.65 mmol) in dichloromethane (10 mL) cooling in an ice bath was added 1-bromopyrrolidine-2,5-dione (472 mg, 2.65 mmol) portionwise. The mixture was stirred for 30 minutes maintaining an internal temperature <10° C. Example 235C (400 mg, 2.038 mmol) in dichloromethane (2 mL) was added slowly. The mixture was stirred in an ice bath for 1 hour and was allowed to warm to ambient temperature. Saturated aqueous NH$_4$Cl (10 mL) and dichloromethane (10 mL) were added. The organic layer was washed with saturated aqueous NaHCO$_3$ and brine, dried over MgSO$_4$, filtered and concentrated. Purification via chromatography on a 24 g silica gel cartridge, eluting with ethyl acetate in heptane at 0-30% gradient provided the title compound. MS (APCI+) m/z 179 (M-Br)$^+$.

Example 235E (2S,3R,4S,5S)-3-tert-butyl-4-{[(5-tert-butyl-2-methoxyphenyl)($^2$H$_2$)methyl]oxy}-5-(2-methylphenyl)-1-[(2S)-oxane-2-carbonyl]pyrrolidine-2-carboxylic acid To Example 188B (70 mg, 0.168 mmol) and Example 235D (47.8 mg, 0.184 mmol) in N,N-dimethylformamide (2 mL) cooling in an ice bath, potassium 2-methylpropan-2-olate (0.22 mL, 1.0M in tetrahydrofuran) was added dropwise. The mixture was stirred in an ice bath for 20 minutes, and stirred at room temperature for 30 minutes. Dichloromethane (20 mL) and saturated aqueous NH$_4$Cl (10 mL) were added. The organic layer was washed with brine, dried over MgSO$_4$, filtered, and concentrated. The residue was purified via chromatography, eluting with ethyl acetate in heptane, 0-40% gradient to yield (2S,3R,4S,5S)-ethyl 3-(tert-butyl)-4-((5-(tert-butyl)-2-methoxy-dideuteriobenzyl)oxy)-1-((S)-tetrahydro-2H-pyran-2-carbonyl)-5-(o-tolyl)pyrrolidine-2-carboxylate, which was dissolved in methanol (2 mL) and 6M aqueous LiOH (0.5 mL). The mixture was stirred at 45° C. for 4 hours. The solvent was removed and residue was adjusted pH to 1~2 by adding 2M aqueous HCl. The mixture was extracted with dichloromethane (10 mL×3). The combined organics were washed with brine, dried over MgSO$_4$, filtered, and concentrated. The residue was purified via HPLC with the trifluoroacetic acid method to provide the title compound. $^1$H NMR (400 MHz, DMSO-d$_6$) δ ppm 8.06-8.01 (m, 1H), 7.12 (d, J=2.6 Hz, 1H), 7.10-7.03 (m, 3H), 6.85 (d, J=2.6 Hz, 1H), 6.72 (d, J=8.6 Hz, 1H), 5.50 (s, 1H), 4.59 (s, 1H), 4.19 (d, J=5.9 Hz, 1H), 3.75 (d, J=11.9 Hz, 1H), 3.61 (s, 3H), 3.39 (d, J=32.7 Hz, 2H), 2.44 (d, J=1.6 Hz, 1H), 2.32 (s, 3H), 1.69-1.27 (m, 6H), 1.17 (s, 9H), 0.97 (s, 9H); MS (ESI+) m/z 568.3 (M+H)+.

Example 236

(2S,3R,4S,5S)-3-tert-butyl-4-[(2-chloro-5,7-dimethylquinolin-3-yl)methoxy]-5-(2-methylphenyl)-1-[(2S)-oxane-2-carbonyl]pyrrolidine-2-carboxylic acid

Example 236A 3-(bromomethyl)-2-chloro-5,7-dimethylquinoline

To triphenylphosphine (355 mg, 1.353 mmol) in dichloromethane (10 mL) cooling in an ice bath was added 1-bromopyrrolidine-2,5-dione (241 mg, 1.353 mmol) portionwise. The mixture was stirred for 30 minutes, maintaining an internal temperature <10° C., and (2-chloro-5,7-dimethylquinolin-3-yl)methanol [CAS#1017464-08-2] (200 mg, 0.902 mmol) in dichloromethane (6 mL) was added portionwise at <10° C. The mixture was stirred in an ice bath for 1 hour and allowed to warm to ambient temperature. Saturated aqueous NH₄Cl (2 mL) was added and the solvent was removed. The residue was partitioned between ethyl acetate and saturated aqueous sodium bicarbonate. The organics were dried over sodium sulfate, filtered, and concentrated. Purification via chromatography on a 24 g silica gel cartridge, eluting with ethyl acetate in heptane using a 0-30% gradient provided the title compound. ¹H NMR (400 MHz, Chloroform-d) δ ppm 8.40-8.32 (m, 1H), 7.70-7.64 (m, 1H), 7.27 (d, J=3.2 Hz, 1H), 4.82 (d, J=42.9 Hz, 2H), 2.69 (dd, J=3.8, 0.8 Hz, 3H), 2.54 (dd, J=2.2, 0.9 Hz, 3H), 2.54 (s, 3H); MS (ESI+) m/z 285 (M+H)+.

Example 236B (2S,3R,4S,5S)-3-tert-butyl-4-[(2-chloro-5,7-dimethylquinolin-3-yl)methoxy]-5-(2-methylphenyl)-1-[(2S)-oxane-2-carbonyl]pyrrolidine-2-carboxylic acid The title compound was prepared according to the procedure described in Example 188, substituting Example 236A for Intermediate 6. ¹H NMR (400 MHz, DMSO-d₆) δ ppm 8.16-8.08 (m, 1H), 7.85 (d, J=1.1 Hz, 1H), 7.45 (s, 1H), 7.25 (s, 1H), 7.10-6.99 (m, 3H), 5.58 (s, 1H), 4.65 (d, J=5.0 Hz, 1H), 4.43 (dd, J=13.6, 1.1 Hz, 1H), 4.38 (d, J=5.7 Hz, 1H), 3.97 (dd, J=13.5, 1.1 Hz, 1H), 3.88(s, 1H), 3.76 (d, J=11.2 Hz, 2H), 2.54 (s, 3H), 2.43 (s, 3H), 2.37 (s, 3H), 2.32 (s, 1H), 1.69-1.33 (m, 6H), 1.03 (d, J=7.4 Hz, 9H); MS (ESI+) m/z 593.3 (M+H)+.

Example 237

(2S,3R,4S,5S)-3-tert-butyl-4-[(2-methoxy-5,8-dimethylquinolin-3-yl)methoxy]-5-(2-methylphenyl)-1-[(2S)-oxane-2-carbonyl]pyrrolidine-2-carboxylic acid

Example 237A (2-chloro-5,8-dimethylquinolin-3-yl)methanol

To 2-chloro-5,8-dimethylquinoline-3-carbaldehyde [cas 323196-71-0] (250 mg, 1.138 mmol) in ethanol (5 mL) cooling in an ice bath, sodium borohydride (64.6 mg, 1.707 mmol) was added in portions. The mixture was stirred in an ice bath for 30 minutes. Saturated aqueous NH₄Cl (2 mL) was added and the solvent was removed under reduced pressure. The residue was dissolved in dichloromethane (20 mL). The mixture was washed with brine, dried over sodium sulfate, filtered, and concentrated to provide the title compound. MS (APCI+) m/z 222.2 (M+H)+.

Example 237B (2-methoxy-5,8-dimethylquinolin-3-yl)methanol

Example 237A (210 mg, 0.947 mmol) was added to a solution of sodium methoxide (6.83 mmol prepared from Na (143 mg) in methanol (5 mL)). The reaction mixture was refluxed overnight. The solvent was removed and water was added. The mixture was extracted with ethyl acetate, dried over MgSO₄, filtered, and concentrated. The residue was purified by chromatography on a 10 g silica gel cartridge, eluting with ethyl acetate in heptane, at a 0-40% gradient to provide the title compound. MS (APCI+) m/z 218.2 (M+H)+.

Example 237C 3-(bromomethyl)-2-methoxy-5,8-dimethylquinoline

The title compound was prepared according to the procedure described in Example 236A, substituting Example 237B for (2-chloro-5,7-dimethylquinolin-3-yl)methanol. MS (APCI+) m/z 282 (M+H)+.

Example 237D (2S,3R,4S,5S)-3-tert-butyl-4-[(2-methoxy-5,8-dimethylquinolin-3-yl)methoxy]-5-(2-methylphenyl)-1-[(2S)-oxane-2-carbonyl]pyrrolidine-2-carboxylic acid The title compound was prepared according to the procedure described in Example 188, substituting Example 237C for Intermediate 6. ¹H NMR (400 MHz, DMSO-d₆) δ ppm 8.13-8.09 (m, 1H), 7.72 (d, J=1.3 Hz, 1H), 7.65-7.47 (m, 2H), 7.29 (d, J=7.2 Hz, 1H), 7.06 (d, J=6.4 Hz, 2H), 5.56 (s, 1H), 4.65 (s, 1H), 4.39-4.30 (m, 2H), 3.97 (d, J=1.3 Hz, 1H), 3.93 (s, 3H), 3.76 (d, J=11.3 Hz, 2H), 3.36(s, 1H), 2.53 (s, 4H), 2.46 (s, 3H), 2.33 (s, 3H), 1.71-1.30 (m, 6H), 1.03 (s, 9H); MS (ESI+) m/z 589.2 (M+H)+.

Example 238

(2S,3R,4S,5S)-3-tert-butyl-4-[(2-methoxy-5,7-dimethylquinolin-3-yl)methoxy]-5-(2-methylphenyl)-1-[(2S)-oxane-2-carbonyl]pyrrolidine-2-carboxylic acid

Example 238A 3-(bromomethyl)-2-methoxy-5,7-dimethylquinoline

The title compound was prepared according to the procedure described in Example 237 B-C, substituting (2-chloro-5,7-dimethylquinolin-3-yl)methanol for (2-chloro-5,8-dimethylquinolin-3-yl)methanol. ¹H NMR (400 MHz, Chloroform-d) δ ppm 8.11 (t, J=1.0 Hz, 1H), 7.66-7.44 (m, 1H), 7.09 (s, 1H), 4.80 (d, J=6.3 Hz, 2H), 4.14

(d, J=0.9 Hz, 3H), 2.63 (s, 3H), 2.50 (s, 3H), 2.40 (t, J=6.5 Hz, 1H); MS (ESI+) m/z 218.1 (M+H)+.

Example 238B (2S,3R,4S,5S)-3-tert-butyl-4-[(2-methoxy-5,7-dimethylquinolin-3-yl)methoxy]-5-(2-methylphenyl)-1-[(2S)-oxane-2-carbonyl]pyrrolidine-2-carboxylic acid The title compound was prepared according to the procedure described in Example 188, substituting Example 238A for Intermediate 6. $^1$H NMR (400 MHz, DMSO-$d_6$) δ ppm 8.08 (dd, J=7.2, 2.6 Hz, 1H), 7.26 (s, 1H), 7.18 (d, J=7.1 Hz, 2H), 7.13 (d, J=4.4 Hz, 3H), 5.56 (s, 1H), 4.66 (s, 1H), 4.36-4.30 (m, 1H), 4.30-4.24 (m, 1H), 3.94 (dd, J=13.9, 1.3 Hz, 1H), 3.91 (s, 3H), 3.77 (d, J=11.4 Hz, 1H), 3.39(m, 2H), 2.54 (s, 3H), 2.52-2.50 (m, 1H), 2.39 (s, 3H), 2.31 (s, 3H), 1.70-1.30 (m, 6H), 1.02 (s, 9H); MS (ESI+) m/z 589.3 (M+H)+.

Example 239

(2S,3R,4S,5S)-3-tert-butyl-4-[(5-cyclobutyl-2-methoxypyridin-3-yl)methoxy]-5-(2-methoxyphenyl)-1-[(2S)-oxane-2-carbonyl]pyrrolidine-2-carboxylic acid Example 239A (2S,3R,4S,5S)-ethyl 3-(tert-butyl)-5-(2-methoxyphenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.168 g, 0.223 mmol) and copper (I) triflate dimer, benzene complex (0.049 g, 0.097 mmol) were dissolved in tetrahydrofuran (43.1 mL) that had been sparged with a nitrogen stream for 1 hour. The resulting mixture was stirred for 1 hour at ambient temperature, and (E)-ethyl 2-((2-methoxybenzylidene)amino)acetate (Core 2A) (5.15 g, 23.28 mmol) was added as a solution in 5 mL of tetrahydrofuran and the resulting solution was cooled to <5° C. in an ice water bath. Potassium 2-methylpropan-2-olate, 1M in tetrahydrofuran (0.155 mL, 0.155 mmol) was added dropwise, followed by addition of (E)-3,3-dimethyl-1-nitrobut-1-ene (2.505 g, 19.40 mmol) over 10 minutes, maintaining a temperature less than 6° C. After 20 minutes in the ice bath, additional potassium 2-methylpropan-2-olate was added, 1M in tetrahydrofuran (0.155 mL, 0.155 mmol), and the mixture was stirred in the ice bath for another 30 minutes. The mixture was poured into saturated aqueous ammonium chloride (50 mL) and diluted with ethyl acetate (250 mL). The organic layer was washed with saturated aqueous ammonium chloride, filtered through a plug of diatomaceous earth topped with silica gel, and dried over sodium sulfate. After filtration, the mixture was concentrated. Heptanes and pentane were added and the solvent was removed in vacuo. Heptane (10 mL) was added and the mixture was cooled in an ice bath. The mixture was concentrated, taken up in heptane (75 mL), brought to reflux, and decanted while hot. The heptane was reduced in volume and the crude material was purified using an 80 g silica gel cartridge eluting with 0-50% ethyl acetate/heptanes over 25 minutes to provide the title compound. $^1$H NMR (501 MHz, Chloroform-d) δ ppm 7.33-7.29 (m, 1H), 7.28-7.24 (m, 1H), 6.98 (td, J=7.6, 1.1 Hz, 1H), 6.90 (dd, J=8.3, 1.0 Hz, 1H), 5.37 (dd, J=5.7, 2.5 Hz, 1H), 4.63-4.54 (m, 1H), 4.34 (qd, J=7.1, 1.5 Hz, 2H), 3.92 (s, 3H), 3.84-3.75 (m, 1H), 3.45-3.34 (m, 1H), 2.92 (dd, J=7.3, 2.5 Hz, 1H), 1.37 (t, J=7.2 Hz, 3H), 1.08 (s, 9H); MS (APCI+) m/z 351 (M+H)+.

Example 239B (2S,3R,4S,5S)-ethyl 3-(tert-butyl)-5-(2-methoxyphenyl)-4-nitro-1-((S)-tetrahydro-2H-pyran-2-carbonyl)pyrrolidine-2-carboxylate To a cooled (ice bath) solution of (2S,3R,4S,5S)-ethyl 3-(tert-butyl)-5-(2-methoxyphenyl)-4-nitropyrrolidine-2-carboxylate from Example 239A (410 mg, 1.170 mmol) in dichloromethane (4.756 mL) was added triethylamine (0.734 mL, 5.27 mmol) followed by the addition of (S)-tetrahydro-2H-pyran-2-carbonyl chloride (362 mg, 2.436 mmol) of as a solution in 2 mL dichloromethane. After stirring for 15 minutes, the mixture was quenched with 10 mL of saturated aqueous sodium bicarbonate. The aqueous layer was extracted with 10 mL dichloromethane. The combined organics were reduced in volume and the crude material was chromatographed using a 40 g silica gel cartridge with a gradient of 0-80% ethyl acetate/heptanes over a period of 20 minutes to provide the title compound. $^1$H NMR (400 MHz, DMSO-$d_6$) δ ppm 7.76 (d, J=7.7 Hz, 1H), 7.25 (t, J=7.8 Hz, 1H), 6.97 (d, J=8.2 Hz, 1H), 6.88 (t, J=7.6 Hz, 1H), 6.12 (s, 1H), 5.42 (dd, J=8.7, 2.7 Hz, 1H), 4.80 (s, 1H), 4.22 (q, J=7.1 Hz, 2H), 3.84 (s, 3H), 3.81-3.71 (m, 1H), 2.93 (td, J=3.4, 0.7 Hz, 2H), 1.73-1.66 (m, 1H), 1.54 (d, J=12.3 Hz, 1H), 1.47-1.32 (m, 3H), 1.27 (t, J=7.1 Hz, 3H), 1.00 (s, 9H), 0.92 (s, 1H), 0.89-0.80 (m, 1H); MS (APCI+) m/z 463 (M+H)+.

Example 239C (2S,3R,5S)-ethyl 3-(tert-butyl)-5-(2-methoxyphenyl)-4-oxo-1-((S)-tetrahydro-2H-pyran-2-carbonyl)pyrrolidine-2-carboxylate A 50 mL flask was charged DBU (1,8-diazabicyclo[5.4.0]undec-7-ene) (0.616 mL, 4.09 mmol), and carbon disulfide (0.352 mL, 5.84 mmol) in 1.4 mL CH$_3$CN and the mixture was stirred at ambient temperature for 30 minutes. The resulting mixture was cooled to 0° C. in an ice bath and (2S,3R,4S,5S)-ethyl 3-(tert-butyl)-5-(2-methoxyphenyl)-4-nitro-1-((S)-tetrahydro-2H-pyran-2-carbonyl)pyrrolidine-2-carboxylate from Example 239B (0.540 g, 1.167 mmol) in 1.4 mL of CH$_3$CN was added dropwise. The reaction was warmed to room temperature over 1 hour, and stirred at ambient temperature for 1 hour. Additional carbon disulfide (0.352 mL, 5.84 mmol) was added. CH$_3$CN (15 mL) was added and 6.0 mL aqueous 20% H$_3$PO$_4$ solution was added to hydrolyze the resulting imine. The mixture was stirred for 3 hours at ambient temperature. Methyl tert-butyl ether (20 mL) and 20 mL brine were added. The organic layer was washed with 18 mL of brine with the addition of 18 mL methyl tert-butyl ether. The mixture was filtered and concentrated. Additional CH$_3$CN (15 mL) and 6.0 mL aqueous 20% H$_3$PO$_4$ solution were added and the mixture was stirred at ambient temperature for 2 hours more. The mixture was extracted again as described, and the crude material was adsorbed onto silica gel, and concentrated. The residue was chromatographed using a 24 g silica gel cartridge with a gradient of 0-60% ethyl acetate/heptanes over a period of 20 minutes to provide the title compound. $^1$H NMR (400 MHz, DMSO-$d_6$) δ ppm 7.63 (dd, J=7.6, 1.7 Hz, 1H), 7.32-7.24

(m, 1H), 7.02 (d, J=8.3 Hz, 1H), 6.95-6.87 (m, 1H), 5.61 (s, 1H), 4.84 (d, J=3.7 Hz, 1H), 4.25-4.08 (m, 2H), 3.85-3.77 (m, 1H), 3.74 (s, 3H), 3.30-3.13 (m, 1H), 2.56 (dd, J=3.8, 1.1 Hz, 1H), 1.67 (dd, J=10.9, 6.5 Hz, 1H), 1.56-1.45 (m, 1H), 1.47-1.34 (m, 3H), 1.33-1.22 (m, 1H), 1.19 (t, J=7.1 Hz, 3H), 1.03 (s, 9H), 0.89-0.78 (m, 1H); MS (APCI+) m/z 432 (M+H)$^+$.

Example 239D (2S,3R,4S,5S)-ethyl 3-(tert-butyl)-4-hydroxy-5-(2-methoxyphenyl)-1-((S)-tetrahydro-2H-pyran-2-carbonyl)pyrrolidine-2-carboxylate To a cooled (ice bath) solution of (2S,3R,5S)-ethyl 3-(tert-butyl)-5-(2-methoxyphenyl)-4-oxo-1-((S)-tetrahydro-2H-pyran-2-carbonyl)pyrrolidine-2-carboxylate from Example 239C (0.426 g, 0.987 mmol) in ethanol (5 mL) was added sodium borohydride (0.056 g, 1.481 mmol) in portions. The reaction was stirred in the ice bath for 30 minutes and at ambient temperature for 60 minutes. The solvent was removed and the crude material was quenched with saturated aqueous NH$_4$Cl (25 mL) and diluted with dichloromethane (100 mL). The organics were removed and washed with brine, dried over sodium sulfate, filtered, and concentrated. The crude material was purified using a 10 g silica gel cartridge, eluting with 5-100% methyl tert-butyl ether/heptanes over 20 minutes to provide the title compound. $^1$H NMR (400 MHz, DMSO-d$_6$) δ ppm 7.80 (s, 1H), 7.19 (t, J=7.9 Hz, 1H), 6.95 (d, J=8.1 Hz, 1H), 6.88 (t, J=7.5 Hz, 1H), 5.60 (s, 1H), 4.45 (s, 1H), 4.38-4.30 (m, 1H), 4.13 (q, J=7.1 Hz, 2H), 3.83 (s, 3H), 3.75 (dq, J=11.5, 2.7, 1.5 Hz, 1H), 2.19 (t, J=3.5 Hz, 1H), 1.73-1.56 (m, 3H), 1.55-1.40 (m, 2H), 1.42-1.27 (m, 4H), 1.22 (t, J=7.0 Hz, 3H), 0.97 (s, 9H).

Example 239E (2S,3R,4S,5S)-ethyl 3-(tert-butyl)-4-((5-cyclobutyl-2-methoxypyridin-3-yl)methoxy)-5-(2-methoxyphenyl)-1-((S)-tetrahydro-2H-pyran-2-carbonyl)pyrrolidine-2-carboxylate (2S,3R,4S,5S)-Ethyl 3-(tert-butyl)-4-hydroxy-5-(2-methoxyphenyl)-1-((S)-tetrahydro-2H-pyran-2-carbonyl)pyrrolidine-2-carboxylate from Example 239D (49 mg, 0.113 mmol) and 3-(bromomethyl)-5-cyclobutyl-2-methoxypyridine (49 mg, 0.191 mmol) were dissolved in dry N,N-dimethylformamide (1 mL). After cooling in an ice bath, a 1M solution of potassium 2-methylpropan-2-olate (0.181 mL, 0.181 mmol) in tetrahydrofuran was added dropwise over 2 minutes. After 10 minutes, the reaction was quenched with saturated aqueous NH$_4$Cl solution (1 mL) and extracted with dichloromethane (2×2 mL). The organic solvent was evaporated and the resulting crude material was loaded onto a 12 g silica gel column and was eluted with 0-70% ethyl acetate/hexanes over 20 minutes to provide the title compound. $^1$H NMR (400 MHz, DMSO-d$_6$) δ ppm 7.89 (d, J=10.0 Hz, 1H), 7.75 (d, J=2.5 Hz, 1H), 7.18 (s, 1H), 6.96-6.84 (m, 3H), 5.77 (s, 1H), 4.61 (s, 1H), 4.24-4.22 (m, 1H), 4.22-4.19 (m, 1H), 4.06 (qd, J=7.1, 1.6 Hz, 2H), 3.89 (d, J=13.0 Hz, 1H), 3.79 (s, 3H), 3.76 (s, 3H), 3.37-3.26 (m, 1H), 2.39 (t, J=2.4 Hz, 1H), 2.29-2.16 (m, 2H), 2.02-1.86 (m, 6H), 1.89-1.77 (m, 2H), 1.72-1.60 (m, 1H), 1.58-1.43 (m, 1H), 1.43-1.30 (m, 3H), 1.12 (t, J=7.1 Hz, 3H), 0.98 (s, 9H); MS (APCI+) m/z 609 (M+H)$^+$.

Example 239F (2S,3R,4S,5S)-3-tert-butyl-4-[(5-cyclobutyl-2-methoxypyridin-3-yl)methoxy]-5-(2-methoxyphenyl)-1-[(2S)-oxane-2-carbonyl]pyrrolidine-2-carboxylic acid To a solution of (2S,3R,4S,5S)-ethyl 3-(tert-butyl)-4-((5-cyclobutyl-2-methoxypyridin-3-yl)methoxy)-5-(2-methoxyphenyl)-1-((S)-tetrahydro-2H-pyran-2-carbonyl)pyrrolidine-2-carboxylate from Example 239E (46 mg, 0.076 mmol) in tetrahydrofuran (0.5 mL), methanol (0.500 mL) and water (0.500 mL) was added lithium hydroxide hydrate (22.20 mg, 0.529 mmol). The reaction was heated at 45° C. for 16 hours. The solvent was removed under a stream of nitrogen. The crude material was acidified with 1M aqueous HCl (0.6 mL) and the resulting residue was taken up in dichloromethane and purified using a 12 g silica gel cartridge with an ethyl acetate/ethanol/heptanes solvent system to provide the title compound. $^1$H NMR (400 MHz, DMSO-d$_6$) δ ppm 8.22 (s, 1H), 7.75 (d, J=2.6 Hz, 1H), 7.16 (s, 1H), 6.92-6.83 (m, 2H), 6.81 (d, J=2.3 Hz, 1H), 5.79 (s, 1H), 4.42 (s, 1H), 4.25 (d, J=13.2 Hz, 1H), 4.14 (dd, J=6.9, 3.0 Hz, 1H), 3.96 (d, J=13.2 Hz, 1H), 3.86-3.72 (m, 8H), 3.37-3.23 (m, 1H), 2.60 (t, J=3.2 Hz, 1H), 2.29-2.14 (m, 2H), 1.99-1.77 (m, 5H), 1.72-1.58 (m, 1H), 1.58-1.43 (m, 1H), 1.44-1.28 (m, 2H), 1.25 (s, 1H), 0.96 (s, 9H), 0.83 (d, J=6.7 Hz, 1H); MS (APCI+) m/z 581 (M+H)$^+$.

Example 240

(2S,3R,4S,5S)-3-tert-butyl-5-(2-methoxyphenyl)-4-{[2-methoxy-5-(trifluoromethyl)pyridin-3-yl]methoxy}-1-[(2S)-oxane-2-carbonyl]pyrrolidine-2-carboxylic acid Example 240A (2S,3R,4S,5S)-ethyl 3-(tert-butyl)-4-((2-methoxy-5-(trifluoromethyl)pyridin-3-yl)methoxy)-5-(2-methoxyphenyl)-1-((S)-tetrahydro-2H-pyran-2-carbonyl)pyrrolidine-2-carboxylate (2S,3R,4S,5S)-Ethyl 3-(tert-butyl)-4-hydroxy-5-(2-methoxyphenyl)-1-((S)-tetrahydro-2H-pyran-2-carbonyl)pyrrolidine-2-carboxylate from Example 239D (53 mg, 0.122 mmol) and 3-(bromomethyl)-2-methoxy-5-(trifluoromethyl)pyridine (44 mg, 0.163 mmol) were dissolved in dry N,N-dimethylformamide (1 mL). After cooling in an ice bath, a 1M solution of potassium 2-methylpropan-2-olate (0.196 mL, 0.196 mmol) in tetrahydrofuran was added dropwise over 2 minutes. After 30 minutes, the mixture was quenched with saturated aqueous NH$_4$Cl solution and extracted with dichloromethane. The organic solvent was evaporated and the crude material was loaded onto a 12 g silica gel column eluting with 0-70% ethyl acetate/hexanes over 20 minutes to provide the title compound. $^1$H NMR (400 MHz, DMSO-d$_6$) δ ppm 8.27 (d, J=2.4 Hz, 1H), 7.85 (s, 1H), 7.17-7.10 (m, 2H), 6.88 (d, J=8.3 Hz, 1H), 6.83 (d, J=7.7 Hz, 1H), 5.78 (s, 1H), 4.62 (s, 1H), 4.30 (d, J=13.7 Hz, 1H), 4.25 (dd, J=6.1, 1.9 Hz, 1H), 4.07 (qq, J=7.2, 3.7 Hz, 2H), 3.92 (d, J=13.8 Hz, 1H), 3.87 (s, 3H), 3.78 (s, 3H), 3.74 (s, 1H), 2.39 (t, J=2.3 Hz, 1H), 1.73-1.60 (m, 2H), 1.60-1.42 (m, 1H), 1.44-1.27 (m, 5H), 1.13 (t, J=7.1 Hz, 3H), 0.99 (s, 9H); MS (APCI+) m/z 623 (M+H)$^+$.

Example 240B (2S,3R,4S,5S)-3-tert-butyl-5-(2-methoxyphenyl)-4-{[2-methoxy-5-(trifluoromethyl)pyridin-3-yl]methoxy}-1-[(2S)-oxane-2-carbonyl]pyrrolidine-2-carboxylic acid To a solution of (2S,3R,4S,5S)-ethyl 3-(tert-butyl)-4-((2-methoxy-5-(trifluoromethyl)pyridin-3-yl)methoxy)-5-(2-methoxyphenyl)-1-((S)-tetrahydro-2H-pyran-2-carbonyl)pyrrolidine-2-carboxylate from Example 240A (57 mg, 0.092 mmol) in tetrahydrofuran (0.5 mL), methanol (0.500 mL) and water (0.500 mL) was added lithium hydroxide, hydrate (26.9 mg, 0.641 mmol) and the reaction mixture was heated at 45° C. for 16 hours. The solvent was removed under a stream of nitrogen. Water (2 mL) was added to the crude material. The mixture was extracted with 2×1 mL heptane (discarded). The desired product was extracted into diethyl ether (3×1 mL), concentrated, and acidified with 1M aqueous HCl (0.5 mL) to pH-2. The precipitate was purified using a 12 g silica gel cartridge with an ethyl acetate/ethanol/heptanes solvent system to provide the title compound. $^1$H NMR (400 MHz, DMSO-$d_6$) δ ppm 8.35-8.25 (m, 1H), 8.25 (s, 1H), 7.15-7.07 (m, 1H), 7.08-7.03 (m, 1H), 6.85-6.69 (m, 2H), 5.99-5.60 (m, 1H), 4.45-4.37 (m, 1H), 4.34 (d, J=14.1 Hz, 1H), 4.21-4.11 (m, 1H), 4.06-3.98 (m, 1H), 3.92-3.85 (m, 3H), 3.84-3.76 (m, 1H), 3.73 (s, 3H), 2.65 (dd, J=10.8, 4.3 Hz, 2H), 1.73-1.60 (m, 1H), 1.59-1.44 (m, 1H), 1.46-1.30 (m, 2H), 1.30-1.21 (m, 2H), 0.97 (s, 9H), 0.83 (d, J=6.7 Hz, 1H); MS (APCI+) m/z 595 (M+H)$^+$.

Example 241

(2S,3R,4S,5S)-3-tert-butyl-4-[(5-tert-butyl-2-methoxypyridin-3-yl)methoxy]-5-(2-methoxyphenyl)-1-[(2S)-oxane-2-carbonyl]pyrrolidine-2-carboxylic acid

Example 241A (2S,3R,4S,5S)-ethyl 3-(tert-butyl)-4-((5-(tert-butyl)-2-methoxypyridin-3-yl)methoxy)-5-(2-methoxyphenyl)-1-((S)-tetrahydro-2H-pyran-2-carbonyl)pyrrolidine-2-carboxylate (2S,3R,4S,5S)-Ethyl 3-(tert-butyl)-4-hydroxy-5-(2-methoxyphenyl)-1-((S)-tetrahydro-2H-pyran-2-carbonyl)pyrrolidine-2-carboxylate from Example 239D (46 mg, 0.106 mmol) and 3-(bromomethyl)-5-(tert-butyl)-2-methoxypyridine (52 mg, 0.201 mmol) were dissolved in dry N,N-dimethylformamide (1 mL). After cooling in an ice bath, 1M potassium 2-methylpropan-2-olate (0.170 mL, 0.170 mmol) solution in tetrahydrofuran was added dropwise over 2 minutes. After 30 minutes, the mixture was quenched with saturated aqueous NH$_4$Cl solution and extracted with dichloromethane. The organic solvent was evaporated and the residue was loaded onto a 12 g silica gel column eluting with 0-70% ethyl acetate/hexanes over 20 minutes to provide the title compound. $^1$H NMR (400 MHz, DMSO-$d_6$) δ ppm 7.98-7.79 (m, 1H), 7.24-7.02 (m, 3H), 6.91 (d, J=8.1 Hz, 1H), 6.84 (t, J=7.4 Hz, 1H), 5.77 (s, 1H), 4.59 (s, 1H), 4.24-4.17 (m, 2H), 4.05 (qd, J=7.1, 1.4 Hz, 2H), 3.87 (d, J=12.9 Hz, 1H), 3.80 (s, 3H), 3.75 (s, 3H), 2.38 (t, J=2.4 Hz, 1H), 1.73-1.57 (m, 2H), 1.57-1.43 (m, 2H), 1.36 (dt, J=10.9, 5.5 Hz, 5H), 1.18 (s, 9H), 1.11 (t, J=7.1 Hz, 3H), 0.97 (s, 9H); MS (APCI+) m/z 611 (M+H)$^+$.

Example 241B (2S,3R,4S,5S)-3-tert-butyl-4-[(5-tert-butyl-2-methoxypyridin-3-yl)methoxy]-5-(2-methoxyphenyl)-1-[(2S)-oxane-2-carbonyl]pyrrolidine-2-carboxylic acid To a solution of (2S,3R,4S,5S)-ethyl 3-(tert-butyl)-4-((5-(tert-butyl)-2-methoxypyridin-3-yl)methoxy)-5-(2-methoxyphenyl)-1-((S)-tetrahydro-2H-pyran-2-carbonyl)pyrrolidine-2-carboxylate from Example 241A (52 mg, 0.085 mmol) in tetrahydrofuran (0.5 mL), methanol (0.500 mL) and water (0.500 mL) was added lithium hydroxide H$_2$O (25.01 mg, 0.596 mmol). The reaction mixture was heated at 45° C. for 16 hours. The solvent was removed under a stream of nitrogen. Water (2 mL) was added to the crude material. The mixture was extracted with 2×1 mL heptane (discarded). The desired product was extracted into diethyl ether (3×1 mL), and the organics were concentrated. Water (0.2 mL water) was added and the mixture was acidified with 1M aqueous HCl (0.3 mL) to pH 2. The water was pipetted off and the precipitate was purified using a 12 g silica gel cartridge with an ethyl acetate/ethanol/heptanes solvent system to provide the title compound. $^1$H NMR (400 MHz, DMSO-$d_6$) δ ppm 7.99 (d, J=7.7 Hz, 1H), 7.91 (d, J=2.7 Hz, 1H), 7.20-7.08 (m, 2H), 6.90 (d, J=8.2 Hz, 1H), 6.83 (t, J=7.4 Hz, 1H), 5.74 (s, 1H), 4.52 (s, 1H), 4.24-4.16 (m, 2H), 3.89 (d, J=13.0 Hz, 1H), 3.79 (s, 3H), 3.76 (s, 3H), 3.64-3.40 (m, 1H), 3.18 (d, J=6.2 Hz, 1H), 1.72-1.60 (m, 2H), 1.58-1.42 (m, 2H), 1.44-1.28 (m, 3H), 1.18 (s, 9H), 0.96 (s, 9H), 0.85-0.77 (m, 1H); MS (APCI+) m/z 583 (M+H)$^+$.

Example 242

(2S,3R,4S,5S)-3-tert-butyl-4-[(2-methoxy-6,8-dimethylquinolin-3-yl)methoxy]-5-(2-methylphenyl)-1-[(2S)-oxane-2-carbonyl]pyrrolidine-2-carboxylic acid

Example 242A (2-methoxy-6,8-dimethylquinolin-3-yl)methanol

To 2-methoxy-6,8-dimethylquinoline-3-carbaldehyde (500 mg, 2.323 mmol) in ethanol (5 mL) cooling in an ice bath, sodium borohydride (132 mg, 3.48 mmol) was added in portions. The mixture was stirred in an ice bath for 30 minutes. Saturated aqueous NH$_4$Cl (2 mL) was added and the solvent was removed under pressure. The residue was partitioned between ethyl acetate and saturated aqueous sodium bicarbonate. The organic extracts was dried over sodium sulfate, filtered, and concentrated to provide the title compound, which was used in next step. MS (APCI+) m/z 218.2 (M+H)$^+$.

Example 242B 3-(bromomethyl)-2-methoxy-6,8-dimethylquinoline

The title compound was prepared according to the procedure described in Example 236A, substituting Example 242A for (2-chloro-5,7-dimethylquinolin-3-yl)methanol, to provide the title compound. MS (APCI+) m/z 280 (M+H)⁺.

Example 242C (2S,3R,4S,5S)-3-tert-butyl-4-[(2-methoxy-6,8-dimethylquinolin-3-yl)methoxy]-5-(2-methylphenyl)-1-[(2S)-oxane-2-carbonyl]pyrrolidine-2-carboxylic acid The title compound was prepared according to the procedure described in Example 188 substituting Example 242B for Intermediate 6. ¹H NMR (400 MHz, DMSO-d₆) δ ppm 8.08 (dd, J=7.2, 2.6 Hz, 1H), 7.26 (s, 1H), 7.18 (d, J=7.1 Hz, 2H), 7.13 (d, J=4.4 Hz, 3H), 5.56 (s, 1H), 4.66 (s, 1H), 4.36-4.30 (m, 1H), 4.30-4.24 (m, 1H), 3.94 (dd, J=13.9, 1.3 Hz, 1H), 3.91 (s, 3H), 3.77 (d, J=11.4 Hz, 1H), 3.39(m, 2H), 2.54 (s, 3H), 2.52-2.50 (m, 1H), 2.39 (s, 3H), 2.31 (s, 3H), 1.70-1.30 (m, 6H), 1.02 (s, 9H); MS (ESI+) m/z 589.3 (M+H)⁺.

Example 243

(2S,3R,4S,5S)-3-tert-butyl-4-{[2-methoxy-5-(1-methylcyclopropyl)pyridin-3-yl]methoxy}-5-(2-methylphenyl)-1-[(2S)-oxane-2-carbonyl]pyrrolidine-2-carboxylic acid

Example 243A 2-methoxy-5-(prop-1-en-2-yl)pyridine

To a thick suspension of methyltriphenylphosphonium iodide (9.75 g, 24.0 mmol) in anhydrous tetrahydrofuran (35 mL) under nitrogen and cooled with a water ice bath, 1.0 M potassium tert-butoxide in tetrahydrofuran (23 mL, 23 mmol) was added slowly. The suspension was stirred cold for seventy minutes and treated over nearly ten minutes with a solution of 1-(6-methoxypyridin-3-yl)ethanone (3.03 g, 20.0 mmol) in tetrahydrofuran (15 mL). After a couple of minutes, the bath was removed and the reaction mixture was stirred another 70 minutes before being quenched with acetone (2 mL). The mixture was stirred about three minutes and concentrated. The residue was slurried with methyl tert-butyl ether (40 mL) and filtered with a thorough methyl tert-butyl ether rinse (60 mL). The filtrate was concentrated and filtered through basic alumina with 25% methyl tert-butyl ether/heptane, and the new filtrate was concentrated to give the title compound. ¹H NMR (400 MHz, DMSO-d₆) δ ppm 8.27 (dd, J=2.6, 0.7 Hz, 1H), 7.86 (dd, J=8.7, 2.6 Hz, 1H), 6.79 (dd, J=8.7, 0.7 Hz, 1H), 5.39 (dq, J=1.5, 0.8 Hz, 1H), 5.05 (qd, J=1.5, 1.5 Hz, 1H), 3.85 (s, 3H), 2.09 (dd, J=1.5, 0.8 Hz, 3H); MS (ESI) m/z 150 (M+H)⁺.

Example 243B 2-methoxy-5-(1-methylcyclopropyl)pyridine

After 1.06 M solution of diethylzinc in heptane (11.3 mL, 12.0 mmol) was added to dichloromethane (25 mL) under nitrogen and cooled to 0° C., a solution of trifluoroacetic acid (920 µL, 12.0 mmol) in dichloromethane (15 mL) was added slowly. The resulting mixture was stirred twelve minutes, treated slowly with a solution of diiodomethane (960 µL, 11.9 mmol) in dichloromethane (10 mL), stirred another twenty minutes and then treated with a solution of 2-methoxy-5-(prop-1-en-2-yl)pyridine (597 mg, 4.00 mmol) in dichloromethane (10 mL). The reaction mixture was allowed to slowly warm to room temperature over the weekend, quenched by the addition of saturated aqueous NaHCO₃ (20 mL), and diluted with heptane (10 mL). The separated aqueous phase was extracted thrice with chloroform and the combined organic phases were dried with sodium sulfate, filtered, concentrated and chromatographed on basic alumina (20 to 50% CHCl₃/heptane) to provide the title compound. ¹H NMR (400 MHz, CDCl₃) δ ppm 8.08 (d, J=2.5 Hz, 1H), 7.45 (dd, J=8.6, 2.5 Hz, 1H), 6.66 (d, J=8.6 Hz, 1H), 3.91 (s, 3H), 1.37 (s, 3H), 0.81-0.77 (m, 2H), 0.72-0.68 (m, 2H); MS (ESI) m/z 164 (M+H)⁺.

Example 243C 2-methoxy-5-(1-methylcyclopropyl)pyridin-3-yl)methanol

To a solution of TMEDA (tetramethylethylenediamine, 132 µL, 0.88 mmol) in anhydrous methyl tert-butyl ether (2.0 mL) under nitrogen and cooled to 0° C. was added 2.05 M n-butyllithium in cyclohexane (410 µL, 0.84 mmol). After a couple of minutes, a dropwise solution of impure 2-methoxy-5-(1-methylcyclopropyl)pyridine (98 mg, <0.6 mmol) in methyl tert-butyl ether (1.5 mL) was added. After a few minutes, the mixture was removed from the bath and stirred at room temperature more than twenty minutes before being cannulated dropwise into a suspension of paraformaldehyde (30 mg, 1.0 mmol) in methyl tert-butyl ether (2.0 mL) under nitrogen. The mixture was cooled with a water ice bath, with a methyl tert-butyl ether (0.5 mL) rinse. After six hours, the reaction mixture was quenched with 3 M aqueous citric acid (400 µL) and diluted with brine (400 µL). The aqueous phase was separated and extracted with methyl tert-butyl ether and the combined organic phases were dried (Na₂SO₄), filtered, and concentrated. The residue was chromatographed on silica (20 to 30% methyl tert-butyl ether/heptane) to provide the title compound. ¹H NMR (500 MHz, CDCl₃) δ ppm 8.00 (d, J=2.4 Hz, 1H), 7.47-7.46 (m, 1H), 4.63 (d, J=5.6 Hz, 2H), 3.97 (s, 3H), 2.36-2.31 (m, 1H), 1.37 (s, 3H), 0.81-0.78 (m, 2H), 0.72-0.69 (m, 2H); MS (ESI) m/z 194 (M+H)⁺.

Example 243D 3-(bromomethyl)-2-methoxy-5-(1-methylcyclopropyl)pyridine

To a solution of Example 243C (60 mg, 0.31 mmol) and triphenylphosphine (97 mg, 0.37 mmol) in anhydrous dichloromethane (1.0 mL) under nitrogen and cooled with a water ice bath was added dropwise a solution of tetrabromomethane (123 mg, 0.37 mmol) in dichloromethane (0.5 mL). After the reaction solution had been stirred a minute, the bath was removed and the mixture was stirred at room temperature about 45 minutes before being concentrated and chromatographed on silica (20 to 40% CHCl₃/heptane) to provide the title compound. ¹H NMR (400 MHz, CDCl₃) δ ppm 8.03 (d, J=2.4 Hz, 1H), 7.49 (d, J=2.4 Hz, 1H), 4.47 (s, 2H), 3.99 (s, 3H), 1.37 (s, 3H), 0.82-0.76 (m, 2H), 0.75-0.70 (m, 2H); MS (ESI) m/z 256, 258 (M+H)⁺.

Example 243E (2S,3R,4S,5S)-ethyl 3-(tert-butyl)-4-((2-methoxy-5-(1-methylcyclopropyl)pyridin-3-yl)methoxy)-1-((S)-tetrahydro-2H-pyran-2-carbonyl)-5-(o-tolyl)pyrrolidine-2-carboxylate Example 170B (74 mg, 0.17 mmol) was dissolved into anhydrous toluene, dried twice over NaSO₄, filtered, and concentrated. The residue was placed under nitrogen, dissolved into anhydrous N,N-dimethylformamide (350 μL), cooled to −40° C., treated first with a solution of Example 243D (51 mg, 0.20 mmol) in N,N-dimethylformamide (250 μL) and then dropwise over several minutes with 1 M potassium tert-butoxide in tetrahydrofuran (190 μL, 0.19 mmol). The reaction mixture was permitted to warm slowly over almost two hours to nearly room temperature before it was quenched with 3 M aqueous citric acid (70 μL). Brine was added and the reaction mixture was extracted thrice with methyl tert-butyl ether. The combined organic phases were dried ($Na_2SO_4$), filtered, concentrated and chromatographed on silica (20 to 30% methyl tert-butyl ether/heptane) to give the crude title compound which was used in the next step without further purification. MS (ESI+) m/z 593 $(M+H)^+$.

Example 243F (2S,3R,4S,5S)-3-tert-butyl-4-{[2-methoxy-5-(1-methylcyclopropyl)pyridin-3-yl]methoxy}-5-(2-methylphenyl)-1-[(2S)-oxane-2-carbonyl]pyrrolidine-2-carboxylic acid Example 243E (80 mg) was dissolved into tetrahydrofuran (900 μL) and methanol (400 μL), treated with 1.5 M aqueous LiOH (900 μL) and heated at 50° C. overnight. The reaction mixture was brought to room temperature and was quenched with 3 M aqueous citric acid (250 μL), diluted with brine (500 μL) and extracted thrice with methyl tert-butyl ether. The combined organic phases were dried ($Na_2SO_4$), filtered, concentrated and chromatographed on silica (10 to 70% methyl tert-butyl ether in 1:3 $CH_2Cl_2$/heptane) to give the title compound. $^1$H NMR (400 MHz, $CDCl_3$) δ ppm 7.83 (d, J=2.4 Hz, 1H), 7.57-7.53 (m, 1H), 7.24-7.12 (m, 3H), 6.77-6.74 (m, 1H), 5.80 (d, J=5.6 Hz, 1H), 4.82-4.79 (m, 1H), 4.38 (d, J=13.8 Hz, 1H), 4.16 (d, J=5.6 Hz, 1H), 3.92 (d, J=13.8 Hz, 1H), 3.87-3.81 (m, 1H), 3.80 (s, 3H), 3.32-3.27 (m, 1H), 2.92-2.89 (m, 1H), 2.86-2.78 (m, 1H), 2.32 (s, 3H), 1.78-1.70 (m, 1H), 1.68-1.42 (m, 3H), 1.36-1.25 (m, 3H), 1.24 (s, 3H), 1.06 (s, 9H), 0.65-0.59 (m, 4H); MS (ESI+) m/z 565 $(M+H)^+$.

Example 244

(2S,3R,4S,5S)-3-tert-butyl-4-[(2-methoxy-8-methylquinolin-3-yl)methoxy]-5-(2-methylphenyl)-1-[(2S)-oxane-2-carbonyl]pyrrolidine-2-carboxylic acid Example 244A 3-(bromomethyl)-2-methoxy-8-methylquinoline The title compound was prepared according to the procedure described in Example 236A, substituting (2-methoxy-8-methylquinolin-3-yl)methanol for (2-chloro-5,7-dimethylquinolin-3-yl)methanol. MS (APCI+) m/z 266 $(M+H)^+$.

Example 244B (2S,3R,4S,5S)-3-tert-butyl-4-[(2-methoxy-8-methylquinolin-3-yl)methoxy]-5-(2-methylphenyl)-1-[(2S)-oxane-2-carbonyl]pyrrolidine-2-carboxylic acid The title compound was prepared according to the procedure described in Example 188 substituting Example 244A for Intermediate 6. $^1$H NMR (400 MHz, DMSO-$d_6$) δ ppm 8.08 (dd, J=6.8, 2.4 Hz, 1H), 7.51-7.37 (m, 2H), 7.36-7.20 (m, 2H), 7.13 (d, J=4.9 Hz, 3H), 5.57 (s, 1H), 4.67 (s, 1H), 4.34 (dd, J=13.9, 1.2 Hz, 1H), 4.29 (d, J=5.9 Hz, 1H), 4.02-3.95 (m, 1H), 3.93 (s, 3H), 3.77 (d, J=11.6 Hz, 1H), 3.39 (m, 2H), 2.58 (s, 3H), 2.53 (d, J=1.8 Hz, 1H), 2.31 (s, 3H), 1.70-1.29 (m, 6H), 1.02 (s, 9H); MS (ESI+):m/e 575.2 $(M+H)^+$.

Example 245

(2S,3R,4S,5S)-3-tert-butyl-4-[(5-tert-butyl-2-methoxyphenyl)methoxy]-1-{[(propan-2-yl)oxy]carbonyl}-5-{2-[(propan-2-yl)oxy]pyridin-3-yl}pyrrolidine-2-carboxylic acid Example 245A (2S,3R,4S,5S)-2-ethyl 1-isopropyl 3-(tert-butyl)-4-hydroxy-5-(2-isopropoxypyridin-3-yl)pyrrolidine-1,2-dicarboxylate To (2S,3R,4S,5S)-ethyl 3-(tert-butyl)-4-hydroxy-5-(2-isopropoxypyridin-3-yl)pyrrolidine-2-carboxylate (Example 169A, 10 g, 28.5 mmol) in dichloromethane (143 mL) was added triethylamine (7.95 mL, 57.1 mmol). The solution was cooled in an ice bath to 5° C., isopropyl carbonochloridate (15.69 mL, 31.4 mmol) was added as a solution in toluene slowly and an exotherm to ~15° C. was noted. A solid formed, so the vial was removed from the bath and stirred at room temperature. The reaction was complete as soon as the chloroformate was added. The mixture was diluted with methyl tert-butyl ether and saturated aqueous sodium bicarbonate was added. The mixture was allowed to stir overnight at room temperature. The organics was washed with brine, dried over $MgSO_4$, filtered, and concentrated to provide the title compound. MS (ESI+) m/z 437 $(M+H)^+$.

Example 245B (2S,3R,4S,5S)-3-tert-butyl-4-[(5-tert-butyl-2-methoxyphenyl)methoxy]-1-{[(propan-2-yl)oxy]carbonyl}-5-{2-[(propan-2-yl)oxy]pyridin-3-yl}pyrrolidine-2-carboxylic acid To Example 245A (80 mg, 0.183 mmol) and 2-(bromomethyl)-4-(tert-butyl)-1-methoxybenzene (Intermediate 6, 47.1 mg, 0.183 mmol) in N,N-dimethylformamide (2 mL) cooling in an ice bath, was added dropwise potassium 2-methylpropan-2-olate (30.8 mg, 0.275 mmol, 0.28 mL, 1.0M in tetrahydrofuran). The mixture was stirred in an ice bath for 20 minutes, and allowed to stir at ambient temperature for 30 minutes. The solvent was concentrated and methanol (2 mL) and 6M aqueous LiOH (0.5 mL) were added. The mixture was stirred at 50° C. for 5 hours, and saturated aqueous $NH_4Cl$ (2 mL) and dichloromethane (20 mL) were added. The organic layer was washed with brine, dried over $MgSO_4$, filtered, and concentrated. The residue was purified via chromatography on a 12 g silica gel cartridge, eluting with ethyl acetate/methanol (9:1) in heptane, at a 0-60% gradient to provide the title compound. $^1$H NMR (400 MHz, DMSO-$d_6$) δ ppm 8.11 (ddd, J=7.4, 2.0, 0.7 Hz, 1H), 7.91 (dd, J=4.9, 2.0 Hz, 1H), 7.10 (dd, J=8.6, 2.6 Hz, 1H), 6.82 (d, J=2.7 Hz, 1H), 6.78 (dd, J=7.4, 5.0 Hz, 1H), 6.72 (d, J=8.5 Hz, 1H), 5.26 (p, J=6.1 Hz, 1H), 5.16 (d, J=6.0 Hz, 1H), 4.65 (dq, J=12.4, 6.2 Hz, 1H), 4.34 (d, J=2.6

Hz, 1H), 4.27 (d, J=12.4 Hz, 1H), 4.19 (dd, J=6.0, 1.7 Hz, 1H), 3.95 (d, J=12.4 Hz, 1H), 3.62 (s, 3H), 1.30 (d, J=6.1 Hz, 3H), 1.25 (d, J=6.2 Hz, 3H), 1.16 (s, 9H), 1.05 (d, J=6.2 Hz, 3H), 0.96 (s, 9H), 0.91 (d, J=6.2 Hz, 3H); MS (ESI+) m/z 585 (M+H)$^+$.

Example 246

(2S,3R,4S,5S)-3-tert-butyl-4-{[2-methoxy-5-(1-methylcyclobutyl)phenyl]methoxy}-1-{[(propan-2-yl)oxy]carbonyl}-5-{2-[(propan-2-yl)oxy]pyridin-3-yl}pyrrolidine-2-carboxylic acid Example 246A 2-methoxy-5-(1-methylcyclobutyl)benzaldehyde 1-Methoxy-4-(1-methylcyclobutyl)benzene (3 g, 17.02 mmol) was dissolved in 110 mL of dichloromethane, and the solution was cooled to <0° C. in an ice brine bath. After addition of dichloro(methoxy)methane (1.693 mL, 18.72 mmol), titanium tetrachloride (2.065 mL, 18.72 mmol) was added dropwise as a solution in 10 mL of dichloromethane over 2 minutes, maintaining an internal temperature <5° C. After 15 minutes at the same temperature, TLC indicated complete conversion. Water (40 mL) was added to quench (exotherm to ~15° C.) the reaction, and the organic layer was concentrated and loaded onto an 80 g silica gel column, eluting with 0-15% ethyl acetate/heptane over 20 minutes to provide the title compound. $^1$H NMR (400 MHz, Chloroform-d) δ ppm 10.49 (d, J=1.0 Hz, 1H), 7.67 (dd, J=2.6, 0.9 Hz, 1H), 7.40 (ddd, J=8.6, 2.5, 1.0 Hz, 1H), 6.96 (d, J=8.6 Hz, 1H), 3.94 (d, J=1.0 Hz, 3H), 2.37 (td, J=10.4, 9.7, 7.3 Hz, 2H), 2.18-2.04 (m, 3H), 1.89-1.81 (m, 1H), 1.46 (s, 3H); MS (ESI+) m/z 205 (M+H)$^+$.

Example 246B (2-methoxy-5-(1-methylcyclobutyl)phenyl)methanol

To Example 246A (1.0 g, 4.9 mmol) in ethanol (20 mL) cooled in an ice bath, sodium borohydride (0.204 g, 5.39 mmol) was added in portions. The mixture was stirred in an ice bath for 30 minutes. Saturated aqueous NH$_4$Cl (2 mL) was added and solvent was removed under reduced pressure, and the residue was partitioned between ethyl acetate and saturated aqueous sodium bicarbonate. The organics were washed with brine, dried over sodium sulfate, filtered, and concentrated to provide the title compound. MS (APCI+) m/z 189 (M-OH)$^+$.

Example 246C 2-(bromomethyl)-1-methoxy-4-(1-methylcyclobutyl)benzene

To triphenylphosphine (2365 mg, 9.02 mmol) in dichloromethane (10 mL) cooling in an ice bath was added 1-bromopyrrolidine-2,5-dione (1605 mg, 9.02 mmol) portionwise. The mixture was stirred for 30 minutes maintaining an internal temperature <10° C., and (2-methoxy-5-(1-methylcyclobutyl)phenyl)methanol (930 mg, 4.51 mmol) in dichloromethane (2 mL) was added slowly at <10° C. The mixture was stirred in ice bath for 1 hour. Saturated aqueous NH$_4$Cl (2 mL) was added and the mixture was concentrated. The residue was partitioned between ethyl acetate and saturated aqueous sodium bicarbonate. The organic extracts were dried over sodium sulfate, filtered, and concentrated to provide the title compound. $^1$H NMR (501 MHz, Chloroform-d) δ ppm 7.17-7.11 (m, 2H), 6.84 (s, 1H), 4.60 (s, 2H), 3.91 (s, 3H), 2.40-2.30 (m, 2H), 2.16-1.98 (m, 3H), 1.87-1.77 (m, 1H), 1.46 (d, J=0.7 Hz, 3H).

Example 246D (2S,3R,4S,5S)-3-tert-butyl-4-{[2-methoxy-5-(1-methylcyclobutyl)phenyl]methoxy}-1-{[(propan-2-yl)oxy]carbonyl}-5-{2-[(propan-2-yl)oxy]pyridin-3-yl}pyrrolidine-2-carboxylic acid The title compound was prepared according to the procedure described in Example 245B, substituting Example 246C for Intermediate 6 to provide the title compound. $^1$H NMR (400 MHz, DMSO-d$_6$) δ ppm 8.09 (dd, J=7.3, 1.9 Hz, 1H), 7.91 (dd, J=4.9, 2.0 Hz, 1H), 6.93 (dd, J=8.4, 2.5 Hz, 1H), 6.78 (dd, J=7.4, 4.9 Hz, 1H), 6.73 (d, J=8.4 Hz, 1H), 6.61 (d, J=2.5 Hz, 1H), 5.30-5.22 (m, 1H), 5.16 (d, J=6.0 Hz, 1H), 4.66 (h, J=6.2 Hz, 1H), 4.34 (d, J=2.5 Hz, 1H), 4.27 (d, J=12.4 Hz, 1H), 4.19 (dd, J=6.0, 1.7 Hz, 1H), 3.94 (d, J=12.5 Hz, 1H), 3.62 (s, 3H), 2.45 (m, 1H), 2.22-2.12 (m, 2H), 2.04-1.91 (m, 3H), 1.78-1.69 (m, 1H), 1.29 (t, J=3.1 Hz, 6H), 1.24 (d, J=6.2 Hz, 3H), 1.04 (d, J=6.2 Hz, 3H), 0.96 (s, 9H), 0.91 (d, J=6.2 Hz, 3H); MS (ESI+) m/z 597 (M+H)$^+$.

Example 247

(2S,3R,4S,5S)-3-tert-butyl-4-[(5-tert-butyl-2-methoxyphenyl)methoxy]-5-(2-methylphenyl)-1-[(2S)-oxolane-2-carbonyl]pyrrolidine-2-carboxylic acid Example 247A ethyl (2S,3R,4S,5S)-3-(tert-butyl)-4-hydroxy-1-((S)-tetrahydrofuran-2-carbonyl)-5-(o-tolyl)pyrrolidine-2-carboxylate A solution of Example 170A ((2S,3R,4S,5S)-ethyl 3-(tert-butyl)-4-hydroxy-5-(o-tolyl)pyrrolidine-2-carboxylate) (1.094 g, 3.58 mmol) in CH$_2$Cl$_2$ (20 mL) under N$_2$ was cooled to 0° C., treated with triethylamine (0.999 mL, 7.17 mmol), treated dropwise with a solution of (S)-tetrahydrofuran-2-carbonyl chloride (0.579 g, 4.3 mmol) in CH$_2$Cl$_2$ (~5 mL) over 5 minutes, stirred at 0° C. for 20 minutes, treated with saturated aqueous NH$_4$Cl solution (15 mL) and the layers were separated. The aqueous layer was diluted with water (10 mL) and extracted with CH$_2$Cl$_2$ (2×25 mL). The combined CH$_2$Cl$_2$ layers were dried (MgSO$_4$), filtered, concentrated and chromatographed on silica gel, eluting with a gradient of 15% to 100% ethyl acetate in heptane to provide the title compound. LC/MS (ESI+) m/z 404 (M+H)$^+$.

Example 247B (2S,3R,4S,5S)-3-(tert-butyl)-4-hydroxy-1-((S)-tetrahydrofuran-2-carbonyl)-5-(o-tolyl)pyrrolidine-2-carboxylic acid A solution of Example 247A ((2S,3R,4S,5S)-ethyl 3-(tert-butyl)-4-hydroxy-1-((S)-tetrahydrofuran-2-carbonyl)-5-(o-tolyl)pyrrolidine-2-carboxylate) (208.5 mg, 0.517 mmol) in tetrahydrofuran (1 mL) was diluted with methanol (1 mL), treated with 1 M aqueous NaOH (1 mL) and stirred at room temperature for 30 minutes. The mixture was treated with methyl tert-butyl ether (5 mL), treated with 1 M aqueous HCl (3 mL) and extracted with methyl tert-butyl ether (2×30 mL). The combined organic layers were washed with brine, dried (MgSO$_4$), filtered, and concentrated to provide the title compound. LC/MS (ESI+) m/z 376 (M+H)$^+$.

Example 247C (2S,3R,4S,5S)-3-tert-butyl-4-[(5-tert-butyl-2-methoxyphenyl)methoxy]-5-(2-methylphenyl)-1-[(2S)-oxolane-2-carbonyl]pyrrolidine-2-carboxylic acid A solution of Example 247B ((2S,3R,4S,5S)-3-(tert-butyl)-4-hydroxy-1-((S)-tetrahydrofuran-2-carbonyl)-5-(o-tolyl)pyrrolidine-2-carboxylic acid) (67.5 mg, 0.180 mmol) in N,N-dimethylformamide (1 mL) under N$_2$ was cooled to 0° C., treated with 1 M potassium tert-butoxide in tetrahydrofuran (539 µL, 0.539 mmol), stirred at room temperature for 15 minutes, cooled to −30° C., treated with a solution of Intermediate 6 (2-(bromomethyl)-4-(tert-butyl)-1-methoxybenzene) (50.9 mg, 0.198 mmol) in tetrahydrofuran (0.5 mL), stirred at −30° C. for 15 minutes, diluted with methyl tert-butyl ether (10 mL) and quenched with 1 M aqueous HCl (2 mL). The mixture was partitioned between methyl tert-butyl ether (40 mL) and water (10 mL). The layers were separated and the aqueous layer was extracted with methyl tert-butyl ether (30 mL). The combined methyl tert-butyl ether layers were washed with brine, dried (MgSO$_4$), filtered, concentrated and chromatographed on silica gel, eluting with a gradient of 10% to 50% [200:1:1 ethyl acetate:HCOOH:H$_2$O] in heptane to provide the title compound. $^1$H NMR (400 MHz, DMSO-d$_6$, 120° C.) δ ppm 7.99-7.90 (m, 1H), 7.14 (dd, J=2.7, 8.6 Hz, 1H), 7.11-7.07 (m, 3H), 6.85 (d, J=2.6 Hz, 1H), 6.76 (d, J=8.5 Hz, 1H), 5.27 (d, J=6.0 Hz, 1H), 4.62 (d, J=2.3 Hz, 1H), 4.27 (d, J=6.0 Hz, 1H), 4.19 (d, J=12.4 Hz, 1H), 3.88-3.80 (m, 2H), 3.65 (s, 4H), 3.60-3.51 (m, 2H), 3.00-2.75 (m, 1H), 2.62-2.56 (m, 1H), 2.37 (s, 3H), 1.90-1.80 (m, 1H), 1.63-1.42 (m, 1H), 1.20 (s, 9H), 1.01 (s, 9H); LC/MS (ESI+) m/z 552 (M+H)$^+$.

Example 248

(2S,3R,4S,5S)-3-tert-butyl-1-(cyclohexanecarbonyl)-4-[(2-methoxy-5,8-dimethylquinolin-3-yl)methoxy]-5-{2-[(propan-2-yl)oxy]pyridin-3-yl}pyrrolidine-2-carboxylic acid The title compound was prepared according to the procedure described in Example 245B, substituting Example 169B for Example 245A, and Example 237C for Intermediate 6. $^1$H NMR (400 MHz, DMSO-d$_6$) δ ppm 7.91 (d, J=5.0 Hz, 1H), 7.62 (s, 1H), 7.29 (d, J=7.2 Hz, 1H), 7.06 (d, J=7.2 Hz, 1H), 6.82 (s, 1H), 5.36 (s, 1H), 5.22 (p, J=6.1 Hz, 1H), 4.56 (d, J=2.8 Hz, 1H), 4.46 (d, J=13.4 Hz, 1H), 4.33 (dd, J=6.2, 2.1 Hz, 1H), 4.14 (d, J=13.4 Hz, 1H), 3.93 (s, 3H), 2.57 (s, 1H), 2.53 (s, 3H), 2.42 (s, 3H), 2.28 (s, 1H), 1.68 (s, 2H), 1.30 (d, J=6.1 Hz, 3H), 1.25 (s, 2H), 1.19 (d, J=6.1 Hz, 3H), 1.12 (d, J=29.0 Hz, 3H), 1.02 (s, 9H); MS (ESI+) m/z 632 (M+H)$^+$.

Example 249

(2S,3R,4S,5S)-3-tert-butyl-4-({2-[2-methoxy-5-(trifluoromethyl)phenyl]prop-2-en-1-yl}oxy)-5-(2-methylphenyl)-1-[(2S)-oxane-2-carbonyl]pyrrolidine-2-carboxylic acid Example 249A 1-(2-methoxy-5-(trifluoromethyl)phenyl)ethan-1-one A 250 mL 3-neck round bottom flask equipped with a thermometer and an addition funnel was charged with trifluoromethanesulfonic acid (29.6 mL, 333 mmol) and then treated dropwise (~6 drops/minute) under N$_2$ over 3 hours with a mixture of 4-(trifluoromethyl)anisole (11.74 g, 66.6 mmol) and acetic anhydride (12.57 mL, 133 mmol) keeping the internal temperature at or below 30° C. The resulting mixture was stirred at room temperature for 3 hours and then poured carefully into 150 mL of ice water, adding more ice during the addition to prevent the mixture from warming. The mixture was extracted with methyl tert-butyl ether (twice, 150 mL and 50 mL). The combined methyl tert-butyl ether layers were washed with saturated aqueous NaHCO$_3$ solution 4 times (100 mL, 100 mL, 50 mL and 50 mL). The methyl tert-butyl ether layer was washed with brine, dried (MgSO$_4$), filtered, concentrated, and chromatographed on silica gel, eluting with a gradient of 5% to 10% ethyl acetate in heptane to provide the title compound. $^1$H NMR (400 MHz, CDCl$_3$) δ ppm 8.00 (dd, J=0.8, 2.5 Hz, 1H), 7.70 (ddd, J=0.8, 2.5, 8.8 Hz, 1H), 7.05 (d, J=8.7 Hz, 1H), 3.97 (s, 3H), 2.62 (s, 3H).

Example 249B 1-methoxy-2-(prop-1-en-2-yl)-4-(trifluoromethyl)benzene

A suspension of methyltriphenoxyphosphonium iodide (1.443 g, 3.19 mmol) in tetrahydrofuran (5 mL) at 0° C. under N$_2$ was treated dropwise with 1 M potassium tert-butoxide in tetrahydrofuran (3.06 mL, 3.06 mmol), stirred at 0° C. for 2 hours, treated with a solution of Example 249A (1-(2-methoxy-5-(trifluoromethyl)phenyl)ethanone) (0.58 g, 2.66 mmol) in tetrahydrofuran (3 mL) and stirred at room temperature for 1 hour. The mixture was diluted with methyl tert-butyl ether (50 mL) and washed with water (20 mL). The layers were separated and the aqueous layer was extracted with methyl tert-butyl ether (30 mL). The combined methyl tert-butyl ether layers were washed with brine, dried (MgSO$_4$), filtered, concentrated and chromatographed on silica gel, eluting with 10% ethyl acetate in heptane to provide the title compound. $^1$H NMR (400 MHz, CDCl$_3$) δ ppm 7.53-7.49 (m, 1H), 7.44 (d, J=2.5 Hz, 1H), 6.93 (d, J=8.5 Hz, 1H), 5.22-5.20 (m, 1H), 5.10 (dd, J=0.9, 2.0 Hz, 1H), 3.89 (s, 3H), 2.12 (dd, J=0.9, 1.5 Hz, 3H).

Example 249C 2-(3-bromoprop-1-en-2-yl)-1-methoxy-4-(trifluoromethyl)benzene

A solution of Example 249B (1-methoxy-2-(prop-1-en-2-yl)-4-(trifluoromethyl)benzene) (233 mg, 1.078 mmol) in tetrahydrofuran (3 mL) was treated with N-bromosuccinimide (201 mg, 1.132 mmol), treated with p-toluenesulfonic acid monohydrate (20.50 mg, 0.108 mmol), stirred at reflux under N₂ for 2 hours, cooled, and diluted with heptanes (30 mL). A solid formed. The solid was removed by filtration and discarded. The filtrate was washed with 50% saturated aqueous NaHCO₃ solution (~10 mL), washed with water (2×20 mL), washed with brine, dried (MgSO₄), filtered, and concentrated. The residue was treated with heptanes (3 mL) and a second solid formed. The heptane solution was decanted away from this solid, and the second solid was decanted with more heptanes. The second solid was discarded. The combined heptane decantations were concentrated and chromatographed on silica gel, eluting first with heptanes, and then eluting with 10% methyl tert-butyl ether in heptanes to provide the title compound. $^1$H NMR (400 MHz, CDCl₃) δ ppm 7.58 (dd, J=2.3, 8.7 Hz, 1H), 7.48 (d, J=2.3 Hz, 1H), 6.95 (d, J=8.6 Hz, 1H), 5.56 (d, J=1.1 Hz, 1H), 5.28 (d, J=1.0 Hz, 1H), 4.43 (d, J=0.8 Hz, 2H), 3.89 (s, 3H).

Example 249D ethyl (2S,3R,4S,5S)-3-(tert-butyl)-4-((2-(2-methoxy-5-(trifluoromethyl)phenyl)allyl)oxy)-1-((S)-tetrahydro-2H-pyran-2-carbonyl)-5-(o-tolyl)pyrrolidine-2-carboxylate A flask containing Example 249C (2-(3-bromoprop-1-en-2-yl)-1-methoxy-4-(trifluoromethyl)benzene) (81 mg, 0.274 mmol) was treated with Example 170B ((2S,3R,4S,5S)-ethyl 3-(tert-butyl)-4-hydroxy-1-((S)-tetrahydro-2H-pyran-2-carbonyl)-5-(o-tolyl)pyrrolidine-2-carboxylate) (88 mg, 0.211 mmol), treated with toluene (~2 mL) and the solution was concentrated. The residue was dissolved in N,N-dimethylformamide (1 mL) under N₂, cooled to −30° C., treated with 1 M potassium tert-butoxide in tetrahydrofuran (253 µL, 0.253 mmol), stirred at −30° C. for 15 minutes, quenched with saturated aqueous NH₄Cl solution (1 mL) and partitioned between water (15 mL) and methyl tert-butyl ether (50 mL). The layers were separated and the aqueous layer was extracted with methyl tert-butyl ether (30 mL). The combined methyl tert-butyl ether layers were washed with brine, dried (MgSO₄), filtered, concentrated and chromatographed on silica gel, eluting with a gradient of 15% to 100% ethyl acetate in heptanes to provide the title compound. LC/MS (ESI+) m/z 632 (M+H)⁺.

Example 249E (2S,3R,4S,5S)-3-tert-butyl-4-({2-[2-methoxy-5-(trifluoromethyl)phenyl]prop-2-en-1-yl}oxy)-5-(2-methylphenyl)-1-[(2S)-oxane-2-carbonyl]pyrrolidine-2-carboxylic acid A solution of Example 249D ((2S,3R,4S,5S)-ethyl 3-(tert-butyl)-4-((2-(2-methoxy-5-(trifluoromethyl)phenyl)allyl)oxy)-1-((S)-tetrahydro-2H-pyran-2-carbonyl)-5-(o-tolyl)pyrrolidine-2-carboxylate) (11 mg, 0.017 mmol) in tetrahydrofuran (0.2), was diluted with methanol (0.1 mL) and water (0.2 mL), treated with lithium hydroxide monohydrate (7.31 mg, 0.174 mmol), stirred at 55° C. for 1 hour, treated with more lithium hydroxide monohydrate (~10 mg), heated to 55° C. overnight, heated to 60° C. for an additional 4 hours, cooled, treated with 1 M aqueous HCl (2 mL) and extracted with ethyl acetate (30 mL). The ethyl acetate layer was washed with brine, dried (MgSO₄), filtered, concentrated and chromatographed on silica gel, eluting with a gradient of 15% to 100% [200:1:1 ethyl acetate:HCOOH:H₂O] in heptane to provide the title compound. $^1$H NMR (400 MHz, DMSO, 120° C.) δ ppm 7.97 (dd, J=2.5, 7.5 Hz, 1H), 7.56-7.51 (m, 1H), 7.16 (d, J=2.4 Hz, 1H), 7.14-7.03 (m, 4H), 5.48 (s, 1H), 4.99-4.95 (m, 2H), 4.62-4.59 (m, 1H), 4.14 (d, J=5.8 Hz, 1H), 3.87-3.83 (m, 1H), 3.81-3.76 (m, 1H), 3.75 (s, 3H), 3.60 (dt, J=1.4, 13.5 Hz, 1H), 2.42-2.40 (m, 1H), 2.32 (s, 3H), 1.72-1.63 (m, 1H), 1.53 (d, J=12.0 Hz, 1H), 1.46-1.25 (m, 4H), 0.99 (s, 9H), 0.93-0.82 (m, 2H); LC/MS (ESI+) m/z 604 (M+H)⁺.

Example 250

(2S,3R,4S,5S)-3-tert-butyl-4-[(5-tert-butyl-2-methoxypyridin-3-yl)methoxy]-1-(cyclohexanecarbonyl)-5-{2-[(propan-2-yl)oxy]pyridin-3-yl}pyrrolidine-2-carboxylic acid The title compound was prepared according to the procedure described in Example 245B, substituting Example 169B for Example 245A, and Intermediate 10 for Intermediate 6. $^1$H NMR (400 MHz, DMSO-d₆) δ ppm 8.19 (s, 1H), 8.03-7.89 (m, 2H), 6.81 (s, 1H), 5.35 (s, 1H), 5.29 (p, J=6.1 Hz, 1H), 4.54-4.51 (m, 1H), 4.30 (s, 1H), 4.26 (dd, J=5.7, 3.5 Hz, 1H), 3.97 (d, J=13.0 Hz, 1H), 3.76 (s, 3H), 2.50 (s, 1H), 2.12 (s, 1H), 1.60 (d, J=64.8 Hz, 4H), 1.33 (s, 2H), 1.29 (d, J=15.3 Hz, 4H), 1.26 (s, 3H), 1.18 (s, 7H), 1.11 (s, 2H), 0.98 (s, 9H); MS (ESI+) m/z 610.3 (M+H)⁺.

Example 251

(2S,3R,4S,5S)-3-tert-butyl-4-[(5-tert-butyl-2-methoxyphenyl)methoxy]-1-(cyclohexanecarbonyl)-5-{2-[(propan-2-yl)oxy]pyridin-3-yl}pyrrolidine-2-carboxylic acid The title compound was prepared according to the procedure described in Example 245B, substituting Example 169B for Example 245A. $^1$H NMR (400 MHz, DMSO-d₆) δ ppm 8.32-8.03 (m, 1H), 7.95 (s, 1H), 7.12-7.06 (m, 1H), 6.83-6.76 (m, 2H), 6.73 (d, J=8.6 Hz, 1H), 5.31 (td, J=12.3, 6.0 Hz, 2H), 4.48 (d, J=3.0 Hz, 1H), 4.28 (d, J=12.3 Hz, 1H), 4.21 (dd, J=6.3, 2.4 Hz, 1H), 3.98 (d, J=12.3 Hz, 1H), 3.63 (s, 3H), 1.67 (s, 3H), 1.51 (s, 3H), 1.32 (d, J=6.1 Hz, 3H), 1.27 (d, J=4.8 Hz, 3H), 1.26 (s, 1H), 1.24 (t, J=2.2 Hz, 1H), 1.16 (s, 9H), 1.14-1.02 (m, 3H), 0.96 (s, 9H); MS (ESI+) m/z 609 (M+H)⁺.

Example 252

(2S,3R,4S,5S)-3-tert-butyl-1-(cyclohexanecarbonyl)-4-[(2-methoxy-5,7-dimethylquinolin-3-yl)methoxy]-5-{2-[(propan-2-yl)oxy]pyridin-3-yl}pyrrolidine-2-carboxylic acid The title compound was prepared according to the procedure described in Example 245B, substituting Example 169B for Example 245A, and Example 238A for Intermediate 6. $^1$H NMR (400 MHz, DMSO-d₆) δ ppm 8.24 (s, 1H), 7.92 (s, 1H), 7.56 (s, 1H), 7.32 (s, 1H), 7.02 (s, 1H), 6.82 (s, 1H), 5.37 (s, 1H), 5.23 (p, J=6.1 Hz, 1H), 4.55 (d, J=2.8 Hz, 1H), 4.43 (dd, J=13.4, 1.2 Hz, 1H), 4.33 (dd, J=6.2, 2.1 Hz, 1H), 4.11 (d, J=13.5 Hz, 1H), 3.89 (s, 3H), 2.56 (s, 1H), 2.53 (s, 1H), 2.43 (s, 3H), 2.38 (s, 3H), 1.67 (s, 3H), 1.52 (s, 3H), 1.37 (d, J=16.9 Hz, 1H), 1.30 (d, J=6.1 Hz, 3H), 1.25 (d, J=3.8 Hz, 1H), 1.20 (d, J=6.2 Hz, 3H), 1.07 (s, 2H), 1.01 (s, 9H); MS (ESI+) m/z 632 (M+H)⁺.

Example 253

(2S,3R,4S,5S)-3-tert-butyl-4-[(2-methoxy-5,7-dimethylquinolin-3-yl)methoxy]-1-{[(propan-2-yl)oxy]carbonyl}-5-{2-[(propan-2-yl)oxy]pyridin-3-yl}pyrrolidine-2-carboxylic acid The title compound was prepared according to the procedure described in Example 245B, substituting Example 238A for Intermediate 6. $^1$H NMR (400 MHz, DMSO-$d_6$) δ ppm 8.14 (d, J=42.2 Hz, 1H), 7.91-7.86 (m, 1H), 7.45 (d, J=23.7 Hz, 1H), 7.32 (s, 1H), 7.02 (s, 1H), 6.88 (dd, J=7.4, 4.9 Hz, 1H), 5.10 (d, J=9.9 Hz, 2H), 4.65 (d, J=43.4 Hz, 2H), 4.44 (d, J=14.0 Hz, 1H), 4.38-4.28 (m, 2H), 4.08 (d, J=14.0 Hz, 1H), 3.84 (s, 3H), 2.37 (s, 3H), 2.35 (s, 3H), 1.23 (d, J=6.0 Hz, 3H), 1.19-1.10 (m, 3H), 1.07 (s, 3H), 0.98 (s, 9H), 0.85-0.57 (m, 3H); MS (ESI+) m/z 608 (M+H)$^+$.

Example 254

(2S,3R,4S,5S)-3-tert-butyl-5-(2-ethylphenyl)-4-[(2-methoxyquinolin-3-yl)methoxy]-1-[(2S)-oxane-2-carbonyl]pyrrolidine-2-carboxylic acid

Example 254A (2S,3R,4S,5S)-ethyl 3-(tert-butyl)-5-(2-ethylphenyl)-4-((2-methoxyquinolin-3-yl)methoxy)-1-((S)-tetrahydro-2H-pyran-2-carbonyl)pyrrolidine-2-carboxylate (2S,3R,4S,5S)-Ethyl 3-(tert-butyl)-5-(2-ethylphenyl)-4-hydroxy-1-((S)-tetrahydro-2H-pyran-2-carbonyl)pyrrolidine-2-carboxylate from Example 278C (184 mg, 0.426 mmol) and 3-(bromomethyl)-2-methoxyquinoline (140 mg, 0.554 mmol) were dissolved in dry N,N-dimethylformamide (2.2 mL). After cooling in an ice bath, potassium 2-methylpropan-2-olate (0.597 mL, 0.597 mmol) 1 M solution in tetrahydrofuran was added dropwise over 2 minutes. After 30 minutes, the mixture was quenched with saturated aqueous NH$_4$Cl solution and extracted with dichloromethane. The organic solvent was evaporated and the crude residue was loaded onto a 24 g silica gel column eluting with 0-70% ethyl acetate/heptanes over 20 minutes to provide the title compound. $^1$H NMR (501 MHz, DMSO-$d_6$) δ ppm 8.15-8.07 (m, 1H), 7.68 (d, J=8.6 Hz, 1H), 7.60-7.54 (m, 1H), 7.52-7.48 (m, 1H), 7.42-7.36 (m, 1H), 7.32 (dd, J=7.4, 1.6 Hz, 1H), 7.27 (tt, J=7.7, 3.5 Hz, 1H), 7.19-7.09 (m, 1H), 7.04 (d, J=8.6 Hz, 1H), 5.67 (d, J=5.5 Hz, 1H), 4.66 (dd, J=15.2, 1.6 Hz, 1H), 4.37 (dd, J=14.3, 1.6 Hz, 1H), 4.28 (dd, J=14.5, 5.7 Hz, 1H), 4.09 (q, J=7.0 Hz, 1H), 3.98 (dd, J=14.4, 1.4 Hz, 1H), 3.88 (s, 2H), 3.73 (d, J=11.2 Hz, 1H), 3.23 (dd, J=10.5, 2.5 Hz, 2H), 2.79-2.67 (m, 1H), 2.66-2.53 (m, 1H), 1.64 (dd, J=28.9, 13.0 Hz, 1H), 1.51 (d, J=9.7 Hz, 1H), 1.43 (q, J=10.0 Hz, 1H), 1.33-1.21 (m, 3H), 1.12 (dt, J=13.9, 7.3 Hz, 6H), 1.01 (d, J=1.7 Hz, 9H); MS (APCI+) m/z 604 (M+H)$^+$.

Example 254B (2S,3R,4S,5S)-3-tert-butyl-5-(2-ethylphenyl)-4-((2-methoxyquinolin-3-yl)methoxy)-1-((S)-tetrahydro-2H-pyran-2-carbonyl)pyrrolidine-2-carboxylic acid To a solution of (2S,3R,4S,5S)-ethyl 3-(tert-butyl)-5-(2-ethylphenyl)-4-((2-methoxyquinolin-3-yl)methoxy)-1-((S)-tetrahydro-2H-pyran-2-carbonyl)pyrrolidine-2-carboxylate from Example 254A (145 mg, 0.241 mmol) in tetrahydrofuran (0.7 mL), methanol (0.700 mL) and water (0.700 mL) was added lithium hydroxide hydrate(70.7 mg, 1.684 mmol) and the reaction was heated at 45° C. for 16 hours. The solvent was removed under a stream of nitrogen. Water (2 mL) was added to the crude material, and the mixture was extracted with 5 mL heptane (discarded). The product was extracted into diethyl ether. The mixture was concentrated and 1 mL water was added. The mixture was acidified with 1M aqueous HCl (0.2 mL) to pH~6, and the precipitate was filtered to provide the title compound. $^1$H NMR (400 MHz, DMSO-$d_6$) δ ppm 8.20 (dd, J=7.8, 1.4 Hz, 1H), 7.67 (dt, J=8.8, 0.9 Hz, 1H), 7.54 (ddd, J=7.2, 3.9, 2.2 Hz, 2H), 7.34 (ddd, J=8.0, 6.9, 1.2 Hz, 1H), 7.23 (s, 1H), 7.22-7.09 (m, 3H), 5.58 (s, 1H), 4.63 (s, 1H), 4.35 (dd, J=14.2, 1.3 Hz, 1H), 4.24 (d, J=5.8 Hz, 1H), 3.96 (dd, J=14.1, 1.3 Hz, 1H), 3.92 (s, 3H), 3.76 (d, J=11.2 Hz, 1H), 2.80-2.62 (m, 2H), 2.59 (s, 1H), 1.68 (d, J=12.6 Hz, 1H), 1.55 (m, 2H), 1.36 (m, 3H), 1.19 (t, J=7.5 Hz, 3H), 1.03 (s, 9H); MS (APCI+) m/z 575 (M+H)$^+$.

Example 255

(2S,3R,4S,5S)-3-tert-butyl-4-[(1-methyl-1H-benzimidaz-2-yl)methoxy]-5-(2-methylphenyl)-1-[(2S)-oxane-2-carbonyl]pyrrolidine-2-carboxylic acid

Example 255A (2S,3R,4S,5S)-ethyl 3-(tert-butyl)-4-((1-methyl-1H-benzo[d]imidazol-2-yl)methoxy)-1-((S)-tetrahydro-2H-pyran-2-carbonyl)-5-(o-tolyl)pyrrolidine-2-carboxylate Example 170B (74 mg, 0.17 mmol) was dissolved into anhydrous toluene, dried twice over NaSO$_4$, filtered, and concentrated. The residue was placed under nitrogen, dissolved into anhydrous N,N-dimethylformamide (500 μL), cooled to near −35° C., treated first with a suspension of 2-(bromomethyl)-1-methyl-1H-benzo[d]imidazole (45 mg, 0.20 mmol) in N,N-dimethylformamide (1.0 mL) and then dropwise with 1 M potassium tert-butoxide in tetrahydrofuran (190 μL, 0.19 mmol). The reaction mixture was permitted to warm to 10° C. over an hour, removed from the bath and stirred five more minutes before it was quenched with 3 M aqueous citric acid (40 μL). The mixture was concentrated and purified by reverse-phase HPLC [Waters XBridge™ C18 5 μm OBD column, 30×100 mm, flow rate 40 mL/minute, 5-60% gradient of acetonitrile in 0.1% aqueous trifluoroacetic acid] to give the title compound. MS (ESI+) m/z 562 (M+H)$^+$.

Example 255B (2S,3R,4S,5S)-3-tert-butyl-4-[(1-methyl-1H-benzimidazol-2-yl)methoxy]-5-(2-methylphenyl)-1-[(2S)-oxane-2-carbonyl]pyrrolidine-2-carboxylic acid Example 255A (18 mg, 32 mol) was dissolved into tetrahydrofuran (200 μL) and methanol (100 μL), treated with 1.5 M aqueous LiOH (150 μL) and stirred at room temperature four days. The reaction mixture was concentrated and placed directly onto silica for chromatography (1% [88% aqueous HCOOH] and 0 to 20% CH$_3$CN in methyl tert-butyl ether) to give the title compound. $^1$H NMR (400 MHz, DMSO-$d_6$, 120° C.) δ ppm 8.01-7.96 (m, 1H), 7.60-7.56 (m, 1H), 7.43-7.39 (m, 1H), 7.30-7.25 (m, 1H), 7.25-7.20 (m, 1H), 7.13-7.06 (m, 2H), 7.03-6.97 (m, 1H), 5.48 (m, 1H), 4.66-4.62 (m, 1H), 4.42 (d, J=13.0 Hz, 1H), 4.34 (d, J=6.0 Hz, 1H), 4.24 (d, J=13.0 Hz, 1H), 3.76-3.69 (m, 1H), 3.1-3.0 (m, 2H), 2.46-2.44 (m, 1H), 2.11 (s, 3H), 1.69-1.60 (m, 1H), 1.58-1.44 (m, 1H), 1.43-1.24 (m, 3H), 1.02-0.95 (m, 1H), 0.99 (s, 9H); MS (ESI+) m/z 534 (M+H)$^+$.

Example 256

(2S,3R,4S,5S)-3-tert-butyl-4-[(5-cyclobutyl-2-methoxypyridin-3-yl)methoxy]-1-(cyclohexanecarbonyl)-5-(2,2-dimethyl-2,3-dihydro-1-benzofuran-7-yl)pyrrolidine-2-carboxylic acid Example 256A (E)-ethyl 2-(((2,2-dimethyl-2,3-dihydrobenzofuran-7-yl)methylene)amino)acetate Ethyl 2-aminoacetate hydrochloride (4.95 g, 35.5 mmol) and magnesium sulfate (6.83 g, 56.7 mmol) were suspended in dichloromethane (47.3 mL) and the suspension was treated with triethylamine (4.94 mL, 35.5 mmol). The mixture was stirred at room temperature for 1 hour, and 2,2-dimethyl-2,3-dihydrobenzofuran-7-carbaldehyde (5 g, 28.4 mmol) was added. The mixture was stirred at room temperature for 20 hours. The solid material was removed via filtration and the filtrate was washed with water (quick wash twice) and brine, dried over sodium sulfate, filtered, and concentrated to provide the title compound. $^1$H NMR (400 MHz, Chloroform-d) δ ppm 8.53 (d, J=1.5 Hz, 1H), 7.78 (dd, J=8.0, 1.2 Hz, 1H), 7.19 (dq, J=7.2, 1.3 Hz, 1H), 6.84 (t, J=7.4 Hz, 1H), 4.39 (d, J=1.3 Hz, 2H), 4.23 (q, J=7.1 Hz, 2H), 3.01 (t, J=1.1 Hz, 2H), 1.50 (s, 6H), 1.30 (t, J=7.1 Hz, 3H); MS (DCI+) m/z 262.0 (M+H)$^+$.

Example 256B (2S,3R,4S,5S)-ethyl 3-(tert-butyl)-5-(2,2-dimethyl-2,3-dihydrobenzofuran-7-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.278 g, 0.369 mmol) and copper (I) triflate dimer, benzene complex (0.071 g, 0.142 mmol) were dissolved in tetrahydrofuran (72.7 mL) that had been sparged with an N$_2$ stream for 4 hours. The resulting solution was stirred for 1.5 hours at room temperature, and (E)-ethyl 2-(((2,2-dimethyl-2,3-dihydrobenzofuran-7-yl)methylene)amino)acetate (7.41 g, 28.4 mmol) in tetrahydrofuran (5 mL) was added after cooling to <5° C. in an ice water bath. Potassium 2-methylpropan-2-olate (0.284 mL, 0.284 mmol) was added dropwise, followed by addition of (E)-3,3-dimethyl-1-nitrobut-1-ene (3.66 g, 28.4 mmol) neat over 25 minutes, maintaining an internal temperature <10° C. After the addition was complete, the mixture was stirred for 15 minutes at the same temperature. The mixture was diluted with methyl tert-butyl ether (200 mL) and stirred with 100 mL of saturated aqueous ammonium chloride at room temperature for 15 minutes. The layers were separated and the organic layer was washed with saturated aqueous sodium bicarbonate and brine, and dried over sodium sulfate. After filtration, the filtrate was concentrated and purified via flash chromatography, eluting with 0-25% ethyl acetate/heptanes over 220 g silica gel column to provide the title compound. $^1$H NMR (501 MHz, Chloroform-d) δ ppm 7.07 (ddt, J=16.1, 7.7, 1.1 Hz, 2H), 6.82 (t, J=7.6 Hz, 1H), 5.31 (dd, J=5.7, 2.4 Hz, 1H), 4.44 (dd, J=13.4, 5.7 Hz, 1H), 4.33 (qd, J=7.1, 1.6 Hz, 2H), 3.81 (dd, J=10.3, 7.2 Hz, 1H), 3.51 (dd, J=13.4, 10.5 Hz, 1H), 3.02 (q, J=1.1 Hz, 2H), 2.89 (dd, J=7.2, 2.3 Hz, 1H), 1.51 (d, J=2.7 Hz, 6H), 1.37 (t, J=7.2 Hz, 3H), 1.08 (s, 9H); MS (ESI+) m/z 391.3 (M+H)$^+$.

Example 256C (2S,3R,4S,5S)-ethyl 3-(tert-butyl)-1-(cyclohexanecarbonyl)-5-(2,2-dimethyl-2,3-dihydrobenzofuran-7-yl)-4-nitropyrrolidine-2-carboxylate To the solution of (2S,3R,4S,5S)-ethyl 3-(tert-butyl)-5-(2,2-dimethyl-2,3-dihydrobenzofuran-7-yl)-4-nitropyrrolidine-2-carboxylate (Example 256B, 2.0 g, 5.12 mmol) and triethylamine (2.142 mL, 15.37 mmol) in dichloromethane (10 mL) was added cyclohexanecarbonyl chloride (0.754 mL, 5.63 mmol) at 0° C. The mixture was stirred at 0° C. for 30 minutes. Dichloromethane (10 mL) and saturated aqueous NH$_4$Cl 95 mL) were added and the organic layer was separated. The solvent was removed and the crude residue was purified via chromatography on a 40 g silica gel cartridge, eluting with ethyl acetate/hexanes at 0-70% gradient to provide the title compound. MS (APCI+) m/z 501 (M+H)$^+$.

Example 256D (2S,3R,5S)-1-allyl 2-ethyl 3-(tert-butyl)-5-(2-isopropoxypyridin-3-yl)-4-oxopyrrolidine-1,2-dicarboxylate A mixture of 2,3,4,6,7,8,9,10-octahydropyrimido[1,2-a]azepine (2.091 mL, 13.98 mmol), carbon disulfide (1.201 mL, 19.97 mmol) in acetonitrile (20 mL) was stirred at room temperature for 1 hour. To the solution was added Example 256C (2.0 g, 3.99 mmol) in 5 mL of CH$_3$CN at 0° C. After the addition, the mixture was warmed to room temperature and stirred for 2 hours. Ethyl acetate (200 mL) and brine (100 mL) were added. The organic layer was washed with brine, dried over Na$_2$SO$_4$, filtered, and concentrated. CH$_3$CN (100 mL) and 20% H$_3$PO$_4$ (100 mL) were added to the reaction mixture to hydrolyze the imine and the mixture was stirred at room temperature for 4 hours. Ethyl acetate (200 mL) was added, and the organic layer was washed with 80 mL of brine, dried over Na$_2$SO$_4$, filtered and concentrated. Purification via chromatography on a 220 g silica gel cartridge eluting with a gradient of 0-30% ethyl acetate/heptane provided the title compound. MS (APCI+) m/z 470 (M+1)$^+$.

Example 256E (2S,3R,4S,5S)-ethyl 3-(tert-butyl)-1-(cyclohexanecarbonyl)-5-(2,2-dimethyl-2,3-dihydrobenzofuran-7-yl)-4-hydroxypyrrolidine-2-carboxylate To (2S,3R,5S)-ethyl 3-(tert-butyl)-1-(cyclohexanecarbonyl)-5-(2,2-dimethyl-2,3-dihydrobenzofuran-7-yl)-4-oxopyrrolidine-2-carboxylate (Example 256D, 1.0 g, 2.129 mmol) in ethanol (5 mL) cooling in an ice bath, sodium borohydride (0.105 g, 2.77 mmol) was added in portions. The mixture was stirred in an ice bath for 30 minutes. Saturated aqueous NH$_4$Cl (2 mL) was added and the solvent was removed under pressure. The residue was partitioned between ethyl acetate and saturated aqueous sodium bicarbonate. The combined organic extracts was washed with brine, dried over sodium sulfate, filtered, and concentrated. The residue was purified via chromatography on 12 g cartridge, eluting with ethyl acetate/methanol (9:1) in heptane at a 0-40% gradient to provide the title compound. MS (APCI+) m/z 472 (M+H)$^+$.

Example 256F (2S,3R,4S,5S)-3-tert-butyl-4-[(5-cyclobutyl-2-methoxypyridin-3-yl)methoxy]-1-(cyclohexanecarbonyl)-5-(2,2-dimethyl-2,3-dihydro-1-benzofuran-7-yl)pyrrolidine-2-carboxylic acid To 3-(bromomethyl)-5-cyclobutyl-2-methoxypyridine (Intermediate 4, 47.8 mg, 0.187 mmol) and Example 256E (80 mg, 0.170 mmol) in N,N-dimethylformamide (2 mL) cooling in an ice bath, potassium 2-methylpropan-2-olate (28.6 mg, 0.254 mmol) (0.35 mL, 1.0 M in tetrahydrofuran) was added dropwise. The mixture was stirred the in ice bath for 20 minutes, and it was allowed to warm to ambient temperature. The mixture was concentrated and methanol (2 mL) and 6N aqueous LiOH (0.5 mL) were added. The mixture was heated to 45° C. and stirred overnight. The pH was adjusted to 1~2 by adding 2M aqueous HCl and the mixture was filtered through a syringe filter. The filtrate was purified via HPLC with the trifluoroacetic acid method to provide the title compound. $^1$H NMR (400 MHz, DMSO-d$_6$) δ ppm 7.77 (d, J=2.5 Hz, 1H), 7.0(m, 1H), 7.03-6.97 (m, 1H), 6.87 (d, J=2.4 Hz, 1H), 6.73 (t, J=7.5 Hz, 1H), 5.33 (d, J=6.9 Hz, 1H), 4.37 (d, J=4.9 Hz, 1H), 4.29 (d, J=13.1 Hz, 1H), 4.21 (dd, J=6.9, 4.4 Hz, 1H), 4.04 (d, J=13.1 Hz, 1H), 3.77 (d, J=0.8 Hz, 3H), 3.36-3.26 (m, 1H), 2.86 (s, 2H), 2.50 (d, J=4.8 Hz, 1H), 2.29-2.15 (m, 3H), 1.99-1.80 (m, 4H), 1.71-1.60 (m, 2H), 1.49 (s, 2H), 1.41 (s, 3H), 1.29 (s, 3H), 1.27-0.99 (m, 6H), 0.96 (s, 9H); MS (ESI+) m/z 619.3 (M+H)$^+$.

Example 257

(2S,3R,4S,5S)-3-tert-butyl-1-(cyclohexanecarbonyl)-5-(2,2-dimethyl-2,3-dihydro-1-benzofuran-7-yl)-4-{[2-methoxy-5-(trifluoromethyl)pyridin-3-yl]methoxy}pyrrolidine-2-carboxylic acid The title compound was prepared according to the procedure described in Example 256, substituting Intermediate 8 for Intermediate 4 to provide the title compound. $^1$H NMR (400 MHz, DMSO-d$_6$) δ ppm 8.29 (dd, J=2.4, 1.2 Hz, 1H), 7.69 (s, 1H), 7.14 (s, 1H), 6.95 (d, J=7.1 Hz, 1H), 6.69 (t, J=7.6 Hz, 1H), 5.34 (d, J=6.9 Hz, 1H), 4.44-4.35 (m, 2H), 4.27 (dd, J=6.9, 4.4 Hz, 1H), 4.09 (d, J=13.9 Hz, 1H), 3.89 (s, 3H), 2.78 (s, 2H), 2.51 (t, J=4.6 Hz, 1H), 2.19 (s, 1H), 1.64 (d, J=12.7 Hz, 2H), 1.49 (s, 2H), 1.40 (s, 3H), 1.29 (s, 1H), 1.26 (s, 3H), 1.24-1.00 (m, 5H), 0.98 (s, 9H); MS (ESI+) m/z 633 (M+H)$^+$.

Example 258

(2S,3R,4S,5S)-1-(cyclohexanecarbonyl)-3-(2-methoxypropan-2-yl)-4-{[2-methoxy-5-(trifluoromethyl)pyridin-3-yl]methoxy}-5-[2-(propan-2-yl)phenyl]pyrrolidine-2-carboxylic acid Example 258A (2S,3R,4S,5S)-ethyl 5-(2-isopropylphenyl)-3-(2-methoxypropan-2-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.378 g, 0.501 mmol) and copper (I) triflate dimer, benzene complex (0.097 g, 0.193 mmol) were dissolved in tetrahydrofuran (99 mL) that had been sparged with a N$_2$ stream for 4 hours. The resulting solution was stirred for 1.5 hours at ambient temperature, and (E)-ethyl 2-((2-isopropylbenzylidene)amino)acetate (Core 13A) (9 g, 38.6 mmol) in tetrahydrofuran (50 mL) was added after cooling to <5° C. in an ice water bath. Potassium 2-methylpropan-2-olate (0.386 mL, 0.386 mmol) 1M in tetrahydrofuran, was added dropwise, followed by addition of (E)-3-methoxy-3-methyl-1-nitrobut-1-ene (5.60 g, 38.6 mmol) neat over 25 minutes, maintaining an internal temperature <10° C. After the addition was complete, the mixture was stirred for 15 minutes at the same temperature. The mixture was diluted with methyl tert-butyl ether (200 mL) and stirred with 100 mL of saturated aqueous ammonium chloride at ambient temperature for 15 minutes. The layers were separated and the organic layer was washed with saturated aqueous sodium bicarbonate and brine, dried over sodium sulfate, filtered, and concentrated in vacuo. The crude product was purified via flash chromatography, eluting with 0-25% ethyl acetate/heptanes over a 220 g silica gel column to provide the title compound; MS (ESI+) m/z 379 (M+H)$^+$.

Example 258B (2S,3R,4S,5S)-1-allyl 2-ethyl 5-(2-isopropylphenyl)-3-(2-methoxypropan-2-yl)-4-nitropyrrolidine-1,2-dicarboxylate (2S,3R,4S,5S)-Ethyl 5-(2-isopropylphenyl)-3-(2-methoxypropan-2-yl)-4-nitropyrrolidine-2-carboxylate from Example 258A (10.2 g, 27.0 mmol) was dissolved in ethyl acetate (67.4 mL) and saturated aqueous sodium bicarbonate (67.4 mL) was added. While stirring vigorously, allyl chloroformate (3.02 mL, 28.3 mmol) was added via additional funnel over 10 minutes. The mixture was stirred for 20 minutes at ambient temperature and the layers were separated. The organic layer was washed with water and brine, dried over sodium sulfate, filtered, and concentrated in vacuo. The crude material was purified via flash chromatography, eluting with 0-25% ethyl acetate/heptanes on a 220 g silica gel column to provide the title compound. MS (ESI+) m/z 463 (M+H)$^+$.

Example 258C (2S,3S,5S)-1-allyl 2-ethyl 5-(2-isopropylphenyl)-3-(2-methoxypropan-2-yl)-4-oxopyrrolidine-1,2-dicarboxylate Into a 500 mL flask was charged DBU (1,8-diazabicyclo[5.4.0]undec-7-ene) (12.65 mL, 84 mmol) and carbon disulfide (7.23 mL, 120 mmol) in acetonitrile (48.0 mL) and the mixture was stirred at ambient temperature for 1 hour. To the resulting solution at 0° C. was added (2S,3R,4S,5S)-1-allyl 2-ethyl 5-(2-isopropylphenyl)-3-(2-methoxypropan-2-yl)-4-nitropyrrolidine-1,2-dicarboxylate from Example 258B (11.09 g, 23.98 mmol) in 5 mL of $CH_3CN$. The reaction was allowed to warm to room temperature over 2 hours and 100 mL of $CH_3CN$ and 100 mL 20% aqueous $H_3PO_4$ were added. The mixture was stirred at ambient temperature for 16 hours. Ethyl acetate (200 mL) and 100 mL brine were added. The organic layer was filtered and concentrated. Further hydrolysis was done for 4 hours at ambient temperature using 100 mL $CH_3CN$ and 100 mL 20% aqueous $H_3PO_4$. Ethyl acetate (200 mL) and 100 mL brine were added. The organic layer was separated and washed with 80 mL of brine. The mixture was filtered and concentrated. The residue was chromatographed using a 220 g silica gel cartridge with a gradient of 0-30% ethyl acetate/heptanes to provide the title compound; MS (ESI+) m/z 432 (M+H)$^+$.

Example 258D (2S,3R,4S,5S)-1-allyl 2-ethyl 4-hydroxy-5-(2-isopropylphenyl)-3-(2-methoxypropan-2-yl)pyrrolidine-1,2-dicarboxylate (2S,3S,5S)-1-Allyl 2-ethyl 5-(2-isopropylphenyl)-3-(2-methoxypropan-2-yl)-4-oxopyrrolidine-1,2-dicarboxylate from Example 258C (2.58 g, 5.98 mmol) was dissolved in ethanol (29.9 mL) and the resulting solution was cooled to <−10° C. in a brine ice bath before addition of sodium borohydride (0.249 g, 6.58 mmol) in one portion. After 40 minutes, the reaction was quenched with the slow addition of acetone over 10 minutes. The reaction was concentrated in vacuo and the residual material was partitioned between saturated aqueous sodium bicarbonate and methyl tert-butyl ether. The organic extracts were washed with brine, dried over sodium sulfate, filtered, and concentrated. The residue was purified via flash chromatography, eluting with 0-30% ethyl acetate/heptanes to provide the title compound. MS (ESI+) m/z 434 (M+H)$^+$.

Example 258E (2S,3R,4S,5S)-1-allyl 2-ethyl 5-(2-isopropylphenyl)-4-((2-methoxy-5-(trifluoromethyl)pyridin-3-yl)methoxy)-3-(2-methoxypropan-2-yl)pyrrolidine-1,2-dicarboxylate (2S,3R,4S,5S)-1-Allyl 2-ethyl 4-hydroxy-5-(2-isopropylphenyl)-3-(2-methoxypropan-2-yl)pyrrolidine-1,2-dicarboxylate from Example 258D (500 mg, 1.153 mmol) and 3-(bromomethyl)-2-methoxy-5-(trifluoromethyl)pyridine (436 mg, 1.615 mmol) were dissolved in dry N,N-dimethylformamide (7 mL). After cooling in an ice bath, potassium 2-methylpropan-2-olate (1.615 mL, 1.615 mmol) as a 1M solution in tetrahydrofuran was added dropwise over 4 minutes. After 30 minutes, the mixture was quenched with saturated aqueous $NH_4Cl$ solution and extracted with dichloromethane. The organic solvent was evaporated. The crude residue was loaded onto a 24 g silica gel column and eluted with 0-70% ethyl acetate/heptanes over 20 minute to provide the title compound. $^1$H NMR (501 MHz, DMSO-$d_6$) δ ppm 8.45-8.29 (m, 1H), 7.93 (s, 1H), 7.19 (d, J=7.7 Hz, 1H), 7.13 (t, J=7.4 Hz, 1H), 7.03 (d, J=7.6 Hz, 2H), 5.71 (d, J=153.3 Hz, 1H), 5.36 (s, 1H), 5.31-4.80 (m, 1H), 4.65 (d, J=2.0 Hz, 1H), 4.50 (m, 1H), 4.36 (d, J=14.4 Hz, 1H), 4.32 (d, J=5.6 Hz, 1H), 4.10 (qd, J=7.1, 2.1 Hz, 2H), 3.85 (d, 4H), 3.19 (s, 3H), 2.82 (s, 1H), 1.27 (d, J=31.0 Hz, 6H), 1.19 (s, 6H), 1.15-1.07 (m, 3H); MS (APCI+) m/z 613 (M+H)$^+$.

Example 258F (2S,3R,4S,5S)-ethyl 5-(2-isopropylphenyl)-4-((2-methoxy-5-(trifluoromethyl)pyridin-3-yl)methoxy)-3-(2-methoxypropan-2-yl)pyrrolidine-2-carboxylate To a solution of (2S,3R,4S,5S)-1-allyl 2-ethyl 5-(2-isopropylphenyl)-4-((2-methoxy-5-(trifluoromethyl)pyridin-3-yl)methoxy)-3-(2-methoxypropan-2-yl)pyrrolidine-1,2-dicarboxylate from Example 258E (370 mg, 0.594 mmol) in acetonitrile/water (4.29 mL, 10:1) was added tetrakis(triphenylphosphine)palladium(0) (15.11 mg, 0.013 mmol) and diethylamine (0.123 mL, 1.188 mmol). The mixture was stirred at ambient temperature for 90 minutes. The mixture was concentrated to a 1 mL volume. Dichloromethane and water were added, and the organic layer was washed with brine, dried over $Na_2SO_4$, filtered, and concentrated. Purified via chromatography, eluting on 24 g cartridge with a gradient 0-70% ethyl acetate/heptanes over 20 minutes provided the title compound. $^1$H NMR (400 MHz, DMSO-$d_6$) δ ppm 8.34 (d, J=1.4 Hz, 1H), 7.57 (dd, J=7.8, 1.4 Hz, 1H), 7.19 (td, J=7.5, 1.9 Hz, 2H), 7.13 (td, J=7.5, 1.4 Hz, 1H), 7.02 (td, J=7.5, 1.4 Hz, 1H), 4.38 (dd, J=8.0, 4.6 Hz, 1H), 4.24 (d, J=14.1 Hz, 1H), 4.10 (p, J=7.0 Hz, 2H), 4.00 (dd, J=4.6, 1.7 Hz, 1H), 3.80 (s, 3H), 3.74 (d, J=14.1 Hz, 1H), 3.67 (t, J=7.1 Hz, 1H), 3.12 (s, 5H), 2.58 (dd, J=6.9, 1.7 Hz, 1H), 1.21-1.09 (m, 16H); MS (APCI+) m/z 539 (M+H)$^+$.

Example 258G (2S,3R,4S,5S)-ethyl 1-(cyclohexanecarbonyl)-5-(2-isopropylphenyl)-4-((2-methoxy-5-(trifluoromethyl)pyridin-3-yl)methoxy)-3-(2-methoxypropan-2-yl)pyrrolidine-2-carboxylate A solution of (2S,3R,4S,5S)-ethyl 5-(2-isopropylphenyl)-4-((2-methoxy-5-(trifluoromethyl)pyridin-3-yl)methoxy)-3-(2-methoxypropan-2-yl)pyrrolidine-2-carboxylate from Example 258F (100 mg, 0.186 mmol) and triethylamine (0.052 mL, 0.371 mmol) in dichloromethane (1 mL) at 25° C. was treated with cyclohexanecarbonyl chloride (0.031 mL, 0.232 mmol) dropwise, stirred for 2 hours, washed with saturated aqueous $NaHCO_3$ (3 mL) and with 1N aqueous $NH_4OH$ (1 mL) solution to convert any leftover acid chloride to the corresponding amide, and concentrated. The residue was dissolved in 1 mL dichloromethane and loaded onto a 12 g column eluting with a gradient of 0-70% ethyl acetate/heptanes over a period of 20 minutes to provide the title compound. $^1$H NMR (400 MHz, DMSO-$d_6$) δ ppm 8.28 (d, J=2.4 Hz, 1H), 7.91 (s, 1H), 7.23 (d, J=7.8 Hz, 1H), 7.14 (d, J=12.0 Hz, 2H), 7.01 (t, J=7.5 Hz, 1H), 5.45 (d, J=5.6 Hz, 1H), 4.79 (d, J=1.8 Hz, 1H), 4.38-4.20 (m, 2H), 4.10 (qd, J=7.1, 2.3 Hz, 2H), 3.86 (s, 3H), 3.82 (d, J=13.9 Hz, 1H), 3.28-3.20 (m, 1H), 3.19 (s, 3H), 2.77 (s, 1H), 2.11 (s, 1H), 1.63 (t, J=13.4 Hz, 3H), 1.47 (s, 2H), 1.30-1.25 (m, 9H), 1.23 (m, 2H), 1.18 (d, J=6.8 Hz, 3H), 1.15 (t, J=7.1 Hz, 3H), 1.06 (t, J=11.6 Hz, 2H); MS (APCI+) m/z 648 (M+H)$^+$.

Example 258H (2S,3R,4S,5S)-1-(cyclohexanecarbonyl)-5-(2-isopropylphenyl)-4-((2-methoxy-5-(trifluoromethyl)pyridin-3-yl)methoxy)-3-(2-methoxypropan-2-yl)pyrrolidine-2-carboxylic acid To a solution of (2S,3R,4S,5S)-ethyl 1-(cyclohexanecarbonyl)-5-(2-isopropylphenyl)-4-((2-methoxy-5-(trifluoromethyl)pyridin-3-yl)methoxy)-3-(2-methoxypropan-2-yl)pyrrolidine-2-carboxylate from Example 258G (107 mg, 0.165 mmol) in tetrahydrofuran (0.5 mL), methanol (0.500 mL) and water (0.500 mL) was added lithium hydroxide hydrate (48.5 mg, 1.155 mmol) and the reaction was heated at 45° C. for 16 hours. The solvent was removed under a stream of nitrogen. Water (2 mL) was added to the crude material and the mixture was extracted with 5 mL heptane (discarded). The desired product was extracted into diethyl ether and the mixture was concentrated. Water was added and the mixture was acidified with 1M aqueous HCl (0.02 mL) to pH~6. The mixture was filtered to provide the title compound. $^1$H NMR (400 MHz, DMSO-d$_6$) δ ppm 8.24 (s, 1H), 8.17 (d, J=8.1 Hz, 1H), 7.15 (d, J=7.7 Hz, 1H), 7.08 (d, 1H), 7.04 (s, 1H), 6.96 (m, 1H), 5.43 (d, J=6.2 Hz, 1H), 4.47 (s, 1H), 4.35 (d, J=14.2 Hz, 1H), 4.24 (s, 1H) 3.87 (m, 4H), 3.21 (m, 4H), 3.02 (bs, 2H)1.65 (bs, 2H), 1.52 (bs, 2H), 1.27 (d, J=6.7 Hz, 3H), 1.23 (d, J=6.3 Hz, 8H), 1.12 (d, J=6.8 Hz, 3H), 1.09 (bs, 3H); MS (APCI+) m/z 621 (M+H)$^+$.

Example 259

(2S,3R,4S,5S)-3-(2-methoxypropan-2-yl)-4-{[2-methoxy-5-(trifluoromethyl)pyridin-3-yl]methoxy}-1-{[(propan-2-yl)oxy]carbonyl}-5-[2-(propan-2-yl)phenyl]pyrrolidine-2-carboxylic acid Example 259A (2S,3R,4S,5S)-2-ethyl 1-isopropyl 5-(2-isopropylphenyl)-4-((2-methoxy-5-(trifluoromethyl)pyridin-3-yl)methoxy)-3-(2-methoxypropan-2-yl)pyrrolidine-1,2-dicarboxylate (2S,3R,4S,5S)-Ethyl 5-(2-isopropylphenyl)-4-((2-methoxy-5-(trifluoromethyl)pyridin-3-yl)methoxy)-3-(2-methoxypropan-2-yl)pyrrolidine-2-carboxylate from Example 258F (100 mg, 0.186 mmol) was dissolved in toluene (0.5 mL) and triethylamine (0.065 mL, 0.464 mmol) was added, followed by slow addition of isopropyl carbonochloridate (0.111 mL, 0.223 mmol) solution after cooling in an ice water bath to ~10° C. The addition was at such a rate that the temperature was maintained at or below ambient temperature during the addition (2 minutes). After the addition was complete, the mixture was removed from water bath and stirred at ambient temperature for 2 hours. The mixture was diluted with diethyl ether and stirred with saturated aqueous sodium bicarbonate for 20 minutes before separating the layers. The organic layer was washed with 1M aqueous HCl×3 and brine, dried over sodium sulfate, filtered and concentrated. The residue was dissolved in 1 mL heptanes and loaded onto a 12 g cartridge eluting with a gradient of 0-60% ethyl acetate/heptanes over a period of 20 minutes to provide the title compound. $^1$H NMR (400 MHz, DMSO-d$_6$) δ ppm 8.36 (dd, J=2.5, 1.2 Hz, 1H), 7.93 (d, J=7.8 Hz, 1H), 7.18 (dd, J=7.9, 1.4 Hz, 1H), 7.11 (td, J=7.5, 1.5 Hz, 2H), 7.01 (td, J=7.5, 1.4 Hz, 1H), 5.30 (s, 1H), 4.57 (d, J=2.0 Hz, 1H), 4.35 (d, J=14.5 Hz, 1H), 4.32-4.28 (m, 1H), 4.10 (qd, J=7.1, 4.7 Hz, 2H), 3.85 (s, 4H), 3.31 (m, 1H), 3.19 (s, 4H), 2.79 (s, 1H), 1.29 (s, 3H), 1.22 (d, J=7.0 Hz, 6H), 1.13 (t, J=7.1 Hz, 6H), 0.97 (s, 3H), 0.62 (s, 3H); MS (ESI+) m/z 625 (M+H)$^+$.

Example 259B (2S,3R,4S,5S)-1-(isopropoxycarbonyl)-5-(2-isopropylphenyl)-4-((2-methoxy-5-(trifluoromethyl)pyridin-3-yl)methoxy)-3-(2-methoxypropan-2-yl)pyrrolidine-2-carboxylic acid To a solution of (2S,3R,4S,5S)-2-ethyl 1-isopropyl 5-(2-isopropylphenyl)-4-((2-methoxy-5-(trifluoromethyl)pyridin-3-yl)methoxy)-3-(2-methoxypropan-2-yl)pyrrolidine-1,2-dicarboxylate from Example 259A (92 mg, 0.147 mmol) in tetrahydrofuran (0.5 mL), methanol (0.500 mL) and water (0.500 mL) was added lithium hydroxide hydrate (43.3 mg, 1.031 mmol) and the reaction was heated at 45° C. for 16 hours. The solvent was removed under a stream of nitrogen. Water (2 mL) was added to the crude material, and the mixture was extracted with 5 mL heptane (discarded). The desired product was extracted into diethyl ether and concentrated. The mixture was acidified with 1M aqueous HCl (0.02 mL) to pH-6 and filtered to provide the title compound. $^1$H NMR (400 MHz, DMSO-d$_6$) δ ppm 8.34 (d, J=2.3 Hz, 1H), 8.03 (d, J=7.9 Hz, 1H), 7.17 (dd, J=7.8, 1.4 Hz, 1H), 7.10 (td, J=7.5, 1.4 Hz, 1H), 7.00 (m, 2H), 5.28 (d, J=5.5 Hz, 1H), 4.67-4.52 (m, 1H), 4.50-4.44 (m, 1H), 4.36 (d, J=14.6 Hz, 1H), 4.28 (d, J=5.7 Hz, 1H), 3.85 (m, 4H), 3.19 (s, 3H), 3.15 (m, 1H), 2.81 (s, 1H), 1.27 (s, 3H), 1.21 (d, J=6.2 Hz, 6H), 1.12 (d, J=6.7 Hz, 3H), 0.97 (bs, 3H), 0.61 (bs, 3H); MS (APCI+) m/z 597 (M+H)$^+$.

Example 260

(2S,3R,4S,5S)-3-(2-methoxypropan-2-yl)-4-{[2-methoxy-5-(trifluoromethyl)pyridin-3-yl]methoxy}-1-[(2S)-oxane-2-carbonyl]-5-[2-(propan-2-yl)phenyl]pyrrolidine-2-carboxylic acid Example 260A (2S,3R,4S,5S)-ethyl 5-(2-isopropylphenyl)-4-((2-methoxy-5-(trifluoromethyl)pyridin-3-yl)methoxy)-3-(2-methoxypropan-2-yl)-1-((S)-tetrahydro-2H-pyran-2-carbonyl)pyrrolidine-2-carboxylate To a solution of (2S,3R,4S,5S)-ethyl 5-(2-isopropylphenyl)-4-((2-methoxy-5-(trifluoromethyl)pyridin-3-yl)methoxy)-3-(2-methoxypropan-2-yl)pyrrolidine-2-carboxylate from Example 258F (100 mg, 0.186 mmol) in dichloromethane (1.9 mL) at 0° C. was added triethylamine (0.116 mL, 0.836 mmol) followed by addition of (S)-tetrahydro-2H-pyran-2-carbonyl chloride (46.9 mg, 0.316 mmol) as a solution in 1 mL dichloromethane. After stirring for 15 minutes, the reaction was quenched with 5 mL of saturated aqueous sodium bicarbonate and the crude material was chromatographed using a 24 g silica gel cartridge with a gradient of 0-65% ethyl acetate/heptanes over a period of 20 minutes to provide the title compound. $^1$H NMR (400 MHz, DMSO-d$_6$) δ ppm 8.27 (dd, J=2.5, 1.1 Hz, 1H), 7.96 (dd, J=7.9, 1.5 Hz, 1H), 7.22 (d, J=7.7 Hz, 1H), 7.15 (s, 2H), 7.02 (d, J=7.8 Hz, 1H), 5.64 (s, 1H), 4.80 (d, J=1.8 Hz, 1H), 4.35 (d, 1H), 4.28 (d, J=5.3 Hz, 1H), 4.09 (qd, J=7.1, 2.2 Hz, 2H), 3.86 (s, 3H), 3.81 (d, J=13.9 Hz, 1H), 3.73 (d, J=11.2 Hz, 1H), 3.21 (m, 4H), 3.15 (d, 1H), 2.80 (m, 1H), 2.73 (d, J=1.7 Hz, 1H), 1.67 (m, 1H), 1.54 (m, 2H), 1.38 (m, 3H), 1.29 (d, J=6.7 Hz, 3H), 1.26 (d, J=5.9 Hz, 6H), 1.14 (t, J=7.0 Hz, 6H); MS (APCI+) m/z 651 (M+H)$^+$.

Example 260B (2S,3R,4S,5S)-5-(2-isopropylphenyl)-4-((2-methoxy-5-(trifluoromethyl)pyridin-3-yl)methoxy)-3-(2-methoxypropan-2-yl)-1-((S)-tetrahydro-2H-pyran-2-carbonyl)pyrrolidine-2-carboxylic acid To a solution of (2S,3R,4S,5S)-ethyl 5-(2-isopropylphenyl)-4-((2-methoxy-5-(trifluoromethyl)pyridin-3-yl)methoxy)-3-(2-methoxypropan-2-yl)-1-((S)-tetrahydro-2H-pyran-2-carbonyl)pyrrolidine-2-carboxylate from Example 260A (98 mg, 0.151 mmol) in tetrahydrofuran (0.5 mL), methanol (0.500 mL) and water (0.500 mL) was added lithium hydroxide hydrate (44.2 mg, 1.054 mmol) and the reaction was heated at 45° C. for 16 hours. The solvent was removed under a stream of nitrogen. Water (2 mL) was added to the crude material, and the mixture was extracted with 5 mL heptane (discarded). The desired product was extracted into diethyl ether and the mixture was concentrated. Water was added (15 mL), and the mixture was acidified with 1M aqueous HCl (0.1 mL) to pH~6, and filtered. $^1$H NMR (400 MHz, DMSO-$d_6$) δ ppm 8.26 (d, J=2.4 Hz, 1H), 8.03 (dd, J=7.9, 1.4 Hz, 1H), 7.21 (d, J=7.9 Hz, 1H), 7.14 (d, 1H), 7.10 (s, 1H), 7.01 (m, 1H), 5.64 (s, 1H), 4.73 (d, J=1.8 Hz, 1H), 4.34 (d, J=14.1 Hz, 1H), 4.28 (d, J=5.9 Hz, 1H), 3.87 (m, 4H), 3.75 (d, J=11.4 Hz, 1H), 3.63 (bs, 1H), 3.21 (m, 4H), 3.08 (m, 2H), 1.68 (d, J=13.2 Hz, 1H), 1.56 (m, 2H), 1.37 (m, 3H), 1.29 (d, J=6.7 Hz, 3H), 1.25 (s, 6H), 1.12 (d, J=6.8 Hz, 3H); MS (APCI+) m/z 623 (M+H)$^+$.

Example 261

(2S,3R,4S,5S)-3-tert-butyl-4-{2-[2-methoxy-5-(trifluoromethyl)phenyl]propoxy}-5-(2-methylphenyl)-1-[(2S)-oxane-2-carbonyl]pyrrolidine-2-carboxylic acid

Example 261A ethyl (2S,3R,4S,5S)-3-(tert-butyl)-4-(2-(2-methoxy-5-(trifluoromethyl)phenyl)propoxy)-1-((S)-tetrahydro-2H-pyran-2-carbonyl)-5-(o-tolyl)pyrrolidine-2-carboxylate A mixture of Example 249D ((2S,3R,4S,5S)-ethyl 3-(tert-butyl)-4-((2-(2-methoxy-5-(trifluoromethyl)phenyl)allyl)oxy)-1-((S)-tetrahydro-2H-pyran-2-carbonyl)-5-(o-tolyl)pyrrolidine-2-carboxylate) (120 mg, 0.190 mmol) and 10% Pd/C (25 mg, 0.023 mmol) in ethanol (2 mL) was stirred under an atmosphere of H$_2$ (balloon) for 90 minutes. The mixture was diluted with ethyl acetate (25 mL), stirred for 5 minutes, and filtered to remove the solids. The filtrate was concentrated to dryness to provide the title compound. LC/MS (ESI+) m/z 634 (M+H)$^+$.

Example 261B (2S,3R,4S,5S)-3-tert-butyl-4-{2-[2-methoxy-5-(trifluoromethyl)phenyl]propoxy}-5-(2-methylphenyl)-1-[(2S)-oxane-2-carbonyl]pyrrolidine-2-carboxylic acid A solution of Example 261A ((2S,3R,4S,5S)-ethyl 3-(tert-butyl)-4-(2-(2-methoxy-5-(trifluoromethyl)phenyl)propoxy)-1-((S)-tetrahydro-2H-pyran-2-carbonyl)-5-(o-tolyl)pyrrolidine-2-carboxylate) (37 mg, 0.058 mmol) in tetrahydrofuran (1 mL) was diluted with methanol (0.5 mL), diluted with water (1 mL), treated with lithium hydroxide hydrate (49.0 mg, 1.168 mmol), stirred at 45° C. overnight, cooled, treated with 1 M aqueous HCl (3 mL) and extracted with ethyl acetate (50 mL). The ethyl acetate layer was washed with brine, dried (MgSO$_4$), filtered, concentrated and chromatographed on silica gel, eluting with a gradient of 20% to 50% [200:1:1 ethyl acetate:HCOOH:H$_2$O] in heptane to provide the title compound. $^1$H NMR (400 MHz, DMSO, 120° C.) δ ppm 8.00-7.95 (m, 1H), 7.48-7.42 (m, 1H), 7.22-7.01 (m, 5H), 5.48 (s, 1H), 4.59 (dd, J=2.1, 5.5 Hz, 1H), 4.08-4.04 (m, 1H), 3.81-3.75 (m, 1H), 3.82 (s, 1.5H), 3.78 (s, 1.5H), 3.40 (s, 1H), 3.23 (dd, J=5.4, 9.0 Hz, 1H), 3.19-3.13 (m, 1H), 3.04-2.72 (m, 3H), 2.39-2.35 (m, 1H), 2.36 (s, 1.5H), 2.34 (s, 1.5H), 1.74-1.62 (m, 1H), 1.53 (d, J=11.9 Hz, 1H), 1.32 (d, J=23.8 Hz, 3H), 0.99 (s, 4H), 0.98 (s, 5H), 0.84 (d, J=6.7 Hz, 1.5H), 0.78 (d, J=7.0 Hz, 1.5H); LC/MS (ESI+) m/z 606 (M+H)$^+$.

Example 262

(2S,3R,4S,5S)-3-tert-butyl-4-{(2S)-2,3-dihydroxy-2-[2-methoxy-5-(trifluoromethyl)phenyl]propoxy}-5-(2-methylphenyl)-1-[(2S)-oxane-2-carbonyl]pyrrolidine-2-carboxylic acid

Example 262A ethyl (2S,3R,4S,5S)-3-(tert-butyl)-4-((S)-2,3-dihydroxy-2-(2-methoxy-5-(trifluoromethyl)phenyl)propoxy)-1-((S)-tetrahydro-2H-pyran-2-carbonyl)-5-(o-tolyl)pyrrolidine-2-carboxylate A solution of Example 249D ((2S,3R,4S,5S)-ethyl 3-(tert-butyl)-4-((2-(2-methoxy-5-(trifluoromethyl)phenyl)allyl)oxy)-1-((S)-tetrahydro-2H-pyran-2-carbonyl)-5-(o-tolyl)pyrrolidine-2-carboxylate) (290 mg, 0.459 mmol) in tetrahydrofuran (5 mL) and water (2.5 mL)was treated with a 4% solution of osmium tetroxide in water (146 mg, 0.023 mmol), treated with sodium periodate (196 mg, 0.918 mmol), and stirred overnight at room temperature. The mixture was treated with more 4% osmium tetroxide in water (300 mg, 0.046 mmol) and stirred at room temperature overnight. The mixture was partitioned between ethyl acetate (50 mL) and 1 M aqueous HCl (15 mL). The layers were separated and the aqueous layer was extracted with ethyl acetate (50 mL). The combined ethyl acetate layers were dried (MgSO$_4$), filtered, concentrated and chromatographed on silica gel, eluting with a gradient of 10% to 100% ethyl acetate in heptane to provide three isolated products. The first product to elute was ethyl (2S,3R,4S,5S)-3-(tert-butyl)-4-((S)-2,3-dihydroxy-2-(2-methoxy-5-(trifluoromethyl)phenyl)propoxy)-1-((S)-tetrahydro-2H-pyran-2-carbonyl)-5-(o-tolyl)pyrrolidine-2-carboxylate; LC/MS (ESI+) m/z 634 (M+H)$^+$. The second product to elute was ethyl (2S,3R,4S,5S)-3-(tert-butyl)-4-((S)-2,3-dihydroxy-2-(2-methoxy-5-(trifluoromethyl)phenyl)propoxy)-1-((S)-tetrahydro-2H-pyran-2-carbonyl)-5-(o-tolyl)pyrrolidine-2-carboxylate; LC/MS (ESI+) m/z 666 (M+H)$^+$. The third product to elute was ethyl (2S,3R,4S,5S)-3-(tert-butyl)-4-((R)-2,3-dihydroxy-2-(2-methoxy-5-(trifluoromethyl)phenyl)propoxy)-1-((S)-tetrahydro-2H-pyran-2-carbonyl)-5-(o-tolyl)pyrrolidine-2-carboxylate; LC/MS (ESI+) m/z 666 (M+H)$^+$. The title compound was the second product to elute, Example 262A.

Example 262B (2S,3R,4S,5S)-3-tert-butyl-4-{(2S)-2,3-dihydroxy-2-[2-methoxy-5-(trifluoromethyl)phenyl]propoxy}-5-(2-methylphenyl)-1-[(2S)-oxane-2-carbonyl]pyrrolidine-2-carboxylic acid A solution of Example 262A ((2S,3R,4S,5S)-ethyl 3-(tert-butyl)-4-((S)-2,3-dihydroxy-2-(2-methoxy-5-(trifluoromethyl)phenyl)propoxy)-1-((S)-tetrahydro-2H-pyran-2-carbonyl)-5-(o-tolyl)pyrrolidine-2-carboxylate) (30 mg, 0.045 mmol) in tetrahydrofuran (1 mL) was diluted with methanol (0.5 mL), diluted with water (1 mL), treated with lithium hydroxide hydrate (18.91 mg, 0.451 mmol), stirred at room temperature for 90 minutes, and heated to 45° C. 2.5 for hours. The mixture was treated with 1 M aqueous HCl (3 mL) and extracted twice with ethyl acetate (2×30 mL). The combined ethyl acetate layers were washed with brine, dried (MgSO$_4$), filtered, concentrated and chromatographed on silica gel, eluting with a gradient of 10% to 100% [200:1:1 ethyl acetate:HCOOH:H$_2$O] in heptane to provide the title compound. $^1$H NMR (400 MHz, DMSO-d$_6$, 120° C.) δ ppm 7.90 (d, J=7.5 Hz, 1H), 7.65 (d, J=2.5 Hz, 1H), 7.48 (dd, J=2.5, 8.5 Hz, 1H), 7.17-7.05 (m, 3H), 7.02 (d, J=8.6 Hz, 1H), 5.46 (bs, 1H), 4.56 (d, J=2.0 Hz, 1H), 4.10 (d, J=5.8 Hz, 1H), 3.80-3.72 (m, 4H), 3.40-3.35 (m, 3H), 3.24 (d, J=9.9 Hz, 1H), 3.07-2.79 (m, 2H), 2.37 (bs, 1H), 2.34 (s, 3H), 1.73-1.63 (m, 1H), 1.57-1.46 (m, 1H), 1.44-1.25 (m, 4H), 0.96 (s, 9H); LC/MS (ESI+) m/z 638 (M+H)$^+$.

Example 263

(2S,3R,4S,5S)-3-tert-butyl-4-{(2R)-2,3-dihydroxy-2-[2-methoxy-5-(trifluoromethyl)phenyl]propoxy}-5-(2-methylphenyl)-1-[(2S)-oxane-2-carbonyl]pyrrolidine-2-carboxylic acid

Example 263A ethyl (2S,3R,4S,5S)-3-(tert-butyl)-4-((R)-2,3-dihydroxy-2-(2-methoxy-5-(trifluoromethyl)phenyl)propoxy)-1-((S)-tetrahydro-2H-pyran-2-carbonyl)-5-(o-tolyl)pyrrolidine-2-carboxylate The procedure described for Example 262A provided the title compound as the third product to elute. LC/MS (ESI+) m/z 666 (M+H)$^+$.

Example 263B (2S,3R,4S,5S)-3-tert-butyl-4-{(2R)-2,3-dihydroxy-2-[2-methoxy-5-(trifluoromethyl)phenyl]propoxy}-5-(2-methylphenyl)-1-[(2S)-oxane-2-carbonyl]pyrrolidine-2-carboxylic acid A solution of Example 263A ((2S,3R,4S,5S)-ethyl 3-(tert-butyl)-4-((R)-2,3-dihydroxy-2-(2-methoxy-5-(trifluoromethyl)phenyl)propoxy)-1-((S)-tetrahydro-2H-pyran-2-carbonyl)-5-(o-tolyl)pyrrolidine-2-carboxylate) (30 mg, 0.045 mmol) in tetrahydrofuran (1 mL) was diluted with methanol (0.5 mL), diluted with water (1 mL), treated with lithium hydroxide hydrate (18.91 mg, 0.451 mmol), stirred at room temperature for 90 minutes, and heated to 45° C. for 2.5 hours. The mixture was treated with 1 M aqueous HCl (3 mL) and extracted twice with ethyl acetate (2×30 mL). The combined ethyl acetate layers were washed with brine, dried (MgSO$_4$), filtered, concentrated and chromatographed on silica gel, eluting with a gradient of 10% to 100% [200:1:1 ethyl acetate:HCOOH:H$_2$O] in heptane to provide the title compound. $^1$H NMR (400 MHz, DMSO-d$_6$, 120° C.) δ ppm 7.82 (d, J=7.7 Hz, 1H), 7.60 (d, J=2.5 Hz, 1H), 7.47 (dd, J=2.5, 8.6 Hz, 1H), 7.08-7.02 (m, 2H), 7.02-6.94 (m, 2H), 5.43 (bs, 1H), 4.59 (s, 1H), 4.10 (d, J=5.8 Hz, 1H), 3.80-3.72 (m, 4H), 3.55 (d, J=10.0 Hz, 1H), 3.45 (d, J=11.2 Hz, 1H), 3.40 (d, J=11.2 Hz, 1H), 3.30 (d, J=10.0 Hz, 1H), 3.12-2.66 (m, 2H), 2.35 (s, 1H), 2.26 (s, 3H), 1.72-1.25 (m, 6H), 0.98 (s, 9H); LC/MS (ESI+) m/z 638 (M+H)$^+$.

Example 264

(2S,3R,4S,5S)-3-tert-butyl-4-{2-[2-methoxy-5-(trifluoromethyl)phenyl]-2-oxoethoxy}-5-(2-methylphenyl)-1-[(2S)-oxane-2-carbonyl]pyrrolidine-2-carboxylic acid A solution of Example 249 ((2S,3R,4S,5S)-3-(tert-butyl)-4-((2-(2-methoxy-5-(trifluoromethyl)phenyl)allyl)oxy)-1-((S)-tetrahydro-2H-pyran-2-carbonyl)-5-(o-tolyl)pyrrolidine-2-carboxylic acid) (48 mg, 0.080 mmol) in tetrahydrofuran (2 mL) was diluted with water (1 mL), treated with 4% solution of osmium tetroxide in water (50.5 mg, 7.95 µmol), cooled to 0° C., treated with sodium periodate (51.0 mg, 0.239 mmol) and stirred overnight at room temperature. The mixture was partitioned between ethyl acetate (30 mL) and 1 M aqueous HCl (5 mL). The layers were separated and the aqueous layer was extracted with ethyl acetate (30 mL). The combined ethyl acetate layers were washed with brine, dried (MgSO$_4$), filtered, concentrated and chromatographed on silica gel, eluting with a gradient of 20% to 50% [200:1:1 ethyl acetate:HCOOH:H$_2$O] in heptane to provide the title compound. $^1$H NMR (400 MHz, DMSO-d$_6$, 120° C.) δ ppm 8.00 (d, J=6.7 Hz, 1H), 7.77 (ddd, J=0.8, 2.5, 8.8 Hz, 1H), 7.64 (d, J=2.5 Hz, 1H), 7.22 (d, J=8.8 Hz, 1H), 7.15-7.07 (m, 3H), 5.44 (bs, J=29.9 Hz, 1H), 4.60 (d, J=2.0 Hz, 1H), 4.20 (d, J=5.7 Hz, 1H), 3.95-3.84 (m, 2H), 3.81 (s, 3H), 3.81-3.75 (m, 2H), 2.54 (d, J=2.1 Hz, 1H), 2.38 (s, 3H), 2.37-2.34 (m, 1H), 1.72-1.26 (m, 6H), 1.01 (s, 9H); LC/MS (ESI+) m/z 606 (M+H)$^+$.

Example 265

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-{[(1,1,1-trifluoropropan-2-yl)oxy]carbonyl}pyrrolidine-2-carboxylic acid

Example 265A (2S,3R,4S,5S)-1-allyl 2-ethyl 3-(tert-butyl)-4-((5-cyclobutyl-2-methoxypyridin-3-yl)methoxy)-5-(2-isopropoxypyridin-3-yl)pyrrolidine-1,2-dicarboxylate To (2S,3R,4S,5S)-1-allyl 2-ethyl 3-(tert-butyl)-4-hydroxy-5-(2-isopropoxypyridin-3-yl)pyrrolidine-1,2-dicarboxylate (Example 285C, 800 mg, 1.841 mmol) and 3-(bromomethyl)-5-cyclobutyl-2-methoxypyridine (Intermediate 4, 472 mg, 1.841 mmol) in N,N-dimethylformamide (5 mL) cooling in an ice bath, potassium 2-methylpropan-2-olate (310 mg, 2.76 mmol) (2.8 mL, 1.0 M in tetrahydrofuran) was added dropwise, and the mixture was stirred in an ice bath for 20 minutes. The mixture was allowed to warm to ambient temperature. Dichloromethane (30 mL) was added and the mixture was washed with brine, dried over MgSO$_4$, filtered, and concentrated. Purification via chromatography on a 12 g silica gel cartridge, eluting with ethyl acetate/methanol (9:1) in heptane at 0-45% gradient to provide the title compound. $^1$H NMR (400 MHz, DMSO-d$_6$) δ ppm 8.03-8.00 (m, 1H), 7.93(d, J=5.8 Hz, 1H), 7.75(d, J=5.8 Hz, 1H), 6.85-6.80 (m, 2H), 5.75(m, 1H), 5.27-5.21 (m, 1H), 5.20 (d, J=5.8 Hz, 1H), 5.09-5.05 (m, 1H), 5.03 (t, J=1.6 Hz, 1H), 4.45 (dd, J=21.6, 2.4 Hz, 3H), 4.30-4.22 (m, 2H), 4.10-4.03 (m, 2H), 3.93 (dt, J=13.0, 0.9 Hz, 1H), 3.75 (s, 3H), 3.33 (q, J=8.5 Hz, 1H), 2.28-2.18 (m, 2H), 2.00-1.78 (m, 4H), 1.28 (d, J=6.1 Hz, 3H), 1.21 (d, J=6.1 Hz, 3H), 1.11 (t, J=7.1 Hz, 3H), 1.00 (s, 9H); MS (ESI+) m/z 610 (M+H)$^+$.

Example 265B (2S,3R,4S,5S)-ethyl 3-(tert-butyl)-4-((5-cyclobutyl-2-methoxypyridin-3-yl)methoxy)-5-(2-isopropoxy-pyridin-3-yl)pyrrolidine-2-carboxylate To a solution of (2S,3R,4S,5S)-1-allyl 2-ethyl 3-(tert-butyl)-4-((5-cyclobutyl-2-methoxypyridin-3-yl)methoxy)-5-(2-isopropoxypyridin-3-yl)pyrrolidine-1,2-dicarboxylate (480 mg, 0.787 mmol) and 1,3-dimethylpyrimidine-2,4,6 (1H,3H,5H)-trione (246 mg, 1.574 mmol) in ethyl acetate/dichloromethane (8 mL, 1:1) was added tetrakis(triphenyl-phosphine)palladium(0) (16.24 mg, 0.016 mmol). The mixture was stirred at room temperature for 20 minutes. Dichloromethane (20 mL) and water (10 mL) were added and the organic layer was washed with brine, dried over MgSO$_4$ and concentrated. The residue was purified by chromatography on a 24 g silica gel cartridge, eluting with ethyl acetate in heptane, to provide the title compound. MS (APCI+) m/z 526 (M+H)$^+$.

Example 265C (2S,3R,4S,5S)-3-tert-butyl-4-[(5-cyclobutyl-2-methoxypyridin-3-yl)methoxy]-5-{2-[(propan-2-yl)oxy]pyridin-3-yl}-1-{[(1,1,1-trifluoropropan-2-yl)oxy]carbonyl}pyrrolidine-2-carboxylic acid To a solution of Example 265B (390 mg, 0.742 mmol) in toluene (5 mL) and saturated aqueous sodium bicarbonate (5 mL) was added 1,1,1-trifluoropropan-2-yl carbonochloridate (262 mg, 1.484 mmol) dropwise at room temperature. The mixture was stirred at room temperature for 30 minutes. Dichloromethane (20 mL) and water (10 mL) were added and the organic layer was washed with brine, dried over MgSO$_4$ filtered, and concentrated. Purification by chromatography on a 24 g cartridge, eluting with ethyl acetate in heptane at a 0-40% gradient to yield (2S,3R,4S,5S)-2-ethyl 1-(1,1,1-trifluoropropan-2-yl) 3-(tert-butyl)-4-((5-cyclobutyl-2-methoxypyridin-3-yl)methoxy)-5-(2-isopropoxypyridin-3-yl)pyrrolidine-1,2-dicarboxylate, which was dissolved in methanol (2 mL) and 6 M LiOH (0.5 mL) and stirred at 50° C. overnight. The pH was adjusted to 1~2 by adding 2M aqueous HCl and concentrated to dryness. The residue was loaded onto a 12 gram silica gel cartridge, eluting with ethyl acetate/methanol (9:1) in heptane at a 0-50% gradient to provide the title compound. $^1$H NMR (400 MHz, DMSO-d$_6$) δ ppm 8.09 (dd, J=10.4, 8.2 Hz, 1H), 7.94 (ddd, J=6.7, 4.9, 1.9 Hz, 1H), 7.77 (d, J=2.4 Hz, 1H), 6.86-6.78 (m, 2H), 5.28-5.18 (m, 2H), 5.13 (pd, J=6.8, 5.1 Hz, 1H), 4.39 (d, J=2.2 Hz, 1H), 4.28 (d, J=13.1 Hz, 1H), 4.24 (dd, J=5.9, 1.6 Hz, 1H), 3.95 (d, J=13.1 Hz, 1H), 3.75 (s, 3H), 3.32 (p, J=8.5 Hz, 1H), 2.5 (m, 1H), 2.33-2.21 (m, 2H), 1.91 (dtt, J=22.6, 15.3, 7.6 Hz, 4H), 1.35-1.26 (m, 3H), 1.27-1.23 (m, 3H), 1.21 (d, J=6.1 Hz, 3H), 1.06 (d, J=6.4 Hz, 1H), 1.00 (s, 9H); MS (ESI+) m/z 638.1 (M+H)$^+$.

Example 266

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-({[(2R)-1,1,1-trifluoropropan-2-yl]oxy}carbonyl)pyrrolidine-2-carboxylic acid Example 266A (2S,3R,4S,5S)-2-ethyl 1-((R)-1,1,1-trifluoropropan-2-yl) 3-(tert-butyl)-4-hydroxy-5-(2-isopropoxypyridin-3-yl)pyrrolidine-1,2-dicarboxylate To (R)-1,1,1-trifluoropropan-2-ol [CAS#17628-73-8] (0.397 mL, 4.38 mmol) and bis(trichloromethyl) carbonate (429 mg, 1.447 mmol) in diethyl ether (10 mL) cooling at −10° C. was added triethylamine (0.611 mL, 4.38 mmol) dropwise. The reaction mixture was warmed to 0° C. and stirred for 2 hours, and stirred at room temperature for 2 hours. The mixture was added to a solution of (2S,3R,4S,5S)-ethyl 3-(tert-butyl)-4-hydroxy-5-(2-isopropoxypyridin-3-yl)pyrrolidine-2-carboxylate (Example 169A, 550 mg, 1.569 mmol) in toluene and saturated aqueous sodium bicarbonate (20 mL, 1:1) dropwise. The mixture was stirred at room temperature for 20 minutes. Ethyl acetate (20 mL) was added, and the organic layer was washed with brine, dried over MgSO$_4$, filtered, and concentrated. The residue was purified via chromatography on a 24 g silica gel cartridge, eluting with ethyl acetate in heptane, at a 0-40% gradient to provide the title compound. MS (APCI+) m/z 491 (M+H)$^+$.

Example 266B (2S,3R,4S,5S)-3-tert-butyl-4-[(5-cyclobutyl-2-methoxypyridin-3-yl)methoxy]-5-{2-[(propan-2-yl)oxy]pyridin-3-yl}-1-({[(2R)-1,1,1-trifluoropropan-2-yl]oxy}carbonyl)pyrrolidine-2-carboxylic acid To Example 266A (60 mg, 0.122 mmol) and 3-(bromomethyl)-5-cyclobutyl-2-methoxypyridine (Intermediate 4, 34.5 mg, 0.135 mmol) in N,N-dimethylformamide (2 mL) cooling in an ice bath, potassium 2-methylpropan-2-olate (20.59 mg, 0.183 mmol) (2.8 mL, 1.0 M in tetrahydrofuran) was added dropwise. The mixture was stirred in an ice bath for 20 minutes, and allowed to warm to ambient temperature. The organic layer was washed with brine, dried over MgSO$_4$, filtered, and concentrated. The residue was dissolved in methanol (2 mL) and aqueous LiOH (6M, 0.5 mL) and stirred at 50° C. overnight. The pH was adjusted to 1~2 by adding 2M aqueous HCl and was concentrated. The residue was loaded onto a 12 gram silica gel cartridge, eluting with ethyl acetate/methanol (9:1) in heptane at a 0-45% gradient to provide the title compound. $^1$H NMR (400 MHz, DMSO-d$_6$) δ ppm 8.07 (d, J=1.9 Hz, 1H), 7.93 (m, 1H), 7.87-7.73 (m, 1H), 6.94-6.80 (m, 2H), 5.33-5.22 (m, 1H), 5.22-5.09 (m, 2H), 4.40 (d, J=2.3 Hz, 1H), 4.28 (d, J=13.1 Hz, 1H), 3.96 (t, J=0.8 Hz, 1H), 3.75 (d, J=0.6 Hz, 3H), 3.34 (t, J=8.2 Hz, 1H), 2.21 (s, H), 2.33-2.21 (m, 2H),), 2.07-1.82 (m, 4H), 1.28 (s, 1H), 1.25 (dd, J=5.9, 1.6 Hz, 3H), 1.00 (s, 9H); MS (ESI+) m/z 638.3 (M+H)$^+$.

Example 267

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-({[(2S)-1,1,1-trifluoropropan-2-yl]oxy}carbonyl)pyrrolidine-2-carboxylic acid The title compound was synthesized using the same procedure as described in Example 266A and 266B, replacing (R)-1,1,1-trifluoropropan-2-ol with (S)-1,1,1-trifluoropropan-2-ol [CAS#3539-97-7] to provide title compound. $^1$H NMR (400 MHz, DMSO-d$_6$) δ ppm 8.11 (dd, J=7.4, 1.9 Hz, 1H), 7.95 (dd, J=4.9, 1.9 Hz, 1H), 7.76 (dd, J=2.4, 0.8 Hz, 1H), 6.85 (dt, J=2.4, 0.8 Hz, 1H), 6.82 (dd, J=7.4, 4.9 Hz, 1H), 5.23 (dt, J=12.1, 6.1 Hz, 2H), 5.12 (p, J=6.7 Hz, 1H), 4.39 (d, J=2.3 Hz, 1H), 4.27 (d, J=13.1 Hz, 1H), 4.23 (dd, J=5.8, 1.5 Hz, 1H), 3.95 (dt, J=13.1, 0.9 Hz, 1H), 3.75 (s, 3H), 3.37-3.29 (m, 1H), 2.33-2.20 (m, 2H), 2.06-1.82 (m, 4H), 1.28-1.24 (m, 3H), 1.21 (d, J=6.2 Hz, 3H), 1.05 (d, J=6.5 Hz, 3H), 1.00 (s, 9H); MS (ESI+) m/z 638.2 (M+H)$^+$.

Example 268

(2S,3R,4S,5S)-3-tert-butyl-4-{2-hydroxy-2-[2-methoxy-5-(trifluoromethyl)phenyl]ethoxy}-5-(2-methylphenyl)-1-[(2S)-oxane-2-carbonyl]pyrrolidine-2-carboxylic acid

Example 268A ethyl (2S,3R,4S,5S)-3-(tert-butyl)-4-(2-(2-methoxy-5-(trifluoromethyl)phenyl)-2-oxoethoxy)-1-((S)-tetrahydro-2H-pyran-2-carbonyl)-5-(o-tolyl)pyrrolidine-2-carboxylate The procedure described for Example 262A provided the titled compound as the first product to elute. LC/MS (ESI+) m/z 634 (M+H)$^+$.

Example 268B ethyl (2S,3R,4S,5S)-3-(tert-butyl)-4-(2-hydroxy-2-(2-methoxy-5-(trifluoromethyl)phenyl)ethoxy)-1-((S)-tetrahydro-2H-pyran-2-carbonyl)-5-(o-tolyl)pyrrolidine-2-carboxylate A mixture of Example 268A ((2S,3R,4S,5S)-ethyl 3-(tert-butyl)-4-(2-(2-methoxy-5-(trifluoromethyl)phenyl)-2-oxoethoxy)-1-((S)-tetrahydro-2H-pyran-2-carbonyl)-5-(o-tolyl)pyrrolidine-2-carboxylate) (50 mg, 0.079 mmol) in ethanol (1 mL) was treated with NaBH$_4$ (5.97 mg, 0.158 mmol), stirred at room temperature for 30 minutes, treated with 1 M aqueous HCl (2 mL) and extracted with ethyl acetate (50 mL). The ethyl acetate layer was washed with brine, dried (MgSO$_4$), filtered, concentrated and chromatographed on silica gel, eluting with a gradient of 20% to 50% ethyl acetate in heptane to provide the title compound. LC/MS (ESI+) m/z 635 (M+H)$^+$.

Example 268C (2S,3R,4S,5S)-3-tert-butyl-4-{2-hydroxy-2-[2-methoxy-5-(trifluoromethyl)phenyl]ethoxy}-5-(2-methylphenyl)-1-[(2S)-oxane-2-carbonyl]pyrrolidine-2-carboxylic acid A solution of Example 268B ((2S,3R,4S,5S)-ethyl 3-(tert-butyl)-4-(2-hydroxy-2-(2-methoxy-5-(trifluoromethyl)phenyl)ethoxy)-1-((S)-tetrahydro-2H-pyran-2-carbonyl)-5-(o-tolyl)pyrrolidine-2-carboxylate (30 mg, 0.047 mmol) in tetrahydrofuran (1 mL) was diluted with methanol (0.5 mL), diluted with water (1 mL), treated with lithium hydroxide hydrate (39.6 mg, 0.944 mmol), stirred at 45° C. for 8 hours, and stirred overnight at room temperature. The mixture was partitioned between 1 M aqueous HCl (3 mL) and ethyl acetate (50 mL). The ethyl acetate layer was washed with brine, dried (MgSO$_4$), filtered, concentrated and chromatographed on silica gel, eluting with a gradient of 20% to 50% [200:1:1 ethyl acetate:HCOOH:H$_2$O] in heptane to provide the title compound. $^1$H NMR (400 MHz, DMSO, 120° C.) δ ppm 7.99-7.95 (m, 1H), 7.51-7.46 (m, 2H), 7.13-7.01 (m, 4H), 5.46 (bs, 1H), 4.71 (dd, J=4.0, 6.7 Hz, 0.5H), 4.60 (dd, J=3.9, 7.0 Hz, 0.5H), 4.56 (dd, J=2.2, 5.0 Hz, 1H), 4.19 (d, J=5.8 Hz, 0.5H), 4.16 (d, J=5.9 Hz, 0.5H), 3.82 (s, 1.5H), 3.82-3.75 (m, 2H), 3.77 (s, 1.5H), 3.09 (dd, J=4.0, 10.6 Hz, 1H), 3.02 (d, J=7.1 Hz, 0.5H), 2.99 (d, J=7.1 Hz, 0.5H), 2.97-2.74 (m, 2H), 2.45 (bs, 0.5H), 2.39 (bs, 0.5H), 2.37 (s, 1.5H), 2.34 (s, 1.5H), 1.74-1.19 (m, 6H), 1.00 (s, 4.5H), 1.00 (s, 4.5H); LC/MS (ESI+) m/z 608 (M+H)$^+$.

Example 269

(2S,3R,4S,5S)-3-tert-butyl-4-{2-methoxy-2-[2-methoxy-5-(trifluoromethyl)phenyl]ethoxy}-5-(2-methylphenyl)-1-[(2S)-oxane-2-carbonyl]pyrrolidine-2-carboxylic acid A solution of Example 268B ((2S,3R,4S,5S)-ethyl 3-(tert-butyl)-4-(2-hydroxy-2-(2-methoxy-5-(trifluoromethyl)phenyl)ethoxy)-1-((S)-tetrahydro-2H-pyran-2-carbonyl)-5-(o-tolyl)pyrrolidine-2-carboxylate) (6 mg, 9.44 µmol) in N,N-dimethylformamide (0.5 mL) was treated with iodomethane (5.90 µL, 0.094 mmol), cooled to −20° C., treated dropwise with 1 M potassium tert-butoxide in tetrahydrofuran (18.88 µL, 0.019 mmol), stirred at −20° C. for 15 minutes, warmed to 0° C., stirred for 45 minutes, treated with more 1 M potassium tert-butoxide in tetrahydrofuran (18.88 µL, 0.019 mmol), stirred at room temperature for 15 minutes, treated with 1 M aqueous HCl (3 mL) and extracted with methyl tert-butyl ether (50 mL). The methyl tert-butyl ether layer was washed with water (20 mL), washed with brine, dried (MgSO$_4$), filtered, and concentrated. The residue was taken up in tetrahydrofuran (0.5 mL), diluted with methanol (0.25 mL), diluted with water (0.5 mL), treated with lithium hydroxide hydrate (7.92 mg, 0.189 mmol), stirred at 45° C. overnight, cooled, treated with 1 M aqueous HCl (3 mL) and extracted with ethyl acetate (30 mL). The ethyl acetate layer was washed with brine, dried (MgSO$_4$), filtered, concentrated and chromatographed on silica gel, eluting with a gradient of 20% to 50% [200:1:1 ethyl acetate:HCOOH:H$_2$O] in heptane to provide the title compound, (2S,3R,4S,5S)-3-(tert-butyl)-4-(2-methoxy-2-(2-methoxy-5-(trifluoromethyl)phenyl)ethoxy)-1-((S)-tetrahydro-2H-pyran-2-carbonyl)-5-(o-tolyl)pyrrolidine-2-carboxylic acid. $^1$H NMR (400 MHz, DMSO-d$_6$, 120° C.) δ ppm 8.02-7.96 (m, 1H), 7.57-7.51 (m, 1H), 7.36 (d, J=2.5 Hz, 0.5H), 7.33 (d, J=2.5 Hz, 0.5H), 7.17-7.04 (m, 4H), 5.48 (bs, 1H), 4.58 (d, J=2.2 Hz, 1H), 4.31 (dd, J=3.3, 6.8 Hz, 0.5H), 4.22 (dd, J=3.2, 7.1 Hz, 0.5H), 4.17 (d, J=6.0 Hz, 0.5H), 4.14 (d, J=6.0 Hz, 0.5H), 3.85 (s, 1.5H), 3.80 (s, 1.5H), 3.79-3.75 (m, 1H), 3.14-3.09 (m, 1H), 3.02 (s, 1.5H), 2.99 (s, 1.5H), 2.95-2.80 (m, 2H), 2.42 (bs, 1H), 2.38 (s, 1.5H), 2.35 (s, 1.5H), 1.73-1.22 (m, 6H), 1.00 (s, 4.5H), 0.99 (s, 4.5H), 0.90-0.81 (m, 1H); LC/MS (ESI+) m/z 622 (M+H)⁺.

Example 270

(2S,3R,4S,5S)-4-[(5-tert-butyl-2-methoxyphenyl)methoxy]-3-(2-methoxypropan-2-yl)-1-[(2S)-oxane-2-carbonyl]-5-[2-(propan-2-yl)phenyl]pyrrolidine-2-carboxylic acid Example 270A (2S,3R,4S,5S)-1-allyl 2-ethyl 4-((5-(tert-butyl)-2-methoxybenzyl)oxy)-5-(2-isopropylphenyl)-3-(2-methoxypropan-2-yl)pyrrolidine-1,2-dicarboxylate (2S,3R,4S,5S)-1-Allyl 2-ethyl 4-hydroxy-5-(2-isopropylphenyl)-3-(2-methoxypropan-2-yl)pyrrolidine-1,2-dicarboxylate from Example 258D (200 mg, 0.461 mmol) and 2-(bromomethyl)-4-(tert-butyl)-1-methoxybenzene (166 mg, 0.646 mmol) were dissolved in dry N,N-dimethylformamide (3 mL). After cooling in an ice bath, potassium 2-methylpropan-2-olate (0.646 mL, 0.646 mmol) solution was added dropwise over 4 minutes. After 30 minutes, the reaction was quenched with saturated aqueous NH₄Cl solution and extracted with dichloromethane. The organic solvent was evaporated and the resulting residue was purified using a 24 g silica gel column with a gradient of 0-70% ethyl acetate/heptanes over 20 minutes to give (2S,3R,4S,5S)-1-allyl 2-ethyl 4-((5-(tert-butyl)-2-methoxybenzyl)oxy)-5-(2-isopropylphenyl)-3-(2-methoxypropan-2-yl)pyrrolidine-1,2-dicarboxylate. $^1$H NMR (501 MHz, DMSO-d₆) δ ppm 7.97 (s, 1H), 7.19 (dd, J=7.9, 1.4 Hz, 1H), 7.15-7.12 (m, 1H), 7.10 (dd, J=8.6, 2.7 Hz, 1H), 7.05 (t, J=7.5 Hz, 1H), 6.80 (s, 1H), 6.73 (d, J=8.6 Hz, 1H), 5.69 (d, J=154.4 Hz, 1H), 5.32 (d, J=5.8 Hz, 1H), 5.21-4.80 (m, 1H), 4.59 (d, J=2.1 Hz, 1H), 4.51-4.29 (m, 2H), 4.26-4.19 (m, 2H), 4.12-4.04 (m, 2H), 3.82-3.76 (m, 1H), 3.61 (s, 3H), 3.33 (m, 1H), 3.19 (s, 1H), 3.16 (s, 3H), 2.76 (s, 1H), 1.25 (d, J=1.4 Hz, 3H), 1.18 (d, J=4.7 Hz, 6H), 1.16 (s, 12H), 1.09 (t, J=7.1 Hz, 3H); MS (APCI+) m/z 610 (M+H)⁺.

Example 270B (2S,3R,4S,5S)-ethyl 4-((5-(tert-butyl)-2-methoxybenzyl)oxy)-5-(2-isopropylphenyl)-3-(2-methoxypropan-2-yl)pyrrolidine-2-carboxylate To a solution of Example 270A (150 mg, 0.246 mmol) in acetonitrile/water (4.4 mL, 10:1) was added tetrakis(triphenylphosphine)palladium(0) (6.25 mg, 5.41 μmol) and diethylamine (0.051 mL, 0.492 mmol). The mixture was stirred at ambient temperature for 2 hours. The mixture was concentrated to 1 mL, and dichloromethane and water were added. The organic layer was washed with brine, dried over sodium sulfate, filtered, and concentrated. The crude material was purified using a 12 g silica gel cartridge with a gradient of 0-70% ethyl acetate/heptanes over 20 minutes to yield (2S,3R,4S,5S)-ethyl 4-((5-(tert-butyl)-2-methoxybenzyl)oxy)-5-(2-isopropylphenyl)-3-(2-methoxypropan-2-yl)pyrrolidine-2-carboxylate. $^1$H NMR (400 MHz, DMSO-d₆) δ ppm 7.61 (dd, J=7.9, 1.4 Hz, 1H), 7.27 (dd, J=7.8, 1.5 Hz, 1H), 7.21 (td, J=7.4, 1.5 Hz, 1H), 7.16-7.09 (m, 2H), 6.79 (d, J=2.6 Hz, 1H), 6.75 (d, J=8.6 Hz, 1H), 4.36 (dd, J=8.3, 4.4 Hz, 1H), 4.19-4.07 (m, 3H), 3.98 (dd, J=4.5, 1.9 Hz, 1H), 3.65 (t, J=7.3 Hz, 1H), 3.61 (s, 3H), 3.58 (d, J=12.0 Hz, 1H), 3.21 (p, J=6.8 Hz, 1H), 3.14 (s, 3H), 3.08-3.00 (m, 1H), 2.56-2.52 (m, 1H), 1.23-1.12 (m, 24H); MS (APCI+) m/z 526 (M+H)⁺.

Example 270C (2S,3R,4S,5S)-ethyl 4-((5-(tert-butyl)-2-methoxybenzyl)oxy)-5-(2-isopropylphenyl)-3-(2-methoxypropan-2-yl)-1-((S)-tetrahydro-2H-pyran-2-carbonyl)pyrrolidine-2-carboxylate To a solution of Example 270B (110 mg, 0.209 mmol) in dichloromethane (1.9 mL) at 0° C. was added triethylamine (0.131 mL, 0.942 mmol) followed by addition (S)-tetrahydro-2H-pyran-2-carbonyl chloride (52.9 mg, 0.356 mmol) as a solution in 1 mL of dichloromethane. After stirring for 15 minutes, the reaction was quenched with 5 mL of saturated aqueous sodium bicarbonate. The crude material was chromatographed using a 12 g silica gel cartridge with a gradient of 0-65% ethyl acetate/heptanes over a period of 20 minutes to give (2S,3R,4S,5S)-ethyl 4-((5-(tert-butyl)-2-methoxybenzyl)oxy)-5-(2-isopropylphenyl)-3-(2-methoxypropan-2-yl)-1-((S)-tetrahydro-2H-pyran-2-carbonyl)pyrrolidine-2-carboxylate. $^1$H NMR (400 MHz, DMSO-d₆) δ ppm 8.00 (dd, J=7.8, 1.5 Hz, 1H), 7.22 (s, 1H), 7.16 (d, J=7.3 Hz, 0H), 7.09 (dd, J=8.5, 2.6 Hz, 1H), 7.04 (t, J=7.5 Hz, 1H), 6.84 (d, J=2.6 Hz, 1H), 6.71 (d, J=8.6 Hz, 1H), 5.59 (s, 1H), 4.76 (d, J=1.8 Hz, 1H), 4.24-4.17 (m, 2H), 4.07 (q, J=7.1 Hz, 2H), 3.79 (d, J=12.4 Hz, 1H), 3.75-3.68 (m, 1H), 3.60 (s, 3H), 3.28-3.20 (m, 1H), 3.18 (s, 3H), 3.12 (bs, 1H), 2.72 (s, 1H), 1.71-1.62 (m, 1H), 1.52 (m, 2H), 1.36 (m, 3H), 1.30 (d, J=6.7 Hz, 3H), 1.22 (d, J=12.4 Hz, 6H), 1.17 (m, 12H), 1.12 (t, J=7.1 Hz, 3H); MS (APCI+) m/z 638 (M+H)⁺.

Example 270D (2S,3R,4S,5S)-4-[(5-tert-butyl-2-methoxyphenyl)methoxy]-3-(2-methoxypropan-2-yl)-1-[(2S)-oxane-2-carbonyl]-5-[2-(propan-2-yl)phenyl]pyrrolidine-2-carboxylic acid To a solution of Example 270C (92 mg, 0.144 mmol) in tetrahydrofuran (0.5 mL), methanol (0.500 mL) and water (0.500 mL) was added lithium hydroxide hydrate (42.4 mg, 1.010 mmol) and the reaction was heated at 45° C. for 16 hours. The solvent was removed under a stream of nitrogen. Water (1 mL) was added to the crude material. The mixture was extracted with 5 mL heptane (discarded), and the aqueous layer was acidified with 1M aqueous HCl (0.8 mL) to pH~6, and filtered. The material was chromatographed using a 4 g silica gel cartridge with a gradient of 0-10% methanol/dichloromethane over a period of 10 minutes to give (2S,3R,4S,5S)-4-((5-(tert-butyl)-2-methoxybenzyl)oxy)-5-(2-isopropylphenyl)-3-(2-methoxypropan-2-yl)-1-((S)-tetrahydro-2H-pyran-2-carbonyl)pyrrolidine-2-carboxylic acid. $^1$H NMR (400 MHz, DMSO-d₆) δ ppm 8.08 (dd, J=7.9, 1.5 Hz, 1H), 7.22 (d, J=7.8 Hz, 1H), 7.15 (t, J=7.6 Hz, 1H), 7.09 (dd, J=8.5, 2.6 Hz, 1H), 7.04 (t, J=7.6 Hz, 1H), 6.83 (d, J=2.6 Hz, 1H), 6.71 (d, J=8.5 Hz, 1H), 5.59 (s, 1H), 4.71 (d, J=1.8 Hz, 1H), 4.25-4.18 (m, 2H), 3.80 (d, J=12.6 Hz, 1H), 3.74 (m, 1H), 3.61 (s, 3H), 3.28-3.20 (m, 1H), 3.18 (s, 3H), 2.80-2.77 (m, 3H), 1.73-1.62 (m, 1H), 1.54 (m, 2H), 1.36 (m, 3H), 1.30 (d, J=6.8 Hz, 3H), 1.21 (d, J=8.4 Hz, 6H), 1.16 (m, 12H); MS (APCI+) m/z 610 (M+H)+.

Example 271

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-({[(2S)-1,1,1-trifluoropropan-2-yl]oxy}carbonyl)pyrrolidine-2-carboxylic acid Example 271A (2S,3R,4S,5S)-1-allyl 2-ethyl 3-(tert-butyl)-5-(2-isopropoxypyridin-3-yl)-4-((2-methoxy-5-(trifluoromethyl)pyridin-3-yl)methoxy)pyrrolidine-1,2-dicarboxylate The title compound was prepared according to the procedure described in Example 265A, substituting 3-(bromomethyl)-2-methoxy-5-(trifluoromethyl)pyridine (Intermediate 8, 342 mg, 1.266 mmol) for 3-(bromomethyl)-5-cyclobutyl-2-methoxypyridine to yield the title compound. $^1$H NMR (400 MHz, DMSO-$d_6$) δ ppm 8.28 (dq, J=2.7, 0.9 Hz, 1H), 8.08 (dd, J=7.4, 1.9 Hz, 1H), 7.88 (dd, J=5.0, 1.9 Hz, 1H), 7.13-7.08 (m, 1H), 6.77 (dd, J=7.4, 4.9 Hz, 1H), 5.73 (ddt, J=17.2, 10.4, 5.1 Hz, 1H), 5.28-5.17 (m, 2H), 5.11-4.98 (m, 2H), 4.43 (dt, J=5.2, 1.7 Hz, 3H), 4.37 (dt, J=13.7, 0.9 Hz, 1H), 4.29 (dd, J=6.0, 1.5 Hz, 1H), 3.99 (dt, J=13.9, 0.9 Hz, 1H), 3.87 (s, 3H), 1.28 (d, J=6.1 Hz, 3H), 1.20 (d, J=6.1 Hz, 3H), 1.02 (s, 9H); MS (ESI+) m/z 596.1 (M+H)+.

Example 271B (2S,3R,4S,5S)-ethyl 3-(tert-butyl)-5-(2-isopropoxypyridin-3-yl)-4-((2-methoxy-5-(trifluoromethyl)pyridin-3-yl)methoxy)pyrrolidine-2-carboxylate The title compound was prepared according to the procedure described in Example 265B, substituting Example 271A for Example 265A to yield title compound. MS (APCI+) m/z 540.5 (M+H)+.

Example 271C (2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-({[(2S)-1,1,1-trifluoropropan-2-yl]oxy}carbonyl)pyrrolidine-2-carboxylic acid To a solution of Example 271B (51.3 mg, 0.095 mmol) in toluene and saturated aqueous sodium bicarbonate (4 mL, 1:1) was added (S)-1,1,1-trifluoropropan-2-yl carbonochloridate (16.79 mg, 0.095 mmol) dropwise at room temperature. The mixture was stirred at room temperature for 20 minutes. Ethyl acetate (20 mL) and water (10 mL) were added, and the organic layer was washed with brine, dried over MgSO$_4$, filtered, and concentrated. The residue was purified via chromatography on a 24 g silica gel cartridge, eluting with ethyl acetate in heptane, at a 0-30% gradient to yield the ester. The ester was dissolved in methanol (2 mL) and aqueous LiOH (0.5 mL), and stirred at 50° C. for overnight. The pH was adjusted to 0-1 by adding 2M aqueous HCl and concentrated to dryness. The residue was purified via chromatography on a 12 g silica gel cartridge, eluting with ethyl acetate in heptane, at 0-50% gradient to provide title compound $^1$H NMR (400 MHz, DMSO-$d_6$) δ ppm 8.36-8.27 (m, 1H), 8.08 (dd, J=7.3, 1.9 Hz, 1H), 7.91 (dd, J=5.0, 1.9 Hz, 1H), 7.18-7.12 (m, 1H), 6.78 (dd, J=7.4, 4.9 Hz, 1H), 5.22 (dd, J=6.0, 2.1 Hz, 2H), 5.19-5.10 (m, 1H), 4.41 (d, J=2.3 Hz, 1H), 4.37 (d, J=13.7 Hz, 1H), 4.28 (dd, J=5.9, 1.4 Hz, 1H), 3.99 (d, J=13.8 Hz, 1H), 3.87 (s, 3H), 2.53 (t, J=1.9 Hz, 1H), 1.26 (d, J=6.1 Hz, 3H), 1.20 (d, J=6.2 Hz, 3H), 1.06 (d, J=6.6 Hz, 3H), 1.01 (s, 9H); MS (ESI+) m/z 652.1 (M+H)+.

Example 272

(2S,3R,4S,5S)-3-tert-butyl-4-{(2R)-2-[2-methoxy-5-(trifluoromethyl)phenyl]propoxy}-5-(2-methylphenyl)-1-[(2S)-oxane-2-carbonyl]pyrrolidine-2-carboxylic acid Example 272A ethyl (2S,3R,4S,5S)-3-(tert-butyl)-4-((R)-2-(2-methoxy-5-(trifluoromethyl)phenyl)propoxy)-1-((S)-tetrahydro-2H-pyran-2-carbonyl)-5-(o-tolyl)pyrrolidine-2-carboxylate A mixture of Example 249D ((2S,3R,4S,5S)-ethyl 3-(tert-butyl)-4-((2-(2-methoxy-5-(trifluoromethyl)phenyl)allyl)oxy)-1-((S)-tetrahydro-2H-pyran-2-carbonyl)-5-(o-tolyl)pyrrolidine-2-carboxylate) (120 mg, 0.190 mmol) and 10% Pd/C (25 mg, 0.023 mmol) in ethanol (2 mL) was stirred under an atmosphere of H$_2$ (balloon) for 90 minutes. The mixture was diluted with ethyl acetate (25 mL), stirred for 5 minutes, and filtered to remove the solids. The filtrate was concentrated to dryness. A portion of the crude product was chromatographed on silica gel, eluting with a gradient of 15% to 100% methyl tert-butyl ether in heptane to provide the title compound as the first isomer to elute from the column. LC/MS (ESI+) m/z 634 (M+H)+.

Example 272B (2S,3R,4S,5S)-3-tert-butyl-4-{(2R)-2-[2-methoxy-5-(trifluoromethyl)phenyl]propoxy}-5-(2-methylphenyl)-1-[(2S)-oxane-2-carbonyl]pyrrolidine-2-carboxylic acid A solution of Example 272A ((2S,3R,4S,5S)-ethyl 3-(tert-butyl)-4-((R)-2-(2-methoxy-5-(trifluoromethyl)phenyl)propoxy)-1-((S)-tetrahydro-2H-pyran-2-carbonyl)-5-(o-tolyl)pyrrolidine-2-carboxylate) (41.6 mg, 0.066 mmol) in tetrahydrofuran (1 mL) was diluted with methanol (0.5 mL), diluted with water (1 mL), treated with lithium hydroxide hydrate (33 mg, 0.786 mmol), stirred at 45° C. overnight, heated overnight to 55° C., cooled, treated with 1 M aqueous HCl (3 mL) and extracted with ethyl acetate (50 mL). The ethyl acetate layer was washed with brine, dried (MgSO$_4$), filtered, concentrated and chromatographed on silica gel, eluting with a gradient of 15% to 50% [200:1:1 ethyl acetate:HCOOH:H$_2$O] in heptane to provide the title compound. $^1$H NMR (400 MHz, DMSO, 200° C.) δ ppm 7.99-7.94 (m, 1H), 7.44 (dd, J=2.4, 8.7 Hz, 1H), 7.20 (d, J=2.4 Hz, 1H), 7.11-7.06 (m, 3H), 7.02 (d, J=8.6 Hz, 1H), 5.48 (bs, 1H), 4.59 (s, 1H), 4.06 (d, J=5.9 Hz, 1H), 3.80-3.75 (m, 1H), 3.78 (s, 3H), 3.19-3.13 (m, 1H), 2.98-2.84 (m, 3H), 2.38 (bs, 1H), 2.33 (s, 3H), 1.72-1.26 (m, 6H), 0.98 (s, 9H), 0.92-0.86 (m, 1H), 0.84 (d, J=6.6 Hz, 3H); LC/MS (ESI+) m/z 606 (M+H)+.

Example 273

(2S,3R,4S,5S)-3-tert-butyl-4-{(2S)-2-[2-methoxy-5-(trifluoromethyl)phenyl]propoxy}-5-(2-methylphenyl)-1-[(2S)-oxane-2-carbonyl]pyrrolidine-2-carboxylic acid

Example 273A ethyl (2S,3R,4S,5S)-3-(tert-butyl)-4-((S)-2-(2-methoxy-5-(trifluoromethyl)phenyl)propoxy)-1-((S)-tetrahydro-2H-pyran-2-carbonyl)-5-(o-tolyl)pyrrolidine-2-carboxylate The procedure for Example 272A provided the title compound as the second isomer to elute from the column. LC/MS (ESI+) m/z 634 (M+H)+.

Example 273B (2S,3R,4S,5S)-3-tert-butyl-4-{(2S)-2-[2-methoxy-5-(trifluoromethyl)phenyl]propoxy}-5-(2-methylphenyl)-1-[(2S)-oxane-2-carbonyl]pyrrolidine-2-carboxylic acid A solution of Example 273A ((2S,3R,4S,5S)-ethyl 3-(tert-butyl)-4-((S)-2-(2-methoxy-5-(trifluoromethyl)phenyl) propoxy)-1-((S)-tetrahydro-2H-pyran-2-carbonyl)-5-(o-tolyl)pyrrolidine-2-carboxylate) (41.6 mg, 0.066 mmol) in tetrahydrofuran (1 mL) was diluted with methanol (0.5 mL), diluted with water (1 mL), treated with lithium hydroxide hydrate (34 mg, 0.810 mmol), stirred at 45° C. overnight, heated overnight to 55° C., cooled, treated with 1 M aqueous HCl (3 mL) and extracted with ethyl acetate (50 mL). The ethyl acetate layer was washed with brine, dried (MgSO$_4$), filtered, concentrated and chromatographed on silica gel, eluting with a gradient of 15% to 50% [200:1:1 ethyl acetate:HCOOH:H$_2$O] in heptane to provide the title compound. $^1$H NMR (400 MHz, DMSO-d$_6$, 120° C.) δ ppm 7.99-7.96 (m, 1H), 7.45 (dd, J=2.4, 8.6 Hz, 1H), 7.12-7.07 (m, 4H), 7.05 (d, J=8.6 Hz, 1H), 5.48 (bs, 1H), 4.58 (d, J=2.3 Hz, 1H), 4.06 (d, J=5.8 Hz, 1H), 3.82 (s, 3H), 3.81-3.75 (m, 1H), 3.23 (dd, J=5.4, 9.0 Hz, 1H), 3.05-2.72 (m, 3H), 2.36 (s, 3H), 2.36-2.35 (m, 1H), 1.71-1.27 (m, 6H), 0.98 (s, 9H), 0.92-0.81 (m, 1H), 0.78 (d, J=6.9 Hz, 3H); LC/MS (ESI+) m/z 606 (M+H)+.

Example 274

(2S,3R,4S,5S)-3-tert-butyl-4-[(5-tert-butyl-2-methoxyphenyl)methoxy]-5-{2-[(propan-2-yl)oxy]pyridin-3-yl}-1-({[(2S)-1,1,1-trifluoropropan-2-yl]oxy}carbonyl)pyrrolidine-2-carboxylic acid The title compound was prepared according to the procedure described in Example 266A and 266B, substituting (S)-1,1,1-trifluoropropan-2-ol for (R)-1,1,1-trifluoropropan-2-ol, and Intermediate 6 for Intermediate 4, respectively, to provide title compound. $^1$H NMR (400 MHz, DMSO-d$_6$) δ ppm 8.14 (dd, J=7.4, 2.0 Hz, 1H), 7.97 (dd, J=4.9, 2.0 Hz, 1H), 7.15 (dd, J=8.6, 2.6 Hz, 1H), 6.89-6.81 (m, 2H), 6.77 (d, J=8.5 Hz, 1H), 5.36-5.27 (m, 1H), 5.27-5.23 (m, 1H), 5.15 (hept, J=6.7 Hz, 1H), 4.40 (d, J=2.4 Hz, 1H), 4.30 (d, J=12.4 Hz, 1H), 4.25 (dd, J=5.9, 1.5 Hz, 1H), 3.99 (d, J=12.4 Hz, 1H), 3.66 (s, 3H), 2.55 (d, J=2.0 Hz, 1H), 1.31 (d, J=6.1 Hz, 3H), 1.29 (d, J=6.1 Hz, 3H), 1.20 (s, 9H), 1.08 (d, J=6.7 Hz, 3H), 1.01 (s, 9H); MS (ESI+) m/z 639.2 (M+H)+.

Example 275

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-[1-(trifluoromethyl)cyclopropane-1-carbonyl]pyrrolidine-2-carboxylic acid To a solution of 1-(trifluoromethyl)cyclopropanecarboxylic acid [277756-46-4] (58.6 mg, 0.380 mmol) and one drop of N,N-dimethylformamide in dichloromethane (2 mL) at −10° C. was added oxalyl dichloride (72.4 mg, 0.571 mmol) dropwise. The mixture was stirred at room temperature for 2 hours and was added dropwise to (2S,3R,4S,5S)-ethyl 3-(tert-butyl)-4-((5-cyclobutyl-2-methoxypyridin-3-yl)methoxy)-5-(2-isopropoxypyridin-3-yl)pyrrolidine-2-carboxylate (Example 133G, 100 mg, 0.190 mmol) in toluene and saturated aqueous sodium bicarbonate (4 mL, 1:1) at room temperature. The mixture was stirred for 20 minutes. Ethyl acetate (20 mL) and water (10 mL) were added, and the organic layer was washed with brine, dried over MgSO$_4$, filtered, and concentrated. The residue was dissolved in methanol (2 mL) and 6N aqueous LiOH (0.5 mL) and stirred at 50° C. for 4 hours. The pH was adjusted to 1~2 by adding 2M aqueous HCl, and the mixture was concentrated. The residue was purified via chromatography on a 10 g silica gel cartridge, eluting with ethyl acetate/methanol (9:1) in heptane at a 0-50% gradient to provide the title compound. $^1$H NMR (400 MHz, DMSO-d$_6$) δ ppm 8.02-7.92 (m, 3H), 7.63 (d, J=2.4 Hz, 1H), 6.71 (dd, J=7.4, 4.9 Hz, 1H), 5.50 (d, J=6.5 Hz, 1H), 5.31 (hept, J=6.2 Hz, 1H), 5.17 (d, J=3.1 Hz, 2H), 4.67 (d, J=4.4 Hz, 1H), 4.44 (dd, J=6.6, 3.9 Hz, 1H), 3.92 (s, 3H), 3.51 (p, J=8.5 Hz, 1H), 2.38-2.28 (m, 3H), 2.14-1.82 (m, 4H), 1.35 (d, J=6.1 Hz, 3H), 1.33 (d, J=6.1 Hz, 3H), 1.30-1.25 (m, 1H), 1.15-1.05 (m, 2H), 1.01 (s, 9H), 0.78 (dtd, J=10.1, 5.2, 4.3, 2.7 Hz, 1H); MS (ESI+) m/z 634.3 (M+H)+.

Example 276

(2S,3R,4S,5S)-3-tert-butyl-4-[(5-cyclobutyl-2-methoxypyridin-3-yl)methoxy]-5-{2-[(propan-2-yl)oxy]pyridin-3-yl}-1-[1-(trifluoromethyl)cyclopentane-1-carbonyl]pyrrolidine-2-carboxylic acid The title compound was prepared according to the procedure described in Example 275, substituting 1-(trifluoromethyl)cyclopentanecarboxylic acid [CAS#277756-44-2] for 1-(trifluoromethyl)cyclopropanecarboxylic acid. $^1$H NMR (400 MHz, DMSO-d$_6$) δ ppm 8.21 (dd, J=7.3, 1.9 Hz, 1H), 7.97 (dd, J=4.9, 2.0 Hz, 1H), 7.79 (d, J=2.3 Hz, 1H), 6.89-6.82 (m, 2H), 5.58 (d, J=6.4 Hz, 1H), 5.24 (p, J=6.0 Hz, 1H), 4.72 (d, J=3.0 Hz, 1H), 4.39 (d, J=13.2 Hz, 1H), 4.25 (dd, J=6.4, 2.4 Hz, 1H), 4.09 (d, J=13.2 Hz, 1H), 3.81 (s, 3H), 3.36 (q, J=8.5 Hz, 1H), 2.57 (d, J=2.7 Hz, 1H), 2.45 (t, J=7.4 Hz, 1H), 2.29-2.19 (m, 3H), 2.10-1.84 (m, 6H), 1.68 (dq, J=34.4, 7.3 Hz, 3H), 1.50 (dq, J=13.6, 7.5 Hz, 1H), 1.33 (d, J=6.1 Hz, 3H), 1.29 (s, 1H), 1.22 (d, J=6.1 Hz, 3H), 1.03 (s, 9H), 0.88 (d, J=7.6 Hz, 1H); MS (ESI+) m/z 662.2 (M+H)+.

Example 277

(2S,3R,4S,5S)-3-tert-butyl-4-({3-[2-methoxy-5-(trifluoromethyl)pyridin-3-yl]prop-2-yn-1-yl}oxy)-5-phenyl-1-{[(propan-2-yl)oxy]carbonyl}pyrrolidine-2-carboxylic acid

Example 277A (2S,3R,4S,5S)-2-ethyl 1-isopropyl 3-(tert-butyl)-5-phenyl-4-(prop-2-yn-1-yloxy)pyrrolidine-1,2-dicarboxylate (2S,3R,4S,5S)-2-Ethyl 1-isopropyl 3-(tert-butyl)-4-hydroxy-5-phenylpyrrolidine-1,2-dicarboxylate from Example 38C (49 mg, 0.130 mmol) and propargyl bromide (34.7 mg, 0.234 mmol) were dissolved in dry N,N-dimethylformamide (0.5 mL). After cooling in an ice bath, potassium 2-methylpropan-2-olate (0.208 mL, 0.208 mmol) (1M in tetrahydrofuran) was added dropwise over 2 minutes. After 15 minutes, the mixture was acidified with 1M aqueous HCl (10 drops) and warmed to ambient temperature. The mixture was concentrated and loaded onto a 12 g silica gel column and was eluted with 5-100% methyl tert-butyl ether/heptanes over 20 minutes to give (2S,3R,4S,5S)-2-ethyl 1-isopropyl 3-(tert-butyl)-5-phenyl-4-(prop-2-yn-1-yloxy)pyrrolidine-1,2-dicarboxylate. MS (APCI+) m/z 415 (M+H)$^+$.

Example 277B (2S,3R,4S,5S)-2-ethyl 1-isopropyl 3-(tert-butyl)-4-((3-(2-methoxy-5-(trifluoromethyl)pyridin-3-yl)prop-2-yn-1-yl)oxy)-5-phenylpyrrolidine-1,2-dicarboxylate (2S,3R,4S,5S)-2-Ethyl 1-isopropyl 3-(tert-butyl)-4-((3-(2-methoxy-5-(trifluoromethyl)pyridin-3-yl)prop-2-yn-1-yl)oxy)-5-phenylpyrrolidine-1,2-dicarboxylate from Example 277A (58 mg, 0.098 mmol), 3-bromo-2-methoxy-5-(trifluoromethyl)pyridine (30.5 mg, 0.119 mmol), copper (I) iodide (2.063 mg, 10.83 μmol) and tetrakis(triphenylphosphine)palladium(0) (12.51 mg, 10.83 μmol) were combined under nitrogen with nitrogen sparged toluene (289 μL) and triethylamine (144 μL). The resulting solution was heated to 60° C. for 3.5 hours. The solvent was removed under a stream of nitrogen. Diethyl ether was added, leaving behind a precipitate (PPh$_3$O), which was filtered out. The filtrate was purified using a 10 g silica gel cartridge eluting with 0-20% ethyl acetate/heptanes over 20 minutes to give (2S,3R,4S,5S)-2-ethyl 1-isopropyl 3-(tert-butyl)-4-((3-(2-methoxy-5-(trifluoromethyl)pyridin-3-yl)prop-2-yn-1-yl)oxy)-5-phenylpyrrolidine-1,2-dicarboxylate. MS (APCI+) m/z 591 (M+H)$^+$.

Example 277C (2S,3R,4S,5S)-3-tert-butyl-4-({3-[2-methoxy-5-(trifluoromethyl)pyridin-3-yl]prop-2-yn-1-yl}oxy)-5-phenyl-1-{[(propan-2-yl)oxy]carbonyl}pyrrolidine-2-carboxylic acid (2S,3R,4S,5S)-2-Ethyl 1-isopropyl 3-(tert-butyl)-4-((3-(2-methoxy-5-(trifluoromethyl)pyridin-3-yl)prop-2-yn-1-yl)oxy)-5-phenylpyrrolidine-1,2-dicarboxylate from Example 277B (58 mg, 0.098 mmol) and lithium hydroxide (20 mg, 0.835 mmol) were combined in methanol (0.3 mL), water (0.300 mL) and tetrahydrofuran (0.3 mL). The resulting solution was heated to 50° C. for 17 hours. The solvent was removed under a stream of nitrogen and the crude material was acidified with 2N aqueous HCl (0.42 mL). The crude material was purified using a 10 g silica gel cartridge eluting with an ethyl acetate/ethanol/heptanes solvent system to give (2S,3R,4S,5S)-3-(tert-butyl)-1-(isopropoxycarbonyl)-4-((3-(2-methoxy-5-(trifluoromethyl)pyridin-3-yl)prop-2-yn-1-yl)oxy)-5-phenylpyrrolidine-2-carboxylic acid. $^1$H NMR (400 MHz, DMSO-d$_6$) δ ppm 8.46 (dd, J=2.4, 1.2 Hz, 1H), 7.90 (d, J=2.5 Hz, 1H), 7.61-7.55 (m, 2H), 7.26-7.13 (m, 3H), 4.98 (d, J=6.4 Hz, 1H), 4.62 (p, J=6.2 Hz, 1H), 4.38 (dd, J=6.5, 3.0 Hz, 1H), 4.26 (d, J=3.6 Hz, 1H), 3.99 (s, 3H), 3.95 (d, J=16.7 Hz, 1H), 3.82 (d, J=16.7 Hz, 1H), 1.05 (d, J=6.2 Hz, 3H), 1.02 (s, 10H), 0.88 (d, J=6.2 Hz, 3H); MS (APCI+) m/z 563 (M+H)$^+$.

Example 278

(2S,3R,4S,5S)-3-tert-butyl-5-(2-ethylphenyl)-4-({3-[2-methoxy-5-(trifluoromethyl)pyridin-3-yl]prop-2-yn-1-yl}oxy)-1-[(2S)-oxane-2-carbonyl]pyrrolidine-2-carboxylic acid

Example 278A (2S,3R,4S,5S)-ethyl 3-(tert-butyl)-5-(2-ethylphenyl)-4-nitro-1-((S)-tetrahydro-2H-pyran-2-carbonyl)pyrrolidine-2-carboxylate To a solution of (2S,3R,4S,5S)-ethyl 3-(tert-butyl)-5-(2-ethylphenyl)-4-nitropyrrolidine-2-carboxylate (Core 24B) (500 mg, 1.435 mmol) in dichloromethane (5 mL) at 0° C. was added triethylamine (0.900 mL, 6.46 mmol) followed by addition (S)-tetrahydro-2H-pyran-2-carbonyl chloride (362 mg, 2.436 mmol) as a solution in 2 mL dichloromethane. After stirring for 15 minutes, the mixture was quenched with 5 mL of saturated aqueous sodium bicarbonate and the crude material was chromatographed using a 24 g silica gel cartridge with a gradient of 0-80% ethyl acetate/heptanes over a period of 20 minutes to give (2S,3R,4S,5S)-ethyl 3-(tert-butyl)-5-(2-ethylphenyl)-4-nitro-1-((S)-tetrahydro-2H-pyran-2-carbonyl)pyrrolidine-2-carboxylate. $^1$H NMR (400 MHz, DMSO-d$_6$) δ ppm 8.31 (d, J=2.1 Hz, 1H), 7.73 (s, 1H), 7.55 (d, J=7.5 Hz, 1H), 7.26 (d, J=2.4 Hz, 1H), 7.20 (d, J=17.6 Hz, 2H), 5.40 (s, 1H), 4.63 (s, 1H), 4.38-4.24 (m, 2H), 4.10 (qd, J=7.1, 3.9 Hz, 2H), 3.91 (d, J=13.7 Hz, 1H), 3.88 (s, 3H), 3.78 (d, J=11.3 Hz, 1H), 3.49 (bs, 1H), 3.10 (bs, 1H), 2.39 (t, J=2.3 Hz, 1H), 1.68 (m, 1H), 1.51 (m, 2H), 1.39 (m, 3H), 1.16 (t, J=7.1 Hz, 3H), 1.00 (s, 9H); MS (APCI+) m/z 461 (M+H)$^+$.

Example 278B (2S,3R,5S)-ethyl 3-(tert-butyl)-5-(2-ethylphenyl)-4-oxo-1-((S)-tetrahydro-2H-pyran-2-carbonyl)pyrrolidine-2-carboxylate In a 100 mL flask was charged DBU (1,8-diazabicyclo[5.4.0]undec-7-ene) (0.743 mL, 4.93 mmol) and carbon disulfide (0.425 mL, 7.05 mmol) in 1.4 mL CH$_3$CN and the mixture was stirred at ambient temperature for 30 minutes. To the mixture at 0° C. was added (2S,3R,4S,5S)-ethyl 3-(tert-butyl)-5-(2-ethylphenyl)-4-nitro-1-((S)-tetrahydro-2H-pyran-2-carbonyl)pyrrolidine-2-carboxylate from Example 278A (649 mg, 1.409 mmol) in 1.4 mL of CH$_3$CN. The mixture was allowed to warm to room temperature for 2 hours. CH$_3$CN (28 mL) was added and 7.4 mL of 10%

H₃PO₄ solution was added to hydrolyze the resulting imine in 2 hours at ambient temperature. Methyl tert-butyl ether (10 mL) and 6 mL brine were added, and the organic layer was washed with 18 mL of brine with the addition of 18 mL methyl tert-butyl ether. The organics were filtered and concentrated. The hydrolysis was repeated by stirring the crude material for 5 hours in 24 mL CH₃CN and 10 mL 10% H₃PO₄. Methyl tert-butyl ether (10 mL) and 6 mL brine were added and the organic layer was washed with 18 mL of brine with the addition of 18 mL methyl tert-butyl ether. The mixture was filtered and concentrated, and the residue was chromatographed using a 24 g silica gel cartridge with a gradient of 0-60% ethyl acetate/heptanes over a period of 20 minutes to give (2S,3R,5S)-ethyl 3-(tert-butyl)-5-(2-ethylphenyl)-4-oxo-1-((S)-tetrahydro-2H-pyran-2-carbonyl)pyrrolidine-2-carboxylate. ¹H NMR (400 MHz, DMSO-d₆) δ ppm 7.82 (dd, J=7.8, 1.4 Hz, 1H), 7.24 (dt, J=14.6, 7.5 Hz, 2H), 7.18-7.08 (m, 1H), 5.58 (s, 1H), 4.73 (d, J=4.4 Hz, 1H), 4.20 (qd, J=7.1, 5.0 Hz, 2H), 3.74 (dtd, J=11.4, 3.8, 1.4 Hz, 1H), 3.22-2.99 (m, 2H), 2.81-2.70 (m, 2H), 2.50 (d, J=4.4 Hz, 1H), 1.82-1.61 (m, 1H), 1.50 (m, 2H), 1.37 (m, 3H), 1.28-1.18 (m, 6H), 1.04 (s, 9H); MS (APCI+) m/z 430 (M+H)⁺.

Example 278C (2S,3R,4S,5S)-ethyl 3-(tert-butyl)-5-(2-ethylphenyl)-4-hydroxy-1-((S)-tetrahydro-2H-pyran-2-carbonyl)pyrrolidine-2-carboxylate (2S,3R,5S)-Ethyl 3-(tert-butyl)-5-(2-ethylphenyl)-4-oxo-1-((S)-tetrahydro-2H-pyran-2-carbonyl)pyrrolidine-2-carboxylate from Example 278B (11.48 g, 26.7 mmol) was heated to dissolve in ethanol (200 mL). Sodium borohydride (2.022 g, 53.5 mmol) was added after cooling the reaction to <−10° C. in an ice/acetone bath. The ice bath was removed after 5 minutes and the reaction was allowed to warm to room temperature over 40 minutes. The mixture was concentrated and the residue was partitioned between ethyl acetate and saturated aqueous sodium bicarbonate. After 1.5 hours, the organics were concentrated and the crude material was purified via flash chromatography, eluting with 0-100% ethyl acetate/heptanes over a period of 20 minutes on a 80 g silica gel cartridge to give (2S,3R,4S,5S)-ethyl 3-(tert-butyl)-5-(2-ethylphenyl)-4-hydroxy-1-((S)-tetrahydro-2H-pyran-2-carbonyl)pyrrolidine-2-carboxylate. ¹H NMR (400 MHz, DMSO-d₆) δ ppm 7.95 (d, J=7.6 Hz, 1H), 7.22-7.15 (m, 2H), 7.13 (m, 1H), 5.46 (s, 1H), 4.46 (s, 1H), 4.41-4.32 (m, 1H), 4.16 (q, J=7.1 Hz, 2H), 3.83 (bs, 1H), 3.75 (dd, J=11.4, 3.9 Hz, 1H), 3.43 (bs, 1H), 3.02 (bs, 1H) 2.71 (ddt, J=19.7, 14.7, 7.4 Hz, 2H), 2.22 (t, J=3.5 Hz, 1H), 1.64 (m, 1H), 1.47 (m, 2H), 1.35 (m, 3H), 1.25 (td, J=7.3, 1.8 Hz, 6H), 0.99 (s, 9H); MS (APCI+) m/z 432 (M+H)⁺.

Example 278D (2S,3R,4S,5S)-ethyl 3-(tert-butyl)-5-(2-ethylphenyl)-4-(prop-2-yn-1-yloxy)-1-((S)-tetrahydro-2H-pyran-2-carbonyl)pyrrolidine-2-carboxylate To a cooled solution of (2S,3R,4S,5S)-ethyl 3-(tert-butyl)-5-(2-ethylphenyl)-4-hydroxy-1-((S)-tetrahydro-2H-pyran-2-carbonyl)pyrrolidine-2-carboxylate from Example 278C (324 mg, 0.751 mmol) in N,N-dimethylformamide (1.5 mL) was added potassium 2-methylpropan-2-olate, 1M in tetrahydrofuran (0.901 mL, 0.901 mmol) followed by propargyl bromide (134 mg, 0.901 mmol) dropwise over 2 minutes. After 15 minutes, the mixture was acidified with 1M aqueous HCl (20 drops) and warmed to ambient temperature. The mixture was diluted with methyl tert-butyl ether and water. The mixture was separated and the organics were washed with water and brine, concentrated and loaded onto a 10 g silica gel cartridge. The cartridge was eluted with 5-100% ethyl acetate/heptanes over 20 minutes to give (2S,3R,4S,5S)-ethyl 3-(tert-butyl)-5-(2-ethylphenyl)-4-(prop-2-yn-1-yloxy)-1-((S)-tetrahydro-2H-pyran-2-carbonyl)pyrrolidine-2-carboxylate. ¹H NMR (400 MHz, DMSO-d₆) δ ppm 7.93 (dd, J=7.6, 1.1 Hz, 1H), 7.17 (d, J=4.3 Hz, 2H), 7.15-7.06 (m, 1H), 5.48 (s, 1H), 4.61 (d, J=2.0 Hz, 1H), 4.29 (d, J=5.8 Hz, 1H), 4.16 (q, J=7.1 Hz, 2H), 3.71 (dd, J=11.4, 4.0 Hz, 1H), 3.58 (dd, J=16.2, 2.3 Hz, 1H), 3.42 (dd, J=16.2, 2.4 Hz, 1H), 2.96 (t, J=2.4 Hz, 1H), 2.73 (qd, J=7.5, 5.6 Hz, 2H), 2.36 (d, J=1.9 Hz, 1H), 1.71-1.60 (m, 1H), 1.57-1.42 (m, 1H), 1.41-1.29 (m, 3H), 1.25 (dt, J=13.3, 7.3 Hz, 7H), 1.01 (s, 11H); MS (APCI+) m/z 470 (M+H)⁺.

Example 278E (2S,3R,4S,5S)-ethyl 3-(tert-butyl)-5-(2-ethylphenyl)-4-((3-(2-methoxy-5-(trifluoromethyl)pyridin-3-yl)prop-2-yn-1-yl)oxy)-1-((S)-tetrahydro-2H-pyran-2-carbonyl)pyrrolidine-2-carboxylate (2S,3R,4S,5S)-Ethyl 3-(tert-butyl)-5-(2-ethylphenyl)-4-(prop-2-yn-1-yloxy)-1-((S)-tetrahydro-2H-pyran-2-carbonyl)pyrrolidine-2-carboxylate from Example 278D (100 mg, 0.213 mmol) and 3-bromo-2-methoxy-5-(trifluoromethyl)pyridine (36.0 μL, 0.234 mmol), copper(I) iodide (4.06 mg, 0.021 mmol) and tetrakis(triphenylphosphine)palladium(0) (24.61 mg, 0.021 mmol) were combined under nitrogen with nitrogen sparged toluene (568 μL) and triethylamine (284 μL). The resulting solution was heated to 50° C. for 17 hours. The solvent was removed under a stream of nitrogen and the crude material was added to diethyl ether, leaving behind a precipitate (PPh₃O). After filtration, the solid was rinsed with additional diethyl ether and the combined ether washes were purified using a 10 g silica gel cartridge eluting with 0-20% ethyl acetate/heptanes over 20 minutes to give (2S,3R,4S,5S)-ethyl 3-(tert-butyl)-5-(2-ethylphenyl)-4-((3-(2-methoxy-5-(trifluoromethyl)pyridin-3-yl)prop-2-yn-1-yl)oxy)-1-((S)-tetrahydro-2H-pyran-2-carbonyl)pyrrolidine-2-carboxylate. ¹H NMR (400 MHz, DMSO-d₆) δ ppm 8.47 (dd, J=2.4, 1.2 Hz, 1H), 7.96 (dd, J=7.4, 1.3 Hz, 1H), 7.86 (d, J=2.5 Hz, 1H), 7.21-7.07 (m, 3H), 5.52 (s, 1H), 4.64 (d, J=1.9 Hz, 1H), 4.43 (d, J=5.8 Hz, 1H), 4.16 (qd, J=7.1, 1.8 Hz, 2H), 3.99 (s, 3H), 3.92 (d, J=16.7 Hz, 1H), 3.71 (d, J=16.7 Hz, 1H), 2.78-2.65 (m, 2H), 2.42 (d, J=1.9 Hz, 1H), 1.70-1.59 (m, 2H), 1.57-1.42 (m, 2H), 1.33 (tt, J=7.7, 4.2 Hz, 5H), 1.23 (td, J=7.3, 1.4 Hz, 6H), 1.03 (s, 9H); MS (APCI+) m/z 645 (M+H)⁺.

Example 278F (2S,3R,4S,5S)-3-(tert-butyl)-5-(2-ethylphenyl)-4-((3-(2-methoxy-5-(trifluoromethyl)pyridin-3-yl)prop-2-yn-1-yl)oxy)-1-((S)-tetrahydro-2H-pyran-2-carbonyl)pyrrolidine-2-carboxylic acid (2S,3R,4S,5S)-Ethyl 3-(tert-butyl)-5-(2-ethylphenyl)-4-((3-(2-methoxy-5-(trifluoromethyl)pyridin-3-yl)prop-2-yn-1-yl)oxy)-1-((S)-tetrahydro-2H-pyran-2-carbonyl)pyrrolidine-2-carboxylate from Example 278E (91 mg, 0.141 mmol) and lithium hydroxide (31 mg, 1.294 mmol) were combined in methanol (0.5 mL), water (0.500 mL) and tetrahydrofuran (0.5 mL). The resulting solution was heated to 50° C. for 17 hours. The solvent was removed under a stream of nitrogen and was acidified with 2N aqueous HCl (0.65 mL). The crude material was purified using a 10 g silica gel cartridge eluting with an ethyl acetate/ethanol/heptanes solvent system to give (2S,3R,4S,5S)-3-(tert-butyl)-5-(2-ethylphenyl)-4-((3-(2-methoxy-5-(trifluoromethyl)pyridin-3-yl)prop-2-yn-1-yl)oxy)-1-((S)-tetrahydro-2H-pyran-2-carbonyl)pyrrolidine-2-carboxylic acid. $^1$H NMR (400 MHz, DMSO-$d_6$) δ ppm 8.47 (dd, J=2.4, 1.2 Hz, 1H), 8.02 (d, J=7.7 Hz, 1H), 7.87 (d, J=2.6 Hz, 1H), 7.22-7.08 (m, 3H), 5.53 (s, 1H), 4.60 (d, J=1.8 Hz, 1H), 4.45 (d, J=5.9 Hz, 1H), 3.99 (s, 3H), 3.94 (d, J=16.8 Hz, 1H), 3.78-3.66 (m, 3H), 2.83-2.65 (m, 3H), 2.48 (d, J=1.8 Hz, 2H), 1.65 (d, J=13.1 Hz, 1H), 1.50 (t, J=11.1 Hz, 1H), 1.33 (ddd, J=22.4, 11.7, 5.3 Hz, 4H), 1.23 (t, J=7.6 Hz, 3H), 1.03 (s, 9H); MS (APCI+) m/z 617 (M+H)$^+$.

Example 279

(2S,3R,4S,5S)-3-tert-butyl-1-(cyclohexanecarbonyl)-5-{2-[(propan-2-yl)oxy]pyridin-3-yl}-4-{[5-(trifluoromethyl)-1-benzofuran-3-yl]methoxy}pyrrolidine-2-carboxylic acid Example 279A 1-(allyloxy)-2-iodo-4-(trifluoromethyl)benzene A solution of 2-iodo-4-(trifluoromethyl)phenol (2.28 g, 7.92 mmol) in N,N-dimethylformamide (60 mL) was treated with $K_2CO_3$ (3.61 g, 26.1 mmol), treated with allyl bromide (2.261 mL, 26.1 mmol) and stirred at room temperature for 3 hours. The mixture was diluted with methyl tert-butyl ether (50 mL) and filtered to remove the solids. The filtrate was diluted with methyl tert-butyl ether (100 mL) and heptanes (150 mL). The mixture was washed with water (twice, 500 mL and 100 mL). The organic layer was washed with brine, dried (MgSO$_4$), filtered, and concentrated to provide the title compound, 1-(allyloxy)-2-iodo-4-(trifluoromethyl)benzene. $^1$H NMR (400 MHz, CDCl$_3$) δ ppm 8.03 (d, J=2.2 Hz, 1H), 7.55 (dd, J=2.2, 8.7 Hz, 1H), 6.84 (d, J=8.6 Hz, 1H), 6.05 (ddt, J=4.8, 10.6, 17.3 Hz, 1H), 5.53 (dq, J=1.5, 17.3 Hz, 1H), 5.37-5.33 (m, 1H), 4.66 (dt, J=1.6, 4.7 Hz, 2H).

Example 279B 3-methyl-5-(trifluoromethyl)benzofuran

A solution of Example 279A (1-(allyloxy)-2-iodo-4-(trifluoromethyl)benzene) (2.38 g, 7.25 mmol) in N,N-dimethylformamide (22 mL) was treated with sodium formate (0.523 g, 7.69 mmol), tetrabutylammonium chloride (2.480 g, 8.92 mmol), Na$_2$CO$_3$ (2.307 g, 21.76 mmol) and palladium(II) acetate (0.212 g, 0.943 mmol) and was stirred at 85° C. for 2 hours and then stirred overnight at room temperature. The mixture was diluted with methyl tert-butyl ether (50 mL) and the resulting solids were removed by filtration and discarded. The filtrate was diluted with additional methyl tert-butyl ether (100 mL) and heptanes (150 mL), and washed with water (twice, 500 mL and 100 mL). The organic layer was washed with brine, dried (MgSO$_4$), filtered, concentrated, and chromatographed on silica gel, eluting with pentane to provide the title compound, 3-methyl-5-(trifluoromethyl)benzofuran. $^1$H NMR (501 MHz, CDCl$_3$) δ ppm 7.83-7.81 (m, 1H), 7.55 (dd, J=1.8, 8.6 Hz, 1H), 7.52 (dt, J=0.7, 8.6 Hz, 1H), 7.50 (q, J=1.3 Hz, 1H), 2.28 (d, J=1.4 Hz, 3H).

Example 279C 3-(bromomethyl)-5-(trifluoromethyl)benzofuran

A solution of Example 279B (3-methyl-5-(trifluoromethyl)benzofuran) (95 mg, 0.475 mmol) and benzoyl peroxide (28.7 mg, 0.119 mmol) in chlorobenzene (2 mL) was heated to 120° C. and was treated with N-bromosuccinimide (84 mg, 0.475 mmol) in 4 portions in 10 minute intervals. The mixture was heated a further 2 hours at 120° C. and was cooled. The mixture was diluted with pentane (~30 mL). The solid was removed by filtration and was discarded. The filtrate was concentrated and chromatographed on silica gel, eluting with pentane to provide the title compound, 3-(bromomethyl)-5-(trifluoromethyl)benzofuran. $^1$H NMR (400 MHz, CDCl$_3$) δ ppm 8.00 (d, J=0.9 Hz, 1H), 7.80 (s, 1H), 7.64-7.57 (m, 2H), 4.63 (d, J=0.8 Hz, 2H).

Example 279D ethyl (2S,3R,4S,5S)-3-(tert-butyl)-1-(cyclohexanecarbonyl)-52824-((5-(trifluoromethyl)benzofuran-3-yl)methoxy)pyrrolidine-2-carboxylate Example 169B ((2S,3R,4S,5S)-ethyl 3-(tert-butyl)-1-(cyclohexanecarbonyl)-4-hydroxy-5-(2-isopropoxypyridin-3-yl)pyrrolidine-2-carboxylate) (28 mg, 0.061 mmol) was dissolved in toluene (~2 mL) and the resulting solution was concentrated. The residue was treated with Example 279C (3-(bromomethyl)-5-(trifluoromethyl)benzofuran) (22.05 mg, 0.079 mmol). The mixture was dissolved in N,N-dimethylformamide (0.5 mL) under N$_2$, cooled to −30° C., treated with 1 M potassium tert-butoxide in tetrahydrofuran (72.9 μL, 0.073 mmol), stirred at −20° C. for ~15 minutes, quenched with 1 M aqueous HCl (3 mL) and partitioned between water (5 mL) and ethyl acetate (50 mL). The ethyl acetate layer was washed with brine, dried (MgSO$_4$), filtered, concentrated and chromatographed on silica gel, eluting with a gradient of 15% to 100% ethyl acetate in heptane to provide the title compound, (2S,3R,4S,5S)-ethyl 3-(tert-butyl)-1-(cyclohexanecarbonyl)-5-(2-isopropoxypyridin-3-yl)-4-((5-(trifluoromethyl)benzofuran-3-yl)methoxy)pyrrolidine-2-carboxylate. LC/MS (ESI+) m/z 659 (M+H)$^+$.

Example 279E (2S,3R,4S,5S)-3-tert-butyl-1-(cyclohexanecarbonyl)-5-{2-[(propan-2-yl)oxy]pyridin-3-yl}-4-{[5-(trifluoromethyl)-1-benzofuran-3-yl]methoxy}pyrrolidine-2-carboxylic acid A solution of Example 279D ((2S,3R,4S,5S)-ethyl 3-(tert-butyl)-1-(cyclohexanecarbonyl)-5-(2-isopropoxypyridin-3-yl)-4-((5-(trifluoromethyl)benzofuran-3-yl)methoxy)pyrrolidine-2-carboxylate) (30 mg, 0.046 mmol) in tetrahydrofuran (1 mL) was diluted with methanol (0.5 mL), diluted with water (1 mL), treated with lithium hydroxide hydrate (38.2 mg, 0.911 mmol), heated to 55° C. for 4 hours, heated to 60° C. for 1 hour, and heated to 65° C. for 30 minutes. The mixture was cooled, acidified with 1 M aqueous HCl (4 mL) and extracted with ethyl acetate (30 mL). The ethyl acetate layer was washed with brine, dried (MgSO$_4$), filtered, concentrated and chromatographed on silica gel, eluting with a gradient of 15% to 100% [200:1:1 ethyl acetate:HCOOH:H₂O] in heptane to provide the title compound, (2S,3R,4S,5S)-3-(tert-butyl)-1-(cyclohexanecarbonyl)-5-(2-isopropoxypyridin-3-yl)-4-((5-(trifluoromethyl)benzofuran-3-yl)methoxy)pyrrolidine-2-carboxylic acid. $^1$H NMR (400 MHz, DMSO-d$_6$, 120° C.) δ ppm 8.19 (bs, 1H), 7.97-7.93 (m, 1H), 7.67 (d, J=8.6 Hz, 1H), 7.59-7.55 (m, 1H), 7.52 (s, 2H), 6.86-6.81 (m, 1H), 5.36 (bs, 1H), 5.27-5.17 (m, 1H), 4.56 (d, J=2.6 Hz, 1H), 4.48 (dd, J=1.0, 12.6 Hz, 1H), 4.32-4.25 (m, 2H), 2.56 (bs, 1H), 1.72-1.06 (m, 10H), 1.32 (d, J=5.9 Hz, 3H), 1.21 (d, J=6.2 Hz, 3H), 1.00 (s, 9H), 0.91-0.83 (m, 1H); LC/MS (APCI+) m/z 631 (M+H)$^+$.

Example 280

(2S,3R,4S,5S)-3-tert-butyl-5-(2-ethylphenyl)-4-{3-[2-methoxy-5-(trifluoromethyl)pyridin-3-yl]propoxy}-1-[(2S)-oxane-2-carbonyl]pyrrolidine-2-carboxylic acid (2S,3R,4S,5S)-3-(tert-Butyl)-5-(2-ethylphenyl)-4-((3-(2-methoxy-5-(trifluoromethyl)pyridin-3-yl)prop-2-yn-1-yl)oxy)-1-((S)-tetrahydro-2H-pyran-2-carbonyl)pyrrolidine-2-carboxylic acid from Example 278F (36 mg, 0.058 mmol) in tetrahydrofuran (1.0 mL) was added to 5% Pd/C (wet JM#9) (12.4 mg, 0.052 mmol) in a 20 mL Barnstead reactor. The reactor was purged with argon. The mixture was stirred at 1200 RPM under 50 psi of hydrogen at 25° C. for 17 hours. The mixture was filtered through a polypropylene membrane and the solvent was removed in vacuo to give (2S,3R,4S,5S)-3-(tert-butyl)-5-(2-ethylphenyl)-4-(3-(2-methoxy-5-(trifluoromethyl)pyridin-3-yl)propoxy)-1-((S)-tetrahydro-2H-pyran-2-carbonyl)pyrrolidine-2-carboxylic acid. $^1$H NMR (400 MHz, DMSO-d$_6$) δ ppm 8.30 (d, J=2.3 Hz, 1H), 8.00 (d, J=7.5 Hz, 1H), 7.37 (d, J=2.4 Hz, 1H), 7.11 (s, 3H), 5.52 (s, 1H), 4.57 (s, 1H), 3.97 (q, J=5.3, 4.9 Hz, 1H), 3.90 (s, 3H), 3.79-3.66 (m, 1H), 3.36-3.20 (m, 1H), 3.15-3.07 (m, 2H), 2.72-2.59 (m, 2H), 2.34 (s, 1H), 2.23-2.09 (m, 3H), 1.71-1.55 (m, 1H), 1.55-1.40 (m, 1H), 1.35 (s, 5H), 1.22 (t, J=7.5 Hz, 4H), 0.97 (s, 9H); MS (APCI+) m/z 621 (M+H)$^+$.

Example 281

(2S,3R,4S,5S)-3-tert-butyl-5-(5-iodo-2-methylphenyl)-4-{[2-methoxy-5-(trifluoromethyl)pyridin-3-yl]methoxy}-1-[(2S)-oxane-2-carbonyl]pyrrolidine-2-carboxylic acid Example 141 (207 mg, 0.358 mmol) was dissolved in dichloromethane (3.6 mL) and I$_2$ (100 mg, 0.394 mmol) and silver(I) trifluoromethanesulfonate (193 mg, 0.751 mmol) were added. The reaction mixture was stirred at room temperature for 1 hour. The reaction mixture was diluted with CH$_2$Cl$_2$ (10 mL) and stirred with saturated aqueous sodium thiosulfate (10 mL) for 10 minutes. After the red color disappeared, the mixture was filtered through a fritted funnel and the layers were separated. The organic layer was dried over sodium sulfate, filtered, and concentrated in vacuo. The crude material was separated via reverse-phase HPLC on a Phenomenex® C8(2) Luna® 5 μm AXIA™ 150×30 mm column using an aqueous trifluoroacetic acid (0.1%):CH$_3$CN mobile phase to give the title compound. $^1$H NMR (400 MHz, DMSO-d$_6$) δ ppm 8.42 (d, J=1.9 Hz, 1H), 8.31 (dd, J=2.6, 1.1 Hz, 1H), 7.41 (d, J=7.6 Hz, 1H), 7.19 (d, J=2.3 Hz, 1H), 6.88 (d, J=8.0 Hz, 1H), 5.46 (s, 1H), 4.67 (s, 1H), 4.41-4.22 (m, 2H), 3.89 (m, 1H), 3.89 (s, 3H), 3.82-3.74 (m, 1H), 3.20 (m, 1H), 2.44-2.39 (m, 1H), 2.28 (s, 3H), 1.70 (dt, J=13.2, 4.2 Hz, 1H), 1.57 (d, J=12.4 Hz, 1H), 1.41 (dd, J=19.2, 9.4 Hz, 5H), 1.02 (s, 9H); MS (ESI) m/z 705.0 (M+H)$^+$.

Example 282

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-[(1R,2R)-2-(trifluoromethyl)cyclohexane-1-carbonyl]pyrrolidine-2-carboxylic acid Example 282A (2S,3R,4S,5S)-ethyl 3-(tert-butyl)-5-(2-isopropoxypyridin-3-yl)-4-((2-methoxy-5-(trifluoromethyl)pyridin-3-yl)methoxy)-1-((1R,2R)-2-(trifluoromethyl)cyclohexanecarbonyl) pyrrolidine-2-carboxylate and (2S,3R,4S,5S)-ethyl 3-(tert-butyl)-5-(2-isopropoxypyridin-3-yl)-4-((2-methoxy-5-(trifluoromethyl)pyridin-3-yl)methoxy)-1-((1S,2S)-2-(trifluoromethyl)cyclohexanecarbonyl)pyrrolidine-2-carboxylate To 2-(trifluoromethyl)cyclohexanecarboxylic acid [CAS#384-20-3](160 mg, 0.815 mmol) in dichloromethane (2 mL) and one drop of N,N-dimethylformamide was added oxalyl dichloride (155 mg, 1.223 mmol, 0.62 mL, 2 M in dichloromethane) dropwise. The mixture was stirred at room temperature for 20 minutes, concentrated, and dissolved in dichloromethane (1 mL). The mixture was added to the solution of (2S,3R,4S,5S)-ethyl 3-(tert-butyl)-5-(2-isopropoxypyridin-3-yl)-4-((2-methoxy-5-(trifluoromethyl)pyridin-3-yl)methoxy)pyrrolidine-2-carboxylate (Example 271A, 220 mg, 0.408 mmol) in toluene (3 mL) and saturated aqueous NaHCO$_3$ (3 mL). The mixture was stirred at room temperature for 20 minutes. Dichloromethane (20 mL) and water (10 mL) were added and the organic layer was washed with brine, dried over MgSO$_4$, filtered, and concentrated. Purification via chromatography on a 24 g silica gel cartridge, eluting with ethyl acetate in heptane using a 0-40% gradient to provide the first eluent, arbitrarily assigned as (2S,3R,4S,5S)-ethyl 3-(tert-butyl)-5-(2-isopropoxypyridin-3-yl)-4-((2-methoxy-5-(trifluoromethyl)pyridin-3-yl)methoxy)-1-((1R,2R)-2-(trifluoromethyl)cyclohexanecarbonyl) pyrrolidine-2-carboxylate. MS (APCI) m/z 718.6 (M+H)$^+$; and the second eluent was arbitrarily assigned as (2S,3R,4S,5S)-ethyl 3-(tert-butyl)-5-(2-isopropoxypyridin-3-yl)-4-((2-methoxy-5-(trifluoromethyl)pyridin-3-yl)methoxy)-1-((1S,2S)-2-(trifluoromethyl)cyclohexanecarbonyl) pyrrolidine-2-carboxylate. MS (APCI+) m/z 718.6 (M+H)$^+$.

Example 282B (2S,3R,4S,5S)-3-(tert-butyl)-5-(2-isopropoxypyridin-3-yl)-4-((2-methoxy-5-(trifluoromethyl)pyridin-3-yl)methoxy)-1-((1R,2R)-2-(trifluoromethyl)cyclohexanecarbonyl)pyrrolidine-2-carboxylic acid To (2S,3R,4S,5S)-ethyl 3-(tert-butyl)-5-(2-isopropoxypyridin-3-yl)-4-((2-methoxy-5-(trifluoromethyl)pyridin-3-yl)methoxy)-1-((1R,2R)-2-(trifluoromethyl)cyclohexanecarbonyl) pyrrolidine-2-carboxylate (first eluent from Example 282A, 100 mg, 0.139 mmol) was added methanol (2 mL) and 6N aqueous LiOH (0.5 mL). The mixture was stirred at room temperature overnight. The pH was adjusted to 1~2 by adding 2N aqueous HCl and the precipitate was filtered, washed with water, and dried in vacuo to provide (2S,3R,4S,5S)-3-(tert-butyl)-5-(2-isopropoxypyridin-3-yl)-4-((2-methoxy-5-(trifluoromethyl)pyridin-3-yl)methoxy)-1-((1R,2R)-2-(trifluoromethyl)cyclohexanecarbonyl) pyrrolidine-2-carboxylic acid as a trifluoroacetic acid salt. $^1$H NMR (400 MHz, DMSO-$d_6$) δ ppm 8.41 (d, J=7.3 Hz, 1H), 8.33 (s, 1H), 7.98 (d, J=4.4 Hz, 1H), 7.15 (s, 1H), 6.88 (s, 1H), 5.57 (d, J=6.5 Hz, 1H), 5.25 (s, 1H), 4.46 (d, J=4.1 Hz, 1H), 4.38 (d, J=13.8 Hz, 1H), 4.26 (dd, J=6.6, 2.8 Hz, 1H), 4.00 (d, J=13.8 Hz, 1H), 3.88 (s, 3H), 3.19 (s, 1H), 2.66 (s, 1H), 2.43 (s, 1H), 2.21 (d, J=27.6 Hz, 2H), 1.68 (d, J=12.5 Hz, 2H), 1.50 (s, 1H), 1.26 (d, J=6.4 Hz, 3H), 1.21 (d, J=6.5 Hz, 3H), 1.16 (s, 2H), 1.00 (s, 9H), 0.87 (d, J=25.9 Hz, 2H); MS (ESI+) m/z 690.2 (M+H)$^+$.

Example 283

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-[(1S,2S)-2-(trifluoromethyl)cyclohexane-1-carbonyl]pyrrolidine-2-carboxylic acid The title compound was prepared according to the procedure described in Example 282B, substituting the second eluent from Example 282A for the first eluent from Example 282A, to provide the title compound. $^1$H NMR (400 MHz, DMSO-$d_6$) δ ppm 8.30 (d, J=1.8 Hz, 2H), 7.89 (s, 1H), 7.10 (s, 1H), 6.75 (s, 1H), 5.35 (s, 1H), 5.24 (h, J=6.3 Hz, 1H), 4.55 (d, J=2.9 Hz, 1H), 4.38 (d, J=13.8 Hz, 1H), 4.29 (d, J=6.0 Hz, 1H), 4.04 (d, J=20.9 Hz, 1H), 3.89 (s, 3H), 2.55 (s, 2H), 1.75-1.33 (m, 6H), 1.31 (d, J=6.2 Hz, 3H), 1.27 (d, J=5.0 Hz, 1H), 1.21 (d, J=6.1 Hz, 3H), 1.02 (s, 9H); MS (ESI+) m/z 690.1 (M+H)$^+$.

Example 284

(2S,3R,4S,5S)-3-tert-butyl-4-{2-[(5-chloro-2-methoxypyridin-3-yl)oxy]ethoxy}-5-(2-methylphenyl)-1-[(2S)-oxane-2-carbonyl]pyrrolidine-2-carboxylic acid Example 284A (2S,3R,4S,5S)-ethyl 4-(2-(tert-butoxy)-2-oxoethoxy)-3-(tert-butyl)-1-(tetrahydro-2H-pyran-2-carbonyl)-5-(o-tolyl)pyrrolidine-2-carboxylate A solution of (2S,3R,4S,5S)-ethyl 3-(tert-butyl)-4-hydroxy-1-((S)-tetrahydro-2H-pyran-2-carbonyl)-5-(o-tolyl)pyrrolidine-2-carboxylate (Example 188B, 505 mg, 1.209 mmol) and tert-butyl bromoacetate (894 μL, 6.05 mmol) in N,N-dimethylformamide (6 mL) was cooled to −40 C, treated dropwise with 1 M potassium tert-butoxide in tetrahydrofuran (2419 μL, 2.419 mmol), stirred at −40° C. for 5 minutes, and warmed to −20° C. The mixture was treated with additional 1 M potassium tert-butoxide in tetrahydrofuran (1209 μL, 1.209 mmol), stirred for 5 minutes, warmed to −15 C, treated with more 1 M potassium tert-butoxide in tetrahydrofuran (1209 μL, 1.209 mmol), stirred for 5 minutes, and quenched with saturated aqueous NH$_4$Cl solution (5 mL). The mixture was partitioned between methyl tert-butyl ether (75 mL) and water (75 mL). The layers were separated and the aqueous layer was extracted with methyl tert-butyl ether (50 mL). The combined methyl tert-butyl ether layers were washed with brine, dried (MgSO4), filtered, concentrated and chromatographed on an Analogix IntelliFlash 280 using a 25 g column eluting with 10% (1 minutes), 10 to 30% (over 14 minutes) ethyl acetate in heptane to provide the title compound. MS (APCI+) m/z 532 (M+H)$^+$.

Example 284B 2-(((2S,3S,4R,5S)-4-(tert-butyl)-5-(ethoxycarbonyl)-1-(tetrahydro-2H-pyran-2-carbonyl)-2-(o-tolyl)pyrrolidin-3-yl)oxy)acetic acid A solution of (2S,3R,4S,5S)-ethyl 4-(2-(tert-butoxy)-2-oxoethoxy)-3-(tert-butyl)-1-((S)-tetrahydro-2H-pyran-2-carbonyl)-5-(o-tolyl)pyrrolidine-2-carboxylate (Example 284A, 472 mg, 0.888 mmol) in trifluoroacetic acid (3 mL) was heated to 55° C. for 2 minutes. The reaction mixture was concentrated and dried under vacuum overnight at 50° C. to provide the title compound, 2-(((2S,3S,4R,5S)-4-(tert-butyl)-5-(ethoxycarbonyl)-1-((S)-tetrahydro-2H-pyran-2-carbonyl)-2-(o-tolyl)pyrrolidin-3-yl)oxy)acetic acid. MS (APCI+) m/z 476 (M+H)$^+$.

Example 284C (2S,3R,4S,5S)-ethyl 3-(tert-butyl)-4-(2-hydroxyethoxy)-1-(tetrahydro-2H-pyran-2-carbonyl)-5-(o-tolyl)pyrrolidine-2-carboxylate To a solution of 2-(((2S,3S,4R,5S)-4-(tert-butyl)-5-(ethoxycarbonyl)-1-(tetrahydro-2H-pyran-2-carbonyl)-2-(o-tolyl)pyrrolidin-3-yl)oxy)acetic acid (Example 284B, 360 mg, 0.757 mmol) in tetrahydrofuran (1 mL) at −10° C. was added 4-methylmorpholine (0.092 mL, 0.833 mmol), and isobutyl carbonochloridate (0.107 mL, 0.833 mmol). The mixture was stirred for 30 minutes and added to a solution of sodium borohydride (57.3 mg, 1.514 mmol) in H$_2$O (0.200 mL) at 0° C. After 30 minutes, the mixture was quenched via addition of saturated aqueous NH$_4$Cl and dichloromethane (230 mL). The organic layer was washed with brine, dried over MgSO$_4$, filtered, and concentrated. The residue was purified via chromatography on a 24 g silica gel cartridge, eluting with ethyl acetate in heptane, at 0-40% gradient to yield (2S,3R,4S,5S)-ethyl 3-(tert-butyl)-4-(2-hydroxyethoxy)-1-(tetrahydro-2H-pyran-2-carbonyl)-5-(o-tolyl)pyrrolidine-2-carboxylate. MS (APCI+) m/z 462.4 (M+H)$^+$.

Example 284D (2S,3R,4S,5S)-3-tert-butyl-4-{2-[(5-chloro-2-methoxypyridin-3-yl)oxy]ethoxy}-5-(2-methylphenyl)-1-[(2S)-oxane-2-carbonyl]pyrrolidine-2-carboxylic acid To a mixture of Example 284C (80 mg, 0.173 mmol) and 5-chloro-2-methoxypyridin-3-ol [cas 1261365-86-9] (27.7 mg, 0.173 mmol) in tetrahydrofuran (1 mL) was added triphenylphosphine (68.2 mg, 0.260 mmol), and (E)-di-tert-butyl diazene-1,2-dicarboxylate (59.9 mg, 0.260 mmol) portionwise. After 30 minutes, the mixture was quenched via addition of saturated aqueous NH$_4$Cl (5 mL) and dichloromethane (20 mL). The organic layer was washed with brine, dried over MgSO$_4$, filtered, and concentrated. The residue was purified via chromatography on a 24 g silica gel cartridge, eluting with ethyl acetate in heptane, at 0-40% gradient to yield (2S,3R,4S,5S)-ethyl 3-(tert-butyl)-4-(2-((5-chloro-2-methoxypyridin-3-yl)oxy)ethoxy)-1-(tetrahydro-2H-pyran-2-carbonyl)-5-(o-tolyl)pyrrolidine-2-carboxylate. The ester was dissolved in methanol (2 mL) and 6M aqueous LiOH (0.5 mL), and the mixture was stirred at 50° C. for 4 hours. The pH was adjusted to 0-1 by adding 2M aqueous HCl. The mixture was concentrated to dryness and was purified via HPLC with trifluoroacetic acid method to yield (2S,3R,4S,5S)-3-(tert-butyl)-4-(2-((5-chloro-2-methoxy-pyridin-3-yl)oxy)ethoxy)-1-((S)-tetrahydro-2H-pyran-2-carbonyl)-5-(o-tolyl)pyrrolidine-2-carboxylic acid. $^1$H NMR (400 MHz, DMSO-$d_6$) δ ppm 8.00-7.94 (m, 1H), 7.67 (d, J=2.3 Hz, 1H), 7.07 (d, J=2.8 Hz, 3H), 7.02 (d, J=2.2 Hz, 1H), 5.47 (s, 1H), 4.60-4.51 (m, 1H), 4.25 (dd, J=5.9, 1.3 Hz, 1H), 3.85 (s, 3H), 3.79-3.73 (m, 1H), 3.73-3.68 (m, 1H), 3.62 (ddd, J=11.0, 5.8, 3.8 Hz, 1H), 3.42 (m, 1H), 3.29 (ddd, J=11.8, 6.2, 4.0 Hz, 1H), 3.05 (ddd, J=11.8, 5.8, 3.9 Hz, 2H), 2.40 (d, J=2.2 Hz, 1H), 2.34 (s, 3H), 1.70-1.60 (m, 1H), 1.51 (q, J=11.8, 10.5 Hz, 1H), 1.43-1.06 (m, 4H), 1.00 (s, 9H); MS (ESI+) m/z 575.2 (M+H)$^+$.

Example 285

(2S,3R,4S,5S)-3-tert-butyl-4-[(5-tert-butyl-2-methoxyphenyl)methoxy]-1-[(2S)-oxane-2-carbonyl]-5-{2-[(propan-2-yl)oxy]pyridin-3-yl}pyrrolidine-2-carboxylic acid

Example 285A (2S,3R,4S,5S)-1-allyl 2-ethyl 3-(tert-butyl)-5-(2-isopropoxypyridin-3-yl)-4-nitropyrrolidine-1,2-dicarboxylate To a mixture of (2S,3R,4S,5S)-ethyl 3-(tert-butyl)-5-(2-isopropoxypyridin-3-yl)-4-nitropyrrolidine-2-carboxylate (Core 7, 10.237 g, 27.0 mmol) in toluene (100 mL) and saturated aqueous NaHCO$_3$ (50 mL) was added allyl carbonochloridate (3.0 mL, 28.2 mmol) dropwise at room temperature. The mixture was stirred for 30 minutes. Methyl tert-butyl ether (400 mL) was added and the organic layer was washed sequentially with 1M aqueous HCl, 1M aqueous NaOH, and brine, dried over MgSO$_4$, filtered, and concentrated to dryness to provide the title compound, which used in next step without further purification. $^1$H NMR (400 MHz, DMSO-$d_6$) δ ppm 8.00 (dd, J=4.9, 1.9 Hz, 1H), 7.96 (ddd, J=7.4, 1.9, 0.8 Hz, 1H), 6.85 (dd, J=7.4, 5.0 Hz, 1H), 5.80-5.66 (m, 1H), 5.53 (d, J=8.3 Hz, 1H), 5.42 (dd, J=8.3, 2.8 Hz, 1H), 5.28 (dt, J=12.4, 6.1 Hz, 1H), 5.08 (t, J=1.6 Hz, 1H), 5.05 (dq, J=6.9, 1.6 Hz, 1H), 4.58 (d, J=3.5 Hz, 1H), 4.46 (ddt, J=4.2, 3.1, 1.6 Hz, 2H), 4.28-4.19 (m, 2H), 2.96 (ddd, J=3.6, 2.8, 0.7 Hz, 1H), 2.46 (p, J=1.9 Hz, 1H), 1.32 (dd, J=6.8, 6.2 Hz, 6H), 1.27 (t, J=7.1 Hz, 2H), 1.01 (s, 9H); MS (APCI+) m/z 464 (M+H)$^+$.

Example 285B (2S,3R,5S)-1-allyl 2-ethyl 3-(tert-butyl)-5-(2-isopropoxypyridin-3-yl)-4-oxopyrrolidine-1,2-dicarboxylate A 500 mL flask was charged DBU (1,8-diazabicyclo[5.4.0]undec-7-ene) (14.64 mL, 97 mmol) and CS$_2$ (8.36 mL, 139 mmol) in (55.5 mL). The mixture was stirred at room temperature for 1 hour and was cooled down to 0° C. Example 285A (12.86 g, 27.7 mmol) in acetonitrile (5 mL) was added. After the addition, the mixture allowed to room temperature and was stirred for 2 hours. Ethyl acetate (200 mL) and 100 mL brine were added to the mixture, and the organic layer was washed with brine, dried over Na$_2$SO$_4$, filtered and concentrated. CH$_3$CN (100 mL) and 20% H$_3$PO$_4$ (100 mL) solution were added to hydrolyze the resulted imine at room temperature for 4 hours. Ethyl acetate (200 mL) and brine (100 mL) were added to the reaction mixture. The organic layer was washed with 80 mL of brine, dried over Na$_2$SO$_4$, filtered and concentrated. Purification via chromatography using a 220 g silica gel cartridge, eluting with a gradient of 0-30% ethyl acetate in heptane provided the title compound. HPLC 97.8 PA % at 11.45 minute; MS (APCI+) m/z 444 (M+H)$^+$.

Example 285C (2S,3R,4S,5S)-1-allyl 2-ethyl 3-(tert-butyl)-4-hydroxy-5-(2-isopropoxypyridin-3-yl)pyrrolidine-1,2-dicarboxylate To Example 285B (10.33 g, 23.88 mmol) in ethanol (119 mL) cooled to <-10° C. in a brine-ice bath was added sodium borohydride (0.994 g, 26.3 mmol) in one portion. After the addition, the temperature was allowed to warm to room temperature and the mixture was stirred for 40 minutes. The reaction was quenched by adding acetone (20 mL) slowly over 10 minutes. The mixture was concentrated under reduced pressure and the residue was partitioned between saturated aqueous sodium bicarbonate and methyl tert-butyl ether. The organic layer was washed with 1M aqueous HCl and brine, dried over sodium sulfate, filtered, and concentrated. Purification of the residue via chromatography on a 80 g silica gel cartridge, eluting with ethyl acetate in heptane at 0-30% gradient to provide the title compound. MS (APCI+) m/z 435.5 (M+H)$^+$.

Example 285D 2S,3R,4S,5S)-1-allyl 2-ethyl 3-(tert-butyl)-4-((5-(tert-butyl)-2-methoxybenzyl)oxy)-5-(2-isopropoxypyridin-3-yl)pyrrolidine-1,2-dicarboxylate To Example 285C (500 mg, 1.151 mmol) and 2-(bromomethyl)-4-(tert-butyl)-1-methoxybenzene (Intermediate 6, 355 mg, 1.381 mmol) in N,N-dimethylformamide (5 mL) cooling in an ice bath, potassium 2-methylpropan-2-olate (1.83 mL, 1.0 M in tetrahydrofuran) was added dropwise. The mixture was stirred in ice bath for 20 minutes, and allowed to warm to ambient temperature. Ethyl acetate (30 mL) and water (10 mL) were added. The organic layer was washed with brine, dried over MgSO$_4$, filtered, and concentrated to provide the title compound, which used in next step without further purification. MS (APCI+) m/z 611 (M+H)$^+$.

Example 285E (2S,3R,4S,5S)-ethyl 3-(tert-butyl)-4-((5-(tert-butyl)-2-methoxybenzyl)oxy)-5-(2-isopropoxypyridin-3-yl)pyrrolidine-2-carboxylate To a solution of 285D (700 mg, 1.146 mmol) and 1,3-dimethylpyrimidine-2,4,6(1H,3H,5H)-trione (358 mg, 2.292 mmol) in ethyl acetate/dichloromethane (10 mL, 1:1) was added Pd(Ph$_3$)$_4$ (tetrakis(triphenylphosphine)palladium(0), 23.65 mg, 0.023 mmol). The mixture was stirred at room temperature for 20 minutes. Dichloromethane (20 mL) and water (10 mL) were added, and the organic layer was washed with brine, dried over MgSO$_4$, filtered, and concentrated. The residue was purified via chromatography on a 24 g silica gel cartridge, eluting with ethyl acetate in heptane at 0-40% gradient to provide the title compound. MS (APCI+) m/z 527.6 (M+H)$^+$.

Example 285F (2S,3R,4S,5S)-3-tert-butyl-4-[(5-tert-butyl-2-methoxy-phenyl)methoxy]-5-(2-isopropoxy-3-pyridyl)-1-[(2S)-tetrahydropyran-2-carbonyl]pyrrolidine-2-carboxylic acid To (S)-tetrahydro-2H-pyran-2-carboxylic acid (29.7 mg, 0.228 mmol) in dichloromethane (2 mL) and one drop of N,N-dimethylformamide was added oxalyl dichloride(38.6 mg, 0.304 mmol) dropwise. The mixture was stirred at room temperature for 20 minutes, and the solvent was evaporated under reduced pressure. The residue was dissolved in dichloromethane (1 mL) and added to a solution of Example 285E (80 mg, 0.152 mmol) in a mixture of toluene and saturated aqueous NaHCO$_3$ (6 mL, 1:1) at room temperature. The mixture was stirred at room temperature for 20 minutes. Ethyl acetate (20 mL) and water (10 mL) were added and the organic layer was washed with brine, dried over MgSO$_4$, filtered, and concentrated. The residue was purified via chromatography on a 14 g silica gel cartridge, eluting with ethyl acetate in heptane, at 0-40% gradient to provide (2S,3R,4S,5S)-ethyl 3-(tert-butyl)-4-((5-(tert-butyl)-2-methoxybenzyl)oxy)-5-(2-isopropoxypyridin-3-yl)-1-((S)-tetrahydro-2H-pyran-2-carbonyl)pyrrolidine-2-carboxylate, which dissolved in methanol (2 mL) and 6N aqueous LiOH (0.5 mL). The mixture was stirred at 50° C. overnight. The pH of the reaction mixture was adjusted to 0-1 by adding 2N aqueous HCl and the mixture was concentrated. The residue was purified via a 24 g silica gel cartridge, eluting with ethyl acetate/methanol in heptane to provide the title compound. $^1$H NMR (400 MHz, DMSO-d$_6$) δ ppm 8.21 (s, 1H), 7.96 (s, 1H), 7.11 (dd, J=8.5, 2.6 Hz, 1H), 6.83 (d, J=2.7 Hz, 2H), 6.74 (d, J=8.5 Hz, 1H), 5.61 (s, 1H), 5.29 (p, J=6.1 Hz, 1H), 4.60 (s, 1H), 4.29 (d, J=12.4 Hz, 1H), 4.21 (dd, J=6.2, 1.9 Hz, 1H), 3.96 (d, J=12.4 Hz, 1H), 3.83-3.75 (m, 1H), 3.63 (s, 3H), 3.44 (d, J=10.8 Hz, 1H), 2.45 (d, J=2.3 Hz, 1H), 1.69 (d, J=12.7 Hz, 1H), 1.54 (s, 1H), 1.38 (s, 2H), 1.34 (d, J=6.2 Hz, 3H), 1.29 (s, 1H), 1.26 (d, J=6.1 Hz, 1H), 1.17 (s, 9H), 1.13-1.00 (m, 1H), 0.97 (s, 9H), 0.90-0.79 (m, 1H); MS (ESI+) m/z 611.4 (M+H)$^+$.

Example 286

(2S,3R,4S,5S)-3-tert-butyl-4-{[2-methoxy-5-(trifluoromethyl)pyridin-3-yl]methoxy}-5-[2-($^2$H$_3$)methyl-phenyl]-1-[(2S,3S)-(2,3-$^2$H$_2$)oxane-2-carbonyl](2-$^2$H)pyrrolidine-2-carboxylic acid Example 286A (2S,3R,4S,5S)-ethyl 3-(tert-butyl)-1-((2S,3S)-2,3-d$_2$-tetrahydro-2H-pyran-2-carbonyl)-4-((2-methoxy-5-(trifluoromethyl)pyridin-3-yl)methoxy)-5-(2-bromophenyl)pyrrolidine-2-carboxylate Argon-degassed 3% triethylamine-d$_{15}$ in CH$_3$OD (20 mL) was added to 3,4-dihydro-2H-pyran-6-carboxylic acid (0.976 g, 7.62 mmol), and diacetato[(S)-(−)-5,5'-bis(diphenylphosphino)-4,4'-bi-1,3-benzodioxole]ruthenium(II) (0.134 g, 0.161 mmol) under argon in a 50 mL SS reactor. The mixture was stirred at room temperature under argon. The vessel was vented, pressurized with 50 psi deuterium, and stirred at 60° C. under 120 psi of deuterium for 22 hours. The solvent was removed in vacuo and the residue was taken up in CH$_2$Cl$_2$ (20 mL), washed with D$_2$O (3×5 mL), dried over sodium sulfate, filtered, and concentrated in vacuo. The crude material was dissolved in 21 mL of CH$_2$Cl$_2$ and the solution was treated with oxalyl chloride (0.93 mL, 10.6 mmol, 2 eq) and N,N-dimethylformamide (0.020 mL, 0.05 eq). The reaction mixture was stirred at room temperature for 1 hour and the volatile material was removed in vacuo. The resulting material was azeotroped with 2×10 mL of CH$_2$Cl$_2$ to give the crude acid chloride, which was used immediately without additional purification. In a separate round-bottomed flask, Example 178B (1.25 g, 2.234 mmol) was dissolved in 10 mL of dichloromethane. The resulting solution was cooled to <5° C. in an ice water bath, and triethylamine (0.779 mL, 5.59 mmol) was added, followed by dropwise addition of the freshly-prepared solution of the acid chloride in dichloromethane (7 mL). After five minutes, 1M aqueous HCl (10 mL) was added and the biphasic mixture was stirred for 5 minutes at room temperature. The layers were separated. The organic layer was washed with aqueous 1M HCl (2×10 mL) and aqueous 1M NaOH (10 mL) then brine (10 mL), dried over sodium sulfate, filtered, and concentrated in vacuo to give a crude mixture of diastereomers in approximately a 7:1 ratio, which was purified via flash chromatography, eluting with 0:100 to 10:90 methyl tert-butyl ether:heptanes over 20 minutes on a 120 g silica gel column to provide the title compound. $^1$H NMR (400 MHz, DMSO-d$_6$, 120° C.) δ ppm 8.30 (d, J=2.1 Hz, 1H), 8.06 (d, J=7.9 Hz, 1H), 7.50 (d, J=7.9 Hz, 1H), 7.25 (s, 1H), 7.17 (d, J=2.5 Hz, 1H), 7.12 (s, 1H), 4.74 (s, 1H), 4.39 (d, J=5.9 Hz, 1H), 4.33 (d, J=13.6 Hz, 1H), 4.10 (qd, J=7.1, 2.2 Hz, 2H), 3.95 (d, J=13.7 Hz, 1H), 3.88 (s, 3H), 3.82-3.75 (m, 1H), 2.44 (t, J=1.3 Hz, 1H), 1.68 (d, J=12.9 Hz, 1H), 1.45 (d, J=50.4 Hz, 3H), 1.15 (t, J=7.1 Hz, 3H), 1.03 (s, 9H); MS (ESI) m/z 673.0 (M+H)$^+$.

Example 286B (2S,3R,4S,5S)-ethyl 3-(tert-butyl)-1-((2S,3S)-2,3-d$_2$-tetrahydro-2H-pyran-2-carbonyl)-4-((2-methoxy-5-(trifluoromethyl)pyridin-3-yl)methoxy)-5-(2-(d$_3$-methyl)phenyl)pyrrolidine-2-carboxylate 1,2-Dioxane (17 mL) and D$_2$O (4.3 mL) were degassed with a stream of N$_2$ for 120 minutes. Example 286A (725 mg, 1.076 mmol), cesium carbonate (1.4 g, 4.3 mmol), and 1,1'-bis(diphenylphosphino)ferrocene-palladium(II)dichloride dichloromethane complex (440 mg, 0.538 mmol) were weighed into a 30 mL scintillation vial, and the vial was purged with N$_2$ for 20 minutes. The solvents were added to the vial, followed by methyl-d$_3$-boronic acid (0.53 mL, 3.23 mmol) and the reaction mixture was sealed and heated to 95° C. in a preheated heating block. After 2 hours, the vial was cooled to room temperature, opened, and sampled on LC-MS, which showed complete conversion of the starting material. The reaction mixture was diluted with methyl tert-butyl ether (50 mL) and washed with 10 mL of D$_2$O. The organic layer was dried over sodium sulfate, filtered, and concentrated in vacuo. The residue was purified via flash chromatography, eluting on an 80 g silica gel column with 0:100 to 20:80 methyl tert-butyl ether:heptanes over 25 minutes to provide the title compound. $^1$H NMR (400 MHz, DMSO-d$_6$, 120° C.) δ ppm 8.34-8.25 (m, 1H), 8.05-7.93 (m, 1H), 7.28-7.17 (m, 1H), 7.08 (d, J=8.2 Hz, 3H), 5.56 (s, 1H), 4.69 (s, 1H), 4.33-4.23 (m, 2H), 4.10 (qd, J=7.1, 2.7 Hz, 2H), 3.87 (s, 3H), 3.81 (s, 1H), 3.80-3.72 (m, 1H), 2.44-2.39 (m, 1H), 1.66 (d, J=12.7 Hz, 1H), 1.49 (d, J=11.3 Hz, 1H), 1.34 (t, J=27.6 Hz, 4H), 1.15 (t, J=7.1 Hz, 3H), 1.03 (s, 9H); MS (ESI) m/z 612.1 (M+H)$^+$.

Example 286C 2S,3R,4S,5S)-3-tert-butyl-4-{[2-methoxy-5-(trifluoromethyl)pyridin-3-yl]methoxy}-5-[2-($^2$H$_3$)methylphenyl]-1-[(2S,3S)-(2,3-$^2$H$_2$)oxane-2-carbonyl](2-$^2$H)pyrrolidine-2-carboxylic acid Example 286B (315 mg, 0.515 mmol) was dissolved in 1.5 mL of CD$_3$OD. Sodium hydroxide (103 mg, 2.57 mmol), was added, and the resulting suspension was heated to 50° C. for 4 hours. The solution was cooled to room temperature, washed with heptanes (2×1 mL) and was diluted with D$_2$O (0.5 mL). The resulting sodium salt of the title compound was extracted into methyl tert-butyl ether (3×5 mL). The combined organic extracts were concentrated in vacuo and the residue was redissolved in ethyl acetate and 5 mL of water and 3 mL of HCl were added to give a solution of pH=2. The desired product was extracted into ethyl acetate (3×5 mL), and the combined extracts were dried over sodium sulfate, filtered, and concentrated in vacuo to provide the title compound. (Deuterium exchange of the ester methine proton occurred during the reaction conditions). $^1$H NMR (400 MHz, DMSO-d$_6$, 120° C.) δ ppm 8.28 (dd, J=2.5, 1.1 Hz, 1H), 8.10-7.94 (m, 1H), 7.22-7.16 (m, 1H), 7.15-7.00 (m, 3H), 5.56 (s, 1H), 4.34-4.25 (m, 2H), 3.88 (s, 3H), 3.85 (s, 1H), 3.75 (s, 1H), 2.44-2.39 (m, 1H), 1.72-1.61 (m, 1H), 1.51 (d, J=11.7 Hz, 1H), 1.45-1.21 (m, 4H), 1.03 (s, 9H); MS (ESI) m/z 585.2 (M+H)$^+$.

Example 287

(2S,3R,4S,5S)-3-tert-butyl-1-(cyclohexanecarbonyl)-4-{[2-methoxy-5-(1-methylcyclopropyl)pyridin-3-yl]methoxy}-5-{2-[(propan-2-yl)oxy]pyridin-3-yl}pyrrolidine-2-carboxylic acid Example 169B (60 mg, 0.13 mmol) was dissolved into anhydrous toluene, dried over NaSO$_4$, filtered, and concentrated. The residue was placed under nitrogen, a solution of Example 243D (38 mg, 0.15 mmol) in anhydrous N,N-dimethylformamide (400 µL) was added, and the mixture was cooled to −40° C. Potassium tert-butoxide in tetrahydrofuran (1 M, 0.14 mL, 0.14 mmol) was added dropwise over eight minutes, and the reaction mixture was stirred for 15 minutes near −40° C. The mixture was allowed to warm to −5° C. over an hour before being quenched with 3 M aqueous citric acid (30 µL). Brine was added, the reaction mixture was extracted thrice with methyl tert-butyl ether and the combined organic phases were dried (Na$_2$SO$_4$), filtered, and concentrated. The residue was diluted with methanol (900 µL), treated with 1.5 M aqueous NaOH (1.2 mL) and heated at 55° C. for 24 hours. Methanol (900 µL), tetrahydrofuran (900 µL) and 1.5 M aqueous LiOH (600 µL) were added and the reaction mixture was heated at 65° C. overnight. Additional tetrahydrofuran (1.8 mL) and 1.5 M aqueous LiOH (1.2 mL) were added and the reaction mixture was stirred at room temperature over the weekend. NaOH (50% aqueous 200 µL) was added and the reaction mixture was heated at 55° C. overnight. The reaction mixture was brought to room temperature, concentrated, diluted with methyl tert-butyl ether, acidified with 1 M aqueous citric acid and stirred well. The aqueous phase was separated and extracted with methyl tert-butyl ether and the combined organic phases were concentrated and chromatographed on silica (20 to 50% methyl tert-butyl ether in 1:3 CH$_2$Cl$_2$/heptane) to provide the title compound. MS (ESI+) m/z 608 (M+H)$^+$.

Example 288

(2S,3R,4S,5S)-3-tert-butyl-4-{2-[2-methoxy-5-(trifluoromethyl)phenoxy]ethoxy}-5-(2-methylphenyl)-1-[(2S)-oxane-2-carbonyl]pyrrolidine-2-carboxylic acid The title compound was prepared according to the procedure described in Example 284D, substituting 2-methoxy-5-(trifluoromethyl)phenol [cas 349-67-7] for 5-chloro-2-methoxypyridin-3-ol. $^1$H NMR (400 MHz, DMSO-d$_6$) δ ppm 7.97 (dd, J=5.9, 2.9 Hz, 1H), 7.22 (ddq, J=8.4, 1.7, 0.8 Hz, 1H), 7.07 (d, J=8.4 Hz, 4H), 6.92 (d, J=2.2 Hz, 1H), 5.48 (s, 1H), 4.56 (d, J=2.3 Hz, 1H), 4.27 (dd, J=5.9, 1.3 Hz, 1H), 3.80 (s, 3H), 3.76 (d, J=11.3 Hz, 1H), 3.69 (ddd, J=10.5, 6.1, 4.2 Hz, 1H), 3.60 (ddd, J=10.6, 5.7, 4.2 Hz, 1H), 3.39 (s, 1H), 3.32-3.26 (m, 1H), 3.09-3.04 (m, 2H), 2.41 (d, J=1.9 Hz, 1H), 2.34 (s, 3H), 1.70-1.59 (m, 1H), 1.61-1.45 (m, 1H), 1.45-1.19 (m, 3H), 1.12 (d, J=30.1 Hz, 1H), 1.00 (s, 9H); MS (ESI+) m/z 608.2 (M+H)$^+$.

Example 289

(2S,3R,4S,5S)-4-[(5-bromo-1-benzofuran-2-yl)methoxy]-3-tert-butyl-1-[(2S)-oxane-2-carbonyl]-5-{2-[(propan-2-yl)oxy]pyridin-3-yl}pyrrolidine-2-carboxylic acid The title compound was prepared according to the procedure described in Example 285D to Example 285F, substituting 5-bromo-2-(bromomethyl) benzofuran [CAS#84102-72-7] for (2-(bromomethyl)-4-(tert-butyl)-1-methoxybenzene (Intermediate 6). $^1$H NMR (400 MHz, DMSO-d$_6$) δ ppm 8.20 (s, 1H), 8.04 (d, J=4.7 Hz, 1H), 7.71 (dd, J=1.8, 0.9 Hz, 1H), 7.38-7.36 (m, 2H), 6.90 (t, J=6.1 Hz, 1H), 6.39 (d, J=0.9 Hz, 1H), 5.63 (s, 1H), 5.26 (hept, J=6.0 Hz, 1H), 4.63 (s, 1H), 4.35-4.24 (m, 2H), 4.18 (dd, J=13.7, 0.8 Hz, 1H), 3.80 (d, J=11.4 Hz, 1H), 3.58 (s, 2H), 2.46 (d, J=2.4 Hz, 1H), 1.76-1.36 (m, 5H), 1.35 (d, J=6.1 Hz, 3H), 1.25-1.22 (m, 3H), 1.22-1.12 (m, 1H), 0.99 (s, 9H); MS (ESI+) m/z 643.1 (M+H)$^+$.

Example 290

(2S,3R,4S,5S)-3-tert-butyl-4-[(6-tert-butyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid

Example 290A 3-(bromomethyl)-6-(tert-butyl)-2-methoxypyridine

To triphenylphosphine (2.216 g, 8.45 mmol) in dichloromethane (10 mL) cooling in an ice bath was added 1-bromopyrrolidine-2,5-dione (1.504 g, 8.45 mmol) portionwise. The mixture was stirred for 30 minutes, maintaining an internal temperature <10° C., and (6-(tert-butyl)-2-methoxypyridin-3-yl) methanol (1.1 g, 5.63 mmol) in dichloromethane (10 mL) was added in portions at <10° C. The mixture was stirred in ice bath for 1 hour and was allowed to warm to ambient temperature. The mixture was stirred overnight. Saturated aqueous NH$_4$Cl (2 mL) was added and the mixture was washed with saturated aqueous sodium bicarbonate. The organic layer was dried over MgSO$_4$, filtered, and concentrated. Purification via chromatography on 24 g silica gel cartridge, eluting with ethyl acetate in heptane at 0-30% gradient provided the title compound. $^1$H NMR (400 MHz, Chloroform-d) δ ppm 7.51 (dd, J=7.6, 1.4 Hz, 1H), 6.84 (dd, J=7.7, 1.5 Hz, 1H), 4.49 (d, J=1.5 Hz, 2H), 4.00 (d, J=1.5 Hz, 3H), 1.32 (d, J=1.5 Hz, 9H); MS (ESI+) m/z 258.0 (M+H)$^+$.

Example 290B (2S,3R,4S,5S)-3-tert-butyl-4-[(6-tert-butyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid The title compound was prepared according to the procedures described in Example 285C to Example 285F, substituting Example 290A for Intermediate 6. $^1$H NMR (400 MHz, DMSO-d$_6$) δ ppm 8.16 (s, 1H), 7.98 (s, 1H), 6.86 (t, J=6.8 Hz, 2H), 6.70 (d, J=7.6 Hz, 1H), 5.60 (s, 1H), 5.25 (p, J=6.1 Hz, 1H), 4.63 (s, 1H), 4.23-4.17 (m, 2H), 3.95 (dd, J=13.1, 0.9 Hz, 1H), 3.79 (s, 3H), 3.77 (s, 2H), 3.59-3.44 (m, 2H), 3.47 (d, J=109.1 Hz, 2H), 2.43 (d, J=2.1 Hz, 1H), 1.70 (d, J=12.5 Hz, 1H), 1.63-1.35 (m, 4H), 1.33 (d, J=6.0 Hz, 3H), 1.30 (d, J=1.1 Hz, 1H), 1.25 (s, 9H), 1.23 (d, J=6.1 Hz, 3H), 0.98 (s, 9H); MS (ESI+) m/z 612.2 (M+H)$^+$.

Example 291

(2S,3R,4S,5S)-3-tert-butyl-4-[(6-tert-butyl-2-methoxypyridin-3-yl)methoxy]-1-(cyclohexanecarbonyl)-5-{2-[(propan-2-yl)oxy]pyridin-3-yl}pyrrolidine-2-carboxylic acid The title compound was prepared according to the procedures described in Example 285C to Example 285F, substituting Example 290A for Intermediate 6, and cyclohexanecarbonyl chloride for (S)-tetrahydro-2H-pyran-2-carboxylic acid, respectively. $^1$H NMR (400 MHz, DMSO-d$_6$) δ ppm 8.16 (s, 1H), 7.98 (s, 1H), 6.86 (t, J=8.9 Hz, 2H), 6.70 (d, J=7.6 Hz, 1H), 5.33 (s, 1H), 5.27 (p, J=6.1 Hz, 1H), 4.52 (d, J=2.7 Hz, 1H), 4.24-4.15 (m, 2H), 3.97 (d, J=13.0 Hz, 1H), 3.79 (s, 3H), 2.3-2.15 (m, 2H), 1.67 (d, J=9.3 Hz, 2H), 1.52 (s, 2H), 1.32 (d, J=6.1 Hz, 3H), 1.25 (s, 12H), 1.11 (d, J=14.6 Hz, 3H), 0.98 (s, 9H), 0.91-0.77 (m, 2H); MS (ESI+) m/z 610 (M+H)$^+$.

Example 292

(2S,3R,4S,5S)-3-tert-butyl-5-(2-ethylphenyl)-1-[(2S)-oxane-2-carbonyl]-4-{[7-(trifluoromethyl)-1-benzofuran-2-yl]methoxy}pyrrolidine-2-carboxylic acid Into a 4 mL vial was weighed Example 278D (30 mg, 0.064 mmol, 1.0 eq), tetrakis(triphenylphosphine)palladium (0) (7.38 mg, 0.0064 mmol, 0.10 eq) and CuI (1.2 mg, 0.0064 mmol, 0.10 eq). N,N-dimethylformamide (500 μL) was added, followed by neat 2-iodo-6-(trifluoromethyl)phenol (20.2 mg, 0.070 mmol, 1.1 eq), and neat trimethylamine (90 μL, 0.64 mmol, 10 eq). The reaction was stirred overnight at 60° C. The crude material was purified via preparative reverse phase HPLC/MS method trifluoroacetic acid8 and carried forward without further characterization. The material was dissolved in 500 μL 3:2 tetrahydrofuran/methanol. LiOH monohydrate (5 M in water, 100 L) was added and the reaction was stirred overnight at 50° C. The solvent was removed under a stream of nitrogen. The residue was acidified with 2 M aqueous HCl and extracted with dichloromethane (3×1 mL). The solvent was removed under a stream of nitrogen, and the residue was dissolved in CH$_3$CN and purified using preparative reverse phase HPLC/MS method trifluoroacetic acid8. $^1$H NMR (400 MHz, 120° C., DMSO-d$_6$:D$_2$O=9:1 (v/v)) δ ppm 8.02 (dd, J=7.7, 1.5 Hz, 1H), 7.80 (d, J=7.8 Hz, 1H), 7.54 (dt, J=7.7, 1.0 Hz, 1H), 7.37 (tt, J=7.8, 0.9 Hz, 1H), 7.24-7.09 (m, 3H), 6.53-6.47 (m, 1H), 5.54-5.49 (m, 1H), 4.63 (d, J=1.9 Hz, 1H), 4.28 (d, J=5.7 Hz, 1H), 4.12-3.98 (m, 2H), 3.74 (d, J=11.4 Hz, 1H), 3.61-3.33 (m, 1H), 3.08-2.87 (m, 1H), 2.80-2.52 (m, 2H), 2.46 (d, J=1.9 Hz, 1H), 1.71-1.59 (m, 1H), 1.56-1.45 (m, 1H), 1.42-1.26 (m, 3H), 1.22-1.02 (m, 4H), 0.97 (s, 9H); MS (APCI+) m/z 602.0 (M+H)$^+$.

Example 293

(2S,3R,4S,5S)-3-tert-butyl-4-[(5-chloro-1-benzofuran-2-yl)methoxy]-5-(2-ethylphenyl)-1-[(2S)-oxane-2-carbonyl]pyrrolidine-2-carboxylic acid Example 293 was prepared following the general procedure used to prepare Example 292, substituting 2-iodo-4-chlorophenol for 2-iodo-6-(trifluoromethyl)phenol. $^1$H NMR (400 MHz, 120° C., DMSO-d$_6$:D$_2$O=9:1 (v/v)) δ ppm 8.00 (dd, J=7.7, 1.4 Hz, 1H), 7.52 (d, J=2.2 Hz, 1H), 7.42-7.35 (m, 1H), 7.27-7.08 (m, 4H), 6.36-6.32 (m, 1H), 5.59-5.41 (m, 1H), 4.63 (d, J=1.9 Hz, 1H), 4.22 (d, J=5.6 Hz, 1H), 4.06 (d, J=13.9 Hz, 1H), 3.96 (d, J=13.9 Hz, 1H), 3.78-3.67 (m, 1H), 3.61-3.29 (m, 1H), 2.97 (s, 1H), 2.78-2.55 (m, 2H), 2.46-2.41 (m, 1H), 1.72-1.59 (m, 1H), 1.58-1.45 (m, 1H), 1.44-1.23 (m, 3H), 1.23-1.01 (m, 4H), 0.98 (s, 9H); MS (APCI+) m/z 568.0 (M+H)$^+$.

Example 294

(2S,3R,4S,5S)-3-tert-butyl-4-[(5-cyclobutyl-2-methoxypyridin-3-yl)methoxy]-1-(naphthalene-1-sulfonyl)-5-{2-[(propan-2-yl)oxy]pyridin-3-yl}pyrrolidine-2-carboxylic acid The title compound was prepared according to the procedure described in to Example 265C, substituting naphthalene-1-sulfonyl chloride [cas 85-46-1] for 1,1,1-trifluoropropan-2-yl carbonochloridate to provide the title compound. $^1$H NMR (400 MHz, DMSO-d$_6$) δ ppm 8.74 (dt, J=7.6, 1.4 Hz, 1H), 8.12 (dt, J=8.2, 1.2 Hz, 1H), 8.05 (dd, J=7.4, 1.3 Hz, 1H), 8.00-7.94 (m, 1H), 7.92 (dd, J=7.4, 2.0 Hz, 1H), 7.81-7.73 (m, 2H), 7.64-7.53 (m, 2H), 7.50 (dd, J=8.2, 7.4 Hz, 1H), 6.86-6.81 (m, 1H), 6.39 (dd, J=7.4, 4.9 Hz, 1H), 5.37 (d, J=6.7 Hz, 1H), 5.22-5.10 (m, 1H), 4.40 (dd, J=5.2, 1.0 Hz, 1H), 4.15 (d, J=12.8 Hz, 1H), 3.95 (dd, J=6.7, 4.0 Hz, 1H), 3.87 (d, J=12.9 Hz, 1H), 3.71 (d, J=0.7 Hz, 3H), 3.34-3.26 (p, J=8.4 Hz, 1H), 2.40 (d, J=4.2 Hz, 1H), 2.27-2.14 (m, 2H), 1.98-1.77 (m, 4H), 1.32 (d, J=6.1 Hz, 3H), 1.18 (dd, J=6.2, 1.0 Hz, 3H), 0.79 (d, J=0.9 Hz, 9H); MS (ESI+) m/z 688 (M+H)$^+$.

Example 295

(2S,3R,4S,5S)-3-tert-butyl-4-[(5-cyclobutyl-2-methoxypyridin-3-yl)methoxy]-1-(cyclohexanecarbonyl)-5-[2-(propan-2-yl)phenyl]pyrrolidine-2-carboxylic acid The title compound was prepared according to the procedure described in Example 285C to Example 285F, substituting Example 96B for Example 285B, and cyclohexanecarbonyl chloride for (S)-tetrahydro-2H-pyran-2-carboxylic acid, respectively. $^1$H NMR (400 MHz, DMSO-$d_6$) δ ppm 8.06 (d, J=7.8 Hz, 1H), 7.78 (dd, J=2.3, 0.8 Hz, 1H), 7.32-7.25 (m, 1H), 7.21 (t, J=7.3 Hz, 1H), 7.09 (t, J=7.6 Hz, 1H), 6.87 (d, J=2.4 Hz, 1H), 5.41 (d, J=5.9 Hz, 1H), 4.65 (d, J=1.8 Hz, 1H), 4.28-4.20 (m, 2H), 3.83 (dt, J=13.4, 0.9 Hz, 1H), 3.78 (s, 3H), 3.38-3.25 (m, 3H), 2.57 (s, 1H), 2.30-2.22 (m, 2H), 2.03-1.85 (m, 4H), 1.72-1.40 (m, 5H), 1.32 (d, J=6.7 Hz, 3H), 1.28 (d, J=9.8 Hz, 3H), 1.20 (d, J=6.8 Hz, 3H), 1.09 (t, J=7.0 Hz, 2H), 1.05 (s, 9H); MS (ESI+) m/z 591 (M+H)$^+$.

Example 296

(2S,3R,4S,5S)-3-tert-butyl-4-[(5-cyclobutyl-1-benzofuran-2-yl)methoxy]-1-[(2S)-oxane-2-carbonyl]-5-{2-[(propan-2-yl)oxy]pyridin-3-yl}pyrrolidine-2-carboxylic acid Into a 4 mL vial was added Example 289 (13 mg, 0.020 mmol) and PEPPSI IPentCl (1.737 mg, 2.020 µmol) in tetrahydrofuran (0.5 mL). Cyclobutylzinc(II) bromide (0.202 mL, 0.101 mmol) was added. The reaction was stirred at room temperature for 3 hours. The solvent was removed under a stream of nitrogen. The residue was dissolved in 1 mL dichloromethane, and 1 mL 2M HCl was added. The aqueous layer was extracted with dichloromethane (2×1 mL). The solvent was removed under a stream of nitrogen. The residue was reconstituted in CH$_3$CN and purified using reverse phase HPLC/MS method trifluoroacetic acid8 to provide the title compound. $^1$H NMR (400 MHz, 120° C., DMSO-$d_6$:D$_2$O=9:1 (v/v)) δ ppm 8.23-8.04 (m, 1H), 8.04-7.94 (m, 1H), 7.34-7.26 (m, 1H), 7.24 (d, J=8.4 Hz, 1H), 7.07 (dd, J=8.5, 1.9 Hz, 1H), 6.91-6.77 (m, 1H), 6.28 (s, 1H), 5.28-5.10 (m, 1H), 4.58 (s, 1H), 4.26-4.17 (m, 2H), 4.09 (d, J=13.4 Hz, 1H), 3.75 (d, J=12.1 Hz, 1H), 3.62-3.47 (m, 1H), 2.40 (s, 1H), 2.37-2.26 (m, 2H), 2.13-1.89 (m, 3H), 1.88-0.99 (m, 16H), 0.93 (s, 9H); MS (APCI+) m/z 619.1 (M+H)$^+$.

Determination of Biological Activity

Cell Surface Expression-Horse Radish Peroxidase (CSE-HRP) Assay

A cellular assay for measuring the F508delCFTR cell surface expression after correction with test compounds either without or with a co-corrector (2 µM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid), was developed in human lung derived epithelial cell line (CFBE41o-) (Veit G et al, (2012) Mol Biol Cell. 23(21): 4188-4202). The development was achieved by expressing the F508delCFTR mutation along with a horseradish peroxidase (HRP) in the fourth exofacial loop, and then measuring the HRP activity using luminescence readout from these cells, CFBE41o-F508delCFTR-HRP, that were incubated overnight with the test corrector compounds, either without or with the co-corrector. For this primary assay, the CFBE41o-F508delCFTR-HRP cells were plated in 384-well plates (Greiner Bio-one; Cat 781080) at 4,000 cells/well along with 0.5 µg/mL doxycycline to induce the F508delCFTR-HRP expression and further incubated at 37° C., 5% CO$_2$ for 72 hours. The test compounds were then added either without or with a co-corrector at the required concentrations and further incubated for 18-24 hours at 33° C. The highest concentration tested was 20 µM with an 8-point concentration response curve using a 3-fold dilution in both the test compound without or with the co-corrector. Three replicate plates were run to determine one EC$_{50}$. All plates contained negative controls (dimethyl sulfoxide, DMSO) and positive control (2 µM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) as well as on-plate concentration response of the positive control. Post incubation, the plates were washed 5× times with Dulbecco's phosphate buffered saline (DPBS), followed by the addition of the HRP substrate, luminol (50 µL), and measuring the HRP activity using luminescence readout on EnVision® Multilabel Plate Reader (Perkin Elmer; product number 2104-0010). The raw counts from the experiment were analyzed using Accelrys® Assay Explorer v3.3.

Z' greater than 0.5 was used as passing quality control criteria for the plates.

The Z' is defined as:

$$1 - [3*SD_{Positive\ Control} + 3*SD_{Negative\ Control}]/\text{Absolute} (Mean_{Positive\ Control} - Mean_{Negative\ Control})]$$

wherein "SD" is standard deviation.

The % activity measured at each of the 8 test concentrations of the test compound added either without or with a co-corrector (2 µM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) was normalized to the on-plate positive control using the following formulae:

% activity(Test compound without co-corrector)= [(test compound without co-corrector response–DMSO response)/(positive control response–DMSO response)]*100

% activity(Test compound with co-corrector)=[(test compound with co-corrector response–DMSO response)/(positive control response–DMSO response)]*100

The maximum % activity achieved for the test compound either without or with a co-corrector at any tested concentration is presented in Table 1 along with the respective EC$_{50}$'s calculated using the following general sigmoidal curve with variable Hill slope equation (described as Model 42 in the Accelrys® Assay Explorer v3.3 software):

$$y=(a-d)/(1+(x/c)^b)+d$$

General sigmoidal curve with concentration, response, top, bottom, EC$_{50}$ and Hill slope. This model describes a sigmoidal curve with an adjustable baseline, a. The equation can be used to fit curves where response is either increasing or decreasing with respect to the independent variable, "x".

"x" is a concentration of drug under test.

"y" is the response.

"a" is the maximum response, and "d" is the minimum response

"c" is the inflection point (EC$_{50}$) for the curve. That is, "y" is halfway between the lower and upper asymptotes when x=c.

"b" is the slope-factor or Hill coefficient. The sign of b is positive when the response increases with increasing dose and is negative when the response decreases with increasing dose (inhibition).

The data is presented with the qualifiers shown below:

| EC50 (μM) | | |
|---|---|---|
| Without/with co-corrector | <1 | +++ |
| | ≥1 and <10 | ++ |
| | ≥10 | + |

| Maximum % activity (%) | | |
|---|---|---|
| Without co-corrector | <100 | + |
| | ≥100 and <200 | ++ |
| | ≥200 | +++ |
| With co-corrector | <150 | + |
| | ≥150 and <350 | ++ |
| | ≥350 | +++ |

TABLE 1

CSE-HRP data

| Example | $EC_{50}$ (without co-corrector) (μM) | Maximum % activity (without co-corrector) (%) | $EC_{50}$ (with co-corrector) (μM) | Maximum % activity (with co-corrector) (%) |
|---|---|---|---|---|
| 1 | ++ | + | ++ | +++ |
| 2 | ++ | ++ | ++ | +++ |
| 3 | ++ | ++ | ++ | +++ |
| 4 | ++ | ++ | ++ | +++ |
| 5 | ++ | ++ | ++ | +++ |
| 6 | ++ | + | ++ | +++ |
| 7 | + | + | + | + |
| 8 | + | + | + | + |
| 9 | + | + | + | + |
| 10 | ++ | +++ | ++ | +++ |
| 11 | ++ | ++ | ++ | +++ |
| 12 | ++ | ++ | ++ | ++ |
| 13 | ++ | + | ++ | +++ |
| 14 | ++ | ++ | ++ | +++ |
| 15 | ++ | ++ | ++ | +++ |
| 16 | ++ | + | ++ | ++ |
| 17 | ++ | ++ | ++ | +++ |
| 18 | + | + | ++ | ++ |
| 19 | +++ | +++ | +++ | +++ |
| 20 | +++ | ++ | +++ | +++ |
| 21 | + | + | ++ | ++ |
| 22 | + | + | + | + |
| 23 | + | + | ++ | ++ |
| 24 | + | + | ++ | ++ |
| 25 | + | + | ++ | ++ |
| 26 | ++ | + | ++ | ++ |
| 27 | ++ | ++ | +++ | +++ |
| 28 | ++ | ++ | ++ | +++ |
| 29 | ++ | +++ | ++ | +++ |
| 30 | ++ | ++ | +++ | +++ |
| 31 | ++ | +++ | +++ | +++ |
| 32 | ++ | + | ++ | +++ |
| 33 | ++ | ++ | ++ | +++ |
| 34 | ++ | + | ++ | +++ |
| 35 | ++ | ++ | ++ | +++ |
| 36 | ++ | ++ | ++ | +++ |
| 37 | ++ | +++ | ++ | +++ |
| 38 | ++ | ++ | ++ | +++ |
| 39 | ++ | +++ | ++ | +++ |
| 40 | ++ | ++ | ++ | +++ |
| 41 | +++ | ++ | +++ | +++ |
| 42 | ++ | + | ++ | +++ |
| 43 | ++ | + | ++ | +++ |
| 44 | ++ | + | ++ | +++ |
| 45 | ++ | ++ | ++ | +++ |

TABLE 1-continued

CSE-HRP data

| Example | $EC_{50}$ (without co-corrector) (μM) | Maximum % activity (without co-corrector) (%) | $EC_{50}$ (with co-corrector) (μM) | Maximum % activity (with co-corrector) (%) |
|---|---|---|---|---|
| 46 | +++ | +++ | +++ | +++ |
| 47 | ++ | +++ | ++ | +++ |
| 48 | ++ | ++ | ++ | +++ |
| 49 | ++ | ++ | ++ | +++ |
| 50 | +++ | +++ | +++ | +++ |
| 51 | ++ | ++ | ++ | +++ |
| 52 | ++ | + | ++ | +++ |
| 53 | +++ | ++ | +++ | +++ |
| 54 | +++ | ++ | +++ | +++ |
| 55 | ++ | ++ | ++ | +++ |
| 56 | +++ | ++ | +++ | +++ |
| 57 | ++ | ++ | ++ | +++ |
| 58 | +++ | ++ | +++ | +++ |
| 59 | ++ | + | ++ | ++ |
| 60 | +++ | ++ | +++ | +++ |
| 61 | +++ | +++ | +++ | +++ |
| 62 | +++ | ++ | +++ | +++ |
| 63 | ++ | ++ | ++ | +++ |
| 64 | ++ | ++ | ++ | +++ |
| 65 | +++ | + | +++ | +++ |
| 66 | +++ | + | ++ | +++ |
| 67 | +++ | + | +++ | +++ |
| 68 | +++ | + | ++ | +++ |
| 69 | ++ | + | ++ | ++ |
| 70 | ++ | + | ++ | ++ |
| 71 | ++ | + | ++ | +++ |
| 72 | ++ | + | ++ | +++ |
| 73 | ++ | ++ | +++ | +++ |
| 74 | ++ | ++ | ++ | +++ |
| 75 | + | + | + | + |
| 76 | ++ | ++ | ++ | +++ |
| 77 | ++ | ++ | ++ | +++ |
| 78 | ++ | ++ | ++ | +++ |
| 79 | ++ | + | ++ | ++ |
| 80 | ++ | + | ++ | ++ |
| 81 | ++ | + | ++ | ++ |
| 82 | ++ | + | ++ | ++ |
| 83 | ++ | ++ | +++ | +++ |
| 84 | ++ | + | ++ | ++ |
| 85 | ++ | + | ++ | ++ |
| 86 | ++ | ++ | +++ | +++ |
| 87 | ++ | ++ | ++ | +++ |
| 88 | ++ | ++ | +++ | +++ |
| 89 | ++ | ++ | +++ | +++ |
| 90 | ++ | + | ++ | +++ |
| 91 | ++ | ++ | ++ | +++ |
| 92 | ++ | ++ | ++ | +++ |
| 93 | ++ | ++ | ++ | +++ |
| 94 | + | + | +++ | + |
| 95 | ++ | ++ | +++ | +++ |
| 96 | +++ | +++ | +++ | +++ |
| 97 | ++ | ++ | ++ | +++ |
| 98 | +++ | ++ | +++ | +++ |
| 99 | ++ | ++ | ++ | +++ |
| 100 | ++ | + | ++ | ++ |
| 101 | ++ | ++ | ++ | +++ |
| 102 | ++ | + | ++ | ++ |
| 103 | ++ | ++ | +++ | +++ |
| 104 | ++ | ++ | ++ | +++ |
| 105 | +++ | ++ | +++ | +++ |
| 106 | ++ | + | ++ | ++ |
| 107 | ++ | + | ++ | ++ |
| 108 | ++ | ++ | ++ | +++ |
| 109 | ++ | + | ++ | ++ |
| 110 | ++ | ++ | ++ | +++ |
| 111 | ++ | ++ | ++ | +++ |
| 112 | ++ | ++ | +++ | +++ |
| 113 | ++ | + | ++ | ++ |
| 114 | + | + | + | + |
| 115 | ++ | ++ | +++ | +++ |
| 116 | ++ | ++ | ++ | +++ |
| 117 | +++ | + | +++ | ++ |

TABLE 1-continued

CSE-HRP data

| Example | EC$_{50}$ (without co-corrector) (μM) | Maximum % activity (without co-corrector) (%) | EC$_{50}$ (with co-corrector) (μM) | Maximum % activity (with co-corrector) (%) |
|---|---|---|---|---|
| 118 | ++ | ++ | +++ | +++ |
| 119 | ++ | ++ | ++ | +++ |
| 120 | ++ | + | +++ | ++ |
| 121 | +++ | + | +++ | ++ |
| 122 | + | + | + | + |
| 123 | ++ | ++ | +++ | +++ |
| 124 | ++ | + | +++ | ++ |
| 125 | +++ | + | +++ | ++ |
| 126 | + | + | + | + |
| 127 | + | + | + | + |
| 128 | ++ | ++ | +++ | +++ |
| 129 | ++ | ++ | +++ | +++ |
| 130 | +++ | ++ | +++ | +++ |
| 131 | +++ | + | +++ | ++ |
| 132 | ++ | ++ | +++ | +++ |
| 133 | ++ | ++ | ++ | +++ |
| 134 | ++ | ++ | ++ | ++ |
| 135 | ++ | ++ | +++ | +++ |
| 136 | +++ | ++ | +++ | +++ |
| 137 | ++ | ++ | +++ | ++ |
| 138 | +++ | ++ | +++ | +++ |
| 139 | ++ | ++ | +++ | +++ |
| 140 | +++ | + | +++ | ++ |
| 141 | ++ | +++ | +++ | +++ |
| 142 | +++ | + | +++ | ++ |
| 143 | ++ | ++ | ++ | +++ |
| 144 | +++ | ++ | +++ | +++ |
| 145 | ++ | + | ++ | +++ |
| 146 | ++ | + | +++ | ++ |
| 147 | ++ | ++ | +++ | +++ |
| 148 | + | + | + | + |
| 149 | ++ | ++ | +++ | +++ |
| 150 | ++ | ++ | +++ | +++ |
| 151 | +++ | + | +++ | ++ |
| 152 | +++ | + | ++ | ++ |
| 153 | +++ | + | +++ | ++ |
| 154 | +++ | + | +++ | ++ |
| 155 | ++ | ++ | +++ | +++ |
| 156 | ++ | ++ | +++ | +++ |
| 157 | +++ | + | +++ | ++ |
| 158 | +++ | ++ | +++ | +++ |
| 159 | +++ | + | +++ | +++ |
| 160 | ++ | + | ++ | ++ |
| 161 | ++ | + | ++ | +++ |
| 162 | ++ | +++ | +++ | +++ |
| 163 | + | + | + | + |
| 164 | + | + | + | + |
| 165 | ++ | ++ | ++ | +++ |
| 166 | ++ | + | ++ | +++ |
| 167 | ++ | + | ++ | ++ |
| 168 | ++ | ++ | ++ | +++ |
| 169 | ++ | +++ | ++ | +++ |
| 170 | ++ | +++ | +++ | +++ |
| 171 | ++ | +++ | ++ | +++ |
| 172 | ++ | +++ | ++ | +++ |
| 173 | ++ | +++ | ++ | +++ |
| 174 | +++ | +++ | +++ | +++ |
| 175 | ++ | +++ | +++ | +++ |
| 176 | ++ | +++ | +++ | +++ |
| 177 | ++ | ++ | ++ | +++ |
| 178 | ++ | ++ | ++ | +++ |
| 179 | +++ | +++ | +++ | +++ |
| 180 | +++ | +++ | +++ | +++ |
| 181 | + | + | ++ | ++ |
| 182 | ++ | +++ | +++ | +++ |
| 183 | ++ | ++ | ++ | +++ |
| 184 | +++ | +++ | +++ | +++ |
| 185 | ++ | +++ | +++ | +++ |
| 186 | ++ | +++ | +++ | +++ |
| 187 | ++ | +++ | +++ | +++ |
| 188 | +++ | +++ | +++ | +++ |
| 189 | ++ | +++ | ++ | +++ |
| 190 | ++ | +++ | ++ | +++ |
| 191 | ++ | +++ | ++ | +++ |
| 192 | ++ | + | ++ | ++ |
| 193 | ++ | ++ | ++ | +++ |
| 194 | ++ | +++ | +++ | +++ |
| 195 | ++ | +++ | ++ | +++ |
| 196 | ++ | ++ | ++ | +++ |
| 197 | ++ | + | ++ | ++ |
| 198 | ++ | +++ | ++ | +++ |
| 199 | ++ | +++ | ++ | +++ |
| 200 | ++ | +++ | +++ | +++ |
| 201 | ++ | +++ | ++ | +++ |
| 202 | ++ | +++ | +++ | +++ |
| 203 | ++ | +++ | ++ | +++ |
| 204 | ++ | +++ | +++ | +++ |
| 205 | ++ | ++ | ++ | +++ |
| 206 | ++ | +++ | ++ | +++ |
| 207 | ++ | ++ | ++ | +++ |
| 208 | ++ | +++ | ++ | +++ |
| 209 | ++ | ++ | ++ | +++ |
| 210 | +++ | ++ | +++ | +++ |
| 211 | ++ | +++ | +++ | +++ |
| 212 | ++ | ++ | ++ | +++ |
| 213 | ++ | +++ | +++ | +++ |
| 214 | ++ | + | ++ | ++ |
| 215 | +++ | +++ | +++ | +++ |
| 216 | ++ | + | +++ | +++ |
| 217 | ++ | +++ | +++ | +++ |
| 218 | +++ | +++ | +++ | +++ |
| 219 | +++ | +++ | +++ | +++ |
| 220 | ++ | ++ | +++ | +++ |
| 221 | ++ | +++ | ++ | +++ |
| 222 | ++ | +++ | +++ | +++ |
| 223 | ++ | +++ | +++ | +++ |
| 224 | +++ | +++ | +++ | +++ |
| 225 | ++ | + | ++ | ++ |
| 226 | +++ | +++ | +++ | +++ |
| 227 | ++ | +++ | +++ | +++ |
| 228 | ++ | +++ | +++ | +++ |
| 229 | ++ | + | +++ | ++ |
| 230 | ++ | ++ | +++ | +++ |
| 231 | ++ | +++ | +++ | +++ |
| 232 | ++ | +++ | +++ | +++ |
| 233 | ++ | +++ | +++ | +++ |
| 234 | +++ | +++ | +++ | +++ |
| 235 | +++ | +++ | +++ | +++ |
| 236 | ++ | ++ | ++ | +++ |
| 237 | ++ | +++ | +++ | +++ |
| 238 | ++ | +++ | +++ | +++ |
| 239 | ++ | ++ | +++ | +++ |
| 240 | ++ | ++ | +++ | +++ |
| 241 | ++ | +++ | +++ | +++ |
| 242 | ++ | ++ | ++ | +++ |
| 243 | ++ | +++ | +++ | +++ |
| 244 | ++ | ++ | ++ | +++ |
| 245 | ++ | +++ | ++ | +++ |
| 246 | ++ | +++ | +++ | +++ |
| 247 | ++ | +++ | ++ | +++ |
| 248 | ++ | +++ | ++ | +++ |
| 249 | ++ | +++ | +++ | +++ |
| 250 | +++ | ++ | +++ | +++ |
| 251 | +++ | +++ | +++ | +++ |
| 252 | ++ | +++ | ++ | +++ |
| 253 | ++ | +++ | ++ | +++ |
| 254 | ++ | +++ | +++ | +++ |
| 255 | + | + | ++ | ++ |
| 256 | ++ | + | +++ | +++ |
| 257 | +++ | + | +++ | ++ |
| 258 | +++ | +++ | +++ | +++ |
| 259 | +++ | +++ | +++ | +++ |
| 260 | +++ | +++ | +++ | +++ |
| 261 | ++ | +++ | +++ | +++ |

TABLE 1-continued

CSE-HRP data

| Example | $EC_{50}$ (without co-corrector) (μM) | Maximum % activity (without co-corrector) (%) | $EC_{50}$ (with co-corrector) (μM) | Maximum % activity (with co-corrector) (%) |
|---|---|---|---|---|
| 262 | ++ | + | ++ | ++ |
| 263 | + | + | ++ | ++ |
| 264 | ++ | + | ++ | +++ |
| 265 | +++ | ++ | +++ | +++ |
| 266 | ++ | ++ | +++ | +++ |
| 267 | ++ | ++ | +++ | +++ |
| 268 | ++ | + | ++ | +++ |
| 269 | ++ | +++ | +++ | +++ |
| 270 | +++ | +++ | +++ | +++ |
| 271 | +++ | ++ | +++ | +++ |
| 272 | +++ | +++ | +++ | +++ |
| 273 | +++ | +++ | +++ | +++ |
| 274 | +++ | +++ | +++ | +++ |
| 275 | + | + | ++ | ++ |
| 276 | + | + | +++ | ++ |
| 277 | +++ | + | +++ | +++ |
| 278 | ++ | ++ | +++ | +++ |
| 279 | +++ | ++ | +++ | +++ |
| 280 | +++ | ++ | +++ | +++ |
| 281 | ++ | + | +++ | ++ |
| 282 | +++ | + | +++ | +++ |
| 283 | +++ | + | ++ | +++ |
| 284 | ++ | + | ++ | +++ |
| 285 | +++ | +++ | +++ | +++ |
| 286 | ++ | +++ | +++ | +++ |
| 287 | +++ | ++ | +++ | +++ |
| 288 | ++ | ++ | ++ | +++ |
| 289 | ++ | + | +++ | +++ |
| 290 | +++ | ++ | +++ | +++ |
| 291 | ++ | +++ | ++ | +++ |
| 292 | ++ | ++ | ++ | +++ |
| 293 | +++ | ++ | +++ | +++ |
| 294 | + | + | ++ | ++ |
| 295 | +++ | +++ | +++ | +++ |
| 296 | ++ | + | +++ | ++ |

The data provided in the present application demonstrate that the compounds of the invention demonstrate activity in vitro, and may be useful in vivo in the treatment of cystic fibrosis.

Further benefits of Applicants' invention will be apparent to one skilled in the art from reading this patent application.

It is to be understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed:

1. A compound of Formula (I), or a pharmaceutically acceptable salt thereof,

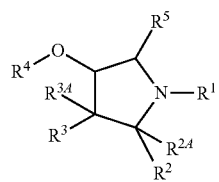

(I)

wherein
R[1] is selected from the group consisting of $SO_2R^6$, $C(O)R^6$, $C(O)OR^6$, and $C(O)NR^7R^8$;
R[2] is C(O)OH or a bioisostere thereof;
$R^{2A}$ is selected from the group consisting of hydrogen, $C_1$-$C_6$ alkyl, $C_1$-$C_6$ haloalkyl, and $C_3$-$C_6$ cycloalkyl;
R[3] is selected from the group consisting of $C_1$-$C_6$ alkyl, $C_3$-$C_6$ cycloalkyl, phenyl, and 5-6 membered heteroaryl; wherein the R[3] $C_1$-$C_6$ alkyl is optionally substituted with one or more substituents independently selected from the group consisting of $C_1$-$C_6$ alkoxy, OH, oxo, CN, $NO_2$, F, Cl, Br and I; wherein the R[3] $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and
$R^{3A}$ is selected from the group consisting of hydrogen, $C_1$-$C_6$ alkyl, and $C_1$-$C_6$ haloalkyl; or
R[3] and $R^{3A}$, together with the carbon to which they are attached, form a $C_3$-$C_6$ cycloalkyl; wherein the $C_3$-$C_6$ cycloalkyl formed from R[3] and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;
R[4] is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the R[4] $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of R[9], $OR^9$, C(O)$OR^9$, C(O)$NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;
$L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo;
R[5] is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the R[5] $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl.

2. The compound of claim 1, or a pharmaceutically acceptable salt thereof, wherein $R^2$ is C(O)OH; and $R^{2A}$ is hydrogen.

3. The compound of claim 1, or a pharmaceutically acceptable salt thereof, wherein $R^2$ is —C(O)NHSO$_2R^{G3a}$ or —C(O)NHSO$_2$N(R$^{G3a}$)$_2$;

R$^{G3a}$, at each occurrence, is independently $C_1$-$C_6$ alkyl, $C_1$-$C_6$ alkyl-O—$C_1$-$C_6$ alkyl, or G$^4$;

G$^4$, at each occurrence, is independently cycloalkyl, which is independently unsubstituted or substituted with 1, 2, or 3 independently selected R$^u$ groups;

R$^u$, at each occurrence, is independently $C_1$-$C_6$ alkyl; and $R^{2A}$ is hydrogen.

4. The compound of claim 1, or a pharmaceutically acceptable salt thereof, wherein $R^3$ is C(CH$_3$)$_3$; and $R^{3A}$ is hydrogen.

5. The compound of claim 1, or a pharmaceutically acceptable salt thereof, wherein $R^5$ is phenyl; wherein the $R^5$ phenyl is optionally substituted with one or more substituents independently selected from the group consisting of $R^{12}$, $OR^{12}$, $NR^{13}R^{14}$, F, Cl, and Br;

$R^{12}$, at each occurrence, is independently selected from the group consisting of $C_1$-$C_6$ alkyl, $C_1$-$C_6$ haloalkyl, 6-10 membered aryl, 5-11 membered heteroaryl, $C_3$-$C_{11}$ cycloalkyl, and 4-12 membered heterocyclyl; and $R^{13}$ and $R^{14}$, at each occurrence, are each independently $C_1$-$C_6$ alkyl.

6. The compound of claim 1, or a pharmaceutically acceptable salt thereof, wherein
$R^5$ is phenyl; wherein the $R^5$ phenyl is unsubstituted.

7. The compound of claim 1, or a pharmaceutically acceptable salt thereof, wherein
$R^5$ is pyridinyl; wherein the $R^5$ pyridinyl is optionally substituted with one or more independently selected $R^{12}$; and
$R^{12}$, at each occurrence, is independently $C_1$-$C_6$ alkyl.

8. The compound of claim 1, or a pharmaceutically acceptable salt thereof, wherein
$R^4$ is $L^1$-$C_6$-$C_{10}$ aryl; wherein the $R^4$ $C_6$-$C_{10}$ aryl is optionally substituted with one or more substituents independently selected from the group consisting of $R^9$ and $OR^9$;
$L^1$ is absent, or is $C_1$-$C_6$ alkylene; and
$R^9$, at each occurrence, is independently selected $C_1$-$C_6$ alkyl; wherein each $R^9$ $C_1$-$C_6$ alkyl is optionally substituted with one or more F.

9. The compound of claim 1, or a pharmaceutically acceptable salt thereof, wherein
$R^4$ is $L^1$-5-11 membered heteroaryl; wherein the $R^4$ 5-11 membered heteroaryl is optionally substituted with one or more substituents independently selected from the group consisting of $R^9$ and $OR^9$;
$L^1$ is absent, or is $C_1$-$C_6$ alkylene; and
$R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F.

10. A compound of Formula (III), or a pharmaceutically acceptable salt thereof,

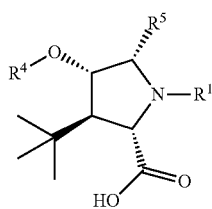

(III)

wherein
$R^1$ is selected from the group consisting of $SO_2R^6$, $C(O)R^6$, $C(O)OR^6$, and $C(O)NR^7R^8$;
$R^4$ is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;
$L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo;
$R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;
$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;
$R^7$ and $R^8$ are each independently hydrogen or $C_1$-$C_6$ alkyl;
$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;
$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;
$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, C₁-C₆ alkoxy, C₁-C₆ haloalkyl, C₁-C₆ haloalkoxy, N(C₁-C₆ alkyl)₂, OH, oxo, CN, NO₂, F, Cl, Br and I;

R¹³ and R¹⁴, at each occurrence, are each independently hydrogen or C₁-C₆ alkyl;

R¹⁵, at each occurrence, is independently selected from the group consisting of C₁-C₆ alkyl, C₂-C₆ alkenyl, C₂-C₆ alkynyl, 6-10 membered aryl, 5-11 membered heteroaryl, C₃-C₁₁ cycloalkyl, C₄-C₁₁ cycloalkenyl, and 4-12 membered heterocyclyl; wherein each R¹⁵ C₁-C₆ alkyl, C₂-C₆ alkenyl, and C₂-C₆ alkynyl is optionally substituted with one or more substituents independently selected from the group consisting of OH, oxo, CN, NO₂, F, Cl, Br and I; wherein each R¹⁵ 6-10 membered aryl, 5-11 membered heteroaryl, C₃-C₁₁ cycloalkyl, C₄-C₁₁ cycloalkenyl, and 4-12 membered heterocyclyl is optionally substituted with one or more substituents independently selected from the group consisting of C₁-C₆ alkyl, C₁-C₆ alkoxy, C₁-C₆ haloalkyl, oxo, OH, CN, NO2, F, Cl, Br and I;

R¹⁶ and R¹⁷, at each occurrence, are each independently hydrogen or C₁-C₆ alkyl;

R¹⁸, at each occurrence, is independently selected from the group consisting of C₁-C₆ alkyl, C₂-C₆ alkenyl, C₂-C₆ alkynyl, C₆-C₁₀ membered aryl, 5-11 membered heteroaryl, C₃-C₁₁ cycloalkyl, C₄-C₁₁ cycloalkenyl, and 4-12 membered heterocyclyl; wherein each R¹⁸ C₁-C₆ alkyl, C₂-C₆ alkenyl, C₂-C₆ alkynyl, C₆-C₁₀ membered aryl, 5-11 membered heteroaryl, C₃-C₁₁ cycloalkyl, C₄-C₁₁ cycloalkenyl, and 4-12 membered heterocyclyl is optionally substituted with one or more substituents independently selected from the group consisting of C₁-C₆ alkyl, C₁-C₆ alkoxy, 5-6 membered heteroaryl, OH, oxo, CN, NO₂, F, Cl, Br and I;

R¹⁹ and R²⁰, at each occurrence, are each independently hydrogen or C₁-C₆ alkyl;

R²¹, at each occurrence, is independently selected from the group consisting of C₁-C₆ alkyl, C₂-C₆ alkenyl, C₂-C₆ alkynyl, 6-10 membered aryl, 5-11 membered heteroaryl, C₃-C₁₁ cycloalkyl, C₄-C₁₁ cycloalkenyl, and 4-12 membered heterocyclyl; wherein each R²¹ C₁-C₆ alkyl, C₂-C₆ alkenyl, C₂-C₆ alkynyl, 6-10 membered aryl, 5-11 membered heteroaryl, C₃-C₁₁ cycloalkyl, C₄-C₁₁ cycloalkenyl, and 4-12 membered heterocyclyl is optionally substituted with one or more substituents independently selected from the group consisting of OH, oxo, CN, NO₂, F, Cl, Br and I;

R²² and R²³, at each occurrence, are each independently hydrogen or C₁-C₆ alkyl;

R²⁴, at each occurrence, is independently selected from the group consisting of C₁-C₆ alkyl, C₁-C₆ haloalkyl, C₁-C₆ alkoxy-C₁-C₆ alkyl, C₂-C₆ alkenyl, C₂-C₆ alkynyl, 6-10 membered aryl, 5-11 membered heteroaryl, C₃-C₁₁ cycloalkyl, C₄-C₁₁ cycloalkenyl, and 4-12 membered heterocyclyl; and R²⁵ and R²⁶, at each occurrence, are each independently hydrogen or C₁-C₆ alkyl.

11. The compound of claim 10, or a pharmaceutically acceptable salt thereof, wherein
R¹ is C(O)R⁶;
R⁴ is L¹-5-11 membered heteroaryl; wherein the R⁴ 5-11 membered heteroaryl is optionally substituted with one or more substituents independently selected from the group consisting of R⁹ and OR⁹;
L¹ is C₁-C₆ alkylene;
R⁵ is C₆-C₁₀ membered aryl; wherein the R⁵ C₆-C₁₀ membered aryl is optionally substituted with one or more R¹²;

R⁶ is 4-12 membered heterocyclyl;
R⁹, at each occurrence, is independently selected C₁-C₆ alkyl; wherein each R⁹ C₁-C₆ alkyl is optionally substituted with one or more F; and
R¹², at each occurrence, is independently selected C₁-C₆ alkyl.

12. The compound of claim 1, or a pharmaceutically acceptable salt thereof, wherein the compound is selected from the group consisting of:

rac-(2R,3S,5R)-3-tert-butyl-1-(cyclopentylacetyl)-4-[(2,5-dichlorophenyl)methoxyl]-5-phenylpyrrolidine-2-carboxylic acid;

rac-(2R,3S,5R)-3-tert-butyl-1-(cyclohexanecarbonyl)-4-{[2-methoxy-5-(trifluoromethyl)phenyl]methoxy}-5-phenylpyrrolidine-2-carboxylic acid;

rac-(2R,3S,5R)-3-tert-butyl-4-[(5-chloro-2-methoxyphenyl)methoxy]-1-(cyclohexanecarbonyl)-5-phenylpyrrolidine-2-carboxylic acid;

rac-(2R,3S,5R)-3-tert-butyl-1-(cyclohexanecarbonyl)-4-[(2,5-dichlorophenyl)methoxy]-5-phenylpyrrolidine-2-carboxylic acid;

rac-(2R,3S,5R)-3-tert-butyl-1-(cyclohexanecarbonyl)-4-{[6-methyl-4-(trifluoromethyl)pyridin-2-yl]oxy}-5-phenylpyrrolidine-2-carboxylic acid;

rac-(2R,3S,5R)-3-tert-butyl-4-[(4,6-dimethoxypyrimidin-2-yl)oxy]-1-[di(propan-2-yl)carbamoyl]-5-phenylpyrrolidine-2-carboxylic acid;

rac-(2R,3S,5R)-3-tert-butyl-1-[di(propan-2-yl)carbamoyl]-4-{[2-methoxy-5-(trifluoromethyl)phenyl]methoxy}-5-phenylpyrrolidine-2-carboxylic acid;

(2R*,3S*,4R*,5R*)-3-tert-butyl-1-[di(propan-2-yl)carbamoyl]-4-{[2-methoxy-5-(trifluoromethyl)phenyl]methoxyl}-5-phenylpyrrolidine-2-carboxylic acid;

(2S*,3R*,4S*,5S*)-3-tert-butyl-1-[di(propan-2-yl)carbamoyl]-4-{[2-methoxy-5-(trifluoromethyl)phenyl]methoxy}-5-phenylpyrrolidine-2-carboxylic acid;

rac-(2R,3S,4R,5R)-3-tert-butyl-1-(cyclohexanecarbonyl)-4-[(4,6-dimethoxypyrimidin-5-yl)methoxy]-5-phenylpyrrolidine-2-carboxylic acid;

rac-(2R,3S,4R,5R)-3-tert-butyl-1-(cyclohexanecarbonyl)-4-[(4,6-dimethoxypyrimidin-2-yl)methoxy]-5-phenylpyrrolidine-2-carboxylic acid;

rac-(2R,3S,4R,5R)-3-tert-butyl-1-(cyclohexanecarbonyl)-4-{[2-(dimethylamino)-5-(trifluoromethyl)pyridin-3-yl]methoxy}-5-phenylpyrrolidine-2-carboxylic acid;

rac-(2R,3S,5R)-3-tert-butyl-1-(cyclohexanecarbonyl)-5-(2-methoxyphenyl)-4-{[2-methoxy-5-(trifluoromethyl)phenyl]methoxy}pyrrolidine-2-carboxylic acid;

rac-(2R,3S,5R)-3-tert-butyl-4-[(4-chloro-2-methoxyphenyl)methoxy]-1-(cyclohexanecarbonyl)-5-(2-methoxyphenyl)pyrrolidine-2-carboxylic acid;

rac-(2R,3S,5R)-3-tert-butyl-1-(cyclohexanecarbonyl)-5-[2-(dimethylamino)pyridin-3-yl]-4-{[2-methoxy-5-(trifluoromethyl)phenyl]methoxy}pyrrolidine-2-carboxylic acid;

rac-(2R,3S,5R)-3-tert-butyl-1-(cyclohexanecarbonyl)-N-(methanesulfonyl)-4-{[2-methoxy-5-(trifluoromethyl)phenyl]methoxy}-5-phenylpyrrolidine-2-carboxamide;

rac-(2R,3S,5R)-3-tert-butyl-4-[(5-chloro-2-methoxyphenyl)methoxy]-5-phenyl-1-{[(propan-2-yl)oxy]carbonyl}pyrrolidine-2-carboxylic acid;

(2R,3S,4R,5R)-3-tert-butyl-1-(cyclohexanecarbonyl)-4-{[2-methoxy-5-(trifluoromethyl)phenyl]methoxy}-5-phenylpyrrolidine-2-carboxylic acid;

(2S,3R,4S,5S)-3-tert-butyl-1-(cyclohexanecarbonyl)-4-
{[2-methoxy-5-(trifluoromethyl)phenyl]methoxy}-5-
phenylpyrrolidine-2-carboxylic acid;

rac-(2R,3S,4R,5R)-3-tert-butyl-1-(cyclohexanecarbonyl)-4-{[2-methoxy-5-(trifluoromethyl)pyridin-3-yl]methoxy}-5-phenylpyrrolidine-2-carboxylic acid;

(2S,3R,4S,5S)-3-tert-butyl-1-(cyclohexanecarbonyl)-N-(2-methoxyethanesulfonyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-4-{[2-methoxy-5-(trifluoromethyl)phenyl]methoxy}-N-(1-methylcyclopropane-1-sulfonyl)-5-phenylpyrrolidine-2-carboxamide;

(2S,3R,4S,5S)-3-tert-butyl-1-(cyclohexanecarbonyl)-N-(cyclopropanesulfonyl)-4{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-N-(ethanesulfonyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-N-(dimethylsulfamoyl)-4-{[2-methoxy-5-(trifluoromethyl)phenyl]methoxy}-5-phenylpyrrolidine-2-carboxamide;

(2S,3R,4S,5S)-3-tert-butyl-1-(cyclohexanecarbonyl)-N-(methanesulfonyl)-4-{[2-methoxy-5-(trifluoromethyl)phenyl]methoxy}-5-phenylpyrrolidine-2-carboxamide;

(2R,3S,4R,5R)-3-tert-butyl-1-[(1S,3S)-3-methoxycyclohexane-1-carbonyl]-4-{[2-methoxy-5-(trifluoromethyl)phenyl]methoxy}-5-phenylpyrrolidine-2-carboxylic acid;

(2R,3S,4R,5R)-3-tert-butyl-1-[(1S,3S)-3-methoxycyclohexane-1-carbonyl]-4-{[6-methyl-4-(trifluoromethyl)pyridin-2-yl]oxy}-5-phenylpyrrolidine-2-carboxylic acid;

rac-(2R,3S,4R,5R)-3-(tert-butyl)-4((2-methoxy-5-(trifluoromethyl)benzyl)oxy)-1-((1R,3R)-3-methoxycyclohexanecarbonyl)-5-phenylpyrrolidine-2-carboxylic acid;

(2S,3R,4S,5S)-3-tert-butyl-1-[(1S,3S)-3-methoxycyclohexane-1-carbonyl]-4-{[2-methoxy-5-(trifluoromethyl)phenyl]methoxy}-5-phenylpyrrolidine-2-carboxylic acid;

(2S,3R,4S,5S)-3-tert-butyl-1-[(1R,3R)-3-methoxycyclohexane-1-carbonyl]-4-{[2-methoxy-5-(trifluoromethyl)phenyl]methoxy}-5-phenylpyrrolidine-2-carboxylic acid;

(2S,3R,4S,5S)-3-tert-butyl-1-[(1S,3S)-3-methoxycyclohexane-1-carbonyl]-4-{[2-methoxy-4-(trifluoromethyl)phenyl]methoxy}-5-phenylpyrrolidine-2-carboxylic acid;

(2S,3R,4S,5S)-3-tert-butyl-1-[(1R,3R)-3-methoxycyclohexane-1-carbonyl]-4-{[2-methoxy-4-(trifluoromethyl)phenyl]methoxy}-5-phenylpyrrolidine-2-carboxylic acid;

rac-(2R,3S,4R,5R)-3-tert-butyl-1-[(cyclobutyloxy)carbonyl]-4-{[2-methoxy-4-(trifluoromethyl)phenyl]methoxy}-5-phenylpyrrolidine-2-carboxylic acid;

rac-(2R,3S,4R,5R)-3-tert-butyl-4-[(5-chloro-2-methoxyphenyl)methoxy]-1-[cyclobutyloxy)carbonyl]-5-phenylpyrrolidine-2-carboxylic acid;

(2S,3R,4S,5S)-4-[(5-bromo-2-methoxyphenyl)methoxy]-3-tert-butyl-5-phenyl-1-{[(propan-2-yl)oxy]carbonyl}pyrrolidine-2-carboxylic acid;

(2S,3R,4S,5S)-4-[(5-bromo-2-methoxyphenyl)methoxy]-3-tert-butyl-1-[(1R,3R)-3-methoxycyclohexane-1-carbonyl]-5-phenylpyrrolidine-2-carboxylic acid;

(2S,3R,4S,5S)-3-tert-butyl-4-[(4-methoxy [1,1'-biphenyl]-3-yl)methoxy]-5-phenyl-1-{[(propan-2-yl)oxy]carbonyl}pyrrolidine-2-carboxylic acid;

(2S,3R,4S,5S)-3-tert-butyl-4-[(4-methoxy [1,1'-biphenyl]-3-yl)methoxy]-1-[(1R,3R)-3-methoxycyclohexane-1-carbonyl]-5-phenylpyrrolidine-2-carboxylic acid;

(2S,3R,4S,5S)-4-[(5-bromo-2-methoxypyridin-3-yl)methoxy]-3-tert-butyl-5-phenyl-1-{[(propan-2-yl)oxy]carbonyl}pyrrolidine-2-carboxylic acid;

(2S,3R,4S,5S)-3-tert-butyl-1-(cyclohexanecarbonyl)-4-{[2-methoxy-5-(trifluoromethyl)pyridin-3-yl]methoxy}-5-phenylpyrrolidine-2-carboxylic acid;

(2S,3R,4S,5S)-3-tert-butyl-4-[(2-methoxy-5-phenylpyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclohexyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclopentyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-[(5-tert-butyl-2-methoxyphenyl)methoxy]-1-[(1R,3R)-3-methoxycyclohexane-1-carbonyl]-5-phenylpyrrolidine-2-carboxylic acid;

(2S,3R,4S,5S)-3-tert-butyl-4-[(5-tert-butyl-2-methoxyphenyl)methoxy]-5-phenyl-1-{[(propan-2-yl)oxy]carbonyl}pyrrolidine-2-carboxylic acid;

(2S,3R,4S,5S)-3-tert-butyl-1-(cyclohexanecarbonyl)-5-(2-fluorophenyl)-4-{[2-methoxy-5-(trifluoromethyl)pyridin-3-yl]methoxy}pyrrolidine-2-carboxylic acid;

(2S,3R,4S,5S)-3-tert-butyl-1-(cyclohexanecarbonyl)-5-(2-fluorophenyl)-4-{[2-methoxy-5-(trifluoromethyl)phenyl]methoxy}pyrrolidine-2-carboxylic acid;

(2S,3R,4S,5S)-3-tert-butyl-4-[(5-tert-butyl-2-methoxyphenyl)methoxy]-1-(cyclohexanecarbonyl)-5-(2-fluorophenyl)pyrrolidine-2-carboxylic acid;

(2S,3R,4S,5S)-4-[(5-bromo-2-methoxypyridin-3-yl)methoxy]-3-tert-butyl-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-5-(2-fluorophenyl)-4-[(2-methoxy-5-phenylpyridin-3-yl)methoxy]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-phenylpyrrolidine-2-carboxylic acid;

(2S,3R,4S,5S)-3-tert-butyl-1-(cyclohexanecarbonyl)-4-[(5-cyclopentyl-2-methoxypyridin-3-yl)methoxy]-5-phenylpyrrolidine-2-carboxylic acid;

(2S,3R,4S,5S)-4-{[5-(bicyclo[2.2.1]heptan-2-yl)-2-methoxypyridin-3-yl]methoxy}-3-tert-butyl-1-(cyclohexanecarbonyl)-5-phenylpyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-4-[(5-cyclopentyl-2-methoxypyridin-3-yl)methoxy]-5-(2-fluorophenyl)pyrrolidine -2-carboxylic acid;

(2S,3R,4S,5S)-4-{[5-(bicyclo[2.2.1]heptan-2-yl)-2-methoxypyridin-3-yl]methoxy}-3-tert-butyl-1-(cyclohexanecarbonyl)-5-(2-fluorophenyl)pyrrolidine-2-carboxylic acid;

(2S,3R,4S,5S)-3-tert-butyl-1-(cyclohexanecarbonyl)-5-(2-fluorophenyl)-4-{[2-methoxy-5-(pyrrolidin-1-yl)pyridin-3-yl]methoxy}pyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-phenylpyrrolidine-2-carboxylic acid;

(2S,3R,4S,5S)-3-tert-butyl-4-[(5-tert-butyl-2-methoxypyridin-3-yl)methoxy]-1-[(1R,3R)-3-methoxycyclohexane-1-carbonyl]-5-phenylpyrrolidine-2-carboxylic acid;

(2S,3R,4S,5S)-3-tert-butyl-4-[(5-tert-butyl-2-methoxypyridin-3-yl)methoxy]-1-(cyclohexanecarbonyl)-5-(2-fluorophenyl)pyrrolidine-2-carboxylic acid;

(2S,3R,4S,5S)-3-tert-butyl-4-[(5-tert-butyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2-fluoro-4-methylphenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2-fluorophenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(4-fluoro-2-methylphenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(2,4-difluorophenyl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(3,6-dihydro-2H-pyran-4-yl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(3-methoxyphenyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(4-methylphenyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-[(6-tert-butyl-2-methoxypyridin-3-yl)methoxy]-5-phenyl-1-{[(propan-2-yl)oxy]carbonyl}pyrrolidine-2-carboxylic acid;

(2S,3R,4S,5S)-3-tert-butyl-5-(2-fluorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-tert-butyl-2-methoxypyridin-3-yl)methoxy]-5-(2-fluorophenyl)-1-{[(propan-2-yl)oxy]carbonyl}pyrrolidine-2-carboxylic acid;

(2S,3R,4R,5S)-3-tert-butyl-4-[(5-tert-butyl-2-methoxypyridin-3-yl)methoxy]-5-(2-fluorophenyl)-1-{[(propan-2-yl)oxy]carbonyl}pyrrolidine-2-carboxylic acid;

(2S,3R,4S,5S)-4-[(5-bromo-2-methoxypyridin-3-yl)methoxy]-3-tert-butyl-5-(2-fluorophenyl)-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-(2-fluorophenyl)-1-{[(propan-2-yl)oxy]carbonyl}pyrrolidine-2-carboxylic acid;

(2S,3R,4S,5S)-3-tert-butyl-4-{[2-methoxy-5-(trifluoromethyl)phenyl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-tert-butyl-2-methoxypyridin-3-yl)methoxy]-5-(3-chlorophenyl)-1-{[(propan-2-yl)oxy]carbonyl}pyrrolidine-2-carboxylic acid;

(2S,3R,4S,5S)-3-tert-butyl-4-{[2-methoxy-5-(piperidin-1-yl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(pyrrolidin-1-yl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-{[(propan-2-yl)oxy]carbonyl}pyrrolidine-2-carboxylic acid;

(2S,3R,4S,5S)-3-tert-butyl-4-{[5-(3,3-difluoroazetidin-1-yl)-2-methoxypyridin-3-yl]methoxy}-5-phenyl-1-{[(propan-2-yl)oxy]carbonyl}pyrrolidine-2-carboxylic acid;

(2S,3R,4S,5S)-3-tert-butyl-4-{[5-(3,3-difluoropyrrolidin-1-yl)-2-methoxypyridin-3-yl]methoxy}-5-phenyl-1-{[(propan-2-yl)oxy]carbonyl}pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-phenylpyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-phenylpyrrolidine-2-carboxylic acid;

(2S,3R,4S,5S)-3-tert-butyl-4-{[2-methoxy-5-(trifluoromethyl)pyridin-3-yl]methoxy}-5-phenyl-1-{[(prop-2-en-1-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxane-2-carbonyl]-5-phenylpyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-[2-(propan-2-yl)phenyl]pyrrolidine-2-carboxylic acid;

(2S,3R,4R,5S)-3-tert-butyl-4-{[2-methoxy-5-(trifluoromethyl)phenyl]methoxy}-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(propan-2-yl)phenyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(2-cyclobutyl-5-methoxypyridin-4-yl)methoxy]-5-phenyl-1-{[(propan-2-yl)oxy]carbonyl}pyrrolidine-2-carboxylic acid;

(2S,3R,4S,5S)-3-tert-butyl-5-(2-cyclobutylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(2R)-oxolane-2-carbonyl]-5-[2-(propan-2-yl)phenyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy]carbonyl}-5-{2-[(propan-2-yl)oxy]phenyl}pyrrolidine-2-carboxylic acid;

(2S,3R,4S,5S)-3-tert-butyl-4-[(2-methoxyquinolin-3-yl)methoxy]-5-phenyl-1-{[(propan-2-yl)oxy]carbonyl}pyrrolidine-2-carboxylic acid;

(2S,3R,4S,5S)-3-tert-butyl-4-{[2-hydroxy-5-(trifluoromethyl)pyridin-3-yl]methoxy}-5-phenyl-1-{[(propan-2-yl)oxy]carbonyl}pyrrolidine-2-carboxylic acid;

(2S,3R,4S,5S)-3-tert-butyl-5-[2-(3,6-dihydro-2H-pyran-4-yl)phenyl]-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-{[2-methoxy-5-(trifluoromethyl)pyridin-3-yl]methoxy}-1-[(3S)-oxolane-3-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-(oxane-4-carbonyl)-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(3R)-oxolane-3-carbonyl]-5-[2-(propan-2-yl)phenyl]pyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-{[2-methoxy-5-(trifluoromethyl)phenyl]methoxy}-1-[(2S)-oxolane-2-carbonyl]-5-[2-(trifluoromethyl)pyridin-3-yl]pyrrolidine-2-carboxylic acid;

(2S,3R,4R,5S)-3-tert-butyl-4-{[2-methoxy-5-(trifluoromethyl)phenyl]methoxy}-1-[(2S)-oxolane-2-carbonyl]-5-[2-(trifluoromethyl)pyridin-3-yl]pyrrolidine-2-carboxylic acid;

(2S,3R,4S,5S)-3-tert-butyl-5-(2-chlorophenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-[(2-methoxyquinolin-3-yl)methoxy]-1-[(2S)-oxolane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[3-(propan-2-yl)phenyl]pyrrolidine-2-carboxylic acid;

(2S,3R,4S,5S)-5-(3-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-cyclopropylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4R,5S)-3-tert-butyl-5-(3-tert-butylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-(3-bromophenyl)-3-tert-butyl-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-5-(3-chlorophenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4R,5S)-5-(2-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-{[2-methoxy-5-(trifluoromethyl)pyridin-3-yl]methoxyl}-1-[(2S)-oxolane-2-carbonyl]-5-[1-(propan-2-yl)-1H-pyrazol-5-yl]pyrrolidine-2-carboxylic acid;

(2S,3R,4S,5S)-3-tert-butyl-5-(2-cyclopropylphenyl)-4-{[2-methoxy-5-(trifluoromethyl)pyridin-3-yl]methoxyl}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-[2-(propan-2-yl)phenyl]pyrrolidine-2-carboxylic acid;

(2S,3R,4S,5S)-3-tert-butyl-4-[(2-methoxyquinolin-3-yl)methoxy]-1-[(2R)-oxane-2-carbonyl]-5-[2-(propan-2-yl)phenyl]pyrrolidine-2-carboxylic acid;

(2S,3R,4S,5S)-3-tert-butyl-4-[(2-methoxyquinolin-3-yl)methoxy]-1-[(2S)-oxane-2-carbonyl]-5-[2-(propan-2-yl)phenyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxolane-2-carbonyl]-5-{2-[(propan-2-yl) oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-(oxane-4-carbonyl)-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-[(2R)-oxane-2-carbonyl]-5-{2-[(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid;

(2S,3R,4S,5S)-5-(2-bromophenyl)-3-tert-butyl-4-[(2-methoxyquinolin-3-yl)methoxyl]-1-{[(propan-2-yl)oxy]carbonyl}pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-{[(propan-2-yl)oxy]carbonyl}pyrrolidine-2-carboxylic acid;

(2S,3R,4S,5S)-3-tert-butyl-5-(2-cyclopropylphenyl)-4-[(2-methoxyquinolin-3-yl)methoxy]-1-[(2S)-oxolane-2-carbonyl]pyrrolidine-2-carboxylic acid;

(2S,3R,4S,5S)-3-tert-butyl-5-(3-cyclobutylphenyl)-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2-methylphenyl)-1-[(2S)-oxane-2-carbonyl]pyrrolidine-2-carboxylic acid;

(2S,3R,4S,5S)-3-tert-butyl-5-(3-chlorophenyl)-4-[(5-cyclobutyl-2-methoxypyridin-3-yl)methoxy]-1-{[(propan-2-yl)oxy]carbonyl}pyrrolidine-2-carboxylic acid;

(2S,3R,4S,5S)-3-tert-butyl-5-(2-cyclopropylphenyl)-4-[(2-methoxyquinolin-3-yl)methoxy]-1-{[(propan-2-yl)oxy]carbonyl}pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-1-{[(propan-2-yl)oxy]carbonyl}-5-[2-(trifluoromethyl)phenyl]pyrrolidine-2-carboxylic acid;

(2S,3R,4S,5S)-3-tert-butyl-4-{[2-methoxy-5-(trifluoromethyl)pyridin-3-yl]methoxyl]-1-[(2S)-oxolane-2-carbonyl]-5-{2[(propan-2-yl)oxy]pyridin-3-yl}pyrrolidine-2-carboxylic acid;

(2S,3R,4S,5S)-3-tert-butyl-4-{[2-methoxy-5-(trifluoromethyl)pyridin-3-yl]methoxy}-1-{[(propan-2-yl)oxy carbonyl}-5-{2[(propan-2-yl)oxy]pyridin-3-yl }pyrrolidine-2-carboxylic acid;

(2S,3R,4S,5S)-3-tert-butyl-4-[(2-methoxyquinolin-3-yl)methoxy]-1-[(2S)-oxolane-2-carbonyl]-5-[1-(propan-2-yl)-11H-pyrazol-5-yl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-[(2S)-oxolane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-(oxane-4-carbonyl)pyrrolidine-2-carboxylic acid;

(2S,3R,4S,5S)-5-(2-bromophenyl)-3-tert-butyl-4-[(2-methoxyquinolin-3-yl)methoxy]-1-[(2S)-oxolane-2-carbonyl]pyrrolidine-2-carboxylic acid;

(2S,3R,4S,5S)-3-tert-butyl-5-(3-tert-butylphenyl)-1-(ethoxycarbonyl)-4-{[2-methoxy-5-(trifluoromethyl)pyridin-3-yl]methoxy}pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(1R,2S,4S)-7-oxabicyclo [2 .2.1]heptane-2-carbonyl]pyrrolidine-2-carboxylic acid ;

(2S,3R,4S,5S)-3-tert-butyl-4-[(5-cyclobutyl-2-methoxypyridin-3-yl)methoxy]-1-[(2S)-oxolane-2-carbonyl]-5-[2-(trifluoromethyl)phenyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxolane-2-carbonyl]-5-[2-(trifluoromethyl)phenyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2R)-oxane-2-carbonyl]pyrrolidine-2-carboxylic acid;

(2S,3R,4S,5S)-3-tert-butyl-5-(3-tert-butylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-[(2S)-oxolane-2-carbonyl]pyrrolidine-2-carboxylic acid;

(2S,3R,4S,5S)-3-tert-butyl-1-(cyclobutanecarbonyl)-4-{[2-methoxy-5-(trifluoromethyl)pyridin-3-yl]methoxyl-}5{-2-[(propan-2-yl)oxy]pyridin-3-yl}pyrrolidine-2-carboxylic acid;

(2S,3R,4S,5S)-3-tert-butyl-1-(cyclobutanecarbonyl)-4-[(5-cyclobutyl-2-methoxypyridin-3-yl)methoxy]-5-{2-[(propan-2-yl)oxy]pyridin-3-yl}pyrrolidine-2-carboxylic acid;

(2S,3R,4S,5S)-5-(2-bromophenyl)-3-tert-butyl-4-[(5-tert-butyl-2-methoxyphenyl)methoxy]-1-[(2S)-oxolane-2-carbonyl]pyrrolidine-2-carboxylic acid;

(2S,3R,4R,5S)-3-tert-butyl-1-(cyclopentanecarbonyl)-4-{[2-methoxy-5-(trifluoromethyl)pyridin-3-yl]methoxy}-5-{2[(propan-2-yl)oxy]pyridin-3-yl}pyrrolidine-2-carboxylic acid;

(2S,3R,4R,5S)-3-tert-butyl-1-(cyclohexanecarbonyl)-4-{[2-methoxy-5-(trifluoromethyl)pyridin-3-yl]methoxy}-5-{2[(propan-2-yl)oxy]pyridin-3-yl }pyrrolidine-2-carboxylic acid;

(2S,3R,4S,5S)-3-tert-butyl-4-[(5-cyclobutyl-2-methoxypyridin-3-yl)methoxy]-5-[2-(difluorome thyl)phenyll ]-1-[(2S)-oxolane-2-carbonyl]pyrrolidine-2-carboxylic acid;

(2S,3R,4R,5S)-5-(2-bromophenyl)-3-tert-butyl-4-[(5-cyclobutyl-2-methoxypyridin-3-yl)methoxy]-1-{[(propan-2-yl)oxy]carbonyl}pyrrolidine-2-carboxylic acid;

(2S,3R,4S,5S)-3-tert-butyl-5-(2,6-difluorophenyl)-4-{[2-methoxy-5-(trifluoromethyl)pyridin-3-yl]methoxy}-1-{[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1{-[(propan-2-yl)oxy]carbonyl}pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-{2 [(propan-2-yl)oxy]pyridin-3-yl}pyrrolidine-2-carboxylic acid;

(2S,3R,4S,5S)-3-tert-butyl-4-[(5-cyclobutyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-(2-cyclopropylphenyl)-1-[(2S)-oxolane-2-carbonyl]pyrrolidine-2-carboxylic acid;

(2S,3R,4S,5S)-4-[5-bromo-2-methoxypyridin-3-yl)methoxyl]-3-tert-butyl-5-(2-cyclopropylphenyl)-1-[(2S)-oxolane-2-carbonyl]pyrrolidine-2-carboxylic acid;

(2S,3R,4S,5S)-3-tert-butyl-4-{[2-methoxy-5-(trifluoromethyl)phenyl]methoxy}-5-(2-methylphenyl)-1-[(2S)-oxane-2-carbonyl]pyrrolidine-2-carboxylic acid;

(2S,3R,4S,5S)-3-tert-butyl-4{-[2-methoxy-4-(trifluoromethyl)phenyl]methoxy}-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-[(2S)-oxane-2-carbonyl]-5-[2-(propan-2-yl)phenyl]pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-[(2S)-oxane-2-carbonyl]pyrrolidine-2-carboxylic acid;

(2S,3R,4S,5S)-5-(2-bromophenyl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2-ethylphenyl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-([1,1'-biphenyl]-2-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-6-oxo-1,6-dihydropyridin-3-yl)phenyl]-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2-cyclopropylphenyl)pyrrolidine-2-carboxylic acid;

(2S,3R,4S,5S)-5-(2-bromophenyl)-3-tert-butyl-4-[(5-cyclobutyl-2-methoxypyridin-3-yl)methoxy]-1-(cyclohexanecarbonyl)pyrrolidine-2-carboxylic acid;

(2S,3R,4S,5S)-3-tert-butyl-5-(2-ethylphenyl)-4-{[2-methoxy-4-(trifluoromethyl)phenyl]methoxy}-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-ethylphenyl)-1-[(2S)-oxane-2-carbonyl]pyrrolidine-2-carboxylic acid;

(2S,3R,4S,5S)-4-[(5-bromo-2-methoxypyridin-3-yl)methoxy]-3-tert-butyl-5-(2-methylphenyl)-1-[(2S)-oxane-2-carbonyl]pyrrolidine-2-carboxylic acid;

(2S,3R,4S,5S)-3-tert-butyl-4-{[5-(2-cyanopropan-2-yl)-2-methoxyphenyl]methoxy}-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxyquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-5-(4'-fluoro [1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(3'-chloro [1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-1,2,3,6-tetrahydropyridin-4-yl)phenyl]-1-[(2S)-oxane-2-carbonyl]pyrrolidine -2-carboxylic acid;

(2S,3R,4S,5S)-3-tert-butyl-4-{[2-methoxy-5-(trifluoromethyl)pyridin-3-yl]methoxy}-5-[2-(1-methyl-1H-pyrazol-4-yl)phenyl]-1-[(2S)-oxane-2-carbonyl]pyrrolidine-2-carboxylic acid;

(2S,3R,4S,5S)-3-tert-butyl-5[3'-(dimethylamino)[1,1'-biphenyl]-2-yl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(2'-methyl [1,1'-biphenyl]-2-yl)-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(pyridin-4-yl)phenyl]pyrrolidine -2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[2-(pyrimidin-5-yl)phenyl]pyrrolidine-2-carboxylic acid;

(2S,3R,4S,5S)-3-tert-butyl-5-[2-(furan-3-yl)phenyl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(1-methyl-1H-1-pyrrol-3-yl)phenyl]-1-[(2S)-oxane-2-carbonyl]pyrrolidine -2-carboxylic acid;

(2S,3R,4S,5S)-3-tert-butyl-5-(2'-chloro [1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[3'-(trifluoromethoxy)[1,1'-biphenyl]-2-yl]pyrrolidine-2-carboxylic acid;

(2S,3R,4S,5S)-3-tert-butyl-5-(4'-chloro [1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-5-[2-(2H-1,3-benzodioxol-5-yl)phenyl]-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-(2'-fluoro [1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-5-[2-(6-methoxypyridin-3-yl)phenyl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-[4-(trifluoromethoxy)[1,1'-biphenyl]-2-yl)]pyrrolidine-2-carboxylic acid;

(2S,3R,4S,5S)-3-tert-butyl-5-(4'-cyano [1,1'-biphenyl]-2-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-1-[(2S)-oxane-2-carbonyl]-5-{2-[6-(trifluoromethyl)pyridin-3-yl]phenyl}pyrrolidine-2-carboxylic acid;

(2S,3R,4S,5S)-3-tert-butyl-5-[2-(5-ethoxypyridin-3-yl)phenyl]-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-(naphthalen-1-yl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-5-(naphthalen-1-yl)-1-[(2S)-oxane-2-carbonyl]pyrrolidine-2-carboxylic acid;

(2S,3R,4S,5S)-5-(1-benzofuran-7-yl)-3-tert-butyl-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-{[2-methoxy-5-(trifluoromethyl)pyridin-3-yl]methoxy}-5-[2-(2-methylpropyl)phenyl]-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-cyclopropylphenyl)-1-(6-methoxypyridine-2-sulfonyl)pyrrolidine-2-carboxylic acid;

(2S,3R,4S,5S)-3-tert-butyl-4-{[2-methoxy-5-(1-methylcyclobutyl)phenyl]methoxy}-5-(2-methylphenyl)-1-[(2S)-oxane-2-carbonyl]pyrrolidine-2-carboxylic acid;

(2S,3R,4S,5S)-3-tert-butyl-5-(2,3-dihydro-1-benzofuran-7-yl)-4-{[2-methoxy-5-(trifluoromethyl)pyridin-3-yl]methoxy}-1-[(2S)-oxane-2-carbonyl]pyrrolidine-2-carboxylic acid;

(2S,3R,4S,5S)-3-tert-butyl-4-[(5-cyclopropyl-2-methoxypyridin-3-yl)methoxy]-5-(2-methylphenyl)-1[(2S)-oxane-2-carbonyl]pyrrolidine-2-carboxylic acid;

(2S,3R,4S,5S)-3-tert-butyl-4[(5-cyclobutyl-2-methoxypyridin-3-yl)methoxyl]-1[(2S)-oxane-2-carbonyl]-5-(5,6,7,8-tetrahydronaphthalen-1-yl)pyrrolidine-2-carboxylic acid;

(2S,3R,4S,5S)-3-tert-butyl-4-{[2-methoxy-5-(trifluoromethyl)pyridin-3-yl]methoxyl]-1[(2S)-oxane-2-carbonyl]-5-(5,6,7,8-tetrahydronaphthalen-l-yl)pyrrolidine-2-carboxylic acid;

(2S,3R,4S,5S)-3-tert-butyl-4[(2-methoxy-7-methylquinolin-3-yl)methoxyl]-5-(2-methylphenyl)-1[(2S)-oxane-2-carbonyl]pyrrolidine-2-carboxylic acid;

(2S,3R,4S,5S)-3-tert-butyl-4[(6-tert-butyl-2-methoxypyridin-3-yl)methoxyl]-5-(2-methylphenyl)-1[(2S)-oxane-2-carbonyl]pyrrolidine-2-carboxylic acid;

(2S,3R,4S,5S)-3-tert-butyl-1-(3,4-dihydro-2H-pyran-6-carbonyl)-4-{[2-methoxy-5-(trifluoromethyl)pyridin-3-yl]methoxy}-5-(2-methylphenyl)pyrrolidine-2-carboxylic acid;

(2S,3R,4S,5S)-3-tert-butyl-4[(5-chloro-2-methoxypyridin-3-yl)methoxyl]-5-(2-methylphenyl)-1-[(2S)-oxane-2-carbonyl]pyrrolidine-2-carboxylic acid;

(2S,3R,4S,5S)-3-tert-butyl-4-{[2-methoxy-5-(trifluoromethoxy)phenyl]methoxy}-5-(2-methylphenyl)-1[(2S)-oxane-2-carbonyl]pyrrolidine-2-carboxylic acid;

(2S,3R,4S,5S)-N-(6-aminopyridine-2-sulfonyl)-3-tert-butyl-[4(5-cyclobutyl-2-methoxypyridin-3-yl)methoxyl]-5-(2-cyclopropylphenyl)-1[(2S)-oxane-2-carbonyl]pyrrolidine-2-carboxamide;

(2S,3R,4S,5S)-3-tert-butyl-4[(6-tert-butyl-3-methoxypyridin-2-yl)methoxyl]-5-(2-methylphenyl)-1[(2S)-oxane-2-carbonyl]pyrrolidine-2-carboxylic acid;

(2S,3R,4S,5S)-3-tert-butyl-4-({[2-methoxy-5-(trifluoromethyl)pyridin-3-yl]($^2$H$_2$)methyl}oxy)-5-(2-methylphenyl)-1[(2S)-oxane-2-carbonyl]pyrrolidine-2-carboxylic acid;

(2S,3R,4S,5S)-3-tert-butyl-4-{[{2-[($^2$H$_3$)methyloxyl]-5-(trifluoromethyl)pyridin-3-yl}($^2$H$_2$)methyl]oxy}-5-(2-methylphenyl)-1-[(2S)-oxane-2-carbonyl]pyrrolidine-2-carboxylic acid;

(2S,3R,4S,5S)-3-tert-butyl-5-(5-chloro-2-methylphenyl)-4[(5-cyclobutyl-2-methoxypyridin-3-yl)methoxyl]-1[(2S)-oxane-2-carbonyl]pyrrolidine-2-carboxylic acid;

(2S,3R,4S,5S)-3-tert-butyl-5-(5-chloro-2-methylphenyl)-4-{[2-methoxy-5-(trifluoromethyl)pyridin-3-yl]methoxy}-1[(2S)-oxane-2-carbonyl]pyrrolidine-2-carboxylic acid;

(2S,3R,4S,5S)-3-tert-butyl-5-(3-chloro-2-methylphenyl)-4[(5-cyclobutyl-2-methoxypyridin-3-yl)methoxyl]-1[(2S)-oxane-2-carbonyl]pyrrolidine-2-carboxylic acid;

(2S,3R,4S,5S)-3-tert-butyl-5-(3-chloro-2-methylphenyl)-4-{[2-methoxy-5-(trifluoromethyl)pyridin-3-yl]methoxy}-1[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[{2-[($^2$H$_3$)methyloxy]-5-(trifluoromethyl)phenyl}($^2$H$_2$)methyl]oxy}-5-(2-methylphenyl)-1-[(2S)-oxane-2-carbonyl]pyrrolidine-2-carboxylic acid;

(2S,3R,4S,5S)-3-tert-butyl-4-{[(5-tert-butyl-2-methoxyphenyl)($^2$H$_2$)methyl]oxy}-5-(2-methylphenyl)-1-[(2S)-oxane-2-carbonyl]pyrrolidine-2-carboxylic acid;

(2S,3R,4S,5S)-3-tert-butyl-4-[(2-chloro-5,7-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxy-5,8-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(2-methoxy-5,7-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-(2-methoxyphenyl)-1-[(2S)-oxane-2-carbonyl]pyrrolidine-2-carboxylic acid;

(2S,3R,4S,5S)-3-tert-butyl-5-(2-methoxyphenyl)-4-{[2-methoxy-5-(trifluoromethyl)pyridin-3-yl]methoxyl}-1-[(2S)-oxane-2-carbonyl]pyrrolidine-2-carboxylic acid;

(2S,3R,4S,5S)-3-tert-butyl-4-[(5-tert-butyl-2-methoxypyridin-3-yl)methoxy]-5-(2-methoxyphenyl)-1-[(2S)-oxane-2-carbonyl]pyrrolidine-2-carboxylic acid;

(2S,3R,4S,5S)-3-tert-butyl-4-[(2-methoxy-6,8-dimethylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-{[2-methoxy-5-(1-methylcyclopropyl)pyridin-3-yl]methoxy}-5-(2-methylphenyl)-1-[(2S)-oxane-2-carbonyl]pyrrolidine-2-carboxylic acid;

(2S,3R,4S,5S)-3-tert-butyl-4-[(2-methoxy-8-methylquinolin-3-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-tert-butyl-2-methoxyphenyl)methoxy]-1-{[(propan-2-yl)oxy]carbonyl}5-{2-[(propan-2-yl)oxy]pyridin-3-yl}pyrrolidine-2-carboxylic acid;

(2S,3R,4S,5S)-3-tert-butyl-4-{[2-methoxy-5-(1-methylcyclobutyl)phenyl]methoxy }-1-{[(propan-2-yl)oxy]carbonyl}-5-{2-[(propan-2-yl)oxy]pyridin-3-yl}pyrrolidine-2-carboxylic acid;

(2S,3R,4S,5S)-3-tert-butyl-4-[(5-tert-butyl-2-methoxyphenyl)methoxy]-5-(2-methylphenyl)-1-[(2S)-oxolane-2-carbonyl]pyrrolidine-2-carboxylic acid;

(2S,3R,4S,5S)-3-tert-butyl-1-(cyclohexanecarbonyl)-4-[(2-methoxy-5,8-dimethylquinolin-3-yl)methoxy]-5-{2-[(propan-2-yl(oxy]pyridin-3-yl}pyrrolidine-2-carboxylic acid;

(2S,3R,4S,5S)-3-tert-butyl-4-({2-[2methoxy-5-(trifluoromethyl)phenyl]prop-2-en-1-yl}oxy)-5-(2-methylphenyl)-1-[(2S)-oxane-2-carbonyl]pyrrolidine -2-carboxylic acid;

(2S,3R,4S,5S)-3-tert-butyl-4-[(5-tert-butyl-2-methoxypyridin-3-yl)methoxy]-1-(cyclohexanecarbonyl)-5-{2-[(propan-2-yl)oxy]pyridin-3-yl}pyrrolidine-2-carboxylic acid;

(2S,3R,4S,5S)-3-tert-butyl-4-[(5-tert-butyl-2-methoxyphenyl)methoxy]-1-(cyclohexanecarbonyl)-5-{2-[(propan-2-yl)oxy]pyridin-3-yl}pyrrolidine -2-carboxylic acid;

(2S,3R,4S,5S)-3-tert-butyl-1-(cyclohexanecarbonyl)-4-[(2-methoxy-5 ,7-dimethylquinolin-3-yl)methoxy]-5-{2[(propan-2-yl)oxy]pyridin-3-yl}pyrrolidine-2-carboxylic acid;

(2S,3R,4S,5S)-3-tert-butyl-4-[(2-methoxy-5,7-dimethylquinolin-3-yl)methoxy]-1-{[(propan-2-yl)oxy]carbonyl }-5-{2-[(propan-2-yl)oxy]pyridin-3-yl}pyrrolidine-2-carboxylic acid;

(2S,3R,4S,5S)-3-tert-butyl-5-(2-ethylphenyl)-4-[(2-methoxyquinolin-3-yl)methoxy]-1-[(2S)-oxane-2-carbonyl]pyrrolidine-2-carboxylic acid;

(2S,3R,4S,5S)-3-tert-butyl-4-[(1-methyl-1H-benzimidazol-2-yl)methoxy]-5-(2-methylphenyl)-1-[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-1-(cyclohexanecarbonyl)-5-(2,2-dimethyl-2, 3-dihydro-1-benzofuran-7-yl)pyrrolidine-2-carboxylic acid;

(2S,3R,4S,5S)-3-tert-butyl-1-(cyclohexanecarbonyl)-5-(2,2-dimethyl-2,3-dihydro-1-benzofuran-7-yl)-4-{[2-methoxy-5-(trifluoromethyl)pyridin-3-yl]methoxy}pyrrolidine-2-carboxylic acid;

(2S,3R,4S,5S)-1-(cyclohexanecarbonyl)-3-(2-methoxypropan-2-yl)-4-{[2-methoxy-5-(trifluoromethyl)pyridin-3-yl]methoxy}-5-[2-(propan-2-yl)phenyl]pyrrolidine-2-carboxylic acid;

(2S,3R,4S,5S)-3-(2-methoxypropan-2-yl)-4-{[2-methoxy-5-(trifluoromethyl)pyridin-3-yl]methoxy}-1-{[(propan-2-yl)oxy]carbonyl }-5-[2-(propan-2-yl)phenyl]pyrrolidine-2-carboxylic acid;

(2S,3R,4S,5S)-3-(2-methoxypropan-2-yl)-4-{[2-methoxy-5-(trifluoromethyl)pyridin-3-yl]methoxy}-1-[(2S)-oxane-2-carbonyl]-5-[2-(propan-2-yl)phenyl]pyrrolidine-2-carboxylic acid;

(2S,3R,4S,5S)-3-tert-butyl-4-{2-[2-methoxy-5-(trifluoromethyl)phenyl]propoxyl}-5-(2-methylphenyl)-1-[(2S)-oxane-2-carbonyl]pyrrolidine-2-carboxylic acid;

(2S,3R,4S,5S)-3-tert-butyl-4-{(2S)-2,3-dihydroxy-2-[2-methoxy-5-(trifluoromethyl)phenyl]propoxy }-5-(2-methylphenyl)-1-[(2S)-oxane-2-carbonyl]pyrrolidine -2-carboxylic acid;

(2S,3R,4S,5S)-3-tert-butyl-4-{(2R)-2,3-dihydroxy-2-[2-methoxy-5-(trifluoromethyl)phenyl]propoxyl }-5-(2-methylphenyl)-1-[(2S)-oxane-2-carbonyl]pyrrolidine -2-carboxylic acid;

(2S,3R,4S,5S)-3-tert-butyl-4-{2-[2-methoxy-5-(trifluoromethyl)phenyl]-2-oxoethoxy}-5-(2-methylphenyl)-1[(2S)-oxane-2-carbonyl]pyrrolidine-2-carboxylic acid;

(2S,3R,4S,5S)-3-tert-butyl-4-[(5-cyclobutyl-2-methoxypyridin-3-yl)methoxy]-5-{2[(propan-2-yl)oxy]pyridin-3-yl}1-{[(1,1,1-trifluoropropan-2-yl)oxy]carbonyl}pyrrolidine-2-carboxylic acid;

(2S,3R,4S,5S)-3-tert-butyl-4[(5-cyclobutyl-2-methoxypyridin-3-yl)methoxy]-5-{2[(propan-2-yl)oxy]pyridin-3-yl}1-({[(2R)-1,1,1-trifluoropropan-2-yl]oxy}carbonyl)pyrrolidine-2-carboxylic acid;

(2S,3R,4S,5S)-3-tert-butyl-4[(5-cyclobutyl-2-methoxypyridin-3-yl)methoxy]-5-{2[(propan-2-yl)oxy]pyridin-3-yl}1-({[(2S)-1,1,1-trifluoropropan-2-yl]oxy}carbonyl)pyrrolidine-2-carboxylic acid;

(2S,3R,4S,5S)-3-tert-butyl-4-{2-hydroxy-2-[2-methoxy-5-(trifluoromethyl)phenyl]ethoxy}-5-(2-methylphenyl)-1[(2S)-oxane-2-carbonyl]pyrrolidine-2-carboxylic acid;

(2S,3R,4S,5S)-3-tert-butyl-4-{2-methoxy-2-[2-methoxy-5-(trifluoromethyl)phenyl]ethoxy}-5-(2-methylphenyl)-1[(2S)-oxane-2-carbonyl]pyrrolidine-2-carboxylic acid;

(2S,3R,4S,5S)-4-[(5-tert-butyl-2-methoxyphenyl)methoxy]-3-(2-methoxypropan-2-yl)-1[(2S)-oxane-2-carbonyl]-5-[2-(propan-2-yl)phenyl]pyrrolidine-2-carboxylic acid;

(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-({[(2S)-1,1,1-trifluoropropan-2-yl]oxy}carbonyl)pyrrolidine-2-carboxylic acid;

(2S,3R,4S,5S)-3-tert-butyl-4-{(2R)-2-[2-methoxy-5-(trifluoromethyl)phenyl]propoxy}-5-(2-methylphenyl)-1[(2S)-oxane-2-carbonyl]pyrrolidine-2-carboxylic acid;

(2S,3R,4S,5S)-3-tert-butyl-4-{(2S)-2-[2-methoxy-5-(trifluoromethyl)phenyl]propoxy}-5-(2-methylphenyl)-1[(2S)-oxane-2-carbonyl]pyrrolidine-2-carboxylic acid;

(2S,3R,4S,5S)-3-tert-butyl-4[(5-tert-butyl-2-methoxyphenyl)methoxy]-5-{2[(propan-2-yl)oxy]pyridin-3-yl}1-({[(2S)-1,1,1-trifluoropropan-2-yl]oxy}carbonyl)pyrrolidine-2-carboxylic acid;

(2S,3R,4S,5S)-3-tert-butyl-4[(5-cyclobutyl-2-methoxypyridin-3-yl)methoxy]-5-{2[(propan-2-yl)oxy]pyridin-3-yl}-1-[1-(trifluoromethyl)cyclopropane-1-carbonyl]pyrrolidine-2-carboxylic acid;

(2S,3R,4S,5S)-3-tert-butyl-4[(5-cyclobutyl-2-methoxypyridin-3-yl)methoxy]-5-{2[(propan-2-yl)oxy]pyridin-3-yl}-1-[1-(trifluoromethyl)cyclopentane-1-carbonyl]pyrrolidine-2-carboxylic acid;

(2S,3R,4S,5S)-3-tert-butyl-4-({3-[2-methoxy-5-(trifluoromethyl)pyridin-3-yl]prop-2-yn-1-yl}oxy)-5-phenyl-1-{[(propan-2-yl)oxy]carbonyl}pyrrolidine-2-carboxylic acid;

(2S,3R,4S,5S)-3-tert-butyl-5-(2-ethylphenyl)-4-({3-[2-methoxy-5-(trifluoromethyl)pyridin-3-yl]prop-2-yn-1-yl}oxy)-1[(2S)-oxane-2-carbonyl]pyrrolidine-2-carboxylic acid;

(2S,3R,4S,5S)-3-tert-butyl-1-(cyclohexanecarbonyl)-5-{2-[(propan-2-yl)oxy]pyridin-3-yl}-4-{[5-(trifluoromethyl)-1-benzofuran-3-yl]methoxy}pyrrolidine-2-carboxylic acid;
(2S,3R,4S,5S)-3-tert-butyl-5-(2-ethylphenyl)-4-{3-[2-methoxy-5-(trifluoromethyl)pyridin-3-yl]propoxy}-1-[(2S)-oxane-2-carbonyl]pyrrolidine-2-carboxylic acid;
(2S,3R,4S,5S)-3-tert-butyl-5-(5-iodo-2-methylphenyl)-4-{[2-methoxy-5-(trifluoromethyl)pyridin-3-yl]methoxy}-1-[(2S)-oxane-2-carbonyl]pyrrolidine-2-carboxylic acid;
(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-[(1R,2R)-2-(trifluoromethyl)cyclohexane-1-carbonyl]pyrrolidine-2-carboxylic acid;
(2S,3R,4S,5S)-3-tert-butyl-4-{[2-methoxy-5-(trifluoromethyl)pyridin-3-yl]methoxy}-5-{2-[(propan-2-yl)oxy]pyridin-3-yl}-1-[(1S,2S)-2-(trifluoromethyl)cyclohexane-1-carbonyl]pyrrolidine-2-carboxylic acid;
(2S,3R,4S,5S)-3-tert-butyl-4-{2-[(5-chloro-2-methoxypyridin-3-yl)oxy]ethoxy}-5-(2-methylphenyl)-1-[(2S)-oxane-2-carbonyl]pyrrolidine-2-carboxylic acid;
(2S,3R,4S,5S)-3-tert-butyl-4-[(5-tert-butyl-2-methoxyphenyl)methoxy]-1-[(2S)-oxane-2-carbonyl]-5-{2-[(propan-2-yl)oxy]pyridin-3-yl}pyrrolidine-2-carboxylic acid;
(2S,3R,4S,5S)-3-tert-butyl-4-{[2-methoxy-5-(trifluoromethyl)pyridin-3-yl]methoxy}-5-[2-($^2$H$_3$)methylphenyl]-1-[(2S,3S)-(2,3-$^2$H$_2$)oxane-2-carbonyl](2-$^2$H)pyrrolidine-2-carboxylic acid;
(2S,3R,4S,5S)-3-tert-butyl-1-(cyclohexanecarbonyl)-4-{[2-methoxy-5-(1-methylcyclopropyl)pyridin-3-yl]methoxy}-5-{2-[(propan-2-yl)oxy]pyridin-3-yl}pyrrolidine-2-carboxylic acid;
(2S,3R,4S,5S)-3-tert-butyl-4-{2-[2-methoxy-5-(trifluoromethyl)phenoxy]ethoxy}-5-(2-methylphenyl)-1-[2S)-oxane-2-carbonyl]pyrrolidine-2-carboxylic acid;
(2S,3R,4S,5S)-4-[(5-bromo-1-benzofuran-2-yl)methoxy]-3-tert-butyl-1-[(2S)-oxane-2-carbonyl]-5-{2-[(propan-2-yl)oxy]pyridin-3-yl}pyrrolidine-2-carboxylic acid;
(2S,3R,4S,5S)-3-tert-butyl-4-[(6-tert-butyl-2-methoxypyridin-3-yl)methoxy]-1-[(2S)-oxane-2-carbonyl]-5-{2-[(propan-2-yl)oxy]pyridin-3-yl}pyrrolidine-2-carboxylic acid;
(2S,3R,4S,5S)-3-tert-butyl-4-[(6-tert-butyl-2-methoxypyridin-3-yl)methoxy]-1-(cyclohexanecarbonyl)-5-{2-[(propan-2-yl)oxy]pyridin-3-yl}pyrrolidine-2-carboxylic acid;
(2S,3R,4S,5S)-3-tert-butyl-5-(2-ethylphenyl)-1-[(2S)-oxane-2-carbonyl]-4-{[7-(trifluoromethyl)-1-benzofuran-2-yl]methoxy}pyrrolidine-2-carboxylic acid;
(2S,3R,4S,5S)-3-tert-butyl-4-[(5-chloro-1-benzofuran-2-yl)methoxy]-5-(2-ethylphenyl)-1-[(2S)-oxane-2-carbonyl]pyrrolidine-2-carboxylic acid;
(2S,3R,4S,5S)-3-tert-butyl-4-[(5-cyclobutyl-2-methoxypyridin-3-yl)methoxy]-1-(naphthalene-1-sulfonyl)-5-{2-[(propan-2-yl)oxy]pyridin-3-yl}pyrrolidine-2-carboxylic acid;
(2S,3R,4S,5S)-3-tert-butyl-4-[(5-cyclobutyl-2-methoxypyridin-3-yl)methoxy]-1-(cyclohexanecarbonyl)-5-[2-(propan-2-yl)phenyl]pyrrolidine-2-carboxylic acid; and
(2S,3R,4S,5S)-3-tert-butyl-4[(5-cyclobutyl-1-benzofuran-2-yl)methoxyl]-1-[(2S)-oxane-2-carbonyl]-5-{2-[(propan-2-yl)oxy]pyridin-3-yl}pyrrolidine-2-carboxylic acid.

13. The compound, or a pharmaceutically acceptable salt thereof, wherein the compound is selected from the group consisting of:
(2S,3R,4S,5S)-3-tert-butyl-4-{[2-methoxy-5-(trifluoromethyl)pyridin-3-yl]methoxy}-1[(2S)-oxolane-2-carbonyl]-5-[2-(propan-2-yl)phenyl]pyrrolidine-2-carboxylic acid;
(2S,3R,4S,5S)-3-tert-butyl-4-{[2-methoxy-5-(trifluoromethyl)pyridin-3-yl]methoxy}-1-[(2,R)-oxolane-2-carbonyl]-5-[2-(propan-2-yl)phenyl]pyrrolidine-2-carboxylic acid;
(2S,3R,4S,5S)-3-tert-butyl-4-{[2-methoxy-5-(trifluoromethyl)pyridin-3-yl]methoxy}-1-[(3S)-oxolane-3-carbonyl]-5-[2-(propan-2-yl)phenyl]pyrrolidine-2-carboxylic acid;
(2S,3R,4S,5S)-3-tert-butyl-4-{[2-methoxy-5-(trifluoromethyl)pyridin-3-yl]methoxy}-1-[3R]-oxolane-3-carbonyl]-5-[2-(propan-2-yl)phenyl]pyrrolidine-2-carboxylic acid;
(2S,3R,4S,5S)-3-tert-butyl-4-{[2-methoxy-5-(trifluoromethyl)pyridin-3-yl]methoxy}-1-[(2,S)-oxolane-2-carbonyl]-5-[3-(propan-2-yl)phenyl]pyrrolidine -2-carboxylic acid;
(2S,3R,4S,5S)-3-tert-butyl-4-{[2-methoxy-5-(trifluoromethyl)pyridin-3-yl]methoxy}-5-(2-methylphenyl)-1[(2S)-oxolane-2-carbonyl]pyrrolidine-2-carboxylic acid; and
(2S,3R,4S,5S)-3-tert-butyl-4-{[2-methoxy-5-(trifluoromethyl)pyridin-3-yl]methoxy}-5-(2-methylphenyl)-1-[(2S)-oxane-2-carbonyl]pyrrolidine -2-carboxylic acid.

14. (2S,3R,4S,5S)-3-tert-butyl-4-{[2-methoxy-5-(trifluoromethyl)phenyl]methoxy}-5-(2-methylphenyl)-1-[(2S)-oxane-2-carbonyl]pyrrolidine-2-carboxylic acid; or a pharmaceutically acceptable salt thereof.

15. (2S,3R,4S,5S)-3-tert-butyl-4-[(5-tert-butyl-2-methoxyphenyl)methoxy]-5-(2-methylphenyl)-1-[(2S)-oxane-2-carbonyl]pyrrolidine-2-carboxylic acid; or a pharmaceutically acceptable salt thereof.

16. (2S,3R,4S,5S)-3-tert-butyl-4-{[2-methoxy-5-(trifluoromethyl)pyridin-3-yl]methoxyl}-1-[(2S)-oxolane-2-carbonyl]-5-[2-(propan-2-yl)phenyl]pyrrolidine-2-carboxylic acid; or a pharmaceutically acceptable salt thereof.

17. (2S,3R,4S,5S)-3-tert-butyl-4-{[2-methoxy-5-(trifluoromethyl)pyridin-3-yl]methoxyl}-1-[(2R)-oxolane-2-carbonyl]-5-[2-(propan-2-yl)phenyl]pyrrolidine-2-carboxylic acid; or a pharmaceutically acceptable salt thereof.

18. The compound, or a pharmaceutically acceptable salt thereof, wherein the compound is selected from the group consisting of:
(2S,3R,4S,5S)-3 -tert-butyl-4-{[2-methoxy-5 -(trifluoromethyl)pyridin-3 -yl]methoxy}-1-[(3S)-oxolane-3-carbonyl]-5-[2,-(propan-2-yl)phenyl]pyrrolidine-2-carboxylic acid; and
(2S,3R,4S,5S)-3 -tert-butyl-4-{[2-methoxy-5 -(trifluoromethyl)pyridin-3 -yl]methoxy}-1-[(3R)-oxolane-3-carbonyl]-5-[2-(propan-2-yl)phenyl]pyrrolidine -2-carboxylic acid; or a pharmaceutically acceptable salt thereof.

19. (2S,3R,4S,5S)-3-tert-butyl-4-{[2-methoxy-5-(trifluoromethyl)pyridin-3-yl]methoxyl}-1[(2S)-oxolane-2-carbonyl]-5-[3-(propan-2-yl)phenyl]pyrrolidine-2-carboxylic acid; or a pharmaceutically acceptable salt thereof.

20. (2S,3R,4S,5S)-3-tert-butyl-4-{[2-methoxy-5-(trifluoromethyl)pyridin-3-yl]methoxyl}-5-(2-methylphenyl)-1-[(2S)-oxolane-2-carbonyl]pyrrolidine-2-carboxylic acid; or a pharmaceutically acceptable salt thereof.

21. (2S,3R,4S,5S)-3-tert-butyl-4-{[2-methoxy-5-(trifluoromethyl)pyridin-3-yl]methoxyl}-5-(2-methylphenyl)-1[(2S)-oxane-2-carbonyl]pyrrolidine-2-carboxylic acid; or a pharmaceutically acceptable salt thereof.

* * * * *